United States Patent
Yamaki et al.

(10) Patent No.: US 12,356,850 B2
(45) Date of Patent: Jul. 8, 2025

(54) COMPOUND, AND ORGANIC ELECTROLUMINESCENCE DEVICE AND ELECTRONIC APPARATUS USING THE SAME

(71) Applicant: IDEMITSU KOSAN CO., LTD., Tokyo (JP)

(72) Inventors: Taro Yamaki, Sodegaura (JP); Satomi Tasaki, Sodegaura (JP); Hiroaki Itoi, Sodegaura (JP); Yuki Nakano, Sodegaura (JP)

(73) Assignee: IDEMITSU KOSAN CO., LTD., Tokyo (JP)

(*) Notice: Subject to any disclaimer, the term of this patent is extended or adjusted under 35 U.S.C. 154(b) by 928 days.

(21) Appl. No.: 17/291,934

(22) PCT Filed: Nov. 8, 2019

(86) PCT No.: PCT/JP2019/043970
§ 371 (c)(1),
(2) Date: May 6, 2021

(87) PCT Pub. No.: WO2020/096053
PCT Pub. Date: May 14, 2020

(65) Prior Publication Data
US 2022/0029099 A1  Jan. 27, 2022

(30) Foreign Application Priority Data
Nov. 8, 2018  (JP) .................................. 2018-210787

(51) Int. Cl.
*H01L 51/50* (2006.01)
*C07C 15/38* (2006.01)
(Continued)

(52) U.S. Cl.
CPC ........... *H10K 85/626* (2023.02); *C07C 15/38* (2013.01); *C09K 11/06* (2013.01); *H10K 85/622* (2023.02);
(Continued)

(58) Field of Classification Search
None
See application file for complete search history.

(56) References Cited

U.S. PATENT DOCUMENTS

| | | | | |
|---|---|---|---|---|
| 2004/0137270 A1* | 7/2004 | Seo | ......... | H05B 33/14 428/690 |
| 2004/0170863 A1* | 9/2004 | Kim | ...... | C07D 409/14 313/506 |

(Continued)

FOREIGN PATENT DOCUMENTS

| | | | | |
|---|---|---|---|---|
| JP | 2005-206551 | * | 8/2005 | ............. C09K 11/06 |
| JP | 2005-206551 A | | 8/2005 | |

(Continued)

OTHER PUBLICATIONS

International Preliminary Report on Patentability from PCT/JP2019/043970 Dtd May 20, 2021 (7 pages).
(Continued)

*Primary Examiner* — Gregory D Clark
(74) *Attorney, Agent, or Firm* — Foley & Lardner LLP

(57) ABSTRACT

A compound represented by the following formula (1), provided that at least one of $R_1$ to $R_8$ is a deuterium atom; and at least one of $Ar_1$ and $Ar_2$ is a substituted or unsubstituted fused aryl group in which only four or more benzene rings are fused.

(Continued)

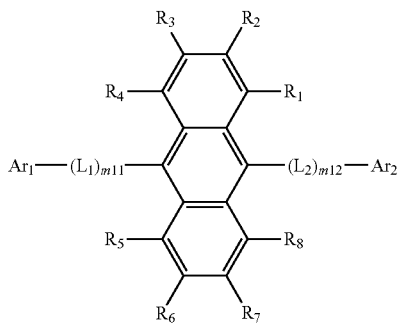

23 Claims, 1 Drawing Sheet

(51) Int. Cl.
*C09K 11/06* (2006.01)
*H10K 85/60* (2023.01)
*H10K 50/11* (2023.01)
*H10K 50/15* (2023.01)
*H10K 50/16* (2023.01)
*H10K 101/10* (2023.01)

(52) U.S. Cl.
CPC ........ *H10K 85/623* (2023.02); *C07B 2200/05* (2013.01); *C07C 2603/24* (2017.05); *C07C 2603/42* (2017.05); *C07C 2603/52* (2017.05); *C09K 2211/1007* (2013.01); *C09K 2211/1011* (2013.01); *H10K 50/11* (2023.02); *H10K 50/15* (2023.02); *H10K 50/16* (2023.02); *H10K 2101/10* (2023.02)

(56) References Cited

U.S. PATENT DOCUMENTS

| | | |
|---|---|---|
| 2012/0217449 A1 | 8/2012 | Spreitzer et al. |
| 2012/0326602 A1 | 12/2012 | Buesing et al. |
| 2018/0261791 A1 | 9/2018 | Yoo et al. |
| 2019/0305227 A1 | 10/2019 | Yoon et al. |
| 2022/0093868 A1* | 3/2022 | Lee .................. C09K 11/06 |
| 2022/0376179 A1 | 11/2022 | Hatakeyama et al. |

FOREIGN PATENT DOCUMENTS

| | | | | |
|---|---|---|---|---|
| JP | 2015-065323 A | | 4/2015 | |
| KR | 10-2014-0058292 A | | 5/2014 | |
| KR | 2014091969 | * | 7/2014 | ............ H01L 51/50 |
| KR | 10-2019-0056338 A | | 5/2019 | |
| WO | WO-2010/071362 A2 | | 6/2010 | |
| WO | WO 2010/099534 | * | 9/2010 | ............ C09K 11/06 |
| WO | WO-2010/099534 A2 | | 9/2010 | |
| WO | WO-2010/135395 A2 | | 11/2010 | |
| WO | WO-2011/028216 A1 | | 3/2011 | |
| WO | WO-2013/175746 A1 | | 11/2013 | |
| WO | WO-2018/146894 A1 | | 8/2018 | |

OTHER PUBLICATIONS

International Search Report and Written Opinion from PCT/JP2019/043970 Dtd Jan. 28, 2020 (16 pages).
Yan, Yong et al., "Porous Metal-Organic Polyhedral Frameworks with Optimal Molecular Dynamics and Pore Geometry for Methane Storage", Journal of the American Chemical Society, 2017, 139(38), pp. 13349-13360, Supporting Information Supporting Information, compound S22.
Office Action issued in corresponding Chinese Patent Application No. 201980073311.1 dated Dec. 23, 2023 (12 pages).

* cited by examiner

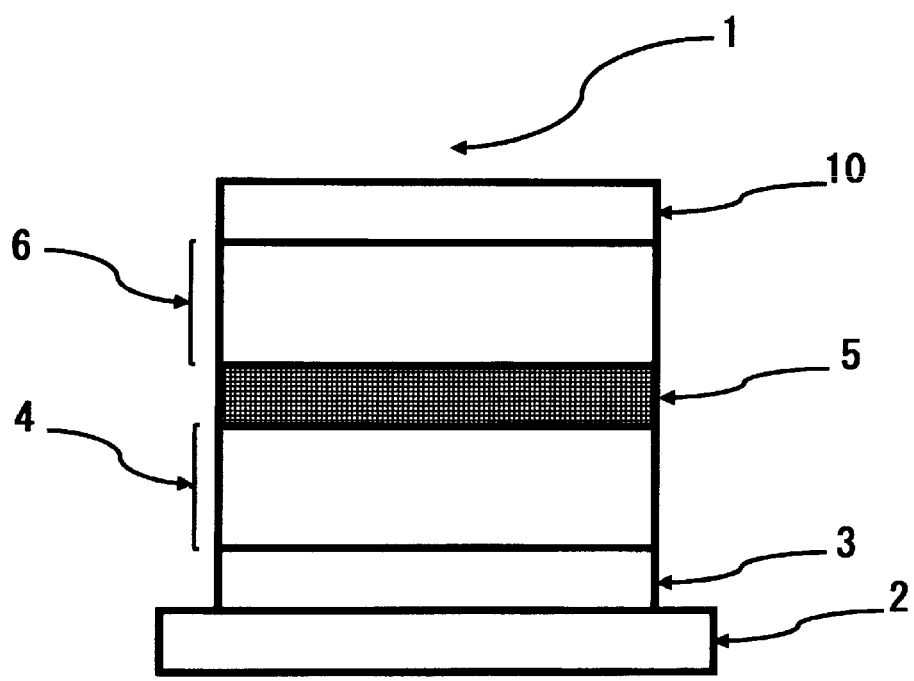

COMPOUND, AND ORGANIC ELECTROLUMINESCENCE DEVICE AND ELECTRONIC APPARATUS USING THE SAME

CROSS-REFERENCE TO RELATED APPLICATIONS

The present application claims priority under 37 U.S.C. § 371 to International Patent Application No. PCT/JP2019/043970, filed Nov. 8, 2019, which claims priority to and the benefit of Japanese Patent Application No. 2018-210787, filed on Nov. 8, 2018. The contents of these applications are hereby incorporated by reference in their entireties.

TECHNICAL FIELD

The invention relates to a novel compound, and an organic electroluminescence device and an electronic apparatus using the same.

BACKGROUND ART

When voltage is applied to an organic electroluminescence device (hereinafter, referred to as an organic EL device in several cases), holes and electrons are injected into an emitting layer from an anode and a cathode, respectively. Then, thus injected holes and electrons are recombined in the emitting layer, and excitons are formed therein.

Patent Documents 1 to 6 disclose the use of an anthracene compound having a specific structure as a host material of an emitting layer of an organic EL device.

RELATED ART DOCUMENTS

Patent Documents

[Patent document 1] WO 2010/099534 A1
[Patent document 2] WO 2010/135395 A1
[Patent document 3] WO 2011/028216 A1
[Patent document 4] WO 2010/071362 A1
[Patent document 5] US 2012/0217449 A1
[Patent document 6] US 2012/0326602 A1

SUMMARY OF THE INVENTION

An object of the invention to provide a novel compound capable of improving (prolonging) device lifetime, and an organic electroluminescent device with improved device lifetime using the compound.

According to the invention, the following compound, material for organic electroluminescent device, composition, organic electroluminescent device, and electronic apparatus are provided.

1. A compound represented by the following formula (1):

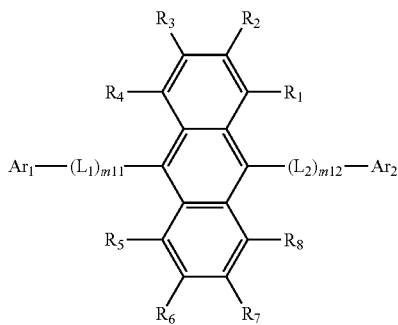

wherein in the formula (1),
$R_1$ to $R_8$ are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si$(R_{901})(R_{902})(R_{903})$,
—O—$(R_{904})$,
—S—$(R_{905})$,
—N$(R_{906})(R_{907})$,
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms;
when two or more of each of $R_{901}$ to $R_{907}$ are present, the two or more of each of $R_{901}$ to $R_{907}$ are the same or different;
adjacent two or more of $R_1$ to $R_8$ do not form a ring by bonding with each other;
provided that at least one of $R_1$ to $R_8$ is a deuterium atom;
$L_1$ and $L_2$ are independently
a substituted or unsubstituted arylene group including 6 to 30 ring carbon atoms, or
a substituted or unsubstituted divalent heterocyclic group including 5 to 30 ring atoms;
m11 and m12 are independently an integer of 0 to 4;
when m11 and m12 are 0, $(L_1)_{m11}$ and $(L_2)_{m12}$ are single bonds;
when m11 or m12 is 2 or more, the two or more m11 or m12 may be the same as or different from each other;
$Ar_1$ and $Ar_2$ are independently
a substituted or unsubstituted aryl group including 6 to 50 ring carbon atoms, or
a substituted or unsubstituted monovalent heterocyclic group including 5 to 50 ring atoms;
provided that at least one of $Ar_1$ and $Ar_2$ is a substituted or unsubstituted fused aryl group in which only four or more benzene rings are fused; and
one or more hydrogen atoms possessed by one or more of the groups selected from $L_1$, $L_2$, $Ar_1$ and $Ar_2$ may be deuterium atoms.

2. A material for an organic electroluminescence device, comprising the compound represented by the formula (1).

3. A composition comprising a compound represented by the formula (1), wherein the content ratio of a compound having the same structure as formula (1) except that only protium atoms are contained as hydrogen atoms to the total of the compound represented by the formula (1) and the compound having the same structure as formula (1) except that only protium atoms are contained as hydrogen atoms is 99 mol % or less.

4. An organic electroluminescence device comprising: a cathode, an anode, and an emitting layer disposed between the cathode and the anode, wherein the emitting layer comprises a compound according to 1.

5. An electronic apparatus, wherein the organic electroluminescence device according to 4 is provided.

According to the invention, a compound capable of improving (prolonging) device lifetime, and an organic electroluminescent device with improved device lifetime using the compound can be provided.

BRIEF DESCRIPTION OF THE DRAWINGS

The FIGURE shows the schematic configuration of an organic EL device according to one embodiment of the invention.

MODE FOR CARRYING OUT THE INVENTION

Definition

In this specification, a hydrogen atom means an atom including isotopes different in the number of neutrons, namely, a protium, a deuterium and a tritium.

In this specification, to a bondable position in which a symbol such as "R", or "D" representing a deuterium atom is not specified in a chemical formula, a hydrogen atom, that is, a light hydrogen atom, a deuterium atom, or a tritium atom is bonded thereto.

In this specification, a term "ring carbon atoms" represents the number of carbon atoms among atoms forming a subject ring itself of a compound having a structure in which atoms are bonded in a ring form (for example, a monocyclic compound, a fused ring compound, a cross-linked compound, a carbocyclic compound or a heterocyclic compound). When the subject ring is substituted by a substituent, the carbon contained in the substituent is not included in the number of ring carbon atoms. The same shall apply to the "ring carbon atoms" described below, unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. Further, for example, a 9,9-diphenylfluorenyl group has 13 ring carbon atoms, and a 9,9'-spirobifluorenyl group has 25 ring carbon atoms.

Further, when the benzene ring or the naphthalene ring is substituted by an alkyl group as a substituent, for example, the number of carbon atoms of the alkyl group is not included in the ring carbon atoms.

In this specification, a term "ring atoms" represents the number of atoms forming a subject ring itself of a compound having a structure in which atoms are bonded in a ring form (for example, a monocycle, a fused ring and a ring assembly) (for example, a monocyclic compound, a fused ring compound, a cross-linked compound, a carbocyclic compound or a heterocyclic compound). The term "ring atoms" does not include atoms which do not form the ring (for example, a hydrogen atom which terminates a bond of the atoms forming the ring) or atoms contained in a substituent when the ring is substituted by the substituent. The same shall apply to the "ring atoms" described below, unless otherwise noted. For example, a pyridine ring has 6 ring atoms, a quinazoline ring has 10 ring atoms, and a furan ring has 5 ring atoms. A hydrogen atom bonded with a carbon atom of the pyridine ring or the quinazoline ring or an atom forming the substituent is not included in the number of the ring atoms.

In this specification, a term "XX to YY carbon atoms" in an expression of "substituted or unsubstituted ZZ group including XX to YY carbon atoms" represents the number of carbon atoms when the ZZ group is unsubstituted. The number of carbon atoms of a substituent when the ZZ group is substituted is not included. Here, "YY" is larger than "XX", and "XX" and "YY" each mean an integer of 1 or more.

In this specification, a term "XX to YY atoms" in an expression of "substituted or unsubstituted ZZ group including XX to YY atoms" represents the number of atoms when the ZZ group is unsubstituted. The number of atoms of a substituent when the group is substituted is not included. Here, "YY" is larger than "XX", and "XX" and "YY" each mean an integer of 1 or more.

A term "unsubstituted" in the case of "substituted or unsubstituted ZZ group" means that the ZZ group is not substituted by a substituent, and a hydrogen atom is bonded therewith. Alternatively, a term "substituted" in the case of "substituted or unsubstituted ZZ group" means that one or more hydrogen atoms in the ZZ group are substituted by a substituent. Similarly, a term "substituted" in the case of "BB group substituted by an AA group" means that one or more hydrogen atoms in the BB group are substituted by the AA group.

Hereinafter, the substituent described in this specification will be described.

The number of the ring carbon atoms of the "unsubstituted aryl group" described in this specification is 6 to 50, preferably 6 to 30, and more preferably 6 to 18, unless otherwise specified.

The number of the ring carbon atoms of the "unsubstituted heterocyclic group" described in this specification is 5 to 50, preferably 5 to 30, and more preferably 5 to 18, unless otherwise specified.

The number of the carbon atoms of the "unsubstituted alkyl group" described in this specification is 1 to 50, preferably 1 to 20, and more preferably 1 to 6, unless otherwise specified.

The number of the carbon atoms of the "unsubstituted alkenyl group" described in this specification is 2 to 50, preferably 2 to 20, and more preferably 2 to 6, unless otherwise specified.

The number of the carbon atoms of the "unsubstituted alkynyl group" described in this specification is 2 to 50, preferably 2 to 20, and more preferably 2 to 6, unless otherwise specified.

The number of the ring carbon atoms of the "unsubstituted cycloalkyl group" described in this specification is 3 to 50, preferably 3 to 20, and more preferably 3 to 6, unless otherwise specified.

The number of the ring carbon atoms of the "unsubstituted arylene group" described in this specification is 6 to 50, preferably 6 to 30, and more preferably 6 to 18, unless otherwise specified.

The number of the ring atoms of the "unsubstituted divalent heterocyclic group" described in this specification is 5 to 50, preferably 5 to 30, and more preferably 5 to 18, unless otherwise specified.

The number of the carbon atoms of the "unsubstituted alkylene group" described in this specification is 1 to 50, preferably 1 to 20, and more preferably 1 to 6, unless otherwise specified.

Specific examples (specific example group G1) of the "substituted or unsubstituted aryl group" described in this specification include an unsubstituted aryl group and a substituted aryl group described below. (Here, a term "unsubstituted aryl group" refers to a case where the "substituted or unsubstituted aryl group" is the "unsubstituted aryl group," and a term "substituted aryl group" refers to a case where the "substituted or unsubstituted aryl group" is the "substituted aryl group". Hereinafter, a case of merely "aryl group" includes both the "unsubstituted aryl group" and the "substituted aryl group".

The "substituted aryl group" refers to a case where the "unsubstituted aryl group" has a substituent, and specific examples thereof include a group in which the "unsubstituted aryl group" has the substituent, and a substituted aryl group described below. It should be noted that examples of the "unsubstituted aryl group" and examples of the "substituted aryl group" listed in this specification are only one example, and the "substituted aryl group" described in this specification also includes a group in which a group in which "unsubstituted aryl group" has a substituent further has a substituent, and a group in which "substituted aryl group" further has a substituent, and the like.

An unsubstituted aryl group:
a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group, and
a perylenyl group.
A substituted aryl group:
an o-tolyl group,
a m-tolyl group,
a p-tolyl group,
a p-xylyl group,
a m-xylyl group,
an o-xylyl group,
a p-isopropyl phenyl group,
a m-isopropyl phenyl group,
an o-isopropyl phenyl group,
a p-t-butylphenyl group,
a m-t-butylphenyl group,
an o-t-butylphenyl group,
a 3,4,5-trimethylphenyl group,
a 9,9-dimethylfluorenyl group,
a 9,9-diphenylfluorenyl group
a 9,9-di(4-methylphenyl)fluorenyl group,
a 9,9-di(4-isopropylphenyl)fluorenyl group,
a 9,9-di(4-t-butylphenyl)fluorenyl group,
a cyanophenyl group,
a triphenylsilylphenyl group,
a trimethylsilylphenyl group,
a phenylnaphthyl group, and
a naphthylphenyl group.

The "heterocyclic group" described in this specification is a ring group including at least one hetero atom in the ring atom. Specific examples of the hetero atom include a nitrogen atom, an oxygen atom, a sulfur atom, a silicon atom, a phosphorus atom and a boron atom.

The "heterocyclic group" described in this specification may be a monocyclic group, or a fused ring group.

The "heterocyclic group" described in this specification may be an aromatic heterocyclic group, or an aliphatic heterocyclic group.

Specific examples (specific example group G2) of the "substituted or unsubstituted heterocyclic group" include an unsubstituted heterocyclic group and a substituted heterocyclic group described below. (Here, the unsubstituted heterocyclic group refers to a case where the "substituted or unsubstituted heterocyclic group" is the "unsubstituted heterocyclic group," and the substituted heterocyclic group refers to a case where the "substituted or unsubstituted heterocyclic group" is the "substituted heterocyclic group". Hereinafter, the case of merely "heterocyclic group" includes both the "unsubstituted heterocyclic group" and the "substituted heterocyclic group".

The "substituted heterocyclic group" refers to a case where the "unsubstituted heterocyclic group" has a substituent, and specific examples thereof include a group in which the "unsubstituted heterocyclic group" has a substituent, and a substituted heterocyclic group described below. It should be noted that examples of the "unsubstituted heterocyclic group" and examples of the "substituted heterocyclic group" listed in this specification are merely one example, and the "substituted heterocyclic group" described in this specification also includes a group in which "unsubstituted heterocyclic group" which has a substituent further has a substituent, and a group in which "substituted heterocyclic group" further has a substituent, and the like.

An unsubstituted heterocyclic group including a nitrogen atom:
a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group, a triazinyl group,
an indolyl group,
an isoindolyl group,
an indolizinyl group,
a quinolizinyl group,
a quinolyl group,
an isoquinolyl group,
a cinnolyl group,
a phthalazinyl group,
a quinazolinyl group,
a quinoxalinyl group,
a benzimidazolyl group,
an indazolyl group,
a phenanthrolinyl group,
a phenanthridinyl group
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

An unsubstituted heterocyclic group including an oxygen atom:
a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

An unsubstituted heterocyclic group including a sulfur atom:
a thienyl group,
a thiazolyl group,
an isothiazolyl group,
a thiadiazolyl group,
a benzothiophenyl group,
an isobenzothiophenyl group,
a dibenzothiophenyl group,
a naphthobenzothiophenyl group,
a benzothiazolyl group,
a benzisothiazolyl group,
a phenothiazinyl group,
a dinaphthothiophenyl group,
an azadibenzothiophenyl group,
a diazadibenzothiophenyl group,
an azanaphthobenzothiophenyl group, and
a diazanaphthobenzothiophenyl group.

A substituted heterocyclic group including a nitrogen atom:
a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenylyltriazinyl group,
a diphenyltriazinyl group,
a phenylquinazolinyl group, and
a biphenylylquinazolinyl group.

A substituted heterocyclic group including an oxygen atom:
a phenyldibenzofuranyl group,
a methyldibenzofuranyl group,
a t-butyldibenzofuranyl group, and
a monovalent residue of spiro[9H-xanthene-9,9'-[9H]fluorene].

A substituted heterocyclic group including a sulfur atom:
a phenyldibenzothiophenyl group,
a methyldibenzothiophenyl group,
a t-butyldibenzothiophenyl group, and
a monovalent residue of spiro[9H-thioxantene-9,9'-[9H]fluorene].

A monovalent group derived from the following unsubstituted heterocyclic ring containing at least one of a nitrogen atom, an oxygen atom and a sulfur atom by removal of one hydrogen atom bonded to the ring atoms thereof, and a monovalent group in which a monovalent group derived from the following unsubstituted heterocyclic ring has a substituent by removal of one hydrogen atom bonded to the ring atoms thereof:

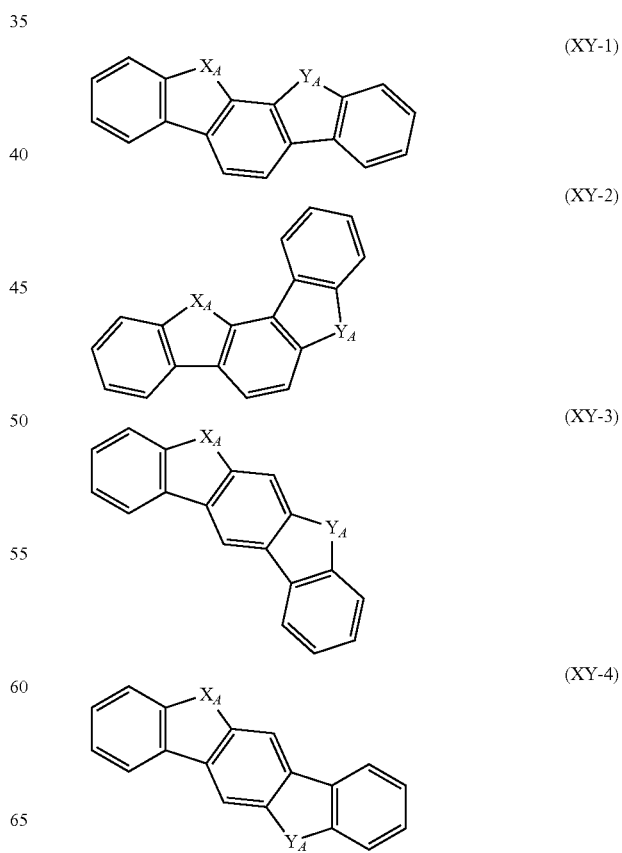

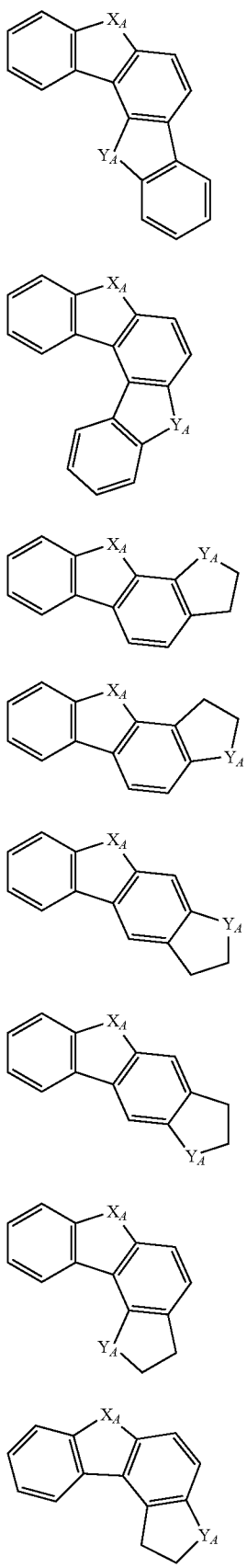
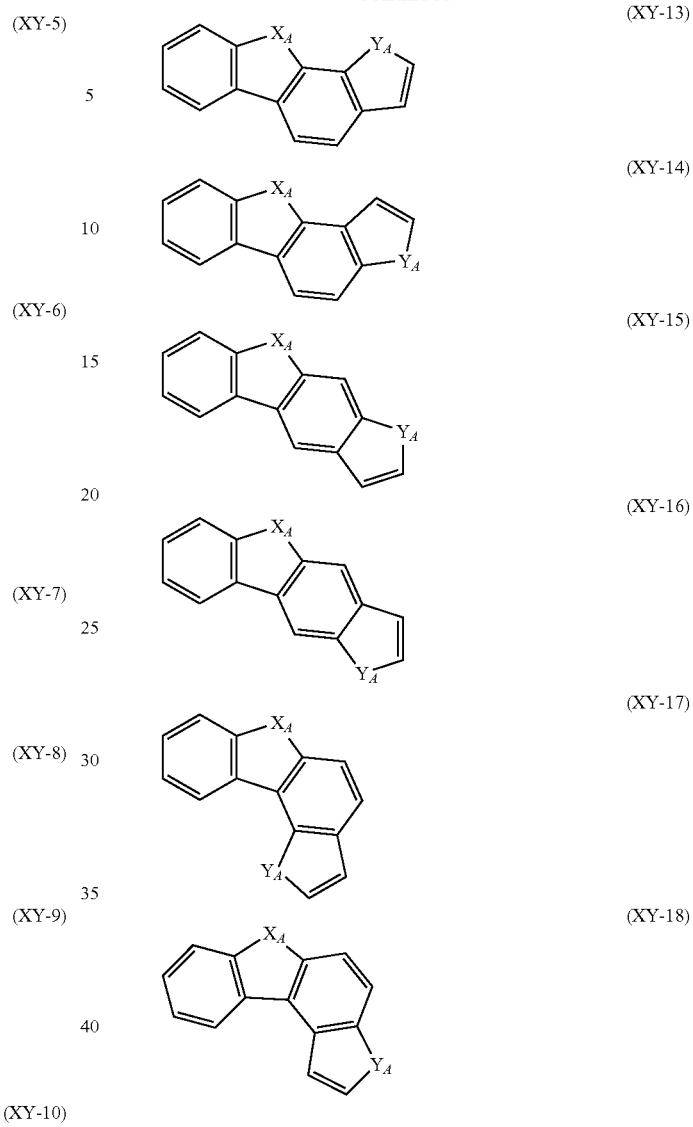

In the formulas (XY-1) to (XY-18), $X_A$ and $Y_A$ are independently an oxygen atom, a sulfur atom, NH or CH$_2$. However, at least one of $X_A$ and $Y_A$ is an oxygen atom, a sulfur atom or NH.

The heterocyclic ring represented by the formulas (XY-1) to (XY-18) becomes a monovalent heterocyclic group including a bond at an arbitrary position.

An expression "the monovalent group derived from the unsubstituted heterocyclic ring represented by the formulas (XY-1) to (XY-18) has a substituent" refers to a case where the hydrogen atom bonded with the carbon atom which constitutes a skeleton of the formulas is substituted by a substituent, or a state in which $X_A$ or $Y_A$ is NH or CH$_2$, and the hydrogen atom in the NH or CH$_2$ is replaced with a substituent.

Specific examples (specific example group G3) of the "substituted or unsubstituted alkyl group" include an unsubstituted alkyl group and a substituted alkyl group described below. (Here, the unsubstituted alkyl group refers to a case where the "substituted or unsubstituted alkyl group" is the "unsubstituted alkyl group," and the substituted alkyl group refers to a case where the "substituted or unsubstituted alkyl group" is the "substituted alkyl group"). Hereinafter, the case of merely "alkyl group" includes both the "unsubstituted alkyl group" and the "substituted alkyl group".

The "substituted alkyl group" refers to a case where the "unsubstituted alkyl group" has a substituent, and specific examples thereof include a group in which the "unsubstituted alkyl group" has a substituent, and a substituted alkyl group described below. It should be noted that examples of the "unsubstituted alkyl group" and examples of the "substituted alkyl group" listed in this specification are merely one example, and the "substituted alkyl group" described in this specification also includes a group in which "unsubstituted alkyl group" has a substituent further has a substituent, a group in which "substituted alkyl group" further has a substituent, and the like.

An unsubstituted alkyl group:
a methyl group,
an ethyl group,
a n-propyl group,
an isopropyl group,
a n-butyl group,
an isobutyl group,
a s-butyl group, and
a t-butyl group.
A substituted alkyl group:
a heptafluoropropyl group (including an isomer),
a pentafluoroethyl group,
a 2,2,2-trifluoroethyl group, and
a trifluoromethyl group.

Specific examples (specific example group G4) of the "substituted or unsubstituted alkenyl group" include an unsubstituted alkenyl group and a substituted alkenyl group described below. (Here, the unsubstituted alkenyl group refers to a case where the "substituted or unsubstituted alkenyl group" is the "unsubstituted alkenyl group," and the substituted alkenyl group refers to a case where the "substituted or unsubstituted alkenyl group" is the "substituted alkenyl group"). Hereinafter, the case of merely "alkenyl group" includes both the "unsubstituted alkenyl group" and the "substituted alkenyl group".

The "substituted alkenyl group" refers to a case where the "unsubstituted alkenyl group" has a substituent, and specific examples thereof include a group in which the "unsubstituted alkenyl group" has a substituent, and a substituted alkenyl group described below. It should be noted that examples of the "unsubstituted alkenyl group" and examples of the "substituted alkenyl group" listed in this specification are merely one example, and the "substituted alkenyl group" described in this specification also includes a group in which "unsubstituted alkenyl group" has a substituent further has a substituent, a group in which "substituted alkenyl group" further has a substituent, and the like.

An unsubstituted alkenyl group and a substituted alkenyl group:
a vinyl group,
an allyl group,
a 1-butenyl group,
a 2-butenyl group,
a 3-butenyl group,
a 1,3-butanedienyl group,
a 1-methylvinyl group,
a 1-methylallyl group,
a 1,1-dimethylallyl group,
a 2-methylallyl group, and
a 1,2-dimethylallyl group.

Specific examples (specific example group G5) of the "substituted or unsubstituted alkynyl group" include an unsubstituted alkynyl group described below. (Here, the unsubstituted alkynyl group refers to a case where the "substituted or unsubstituted alkynyl group" is the "unsubstituted alkynyl group"). Hereinafter, a case of merely "alkynyl group" includes both the "unsubstituted alkynyl group" and the "substituted alkynyl group".

The "substituted alkynyl group" refers to a case where the "unsubstituted alkynyl group" has a substituent, and specific examples thereof include a group in which the "unsubstituted alkynyl group" described below has a substituent.

An unsubstituted alkynyl group:
an ethynyl group.

Specific examples (specific example group G6) of the "substituted or unsubstituted cycloalkyl group" described in this specification include an unsubstituted cycloalkyl group and a substituted cycloalkyl group described below. (Here, the unsubstituted cycloalkyl group refers to a case where the "substituted or unsubstituted cycloalkyl group" is the "unsubstituted cycloalkyl group," and the substituted cycloalkyl group refers to a case where the "substituted or unsubstituted cycloalkyl group" is the "substituted cycloalkyl group"). Hereinafter, a case of merely "cycloalkyl group" includes both the "unsubstituted cycloalkyl group" and the "substituted cycloalkyl group".

The "substituted cycloalkyl group" refers to a case where the "unsubstituted cycloalkyl group" a the substituent, and specific examples thereof include a group in which the "unsubstituted cycloalkyl group" has a substituent, and a substituted cycloalkyl group described below. It should be noted that examples of the "unsubstituted cycloalkyl group" and examples of the "substituted cycloalkyl group" listed in this specification are merely one example, and the "substituted cycloalkyl group" described in this specification also includes a group in which "unsubstituted cycloalkyl group" has a substituent further has a substituent, a group in which "substituted cycloalkyl group" further has a substituent, and the like.

An unsubstituted aliphatic ring group:
a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.
A substituted cycloalkyl group:
a 4-methylcyclohexyl group.

Specific examples (specific example group G7) of the group represented by —Si($R_{901}$)($R_{902}$)($R_{903}$) described in this specification include
—Si(G1)(G1)(G1),
—Si(G1)(G2)(G2),
—Si(G1)(G1)(G2),
—Si(G2)(G2)(G2),
—Si(G3)(G3)(G3),
—Si(G5)(G5)(G5) and
—Si(G6)(G6)(G6).
In which,
G1 is the "aryl group" described in the specific example group G1.
G2 is the "heterocyclic group" described in the specific example group G2.
G3 is the "alkyl group" described in the specific example group G3.
G5 is the "alkynyl group" described in the specific example group G5.

G6 is the "cycloalkyl group" described in the specific example group G6.

Specific examples (specific example group G8) of the group represented by —O—($R_{904}$) described in this specification include
- —O(G1),
- —O(G2),
- —O(G3) and
- —O(G6).

In which,

G1 is the "aryl group" described in the specific example group G1.

G2 is the "heterocyclic group" described in the specific example group G2.

G3 is the "alkyl group" described in the specific example group G3.

G6 is the "cycloalkyl group" described in the specific example group G6.

Specific examples (specific example group G9) of the group represented by —S—(Rsos) described in this specification include
- —S(G1),
- —S(G2),
- —S(G3) and
- —S(G6).

In which,

G1 is the "aryl group" described in the specific example group G1.

G2 is the "heterocycle group" described in the specific example group G2.

G3 is the "alkyl group" described in the specific example group G3.

G6 is the "cycloalkyl group" described in the specific example group G6.

Specific examples (specific example group G10) of the group represented by —N(Re6)($R_{907}$) described in this specification include
- —N(G1)(G1),
- —N(G2)(G2),
- —N(G1)(G2),
- —N(G3)(G3) and
- —N(G6)(G6).

In which,

G1 is the "aryl group" described in the specific example group G1.

G2 is the "heterocycle group" described in the specific example group G2.

G3 is the "alkyl group" described in the specific example group G3.

G6 is the "cycloalkyl group" described in the specific example group G6.

Specific examples (specific example group G11) of the "halogen atom" described in this specification include a fluorine atom, a chlorine atom, a bromine atom and an iodine atom.

Specific examples of the "alkoxy group" described in this specification include a group represented by —O(G3), where G3 is the "alkyl group" described in the specific example group G3. The number of carbon atoms of the "unsubstituted alkoxy group" are 1 to 50, preferably 1 to 30, and more preferably 1 to 18, unless otherwise specified.

Specific examples of the "alkylthio group" described in this specification include a group represented by —S(G3), where G3 is the "alkyl group" described in the specific example group G3. The number of carbon atoms of the "unsubstituted alkylthio group" are 1 to 50, preferably 1 to 30, and more preferably 1 to 18, unless otherwise specified.

Specific examples of the "aryloxy group" described in this specification include a group represented by —O(G1), where G1 is the "aryl group" described in the specific example group G1. The number of ring carbon atoms of the "unsubstituted aryloxy group" are 6 to 50, preferably 6 to 30, and more preferably 6 to 18, unless otherwise specified.

Specific examples of the "arylthio group" described in this specification include a group represented by —S(G1), where G1 is the "aryl group" described in the specific example group G1. The number of ring carbon atoms of the "unsubstituted arylthio group" are 6 to 50, preferably 6 to 30, and more preferably 6 to 18, unless otherwise specified.

Specific examples of the "aralkyl group" described in this specification include a group represented by -(G3)-(G1), where G3 is the "alkyl group" described in the specific example group G3, and G1 is the "aryl group" described in the specific example group G1. Accordingly, the "aralkyl group" is one embodiment of the "substituted alkyl group" substituted by the "aryl group". The number of carbon atoms of the "unsubstituted aralkyl group," which is the "unsubstituted alkyl group" substituted by the "unsubstituted aryl group," are 7 to 50, preferably 7 to 30, and more preferably 7 to 18, unless otherwise specified.

Specific example of the "aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, and a 2-β-naphthylisopropyl group.

The substituted or unsubstituted aryl group described in this specification is, unless otherwise specified, preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-diphenylfluorenyl group, or the like.

The substituted or unsubstituted heterocyclic group described in this specification is, unless otherwise specified, preferably a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazole-9-yl group, a phenylcarbazol-9-yl group, a phenyltriazinyl group, a biphenylyltriazinyl group, diphenyltiiazinyl group, a phenyldibenzofuranyl group, a phenyldibenzothiophenyl group, an indrocarbazolyl group, a pyrazinyl group, a pyridazinyl group, a quinazolinyl group, a cinnolinyl group, a phthalazinyl group, a quinoxalinyl group, a pyrrolyl group, an indolyl group, a pyrrolo[3,2,1-jk]carbazolyl group, a furanyl group, a benzofuranyl group, a thiophenyl group, a benzothiophenyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, an indro[3,2,1-jk]carbazolyl group, a dibenzothiophenyl group, or the like.

The dibenzofuranyl group and the dibenzothiophenyl group as described above are specifically any group described below, unless otherwise specified.

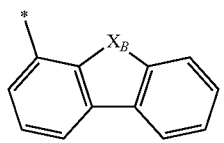
(XY-76)

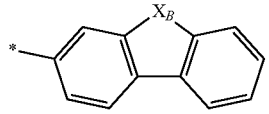
(XY-77)

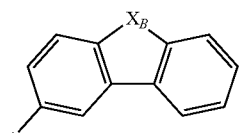
(XY-78)

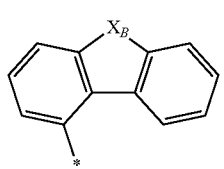
(XY-79)

In the formulas (XY-76) to (XY-79), $X_B$ is an oxygen atom or a sulfur atom.

The substituted or unsubstituted alkyl group described in this specification is, unless otherwise specified, preferably a methyl group, an ethyl group, a propyl group, an isopropyl group, a n-butyl group, an isobutyl group, a t-butyl group, or the like.

The "substituted or unsubstituted arylene group" descried in this specification refers to a group in which the above-described "aryl group" is converted into divalence, unless otherwise specified. Specific examples (specific example group G12) of the "substituted or unsubstituted arylene group" include a group in which the "aryl group" described in the specific example group G1 is converted into divalence. Namely, specific examples (specific example group G12) of the "substituted or unsubstituted arylene group" refer to a group derived from the "aryl group" described in specific example group G1 by removal of one hydrogen atom bonded to the ring carbon atoms thereof.

Specific examples (specific example group G13) of the "substituted or unsubstituted divalent heterocyclic group" include a group in which the "heterocyclic group" described in the specific example group G2 is converted into divalence. Namely, specific examples (specific example group G13) of the "substituted or unsubstituted divalent heterocyclic group" refer to a group derived from the "heterocyclic group" described in specific example group G2 by removal of one hydrogen atom bonded to the ring atoms thereof.

Specific examples (specific example group G14) of the "substituted or unsubstituted alkylene group" include a group in which the "alkyl group" described in the specific example group G3 is converted into divalence. Namely, specific examples (specific example group G14) of the "substituted or unsubstituted alkylene group" refer to a group derived from the "alkyl group" described in specific example group G3 by removal of one hydrogen atom bonded to the carbon atoms constituting the alkane structure thereof.

The substituted or unsubstituted arylene group described in this specification is any group described below, unless otherwise specified.

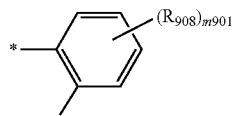
(XY-20)

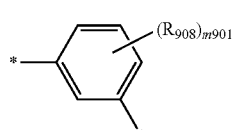
(XY-21)

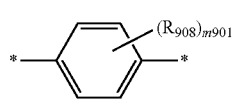
(XY-22)

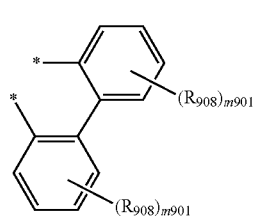
(XY-23)

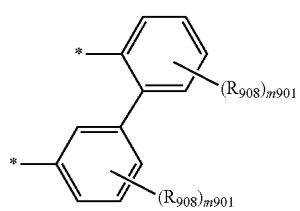
(XY-24)

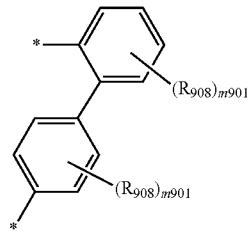
(XY-25)

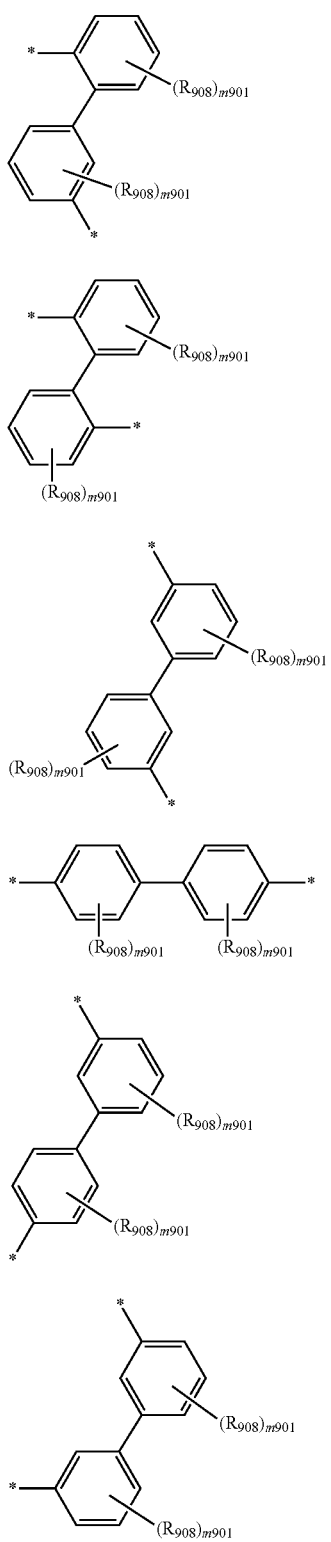
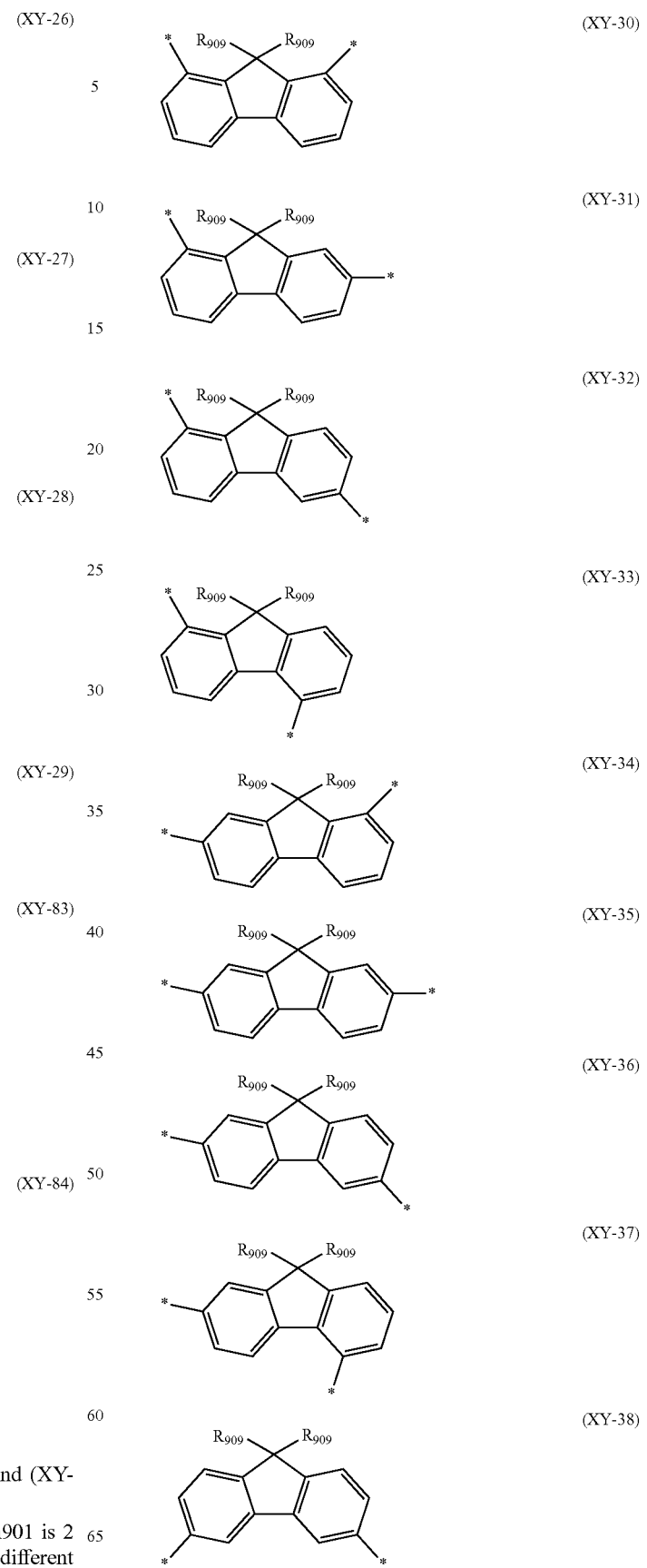
In the formulas (XY-20) to (XY-29), (XY-83) and (XY-84), $R_{908}$ is a substituent.
Then, m901 is an integer of 0 to 4, and when m901 is 2 or more, a plurality of $R_{908}$ may be the same with or different from each other.

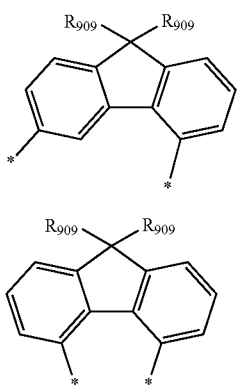
(XY-39)

(XY-40)

In the formulas (XY-30) to (XY-40), $R_{909}$ is independently a hydrogen atom or a substituent. Two of $R_{909}$ may form a ring by bonding with each other through a single bond.

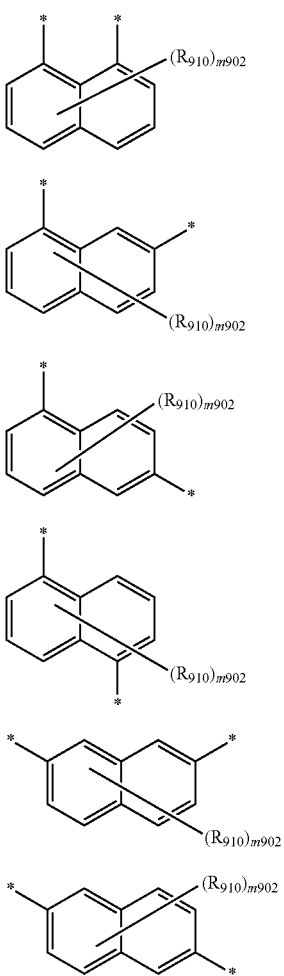
(XY-41)

(XY-42)

(XY-43)

(XY-44)

(XY-45)

(XY-46)

In the formulas (XY-41) to (XY-46), $R_{910}$ is a substituent.

Then, m902 is an integer of 0 to 6. When m902 is 2 or more, a plurality of $R_{910}$ may be the same with or different from each other.

The substituted or unsubstituted divalent heterocyclic group described in this specification is preferably any group described below, unless otherwise specified.

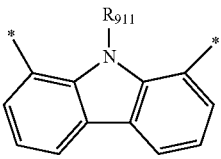
(XY-50)

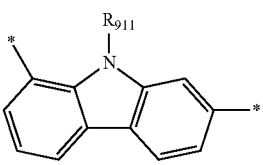
(XY-51)

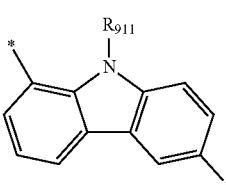
(XY-52)

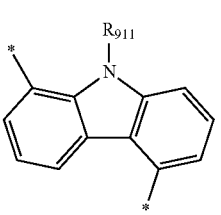
(XY-53)

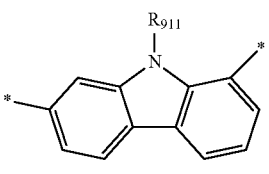
(XY-54)

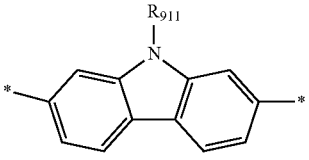
(XY-55)

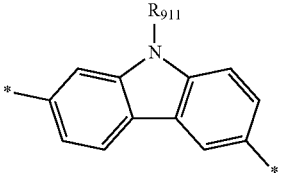
(XY-56)

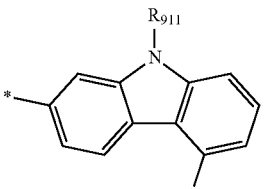
(XY-57)

(XY-58)
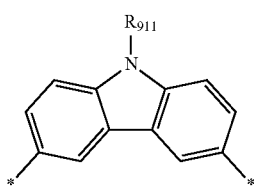
(XY-59)
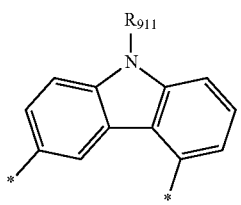
(XY-60)
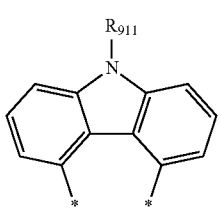
(XY-61)
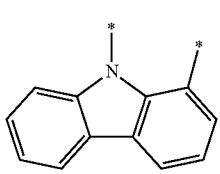
(XY-62)
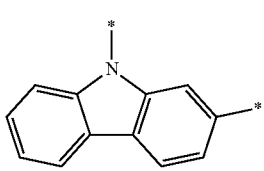
(XY-63)
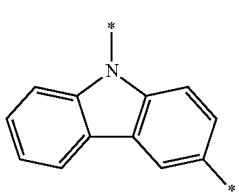
(XY-64)
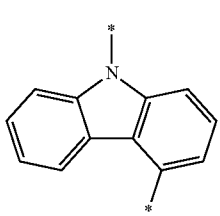
In the formulas (XY-50) to (XY-60), $R_{911}$ is a hydrogen atom or a substituent.
(XY-65)
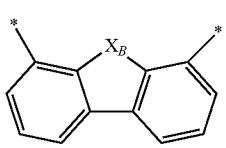
(XY-66)
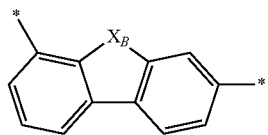
(XY-67)
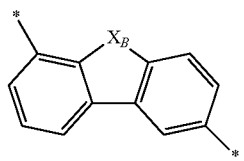
(XY-68)
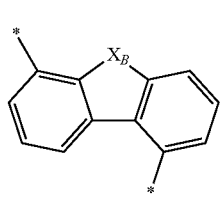
(XY-69)
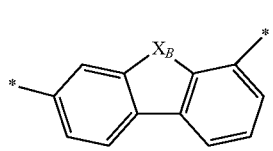
(XY-70)
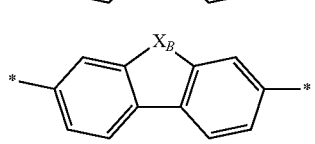
(XY-71)
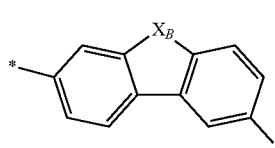
(XY-72)
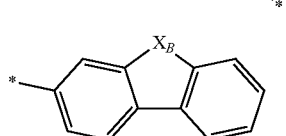
(XY-73)
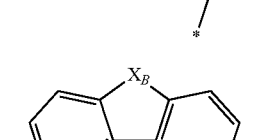
(XY-74)
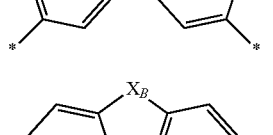
(XY-75)
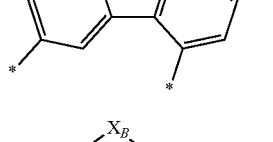
In the formulas (XY-65) to (XY-75), $X_B$ is an oxygen atom or a sulfur atom.

In this specification, a case where "one or more sets of two or more groups adjacent to each other form a substituted or unsubstituted and saturated or unsaturated ring by bonding with each other" will be described by taking, as an example, a case of an anthracene compound represented by the following formula (XY-80) in which a mother skeleton is an anthracene ring.

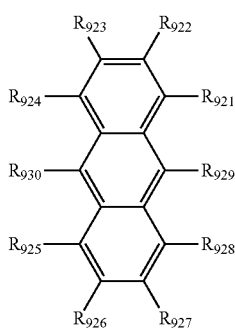

(XY-80)

For example, two adjacent to each other into one set when "one or more sets of two or more groups adjacent to each other form the ring by bonding with each other" among $R_{921}$ to $R_{930}$ include $R_{921}$ and $R_{922}$, $R_{922}$ and $R_{923}$, $R_{923}$ and $R_{924}$, $R_{924}$ and $R_{930}$, $R_{930}$ and $R_{925}$, $R_{925}$ and $R_{926}$, $R_{926}$ and $R_{927}$, $R_{927}$ and $R_{928}$, $R_{928}$ and $R_{929}$, and $R_{929}$ and $R_{921}$.

The above-described "one or more sets" means that two or more sets of two groups adjacent to each other may simultaneously form the ring. For example, a case where $R_{921}$ and $R_{922}$ form a ring A by bonding with each other, and simultaneously $R_{925}$ and $R_{926}$ form a ring B by bonding with each other is represented by the following formula (XY-81).

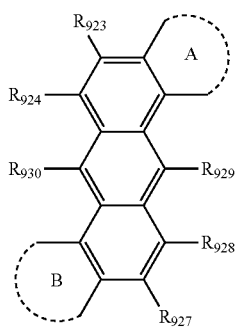

(XY-81)

A case where "two or more groups adjacent to each other" form a ring means that, for example, $R_{921}$ and $R_{922}$ form a ring A by bonding with each other, and $R_{922}$ and $R_{923}$ form a ring C by bonding with each other. A case where the ring A and ring C sharing $R_{922}$ are formed, in which the ring A and the ring C are fused to the anthracene mother skeleton by three of $R_{921}$ to $R_{923}$ adjacent to each other, is represented by the following (XY-82).

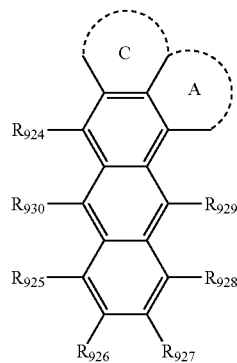

(XY-82)

The rings A to C formed in the formulas (XY-81) and (XY-82) are a saturated or unsaturated ring.

A term "unsaturated ring" means an aromatic hydrocarbon ring or an aromatic heterocyclic ring. A term "saturated ring" means an aliphatic hydrocarbon ring or an aliphatic heterocyclic ring.

For example, the ring A formed by $R_{921}$ and $R_{922}$ being bonded with each other, represented by the formula (XY-81), means a ring formed by a carbon atom of the anthracene skeleton bonded with $R_{921}$, a carbon atom of the anthracene skeleton bonded with $R_{922}$, and one or more arbitrary elements. Specific examples include, when the ring A is formed by $R_{921}$ and $R_{922}$, a case where an unsaturated ring is formed of a carbon atom of an anthracene skeleton bonded with $R_{921}$, a carbon atom of the anthracene skeleton bonded with $R_{922}$, and four carbon atoms, in which a ring formed by $R_{921}$ and $R_{922}$ is formed into a benzene ring. Further, when a saturated ring is formed, the ring is formed into a cyclohexane ring.

Here, "arbitrary elements" are preferably a C element, a N element, an O element and a S element. In the arbitrary elements (for example, a case of the C element or the N element), the bond(s) that is(are) not involved in the formation of the ring may be terminated by a hydrogen atom, or may be substituted by an arbitrary substituent. When the ring contains the arbitrary elements other than the C element, the ring to be formed is a heterocyclic ring.

The number of "one or more arbitrary elements" forming the saturated or unsaturated ring is preferably 2 or more and 15 or less, more preferably 3 or more and 12 or less, and further preferably 3 or more and 5 or less.

As specific examples of the aromatic hydrocarbon ring, a structure in which the aryl group described in specific example group G1 is terminated with a hydrogen atom may be mentioned.

As specific examples of the aromatic heterocyclic ring, a structure in which the aromatic heterocyclic group described in specific example group G2 is terminated with a hydrogen atom may be mentioned.

As specific examples of the aliphatic hydrocarbon ring, a structure in which the cycloalkyl group described in specific example group G6 is terminated with a hydrogen atom may be mentioned.

When the above-described "saturated or unsaturated ring" has a substituent, the substituent is an "arbitrary substituent" as described below, for example. When the above-mentioned "saturated or unsaturated ring" has a substituent, specific examples of the substituent refer to the substituents described in above-mentioned "the substituent described herein".

In one embodiment of this specification, the substituent (hereinafter, referred to as an "arbitrary substituent" in several cases) in the case of the "substituted or unsubstituted" is a group selected from the group consisting of
an unsubstituted alkyl group including 1 to 50 carbon atoms,
an unsubstituted alkenyl group including 2 to 50 carbon atoms,
an unsubstituted alkynyl group including 2 to 50 carbon atoms,
an unsubstituted cycloalkyl group including 3 to 50 ring carbon atoms,
—Si($R_{901}$)($R_{902}$)($R_{903}$),
—O—($R_{904}$),
—S—($R_{905}$)
—N($R_{906}$)($R_{907}$)
wherein,
$R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms; and when two or more
of $R_{901}$ to $R_{907}$ exist, two or more of $R_{901}$ to $R_{907}$ may be the same with or different from each other,
a halogen atom, a cyano group, a nitro group,
an unsubstituted aryl group including 6 to 50 ring carbon atoms, and
an unsubstituted monovalent heterocyclic group including 5 to 50 ring atoms.
In one embodiment, the substituent in the case of "substituted or unsubstituted" is a group selected from the group consisting of
an alkyl group including 1 to 50 carbon atoms,
an aryl group including 6 to 50 ring carbon atoms, and
a monovalent heterocyclic group including 5 to 50 ring atoms.
In one embodiment, the substituent in the case of "substituted or unsubstituted" is a group selected from the group consisting of
an alkyl group including 1 to 18 carbon atoms,
an aryl group including 6 to 18 ring carbon atoms, and
a monovalent heterocyclic group including 5 to 18 ring atoms.
Specific examples of each group of the arbitrary substituent described above are as described above.
In this specification, unless otherwise specified, the saturated or unsaturated ring (preferably substituted or unsubstituted and saturated or unsaturated five-membered or six-membered ring, more preferably a benzene ring) may be formed by the arbitrary substituents adjacent to each other.
In this specification, unless otherwise specified, the arbitrary substituent may further have the substituent. Specific examples of the substituent that the arbitrary substituent further has include to the ones same as the arbitrary substituent described above.
[Compound Represented by the Formula (1)]
The compound according to an aspect of the invention is represented by the following formula (1).

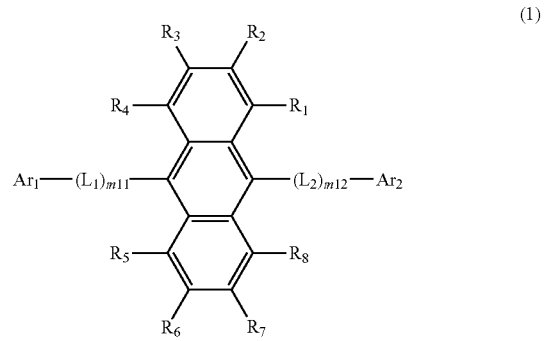

In the formula (1),
$R_1$ to $R_8$ are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms;
when two or more of each of $R_{901}$ to $R_{907}$ are present, the two or more of each of $R_{901}$ to $R_{907}$ are the same or different;
adjacent two or more of $R_1$ to $R_8$ do not form a ring by bonding with each other;
provided that at least one of $R_1$ to $R_8$ is a deuterium atom;
$L_1$ and $L_2$ are independently
a substituted or unsubstituted arylene group including 6 to 30 ring carbon atoms, or
a substituted or unsubstituted divalent heterocyclic group including 5 to 30 ring atoms;
m11 and m12 are independently an integer of 0 to 4;
when m1 and m2 are 0, $(L_1)_{m11}$ and $(L_2)_{m12}$ are single bonds;
when m11 or m12 is 2 or more, the two or more m11 or m12 may be the same as or different from each other;
$Ar_1$ and $Ar_2$ are independently
a substituted or unsubstituted aryl group including 6 to 50 ring carbon atoms, or
a substituted or unsubstituted monovalent heterocyclic group including 5 to 50 ring atoms;

provided that at least one of $Ar_1$ and $Ar_2$ is a substituted or unsubstituted fused aryl group in which only four or more benzene rings are fused; and one or more hydrogen atoms possessed by one or more of the groups selected from $L_1$, $L_2$, $Ar_1$ and $Ar_2$ may be deuterium atoms.

The compound represented by the formula (1) has one or more deuterium atoms in the anthracene skeleton and has a fused aryl group in which only four or more benzene rings are fused in a side chain, and may also have a deuterium atom in the side chain (including the aryl group, an aryl group other than the fused aryl group, and a monovalent heterocyclic group). By using the compound represented by the formula (1) in an emitting layer, an effect of prolonging the device lifetime can be obtained.

Here, a fused aryl group "in which only benzene rings are fused" means that monovalent groups derived from fused aromatic hydrocarbon rings containing rings other than benzene rings are excluded. Specifically, for example, a monovalent group derived from a fused benzofluorene ring containing one 5-membered ring in addition to four benzene rings is excluded.

Note that the fused aryl group in which only benzene rings are fused may be substituted by an arbitrary substituent.

All of $R_1$ to $R_8$ may be deuterium atoms, and some (for example, one or two) of $R_1$ to $R_8$ may be deuterium atoms.

In one embodiment, one to eight of $R_1$ to $R_8$ are deuterium atoms. In one embodiment, one to four of $R_1$ to $R_8$ are deuterium atoms. Also, in one embodiment, 2 to 8 or 2 to 4 of $R_1$ to $R_8$ are deuterium atoms.

In one embodiment, all of $R_1$ to $R_8$ are deuterium atoms.

$R_1$ to $R_8$ which are not deuterium atoms are preferably hydrogen atoms (protium atom).

The presence of deuterium atoms in the compound is confirmed by mass spectrometry or $^1$H-NMR analysis. The binding position of deuterium atoms in the compound is identified by $^1$H-NMR analysis. Specifically, these can be confirmed by the following method.

The target compound is subjected to mass spectrometry, and if the molecular weight is increased by 1, compared to the corresponding compound in which all hydrogen atoms are protium atoms, it can be confirmed that the compound contains one deuterium atom. In addition, the number of deuterium atoms in the molecule can be confirmed by the integral value obtained by $^1$H-NMR analysis of the target compound, since a deuterium atom gives no signal in $^1$H-NMR analysis. In addition, the binding position of deuterium atoms can be identified by subjecting the target compound to $^1$H-NMR analysis, and assigning the obtained signals.

In one embodiment, one of $Ar_1$ and $Ar_2$ is the fused aryl group aryl group in which only four or more benzene rings are fused.

In one embodiment, the fused aryl group aryl group in which only four or more benzene rings are fused is a fused aryl group aryl group in which only four or more and six or less benzene rings are fused.

In one embodiment, the fused aryl group in which only four or more benzene rings are fused is a substituted or unsubstituted monovalent group derived from a polycyclic fused aromatic hydrocarbon selected from the following groups:

naphthacene,
pyrene,
chrysene,
triphenylene,
benzoanthracene,
benzophenanthrene,
perylene,
pentacene,
benzopyrene,
benzotriphenylene,
dibenzanthracene,
picene,
naphthopyrene,
anthanthrene
dibenzopyrene, and
coronene.

In one embodiment, one or both of $Ar_1$-$(L_1)_{m11}$- and $Ar_2$-$(L_2)_{m12}$- in the formula (1) are not a group represented by the following formula (BA).

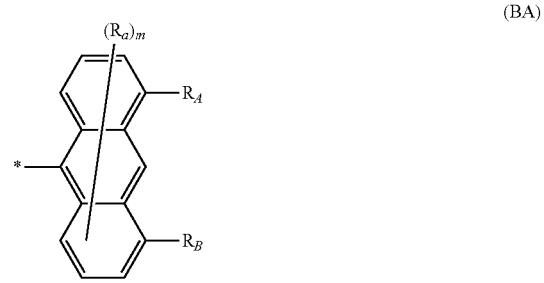

(BA)

In the formula (BA), $R_A$ and $R_B$ are independently a substituent;

$R_a$ is a substituent;

m is an integer of 0 to 7; when m is 2 or more, a plurality of $R_a$'s may be the same as or different to each other.

In one embodiment, one or both of $Ar_1$-$(L_1)_{m11}$- and $Ar_2$-$(L_2)_{m12}$- in the formula (1) are not substituted or unsubstituted anthryl groups.

In one embodiment, one or both of $Ar_1$ and $Ar_2$ in the formula (1) are not triphenylenyl groups.

In one embodiment, $(L_1)_{m11}$ and $(L_2)_{m12}$ are independently a single bond, a substituted or unsubstituted phenylene group, a substituted or unsubstituted biphenylene group, or a substituted or unsubstituted naphthylene group.

More specifically, in one embodiment, at least one of m11 and m12 is 0, and $(L_1)_{m11}$ and $(L_2)_{m12}$ are independently a single bond.

In one embodiment, at least one of m11 and m12 is 1, and $L_1$ and $L_2$ are independently a substituted or unsubstituted phenylene group, a substituted or unsubstituted biphenylene group, or a substituted or unsubstituted naphthylene group.

In one embodiment, m11 and m12 are 1 or more and $(L_1)_{m11}$ and $(L_2)_{m12}$ are independently selected from the group consisting of divalent groups represented by the following formulas (a1) to (a17).

(a1)

(a2) 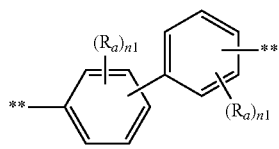
(a3) 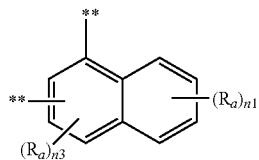
(a4) 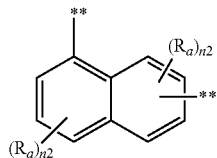
(a5) 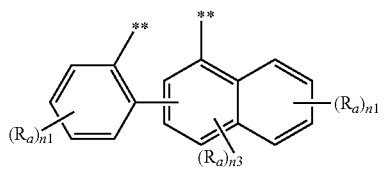
(a6) 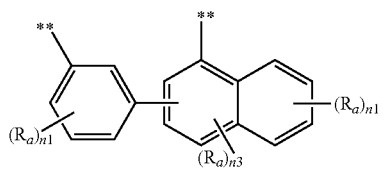
(a7) 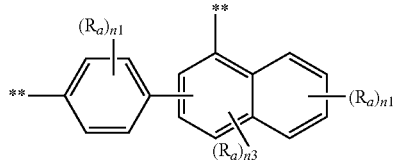
(a8) 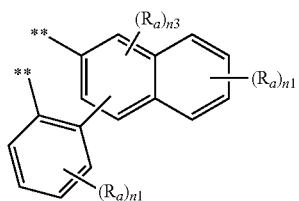
(a9) 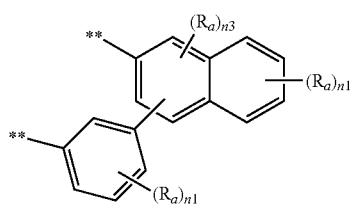
(a10) 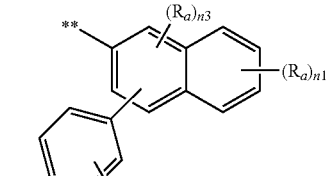
(a11) 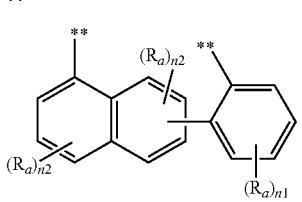
(a12) 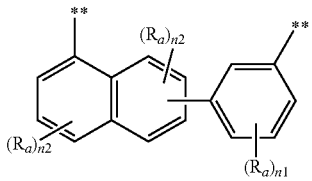
(a13) 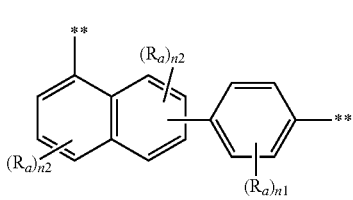
(a14) 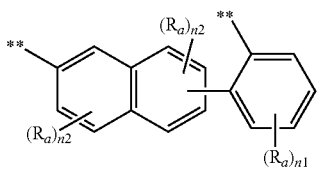
(a15) 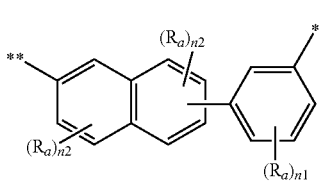
(a16) 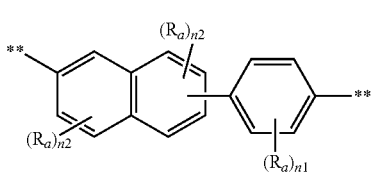
(a17) 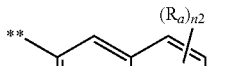
In the formulas (a1) to (a17),
*'s respectively represent binding positions with anthracene skeleton and $Ar_1$ or $Ar_2$;
$R_a$ is a substituent;
n1 is an integer of 0 to 4;
n2 is an integer of 0 to 3;

n3 is an integer of 0 to 2; and when n1, n2, and n3 are 2 or more, a plurality of $R_a$'s may be the same as or different from each other.

In one embodiment, one or both of m11 and m12 is 0, that is, at least one of $(L_1)_{m11}$ and $(L_2)_{m12}$ is a single bond. In one embodiment, both m11 and m12 are 0, that is, $(L_1)_{m11}$ and $(L_2)_{m12}$ are single bonds.

In one embodiment, at least one of m11 and m12 is 2, $(L_1)_{m11}$ and $(L_2)_{m12}$ are independently represented by $(L_1)$-$(L_1)$ and $(L_2)$-$(L_2)$; and the plurality of each of $L_1$'s and $L_2$'s are independently a substituted or unsubstituted phenylene group, or a substituted or unsubstituted naphthylene group.

In one embodiment, both m11 and m12 are 2.

In one embodiment, $L_1$ and $L_2$ are independently selected from divalent groups represented by the following formulas.

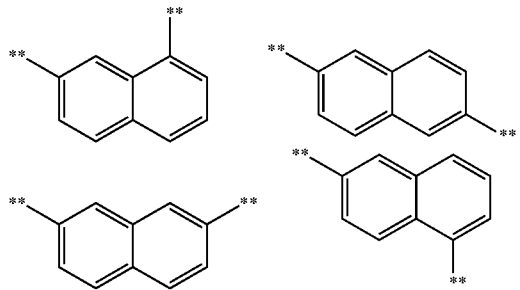

In the formulas, **'s respectively represent binding positions with anthracene skeleton and $Ar_1$ or $Ar_2$.

In one embodiment, n1, n2, and n3 in the formulas (a1) to (a17) are independently 0. More specifically, the divalent groups represented by the following formulas (a1) to (a17) do not have a substituent $R_a$.

In one embodiment, the compound represented by the formula (1) is a compound represented by the following formula (1-1).

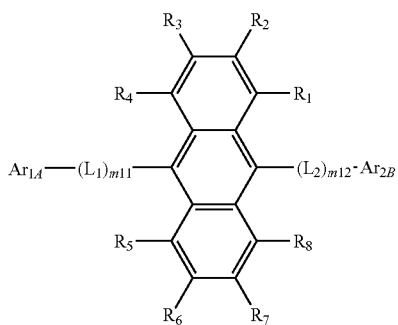

In the formula (1-1), $R_1$ to $R_8$, $L_1$, $L_2$, m11, and m12 are as defined in the formula (1);

$Ar_{1A}$ is a substituted or unsubstituted aryl group including 6 to 50 ring carbon atoms other than a fused aryl group in which only four or more benzene rings are fused;

$Ar_{2B}$ is a fused aryl group in which only four or more and six or less benzene rings are fused;

one or more hydrogen atoms possessed by one or more of the groups selected from $L_1$, $L_2$, $Ar_{1A}$, and $Ar_{2B}$ may be deuterium atoms.

In one embodiment, the compound represented by the formula (1) is a compound represented by the following formula (1-2).

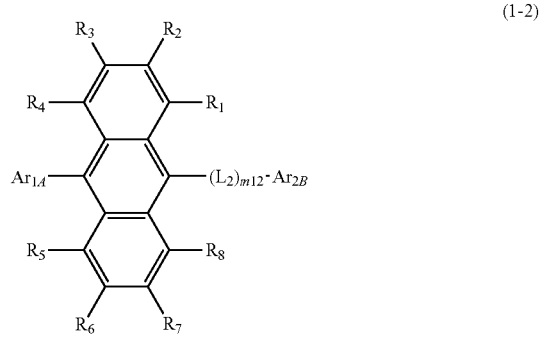

In the formula (1-2), $R_1$ to $R_8$, $L_2$, and m12 are as defined in the formula (1);

$Ar_{1A}$ is a substituted or unsubstituted aryl group including 6 to 50 ring carbon atoms other than a fused aryl group in which only four or more benzene rings are fused;

$Ar_{2B}$ is a fused aryl group in which only four or more and six or less benzene rings are fused;

one or more hydrogen atoms possessed by one or more of the groups selected from $L_2$, $Ar_{1A}$ and $Ar_{2B}$ may be deuterium atoms.

In one embodiment, the compound represented by the formula (1) is a compound represented by the following formula (1-3).

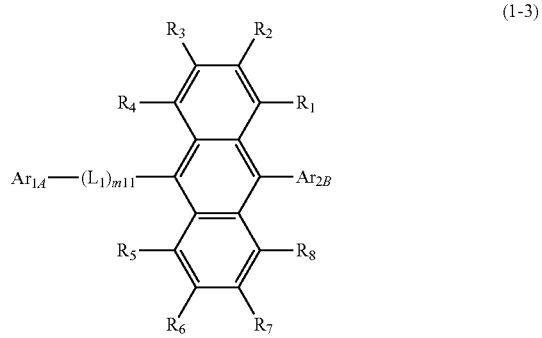

In the formula (1-3), $R_1$ to $R_8$, $L_1$, and m11 are as defined in the formula (1);

$Ar_{1A}$ is a substituted or unsubstituted aryl group including 6 to 50 ring carbon atoms other than a fused aryl group in which only four or more benzene rings are fused;

$Ar_{2B}$ is a fused aryl group in which only four or more and six or less benzene rings are fused;

one or more hydrogen atoms possessed by one or more of the groups selected from $L_1$, $Ar_{1A}$ and $Ar_{2B}$ may be deuterium atoms.

In one embodiment, the substituted or unsubstituted fused aryl group in which only four or more benzene rings are fused is a substituted or unsubstituted monovalent group derived from a polycyclic fused aromatic hydrocarbon selected from the group consisting of the following formulas (b1) to (b4).

(b1)
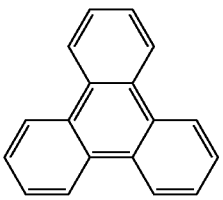

(b2)
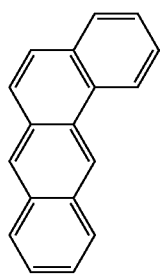

(b3)
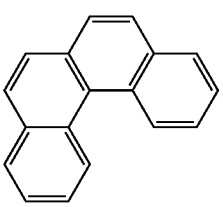

(b4)
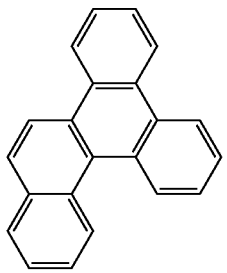

In one embodiment, the substituted or unsubstituted fused aryl group in which only four or more benzene rings are fused is a substituted or unsubstituted monovalent group derived from a polycyclic fused aromatic hydrocarbon selected from the group consisting of the formulas (b2) to (b4).

In one embodiment, $Ar_{1A}$ is
a substituted or unsubstituted phenyl group,
a substituted or unsubstituted naphthyl group,
a substituted or unsubstituted biphenylyl group, or
a substituted or unsubstituted phenanthryl group.

In one embodiment, one or more hydrogen atoms possessed by one or more groups selected from $L_1$, $L_2$, $Ar_1$, and $Ar_2$ are deuterium atoms.

In one embodiment, one or more hydrogen atoms possessed by one or more groups selected from $Ar_1$ or $Ar_2$ which are not the fused aryl group aryl group in which only four or more benzene rings are fused are deuterium atoms.

In one embodiment, all hydrogen atoms possessed by $L_1$, $L_2$, $Ar_1$, and $Ar_2$ are protium atoms.

Details of each substituent in the formulas (1), (a1) to (a17), (1-1), (1-2), (1-3), and (b1) to (b4), and each substituent in the case of "a substituted or unsubstituted" are as defined in the [Definition] part of this specification.

The compound represented by the formula (1) within the scope of the invention can be synthesized in accordance with the synthetic methods described in Examples by using known alternative reactions or raw materials tailored to the target compound.

Specific examples of the compound represented by the formula (1) include the following compounds. In the following specific examples, D represents a deuterium atom.

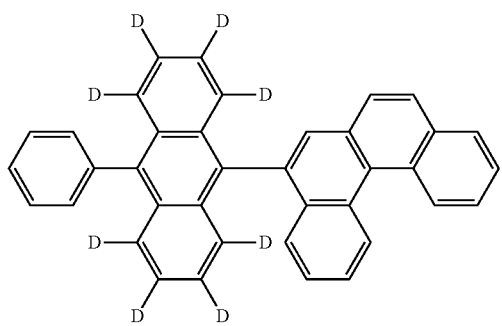

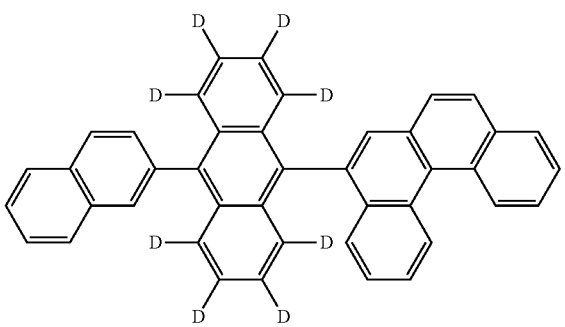

-continued
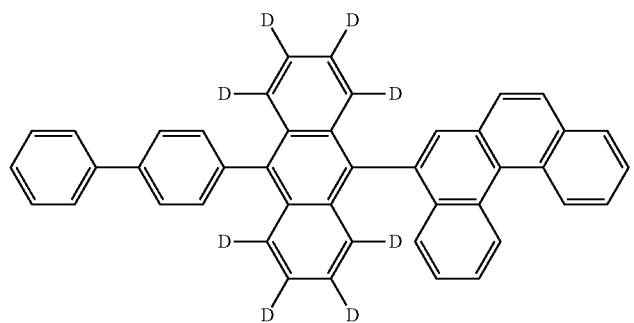
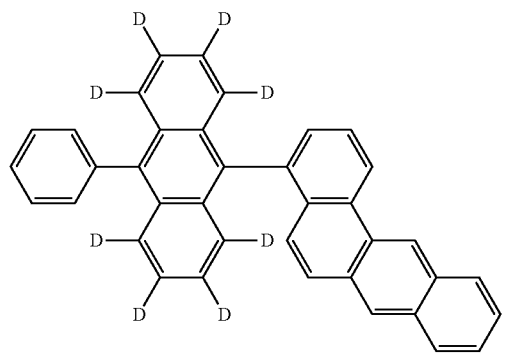
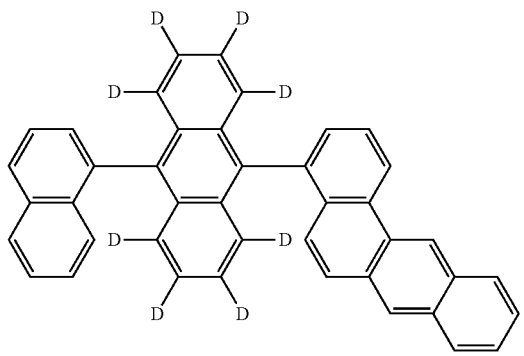
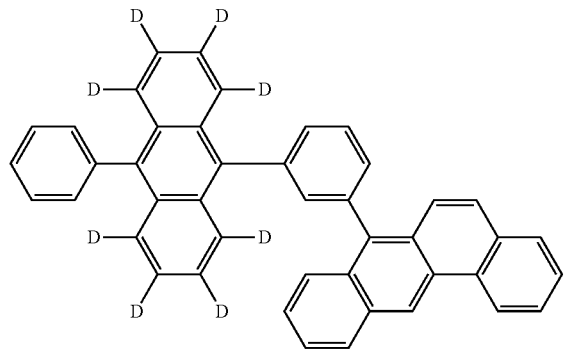
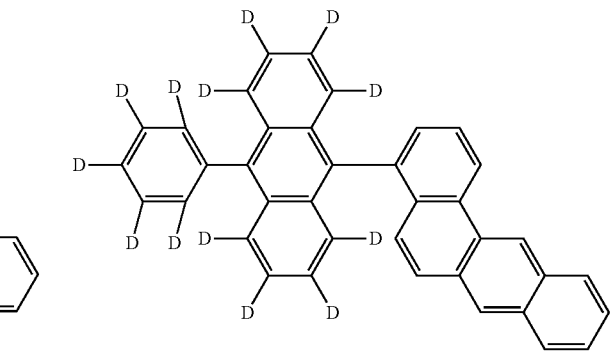
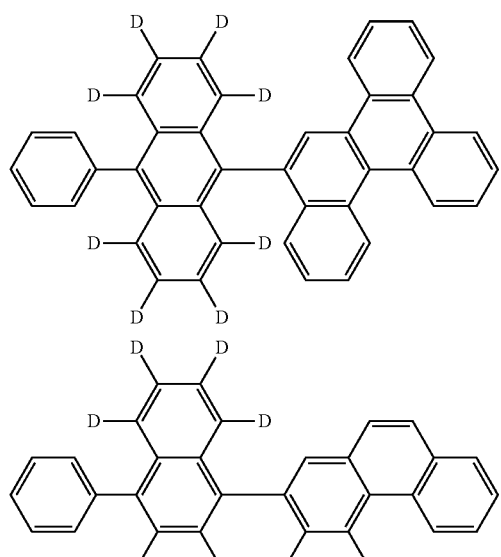
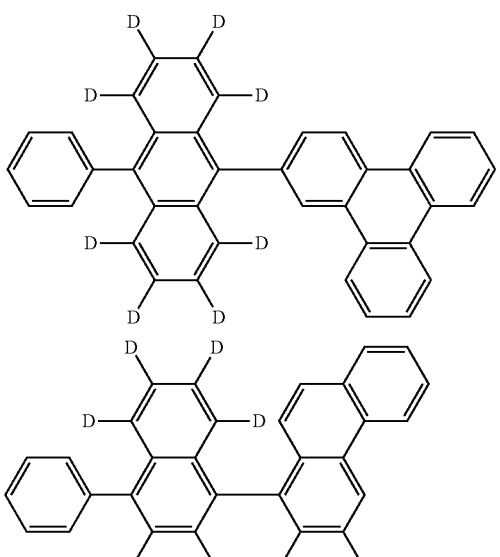

-continued
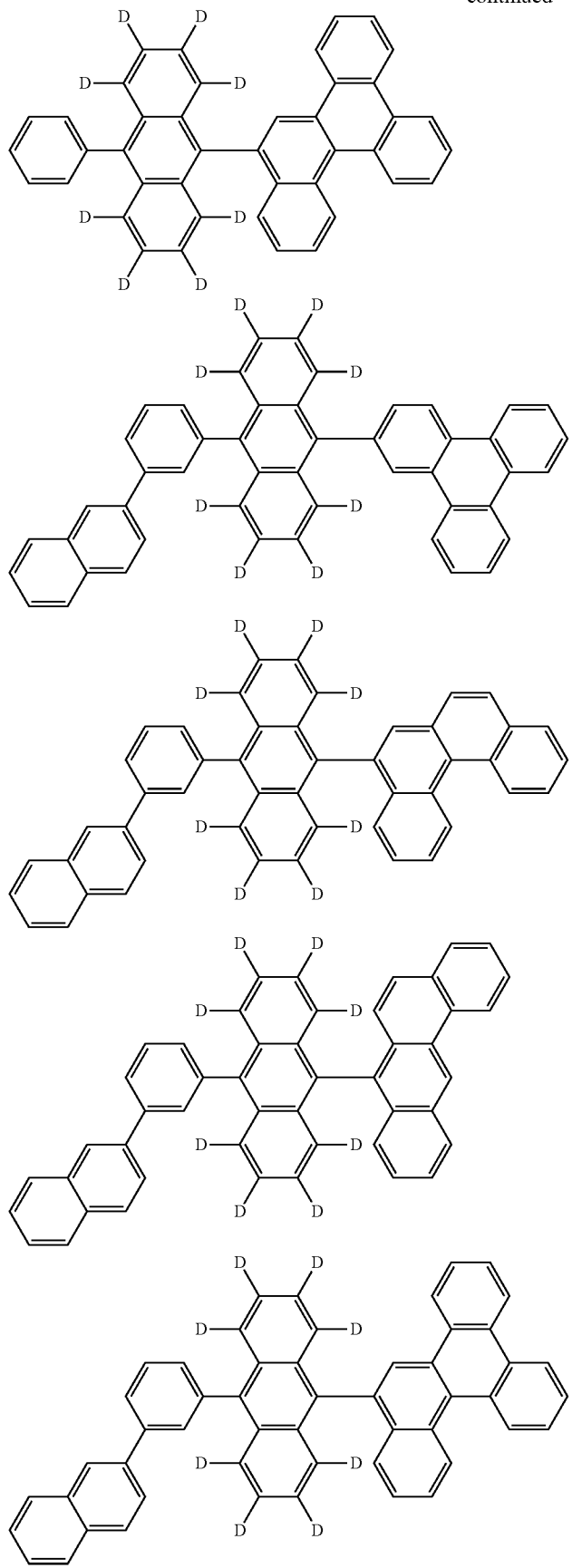

-continued
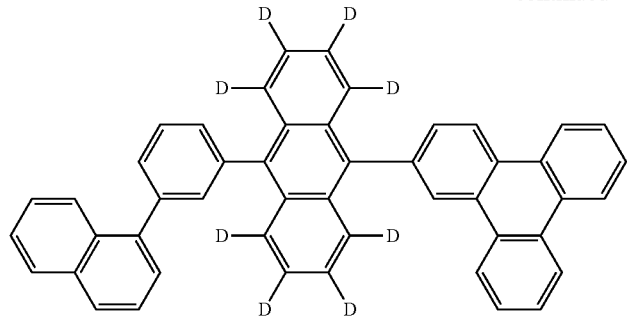
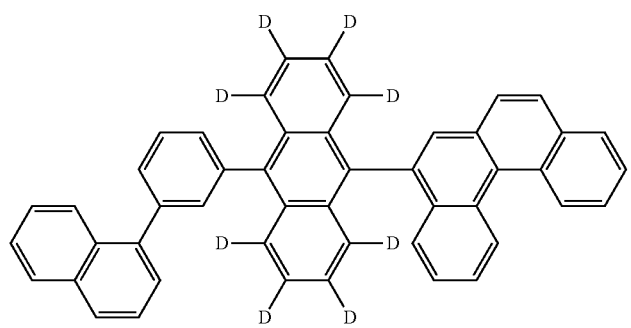
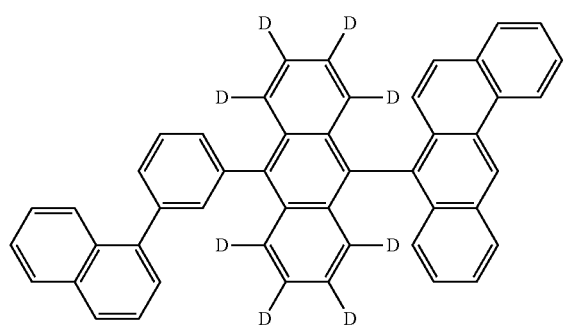
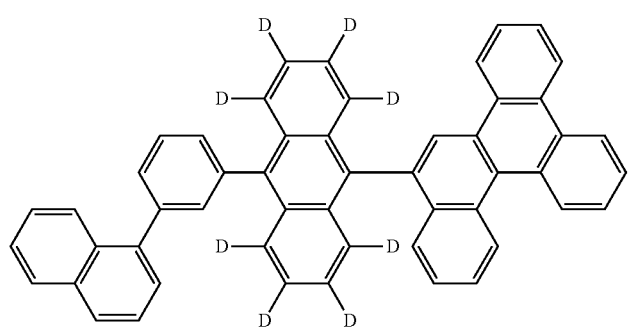
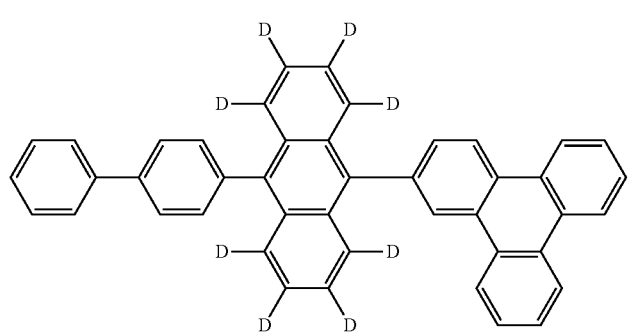

-continued
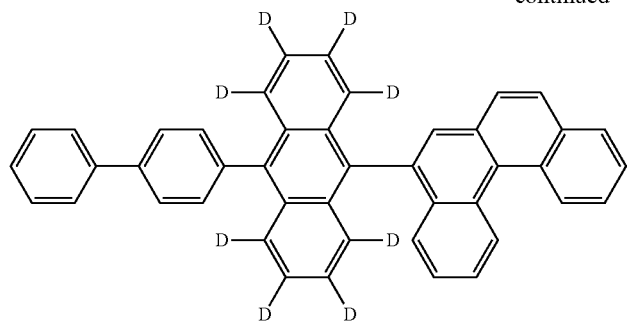
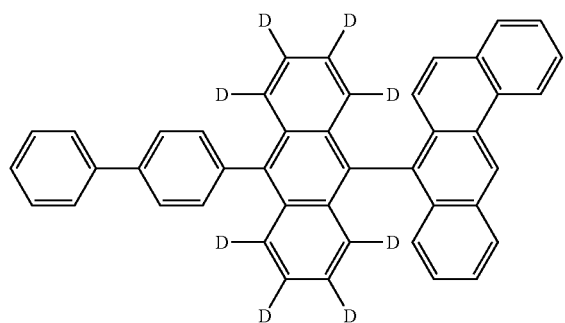
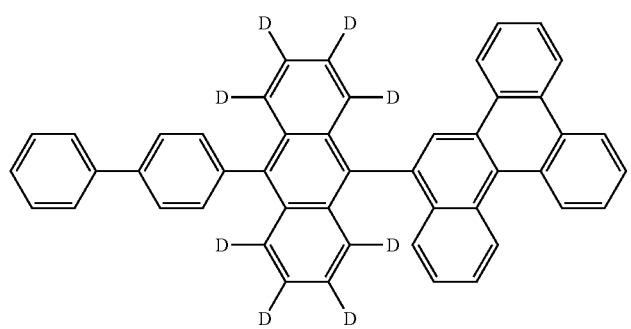
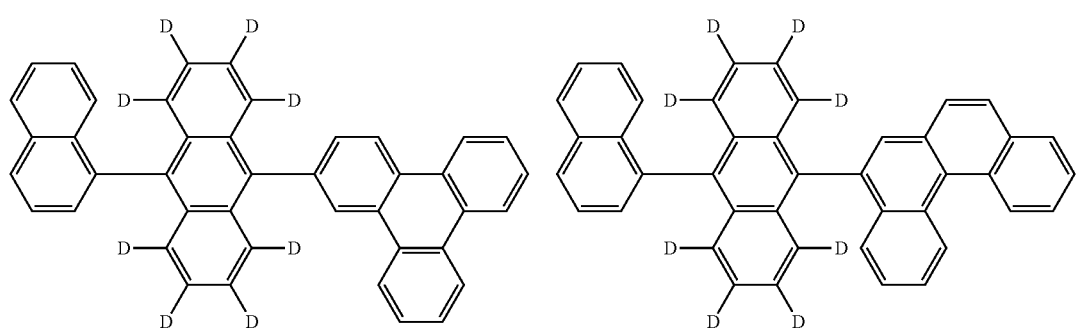
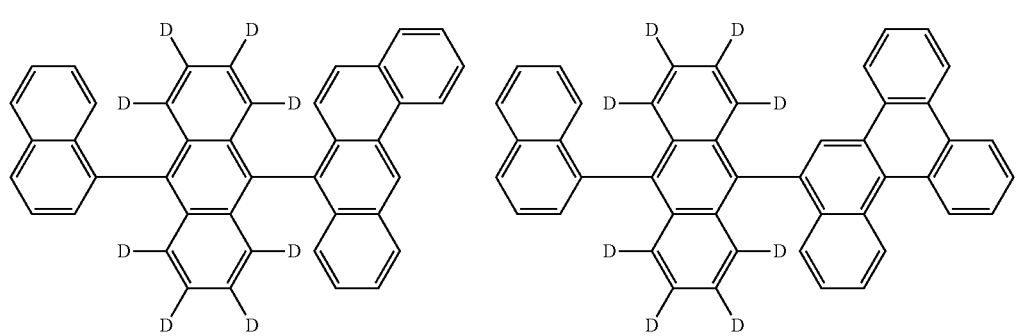

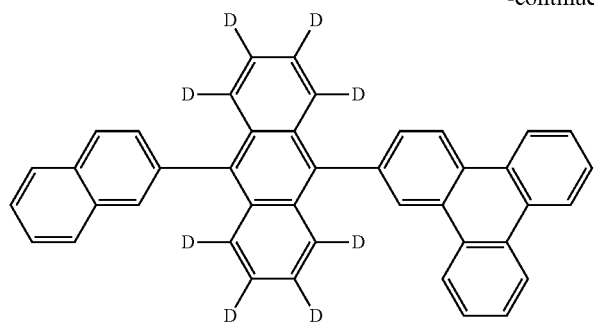
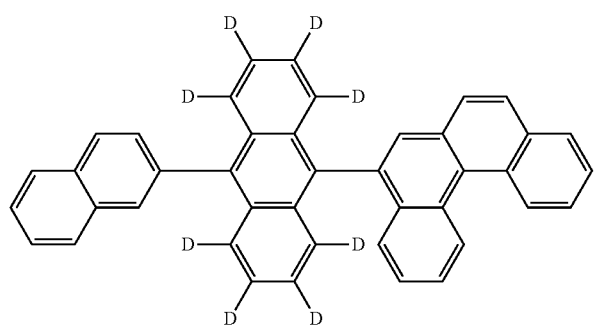
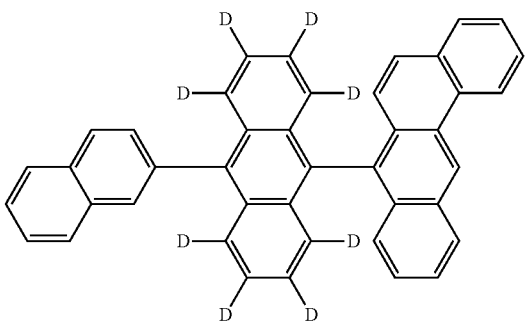
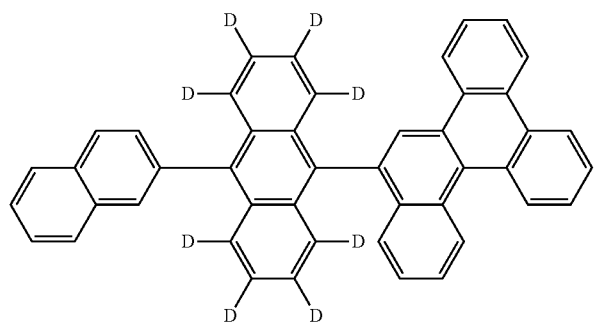
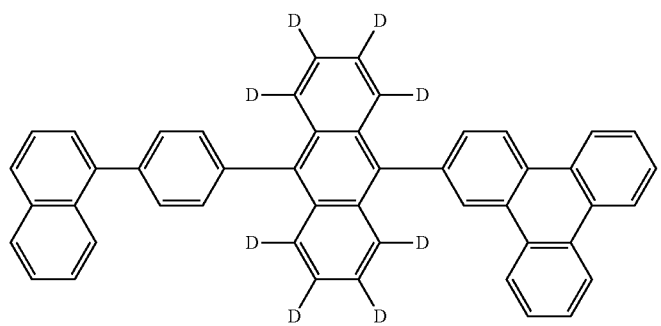
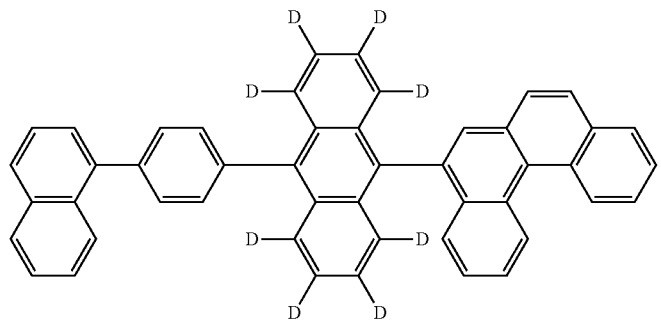

-continued
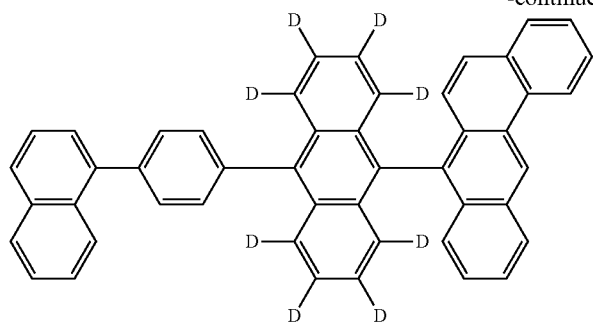
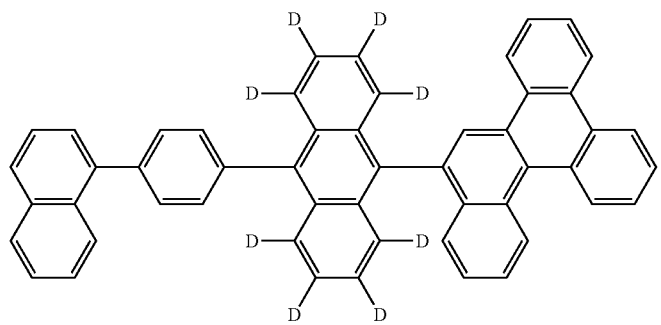
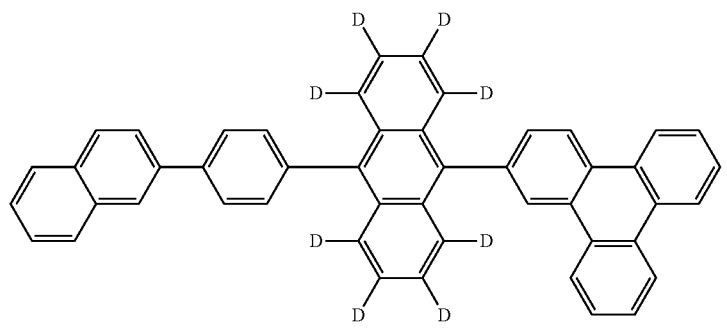
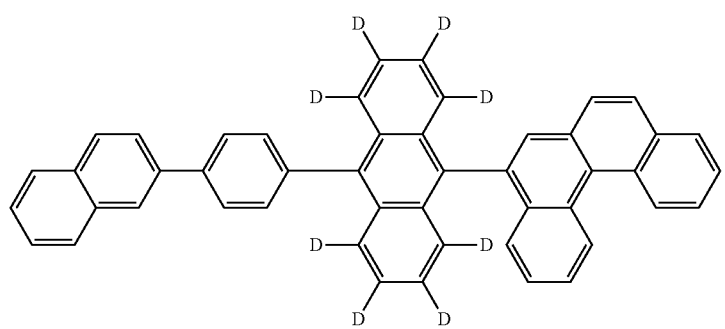
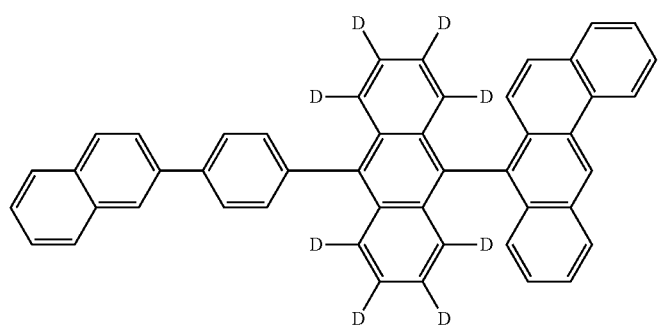

-continued
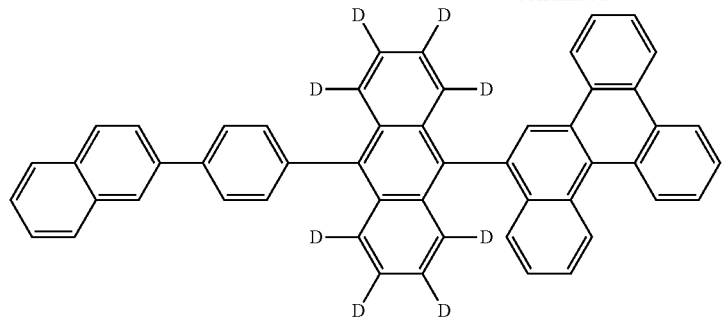
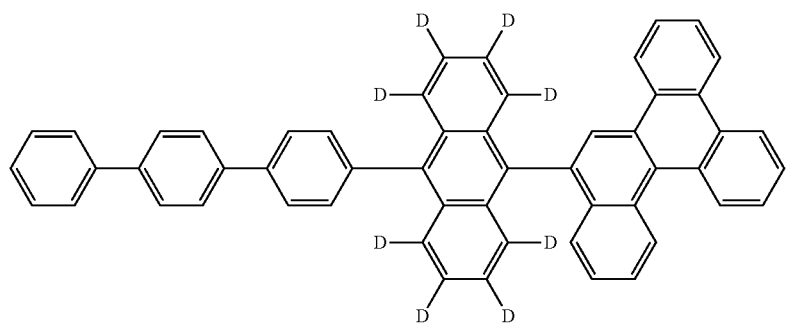
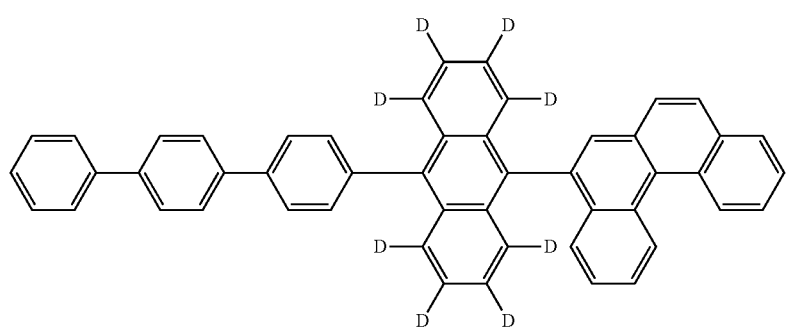
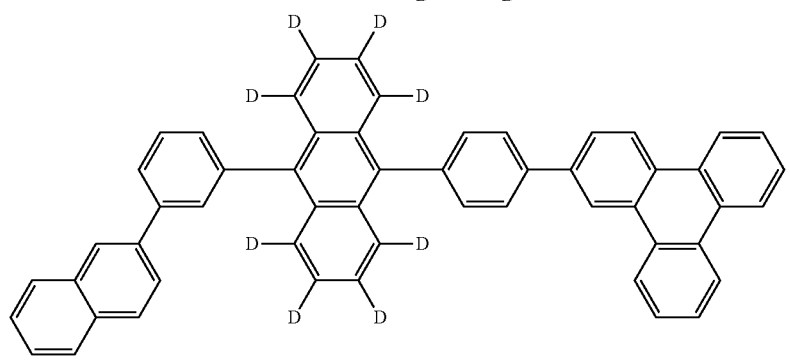
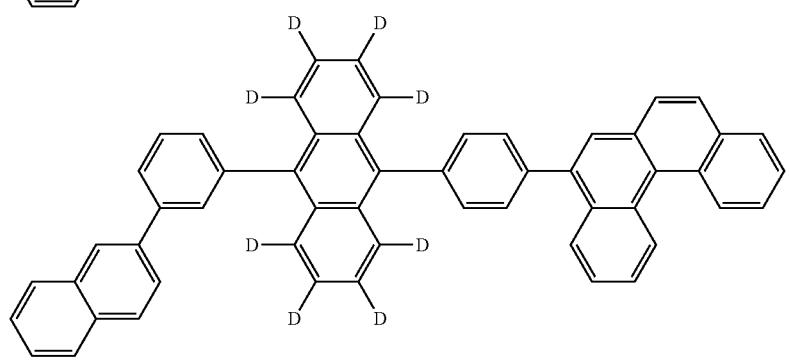

-continued
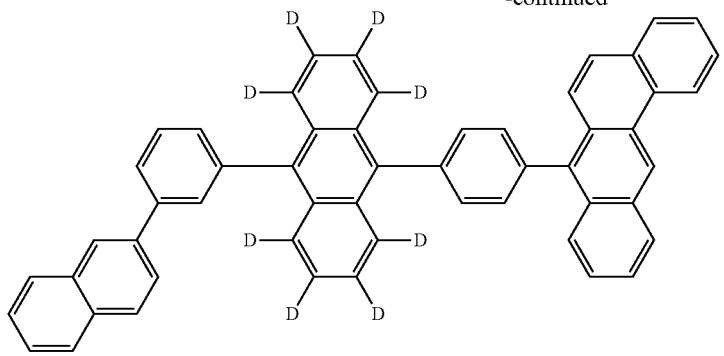
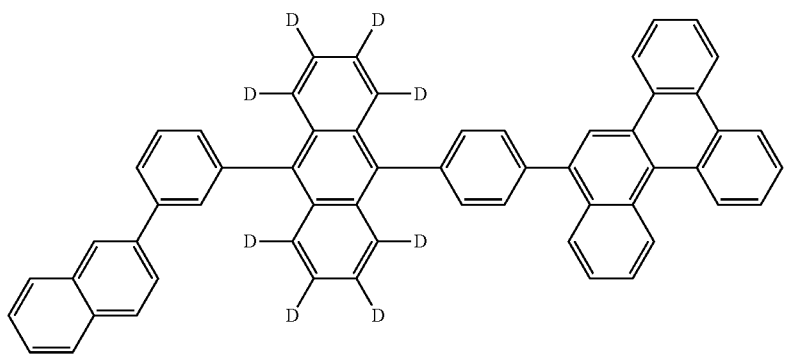
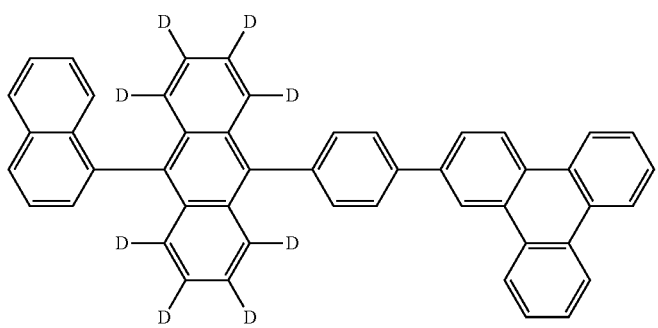
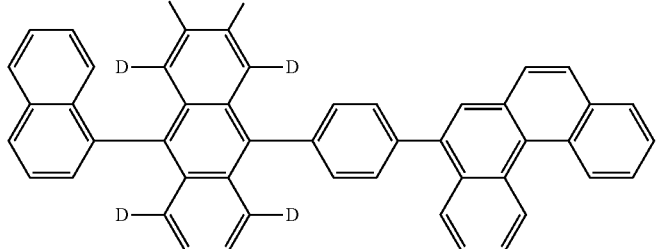
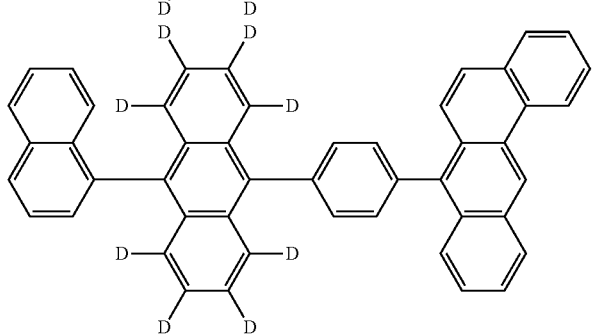

-continued
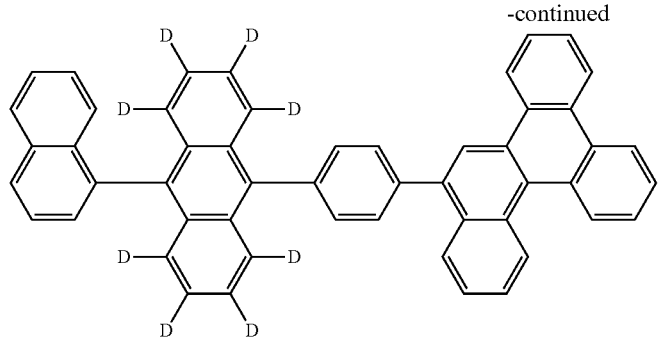
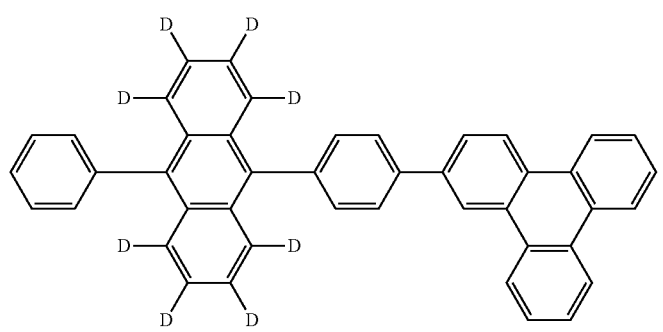
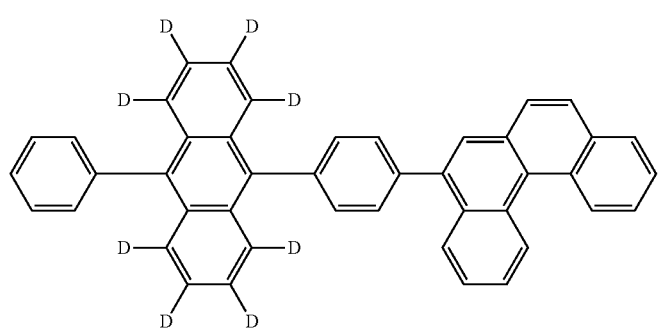
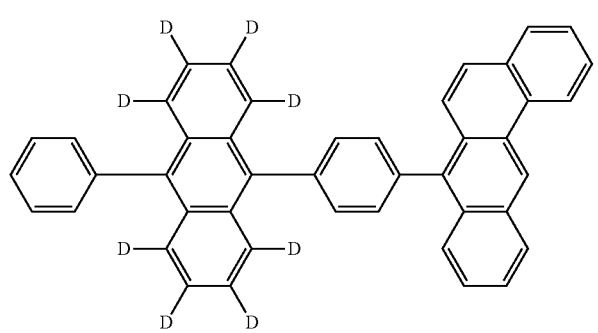
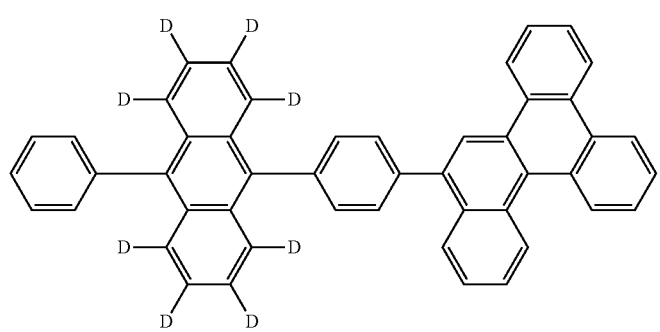

-continued
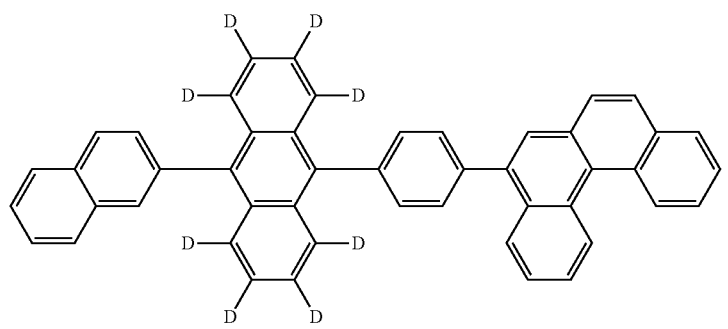
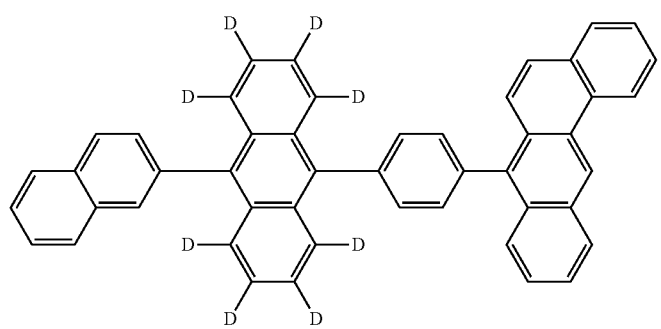
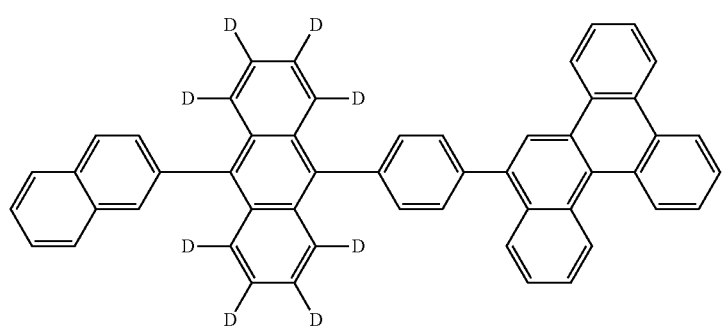
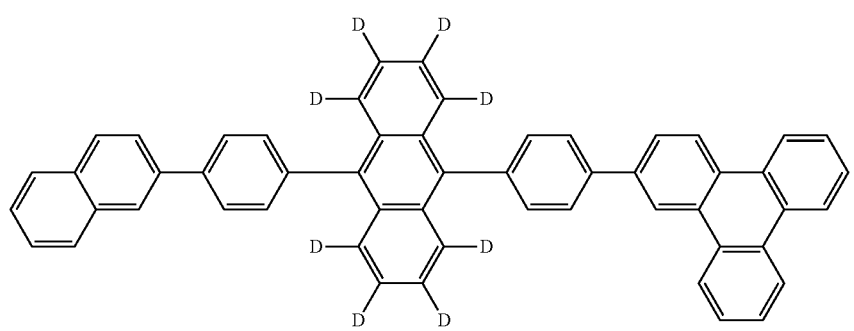

-continued
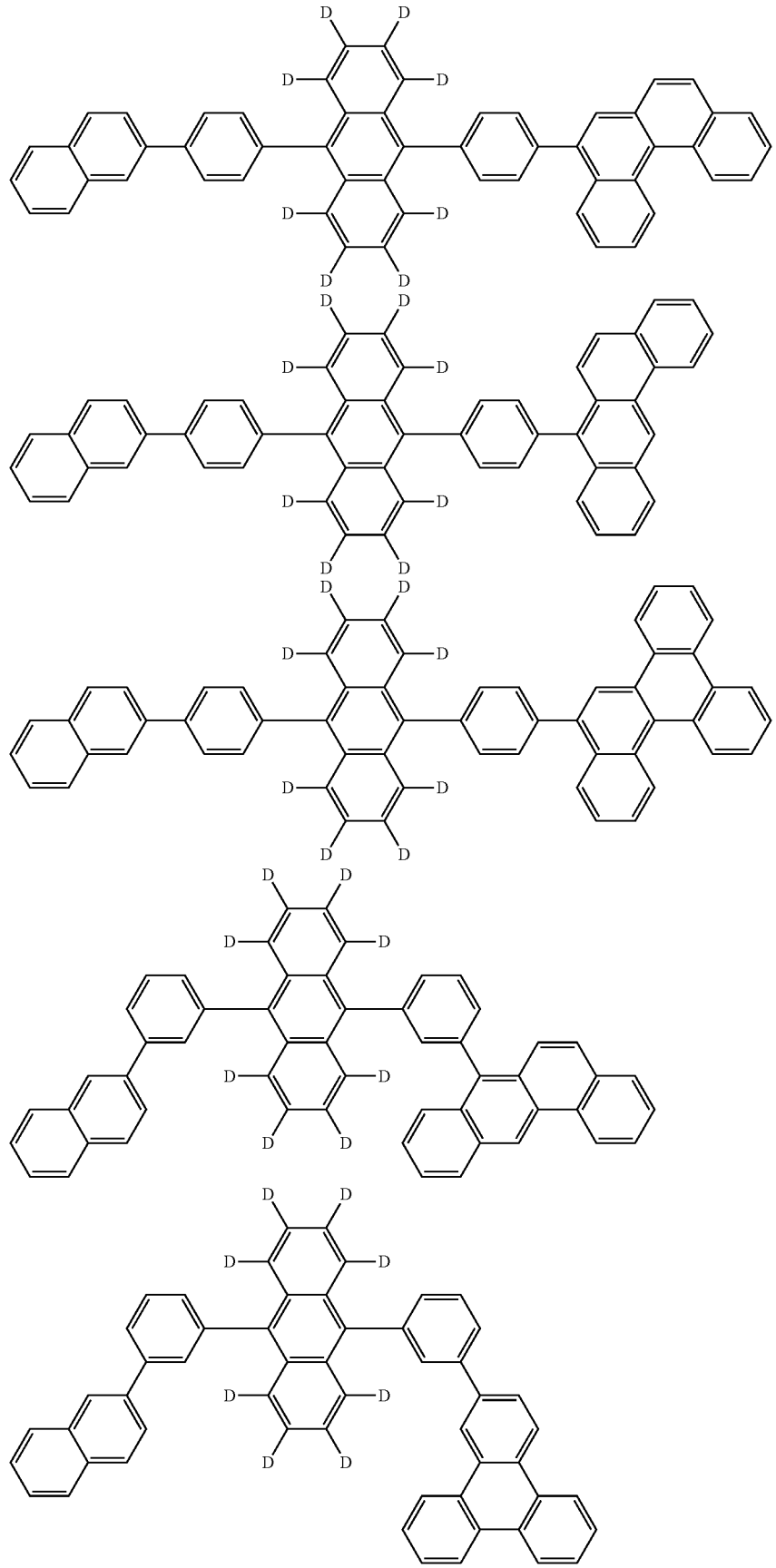

-continued
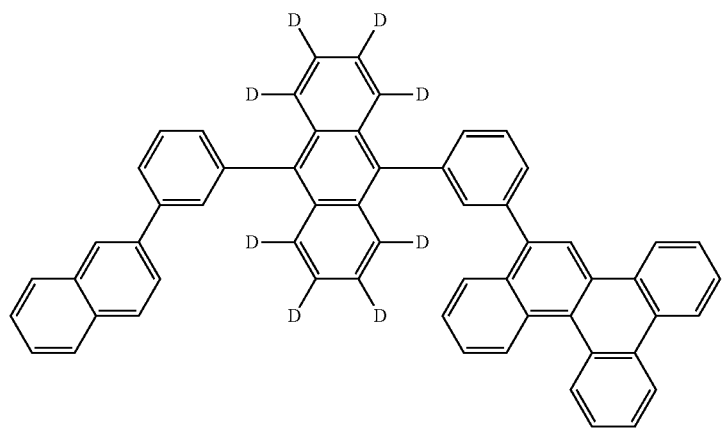
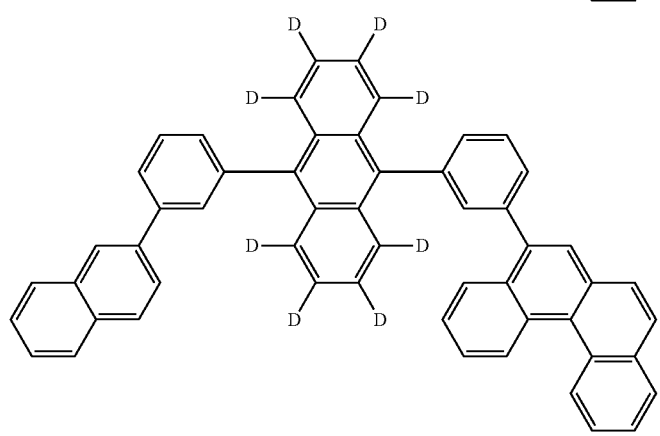
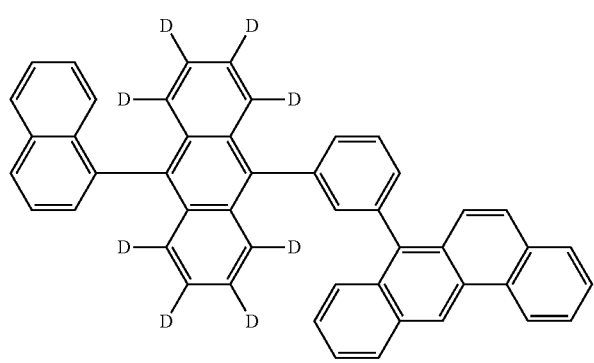
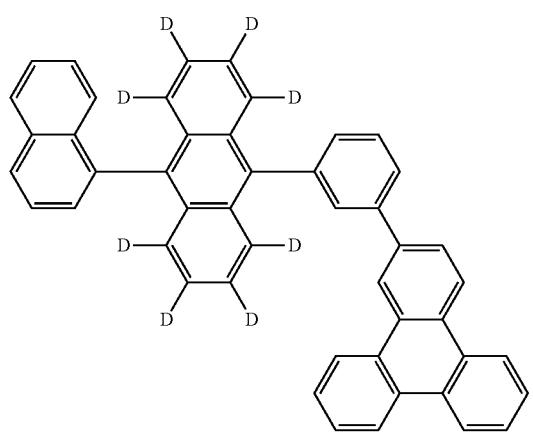
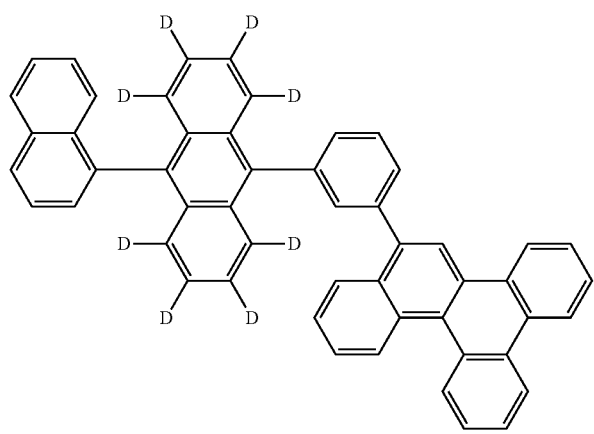

-continued
| 59 | 60 |
|---|---|
| 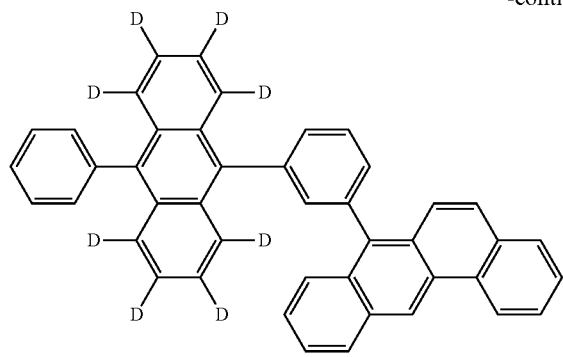 | 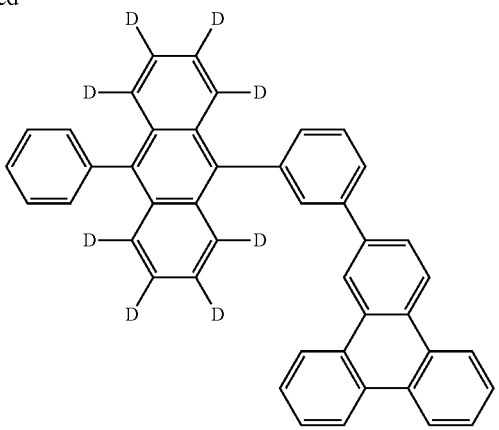 |
| 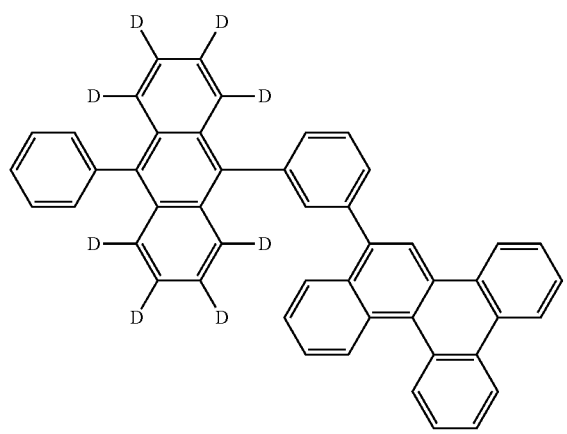 | 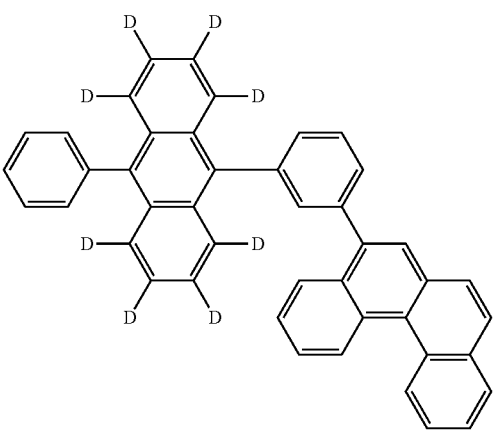 |
| 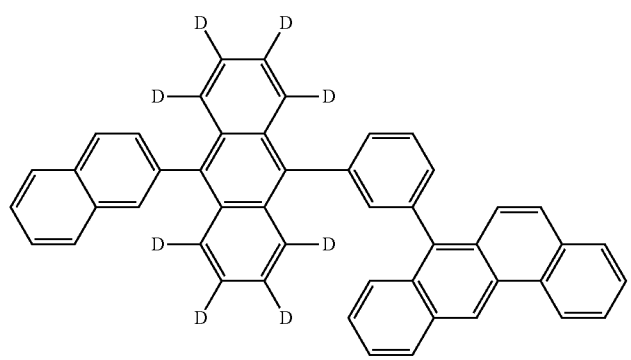 | |
| 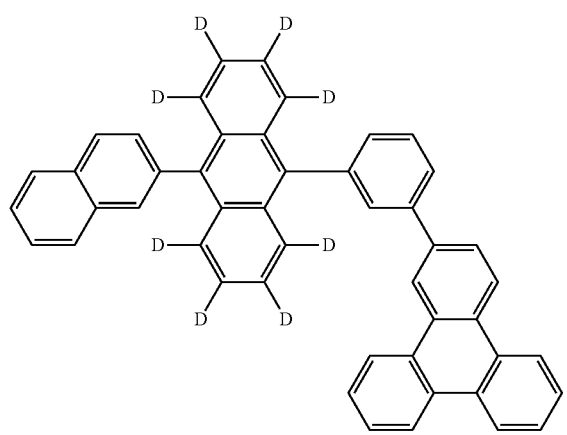 | |

-continued
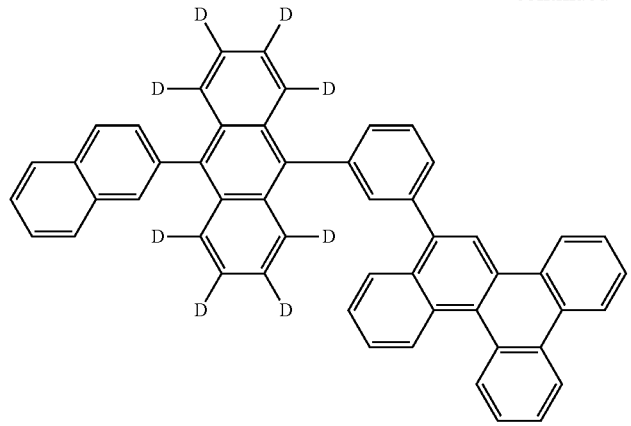
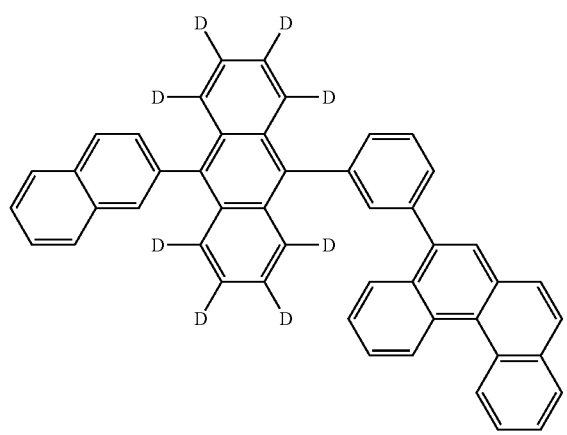
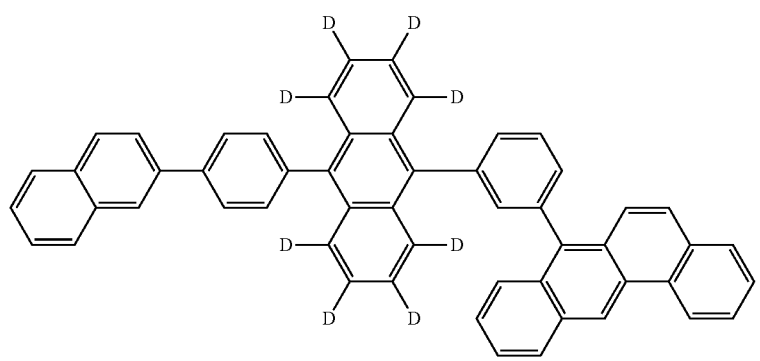
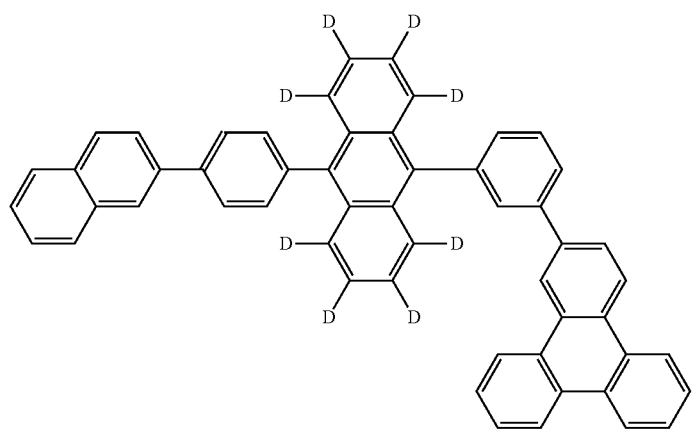

-continued
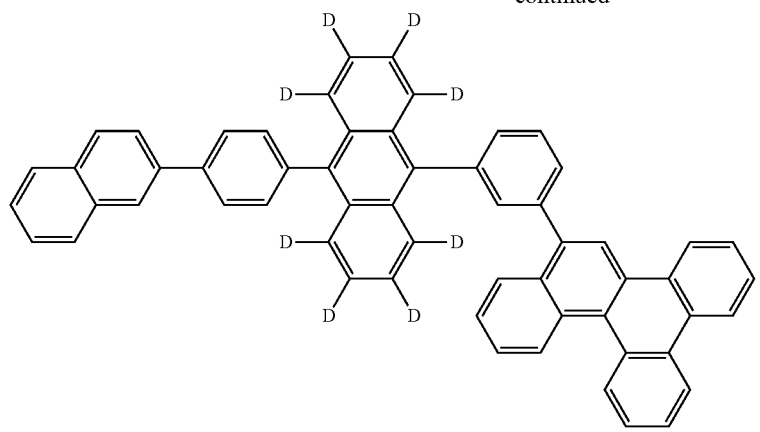
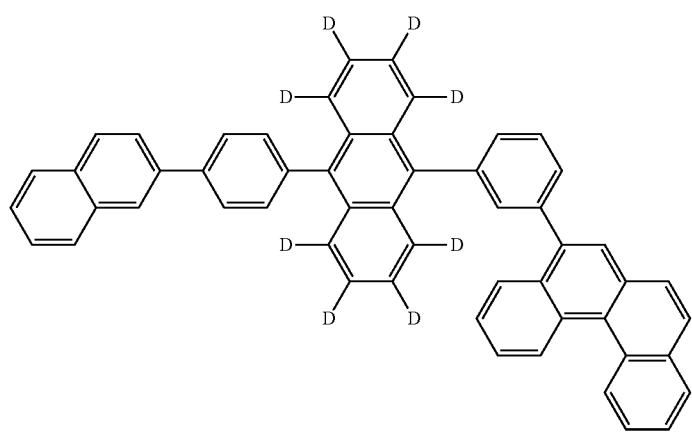
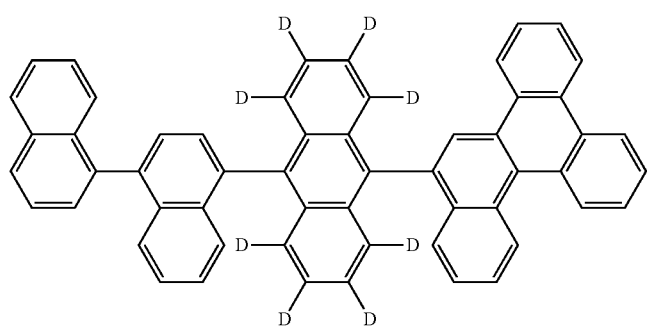
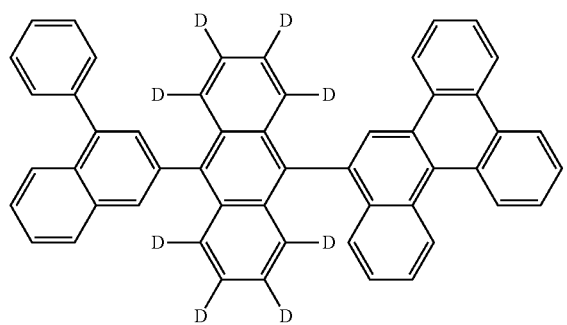

-continued
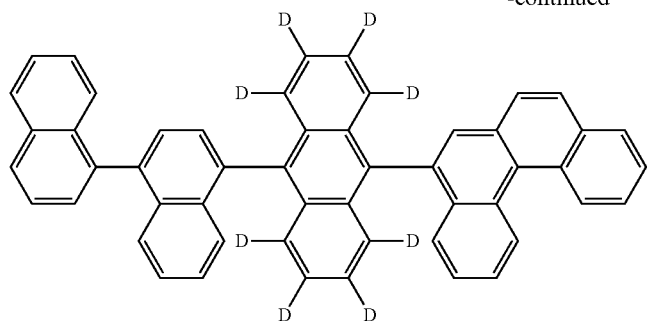

-continued
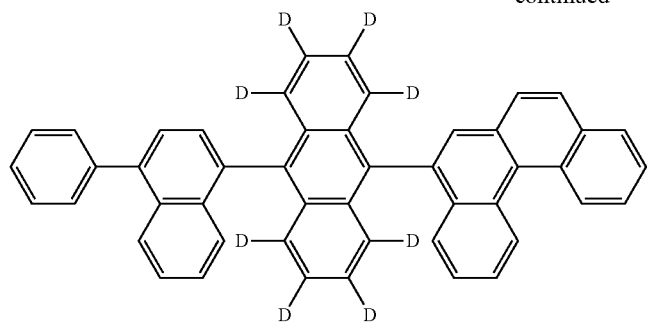
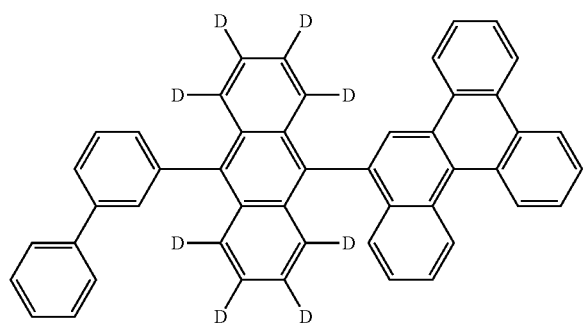
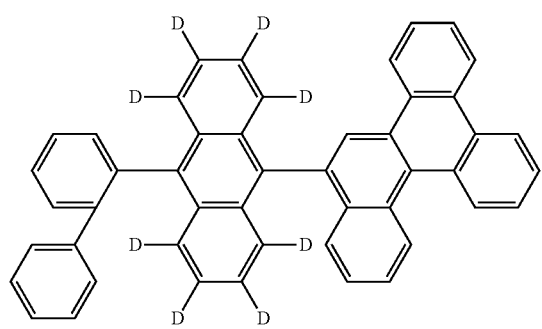
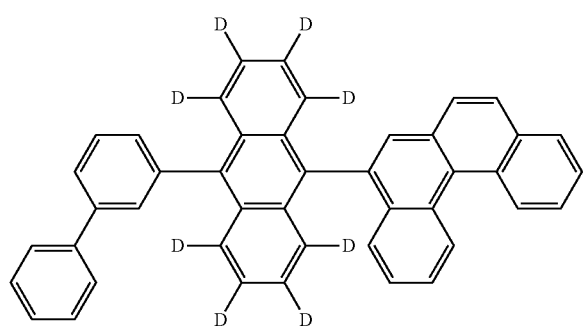
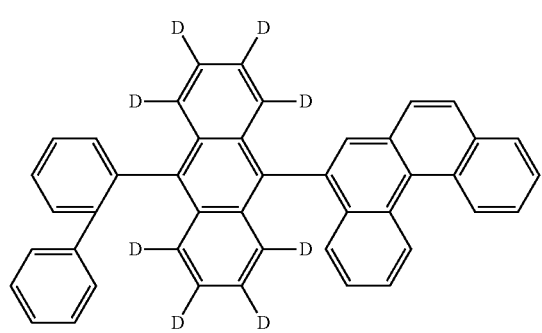

-continued
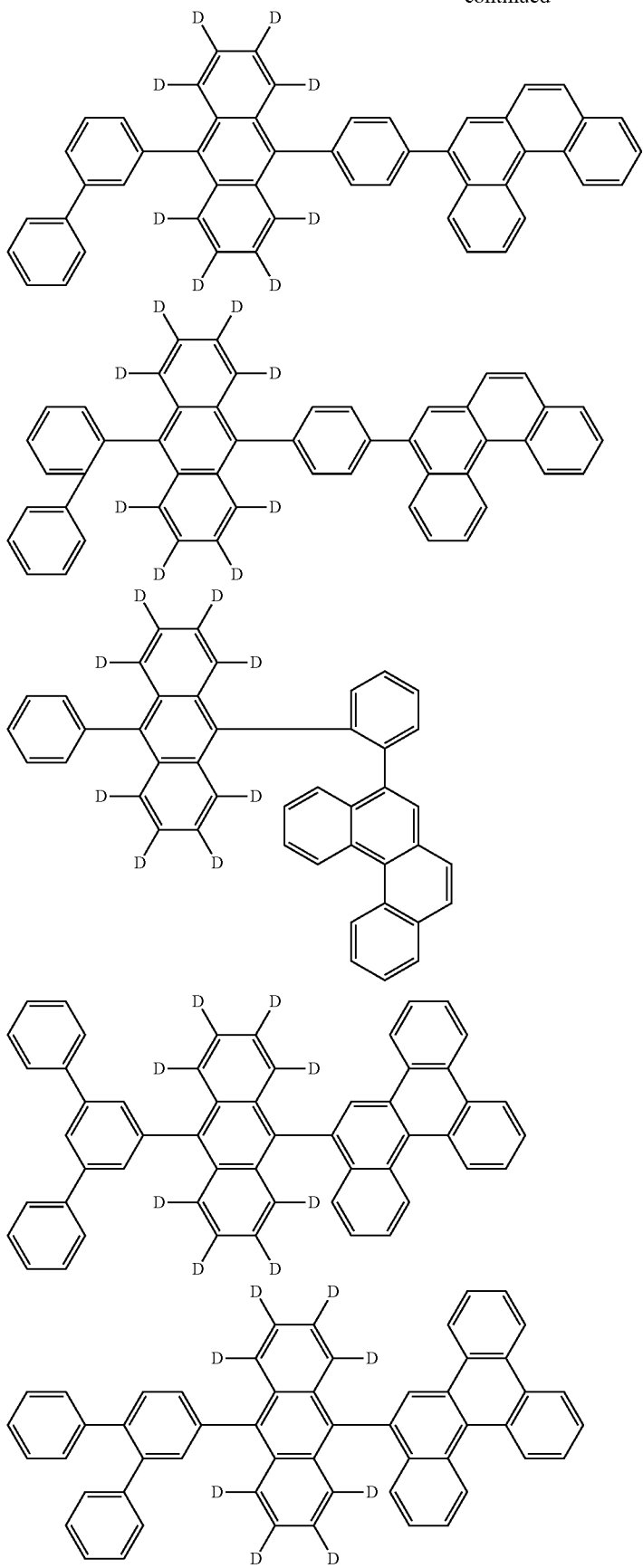

-continued
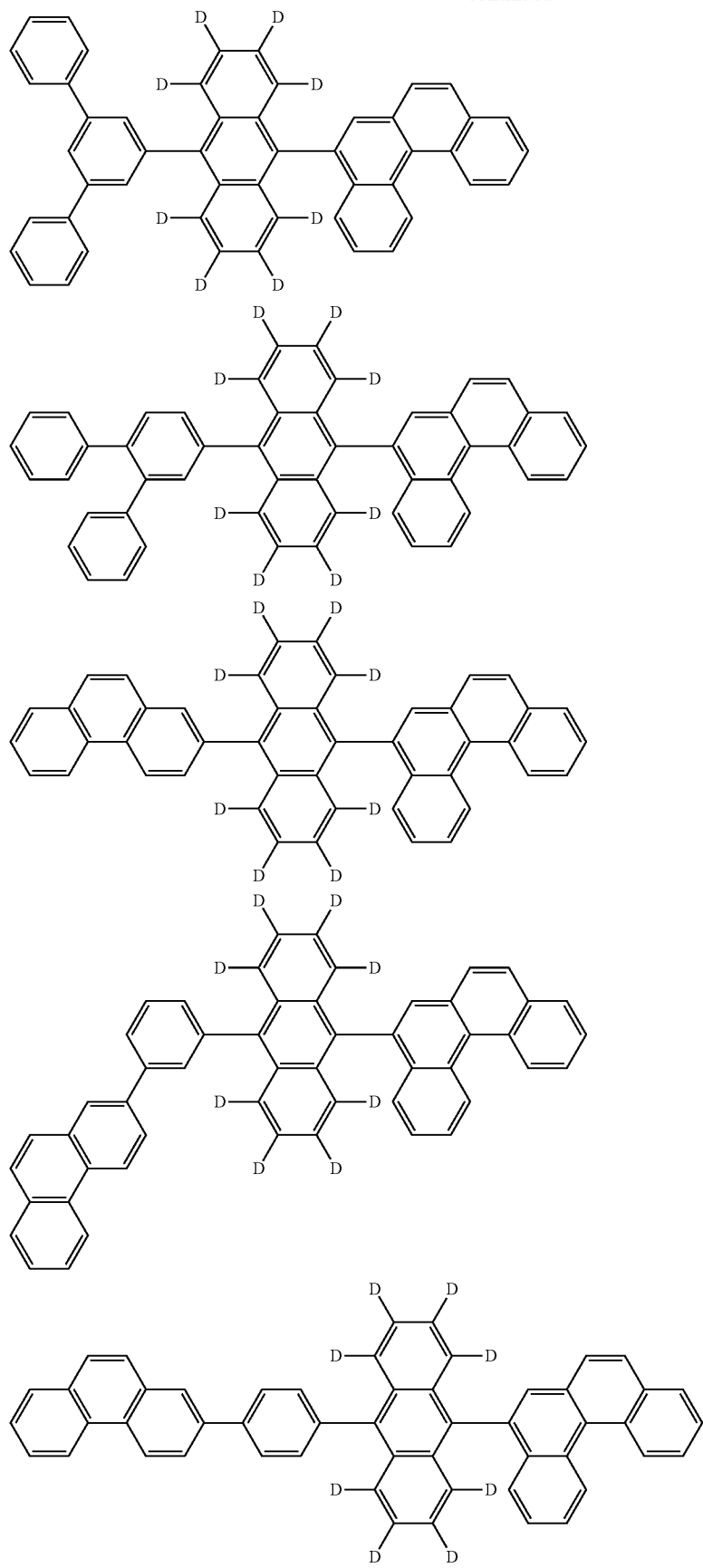

-continued
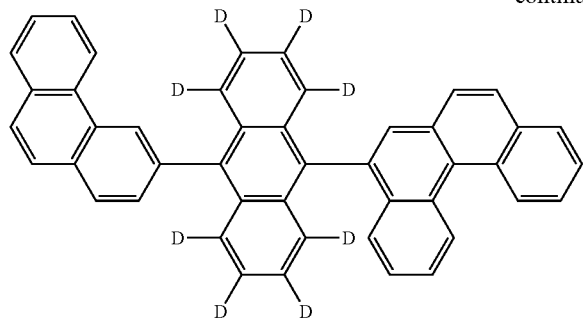
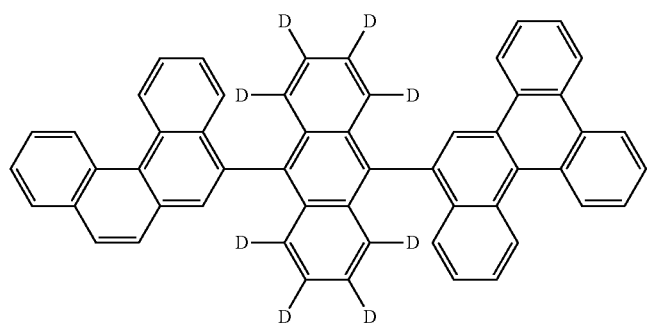
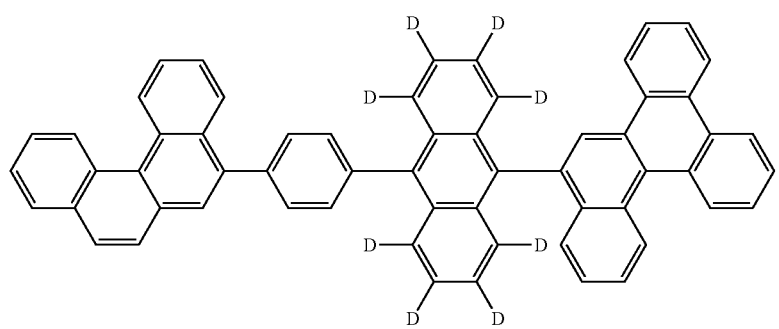
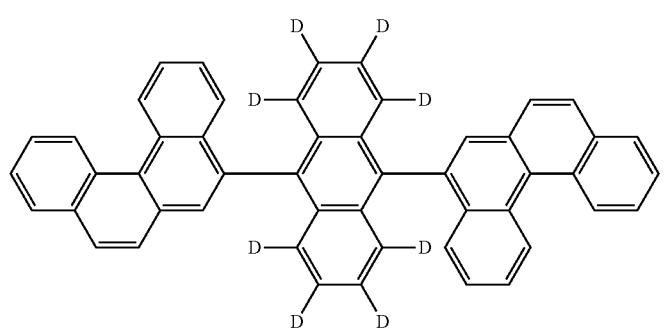
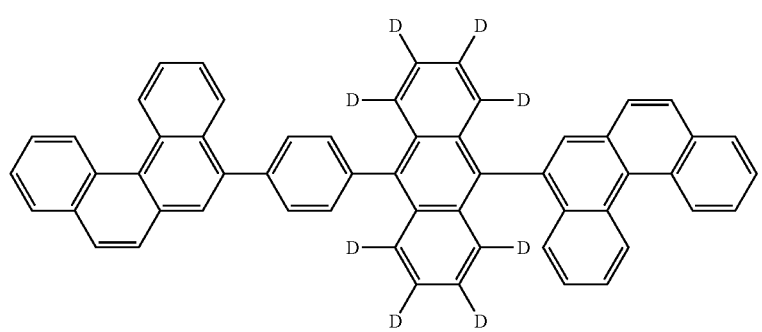

75 76
-continued
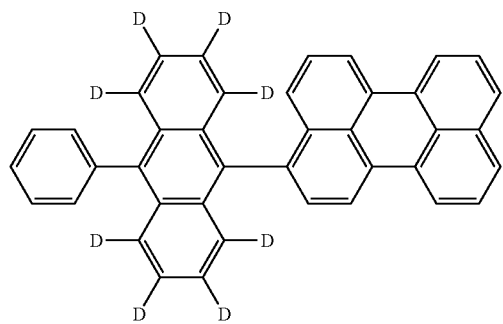
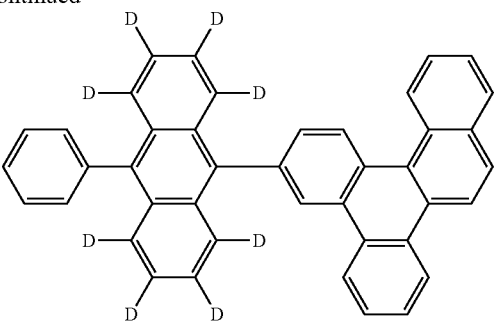
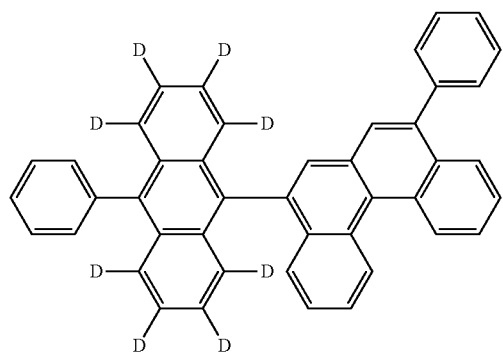
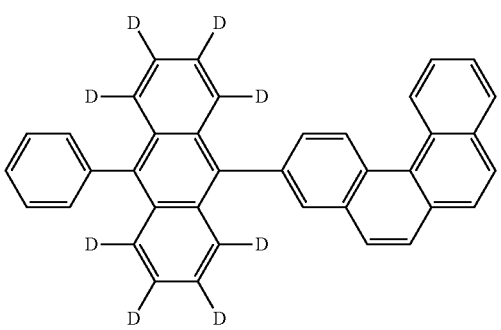
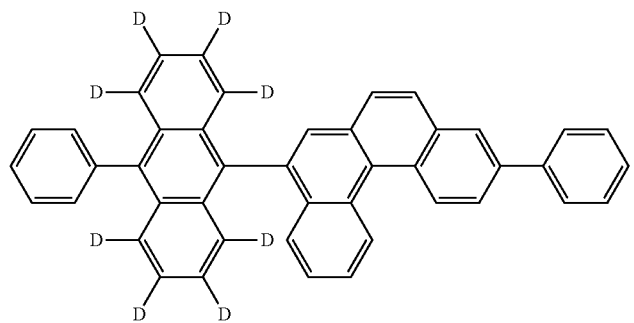
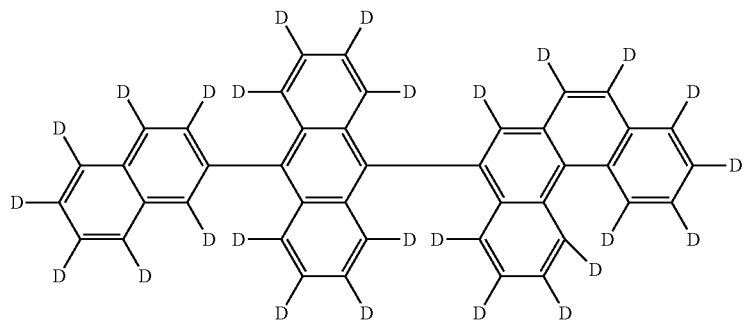
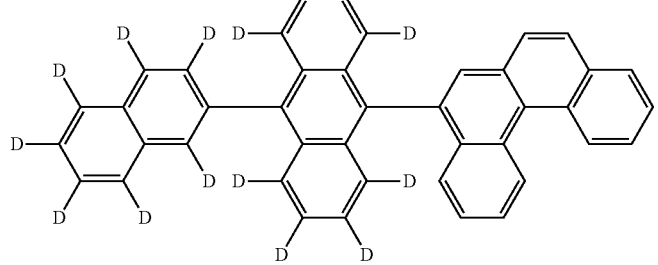

-continued

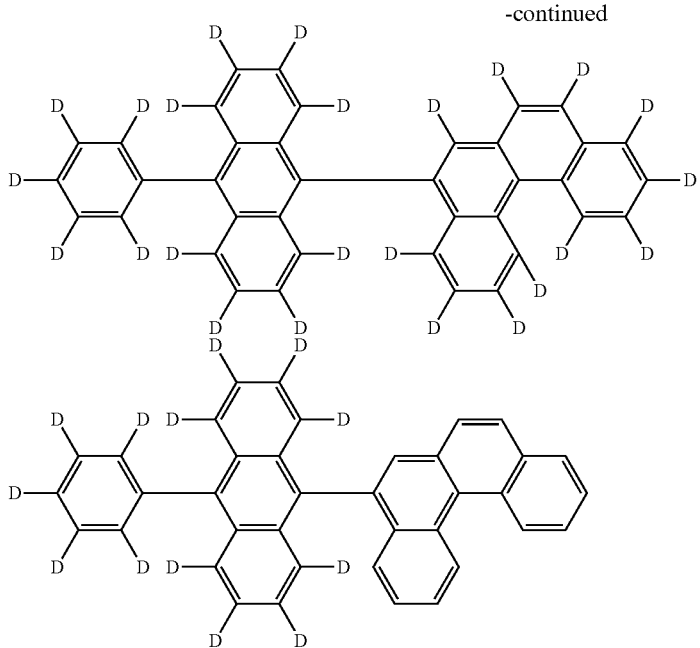

[Material for an Organic Electroluminescence Device Containing the Compound Represented by Formula (1)]

The material for an organic EL device according to an aspect of the invention contains the compound represented by the formula (1).

In one embodiment, the material for an organic EL device is useful as a host material for an emitting layer.

[Composition Containing the Compound Represented by the Formula (1)]

The composition according to an aspect of the invention contains the compound represented by the formula (1), and based on the total amount of a compound represented by the formula (1)(hereinafter also referred to as a "deuterium compound") and a compound having the same structure as the compound represented by the formula (1) except that only protium atoms are contained as hydrogen atoms (hereinafter also referred to as a "protium compound"), the content proportion of the protium compound is 99 mol % or less. The proportion of the protium compound is confirmed by mass spectrometry.

[Organic Electroluminescence Device and Electronic Apparatus]

The organic electroluminescence device according to an aspect of the invention contains
a cathode,
an anode; and
an emitting layer disposed between the cathode and the anode, wherein
the emitting layer contains a compound represented by the formula (1).

In one embodiment, the emitting layer further contains a dopant material.

In one embodiment, the dopant material is one or more compounds selected from the group consisting of a compound represented by the following formula (11), a compound represented by the following formula (21), a compound represented by the following formula (31), a compound represented by the following formula (41), a compound represented by the following formula (51), a compound represented by the following formula (61), a compound represented by the following formula (71), and a compound represented by the following compound (81).

Schematic configuration of organic EL device according to one aspect of the invention will be explained referring to the Figure.

The organic EL device 1 according to an aspect of the invention contains a substrate 2, an anode 3, an emitting layer 5, a cathode 10, an organic layer 4 between the anode 3 and the emitting layer 5, and an organic layer 6 between the emitting layer 5 and the cathode 10. The compound represented by the formula (1) is contained in the emitting layer 5.

In one embodiment, a compound represented by the formula (1) and one or more compounds selected from the group consisting of the formulas (11), (21), (31), (41), (51), (61), (71), and (81) are contained in the emitting layer 5 between the anode 3 and the cathode 10. Each of these compounds may be contained singly or in combination of two or more.

Hereinafter, each compound represented by the formulas (11), (21), (31), (41), (51), (61), (71), and (81) will be described.

(Compound Represented by the Formula (11))

The compound represented by the formula (11) is explained below.

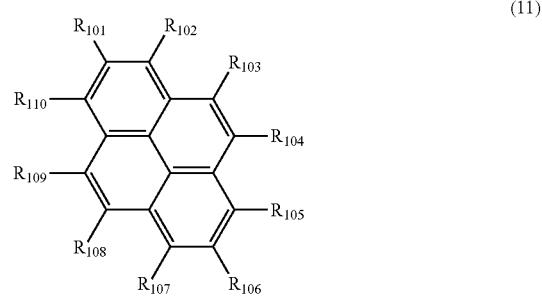

(11)

In the formula (11), one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;

at least one of $R_{101}$ to $R_{110}$ is a monovalent group represented by the formula (12);

$R_{101}$ to $R_{110}$ that do not form the substituted or unsubstituted, saturated or unsaturated ring and that are not a monovalent group represented by the following formula (12) are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms;

$R_{901}$ to $R_{907}$ are as defined in the formula (1);

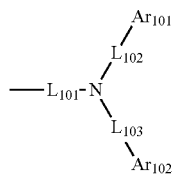

(12)

In the formula (12), $Ar_{101}$ and $Ar_{102}$ are independently a substituted or unsubstituted aryl group including 6 to 50 ring carbon atoms, or a substituted or unsubstituted monovalent heterocyclic group including 5 to 50 ring atoms;

$L_{101}$ to $L_{103}$ are independently a single bond, a substituted or unsubstituted arylene group including 6 to 30 ring carbon atoms, or a substituted or unsubstituted divalent heterocyclic group including 5 to 30 ring atoms.

In the formula (11), it is preferable that two of $R_{101}$ to $R_{110}$ are the group represented by the formula (12).

In one embodiment, the compound represented by the formula (11) is represented by the following formula (13).

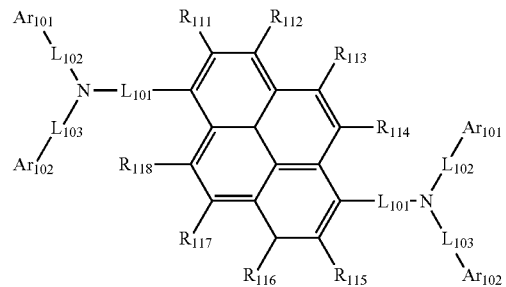

(13)

In the formula (13), $R_{111}$ to $R_{118}$ are the same as $R_{101}$ to $R_{110}$ that is not a monovalent group represented by the formula (12) in the formula (11). $Ar_{101}$, $Ar_{102}$, $L_{101}$, $L_{102}$ and $L_{103}$ are as defined in the formula (12).

In the formula (11), $L_{101}$ is preferably a single bond and $L_{102}$ and $L_{103}$ are preferably a single bond.

In one embodiment, the compound represented by the formula (11) is represented by the formula (14) or (15).

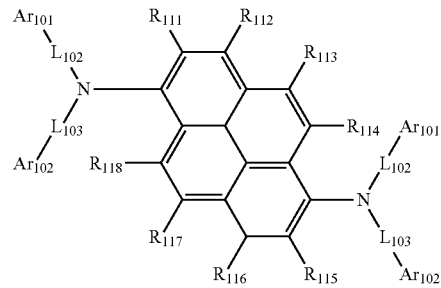

(14)

In the formula (14), $R_{111}$ to $R_{118}$ are as defined in the formula (13). $Ar_{101}$, $Ar_{102}$, $L_{102}$ and $L_{103}$ are as defined in the formula (12).

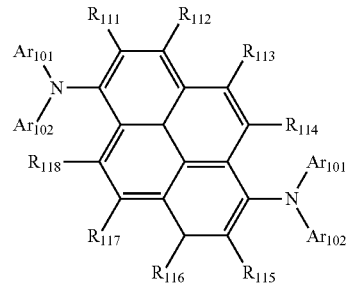

(15)

In the formula (15), $R_{111}$ to $R_{118}$ are as defined in the formula (13). $Ar_{101}$ and $Ar_{102}$ areas defined in the formula (12).

In the formula (11)(formula (12)), it is preferable that at least one of $Ar_{101}$ and $Ar_{102}$ is the group represented by the following formula (16).

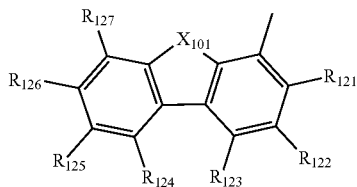

(16)

In the formula (16), $X_{101}$ is an oxygen atom or a sulfur atom;

one or more pairs of two or more adjacent groups of $R_{121}$ to $R_{127}$ are bonded with each other to form a substituted or unsubstituted, saturated or unsaturated ring, or do not form a substituted or unsubstituted, saturated or unsaturated ring:

$R_{121}$ to $R_{127}$ that do not form the substituted or unsubstituted, saturated or unsaturated ring are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms; and $R_{901}$ to $R_{907}$ are as defined in the formula (1).

It is preferable that $X_{101}$ is an oxygen atom.

It is preferable that at least one of $R_{121}$ to $R_{127}$ is a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms.

It is preferable that in the formula (11)(formula (12)), $Ar_{101}$ is a group represented by the formula (16) and $Ar_{102}$ is a substituted or unsubstituted aryl group including 6 to 50 ring carbon atoms.

In one embodiment, the compound represented by the formula (11) is represented by the following formula (17).

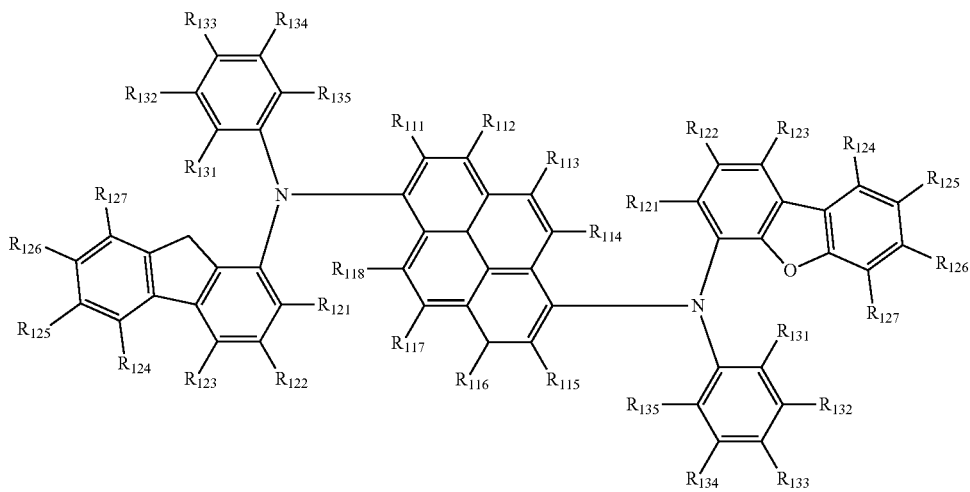

(17)

In the formula (17), $R_{111}$ to $R_{118}$ are as defined in the formula (13), and $R_{121}$ to $R_{127}$ are as defined in the formula (16);

$R_{131}$ to $R_{135}$ are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms; and $R_{901}$ to $R_{907}$ are as defined in the formula (1).

As the compound represented by the formula (11), the following compounds can be given as specific examples, for example. In the following example compounds, Me represents methyl group.

83
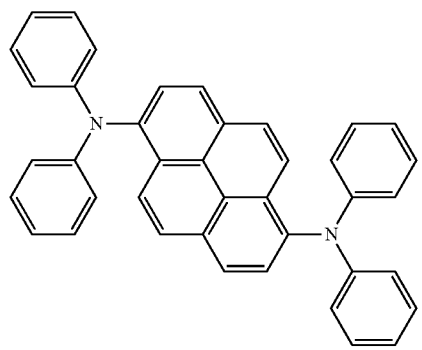
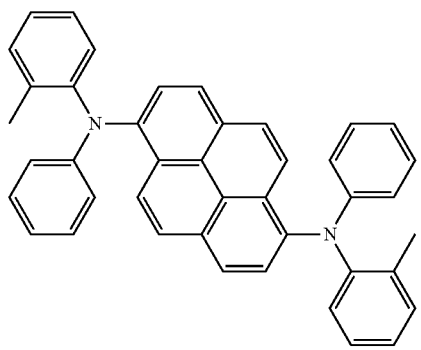
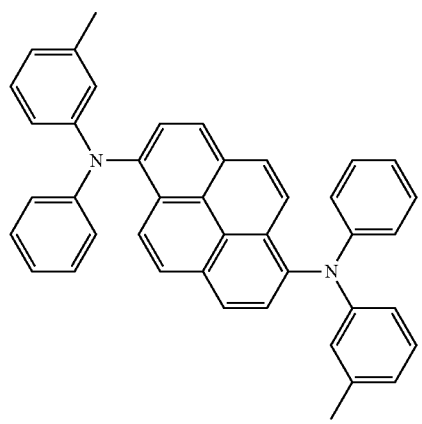
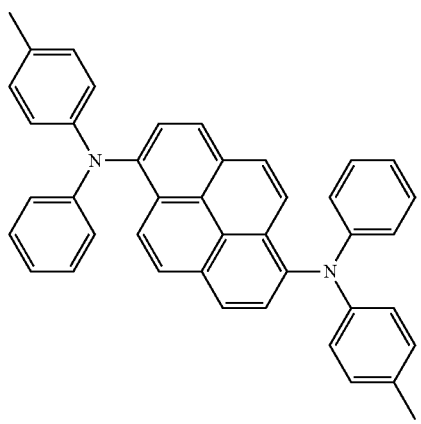
84
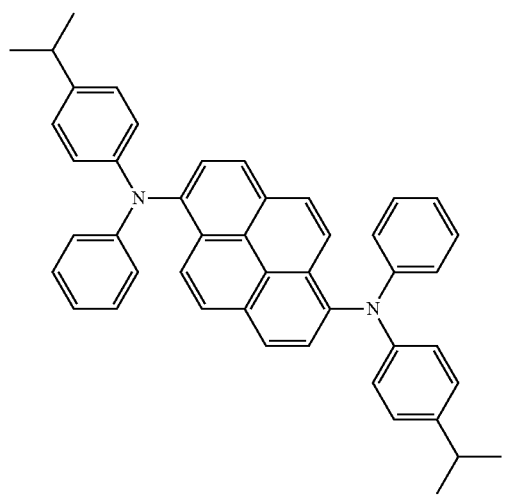
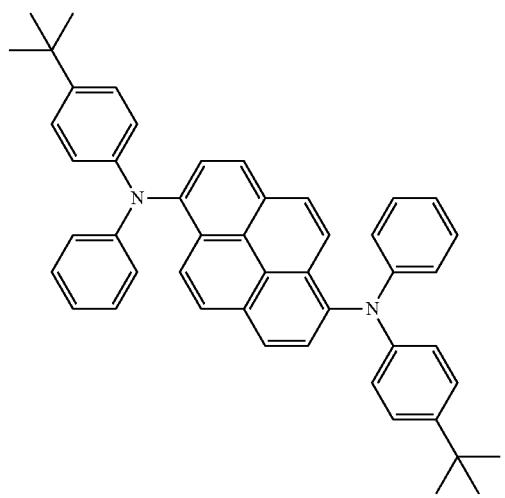

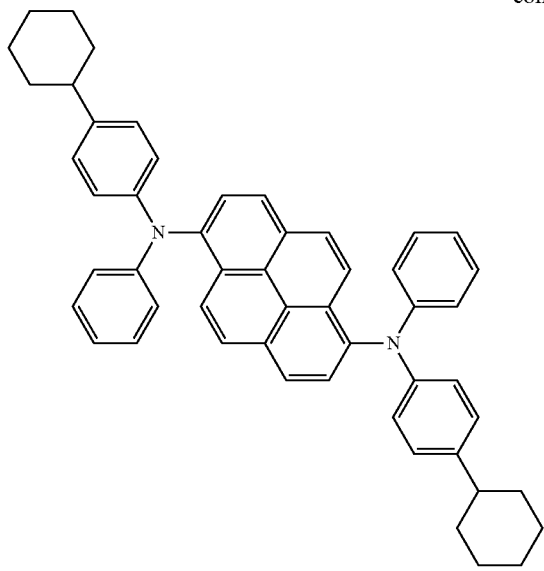
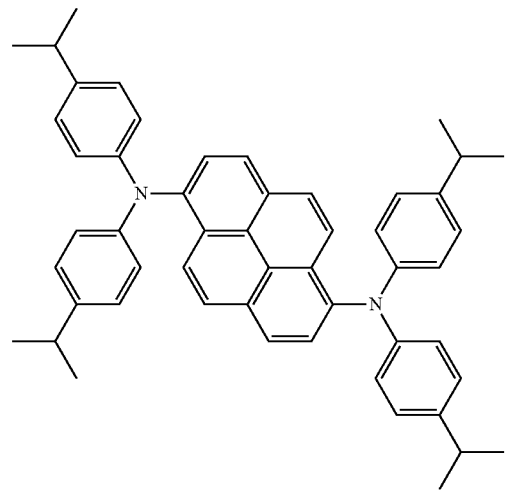
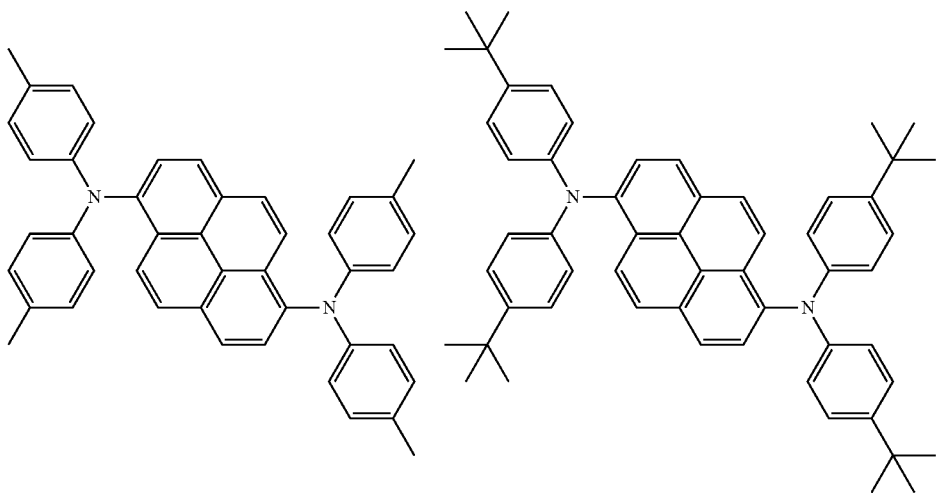
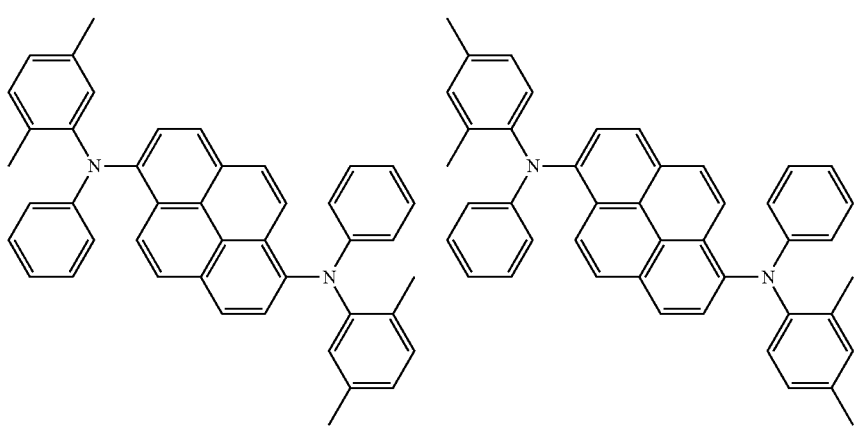

-continued
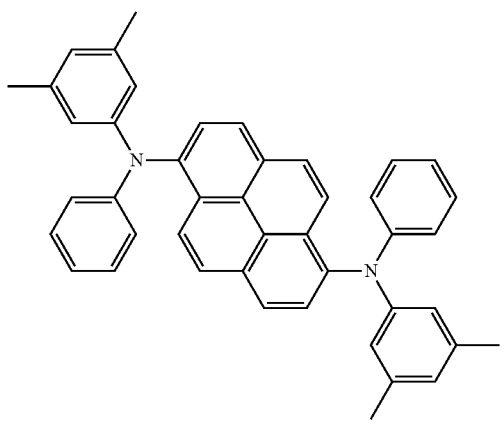
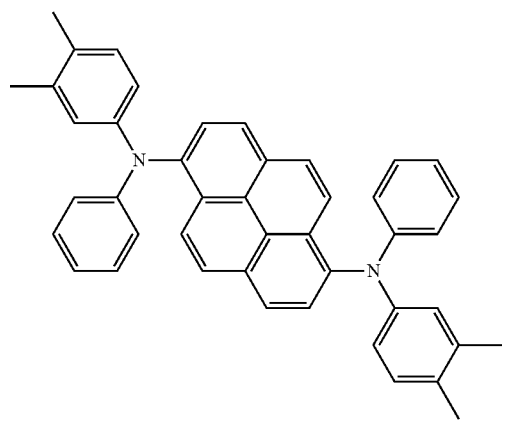
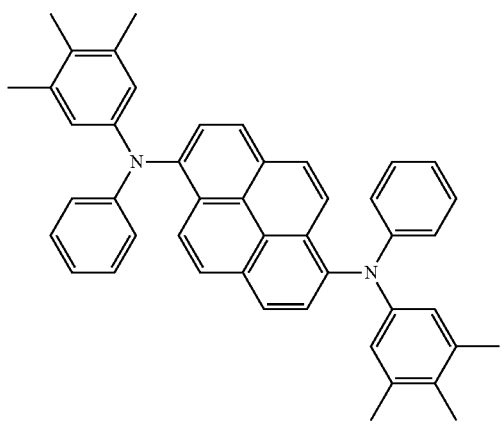
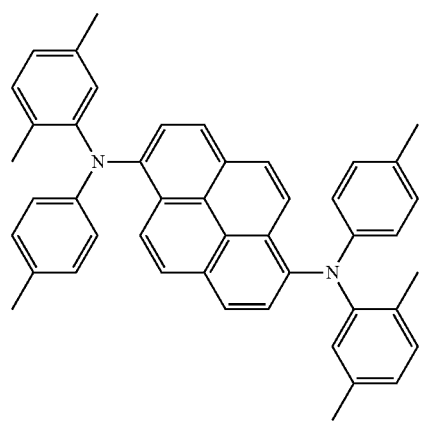
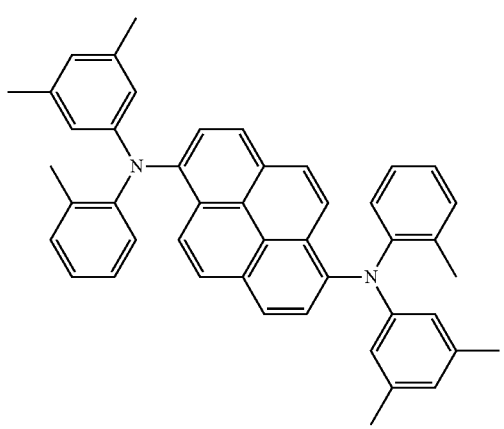
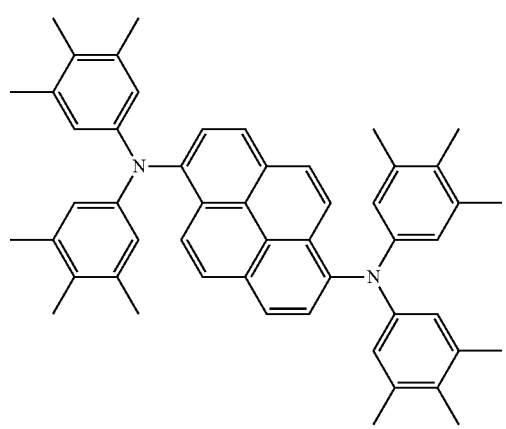

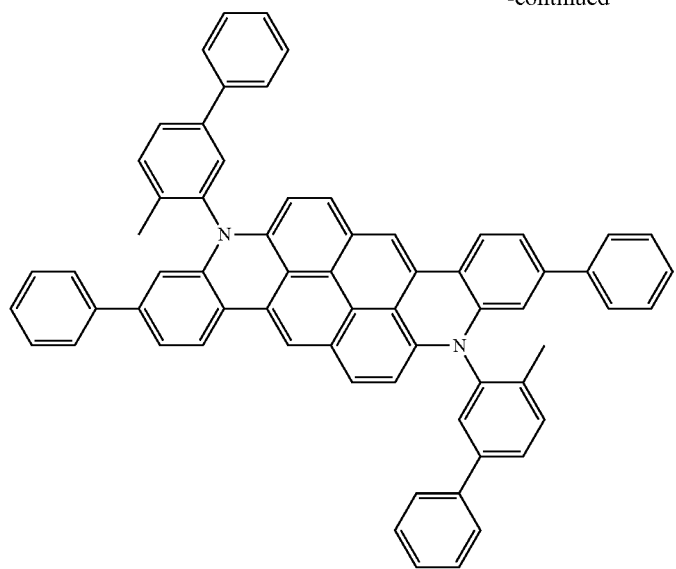
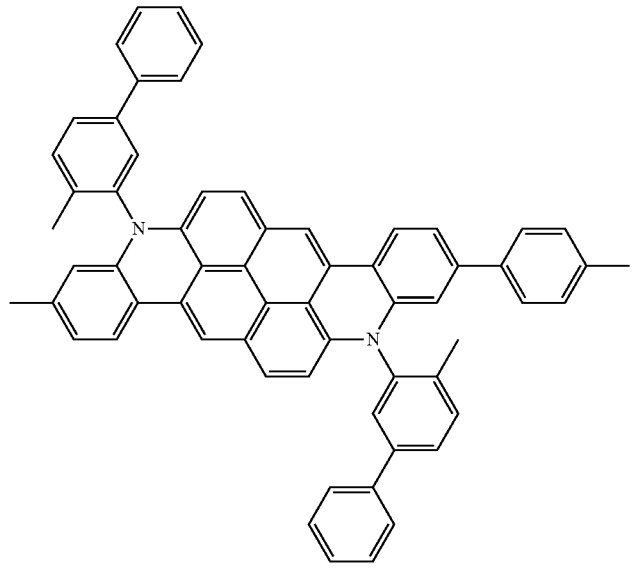
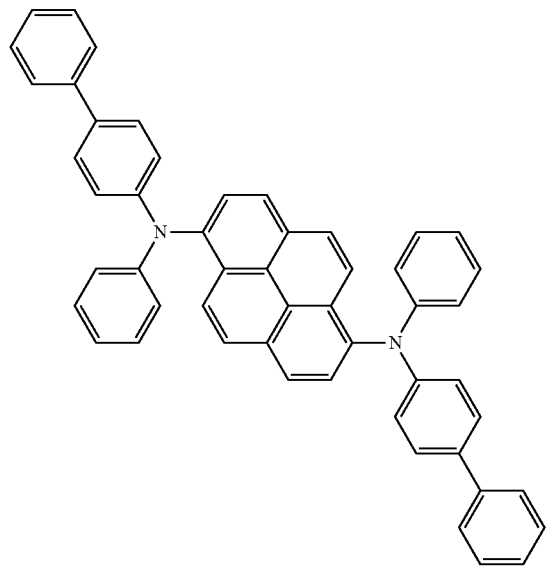
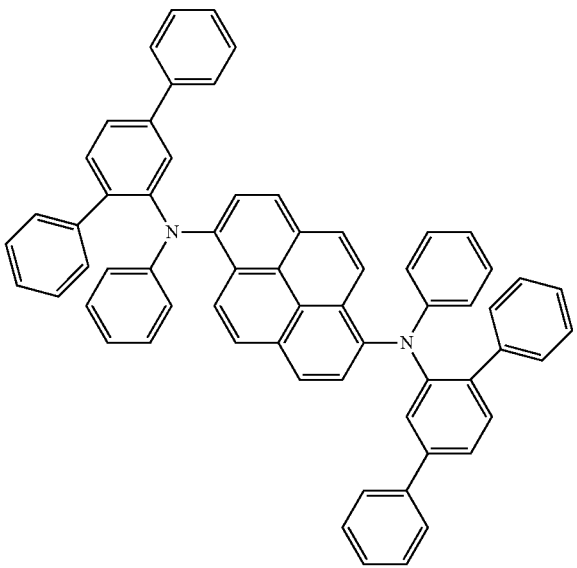

91
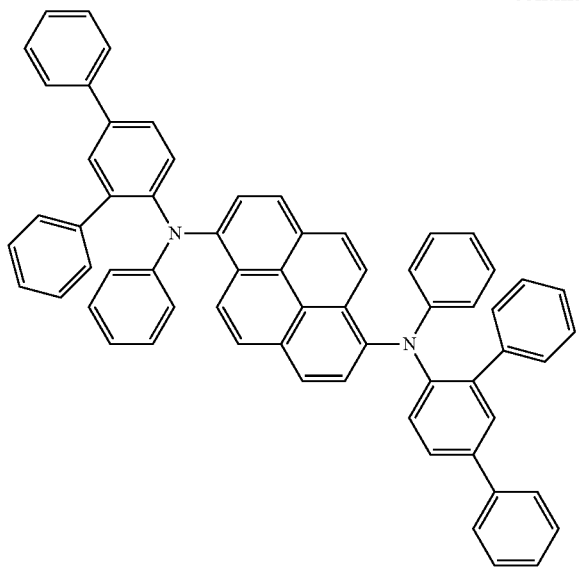
92
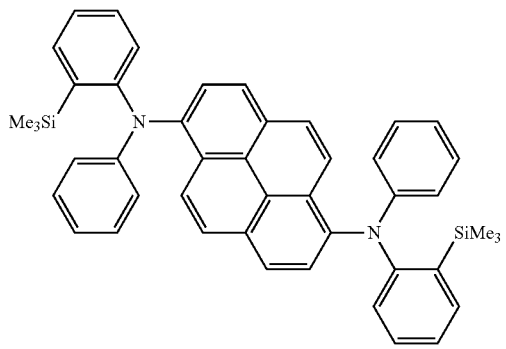
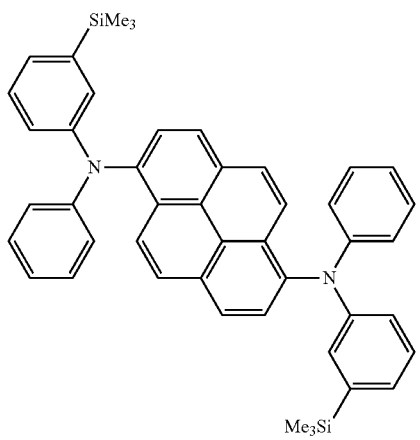
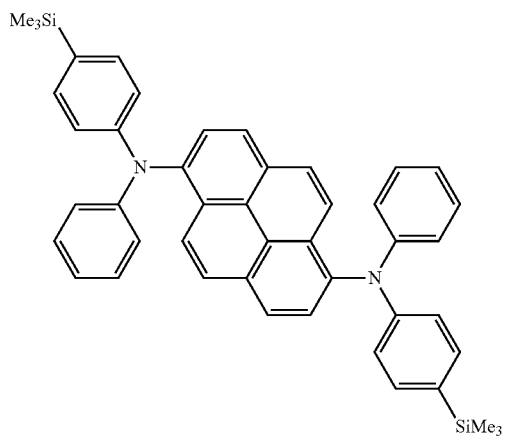
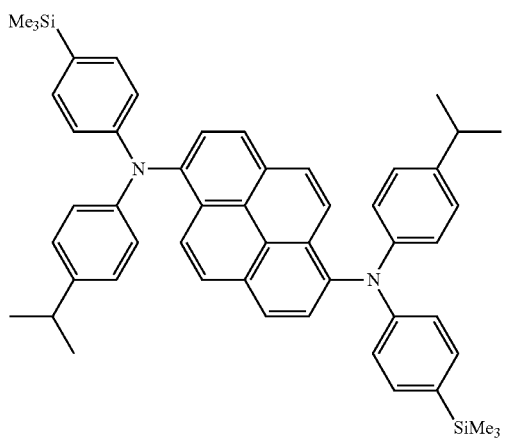
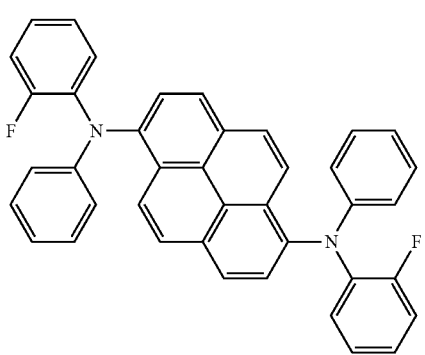

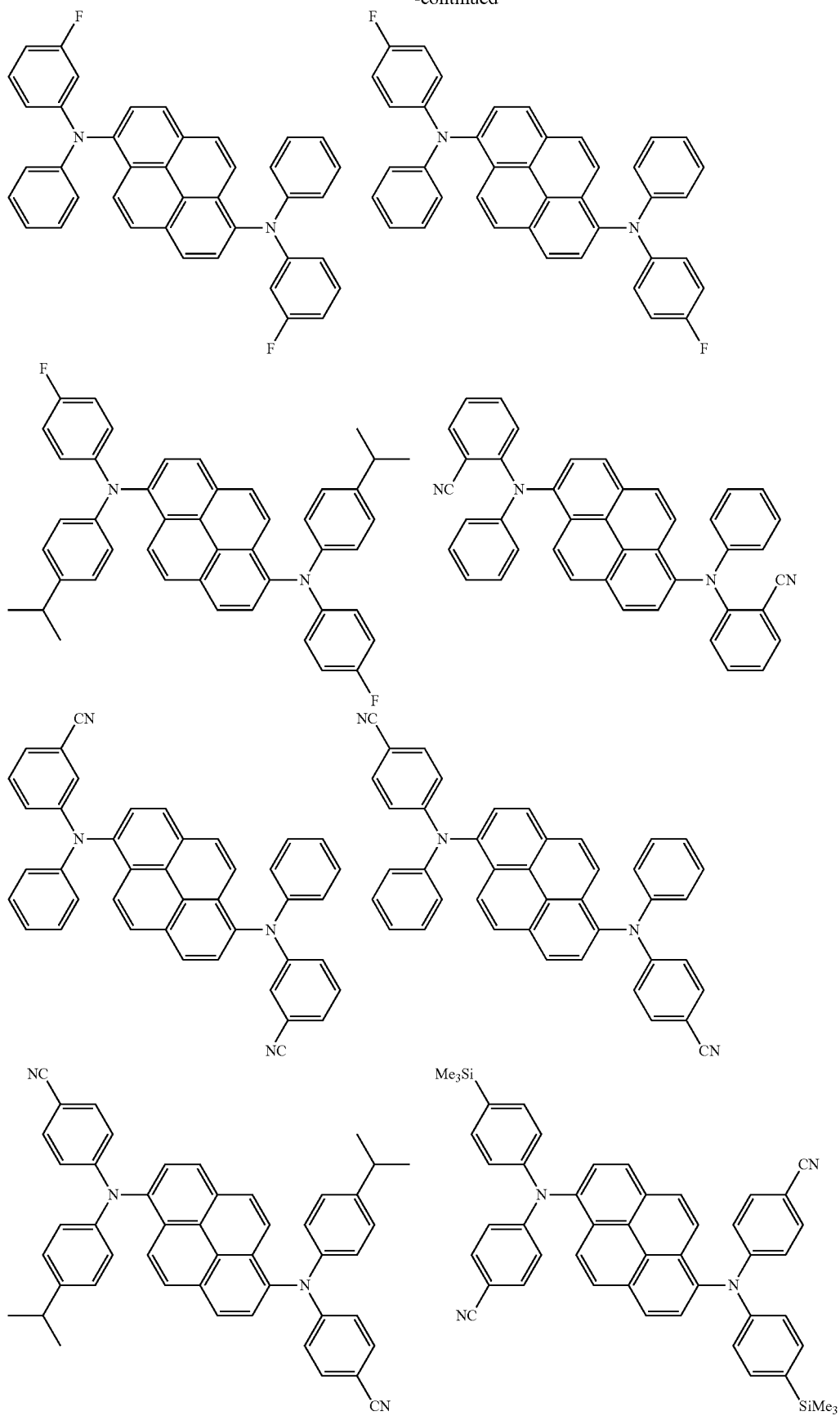

-continued
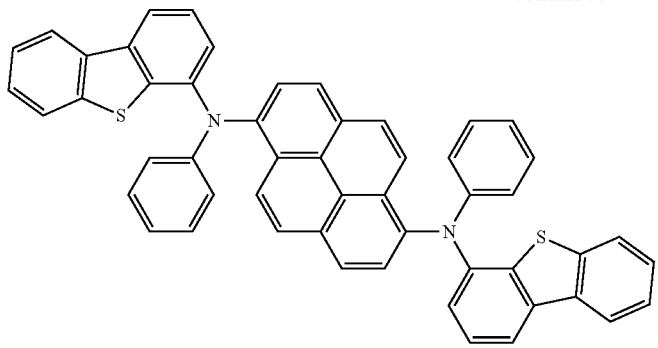
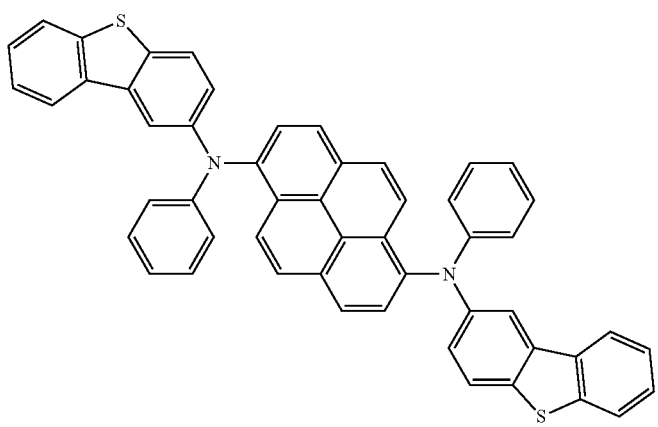
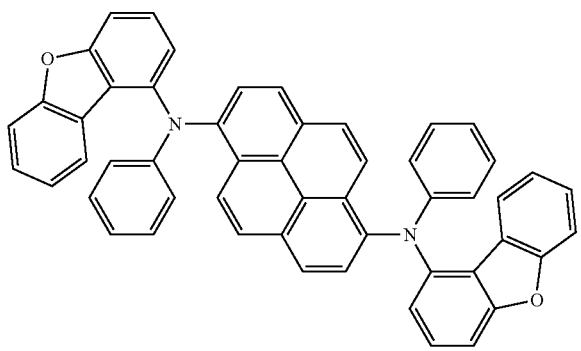
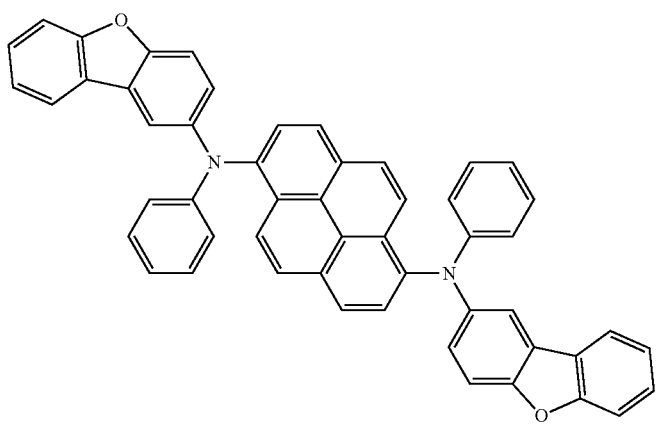

-continued
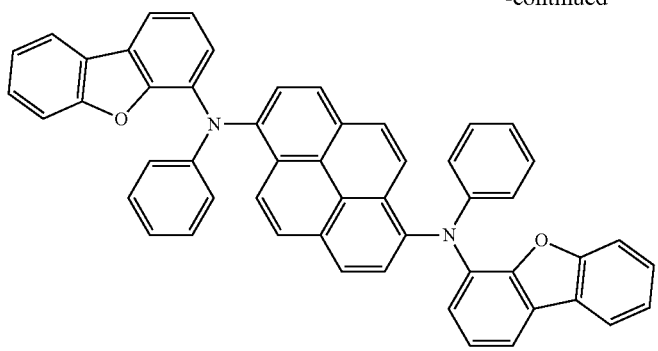
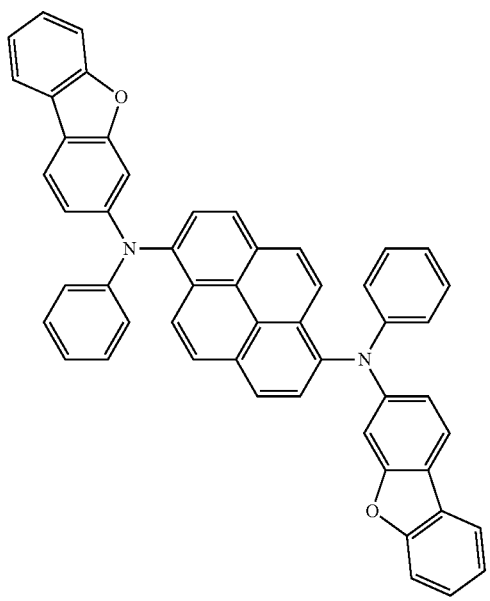
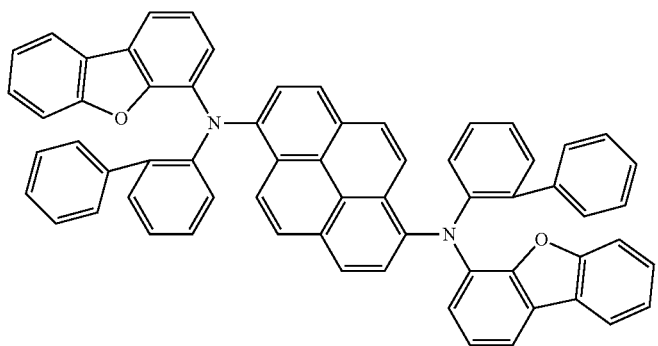
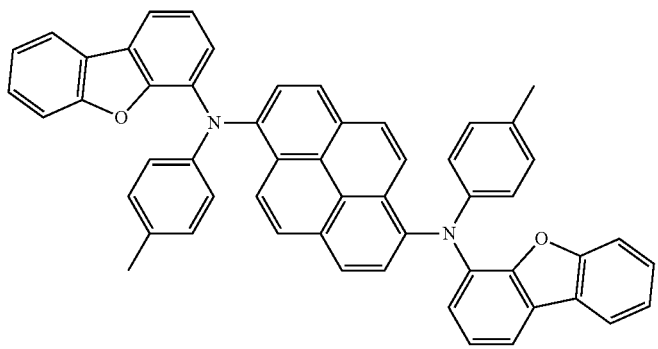

-continued
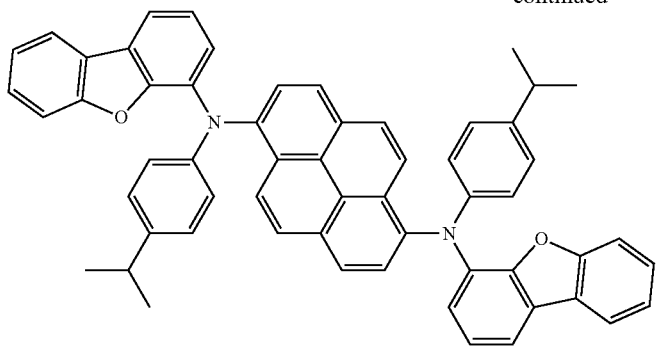
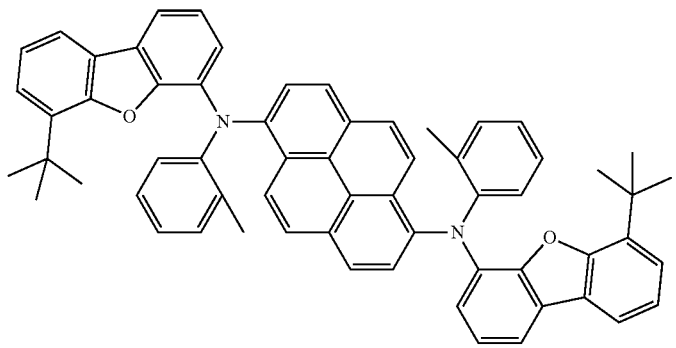
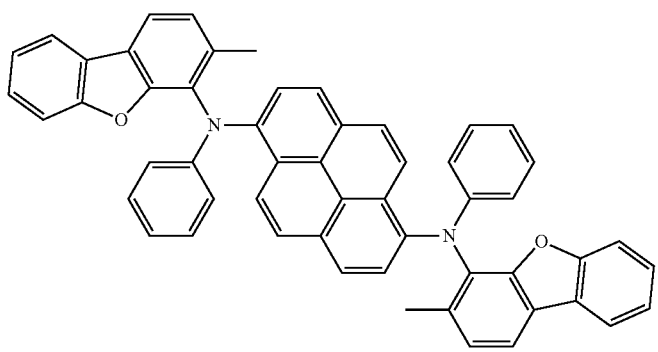
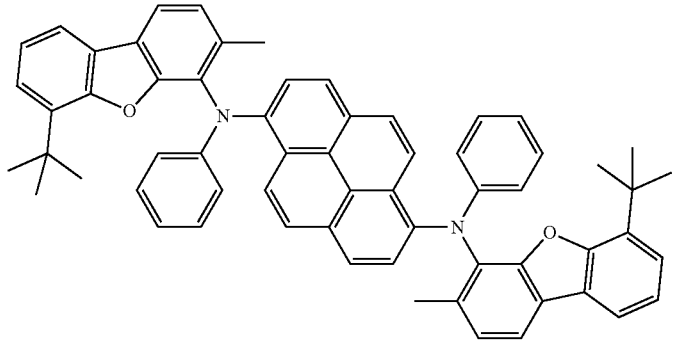
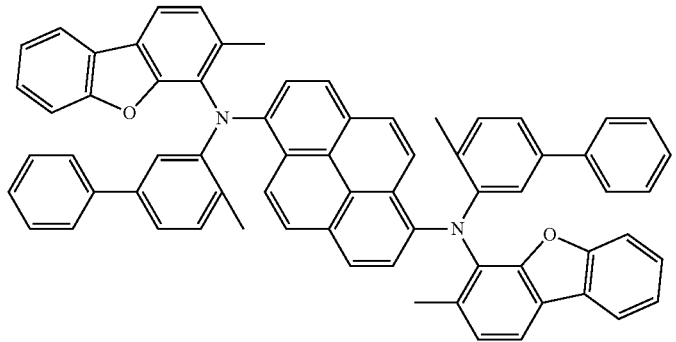

-continued
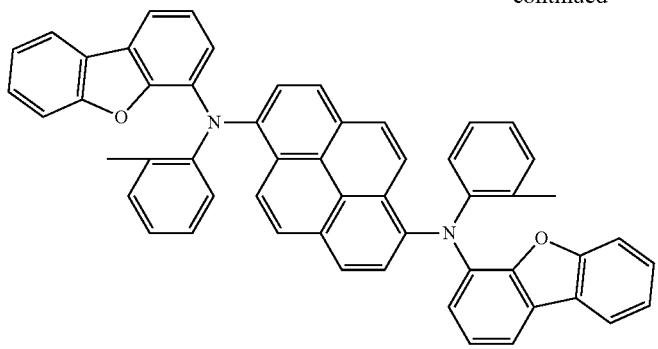
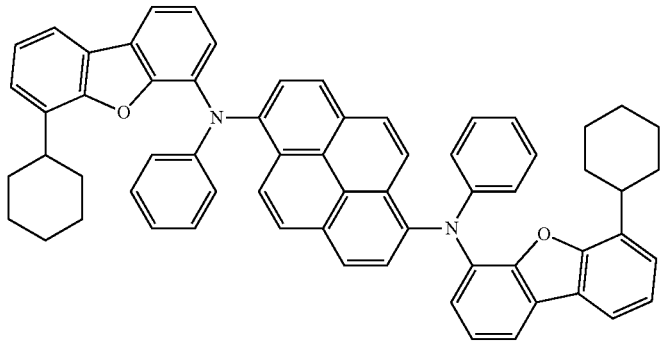
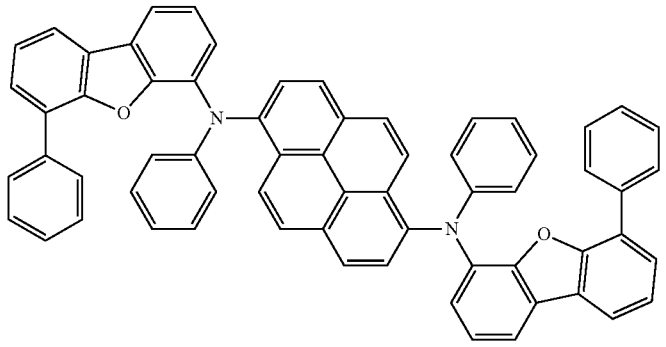
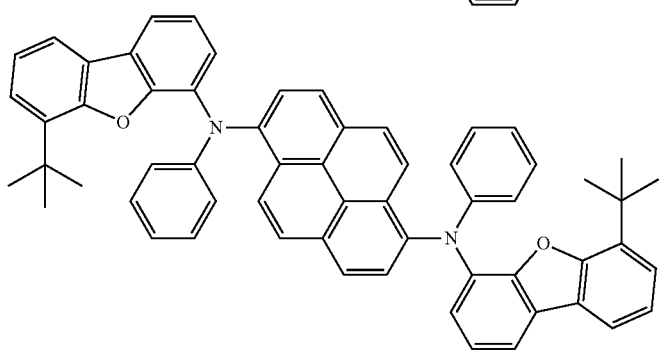
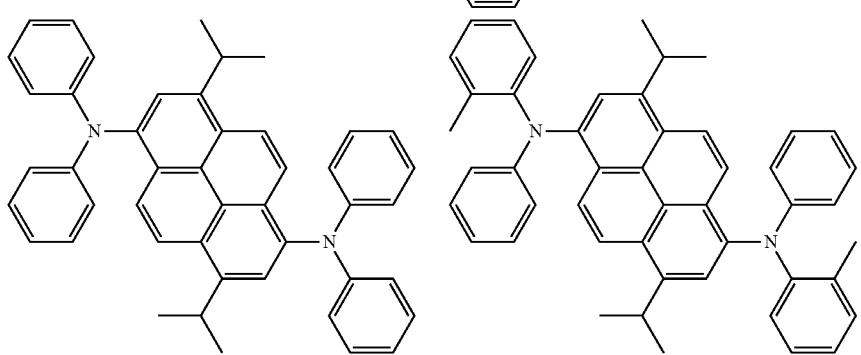

103
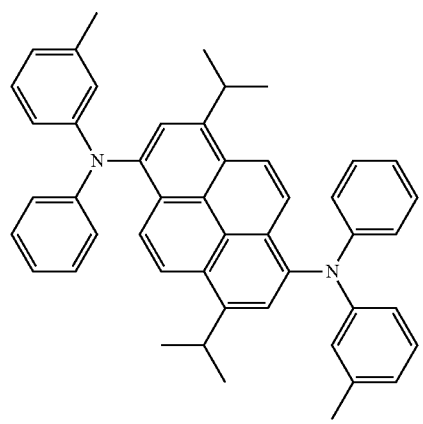
104
-continued
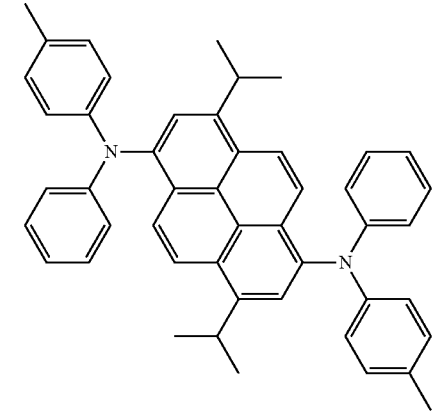
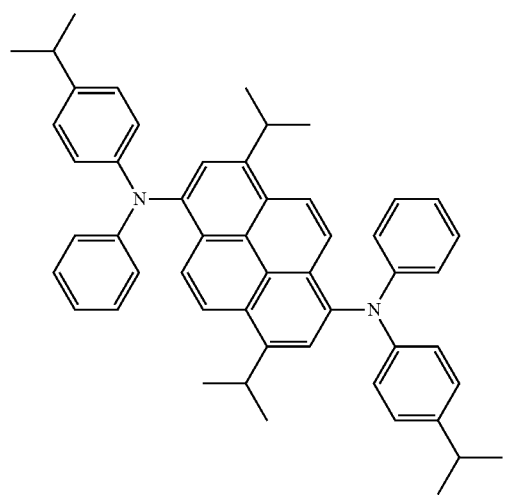
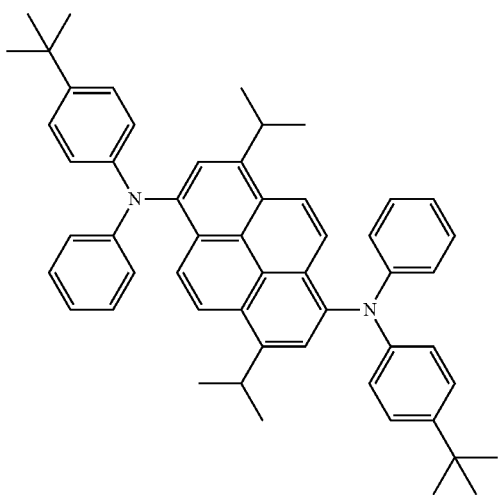
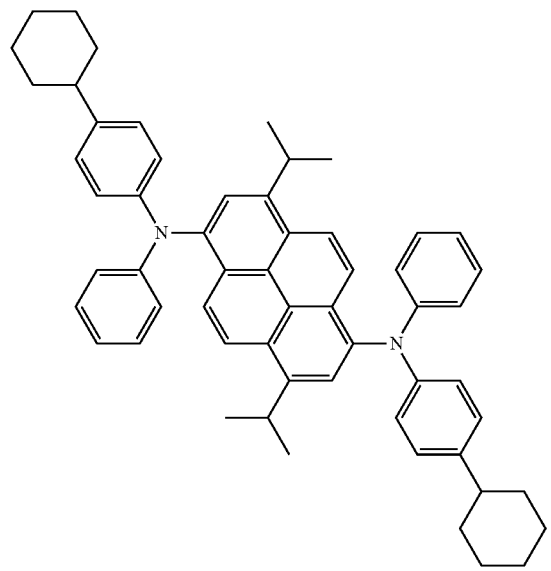
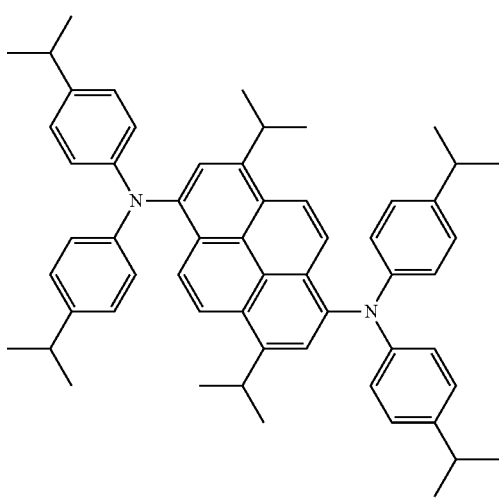

105
106
-continued
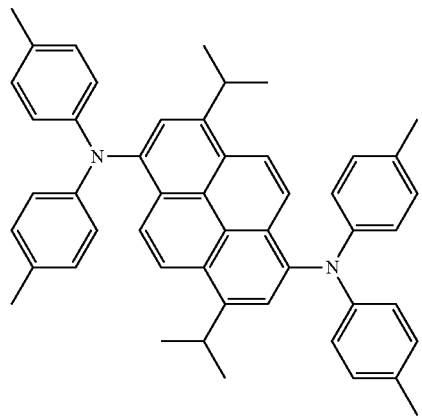
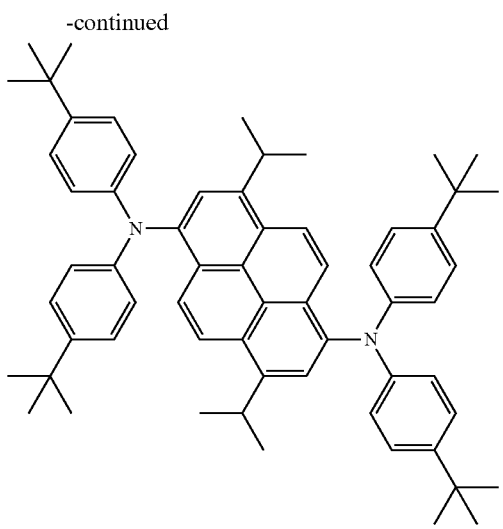
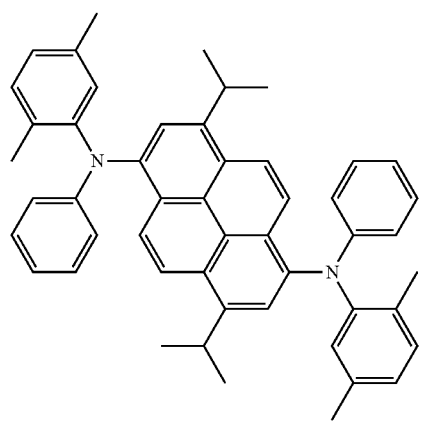
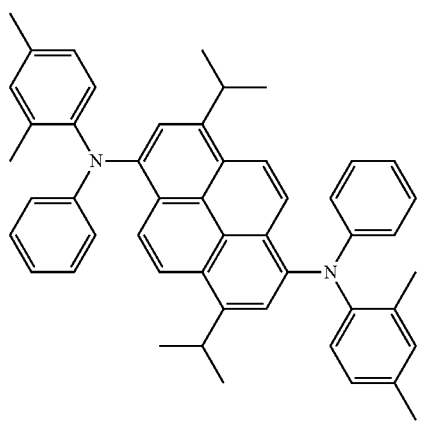
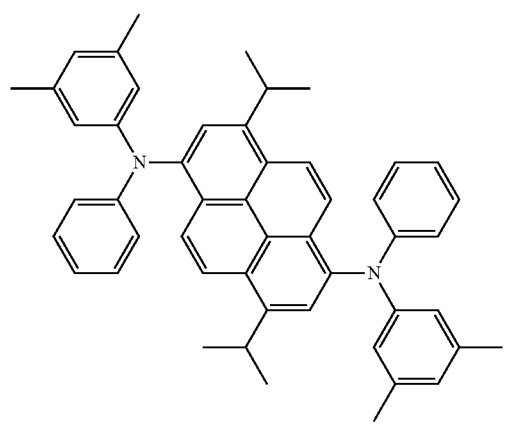
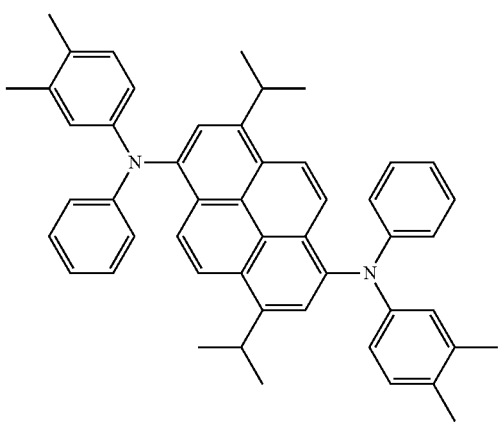

-continued
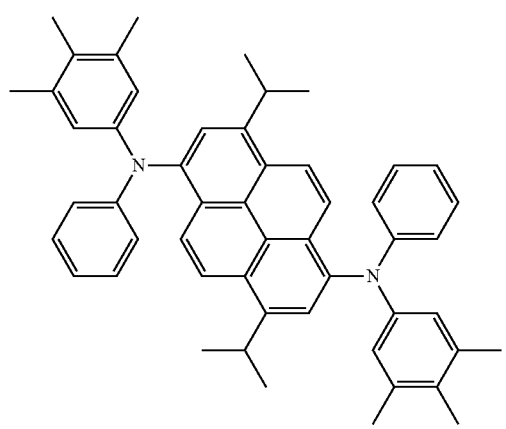
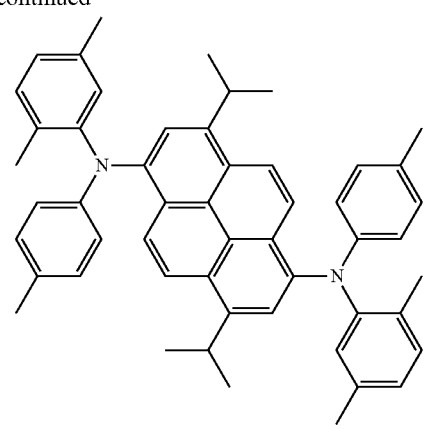
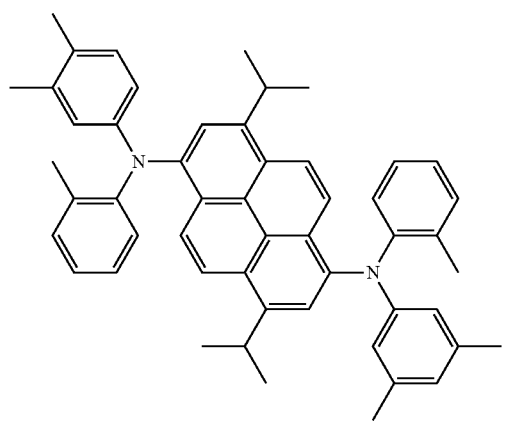
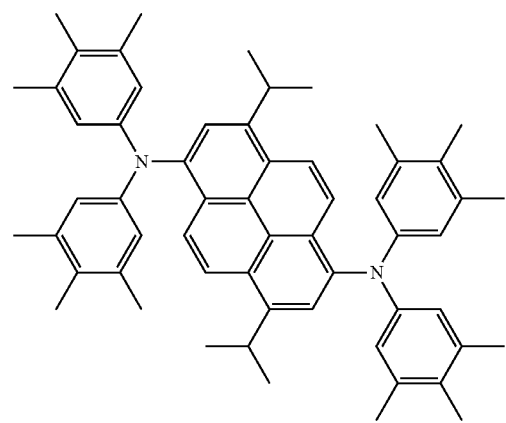
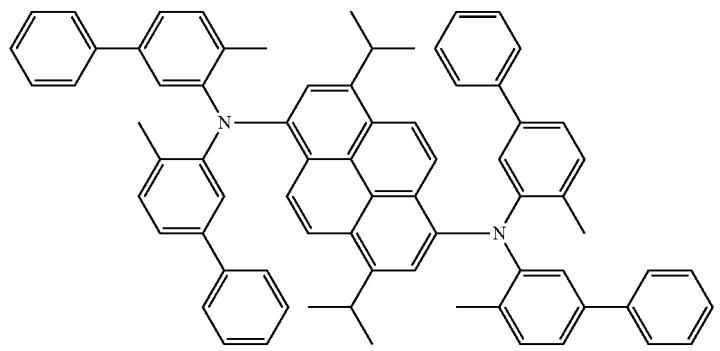
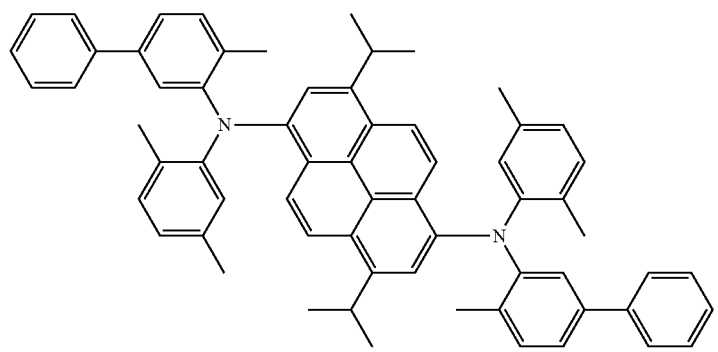

109
110
-continued
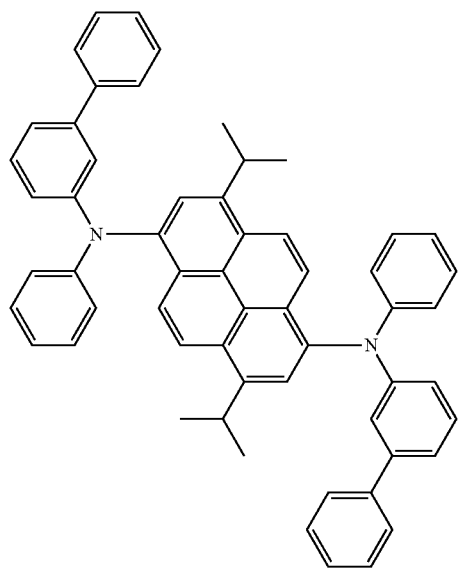
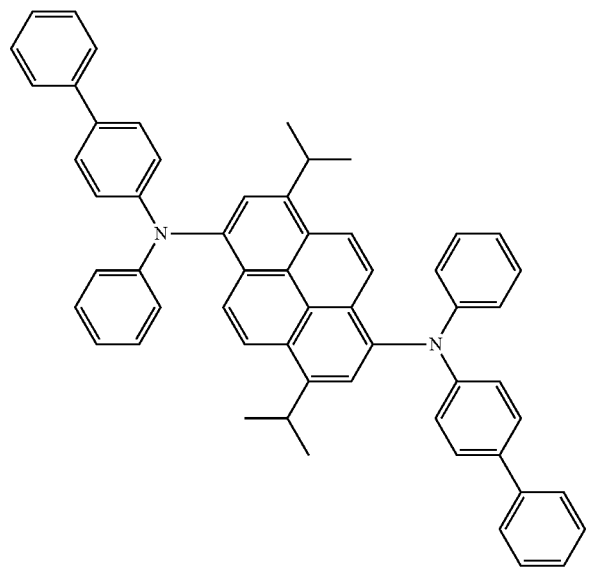
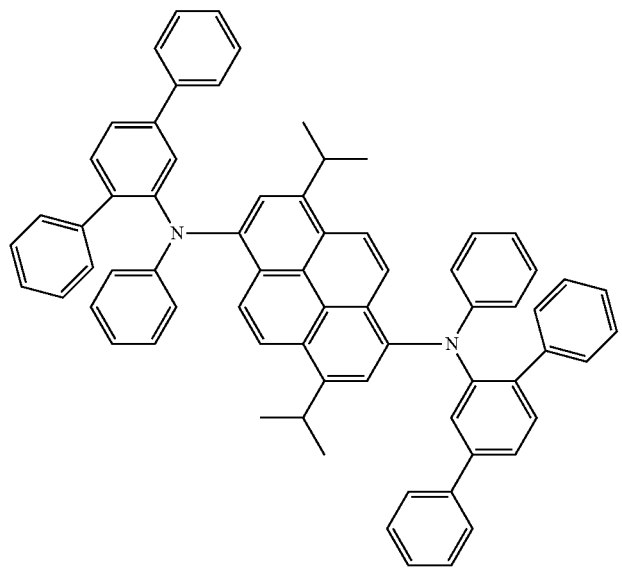
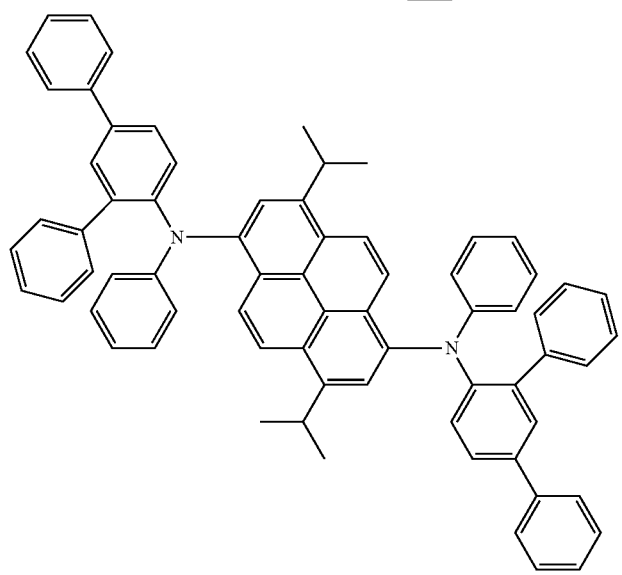

-continued
111
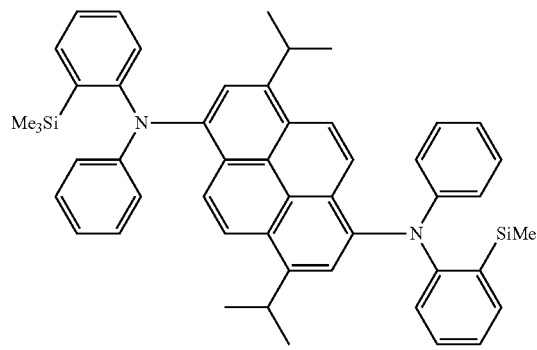
112
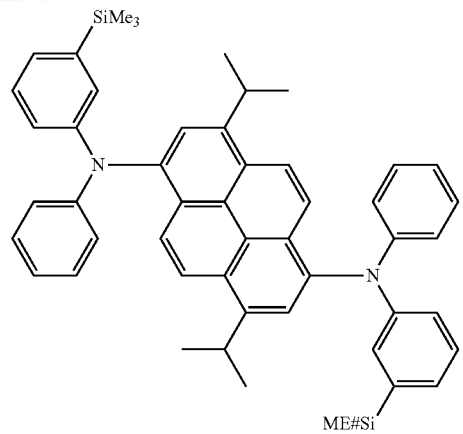
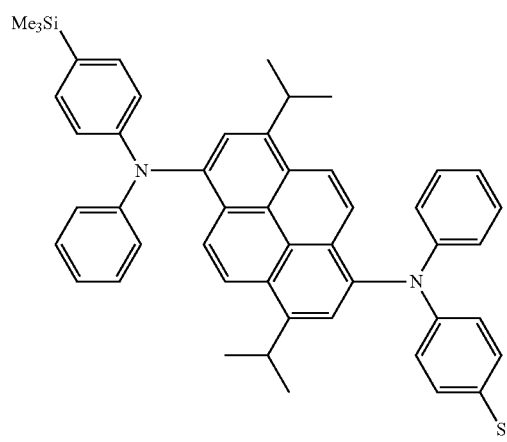
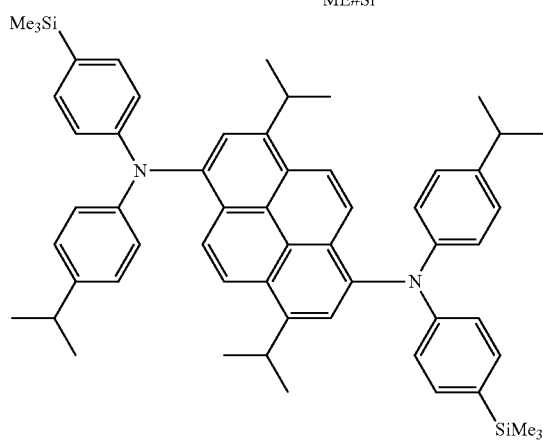
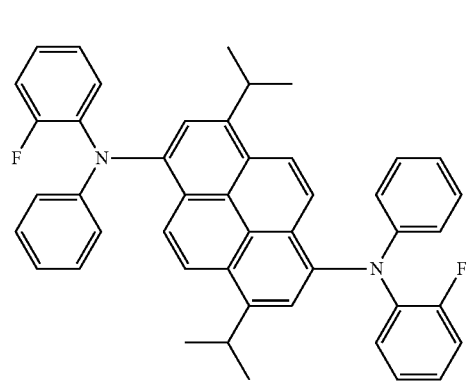
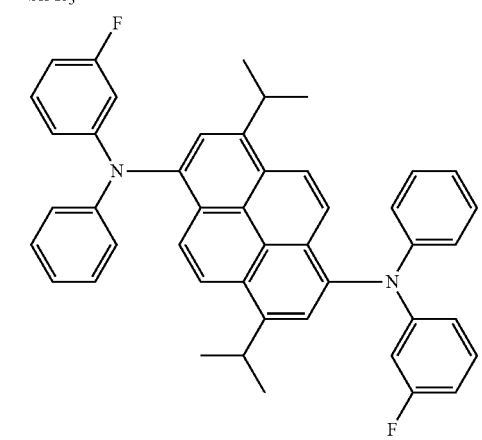
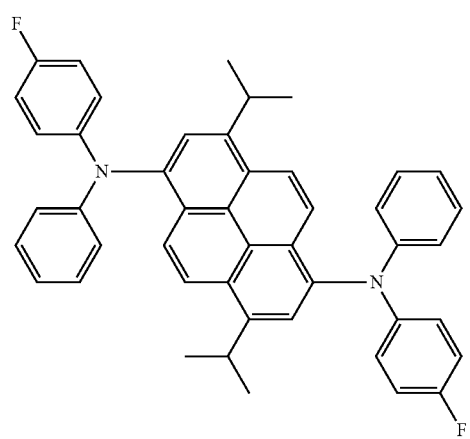
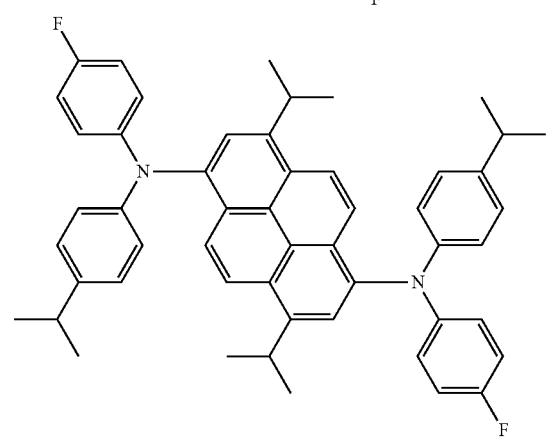

-continued
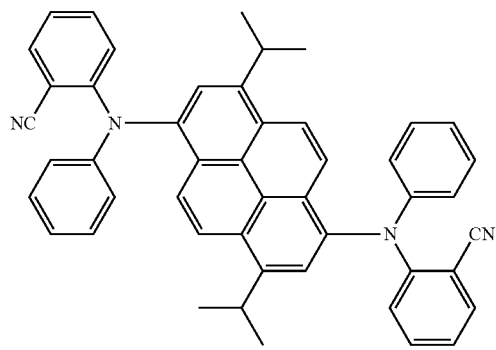
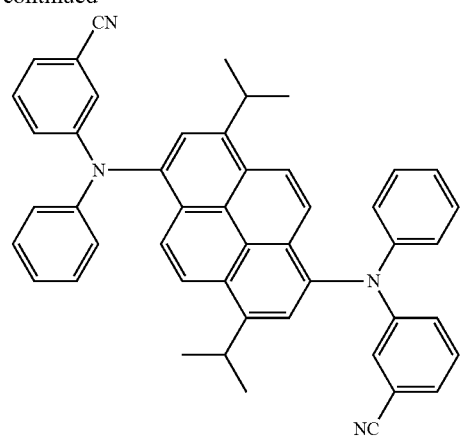
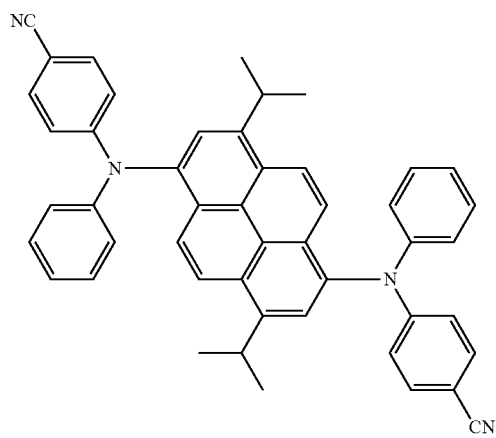
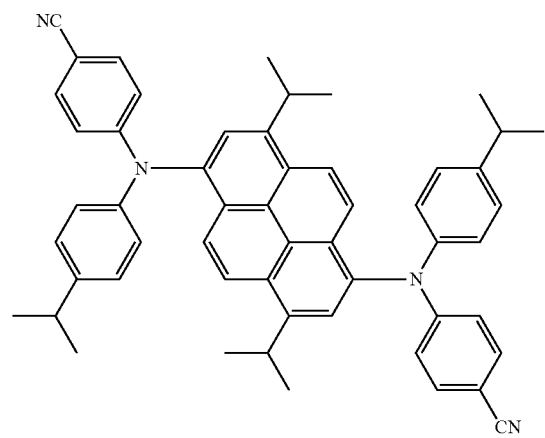
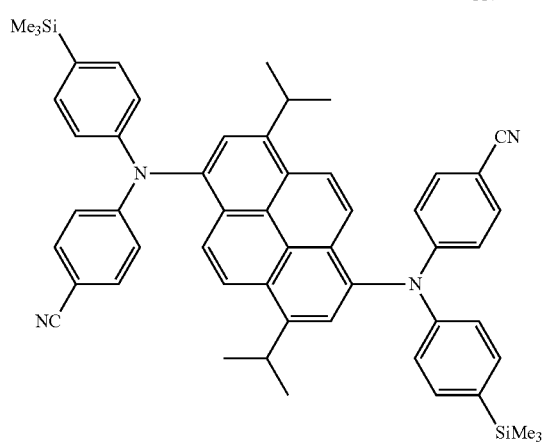
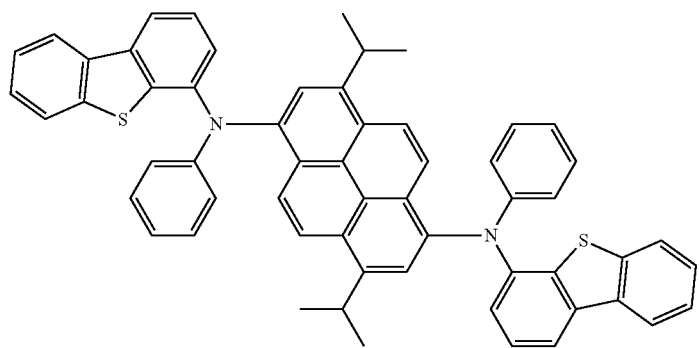

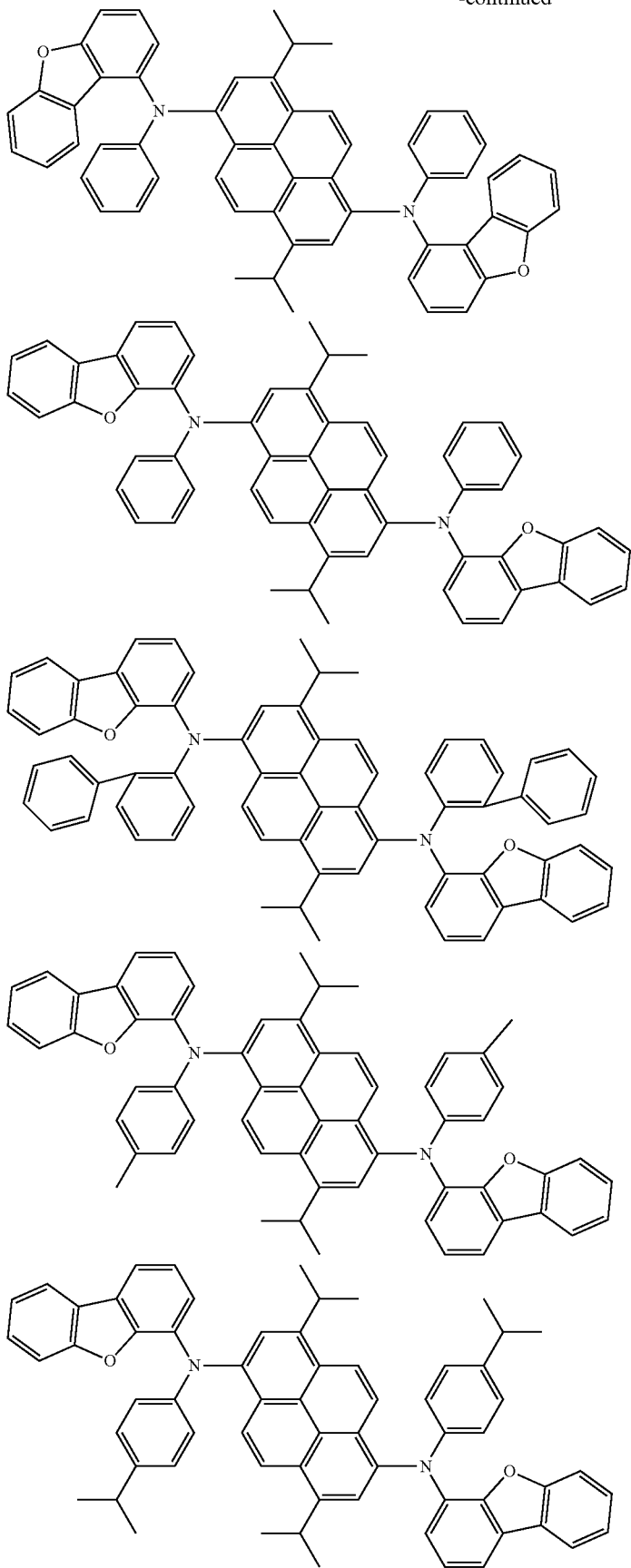

-continued
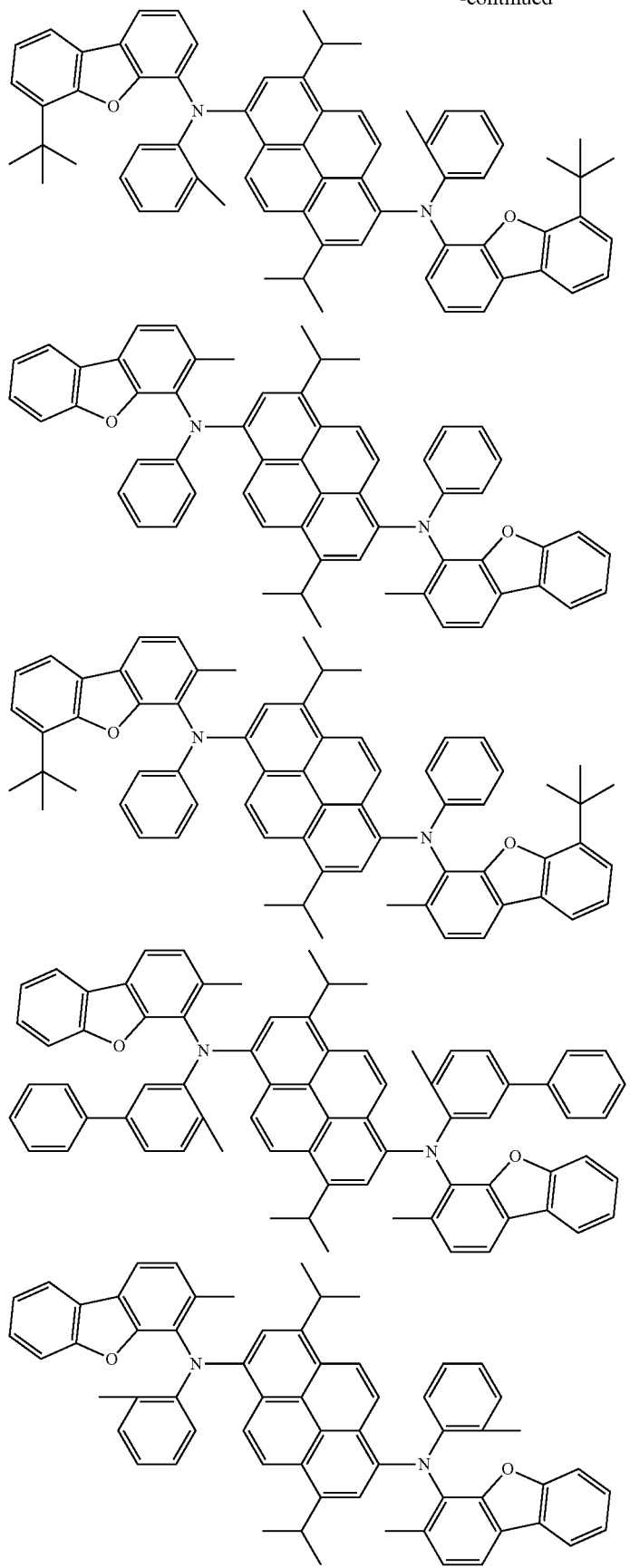

-continued
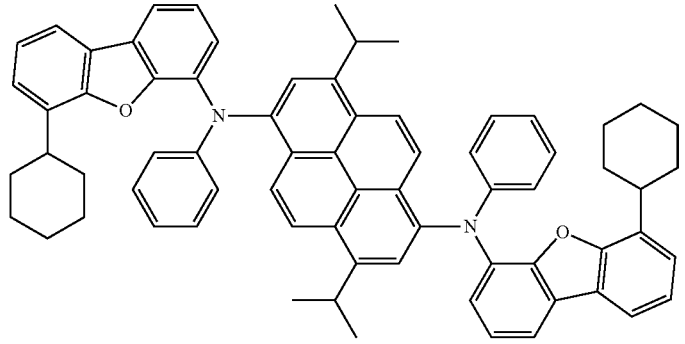
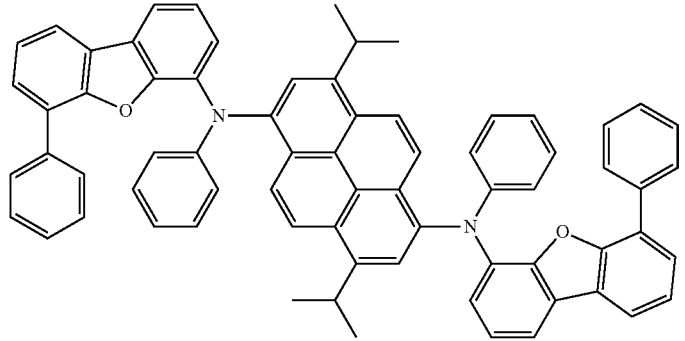
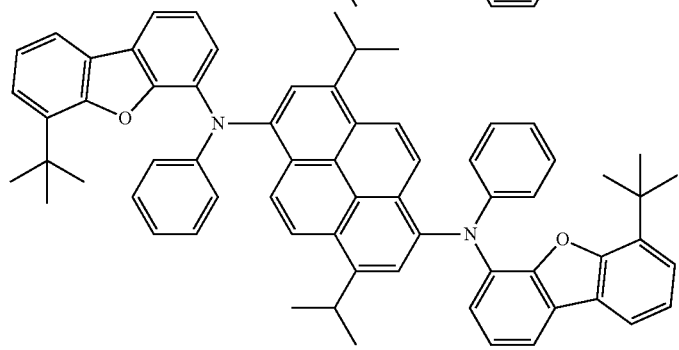
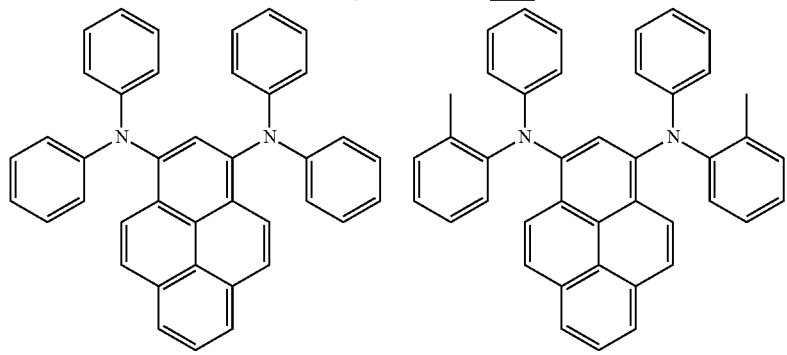
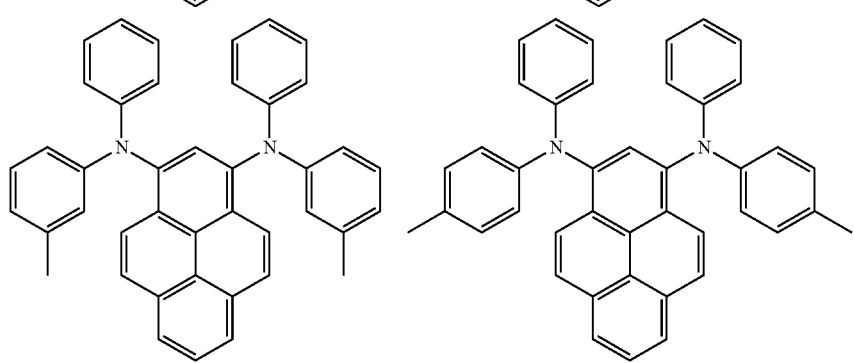

-continued
121
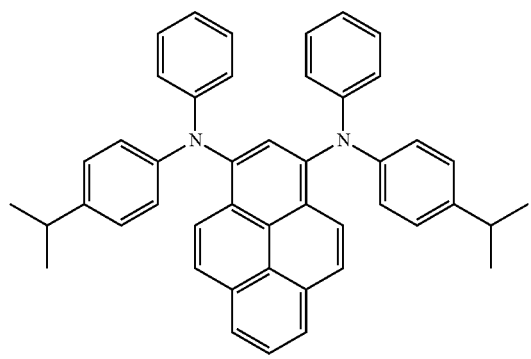
122
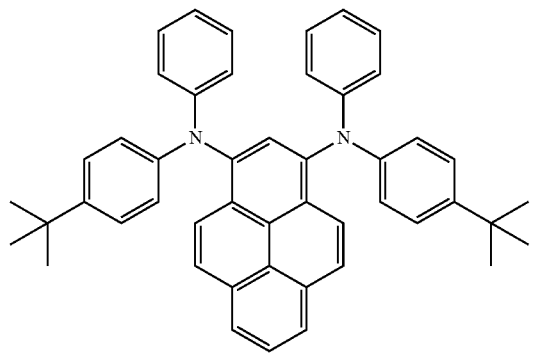
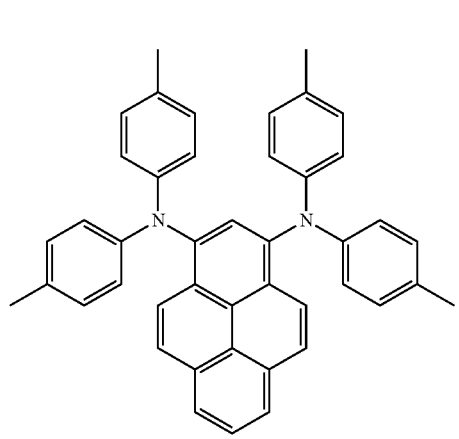
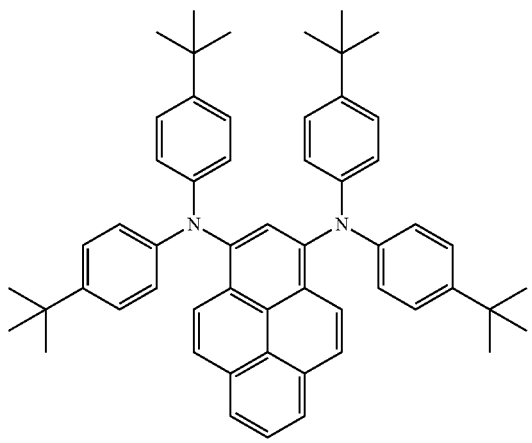
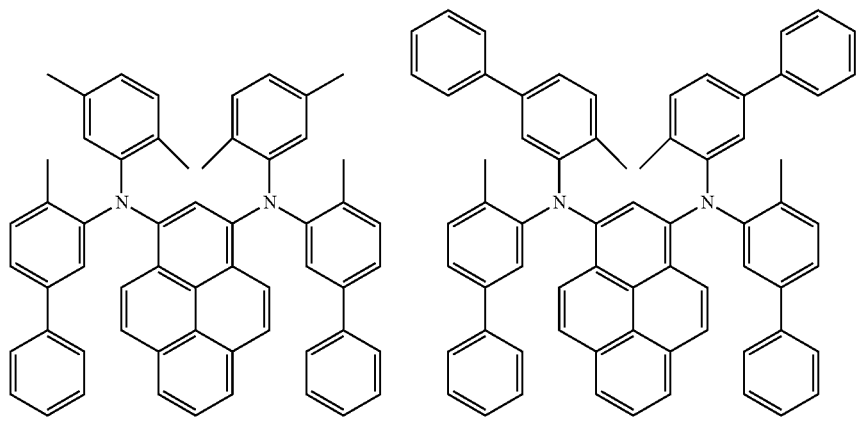
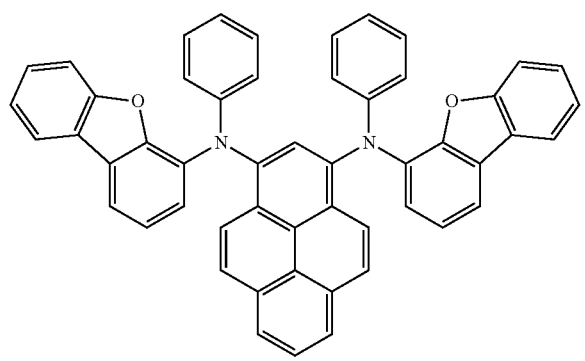

123
-continued
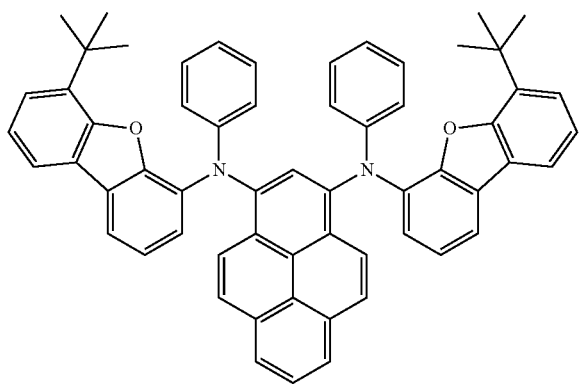
124
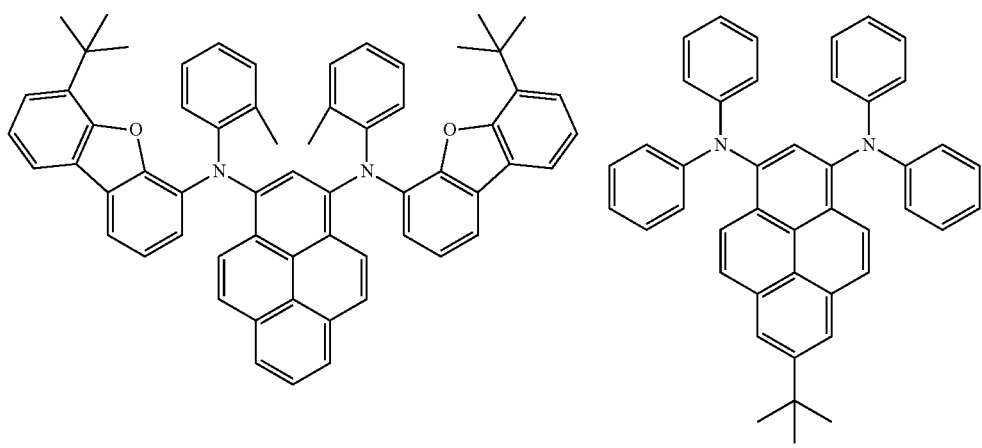
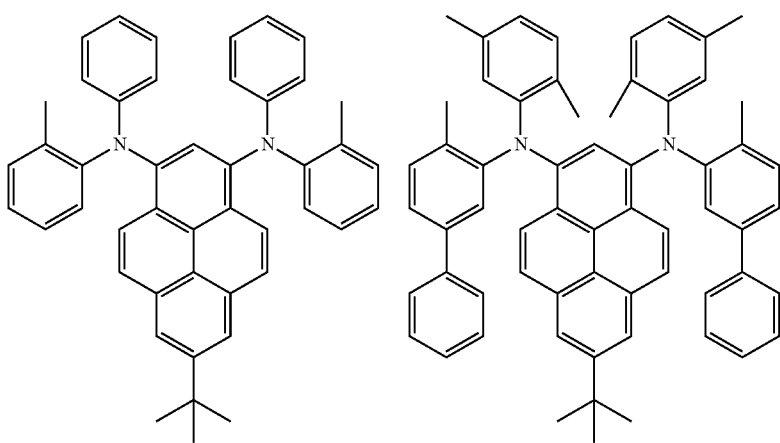

-continued
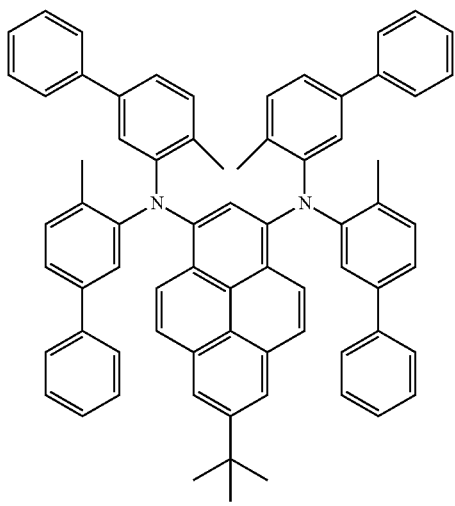
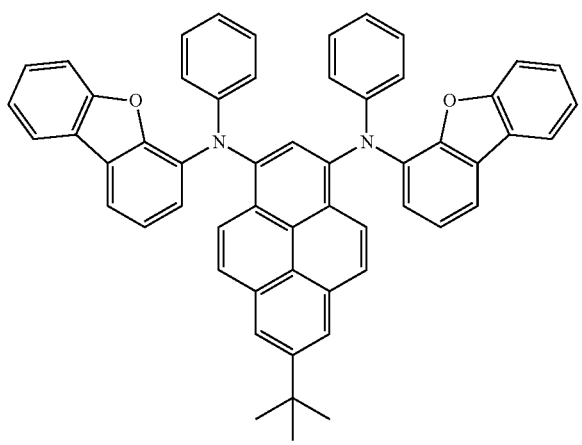
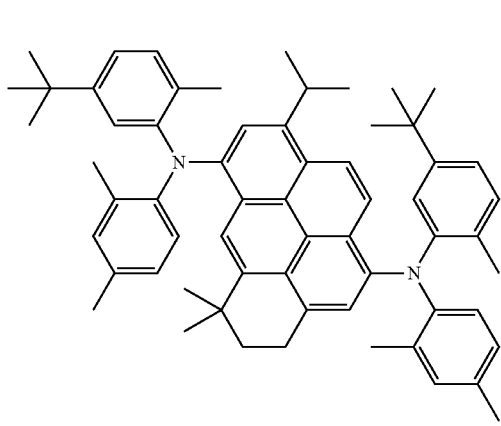
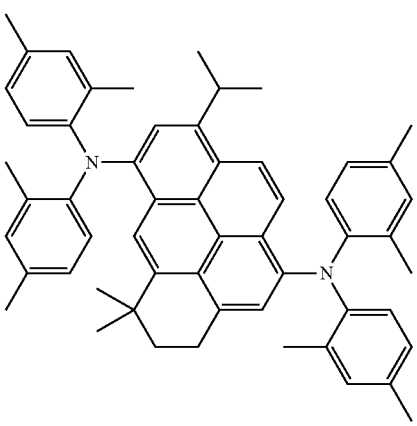
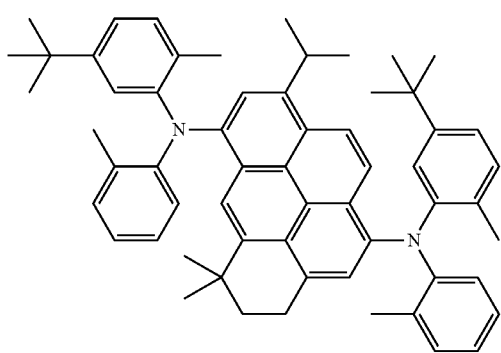
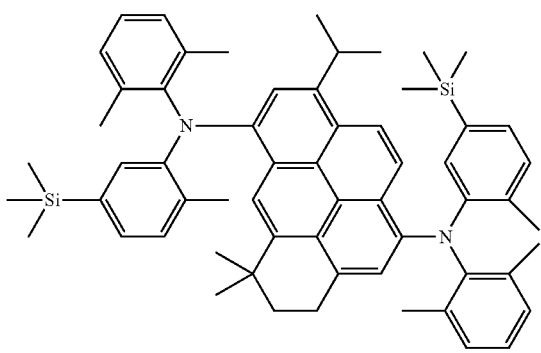
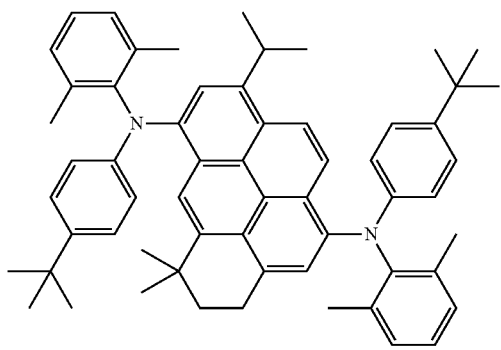

-continued
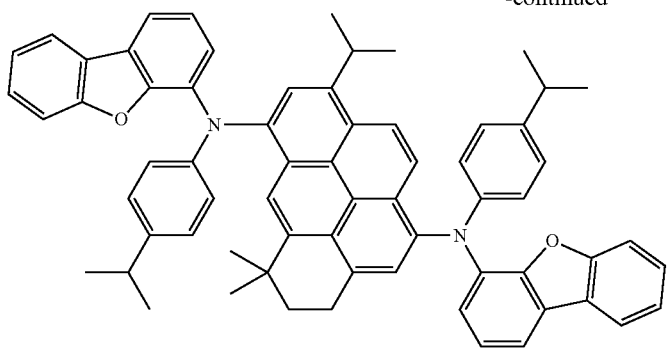
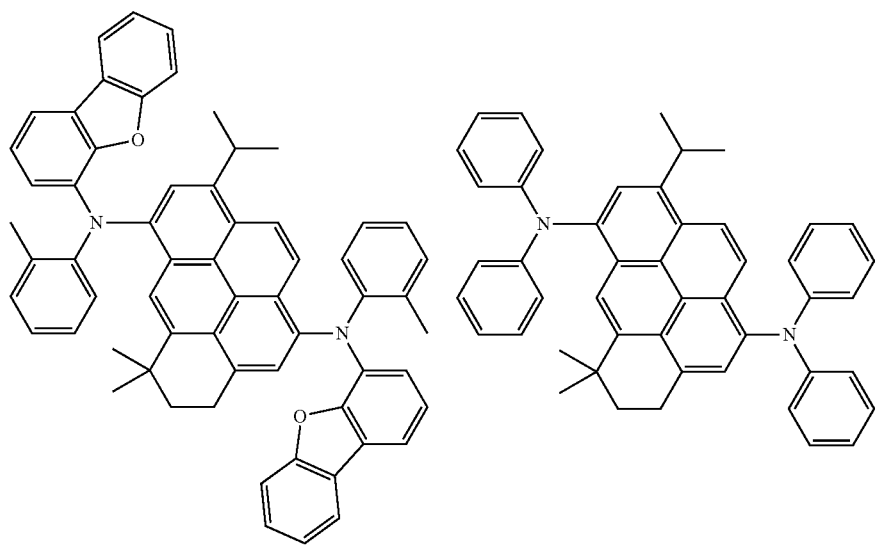
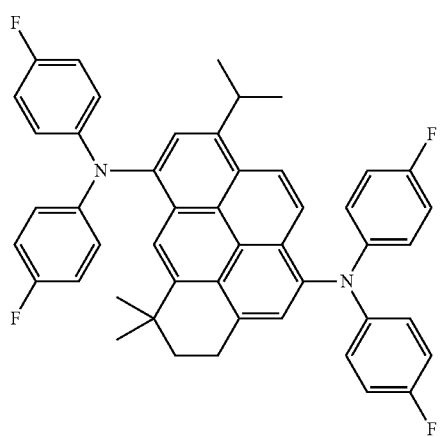
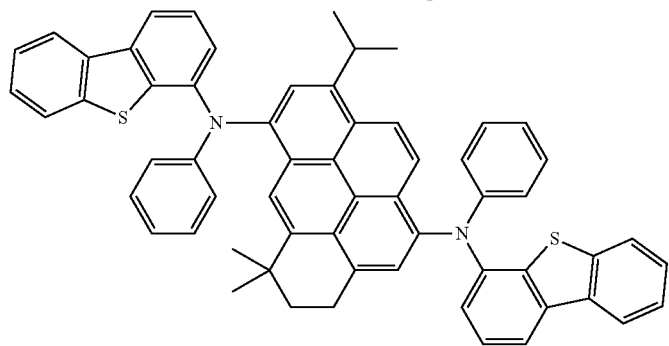

-continued
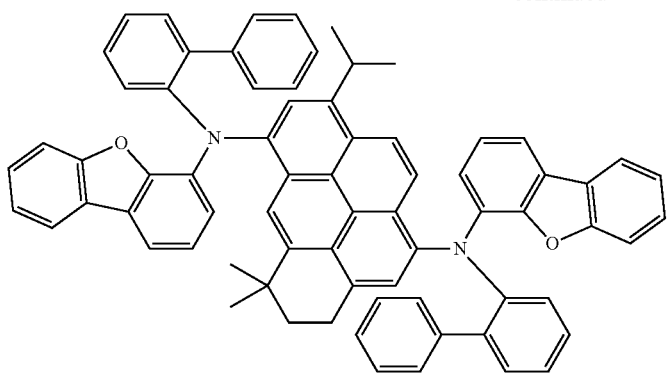
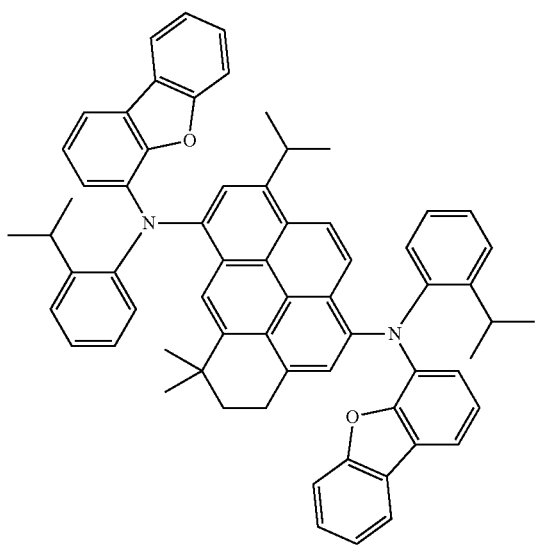
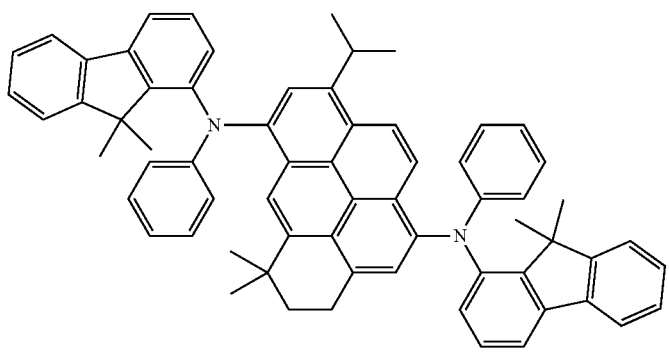
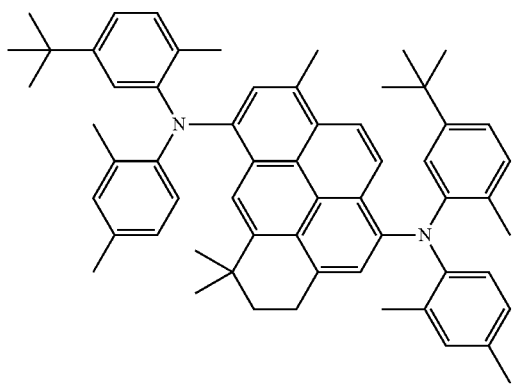

-continued
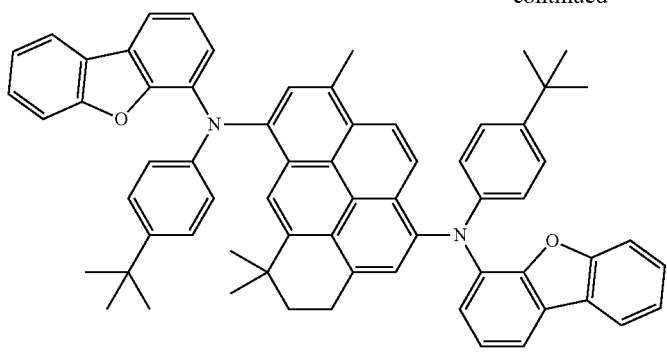
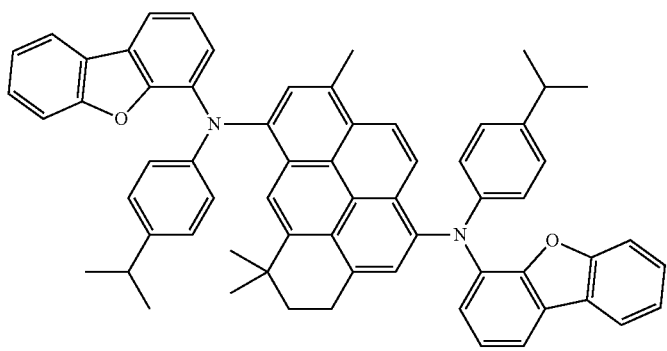
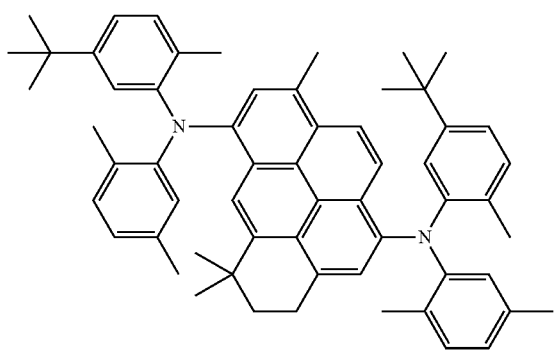
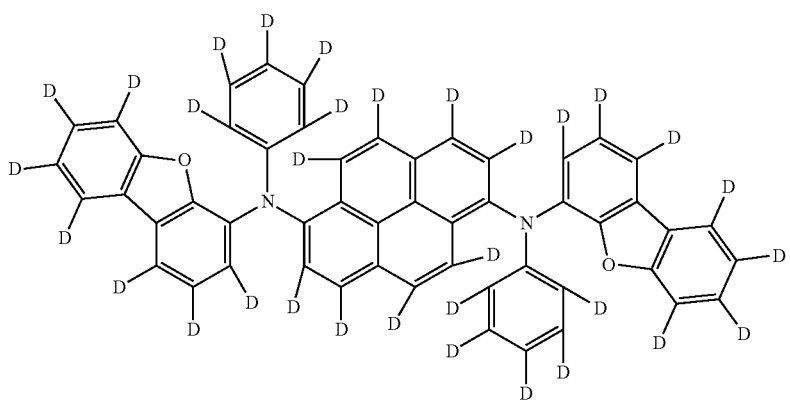

-continued

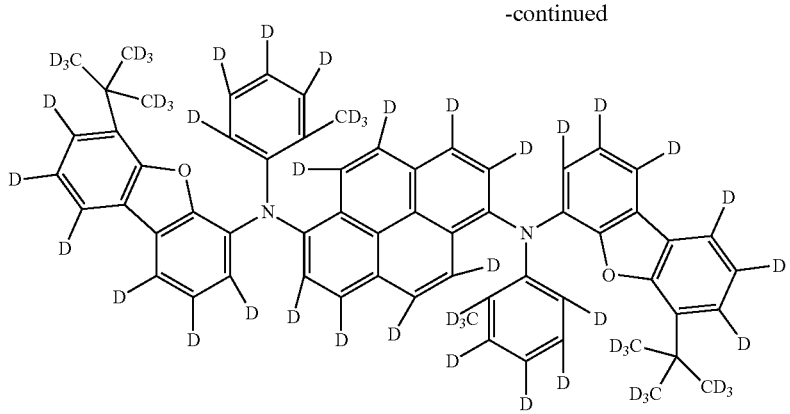

(Compound Represented by Formula (21))
The compound represented by the formula (21) is explained below.

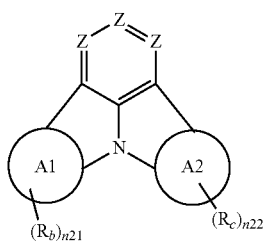

(21)

In the formula (21),
Zs are independently $CR_a$ or N;
A1 ring and A2 ring are independently a substituted or unsubstituted aromatic hydrocarbon ring including 6 to 50 ring carbon atoms, or a substituted or unsubstituted heterocyclic ring including 5 to 50 ring atoms;
when plural $R_a$s exist, one or more pairs of two or more adjacent groups of $R_a$ are bonded with each other to form a substituted or unsubstituted, saturated or unsaturated ring, or do not form a substituted or unsubstituted, saturated or unsaturated ring;
when plural $R_b$s exist, one or more pairs of two or more adjacent groups of $R_b$ are bonded with each other to form a substituted or unsubstituted, saturated or unsaturated ring, or do not form a substituted or unsubstituted, saturated or unsaturated ring;
when plural $R_c$s exist, one or more pairs of two or more adjacent groups of $R_c$ are bonded with each other to form a substituted or unsubstituted, saturated or unsaturated ring, or do not form a substituted or unsubstituted, saturated or unsaturated ring;
n21 and n22 are independently an integer of 0 to 4;
$R_a$ to $R_c$ that do not form the substituted or unsubstituted, saturated or unsaturated ring are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms, —$Si(R_{901})(R_{902})(R_{903})$,
—$O$—$(R_{904})$,
—$S$—$(R_{905})$,
—$N(R_{906})(R_{907})$,
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are as defined in the formula (1).
The "aromatic hydrocarbon ring" of A1 ring and A2 ring has the same structure as the compound obtained by introducing a hydrogen atom into the "aryl group" described above. The "aromatic hydrocarbon ring" of the A1 ring and the A2 ring contains two carbon atoms in the fused bicyclic structure at the center of the formula (21) as ring atoms. Examples of "substituted or unsubstituted aromatic hydrocarbon ring including 6 to 50 ring carbon atoms" include compounds in which a hydrogen atom is introduced into the "aryl group" described in the example group G1.
The "heterocyclic ring" of A1 ring and A2 ring has the same structure as the compound obtained by introducing a hydrogen atom into the "heterocyclic group" described above. The "heterocyclic ring" of the A1 ring and the A2 ring contains two carbon atoms in the fused bicyclic structure at the center of the formula (21) as ring atoms. Examples of "substituted or unsubstituted heterocyclic ring including 5 to 50 ring atoms" include compounds in which a hydrogen atom is introduced into the "heterocyclic group" described in the example group G2.
$R_b$ is bonded to one of carbon atoms which form the aromatic hydrocarbon ring of A1 ring, or one of atoms which form the heterocycle of A1 ring.
$R_c$ is bonded to one of carbon atoms which form the aromatic hydrocarbon ring of A2 ring, or one of atoms which form the heterocycle of A2 ring.
It is preferable that at least one (preferably two) of $R_a$ to $R_c$ is a group represented by the following formula (21a).

-$L_{201}$-$Ar_{201}$ (21a)

In the formula (21a),
$L_{201}$ is
a single bond,
a substituted or unsubstituted arylene group including 6 to 30 ring carbon atoms, or
a substituted or unsubstituted bivalent heterocyclic group including 5 to 30 ring atoms;

$Ar_{201}$ is
a substituted or unsubstituted arylene group including 6 to 50 ring carbon atoms,
a substituted or unsubstituted monovalent heterocyclic group including 5 to 50 ring atoms, or
a group represented by the following formula (21b):

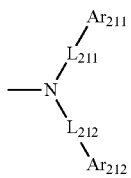

(21b)

In the formula (21b),
$L_{211}$ and $L_{212}$ are independently
a single bond,
a substituted or unsubstituted arylene group including 6 to 30 ring carbon atoms, or
a substituted or unsubstituted divalent heterocyclic group including 5 to 30 ring atoms;
$Ar_{211}$ and $Ar_{212}$ are bonded with each other to form a substituted or unsubstituted, saturated or unsaturated ring, or do not form a substituted or unsubstituted, saturated or unsaturated ring; and
$Ar_{211}$ and $Ar_{212}$ that do not form a substituted or unsubstituted, saturated or unsaturated ring are independently
a substituted or unsubstituted aryl group including 6 to 50 ring carbon atoms or
a substituted or unsubstituted monovalent heterocyclic group including 5 to 50 ring atoms.

In one embodiment, the compound represented by the formula (21) is represented by the following formula (22).

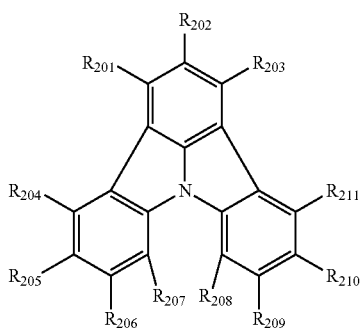

(22)

In the formula (22),
one or more pairs of two or more adjacent groups of $R_{201}$ to $R_{211}$ are bonded with each other to form a substituted or unsubstituted, saturated or unsaturated ring, or do not form a substituted or unsubstituted saturated or unsaturated ring;
$R_{201}$ to $R_{211}$ that do not form the substituted or unsubstituted, saturated or unsaturated ring are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms, —$Si(R_{901})(R_{902})(R_{903})$,
—$O$—$(R_{904})$,
—$S$—$(R_{905})$,
—$N(R_{906})(R_{907})$,
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms; and
$R_{901}$ to $R_{907}$ are as defined in the formula (1).

It is preferable that at least one (preferably two) of $R_{201}$ to $R_{211}$ is the group represented by the formula (21a). It is preferable that $R_{204}$ and $R_{211}$ are the group represented by the formula (21a).

In one embodiment, the compound represented by the formula (21) is a compound obtained by bonding the structure represented by the following formula (21-1) or (21-2) to A1 ring. In one embodiment, the compound represented by the formula (22) is a compound obtained by bonding the structure represented by the following formula (21-1) or (21-2) to the ring to which $R_{204}$ to $R_{207}$ bonds to.

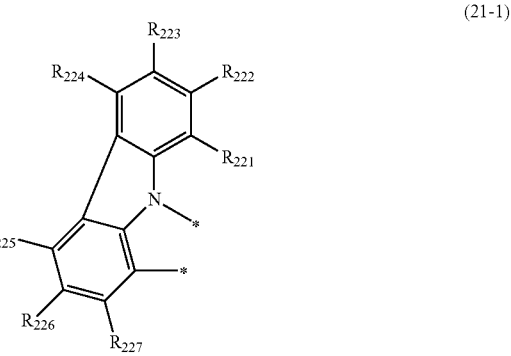

(21-1)

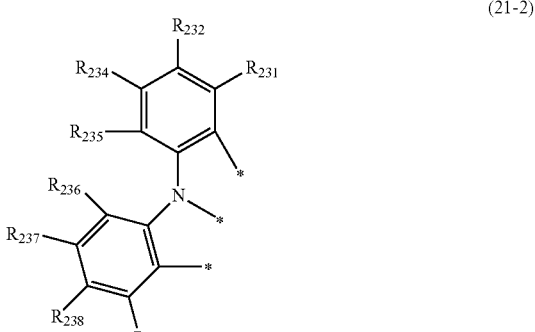

(21-2)

In the formula (21-1), two *'s independently bond to a ring carbon atom in the aromatic hydrocarbon ring or a ring atom in the heterocyclic group in A1 ring in the formula (21), or bond to one of $R_{204}$ to $R_{207}$ in the formula (22);

In the formula (21-2), three *'s independently bond to a ring carbon atom in the aromatic hydrocarbon ring or a ring atom in the heterocyclic group in A1 ring in the formula (21), or bond to one of $R_{204}$ to $R_{207}$ in the formula (22);

One or more pairs of two or more adjacent groups of $R_{221}$ to $R_{227}$ and $R_{231}$ to $R_{239}$ are bonded with each other to form a substituted or unsubstituted, saturated or unsaturated ring, or do not form a substituted or unsubstituted, saturated or unsaturated ring;

$R_{221}$ to $R_{227}$ and $R_{231}$ to $R_{239}$ that do not form the substituted or unsubstituted, saturated or unsaturated ring are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms; and $R_{901}$ to $R_{907}$ are as defined in the formula (1).

In one embodiment, the compound represented by the formula (21) is a compound represented by the following formula (21-3), (21-4), or (21-5).

(21-3)

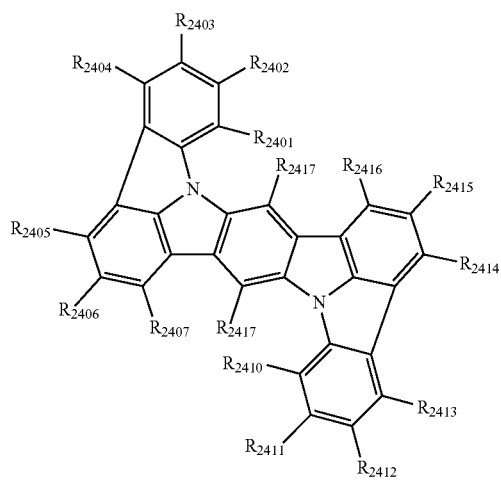

(21-4)

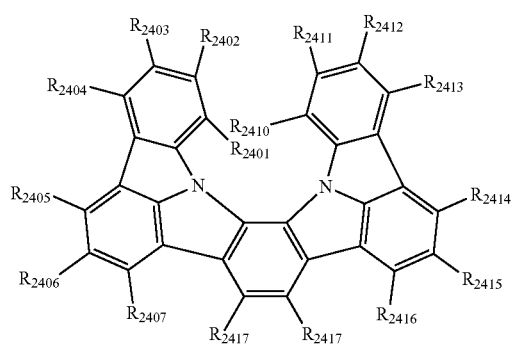

(21-5)

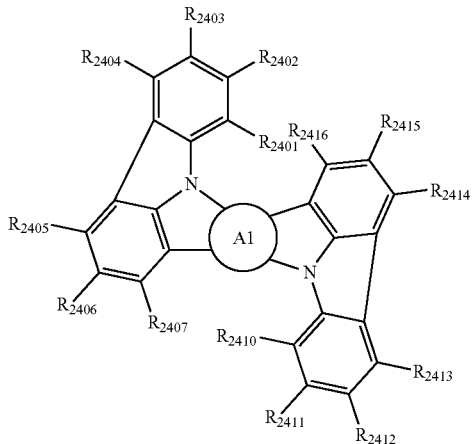

In the formulas (21-3), (21-4) and (21-5),

A1 ring is as defined in the formula (21);

$R_{2401}$ to $R_{2407}$ are the same as $R_{221}$ to $R_{227}$ in the formulas (21-1) and (21-2); and $R_{2410}$ to $R_{2417}$ are the same as $R_{211}$ to $R_{211}$ in the formula (22).

In one embodiment, the substituted or unsubstituted aromatic hydrocarbon ring including 6 to 50 ring carbon atoms of A1 ring in the formula (21-5) is a substituted or unsubstituted napthalene ring, or a substituted or unsubstituted fluorene ring.

In one embodiment, the substituted or unsubstituted heterocycle including 5 to 50 ring atoms of A1 ring in the formula (21-5) is a substituted or unsubstituted dibenzofuran ring, a substituted or unsubstituted carbazole ring, or a substituted or unsubstituted dibenzothiophene ring.

In one embodiment, the compound represented by the formula (21) or (22) is selected from the group consisting of the compounds represented by the following formulas (21-6-1) to (21-6-7).

(21-6-1)

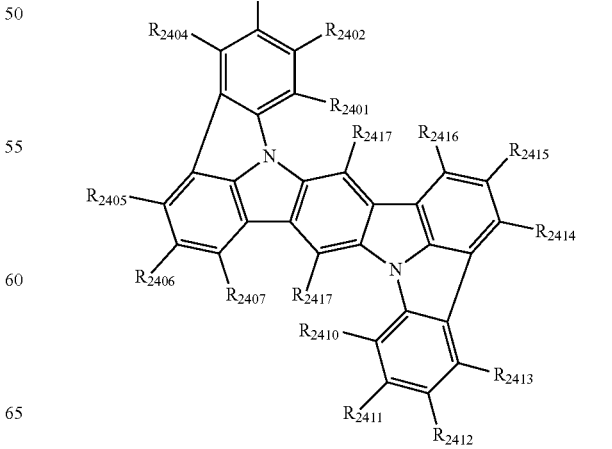

(21-6-2)
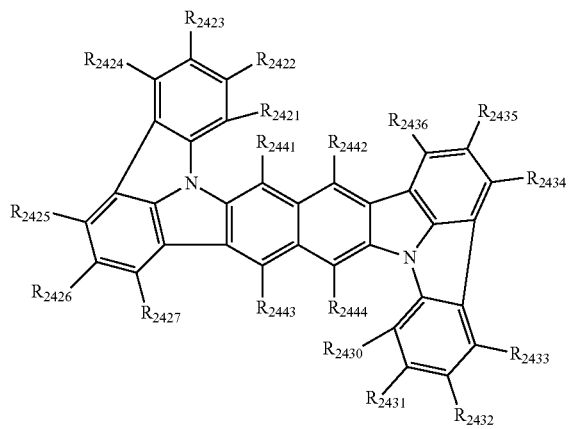

(21-6-3)

(21-6-4)
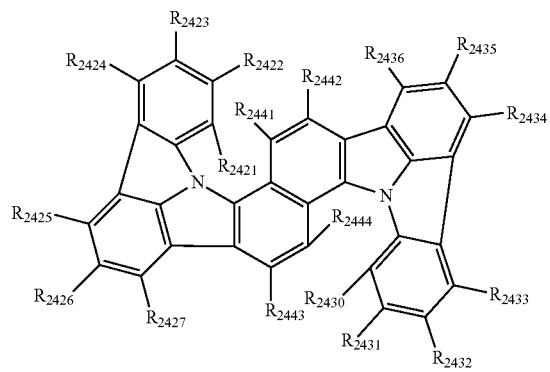

(21-6-5)
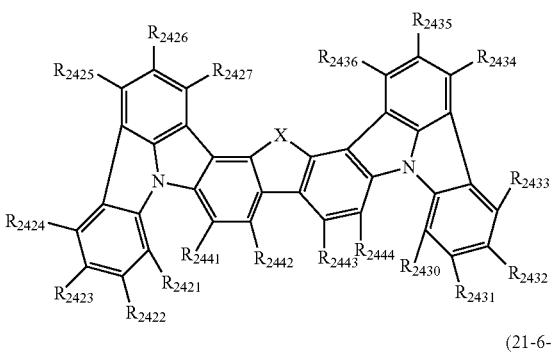

(21-6-6)
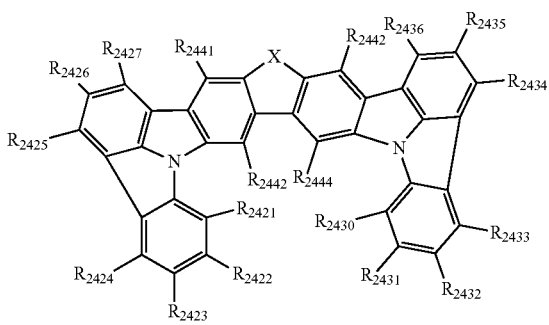

(21-6-7)
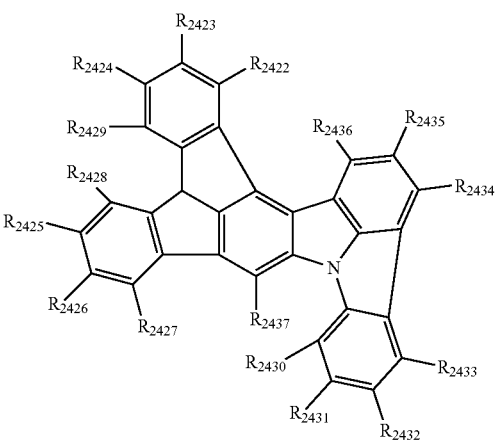

In the formulas (21-6-1) to (21-6-7), $R_{2421}$ to $R_{2427}$ are the same as $R_{221}$ to $R_{227}$ in the formulas (21-1) and (21-2);

$R_{2430}$ to $R_{2437}$ and $R_{2441}$ to $R_{2444}$ are the same as $R_{201}$ to $R_{211}$ in the formula (22);

X is O, $NR_{901}$, or $C(R_{902})(R_{903})$; and $R_{901}$ to $R_{903}$ are as defined in the formula (1).

In one embodiment, in the compound represented by the formula (22), one or more pairs of two or more adjacent groups of $R_{201}$ to $R_{211}$ are bonded with each other to form a substituted or unsubstituted, saturated or unsaturated ring. This embodiment is described in the following formula (25).

(Compound Represented by Formula (25))

The compound represented by the formula (25) is explained below.

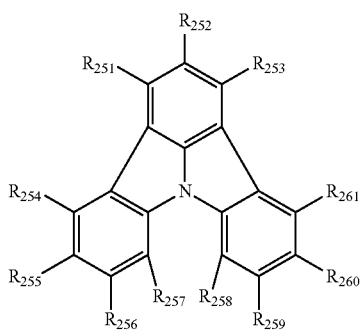

(25)

In the formula (25), two or more pairs selected from a group consisting of $R_{251}$ and $R_{252}$, $R_{252}$ and $R_{253}$, $R_{254}$ and $R_{255}$, $R_{255}$ and $R_{256}$, $R_{256}$ and $R_{257}$, $R_{258}$ and $R_{259}$, $R_{259}$ and $R_{260}$ and $R_{260}$ and $R_{261}$ bond with each other to form a substituted or unsubstituted, saturated or unsaturated ring;

Provided that the pair of $R_{251}$ and $R_{252}$ and the pair of $R_{252}$ and $R_{253}$ do not form a ring simultaneously; the pair of $R_{254}$ and $R_{255}$ and the pair of $R_{255}$ and $R_{256}$ do not form a ring simultaneously; the pair of $R_{255}$ and $R_{256}$ and the pair of $R_{256}$ and $R_{257}$ do not form a ring simultaneously; the pair of $R_{258}$ and $R_{259}$ and the pair of $R_{259}$ and $R_{260}$ do not form a ring simultaneously; and the pair of $R_{259}$ and $R_{260}$ and the pair of $R_{260}$ and $R_{261}$ do not form a ring simultaneously;

when two or more rings are formed by $R_{251}$ to $R_{261}$, the rings may be the same or different;

$R_{251}$ to $R_{261}$ that do not form the substituted or unsubstituted, saturated or unsaturated ring are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms, or
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms; and $R_{901}$ to $R_{907}$ are as defined in the formula (1).

In the formula (25), $R_n$ and $R_{n+1}$ (n is an integer selected from 251, 252, 254 to 256 and 258 to 260) bond with each other to form a substituted or unsubstituted, saturated or unsaturated ring together with two ring carbon atoms to which $R_n$ and $R_{n+1}$ bond with. The ring is preferably configured with atoms selected from C atom, O atom, S atom and N atom, and the number of atoms is preferably 3 to 7, more preferably 5 or 6.

The number of the above-described ring structures in the compound represented by the formula (25) is, for example, 2, 3 or 4. Two or more ring structures may exist in the same benzene ring of the main skeleton in the formula (25), or may exist in different benzene rings. For example, the compound has three ring structures, one ring structure may exist in each of the three benzene rings in the formula (25).

As the above-mentioned ring structure in the compound represented by the formula (25), structures represented by the following formulas (251) to (260) can be given, for example.

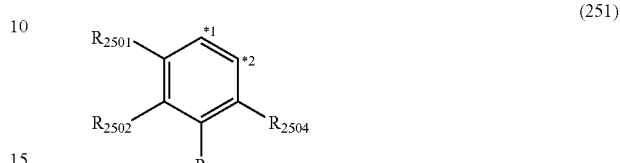

(251)

(252)

(253)

(254)

(255)

(256)

(257)

In the formulas (251) to (257), each of *1 and *2, *3 and *4, *5 and *6, *7 and *8, *9 and *10, *11 and *12, and *13 and *14 represents two ring carbon atoms to which $R_n$ and $R_{n+1}$ bond, and $R_n$ may bond to either one of the two ring carbon atoms of *1 and *2, *3 and *4, *5 and *6, *7 and *8, *9 and *10, *11 and *12, and *13 and *14;

$X_{2501}$ is C($R_{2512}$)($R_{2513}$), N$R_{2514}$, O or S;

One or more pairs of two or more adjacent groups of $R_{2501}$ to $R_{2506}$ and $R_{2512}$ to $R_{2513}$ are bonded with each other to form a substituted or unsubstituted, saturated or unsaturated ring, or do not form a substituted or unsubstituted saturated or unsaturated ring; and $R_{2501}$ to $R_{2514}$ that do not form a substituted or unsubstituted saturated or unsaturated ring are the same as $R_{251}$ to $R_{261}$.

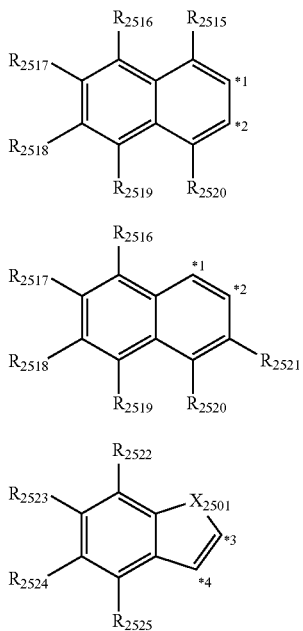

(258)

(259)

(260)

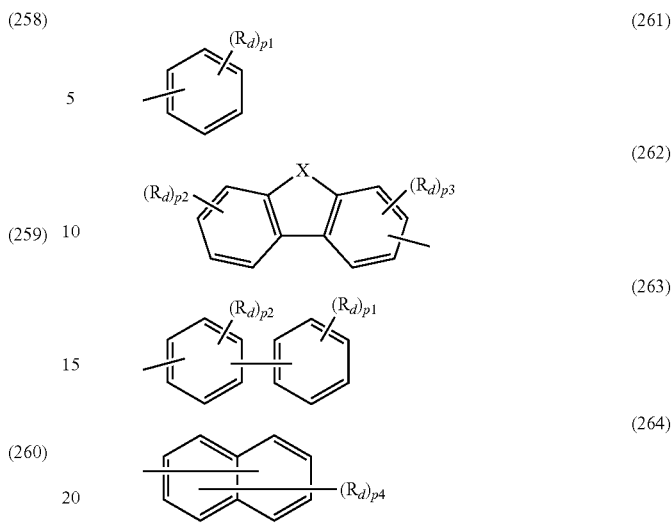

(261)

(262)

(263)

(264)

In the formulas (258) to (260),
each of *1 and *2, and *3 and *4 represents two ring carbon atoms to which $R_n$ and $R_{n+1}$ bond, and $R_n$ may bond to either one of the two ring carbon atoms of *1 and*2, or *3 and*4;

$X_{2501}$ is $C(R_{2512})(R_{2513})$, $NR_{2514}$, O or S;

One or more pairs of two or more adjacent groups of $R_{2515}$ to $R_{2525}$ bond to each other to form a substituted or unsubstituted, saturated or unsaturated ring, or do not form a substituted or unsubstituted saturated or unsaturated ring; and $R_{2515}$ to $R_{2521}$ and $R_{2522}$ to $R_{2525}$ that do not form a substituted or unsubstituted saturated or unsaturated ring are the same as $R_{251}$ to $R_{261}$.

In the formula (25), it is preferable that at least one of $R_{252}$, $R_{254}$, $R_{255}$, $R_{260}$ and $R_{261}$ (preferably at least one of $R_{252}$, $R_{255}$, and $R_{260}$, more preferably $R_{252}$) is a group which does not form a ring.

(i) Substituent in the case where the ring structure formed by $R_n$ and $R_{n+1}$ has a substituent in the formula (25),
(ii) $R_{251}$ to $R_{261}$ that do not form a ring structure in the formula (25), and
(iii) $R_{2501}$ to $R_{2514}$ and $R_{2515}$ to $R_{2525}$ in the formulas (251) to (260)

are preferably independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—$N(R_{906})(R_{907})$,
a substituted or unsubstituted aryl group including 6 to 50 ring carbon atoms,
a substituted or unsubstituted monovalent heterocyclic group including 5 to 50 ring atoms, or
a group selected from the following groups.

In the formulas (261) to (264),
$R_d$s are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—$Si(R_{901})(R_{902})(R_{903})$,
—O—$(R_{904})$,
—S—$(R_{905})$,
—$N(R_{906})(R_{907})$,
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;

X is $C(R_{901})(R_{902})$, $NR_{903}$, O, or S;
$R_{901}$ to $R_{907}$ are as defined in the formula (1); and
p1 is independently an integer of 0 to 5, $p^2$ is independently an integer of 0 to 4, p3 is an integer of 0 to 3, and p4 is an integer of 0 to 7.

In one embodiment, the compound represented by the formula (25) is represented by the following formulas (25-1) to (25-6).

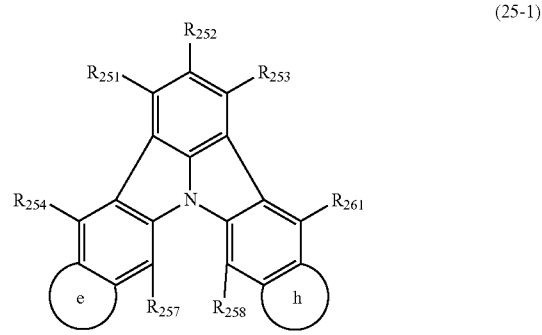

(25-1)

(25-2)
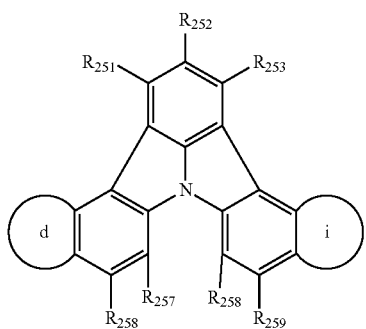
(25-3)
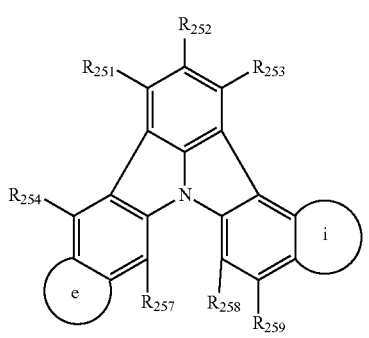
(25-4)
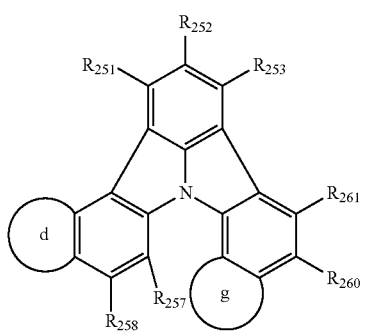
(25-5)
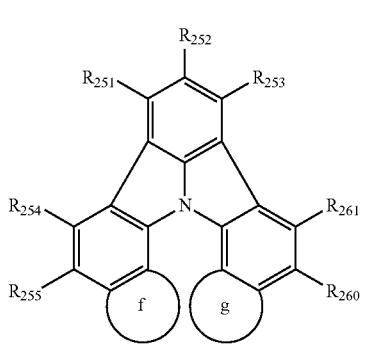
(25-6)
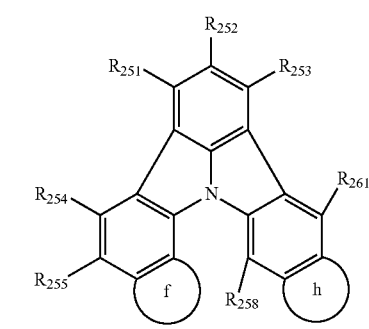
In the formulas (25-1) to (25-6), ring d to ring i are independently a substituted or unsubstituted, saturated or unsaturated ring; and $R_{251}$ to $R_{261}$ are the same as defined in the formula (25).
In one embodiment, the compound represented by the formula (25) is represented by the following formulas (25-7) to (25-12).
(25-7)
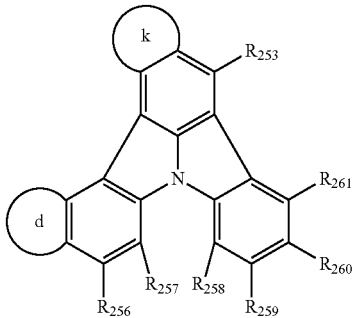
(25-8)
(25-9)

(25-10)
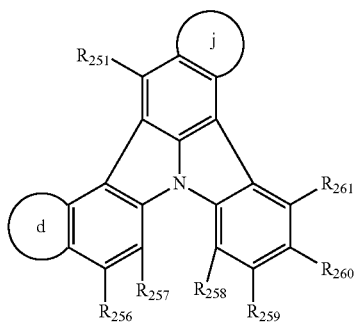
(25-11)
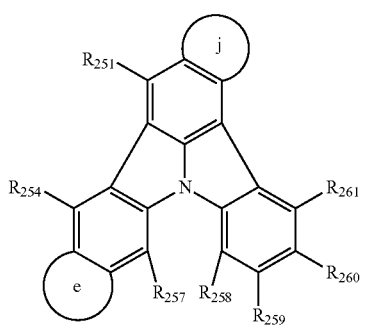
(25-12)
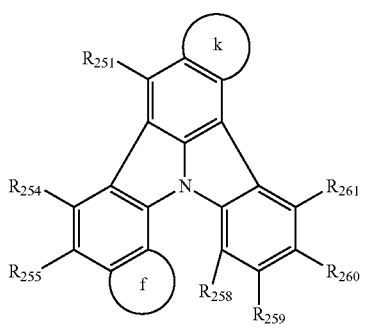
In the formulas (25-7) to (25-12), ring d to ring f, ring k, and ring j are independently a substituted or unsubstituted, saturated or unsaturated ring; and $R_{251}$ to $R_{261}$ are the same as defined in the formula (25).
In one embodiment, the compound represented by the formula (25) is represented by the following formulas (25-13) to (25-21).
(25-13)
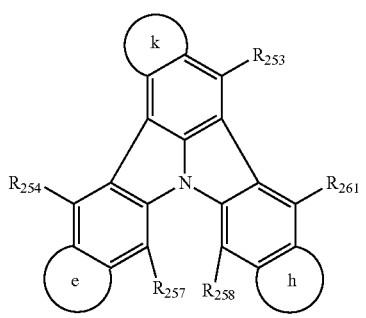
(25-14)
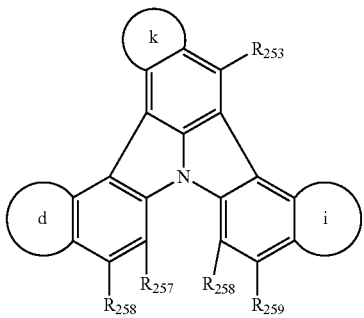
(25-15)
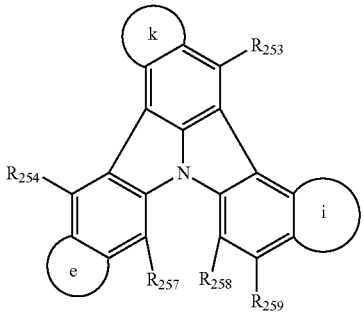
(25-16)
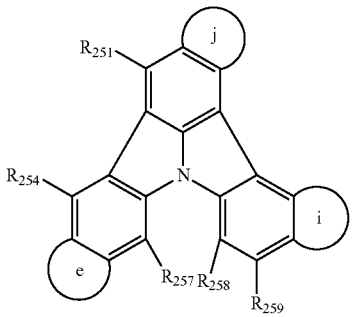
(25-17)
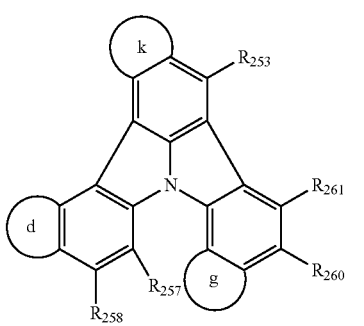
(25-18)
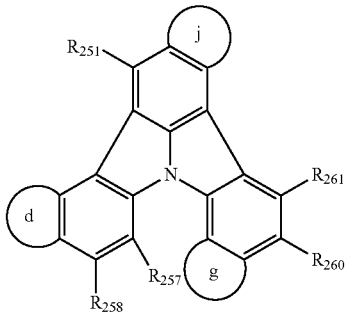

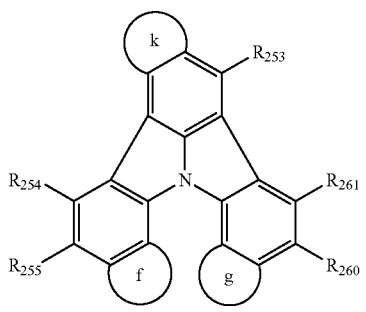

(25-19)

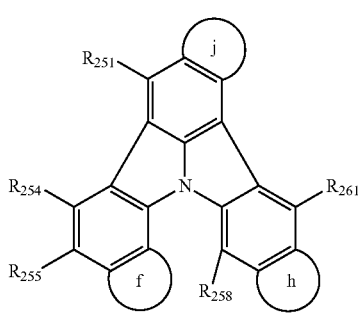

(25-20)

(25-21)

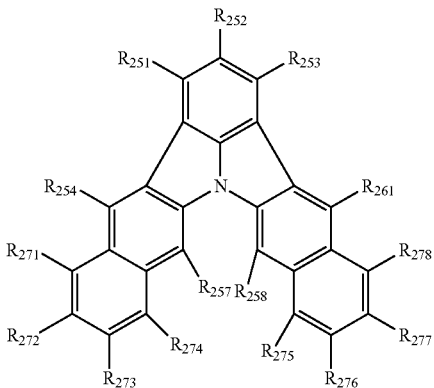

(25-22)

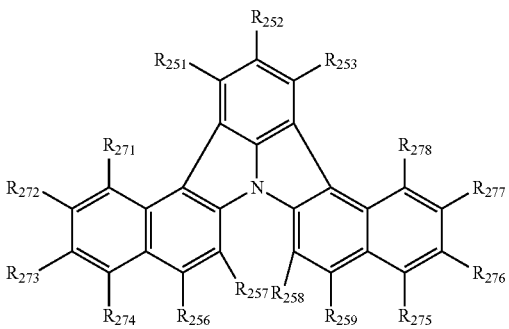

(25-23)

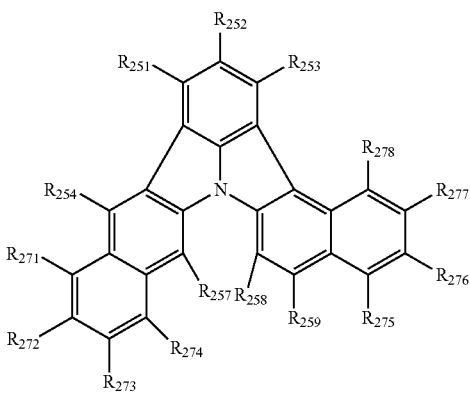

(25-24)

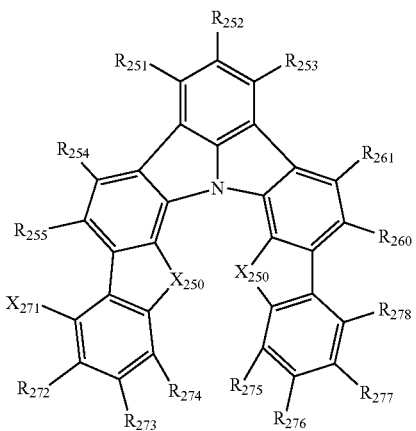

(25-25)

In the formulas (25-13) to (25-21), ring d to ring k are independently a substituted or unsubstituted, saturated or unsaturated ring; and $R_{251}$ to $R_{261}$ are the same as defined in the formula (25).

As a substituent in the case where the ring g or ring h further has a substituent,

- a substituted or unsubstituted alkyl group including 1 to 50 carbon atoms,
- a substituted or unsubstituted aryl group including 6 to 50 ring carbon atoms, or
- a group represented by the formula (261), (263) or (264) can be given for example.

In one embodiment, the compound represented by the formula (25) is represented by one of the following formulas (25-22) to (25-25).

In the formulas (25-22) to (25-25), $X_{250}$ is independently $C(R_{901})(R_{902})$, $NR_{903}$, O or S; $R_{251}$ to $R_{261}$, and $R_{271}$ to $R_{273}$ are the same as $R_{251}$ to $R_{261}$ in the formula (25); and $R_{901}$ to $R_{903}$ are as defined in the formula (1).

In one embodiment, the compound represented by the formula (25) is represented by the following formula (25-26).

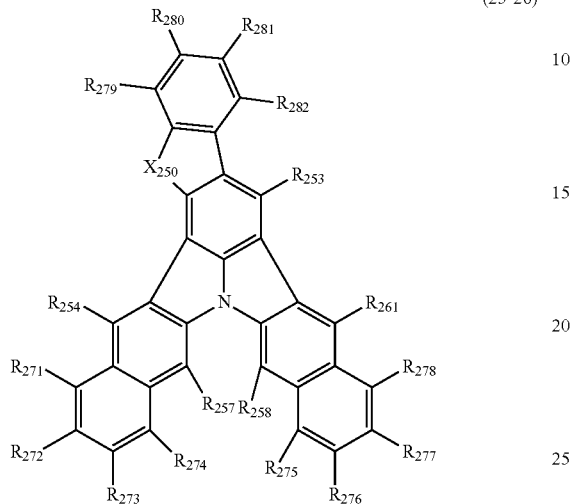

(25-26)

In the formula (25-26), $X_{250}$ are independently $C(R_{901})(R_{902})$, $NR_{903}$, O or S; $R_{253}$, $R_{254}$, $R_{257}$, $R_{258}$, $R_{261}$, and $R_{271}$ to $R_{282}$ are the same as $R_{251}$ to $R_{261}$ in the formula (25); and $R_{901}$ to $R_{903}$ are as defined in the formula (1).

As the compound represented by the formula (21), the following compounds can be shown for example. In the following example compounds, Me represents methyl group.

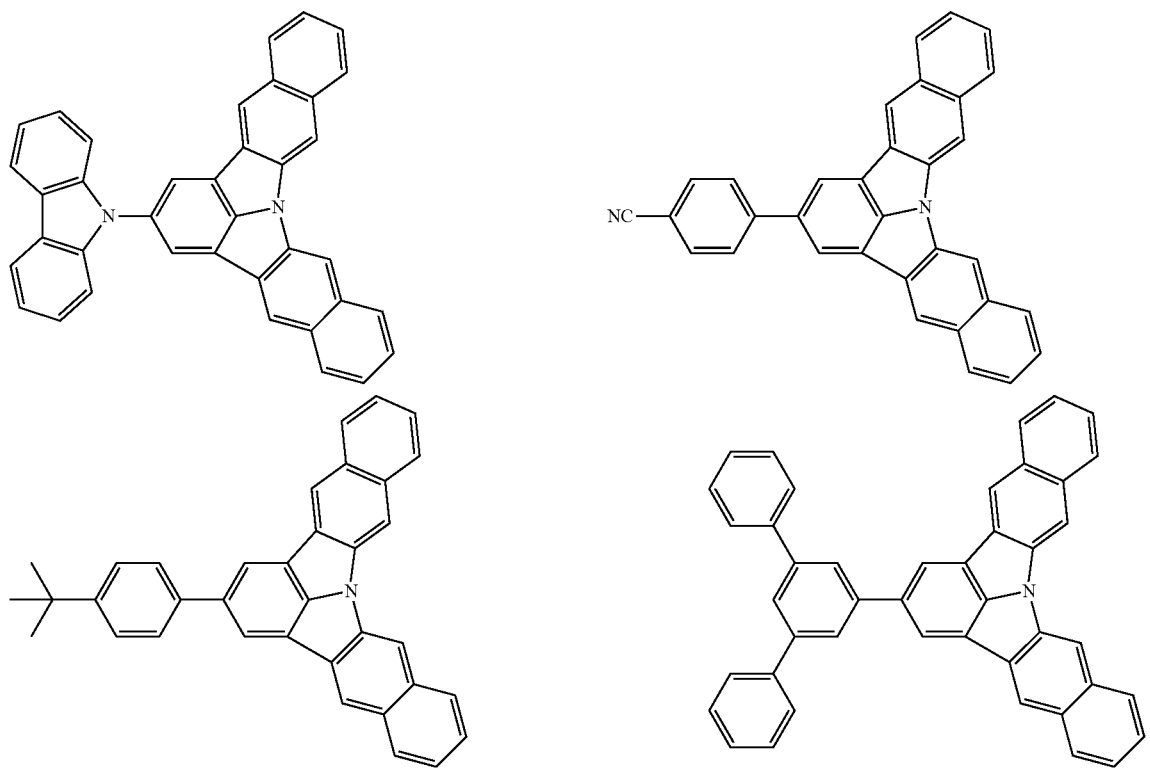

-continued
153
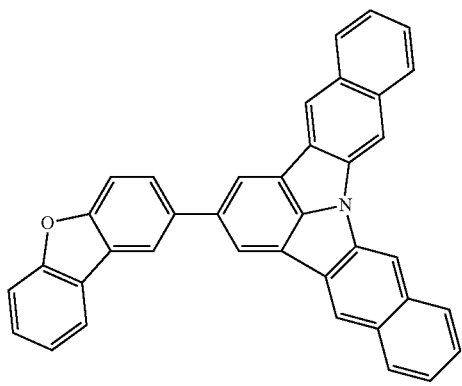
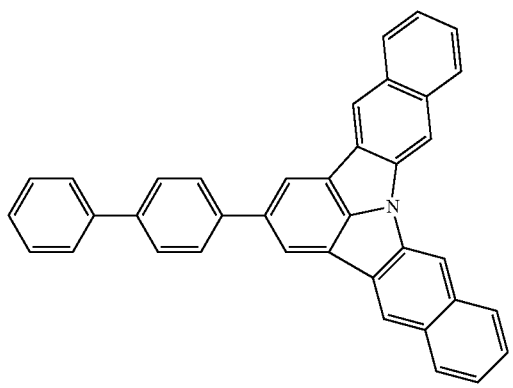
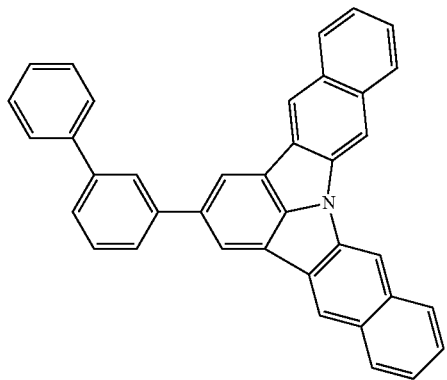
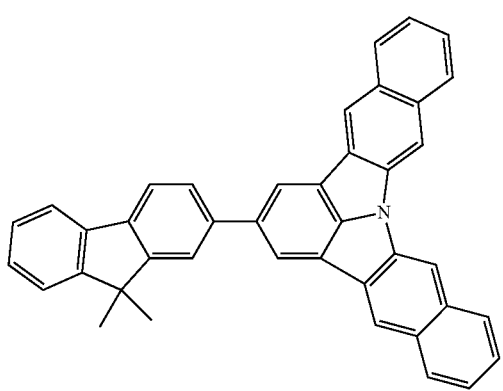
154
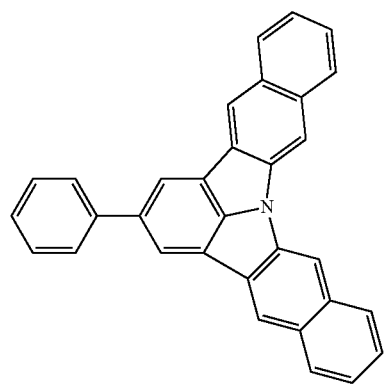
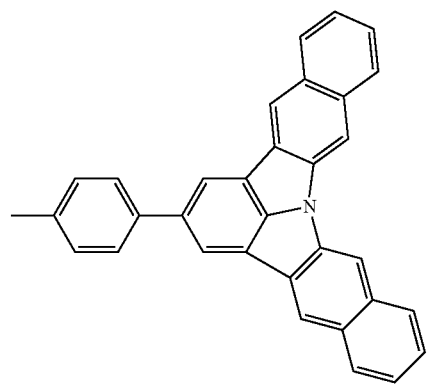
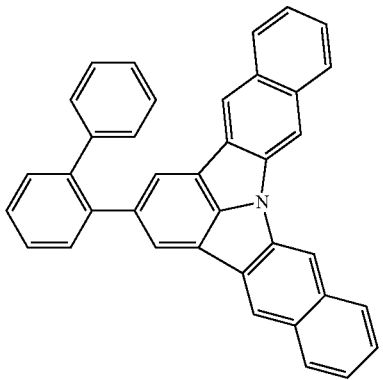
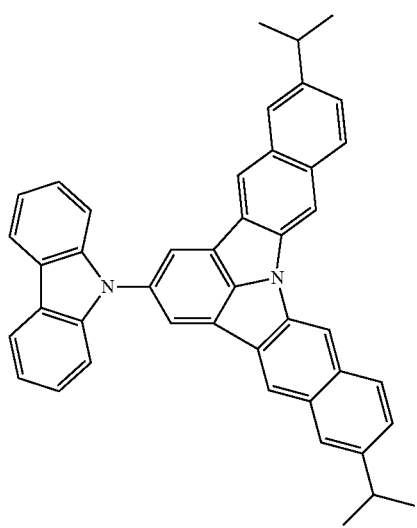

-continued
155
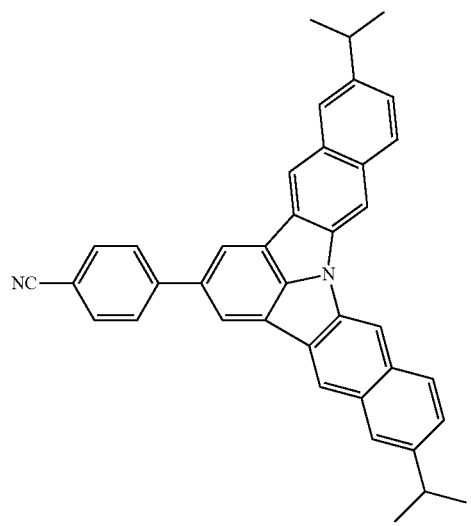
156
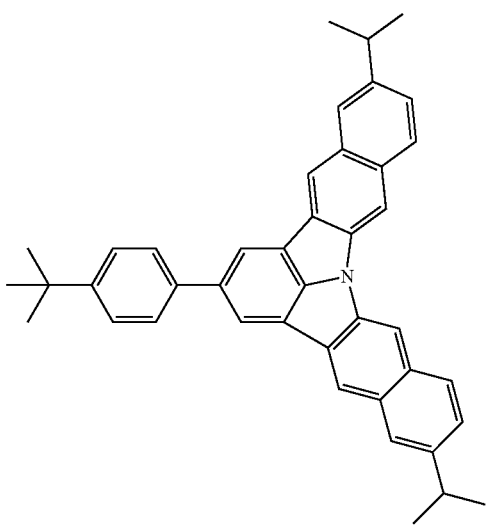
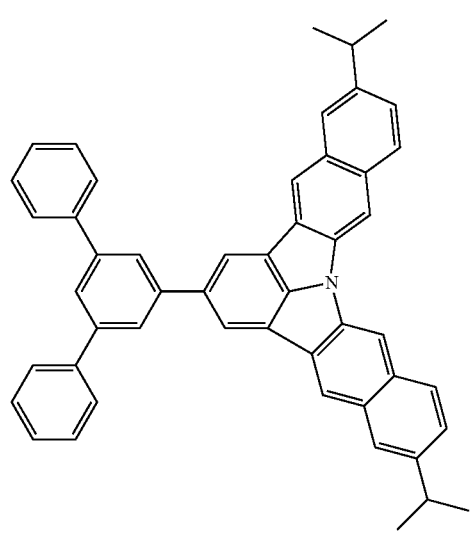
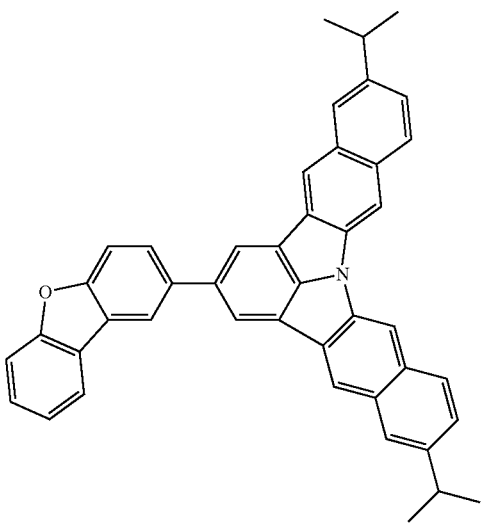
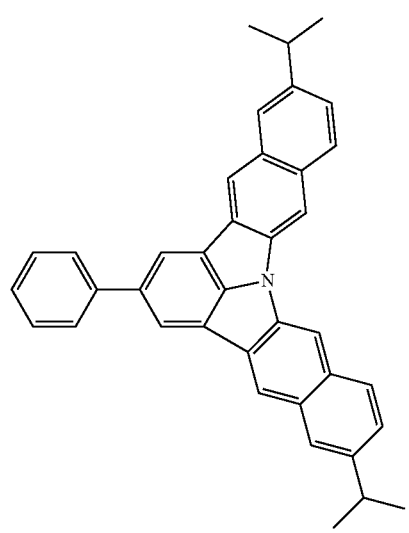
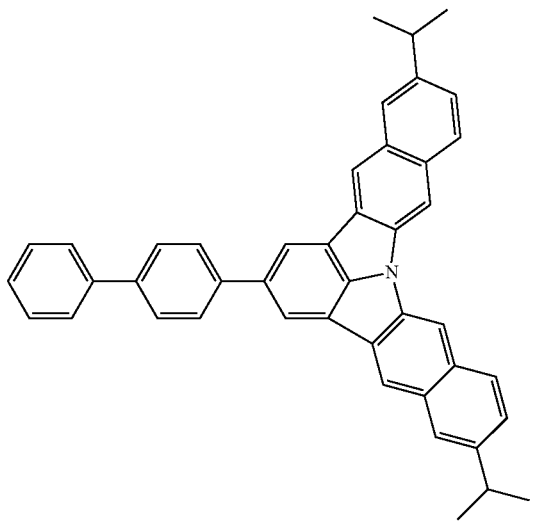

-continued
157 158
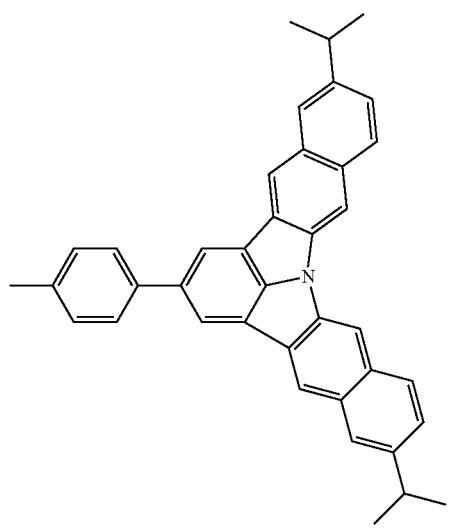
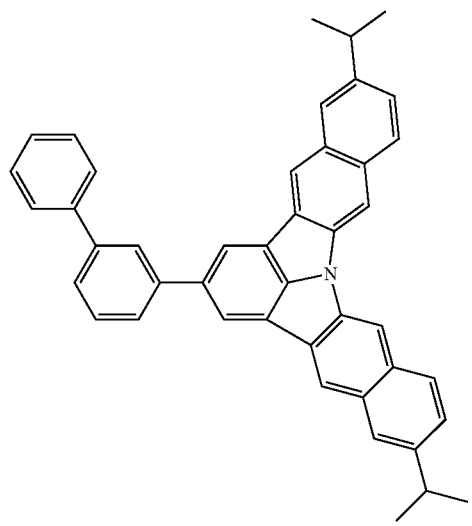
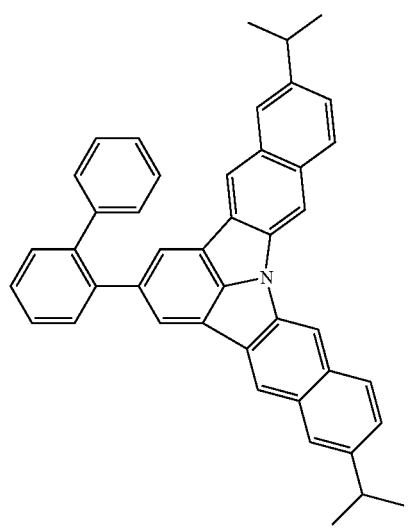
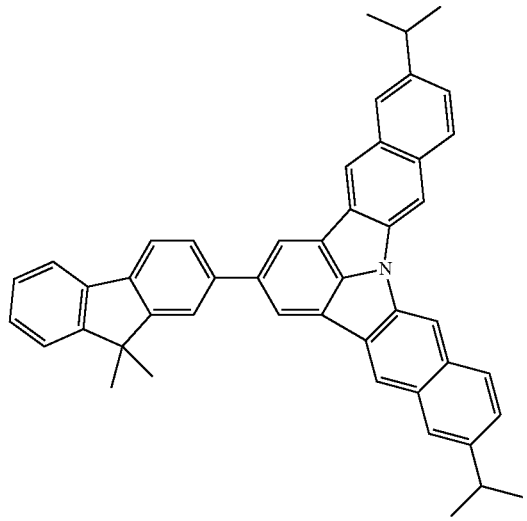
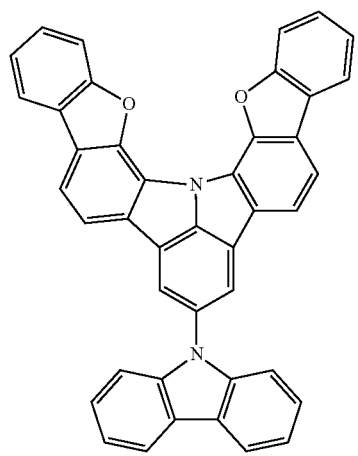
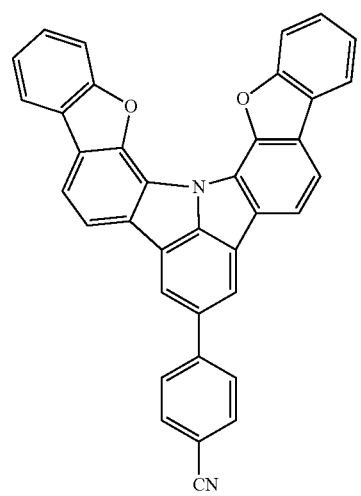
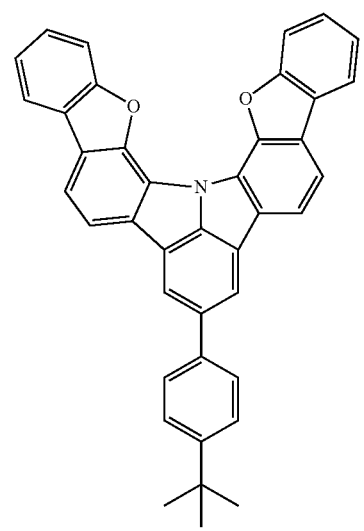

159
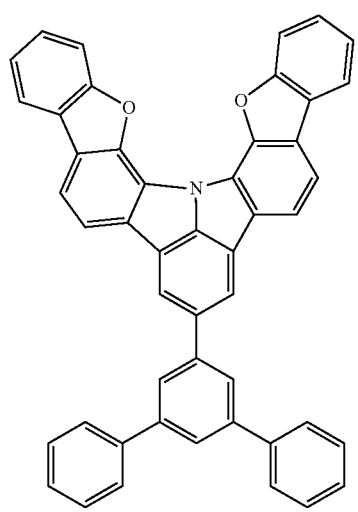
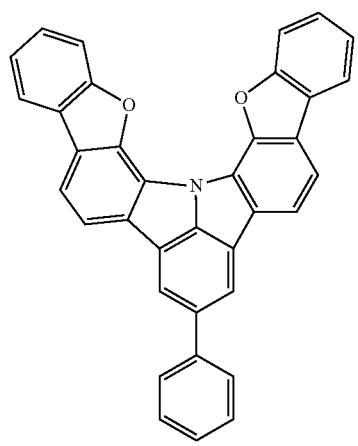
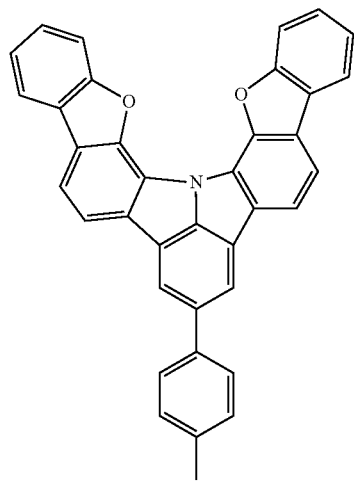
160
-continued
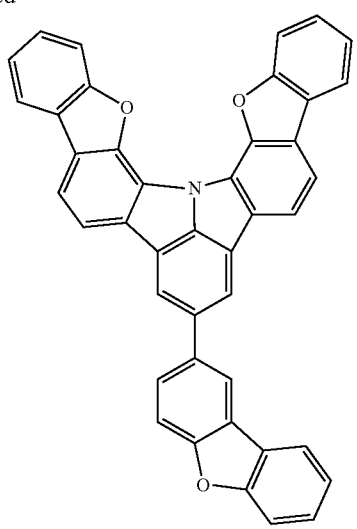
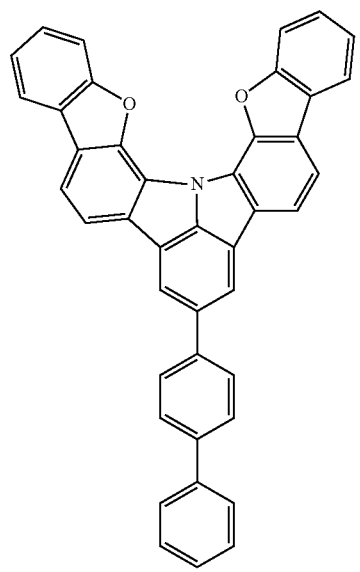
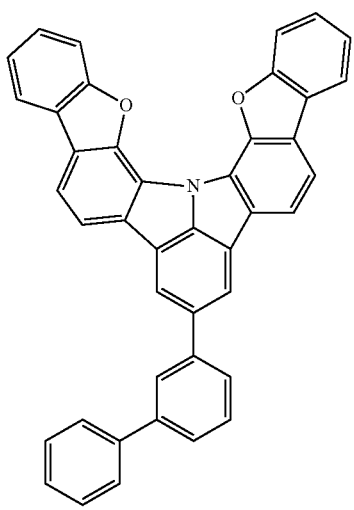

-continued
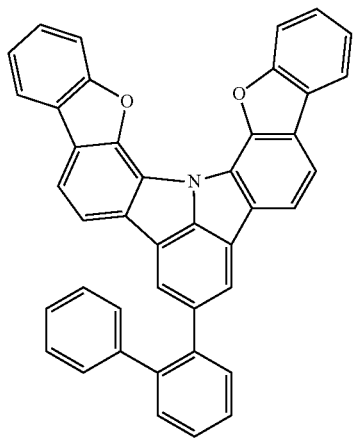
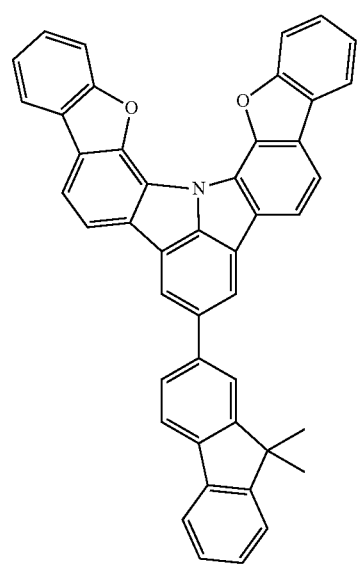
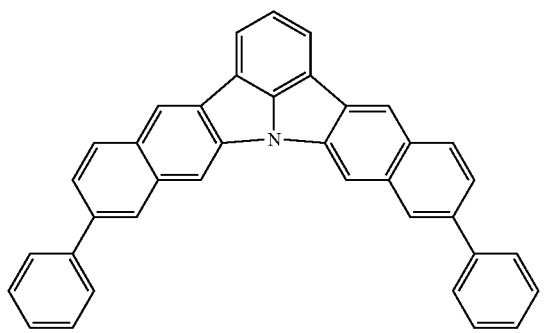
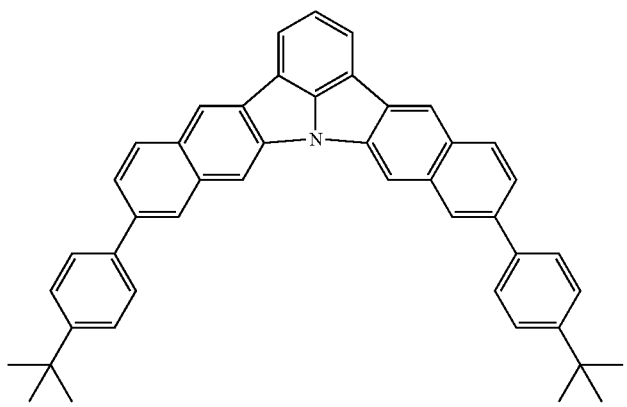
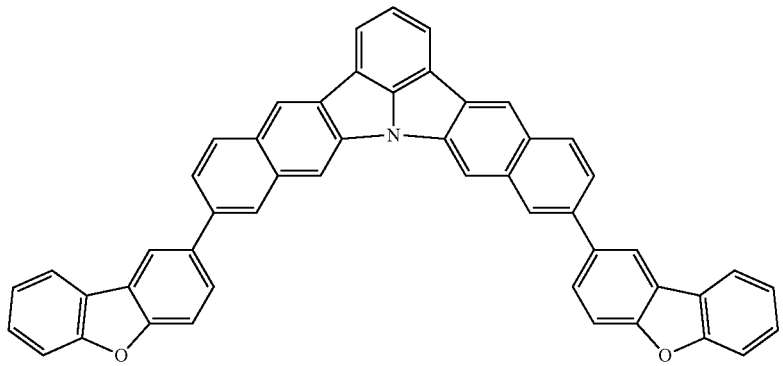

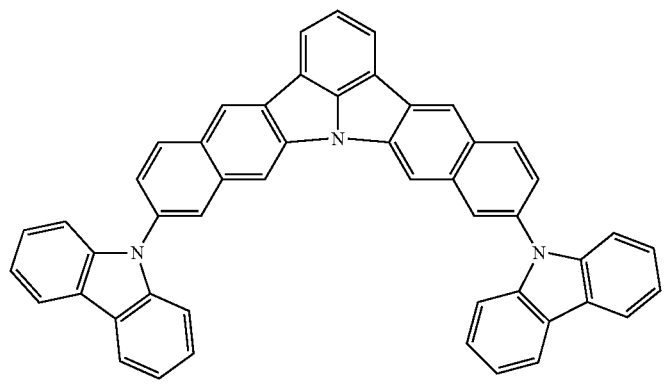
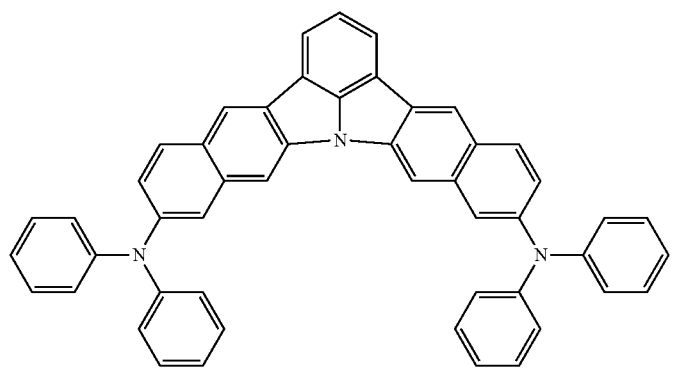
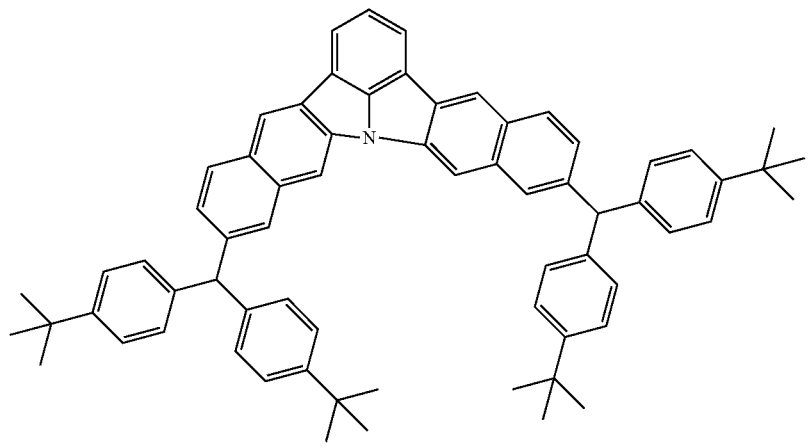
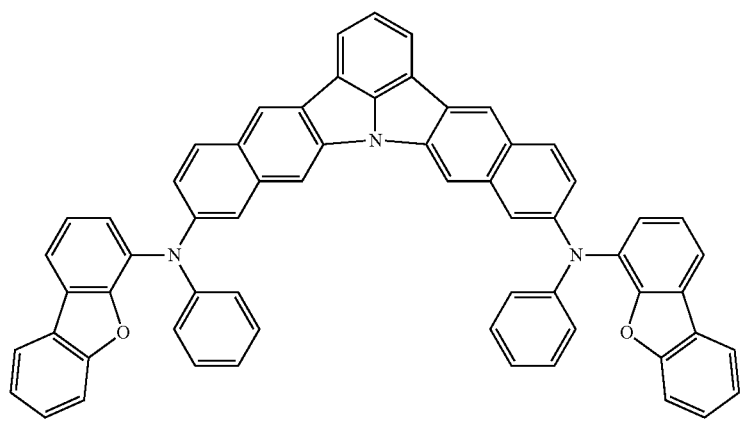

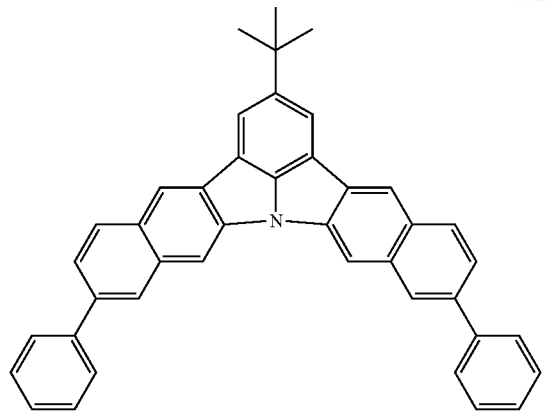
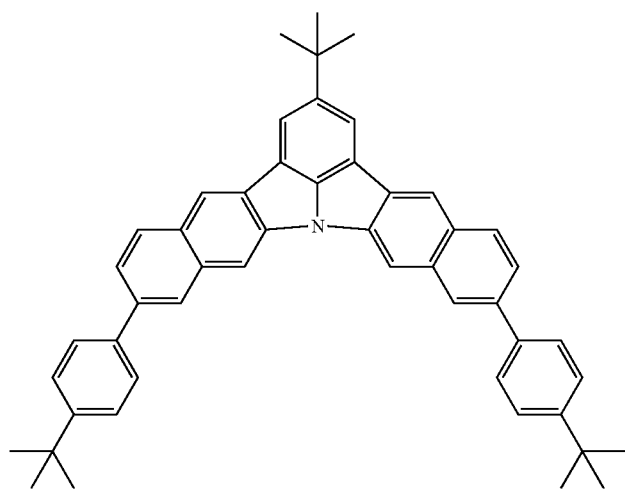
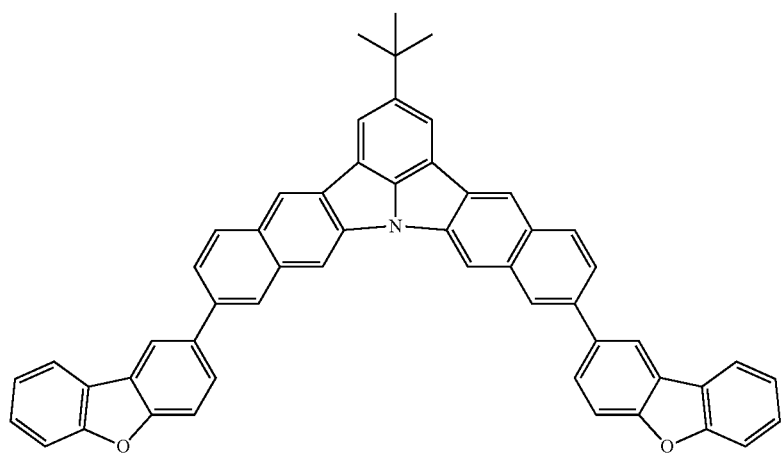

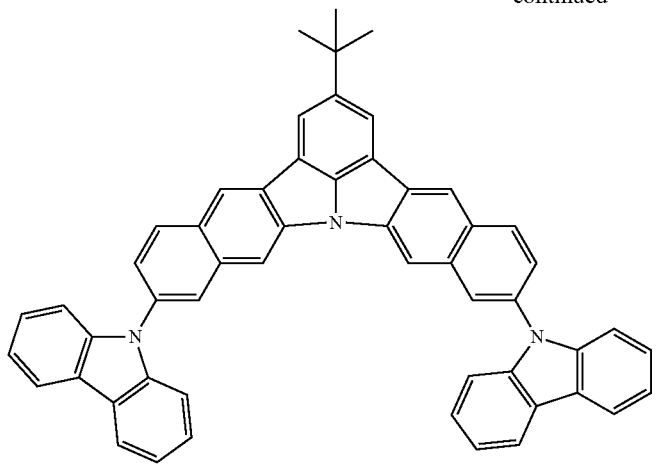
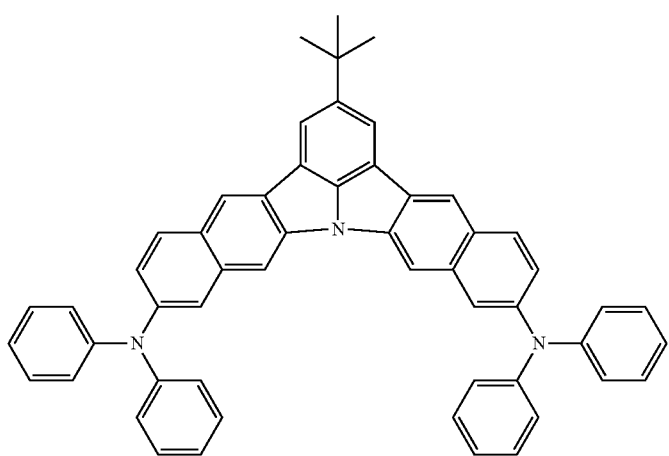
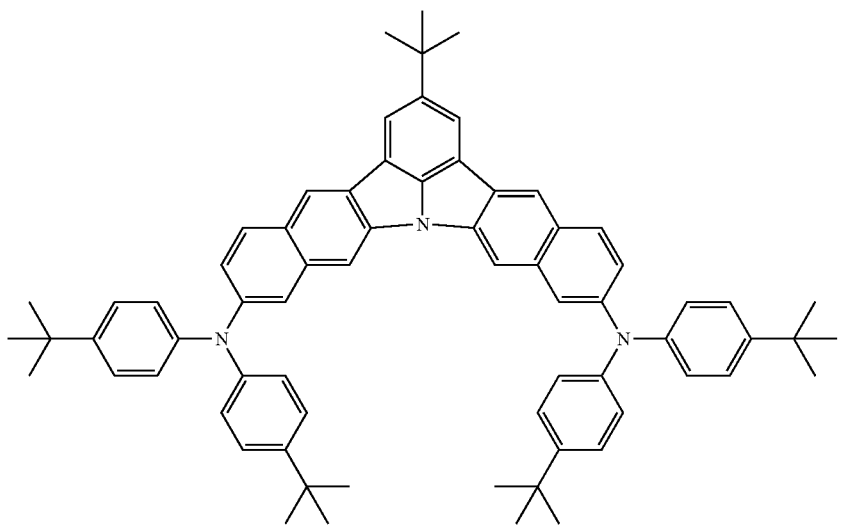

-continued
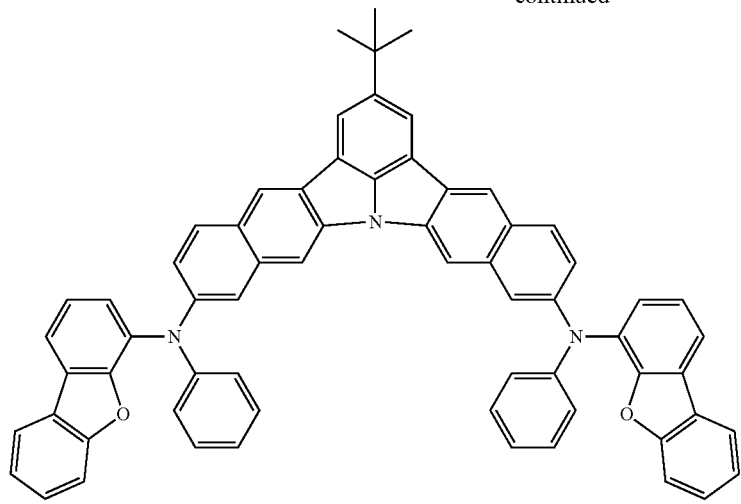
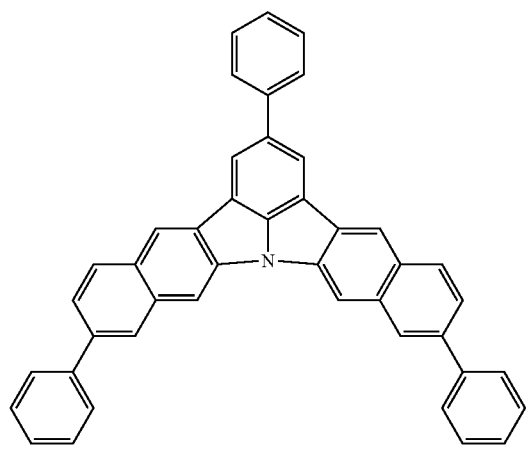
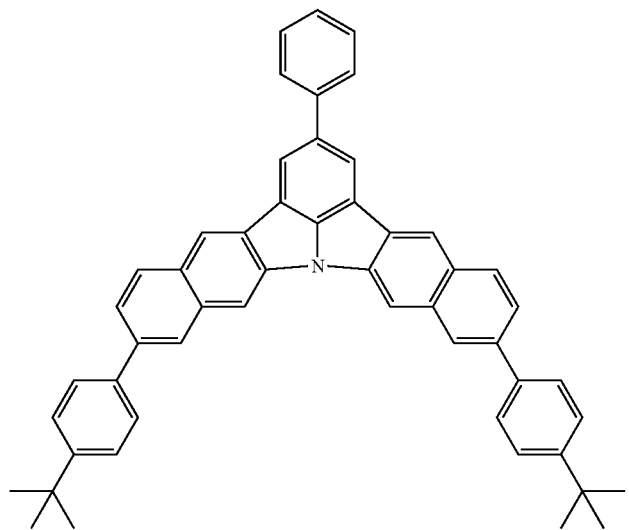

-continued
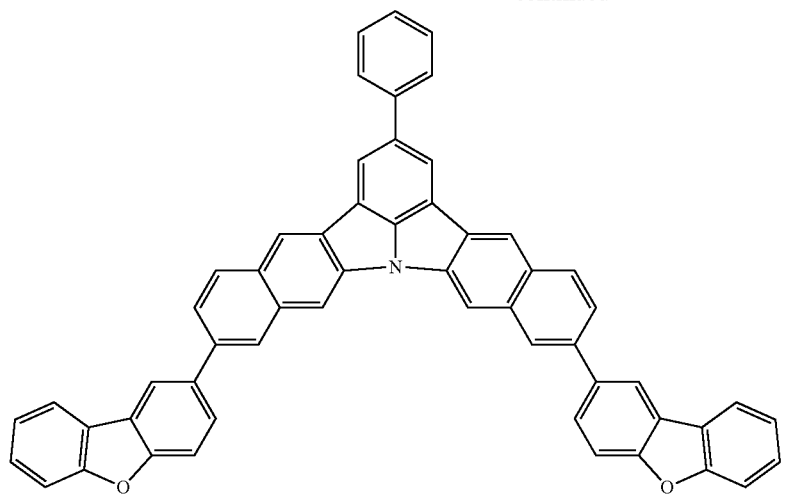
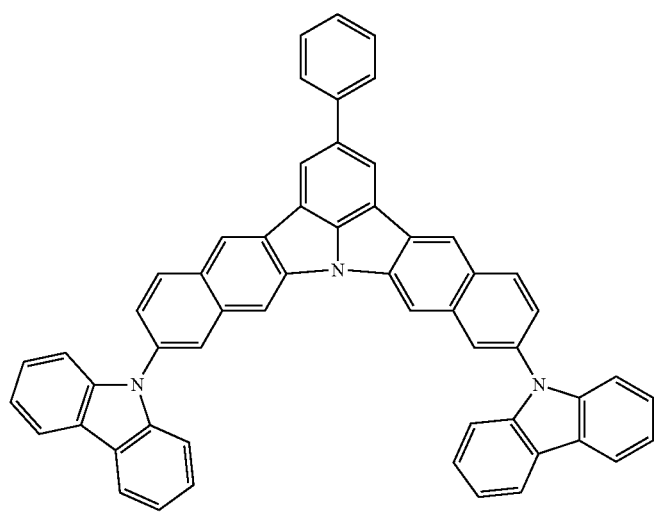
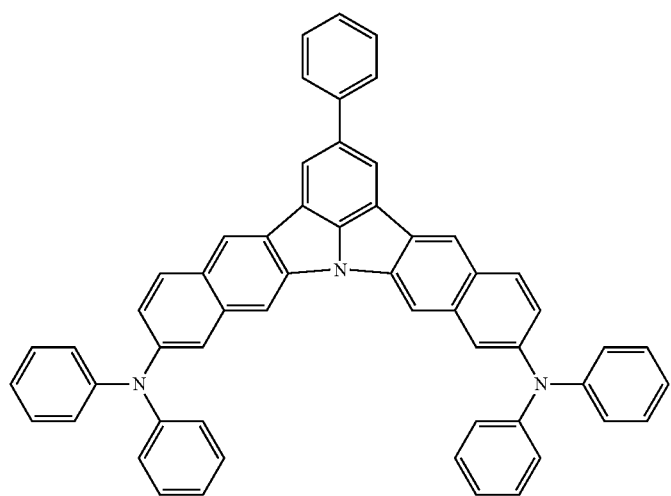

-continued
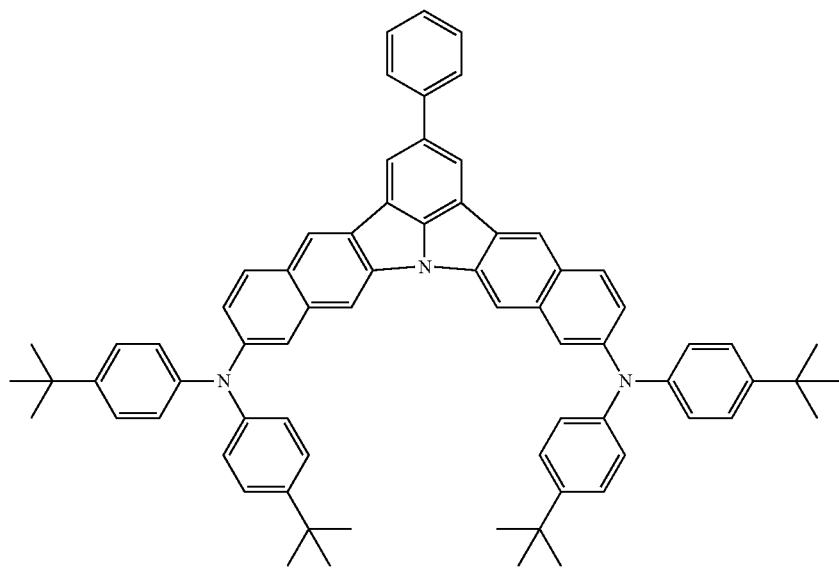
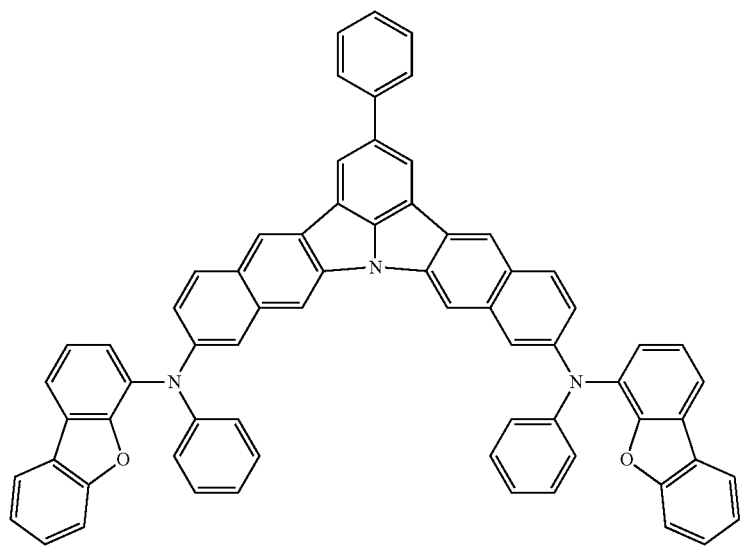
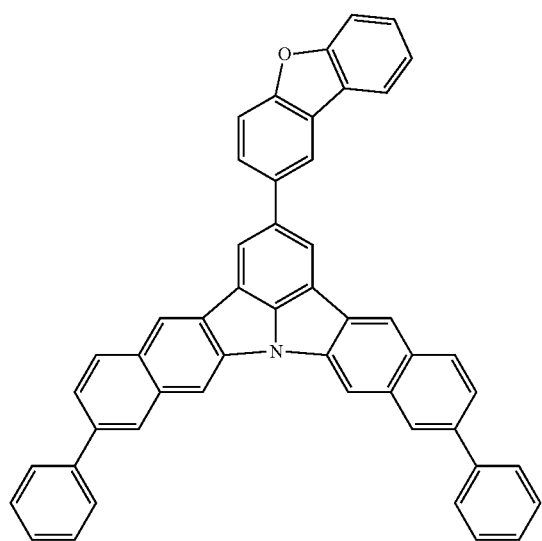

-continued
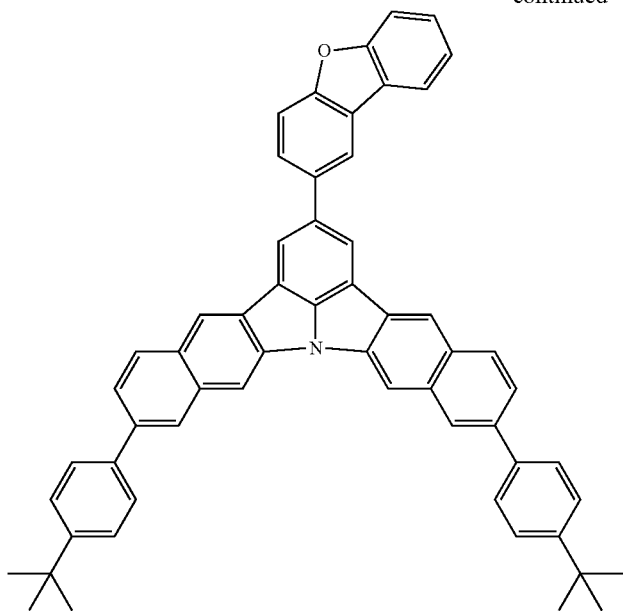
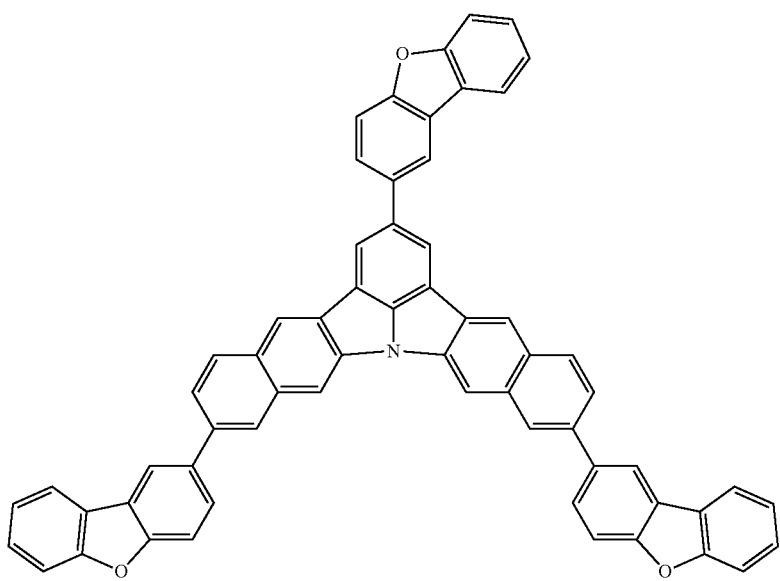

-continued
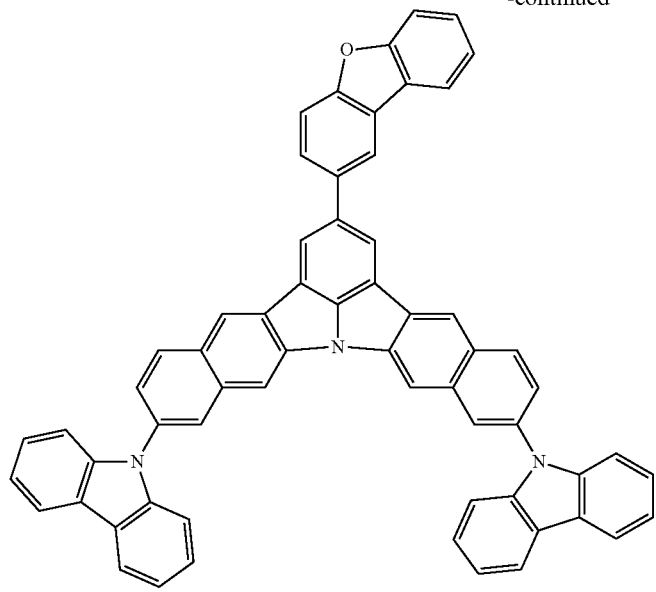
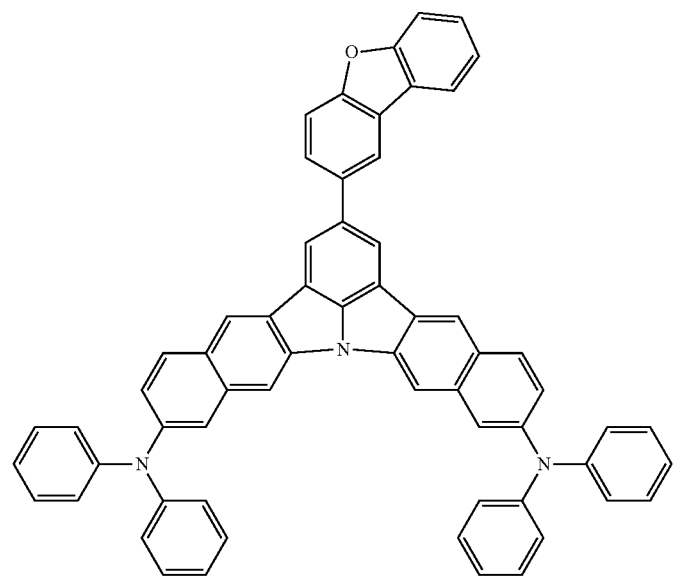

-continued
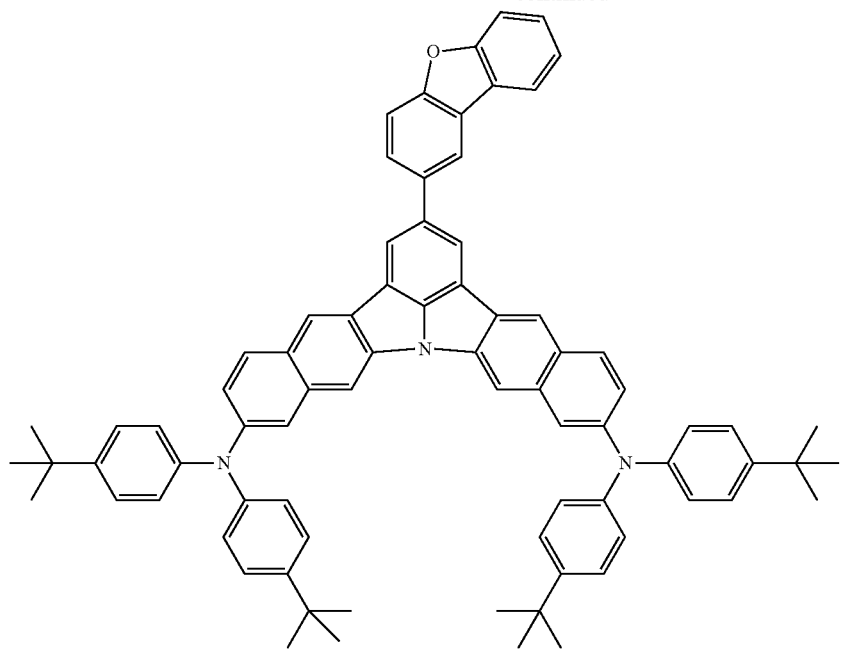
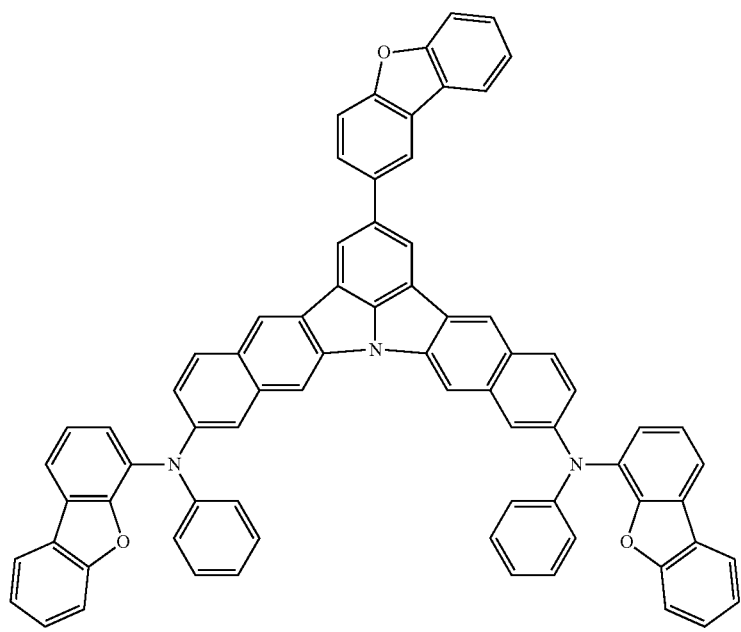
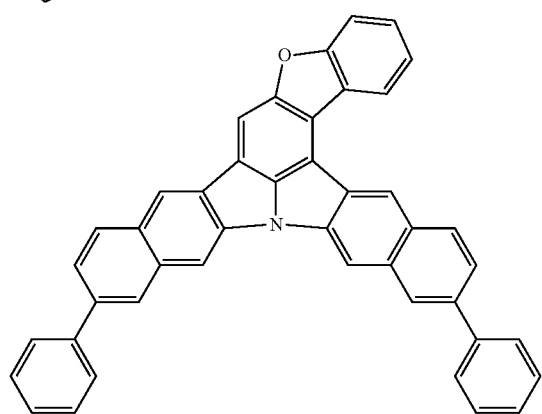

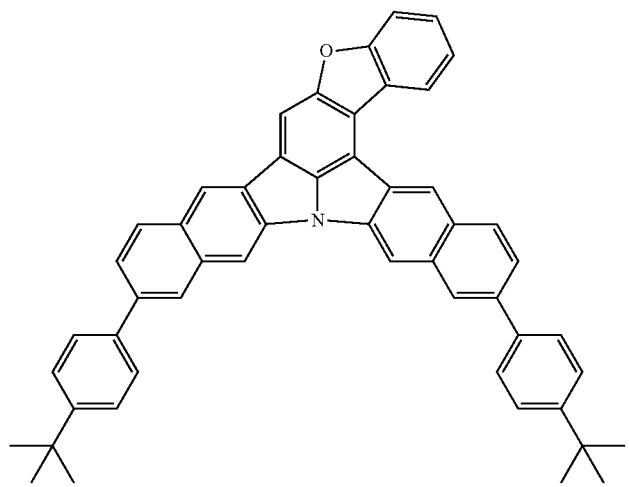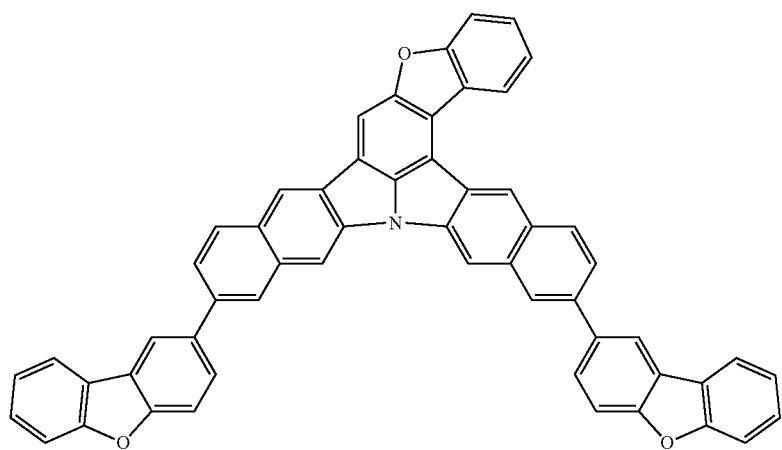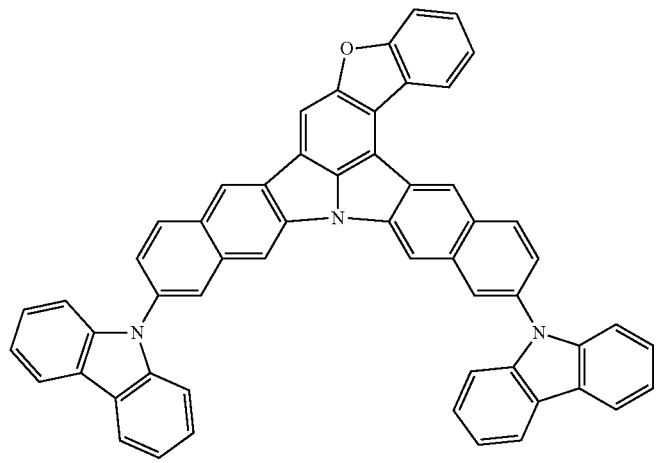

-continued
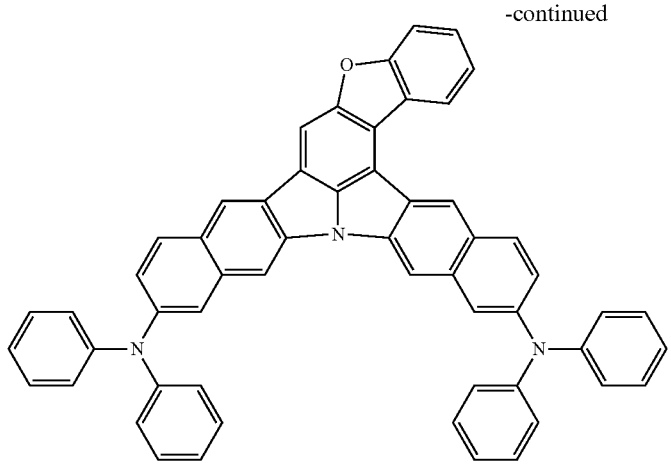
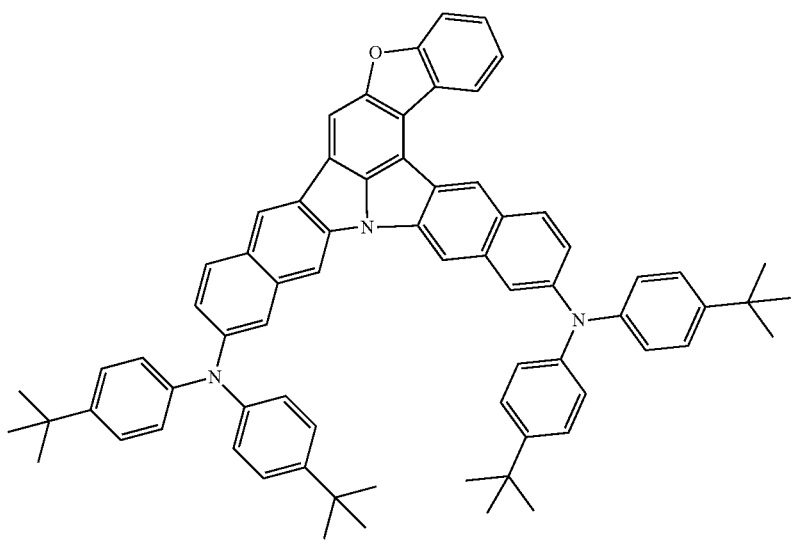
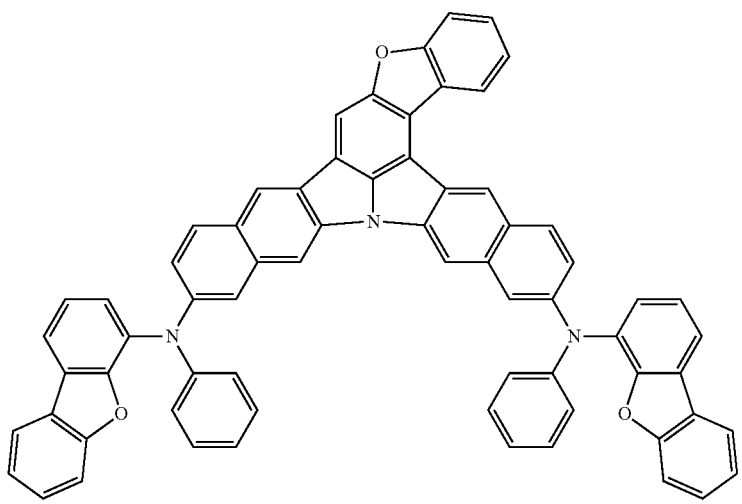

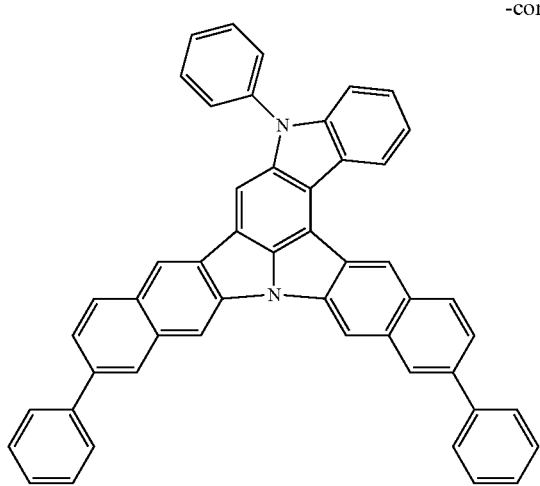
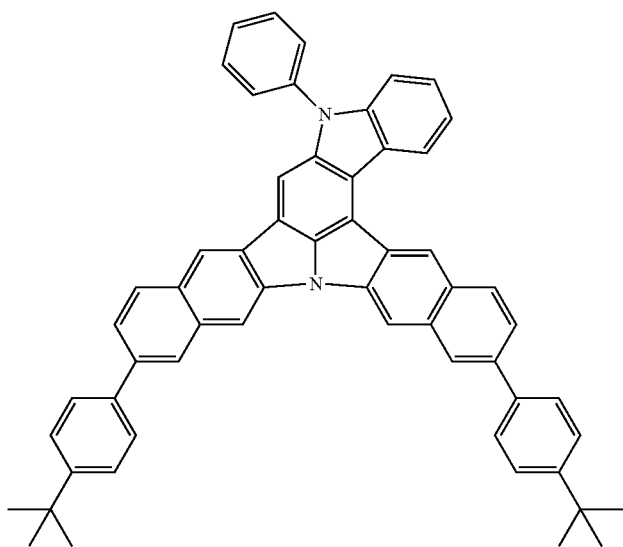
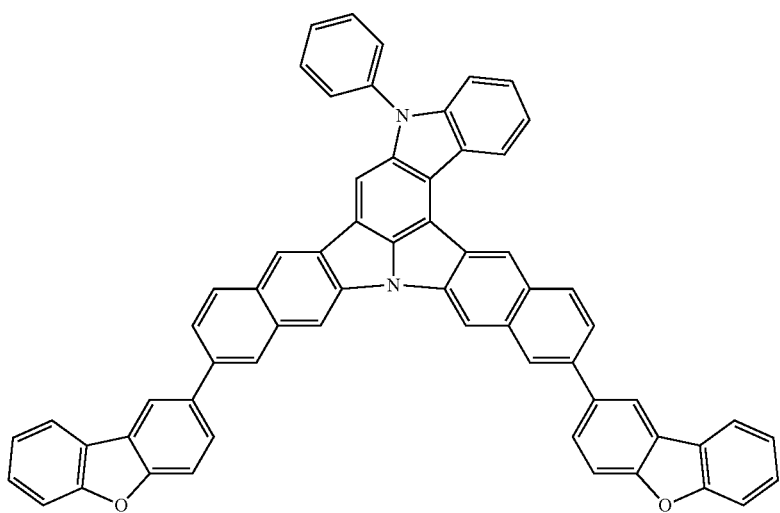

-continued
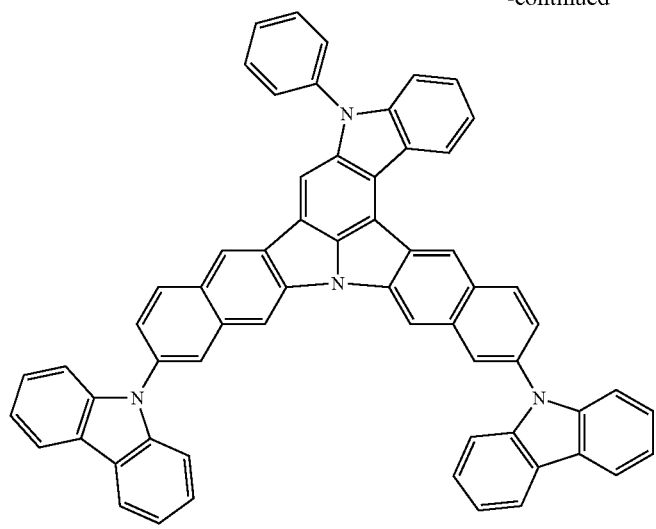
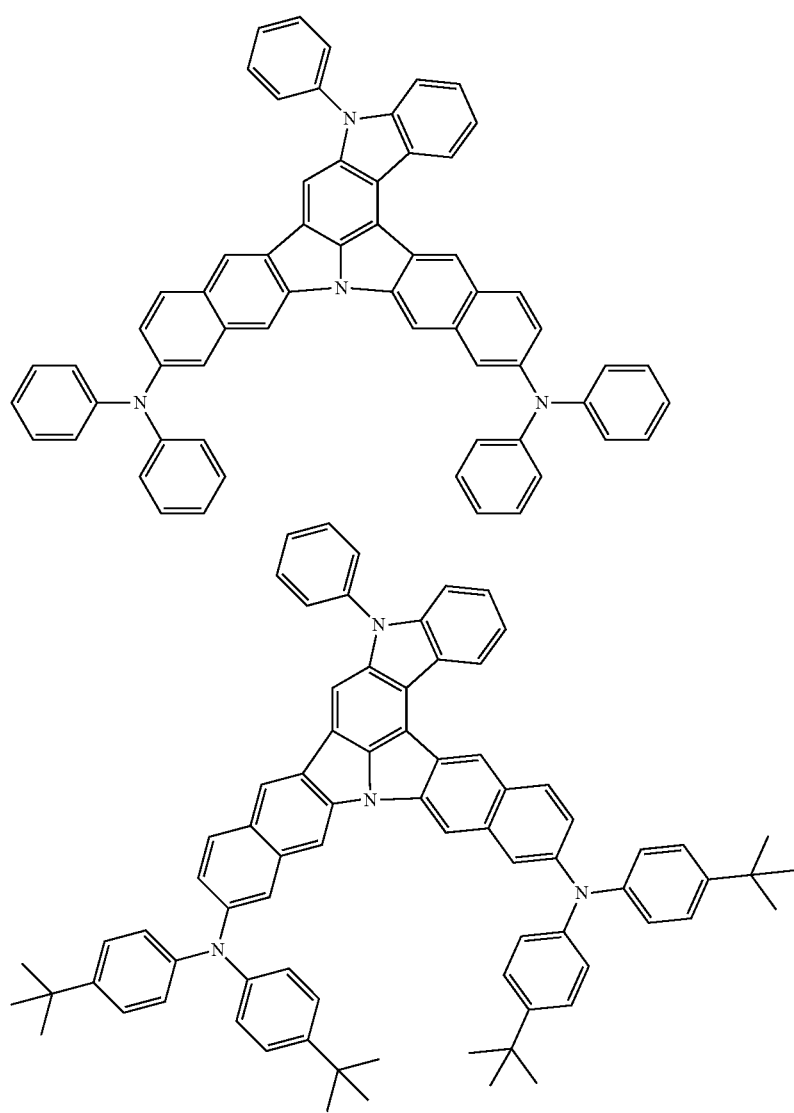

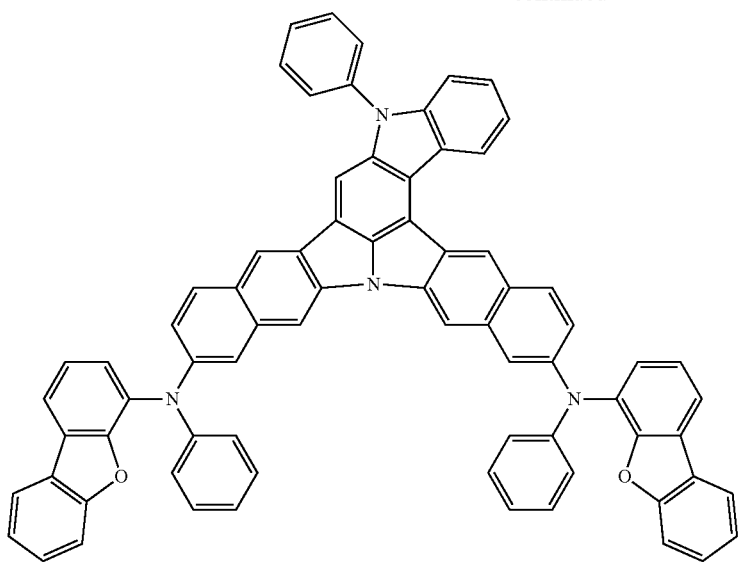
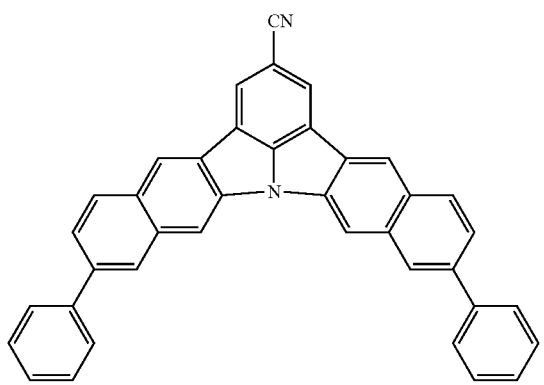
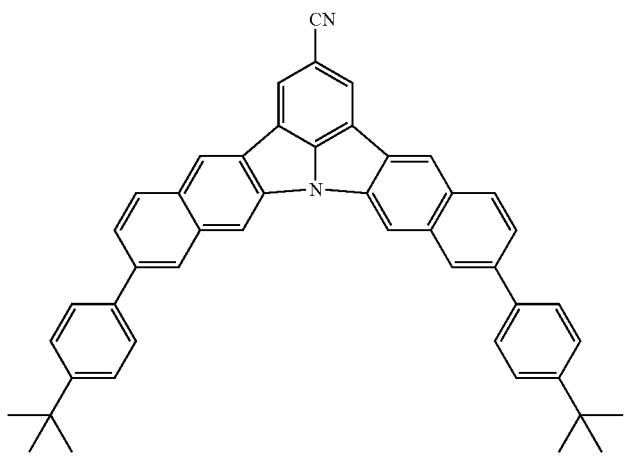

-continued
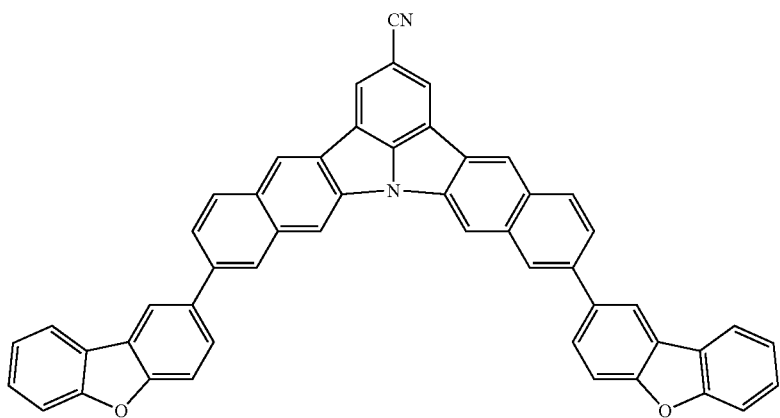
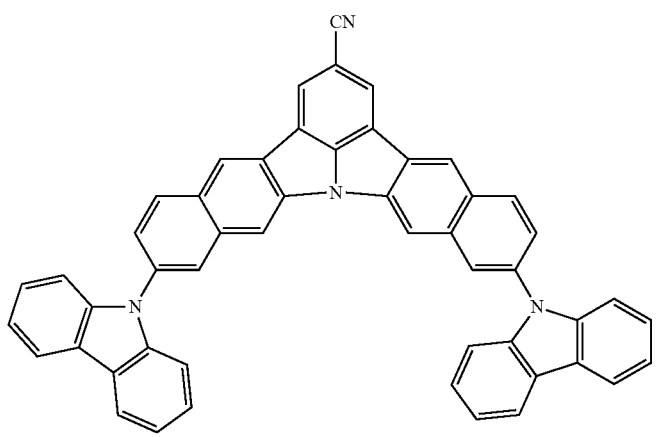
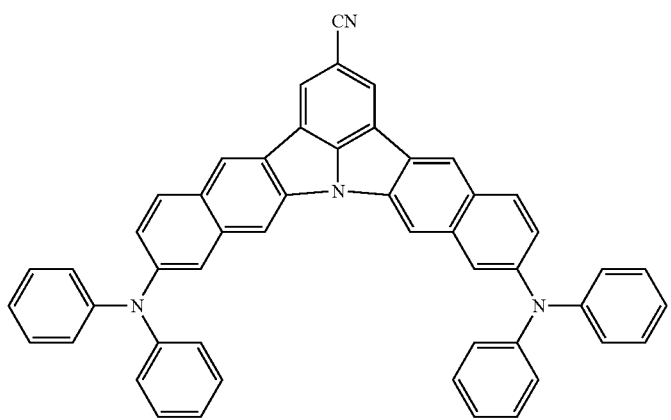

-continued
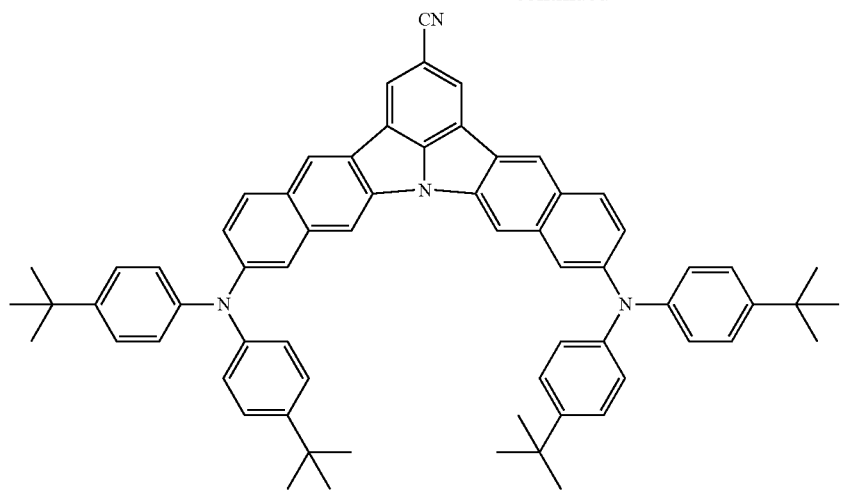
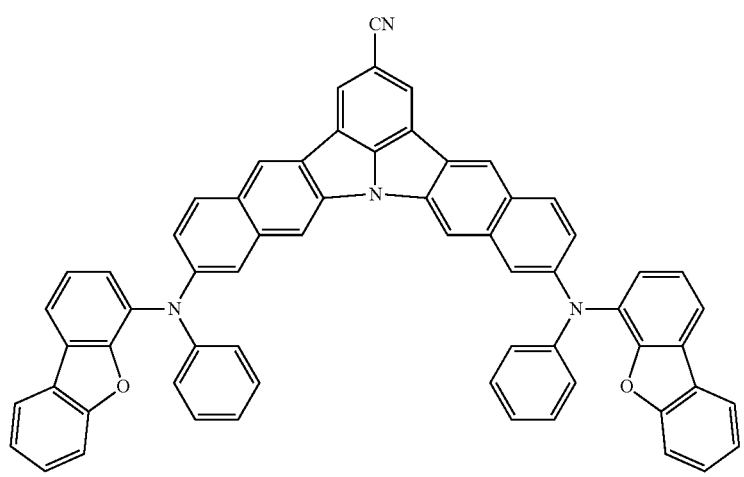
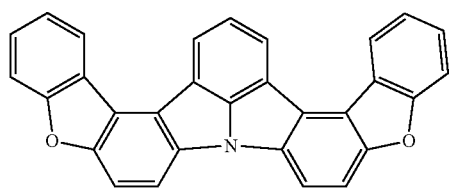
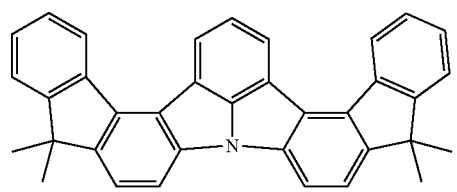
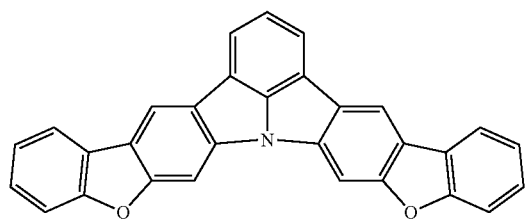
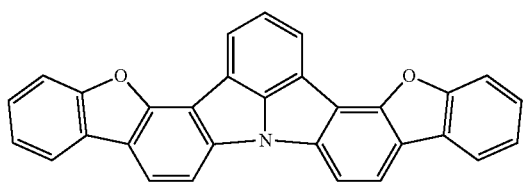
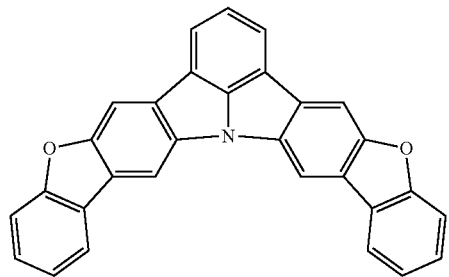
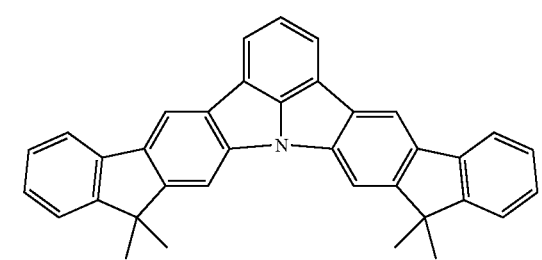

-continued
| 195 | 196 |
|---|---|
| 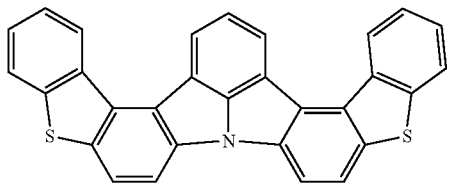 | 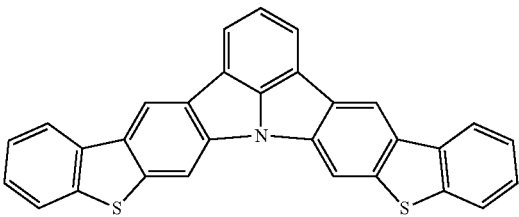 |
| 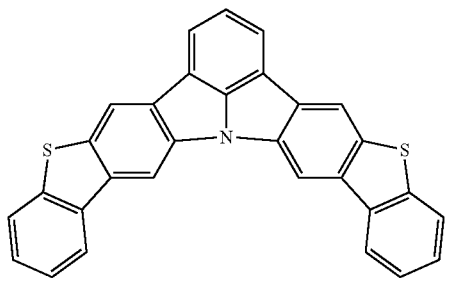 | 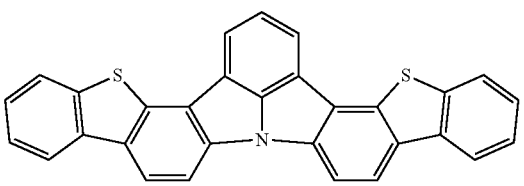 |
| 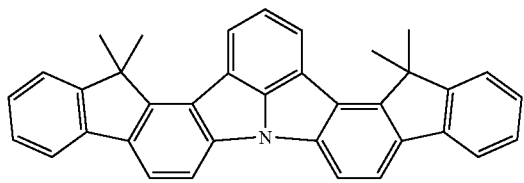 | 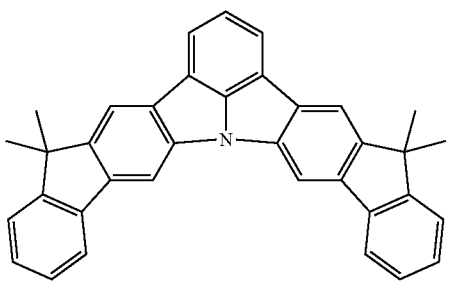 |
| 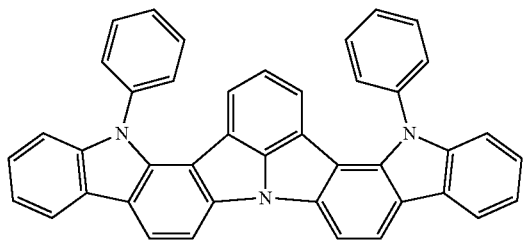 | 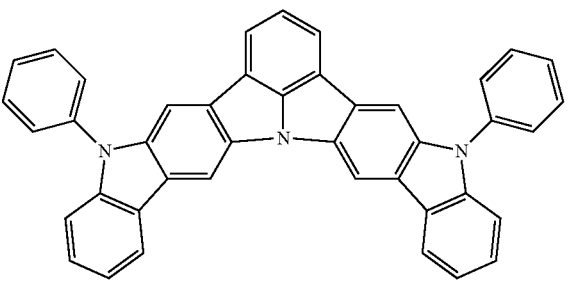 |
| 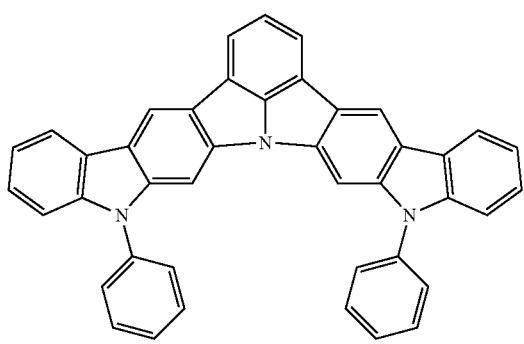 | 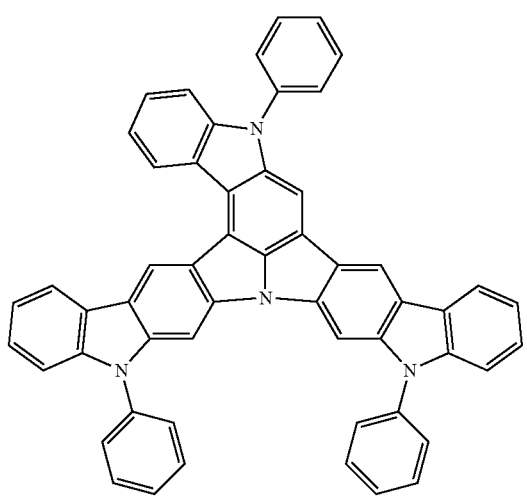 |

197 198
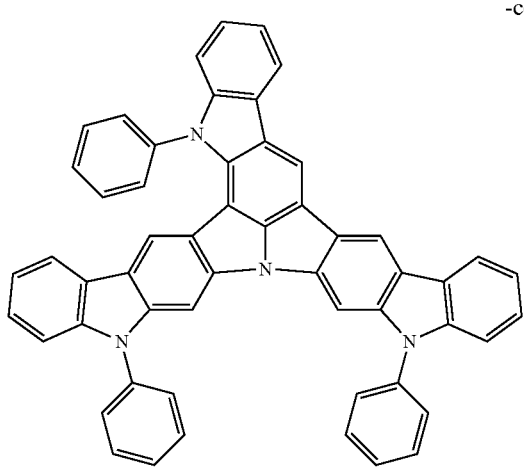 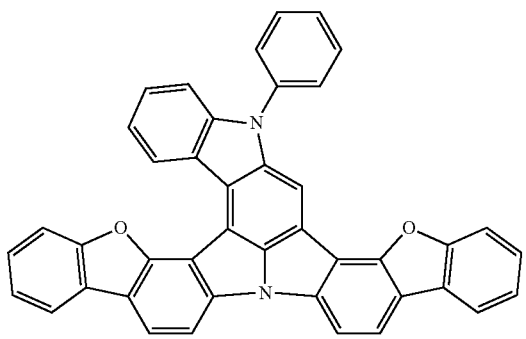
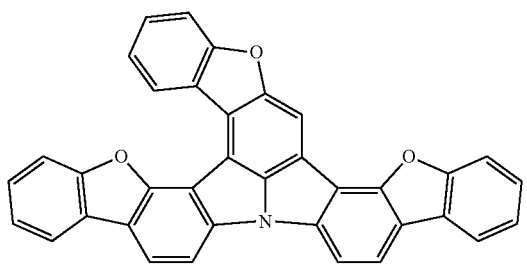 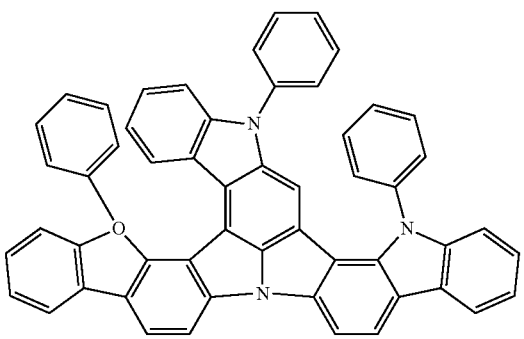
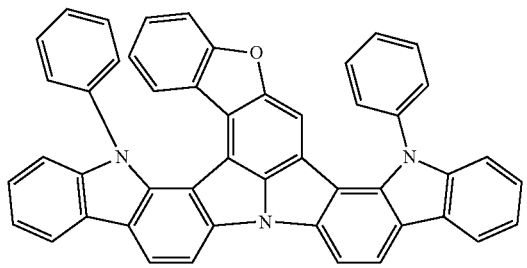 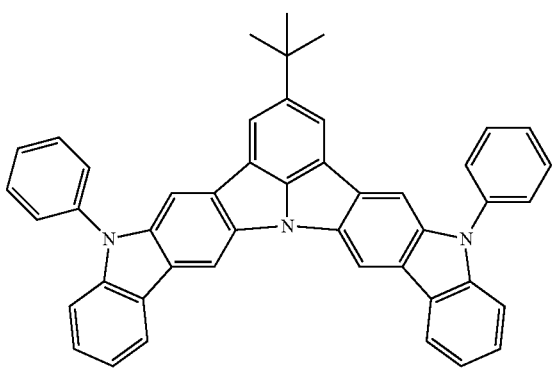
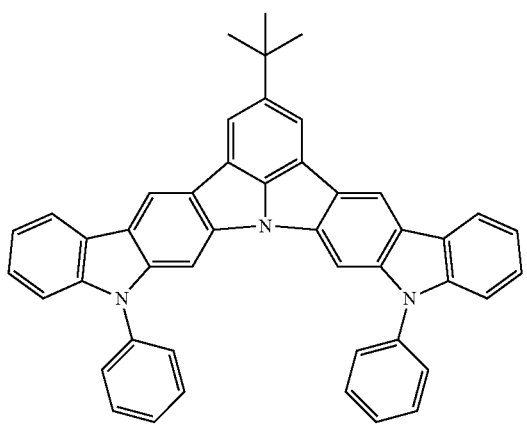 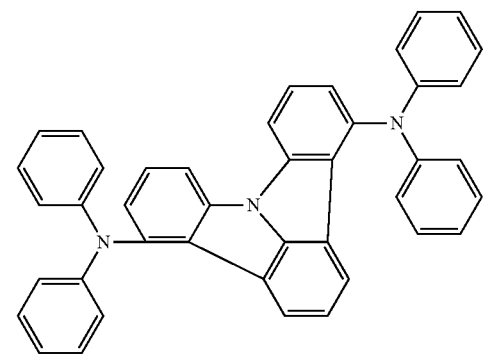

-continued
| 199 | 200 |
|---|---|
| 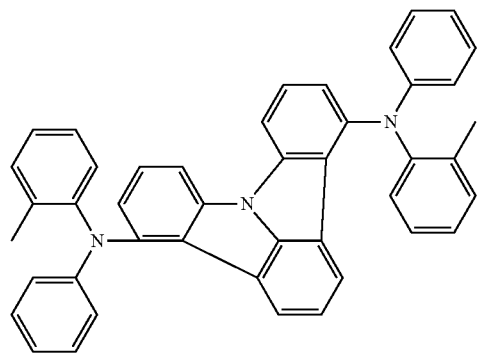 | 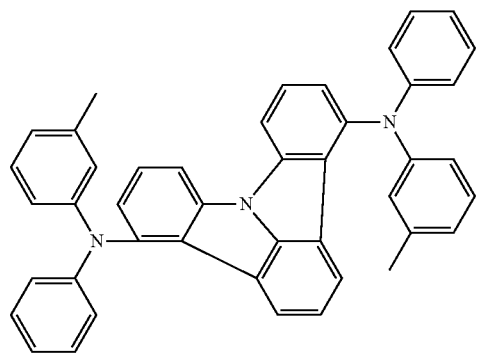 |
| 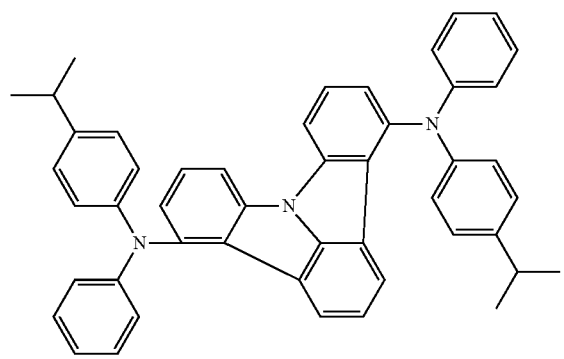 | |
| 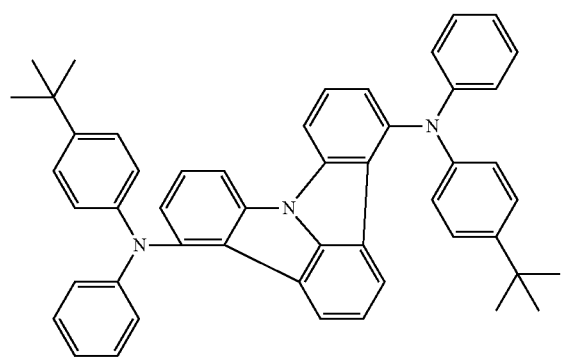 | 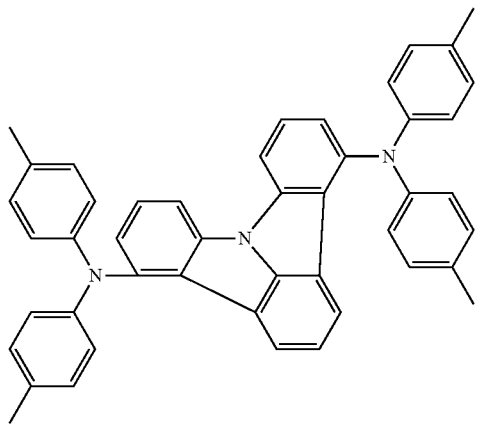 |
| 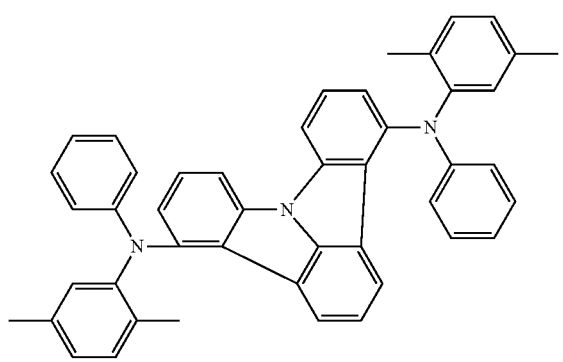 | 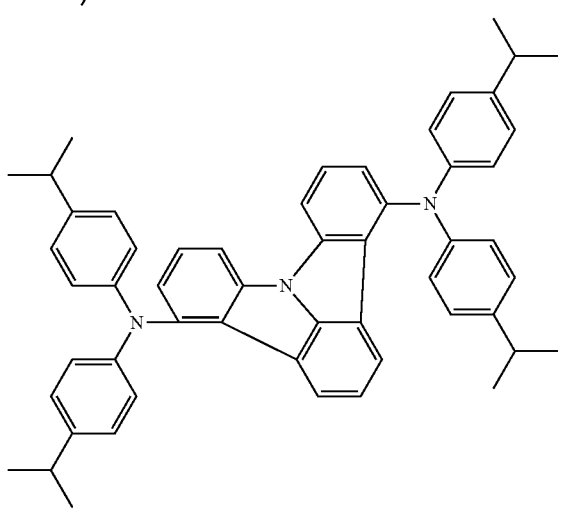 |

-continued
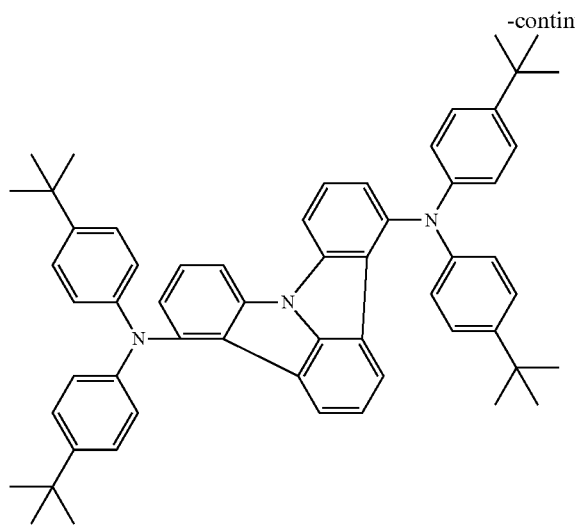
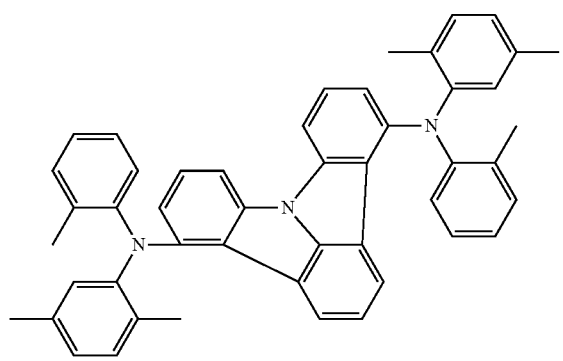
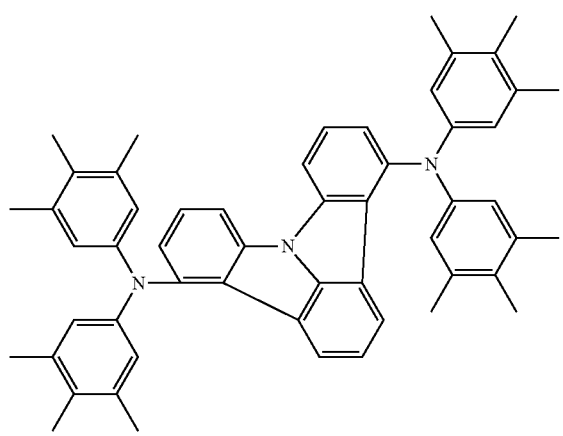
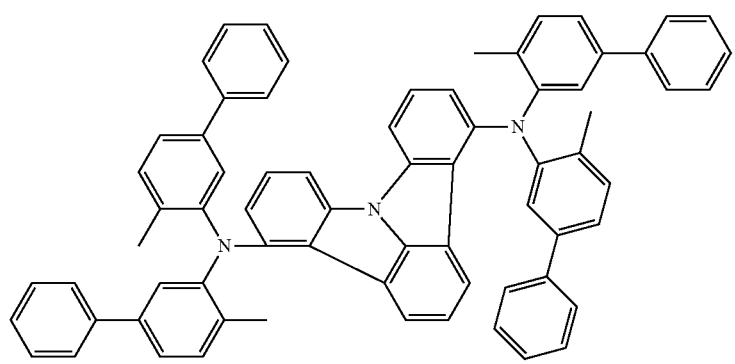

203                                              204
-continued
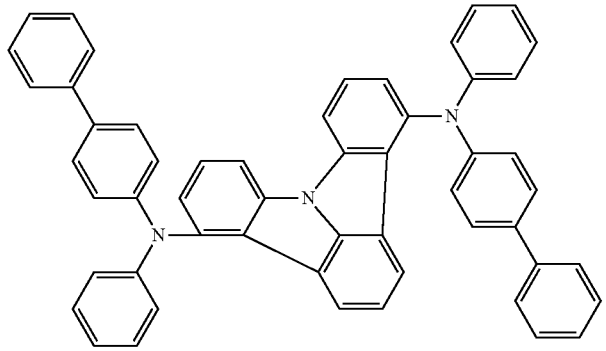
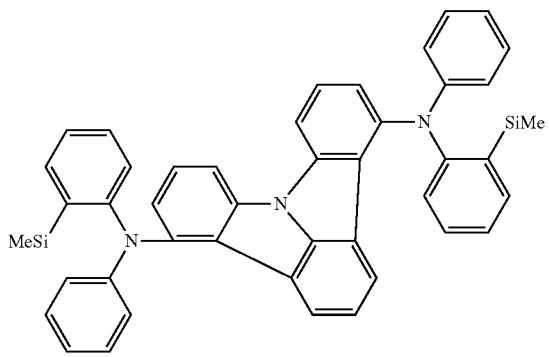
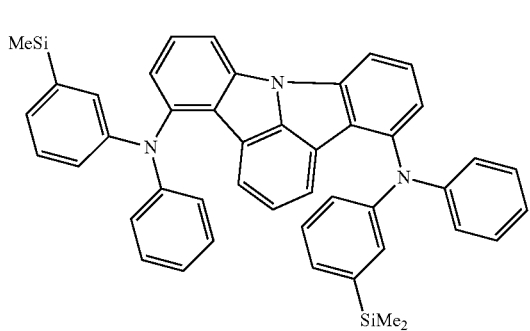
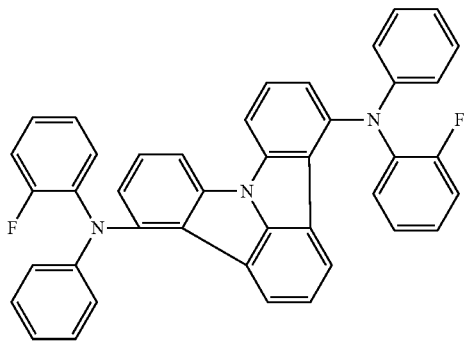
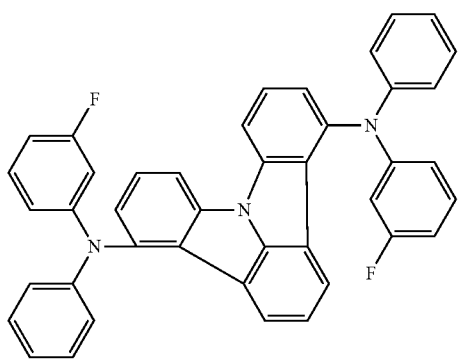
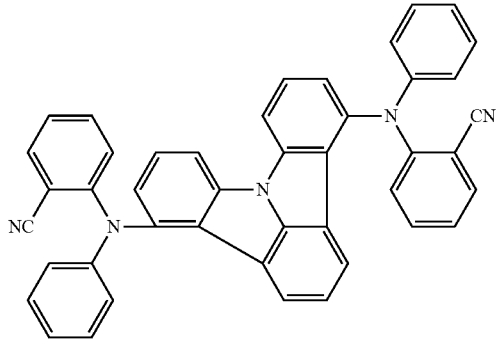

-continued
205
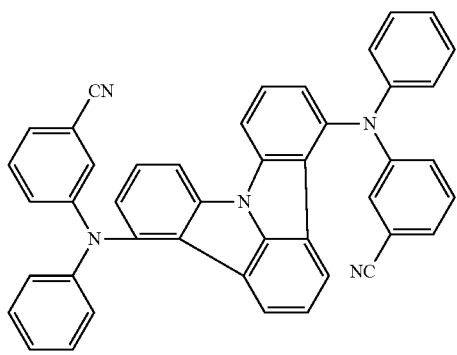
206
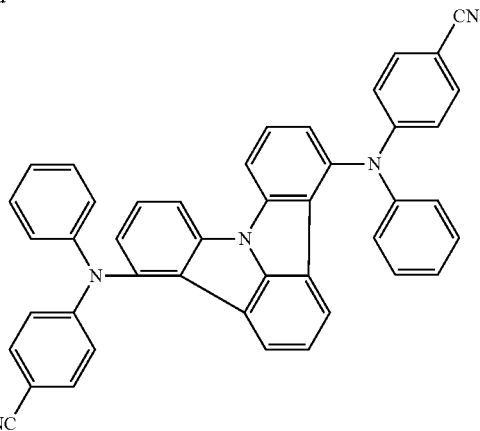
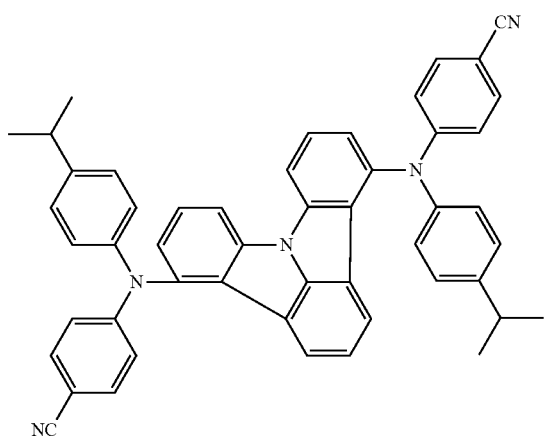
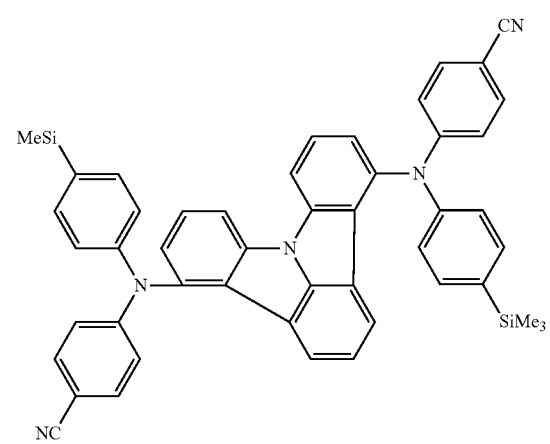
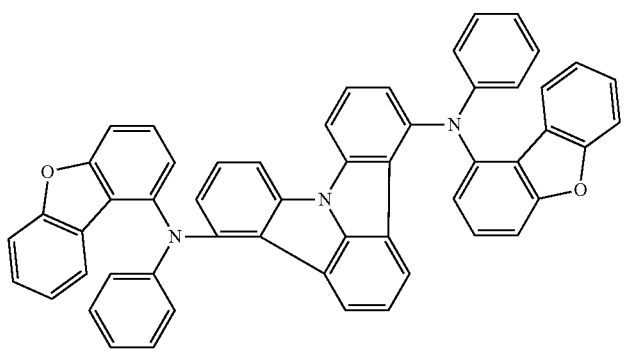
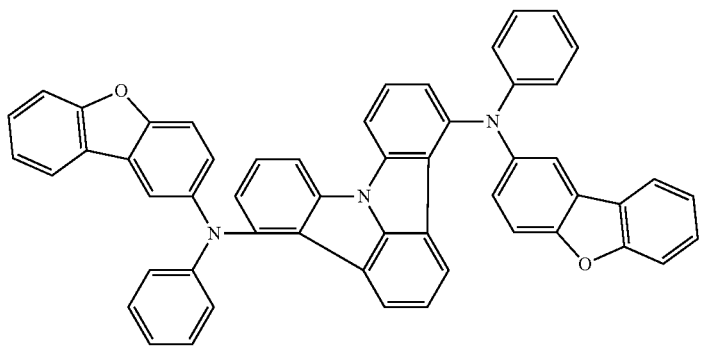

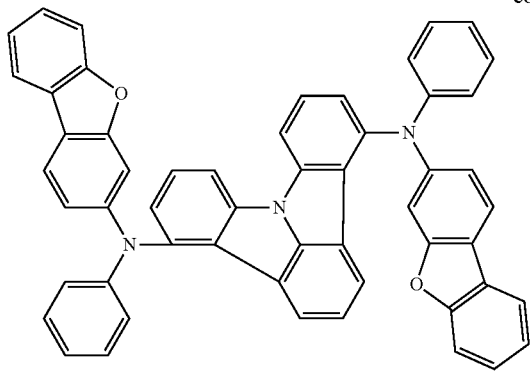
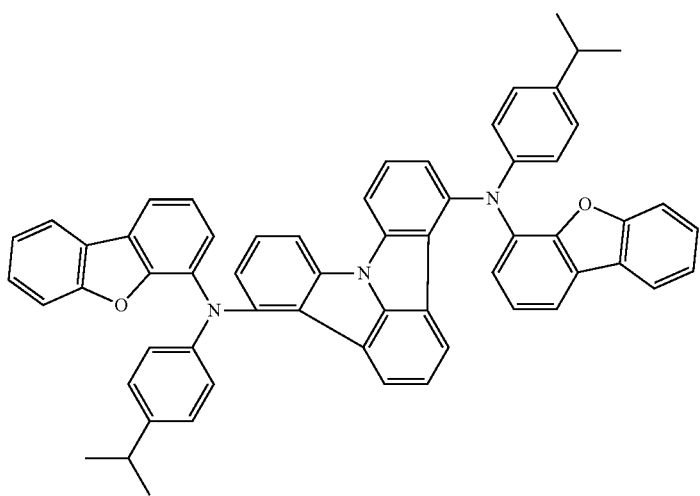
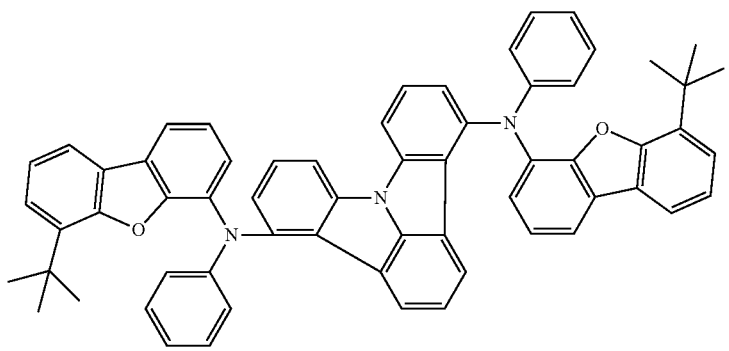
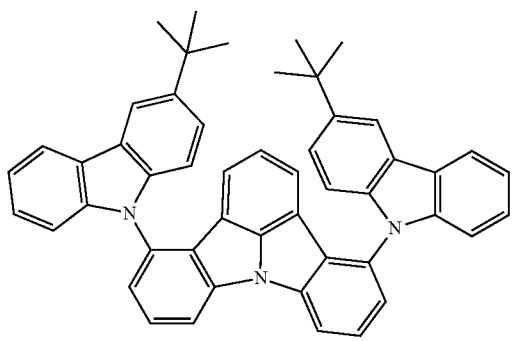

-continued
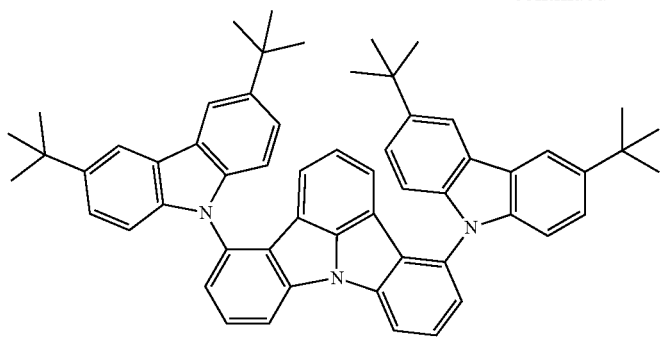
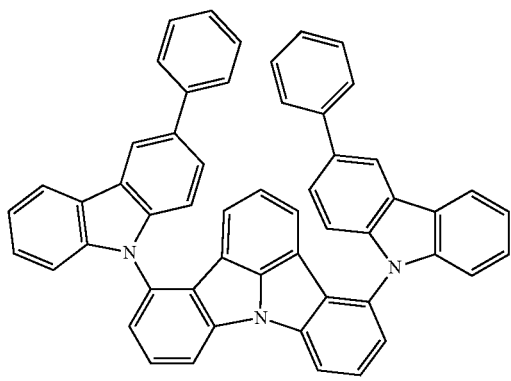
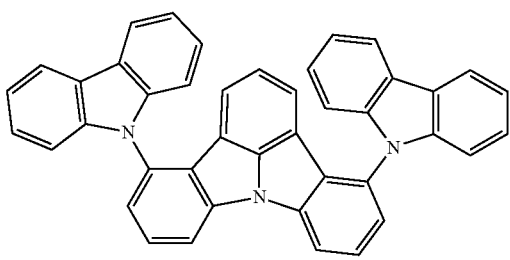
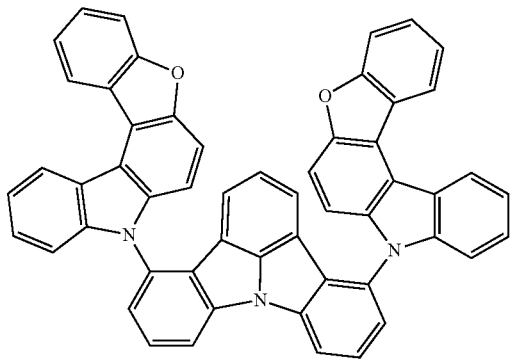
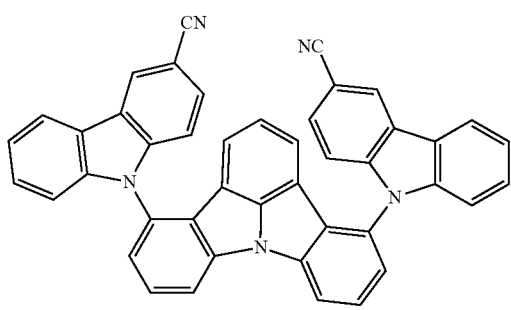
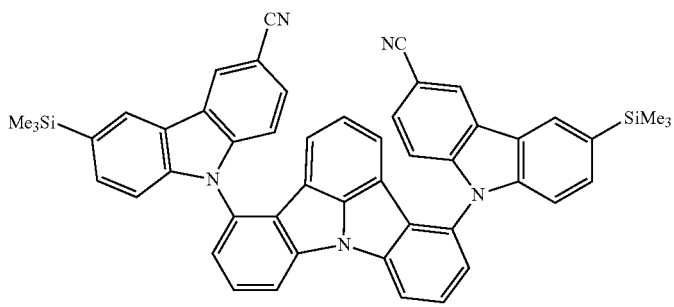

-continued
211 212
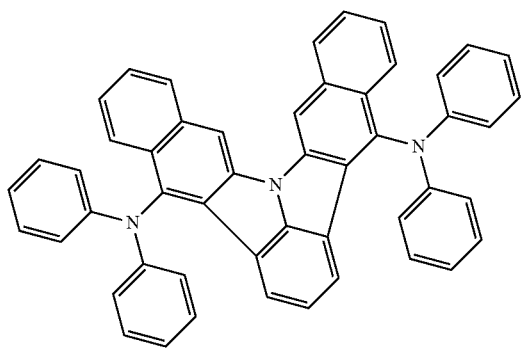 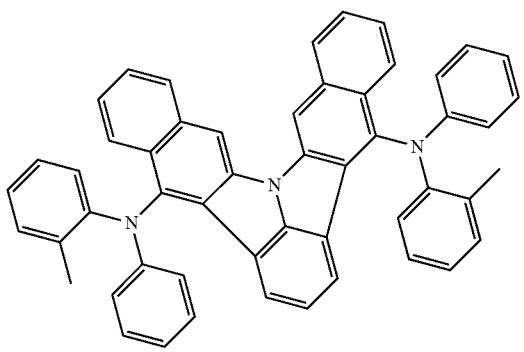
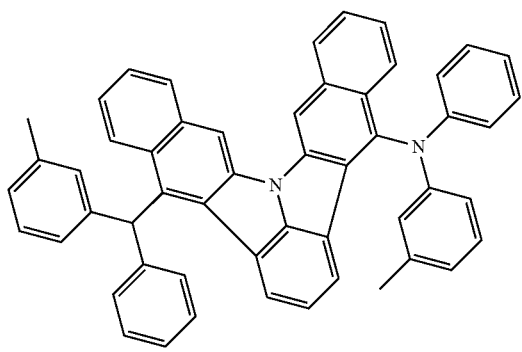
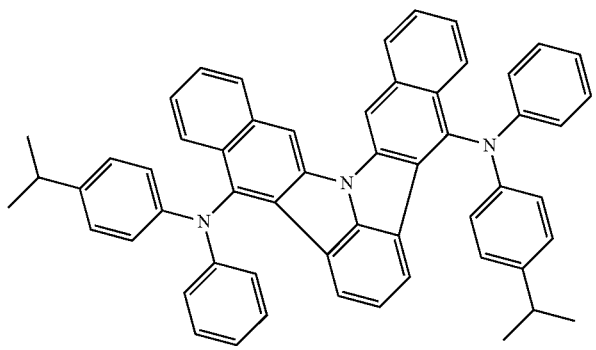
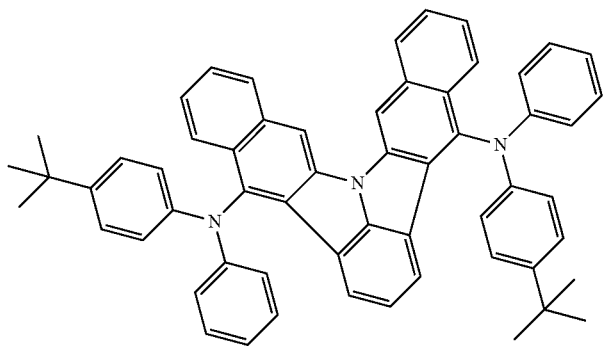

-continued
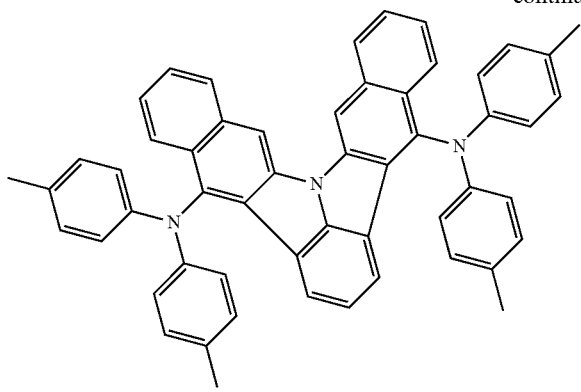
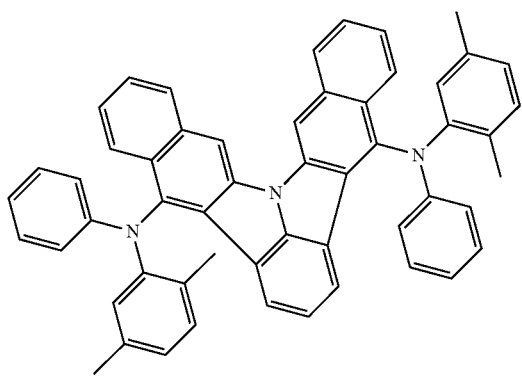
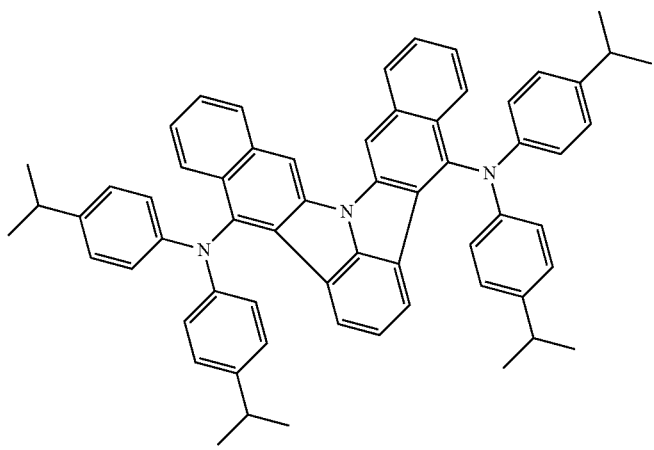
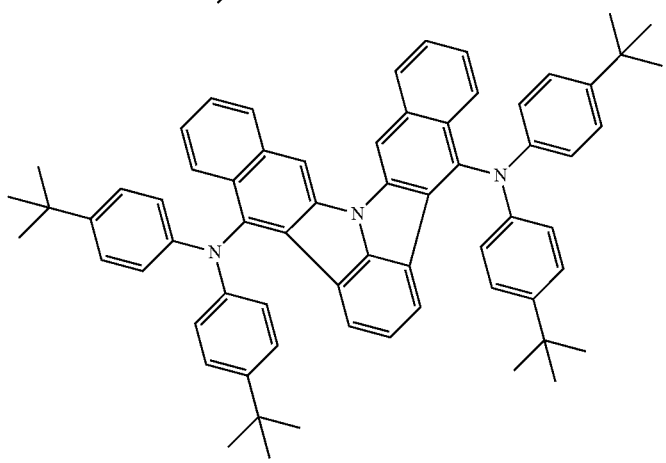

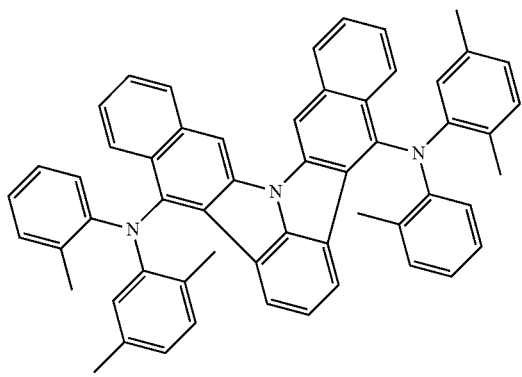
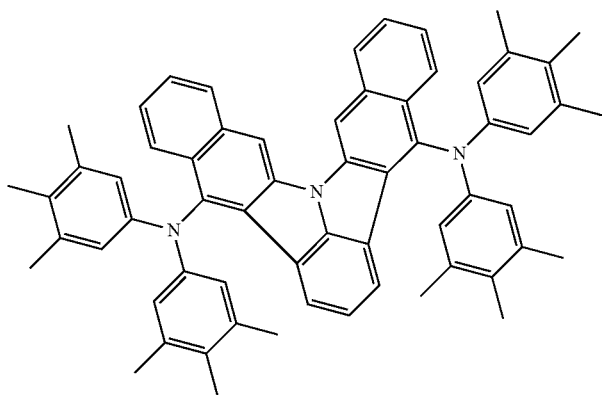
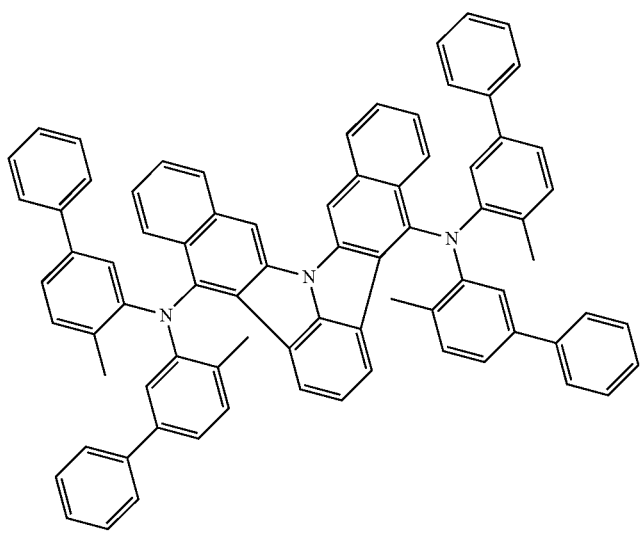
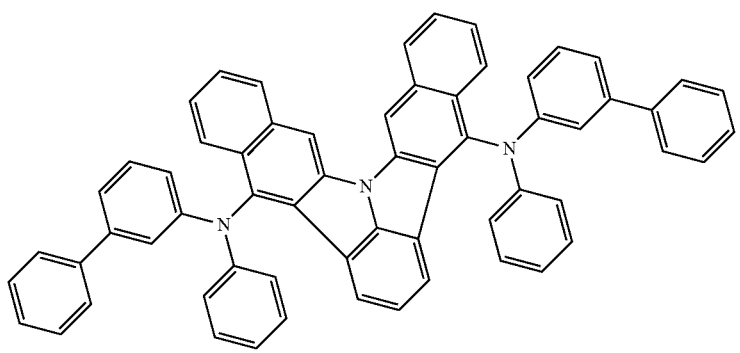

217 218
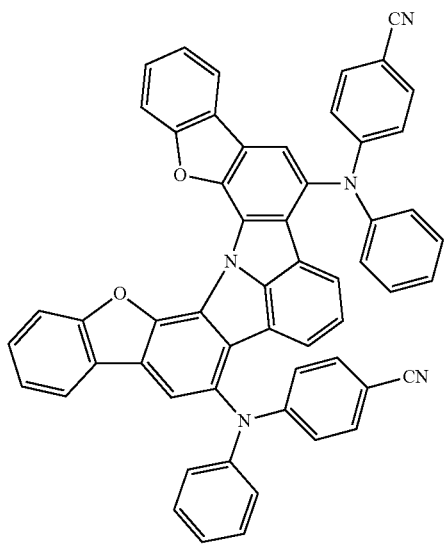
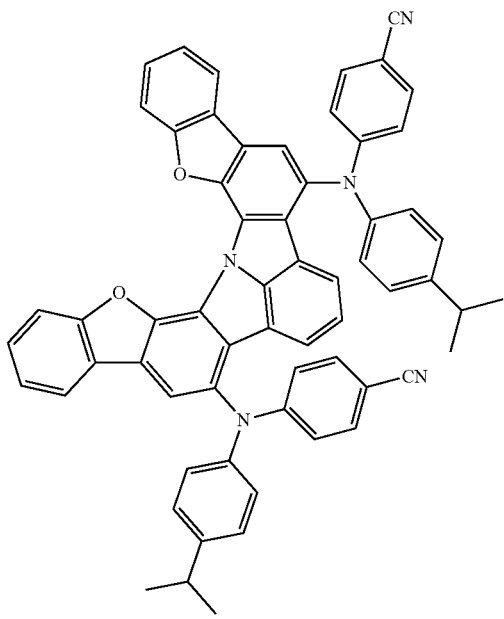
-continued
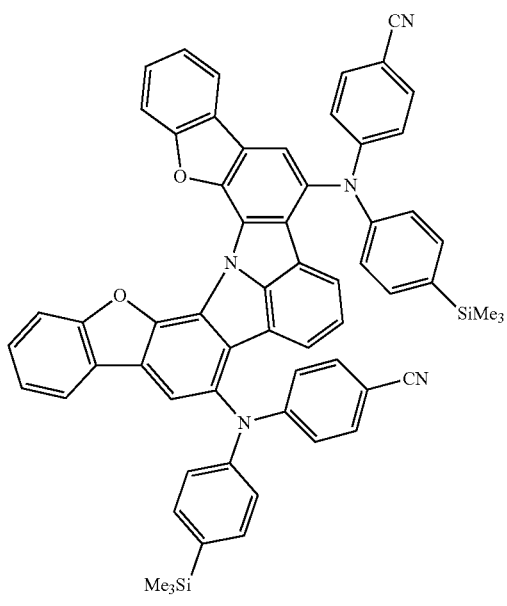
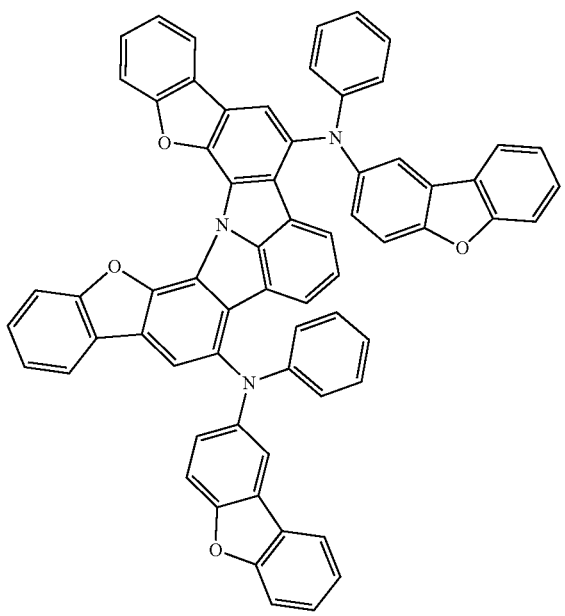

219
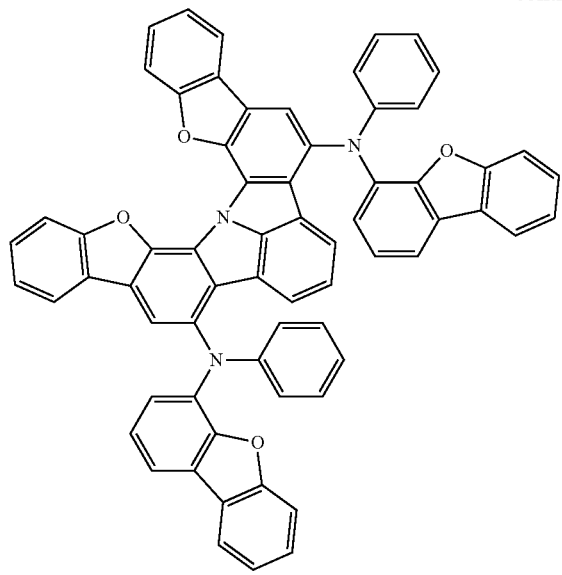
220
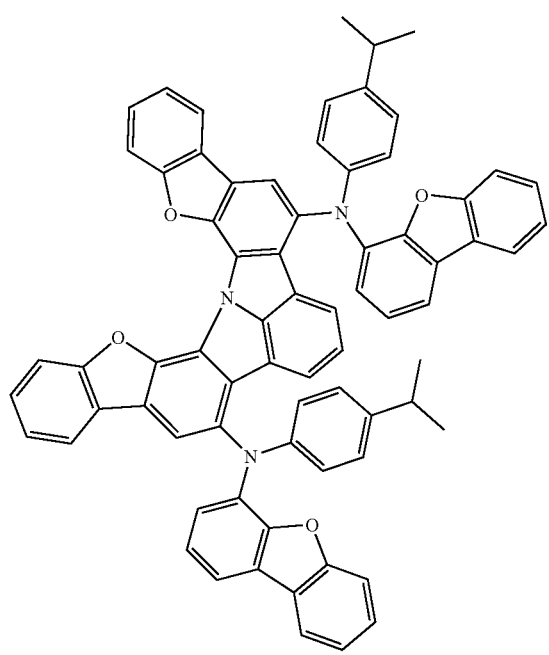
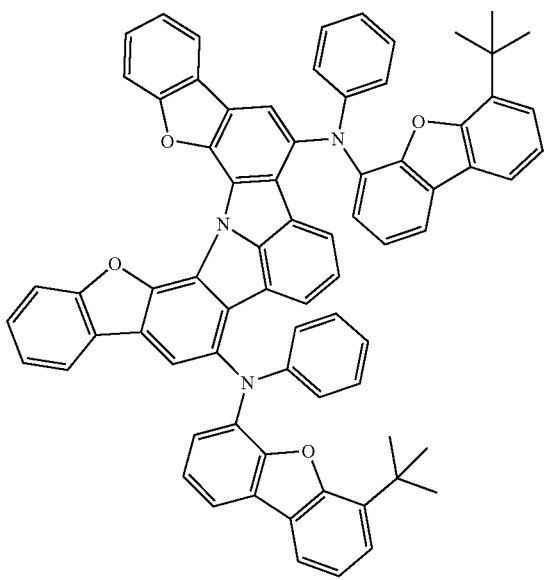

-continued
221
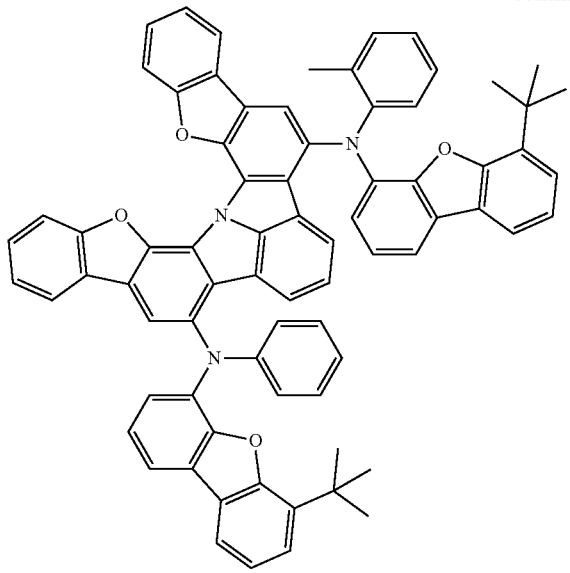
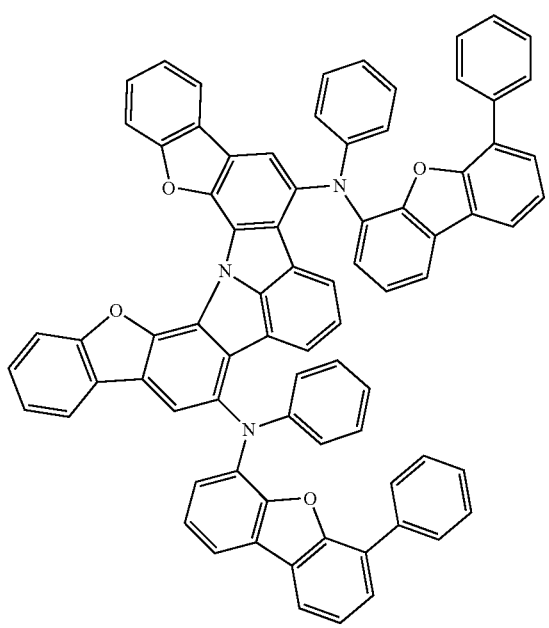
222
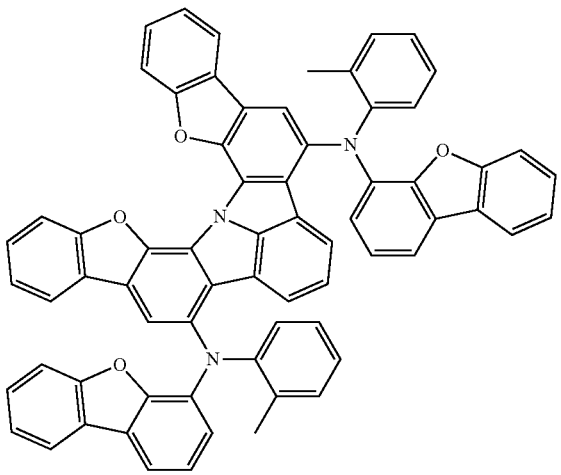
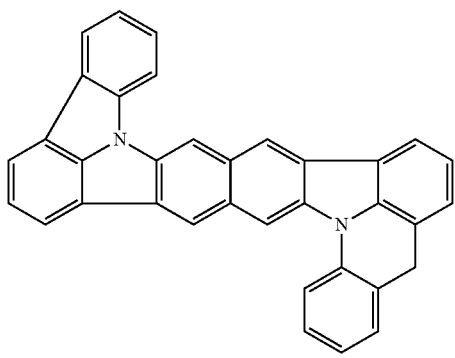
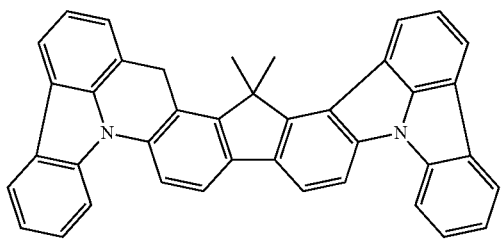

223 224
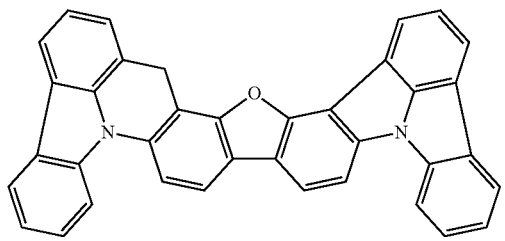 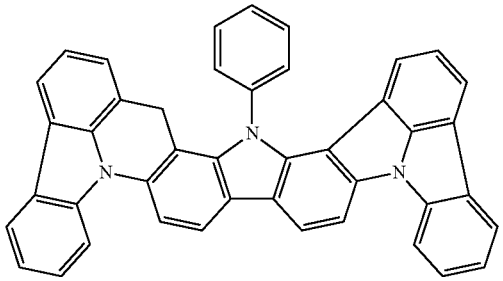
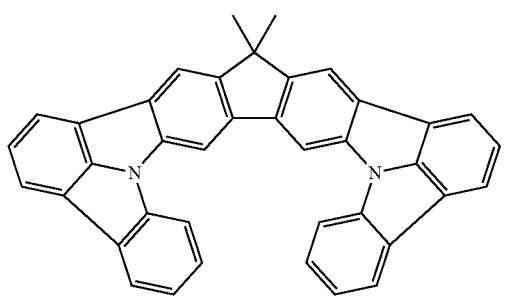 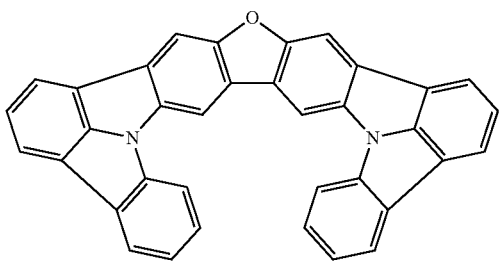
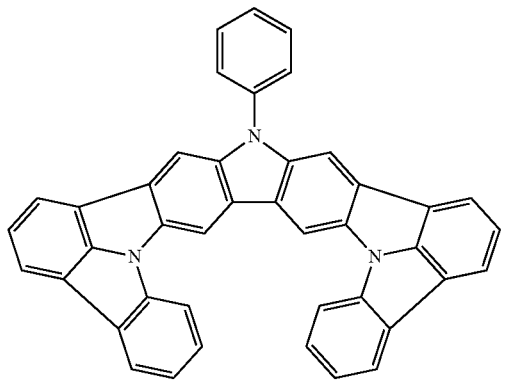 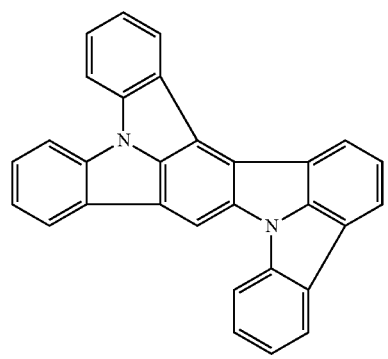
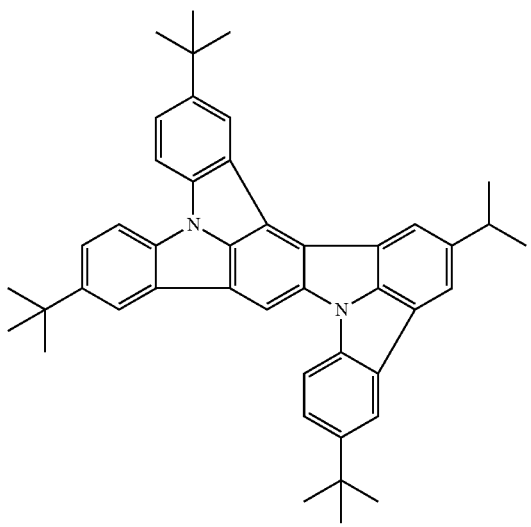

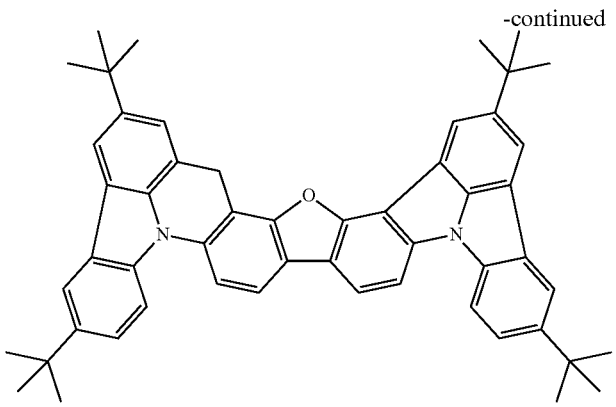

(Compound Represented by Formula (31))

The compound represented by the formula (31) is explained below.

The compound represented by formula (31) is a compound corresponding to the compound represented by the formula (21-3).

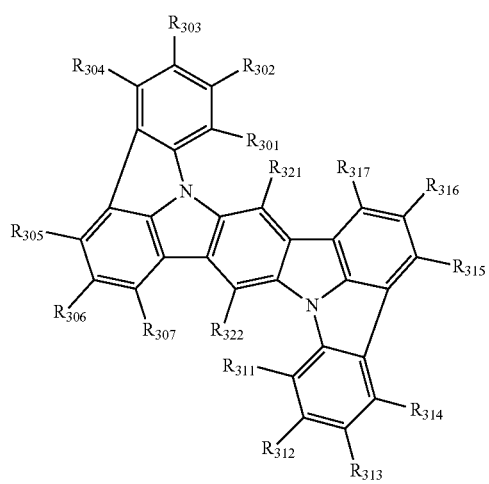

In the formula (31), one or more pairs of two or more adjacent groups of $R_{301}$ to $R_{307}$ and $R_{311}$ to $R_{317}$ form a substituted or unsubstituted, saturated or unsaturated ring, or do not form a substituted or unsubstituted, saturated or unsaturated ring;

$R_{301}$ to $R_{307}$ and $R_{311}$ to $R_{317}$ that do not form the substituted or unsubstituted, saturated or unsaturated ring are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms;

$R_{321}$ and $R_{322}$ are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms; and $R_{901}$ to $R_{907}$ are as defined in the formula (1).

Example of "One pair of two or more adjacent groups of $R_{301}$ to $R_{307}$ and $R_{311}$ to $R_{317}$" is pairs of $R_{301}$ and $R_{302}$, $R_{302}$ and $R_{303}$ $R_{303}$ and $R_{304}$, $R_{305}$ and $R_{306}$, $R_{306}$ and $R_{307}$, and $R_{301}$, $R_{302}$ and $R_{303}$, and the like.

In one embodiment, at least one of $R_{301}$ to $R_{307}$ and $R_{311}$ to $R_{317}$, preferably two of $R_{301}$ to $R_{307}$ and $R_{311}$ to $R_{317}$ are groups represented by —N($R_{906}$)($R_{907}$).

In one embodiment, $R_{301}$ to $R_{307}$ and $R_{311}$ to $R_{317}$ are independently a hydrogen atom, a substituted or unsubstituted aryl group including 6 to 50 ring carbon atoms, or a substituted or unsubstituted monovalent heterocyclic group including 5 to 50 ring atoms.

In one embodiment, the compound represented by the formula (31) is a compound represented by the following formula (32).

(32)

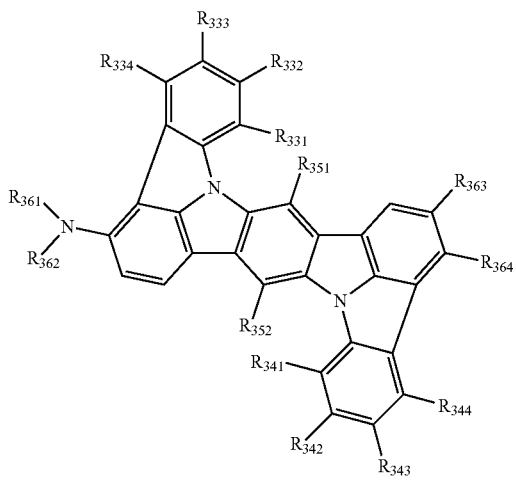

In the formula (32), one or more pairs of two or more adjacent groups of $R_{331}$ to $R_{334}$ and $R_{341}$ to $R_{344}$ form a substituted or unsubstituted, saturated or unsaturated ring, or do not form a substituted or unsubstituted saturated or unsaturated ring;

$R_{331}$ to $R_{334}$ and $R_{341}$ to $R_{344}$ that do not form the substituted or unsubstituted, saturated or unsaturated ring and $R_{351}$ and $R_{352}$ are independently a hydrogen atom, a substituted or unsubstituted aryl group including 6 to 50 ring carbon atoms, or a substituted or unsubstituted monovalent heterocyclic group including 5 to 50 ring atoms; and $R_{361}$ to $R_{364}$ are independently a substituted or unsubstituted aryl group including 6 to 50 ring carbon atoms, or a substituted or unsubstituted monovalent heterocyclic group including 5 to 50 ring atoms.

In one embodiment, the compound represented by the formula (31) is a compound represented by the formula (33).

(33)

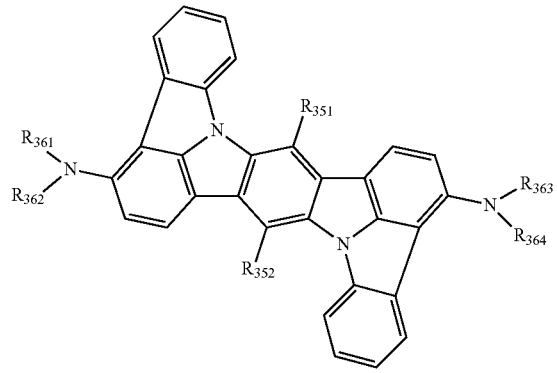

In the formula (33), $R_{351}$, $R_{352}$, and $R_{361}$ to $R_{364}$ are as defined in the formula (32).

In one embodiment, $R_{361}$ to $R_{364}$ in the formulas (32) and (33) are independently a substituted or unsubstituted aryl group including 6 to 50 ring carbon atoms (preferably a phenyl group).

In one embodiment, $R_{321}$ and $R_{322}$ in the formula (31), and $R_{351}$ and $R_{352}$ in the formulas (32) and (33) are hydrogen atoms.

In one embodiment, a substituent in the case of "substituted or unsubstituted" in the formulas (31) to (33) is a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms.

As the compound represented by the formula (31), the following compounds can be given for example. In the following example compounds, Me represents methyl group.

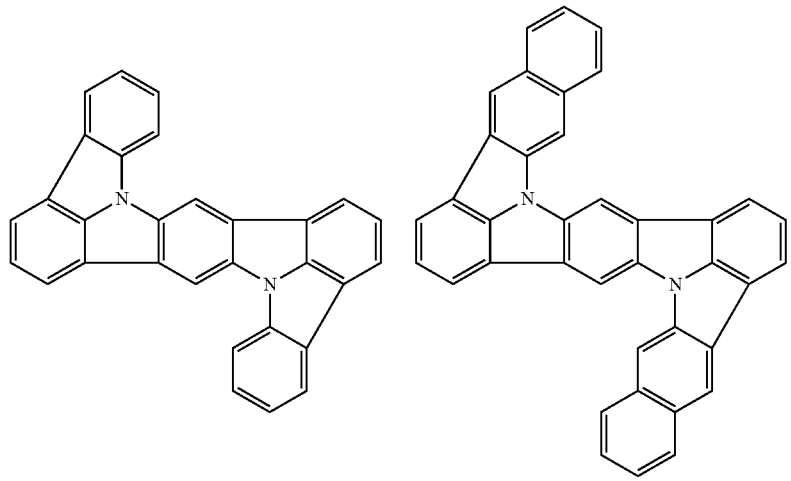

229 230
-continued
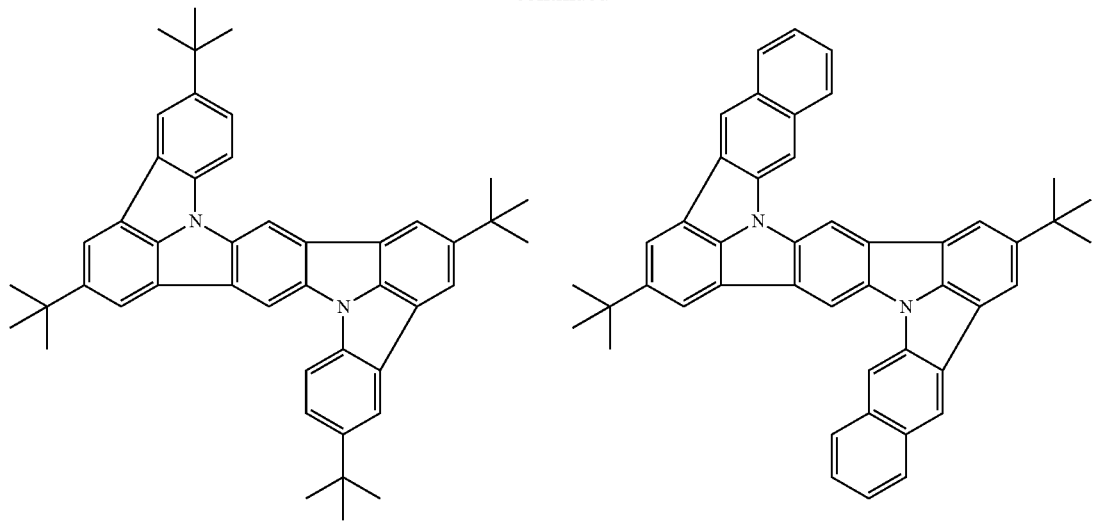
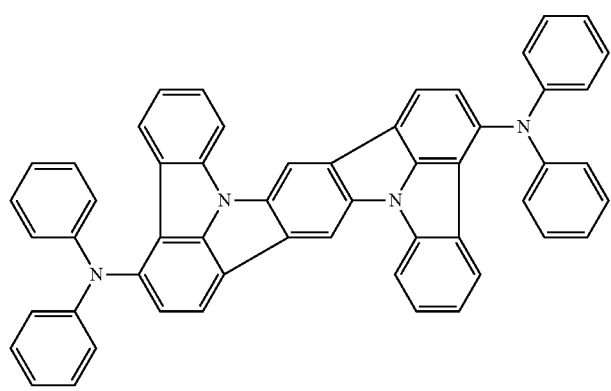
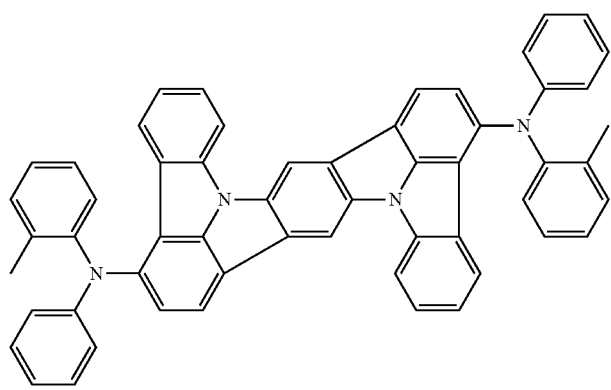
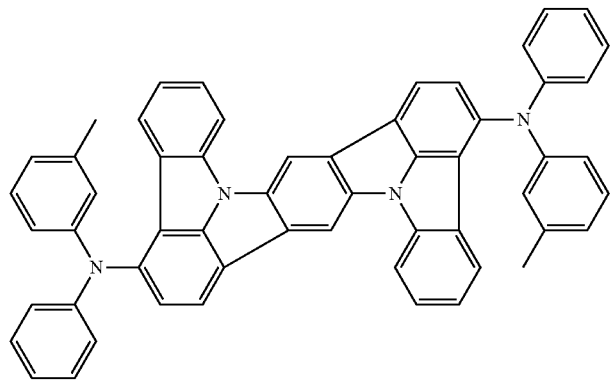

-continued
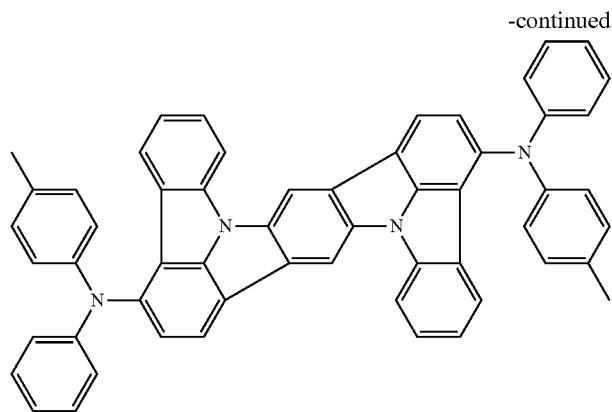
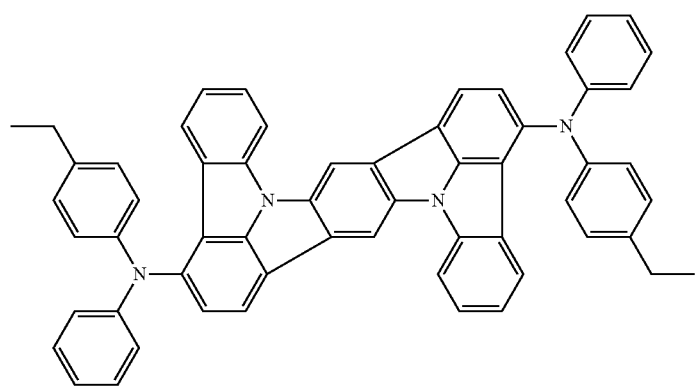
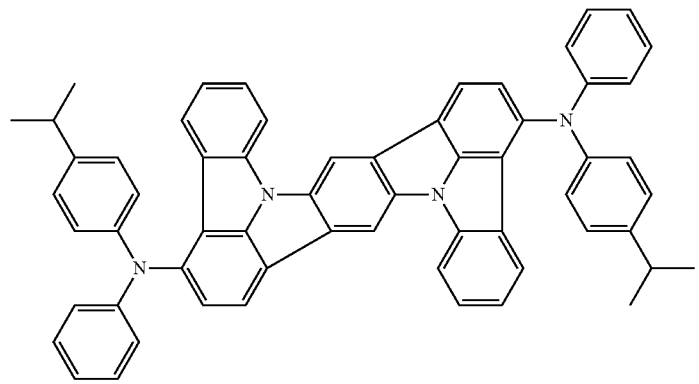
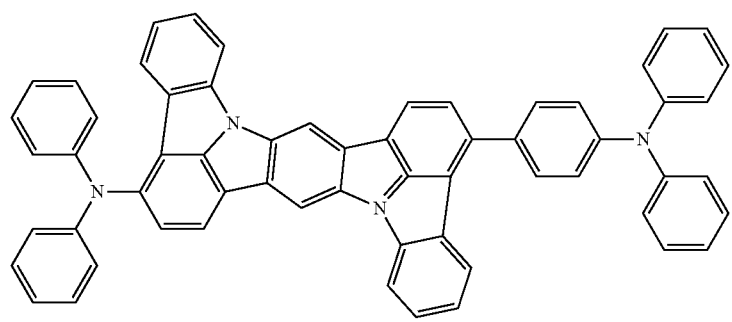

-continued
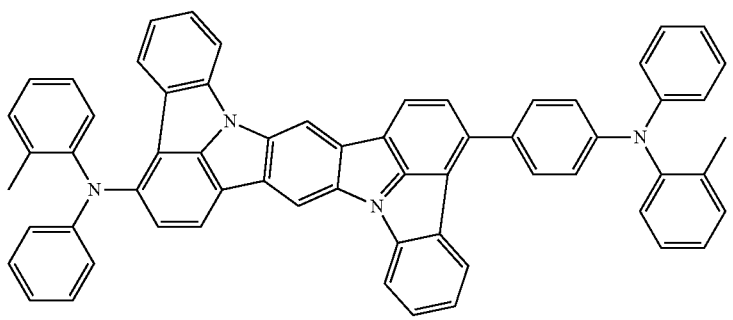
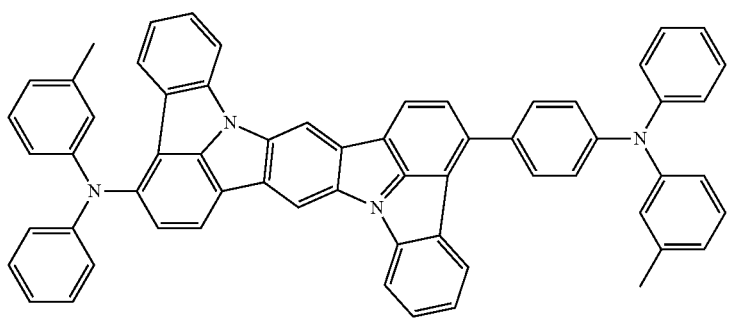
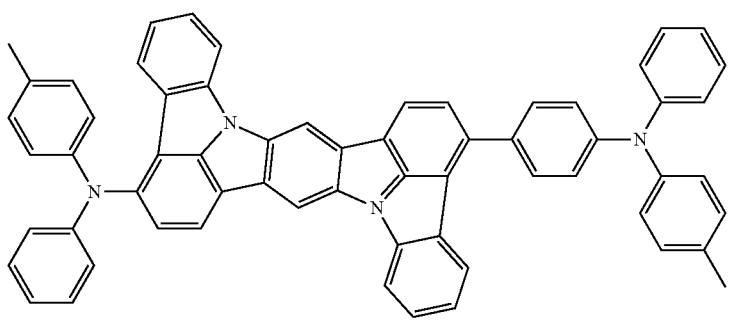
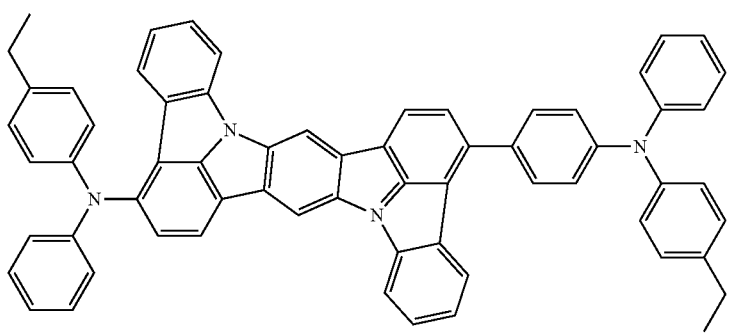
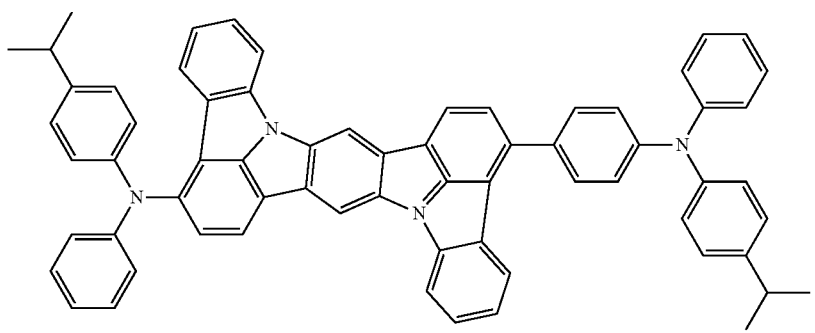

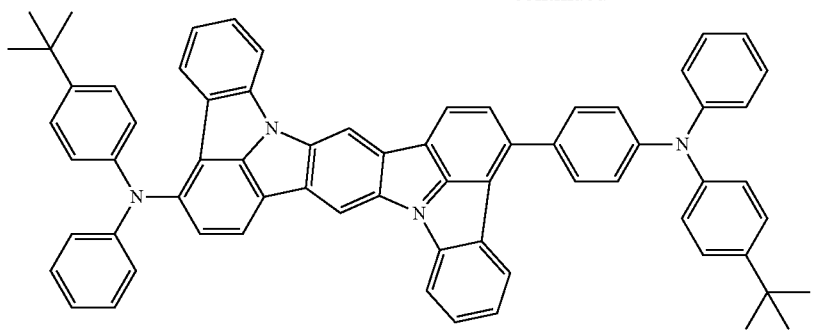
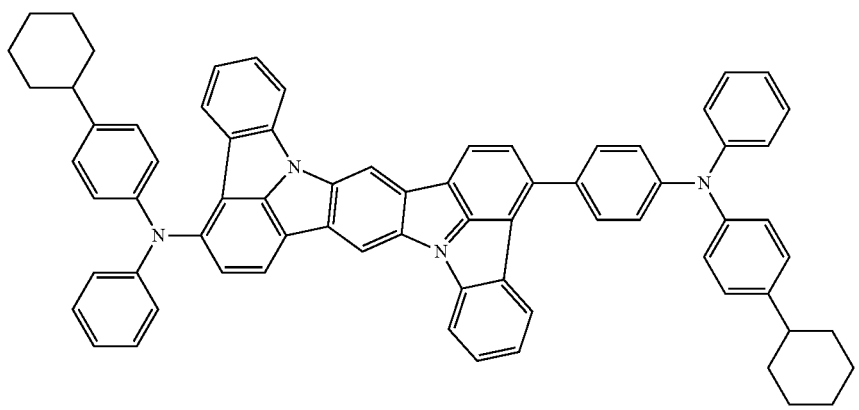
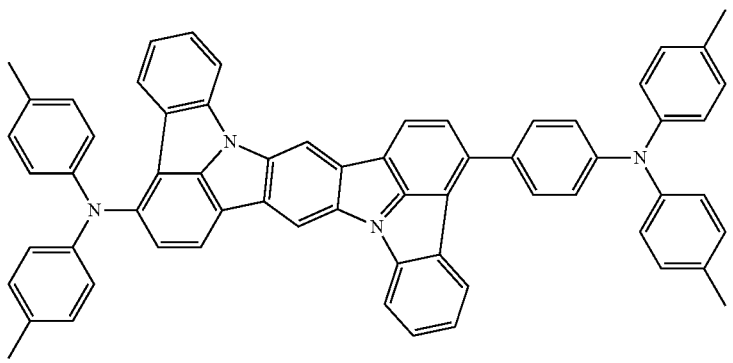
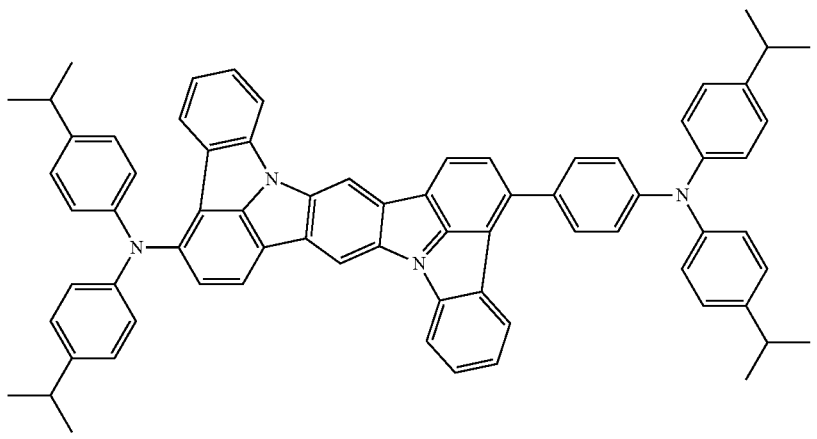

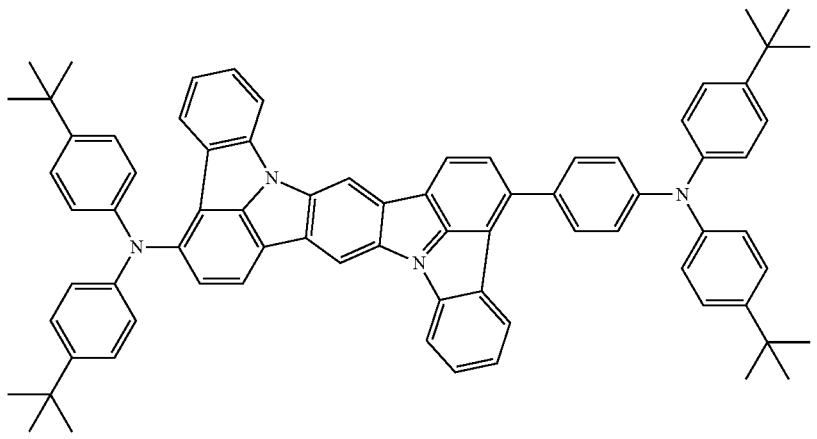
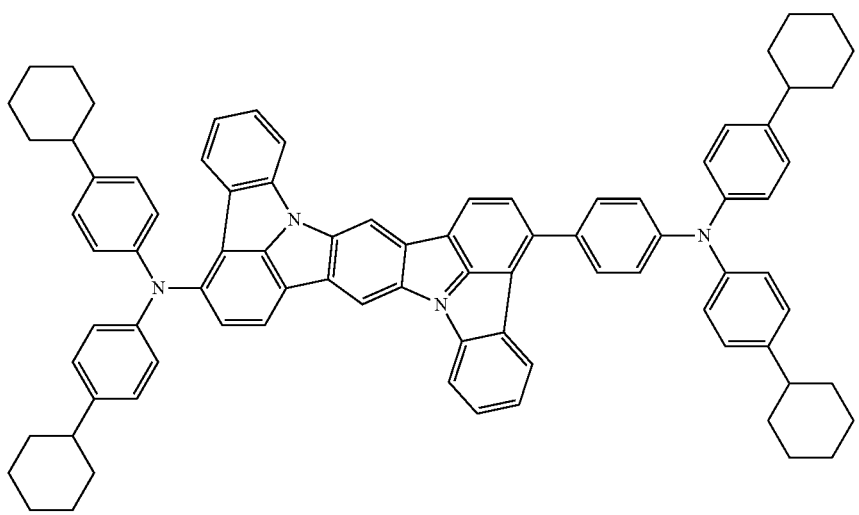
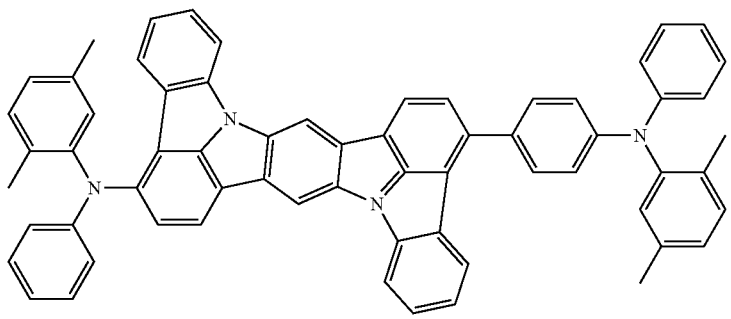
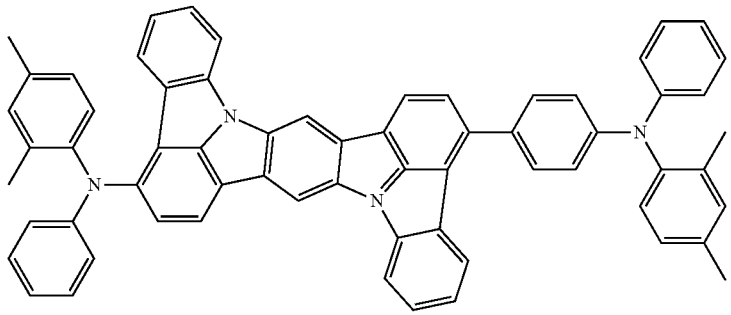

-continued
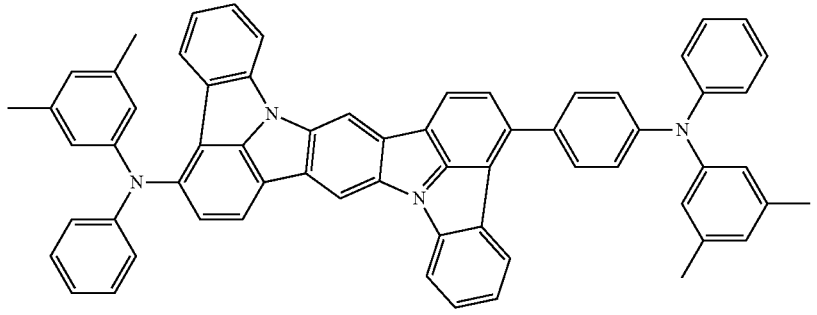
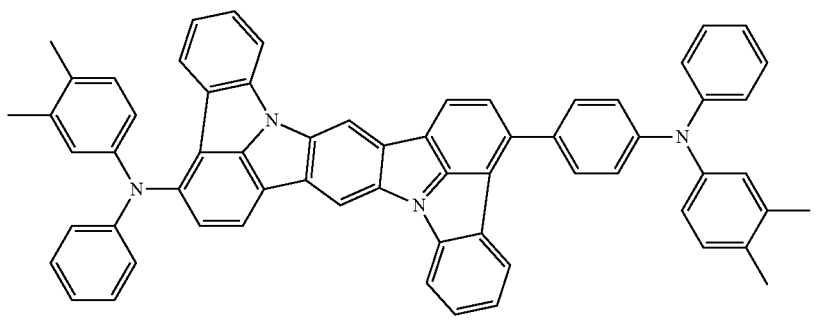
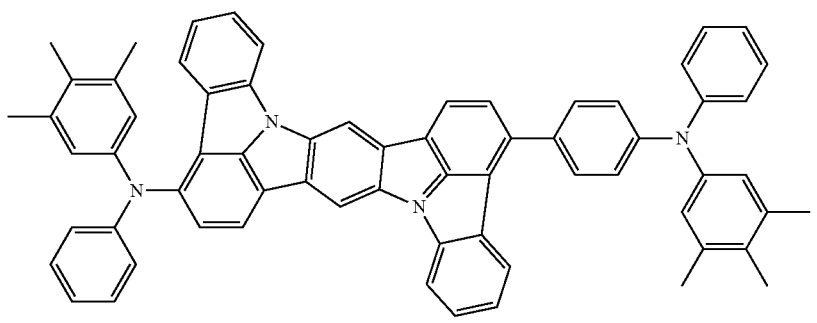
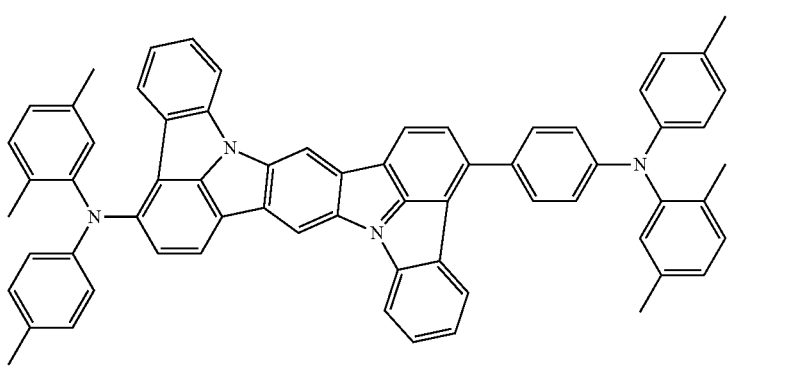
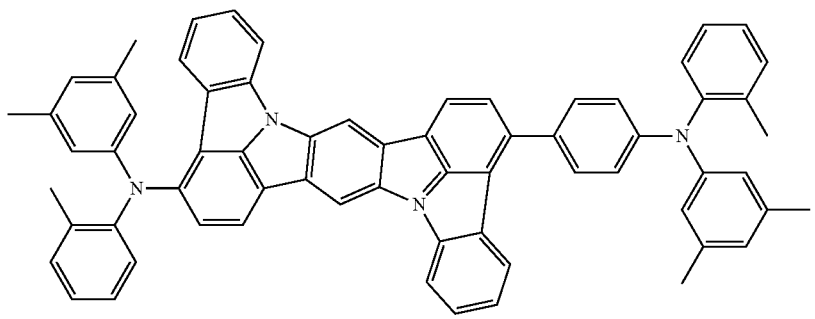

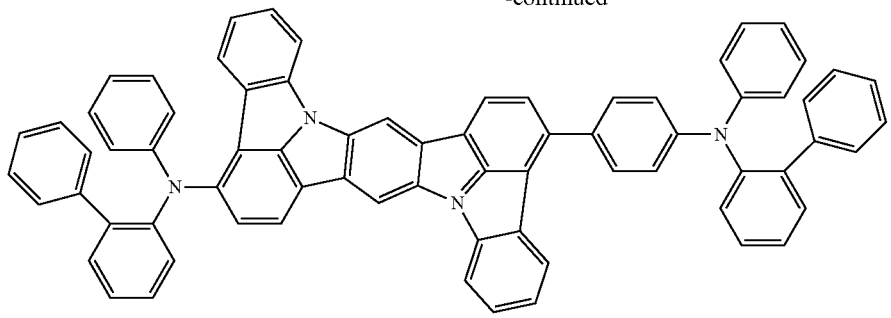
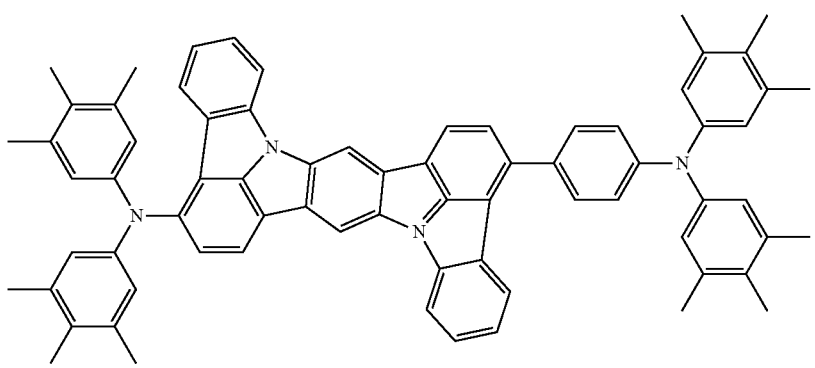
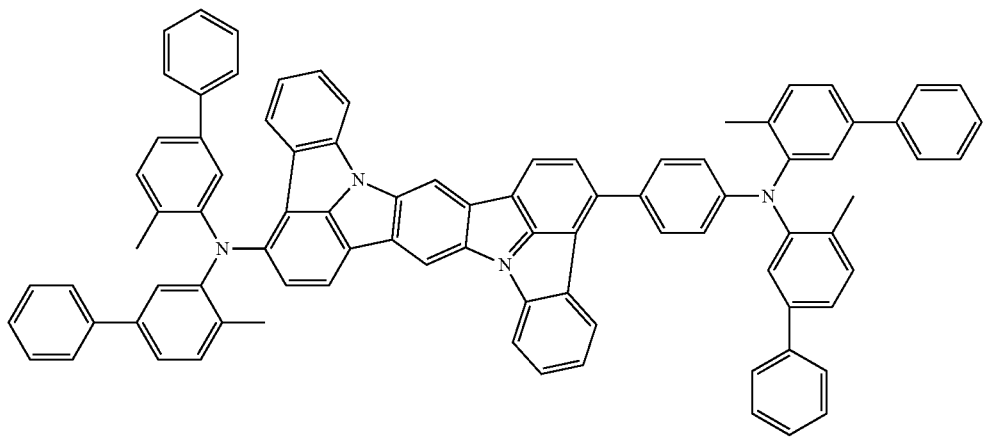
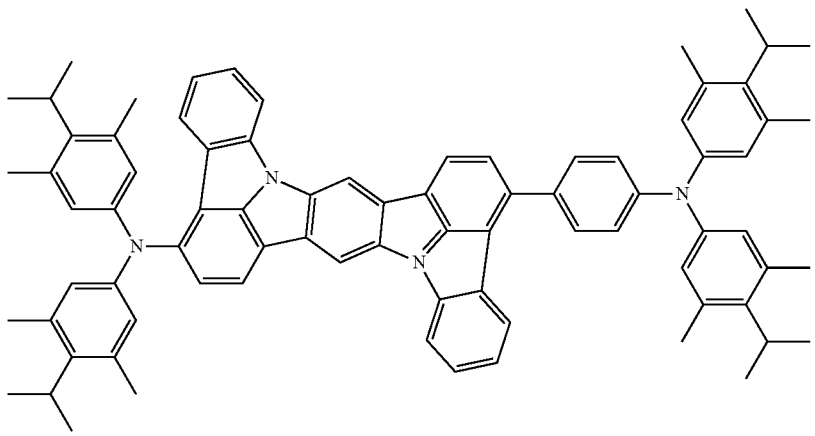

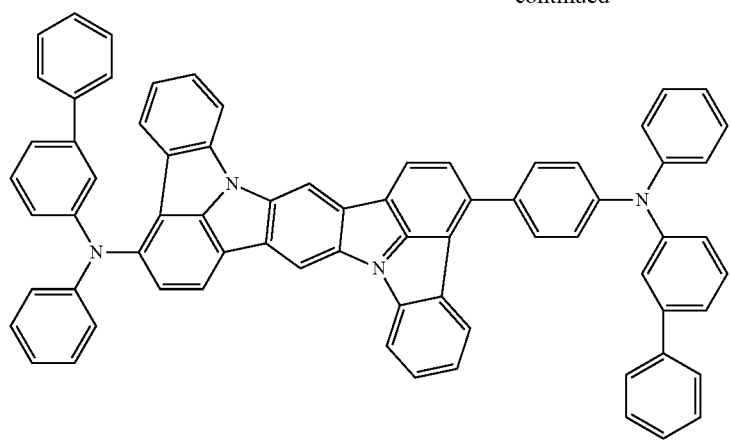
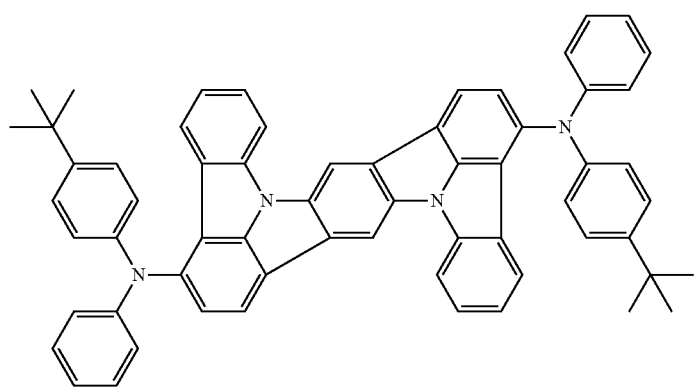
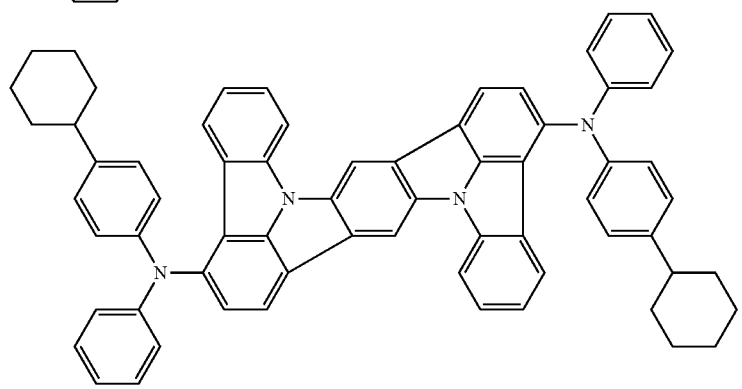
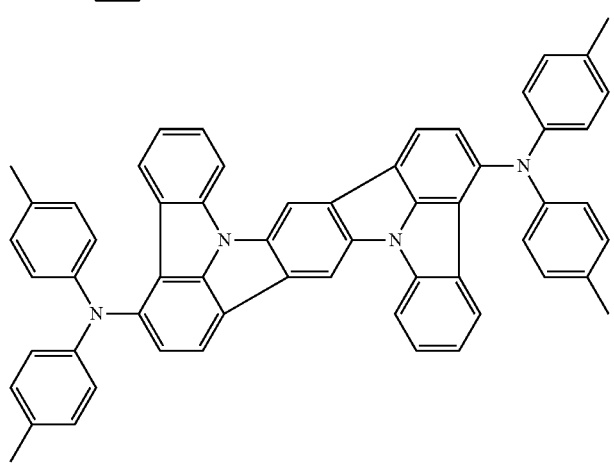

-continued
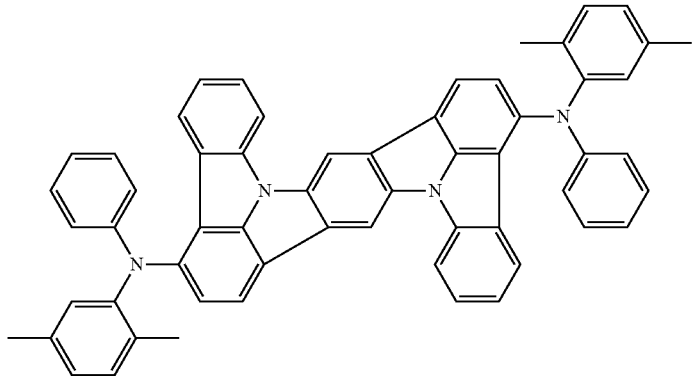
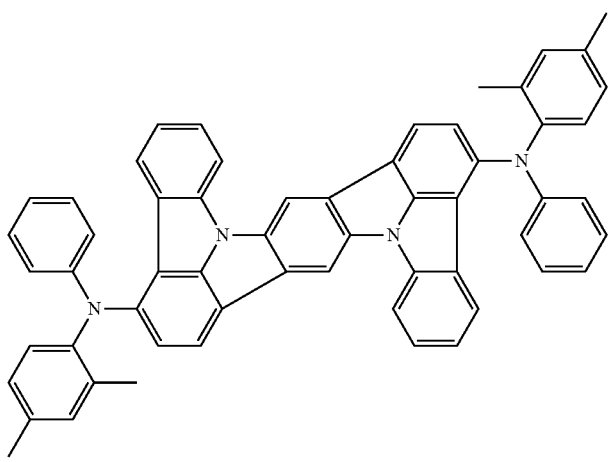
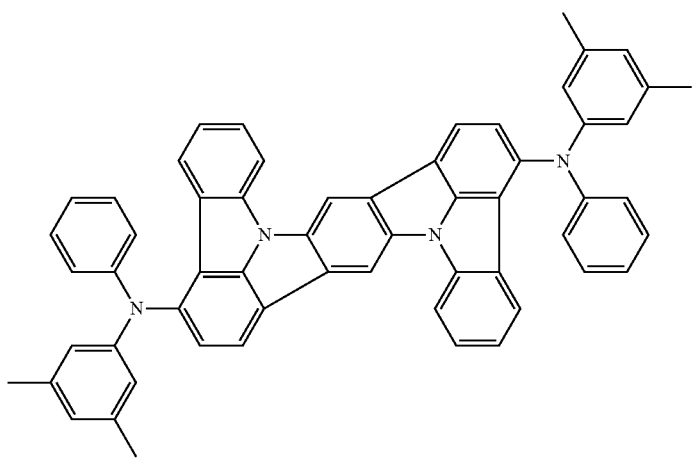

-continued
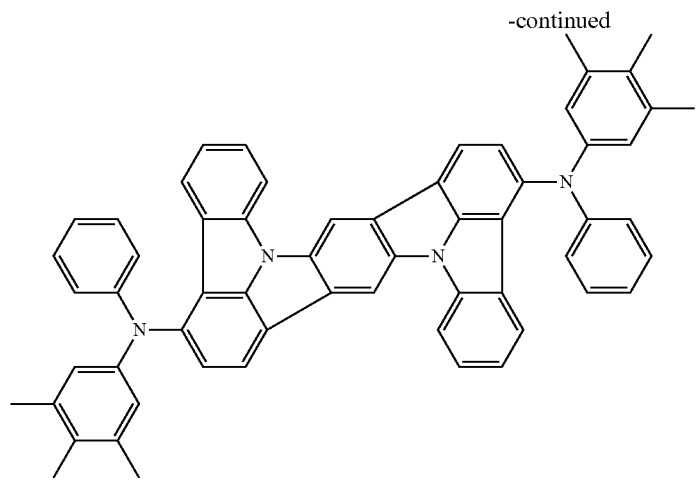
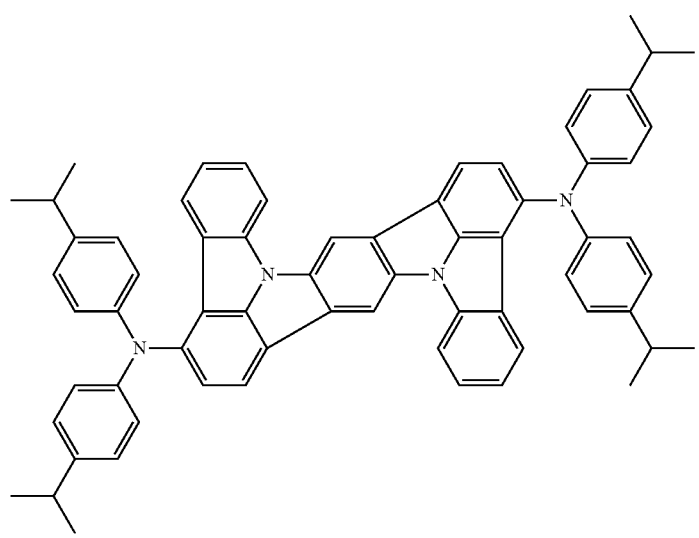
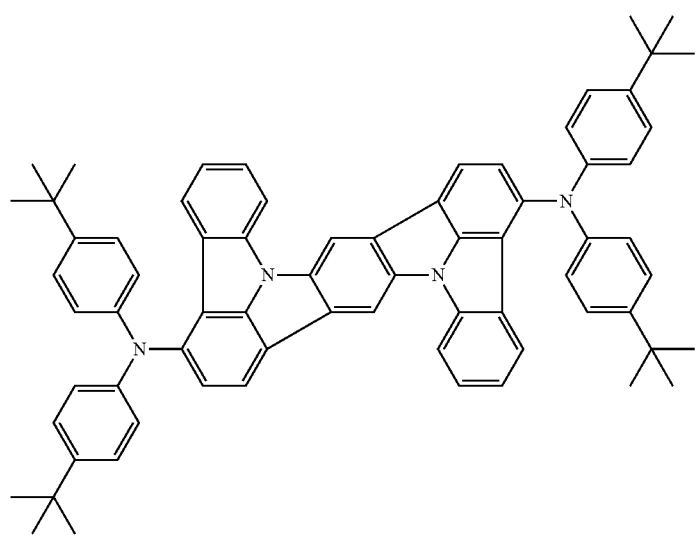

-continued
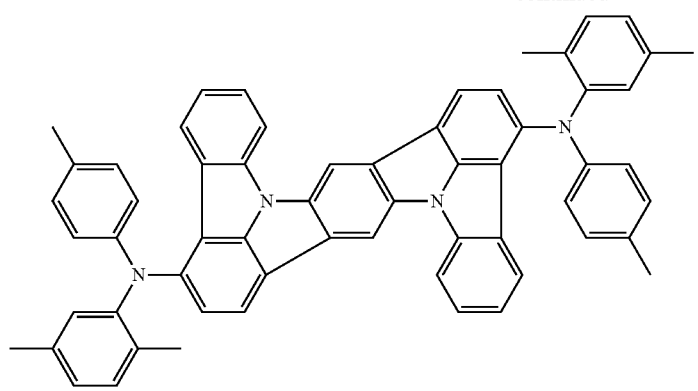
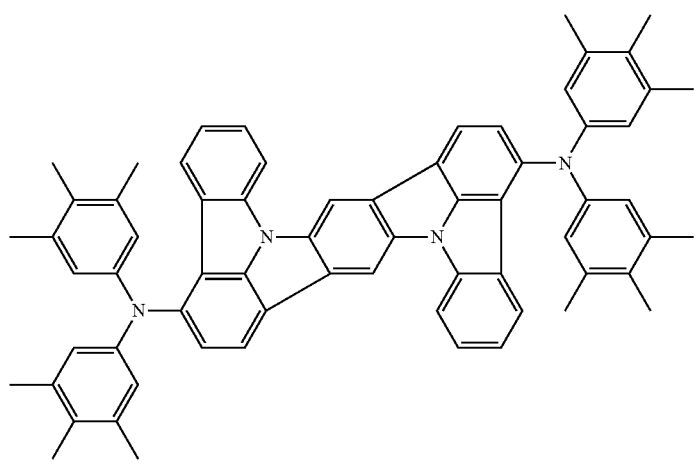
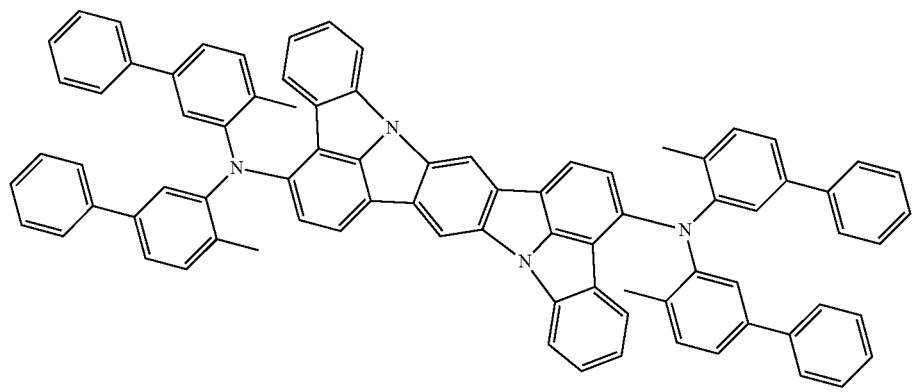
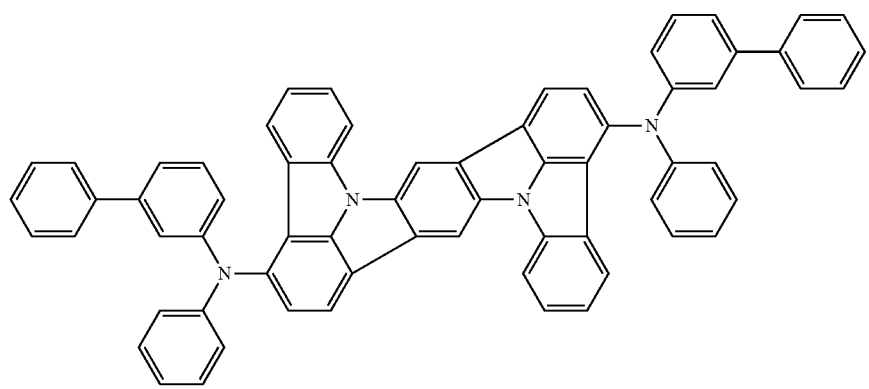

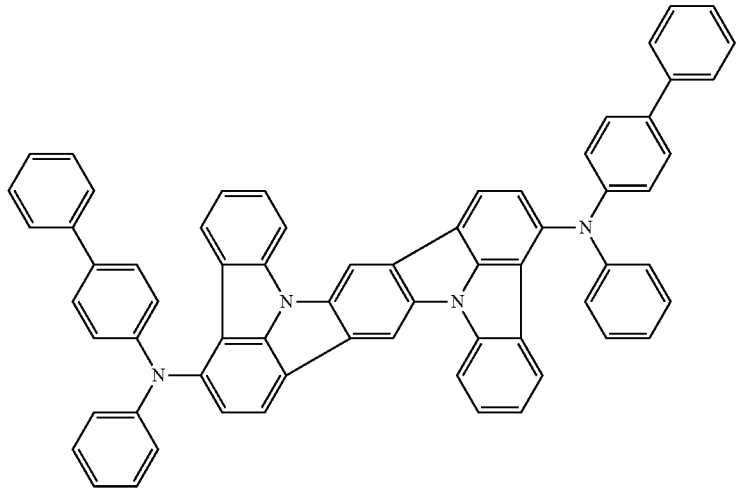
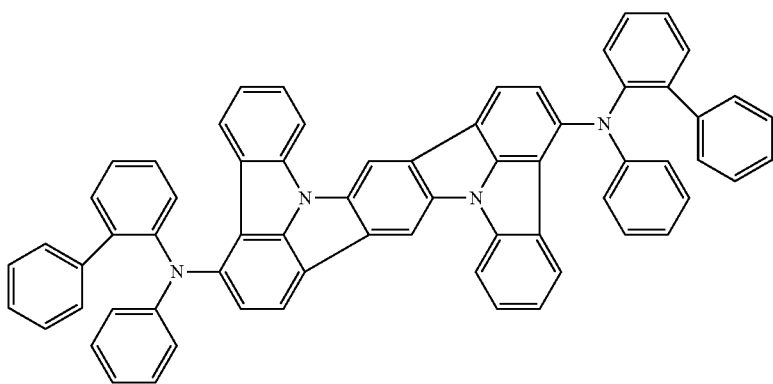
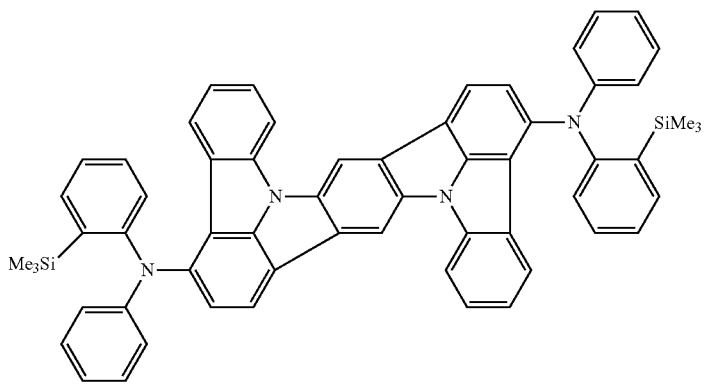
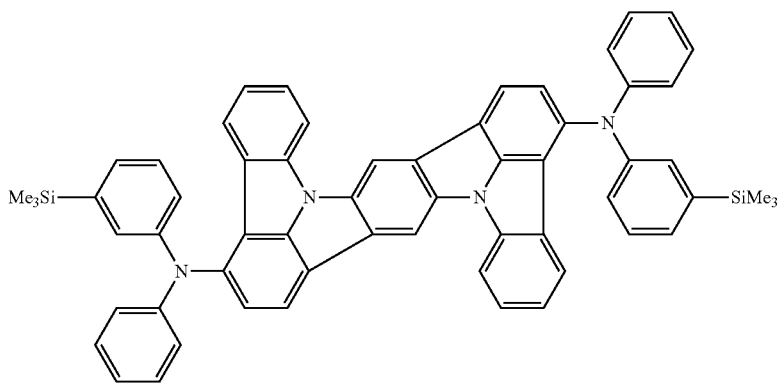

-continued
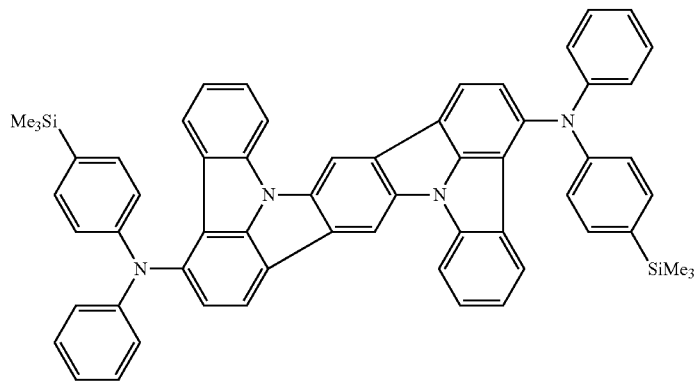
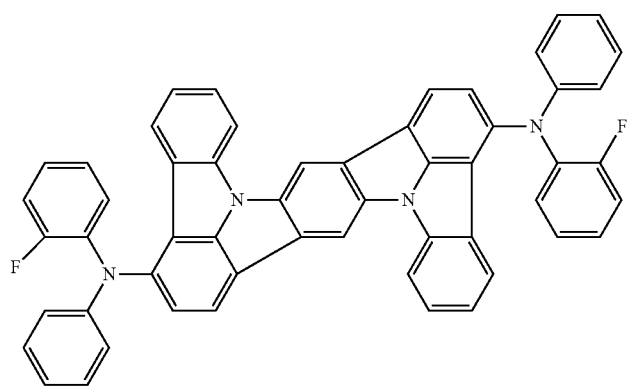
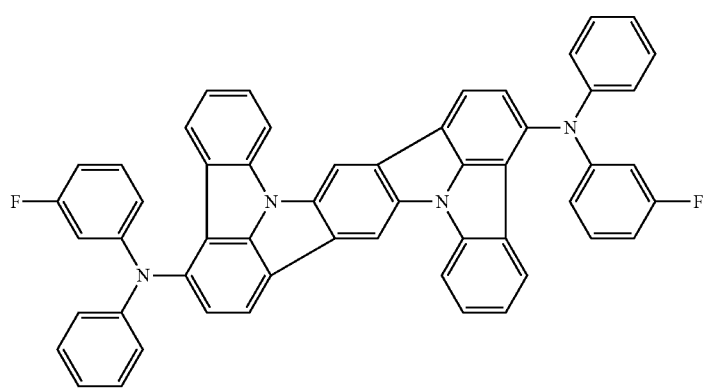
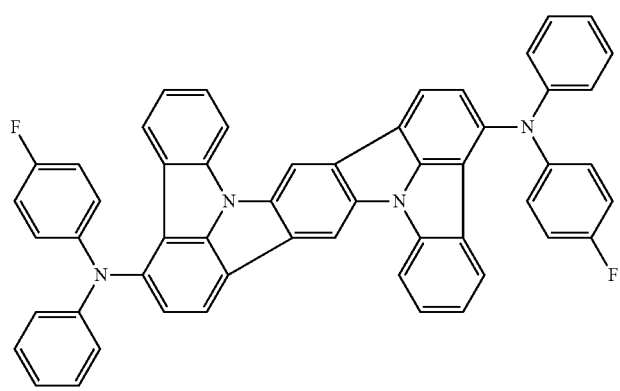

-continued
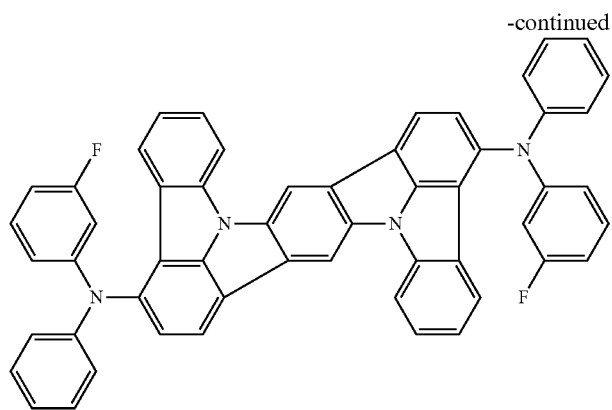
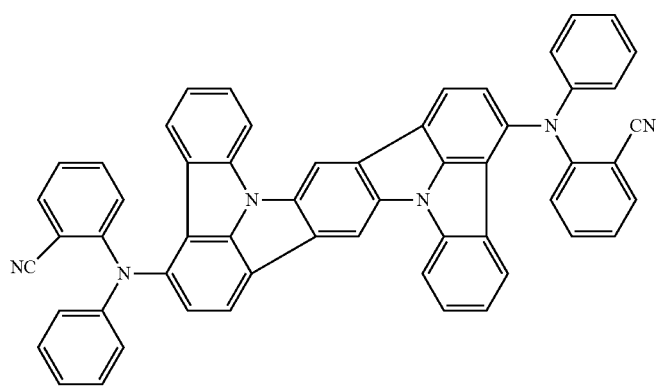
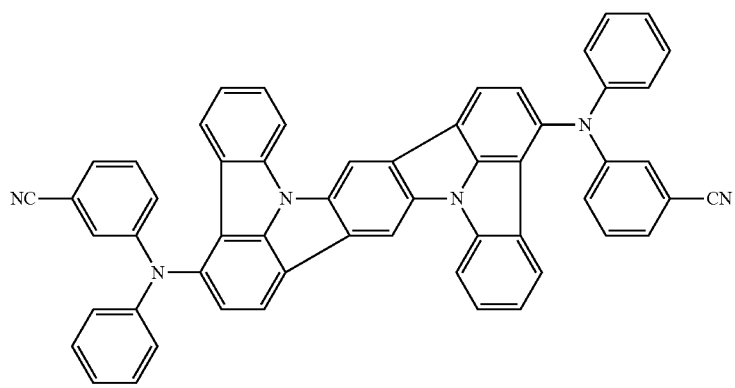
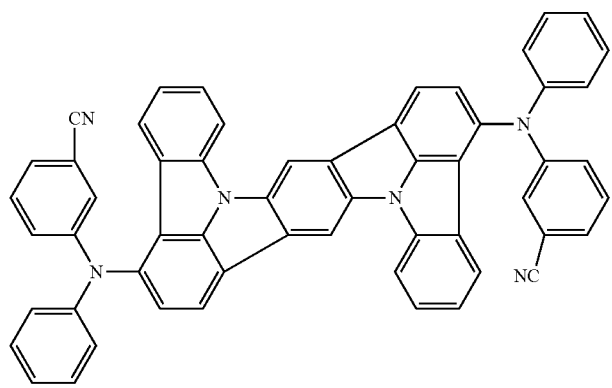

-continued
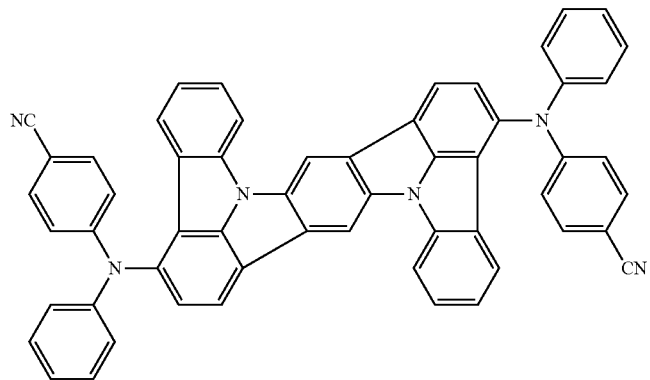
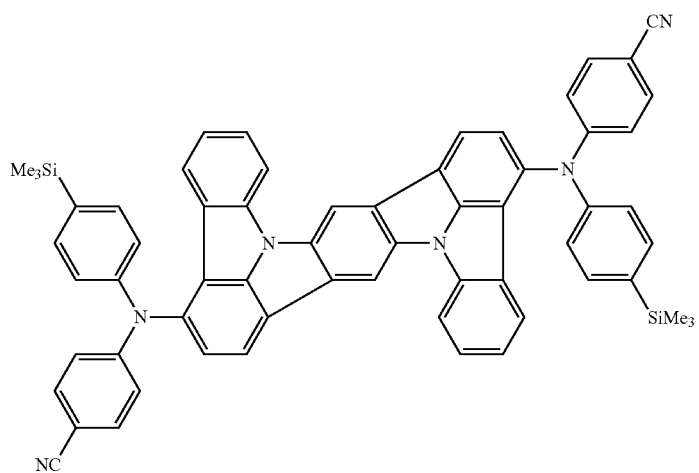 [SMILES: C[Si](C)(C)c1ccc(N(c2ccc(C#N)cc2)c2ccc3c4cc5c(cc4n4c6ccccc6c2c34)c2ccc(N(c3ccc(C#N)cc3)c3ccc([Si](C)(C)C)cc3)c3c4ccccc4n5c23)cc1]
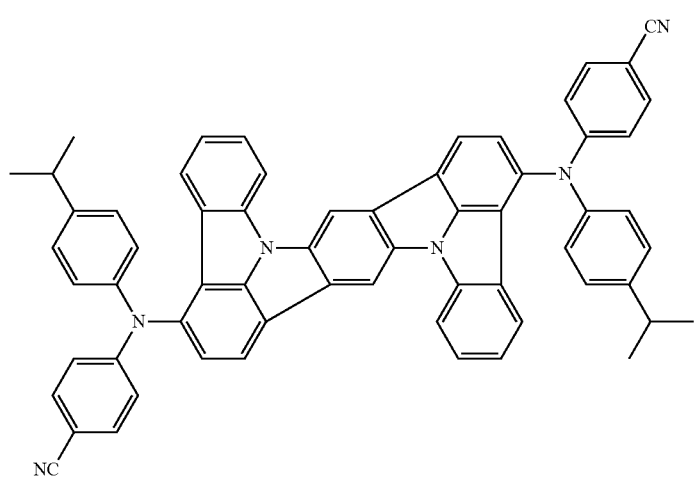
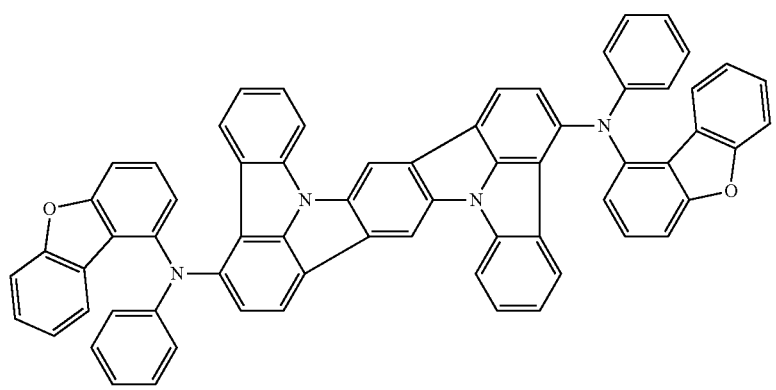

-continued
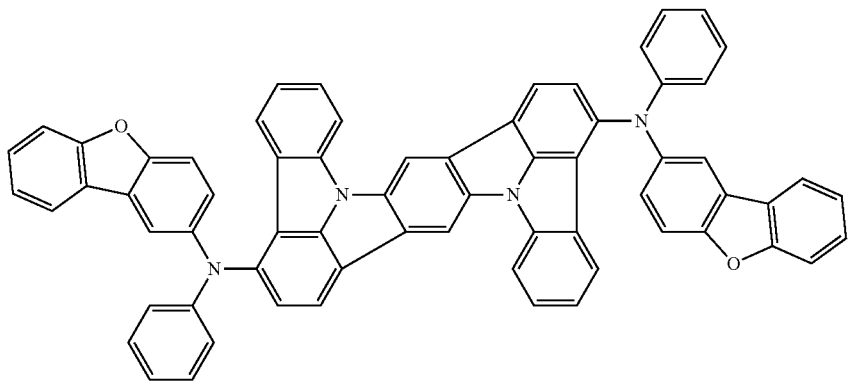
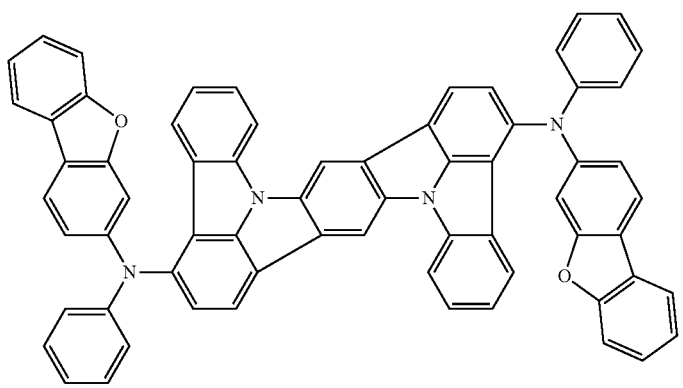
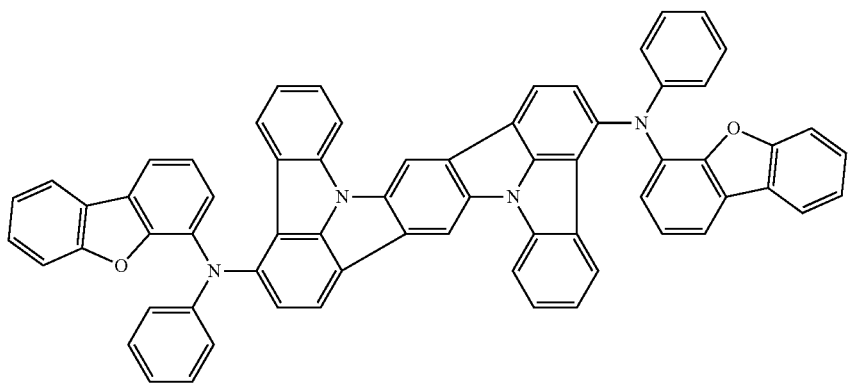
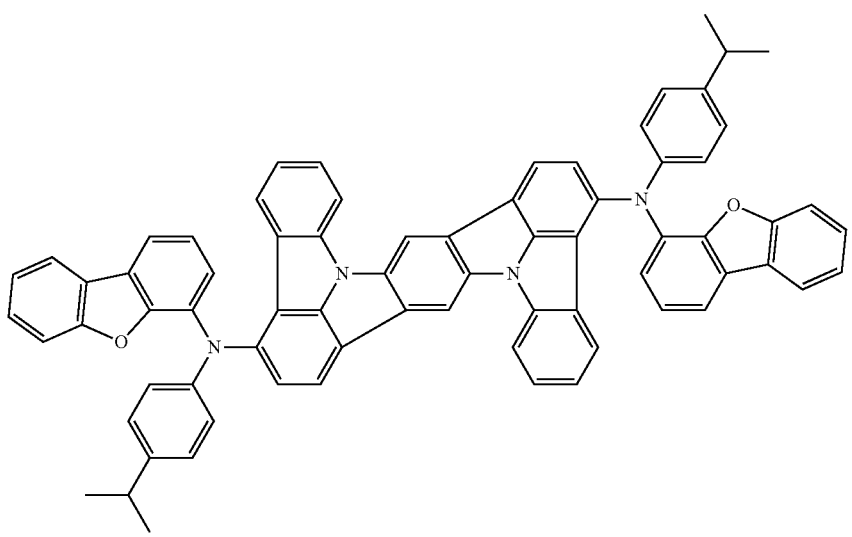

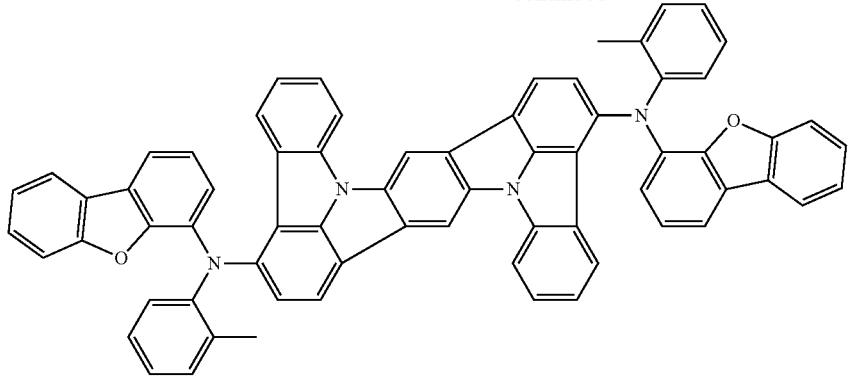
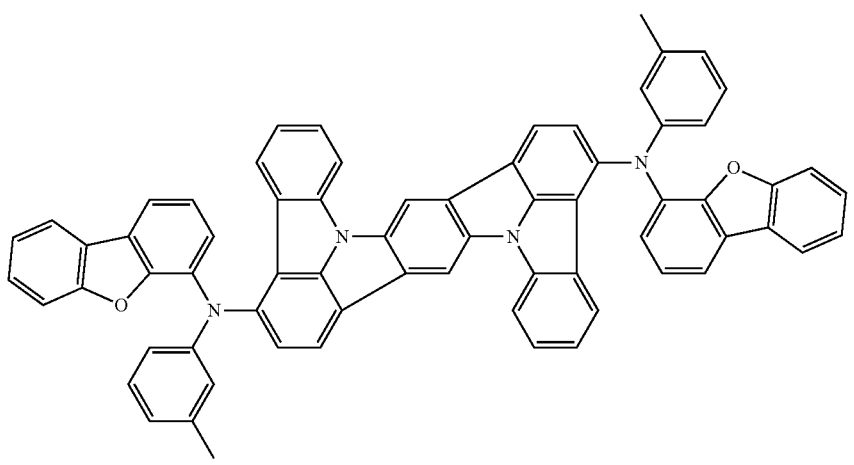
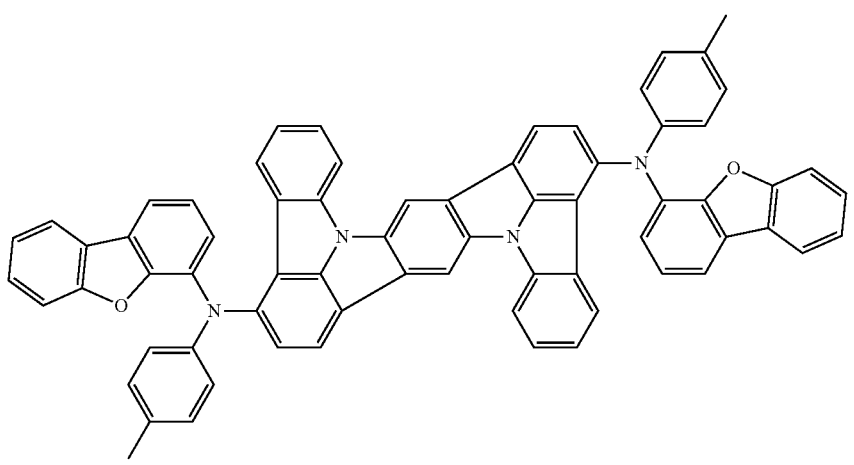

-continued
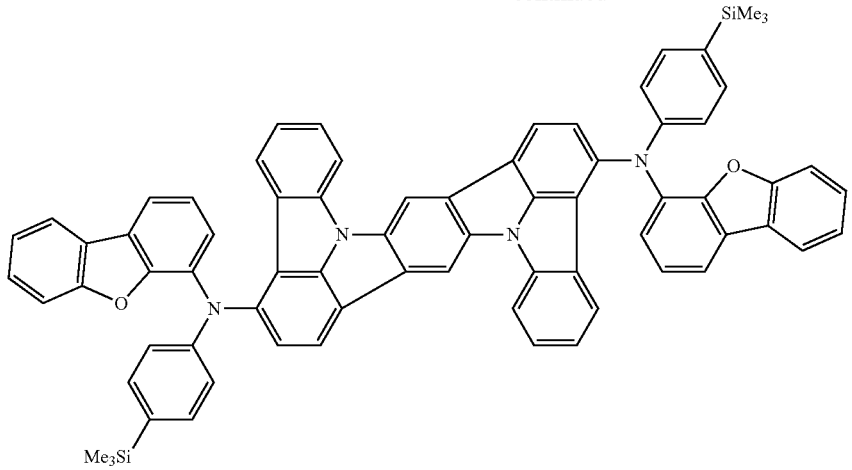
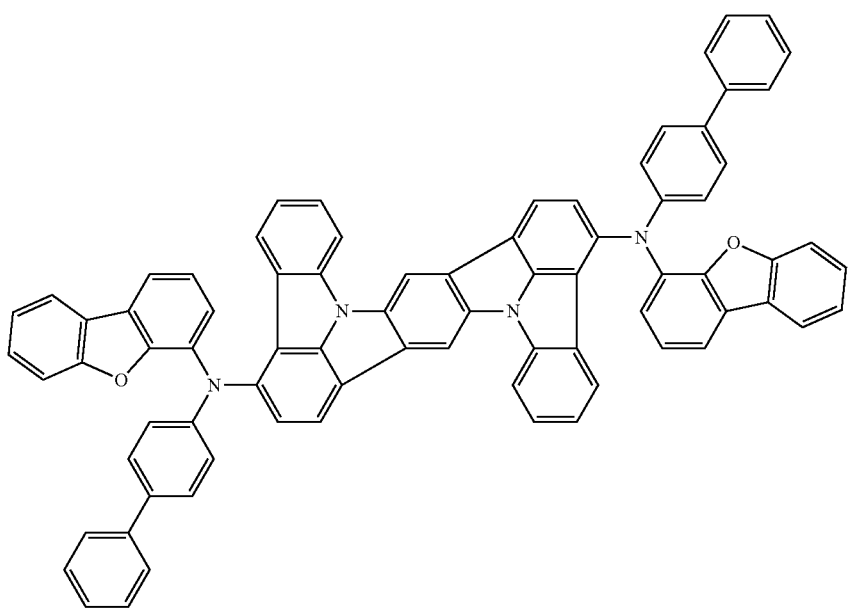
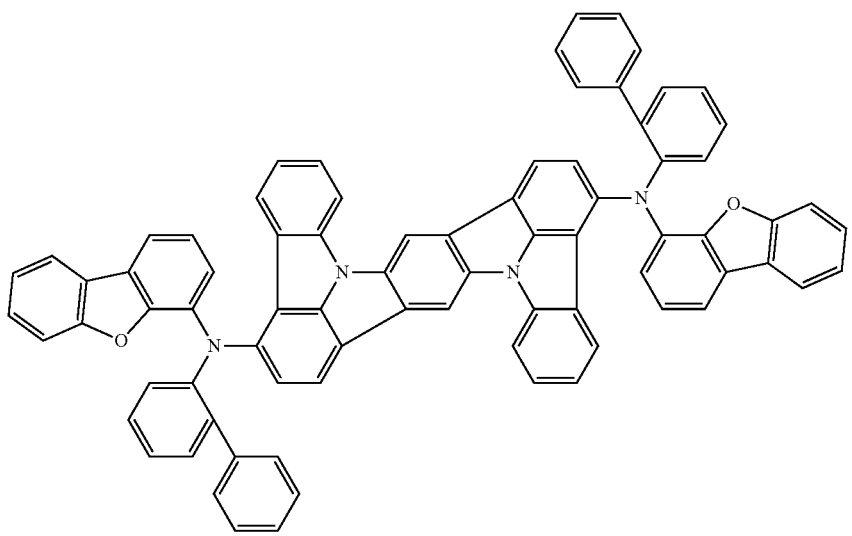

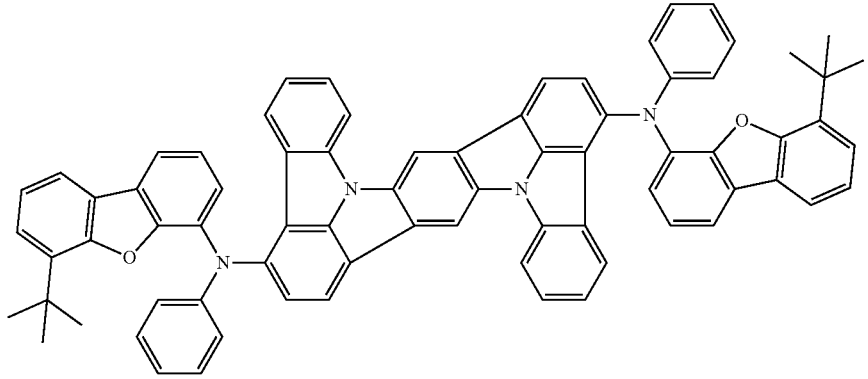
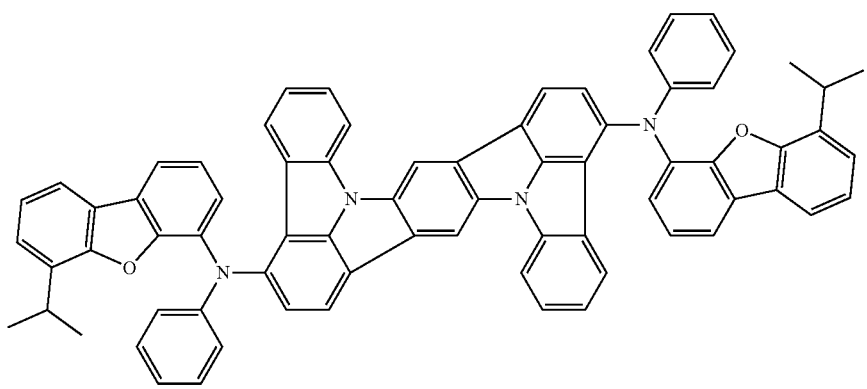
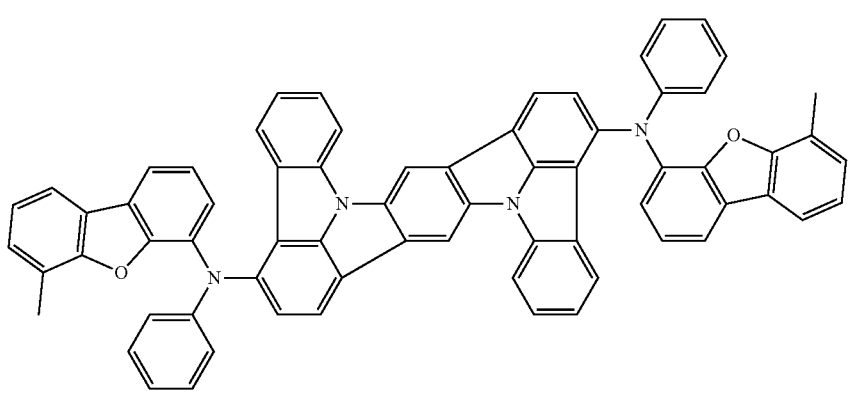
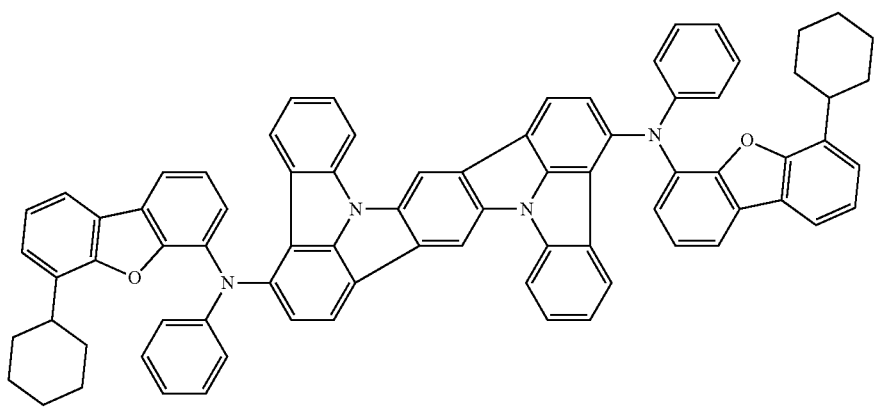

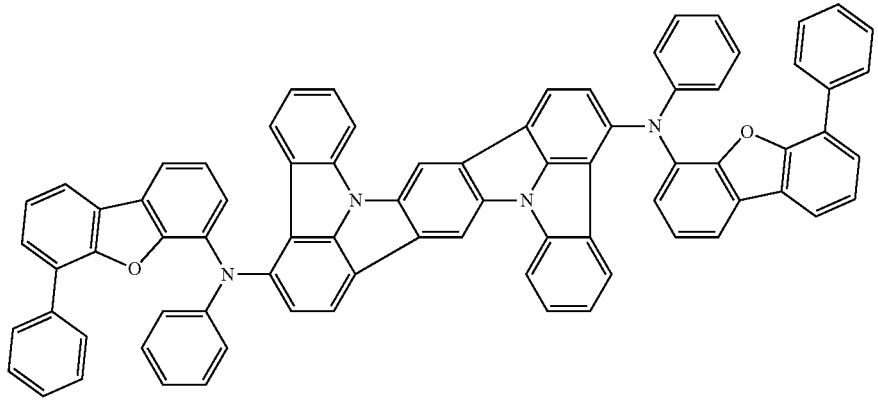
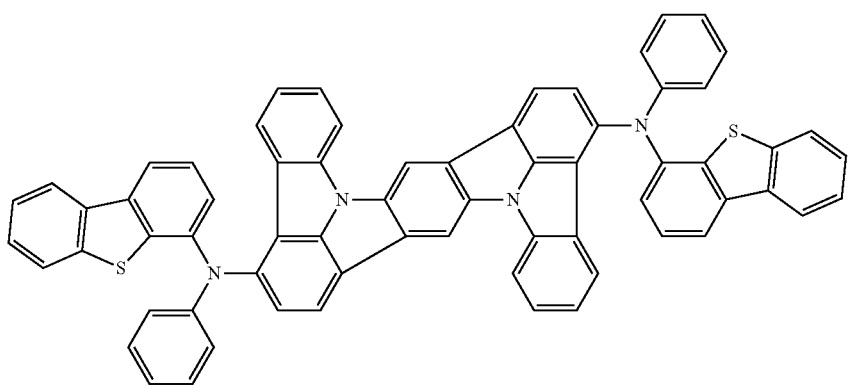
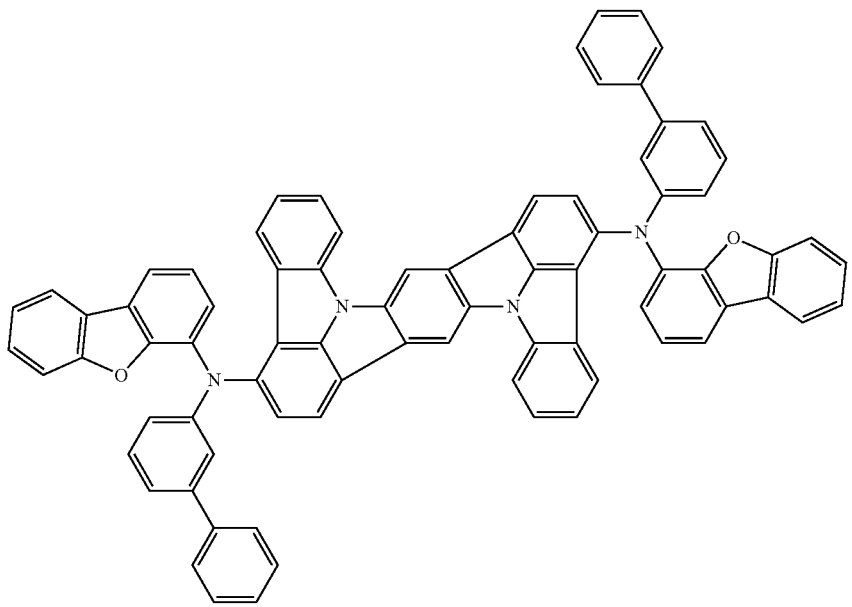
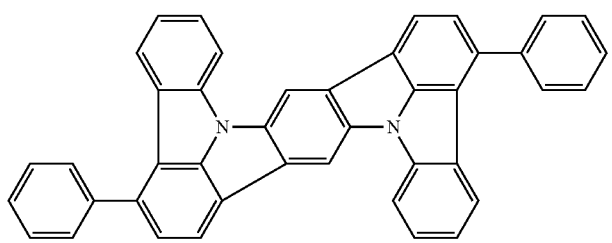

-continued
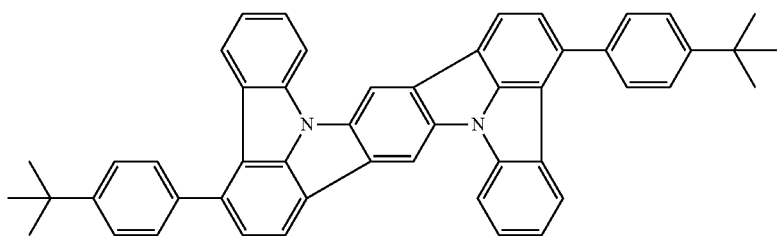
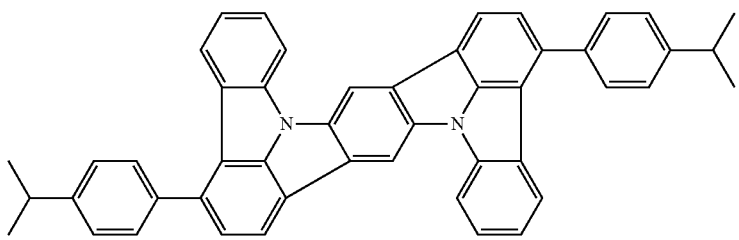
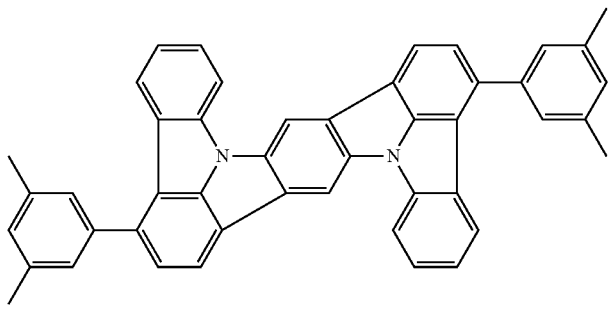
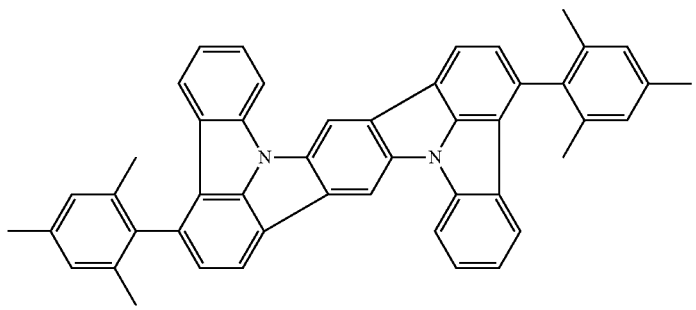
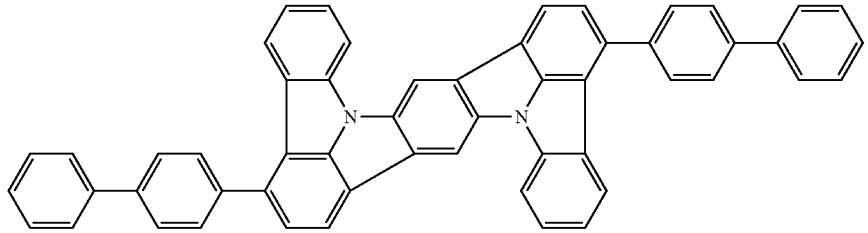
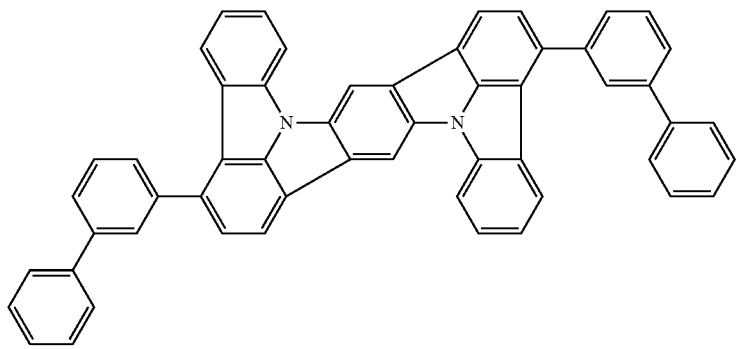

-continued
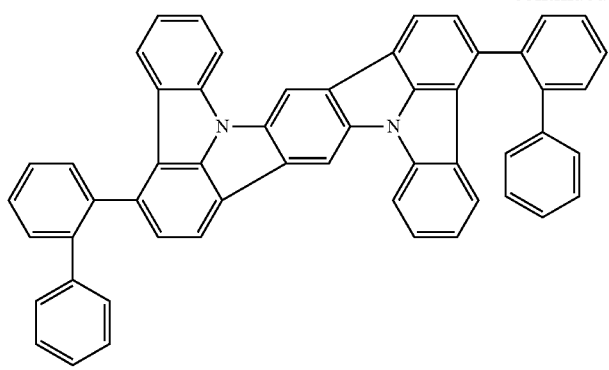
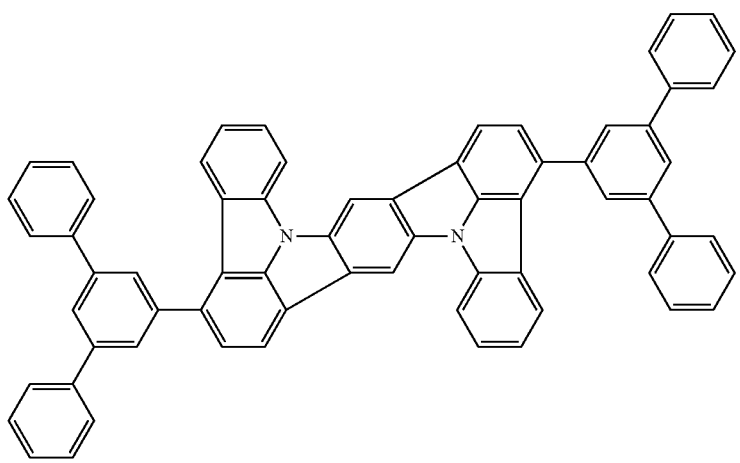
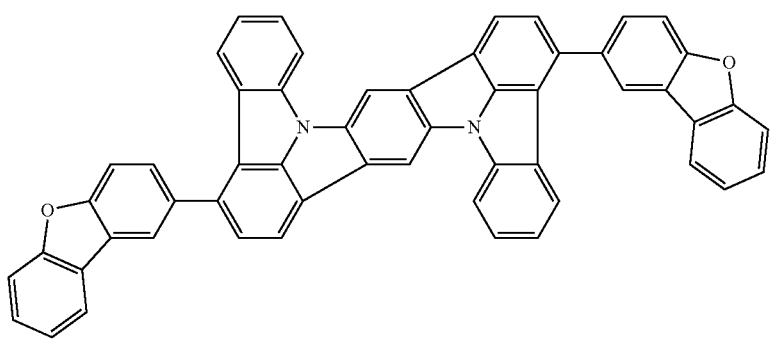
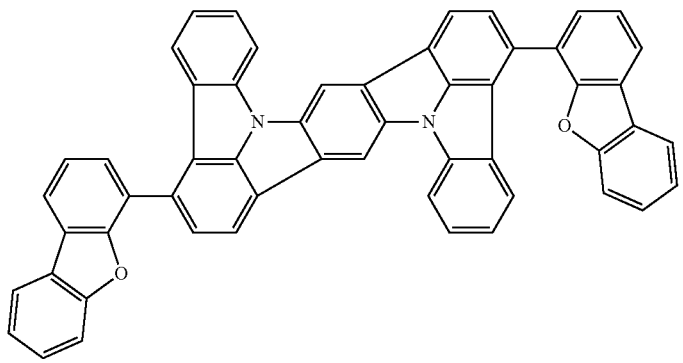

-continued
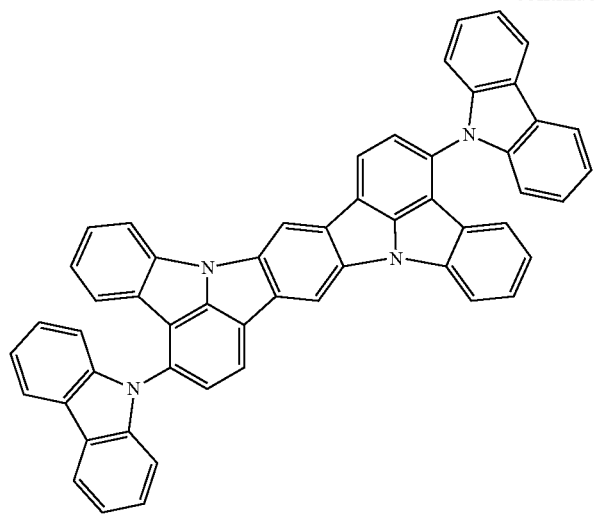
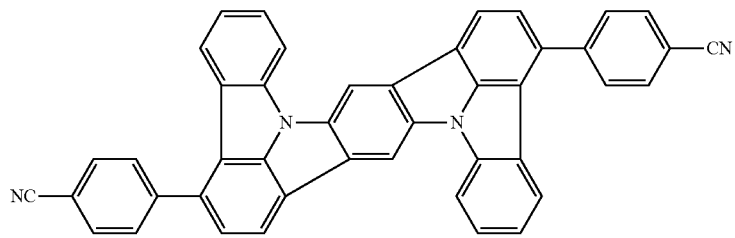
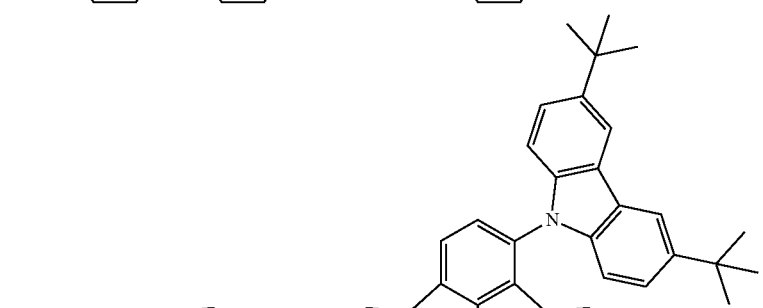
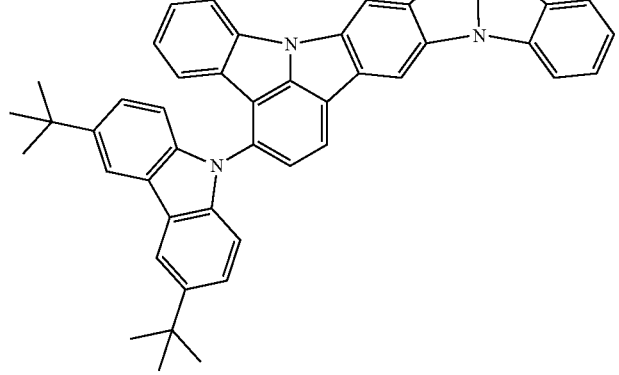
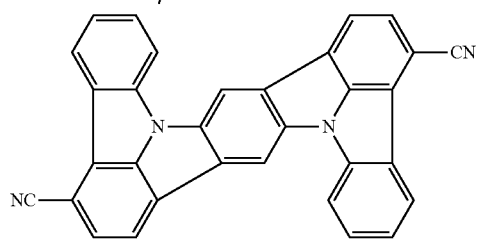

-continued
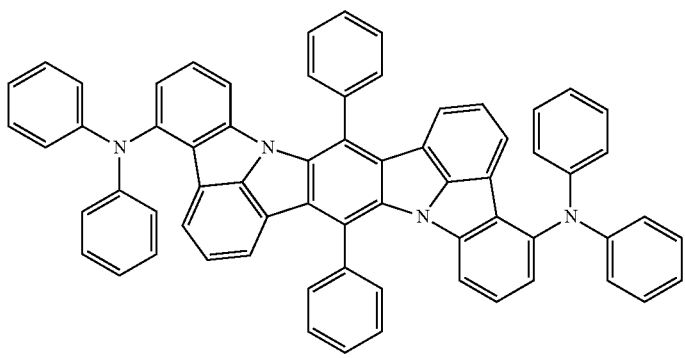
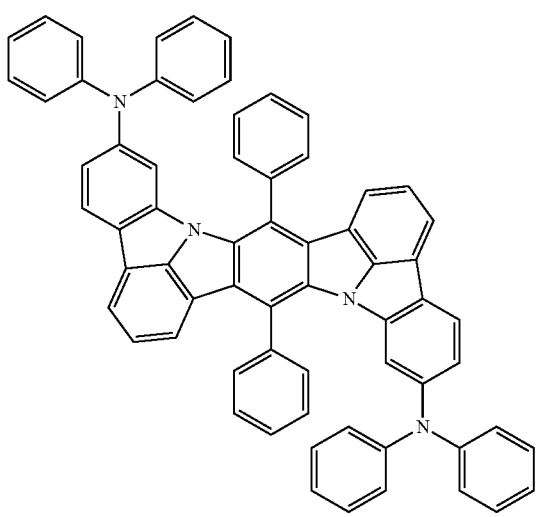
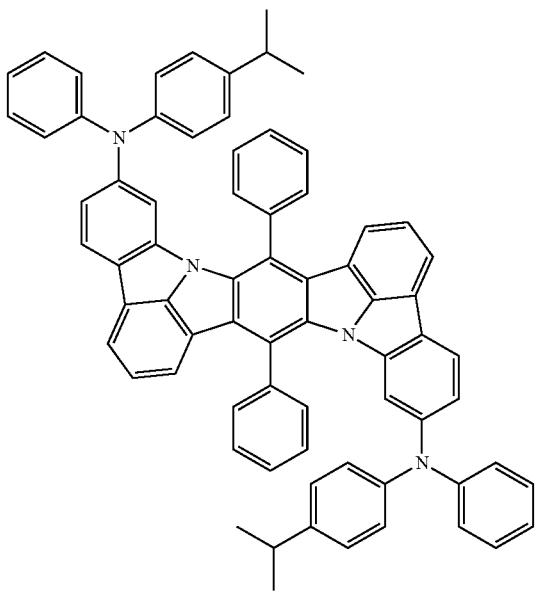
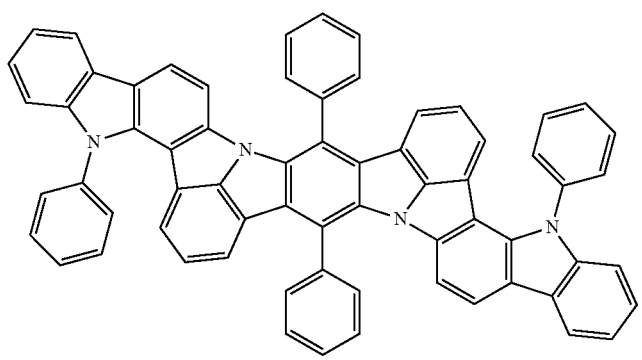
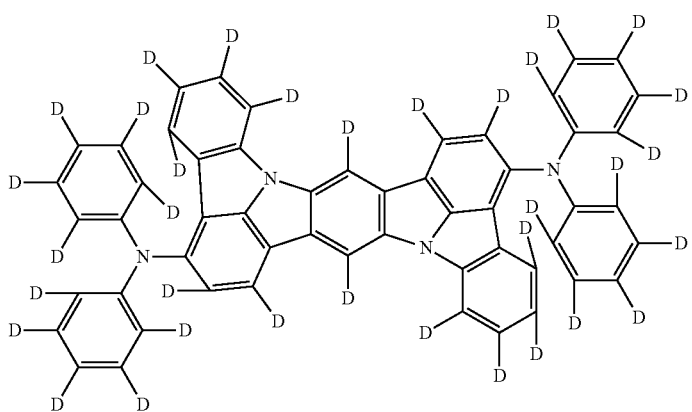

277
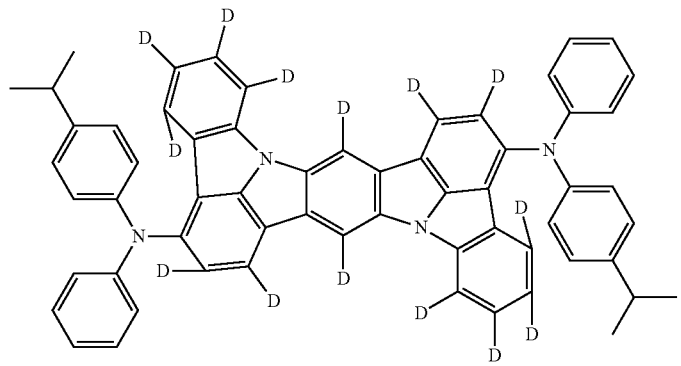
278
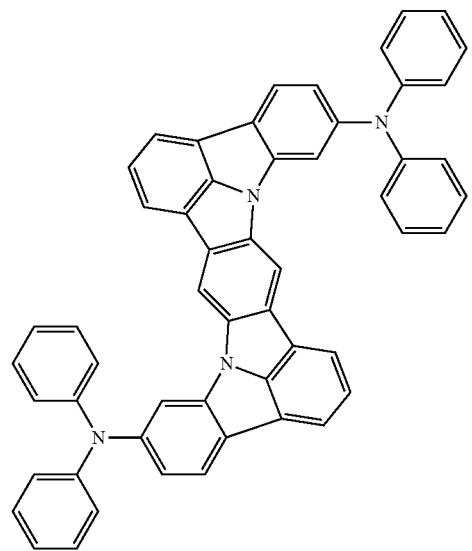
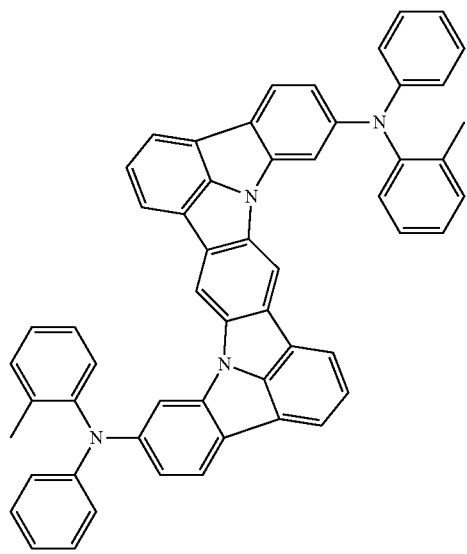
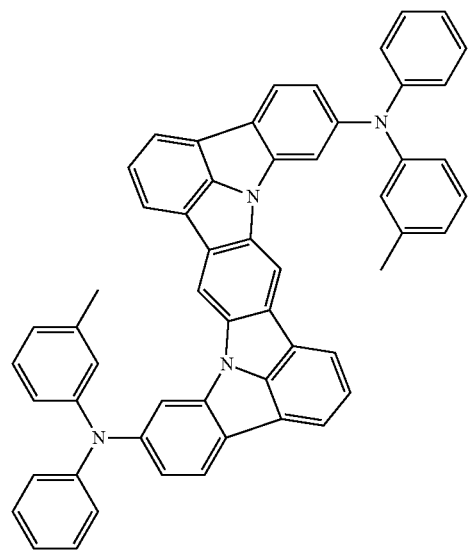
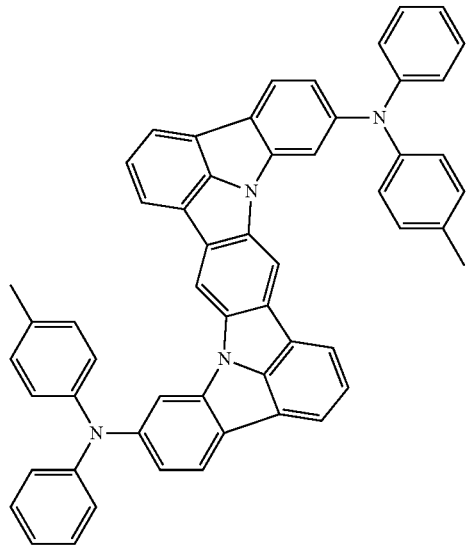
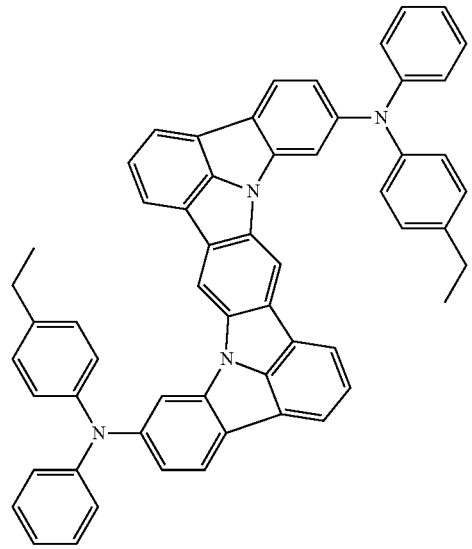

-continued
| 279 | 280 |
|---|---|
| 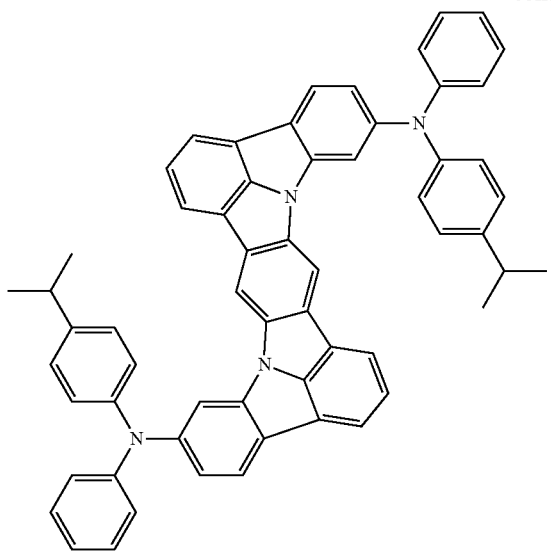 | 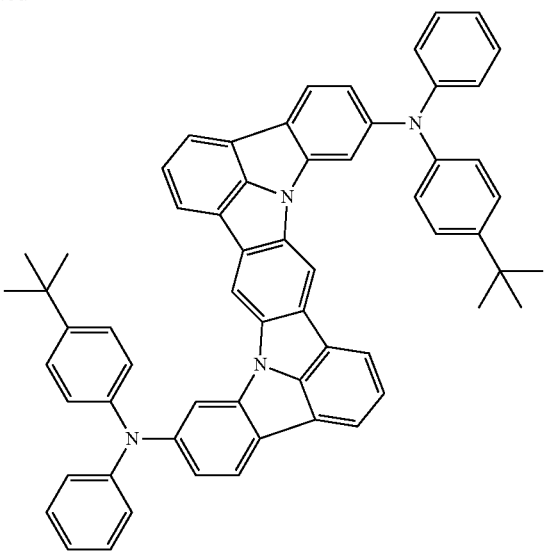 |
| 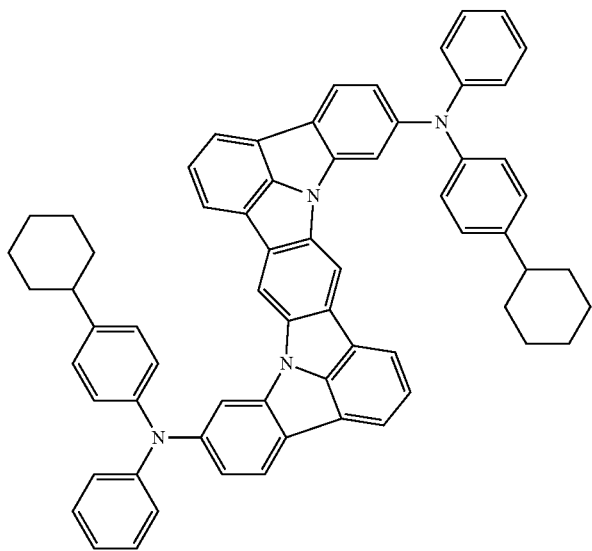 | 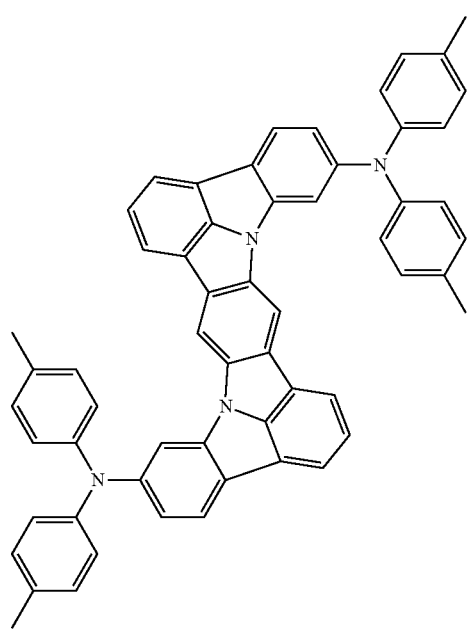 |

-continued
281
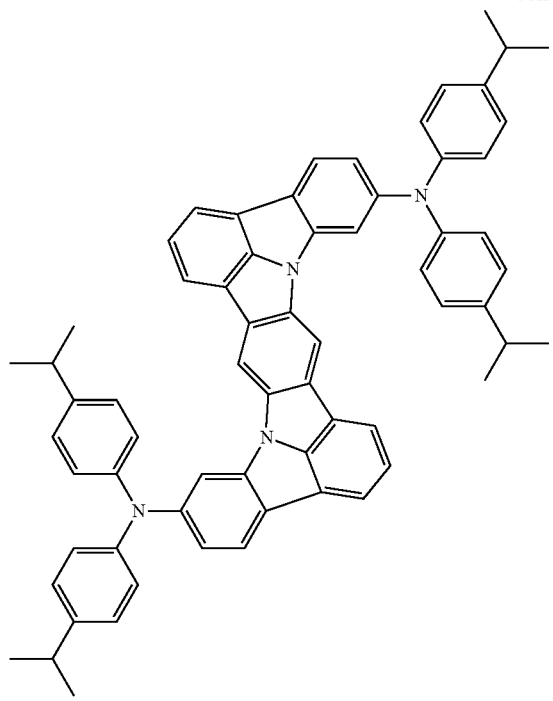
282
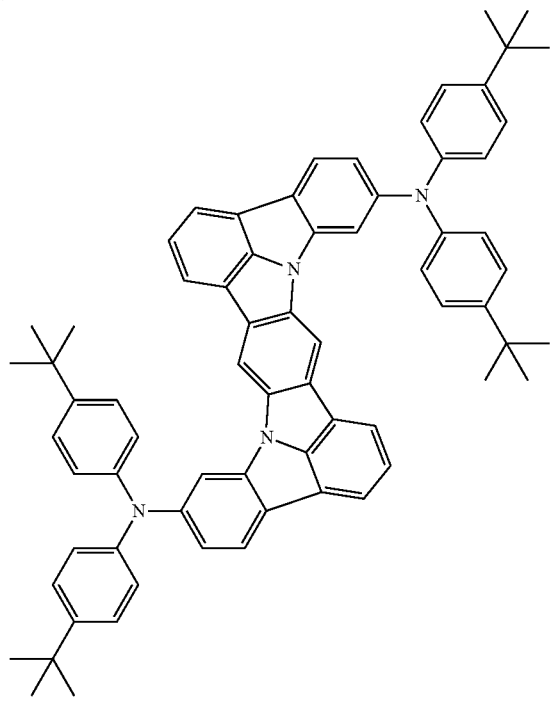
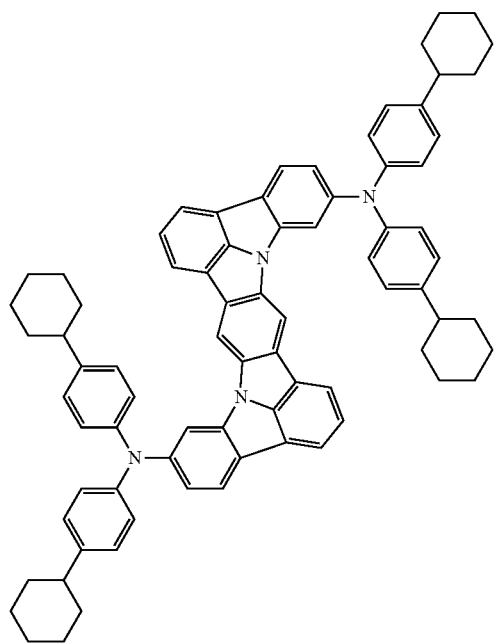
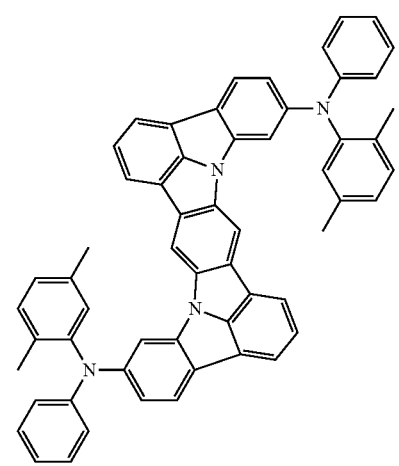

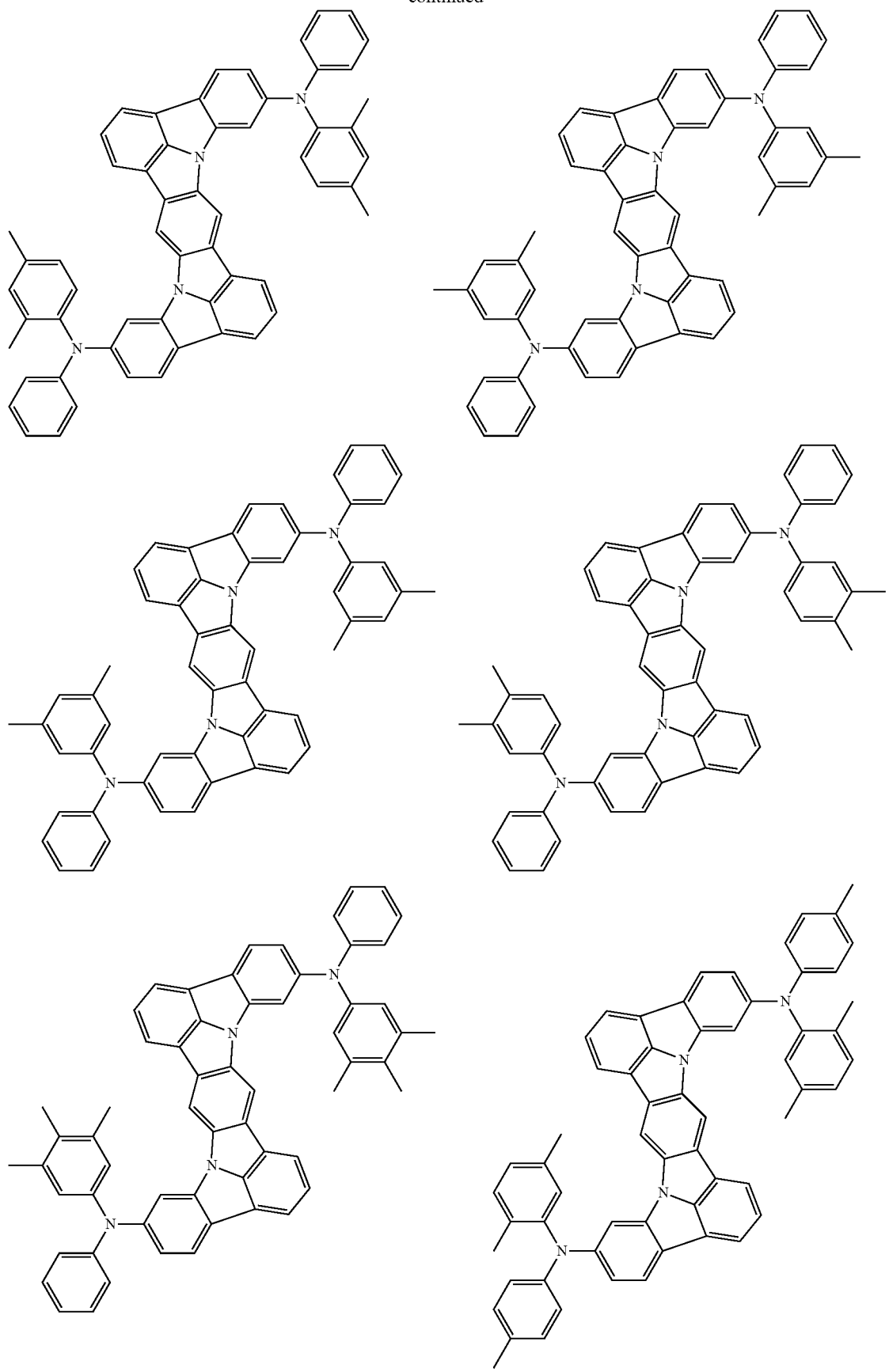

-continued
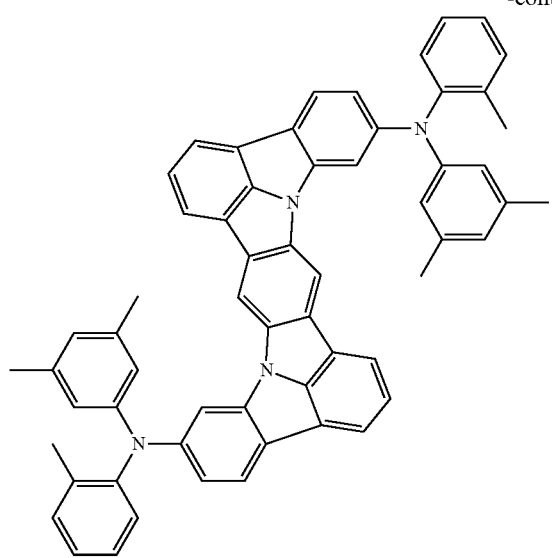
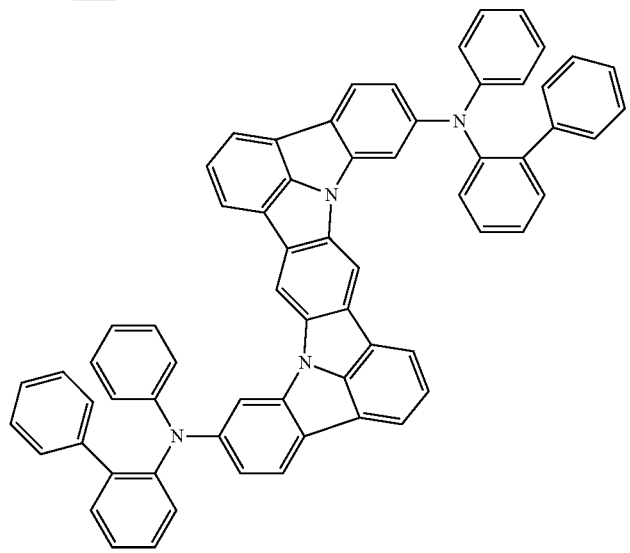
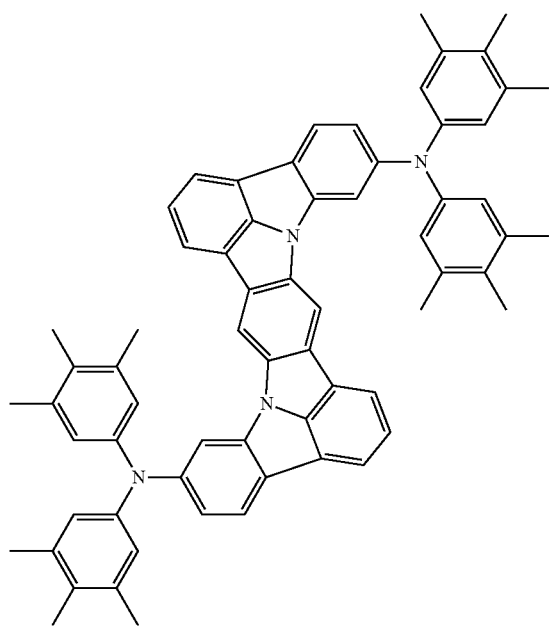

287
-continued
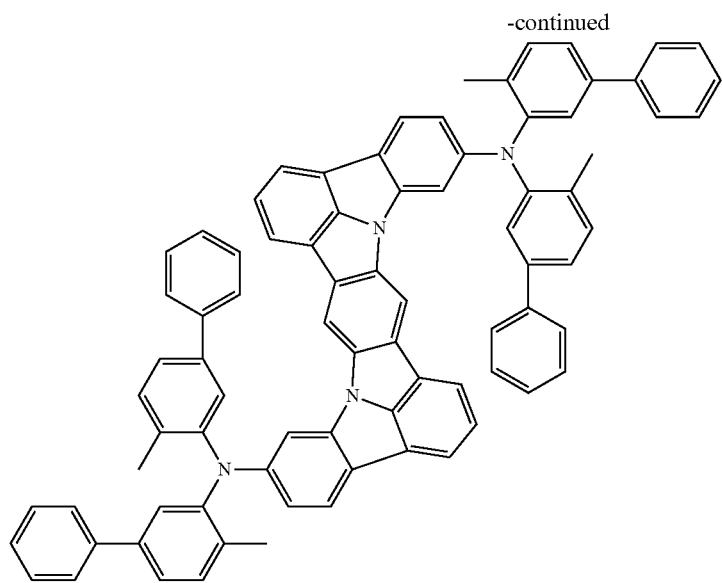
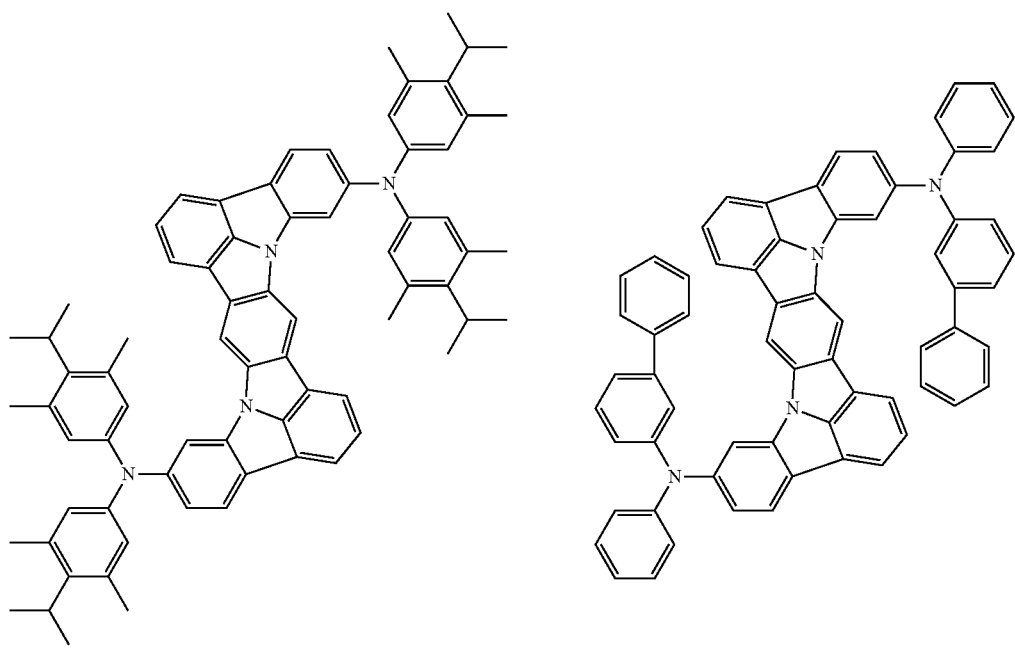

-continued
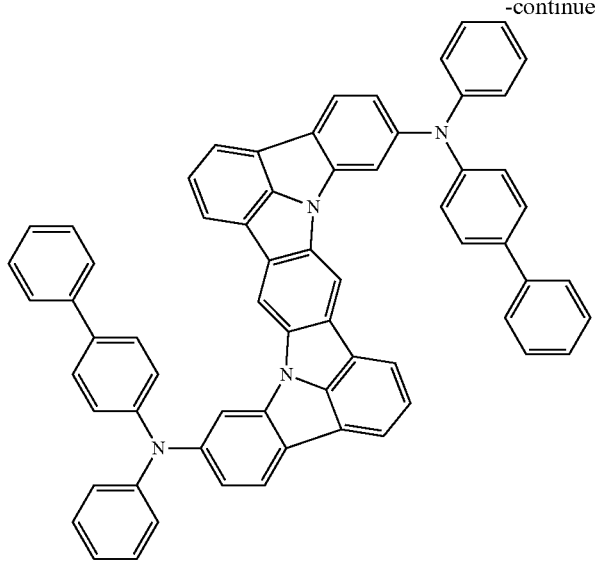
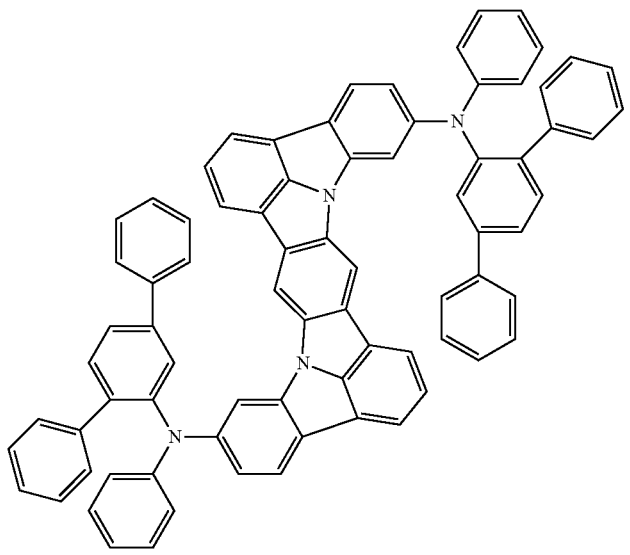
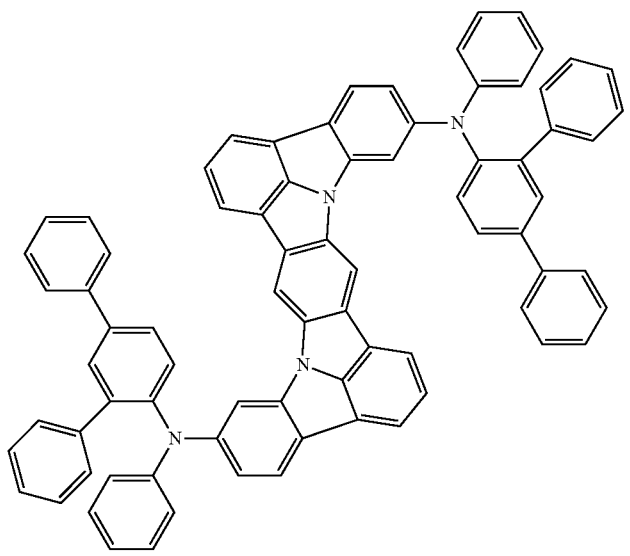

291 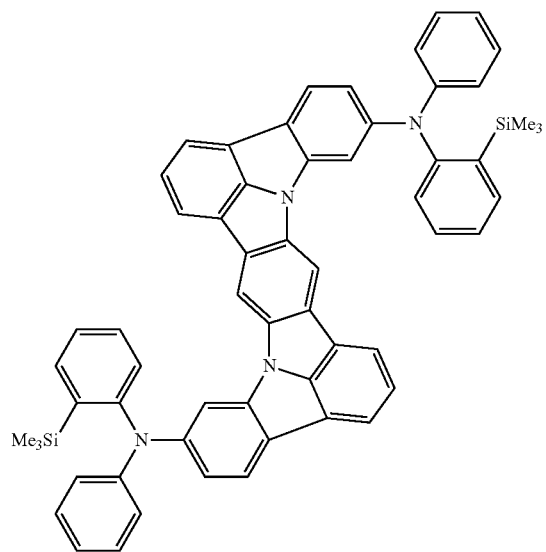 292 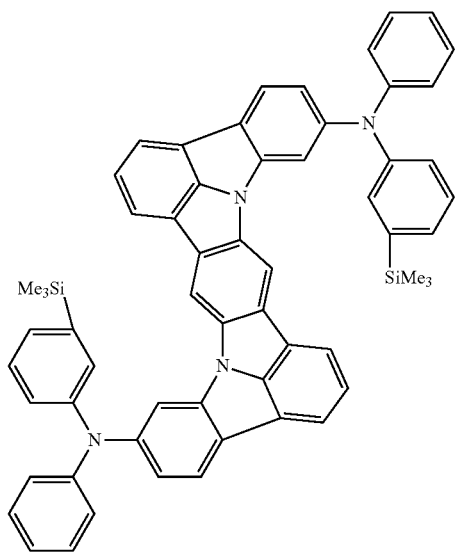
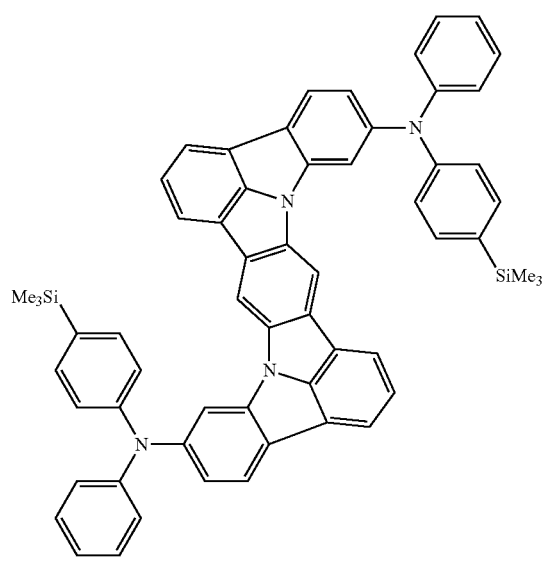 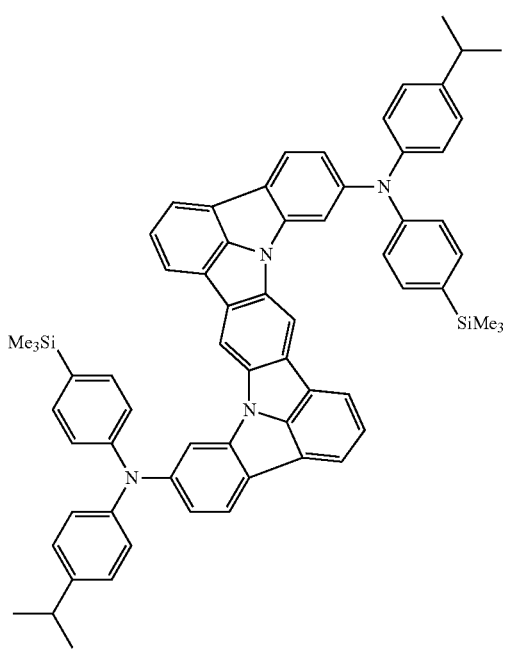

293 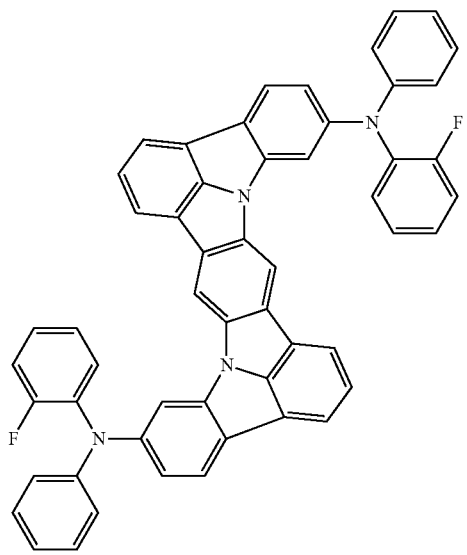 294 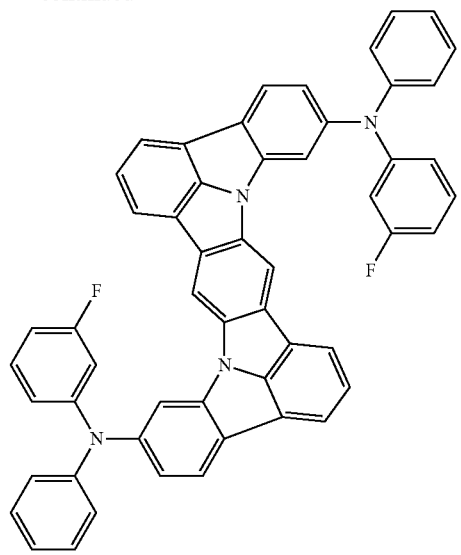
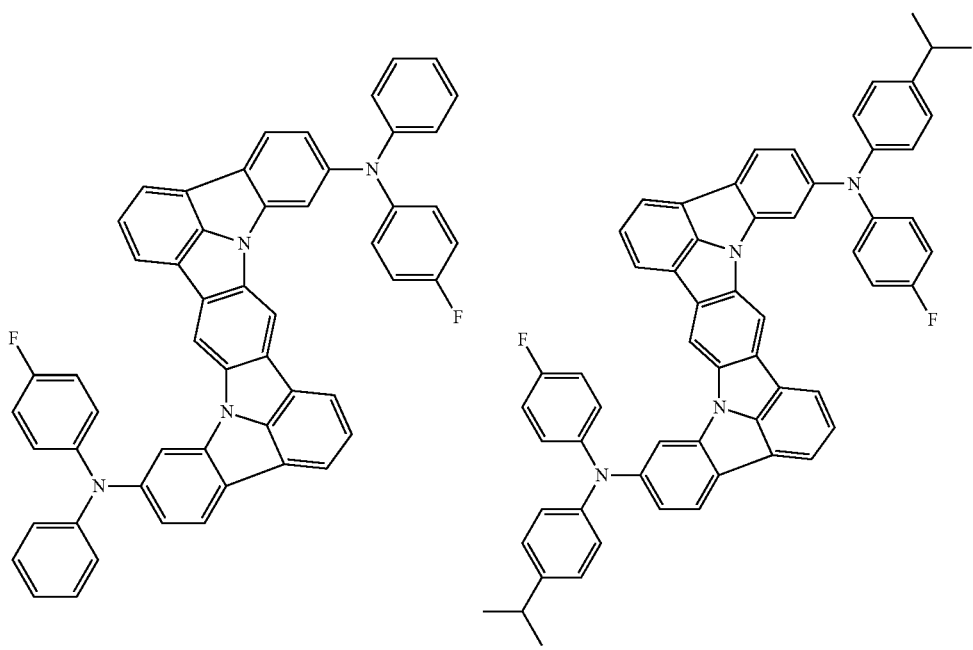

-continued
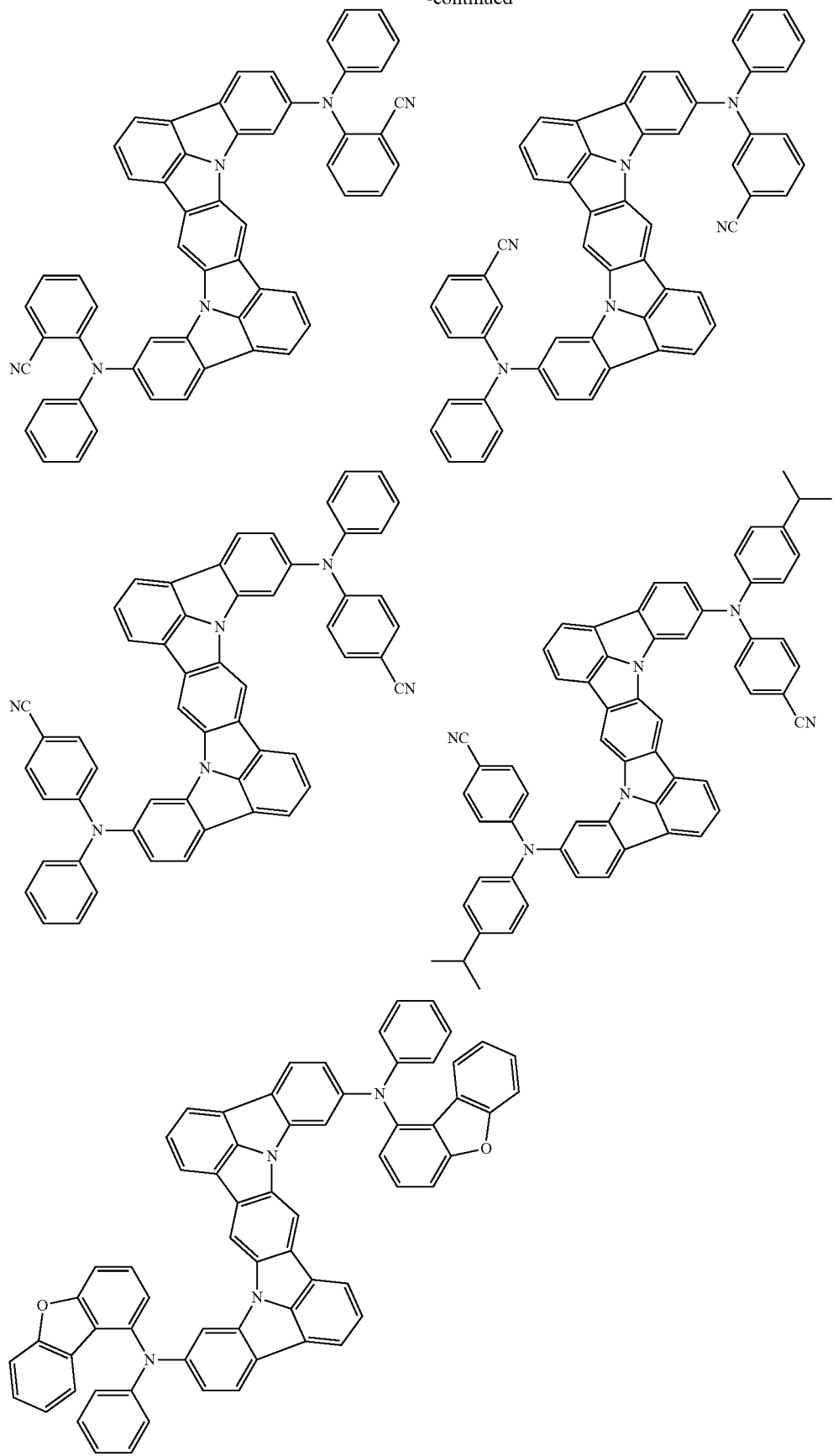

-continued
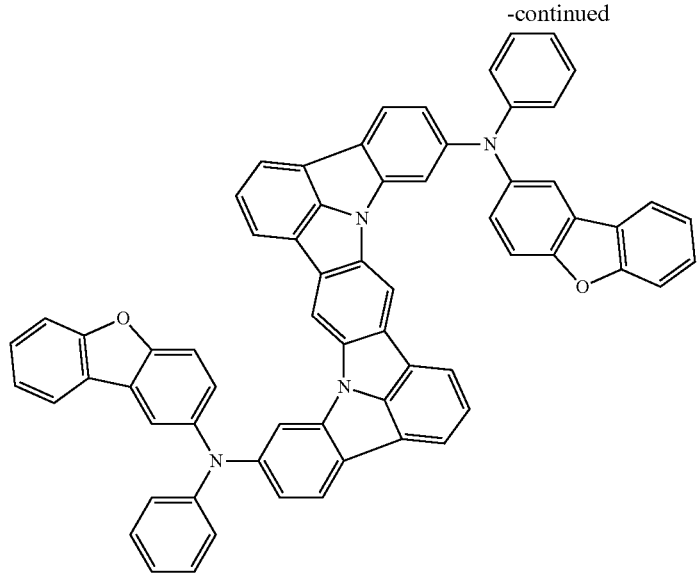
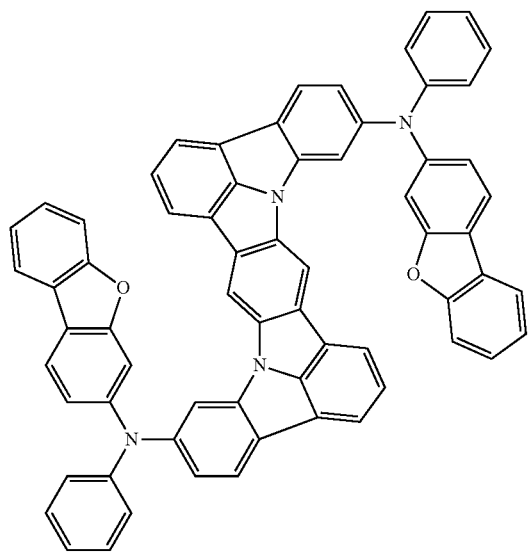
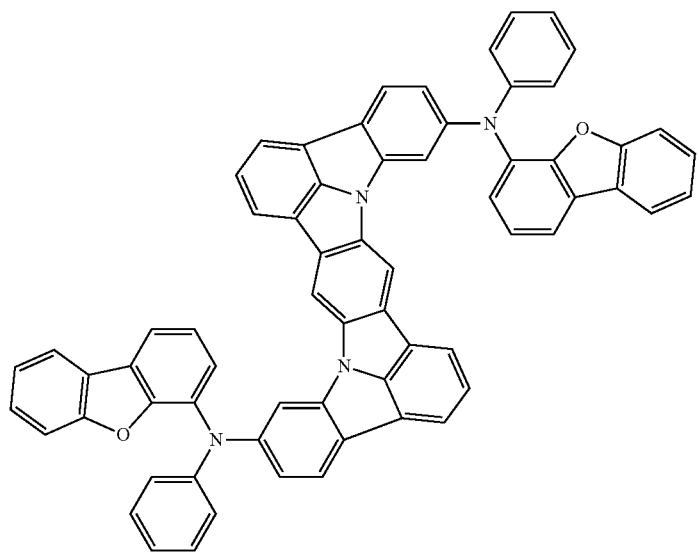

-continued
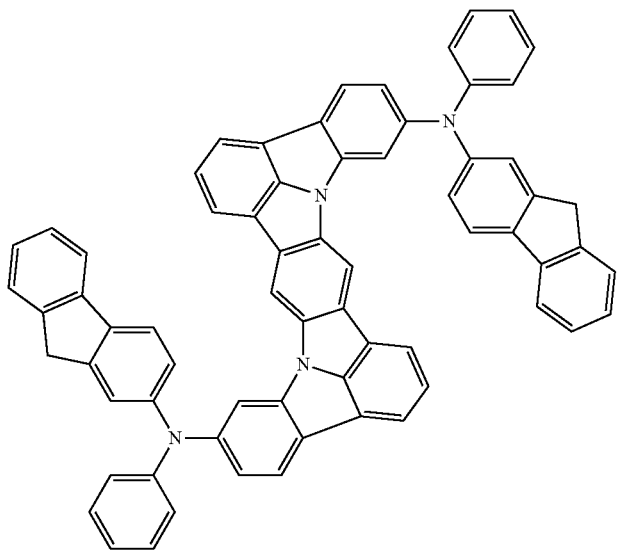
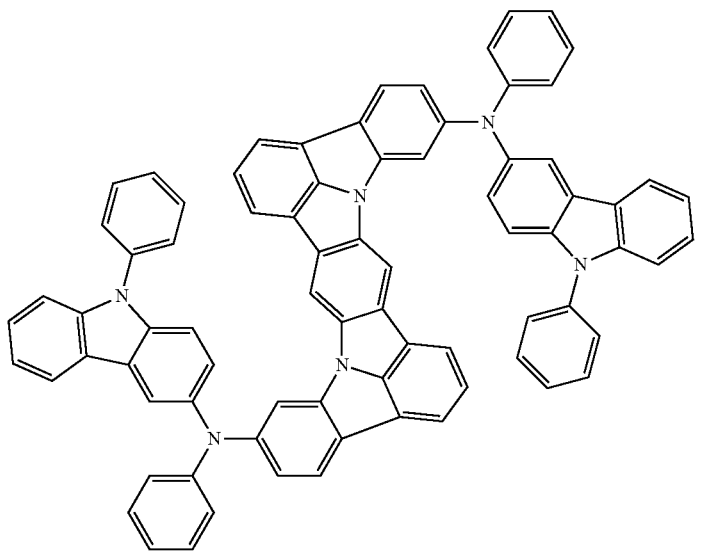
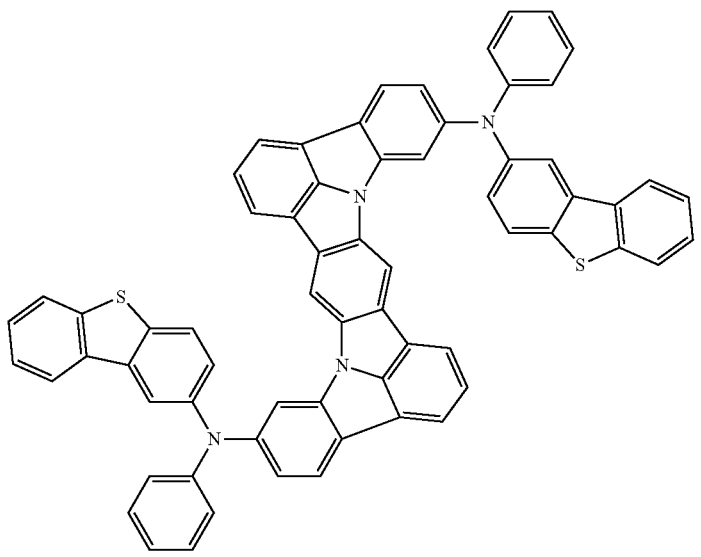

-continued
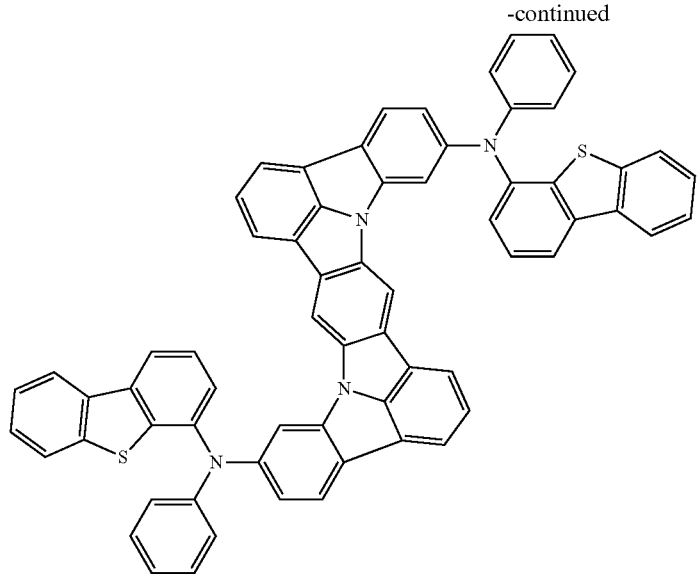
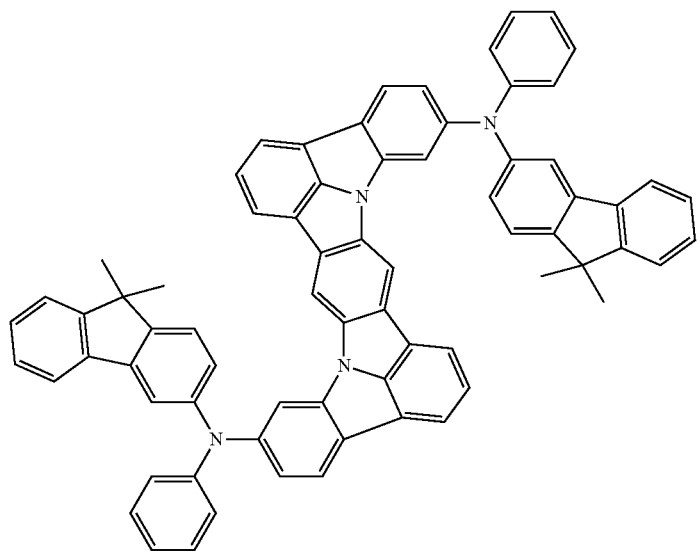
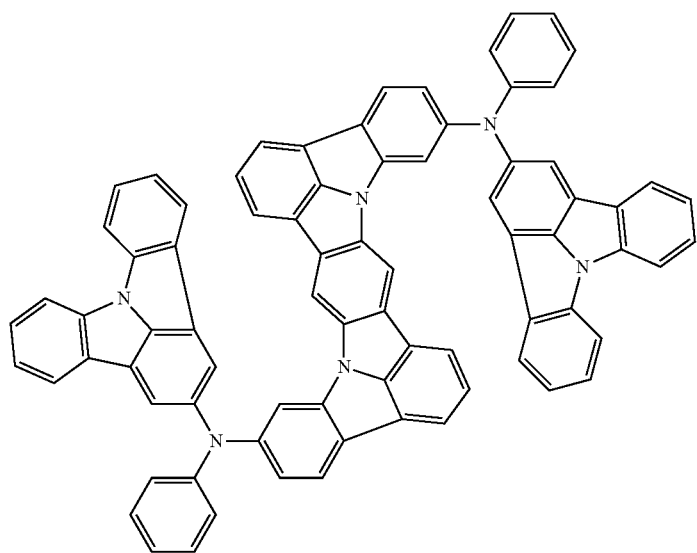

-continued
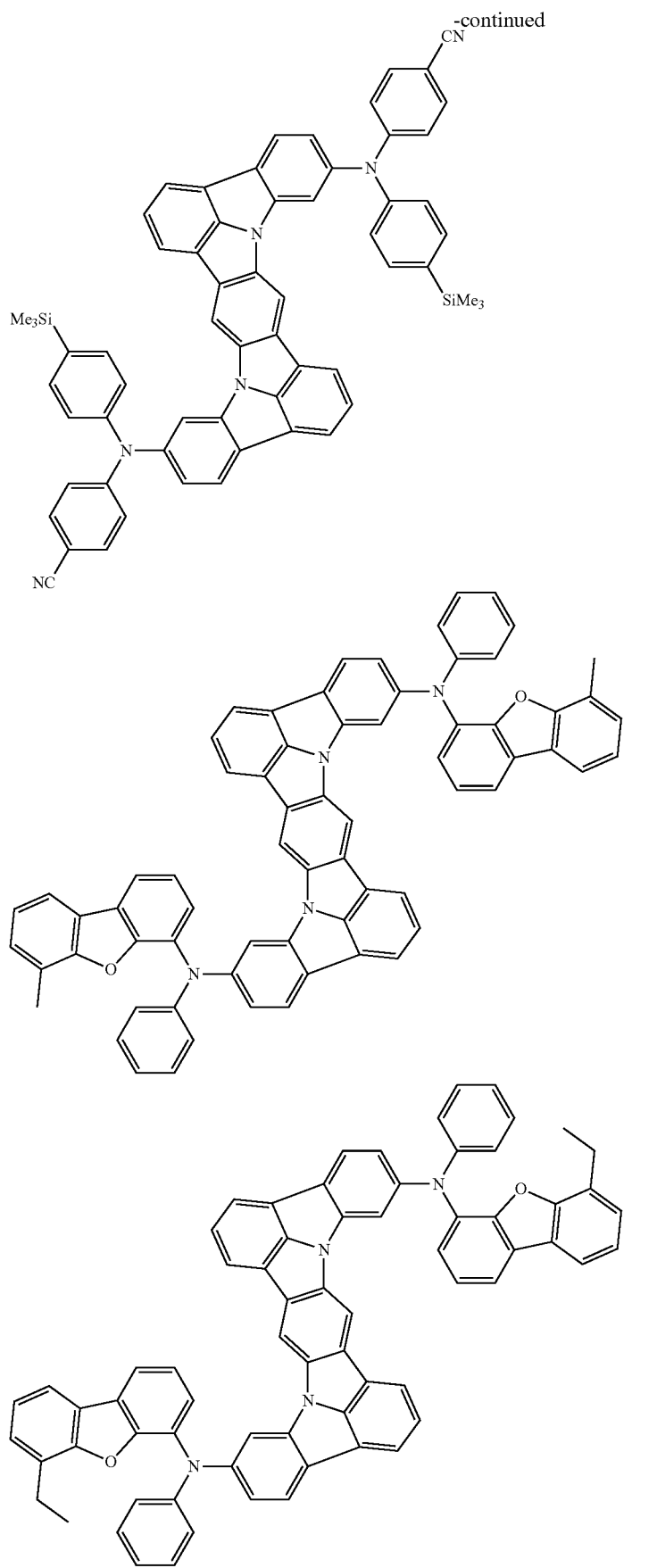

-continued
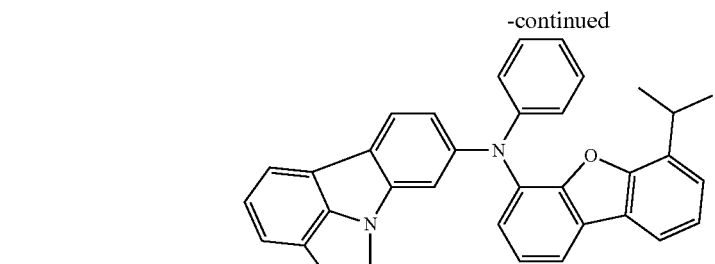
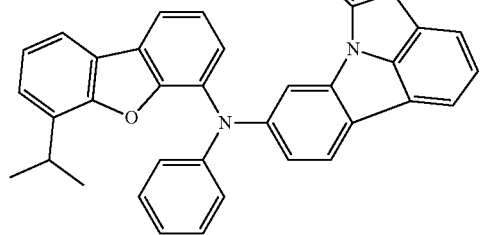
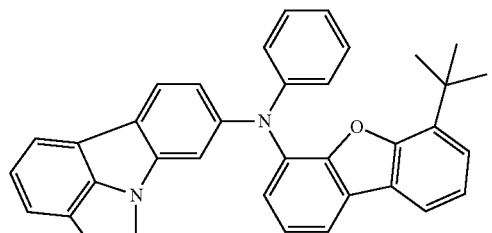
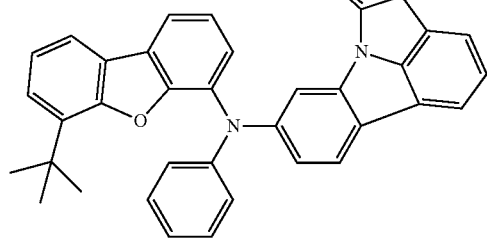
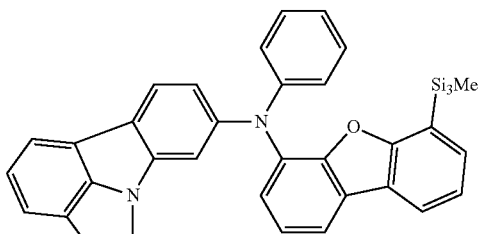
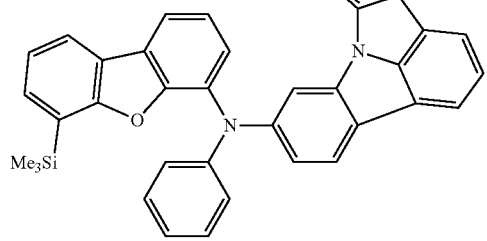

-continued
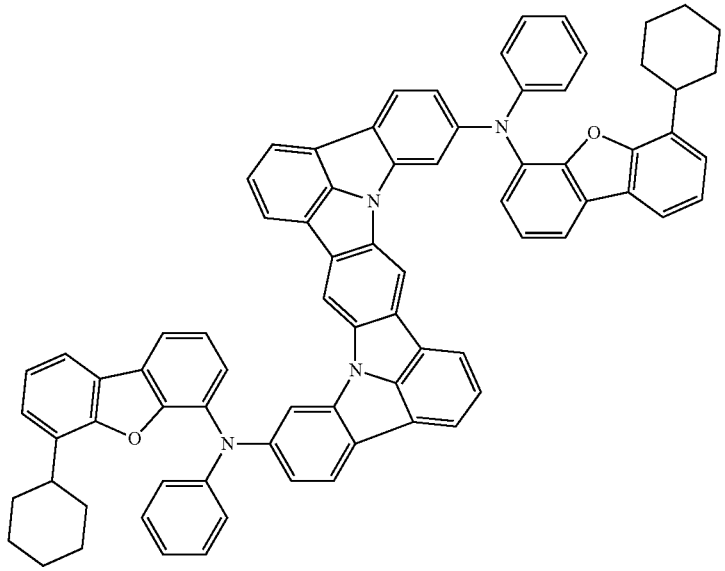
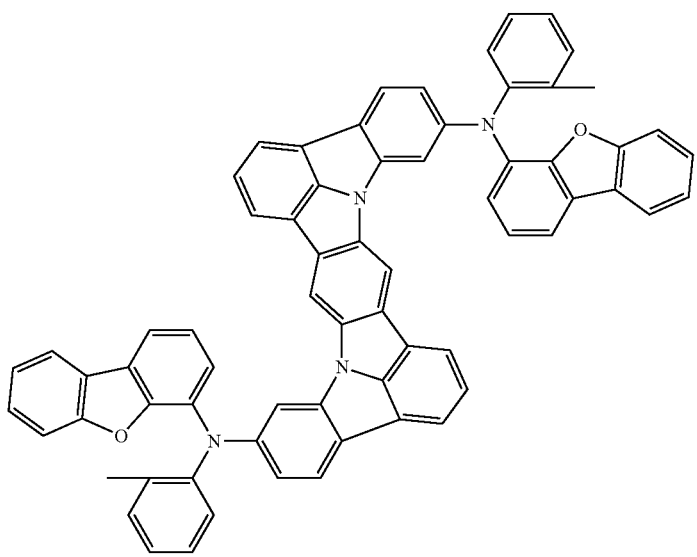
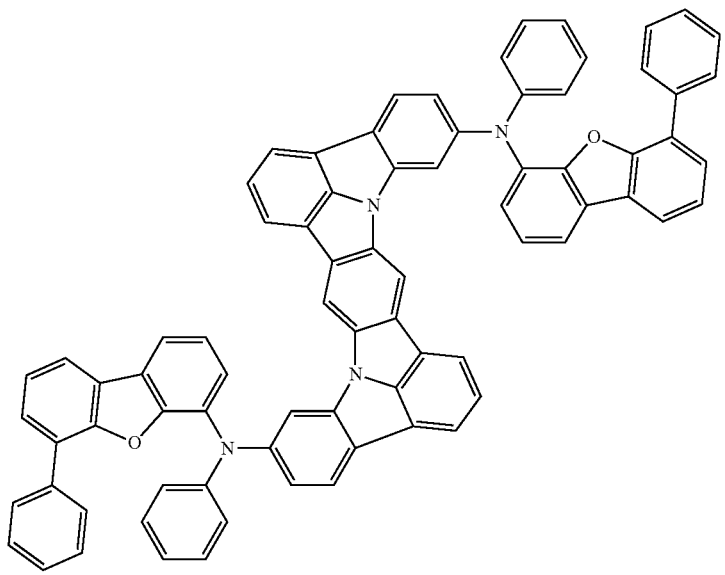

-continued
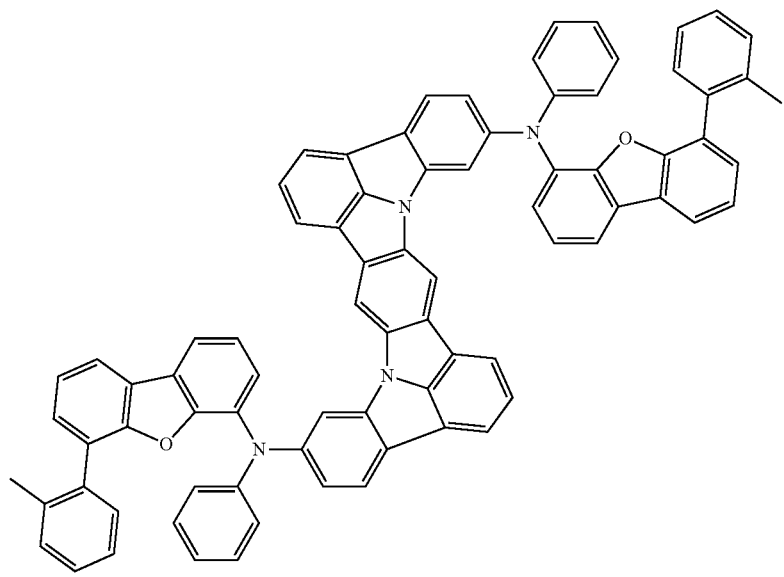
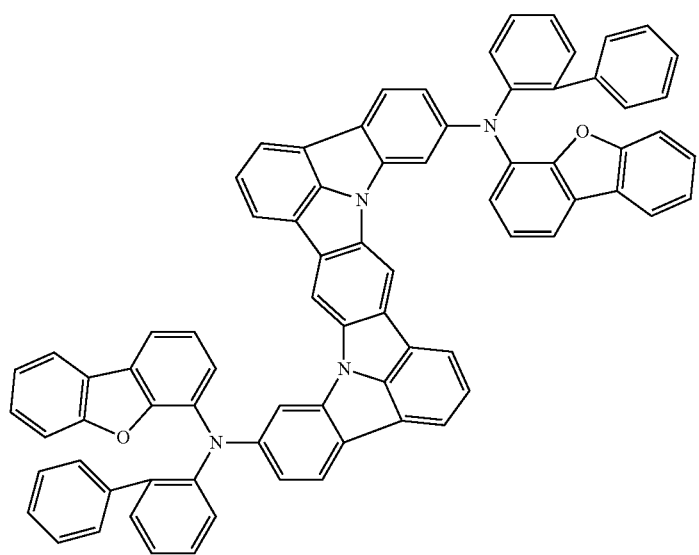

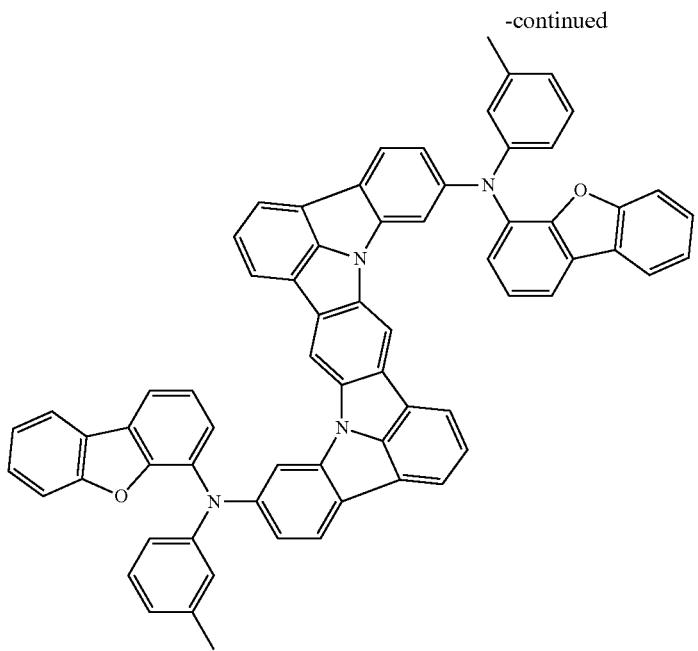
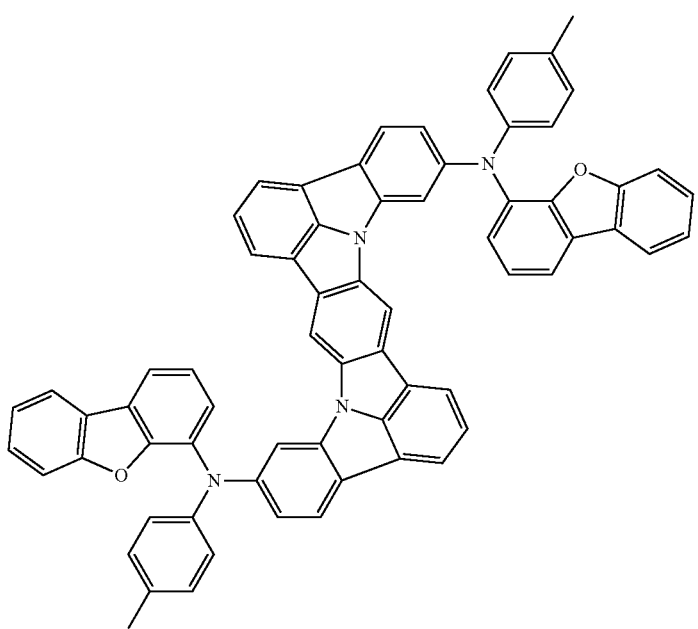

-continued
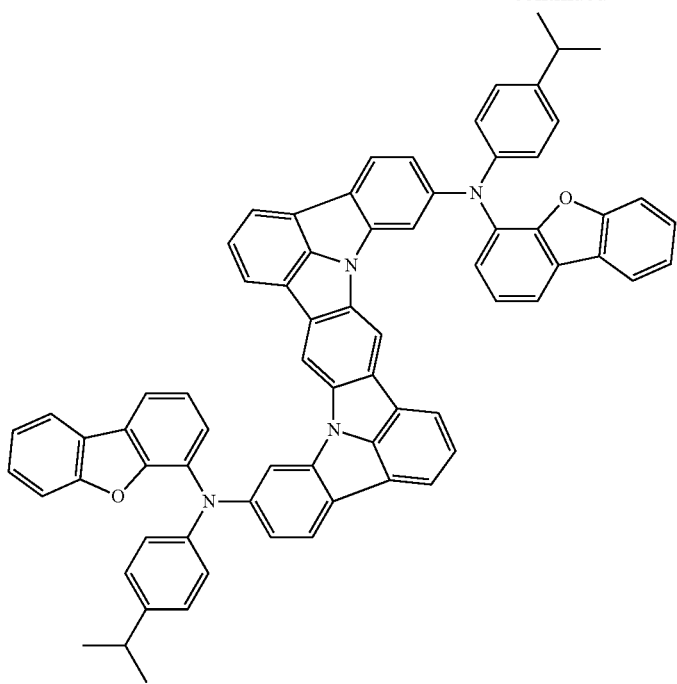
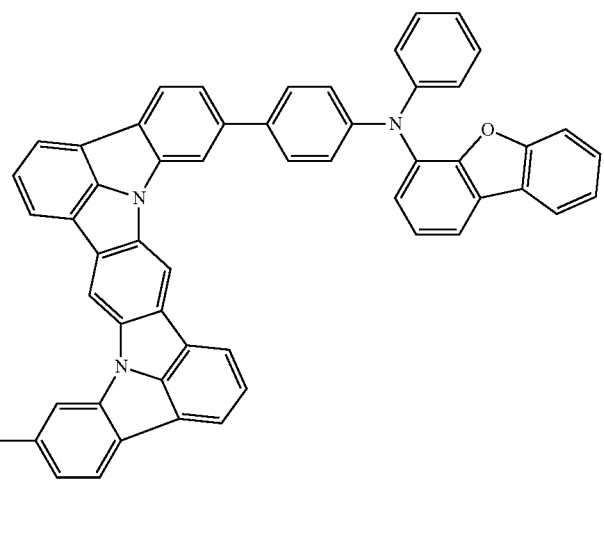

-continued
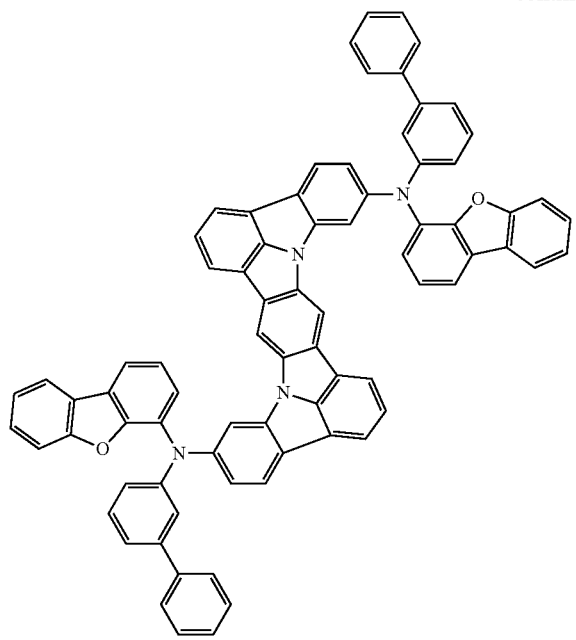
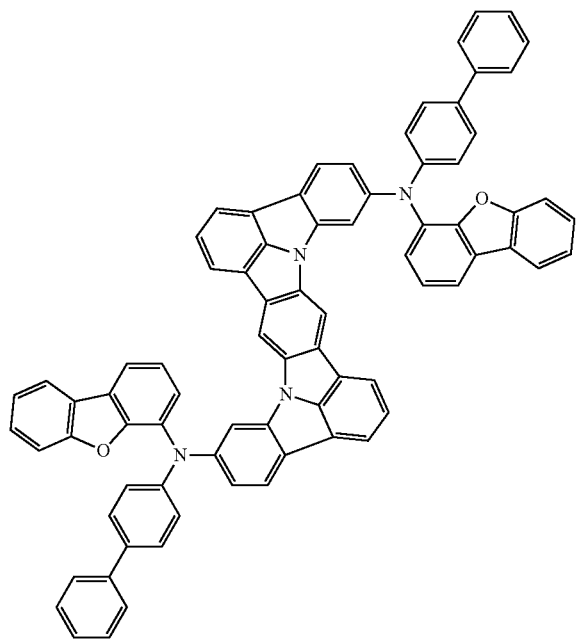

-continued
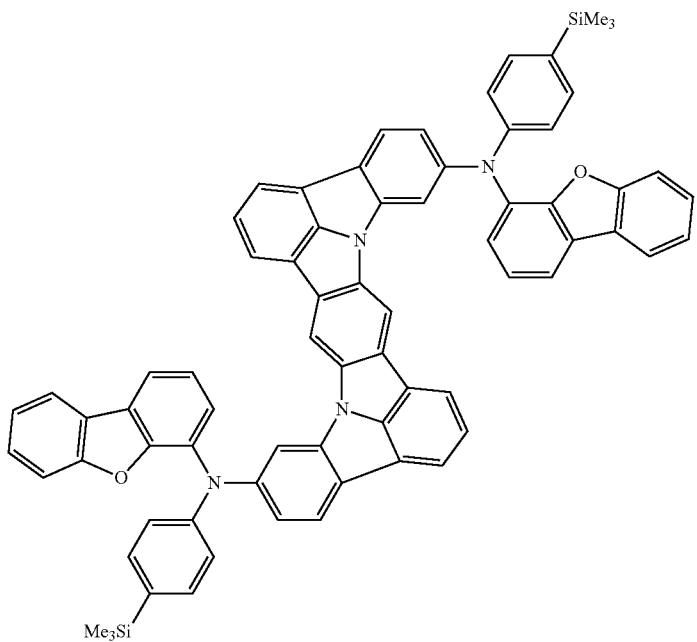
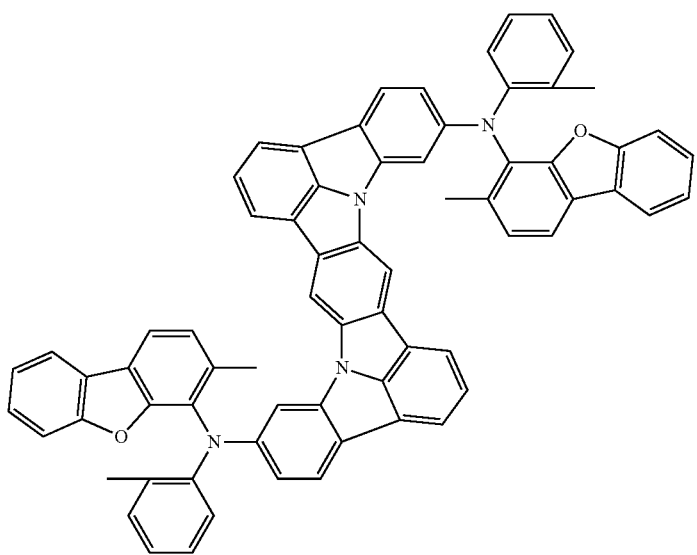

-continued
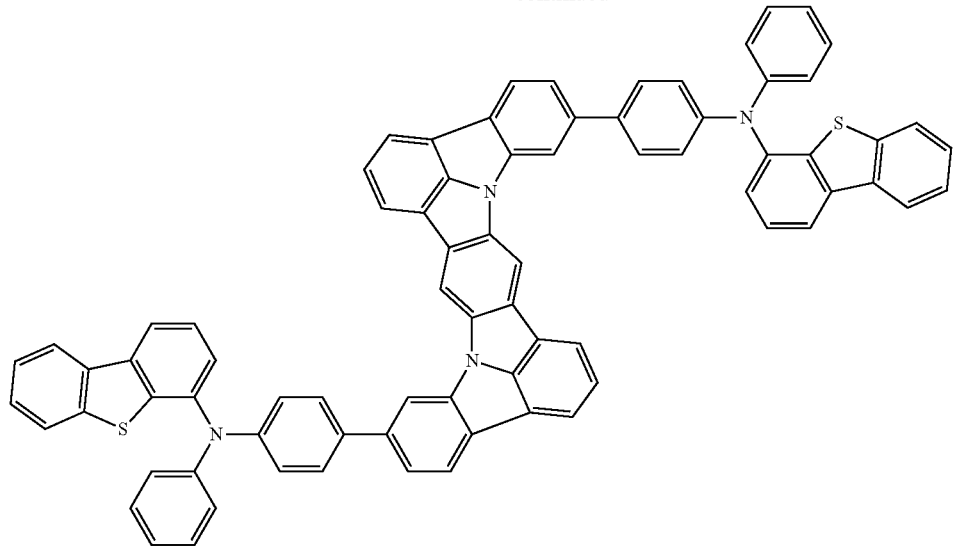
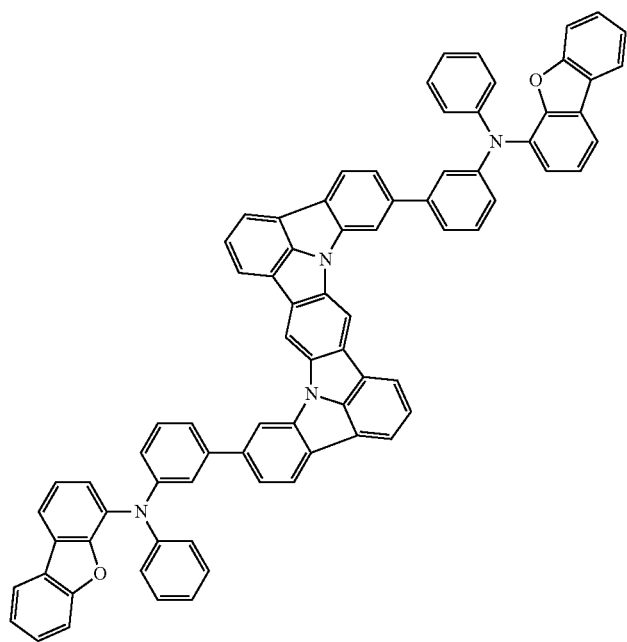

-continued
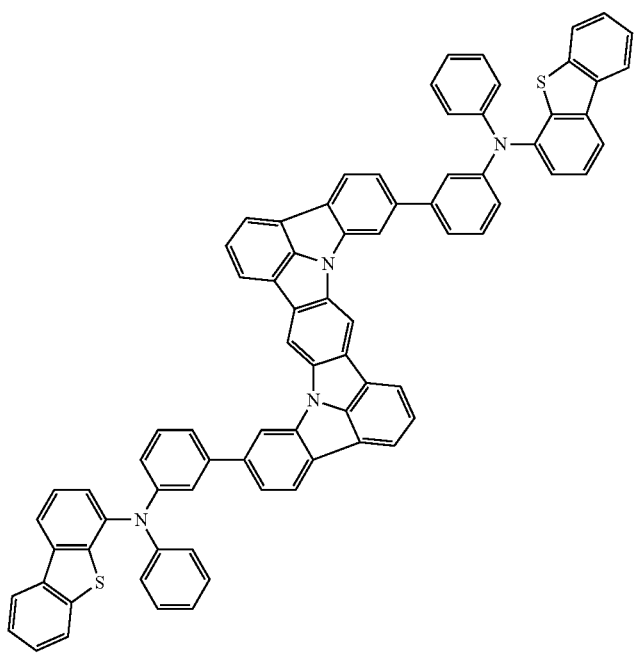
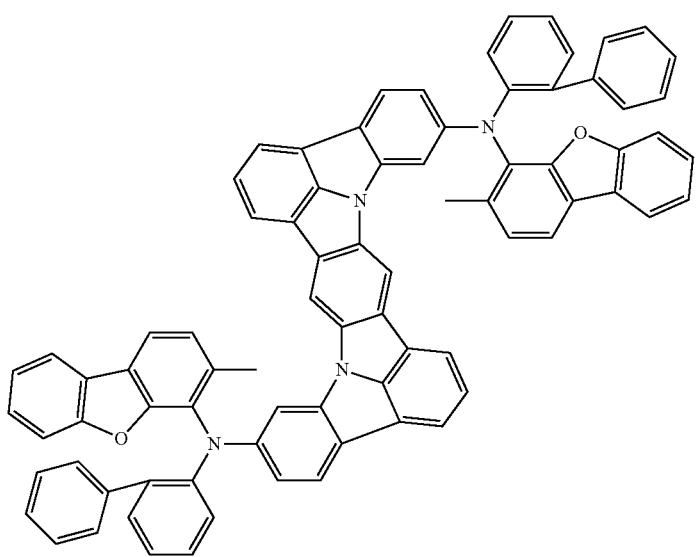

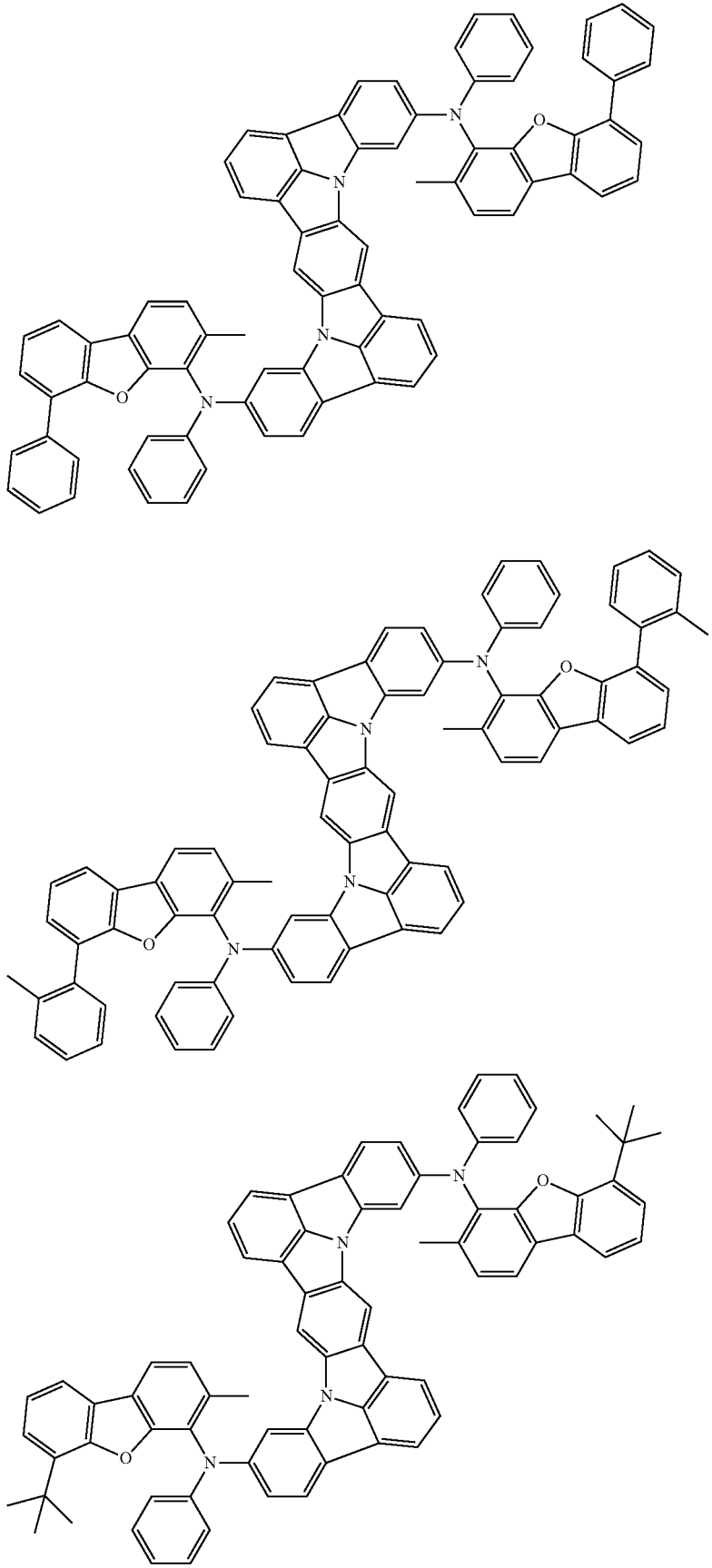

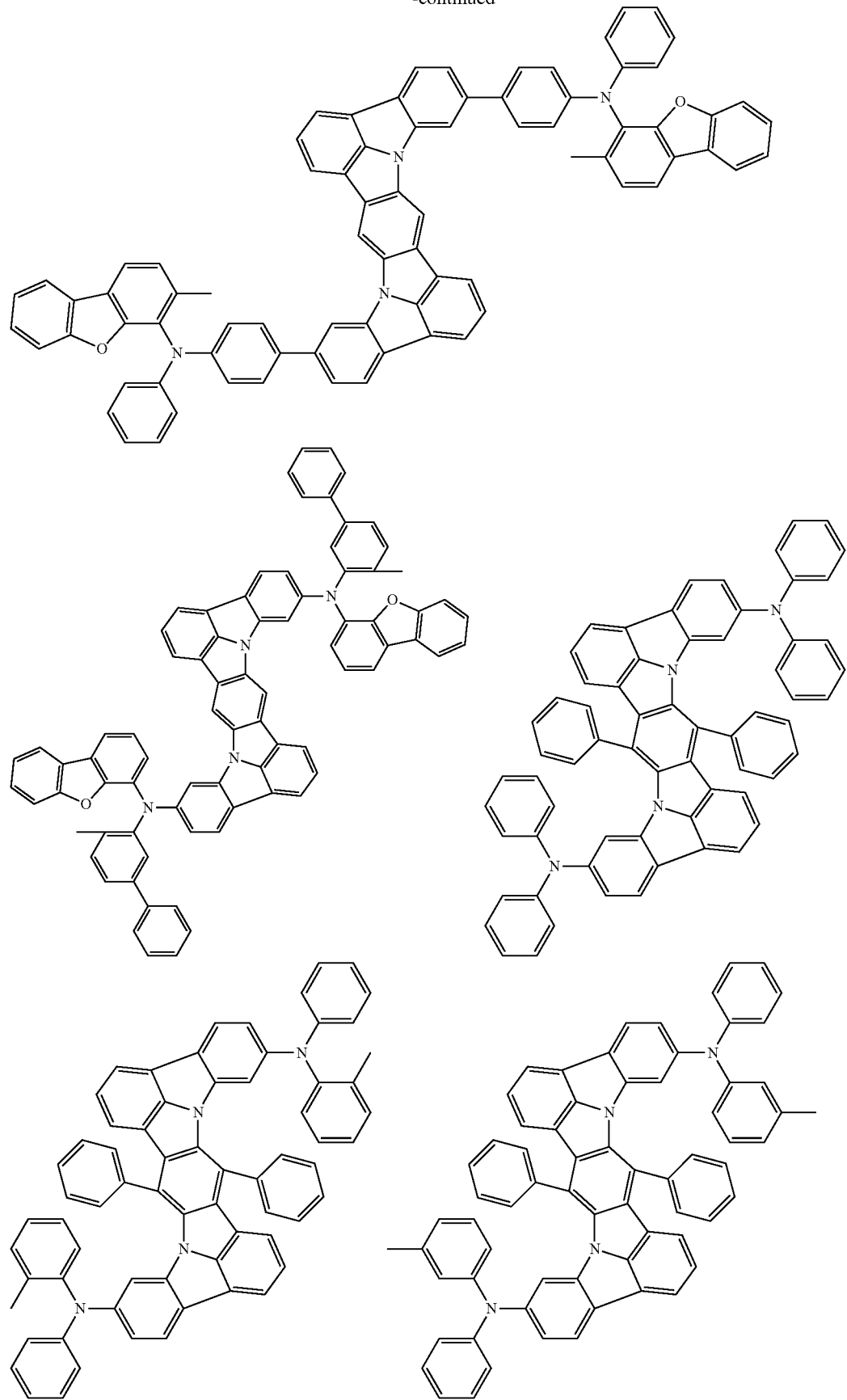

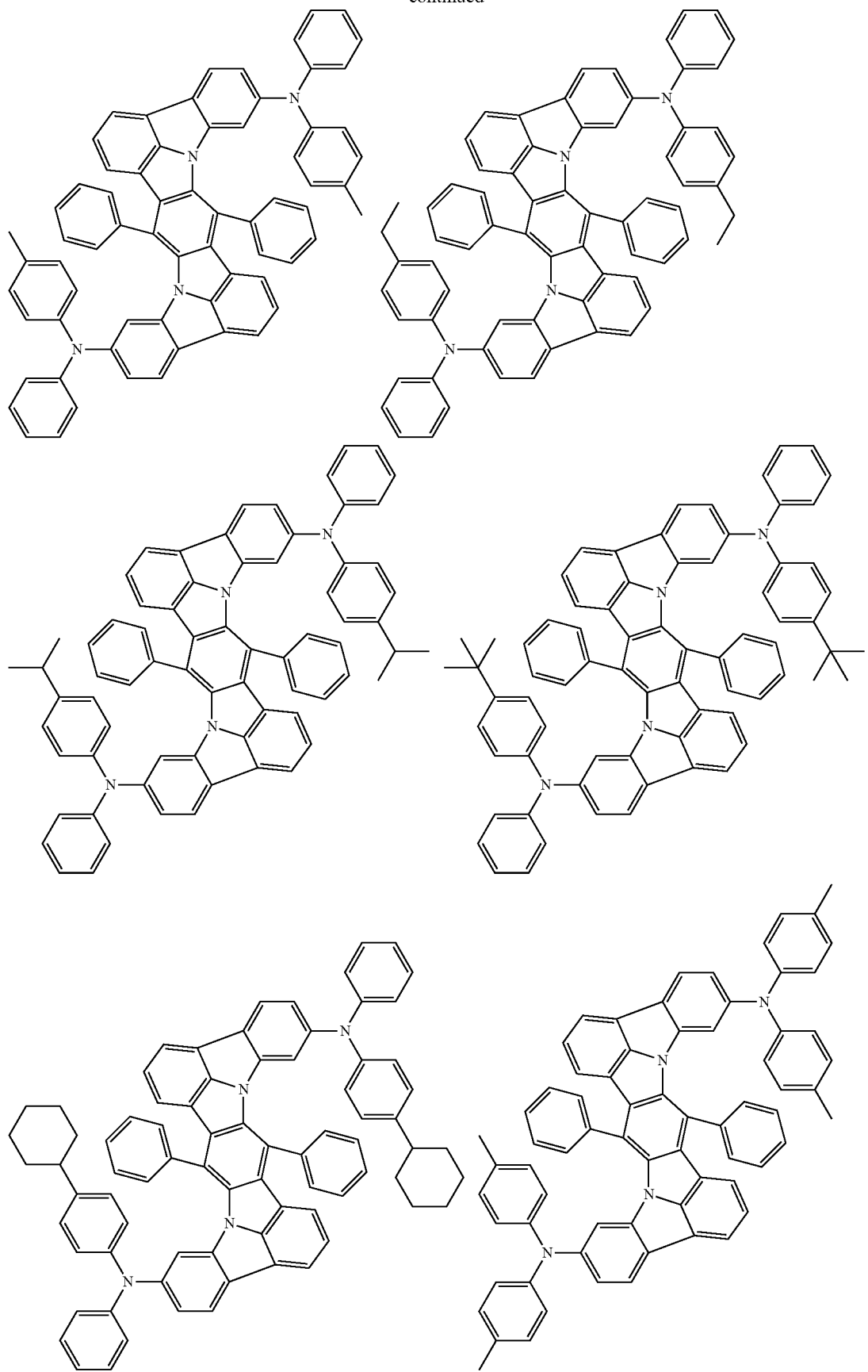

329 330
-continued
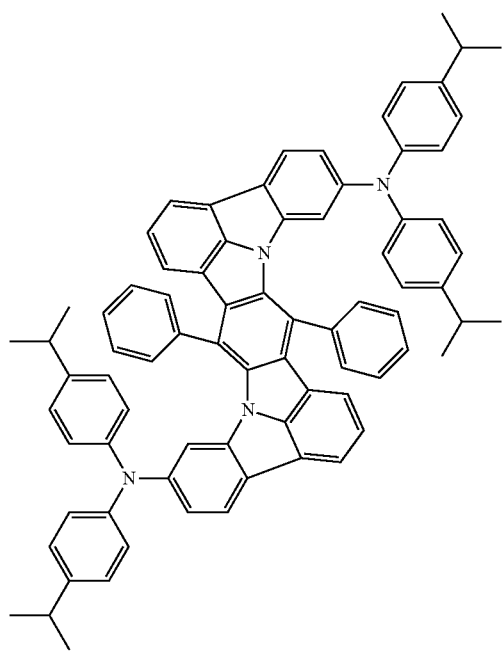 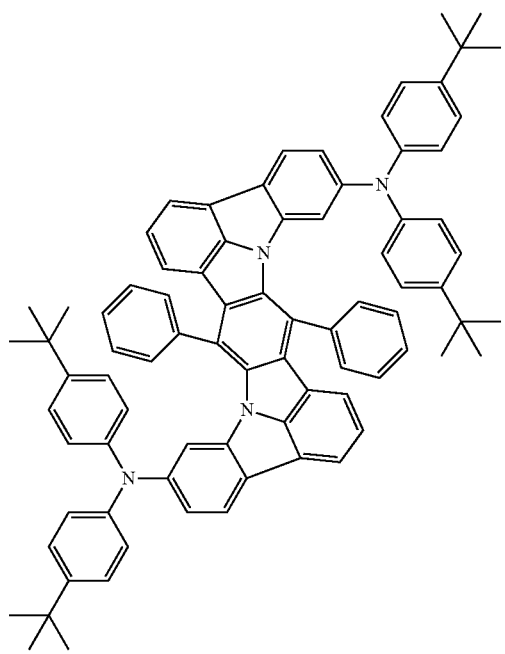
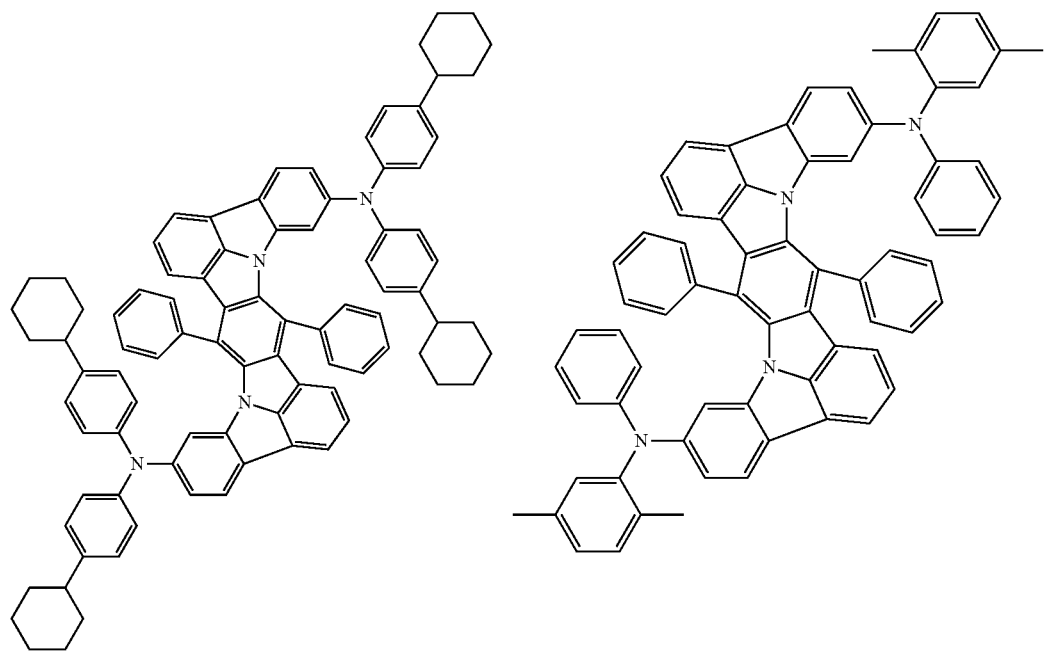

-continued
| 331 | 332 |
|---|---|
| 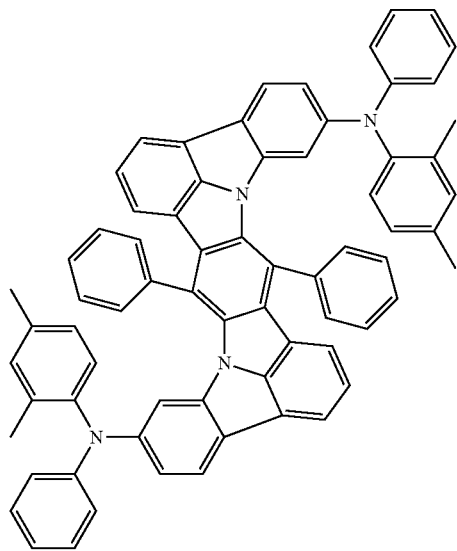 | 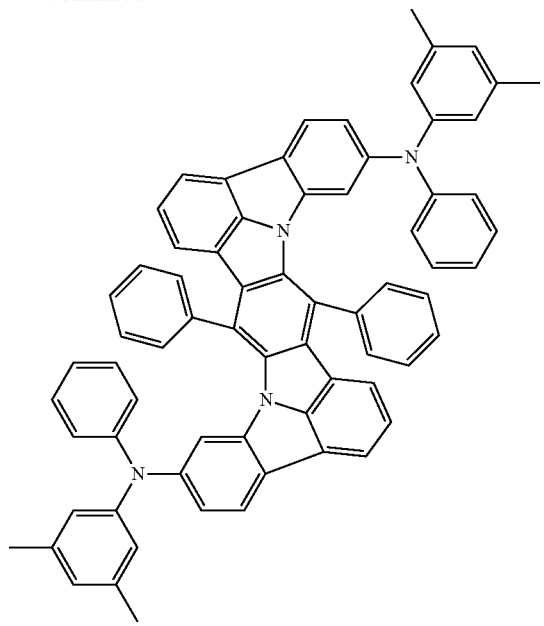 |
| 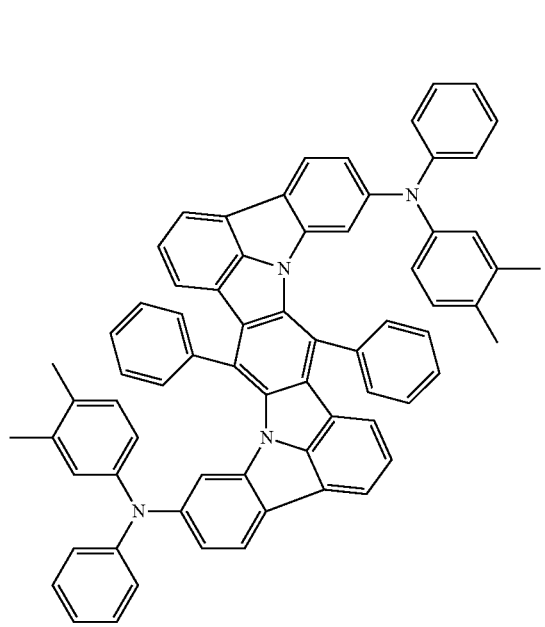 | 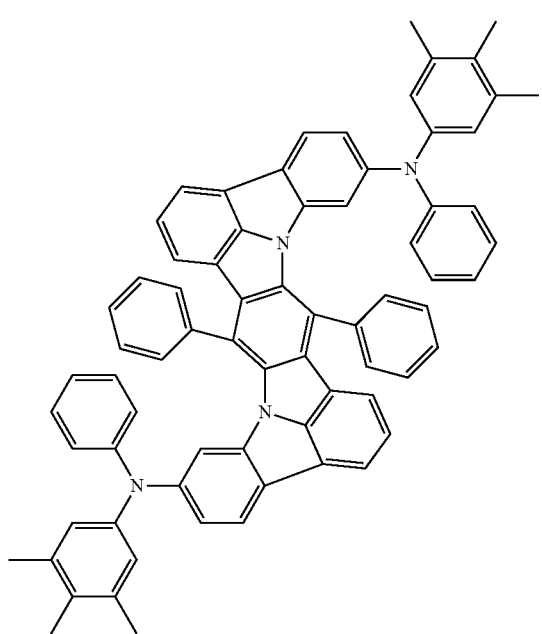 |

333
334
-continued
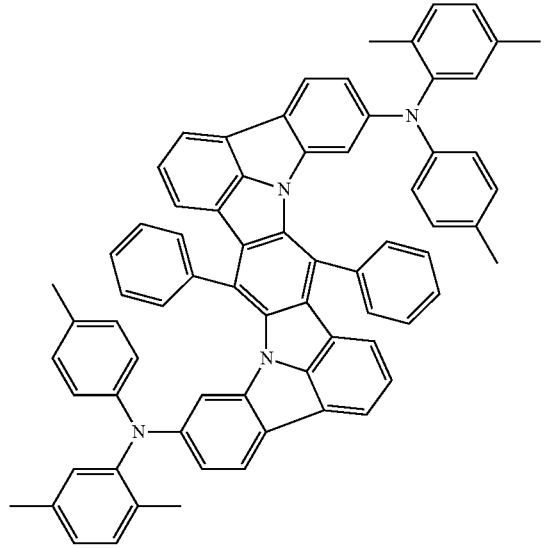
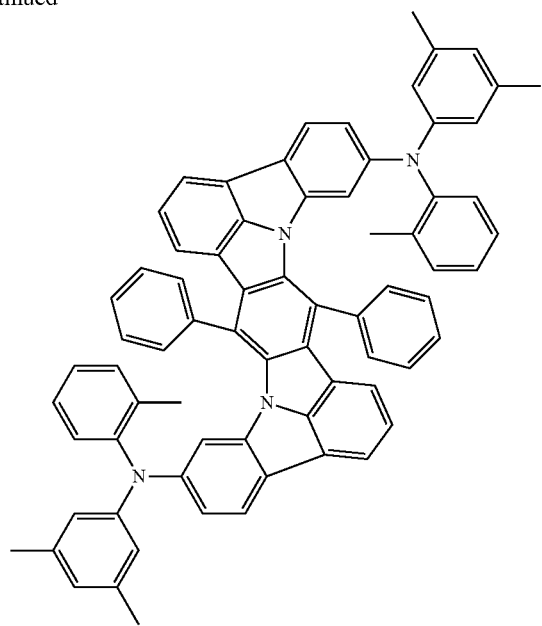
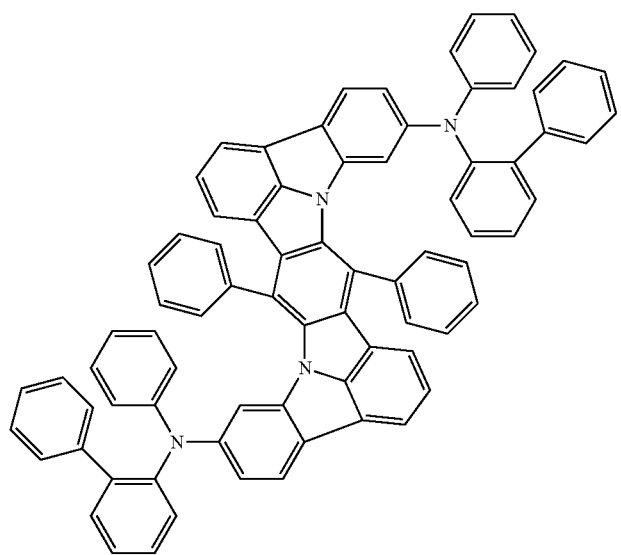
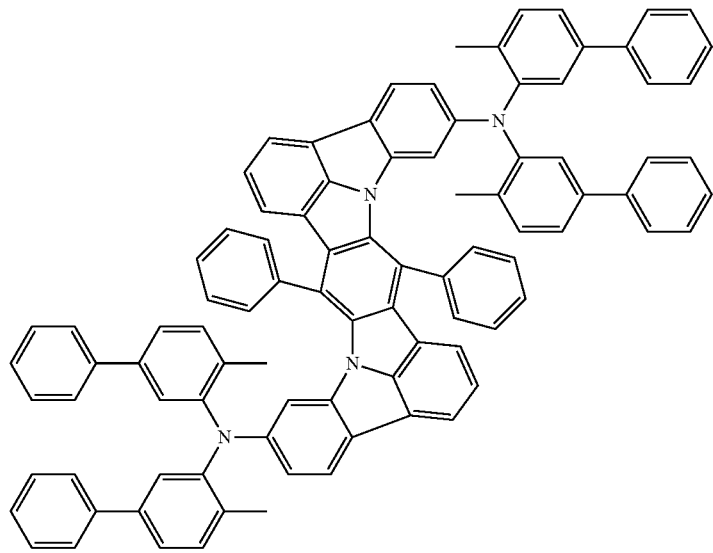

-continued
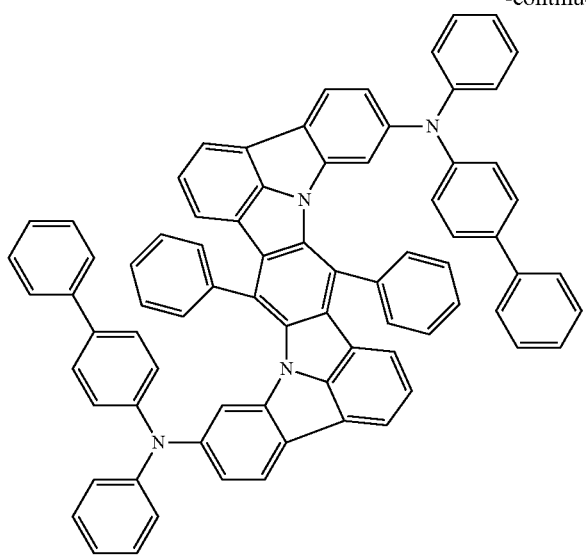
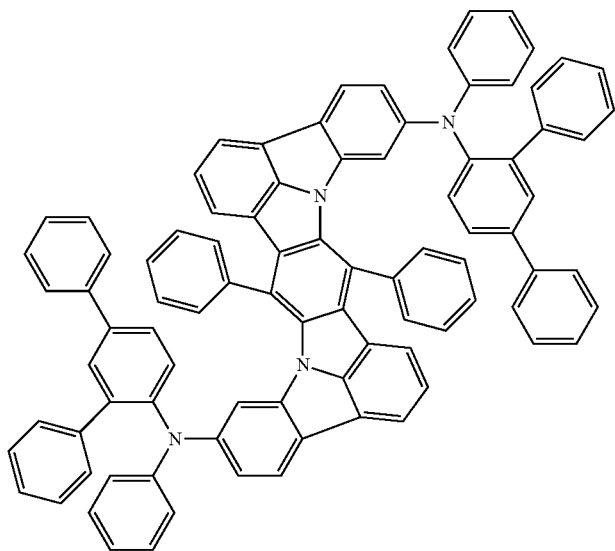
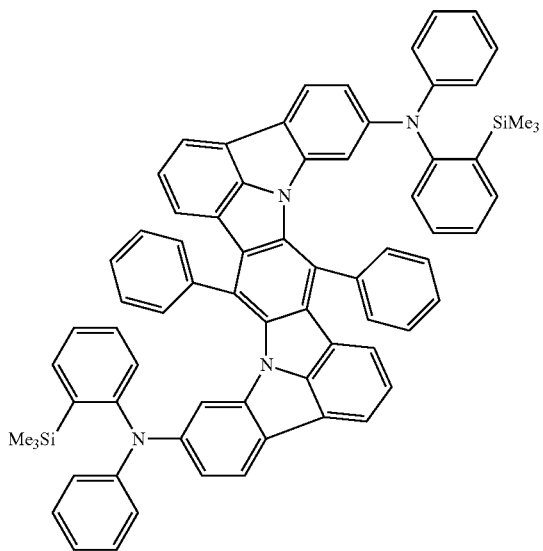

-continued
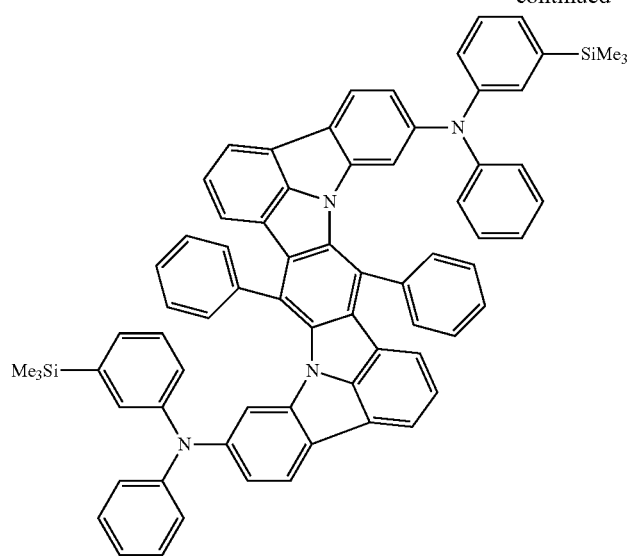
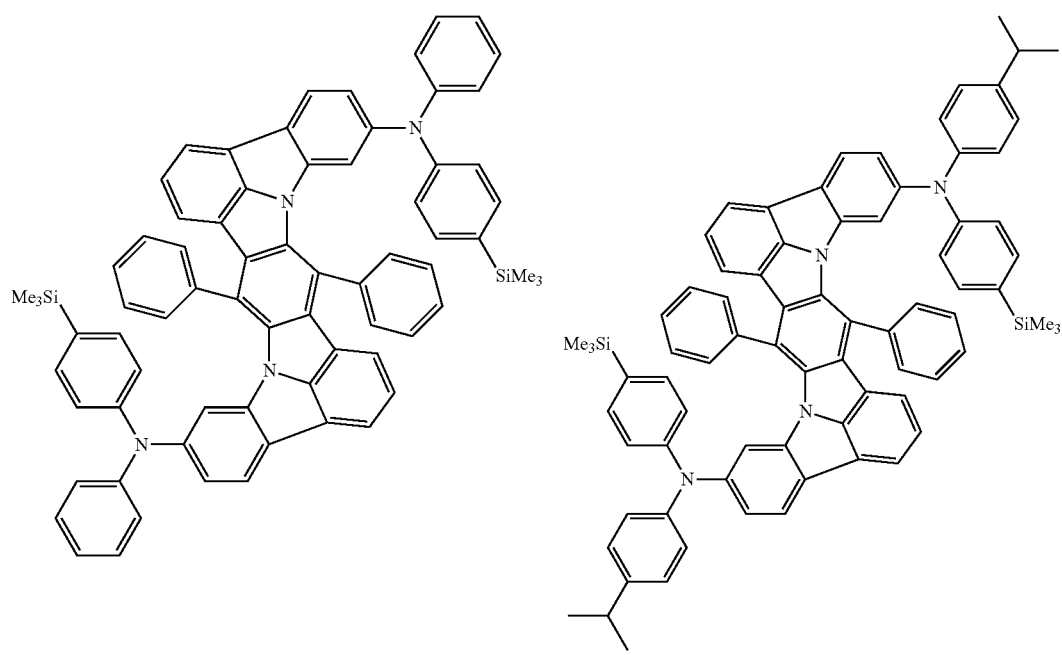

-continued
339
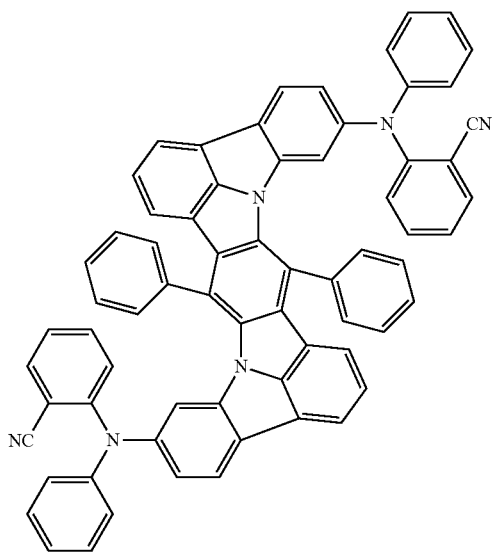
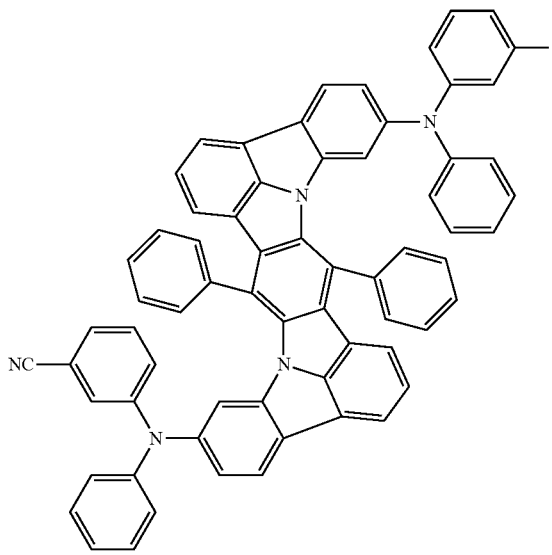
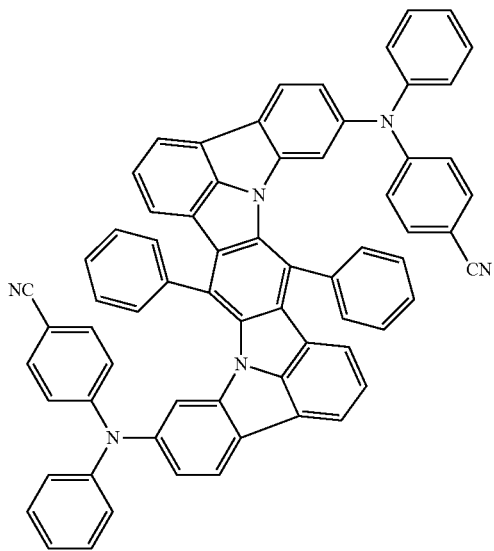
340
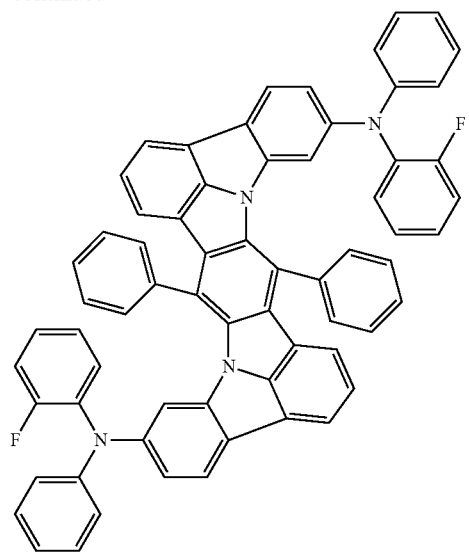
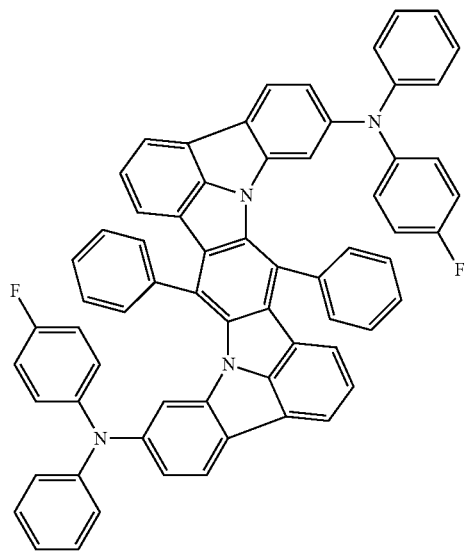
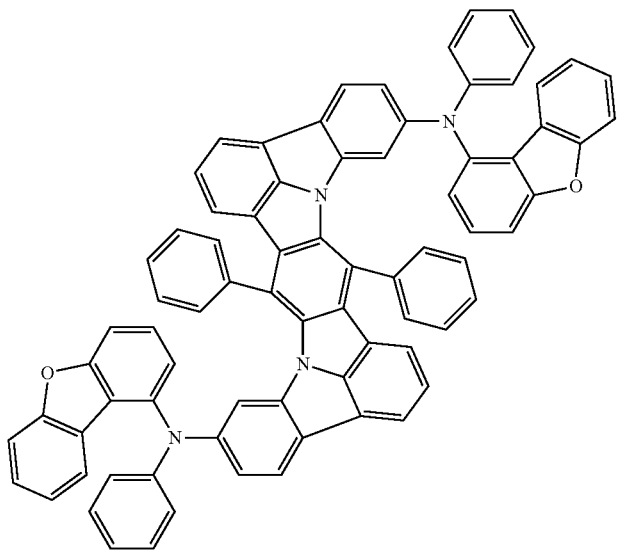

-continued
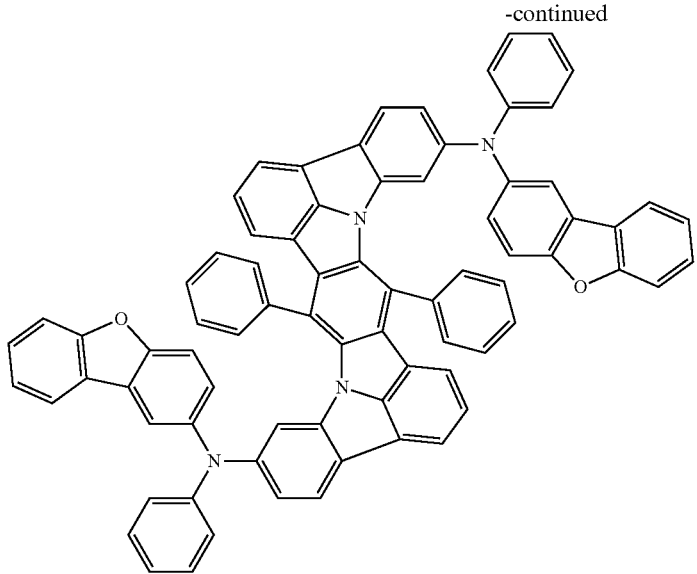
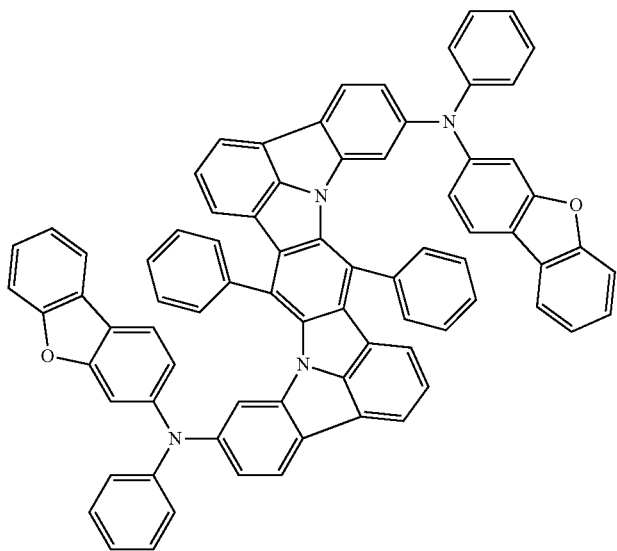
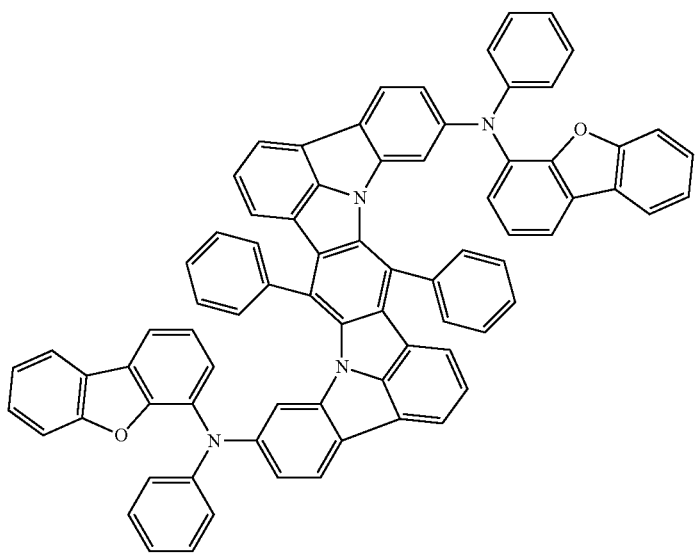

-continued
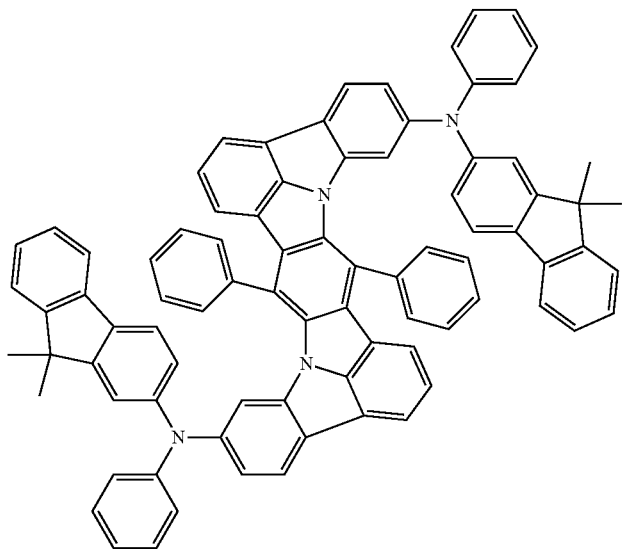
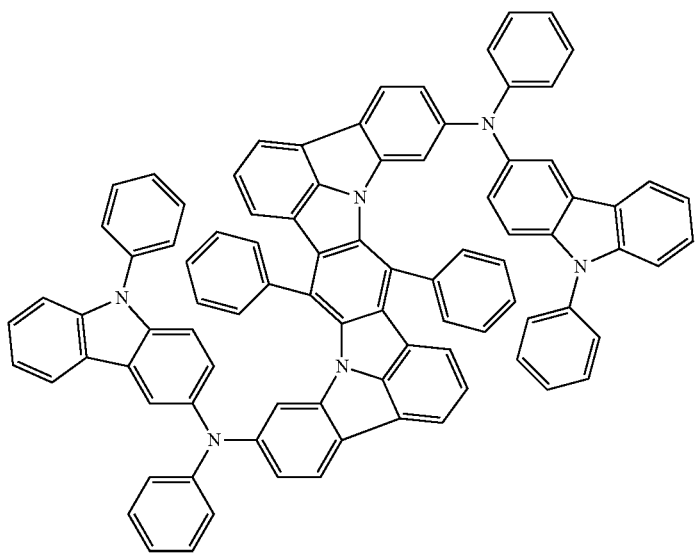
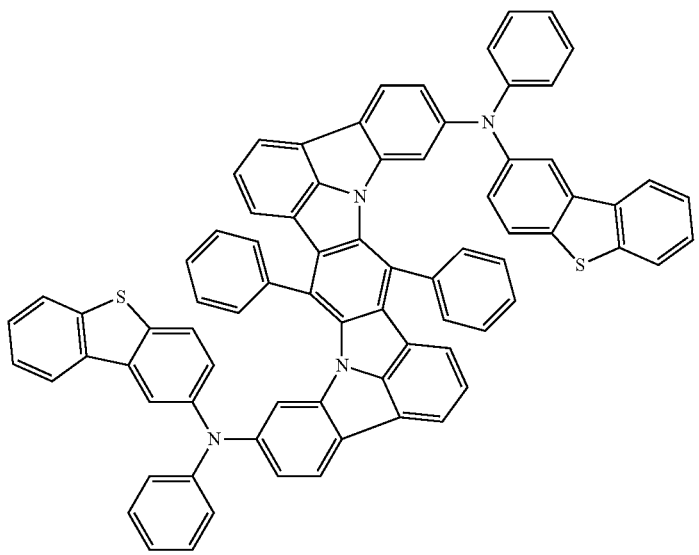

-continued
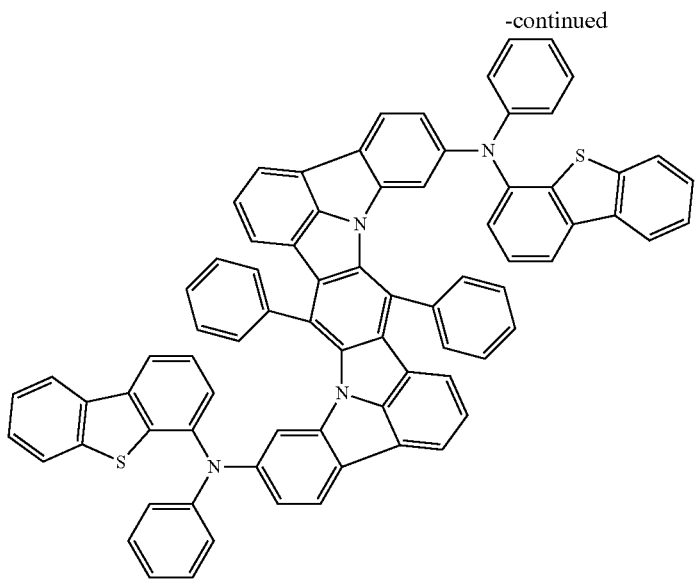
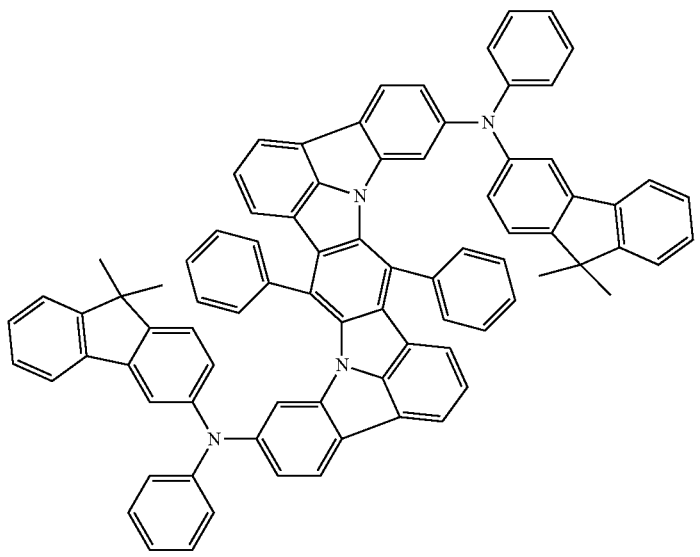
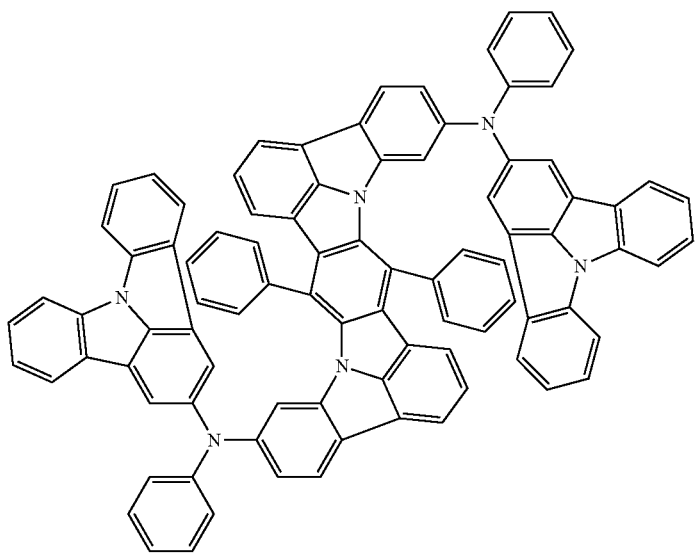

-continued
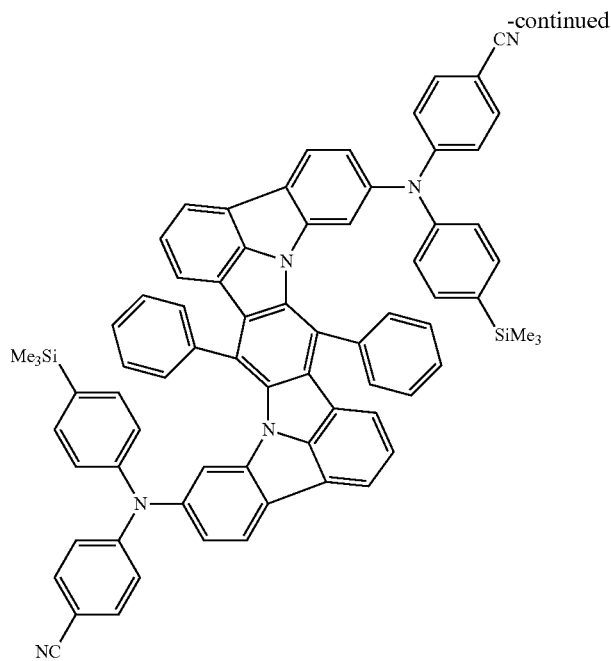
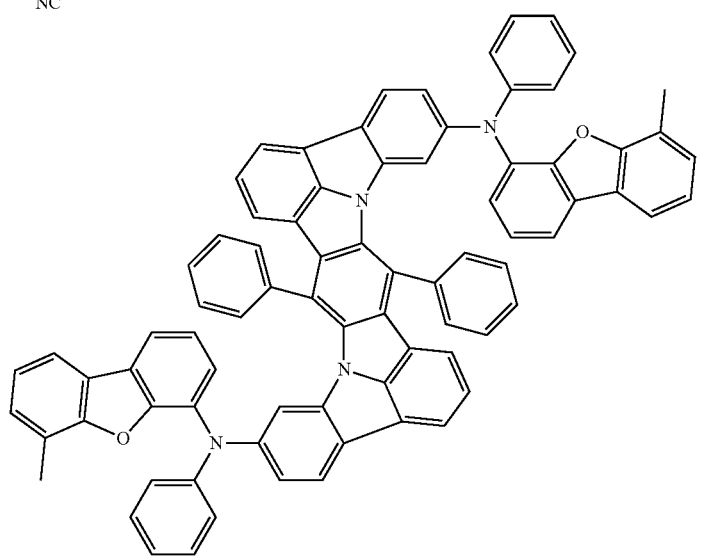
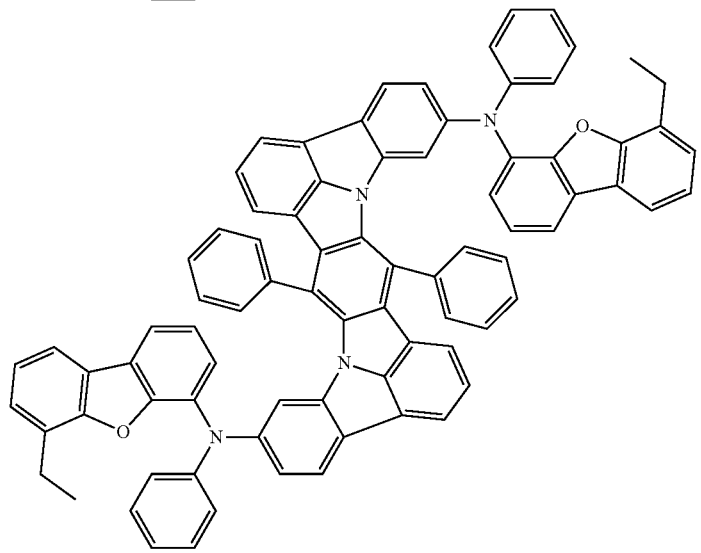

-continued
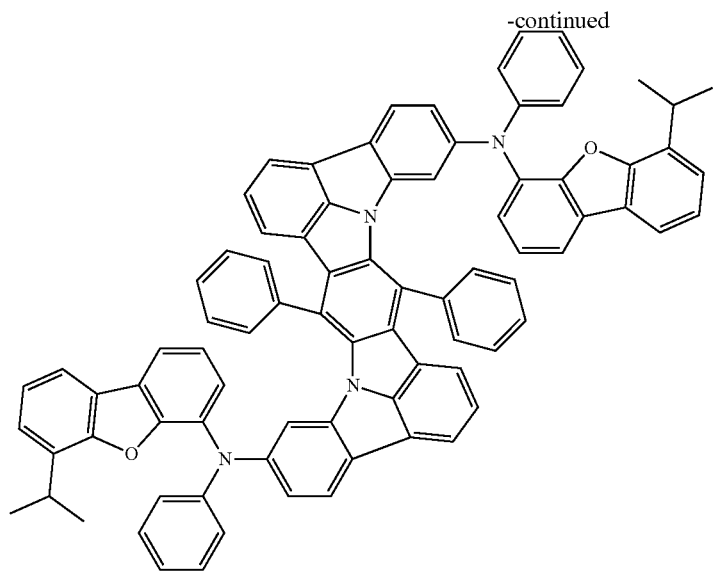
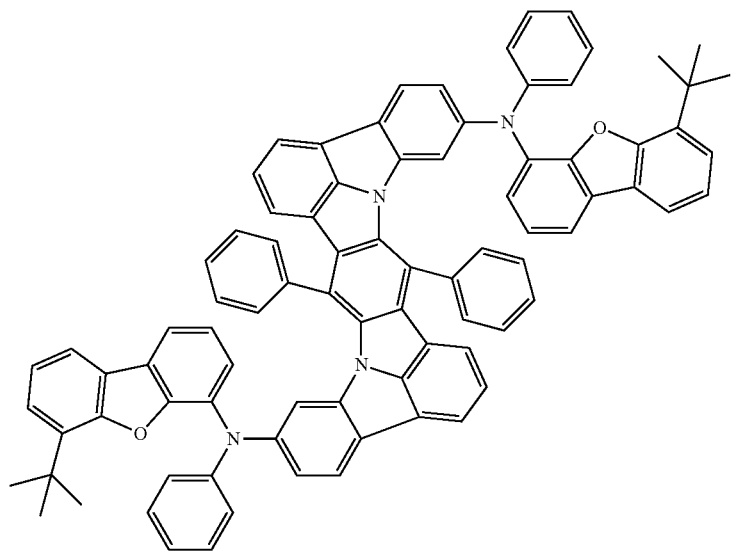
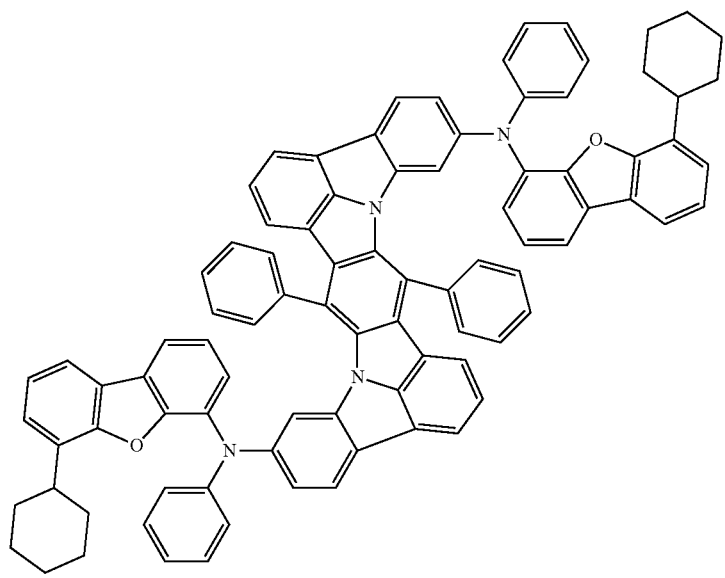

-continued
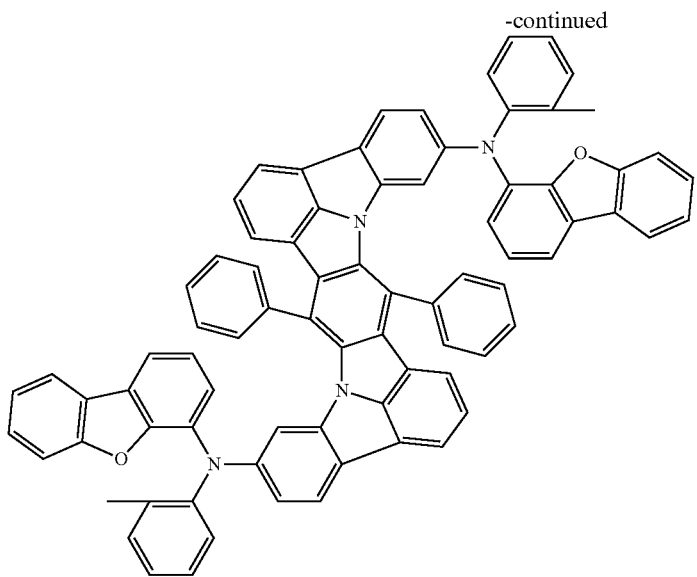
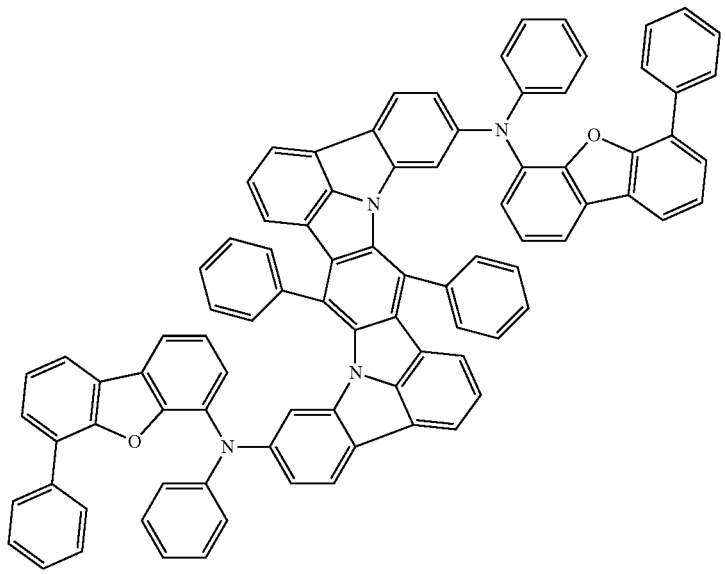
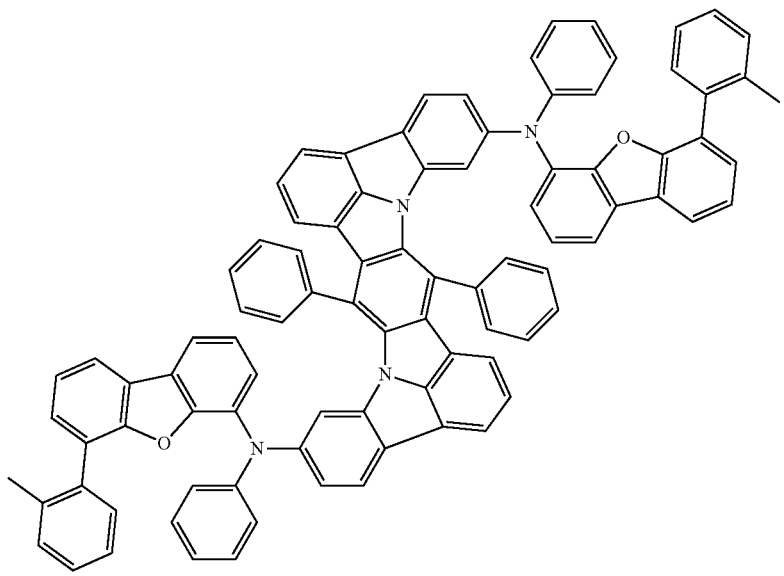

-continued
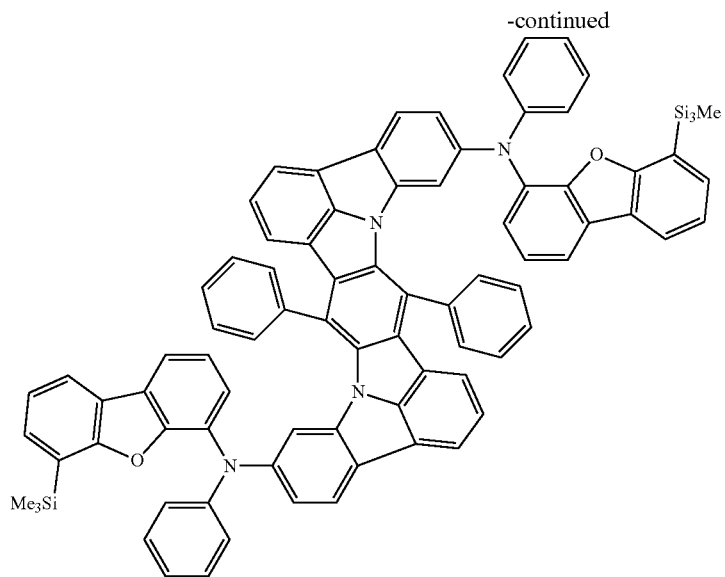
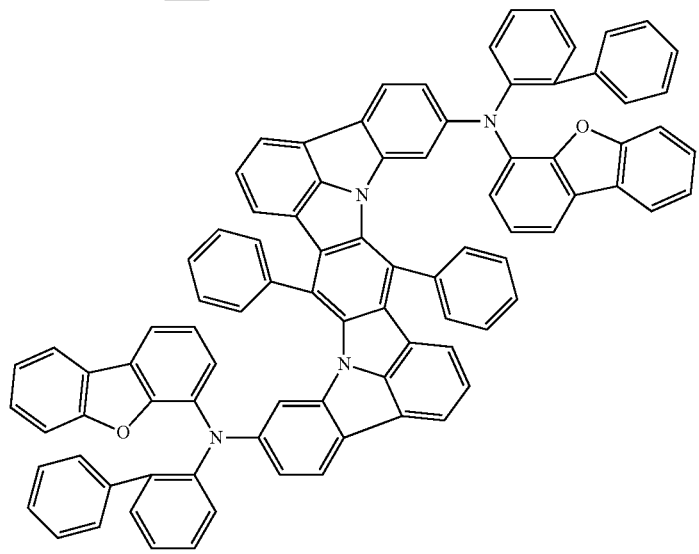
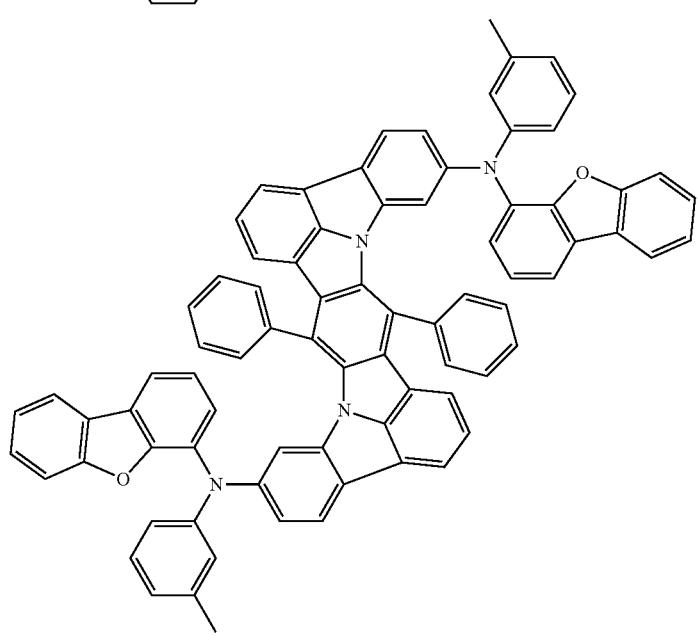

-continued
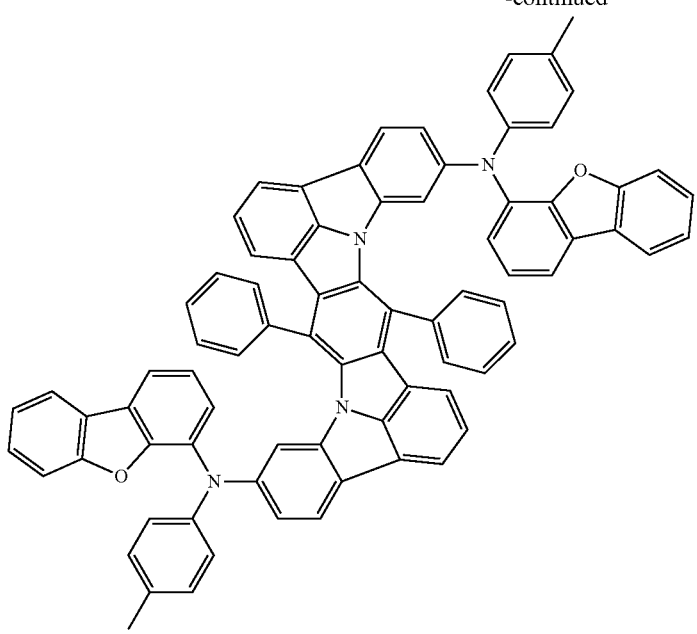
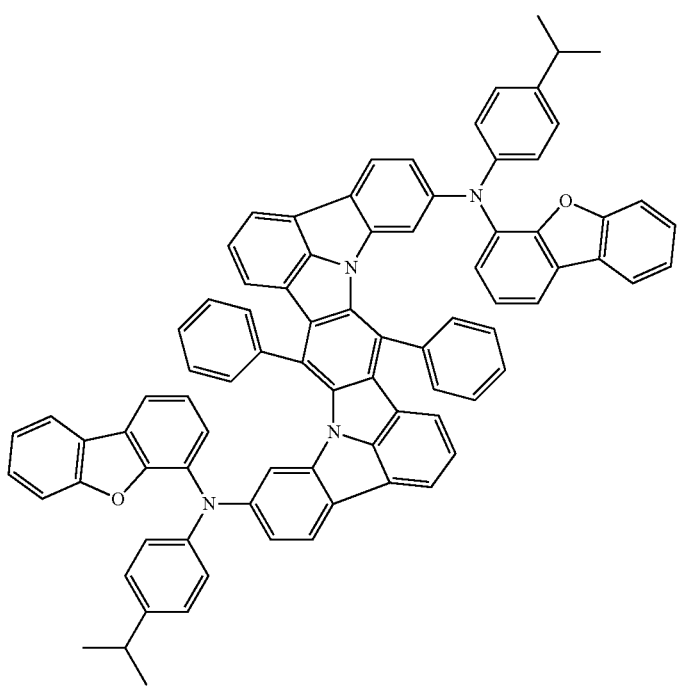

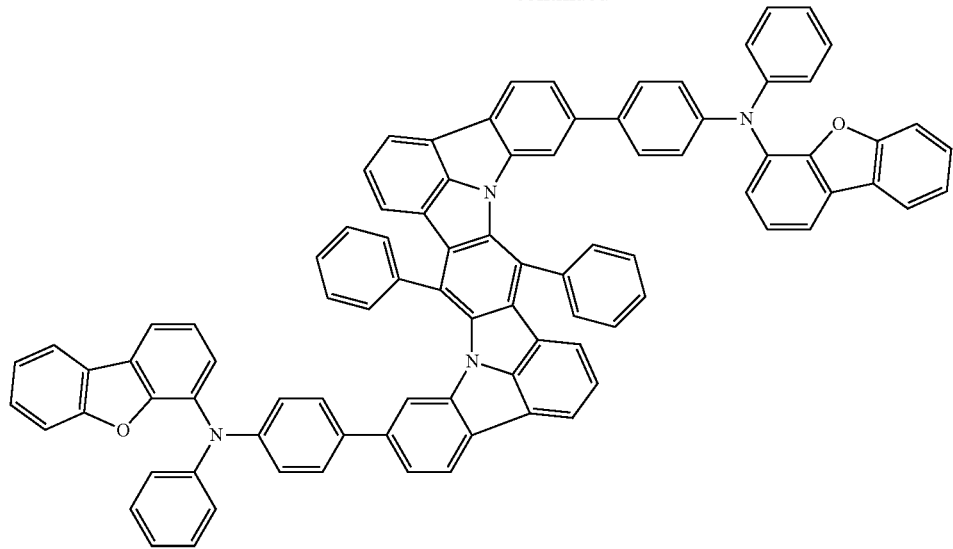
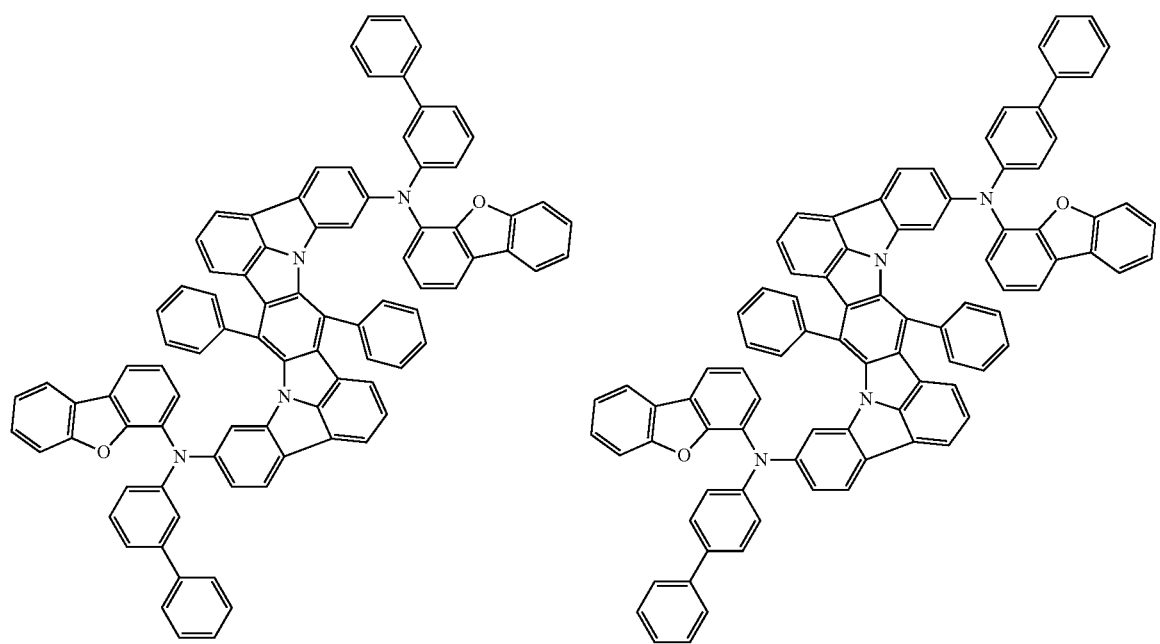

-continued
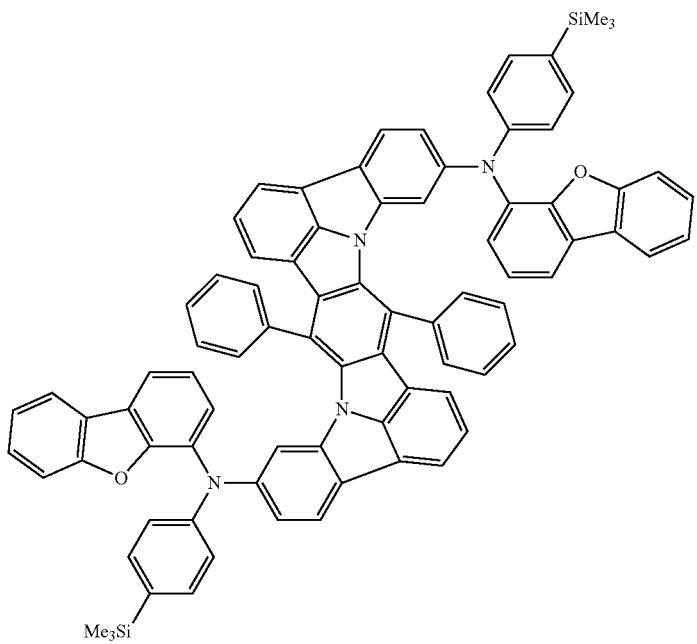
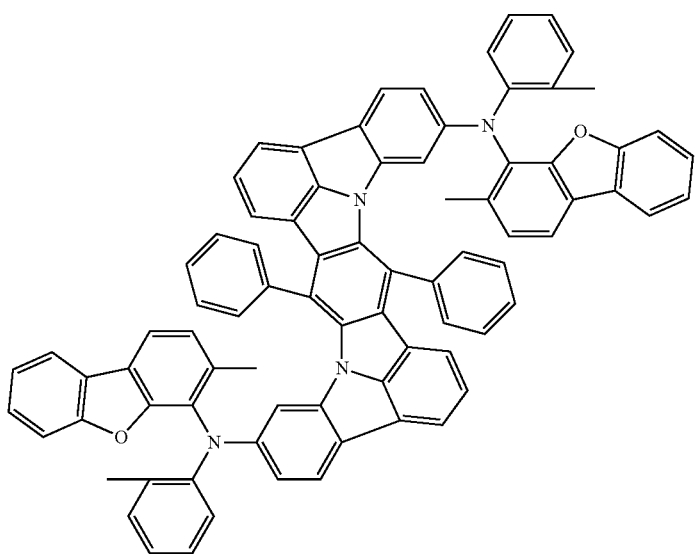

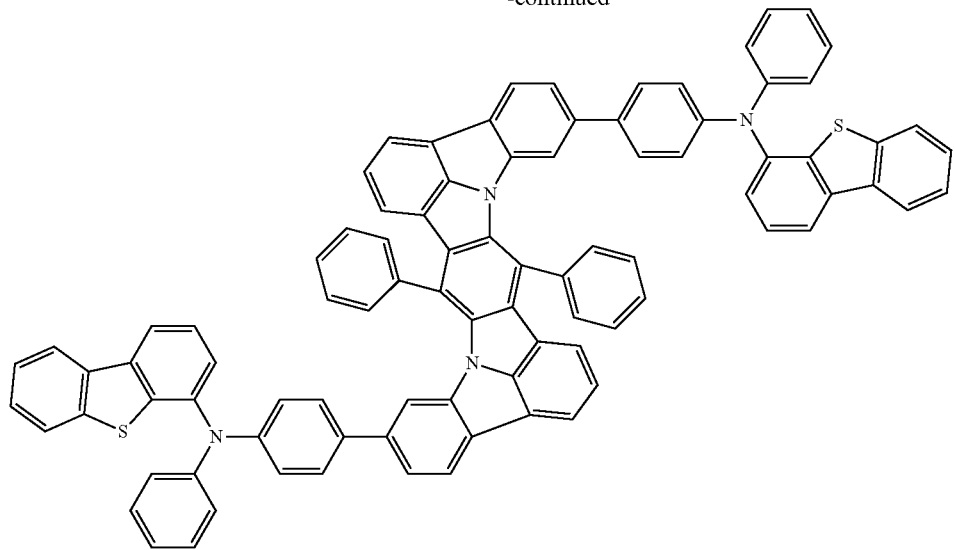
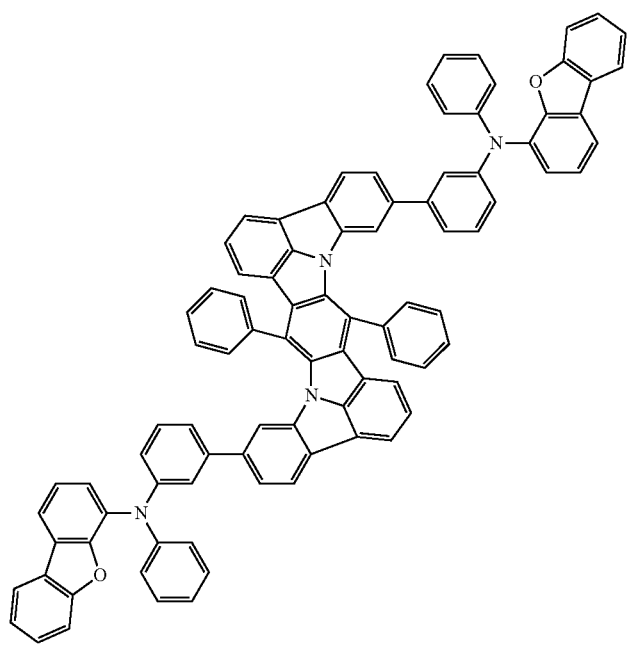

-continued
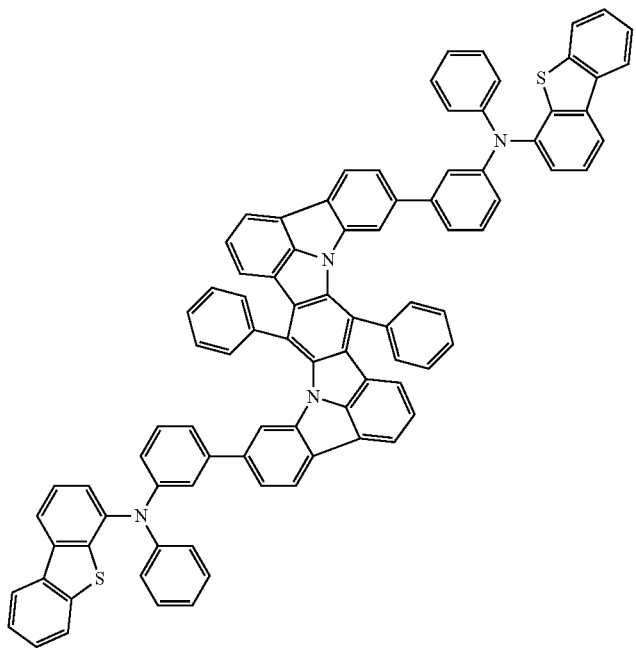
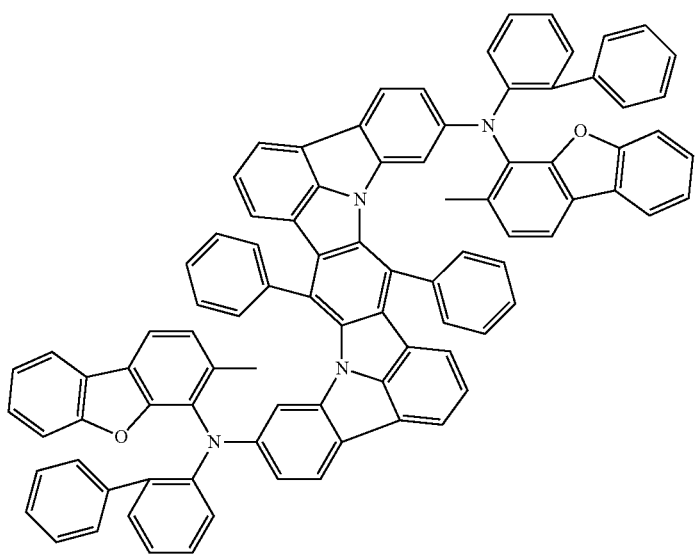

-continued
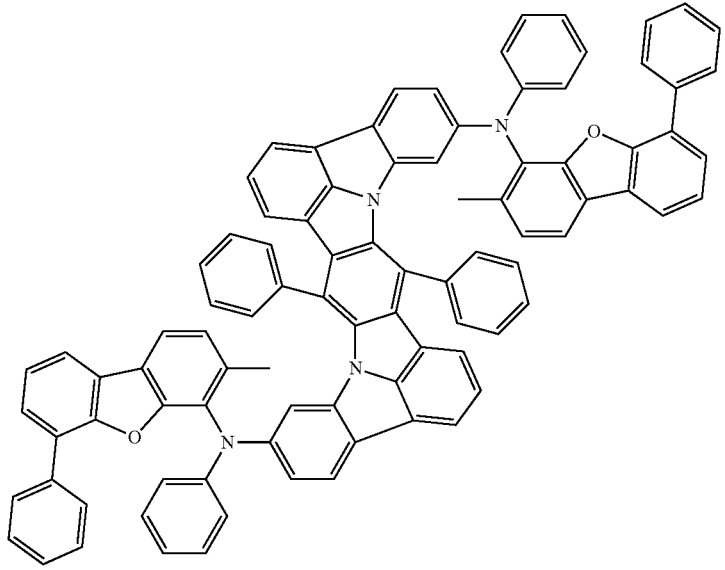
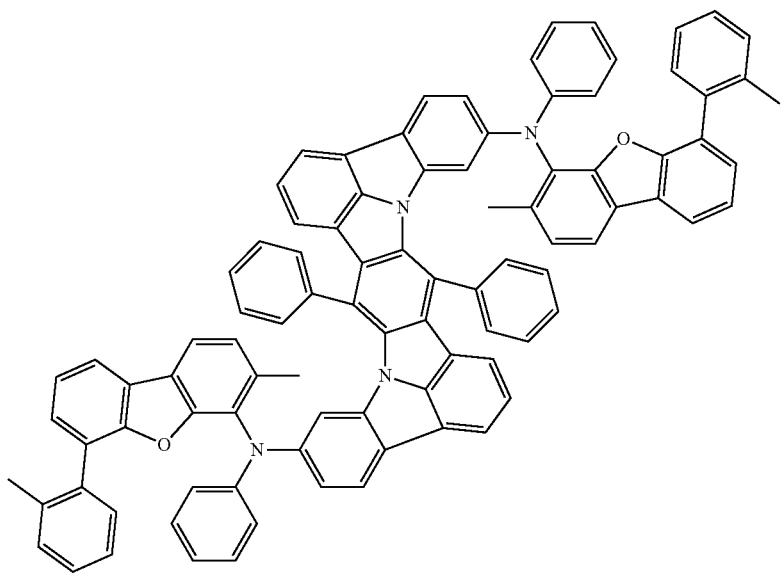
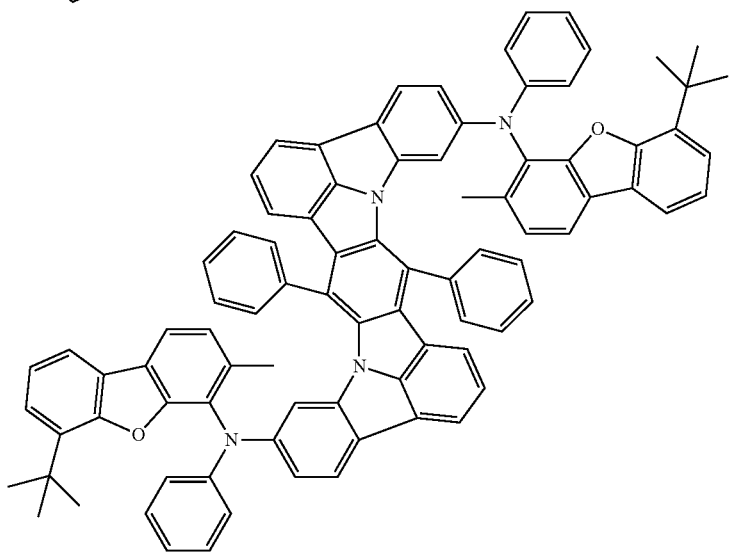

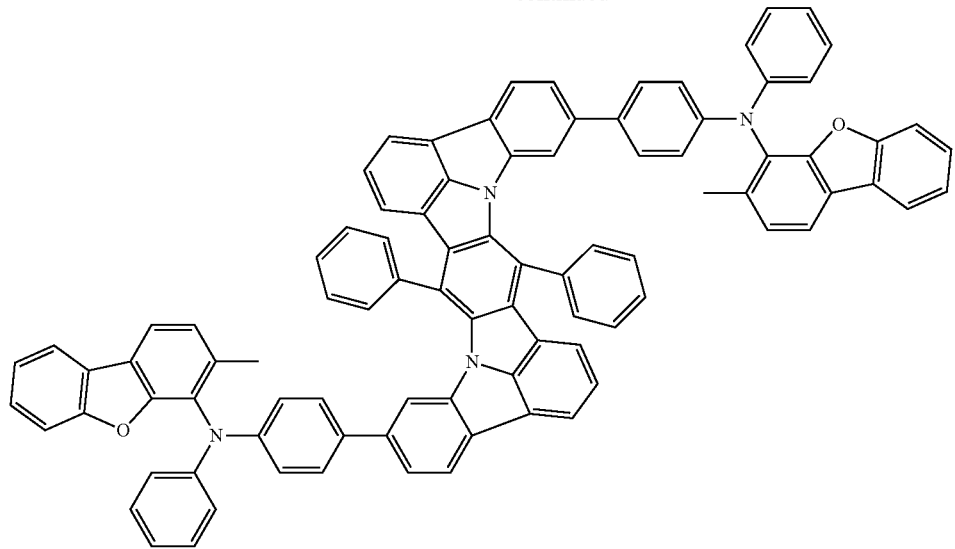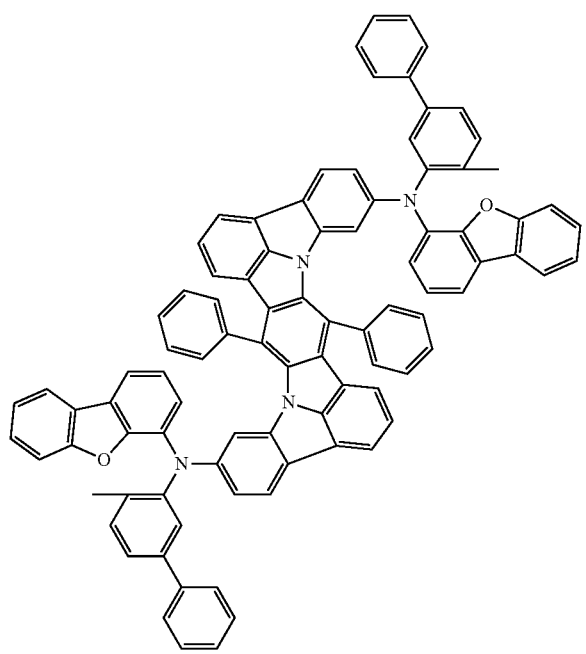 [SMILES: Cc1ccc(-c2ccccc2)cc1N(c1ccc2c3cccc4c5c(-c6ccccc6)c6c(c(-c7ccccc7)c5n(c2c1)c34)c1cccc2c3ccc(N(c4cc(-c5ccccc5)ccc4C)c4cccc5c4oc4ccccc45)cc3n6c21)c1cccc2c1oc1ccccc12]

369 370
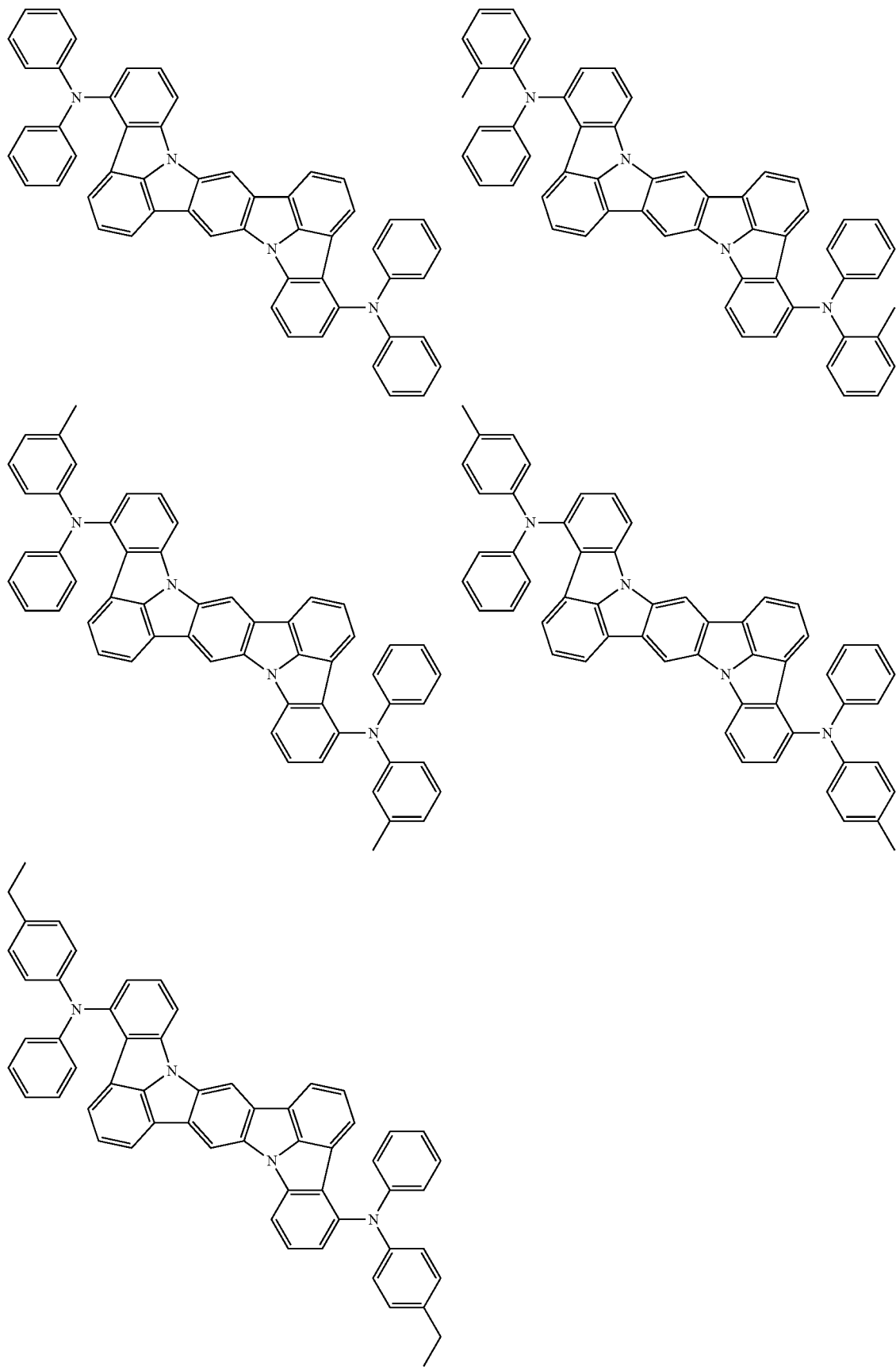

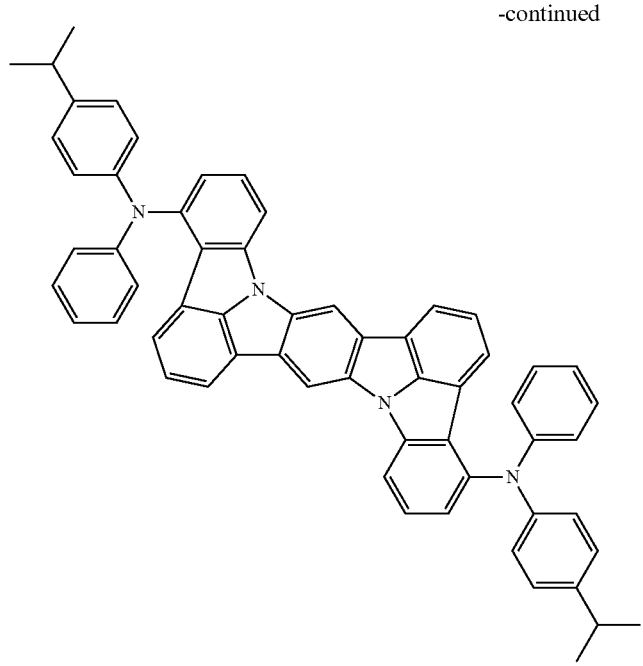
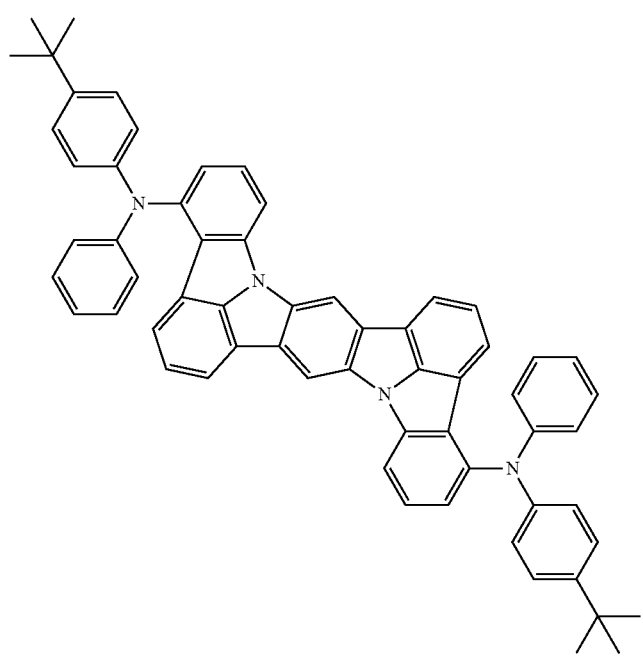

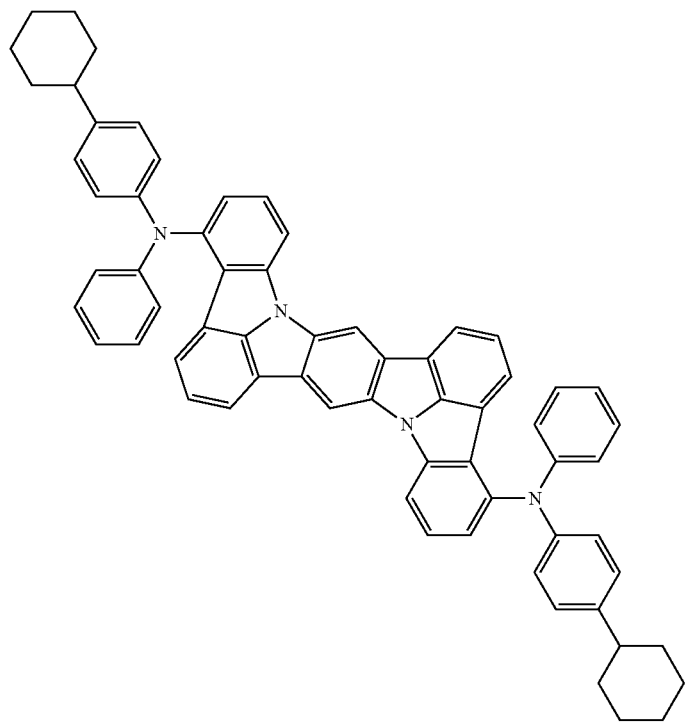
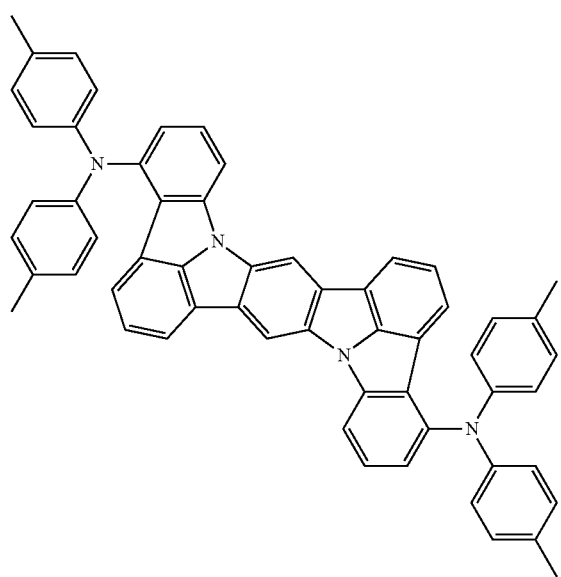

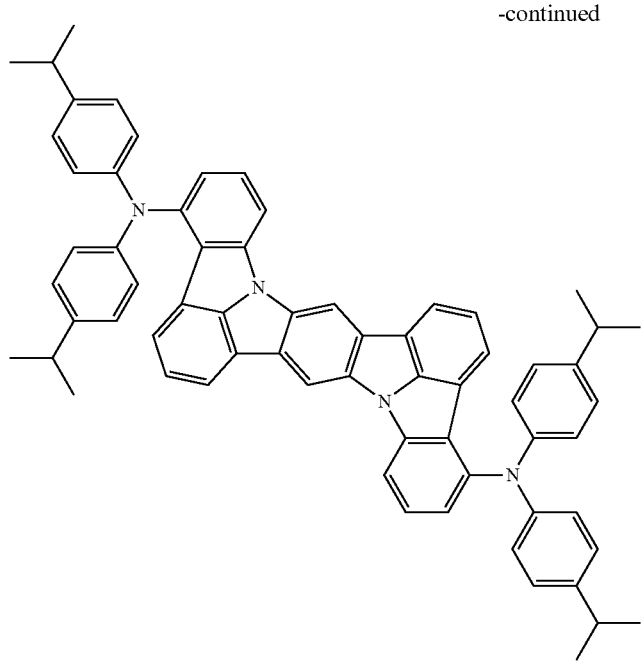
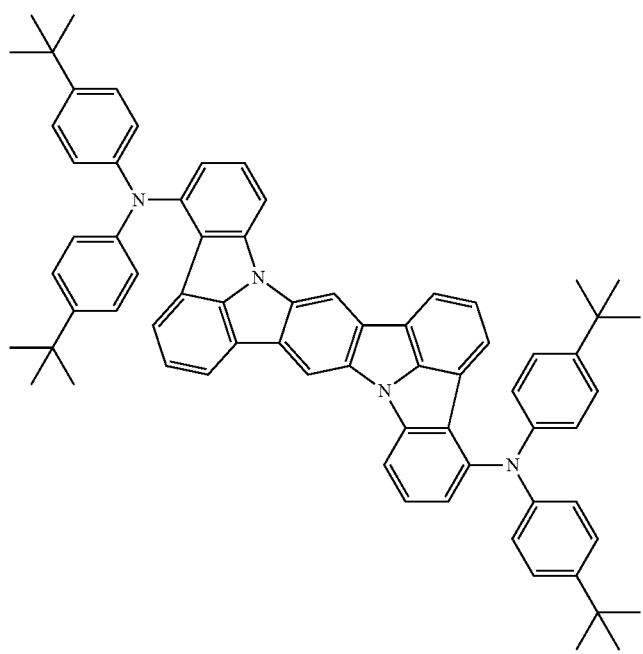

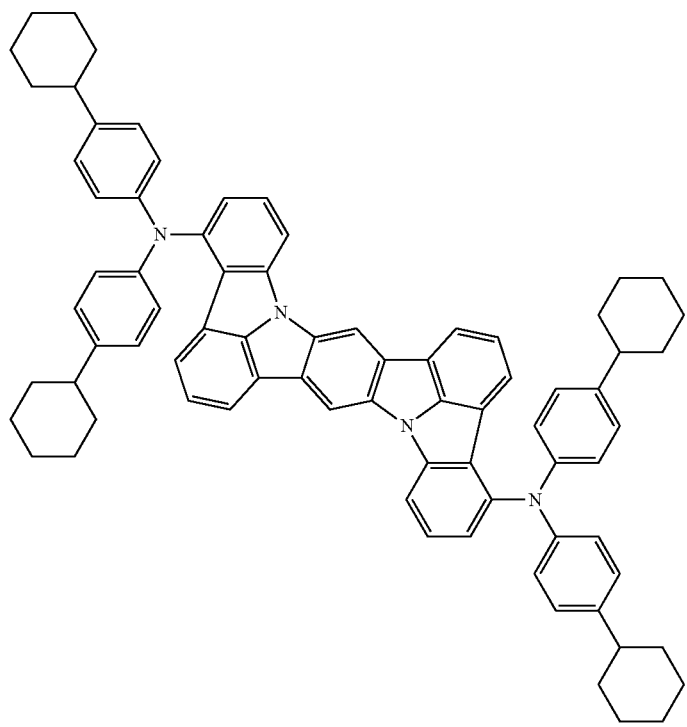
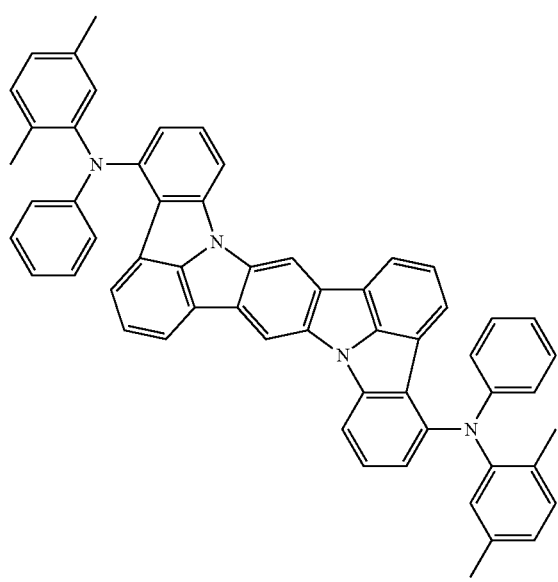

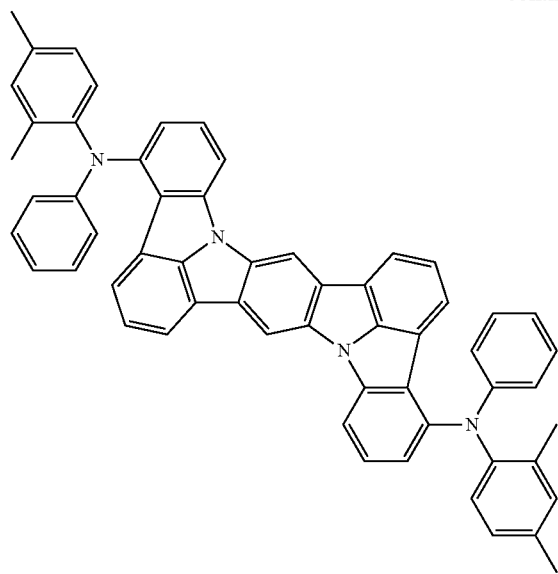
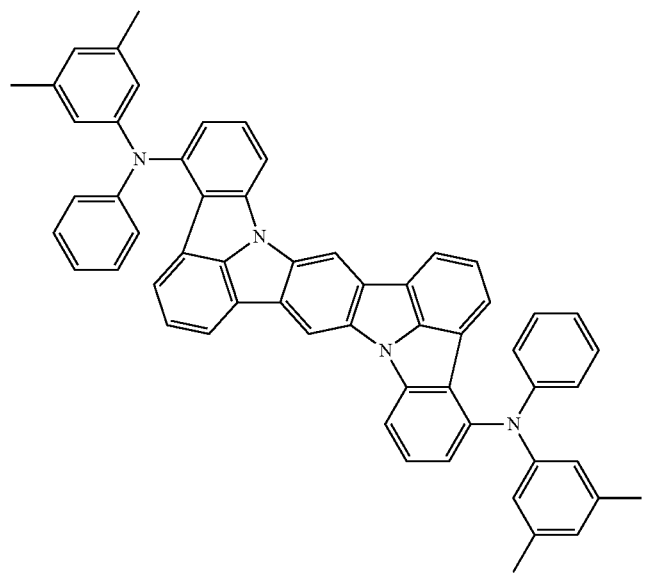
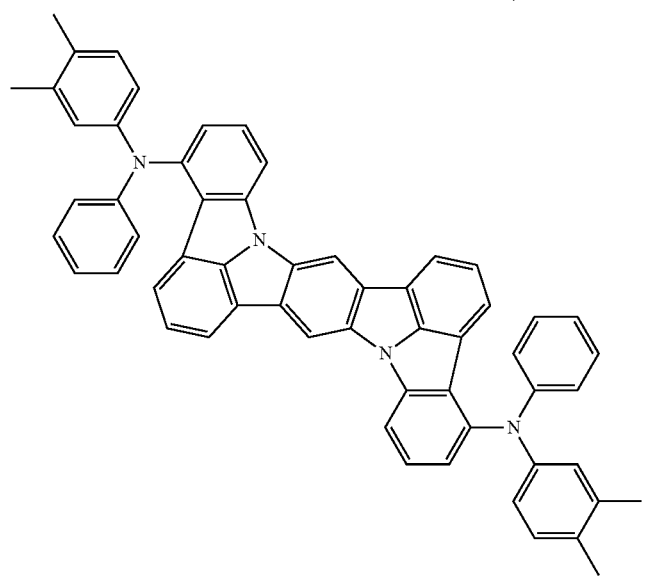

-continued
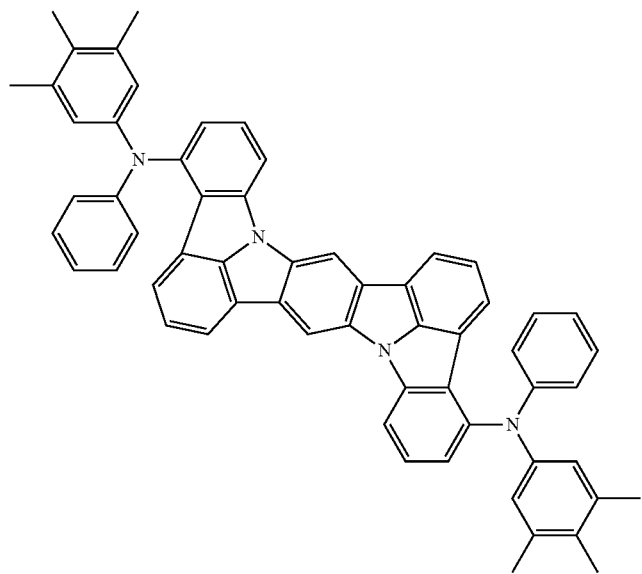
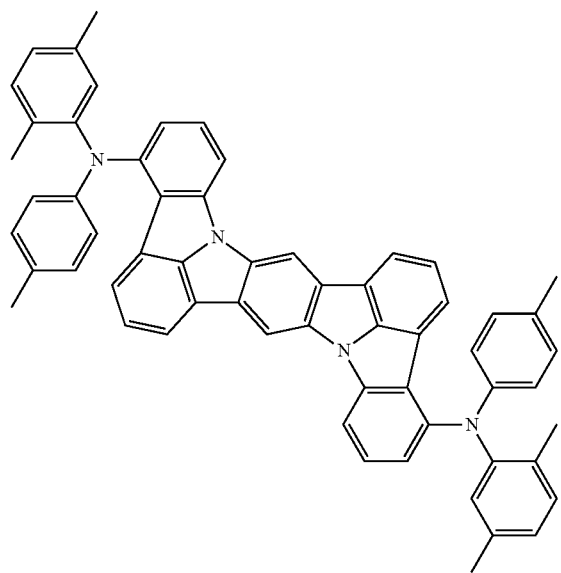
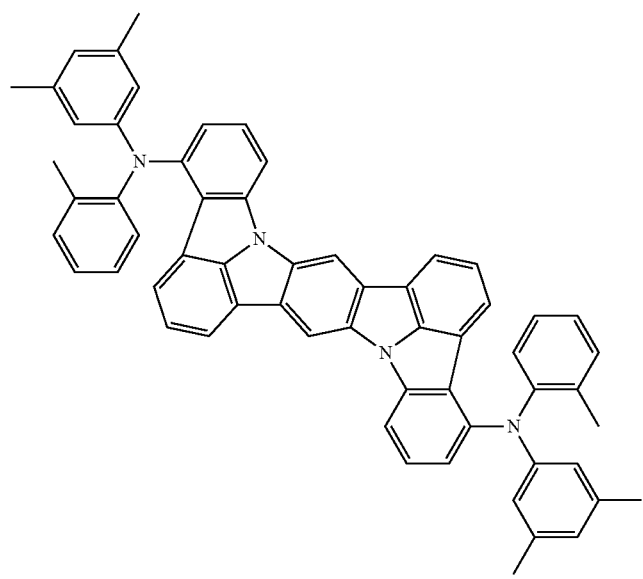

-continued
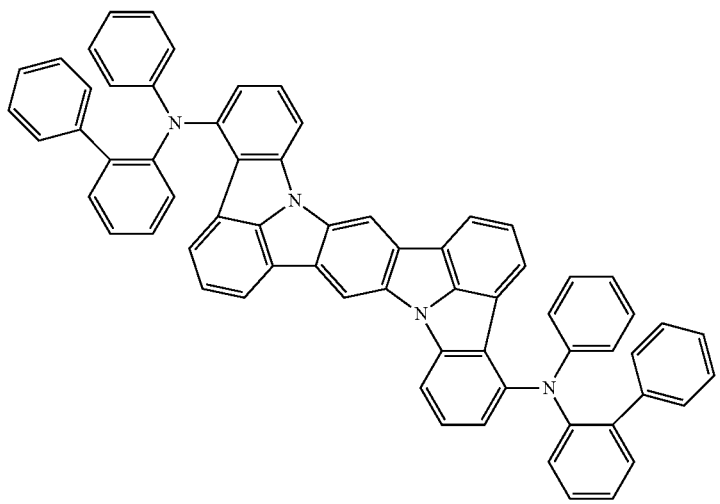
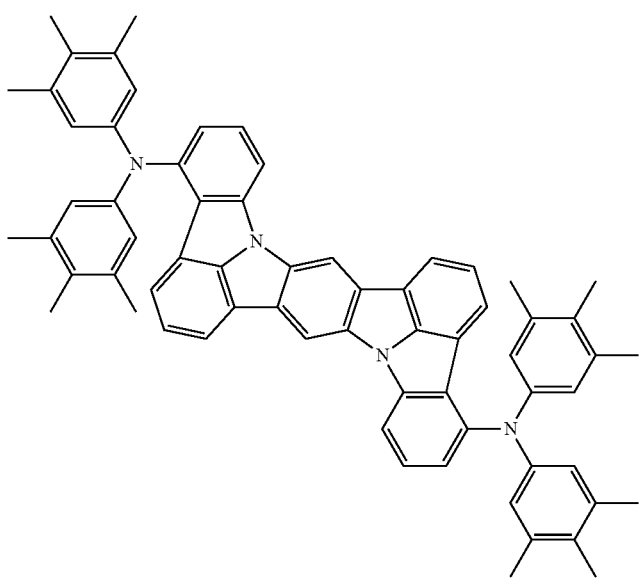

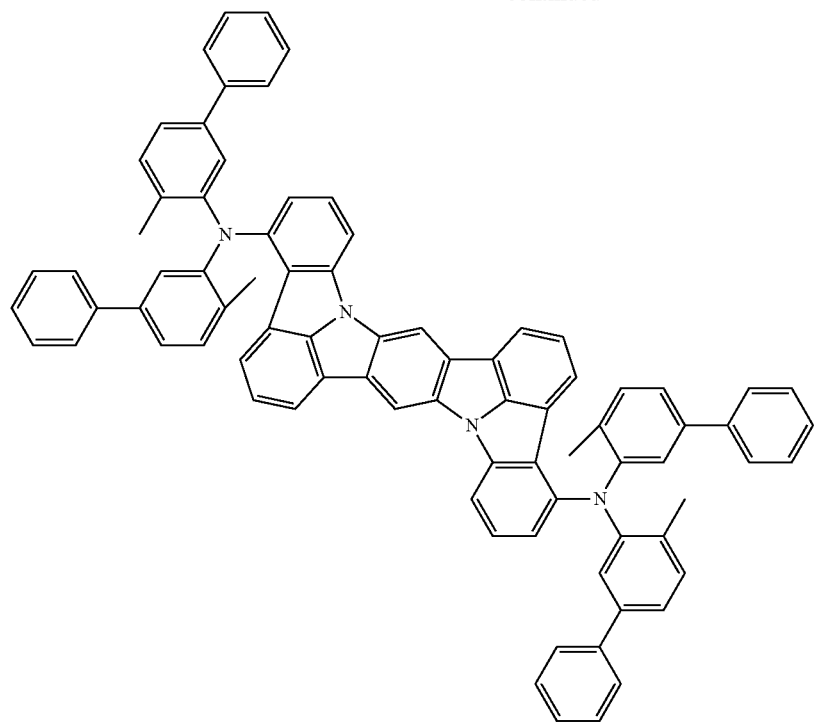
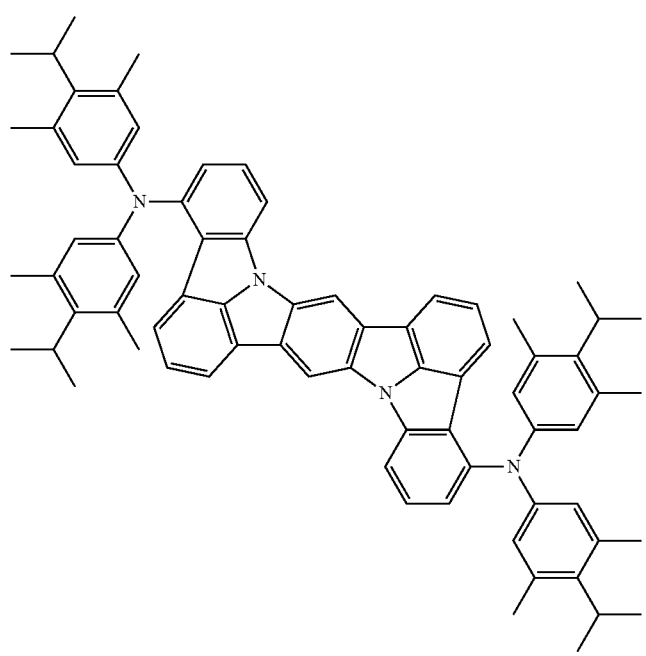

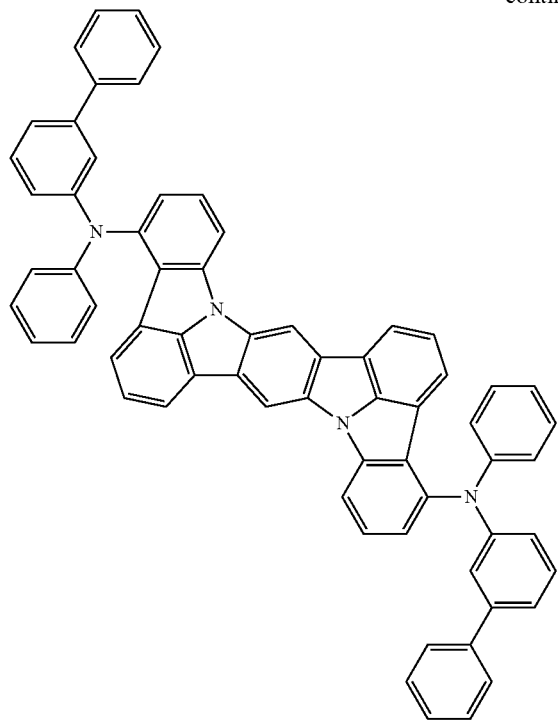
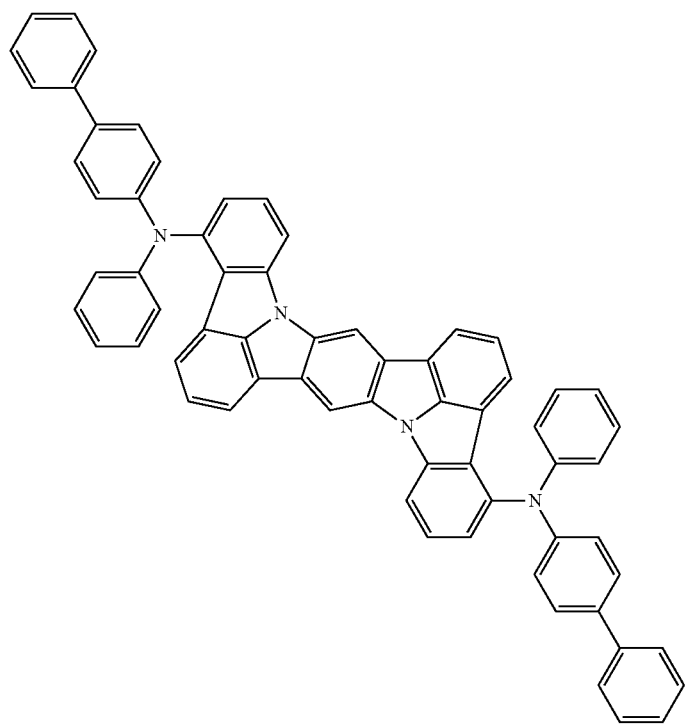

-continued
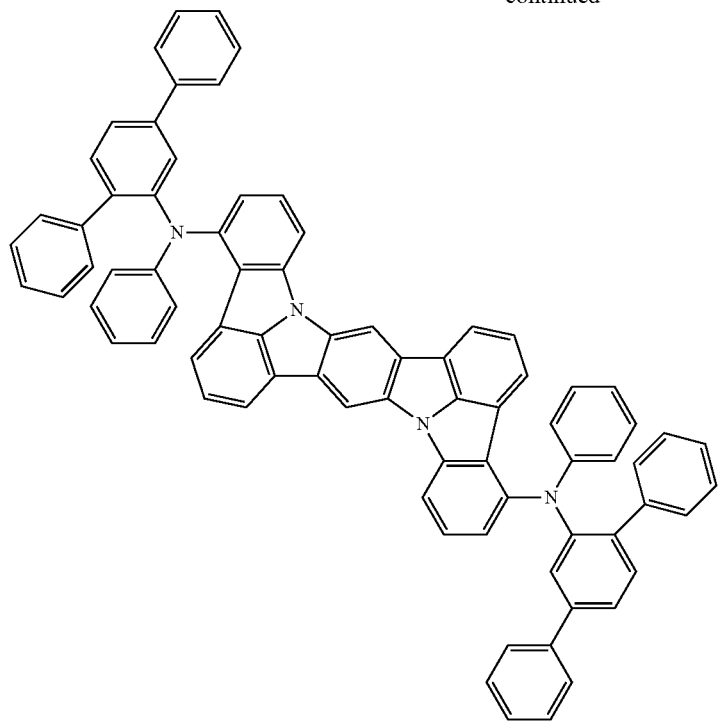
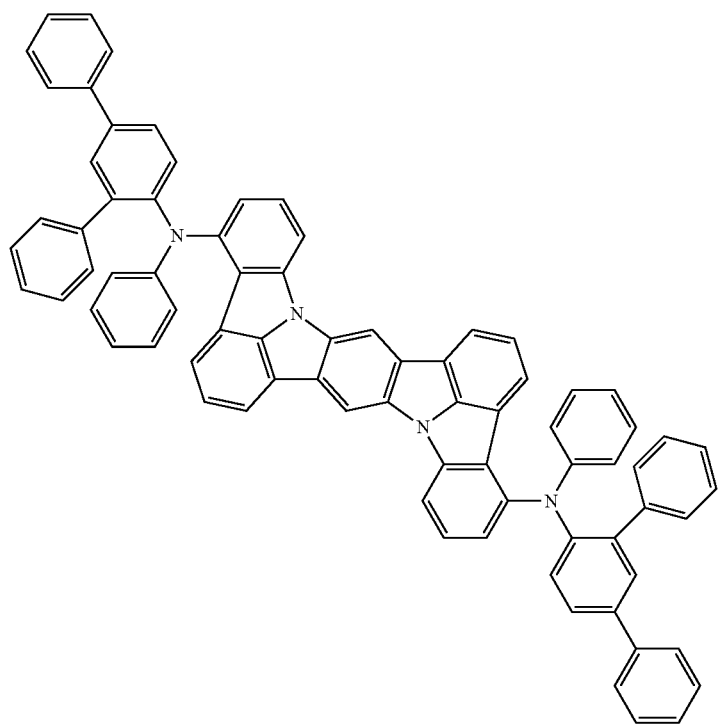 [SMILES: c1ccc(-c2ccc(N(c3ccccc3)c3cccc4c3c3cccc5c6cc7c(cc6n4c53)c3cccc4c5c(N(c6ccccc6)c6ccc(-c8ccccc8)cc6-c6ccccc6)cccc5n7c34)c(-c3ccccc3)c2)cc1]

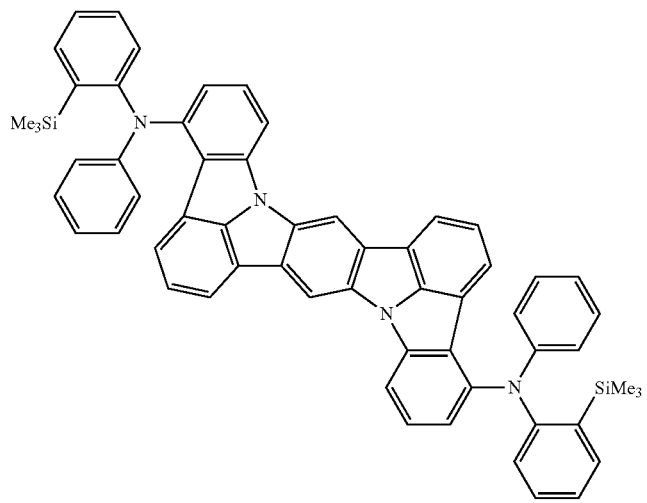
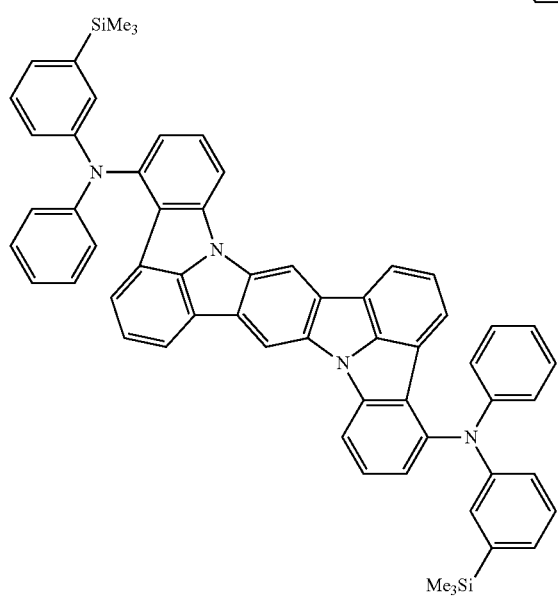
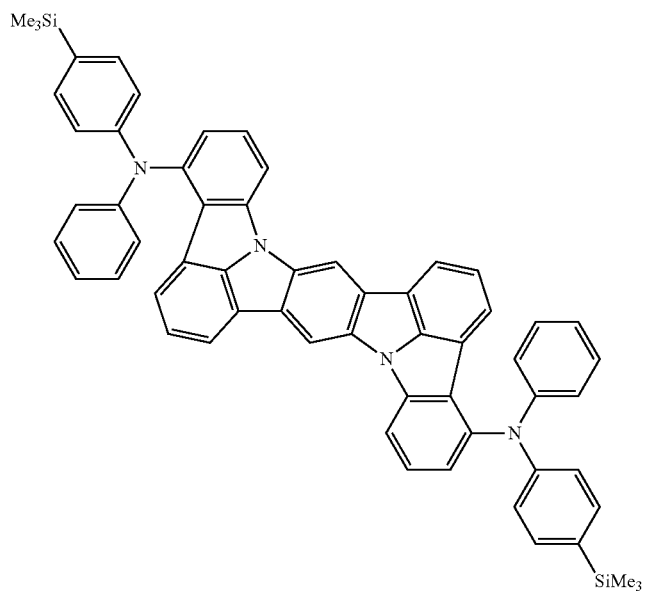

-continued
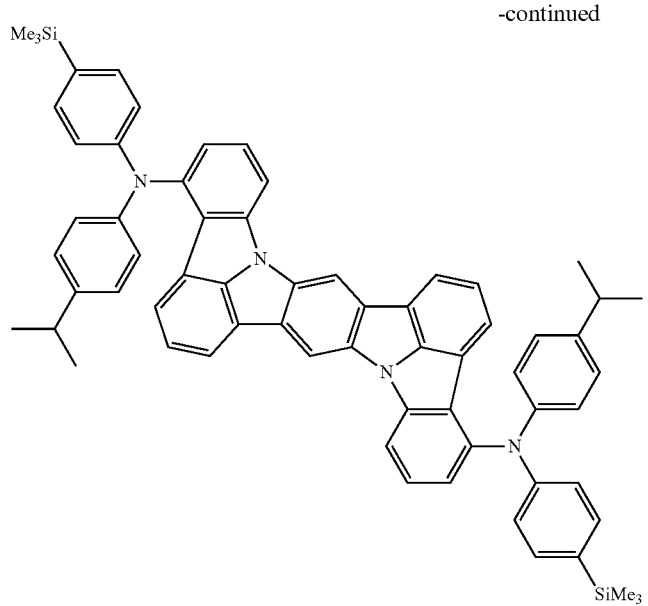
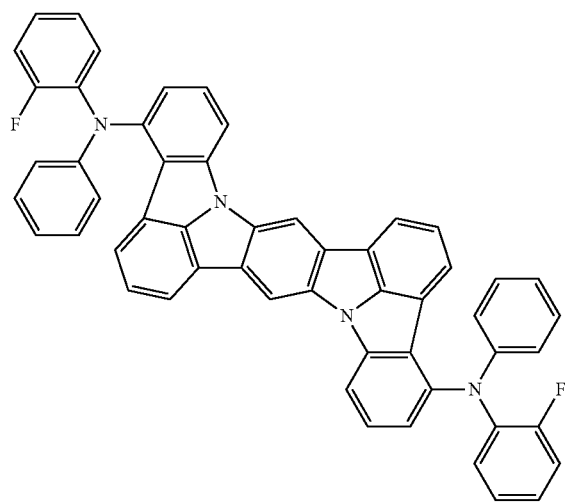
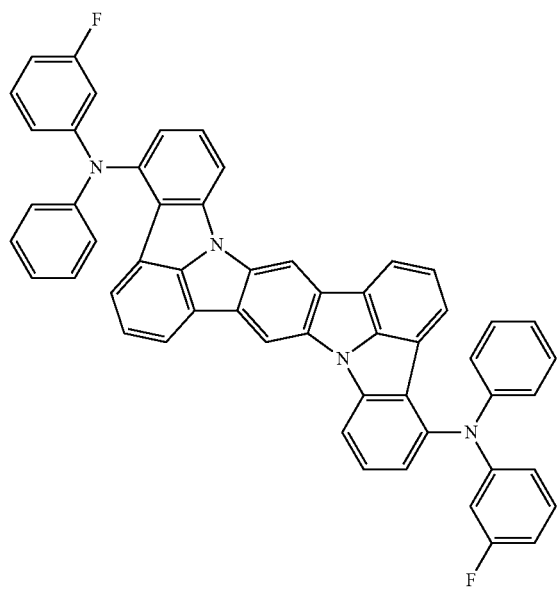

-continued
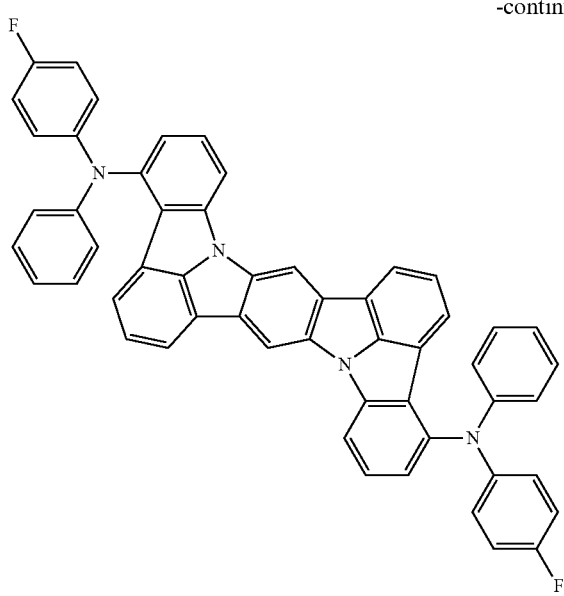
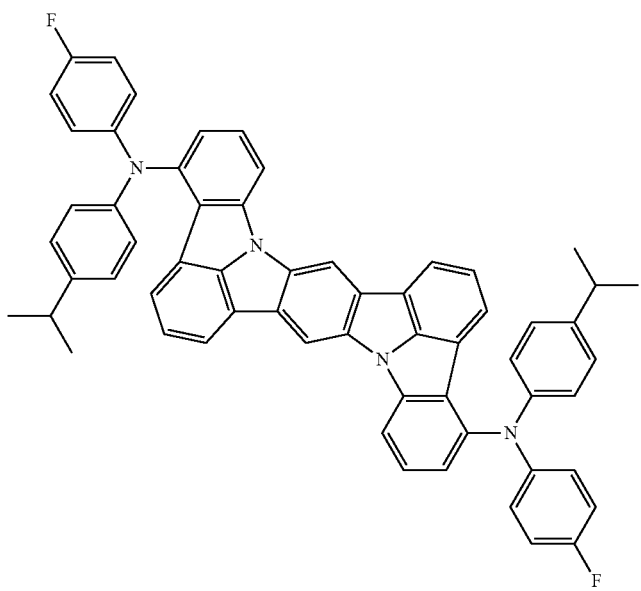
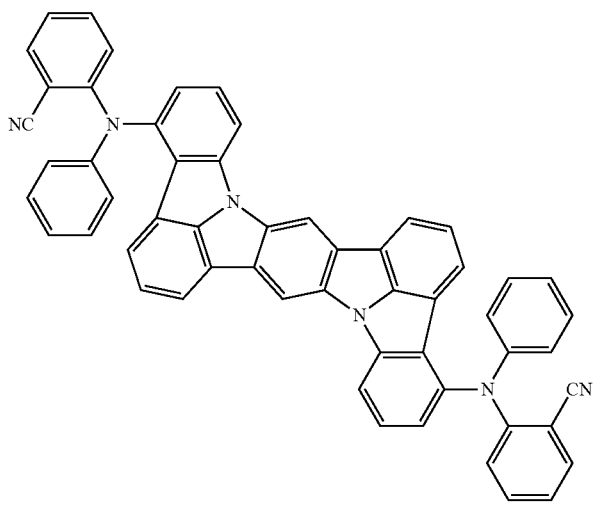

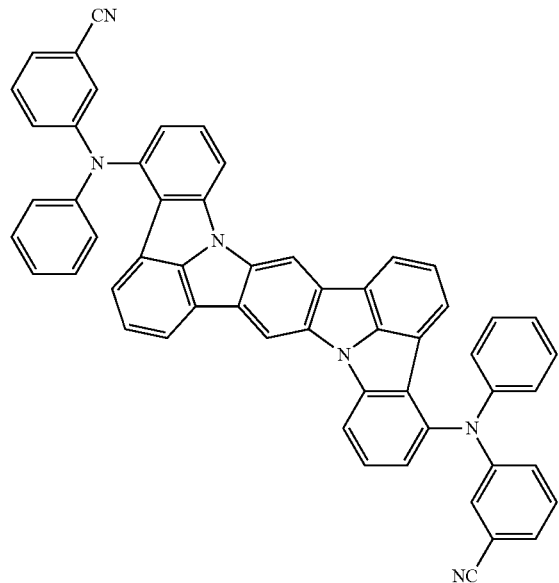
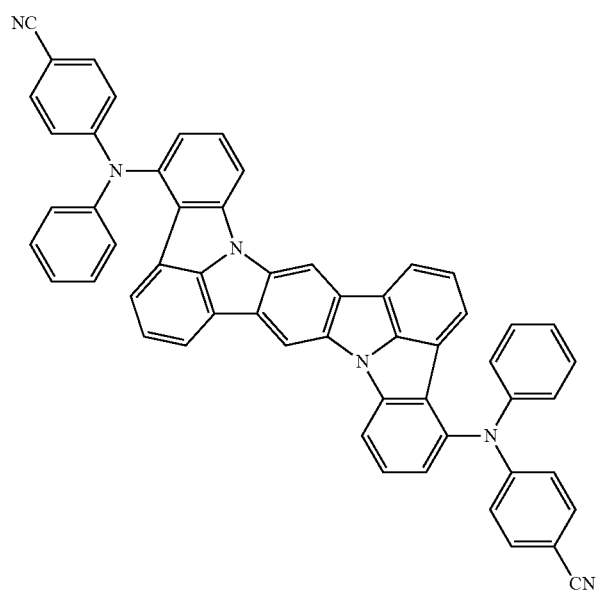

-continued
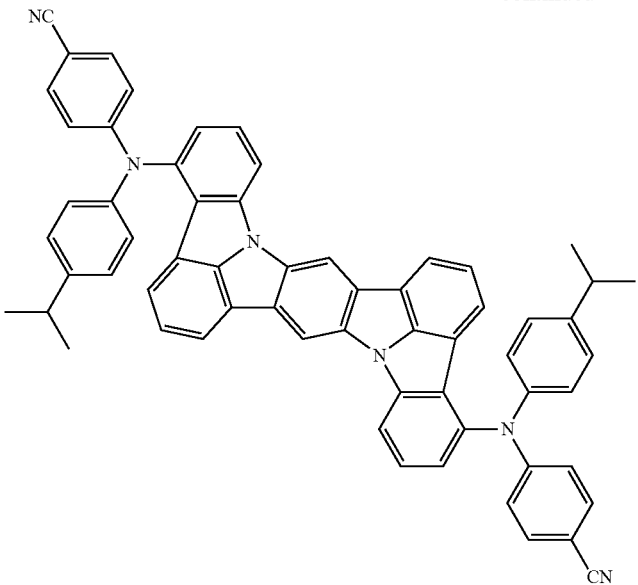
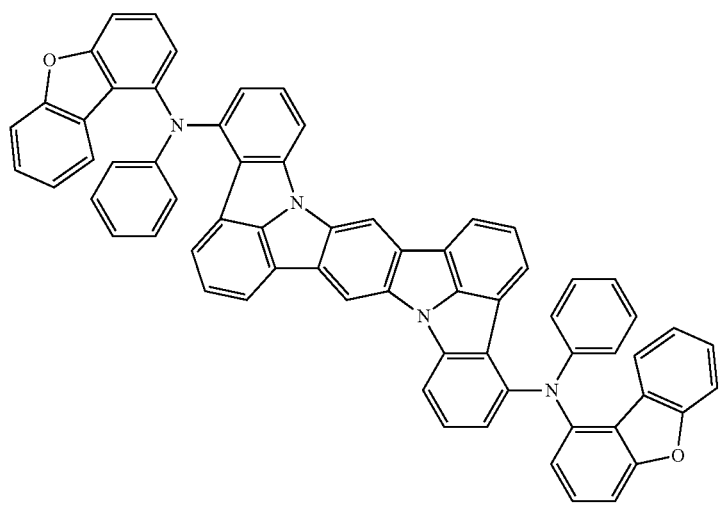
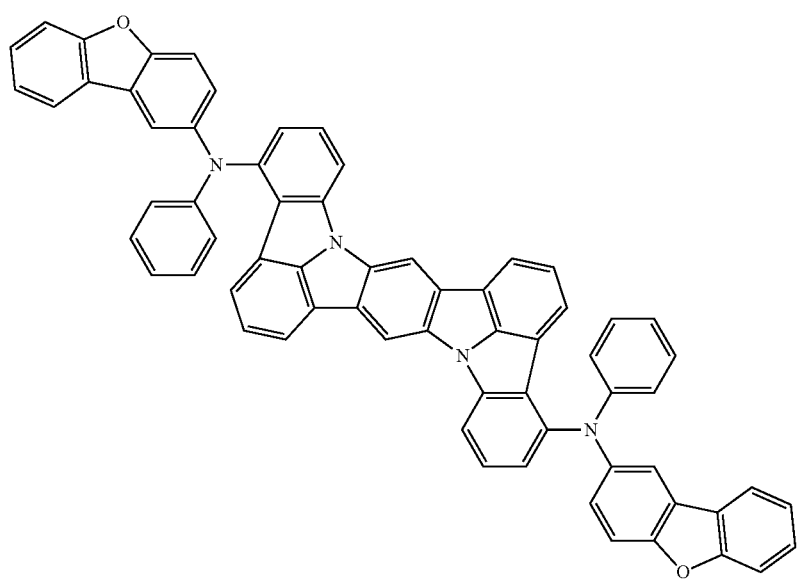

401
-continued
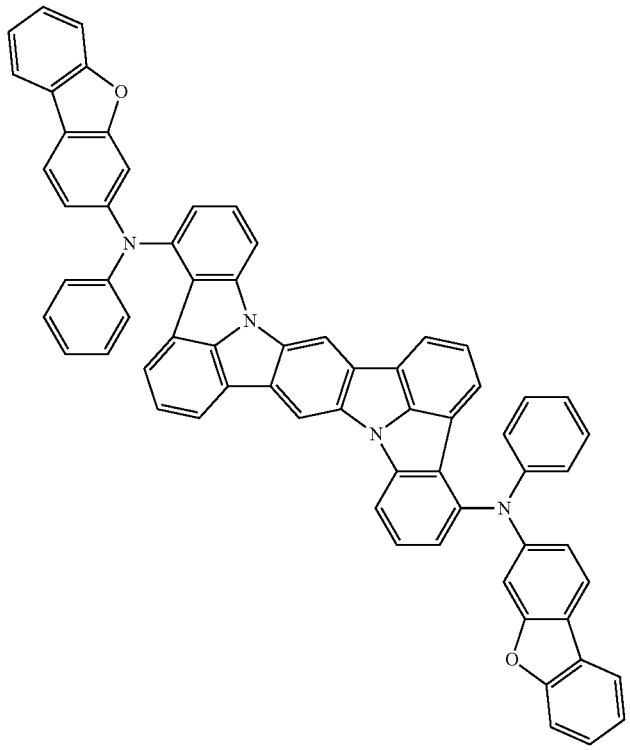
402
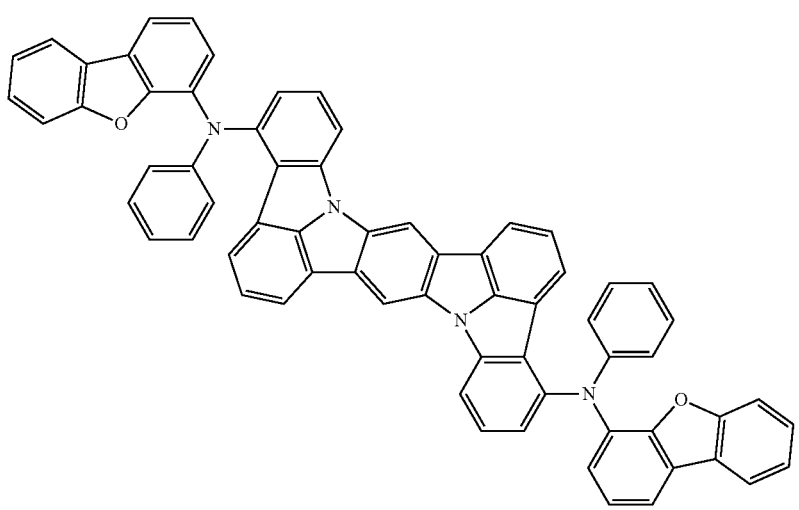

-continued
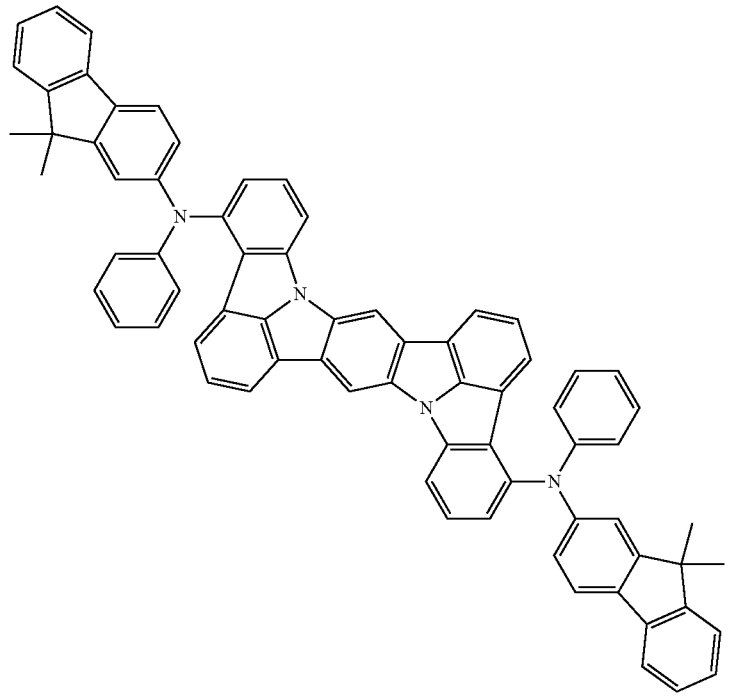
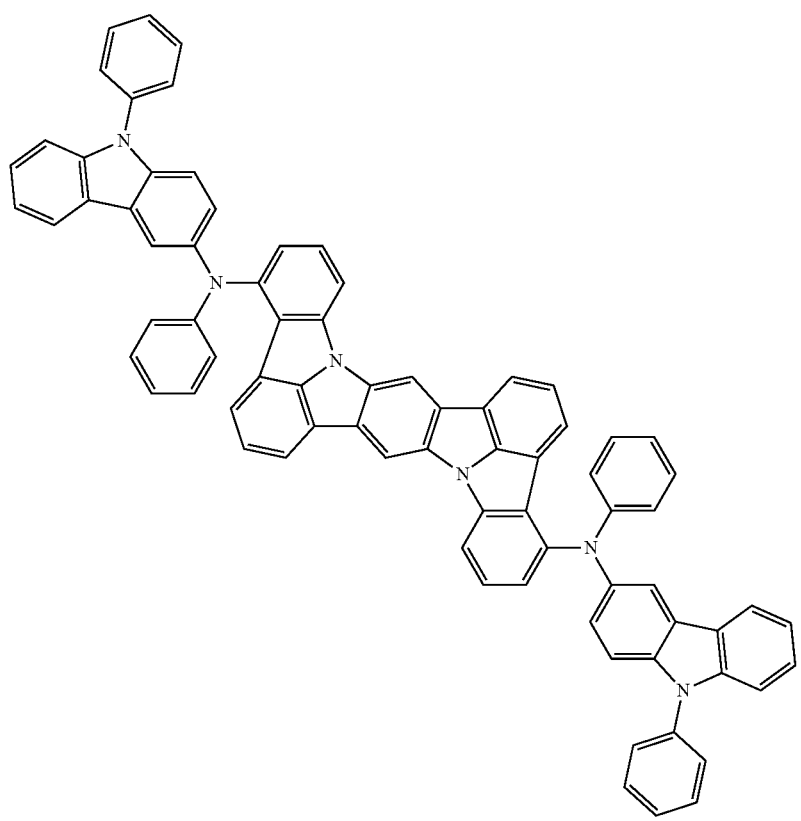

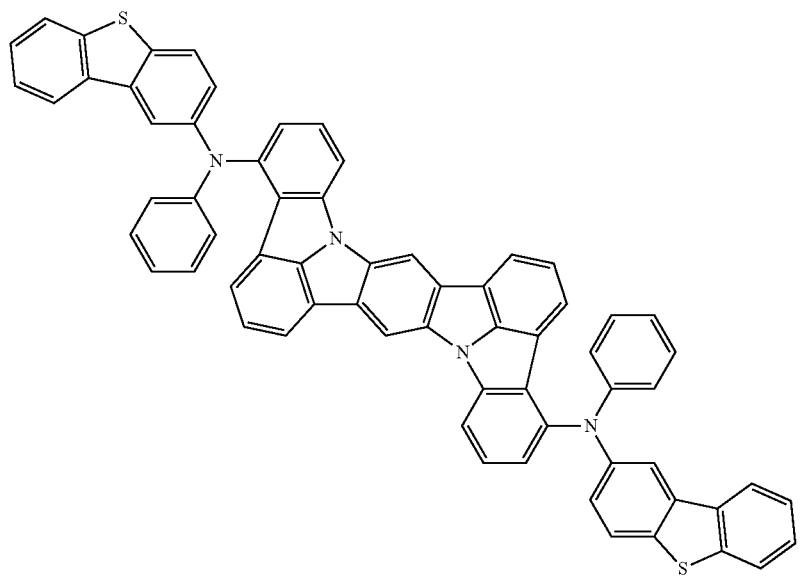
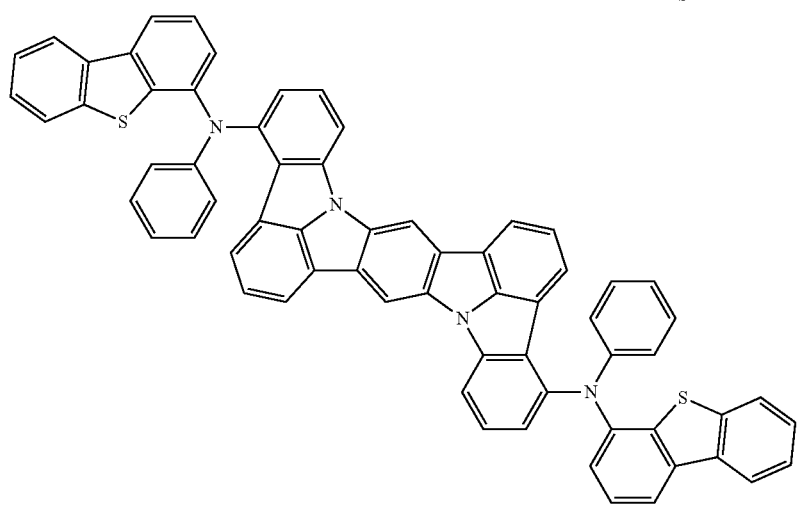
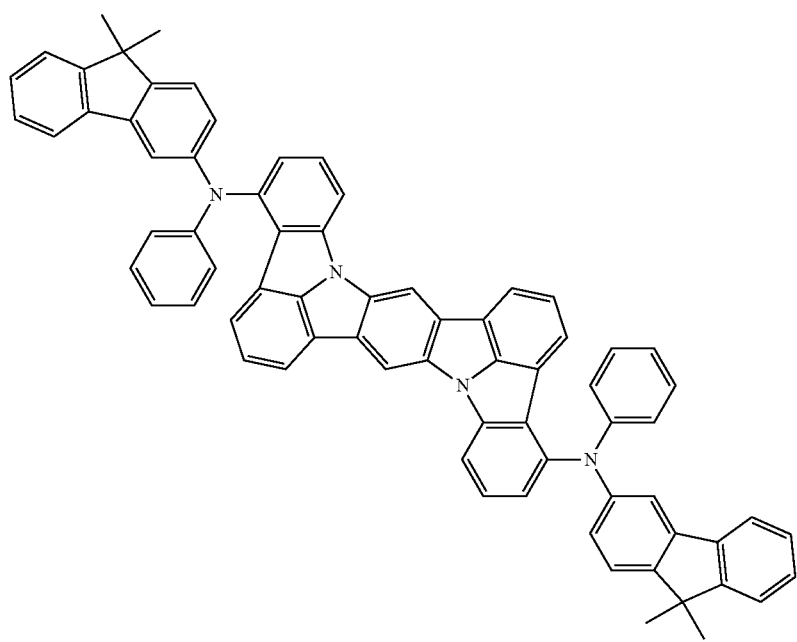

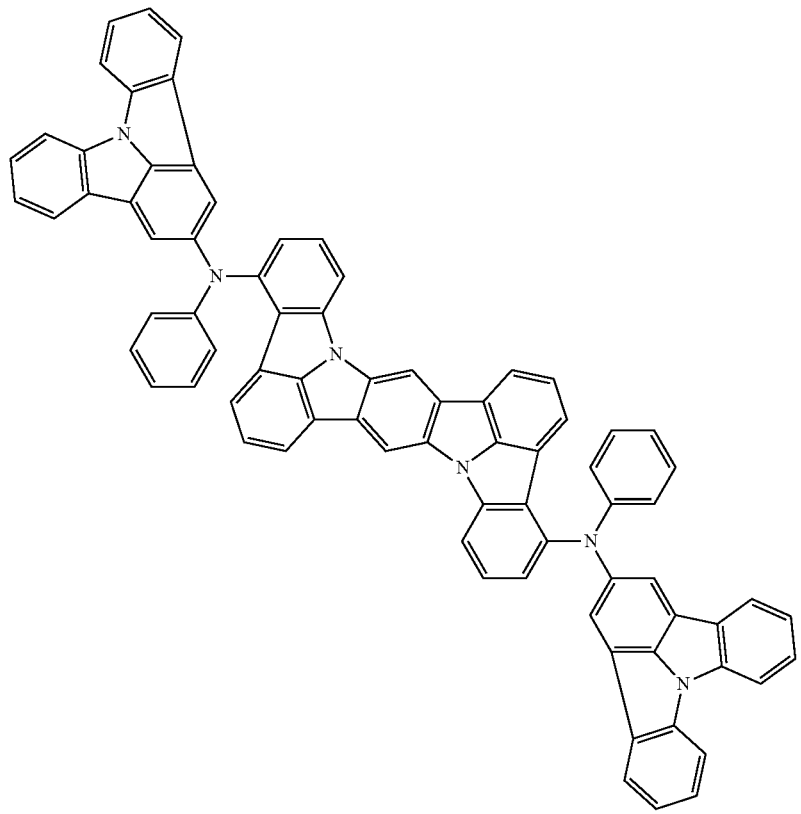
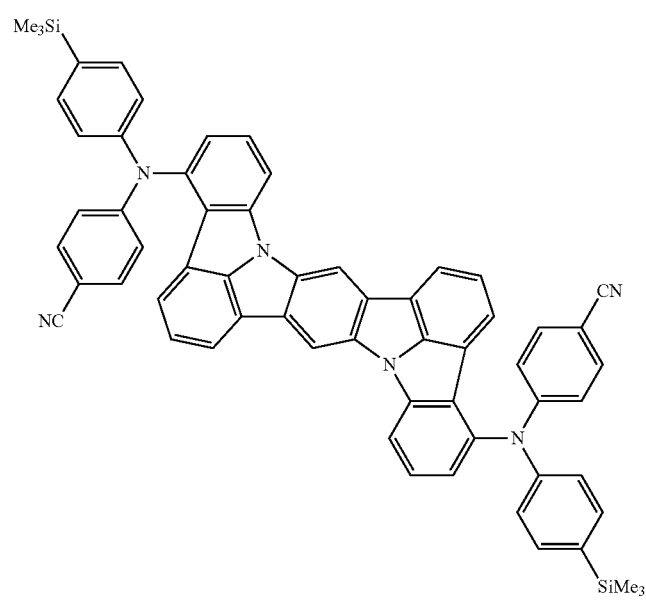

-continued
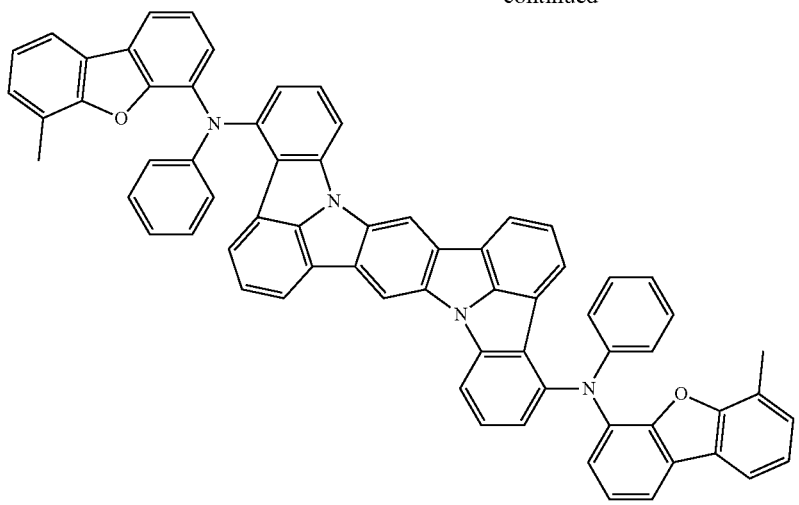
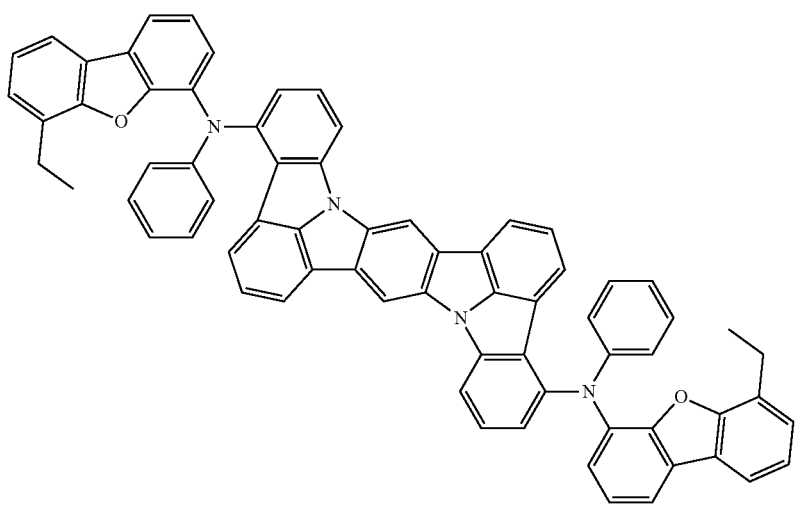
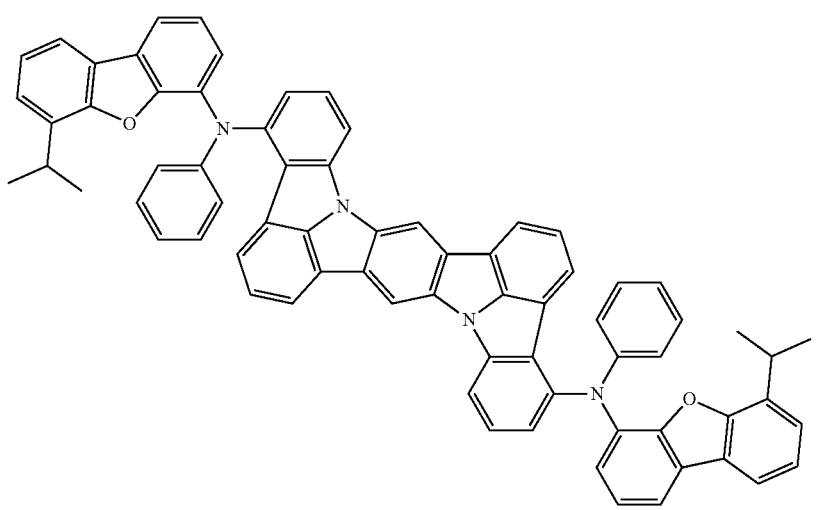

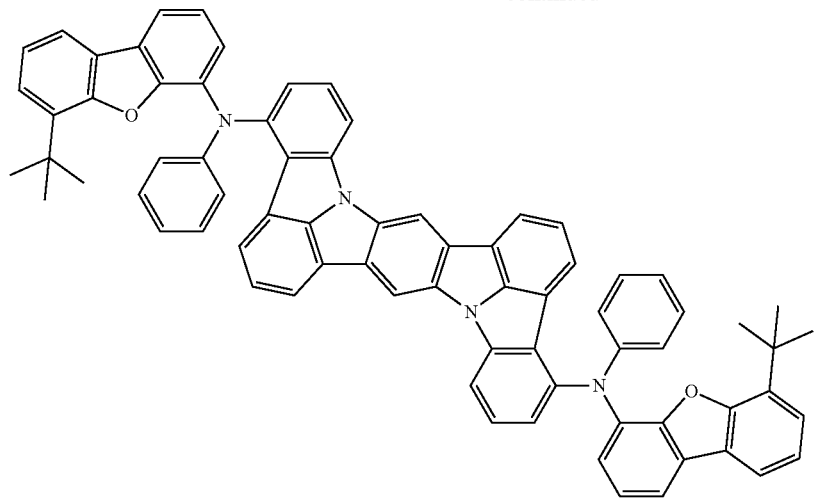
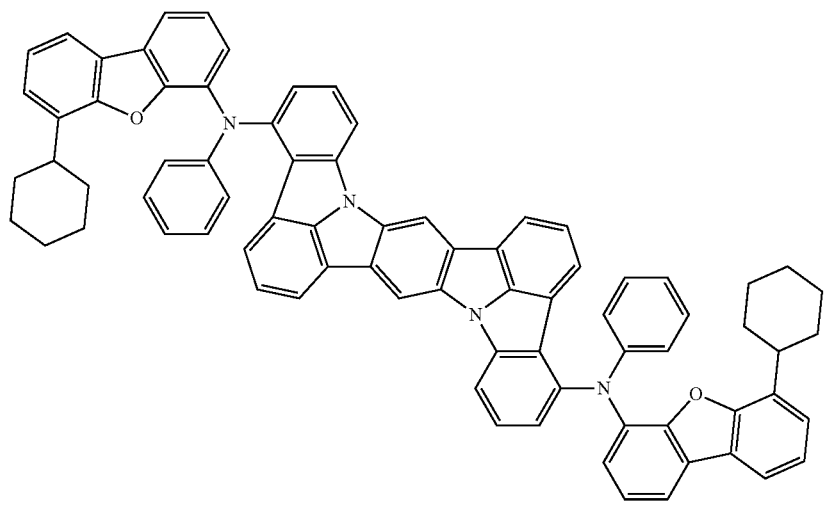
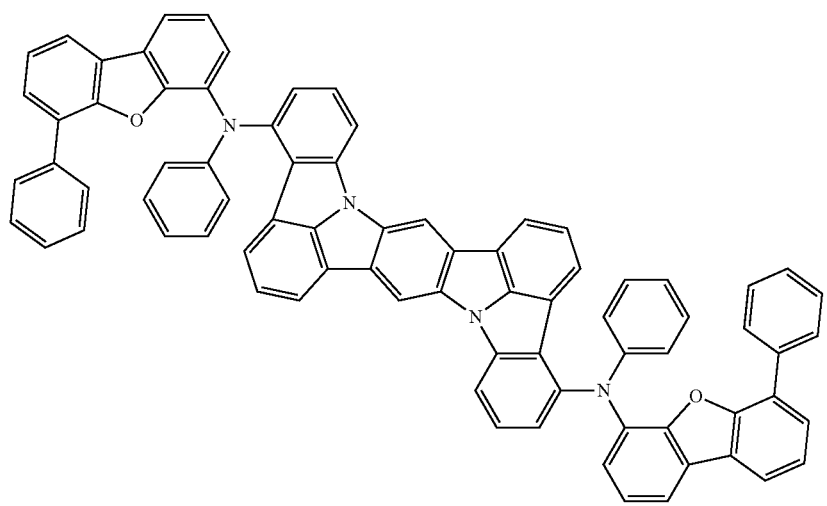

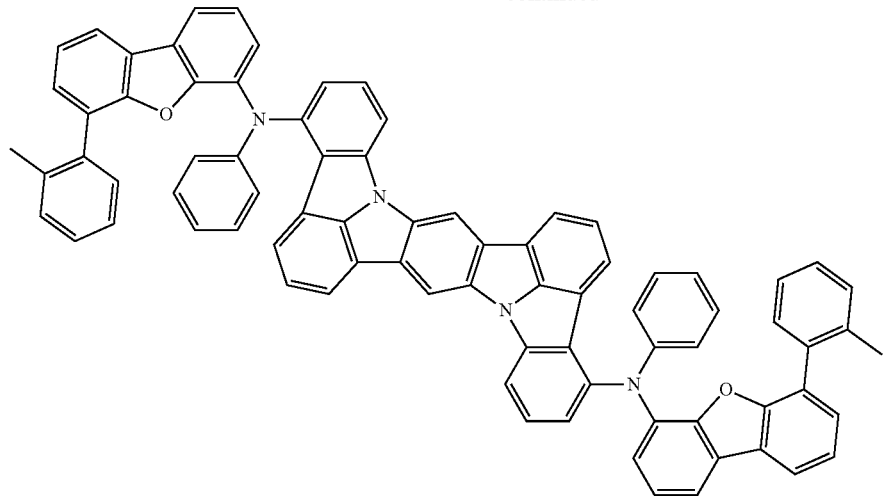
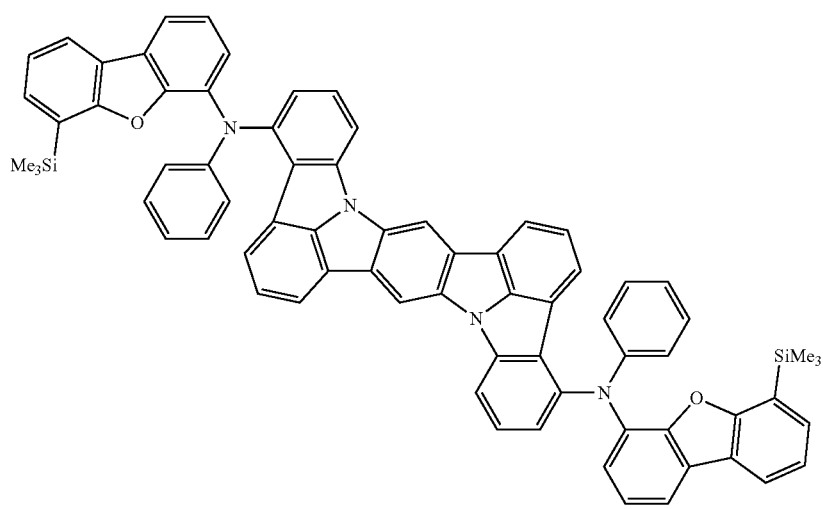
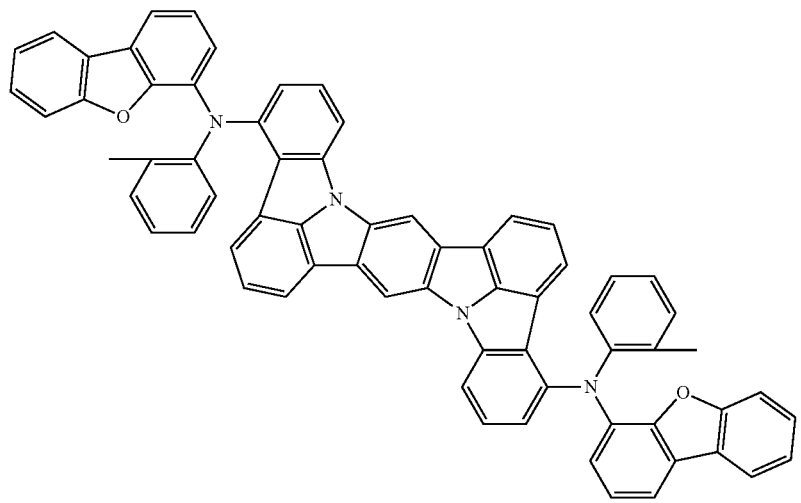

-continued
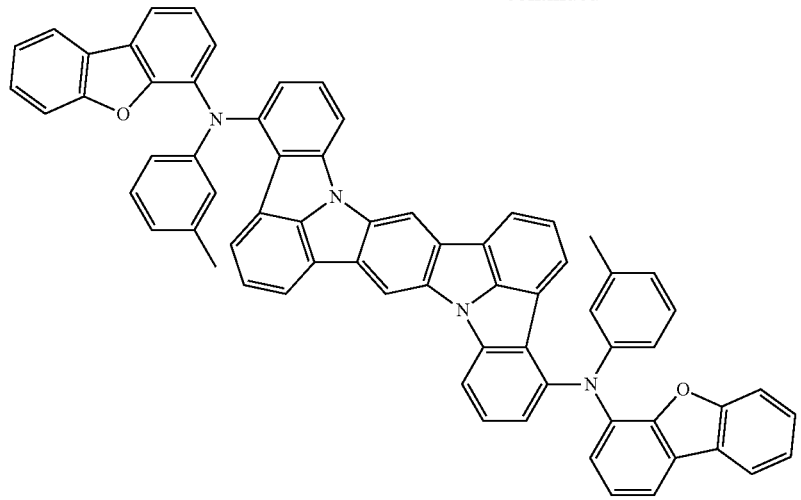
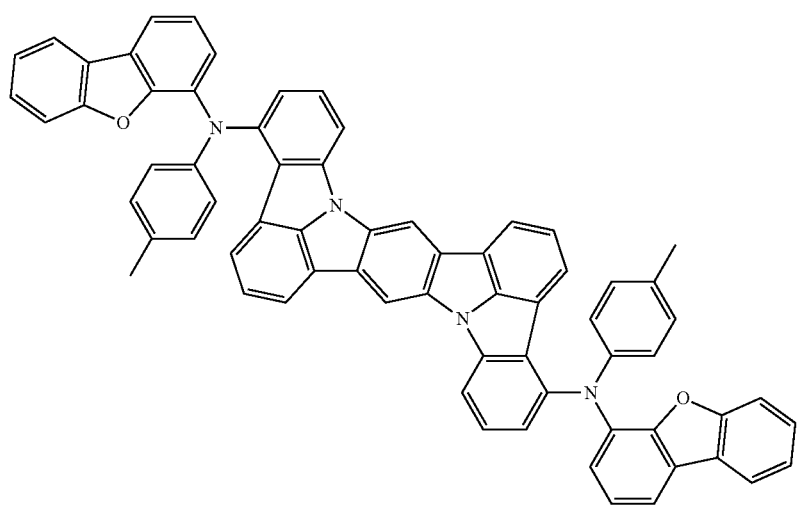
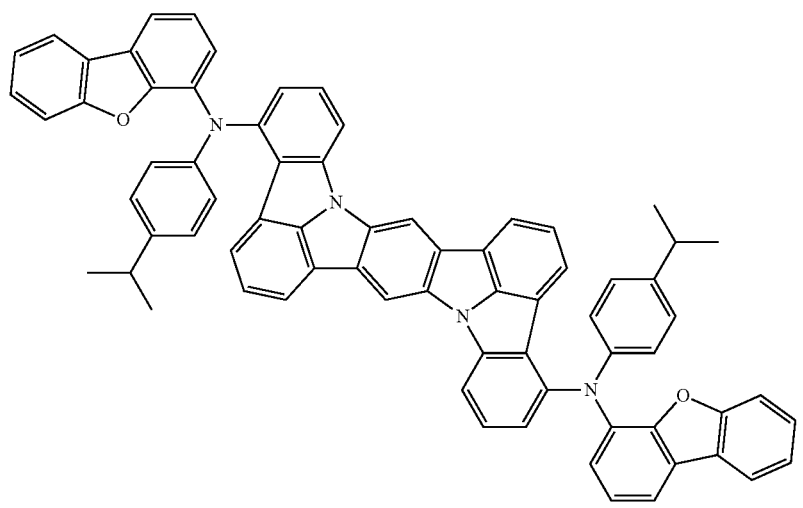

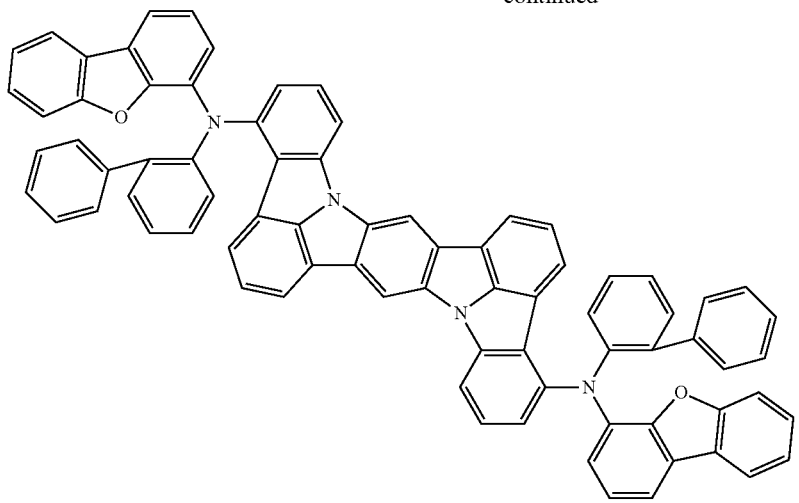
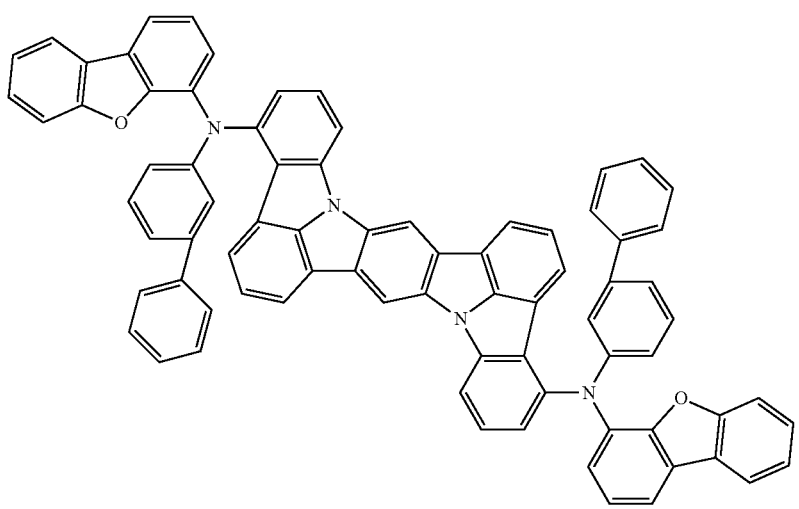
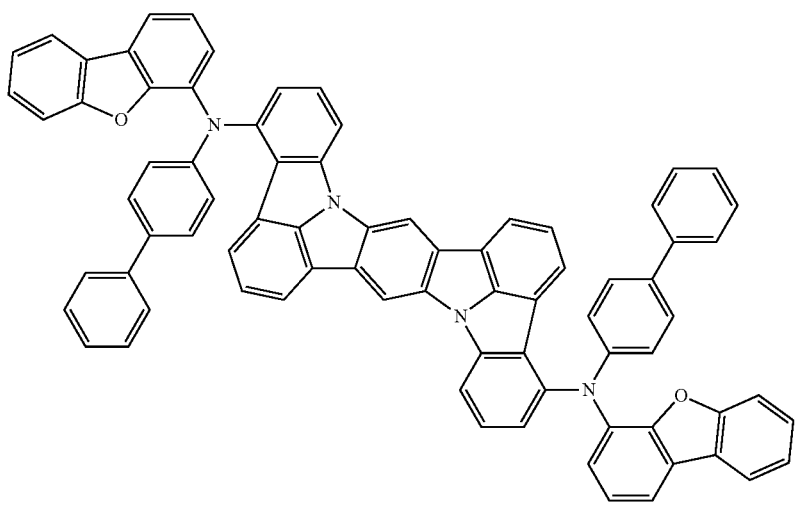

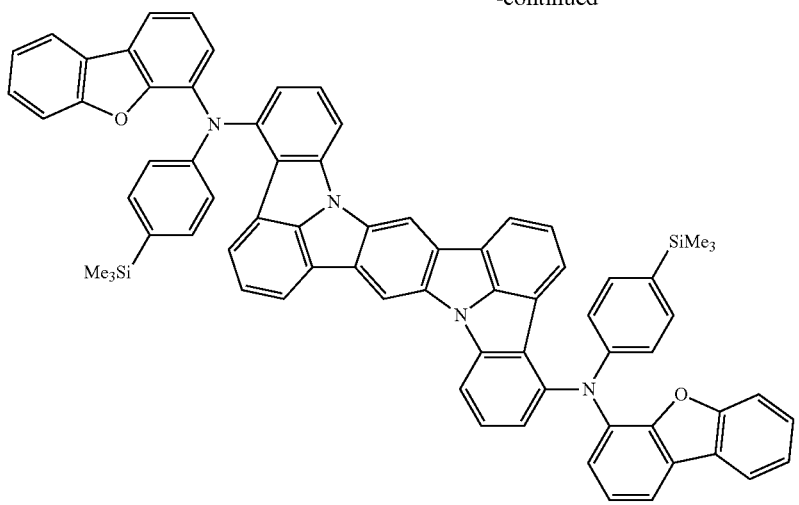
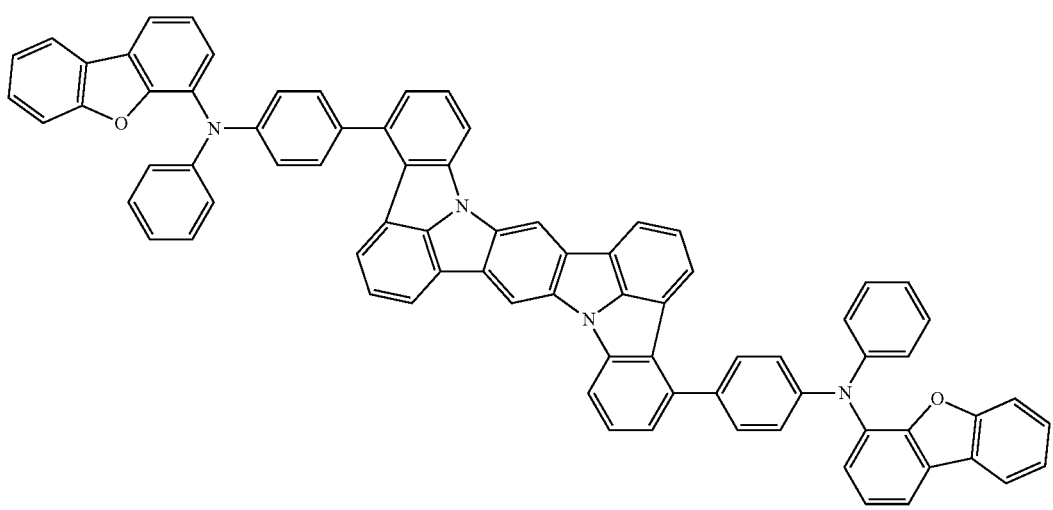
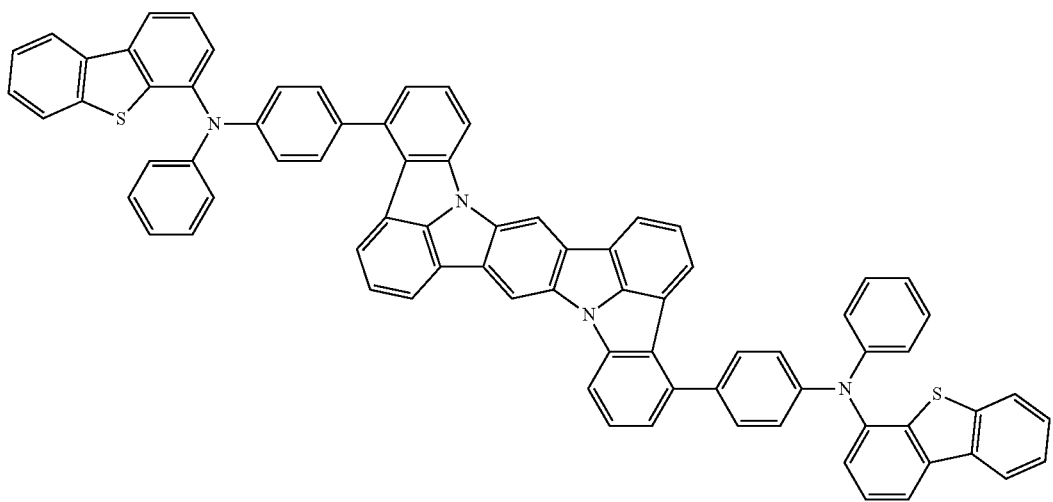

-continued
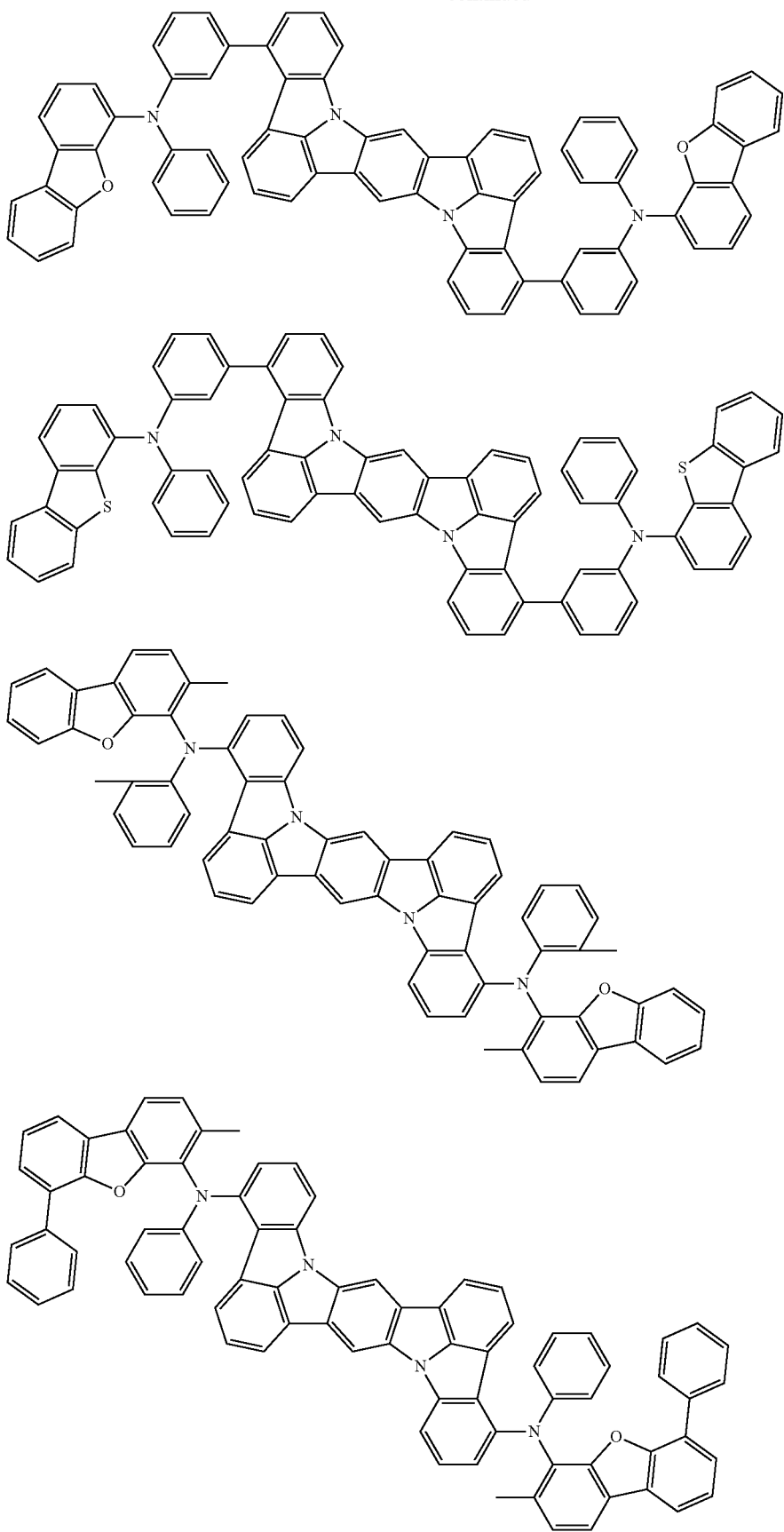

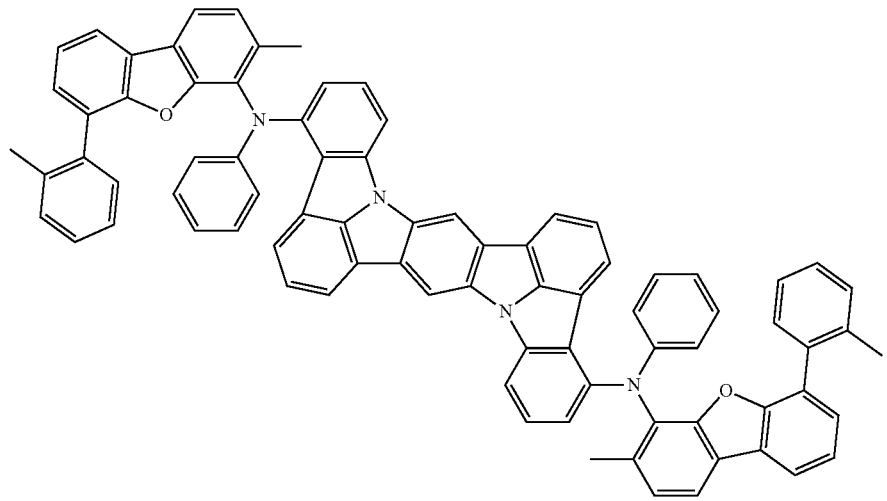
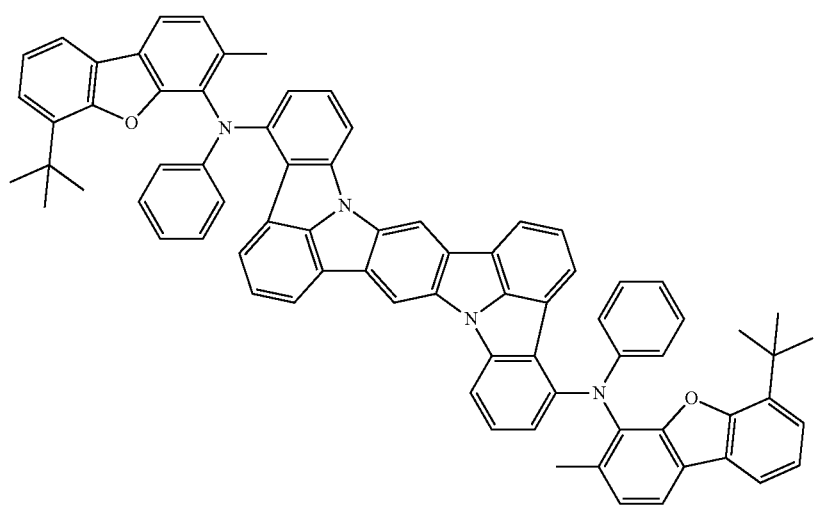
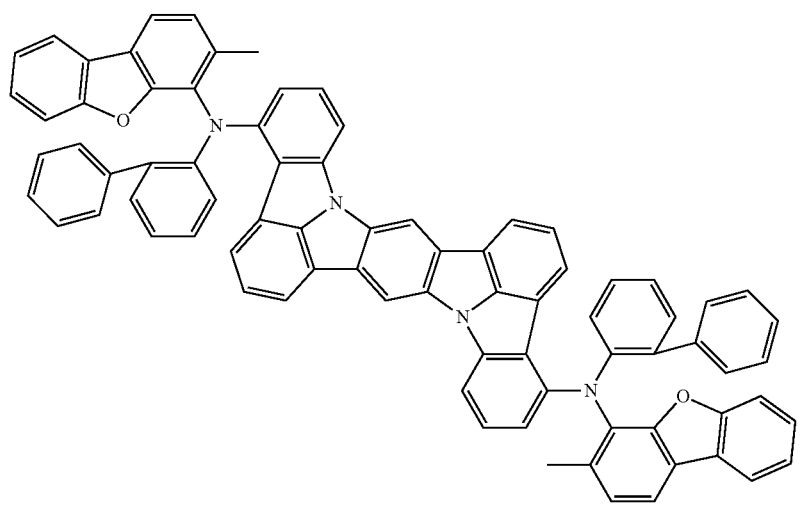

425 426
-continued
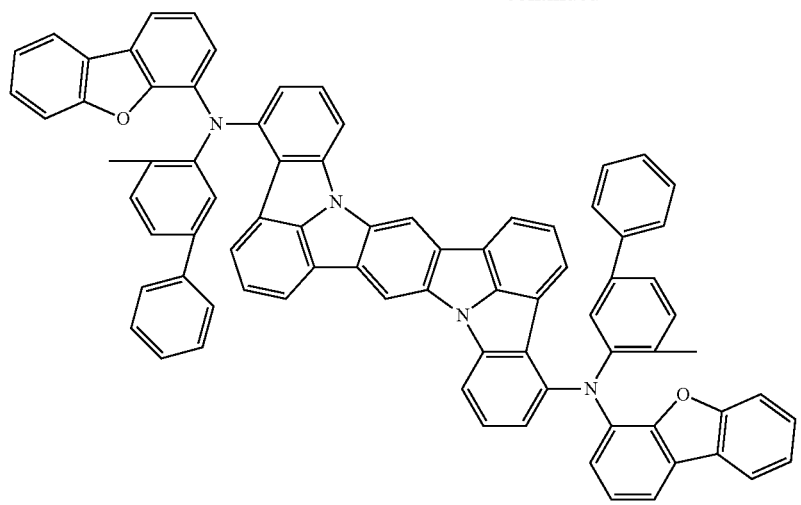
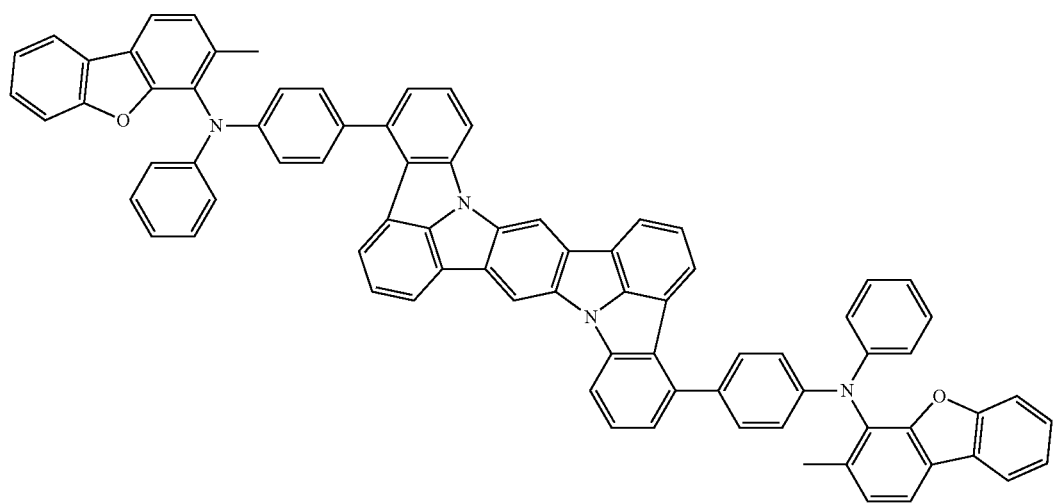
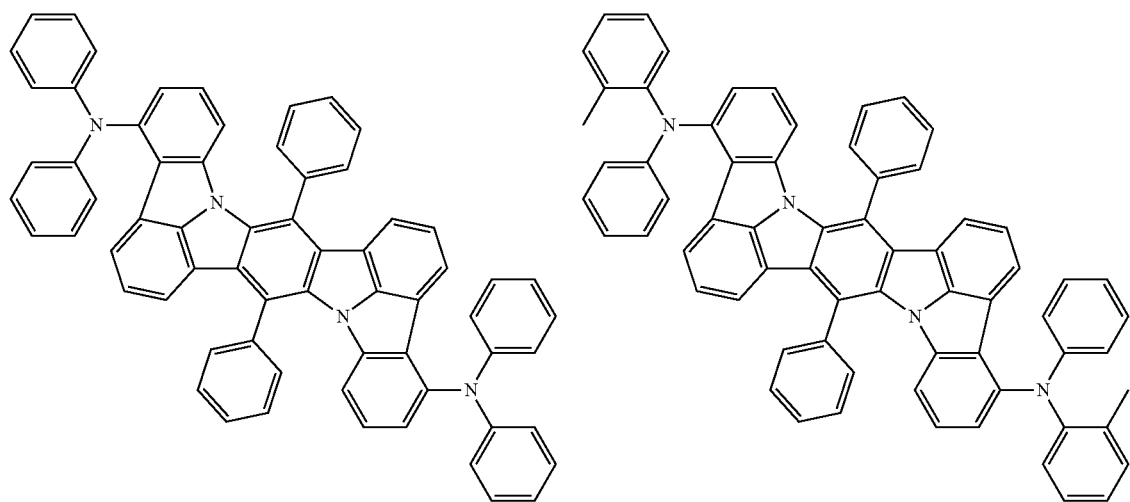

427 428
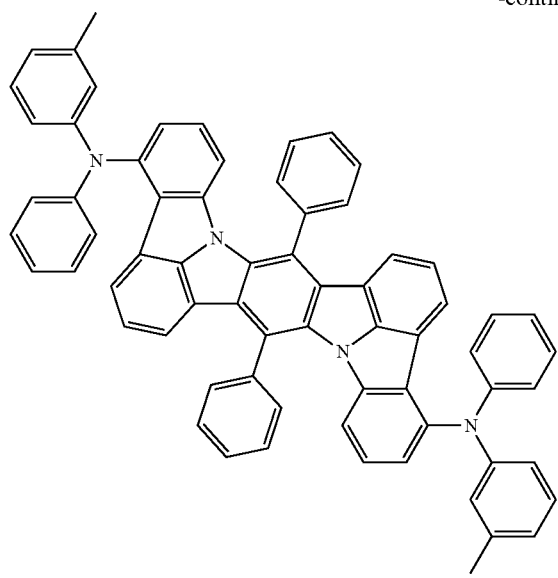
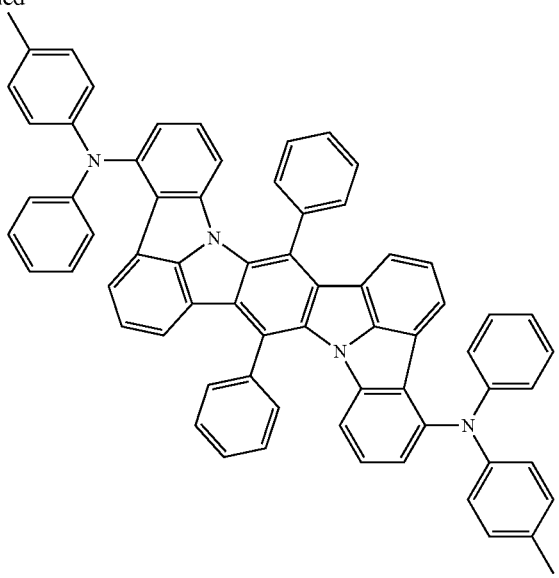
-continued
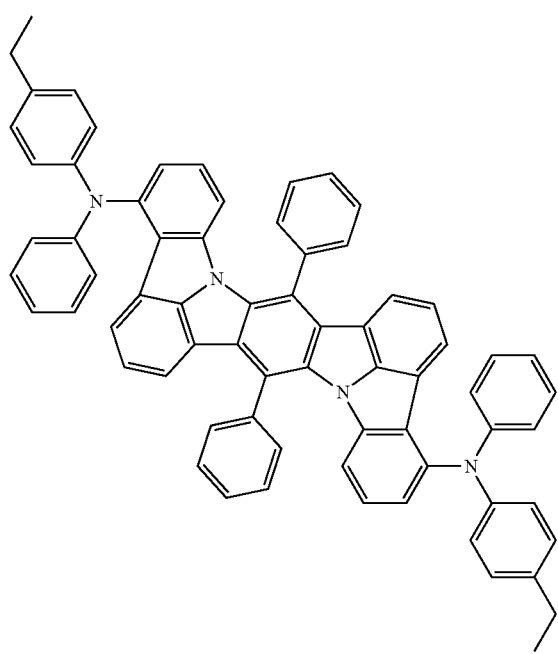

-continued
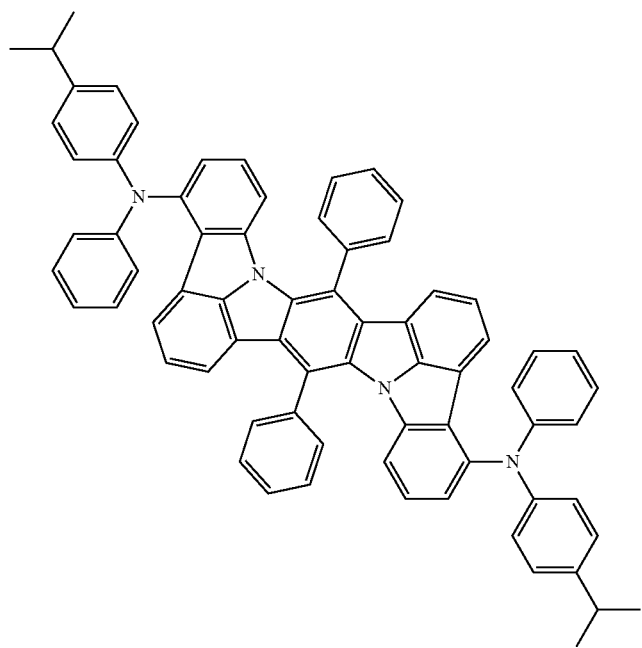
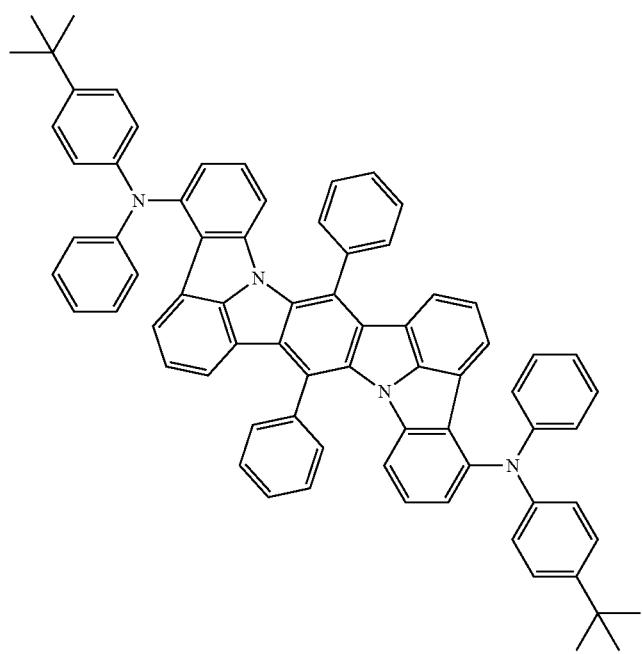

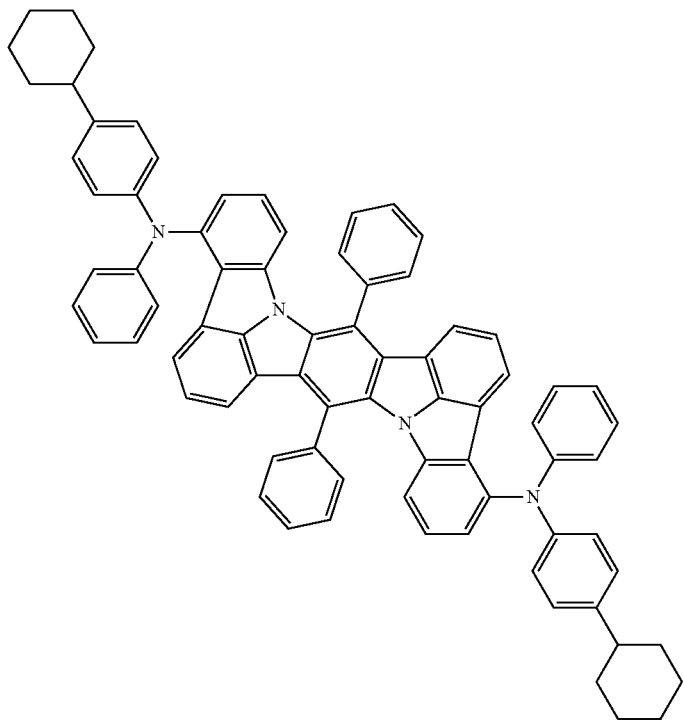
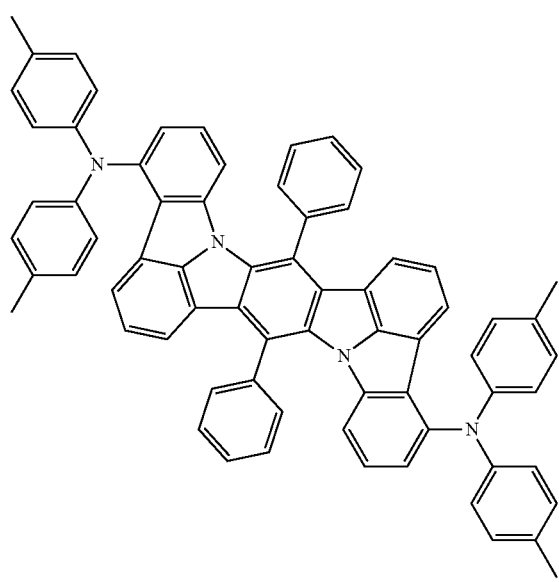

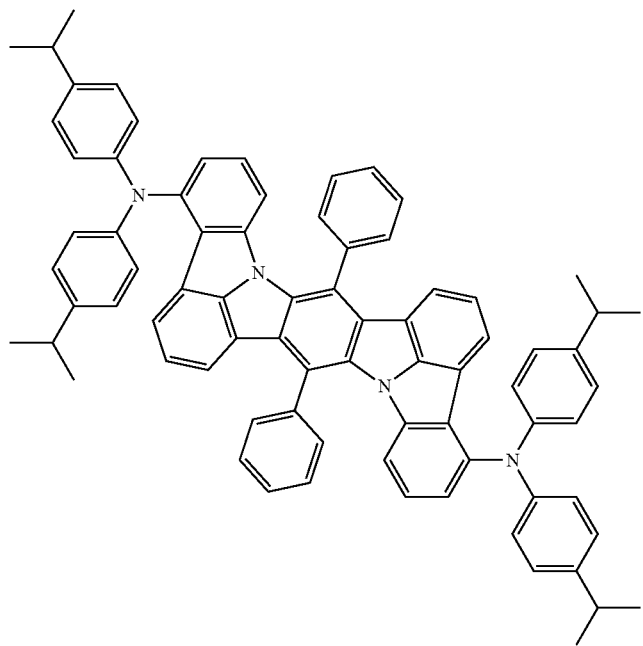
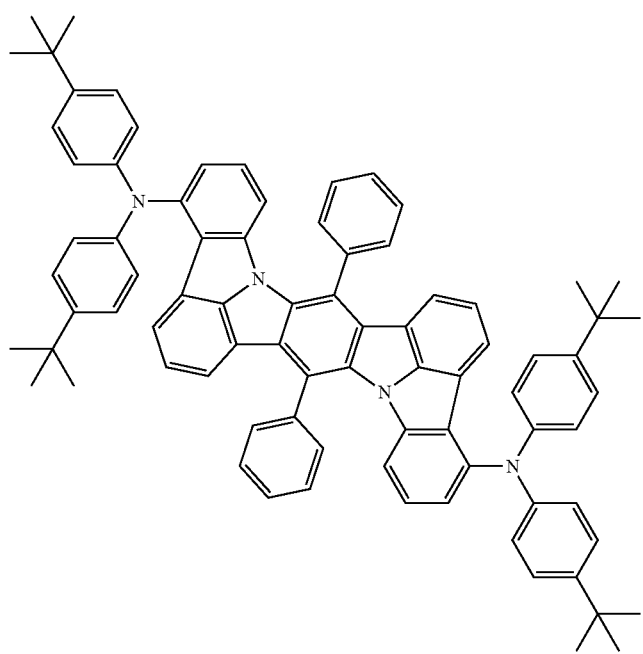

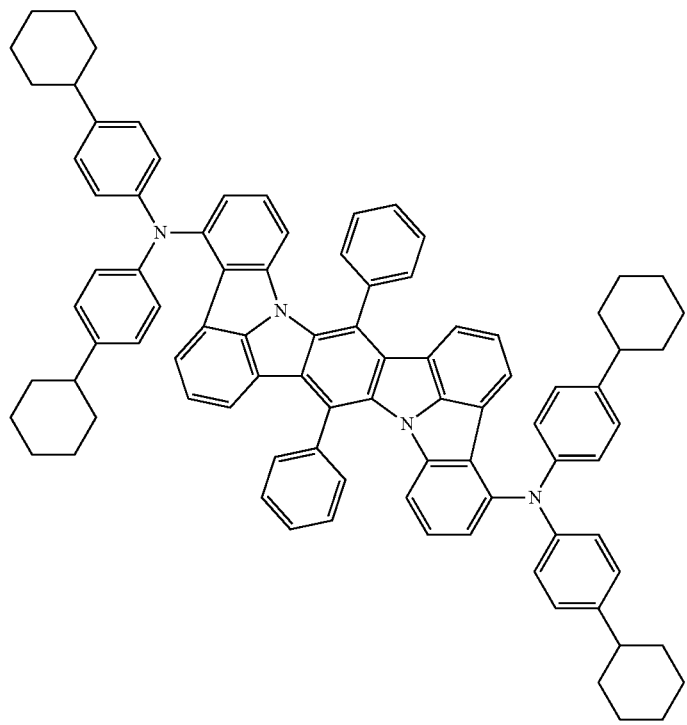
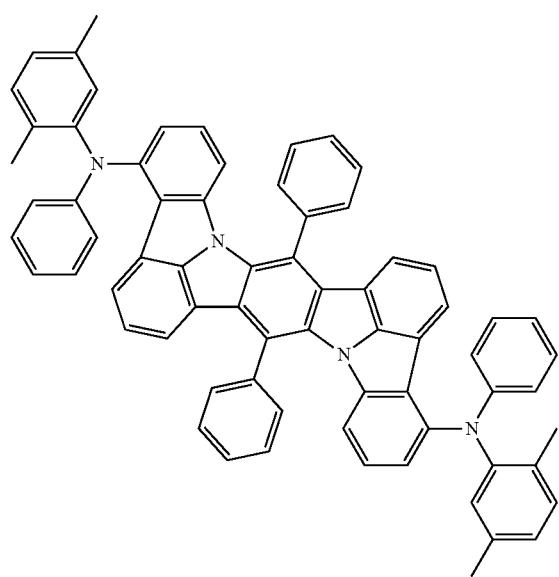

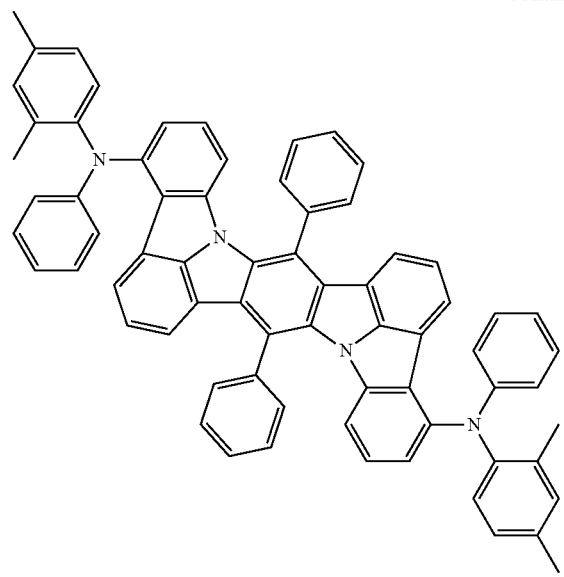
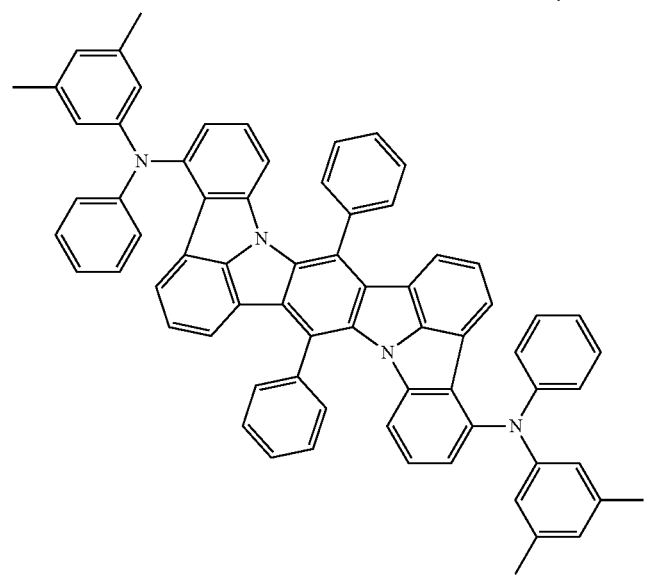
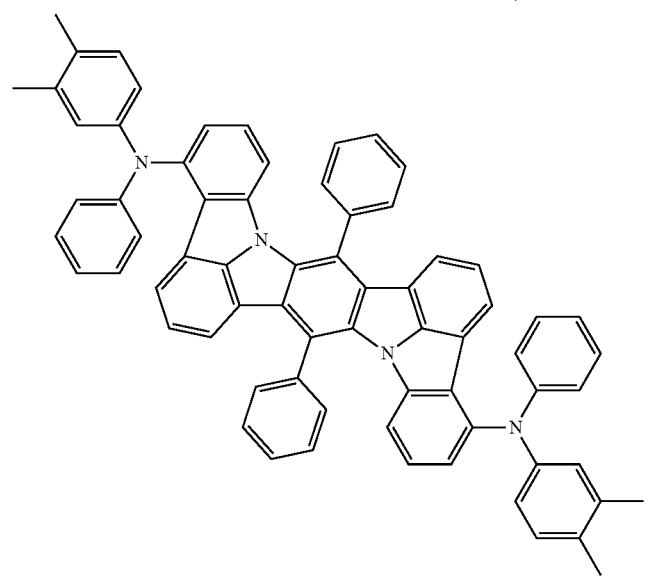

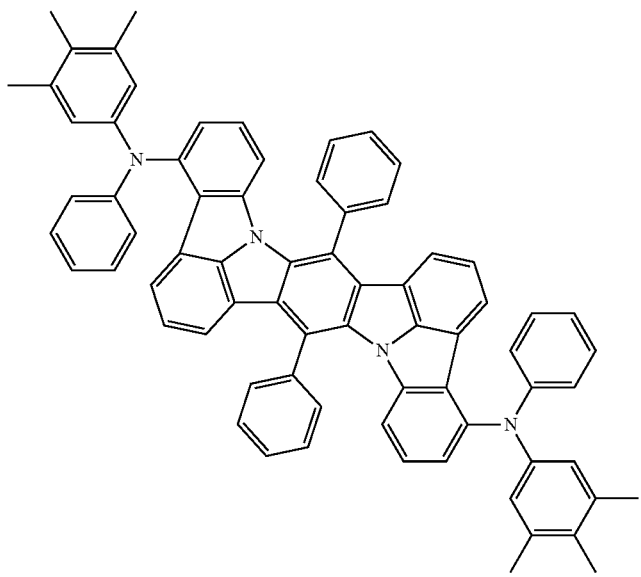
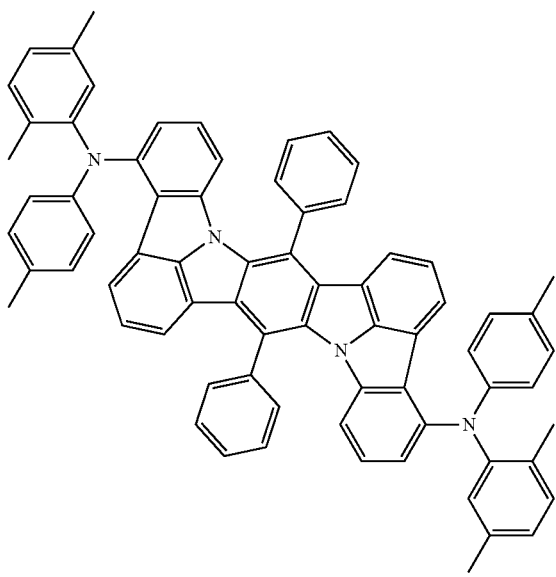
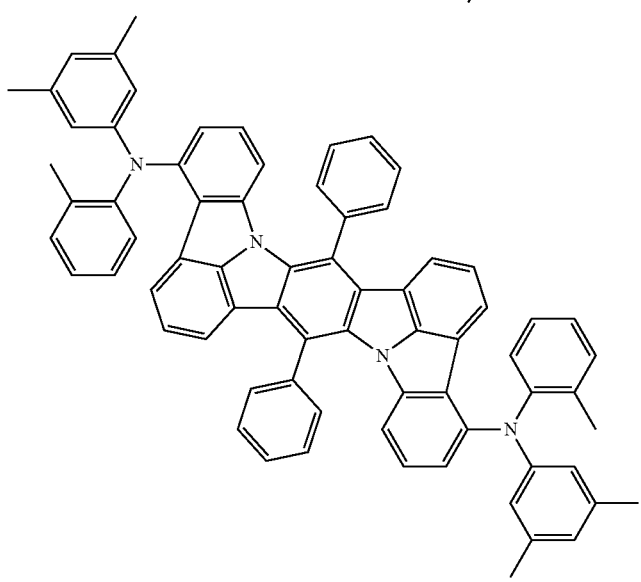

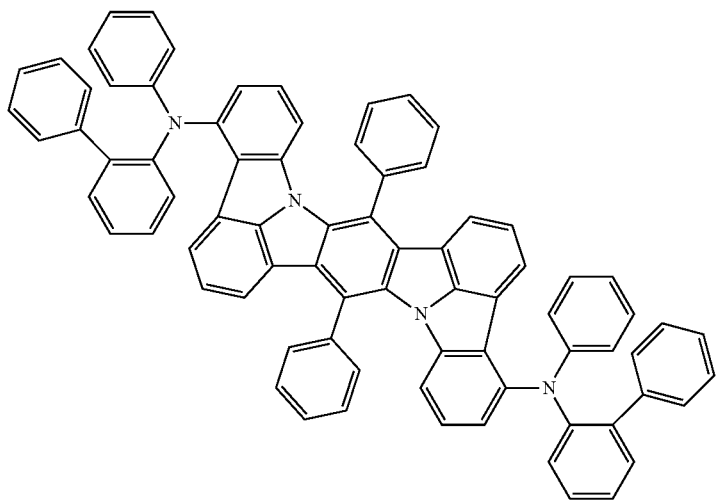
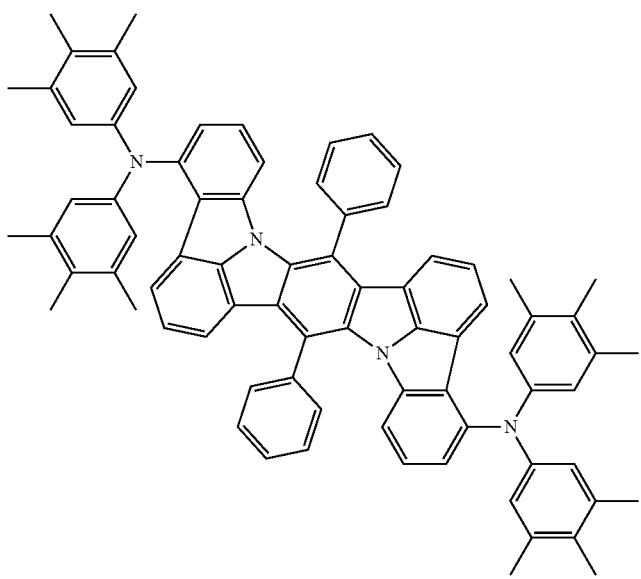

-continued
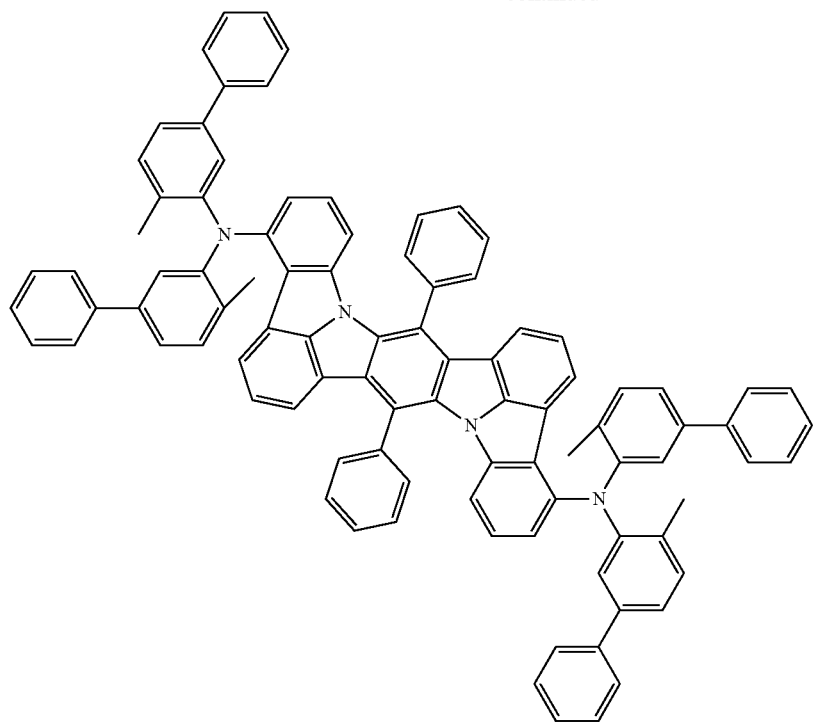
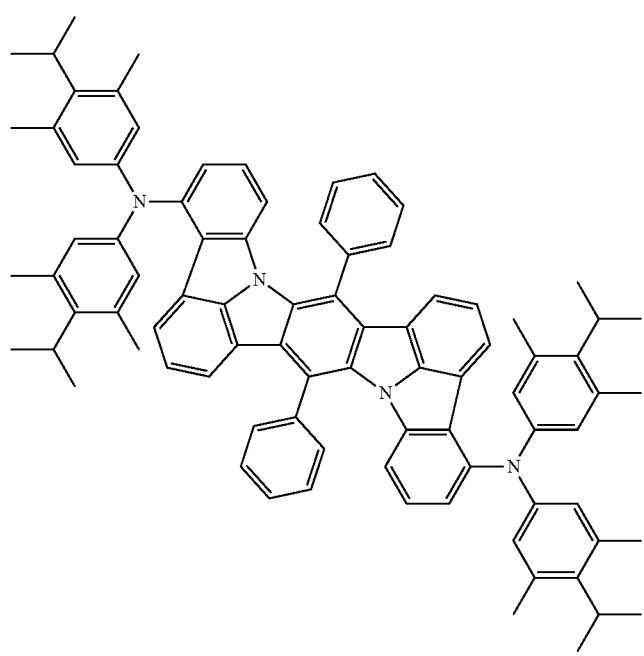

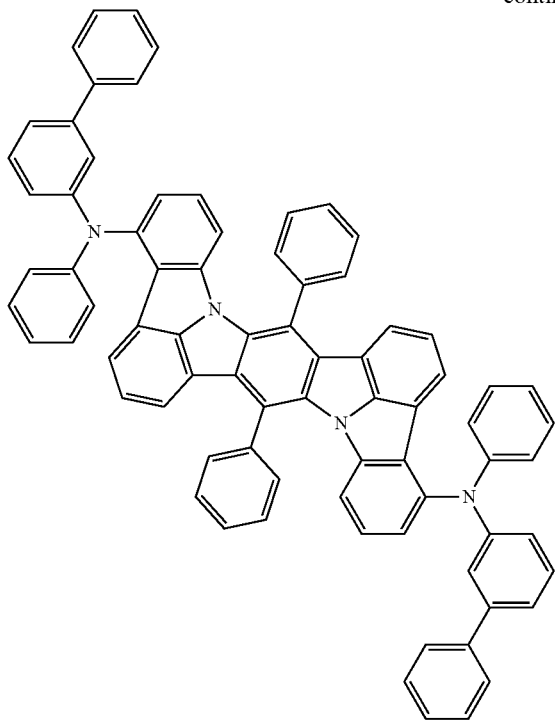
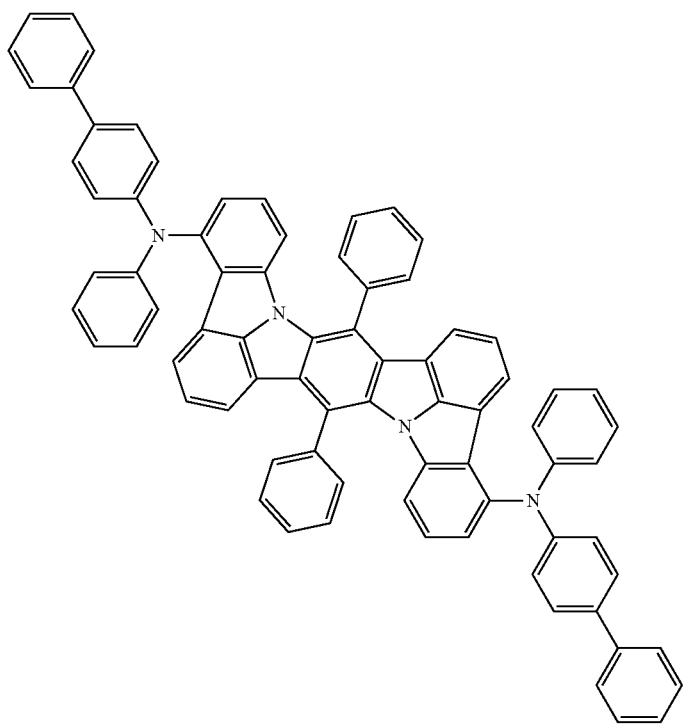

-continued
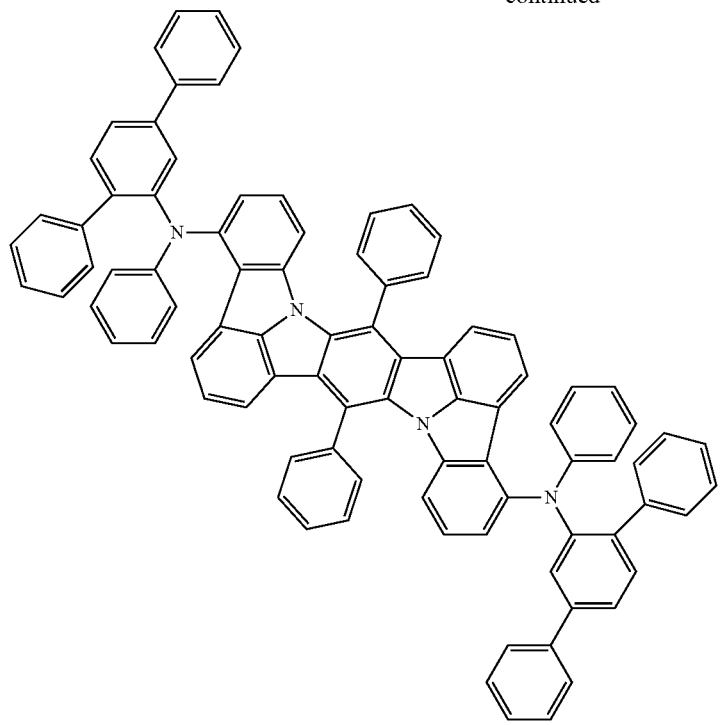
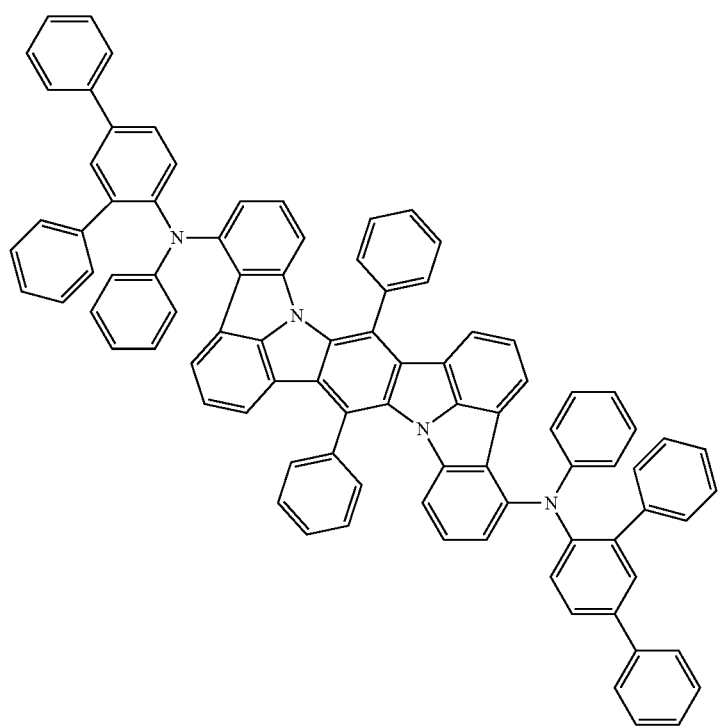 [SMILES: c1ccc(-c2ccc(N(c3ccccc3)c3cccc4c3c3cccc5c6c(-c7ccccc7)c7c(c(-c8ccccc8)c6n4c35)c3cccc4c5c(N(c6ccccc6)c6ccc(-c8ccccc8)cc6-c6ccccc6)cccc5n7c43)c(-c3ccccc3)c2)cc1]

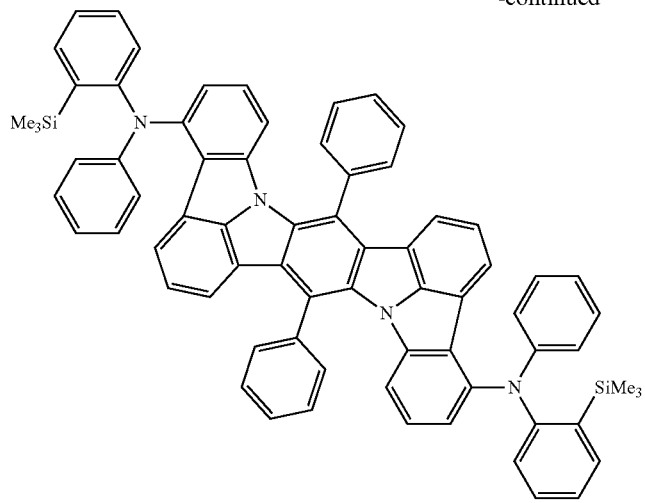

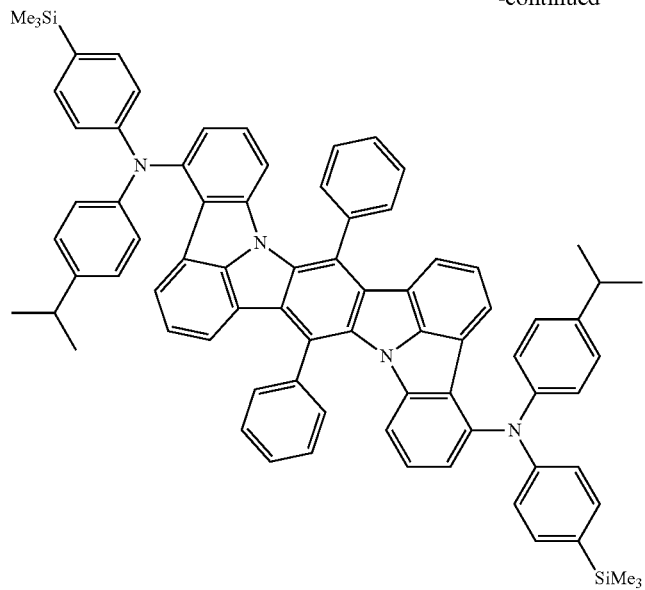
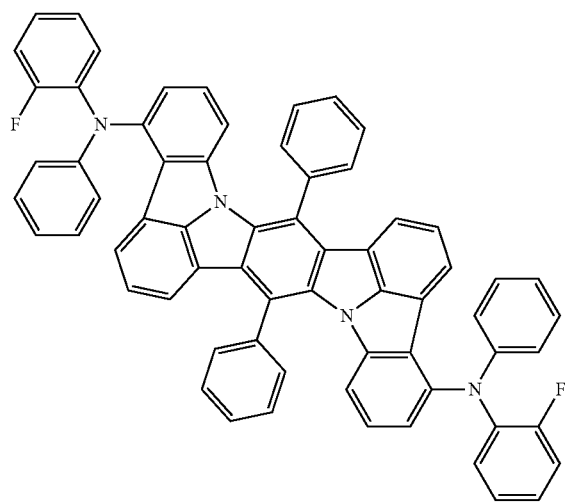
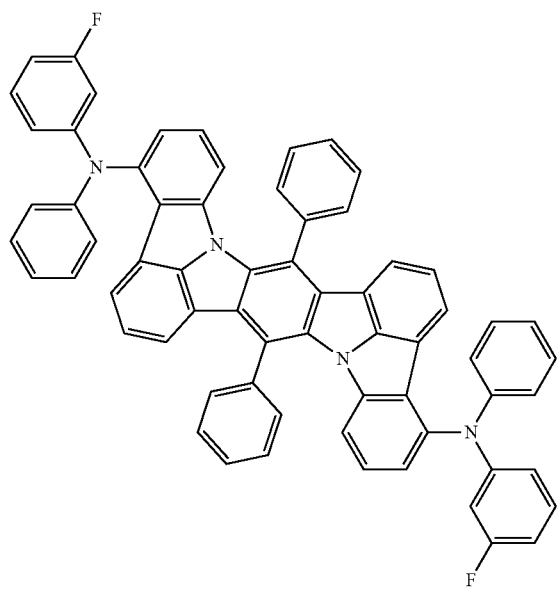

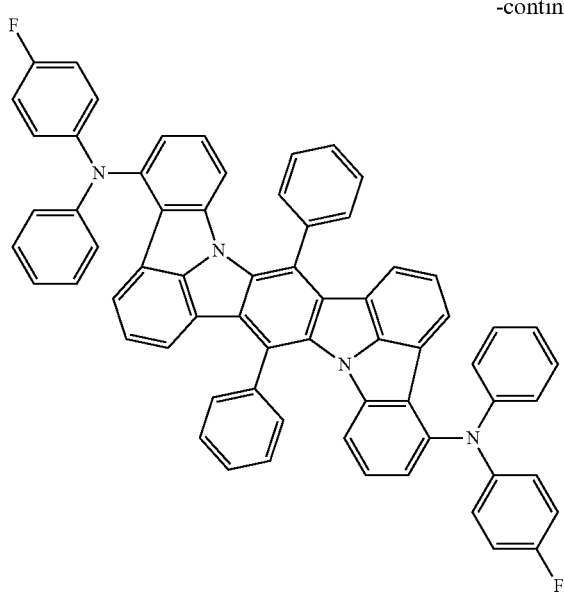
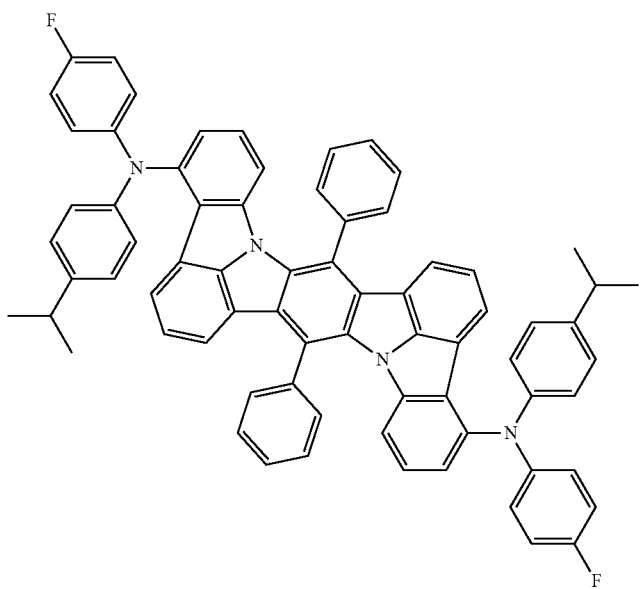
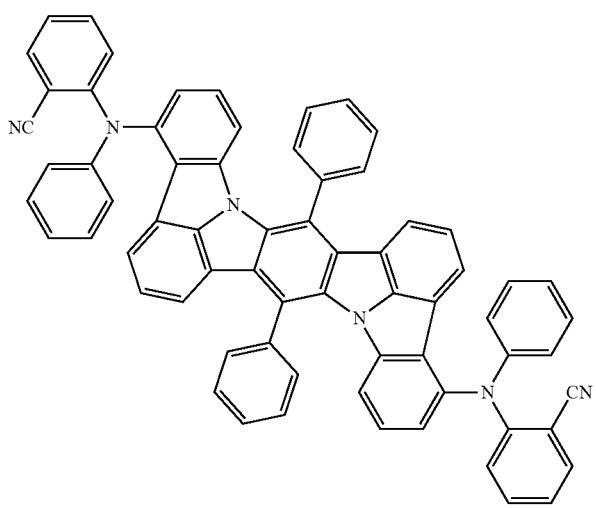

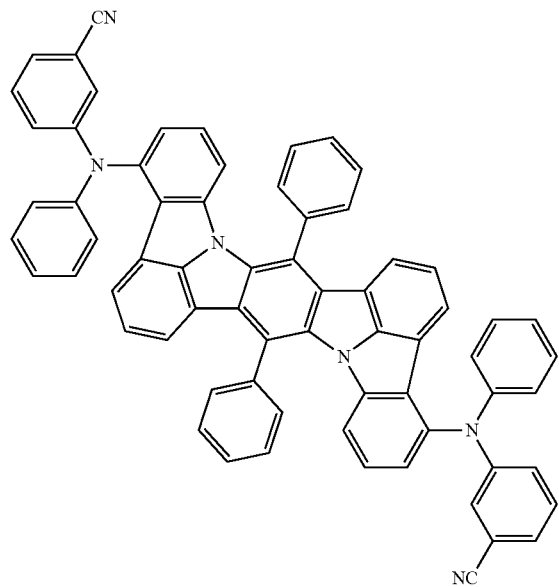
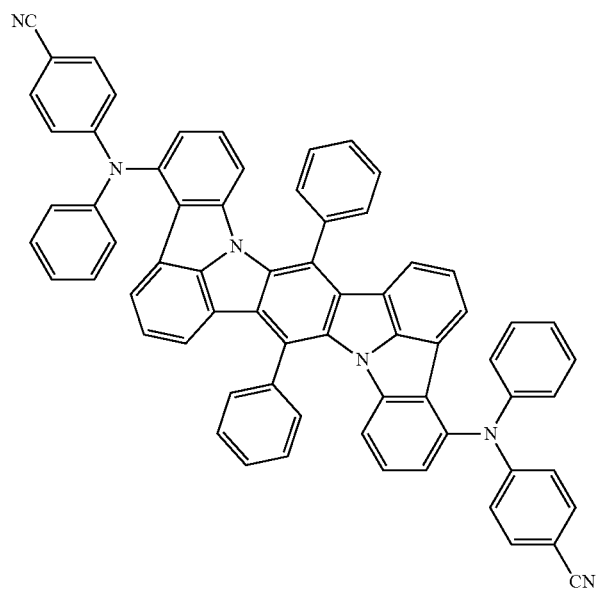

-continued
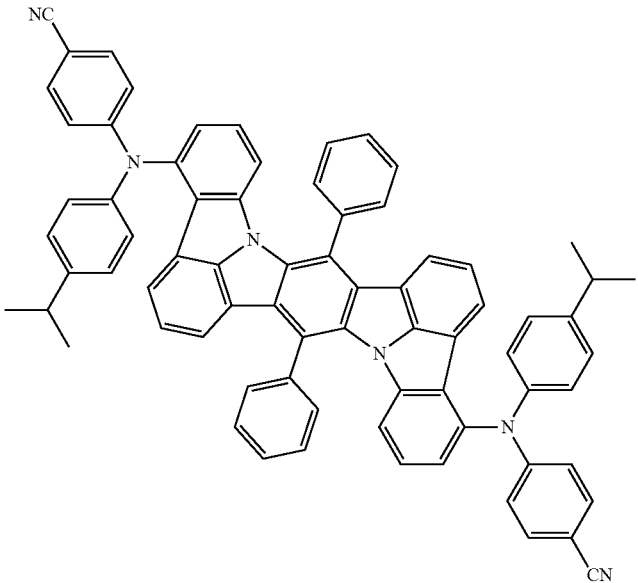
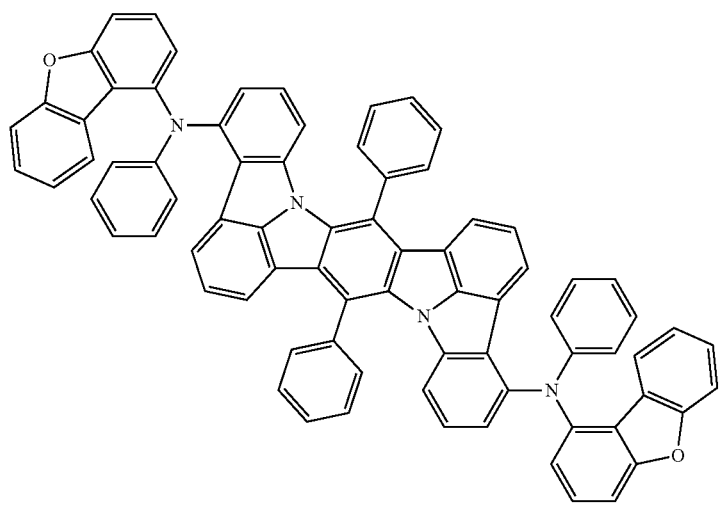
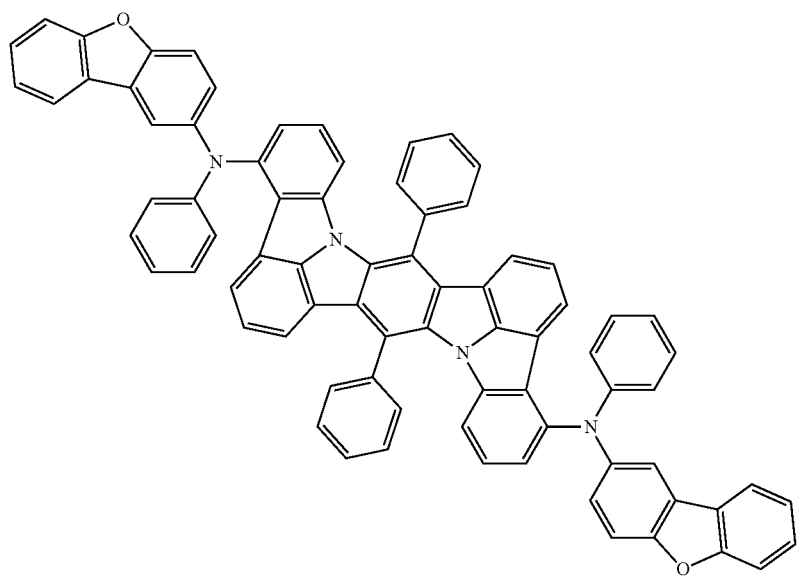

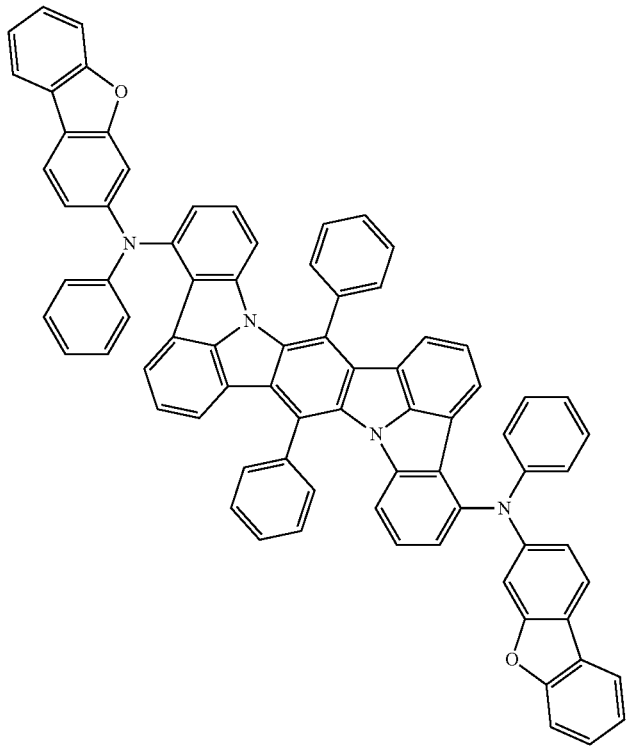
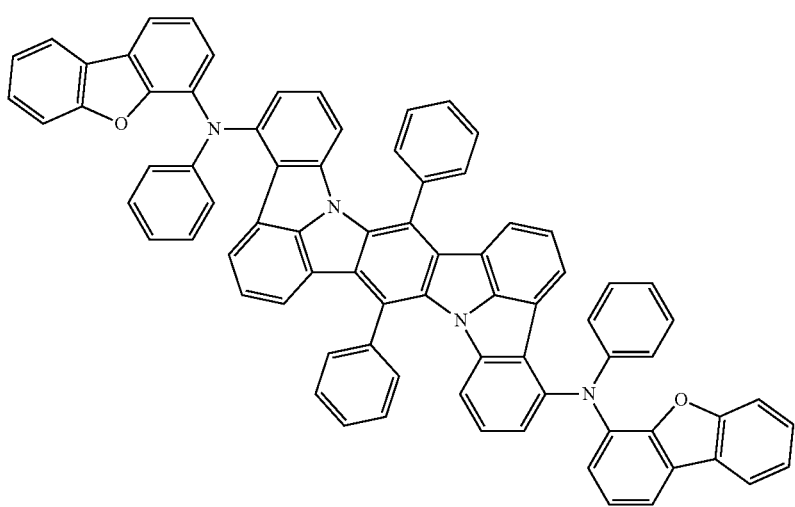

-continued
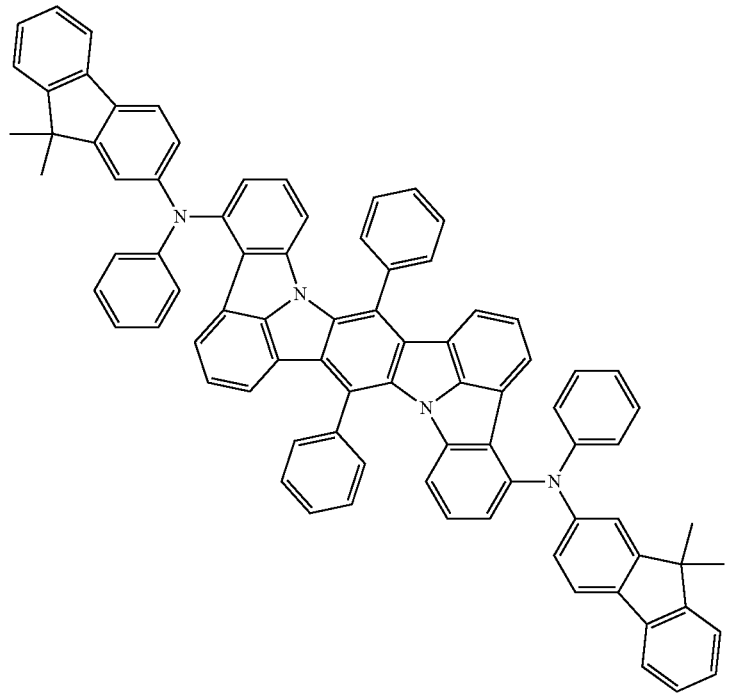
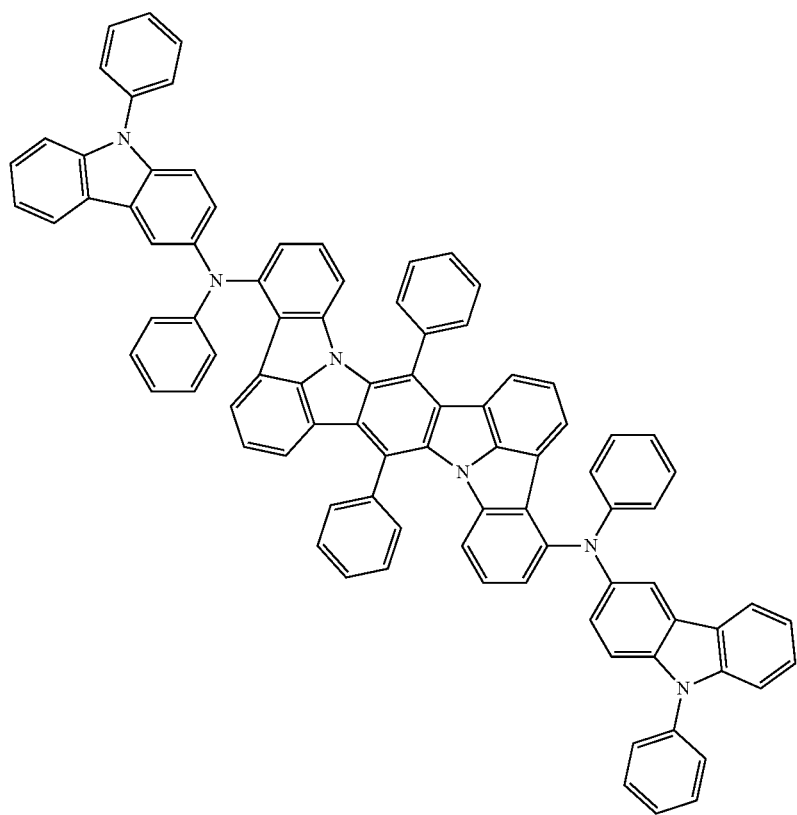

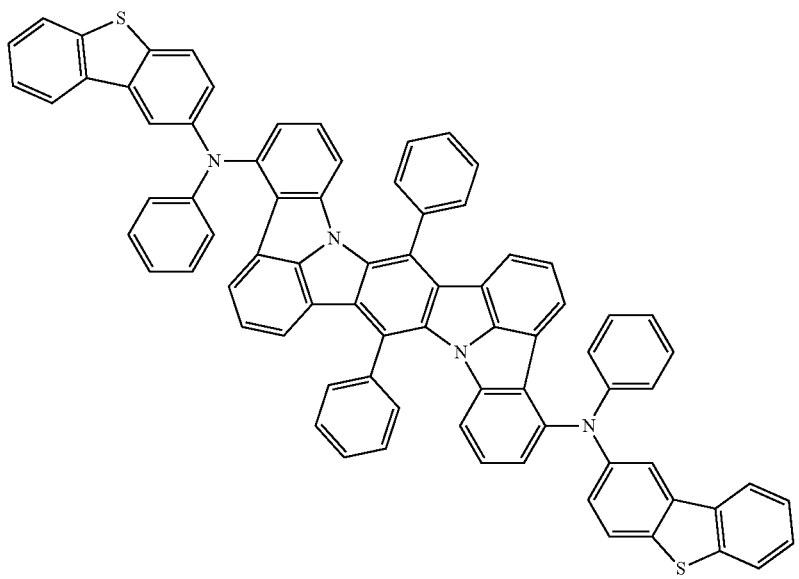
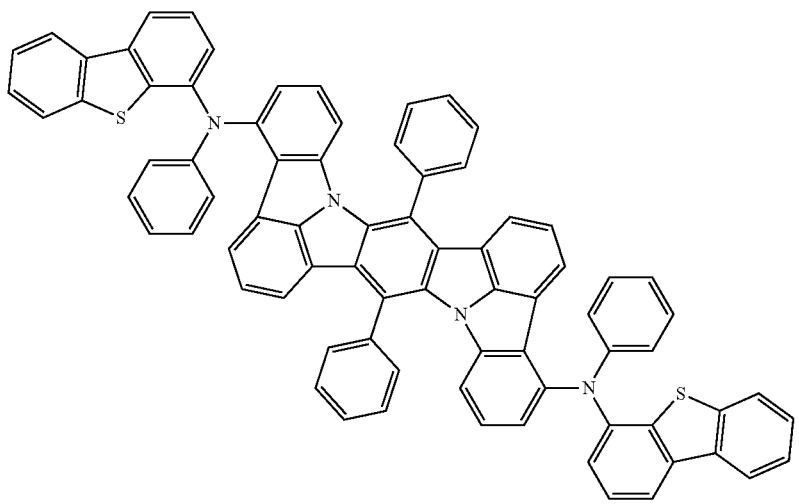
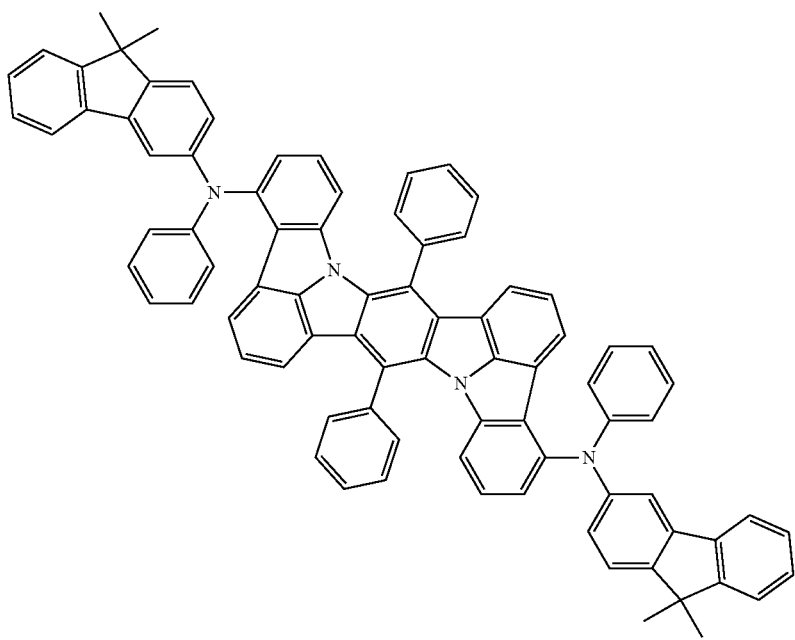

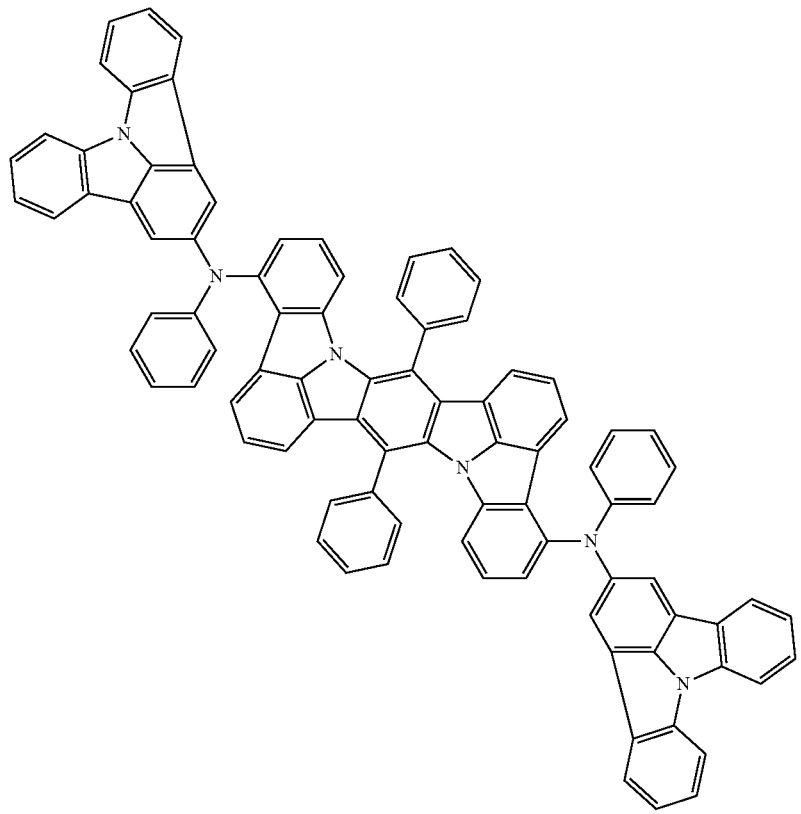
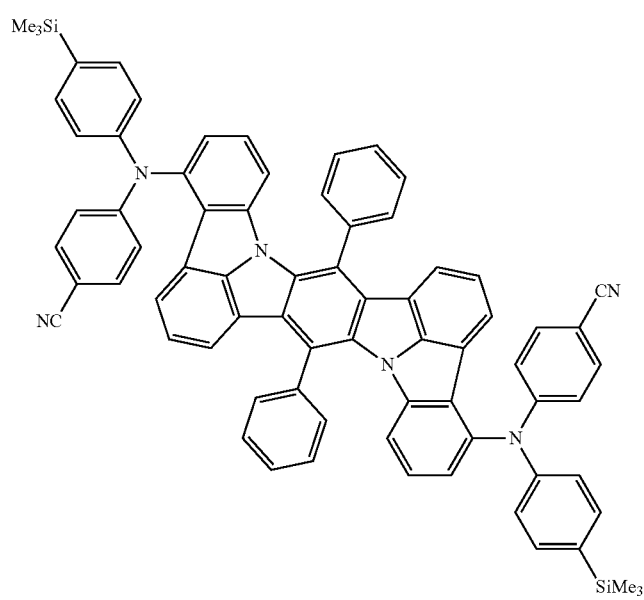

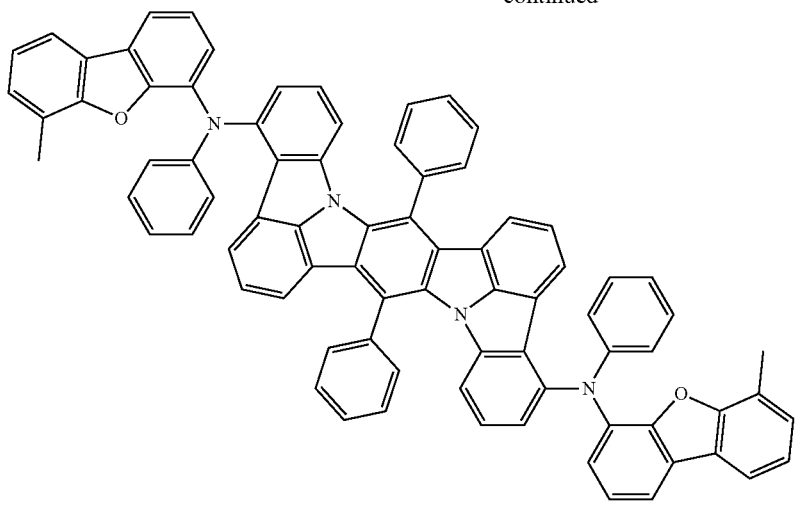
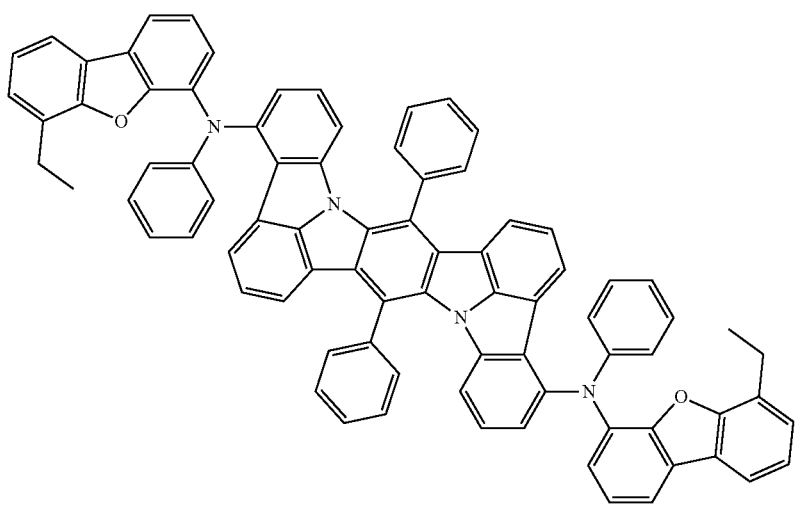
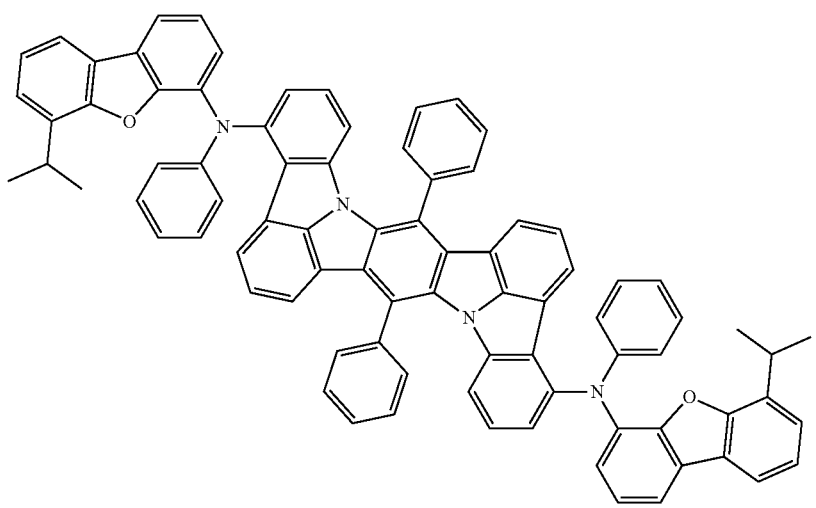

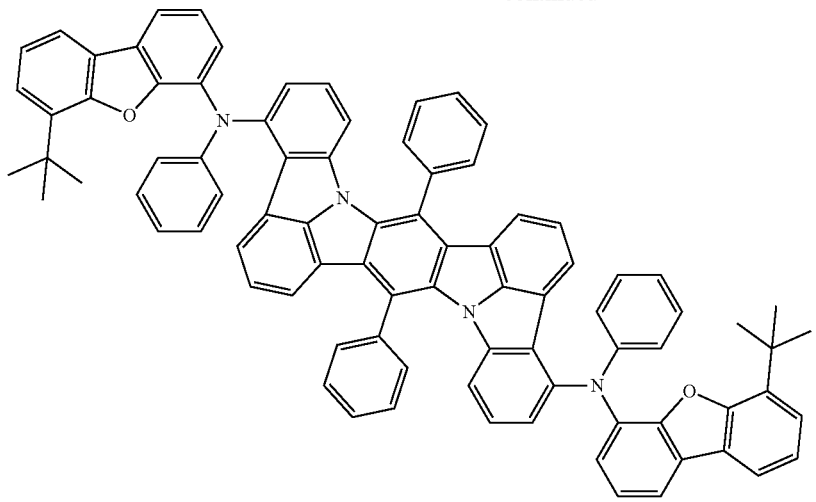
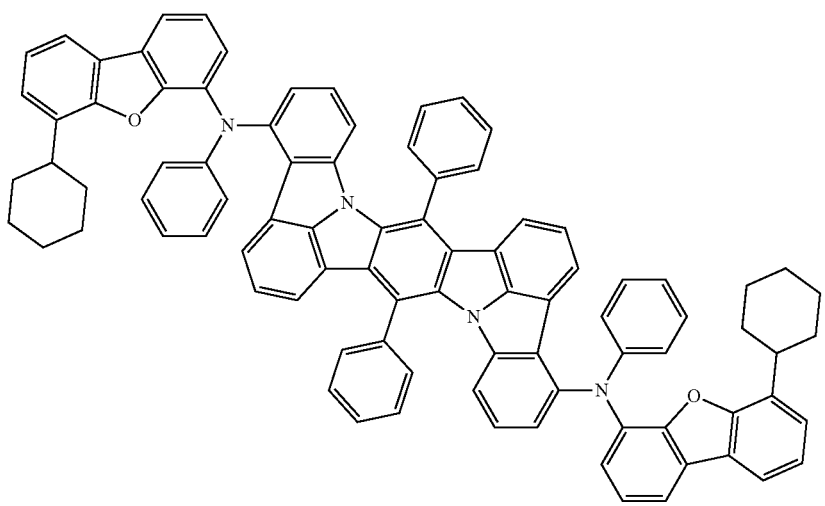
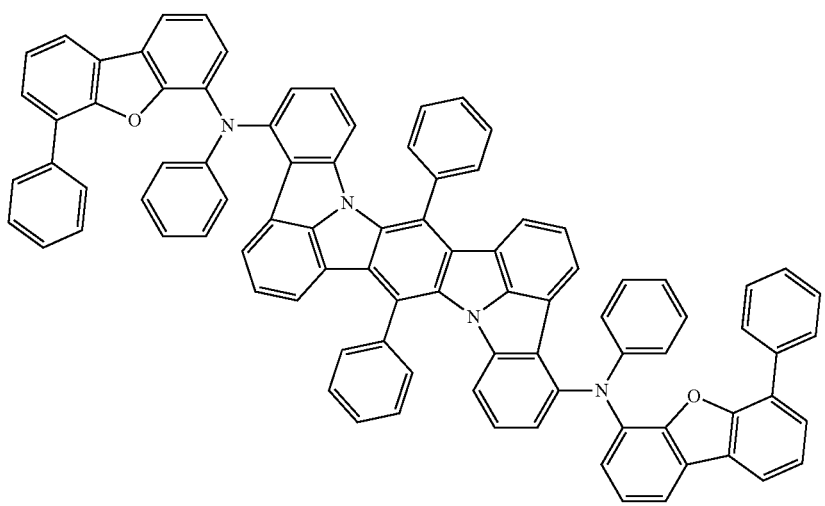

-continued
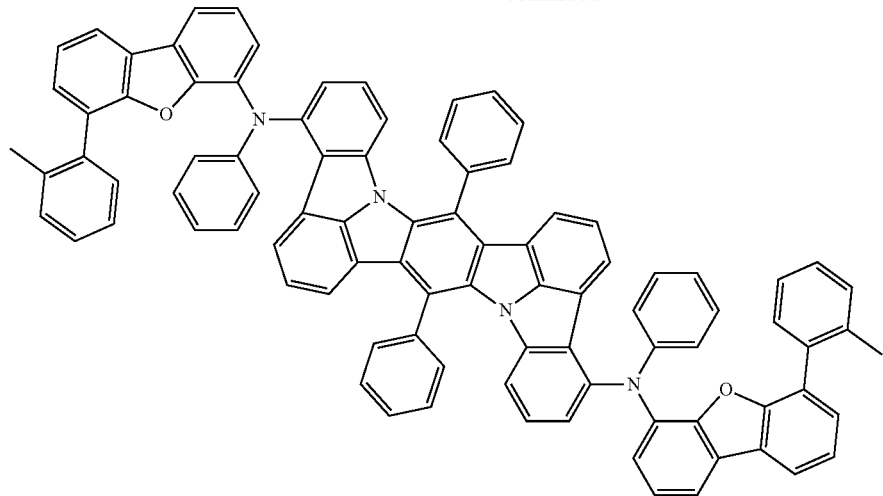
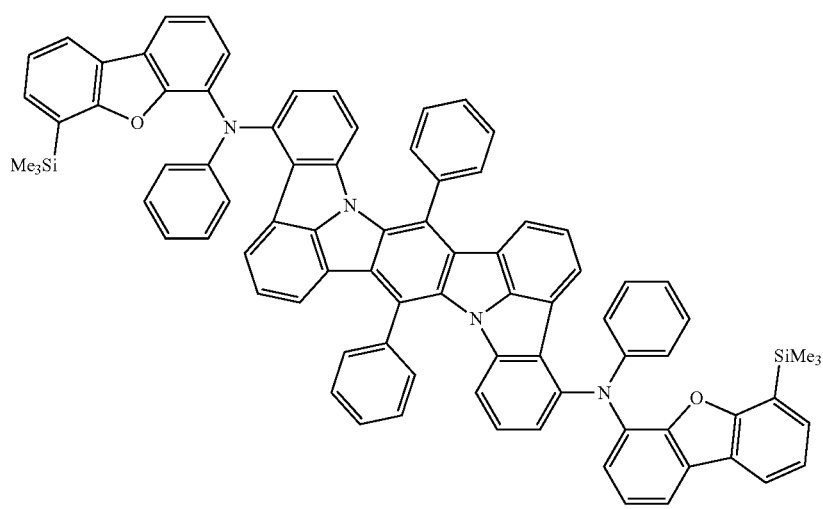
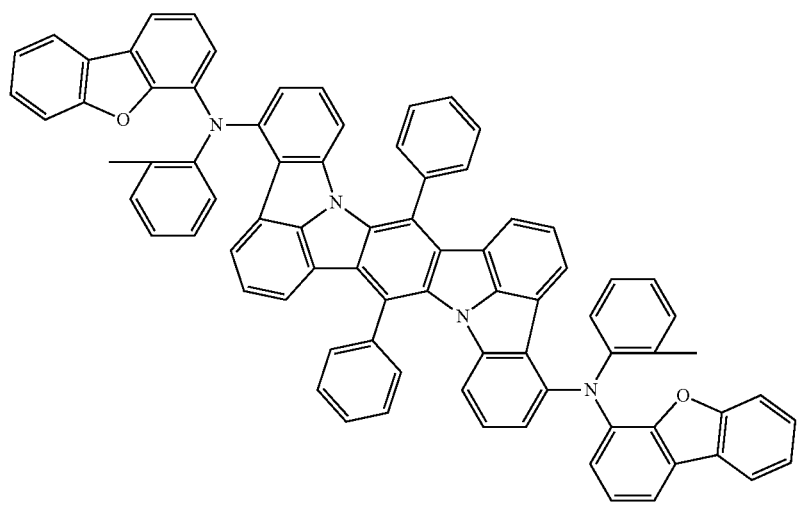

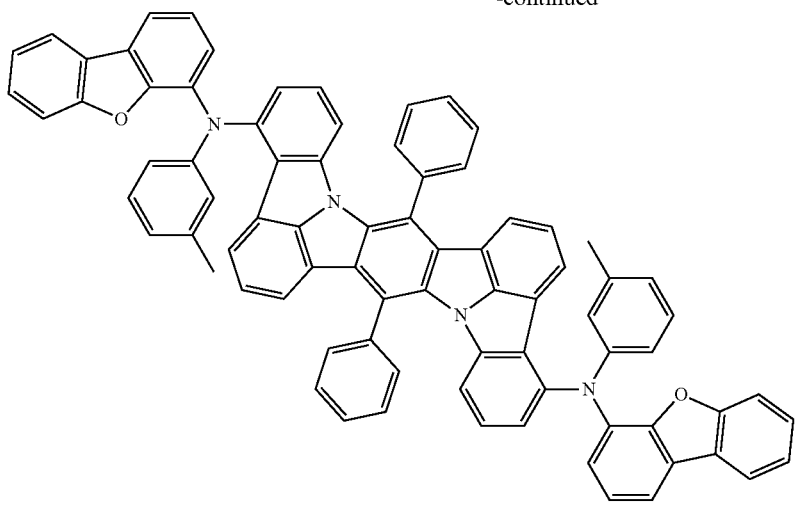
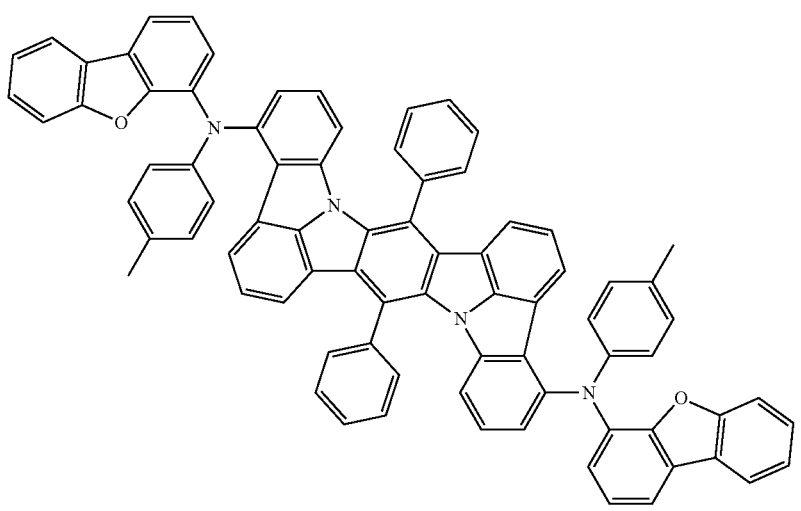
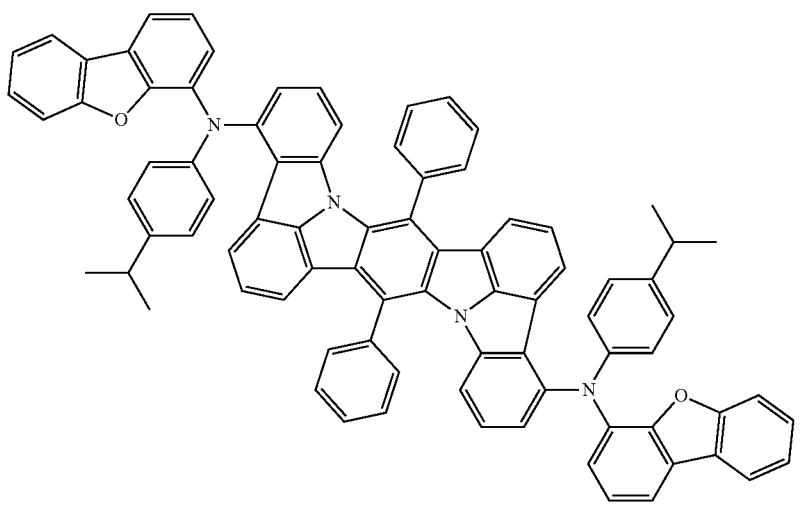

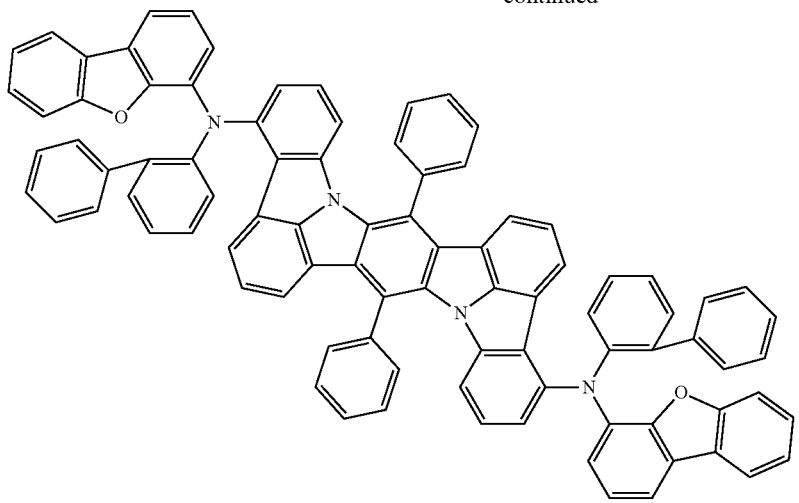
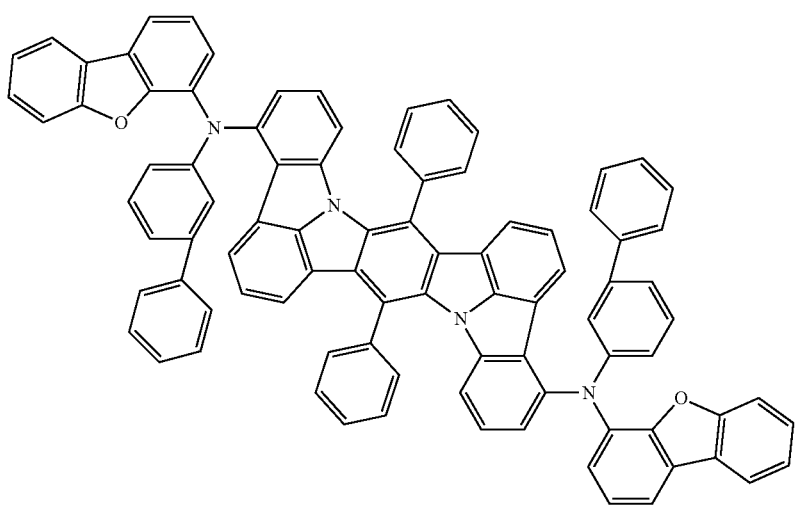
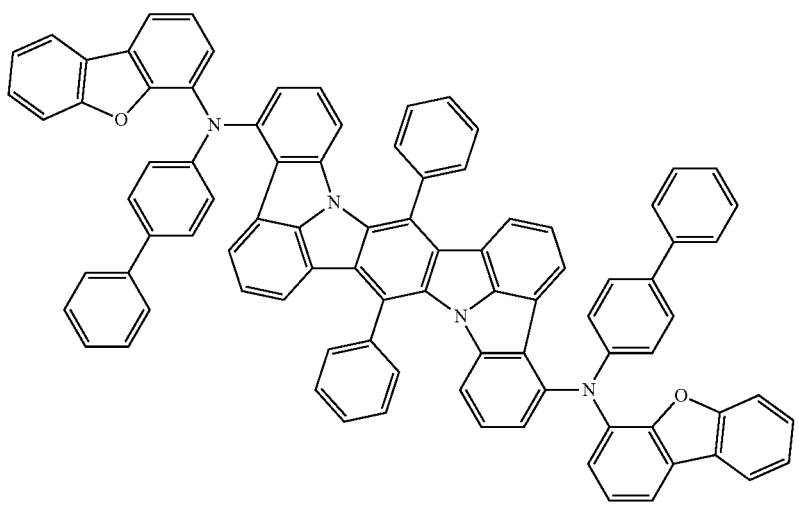

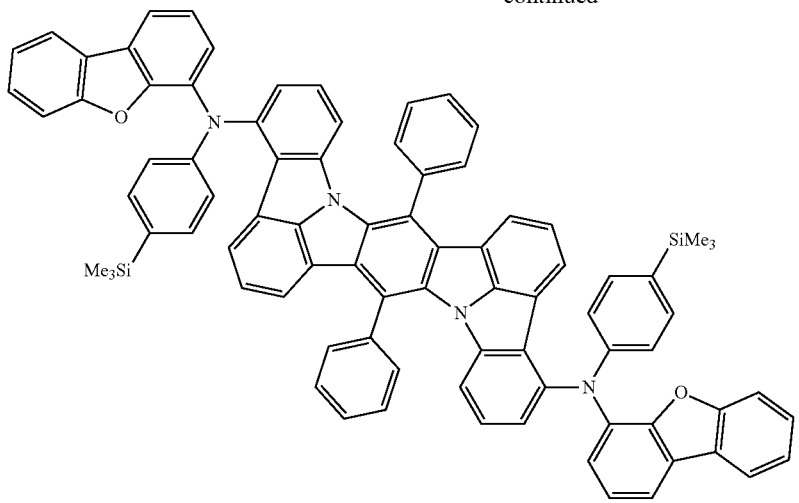
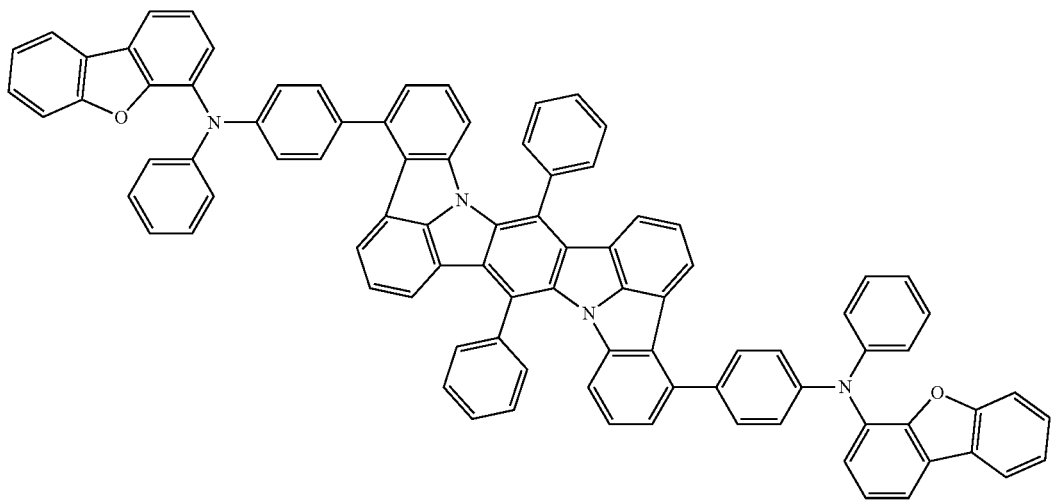
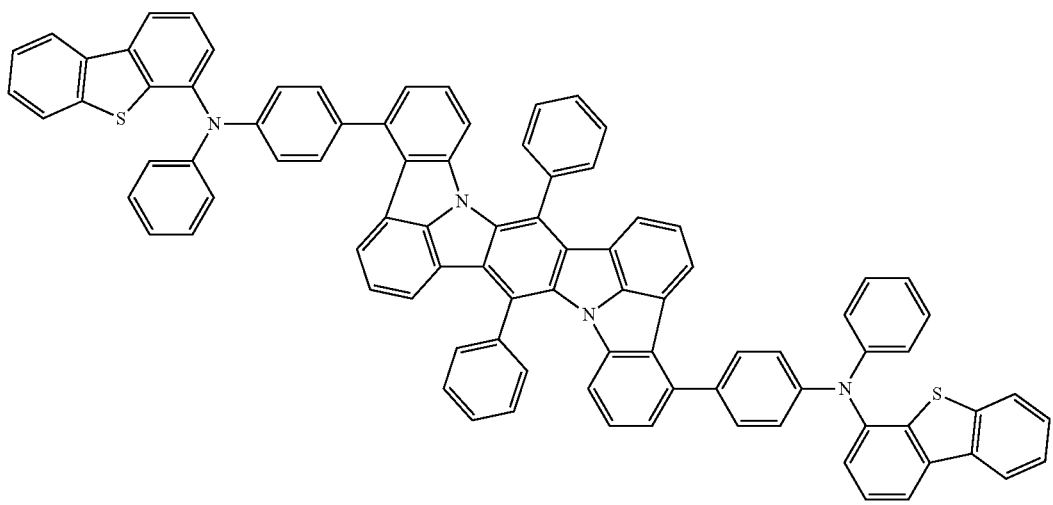

-continued
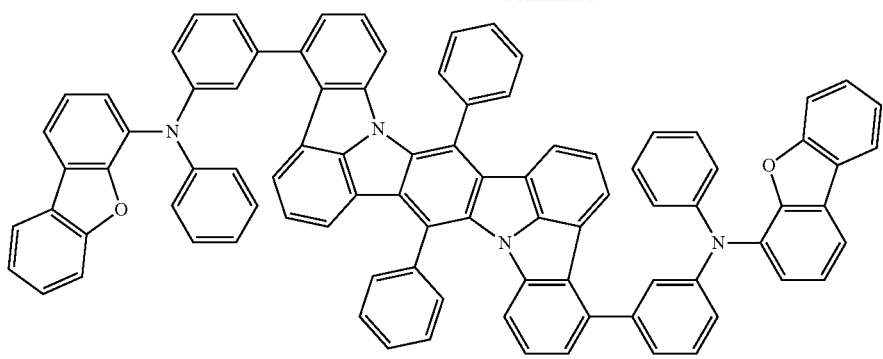
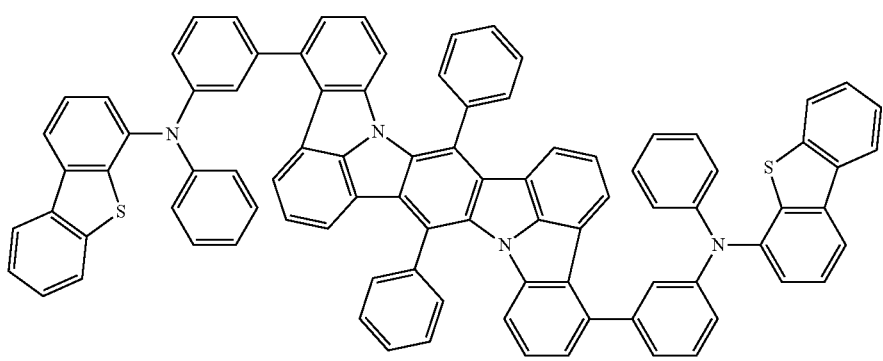
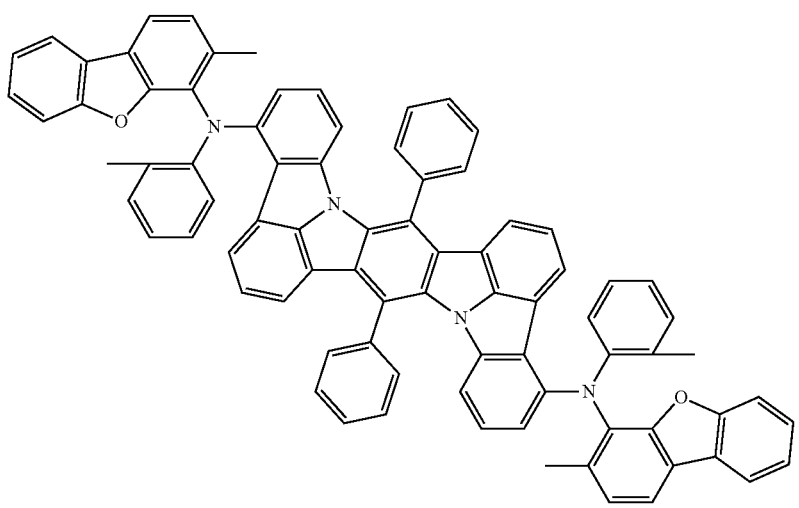
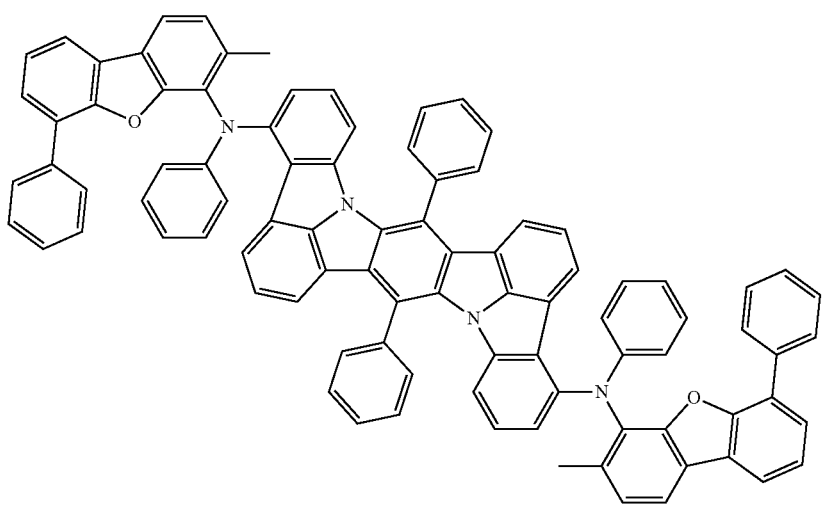

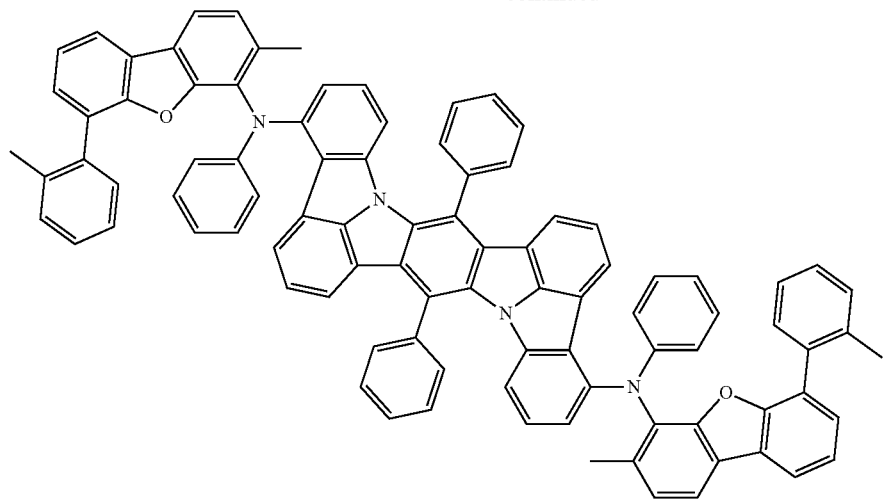
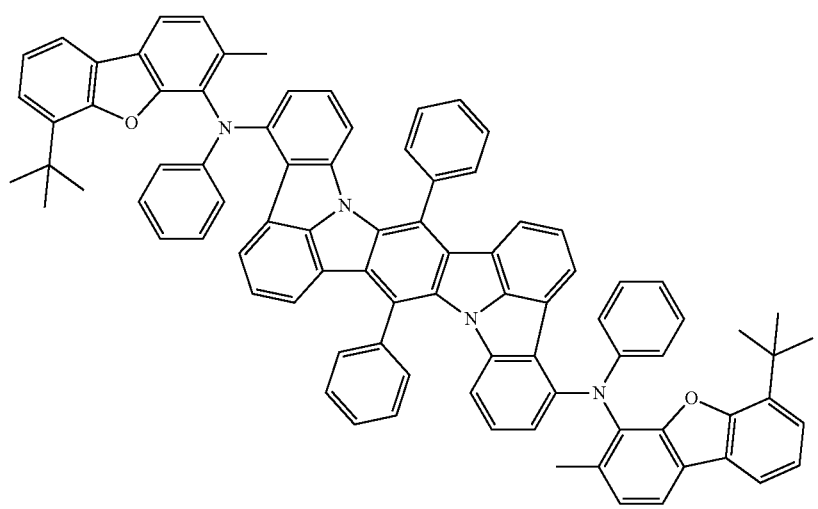
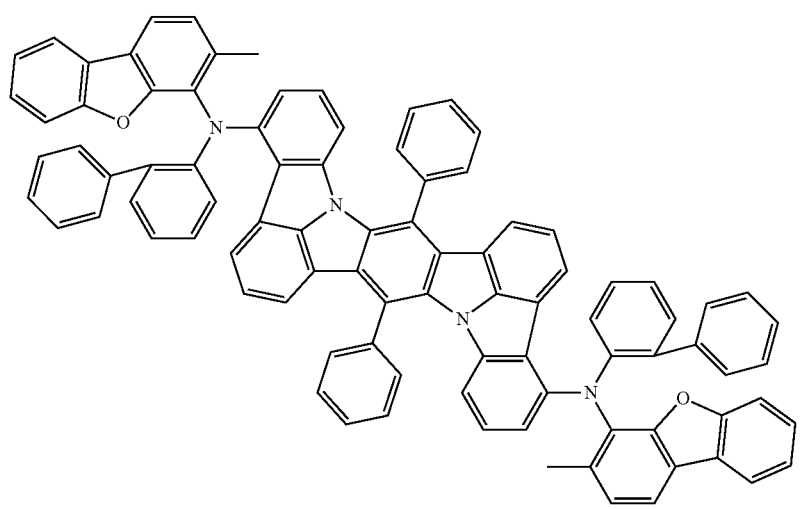

-continued
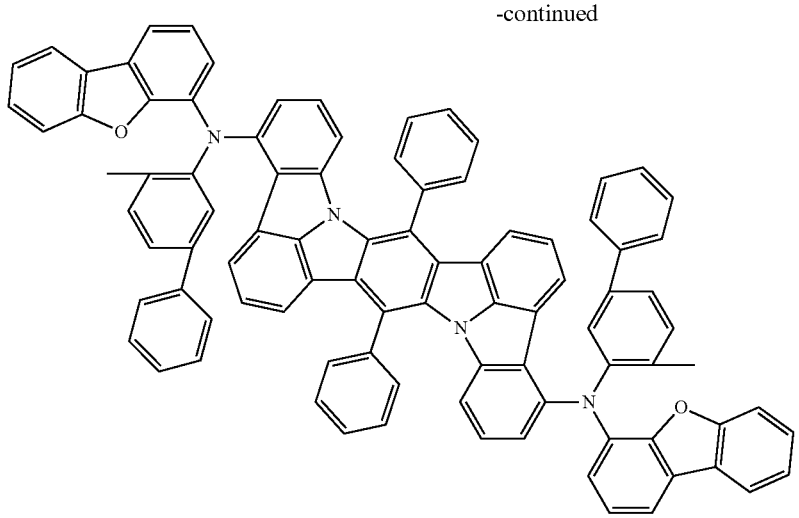
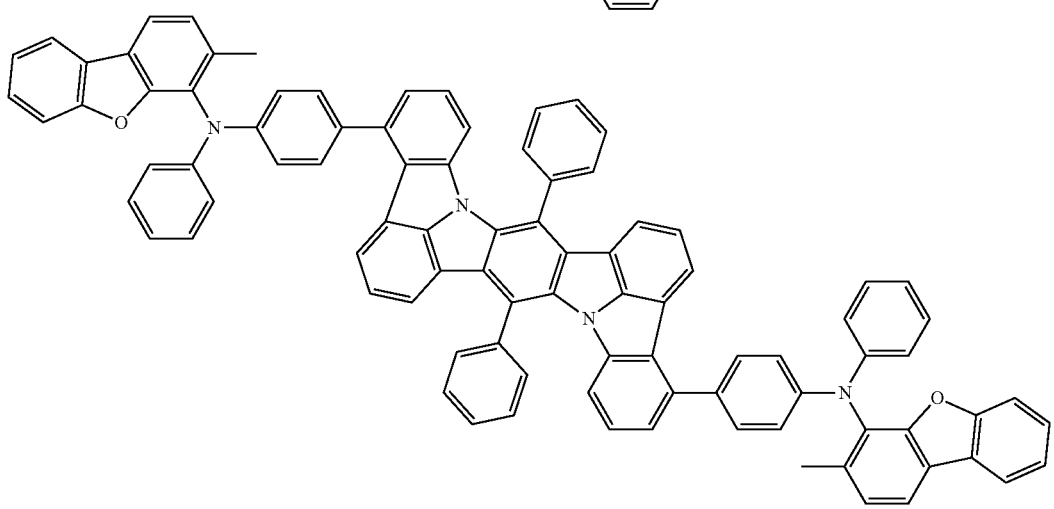
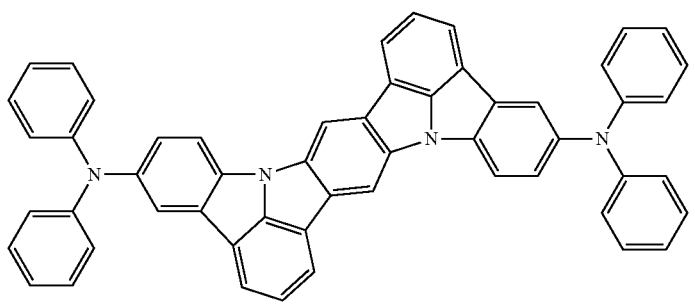
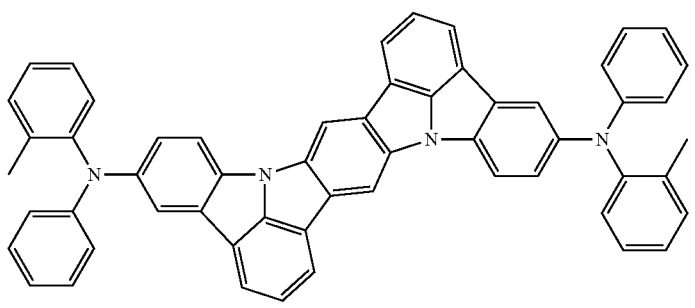

-continued
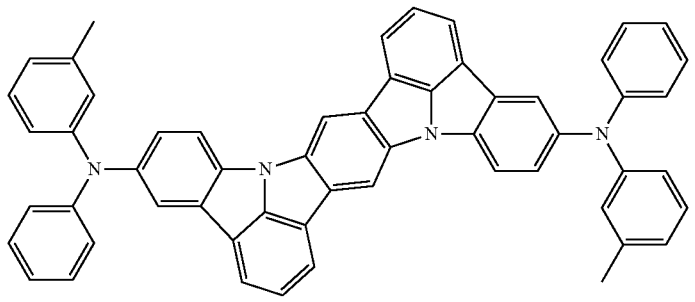
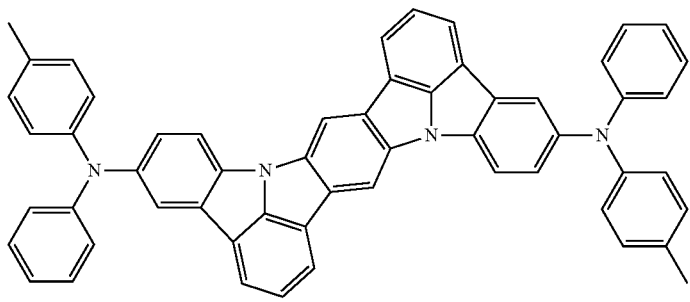
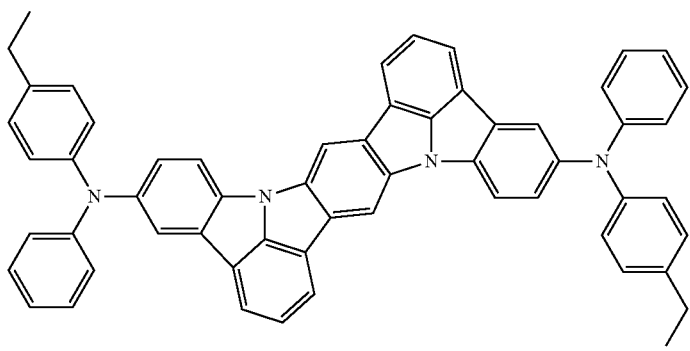
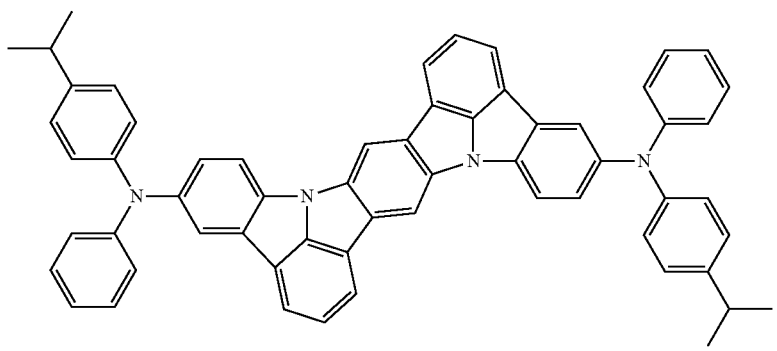
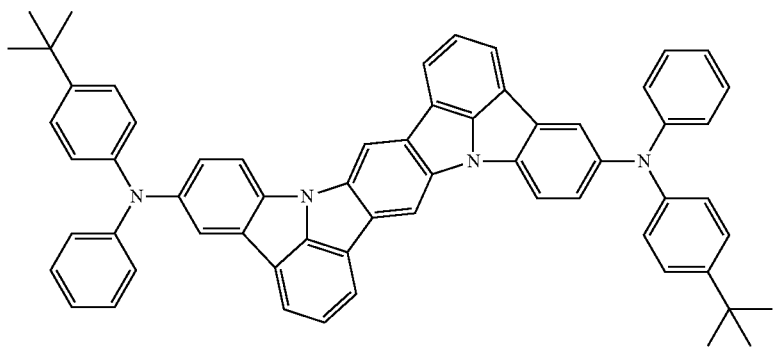

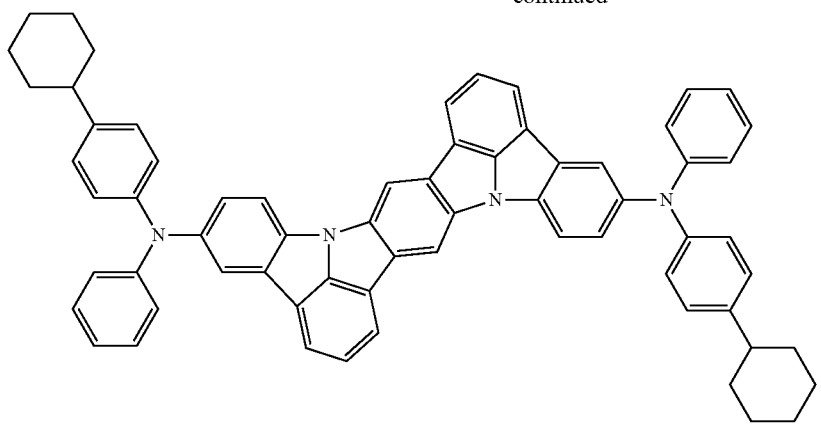
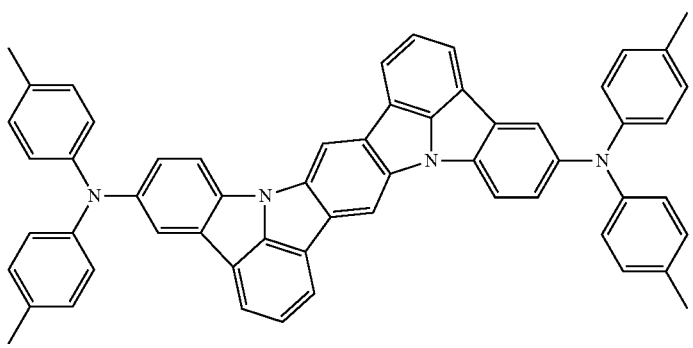
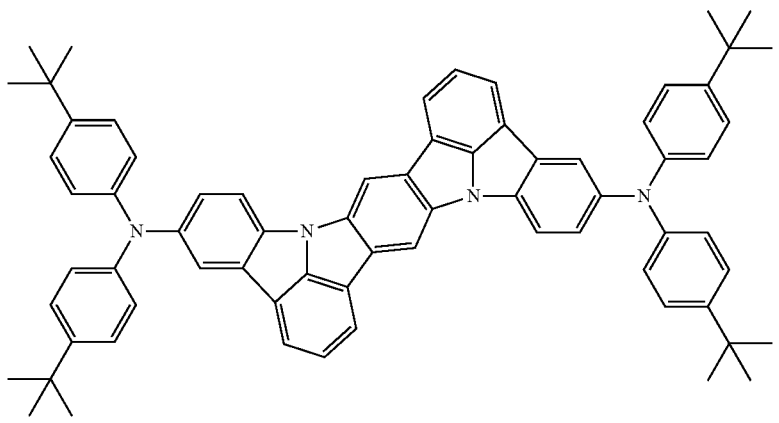

-continued
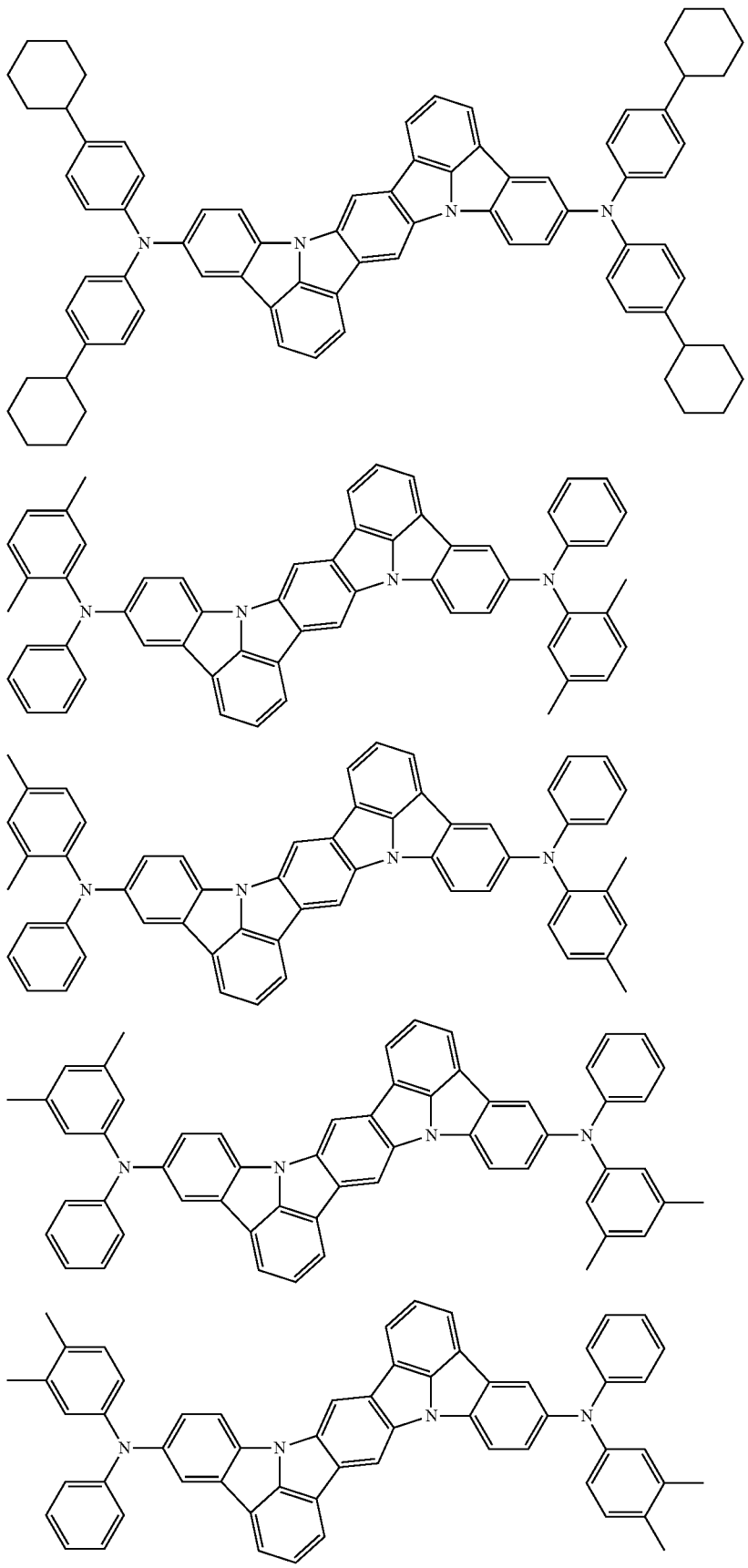

-continued
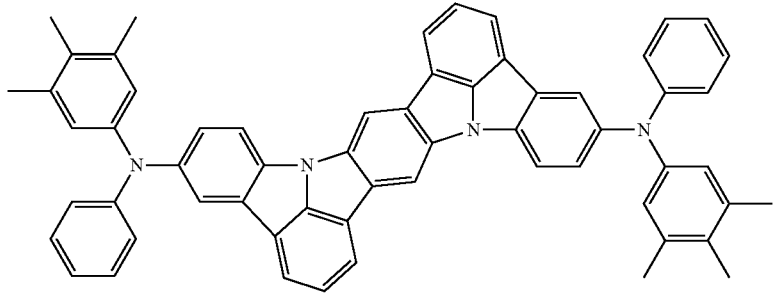
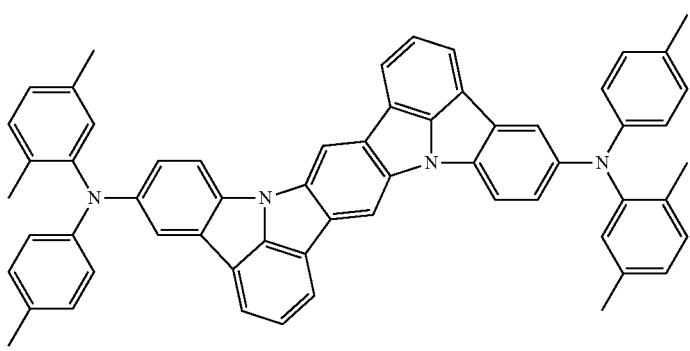
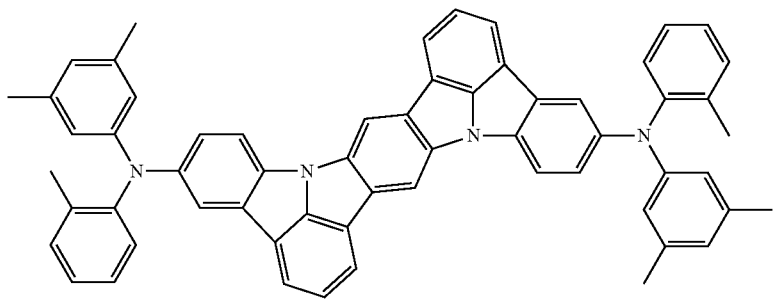
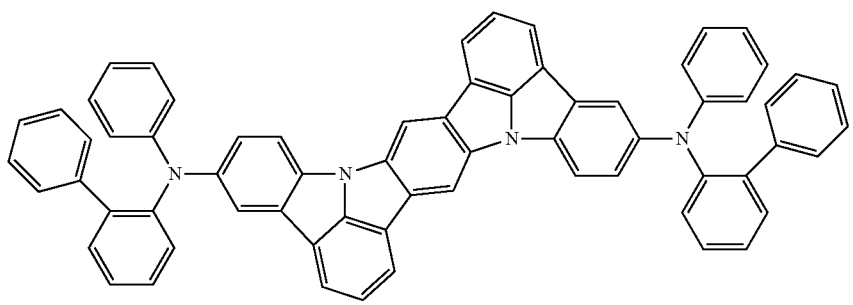
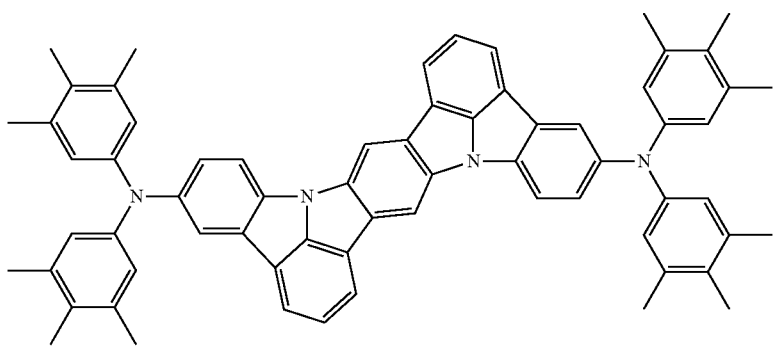

-continued
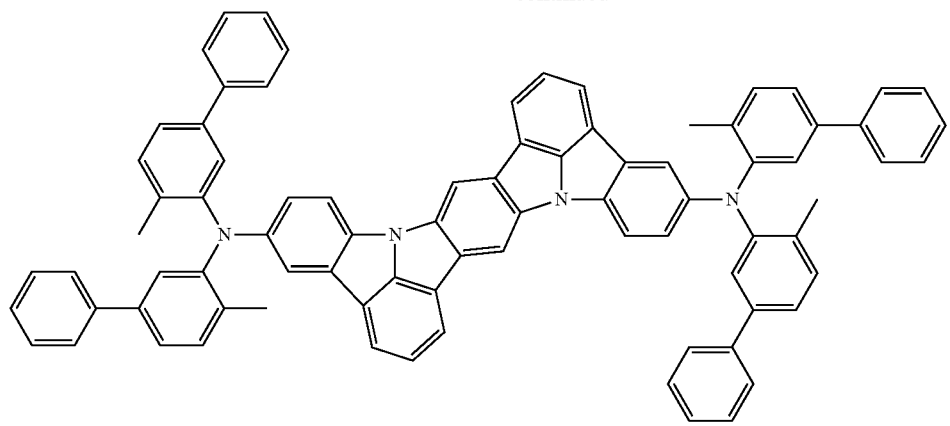
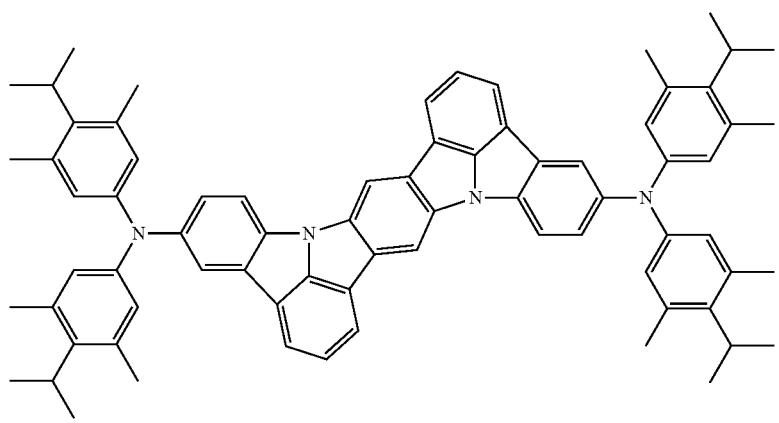
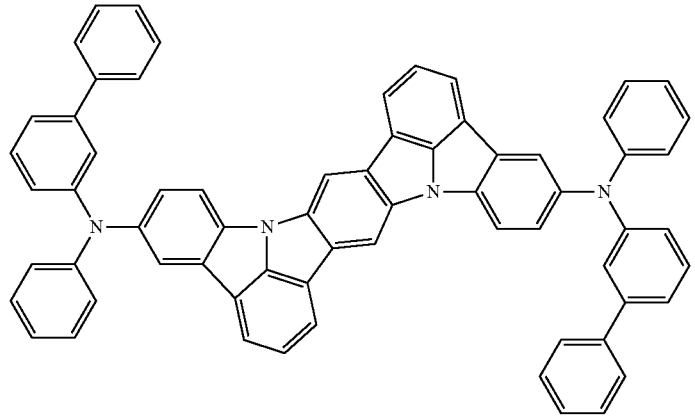
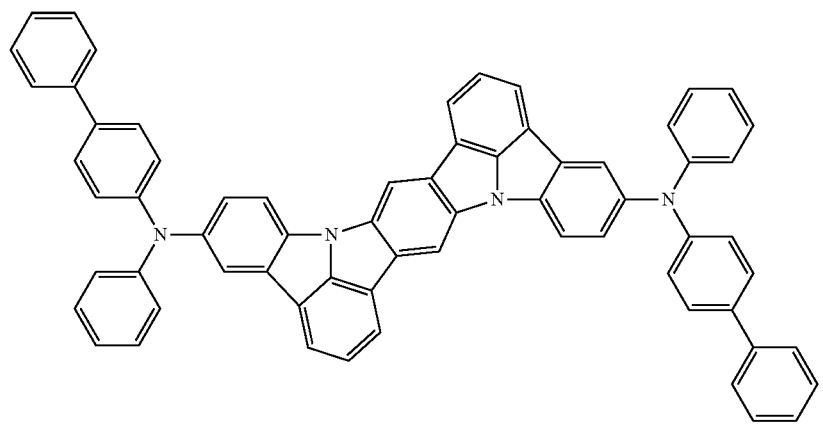

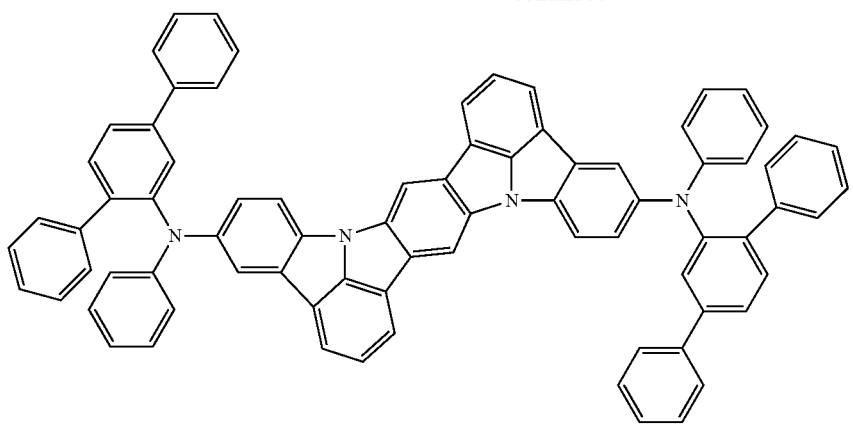
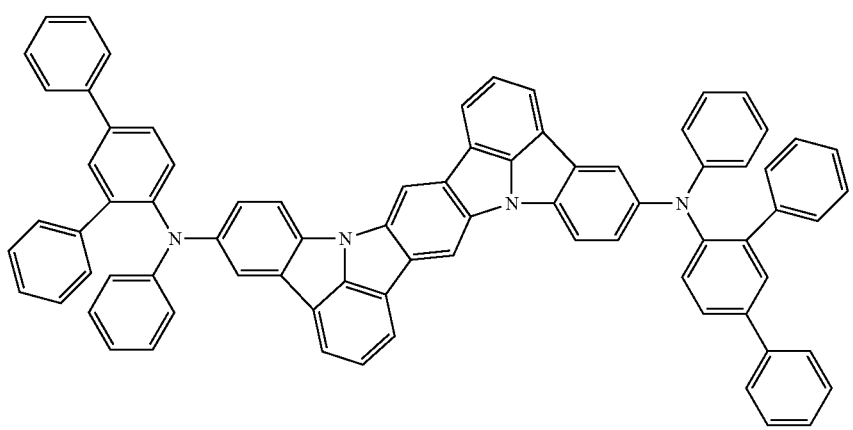
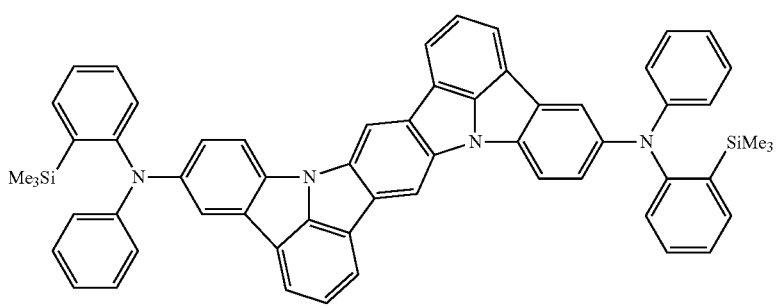
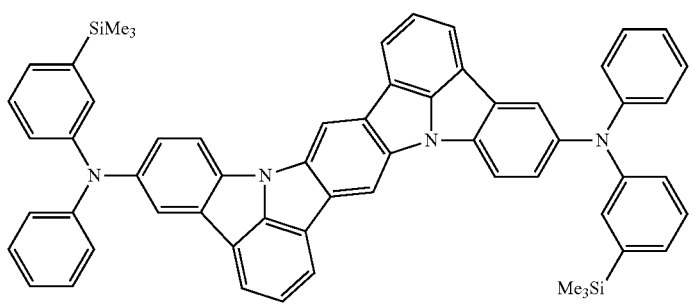

-continued
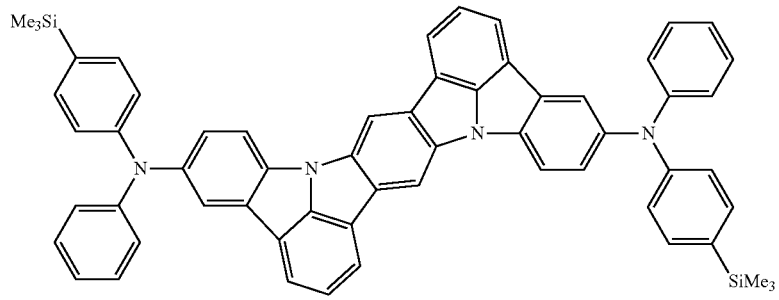
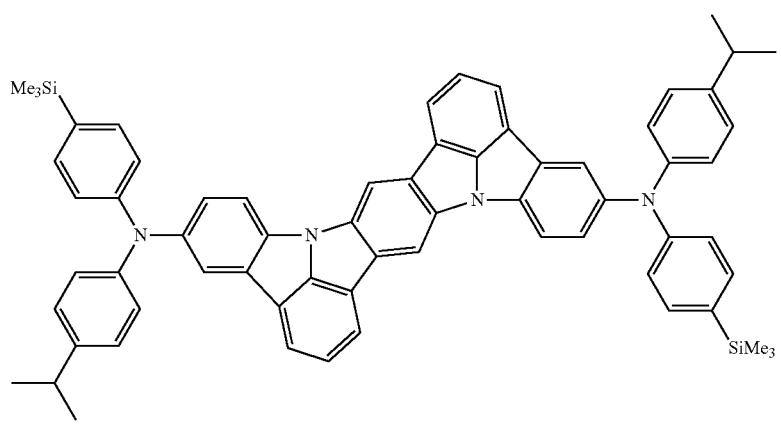
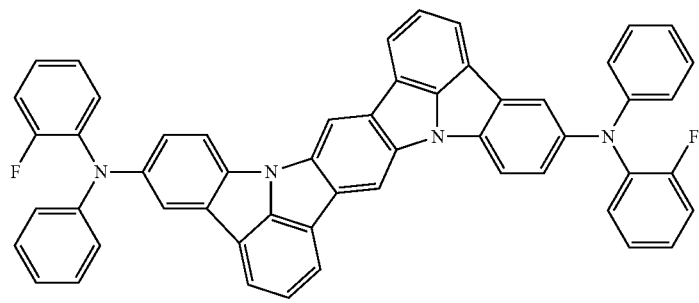
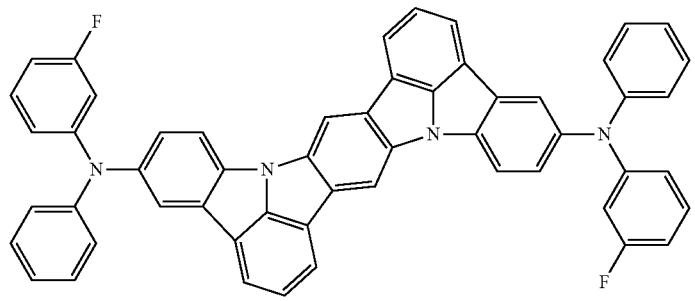
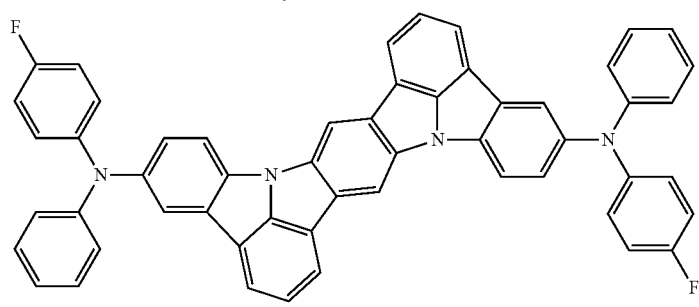

-continued
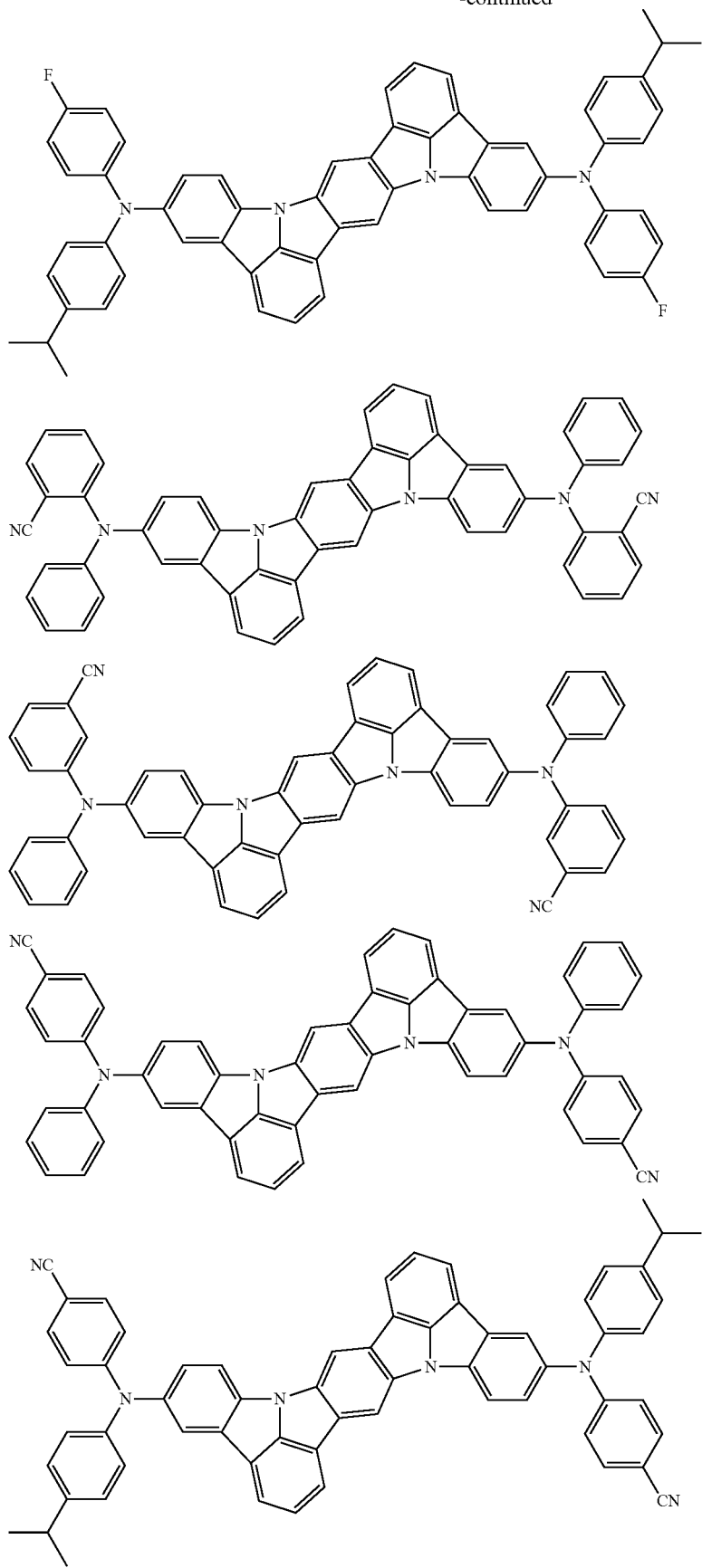

-continued
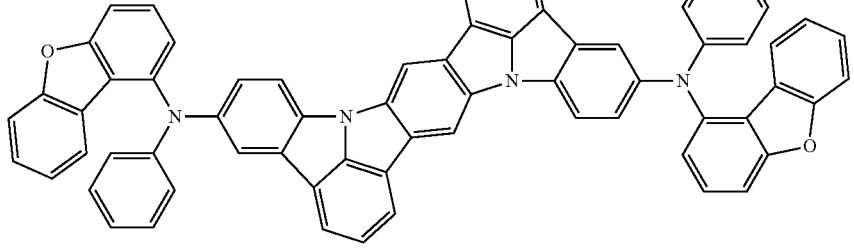
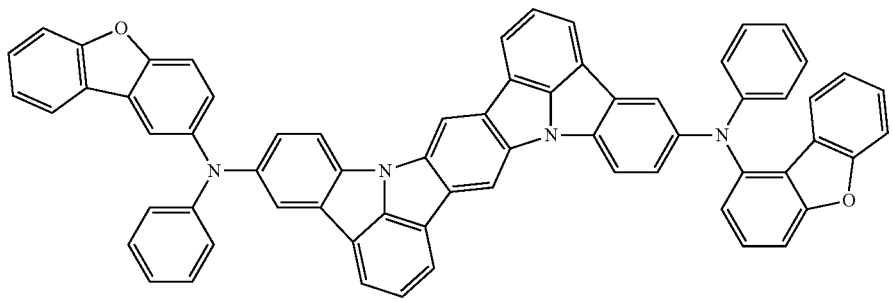
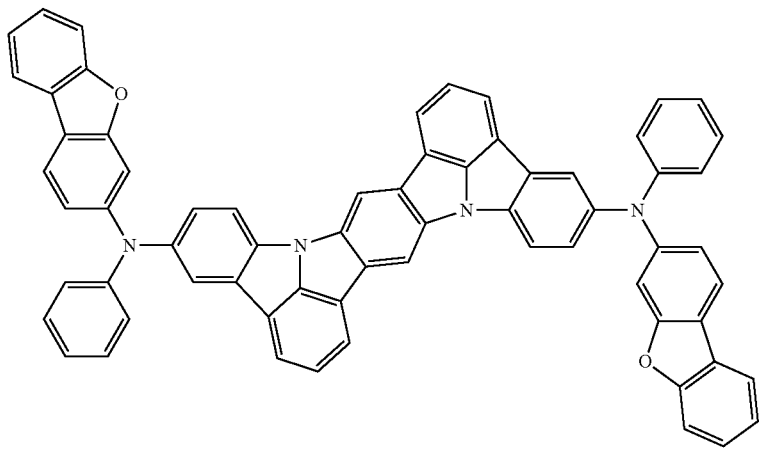
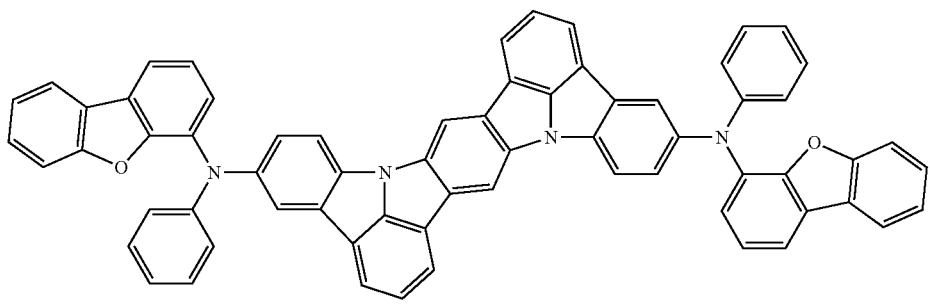

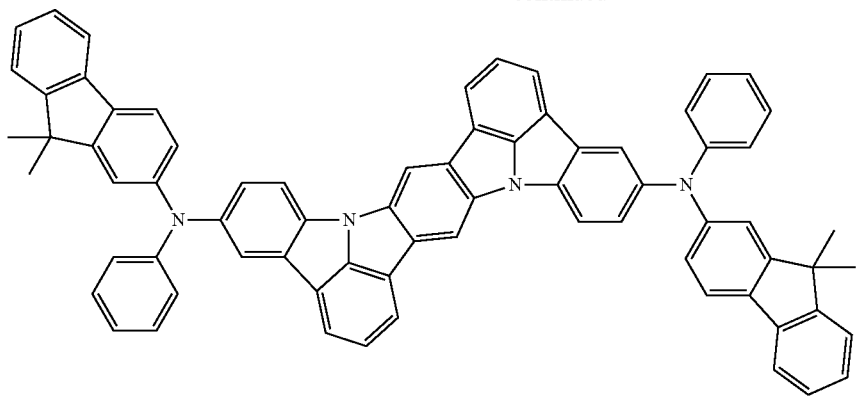

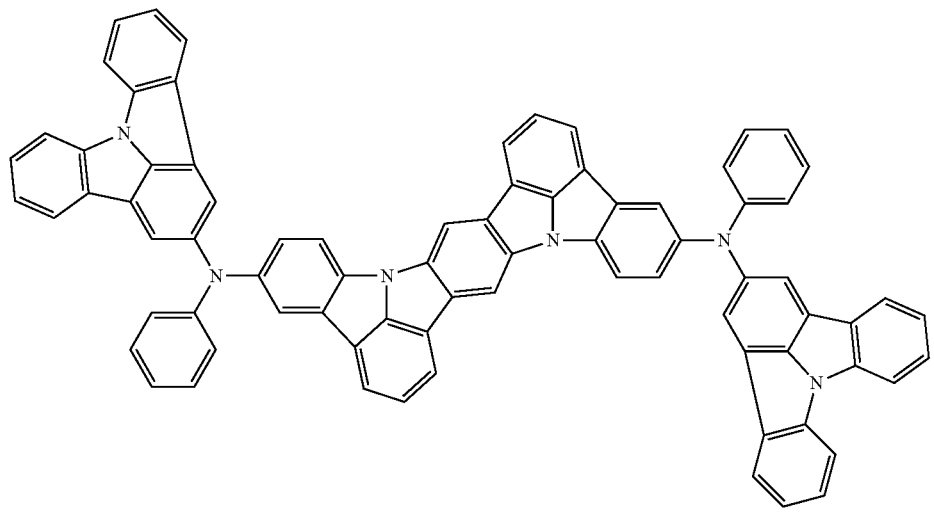
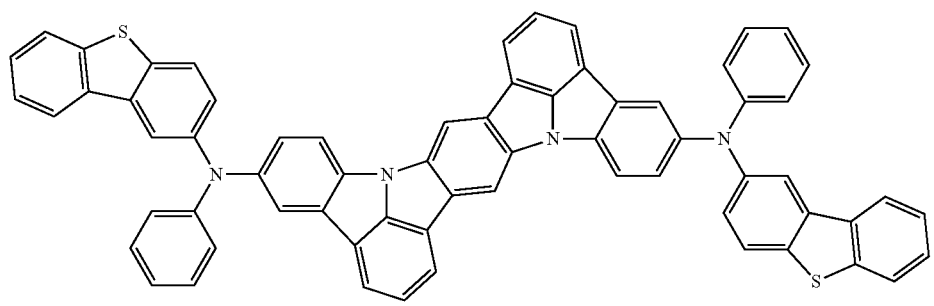
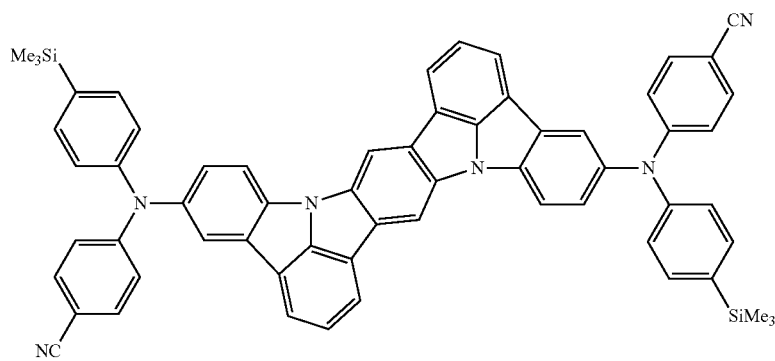
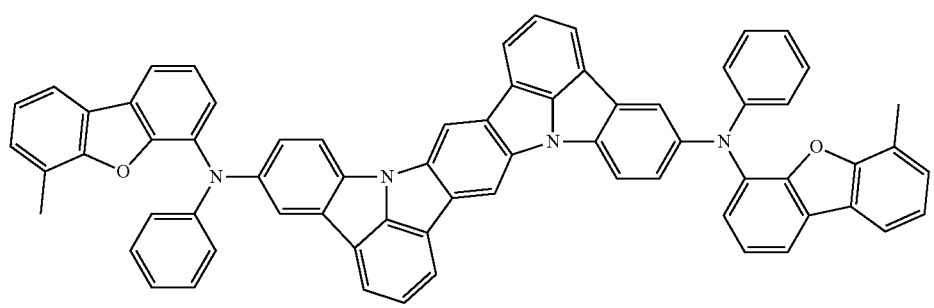

-continued
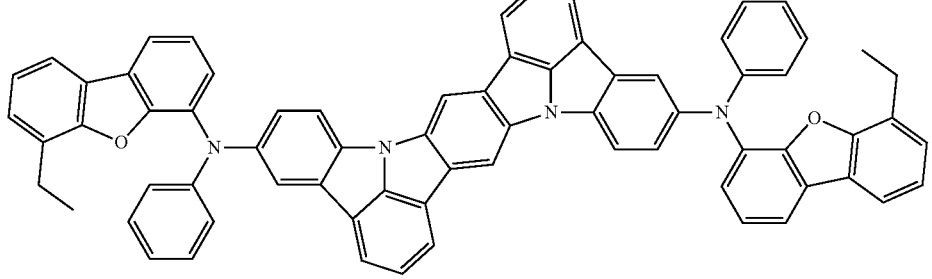
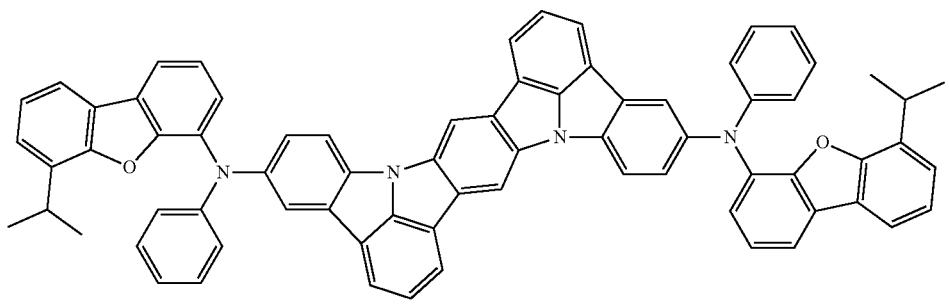
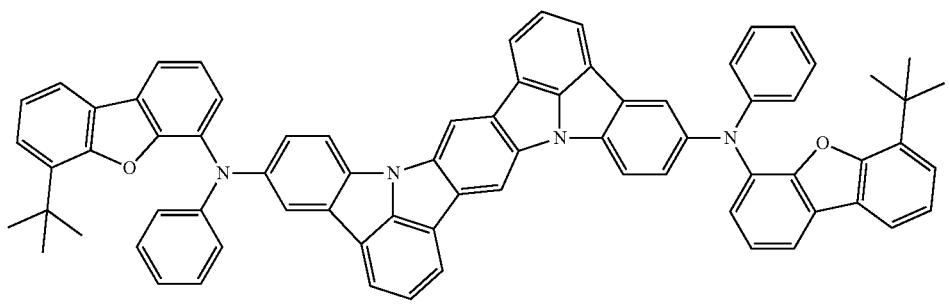
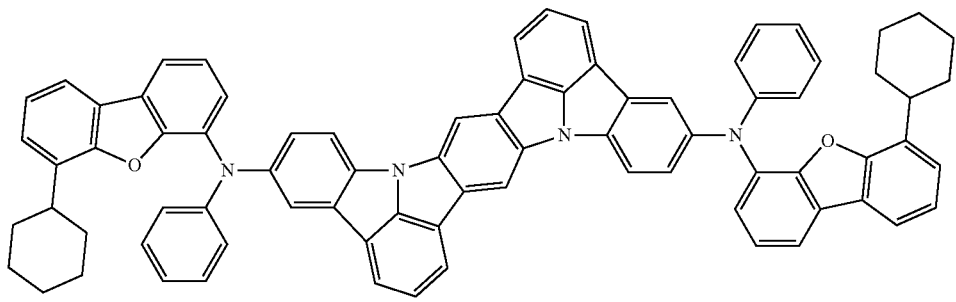
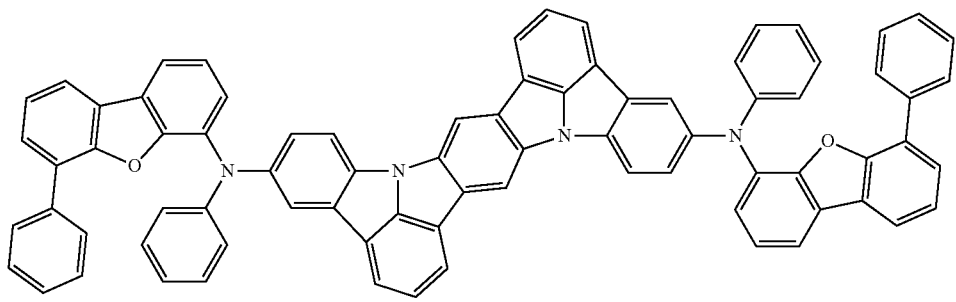

-continued
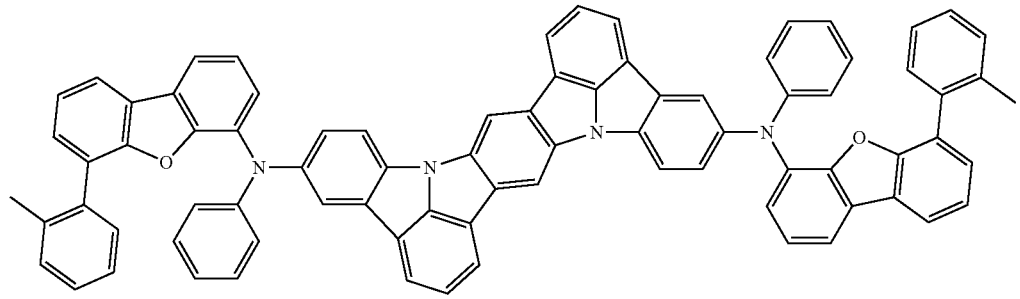
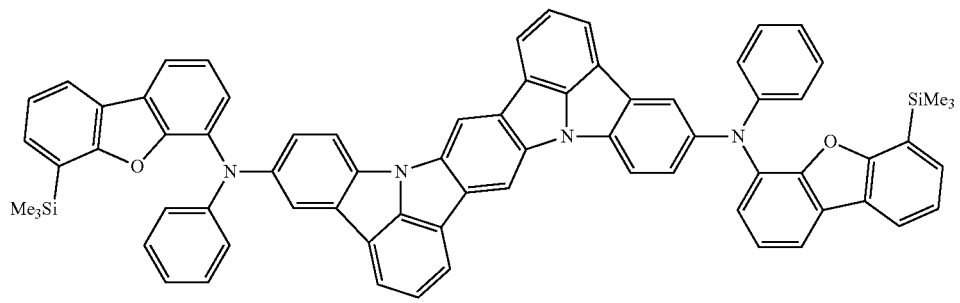
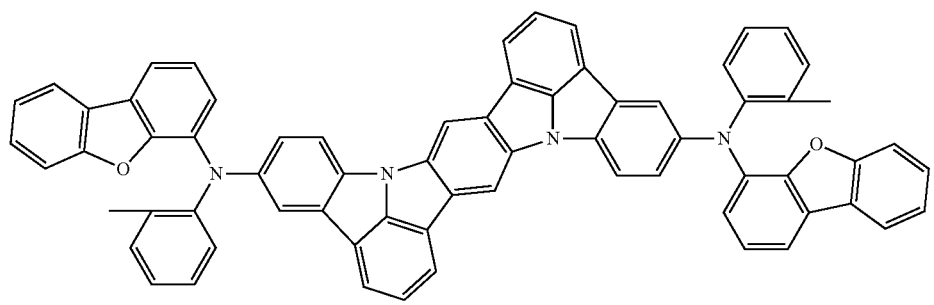
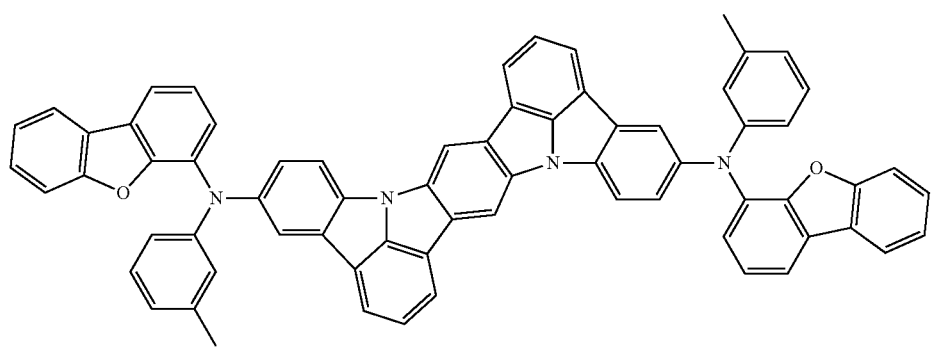
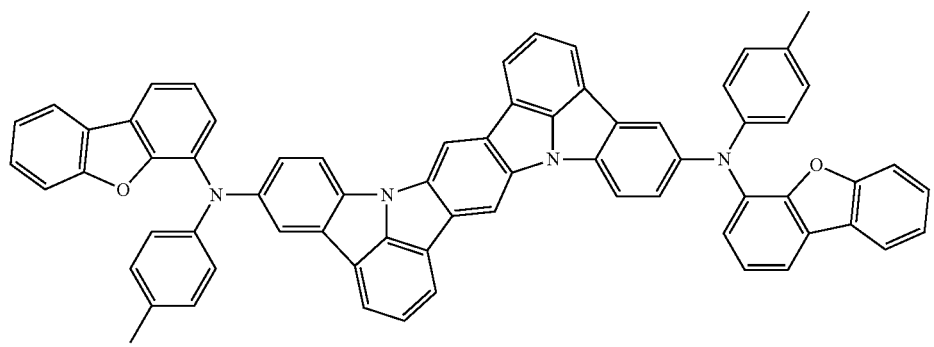

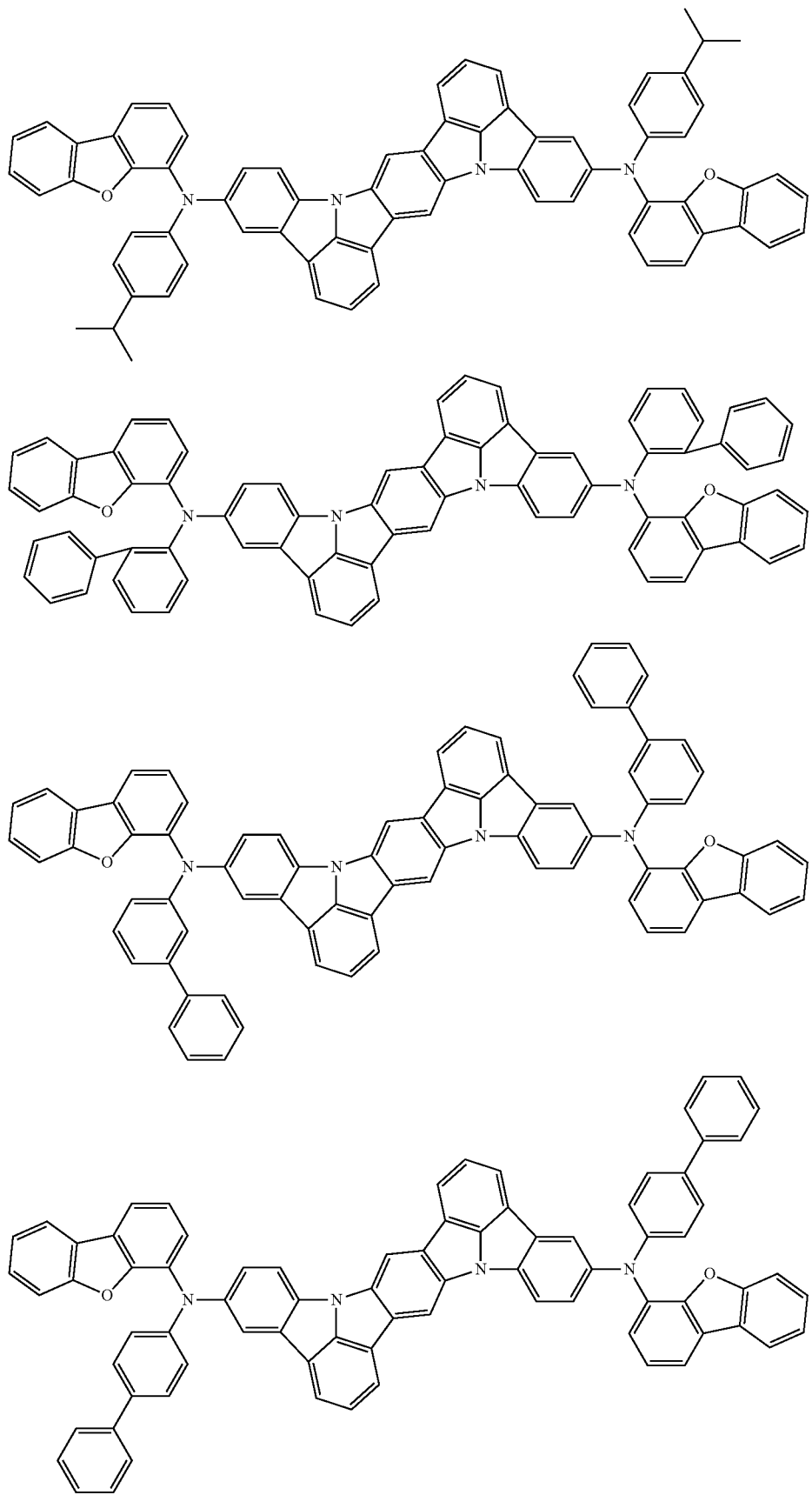

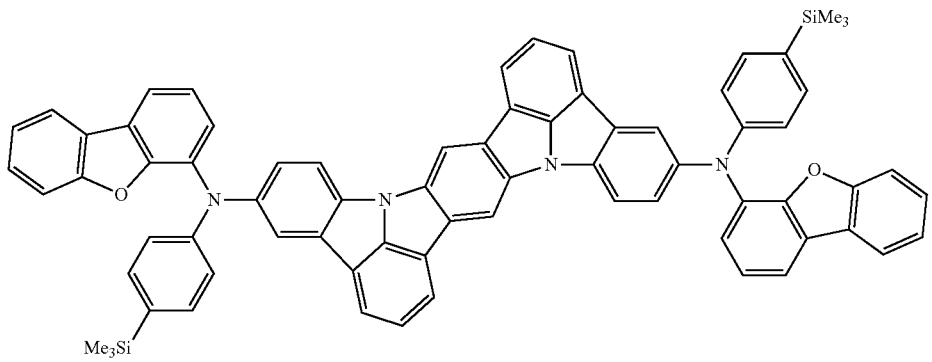

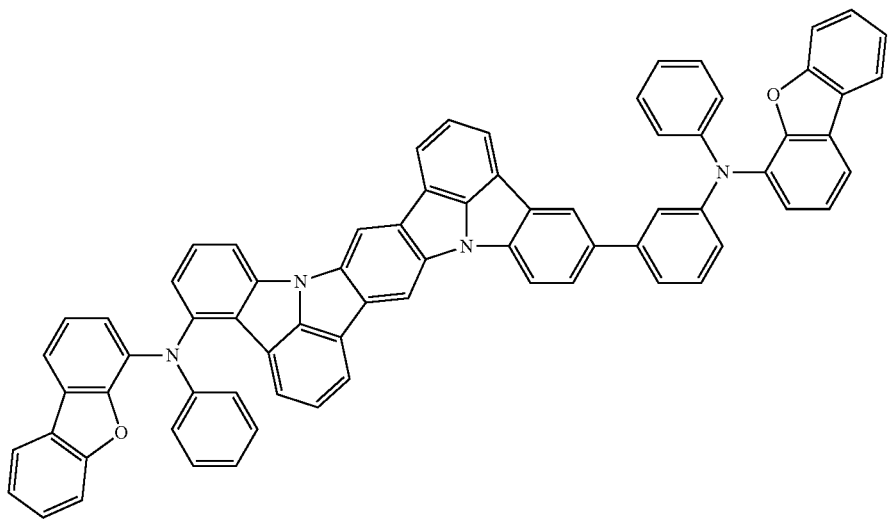

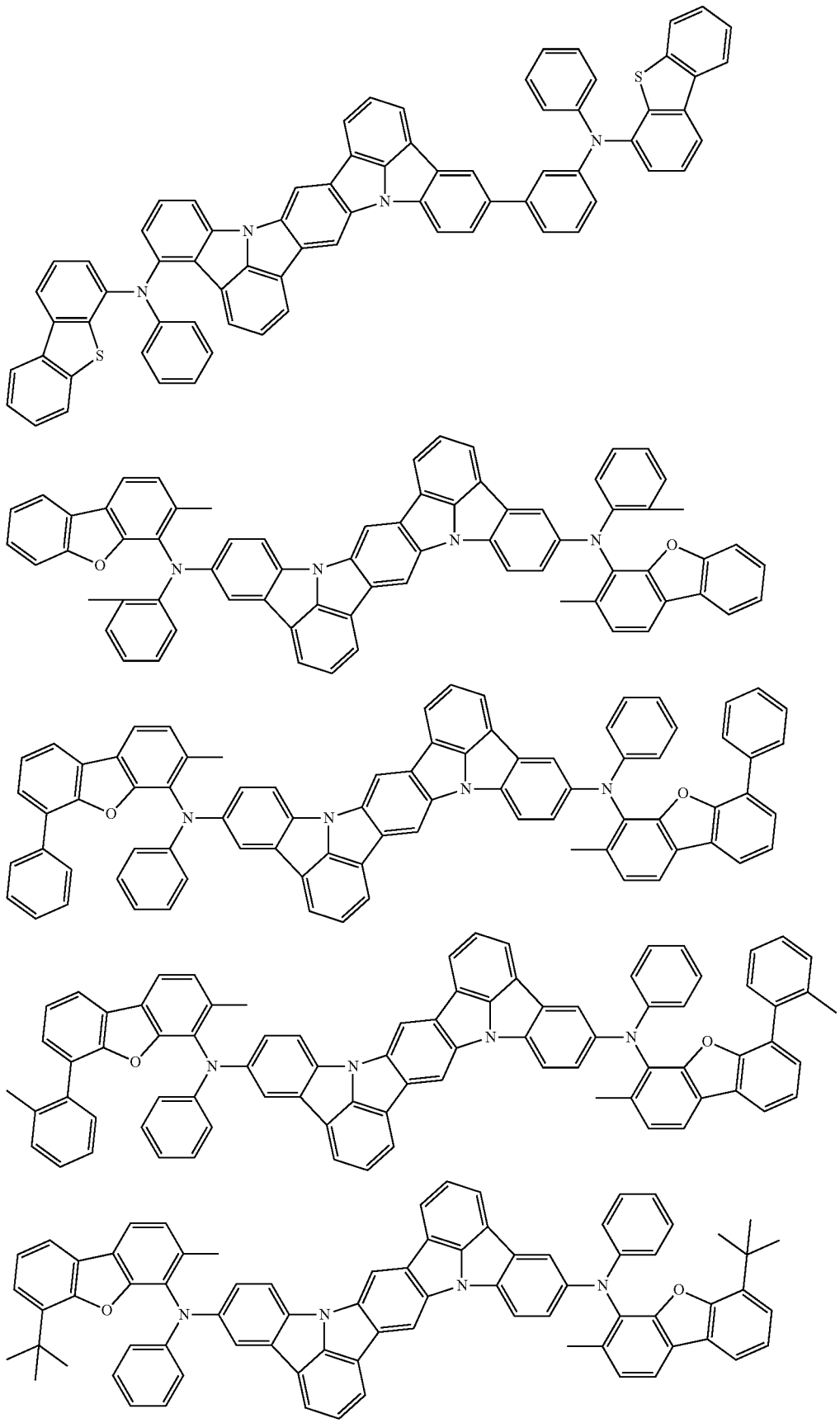

-continued
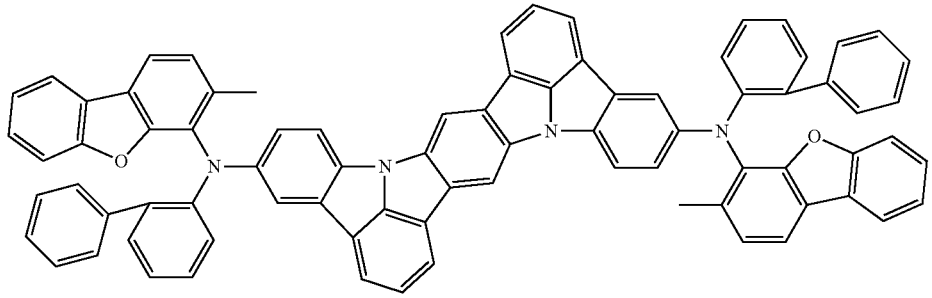
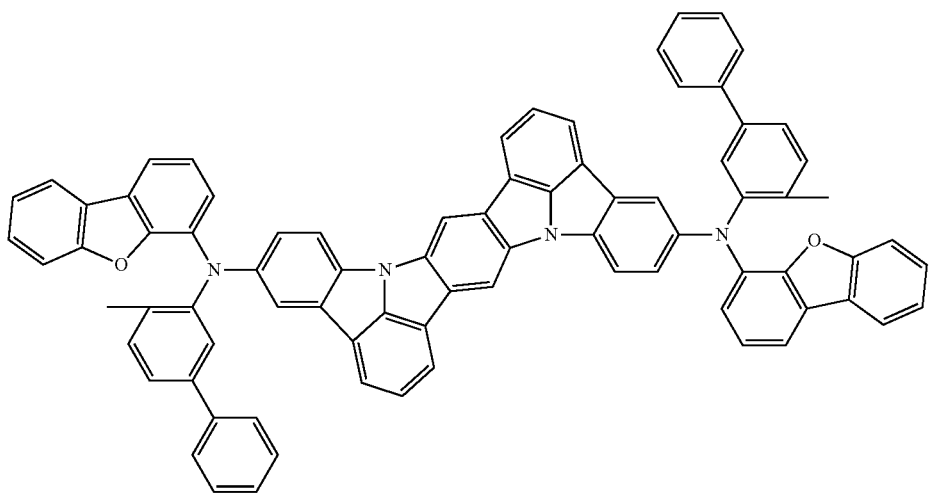
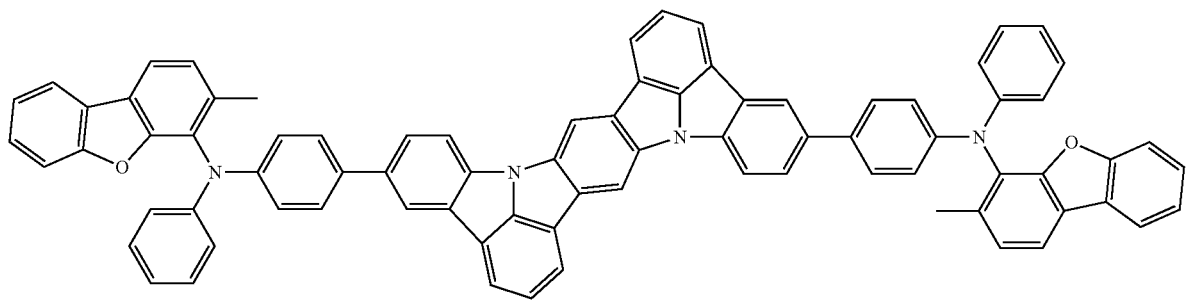
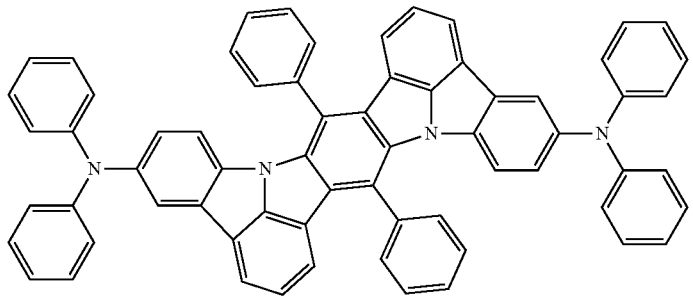
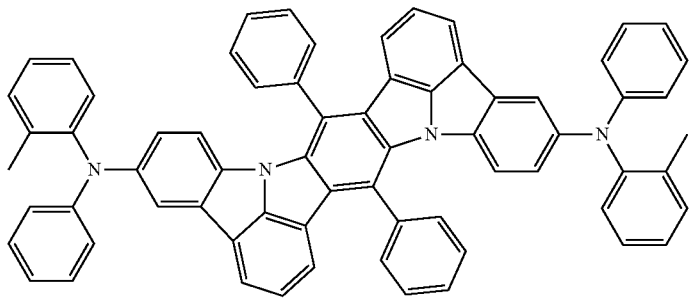

-continued
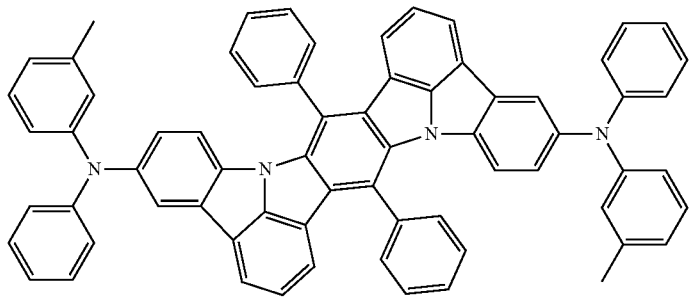
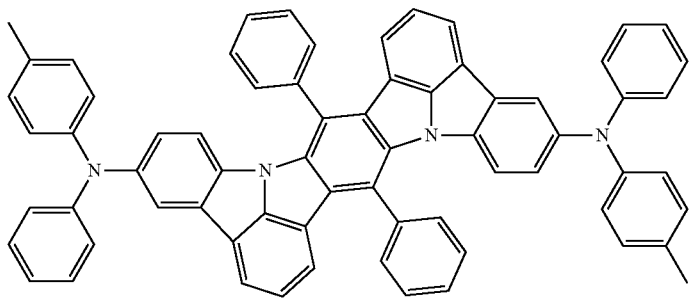
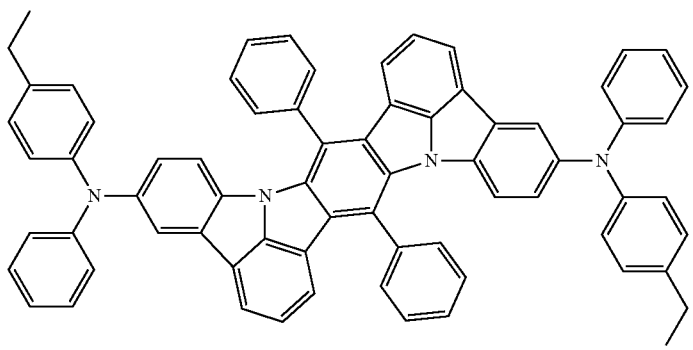
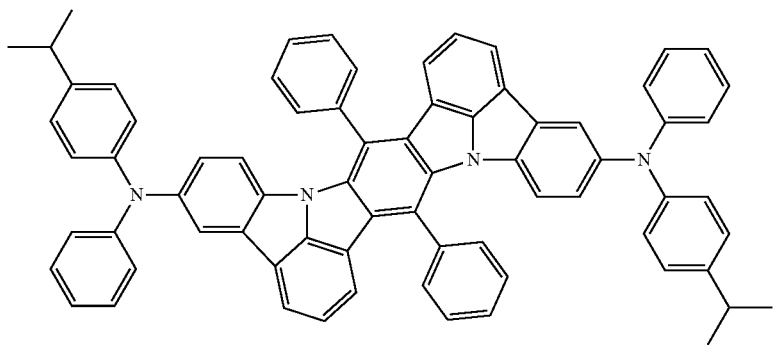

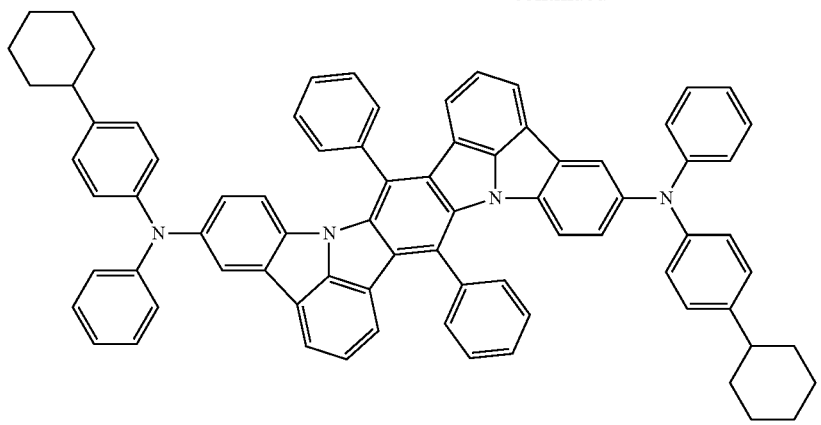
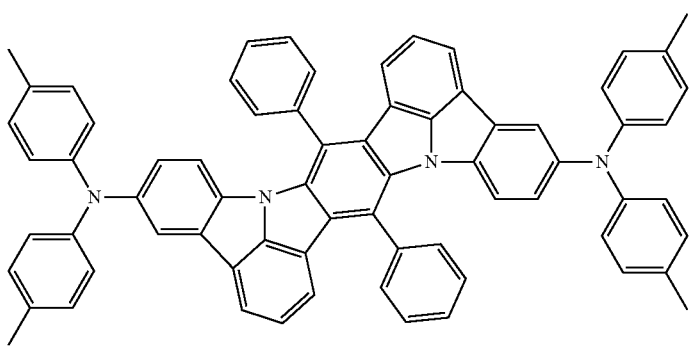
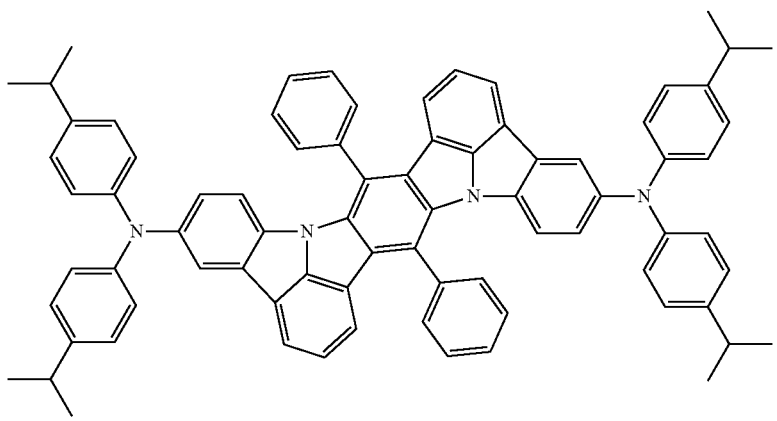
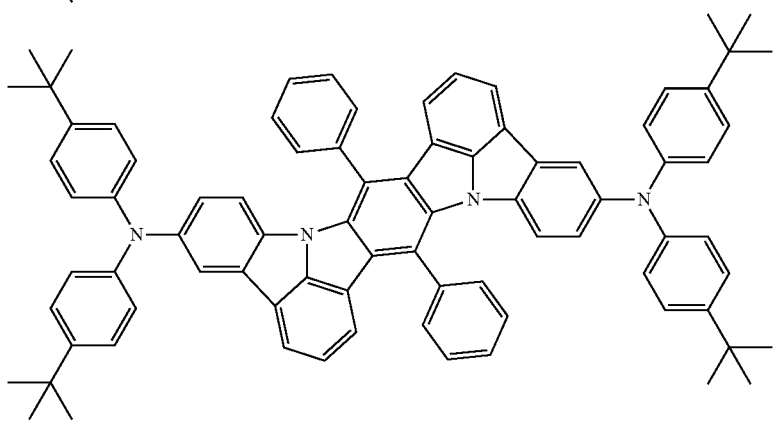

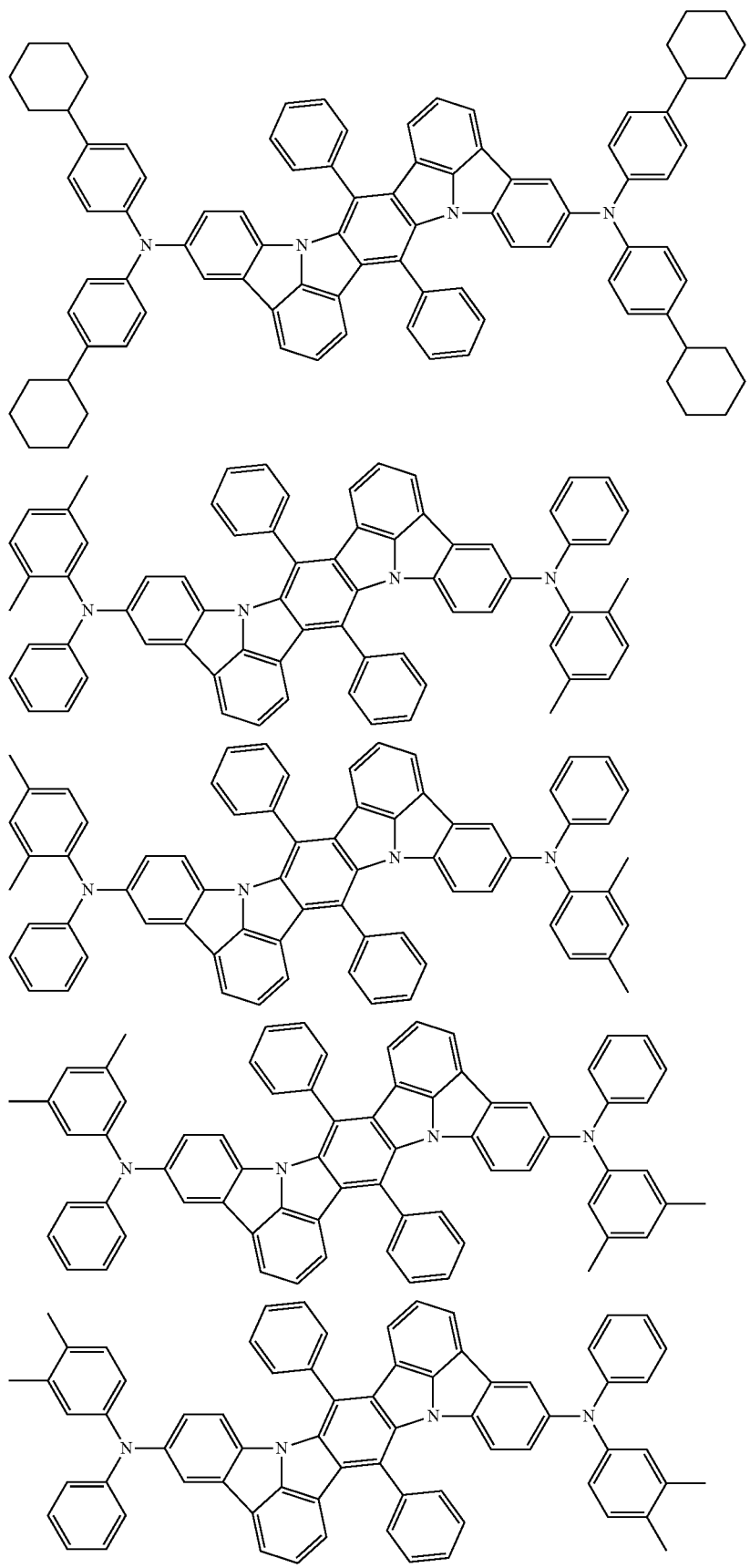

-continued
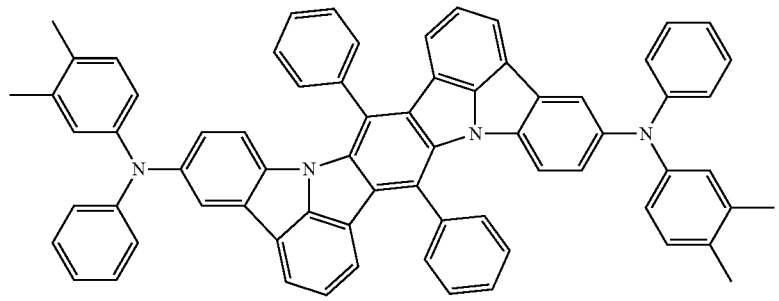
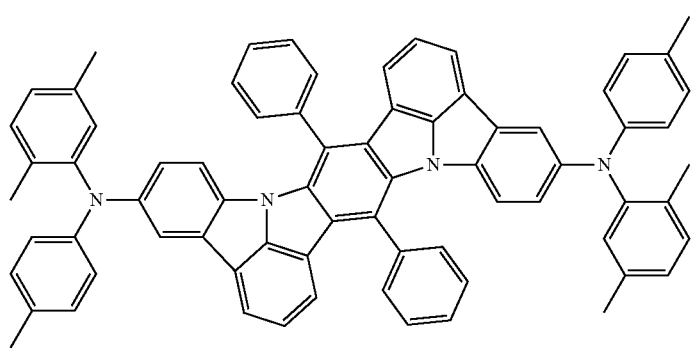
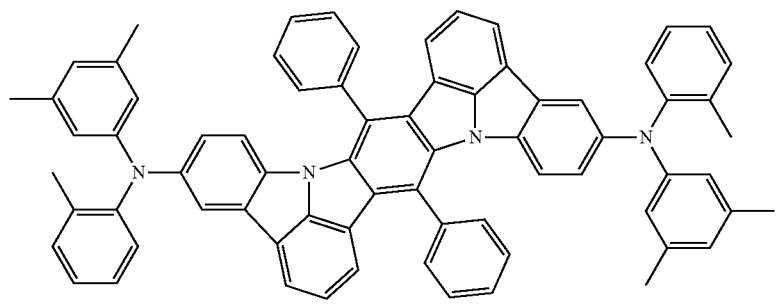
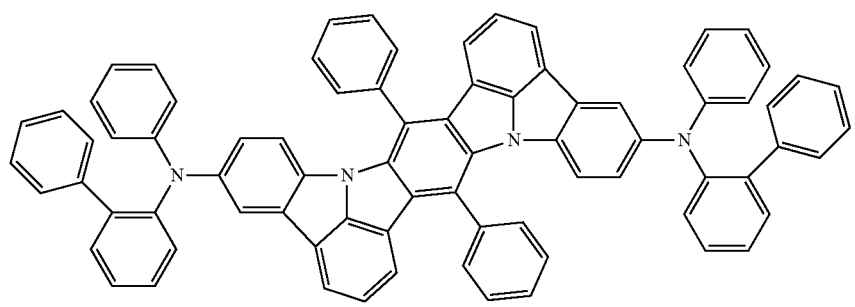
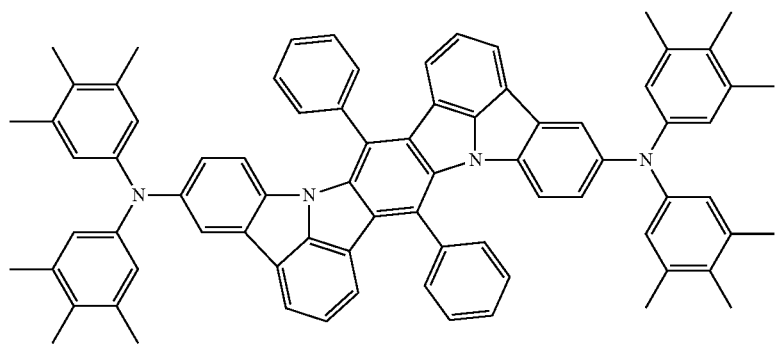

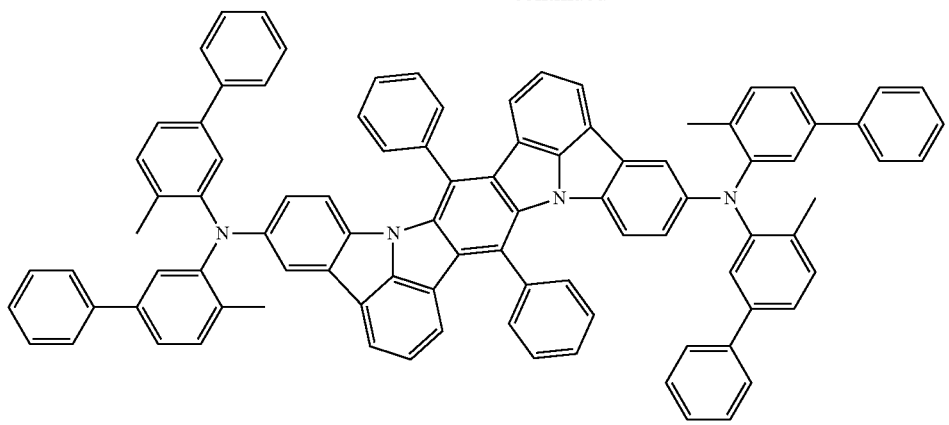
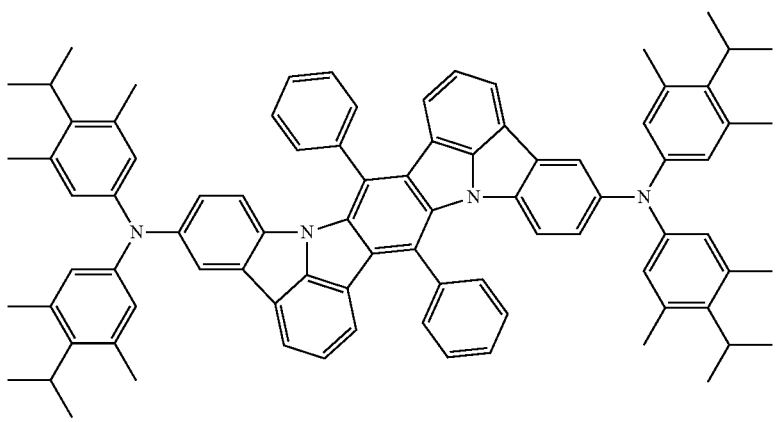
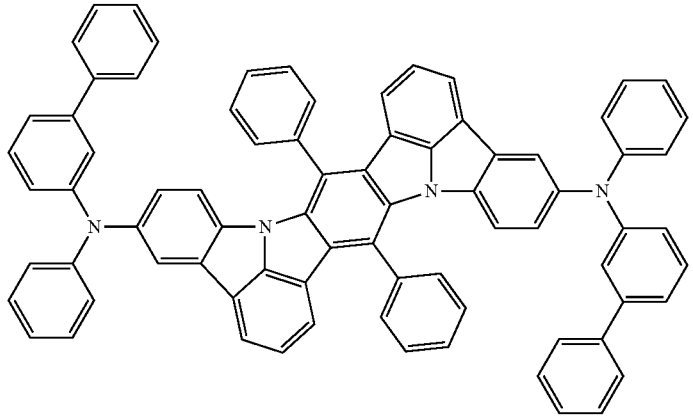
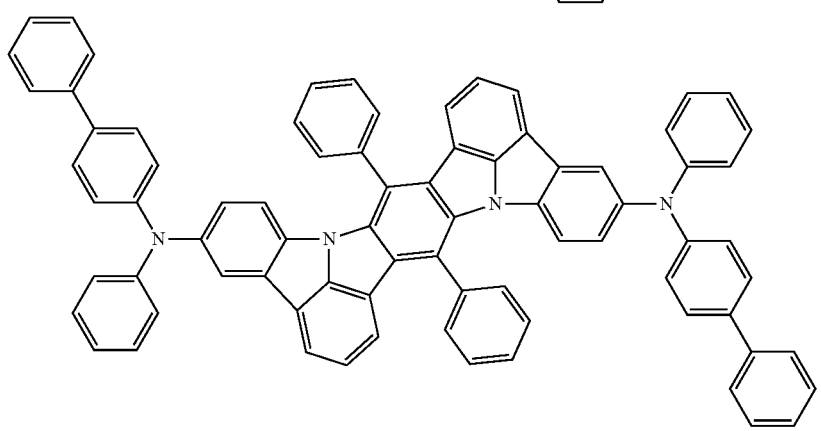

-continued
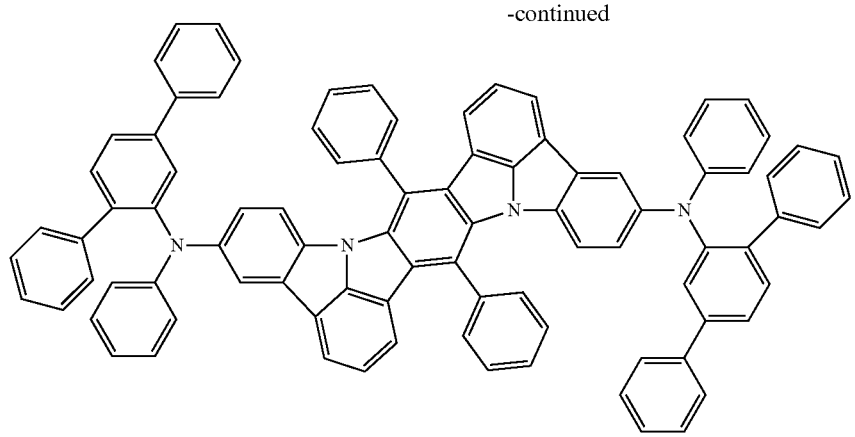
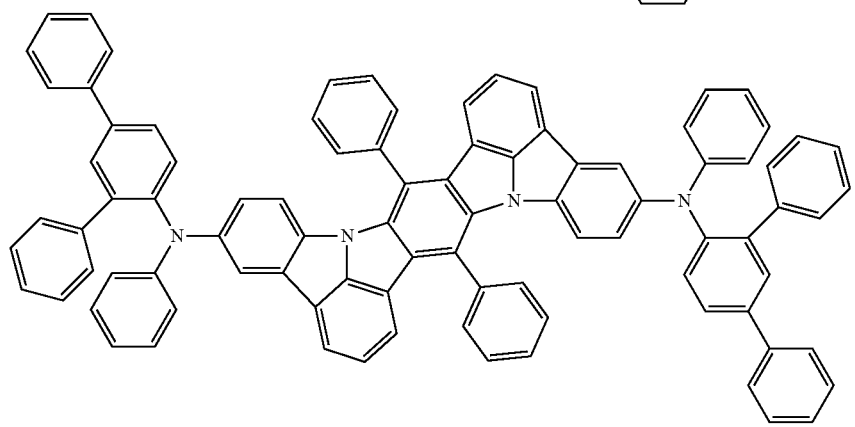
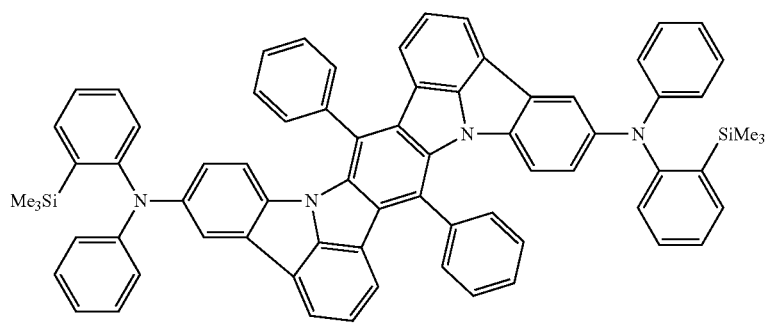
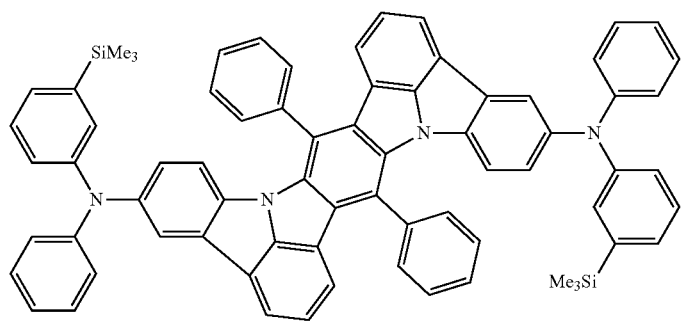

-continued
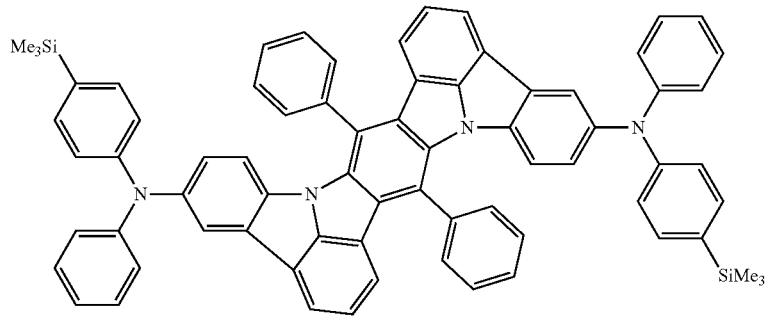
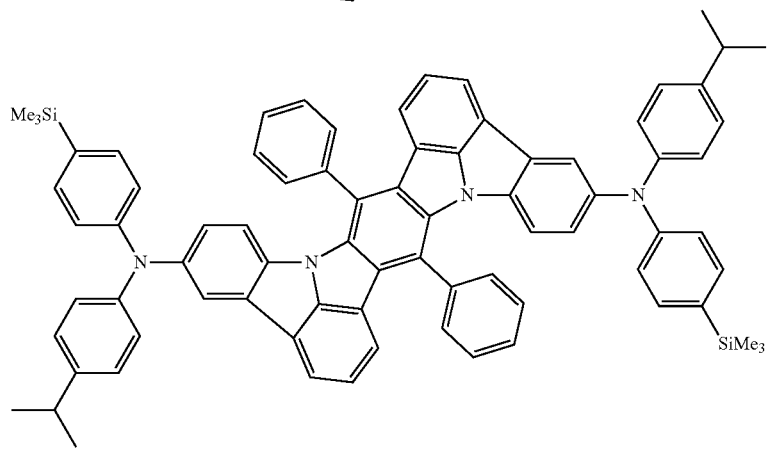
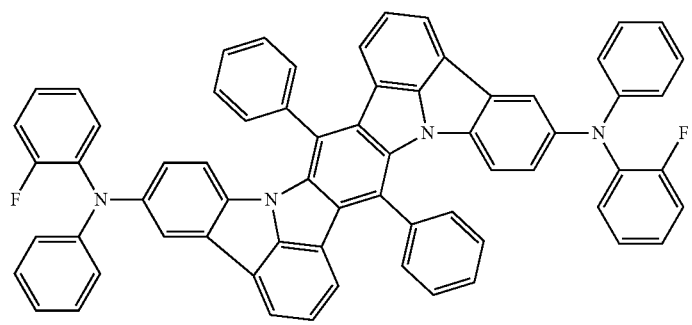
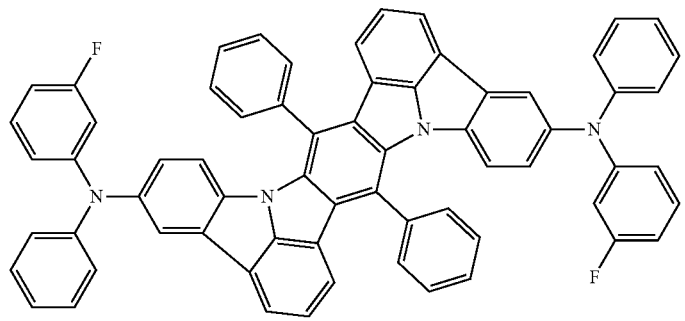
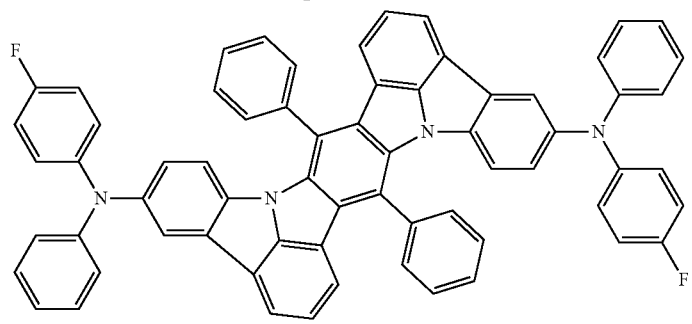

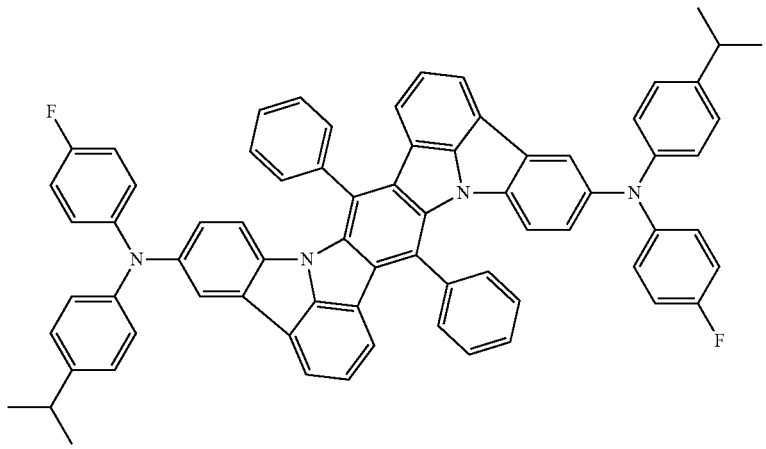
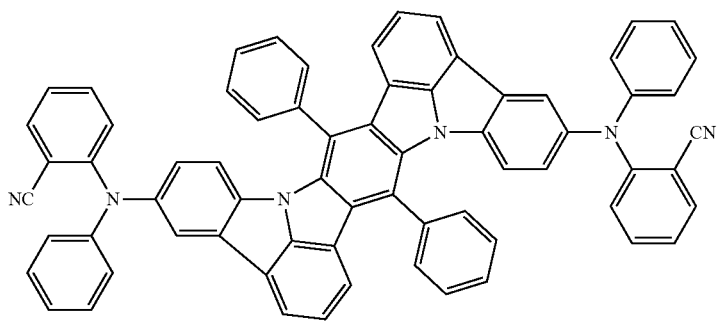
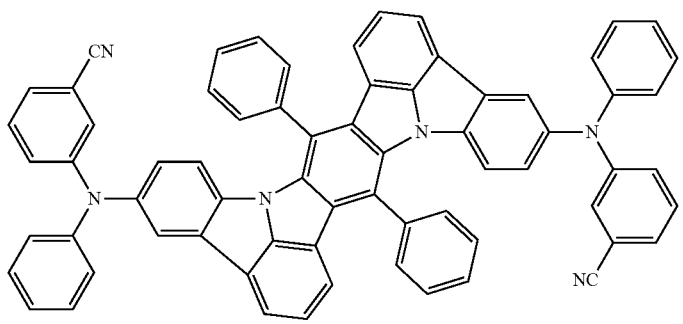
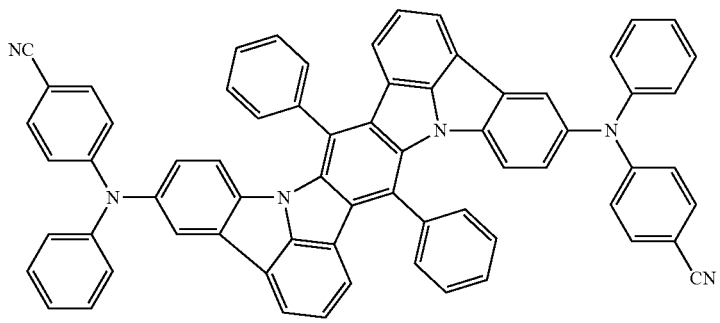

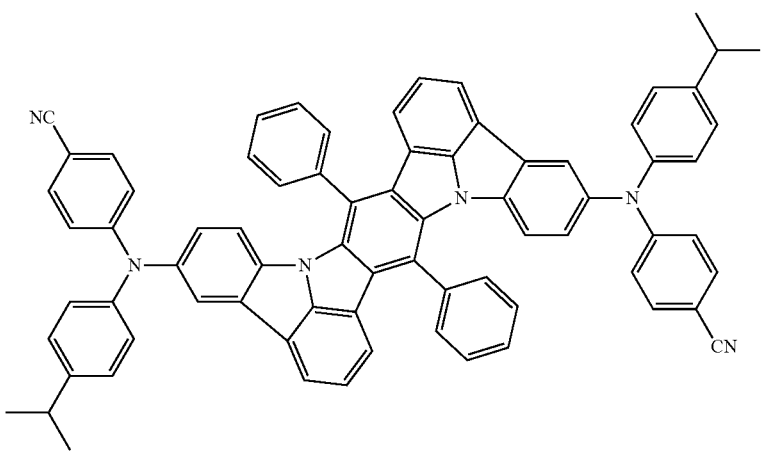
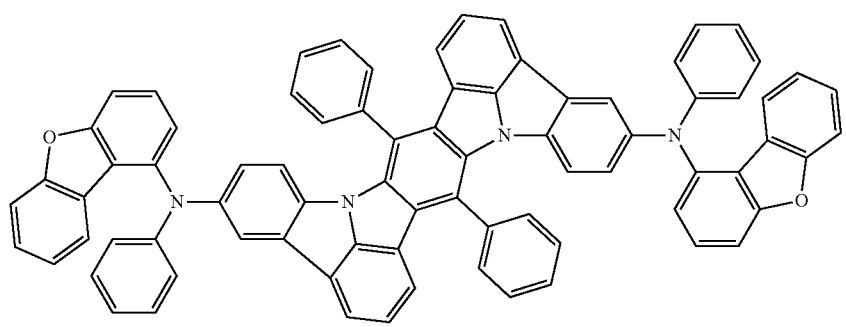
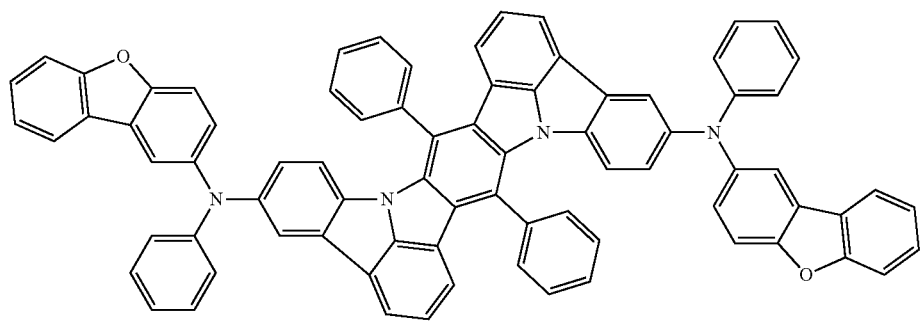
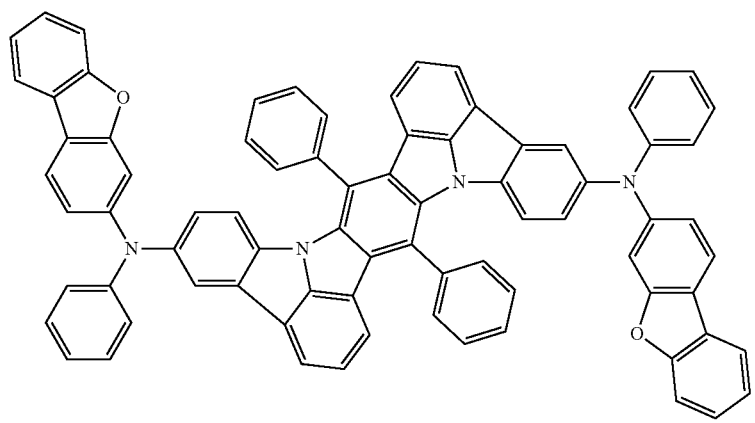

-continued
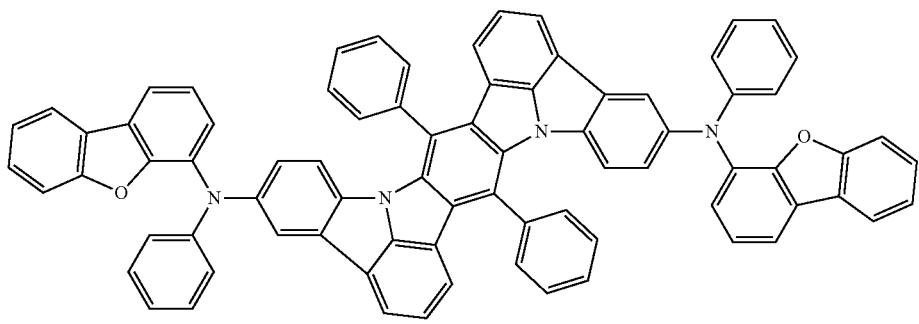

-continued
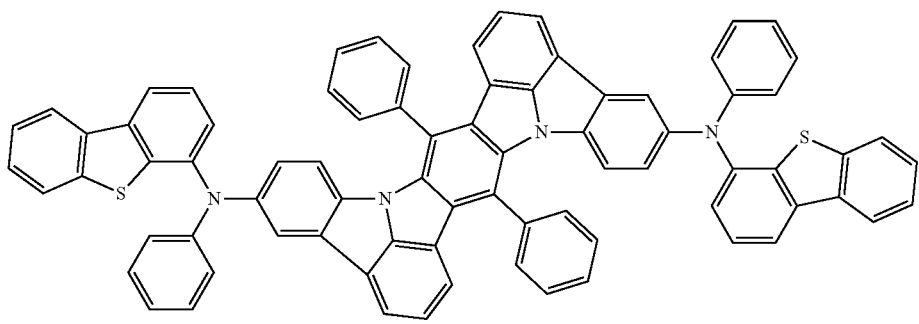
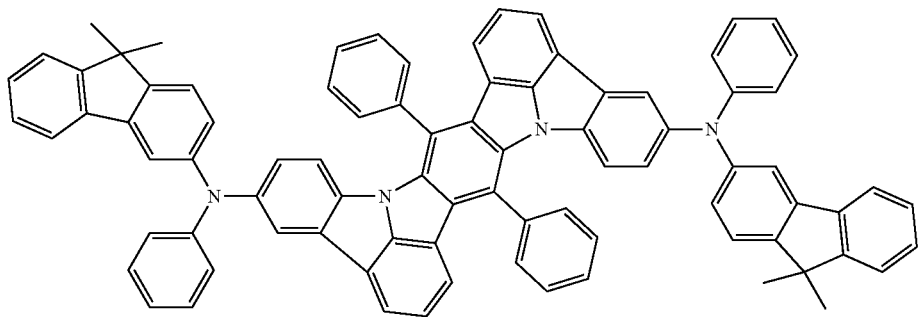
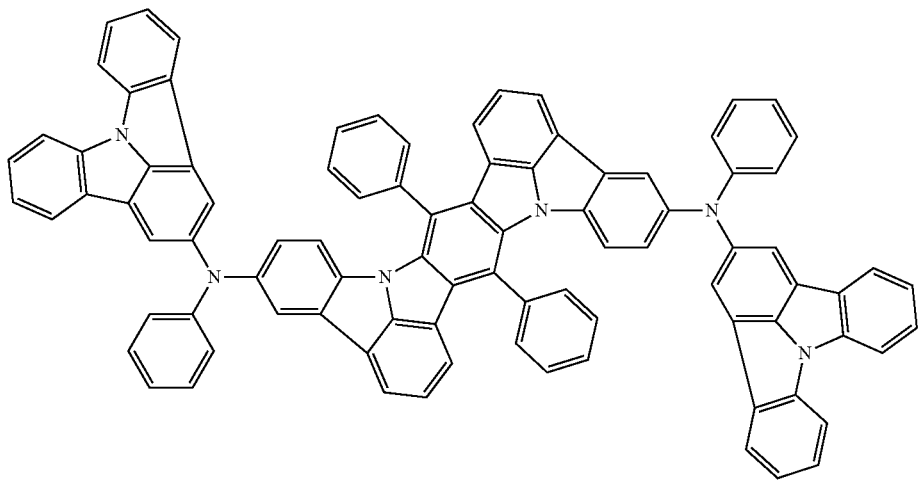
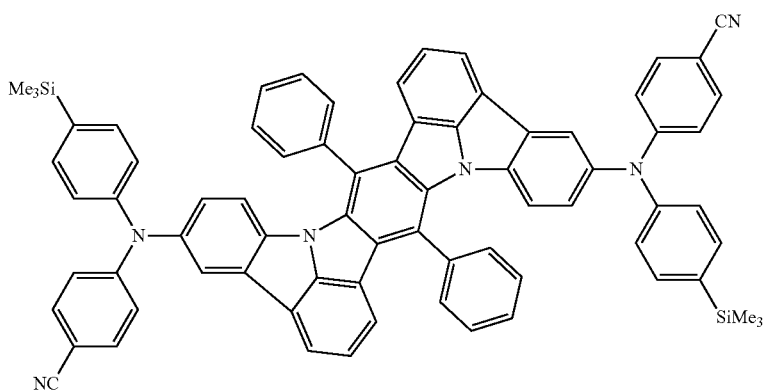

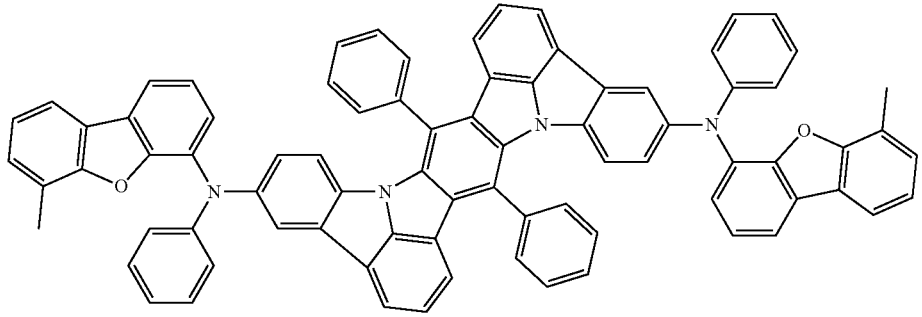
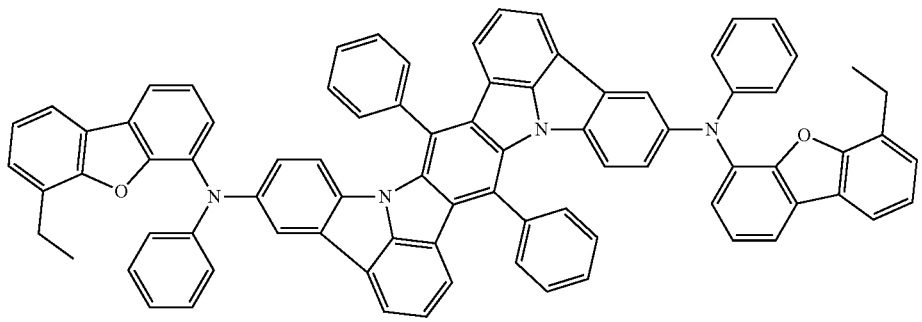
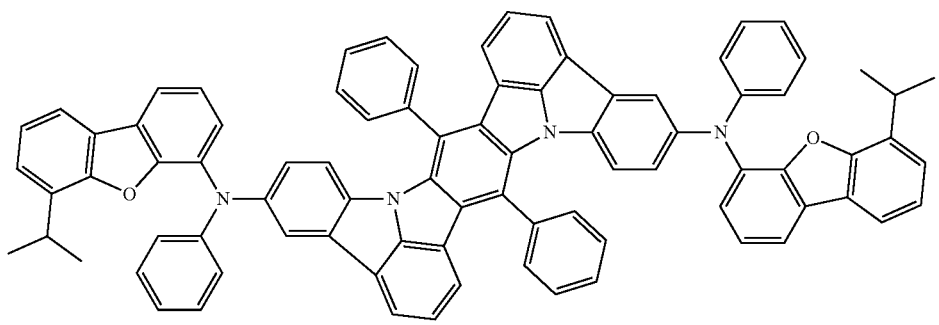
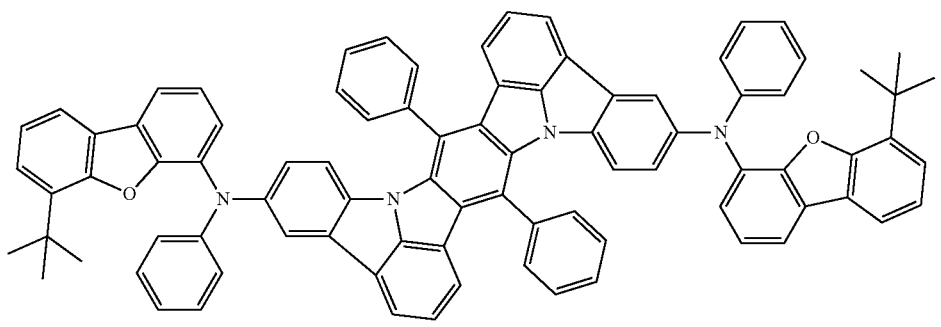
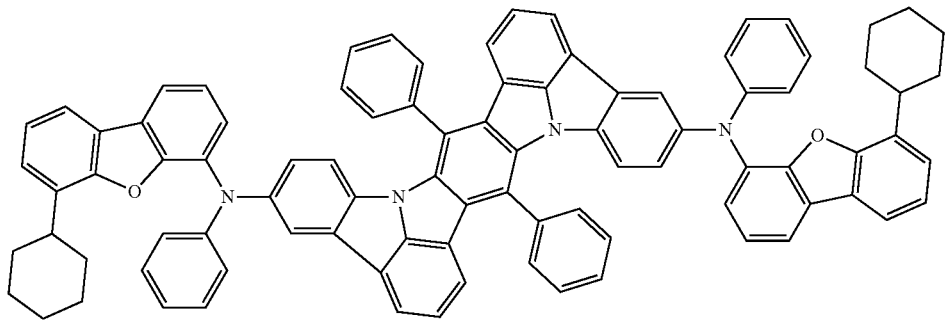

-continued
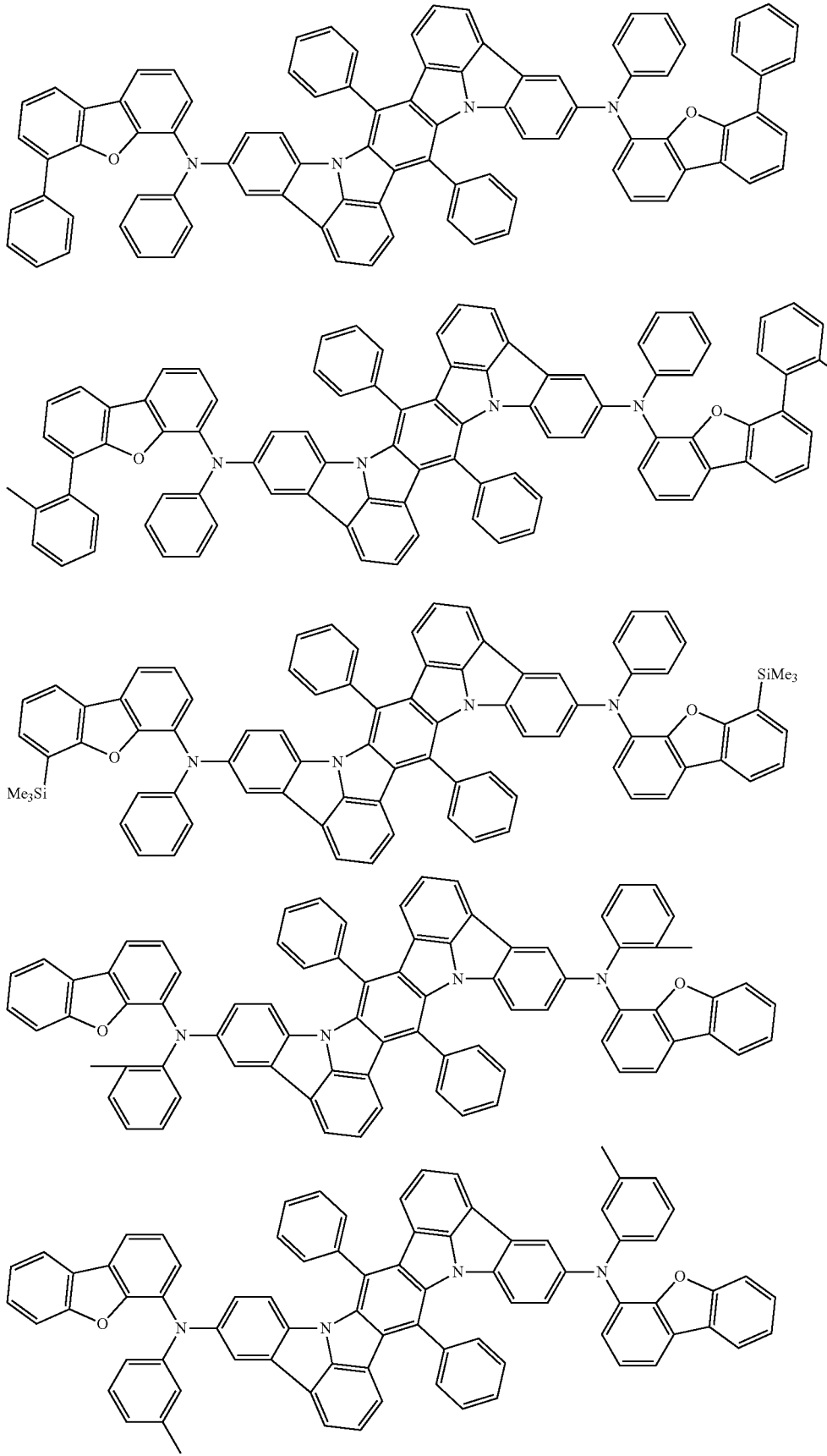

-continued
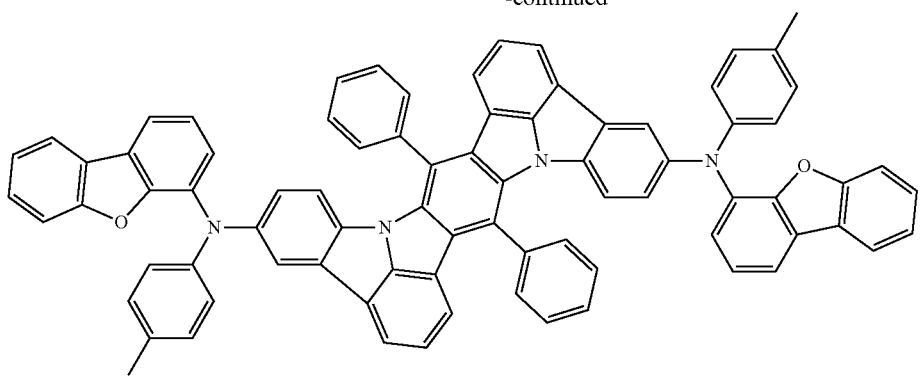
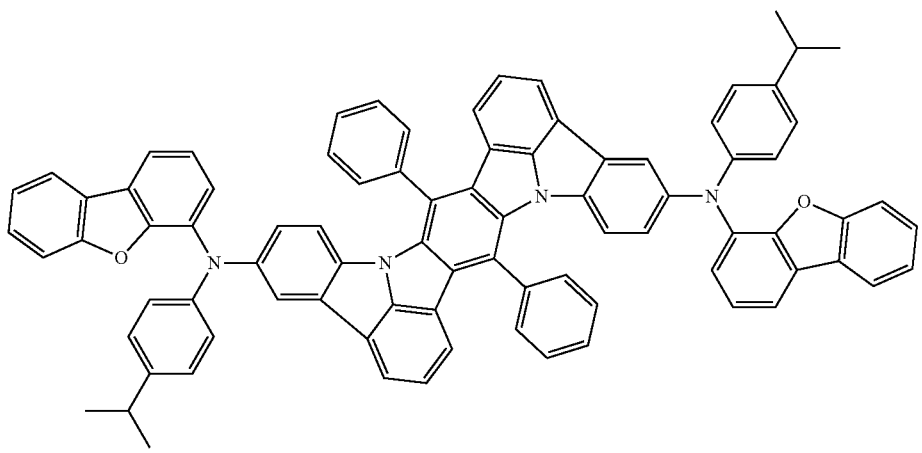
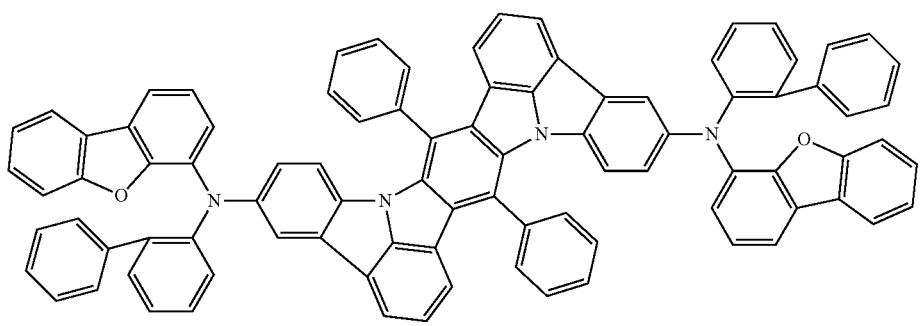
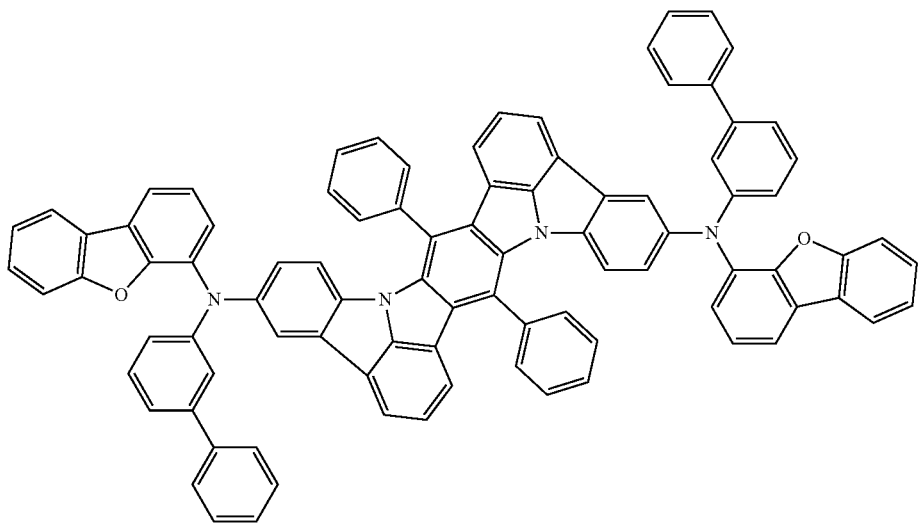

-continued
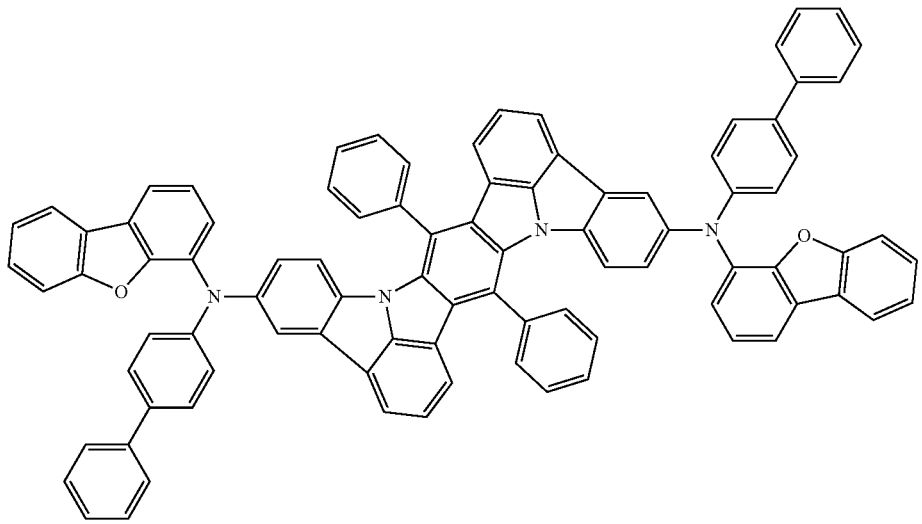
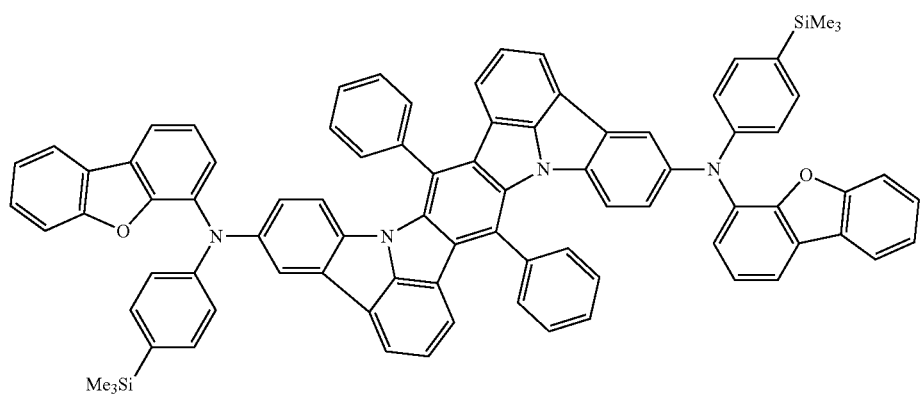
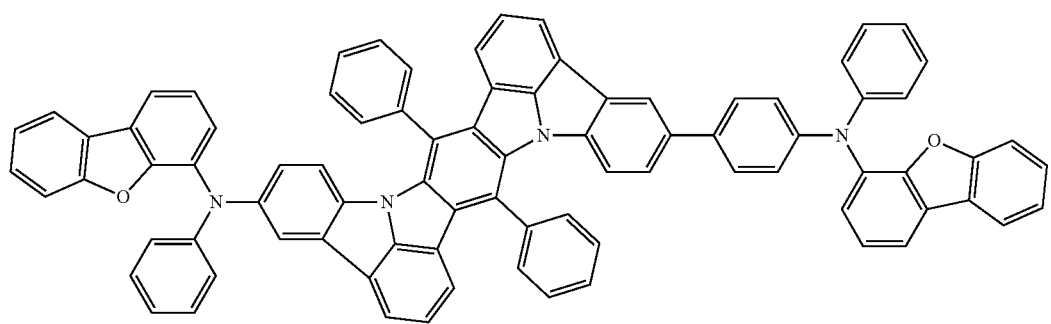
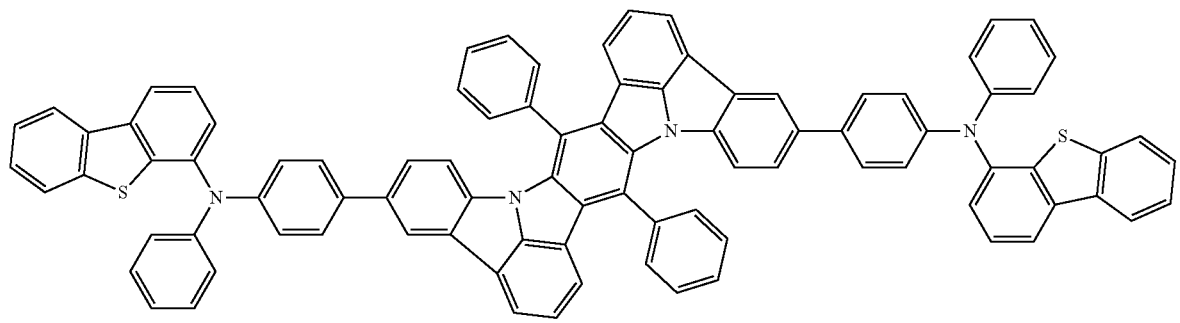

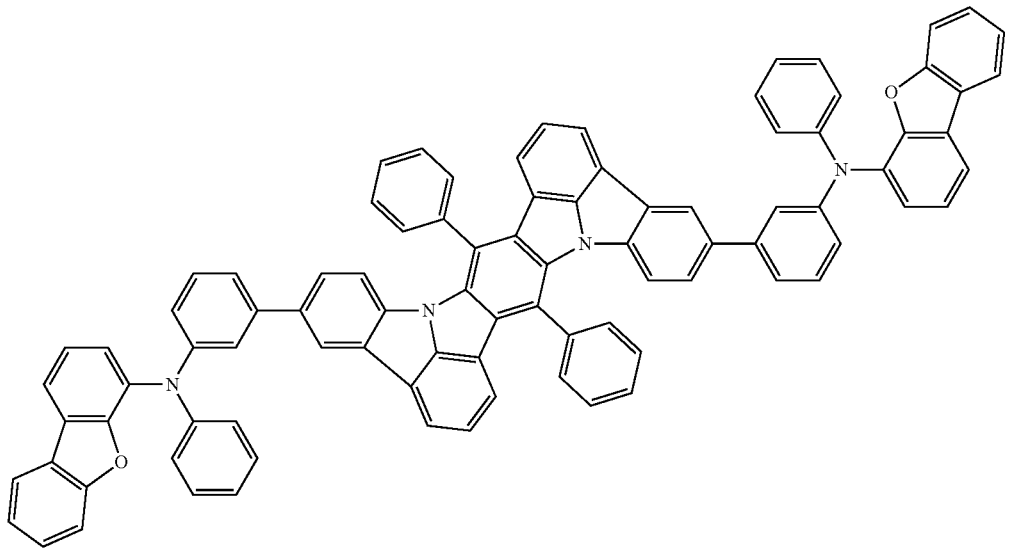
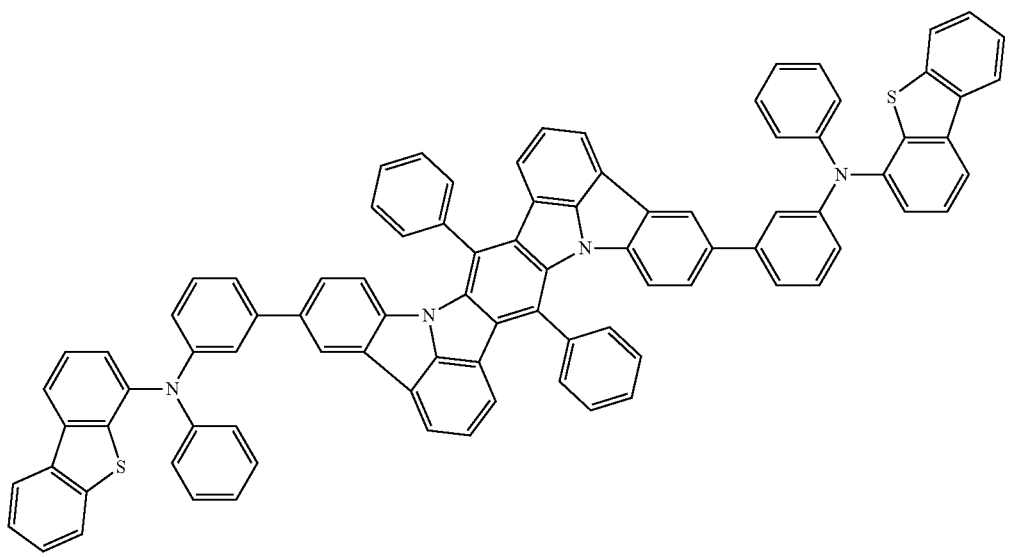
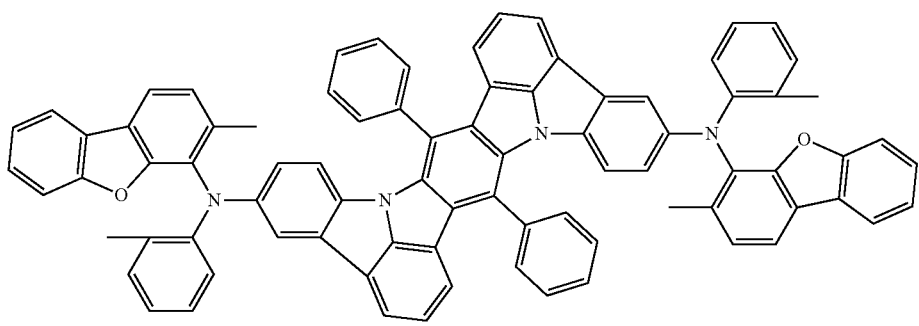

-continued
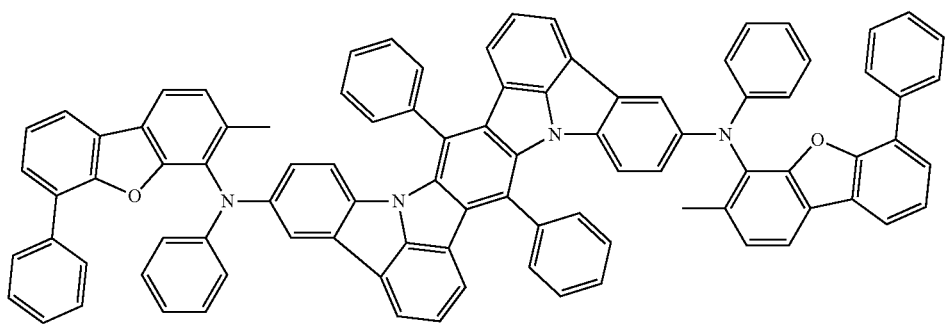
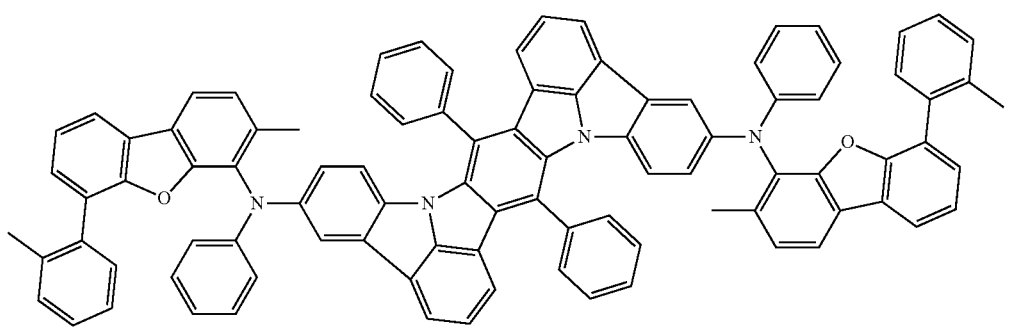
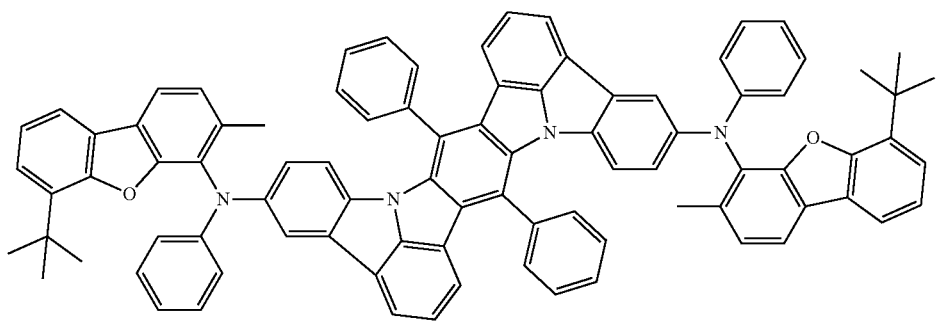
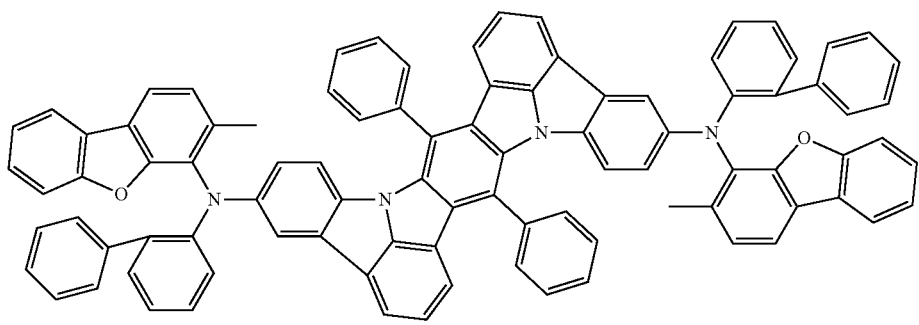

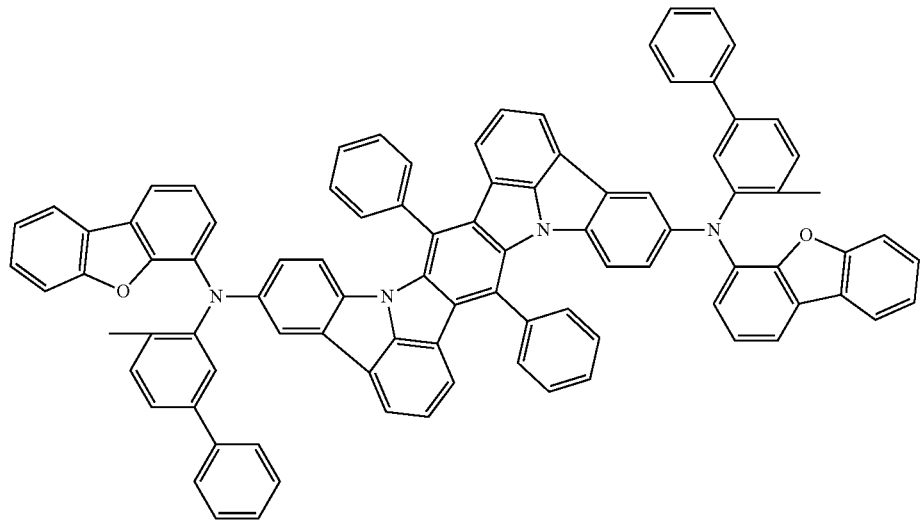
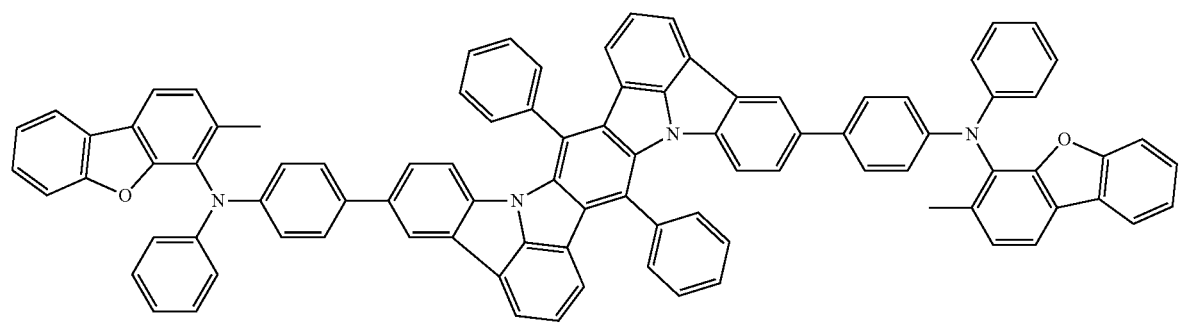
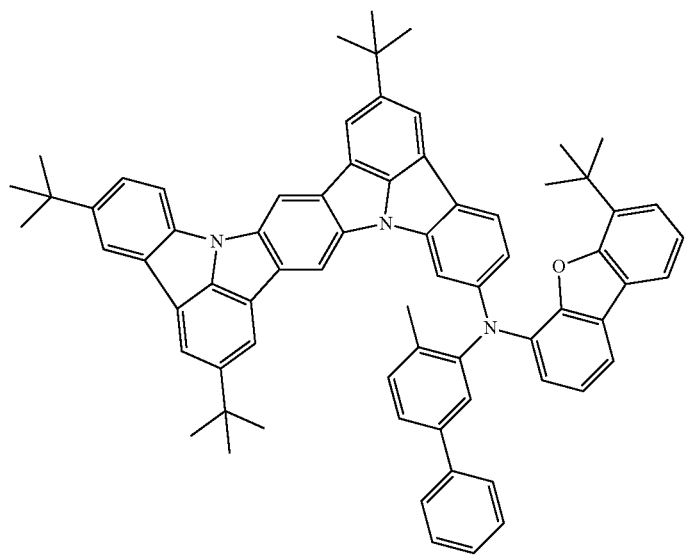

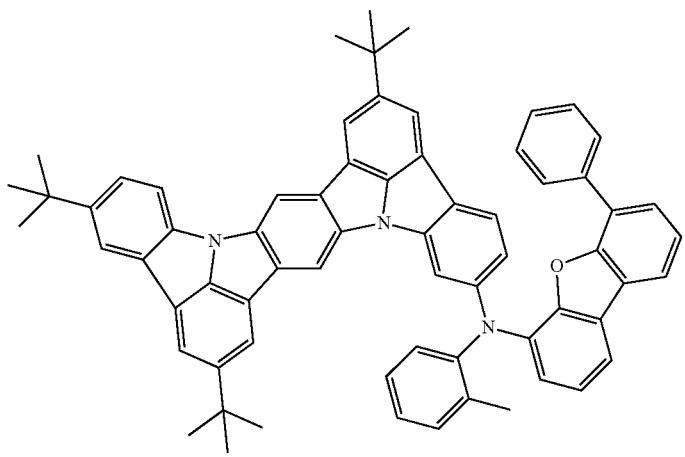
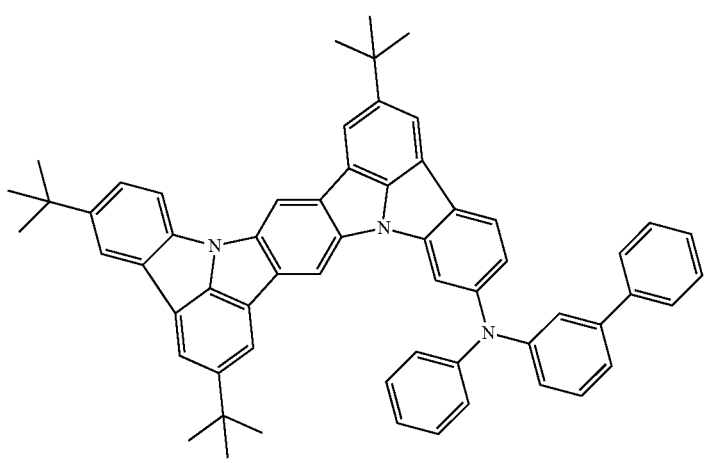
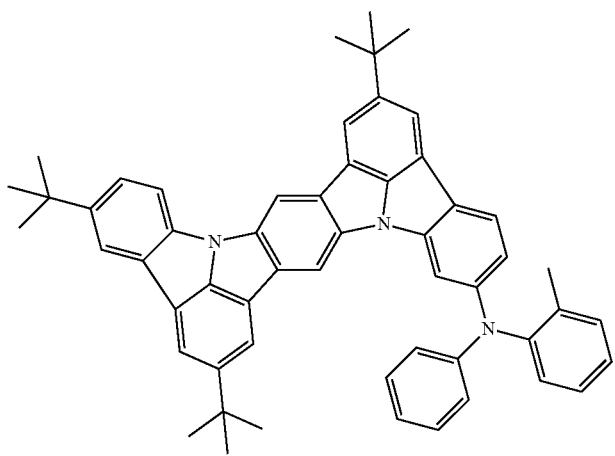

-continued
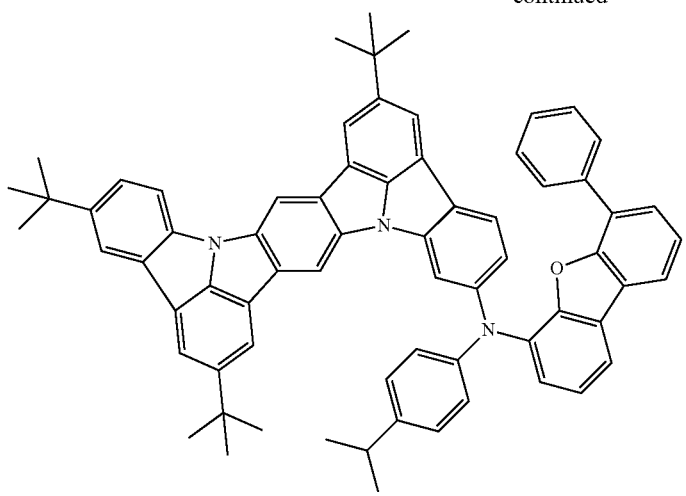
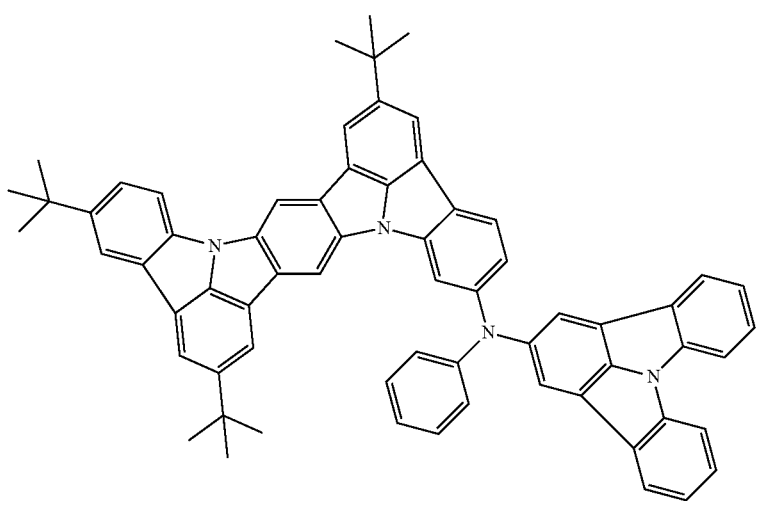
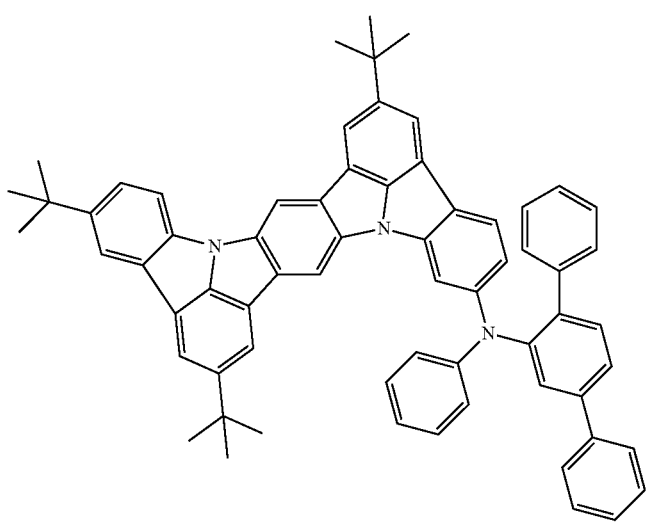

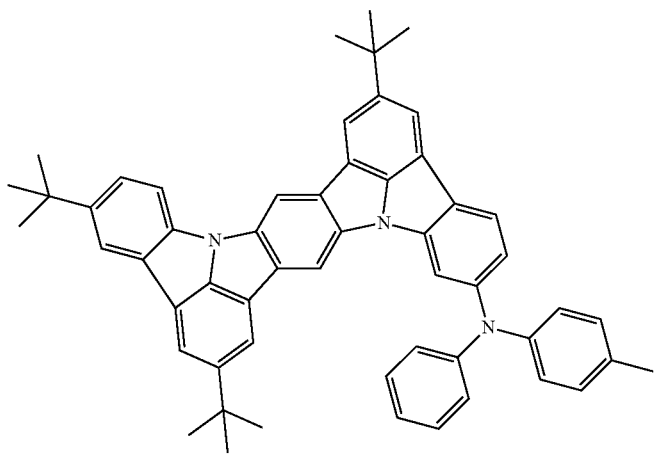
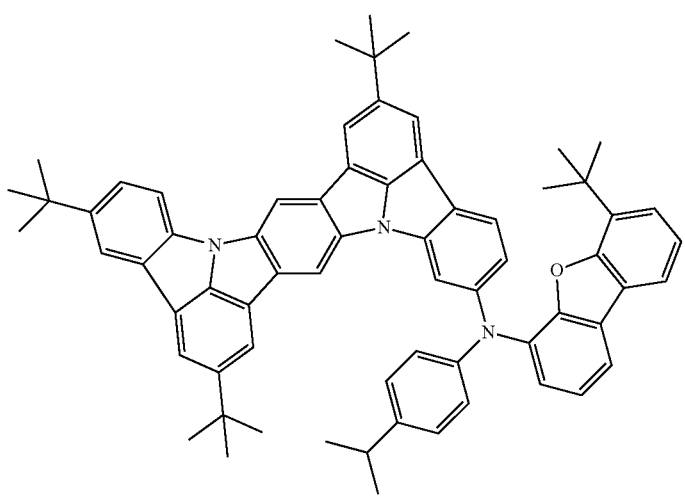
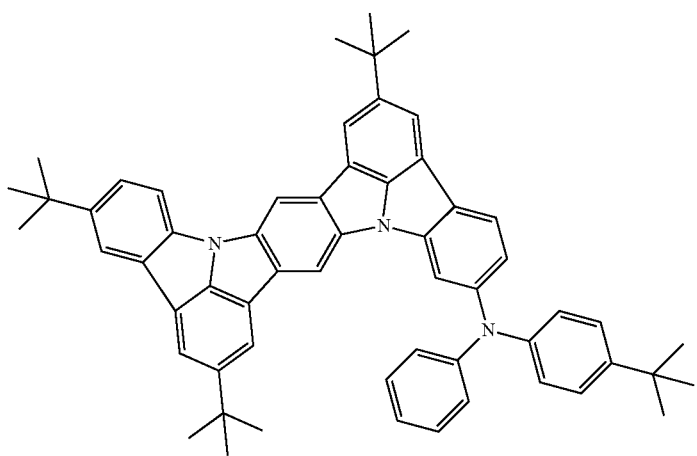

-continued
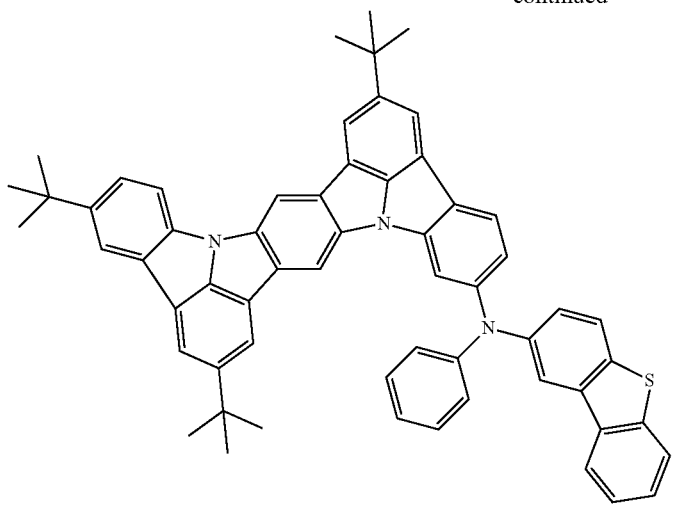
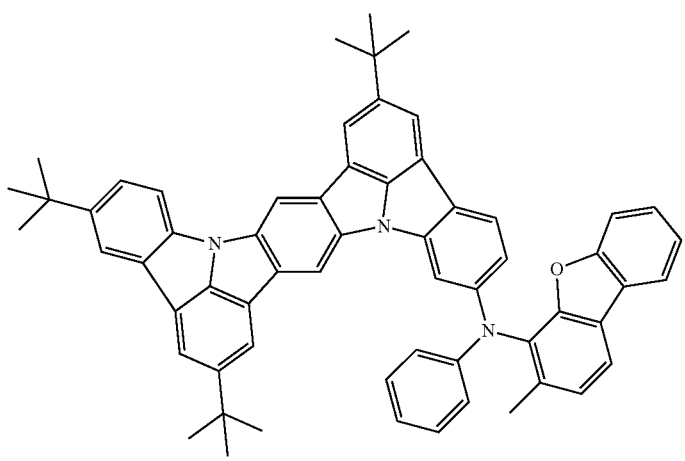
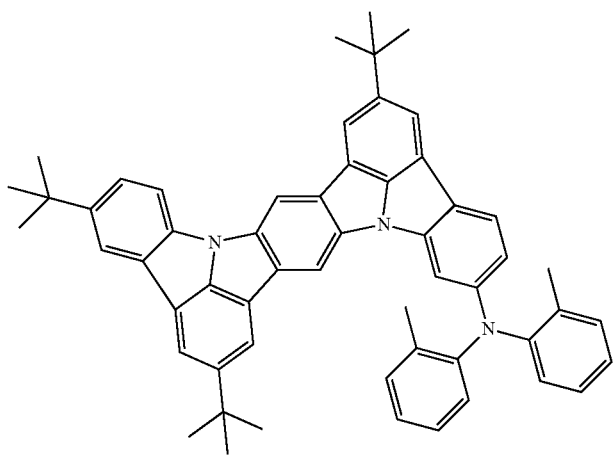

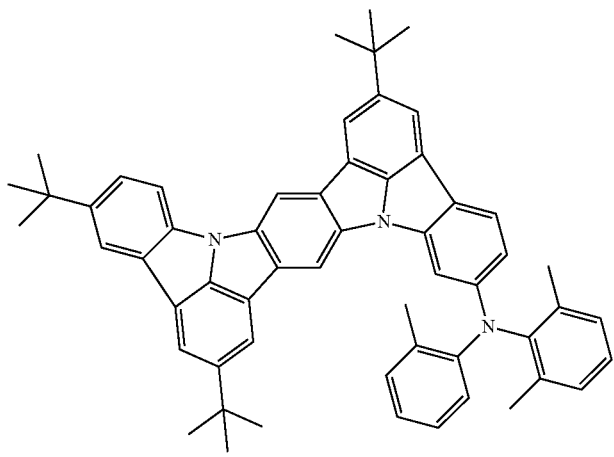
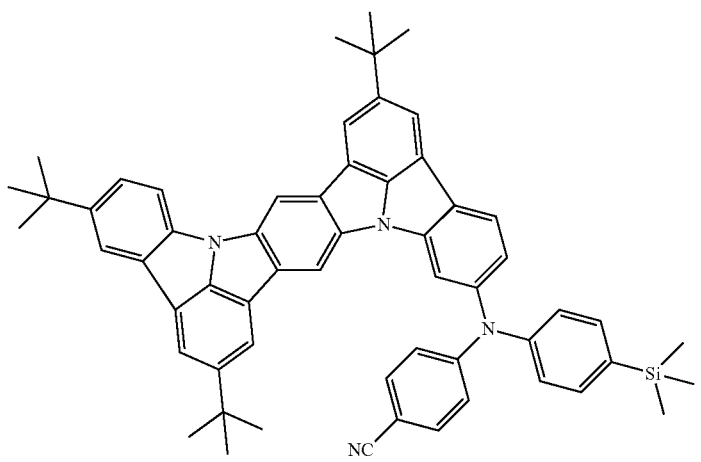
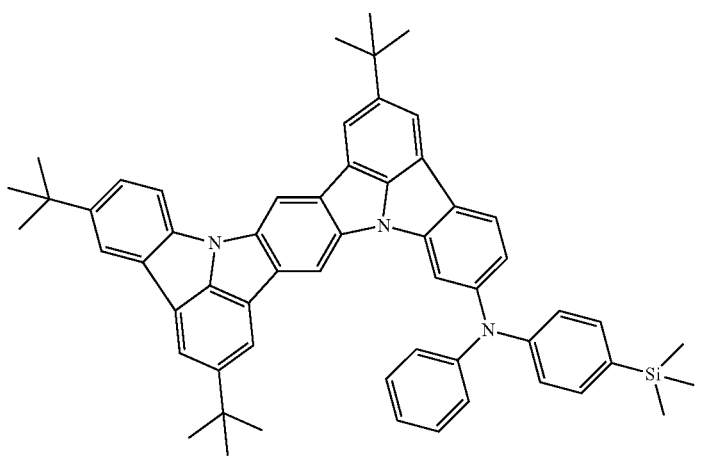

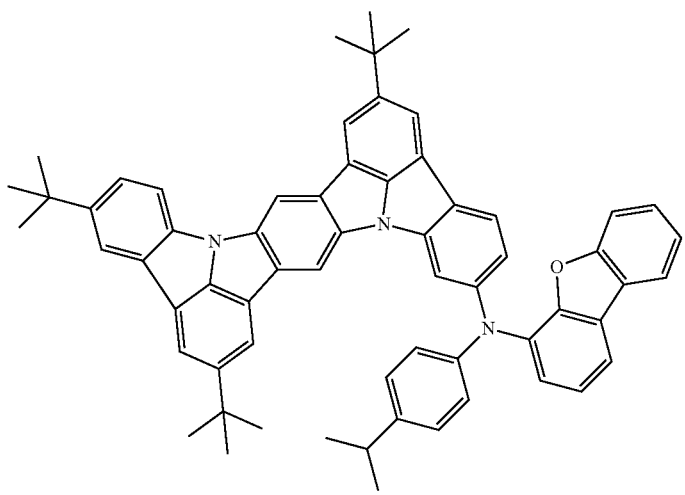
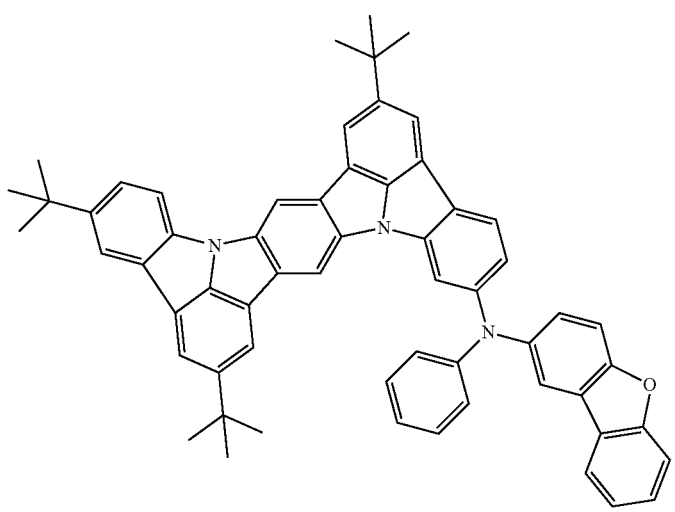
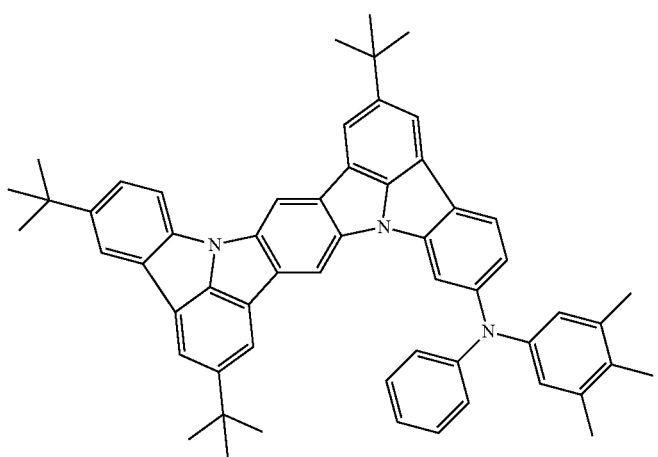

-continued
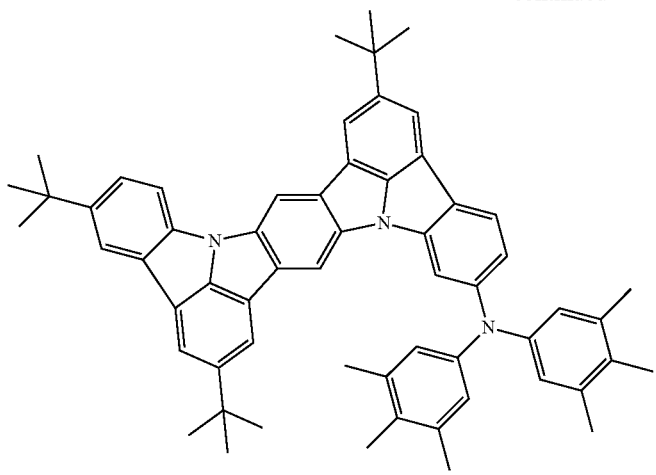
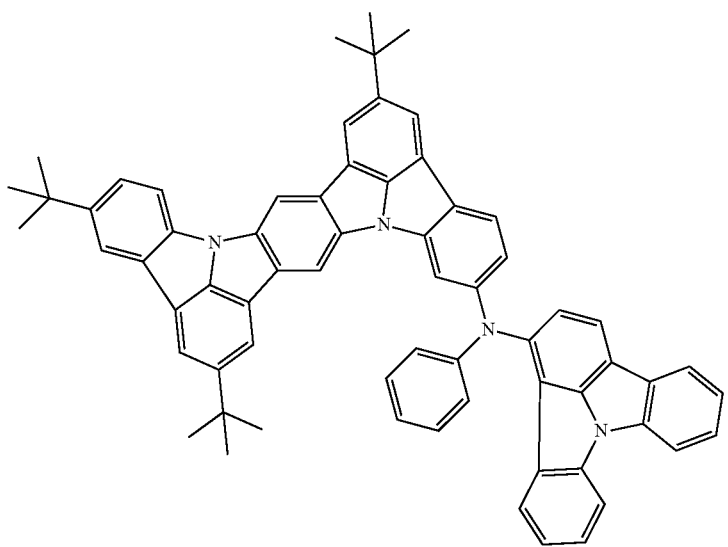
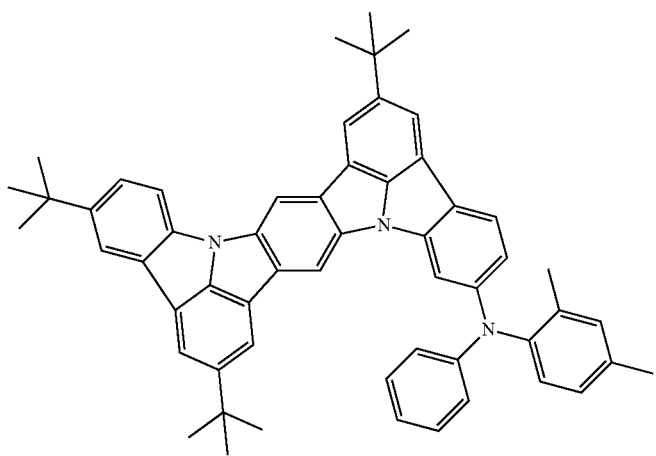

-continued
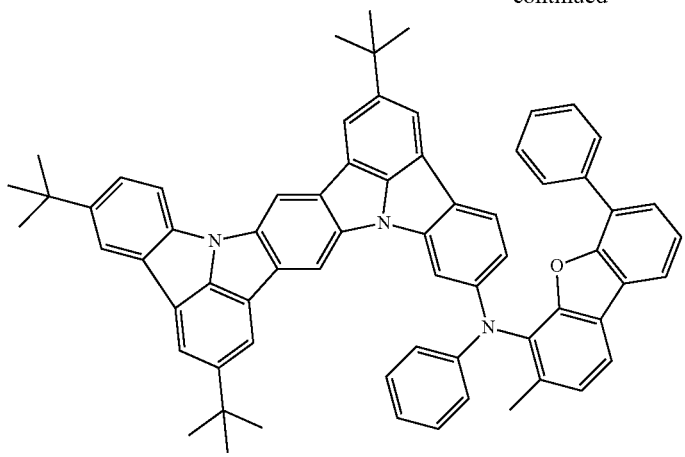
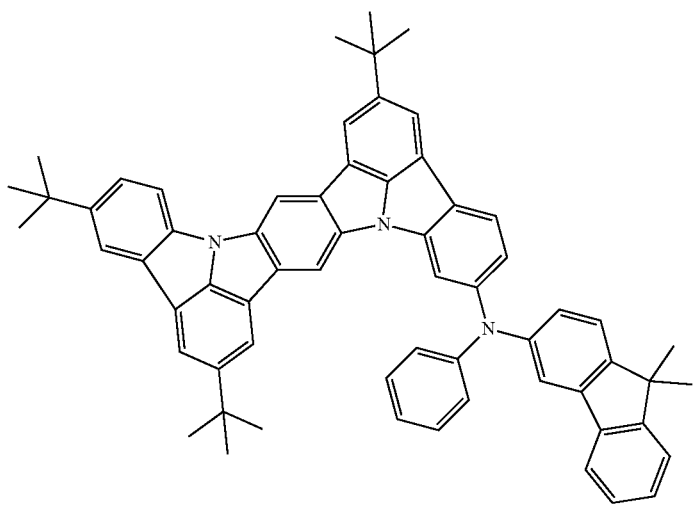
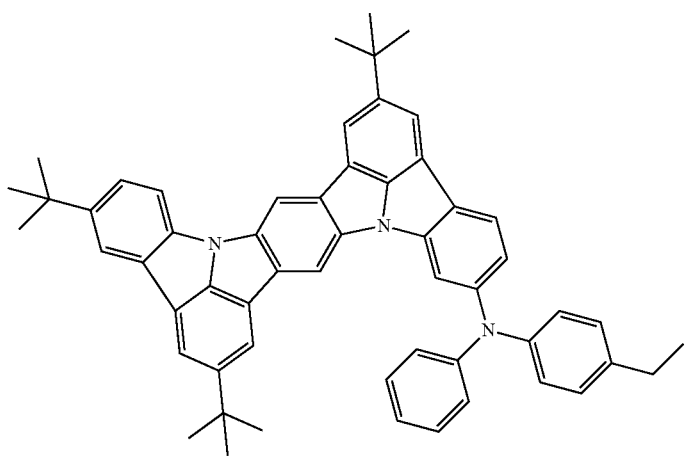

-continued
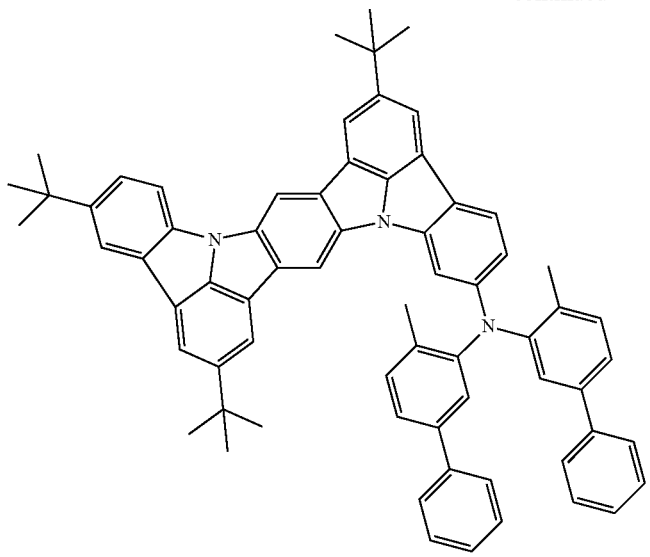
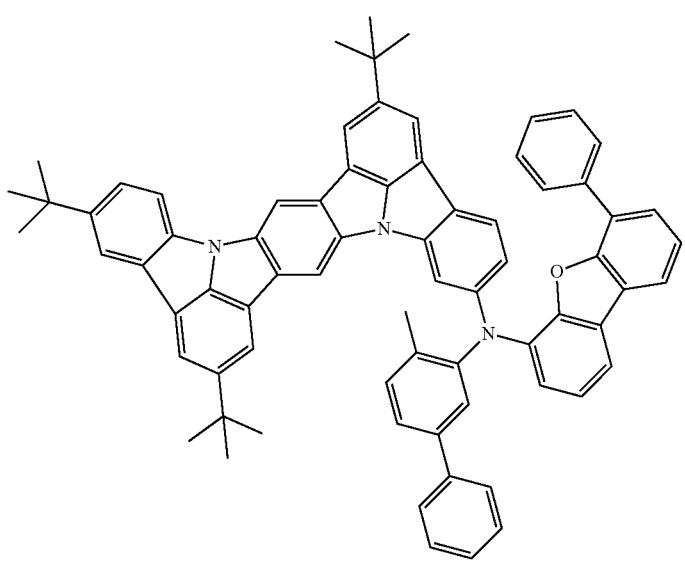
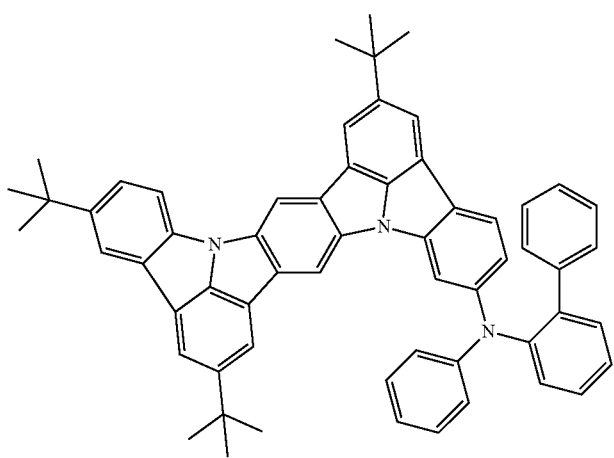

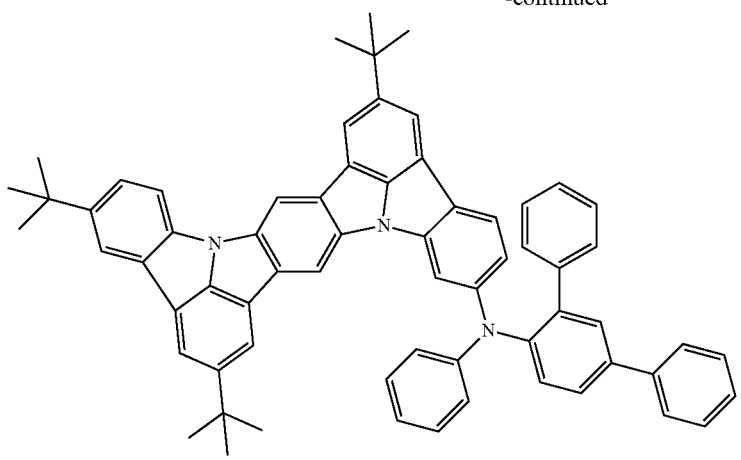
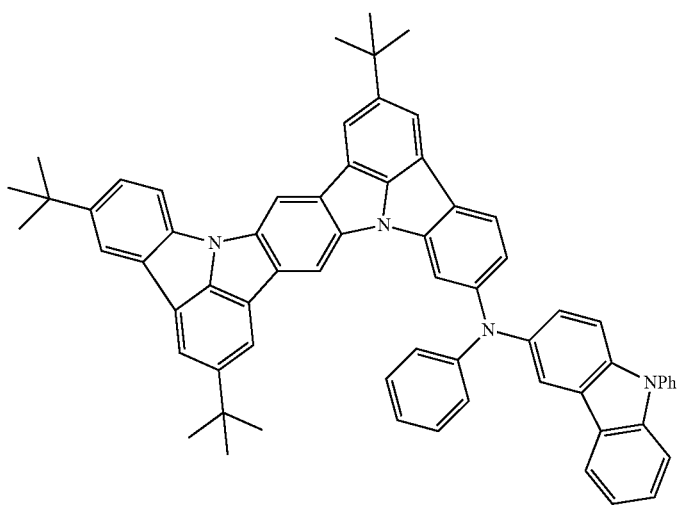
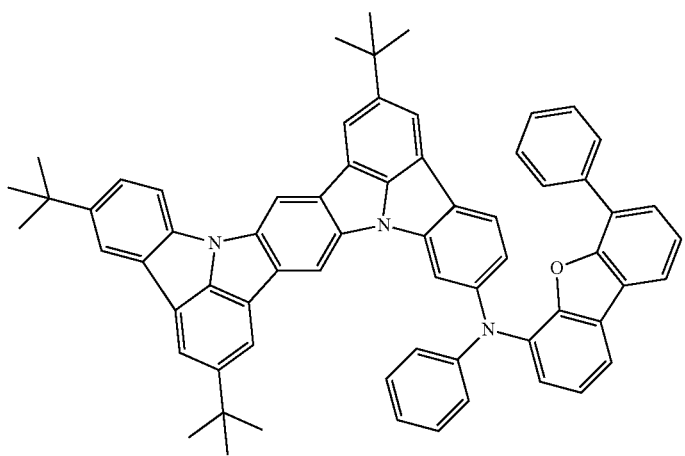

-continued
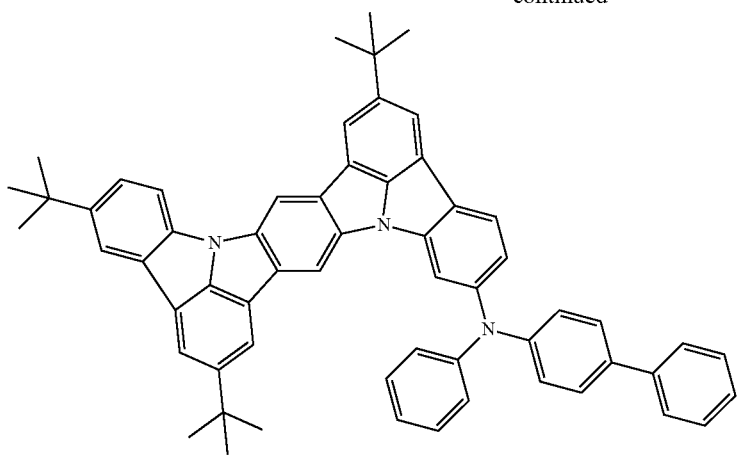
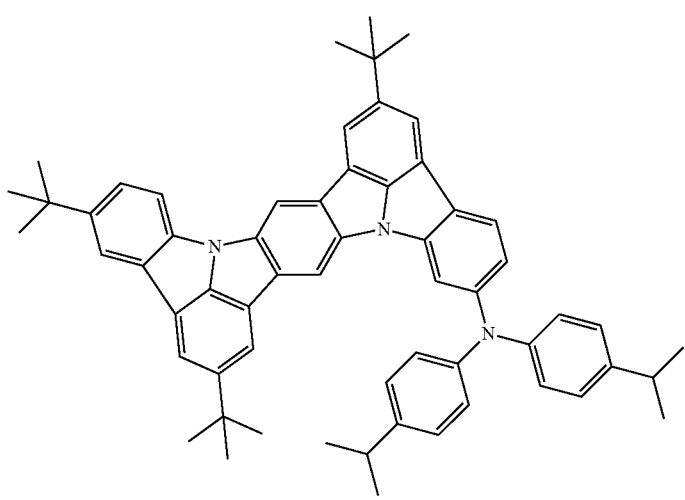
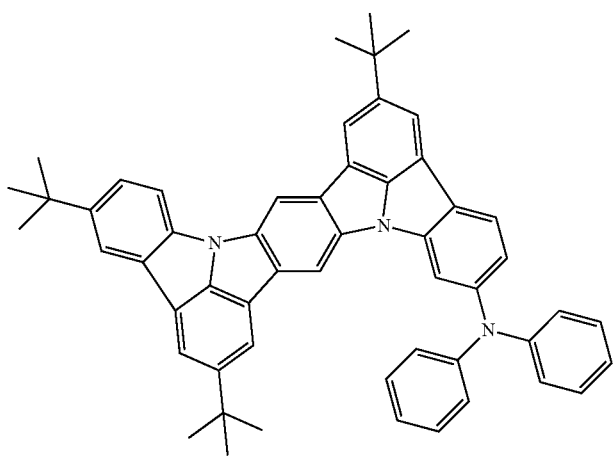

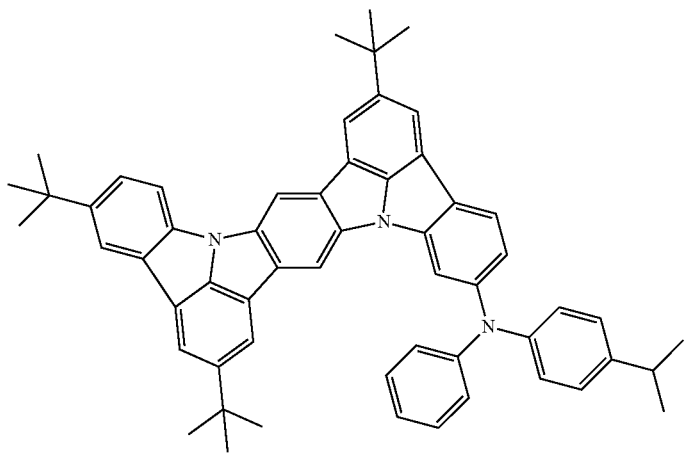
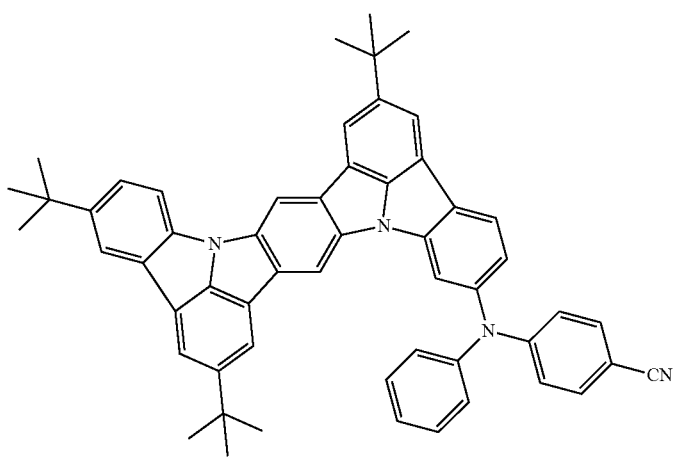
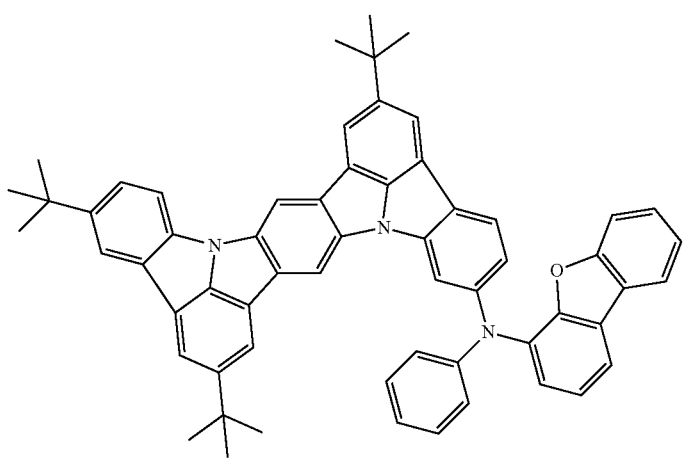

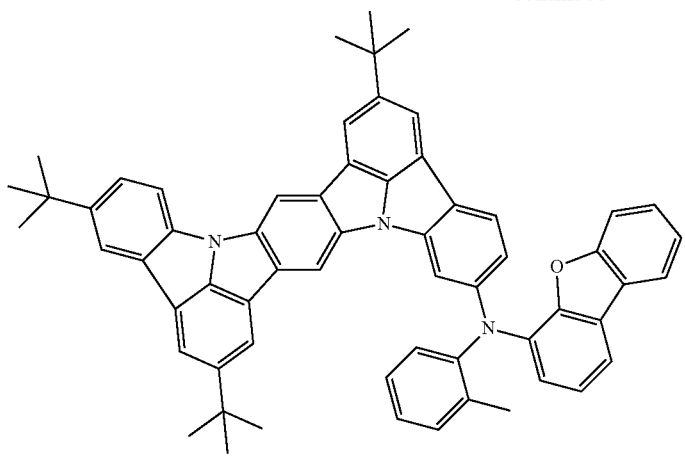
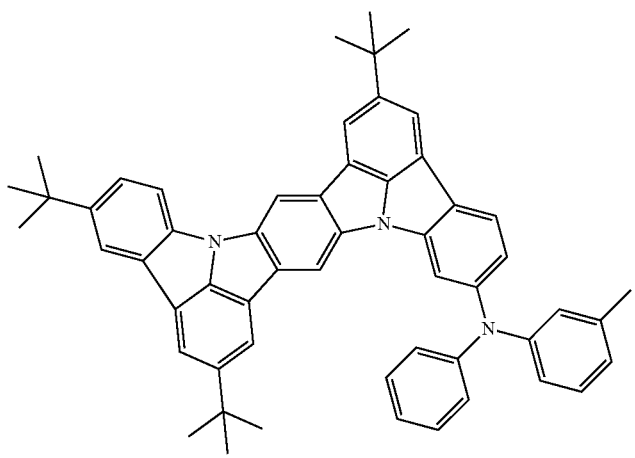
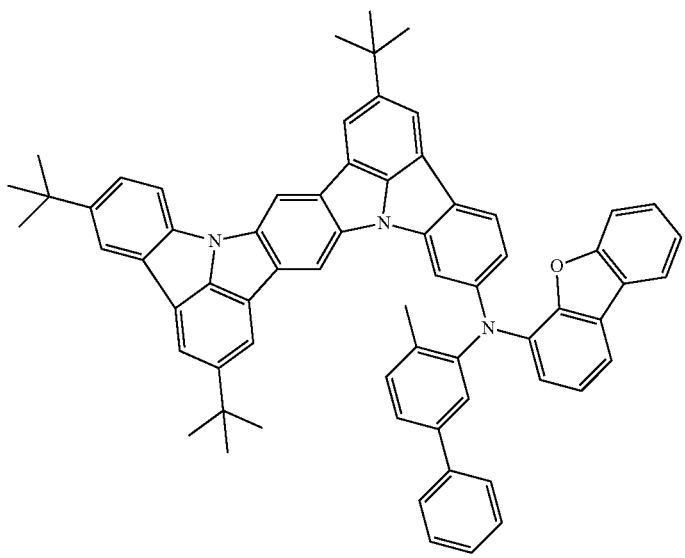

-continued
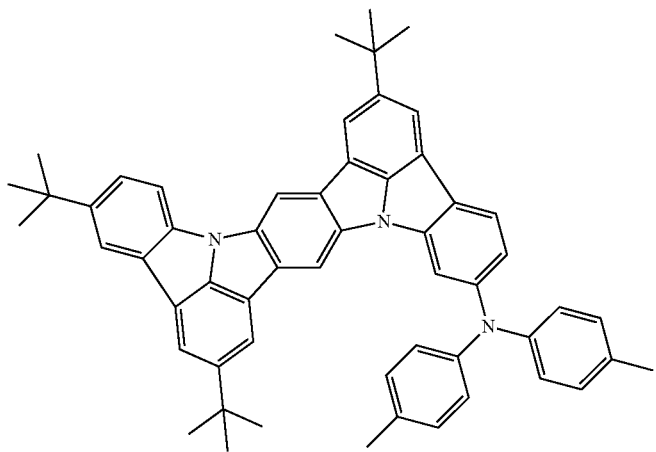
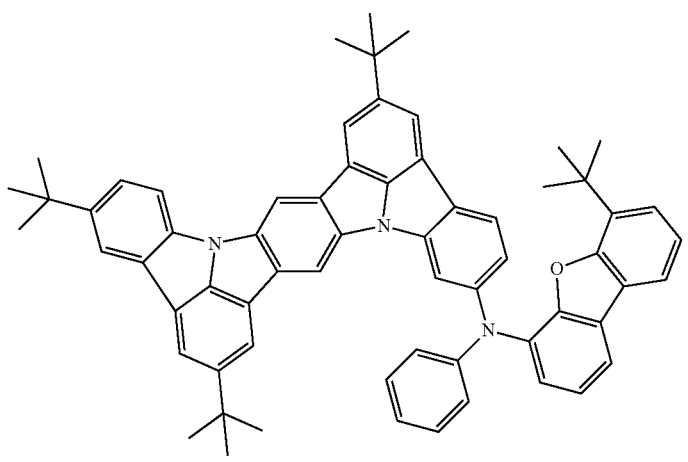
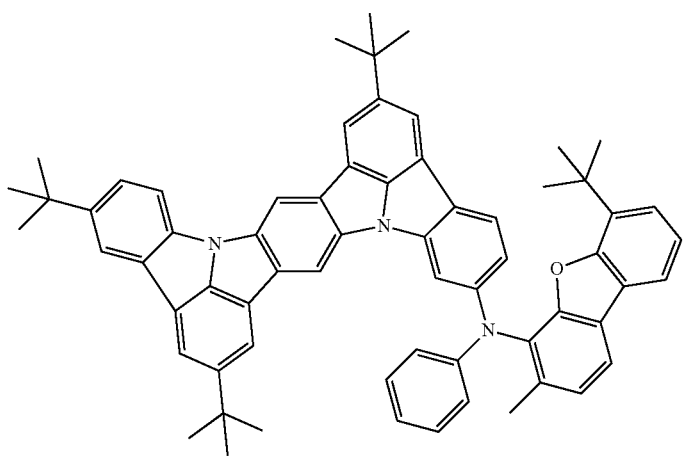

-continued
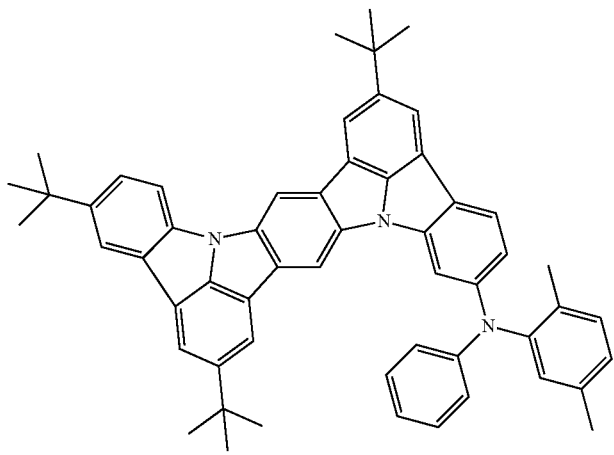
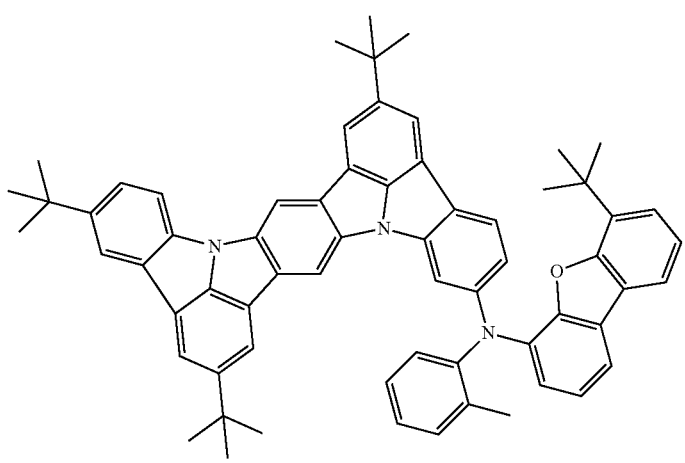
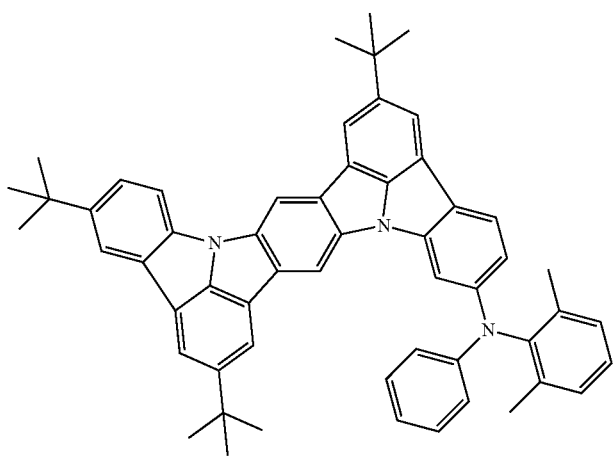

-continued
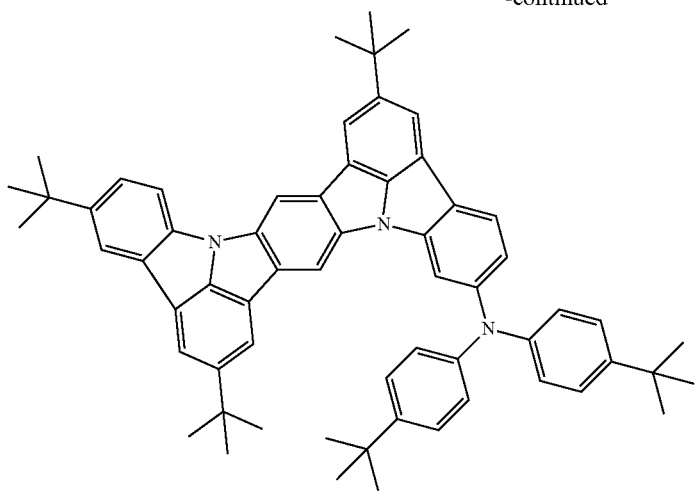
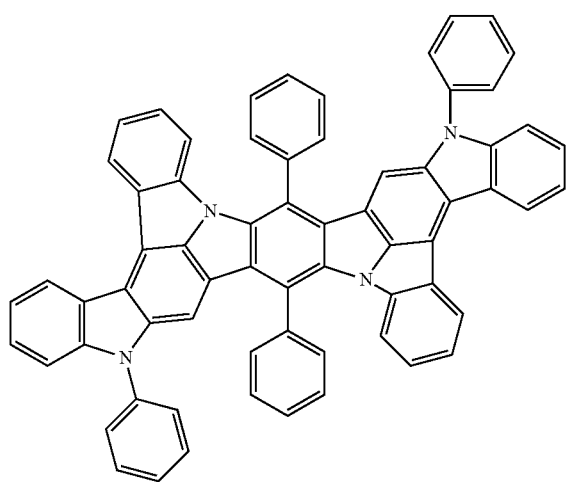
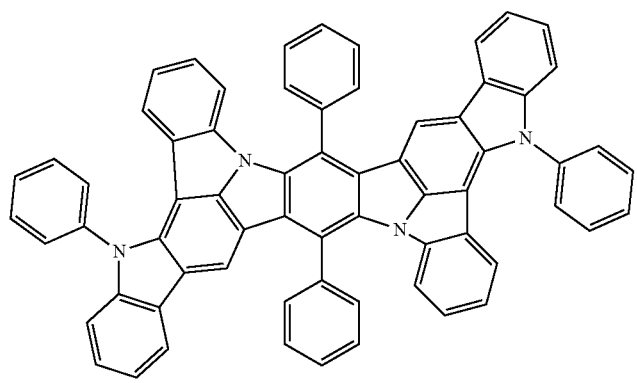

-continued
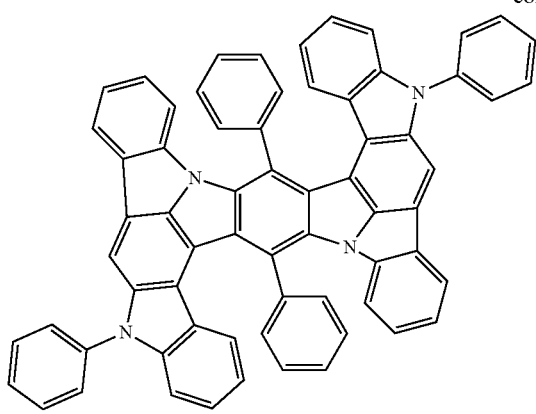
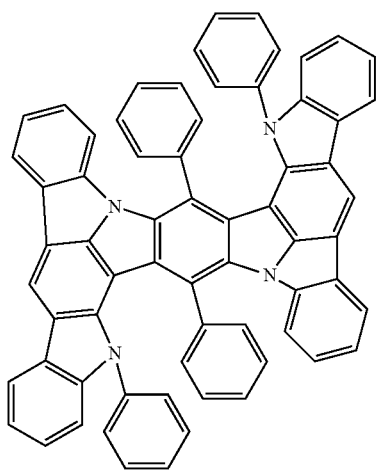
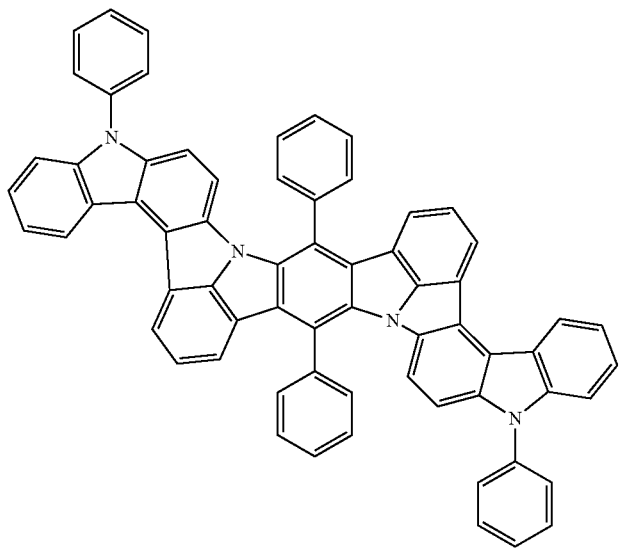

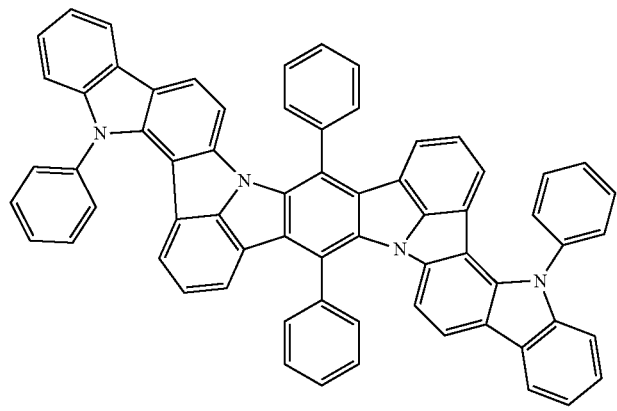
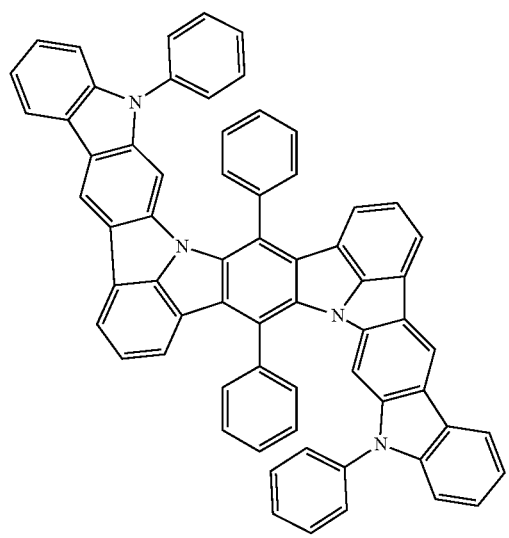
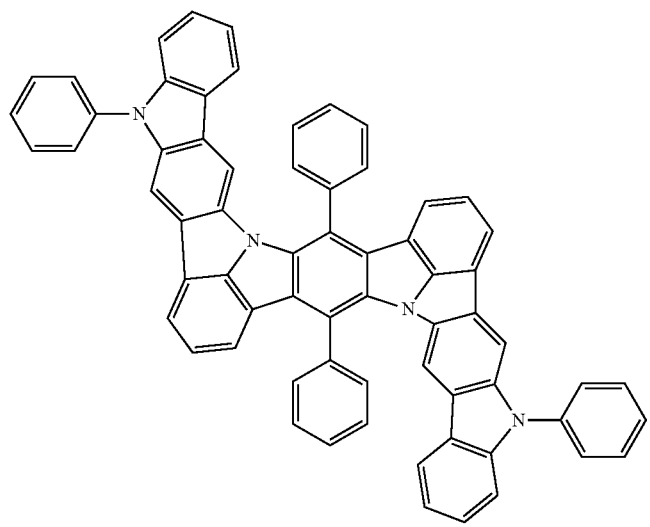

-continued
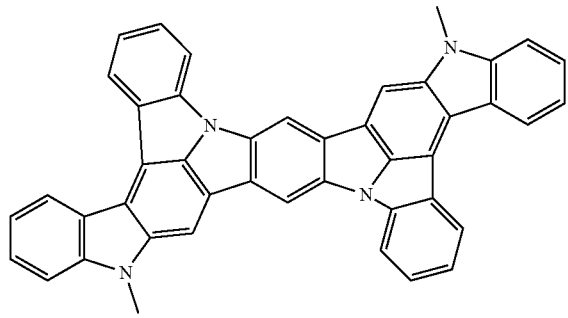
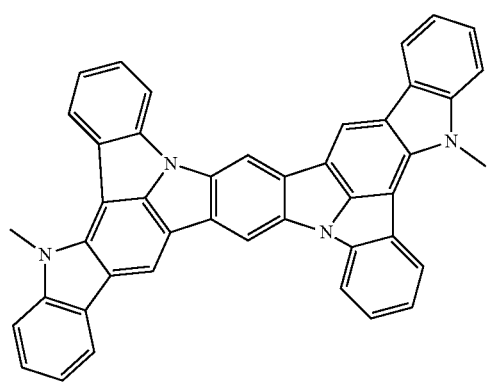
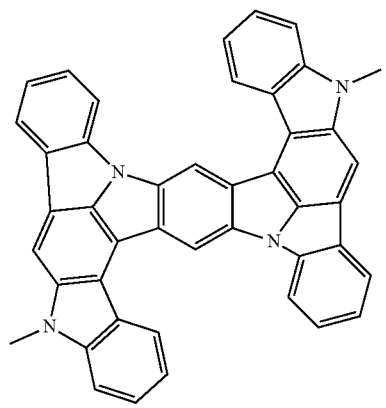
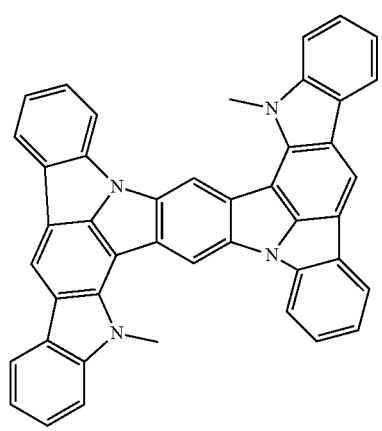

-continued
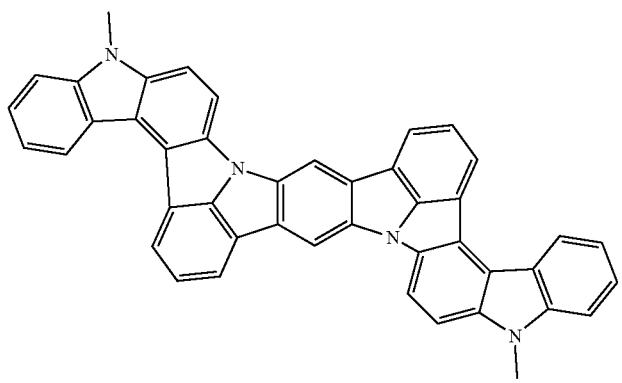
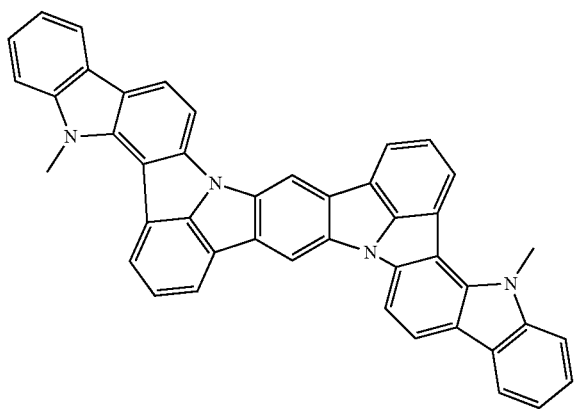
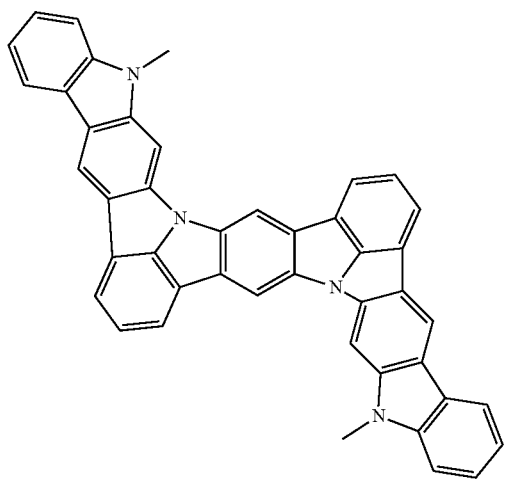

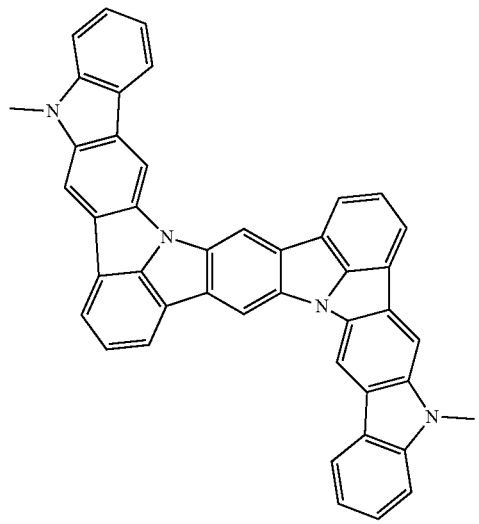
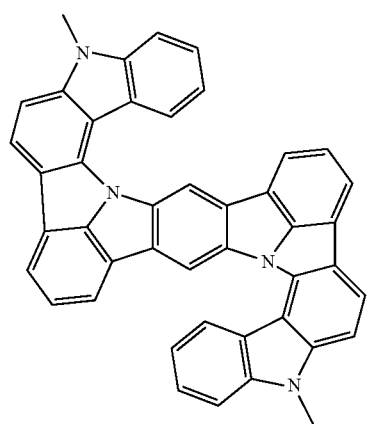
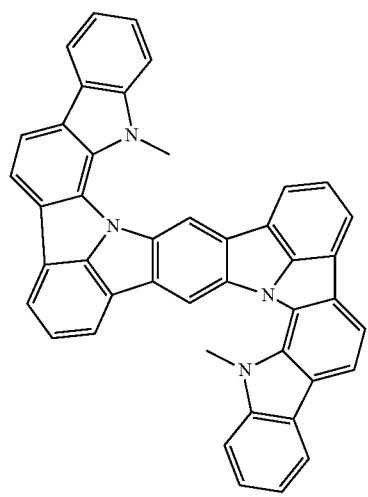

-continued
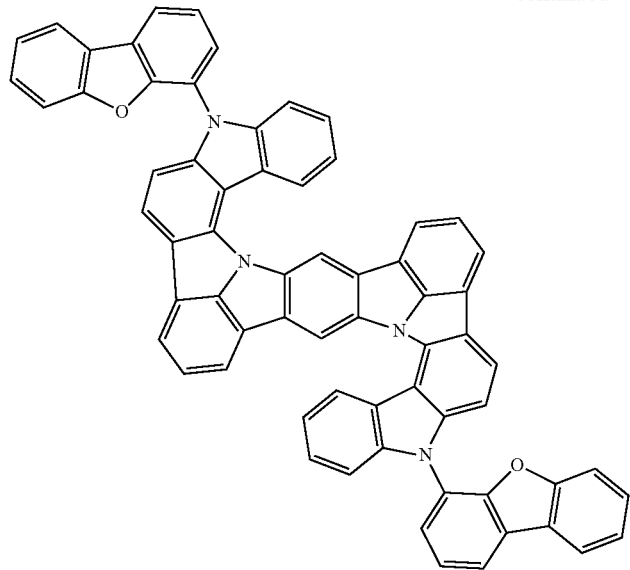
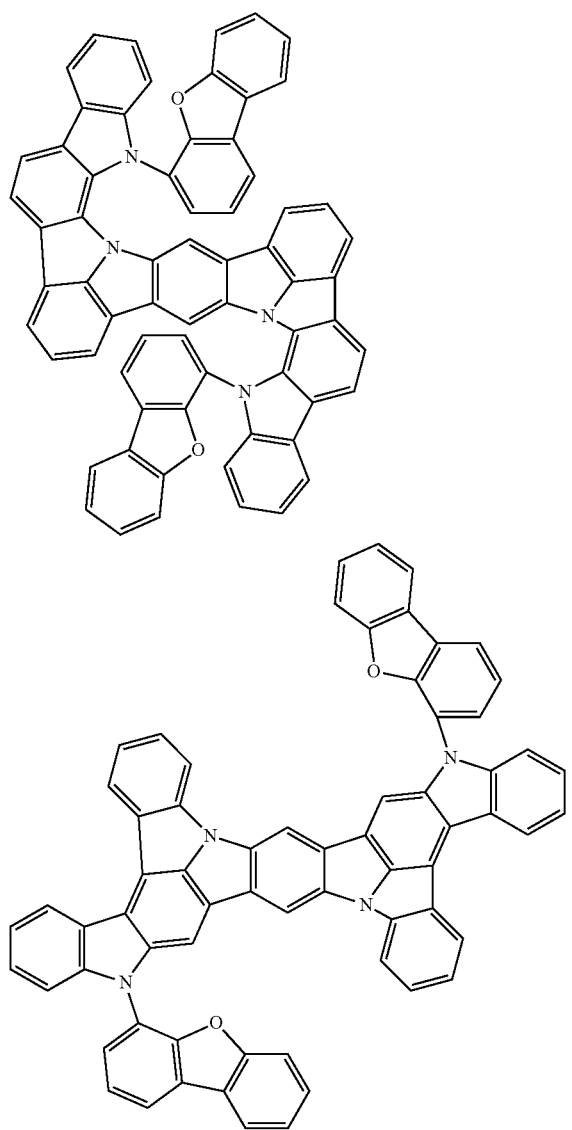

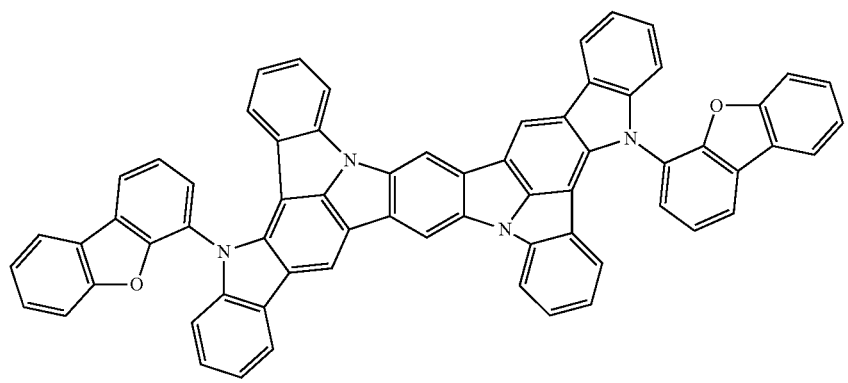
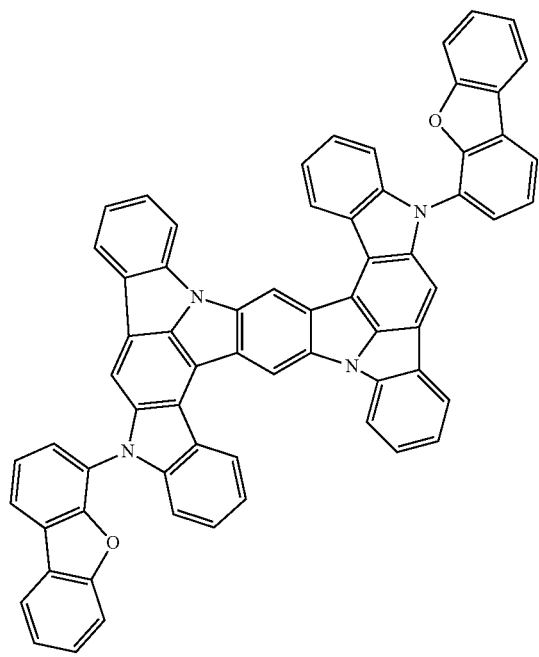
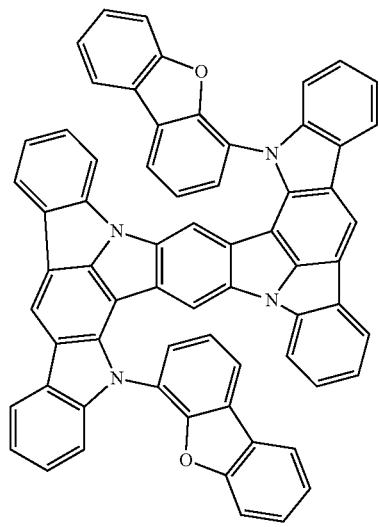

-continued
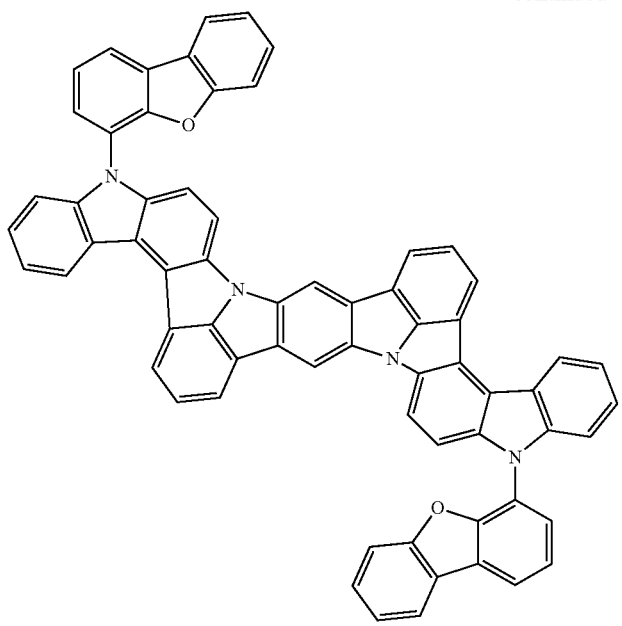
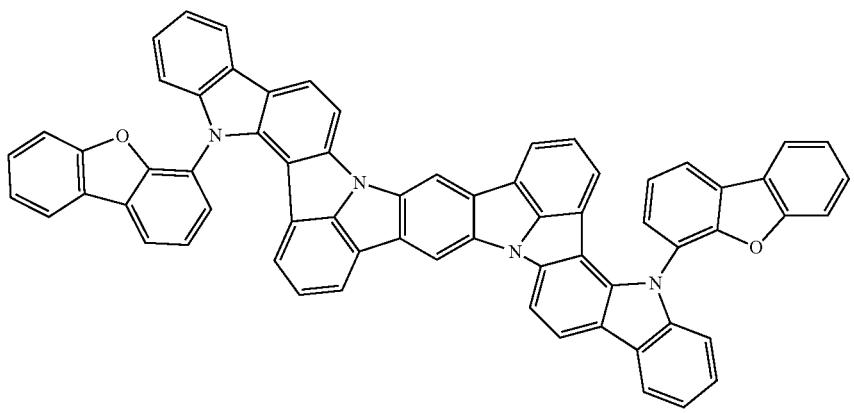
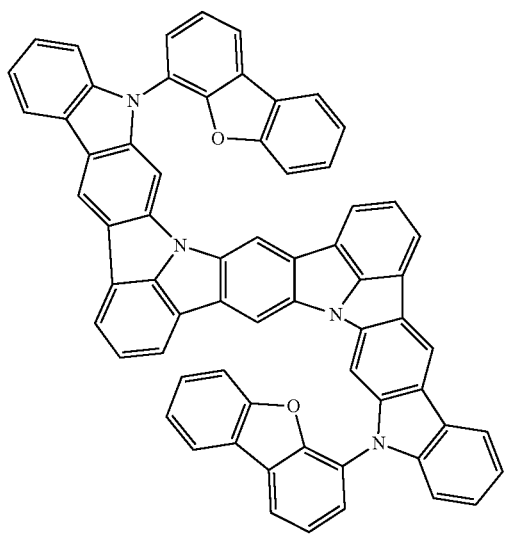

603
-continued
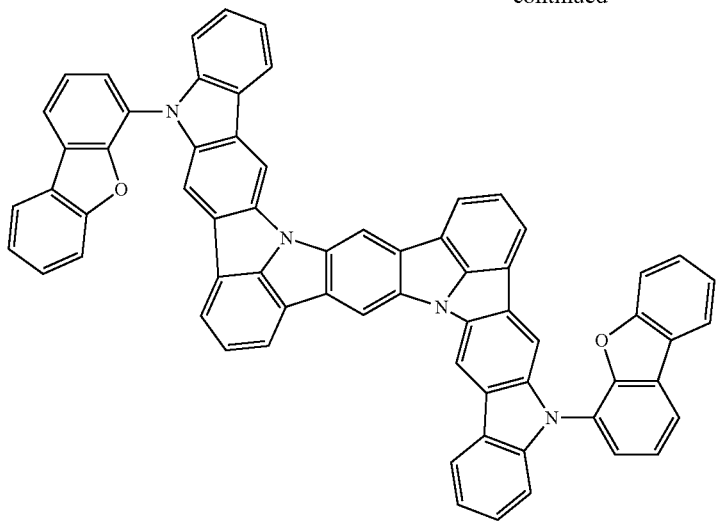
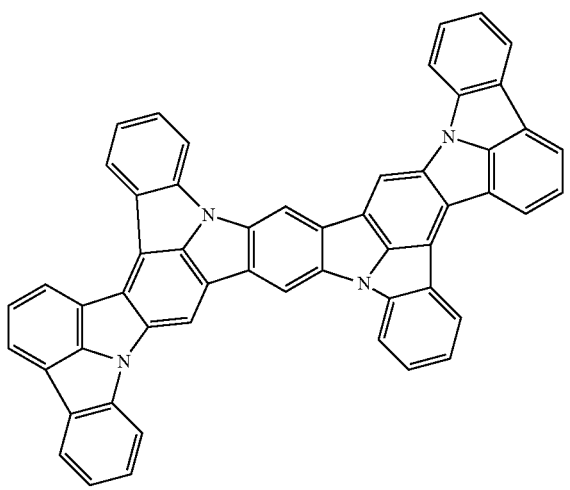
604
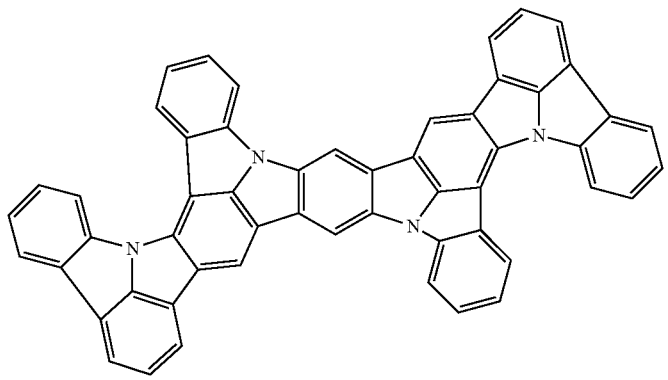

-continued
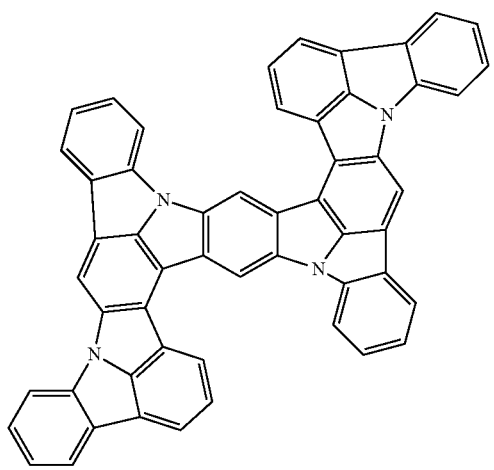
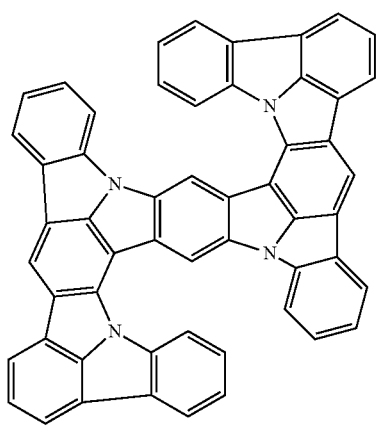
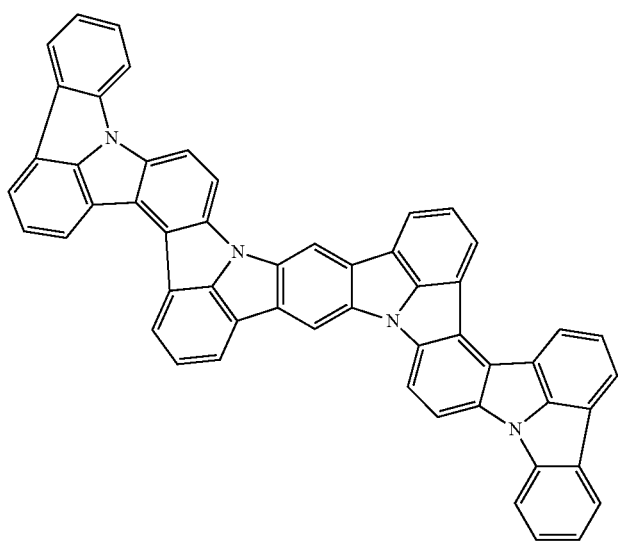

607 608
-continued
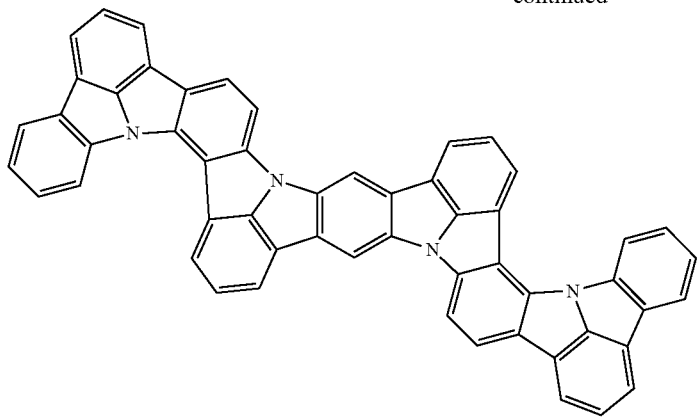
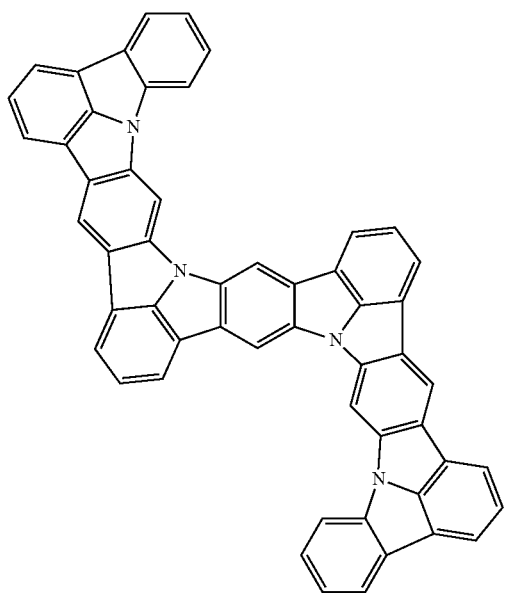
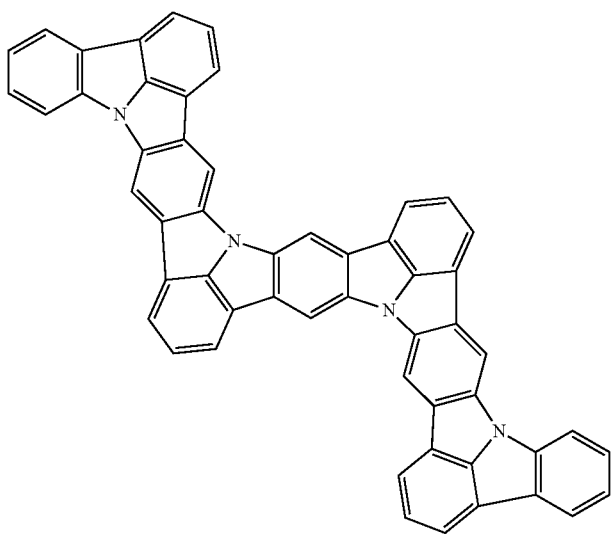

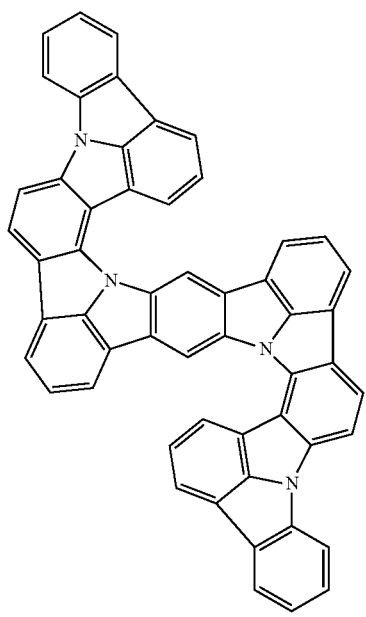
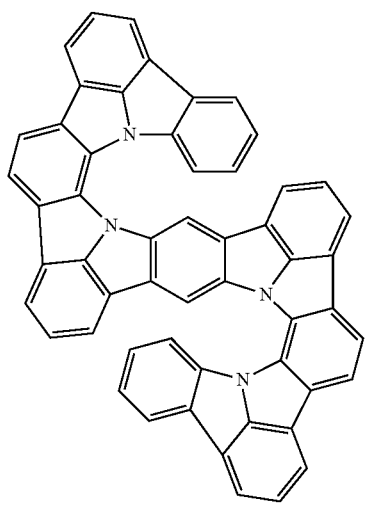
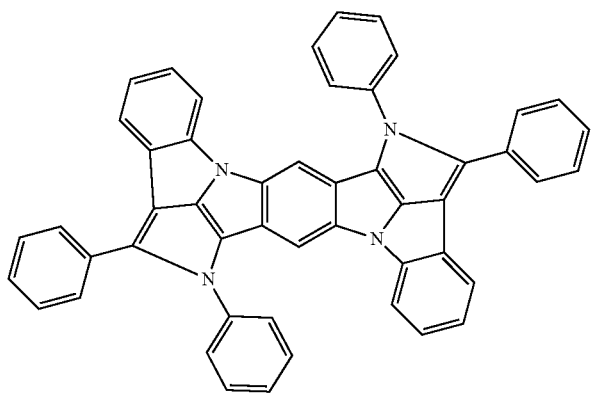

-continued
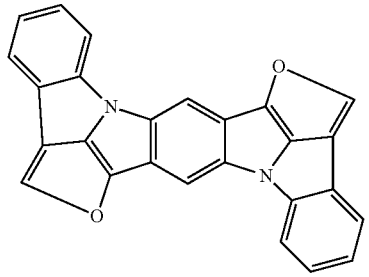
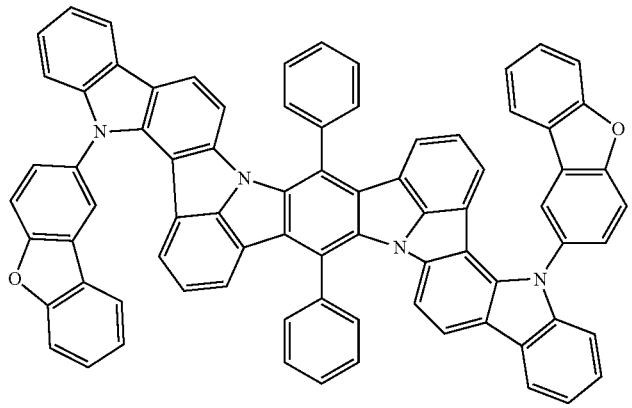
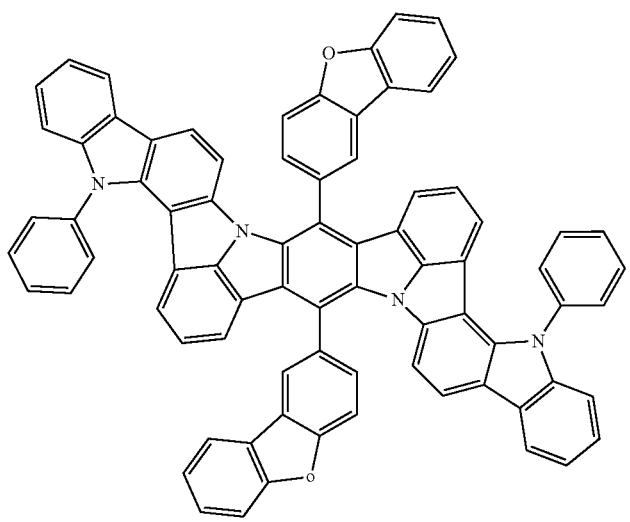
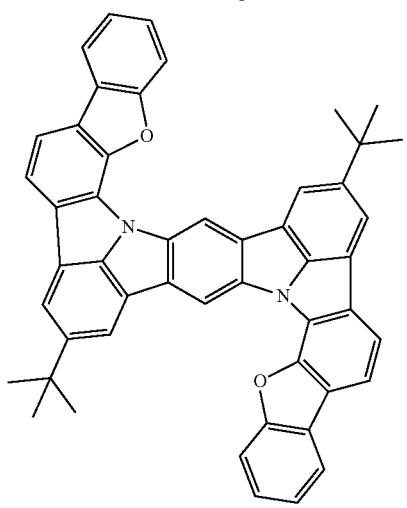

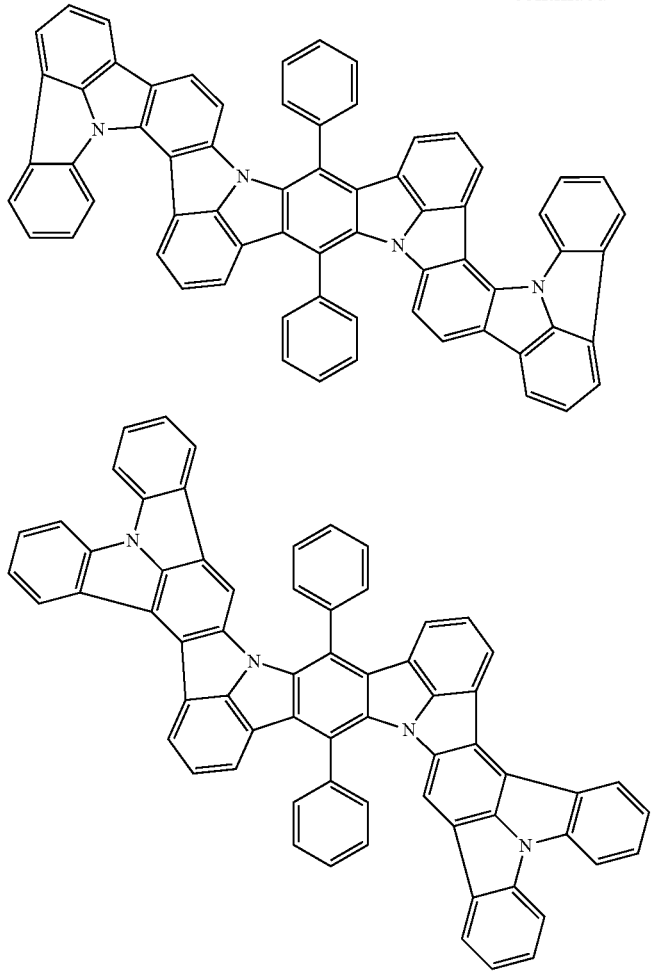

(Compound Represented by Formula (41))

The compound represented by the formula (41) is explained below.

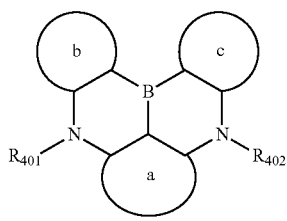

(41)

In the formula (41), a ring, b ring and c ring are independently
a substituted or unsubstituted aromatic hydrocarbon ring including 6 to 50 ring carbon atoms, or
a substituted or unsubstituted heterocyclic ring including 5 to 50 ring atoms;

$R_{401}$ and $R_{402}$ are independently bonded to the a ring, the b ring or the c ring to form a substituted or unsubstituted heterocyclic ring or do not form a substituted or unsubstituted heterocyclic ring;

$R_{401}$ and $R_{402}$ that do not form the substituted or unsubstituted heterocyclic ring are independently a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms.

The a ring, b ring and c ring are rings (a substituted or unsubstituted aromatic hydrocarbon ring including 6 to 50 ring carbon atoms or a substituted or unsubstituted heterocyclic ring including 5 to 50 ring atoms) fuse to the fused bicyclic structure composed of B atom and two N atoms in the center of the formula (41).

The "aromatic hydrocarbon ring" of the a ring, the b ring and the c ring has the same structure as the compound obtained by introducing a hydrogen atom into the "aryl group" described above. The "aromatic hydrocarbon ring" of the a ring contains three carbon atoms in the fused bicyclic structure in the center of the formula (41) as ring atoms. The "aromatic hydrocarbon ring" of the b ring and the c ring contain two carbon atoms in the fused bicyclic structure in the center of the formula (41) as ring atoms. As examples of "substituted or unsubstituted aromatic hydrocarbon ring including 6 to 50 ring carbon atoms", compounds in which a hydrogen atom is introduced into the "aryl group" described in the group G1 and the like can be given.

The "heterocyclic ring" of the a ring, the b ring and the c ring has the same structure as the compound obtained by introducing a hydrogen atom into the "heterocyclic group" described above. The "heterocyclic ring" of the a ring contains three carbon atoms in the fused bicyclic structure in the center of the formula (41) as ring atoms. The "heterocyclic ring" of the b ring and the c ring contain two carbon atoms in the fused bicyclic structure in the center of the formula (41) as ring atoms. As examples of "substituted or unsubstituted heterocyclic ring including 5 to 50 ring atoms", compounds in which a hydrogen atom is introduced into the "heterocyclic group" described in the group G2.

$R_{401}$ and $R_{402}$ may be independently bonded to the a ring, the b ring or the c ring to form a substituted or unsubstituted heterocyclic ring. This heterocyclic ring contains the nitrogen atom in the fused bicyclic structure in the center of the formula (41). This heterocyclic ring may contain a heteroatom other than the nitrogen atom. "$R_{401}$ and $R_{402}$ are bonded to the a ring, the b ring or the c ring" means, specifically, an atom forming the a ring, the b ring or the c ring is bonded to an atom forming $R_{401}$ and $R_{402}$. For example, it is possible that $R_{401}$ is bonded to the a ring to form a nitrogen-containing heterocyclic ring including a two-ring fused structure (or three or more rings fused structure) in which a ring containing $R_{401}$ and the a ring are fused. Specific examples of the nitrogen-containing heterocyclic ring include compound and the like corresponding to a heterocyclic group of 2 ring condensation or more containing nitrogen among specific example groups G2.

The same applies to the case where $R_{401}$ is bonded to the b ring, $R_{402}$ is bonded to the a ring, and $R_{402}$ is bonded to the c ring.

In one embodiment, the a ring, the b ring and the c ring in the formula (41) are independently a substituted or unsubstituted aromatic hydrocarbon ring including 6 to 50 ring carbon atoms.

In one embodiment, the a ring, the b ring and the c ring in the formula (41) are independently a substituted or unsubstituted benzene ring or a substituted or unsubstituted naphthalene ring.

In one embodiment, $R_{401}$ and $R_{402}$ in the formula (41) are independently a substituted or unsubstituted aryl group including 6 to 50 ring carbon atoms, or a substituted or unsubstituted monovalent heterocyclic group including 5 to 50 ring atoms, and preferably a substituted or unsubstituted aryl group including 6 to 50 ring carbon atoms.

In one embodiment, the compound represented by the formula (41) is a compound represented by the following formula (42):

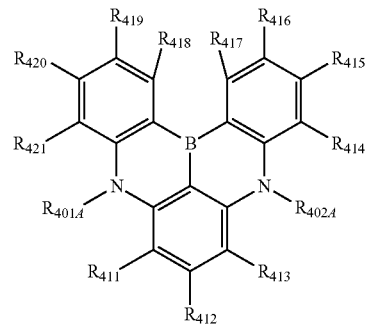

(42)

In the formula (42), $R_{401A}$ is bonded with one or more groups selected from $R_{411}$ and $R_{421}$ to form a substituted or unsubstituted heterocyclic ring, or does not form a substituted or unsubstituted heterocyclic ring; $R_{402A}$ is bonded with one or more group selected from $R_{413}$ or $R_{414}$ to form a substituted or unsubstituted heterocyclic ring, or does not form a substituted or unsubstituted heterocyclic ring;

$R_{401A}$ and $R_{402A}$ that do not form a substituted or unsubstituted heterocyclic ring are independently
  a substituted or unsubstituted alkyl group including 1 to 50 carbon atoms,
  a substituted or unsubstituted alkenyl group including 2 to 50 carbon atoms,
  a substituted or unsubstituted alkynyl group including 2 to 50 carbon atoms,
  a substituted or unsubstituted cycloalkyl group including 3 to 50 ring carbon atoms,
  a substituted or unsubstituted aryl group including 6 to 50 ring carbon atoms, or
  a substituted or unsubstituted monovalent heterocyclic group including 5 to 50 ring atoms;

One or more pairs of two or more adjacent groups of $R_{411}$ to $R_{421}$ are bonded with each other to form a substituted or unsubstituted, saturated or unsaturated ring, or do not form a substituted or unsubstituted, saturated or unsaturated ring;

$R_{411}$ to $R_{421}$ that do not form the substituted or unsubstituted heterocyclic ring or the substituted or unsubstituted, saturated or unsaturated ring are independently
  a hydrogen atom,
  a substituted or unsubstituted alkyl group including 1 to 50 carbon atoms,
  a substituted or unsubstituted alkenyl group including 2 to 50 carbon atoms,
  a substituted or unsubstituted alkynyl group including 2 to 50 carbon atoms,
  a substituted or unsubstituted cycloalkyl group including 3 to 50 ring carbon atoms,
  —Si($R_{901}$)($R_{902}$)($R_{903}$),
  —O—($R_{904}$),
  —S—($R_{905}$),
  —N($R_{906}$)($R_{907}$),
  a halogen atom, a cyano group, a nitro group,
  a substituted or unsubstituted aryl group including 6 to 50 ring carbon atoms, or
  a substituted or unsubstituted monovalent heterocyclic group including 5 to 50 ring atoms; and
  $R_{901}$ to $R_{907}$ are as defined in the formula (1).

$R_{401A}$ and $R_{402A}$ in the formula (42) correspond to $R_{401}$ and $R_{402}$ in the formula (41).

$R_{401A}$ and $R_{411}$ may be bonded with each other to form a nitrogen-containing heterocyclic ring including two-ring fused structure (or three or more rings fused structure) which is a fused ring of a ring containing $R_{401A}$ and $R_{411}$ and the benzene ring of the a ring, for example. As examples of the nitrogen-containing heterocyclic ring, compounds correspond to nitrogen-containing heterocyclic group including two or more ring fused structure in the group G2 can be given. The same applies to the cases where $R_{401A}$ and $R_{412}$ are bonded, $R_{402A}$ and $R_{413}$ are bonded, and $R_{402A}$ and $R_{414}$ are bonded.

One or more pairs of two or more adjacent groups of $R_{411}$ to $R_{421}$ are bonded with each other to form a substituted or unsubstituted, saturated or unsaturated ring. For example, $R_{411}$ and $R_{412}$ are bonded to forma benzene ring, an indole ring, a pyrrole ring, a benzofuran ring, a benzothiophene ring or the like which fuses to the six-membered ring to which $R_{411}$ and $R_{412}$ bond, and the formed fused ring is a naphthalene ring, a carbazole ring, an indole ring, a dibenzofuran ring or a dibenzothiophene ring.

In one embodiment, $R_{411}$ to $R_{421}$ that do not contribute to form a ring are independently a hydrogen atom, a substituted or unsubstituted alkyl group including 1 to 50 carbon atoms, a substituted or unsubstituted aryl group including 6 to 50 ring carbon atoms, or a substituted or unsubstituted monovalent heterocyclic group including 5 to 50 ring atoms.

In one embodiment, $R_{411}$ to $R_{421}$ that do not contribute to form a ring are independently a hydrogen atom, a substituted or unsubstituted aryl group including 6 to 50 ring carbon atoms, or a substituted or unsubstituted monovalent heterocyclic group including 5 to 50 ring atoms.

In one embodiment, $R_{411}$ to $R_{421}$ that do not contribute to form a ring are independently a hydrogen atom or a substituted or unsubstituted alkyl group including 1 to 50 carbon atoms.

In one embodiment, $R_{411}$ to $R_{421}$ that do not contribute to form a ring are independently a hydrogen atom, a substituted or unsubstituted alkyl group including 1 to 50 carbon atoms, and at least one of $R_{411}$ to $R_{421}$ is a substituted or unsubstituted alkyl group including 1 to 50 carbon atoms.

In one embodiment, the compound represented by the formula (42) is a compound represented by the following formula (43).

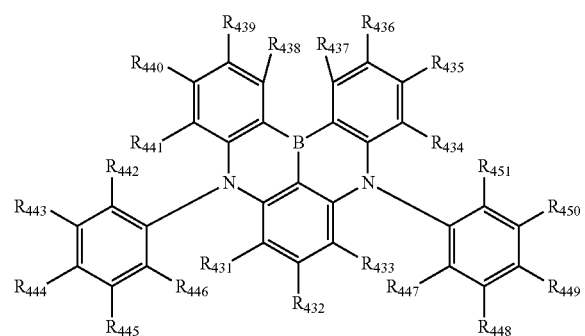

(43)

In the formula (43),
$R_{41}$ is bonded with $R_{446}$ to form a substituted or unsubstituted heterocyclic ring, or does not form a substituted or unsubstituted heterocyclic ring; $R_{433}$ is bonded with $R_{447}$ to form a substituted or unsubstituted heterocyclic ring, or does not form a substituted or unsubstituted heterocyclic ring; $R_{434}$ is bonded with $R_{451}$ to form a substituted or unsubstituted heterocyclic ring, or does not form a substituted or unsubstituted heterocyclic ring; $R_{441}$ is bonded with $R_{442}$ to form a substituted or unsubstituted heterocyclic ring, or does not form a substituted or unsubstituted heterocyclic ring;

one or more pairs of two or more adjacent groups of $R_{431}$ to $R_{451}$ are bonded with each other to form a substituted or unsubstituted, saturated or unsaturated ring, or do not form a substituted or unsubstituted, saturated or unsaturated ring;

$R_{431}$ to $R_{451}$ that do not form a substituted or unsubstituted heterocyclic ring are independently a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si$(R_{901})(R_{902})(R_{903})$,
—O—$(R_{904})$,
—S—$(R_{905})$,
—N$(R_{906})(R_{907})$,
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms; and
$R_{901}$ to $R_{907}$ are as defined in the formula (1).

$R_{431}$ may bond to $R_{446}$ to forma substituted or unsubstituted heterocyclic ring. For example, $R_{431}$ may bonds with $R_{446}$ to form a nitrogen-containing heterocyclic ring with three or more fused rings of the benzene ring to which $R_{446}$ bond, a nitrogen-containing ring and the benzene ring of the a ring. As examples of the nitrogen-containing heterocyclic ring, compounds correspond to nitrogen-containing heterocyclic group including three or more ring fused structure in the group G2 can be given. The same applies to the cases where $R_{433}$ and $R_{447}$ are bonded, $R_{434}$ and $R_{451}$ are bonded, and $R_{441}$ and $R_{442}$ are bonded.

In one embodiment, $R_{431}$ to $R_{451}$ that do not contribute to form a ring are independently, a hydrogen atom, a substituted or unsubstituted alkyl group including 1 to 50 carbon atoms, a substituted or unsubstituted aryl group including 6 to 50 carbon atoms, or a substituted or unsubstituted monovalent heterocyclic group including 5 to 50 ring atoms.

In one embodiment, $R_{431}$ to $R_{451}$ that do not contribute to form a ring are independently, a hydrogen atom, a substituted or unsubstituted aryl group including 6 to 50 carbon atoms, or a substituted or unsubstituted monovalent heterocyclic group including 5 to 50 ring atoms.

In one embodiment, $R_{431}$ to $R_{451}$ that do not contribute to form a ring are independently a hydrogen atom or a substituted or unsubstituted alkyl group including 1 to 50 carbon atoms.

In one embodiment, $R_{431}$ to $R_{451}$ that do not contribute to form a ring are independently a hydrogen atom, a substituted or unsubstituted alkyl group including 1 to 50 carbon atoms, and at least one of $R_{431}$ to $R_{451}$ is a substituted or unsubstituted alkyl group including 1 to 50 carbon atoms.

In one embodiment, the compound represented by the formula (43) is a compound represented by the following formula (43A).

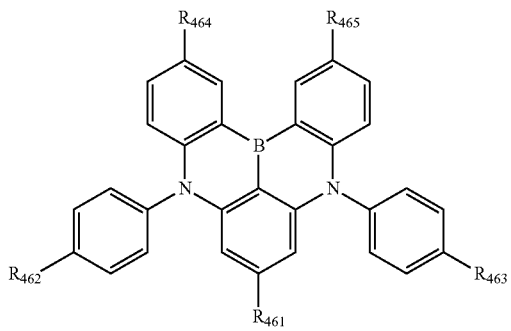

(43A)

In the formula (43A),
$R_{461}$ is
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms, or
a substituted or unsubstituted aryl group including 6 to 50 ring carbon atoms; and
$R_{462}$ to $R_{465}$ are independently
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms, or
a substituted or unsubstituted aryl group including 6 to 50 ring carbon atoms.

In one embodiment, $R_{461}$ to $R_{465}$ are independently a substituted or unsubstituted alkyl group including 1 to 50 carbon atoms or a substituted or unsubstituted aryl group including 6 to 50 ring carbon atoms.

In one embodiment, $R_{461}$ and $R_{465}$ are independently a substituted or unsubstituted alkyl group including 1 to 50 carbon atoms.

In one embodiment, the compound represented by the formula (43) is a compound represented by the following formula (43B).

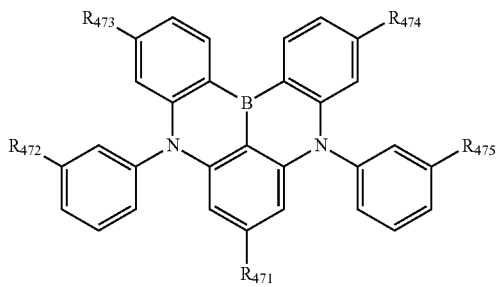

(43B)

In the formula (43B),
$R_{471}$ and $R_{472}$ are independently,
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—$N(R_{906})(R_{907})$, or
a substituted or unsubstituted aryl group including 6 to 50 ring carbon atoms;
$R_{473}$ to $R_{475}$ are independently,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—$N(R_{906})(R_{907})$, or
a substituted or unsubstituted aryl group including 6 to 50 ring carbon atoms; and
$R_{906}$ and $R_{907}$ are as defined in the formula (1).

In one embodiment, the compound represented by the formula (43) is the compound represented by the following formula (43B').

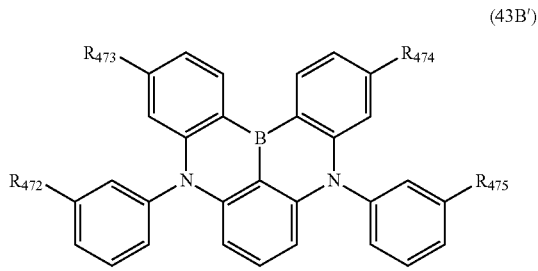

(43B')

In the formula (43B'), $R_{472}$ to $R_{475}$ are as defined in the formula (43B).

In one embodiment, at least one of $R_{471}$ to $R_{475}$ is
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—$N(R_{906})(R_{907})$, or
a substituted or unsubstituted aryl group including 6 to 50 ring carbon atoms.

In one embodiment,
$R_{472}$ is
a hydrogen atom,
a substituted or unsubstituted alkyl group including 1 to 50 carbon atoms,
—$N(R_{906})(R_{907})$, or
a substituted or unsubstituted aryl group including 6 to 50 ring carbon atoms; and
$R_{471}$ and $R_{473}$ to $R_{475}$ are independently
a substituted or unsubstituted alkyl group including 1 to 50 carbon atoms,
—$N(R_{906})(R_{907})$, or
a substituted or unsubstituted aryl group including 6 to 50 ring carbon atoms.

In one embodiment, the compound represented by the formula (43) is a compound represented by the formula (43C).

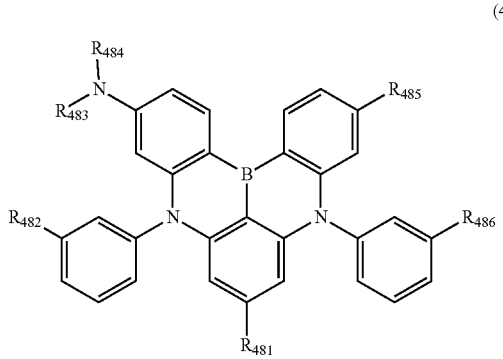

(43C)

In the formula (43C),
$R_{481}$ and $R_{482}$ are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms, or
a substituted or unsubstituted aryl group including 6 to 50 ring carbon atoms; and
$R_{483}$ to $R_{486}$ are independently
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms, or
a substituted or unsubstituted aryl group including 6 to 50 ring carbon atoms.

In one embodiment, the compound represented by the formula (43) is the compound represented by the following formula (43C').

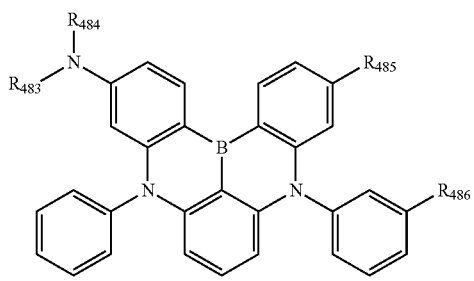

(43C')

In the formula (43C'), $R_{483}$ to $R_{486}$ are as defined in the formula (43C).

In one embodiment, $R_{481}$ to $R_{486}$ are independently a substituted or unsubstituted alkyl group including 1 to 50 carbon atoms or a substituted or unsubstituted aryl group including 6 to 50 ring carbon atoms.

In one embodiment, $R_{481}$ to $R_{486}$ are independently a substituted or unsubstituted aryl group including 6 to 50 ring carbon atoms.

The compound represented by the formula (41) can be synthesized by the following method. An intermediate is obtained by bonding the a ring, the b ring and the c ring with linking groups (a group containing N—$R_1$ and a group containing N—$R_2$)(first reaction), and a final compound is obtained by bonding the a ring, the b ring and the c ring with a linking group (a group containing B)(second reaction). In the first reaction, an amination reaction such as Buchwald-Hartwig reaction can be applied. In the second reaction, tandem hetero-Friedel-Crafts reaction or the like can be applied.

Examples of the compound represented by the formula (41) are described below. They are just exemplified compounds and the compound represented by the formula (41) is not limited to the following examples. In the following example compounds, Me represents methyl group, tBu represents tert-butyl group, and D represents a deuterium atom.

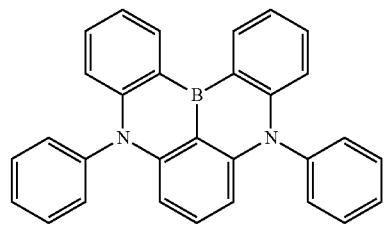

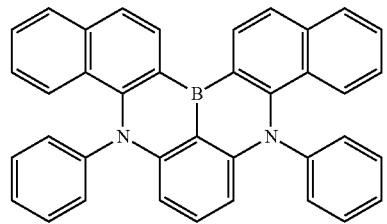

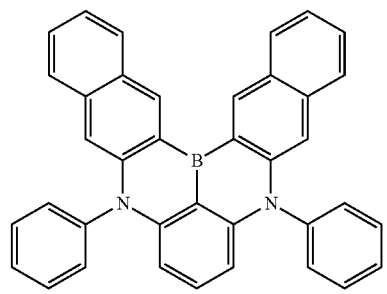

623
-continued
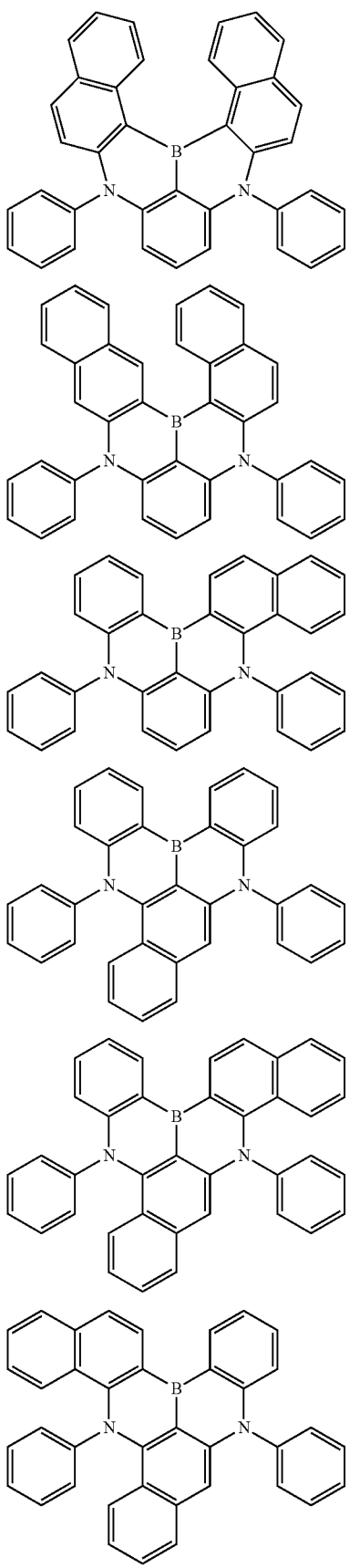
624
-continued
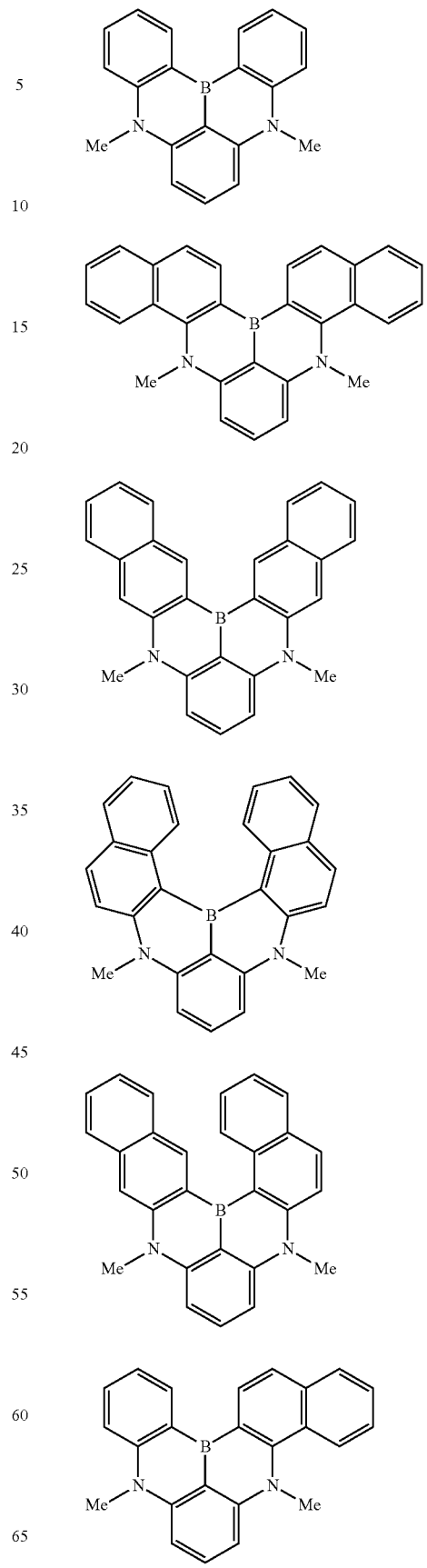

625
-continued
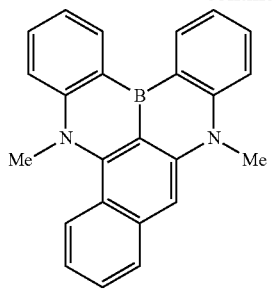
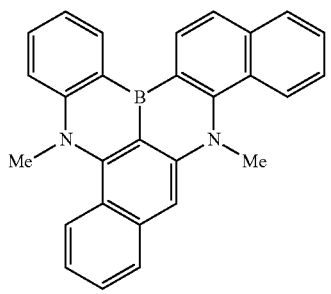
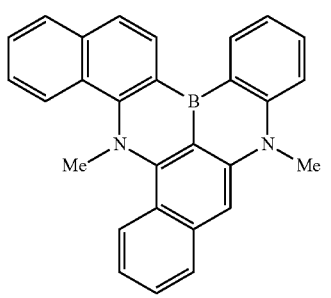
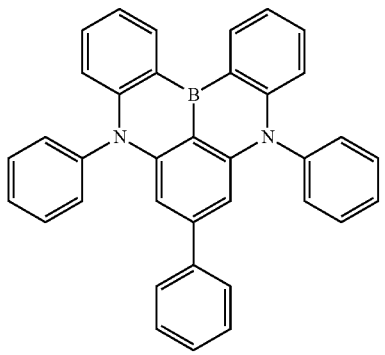
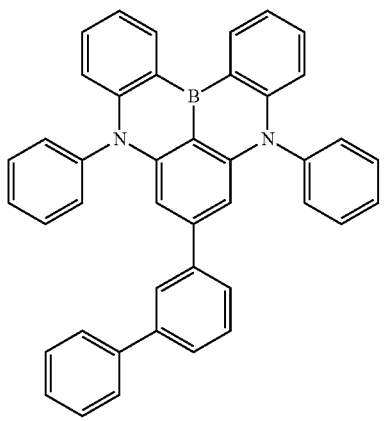
626
-continued
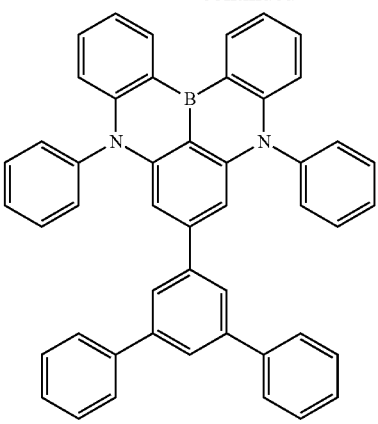
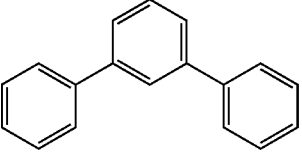
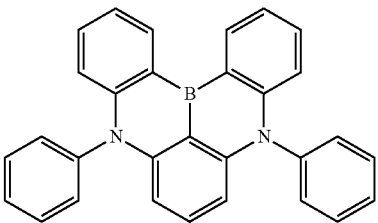
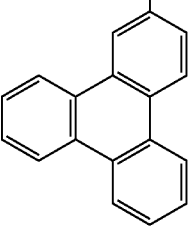
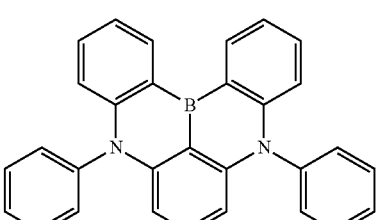
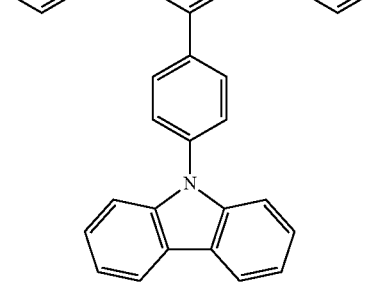

627
-continued
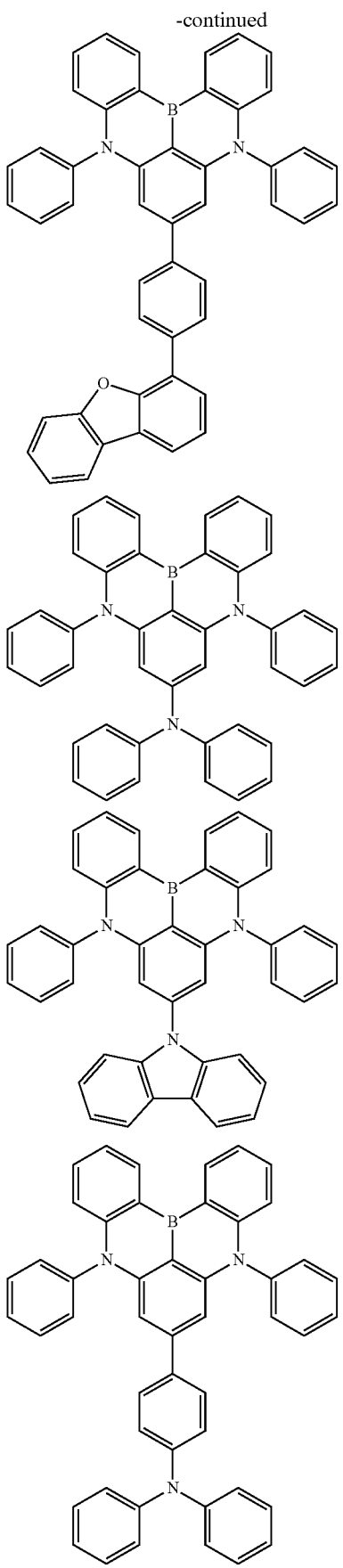
628
-continued
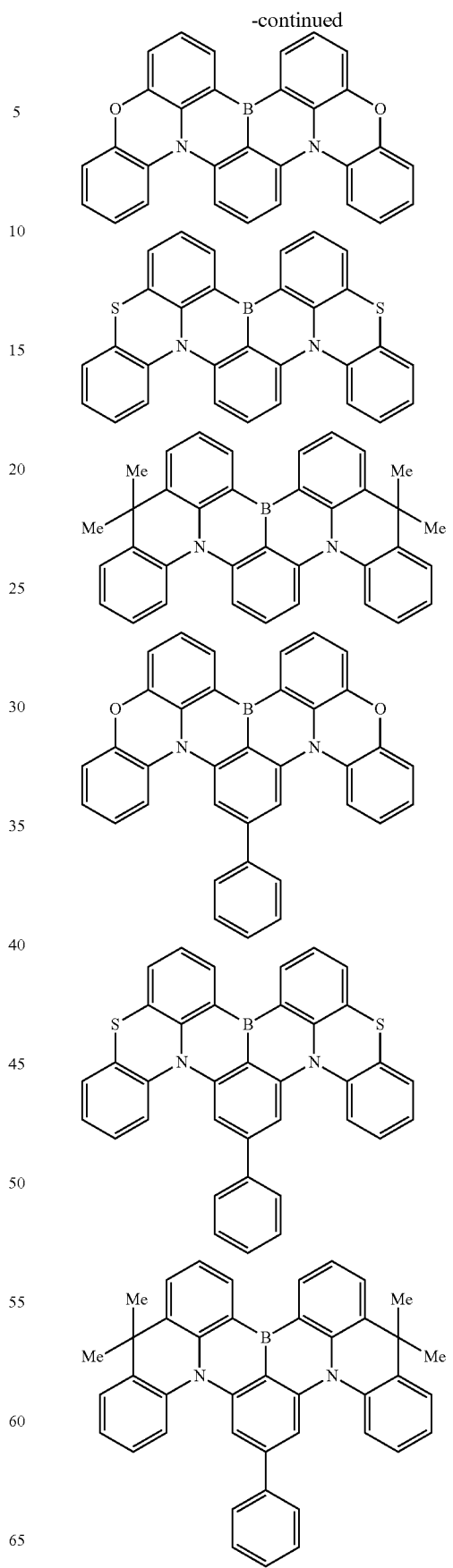

629
-continued
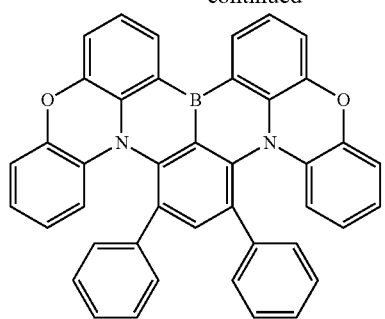
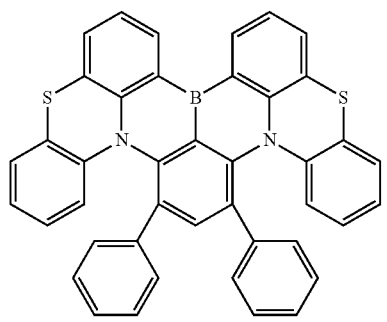
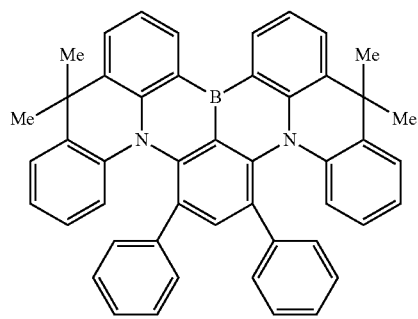
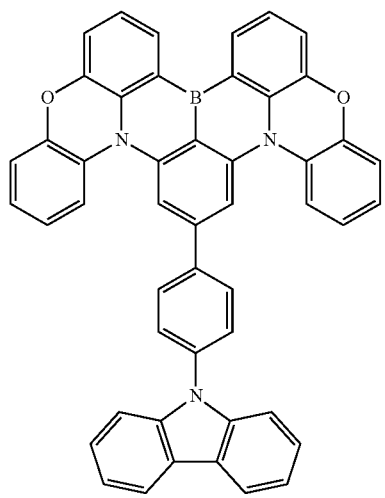
630
-continued
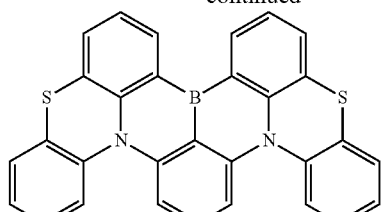
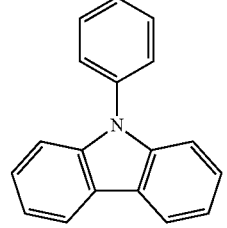
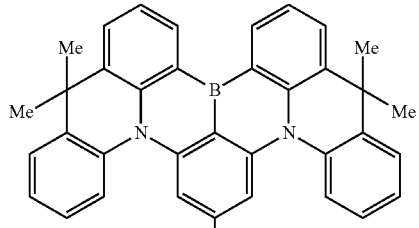
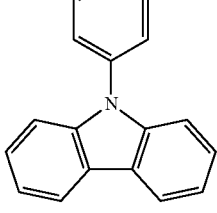
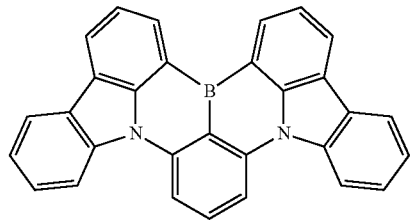
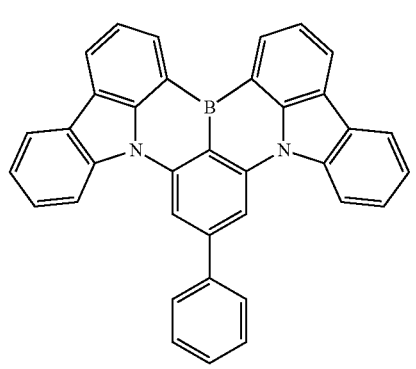

631
-continued
632
-continued
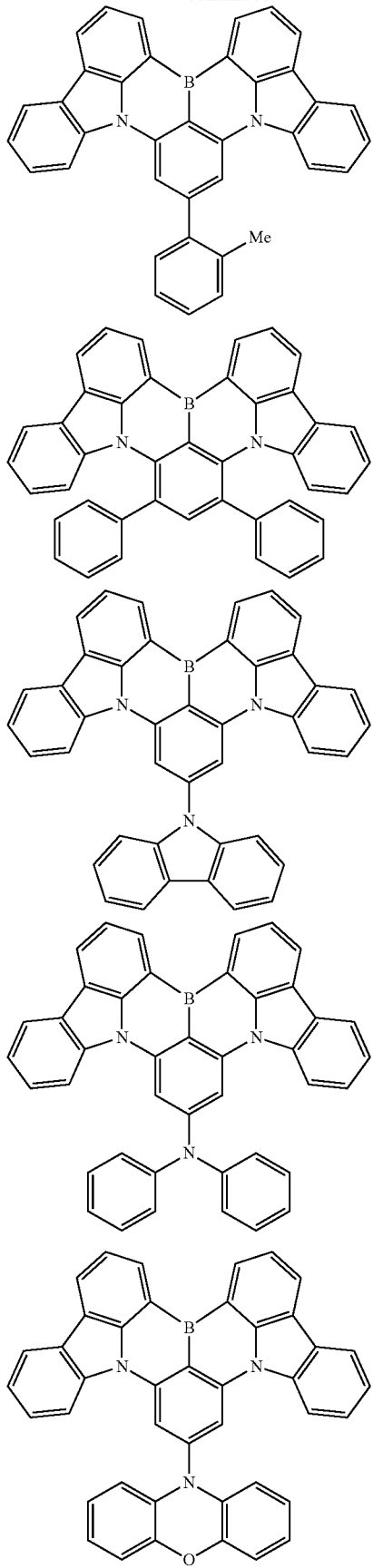
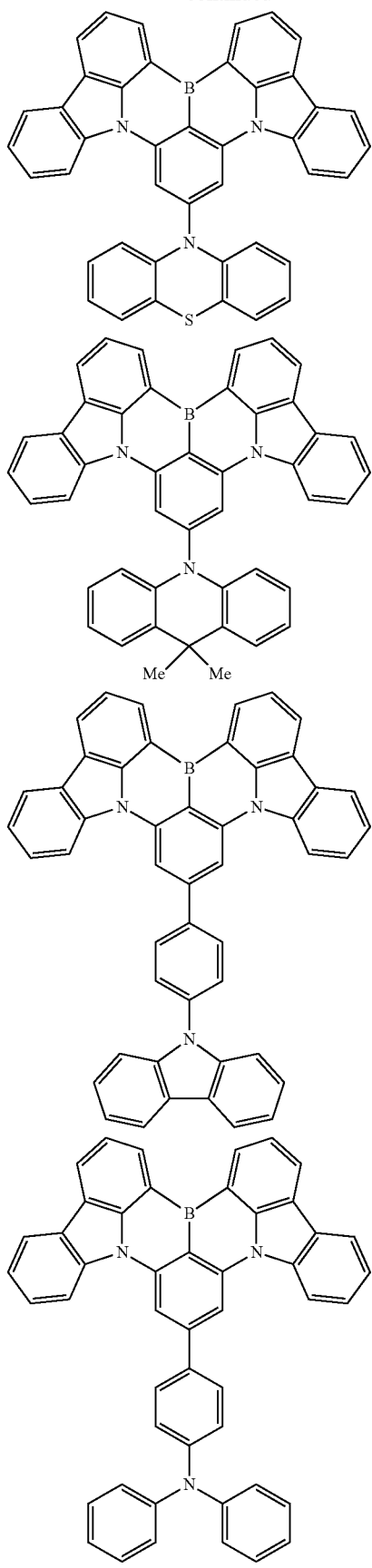

633
-continued
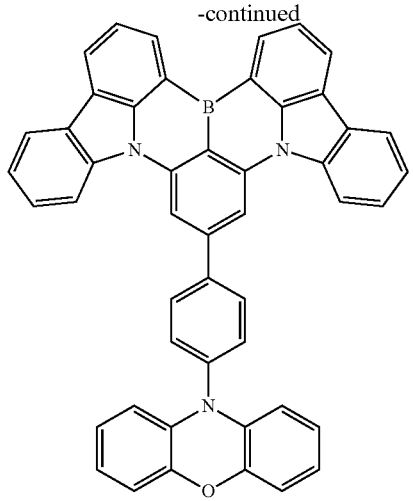
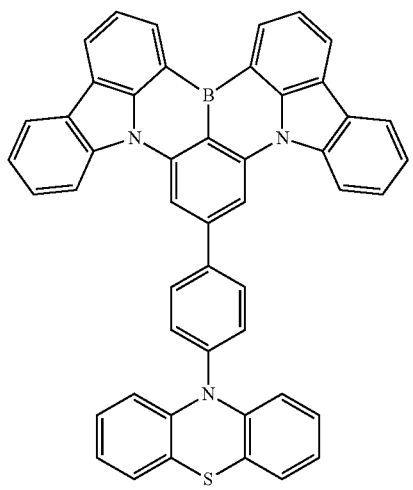
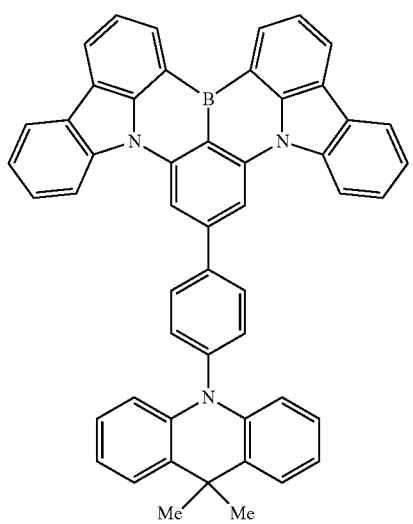
634
-continued
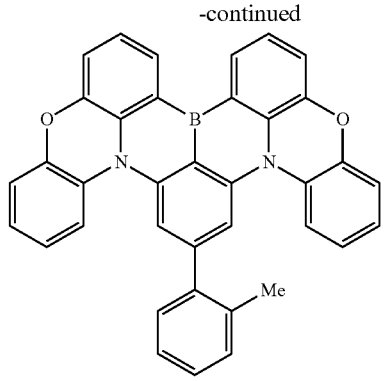
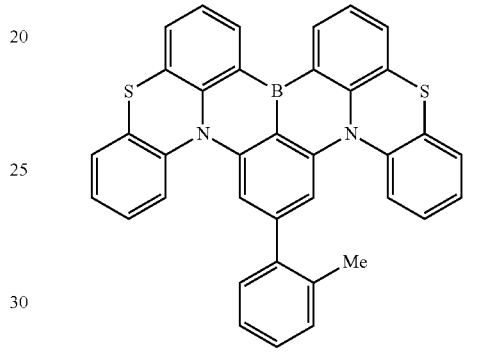
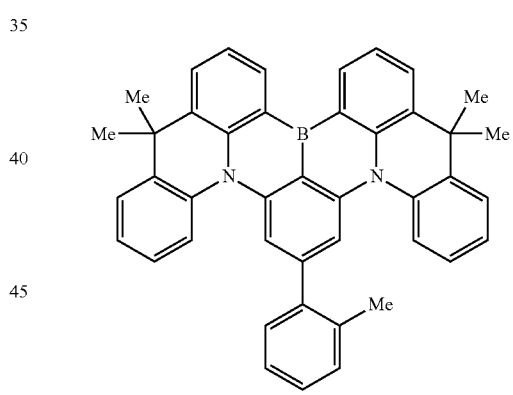
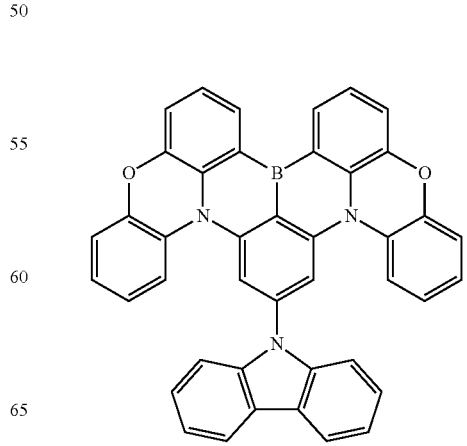

635
-continued
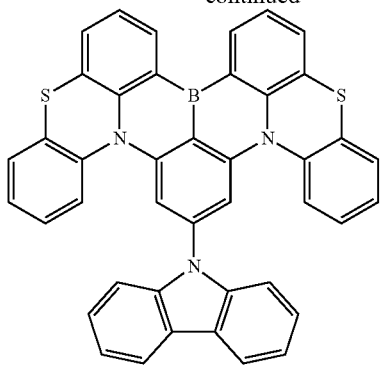
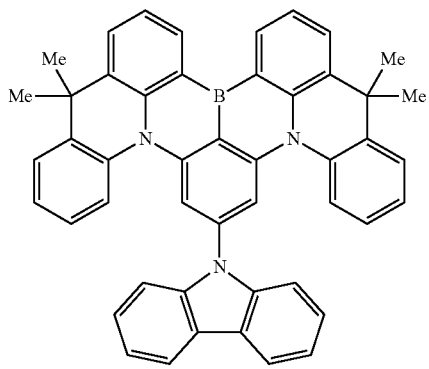
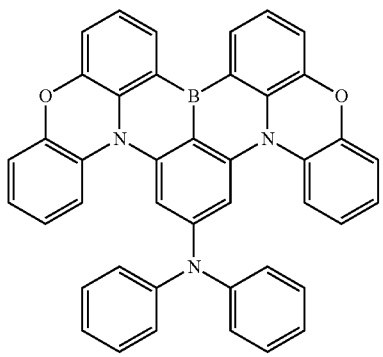
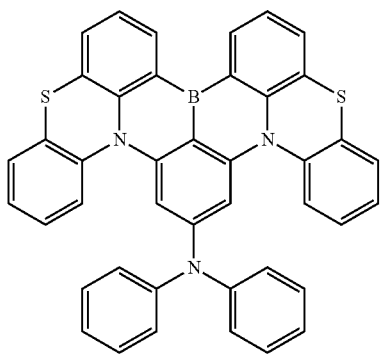
636
-continued
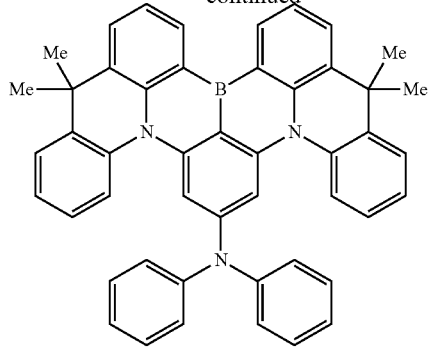
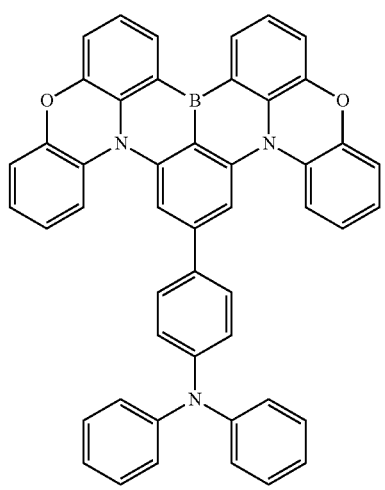

637
-continued
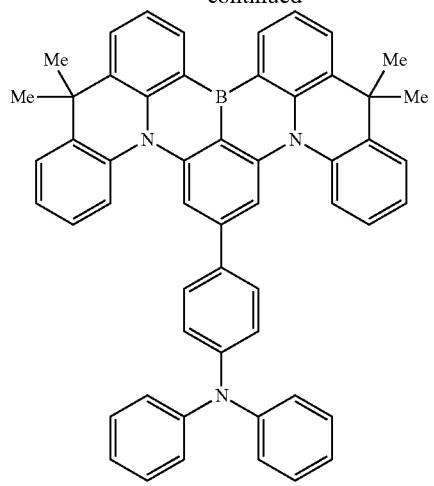
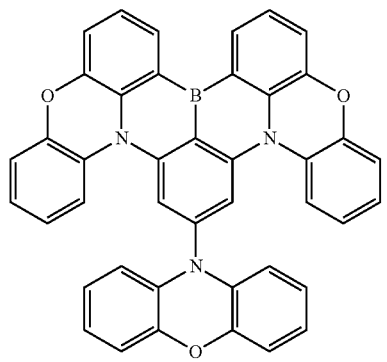
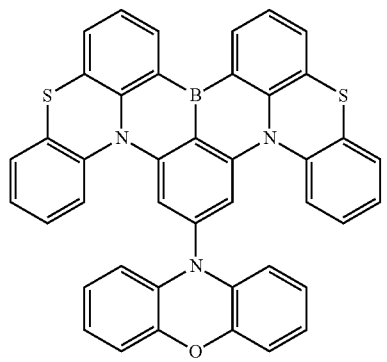
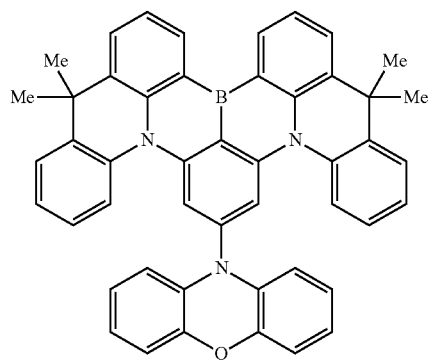
638
-continued
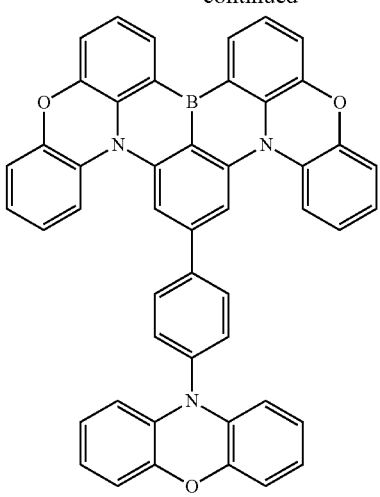
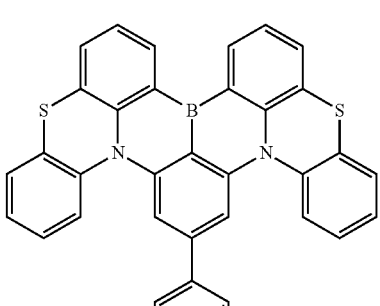
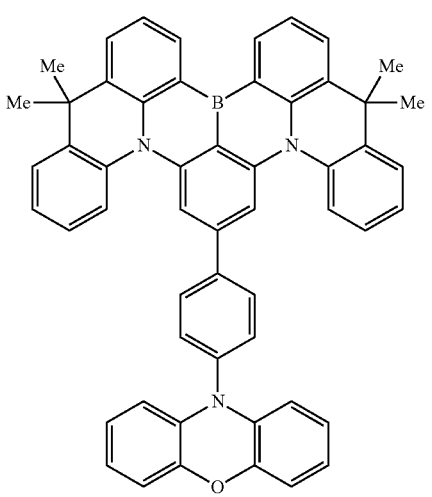

639
-continued
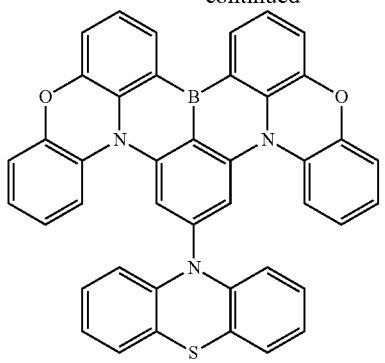
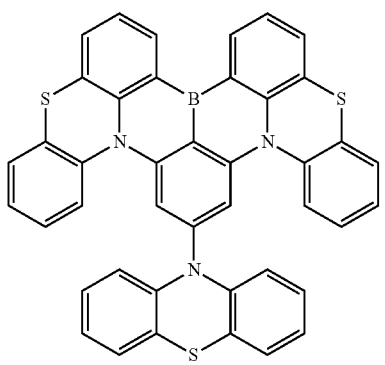
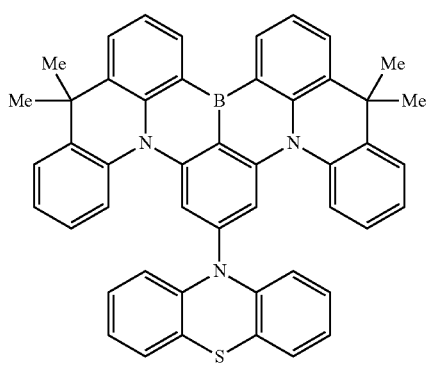
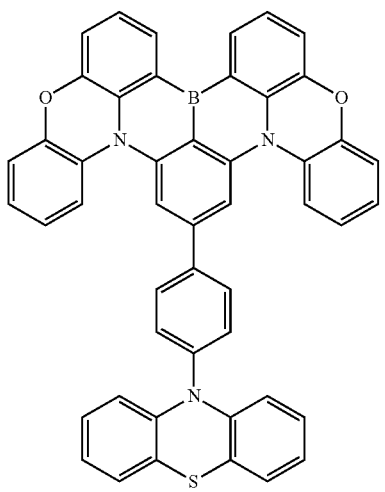
640
-continued
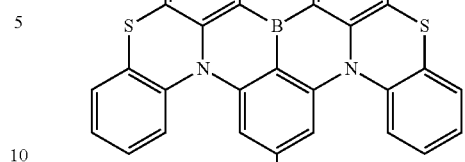
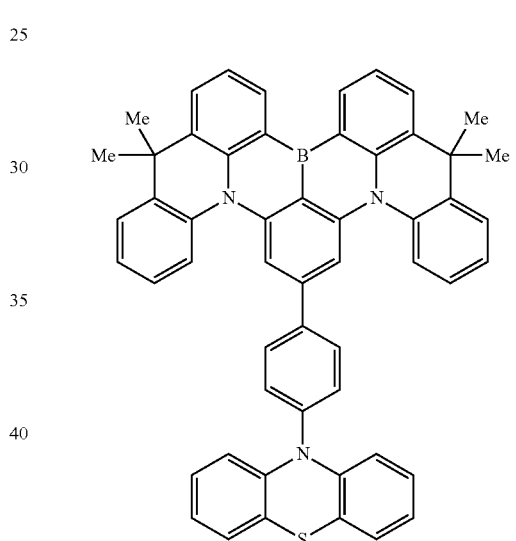
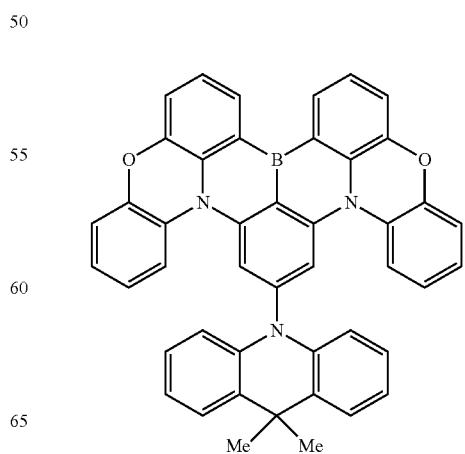

641
-continued
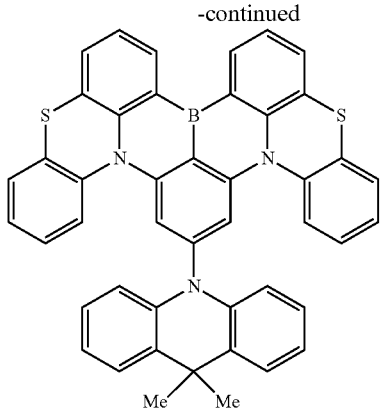
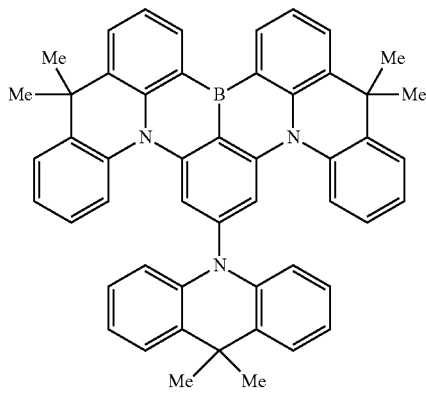
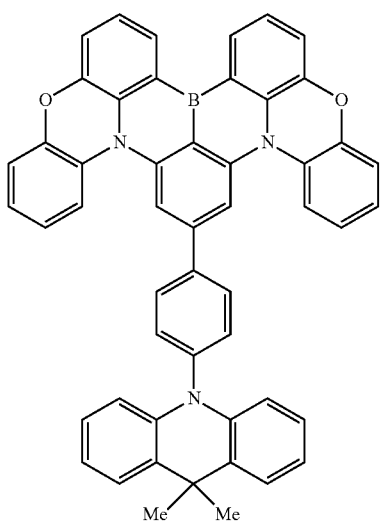
642
-continued
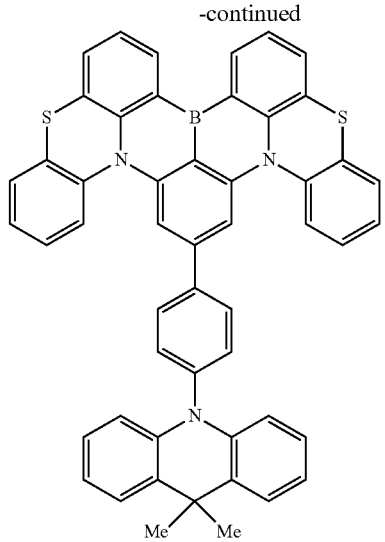
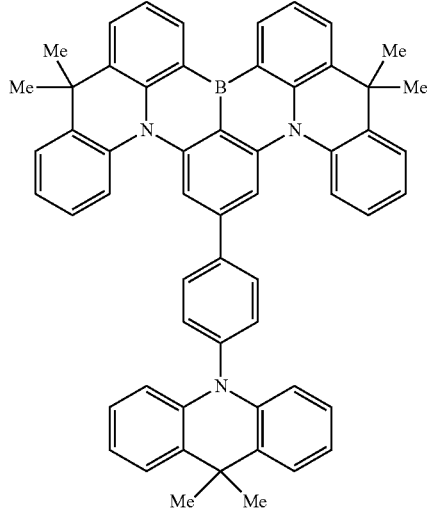
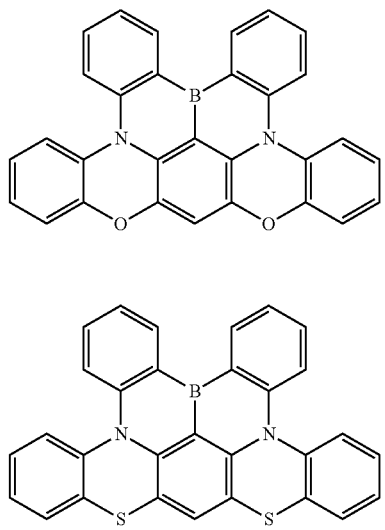

643
-continued
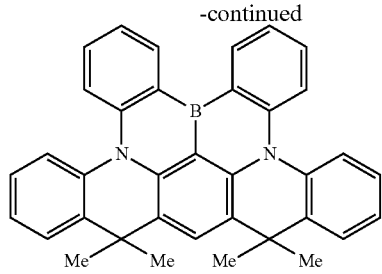
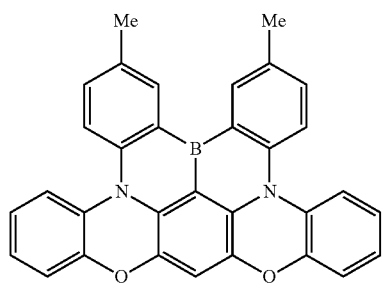
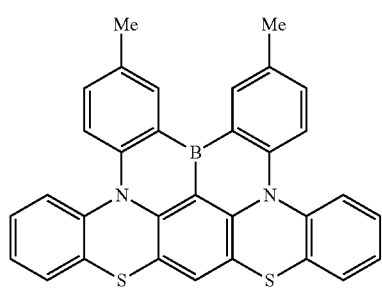
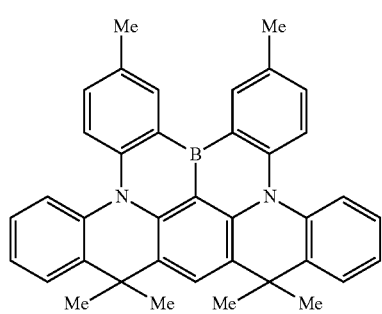
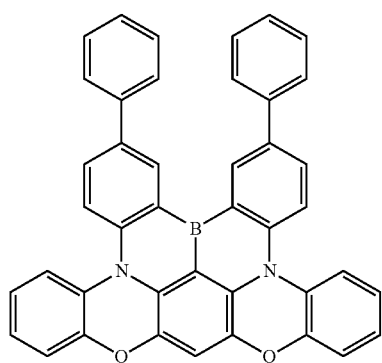
644
-continued
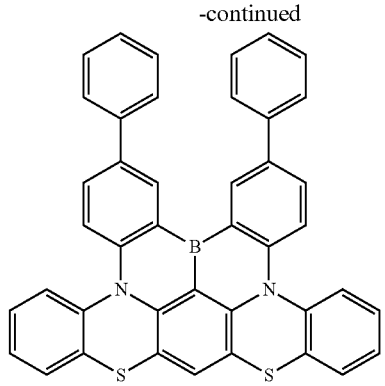
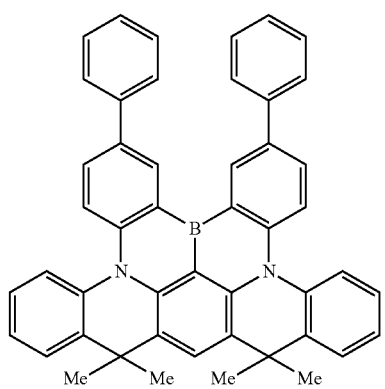
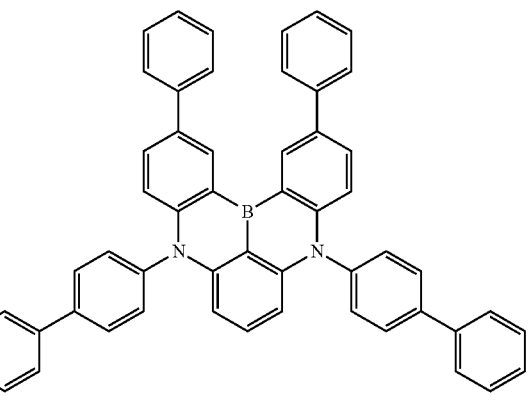
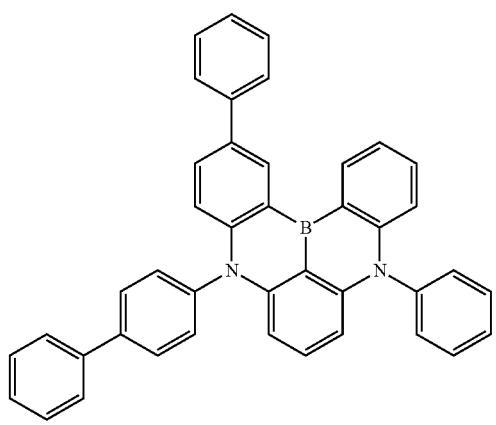

645
-continued
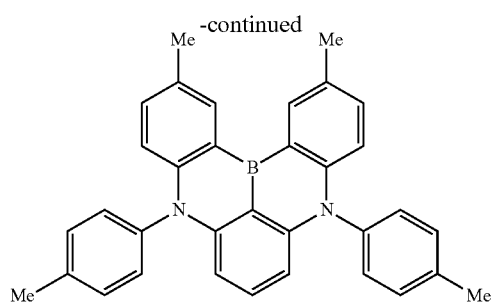
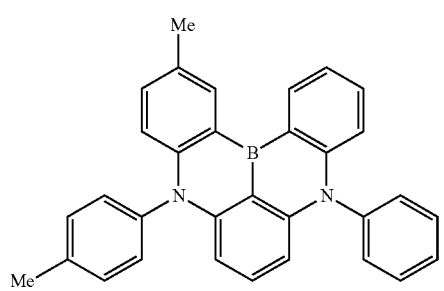
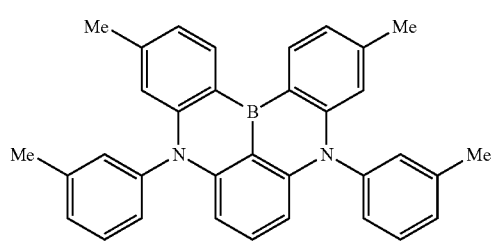
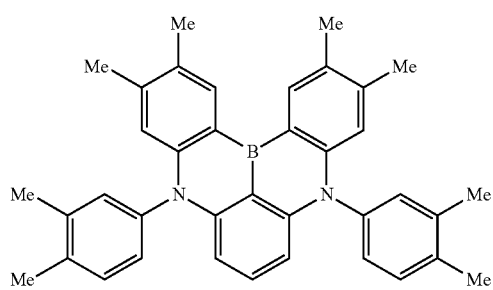
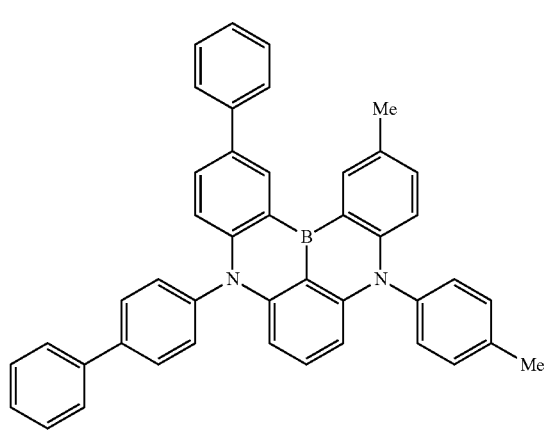
646
-continued
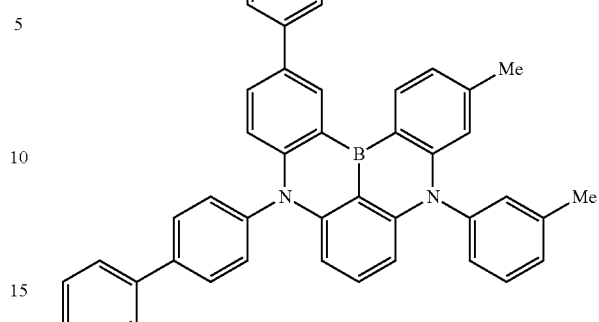
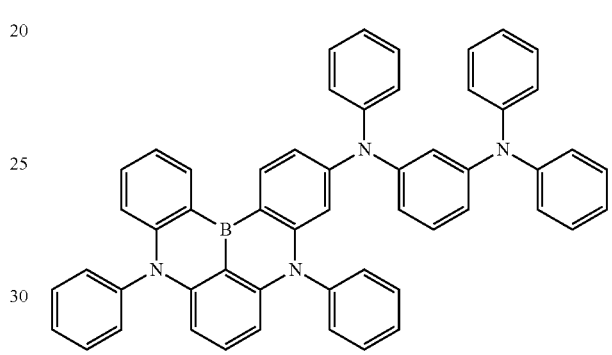
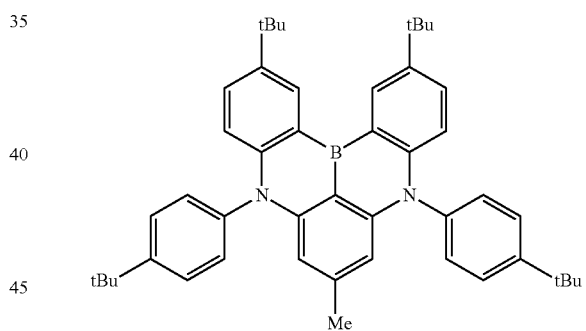

647
-continued
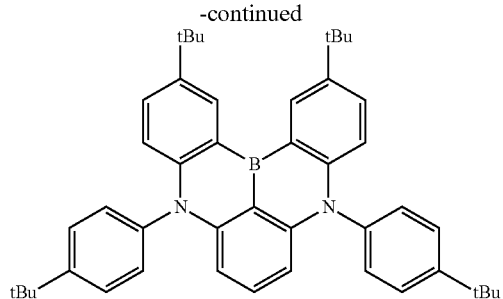
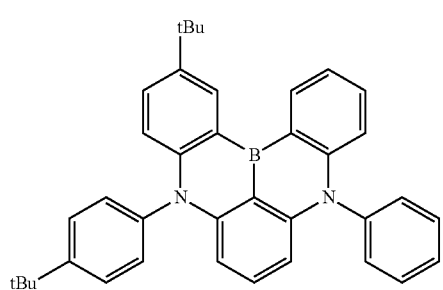
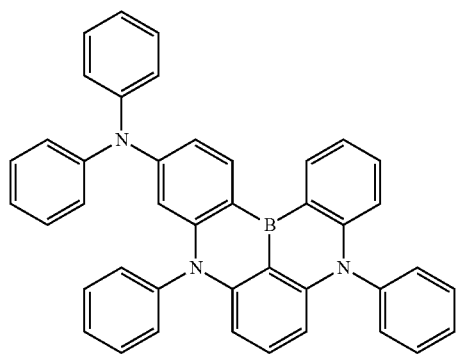
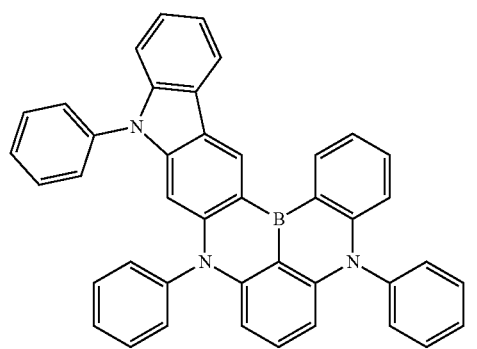
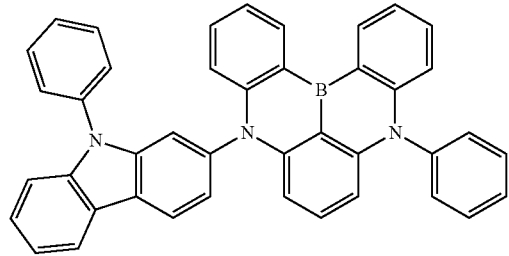
648
-continued
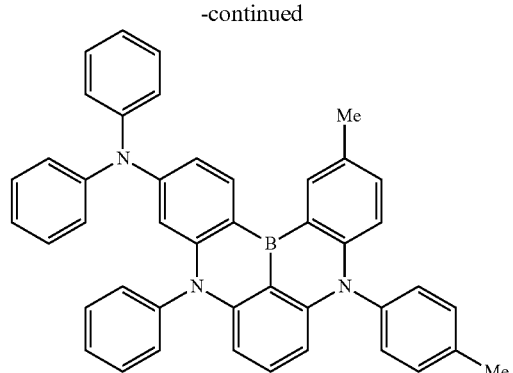
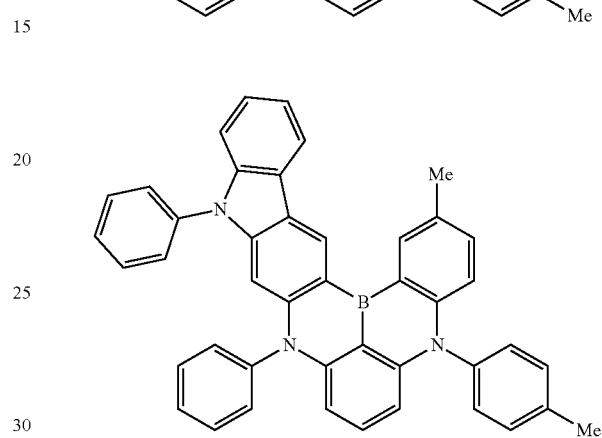
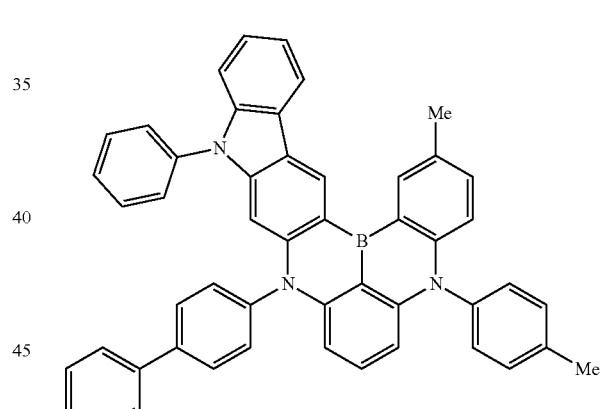
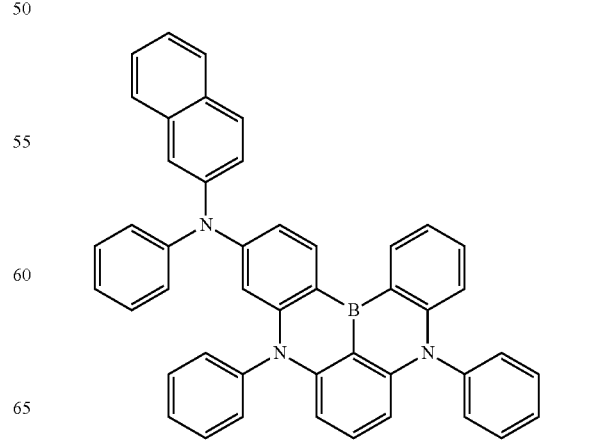

-continued
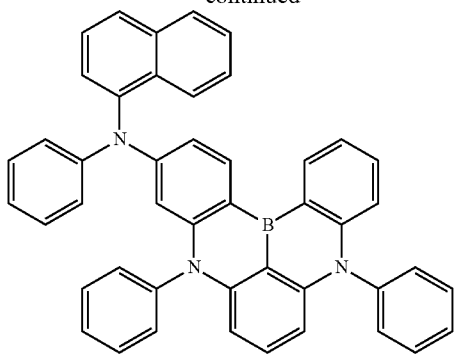
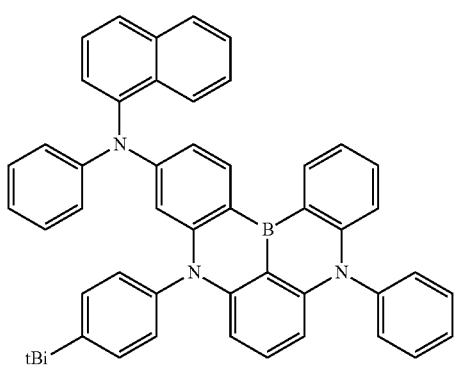
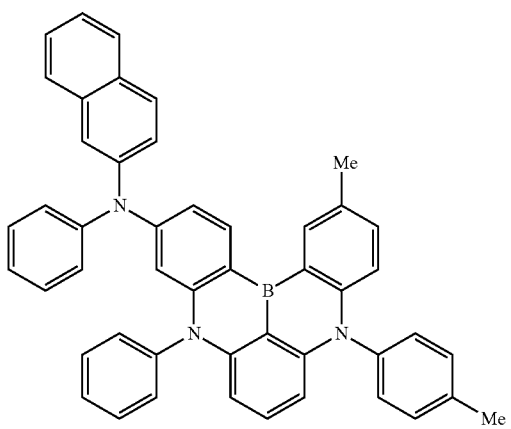
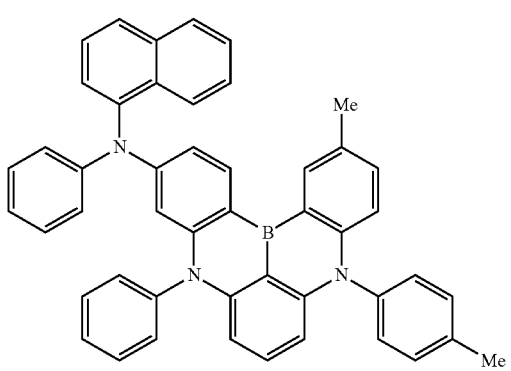
-continued
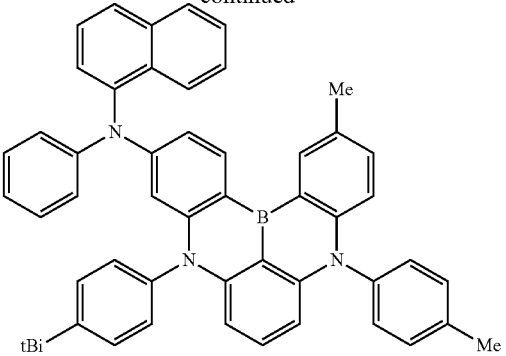
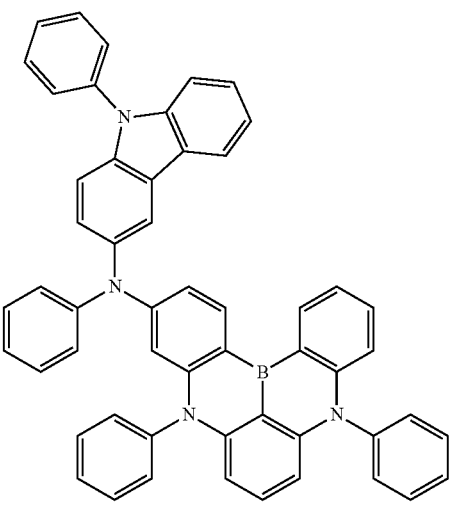
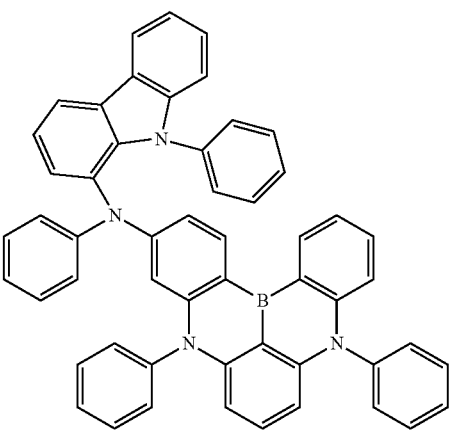

651
-continued
652
-continued
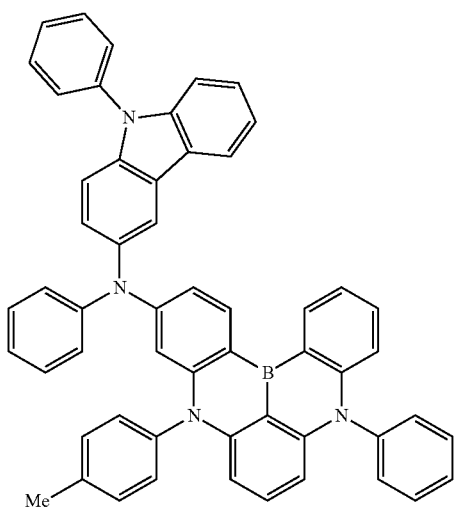
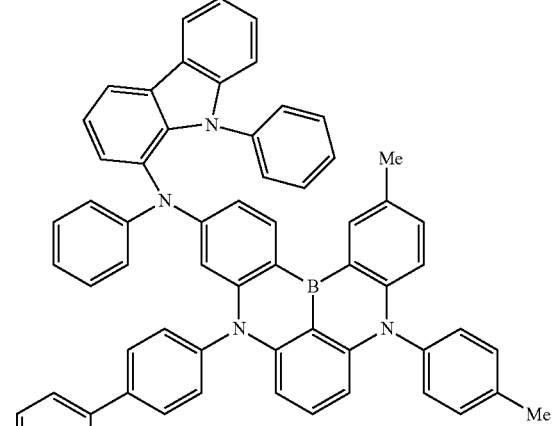
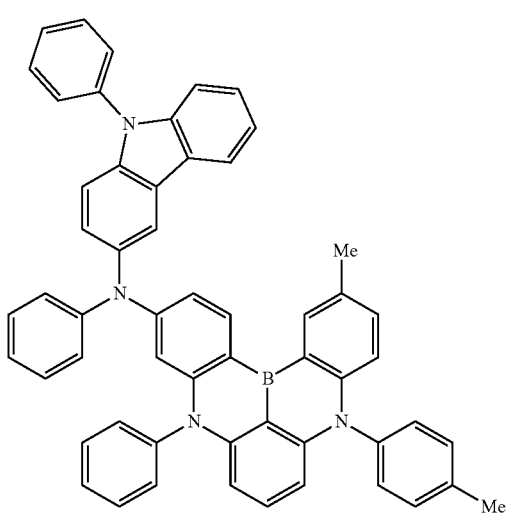
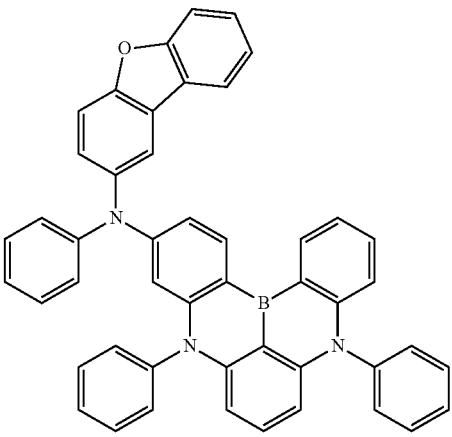
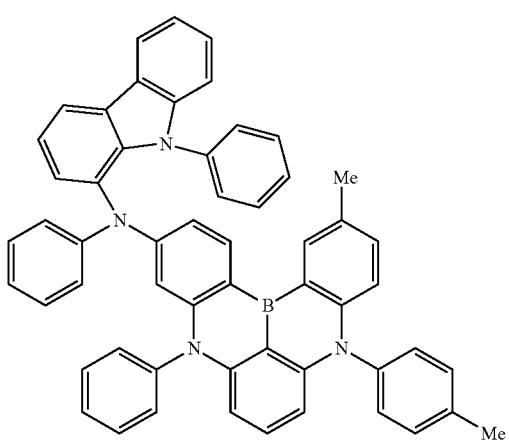
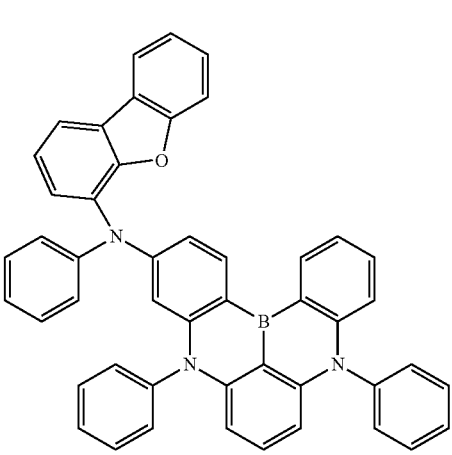

653
-continued
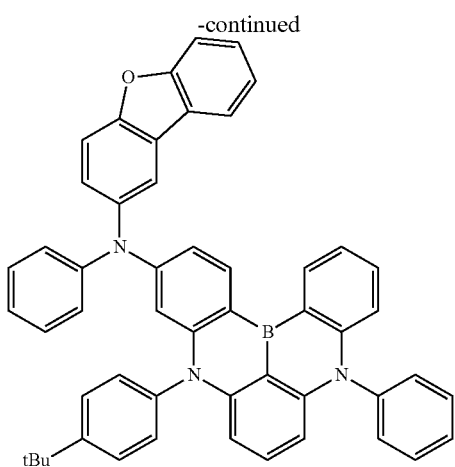
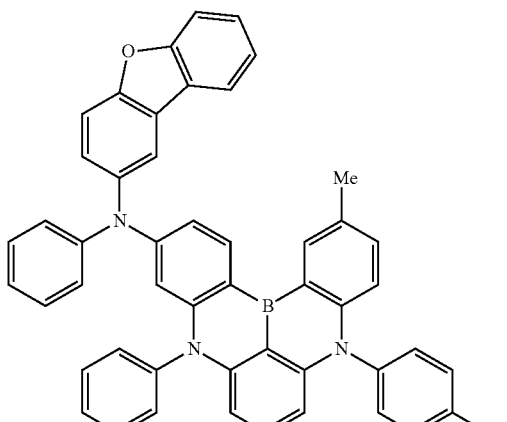
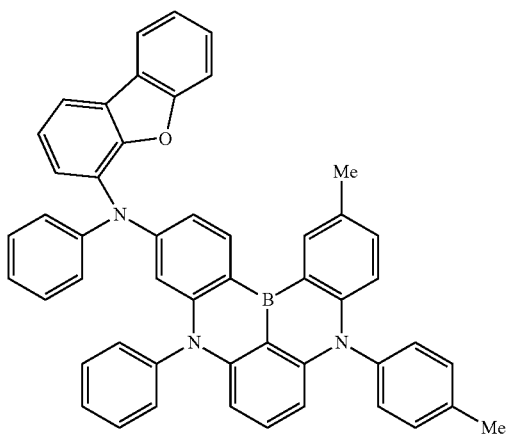
654
-continued
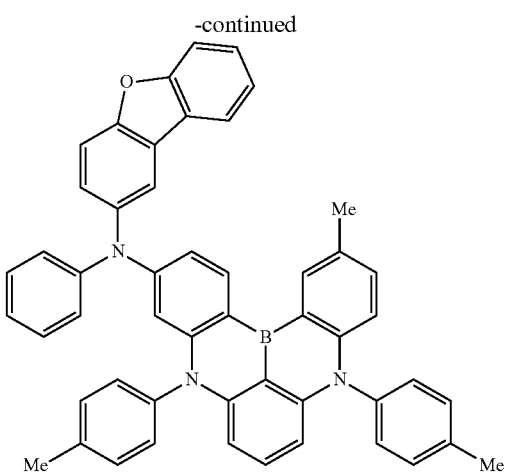
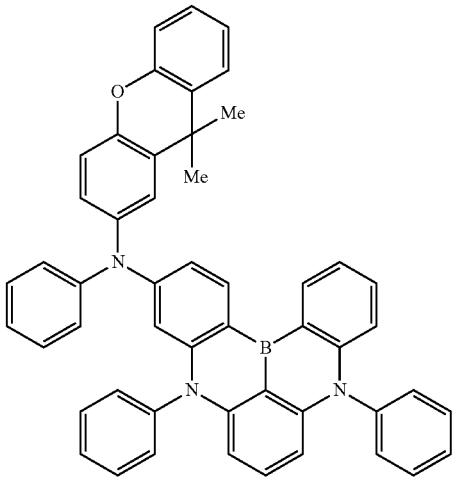
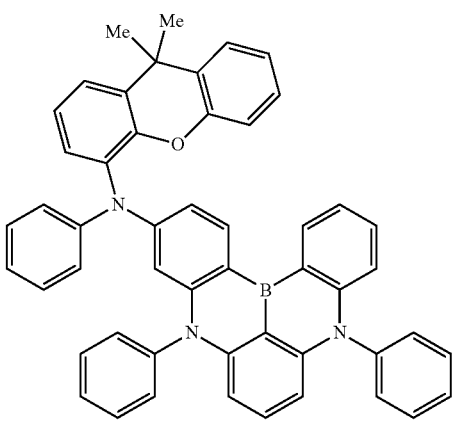

655
-continued
656
-continued
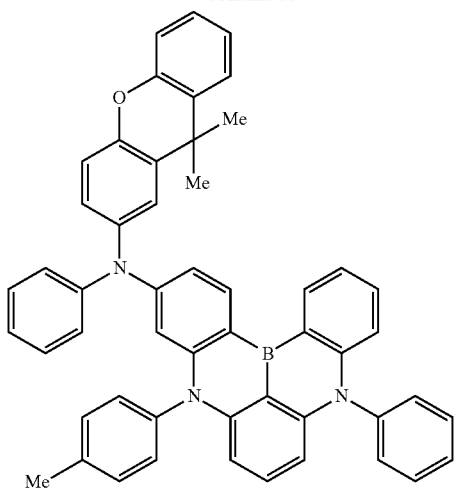
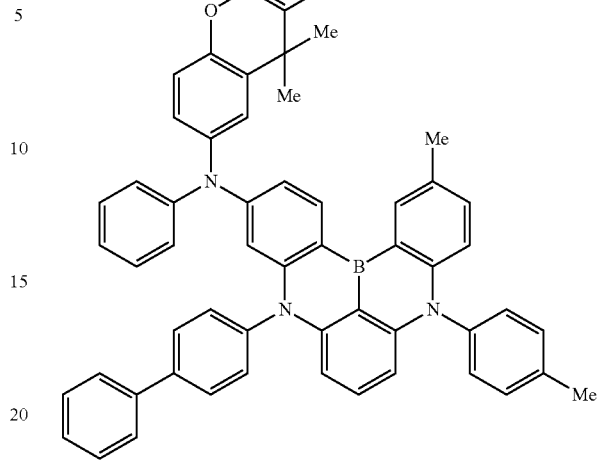
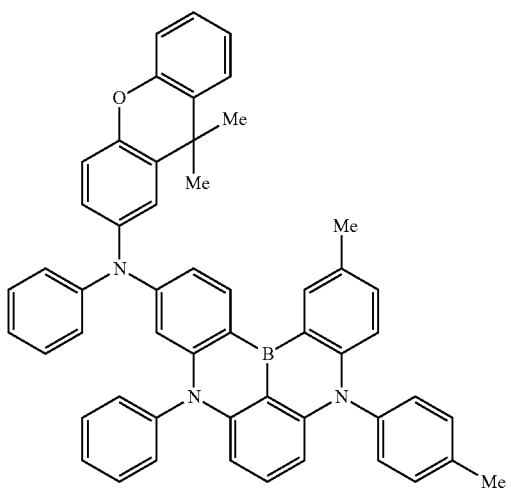
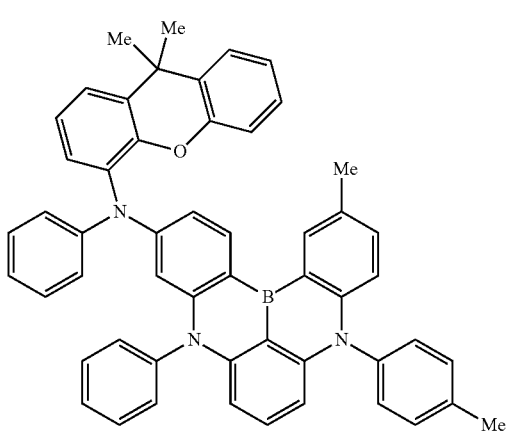
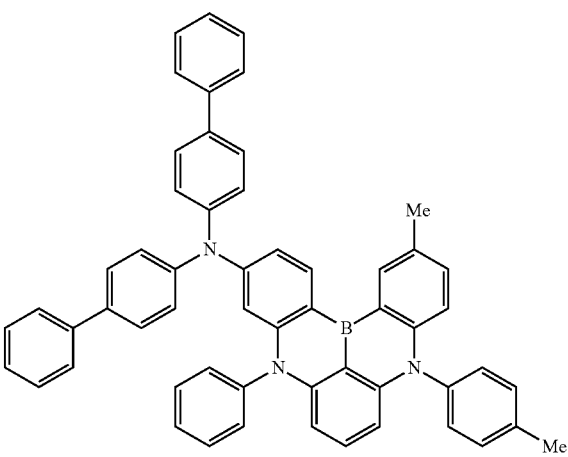

-continued
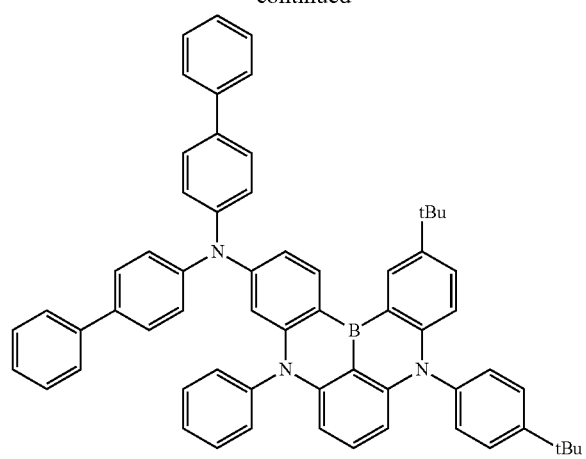
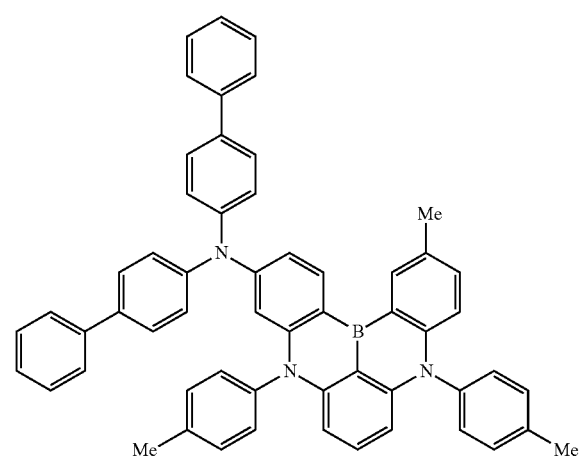
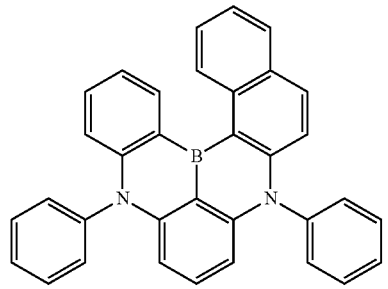
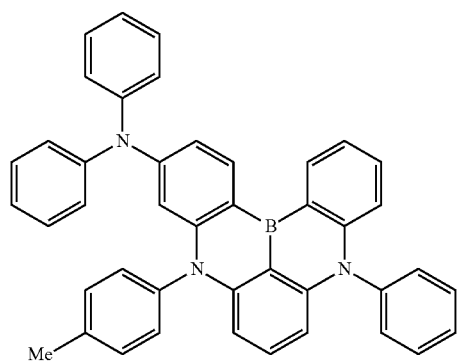
-continued
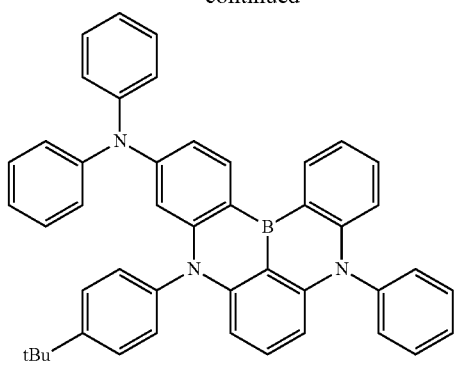
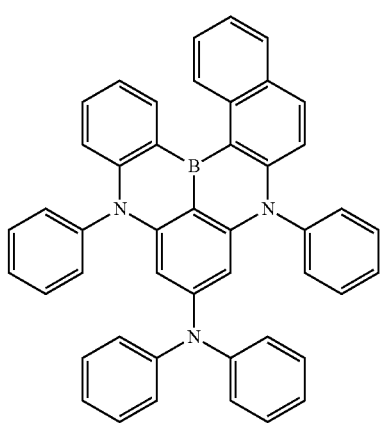
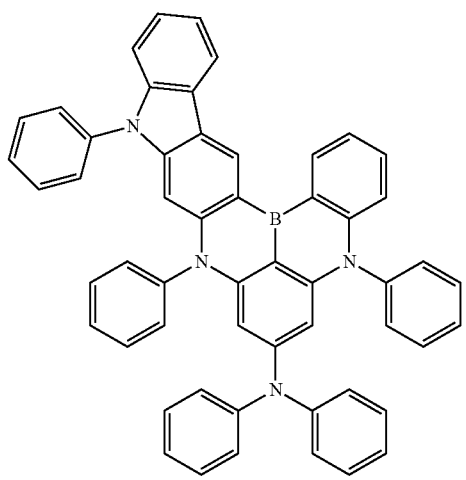
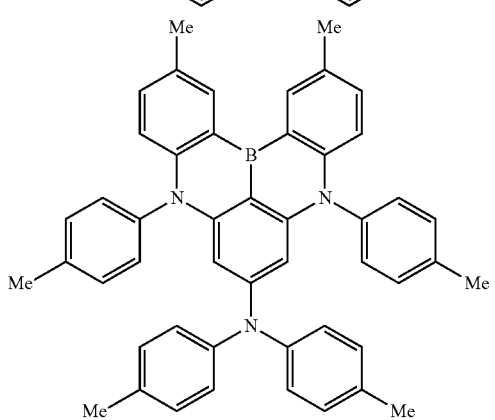

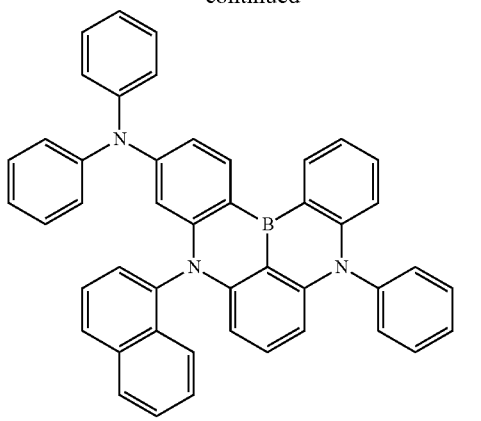
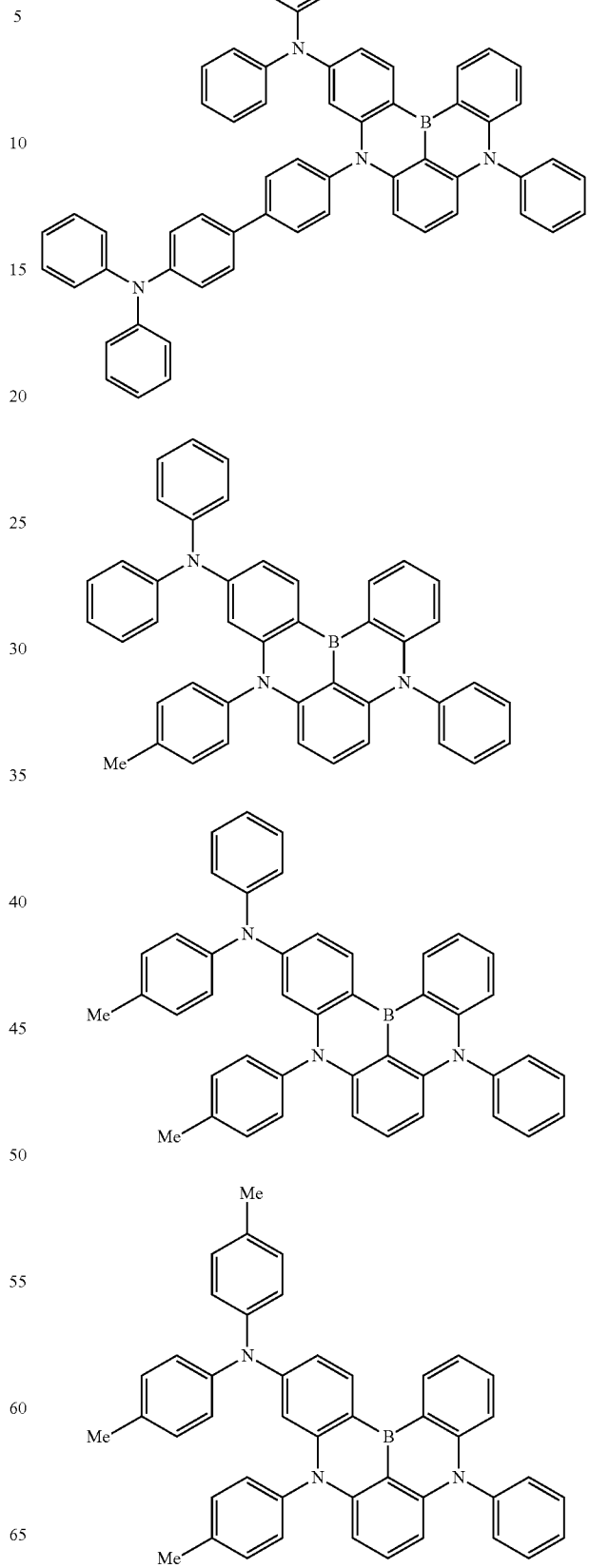

661
-continued
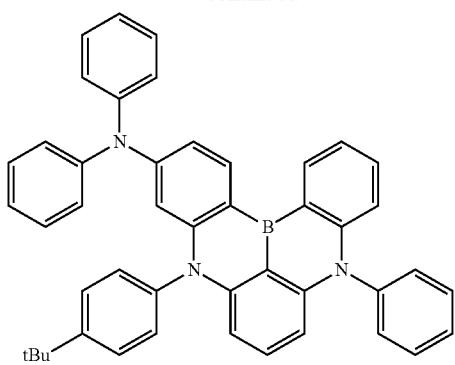
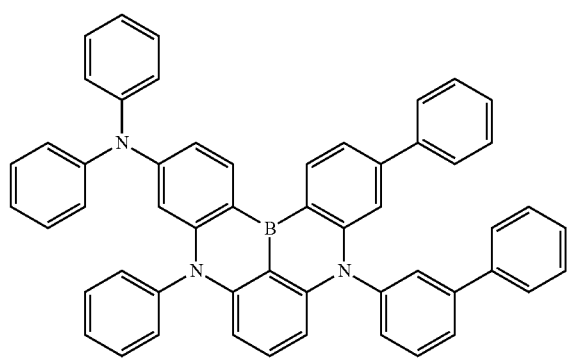
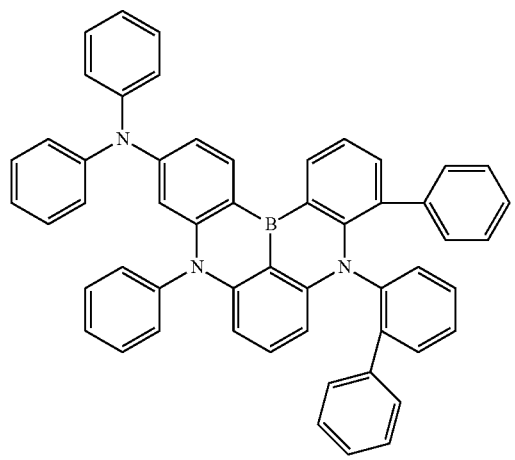
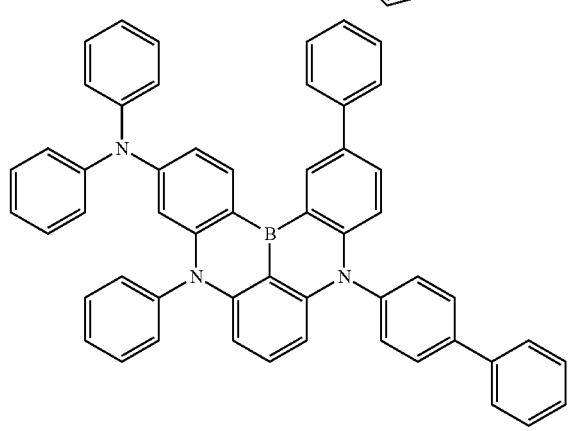
662
-continued
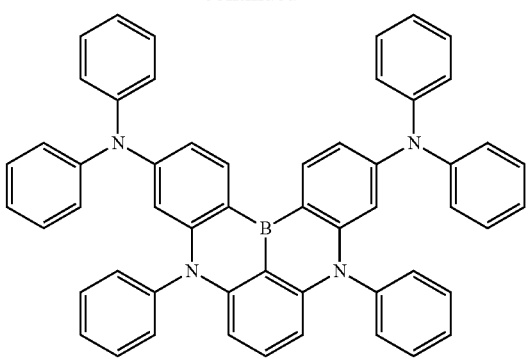
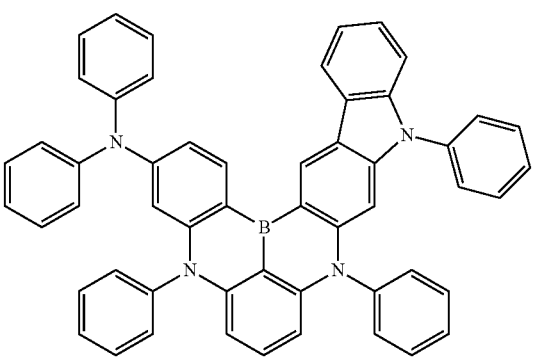
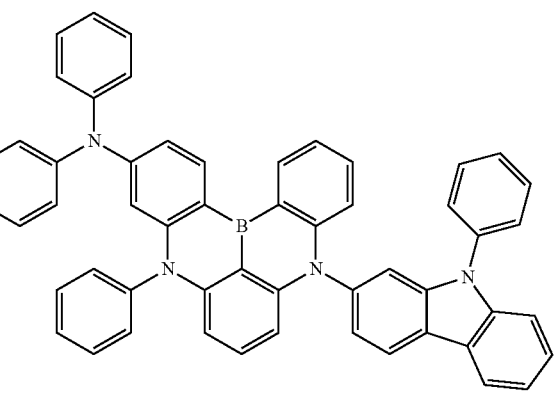
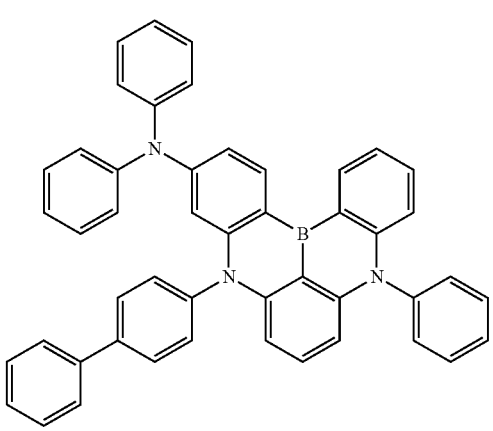

663
-continued
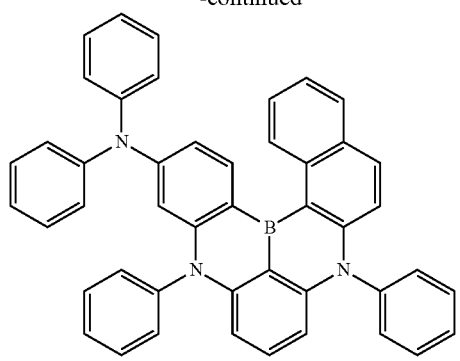
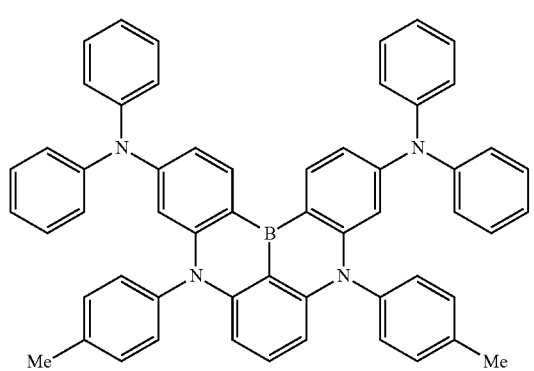
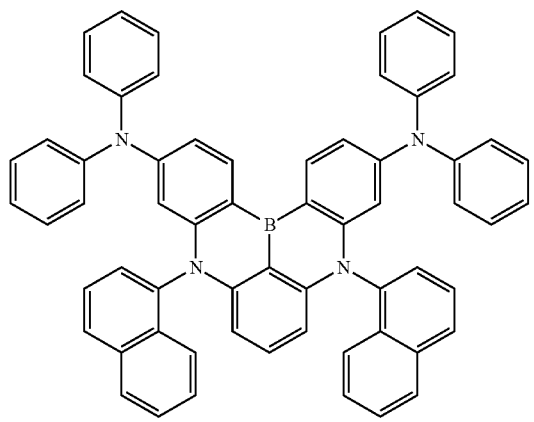
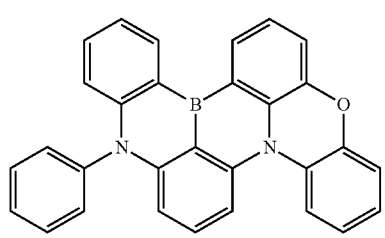
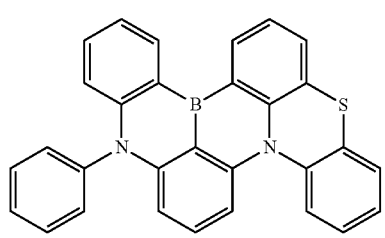
664
-continued
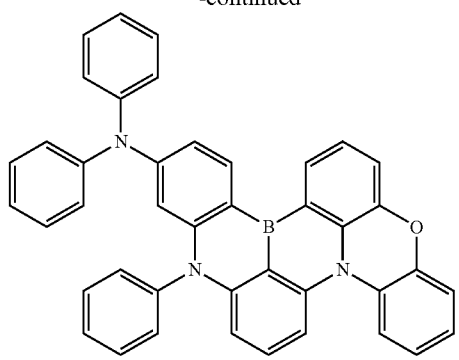
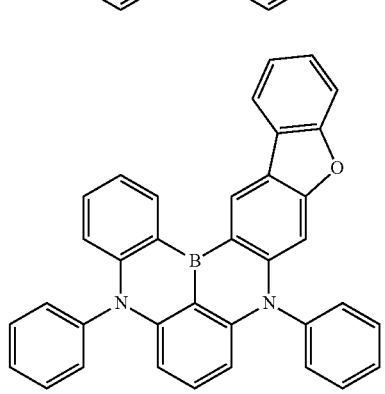
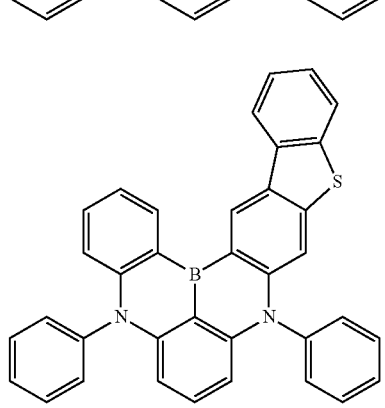
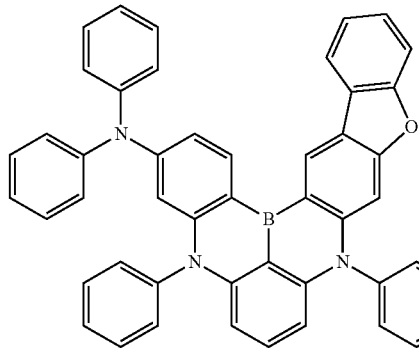
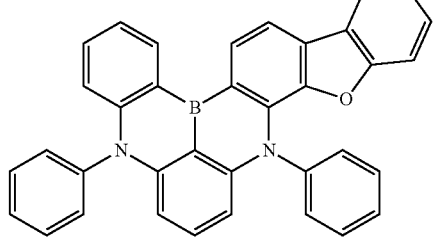

665
-continued
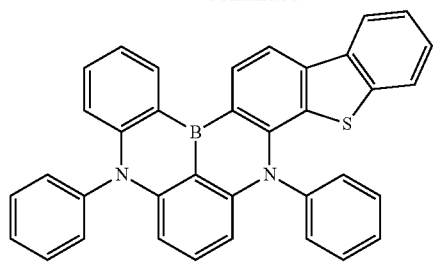
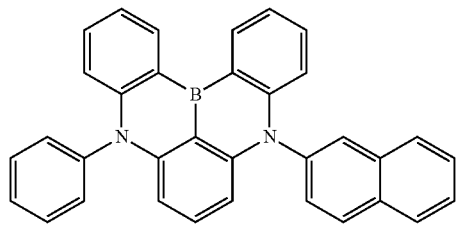
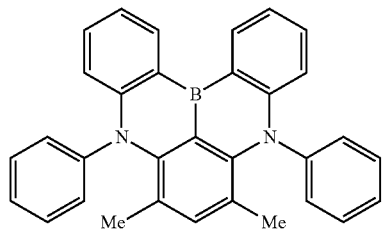
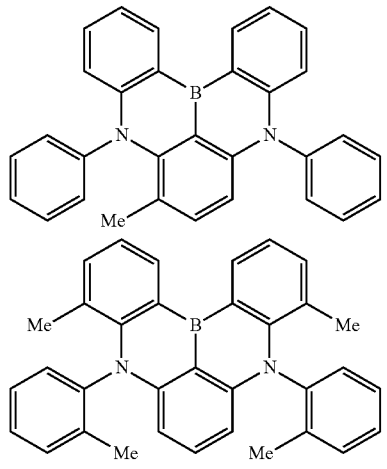
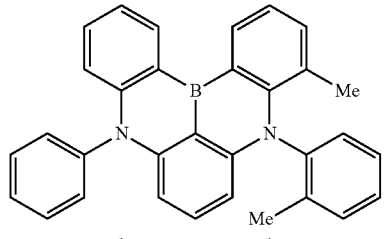
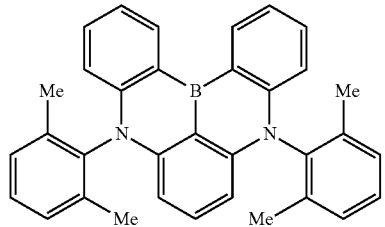
666
-continued
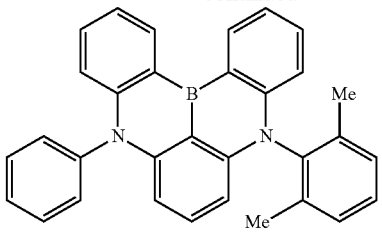
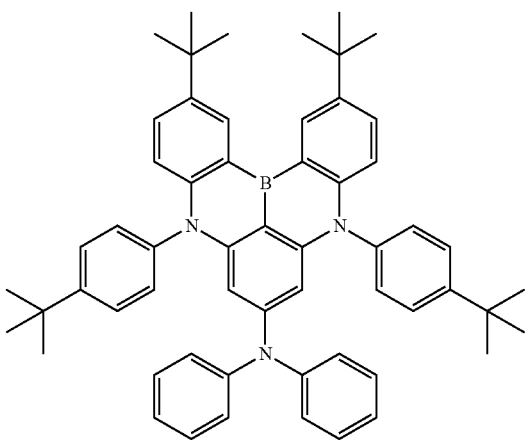
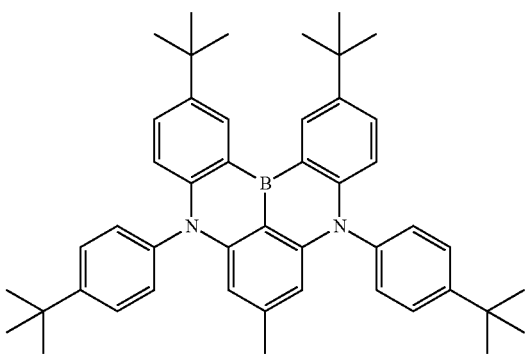
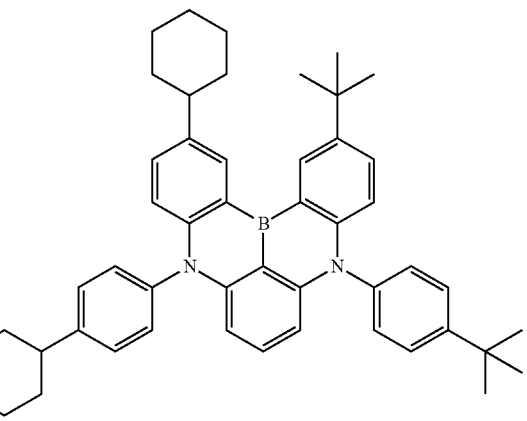

667
-continued
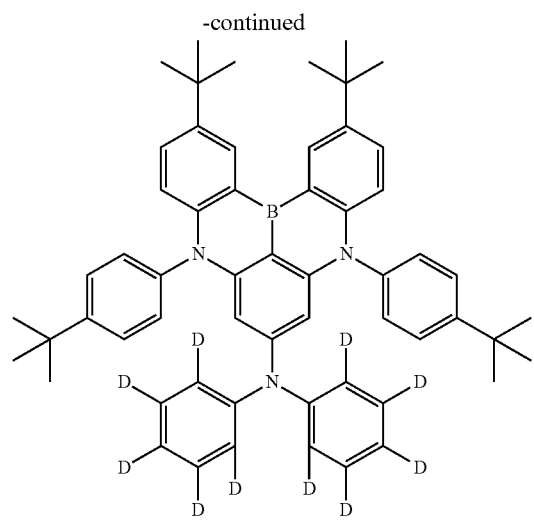
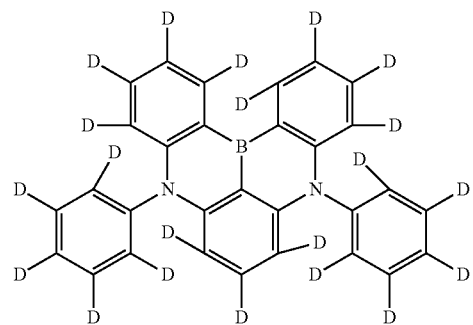
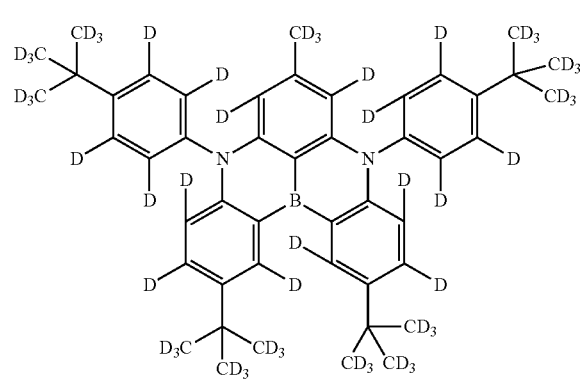
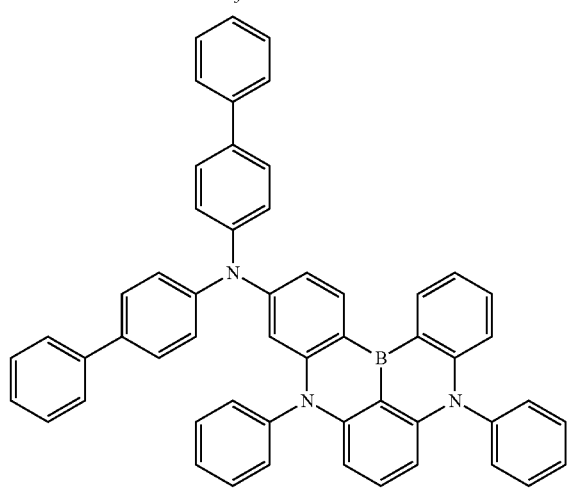
668
-continued
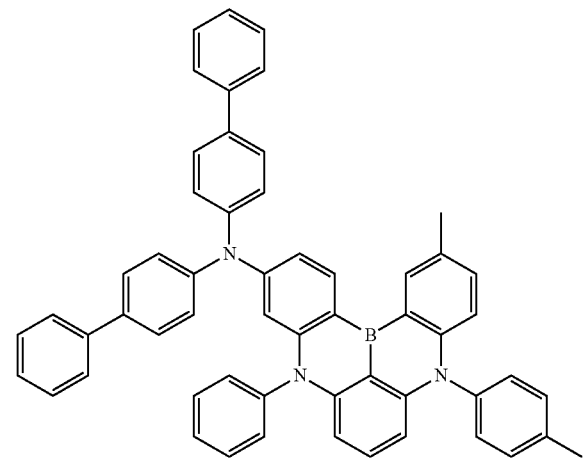
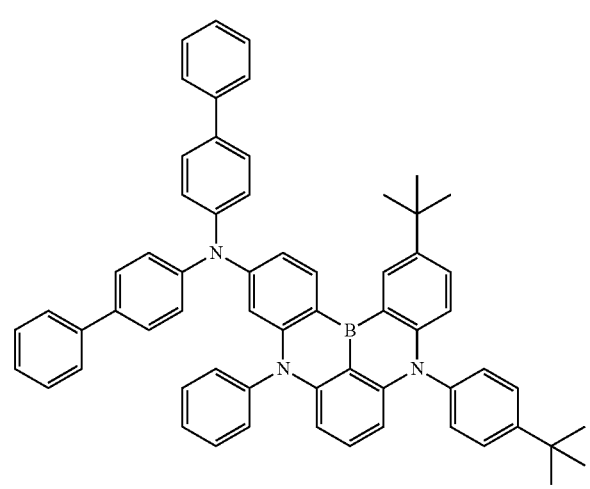
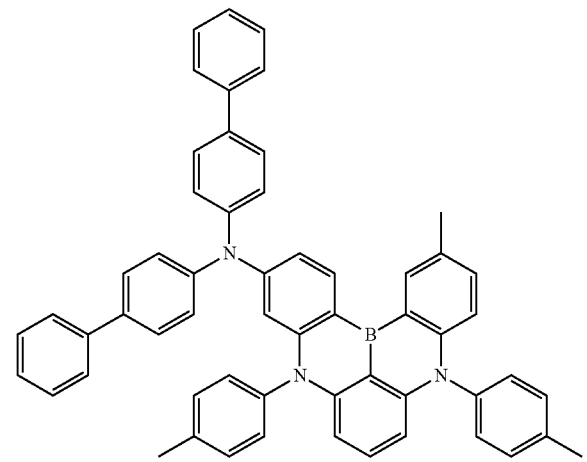

669
-continued
670
-continued
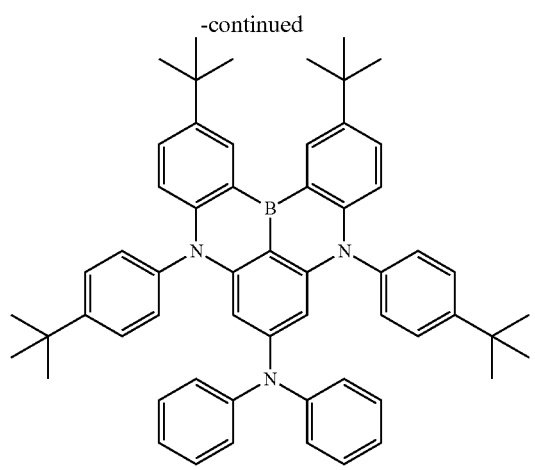
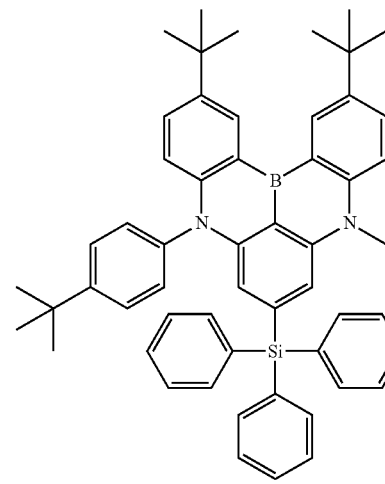
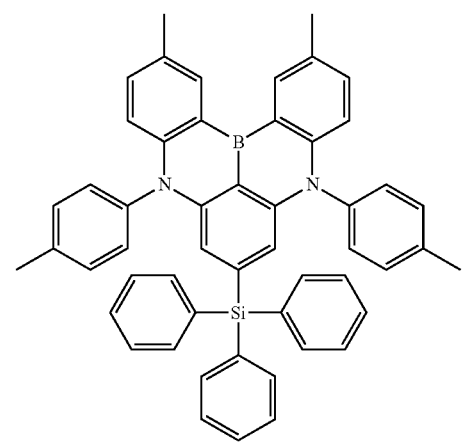
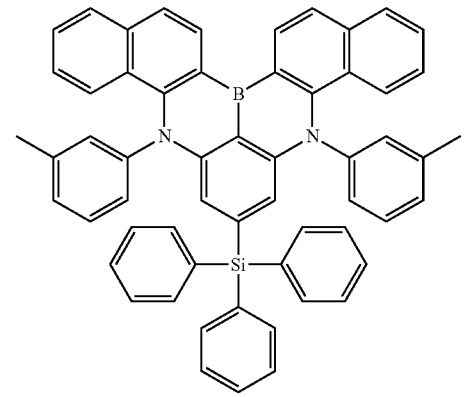

671
-continued
672
-continued
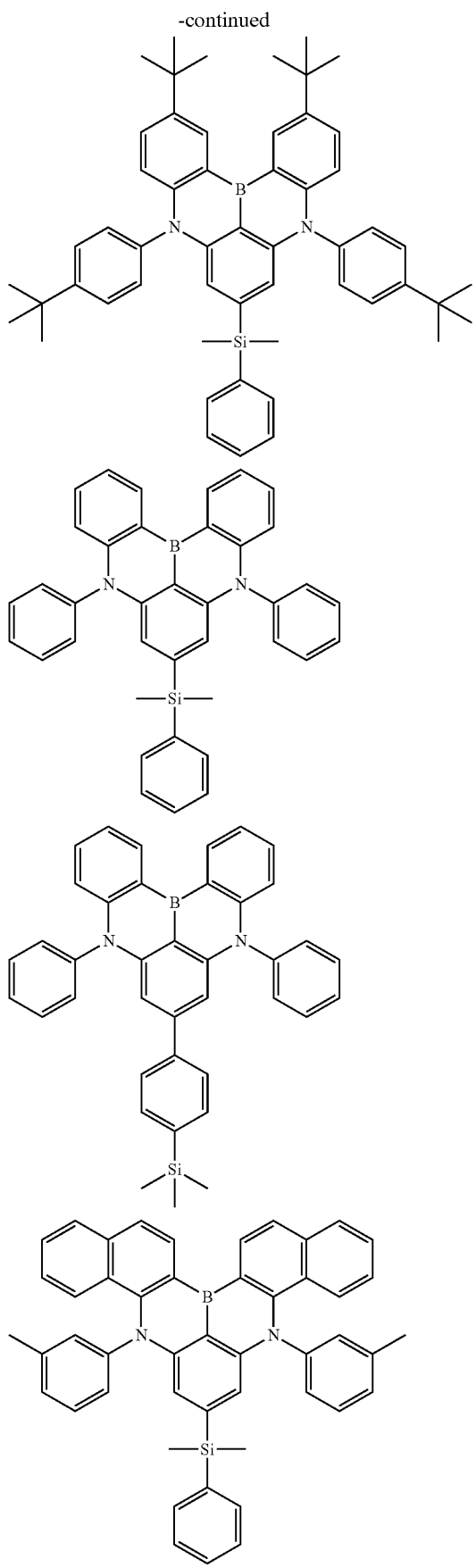
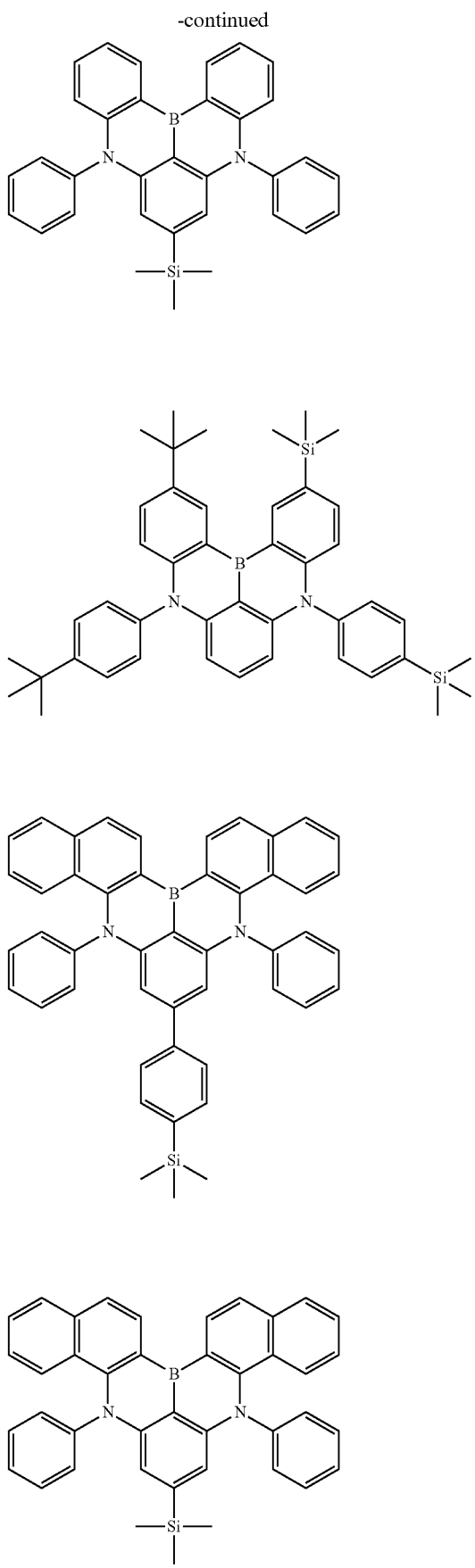

-continued
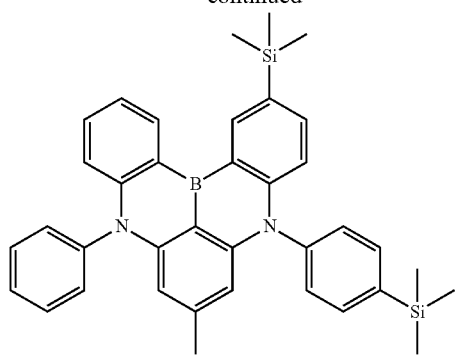
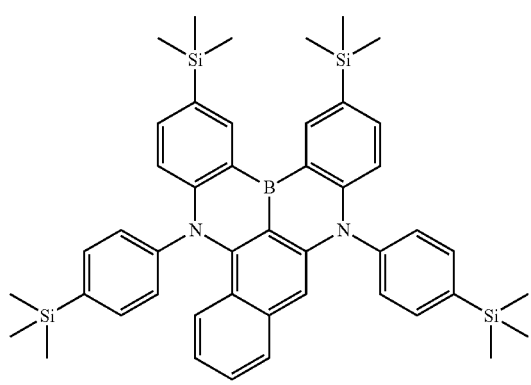
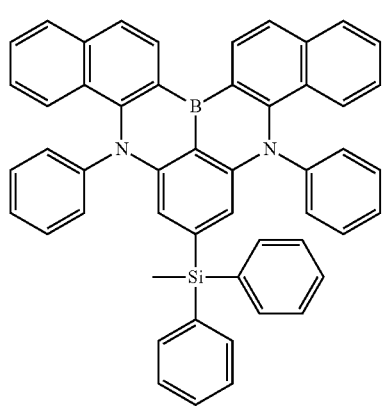
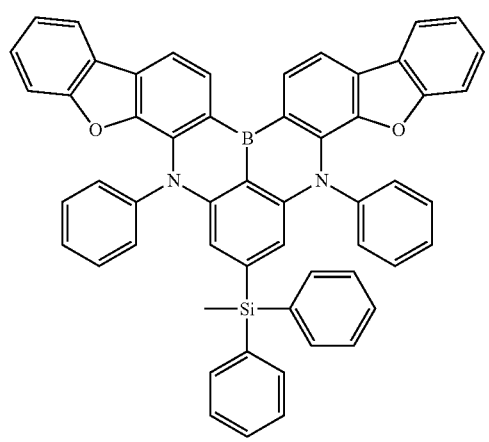
-continued
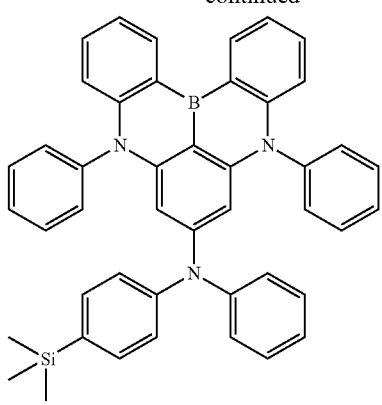
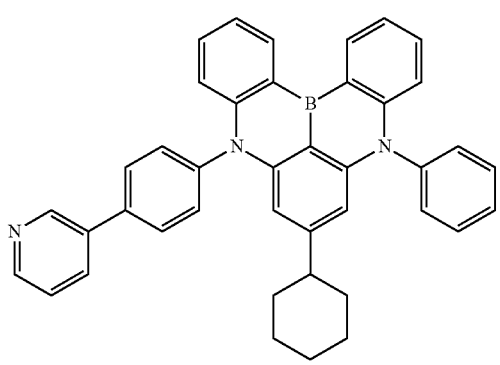
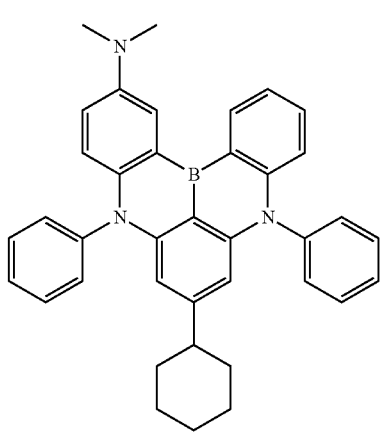

675
-continued
676
-continued
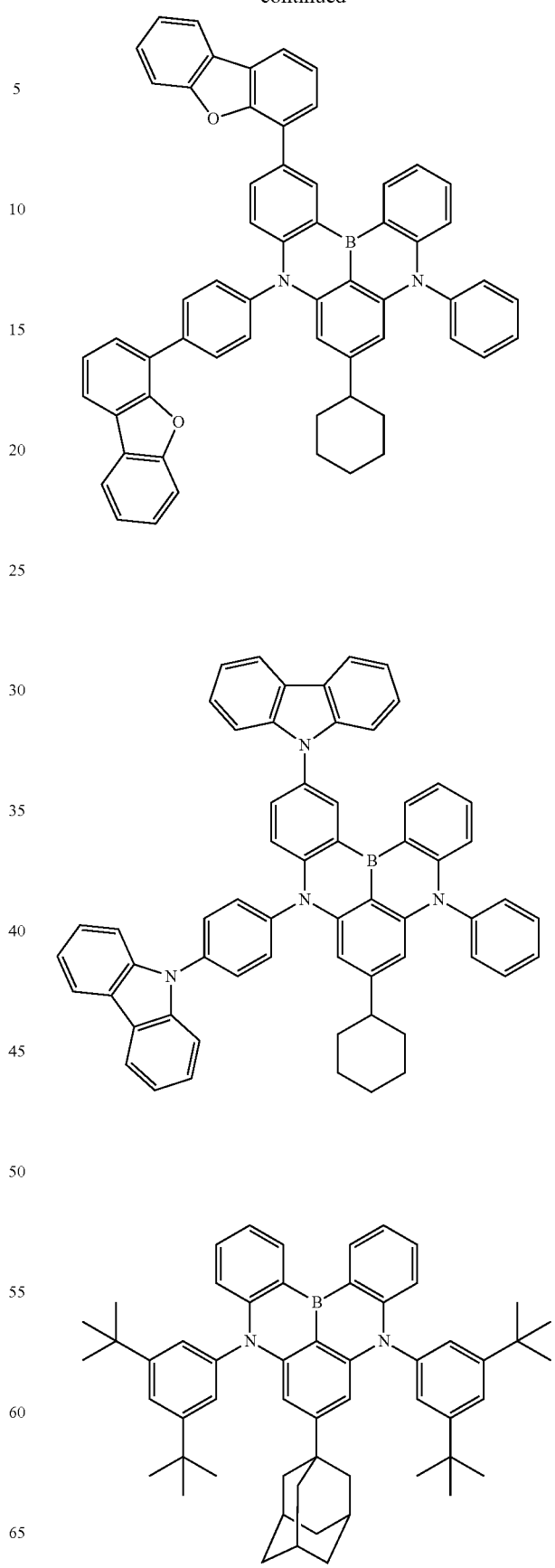

677
-continued
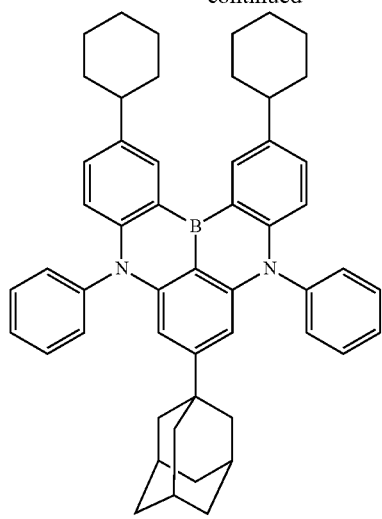
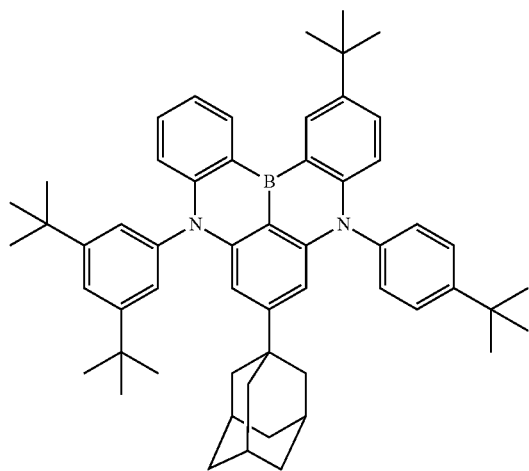
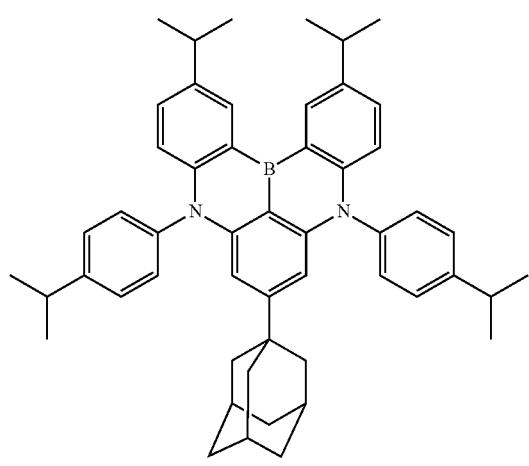
678
-continued
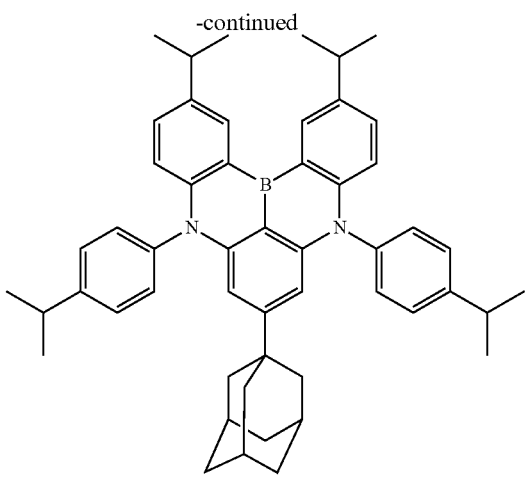
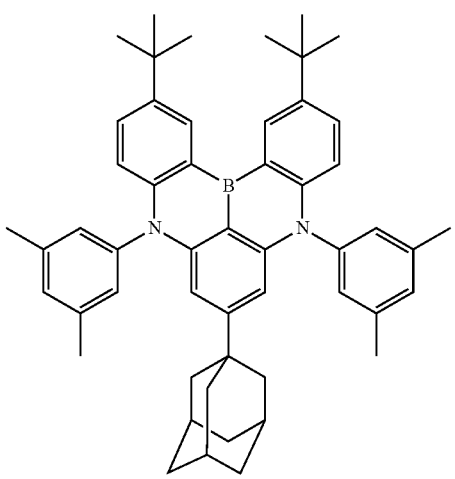
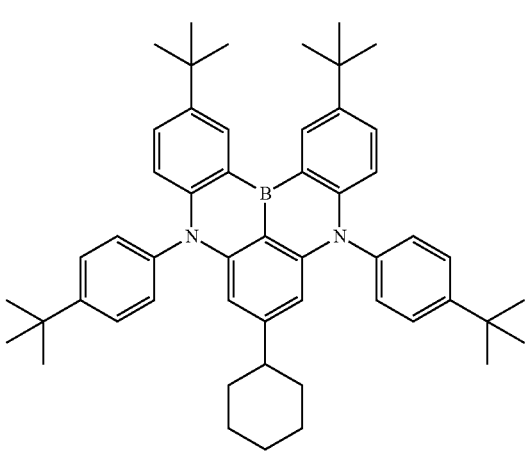

679
-continued
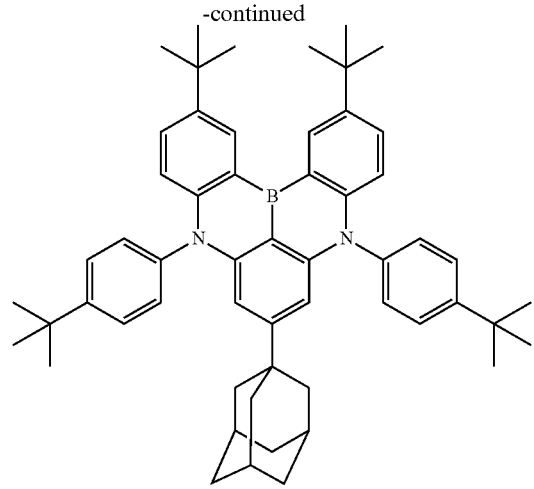
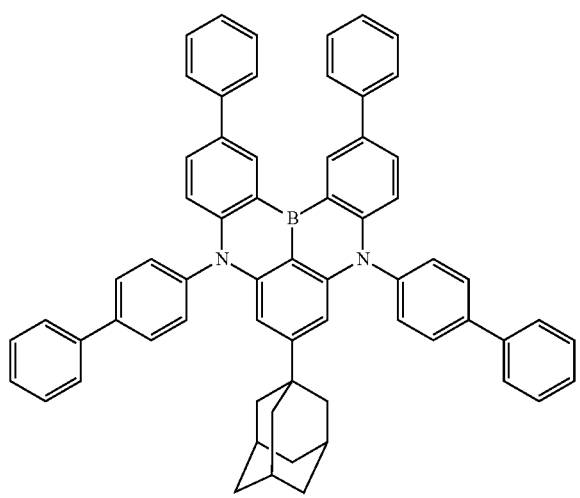
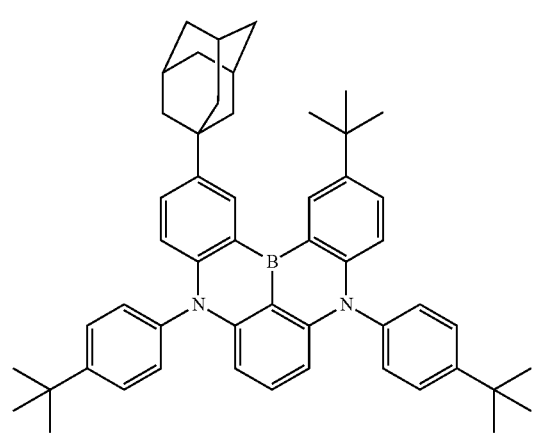
680
-continued
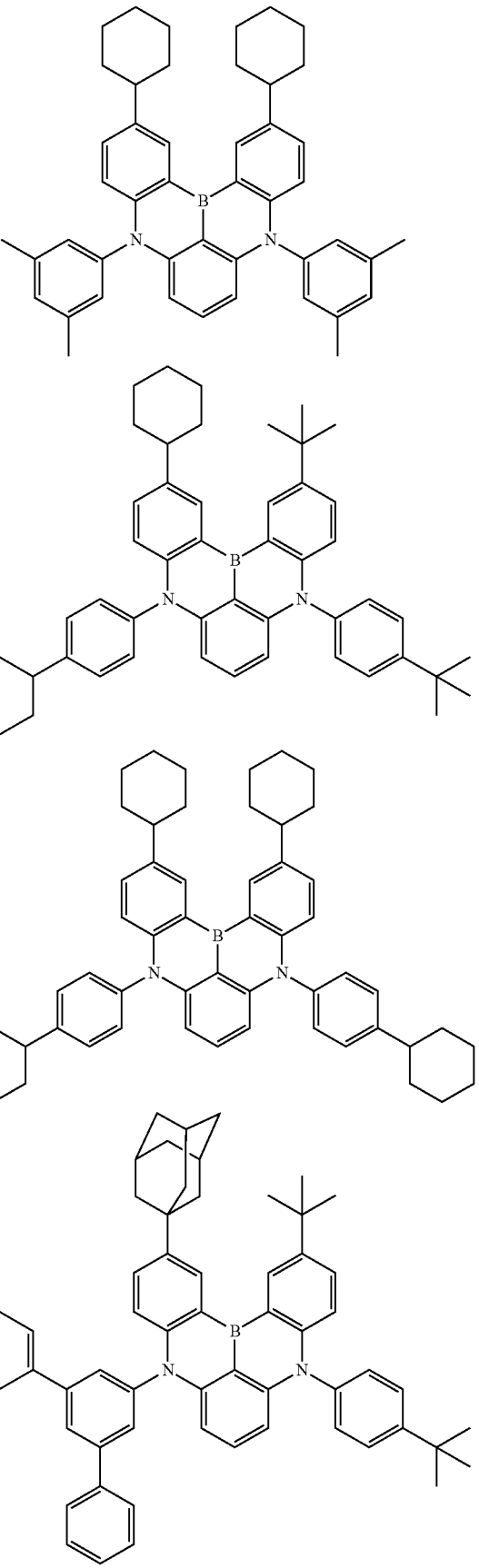

681
-continued
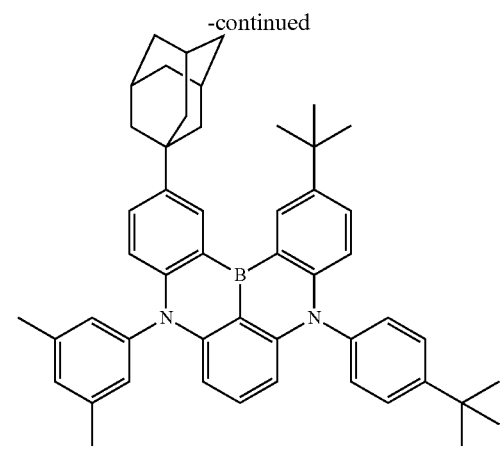
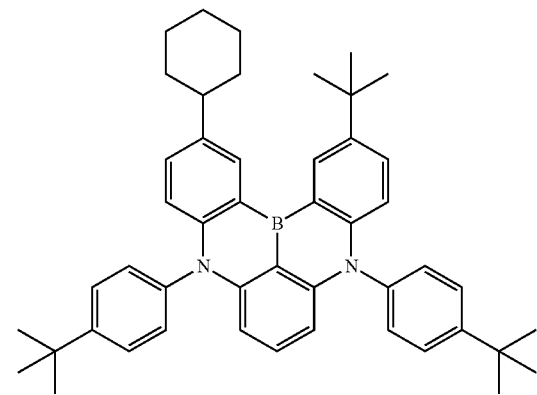
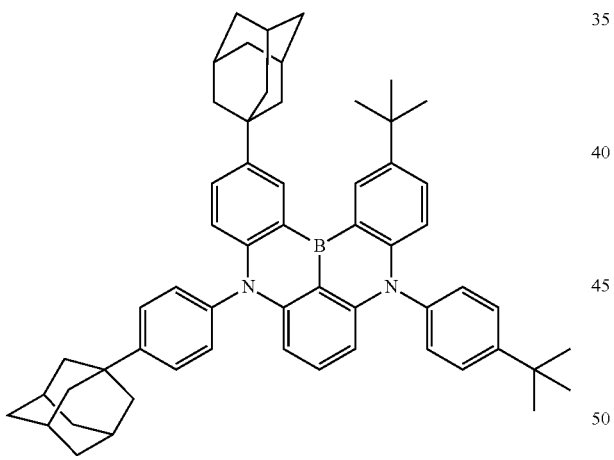
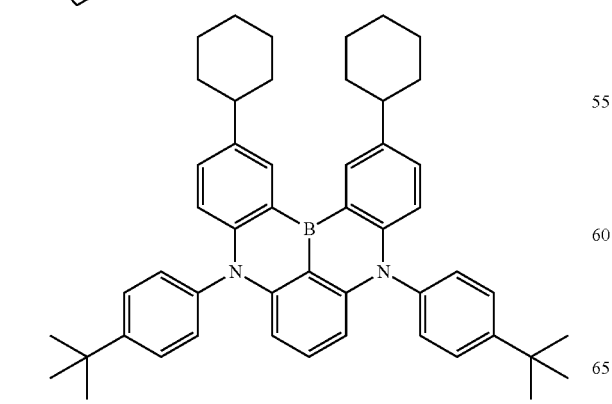
682
-continued
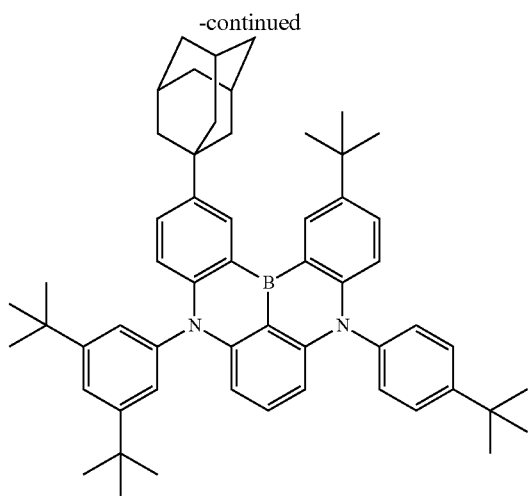
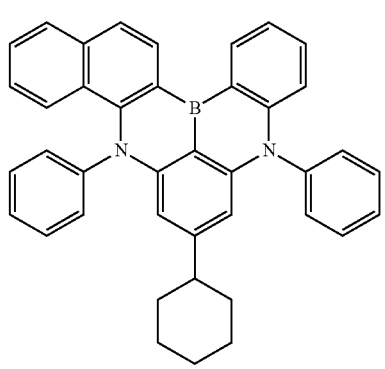
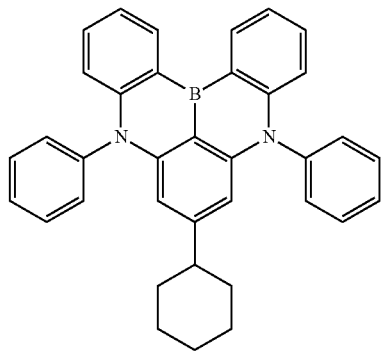
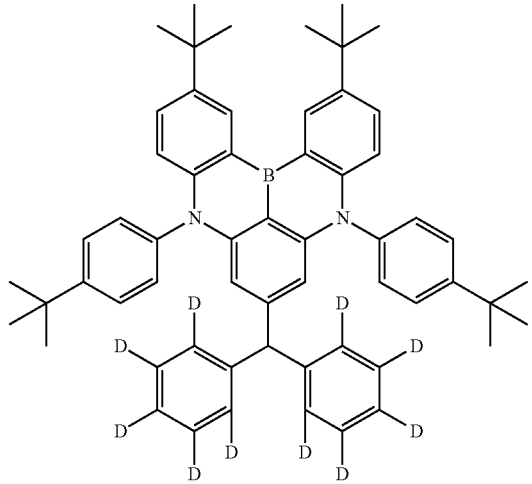

683
-continued
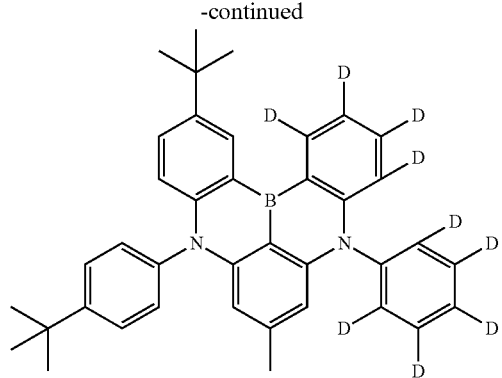
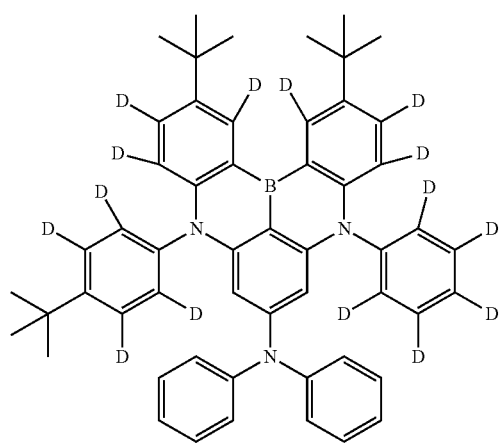
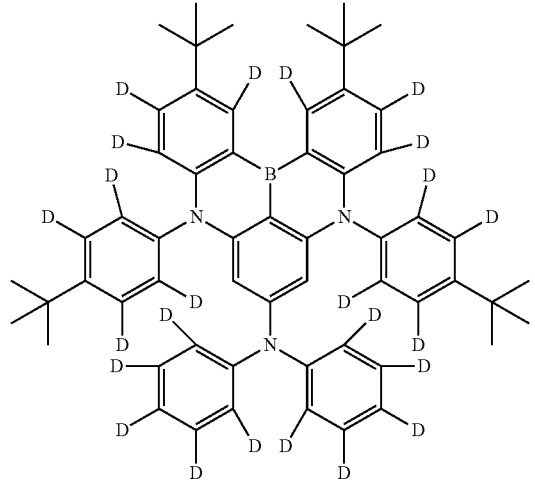
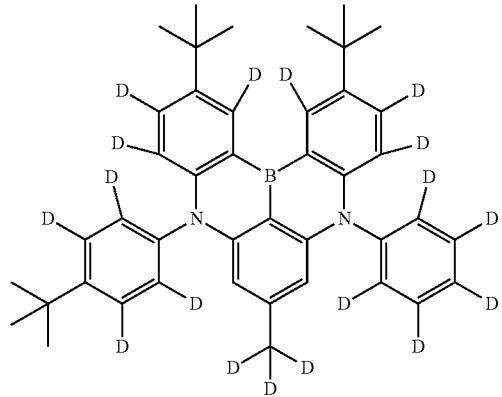
684
-continued
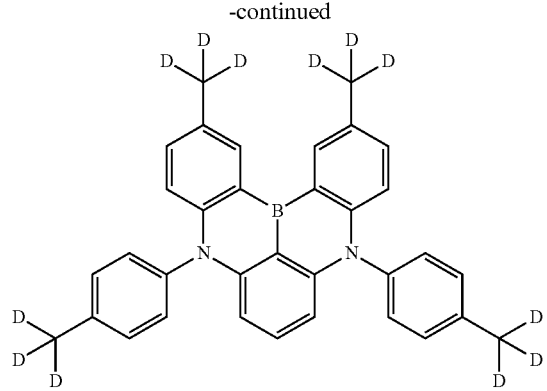
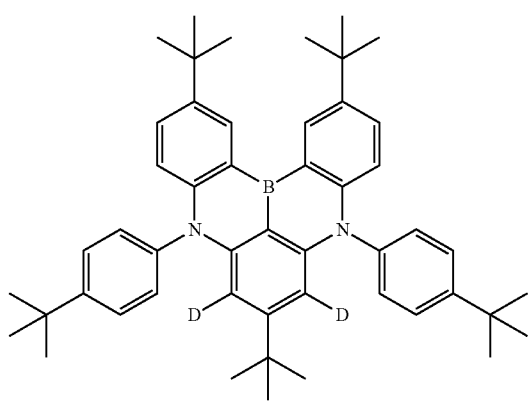
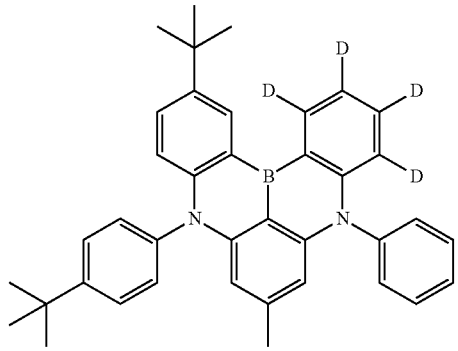
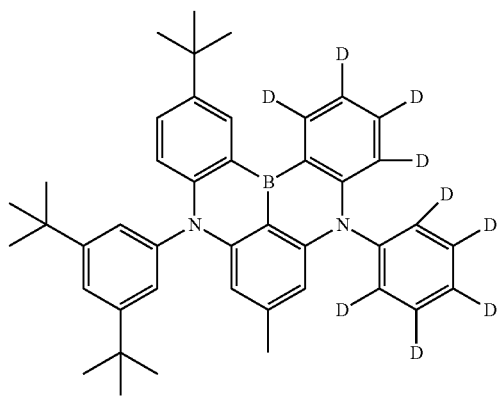

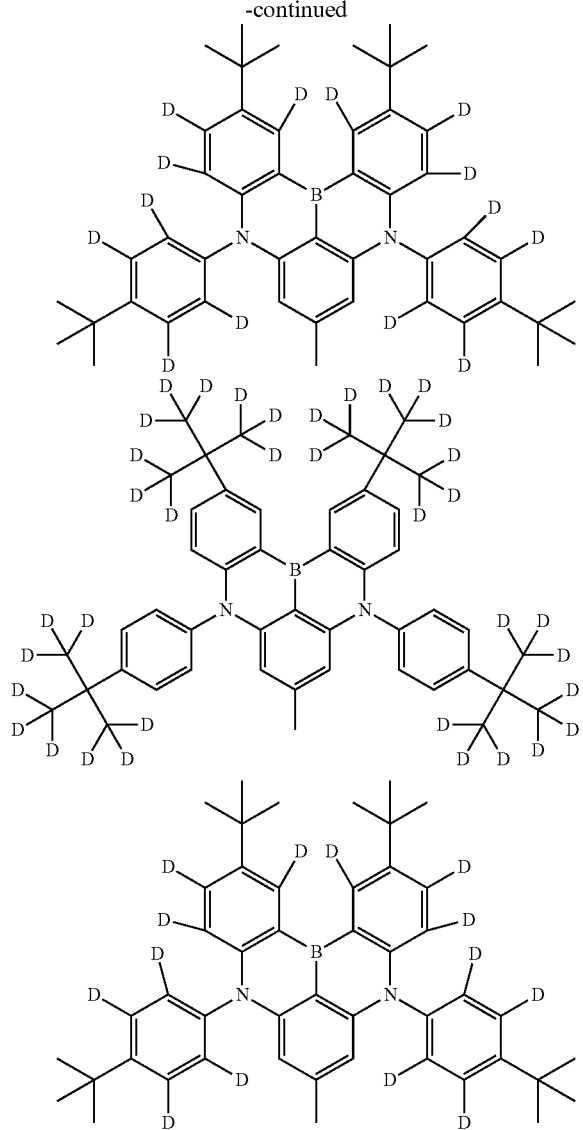

(Compound Represented by Formula (51))

The compound represented by the formula (51) is explained below.

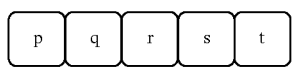

(51)

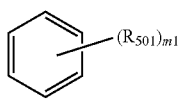

(52)

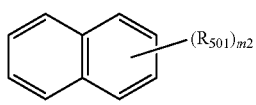

(53)

(54)

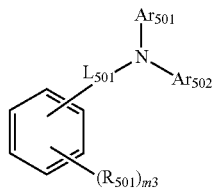

(55)

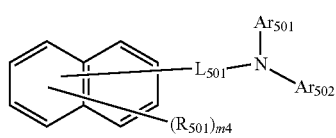

(56)

In the formula (51), r ring is a ring represented by the formula (52) or formula (53) which is fused to an adjacent ring at an arbitrary position;

q ring and s ring are independently a ring represented by the formula (54) which is fused to an adjacent ring at an arbitrary position;

p ring and t ring are independently a ring represented by the formula (55) or the formula (56) which is fused to an adjacent ring at an arbitrary position;

when plural $R_{901}$'s exist, adjacent plural $R_{901}$'s are bonded with each other to form a substituted or unsubstituted, saturated or unsaturated ring, or do not form a substituted or unsubstituted, saturated or unsaturated ring;

$X_{501}$ is an oxygen atom, a sulfur atom, or $NR_{502}$;

$R_{501}$ and $R_{502}$ that do not form the substituted or unsubstituted saturated or unsaturated ring are a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms;

$R_{901}$ to $R_{907}$ are as defined in the formula (1);

$Ar_{501}$ and $Ar_{502}$ are independently a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms;

$L_{501}$ is a substituted or unsubstituted alkylene group including 1 to 50 carbon atoms, a substituted or unsubstituted alkenylene group including 2 to 50 carbon atoms, a substituted or unsubstituted alkynylene group including 2 to 50 carbon atoms, a substituted or unsubstituted cycloalkylene group including 3 to 50 ring carbon atoms, a substituted or unsubstituted arylene group including 6 to 50 ring carbon atoms, or a substituted or unsubstituted divalent heterocyclic group including 5 to 50 ring atoms;

m1 is independently an integer of 0 to 2, m2 is independently an integer of 0 to 4, m3 is independently an integer of 0 to 3, and m4 is independently an integer of 0 to 5; when plural $R_{901}$'s exist, the plural $R_{901}$'s may be the same or different;

In the formula (51), each of the p ring to the t ring is fused to an adjacent ring by sharing two carbon atoms. The position and direction of fusing are not limited, and condensation is possible at any position and direction.

In one embodiment, in the formula (52) or (53) of the r ring, $R_{501}$ is a hydrogen atom.

In one embodiment, the compound represented by the formula (51) is represented by any one of the following formulas (51-1) to (51-6).

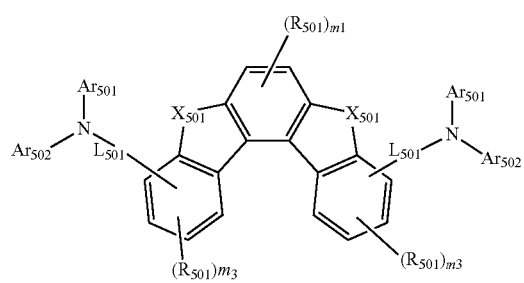

(51-1)

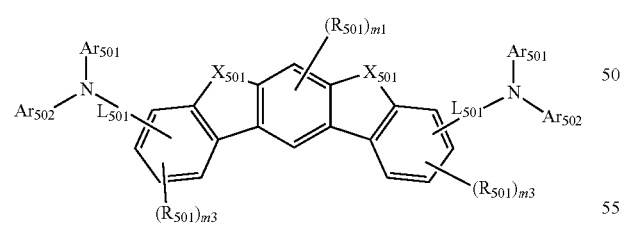

(51-2)

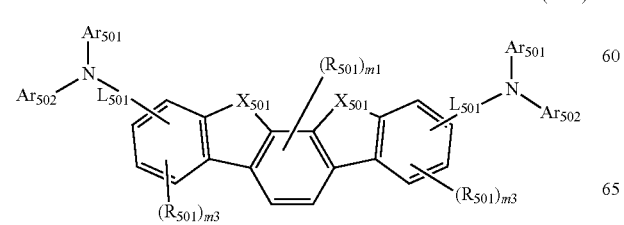

(51-3)

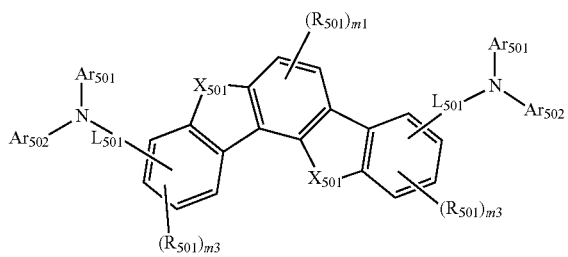

(51-4)

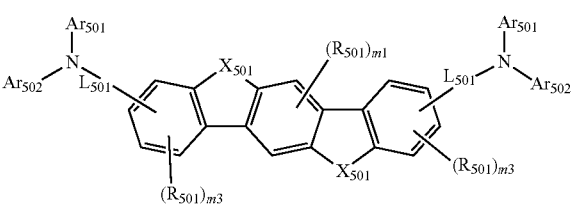

(51-5)

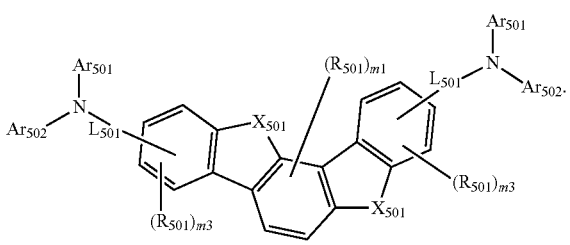

(51-6)

In the formulas (51-1) to (51-6), $R_{501}$, $X_{501}$, $Ar_{501}$, $Ar_{502}$, $L_{501}$, m1 and m3 are as defined in the formula (51).

In one embodiment, the compound represented by the formula (51) is represented by any one of the following formulas (51-11) to (51-13).

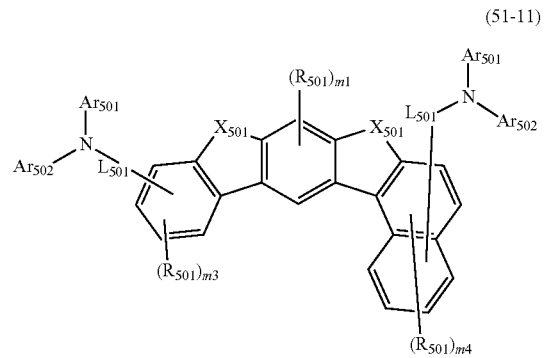

(51-11)

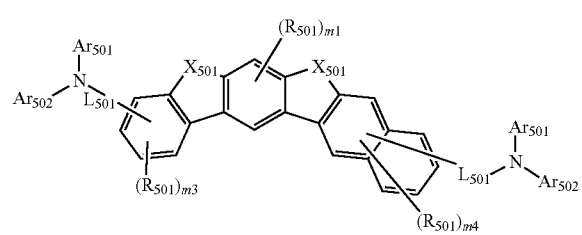

(51-12)

-continued
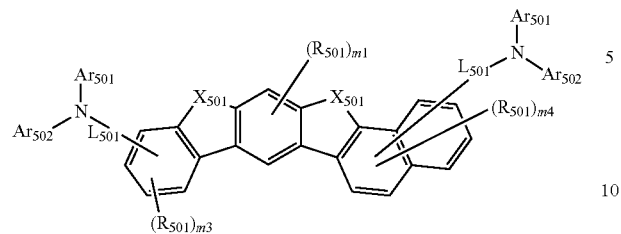
(51-13)
In the formulas (51-11) to (51-13), $R_{501}$, $X_{501}$, $Ar_{501}$, $Ar_{502}$, $L_{501}$, m1, m3 and m4 are as defined in the formula (51).
In one embodiment, the compound represented by the formula (51) is represented by any one of the following formulas (51-21) to (51-25).
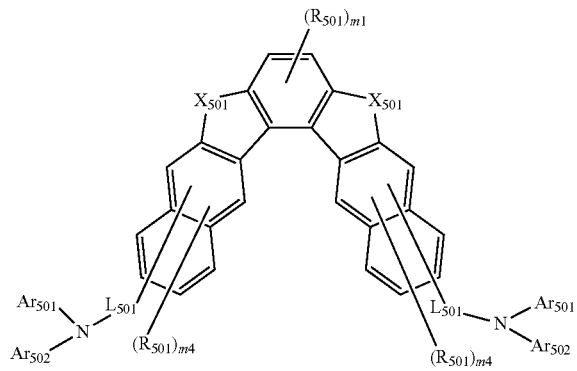
(51-21)
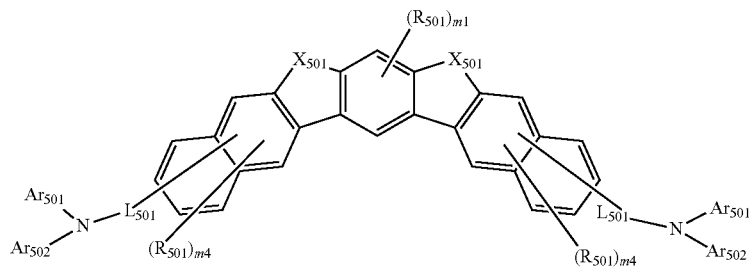
(51-22)
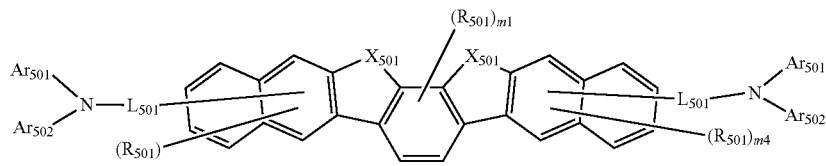
(51-23)
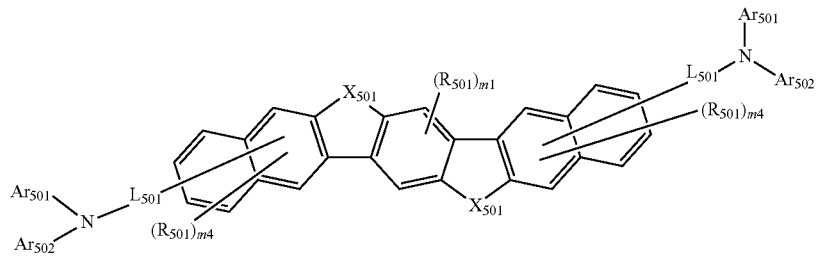
(51-24)

-continued (51-25)

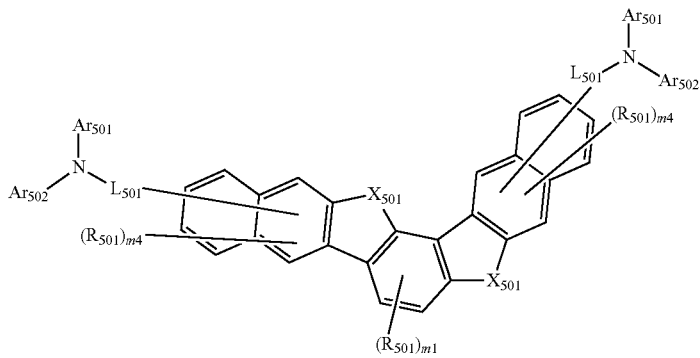

In the formulas (51-21) to (51-25), $R_{501}$, $X_{501}$, $Ar_{501}$, $Ar_{502}$, $L_{501}$, m1 and m4 are as defined in the formula (51).

In one embodiment, the compound represented by the formula (51) is represented by any one of the following formulas (51-31) to (51-33).

(51-31)

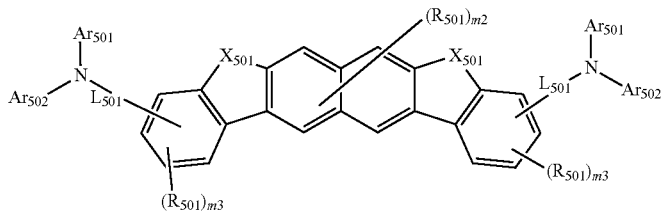

(51-32)

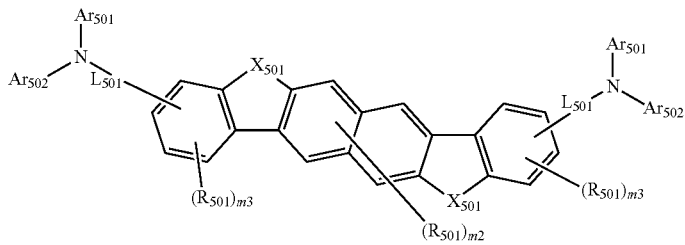

(51-33)

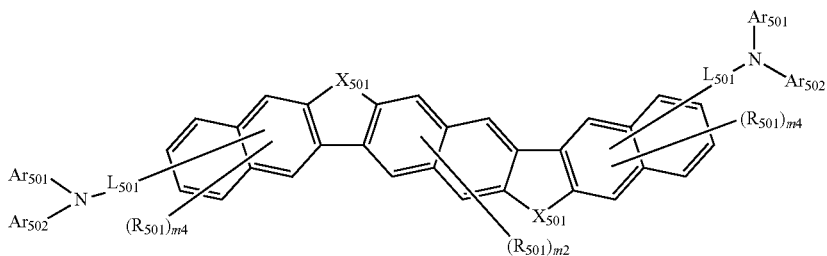

In the formulas (51-31) to (51-33), $R_{501}$, $X_{501}$, $Ar_{501}$, $Ar_{502}$, $L_{501}$, m2 to m4 are as defined in the formula (51).

In one embodiment, $Ar_{501}$ and $Ar_{502}$ are independently a substituted or unsubstituted aryl group including 6 to 50 ring carbon atoms.

In one embodiment, one of $Ar_{501}$ and $Ar_{502}$ is a substituted or unsubstituted aryl group including 6 to 50 ring carbon atoms and the other is a substituted or unsubstituted monovalent heterocyclic ring including 5 to 50 ring atoms.

As examples of the compound represented by the formula (51), the following compounds can be given, for example. In the following example compounds, Me represents methyl group.

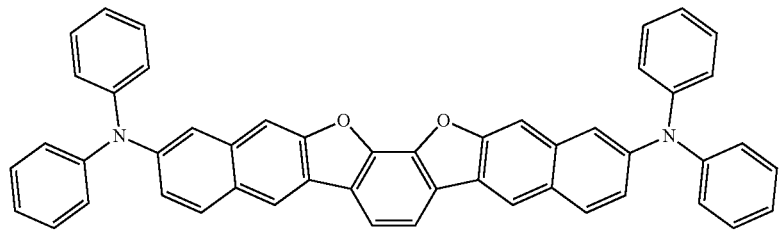
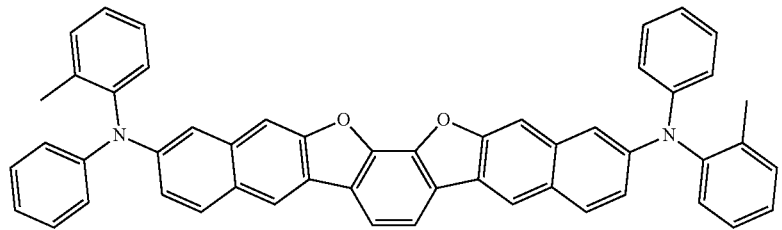
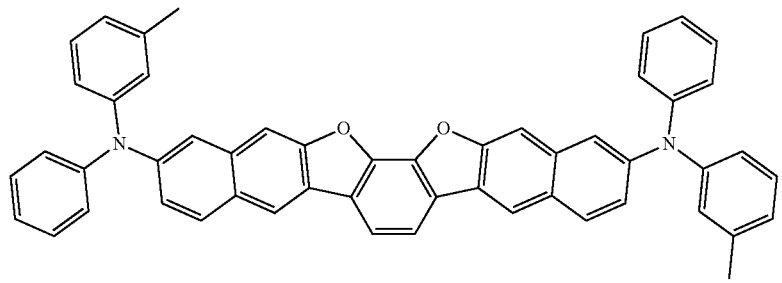
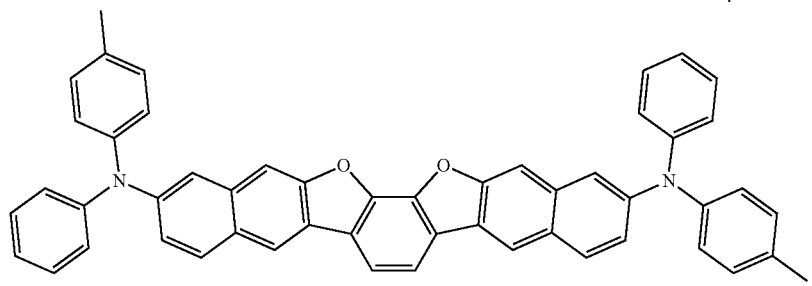
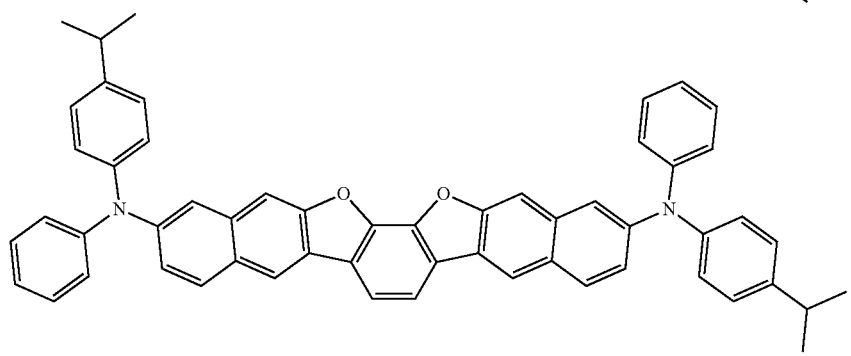
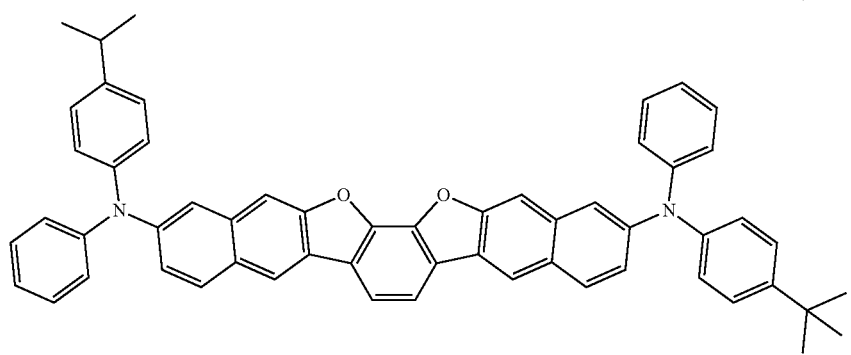

-continued
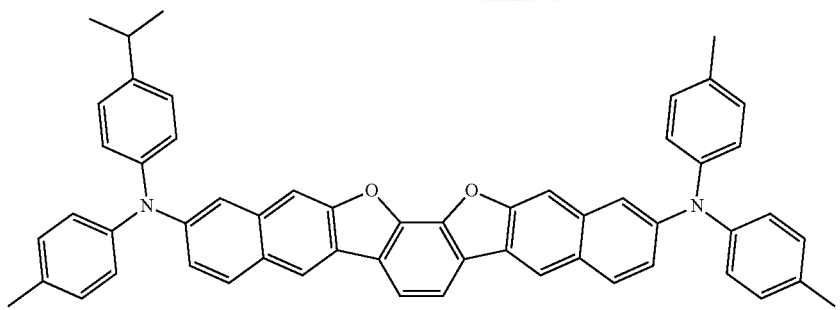
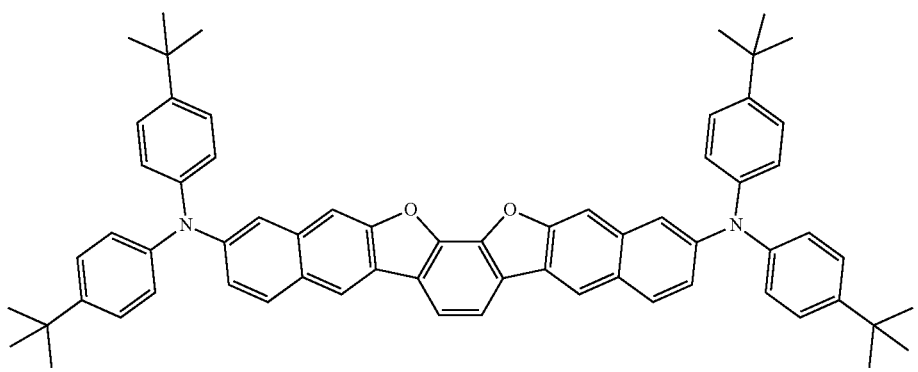
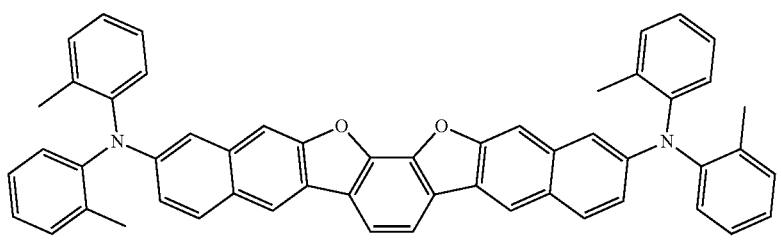
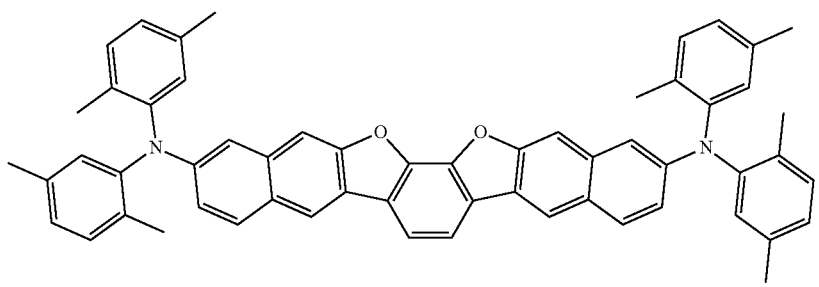
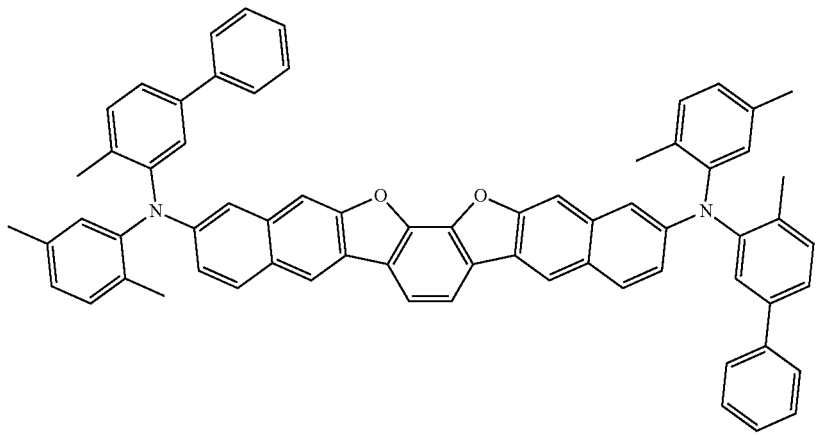

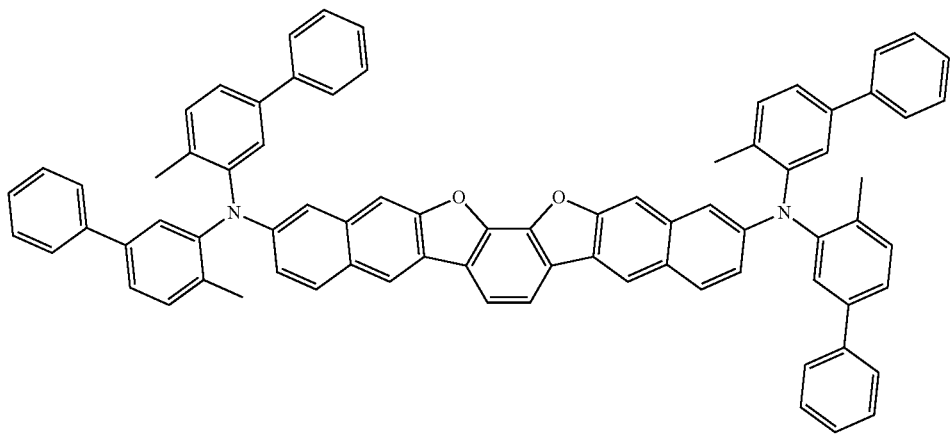
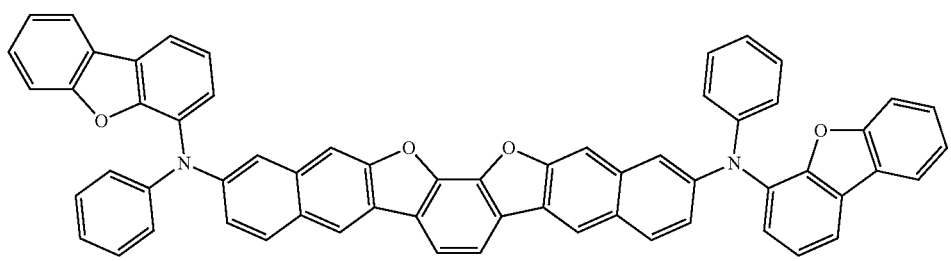
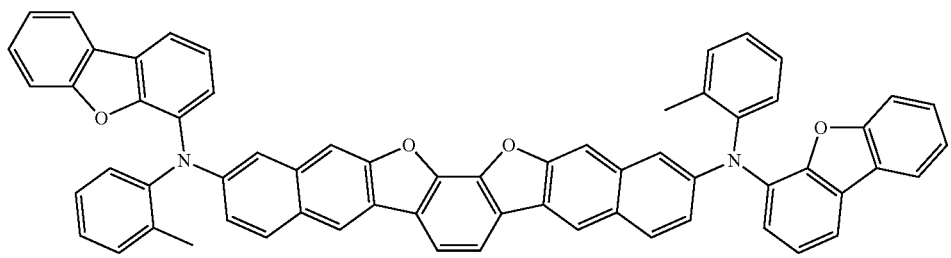
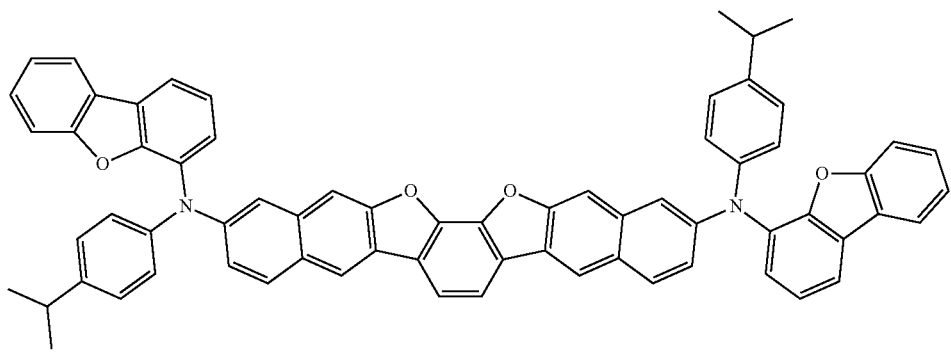
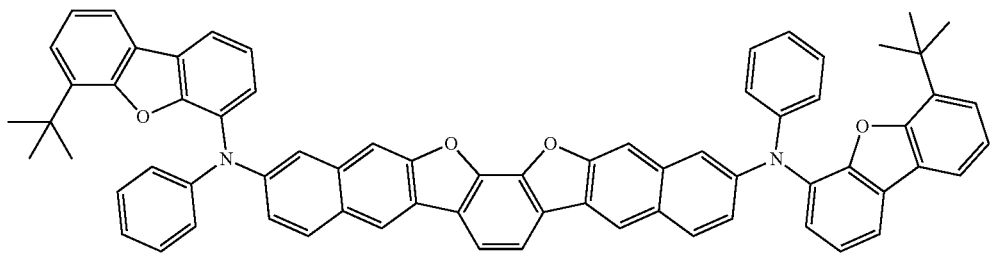

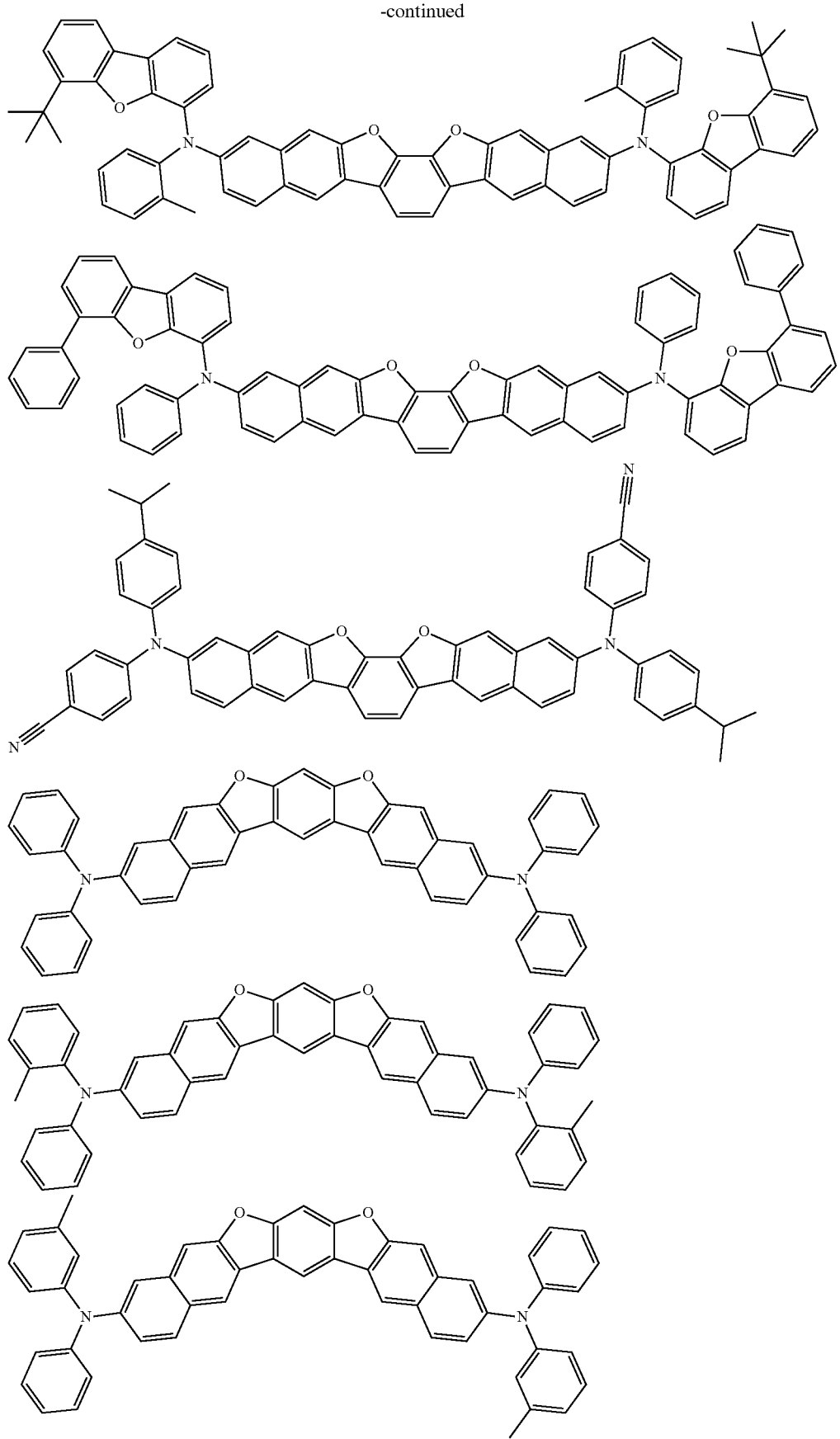

-continued
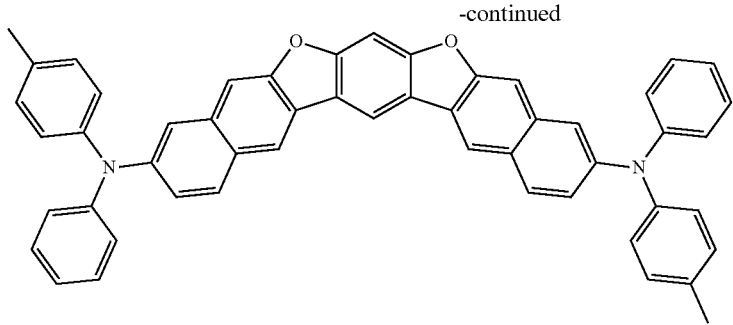
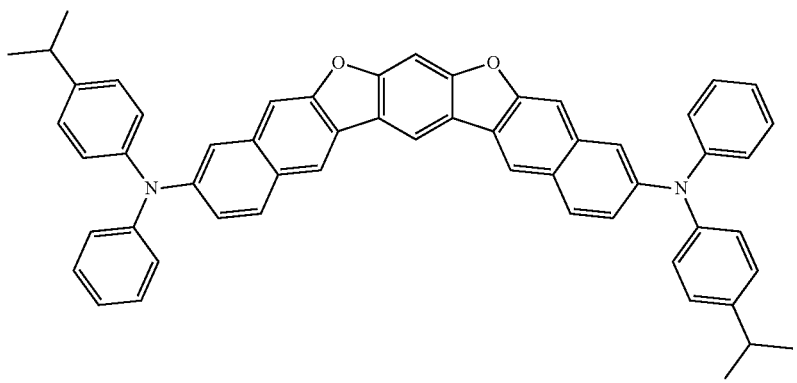
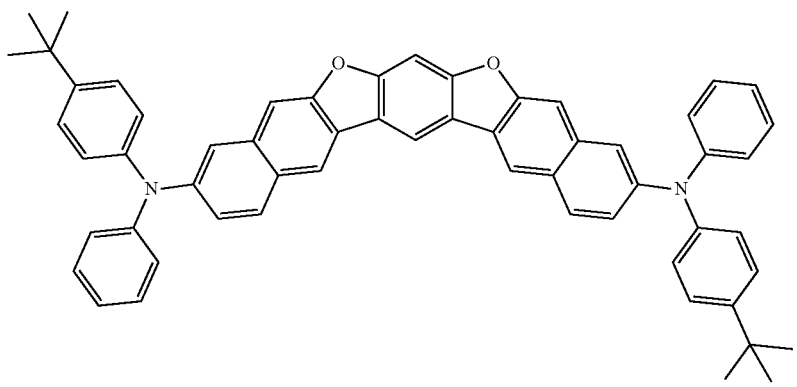
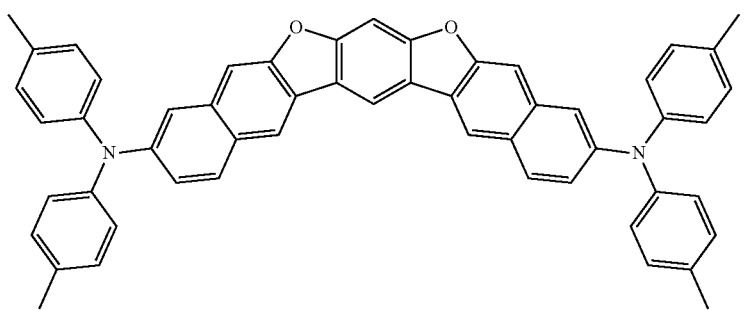

703
-continued
704
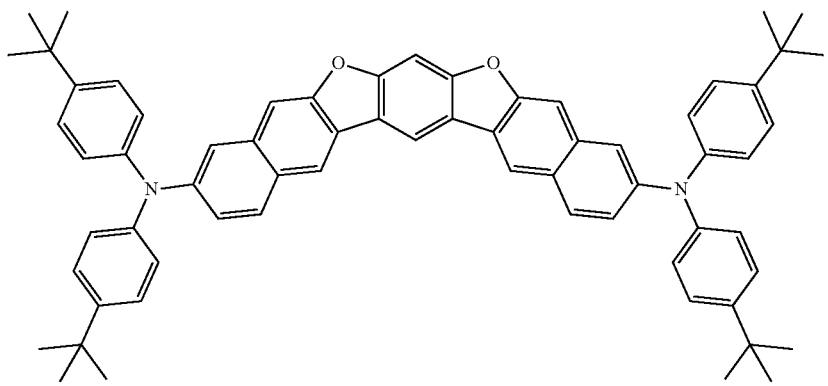
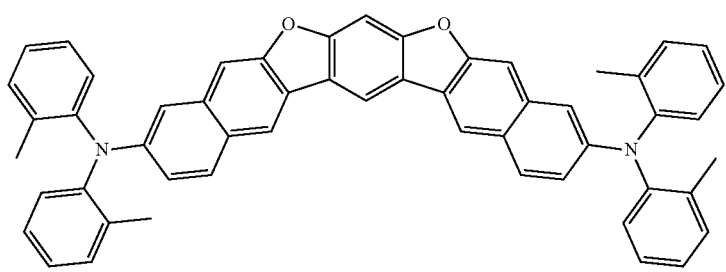
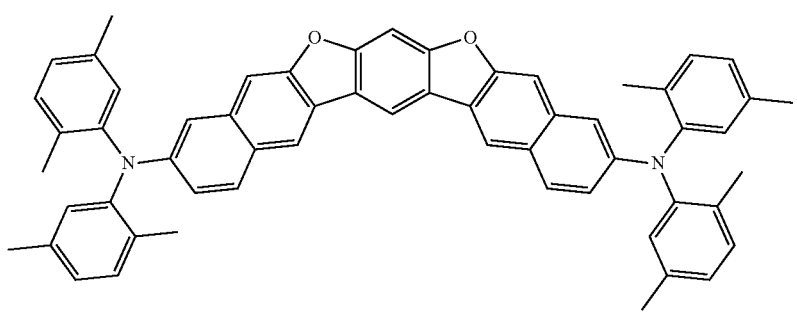
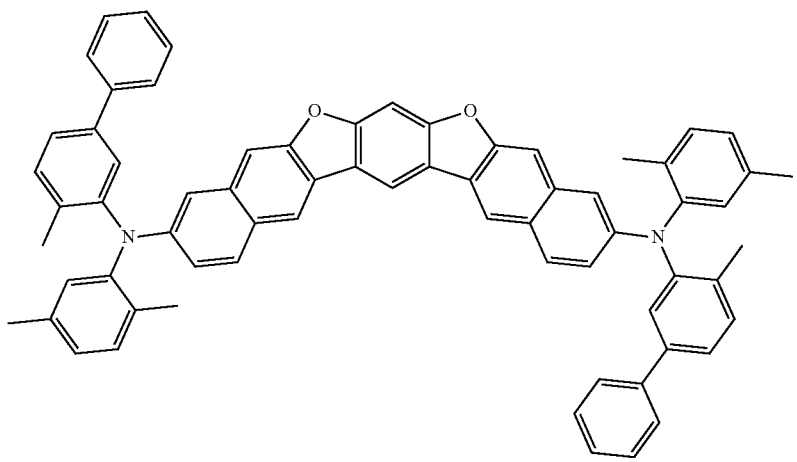

-continued
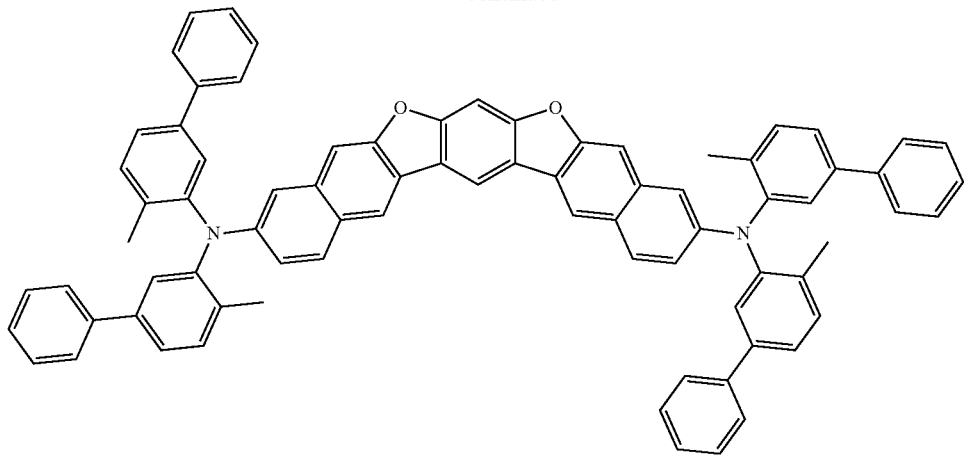
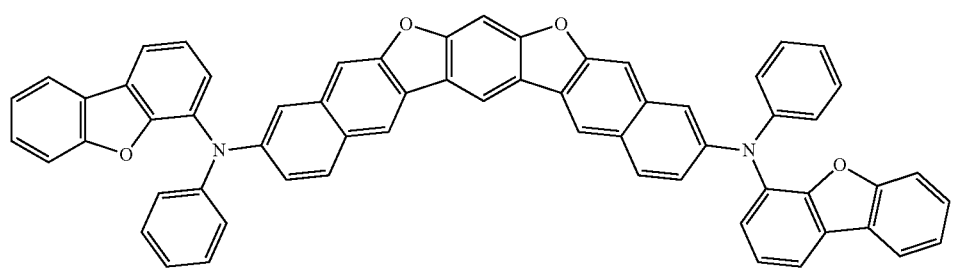
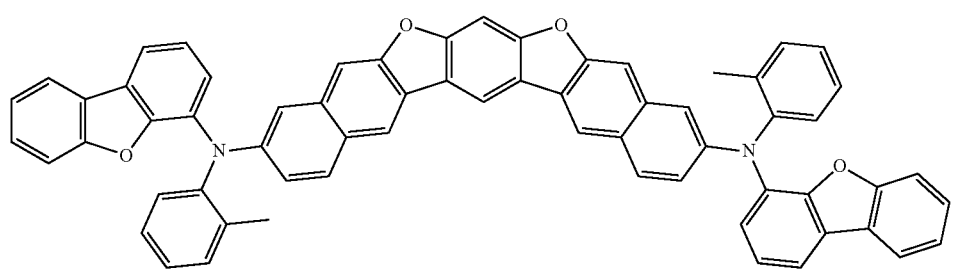
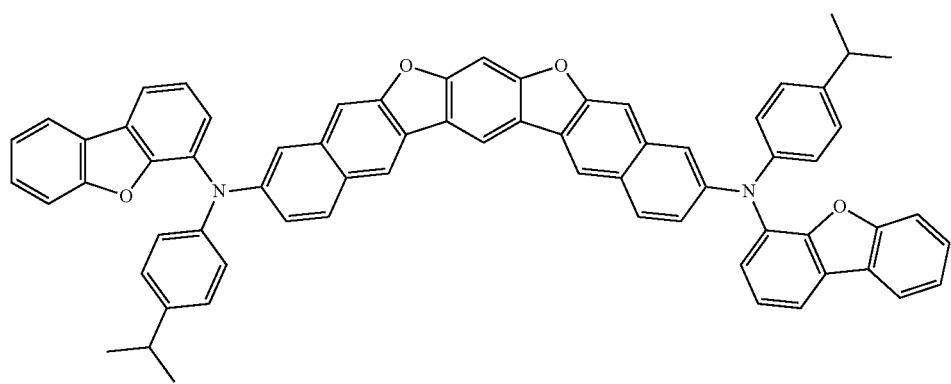
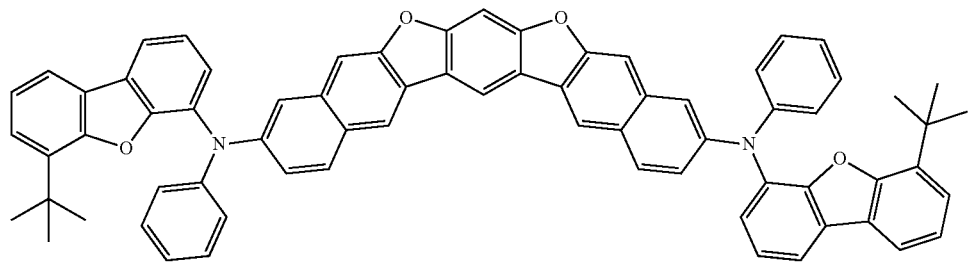

-continued
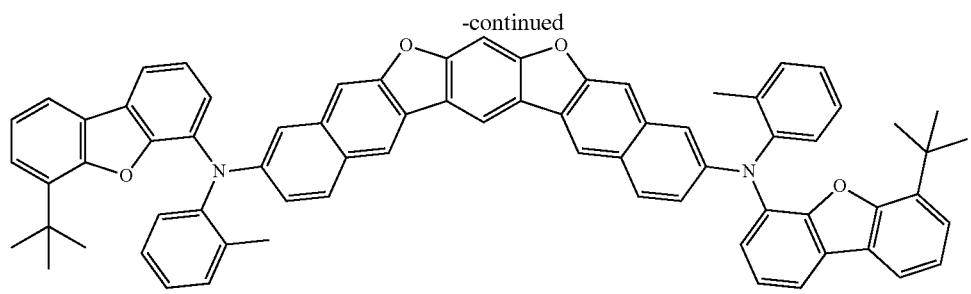
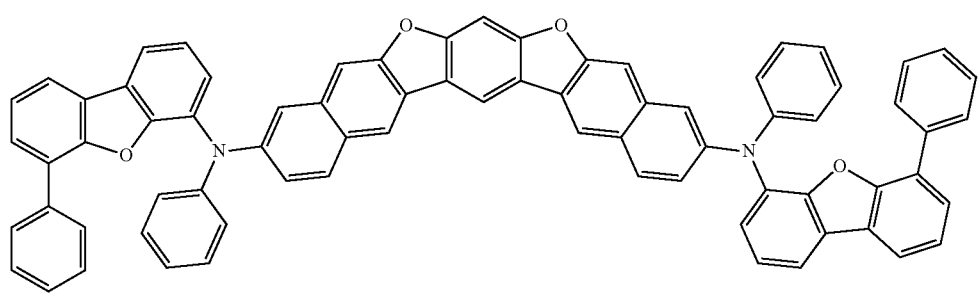
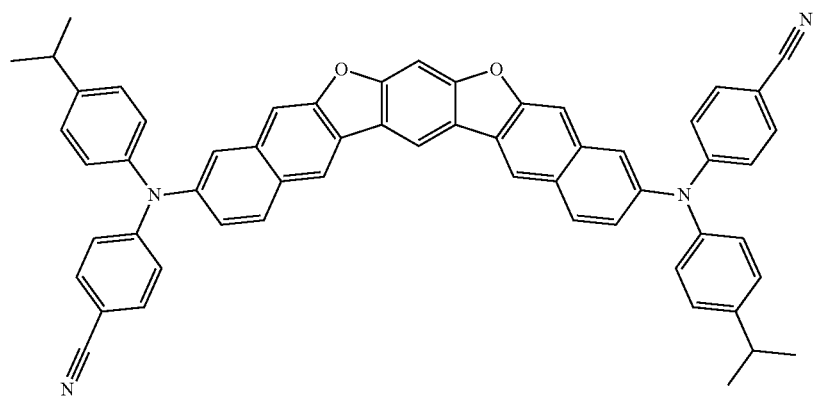
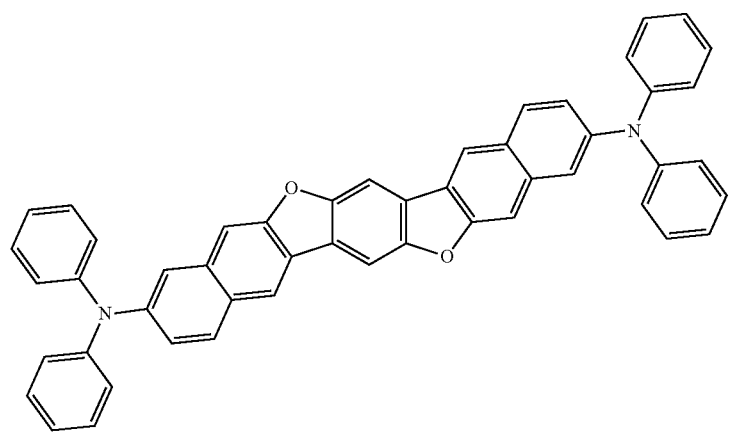

-continued
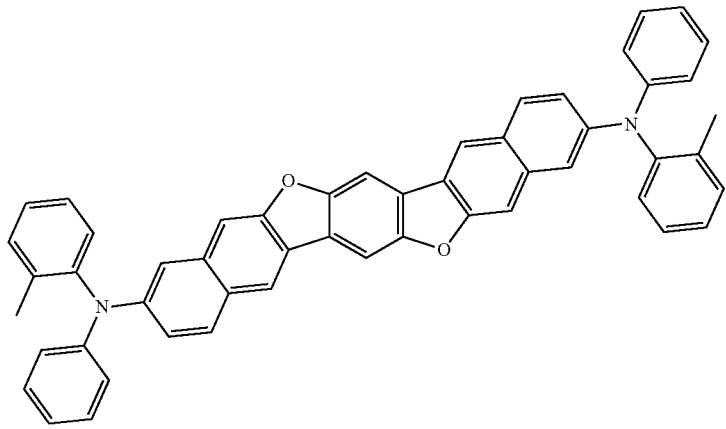
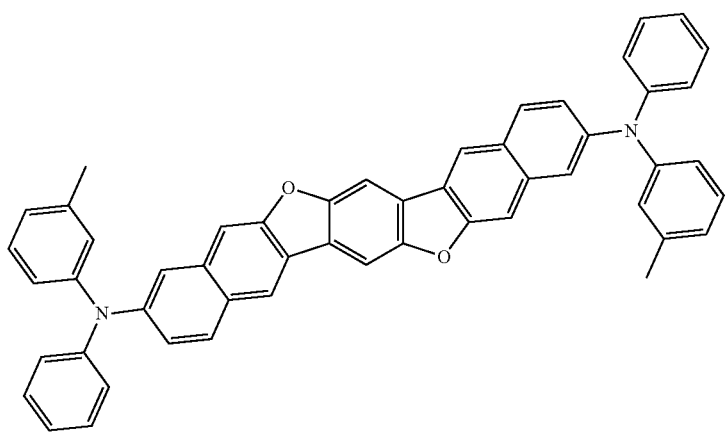
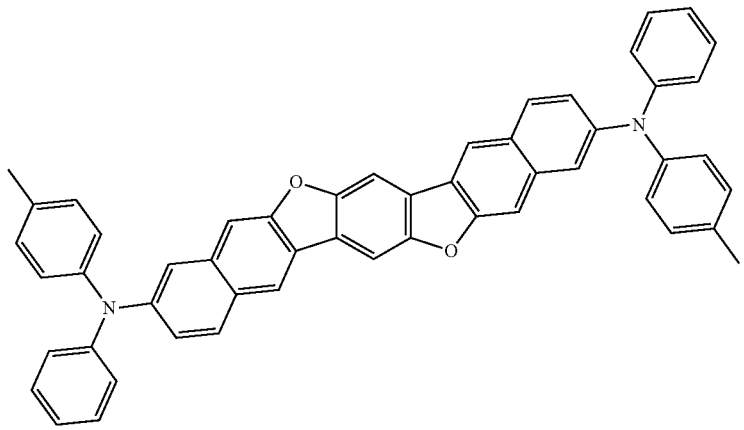
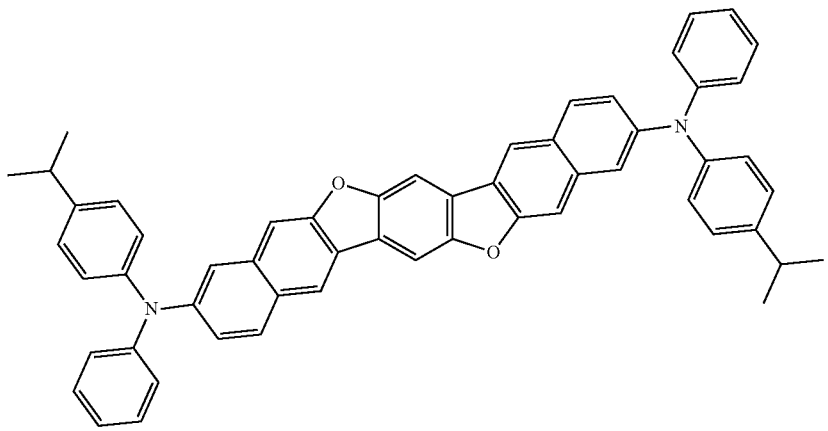

-continued
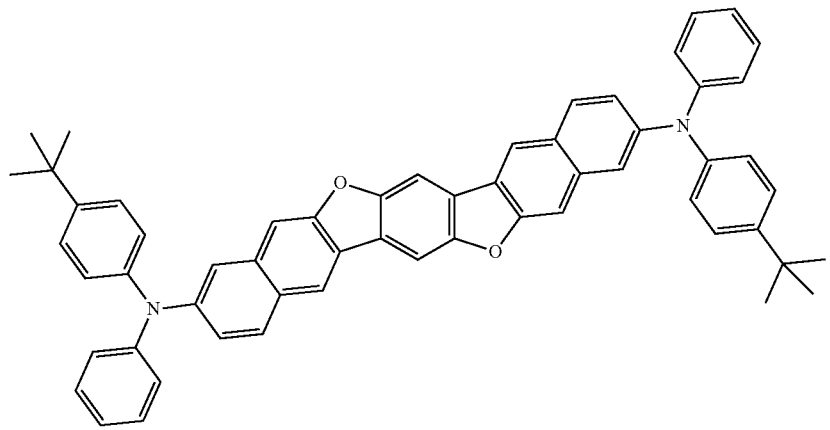
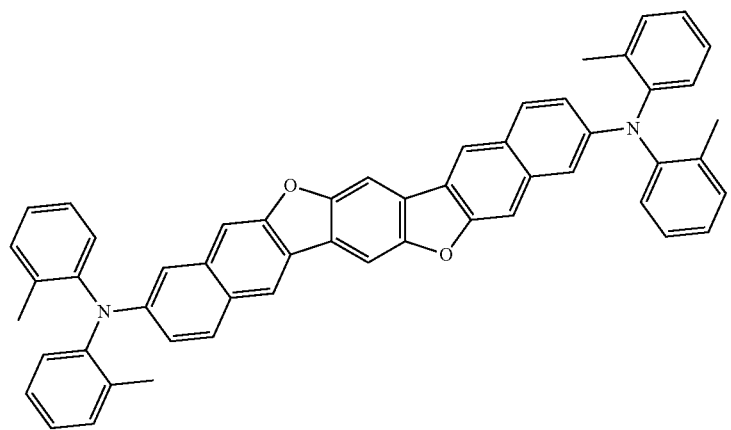
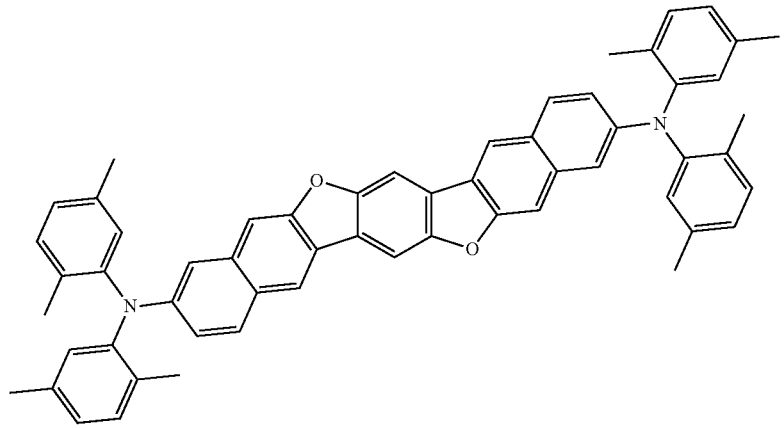
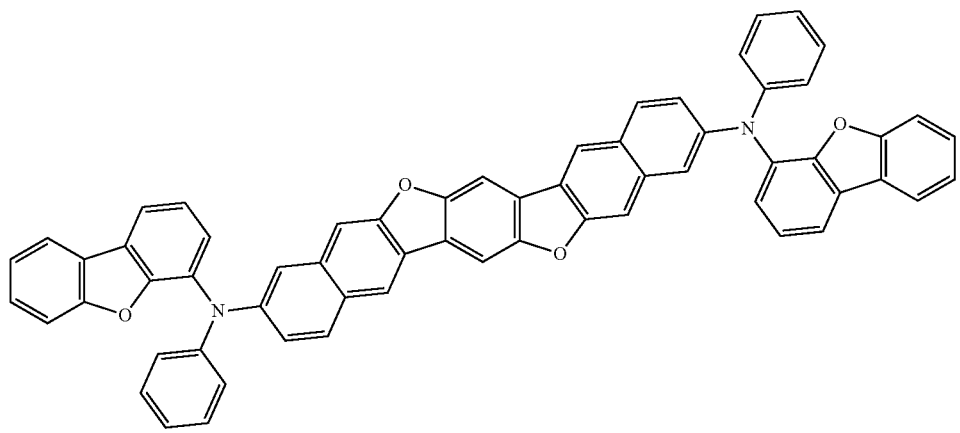

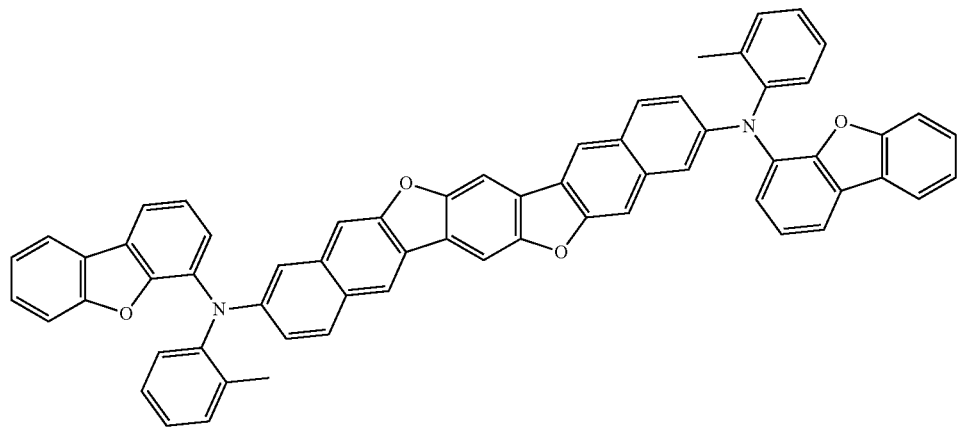
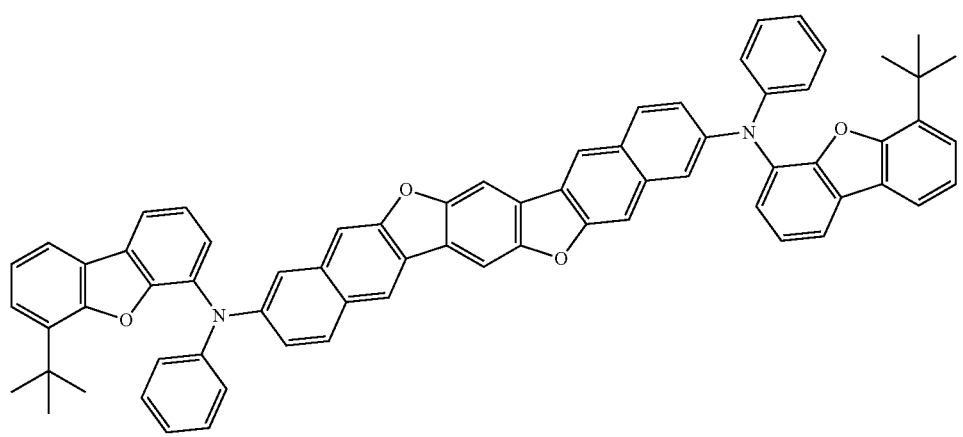
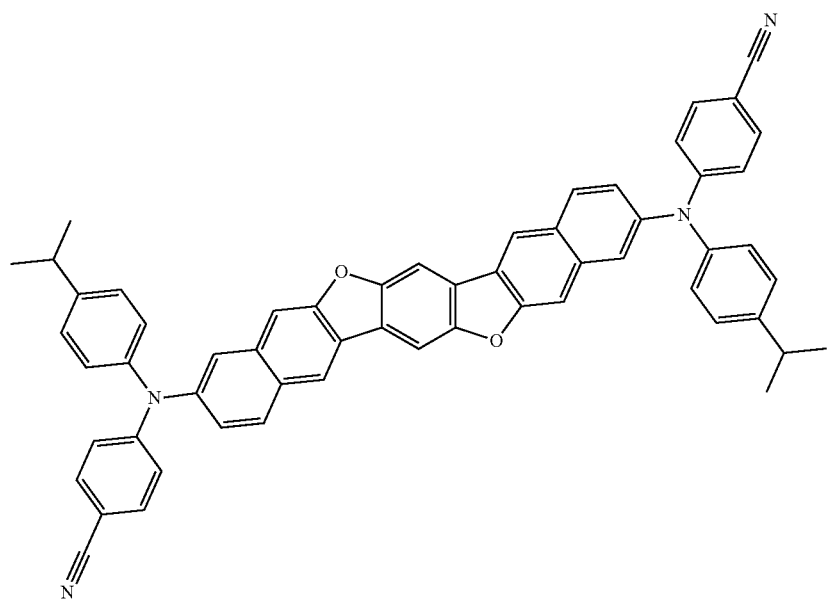

-continued
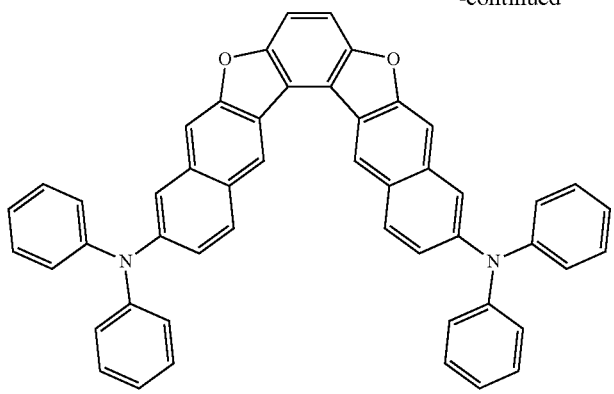
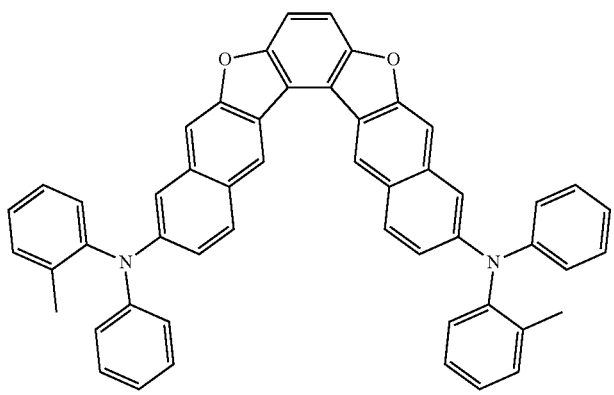
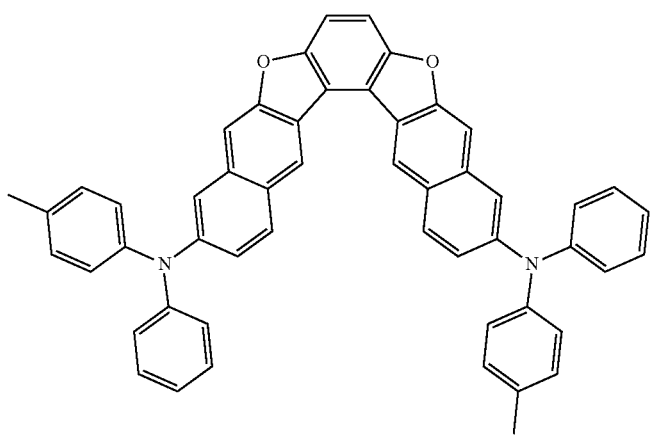
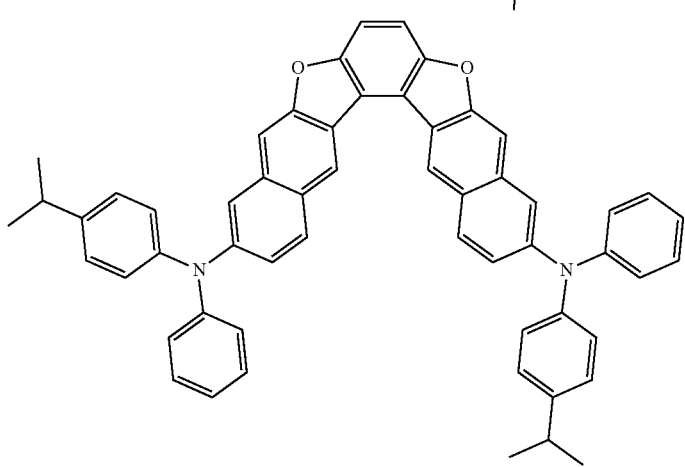

-continued
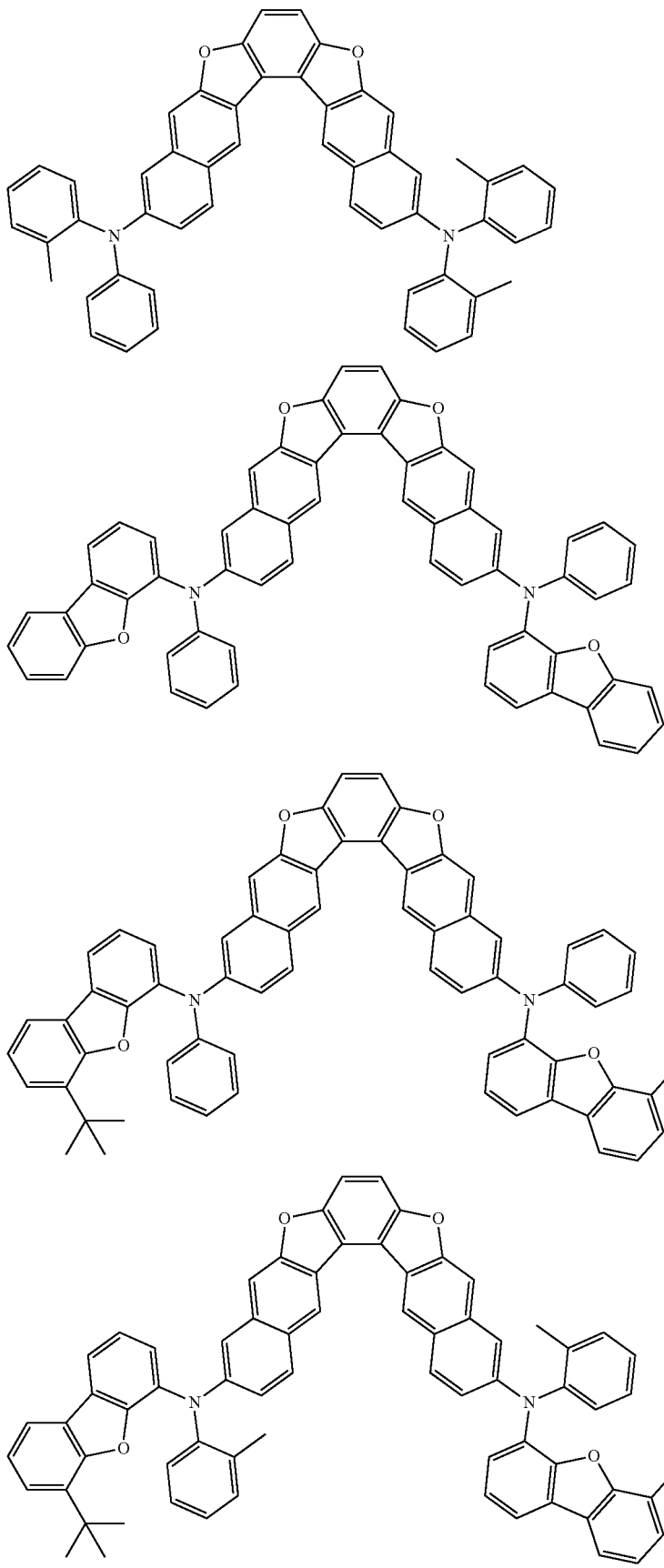

-continued
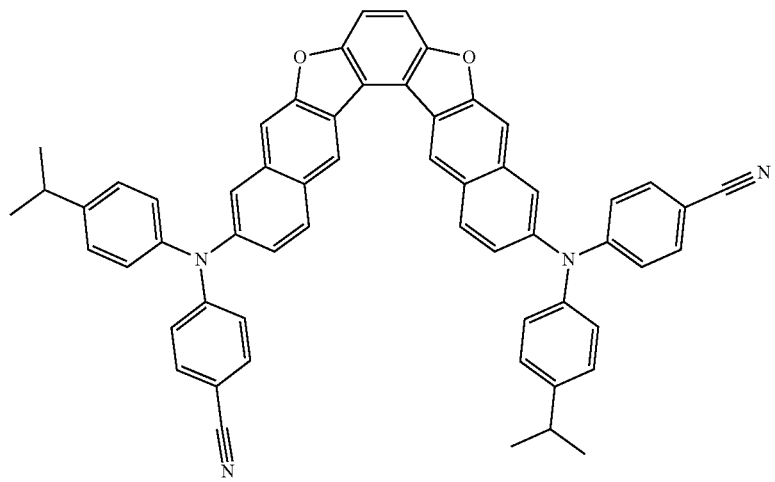
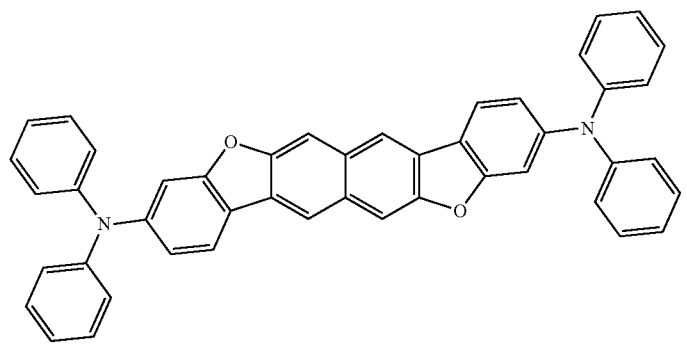
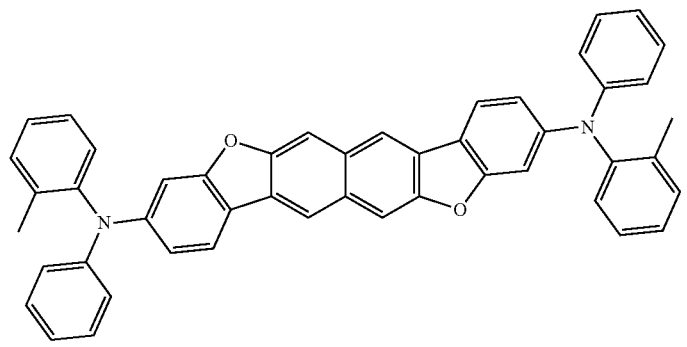
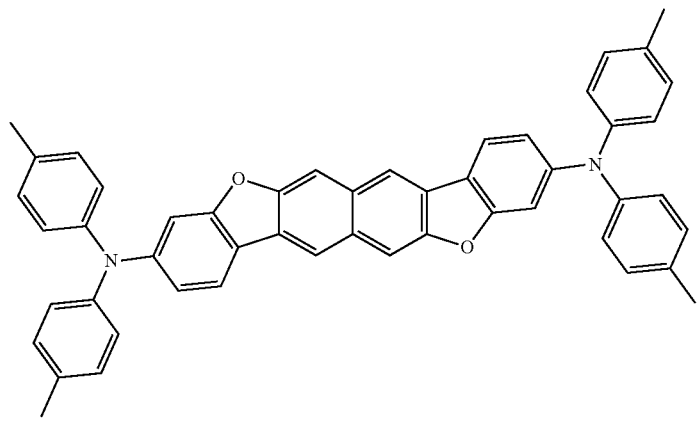

-continued
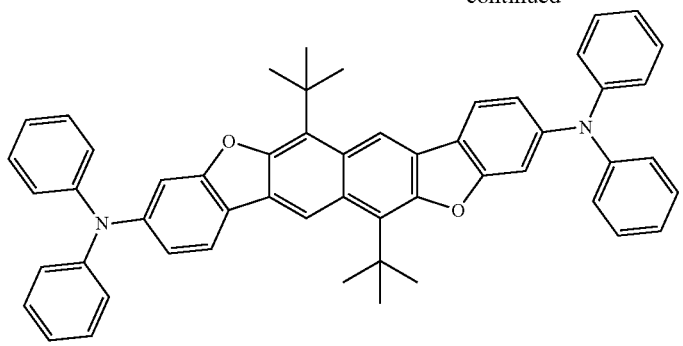
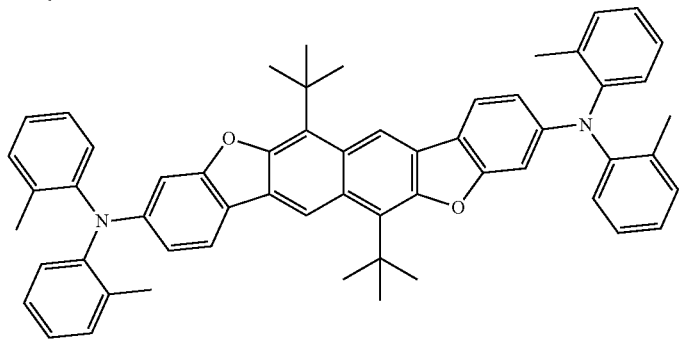
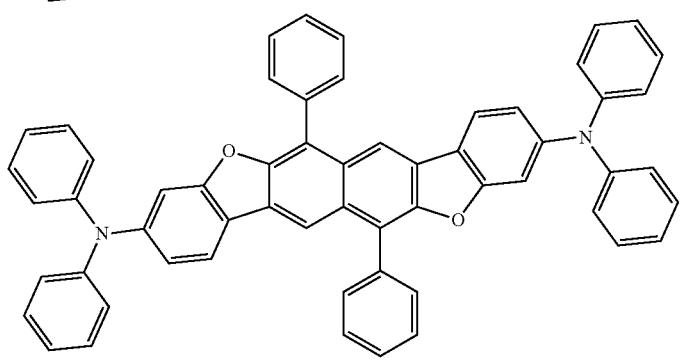
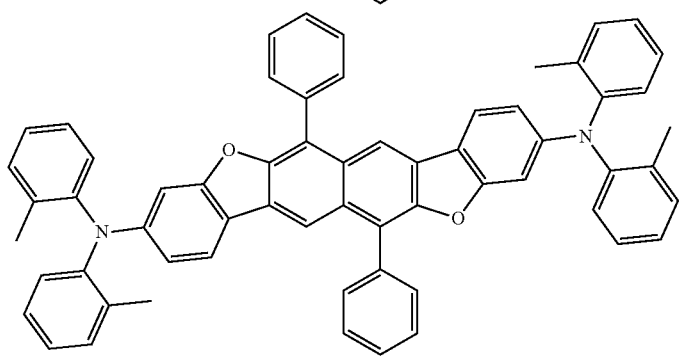
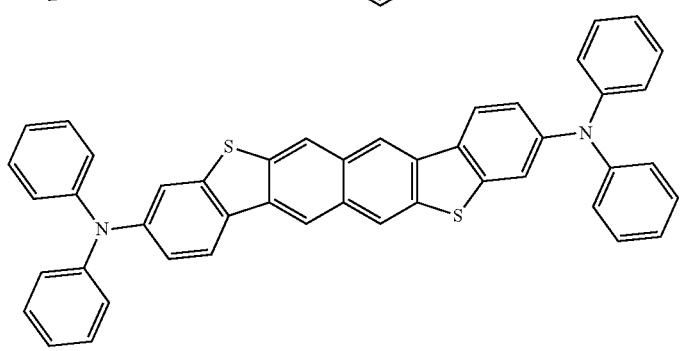

-continued
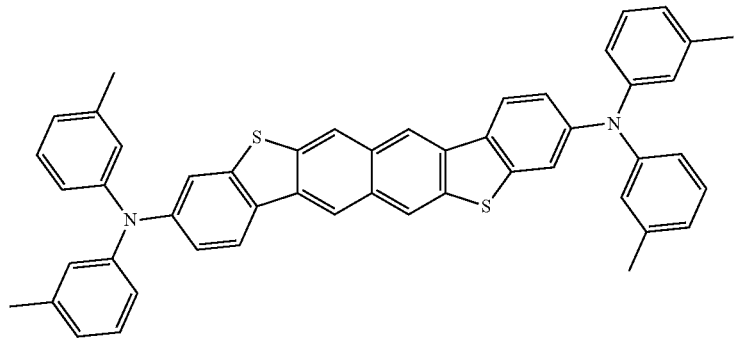
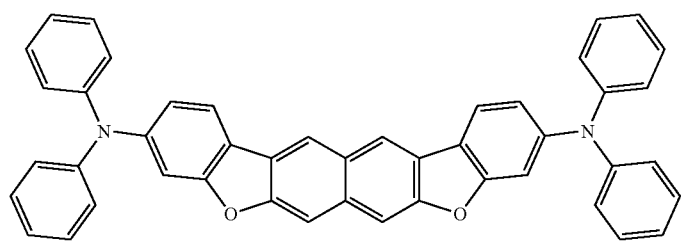
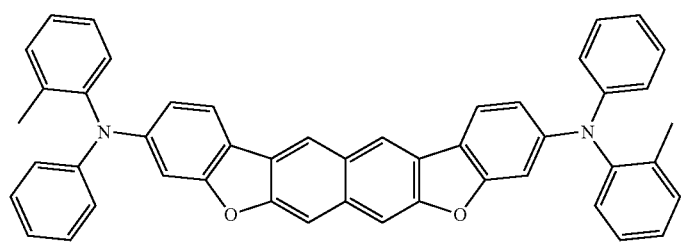
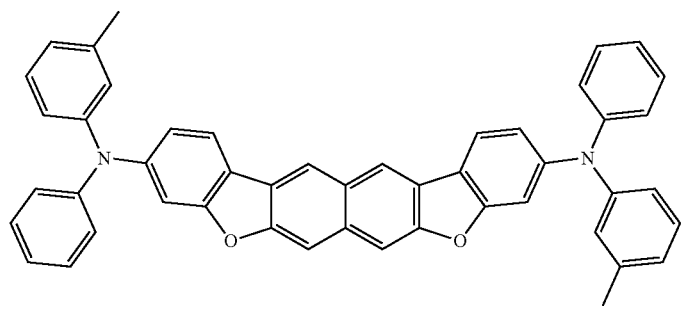

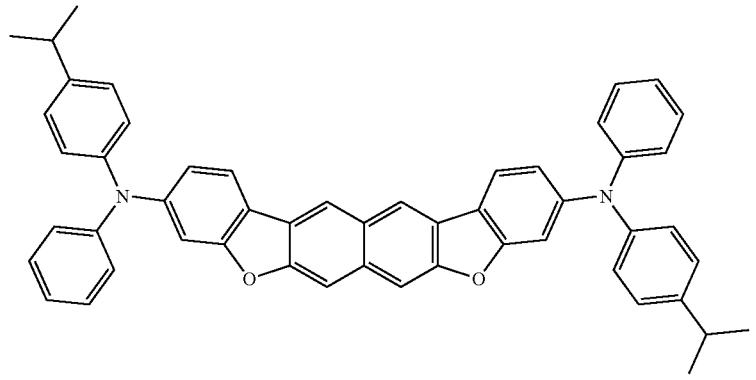
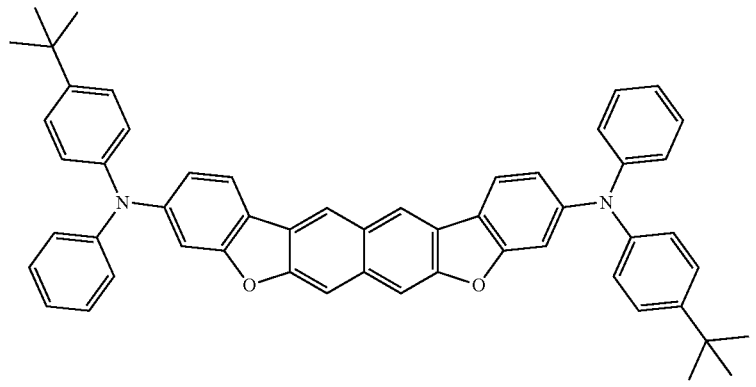
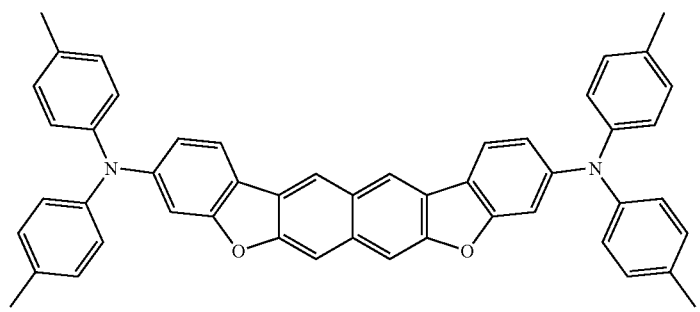
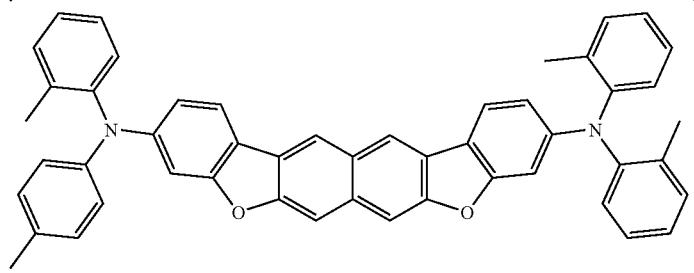
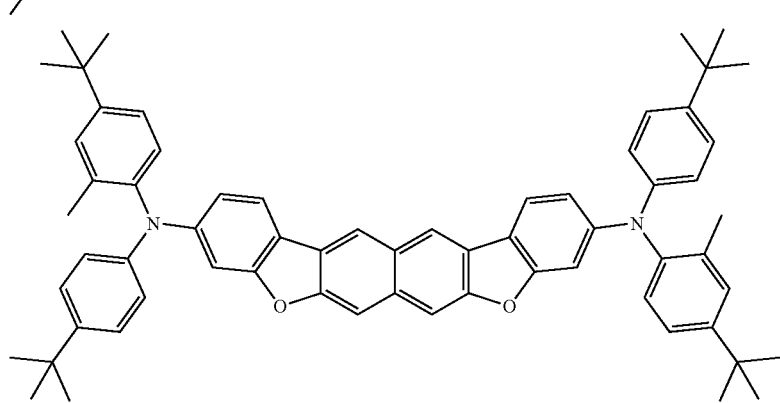

-continued
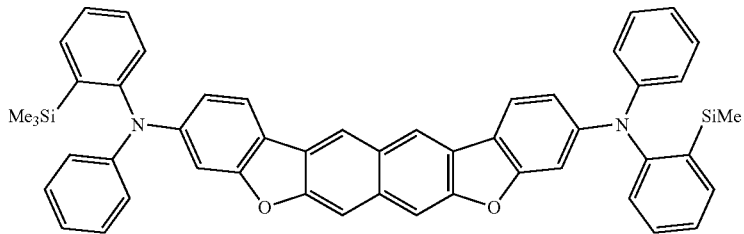
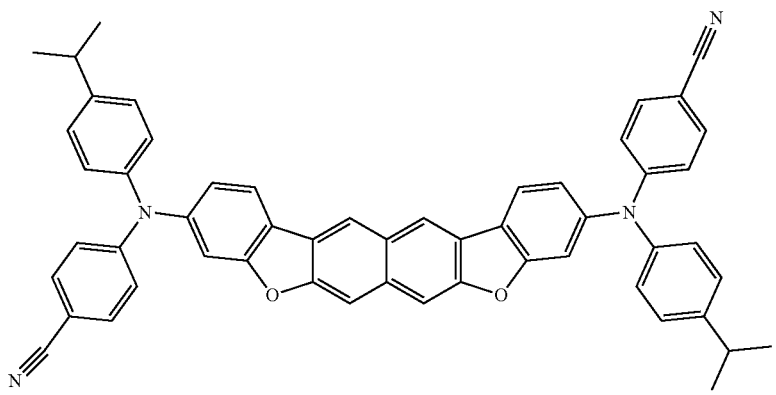
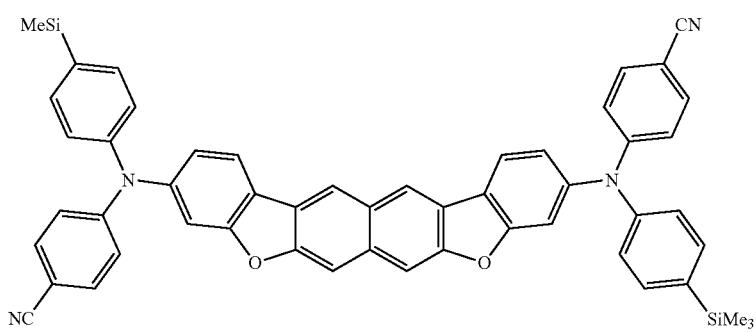
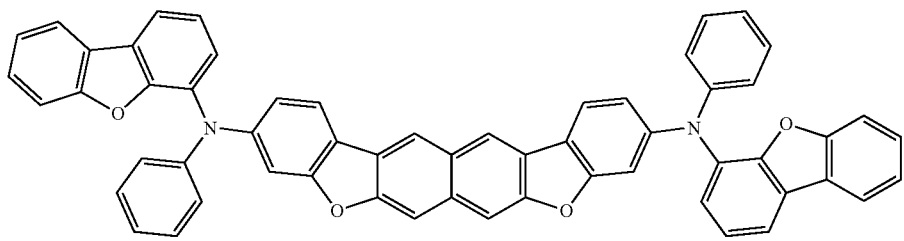
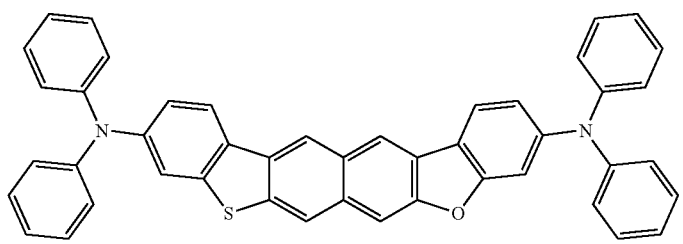

-continued
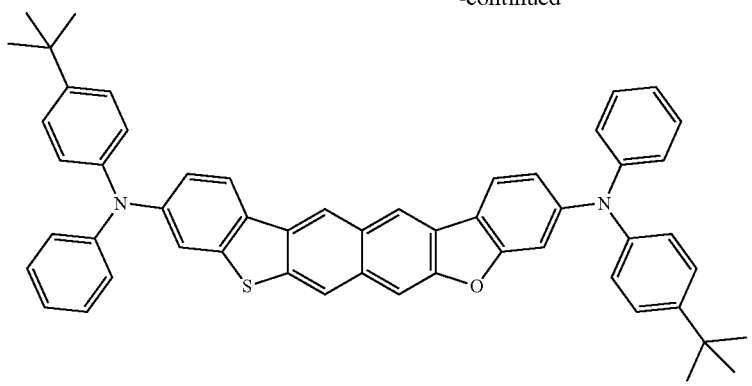
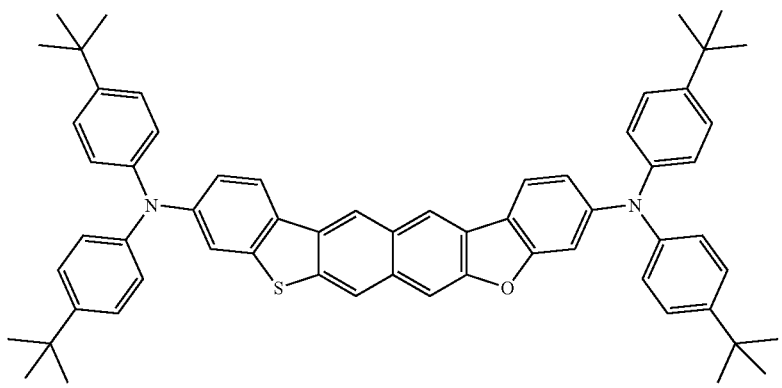
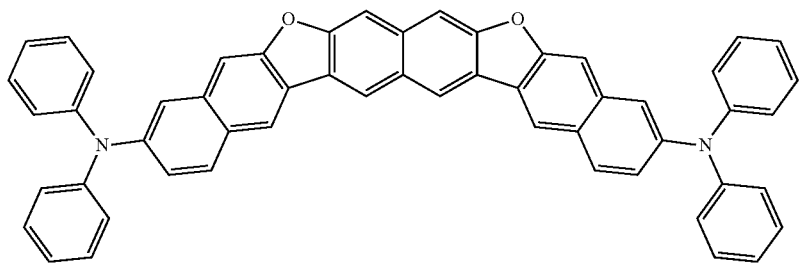
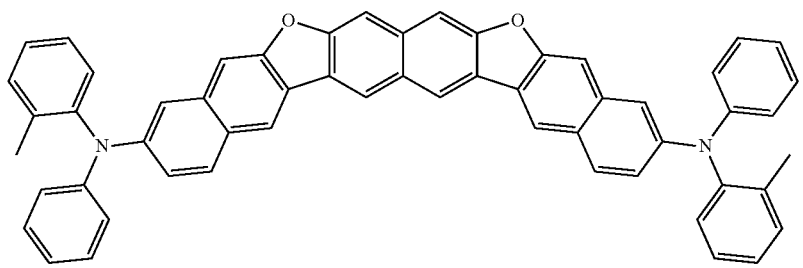
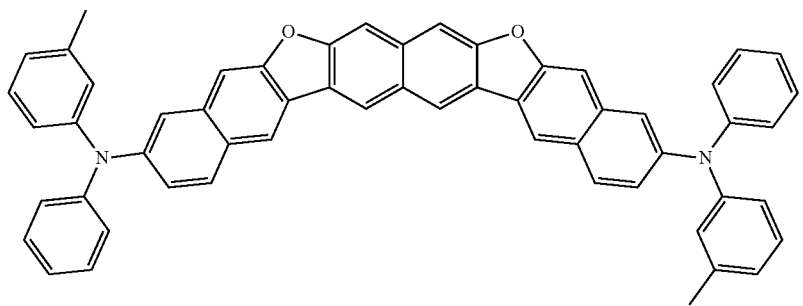

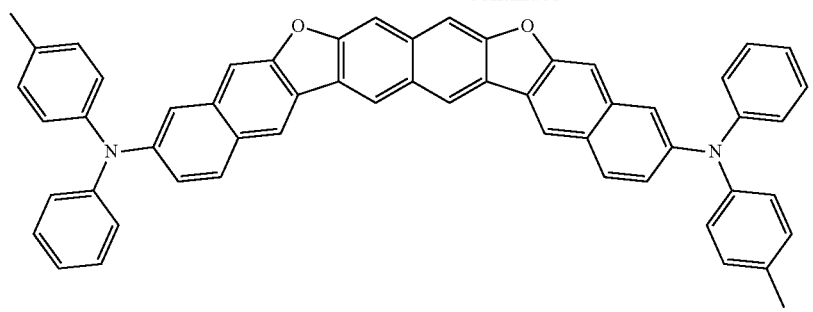
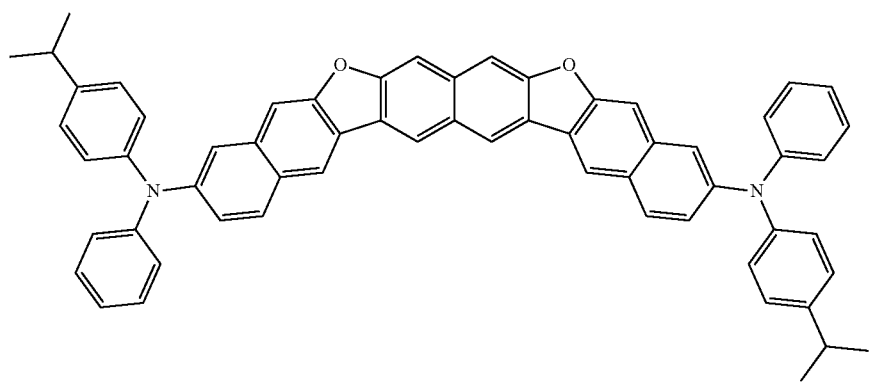
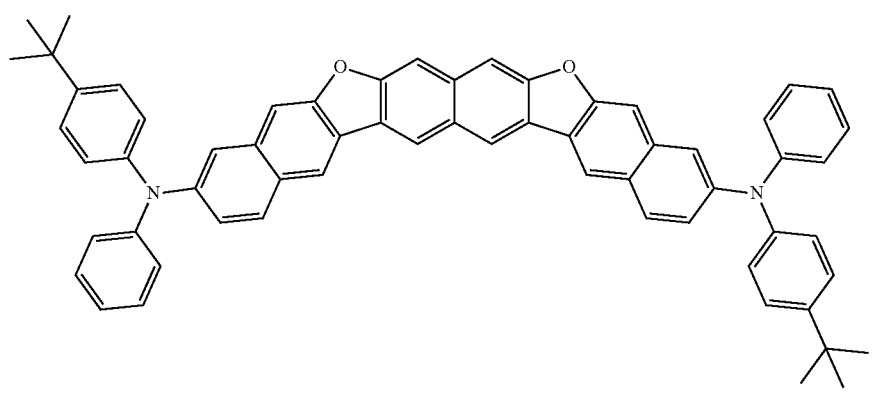
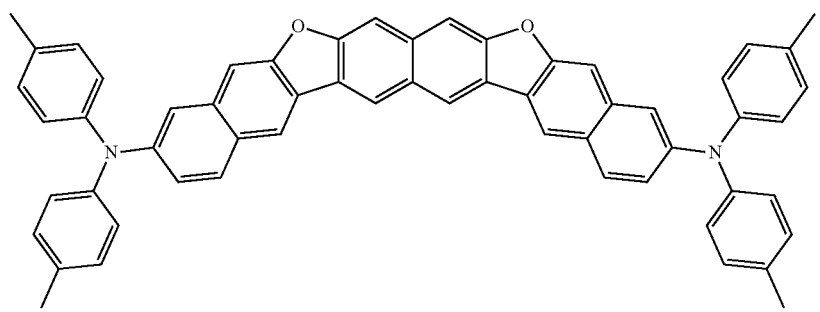
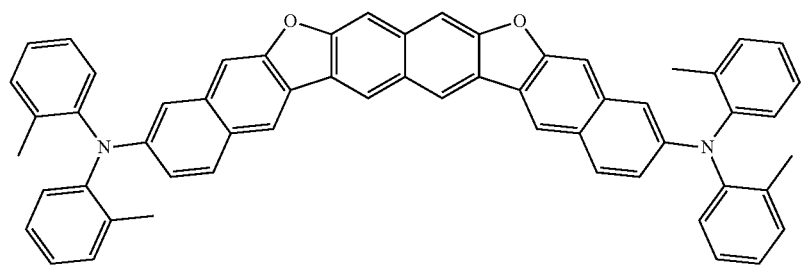

-continued

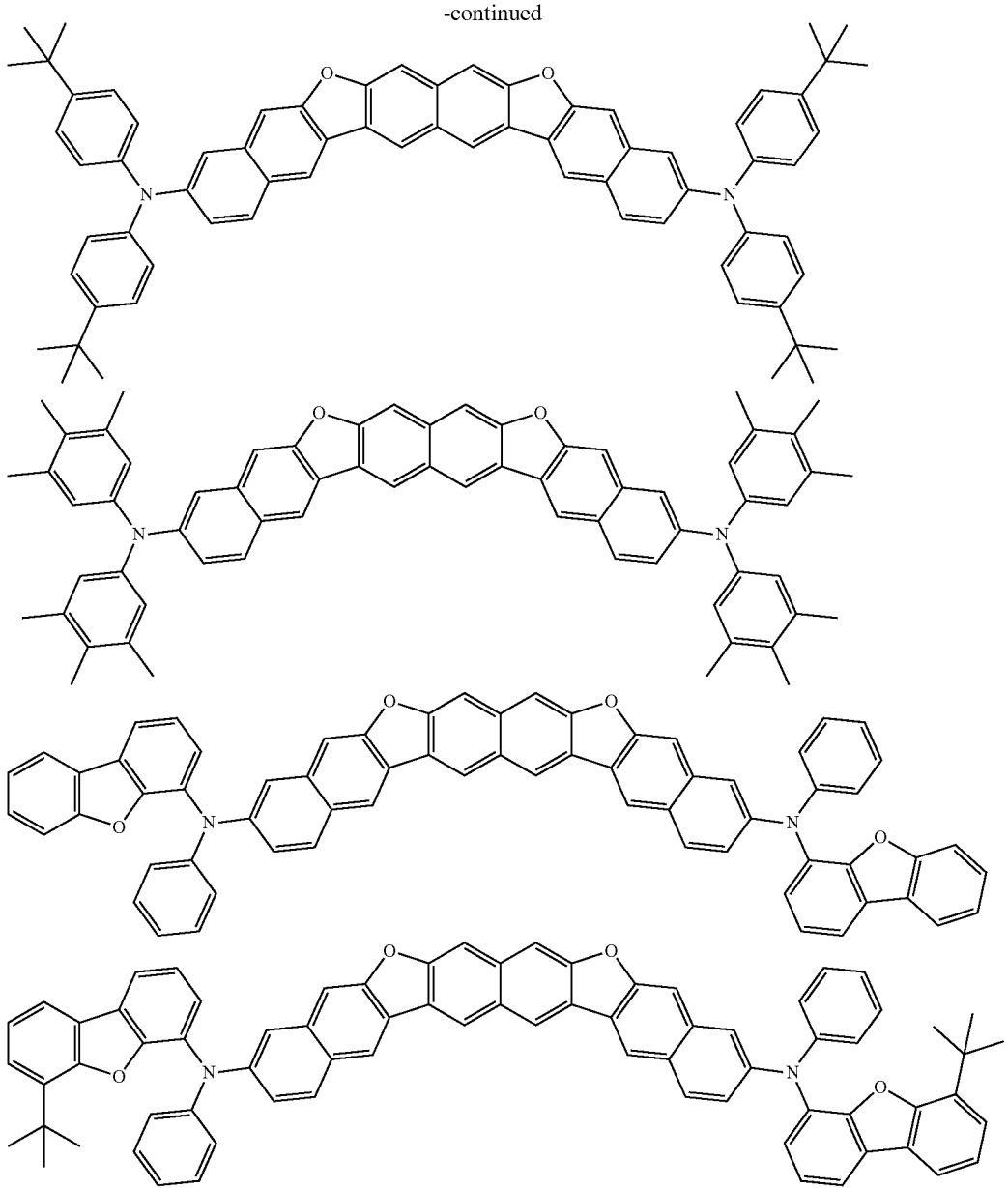

(Compound Represented by Formula (61))

The compound represented by the formula (61) is explained below.

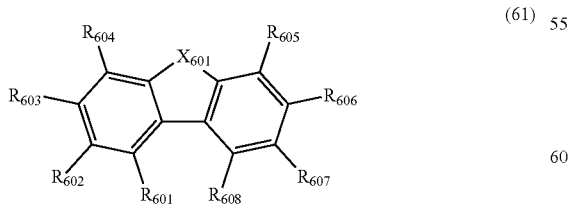

In the formula (61), at least one pair of $R_{601}$ and $R_{602}$, $R_{602}$ and $R_{603}$, and $R_{603}$ and $R_{604}$ are bonded with each other to form a divalent group represented by the formula (62);

at least one pair of $R_{605}$ and $R_{606}$, $R_{606}$ and $R_{607}$, and $R_{607}$ and $R_{608}$ are bonded with each other to form a divalent group represented by formula (63).

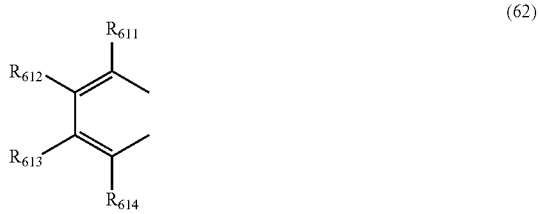

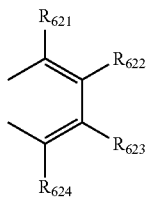
(63)

At least one of $R_{601}$ to $R_{904}$ that does not form the divalent group represented by the formula (62), and $R_{611}$ to $R_{614}$ is a monovalent group represented by the following formula (64);

at least one of $R_{605}$ to $R_{608}$ that do not form the divalent group represented by the formula (63), and $R_{621}$ to $R_{624}$ is a monovalent group represented by the following formula (64);

$X_{601}$ is an oxygen atom, a sulfur atom, or $NR_{609}$;

$R_{601}$ to $R_{608}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are as defined in the formula (1).

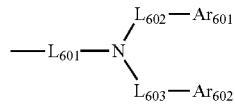
(64)

In the formula (64), $Ar_{601}$ and $Ar_{602}$ are independently
a substituted or unsubstituted aryl group including 6 to 50 ring carbon atoms, or
a substituted or unsubstituted monovalent heterocyclic group including 5 to 50 ring atoms;
$L_{601}$ to $L_{603}$ are independently
a single bond,
a substituted or unsubstituted arylene group including 6 to 30 ring carbon atoms,
a substituted or unsubstituted divalent heterocyclic group including 5 to 30 ring atoms, or
a divalent linking group formed by bonding 2 to 4 above mentioned groups.

In the formula (61), positions at which the divalent group represented by the formula (62) and the divalent group represented by the formula (63) are formed are not limited, and said groups can be formed at possible positions in $R_{601}$ to $R_{608}$.

In one embodiment, the compound represented by the formula (61) is represented by any one of the following formulas (61-1) to (61-6).

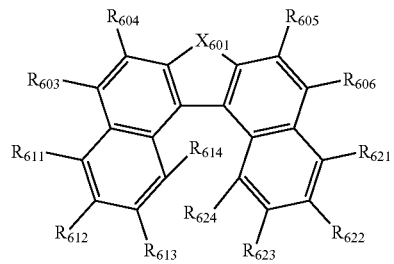
(61-1)

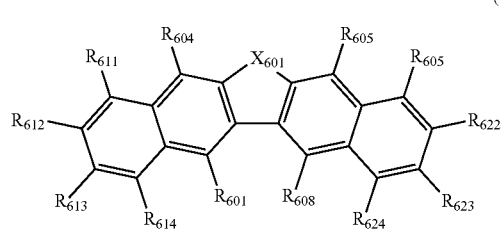
(61-2)

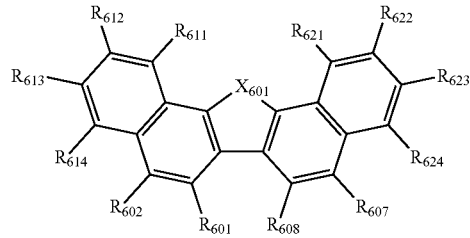
(61-3)

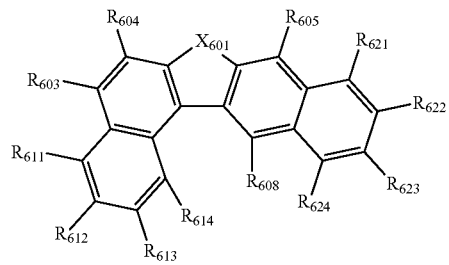
(61-4)

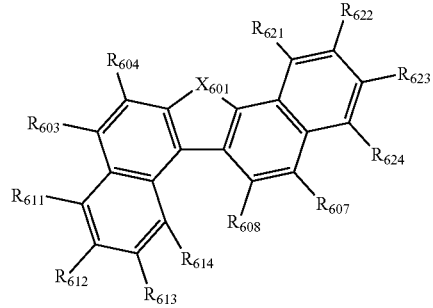
(61-5)

(61-6)

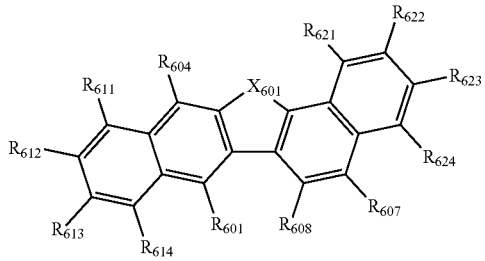

(61-9)

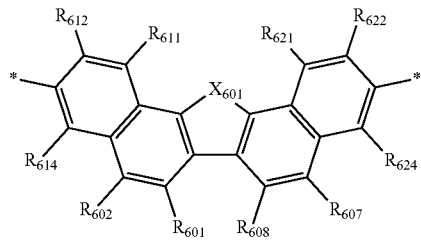

(61-10)

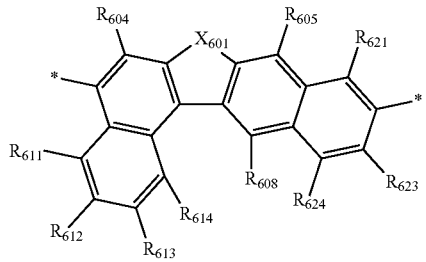

(61-11)

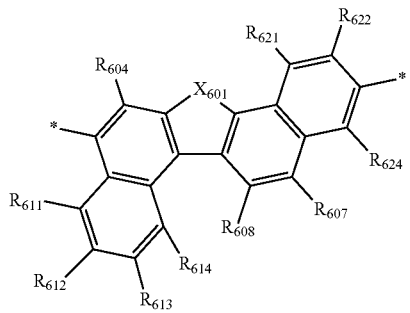

In the formulas (61-1) to (61-6), $X_{601}$ is as defined in the formula (61);

at least two of $R_{601}$ to $R_{624}$ are monovalent groups represented by the formula (64);

$R_{601}$ to $R_{624}$ that are not monovalent groups represented by the formula (64) are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si$(R_{901})(R_{902})(R_{903})$,

—O—$(R_{904})$,

—S—$(R_{905})$,

—N$(R_{906})(R_{907})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms; and $R_{901}$ to $R_{907}$ are as defined in the formula (1).

In one embodiment, the compound represented by the formula (61) is represented by any one of the following formulas (61-7) to (61-18).

(61-7)

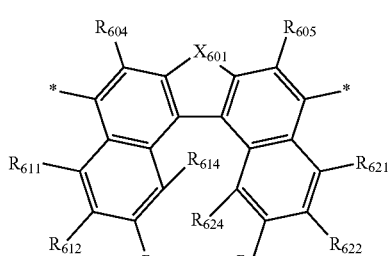

(61-8)

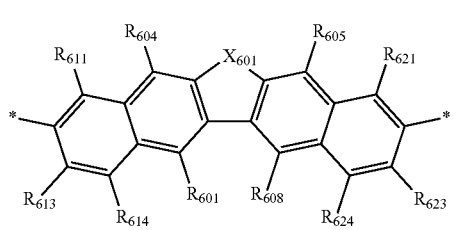

(61-12)

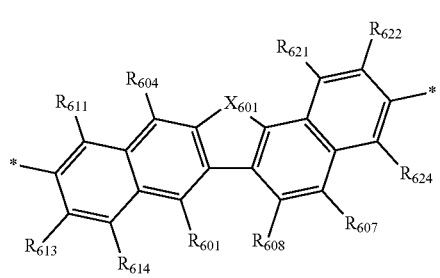

(61-13)

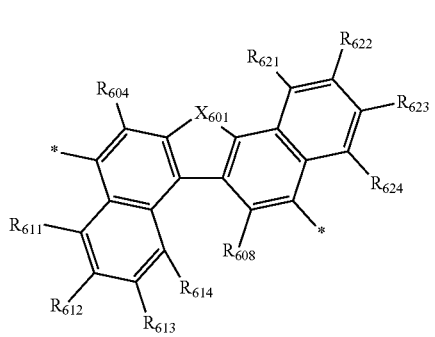

-continued (61-14)
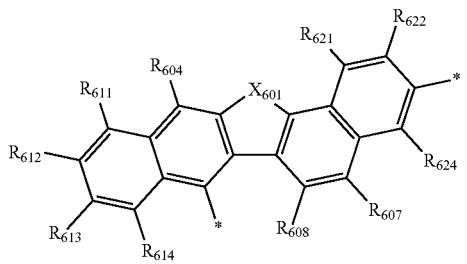

(61-15)
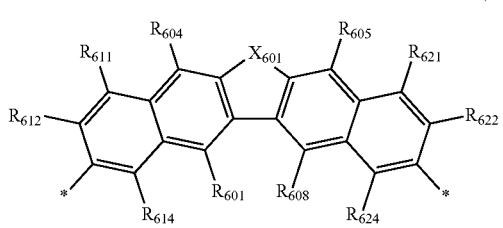

(61-16)
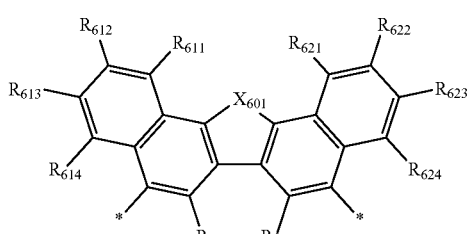

(61-17)
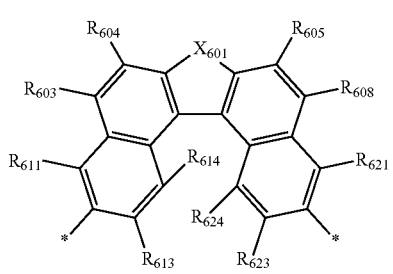

(61-18)
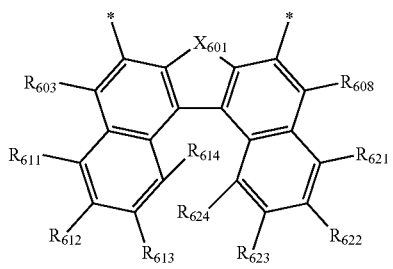

In the formulas (61-7) to (61-18), $X_{601}$ is as defined in the formula (61); * is a single bond bonding to the monovalent group represented by the formula (64); and $R_{601}$ to $R_{624}$ are the same as $R_{601}$ to $R_{624}$ that are not monovalent groups represented by the formula (64).

$R_{601}$ to $R_{608}$ which do not form the divalent group represented by the formula (62) and (63) and are not monovalent groups represented by the formula (64), and $R_{611}$ to $R_{614}$ and $R_{621}$ to $R_{624}$ which are not monovalent groups represented by the formula (64) are preferably independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms.

The monovalent group represented by the formula (64) is preferably represented by the following formulas (65) or (66).

(65)
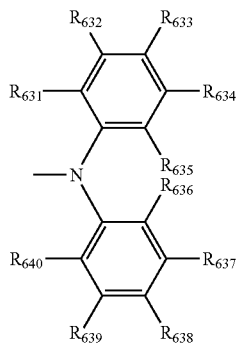

In the formula (65), $R_{631}$ to $R_{640}$ are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms; and
$R_{901}$ to $R_{907}$ are as defined in the formula (1).

(66)
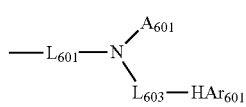

In the formula (66), $Ar_{601}$, $L_{601}$ and $L_{603}$ are as defined in the formula (64); and $HAr_{601}$ is a structure represented by the following formula (67).

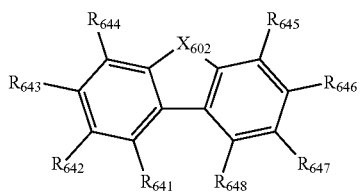
(67)

In the formula (67) $X_{602}$ is an oxygen atom or a sulfur atom;
any one of $R_{641}$ to $R_{648}$ is a single bond bonding to $L_{603}$; $R_{641}$ to $R_{43}$ which are not single bonds are independently a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms; and
$R_{901}$ to $R_{907}$ are as defined in the formula (1).

As specific example of the compound represented by the formula (61), in addition to the compounds described in WO2014/104144, the following compounds can be given, for example. In the following example compounds, Me represents methyl group.

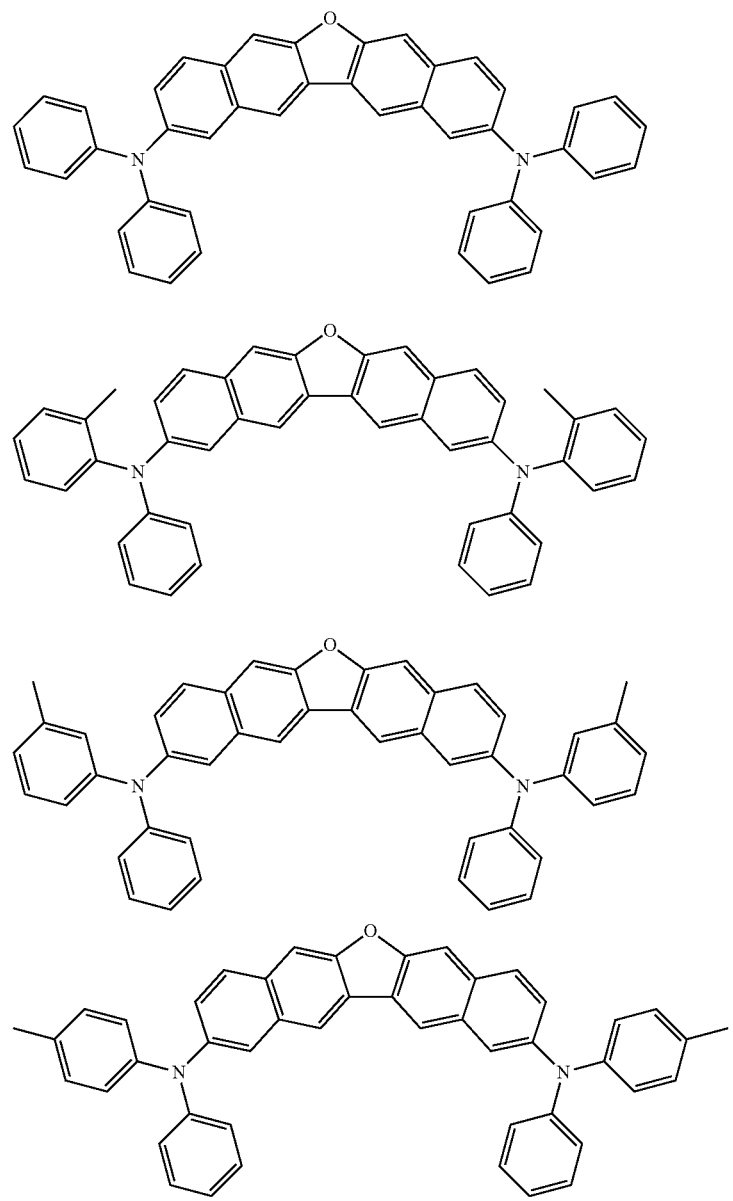

-continued
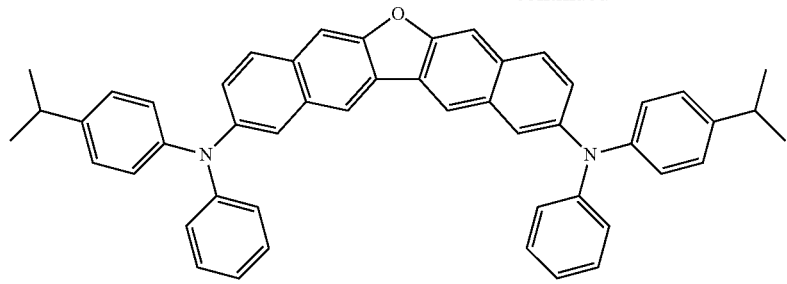
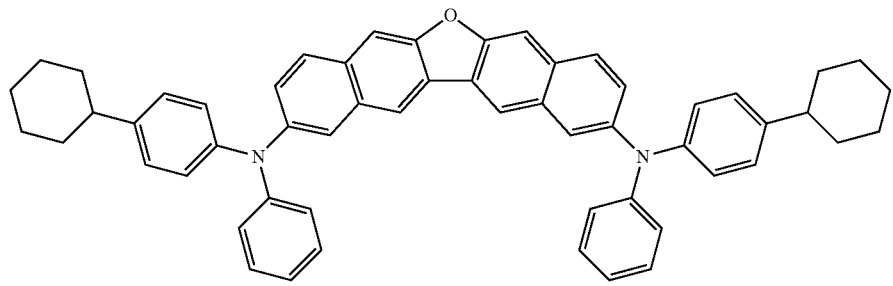
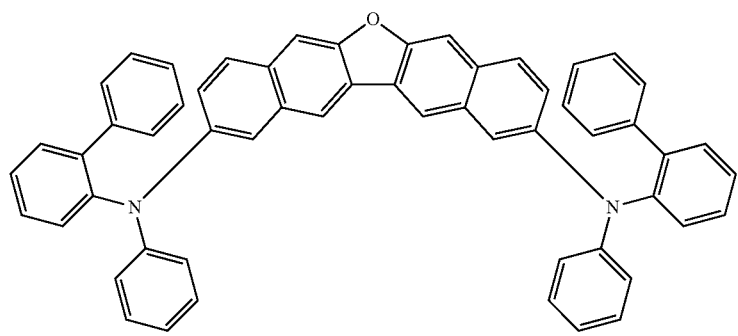
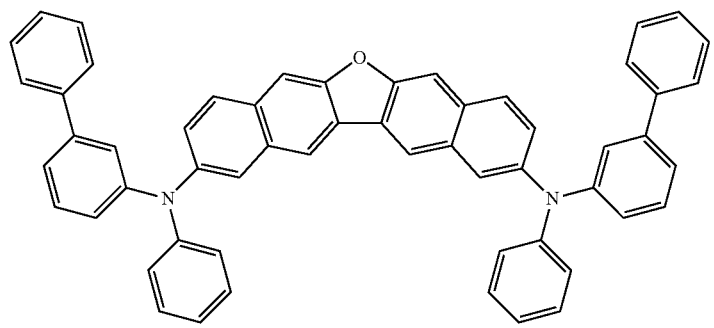
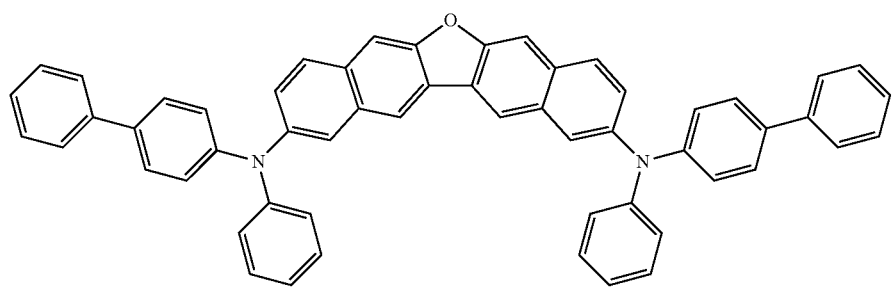

-continued
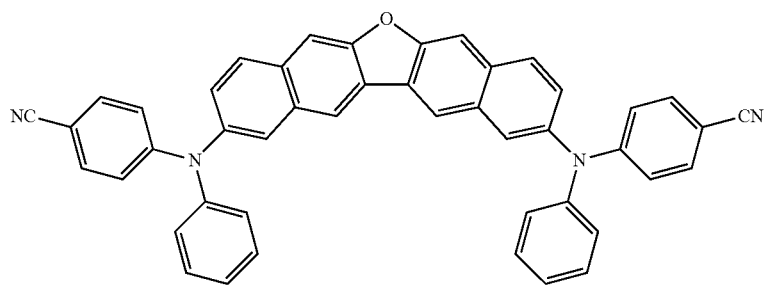
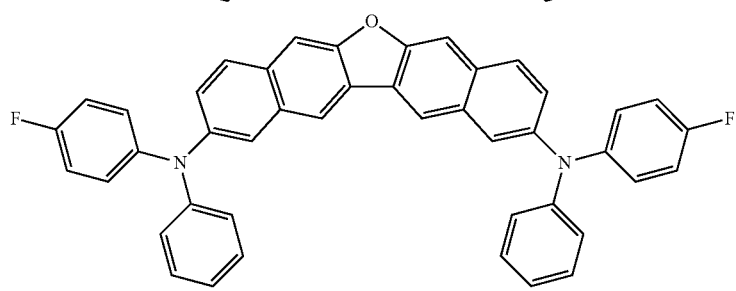
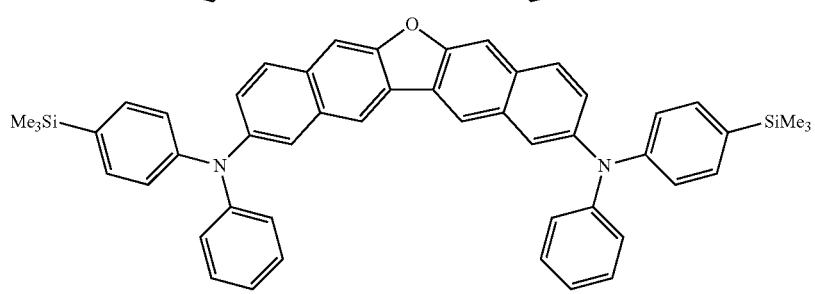
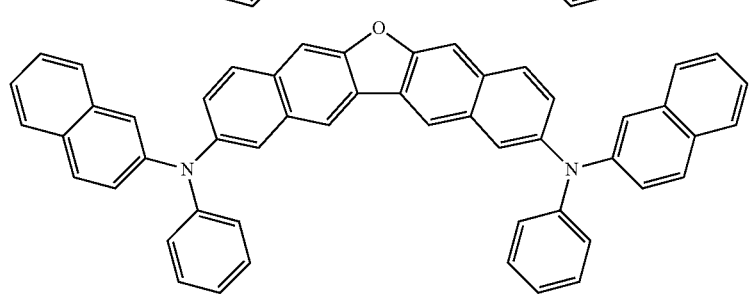
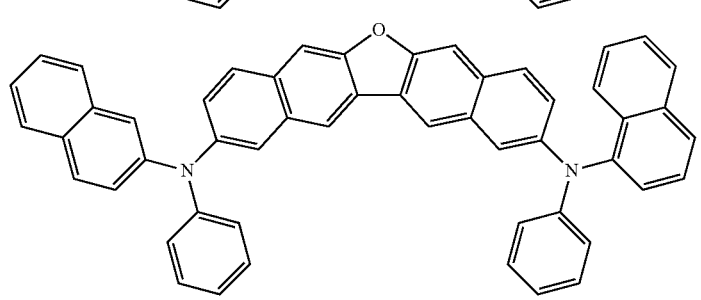
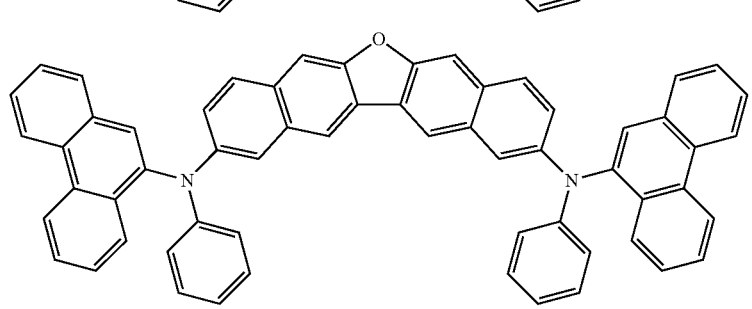

-continued
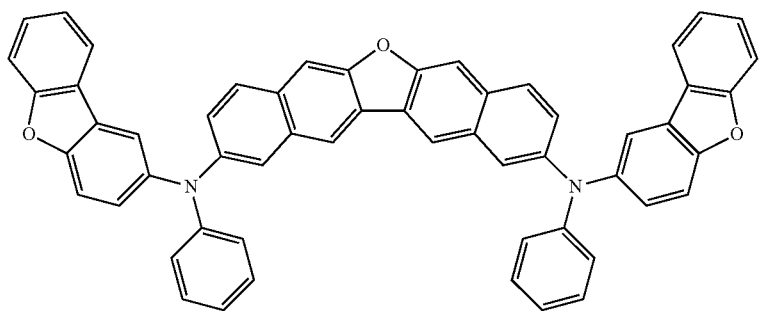
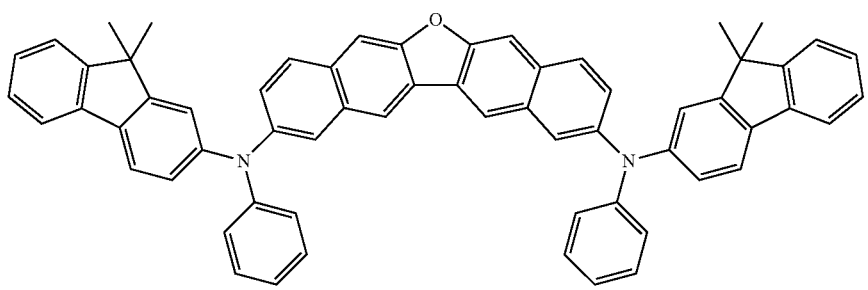
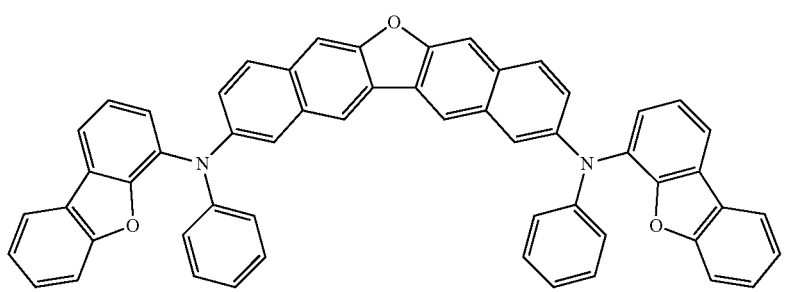
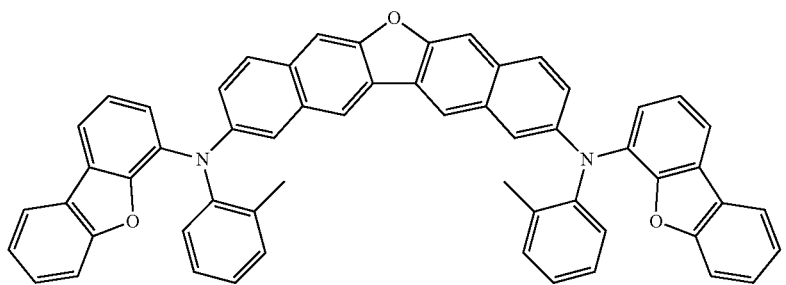
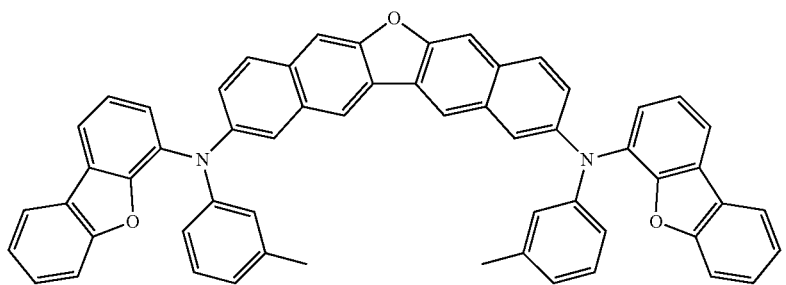

-continued
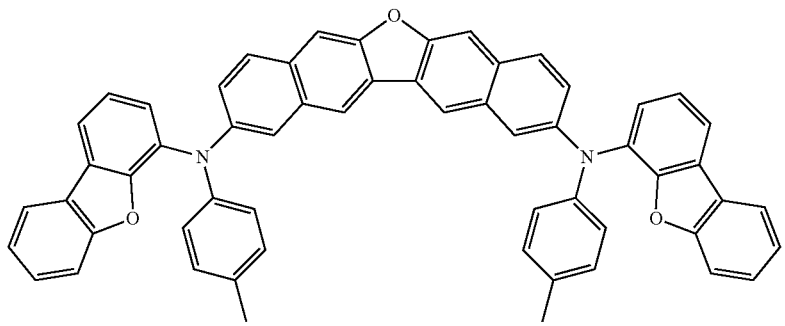
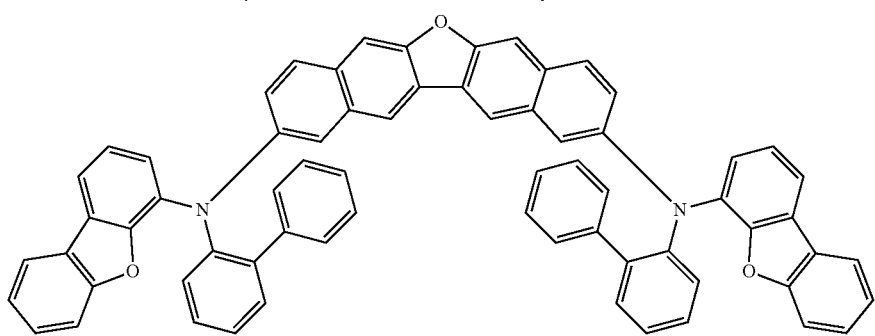
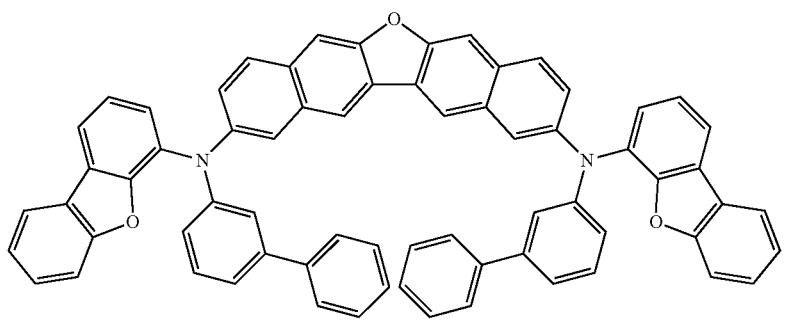
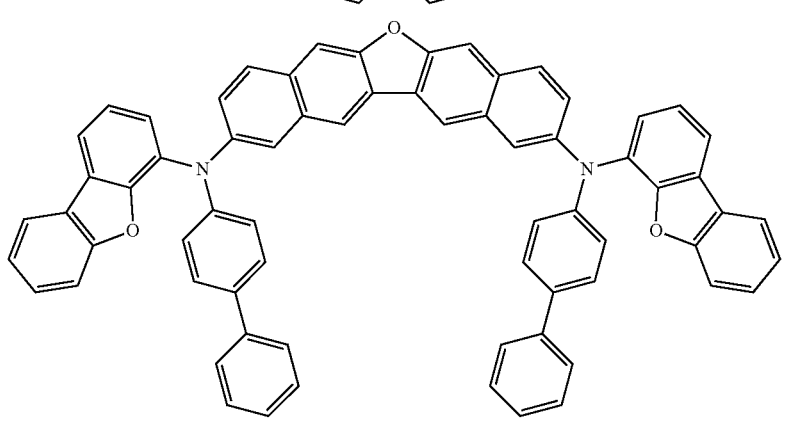
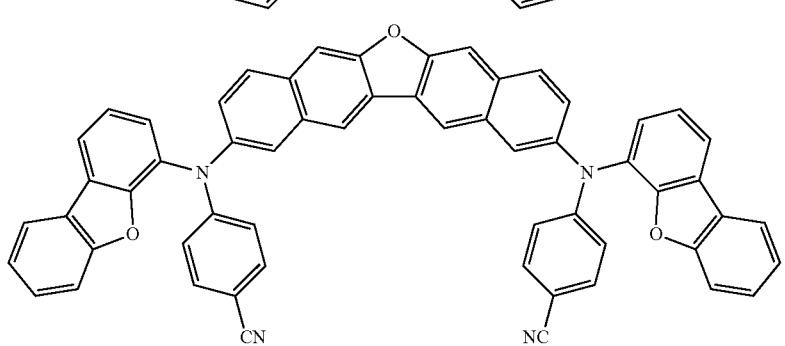

-continued
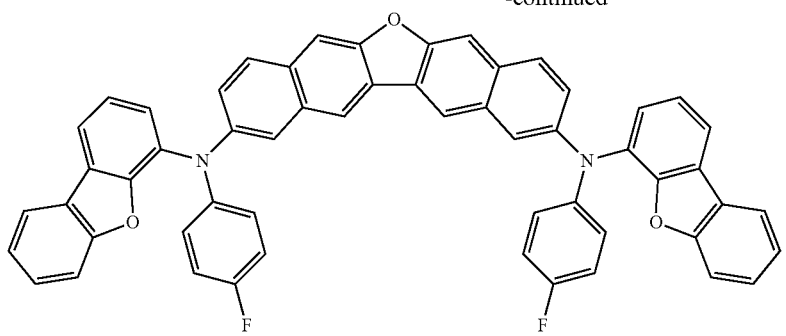
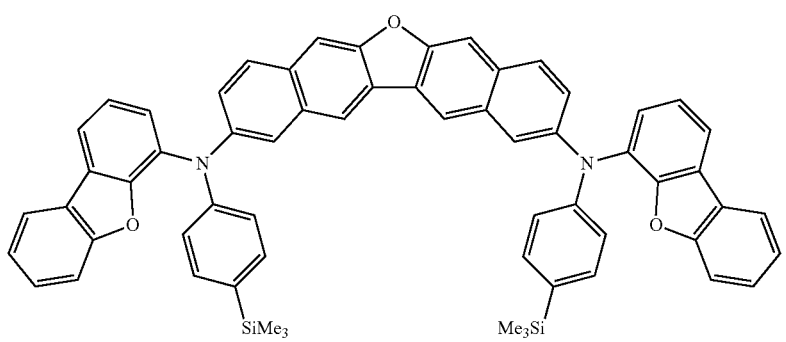
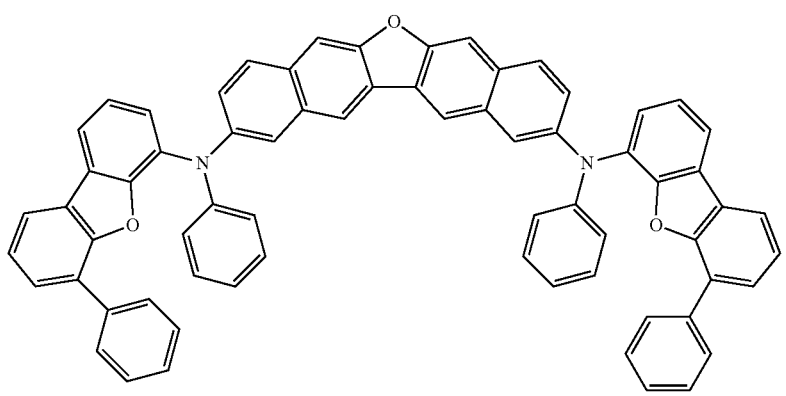
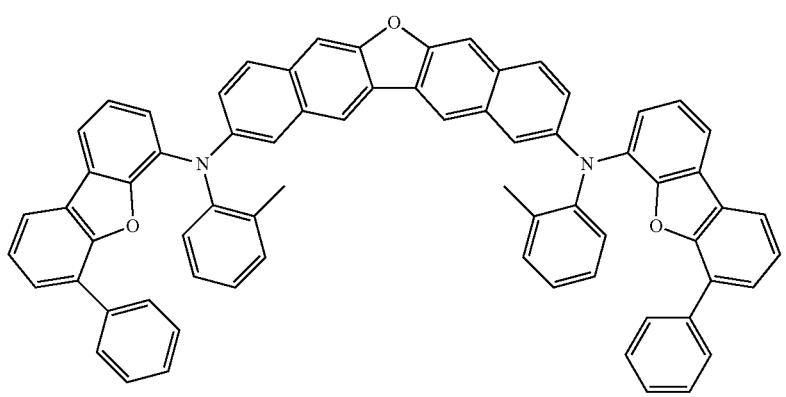

-continued
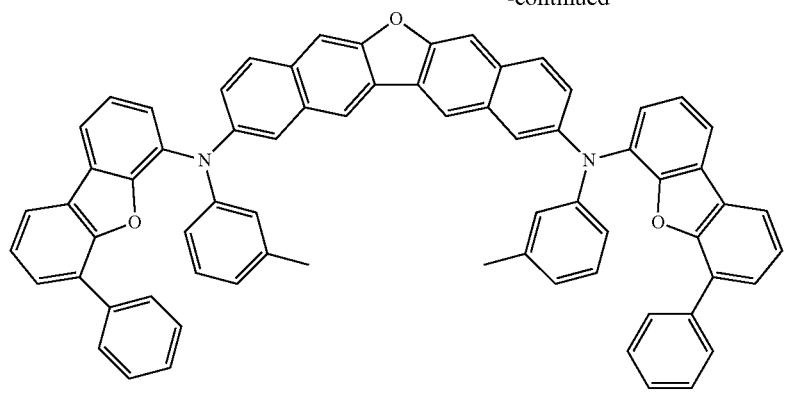
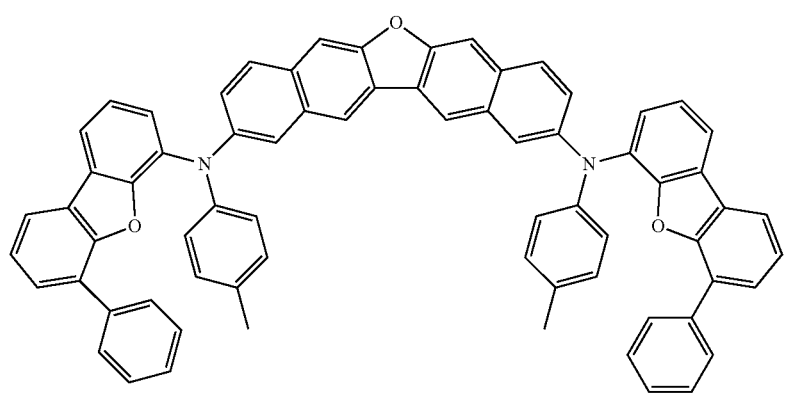
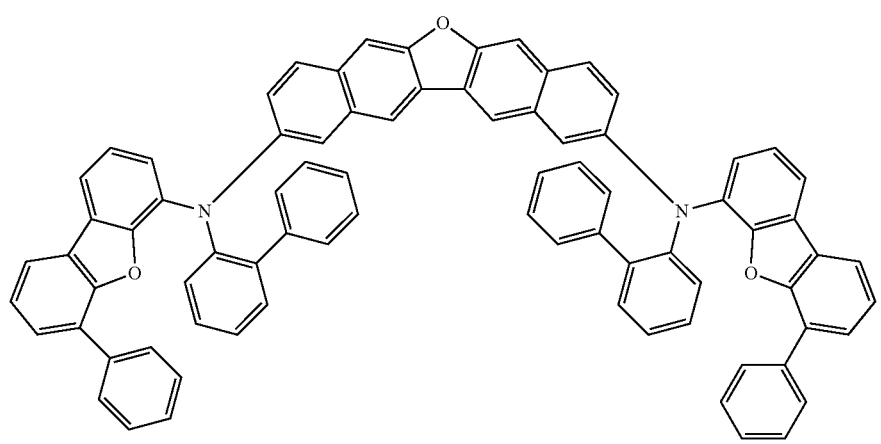
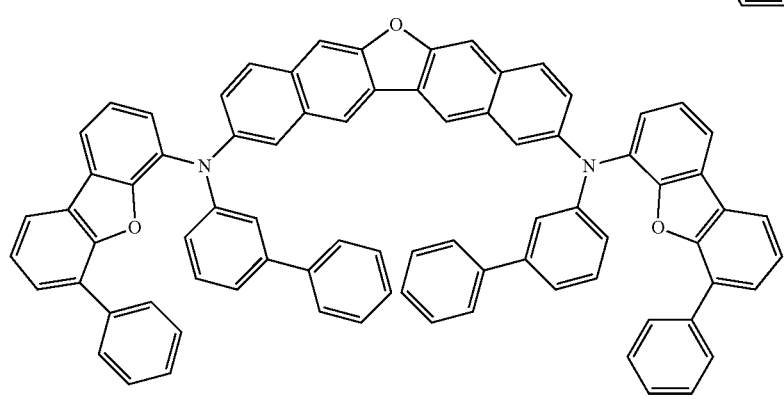

-continued
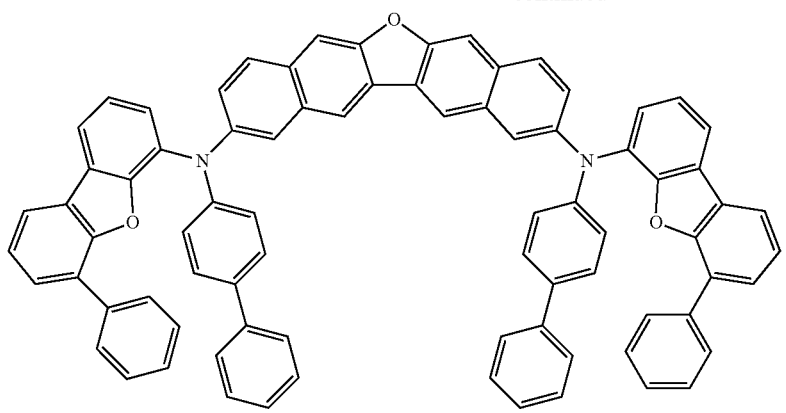
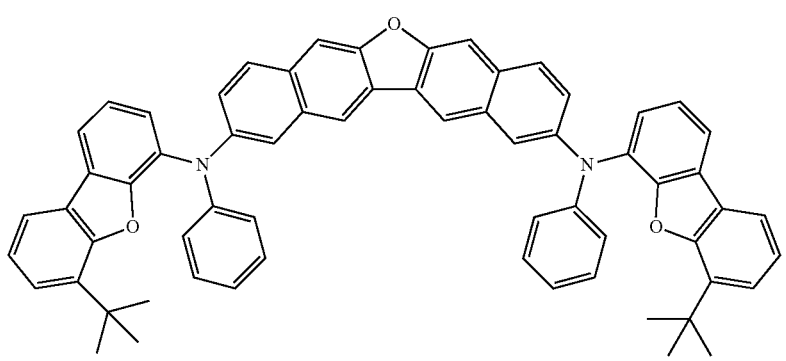
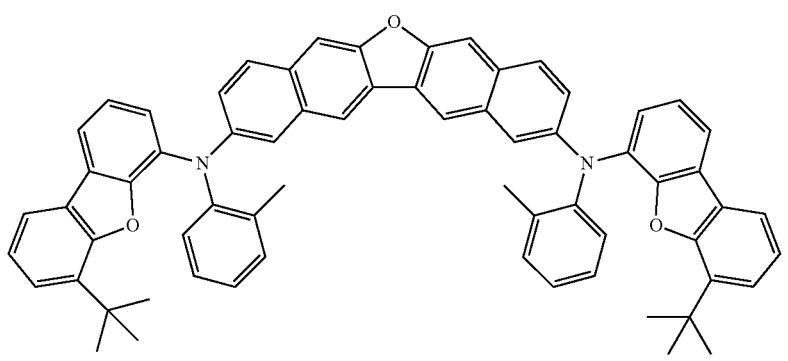
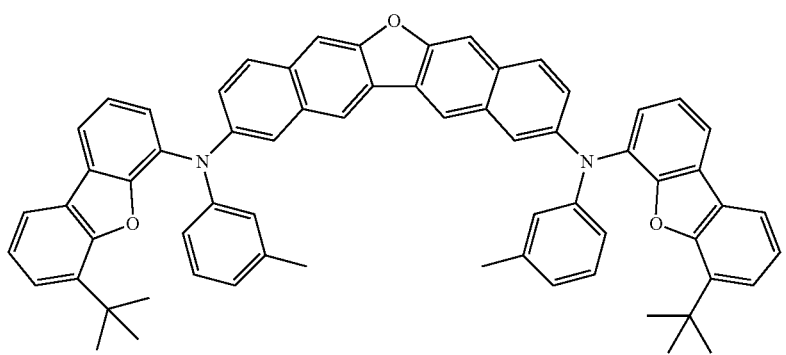

-continued
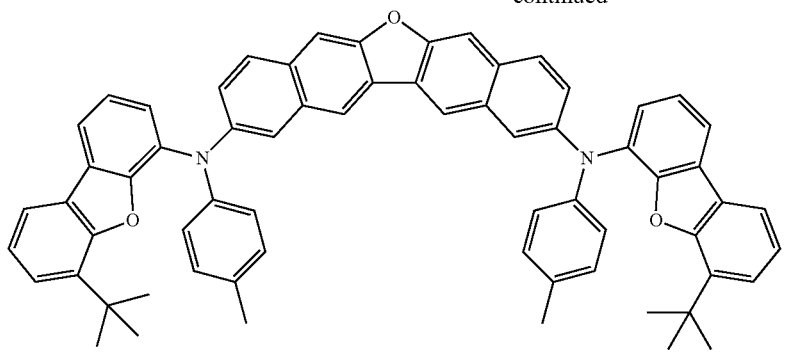
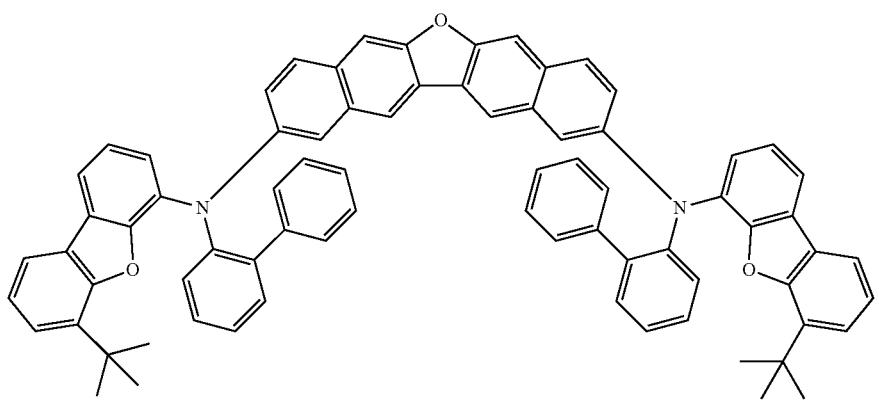
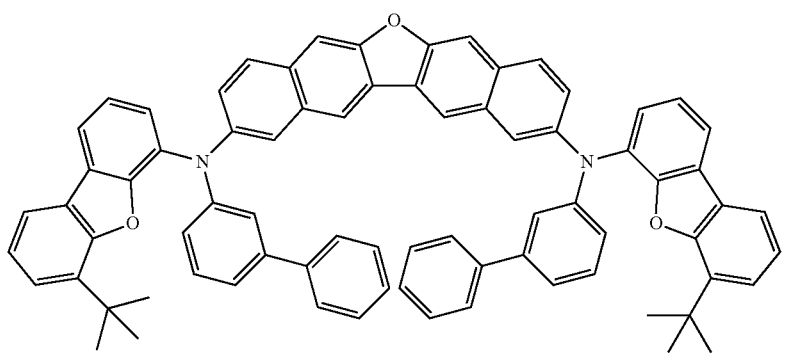
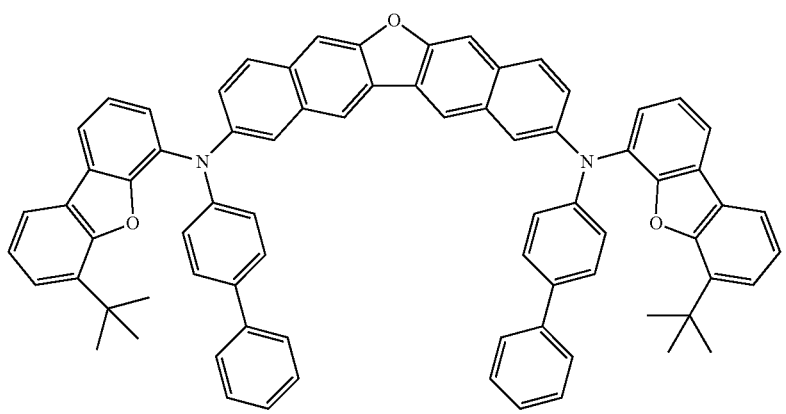

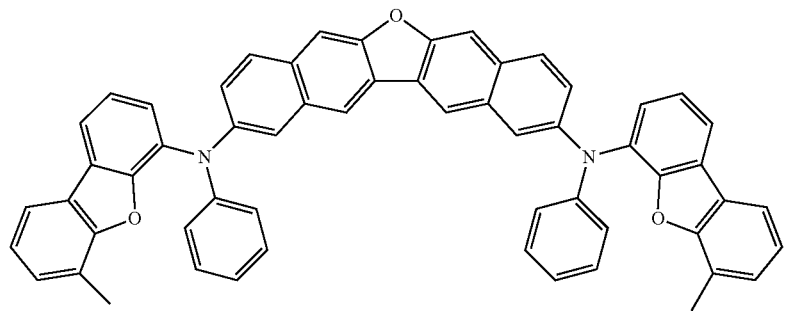
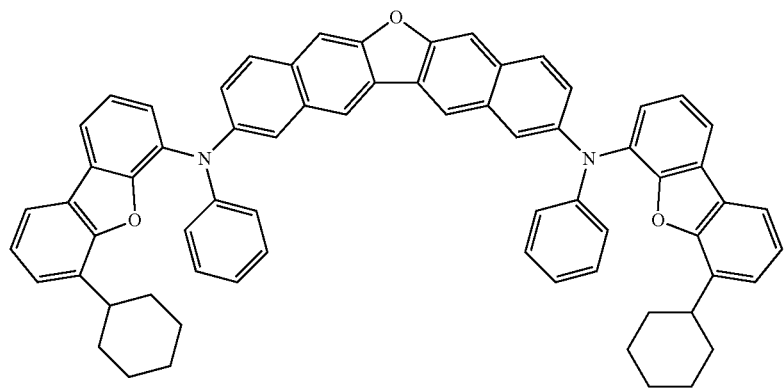
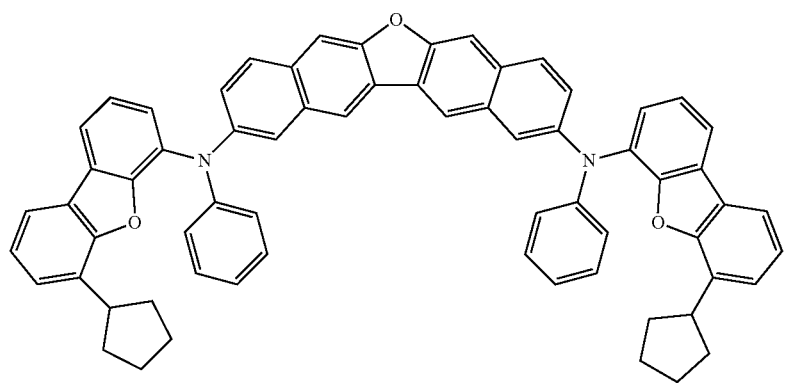
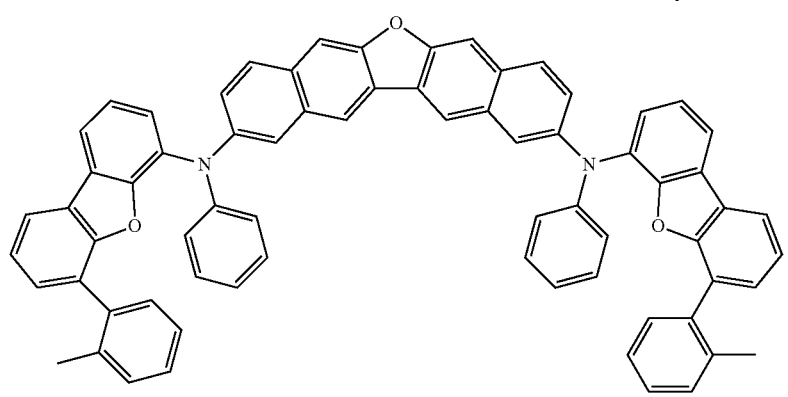
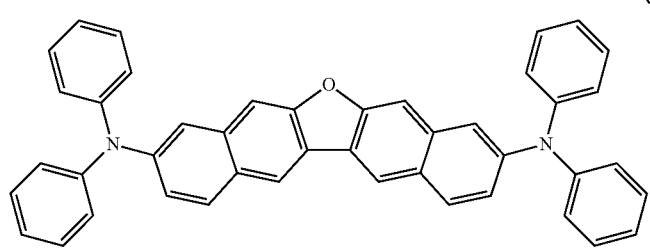

-continued
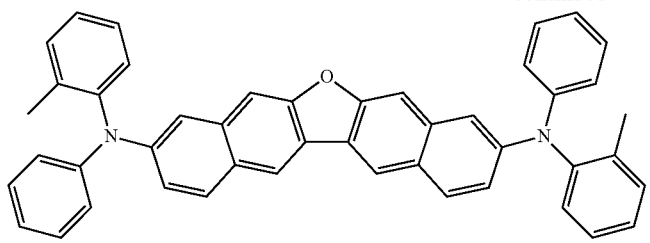
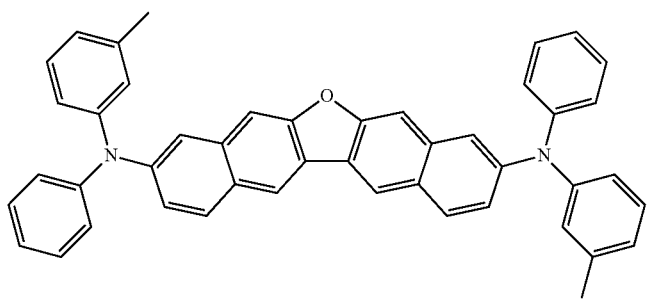
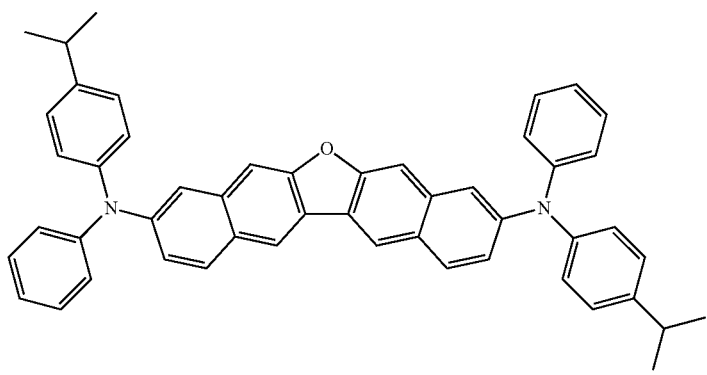
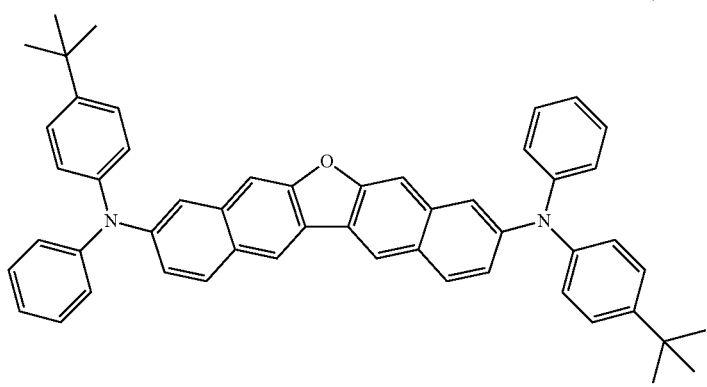
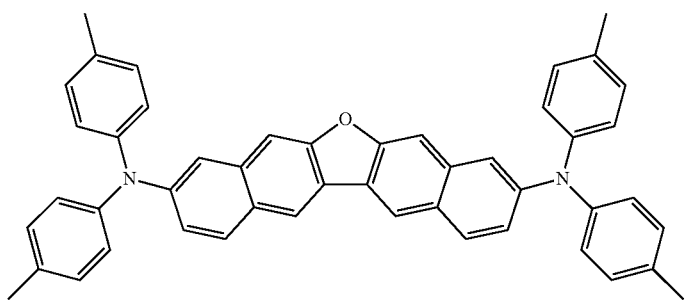

-continued
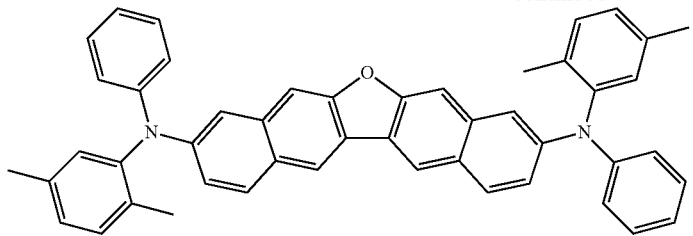
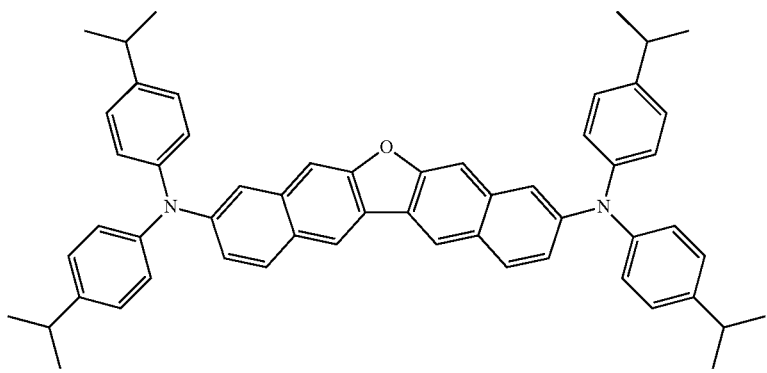
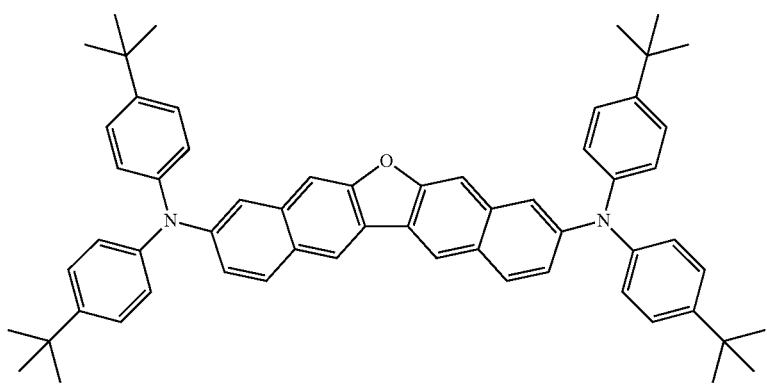
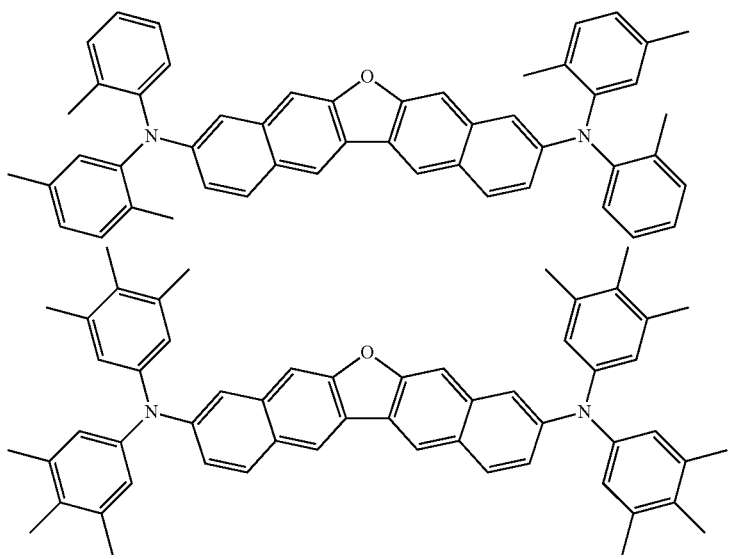

-continued
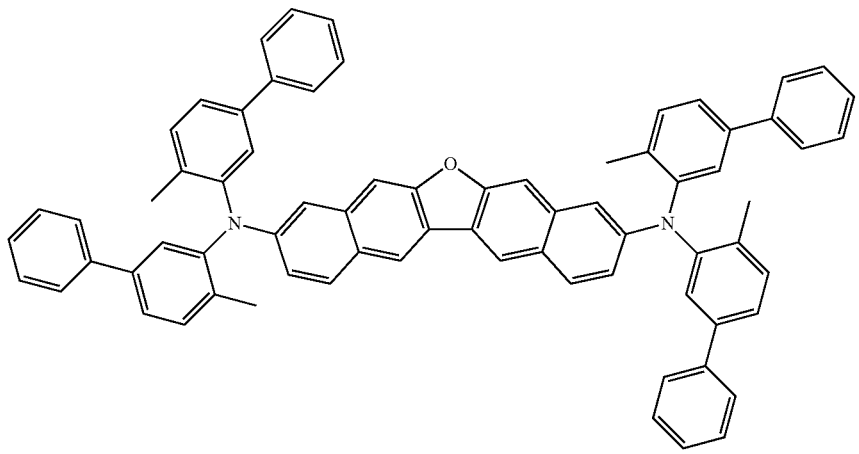
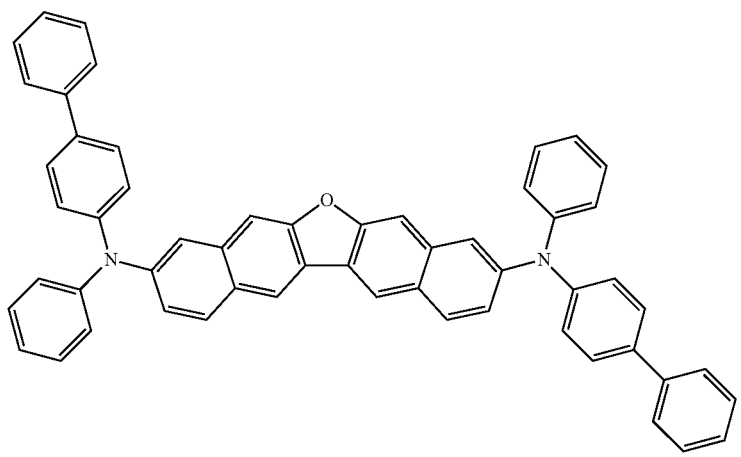
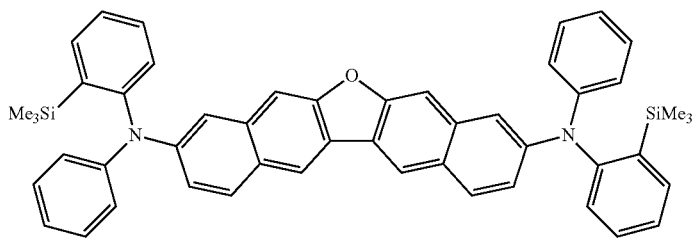
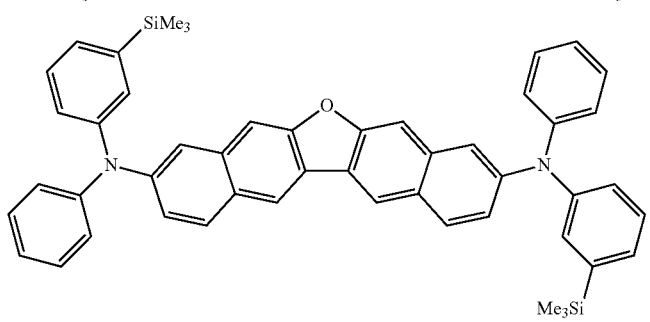
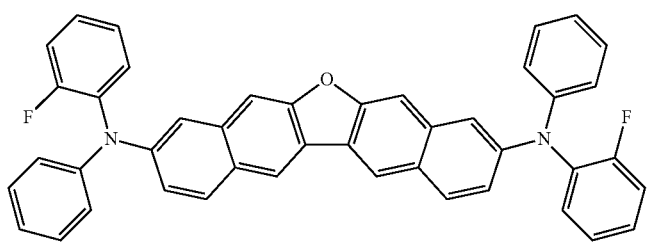

-continued
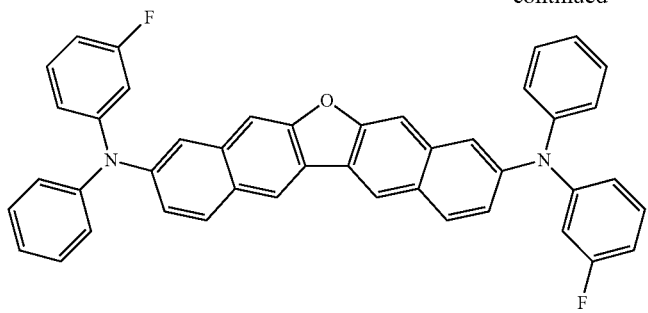
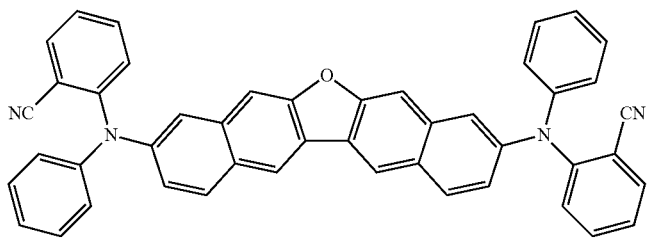
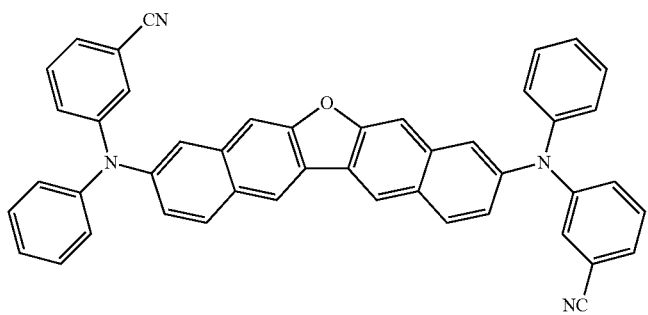
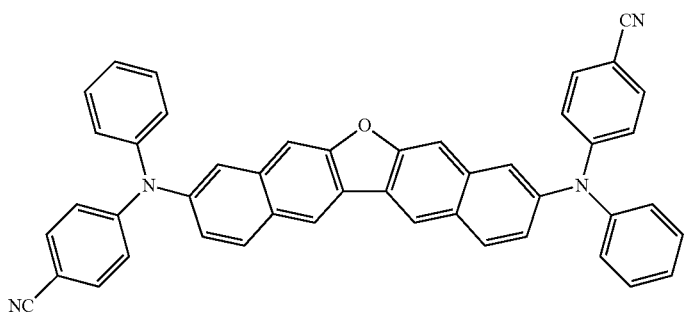
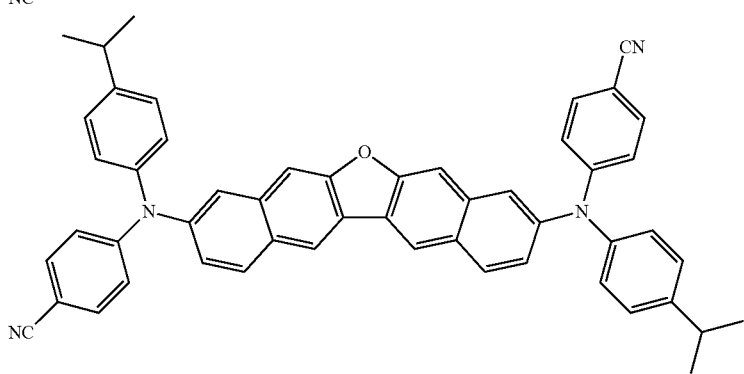

-continued
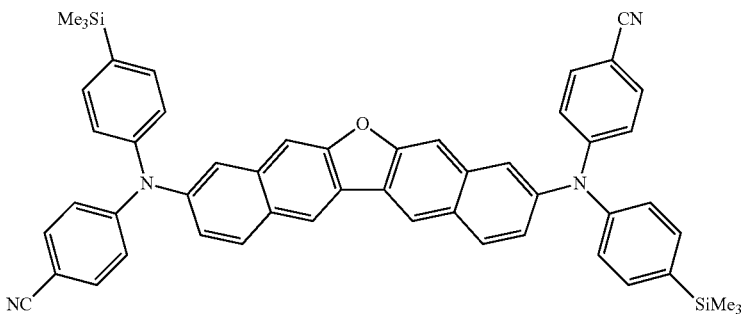
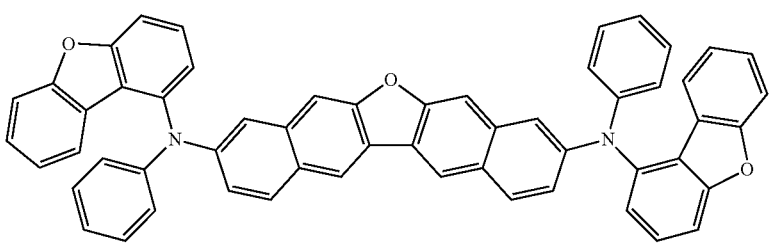
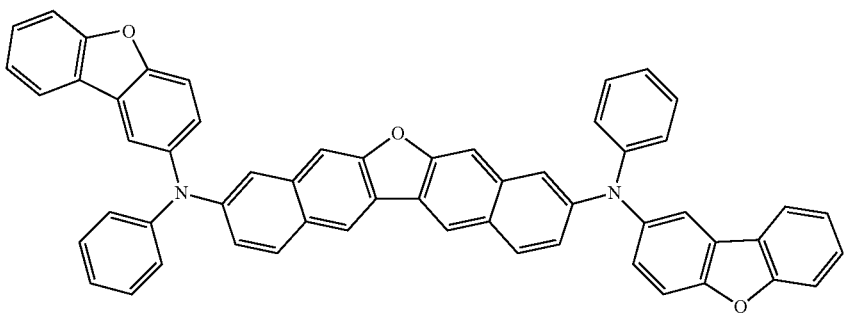
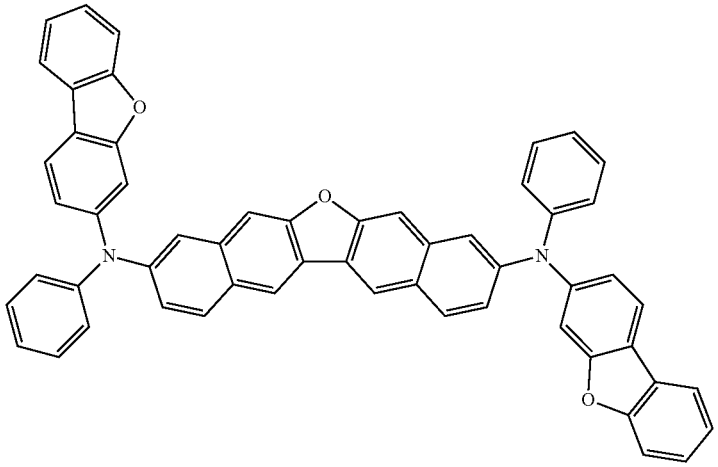
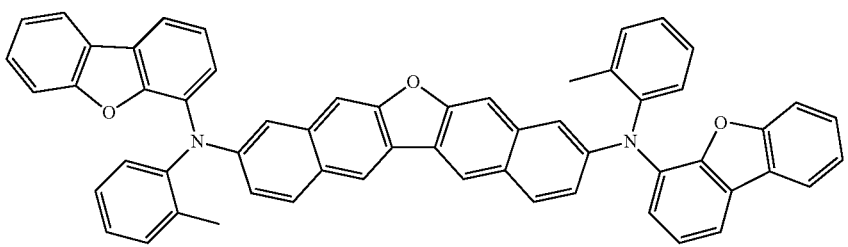

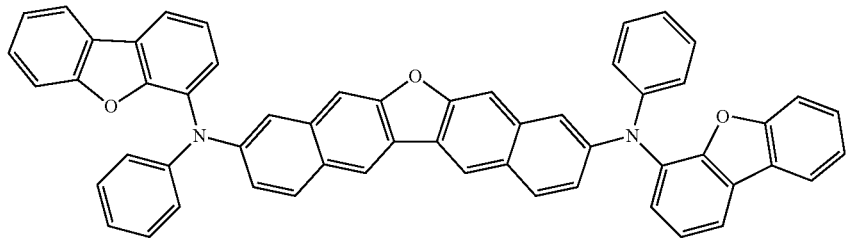
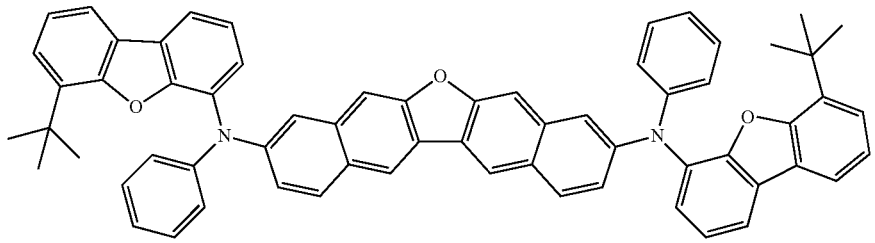
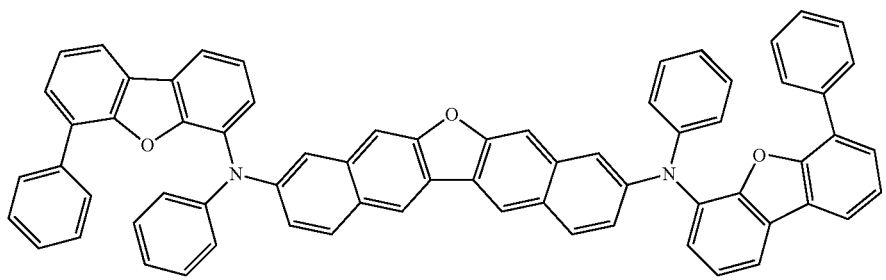
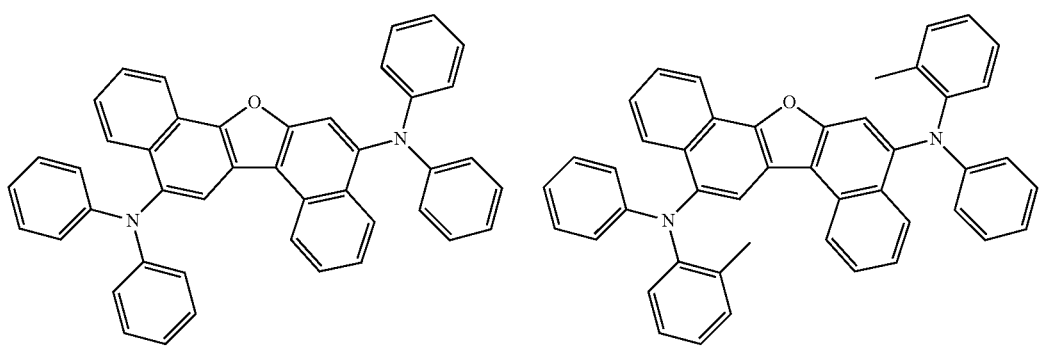
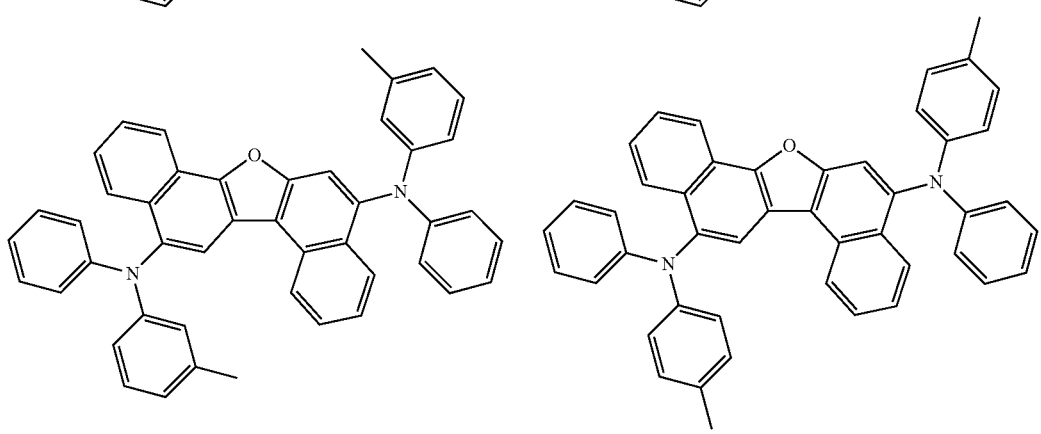

773 774
-continued
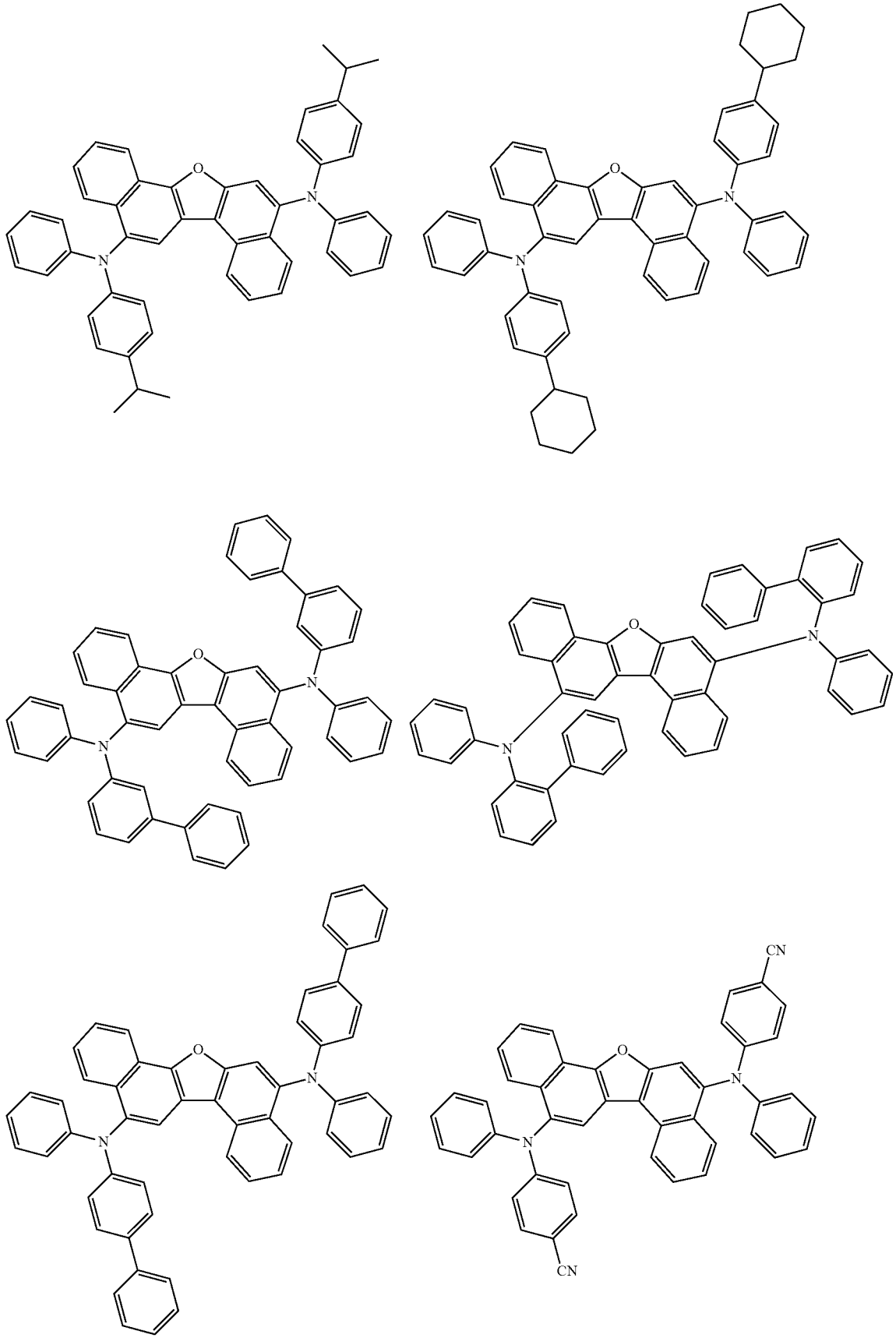

-continued
| 775 | 776 |
|---|---|
| 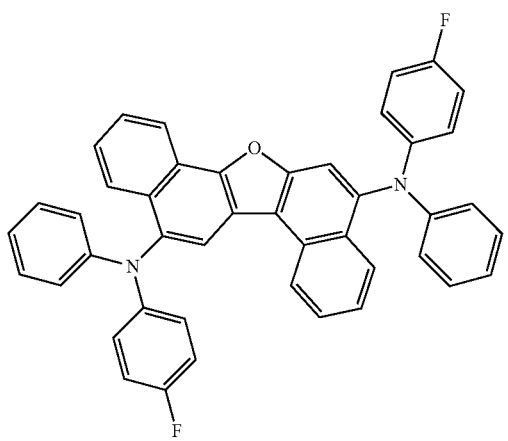 | 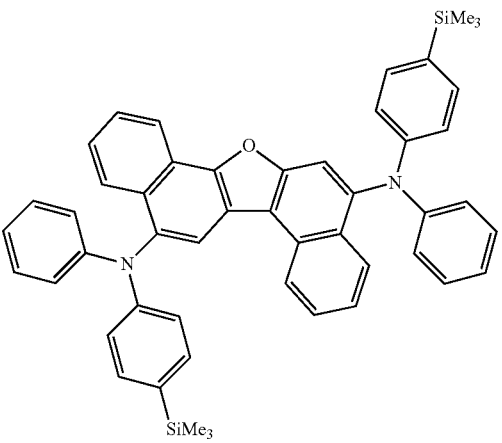 |
| 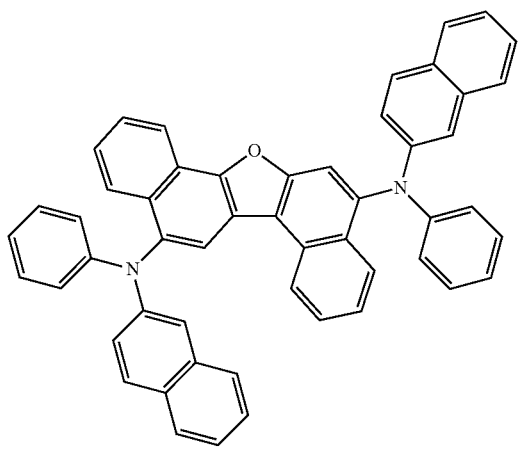 | 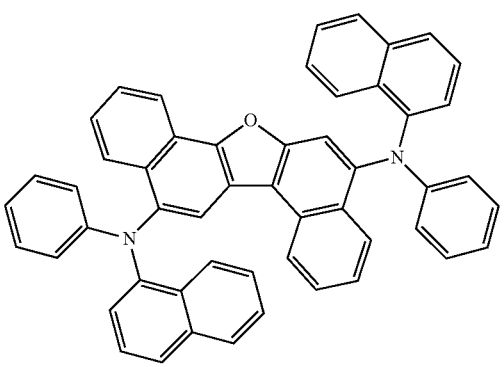 |
| 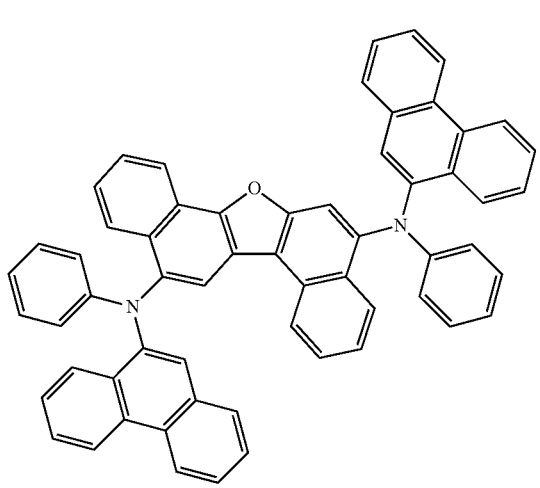 | 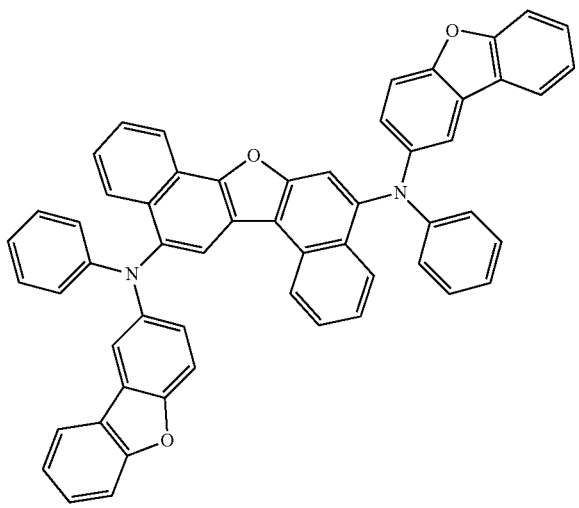 |

-continued
777 778
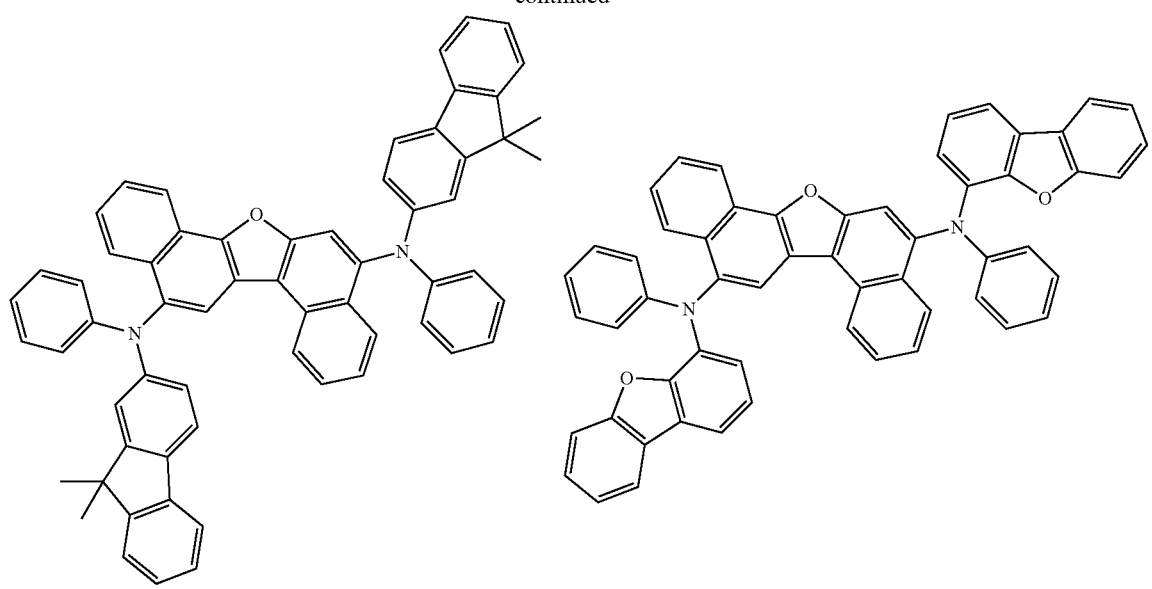
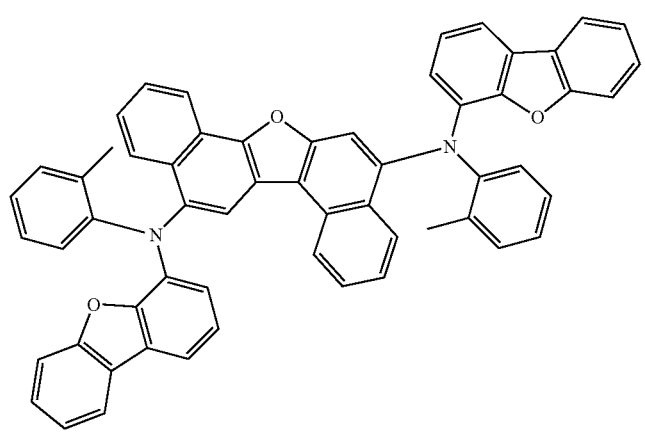
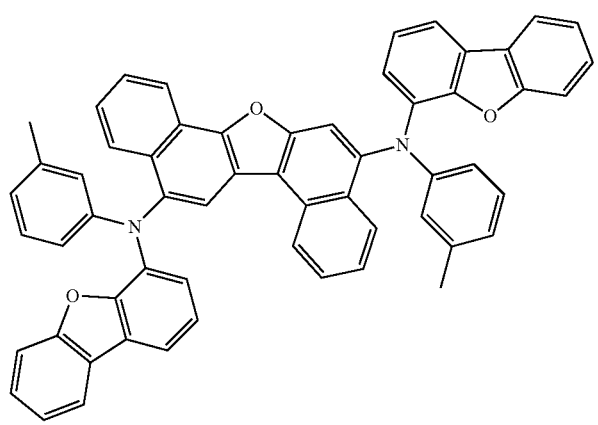

-continued
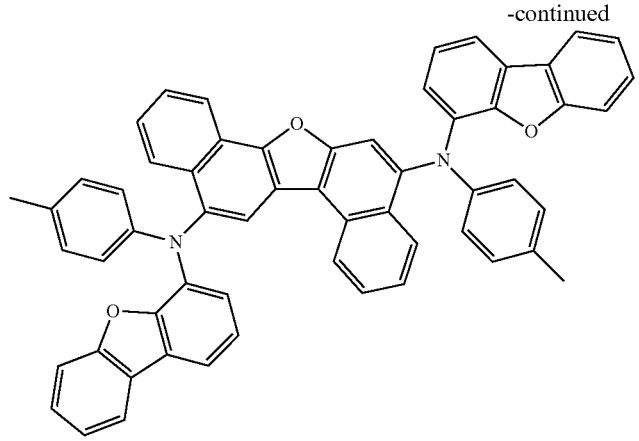
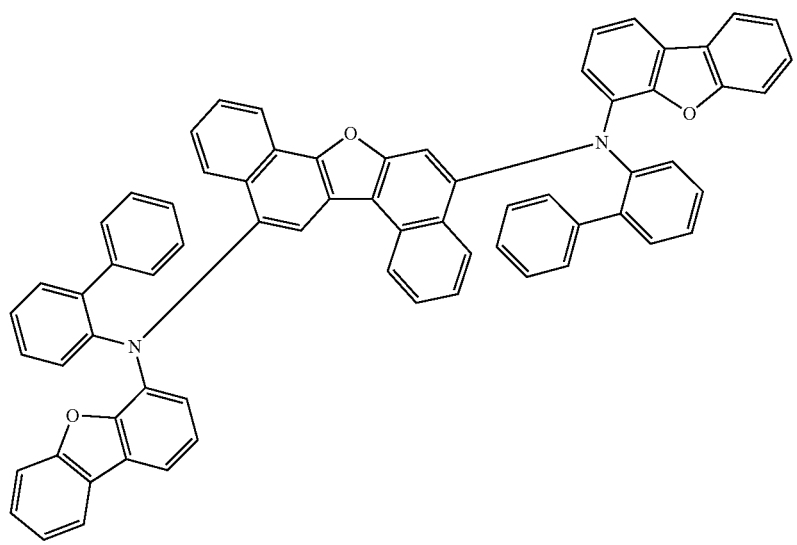
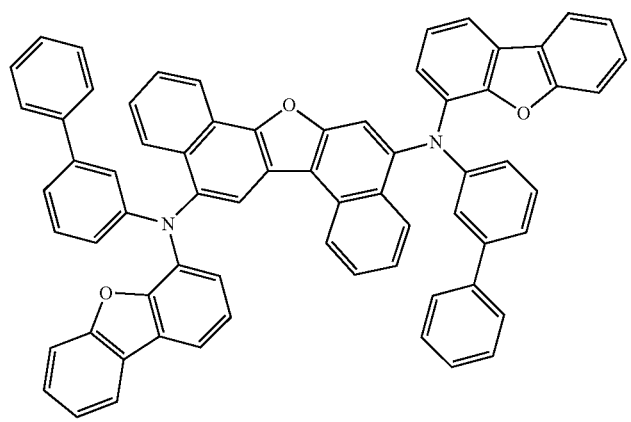

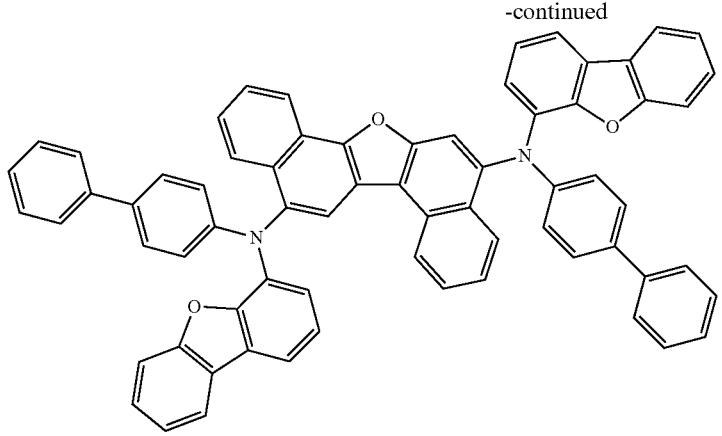
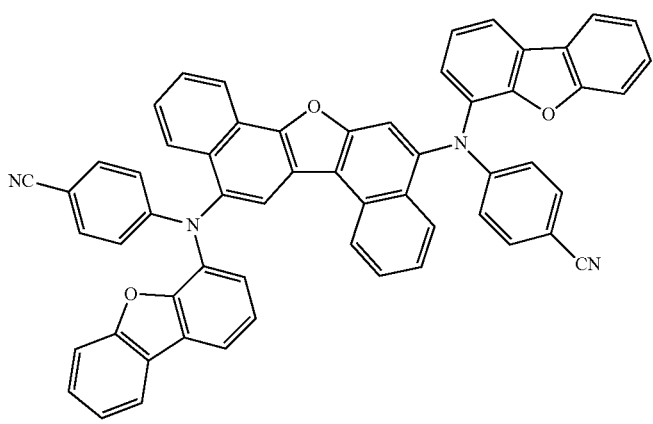
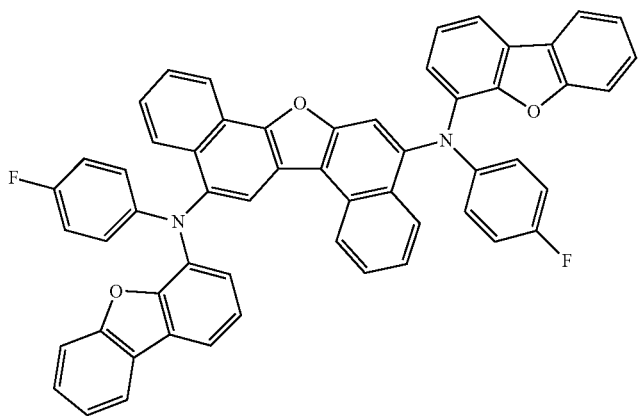
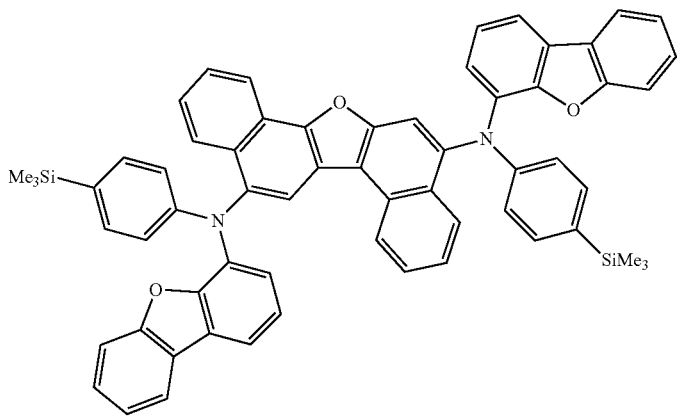

-continued
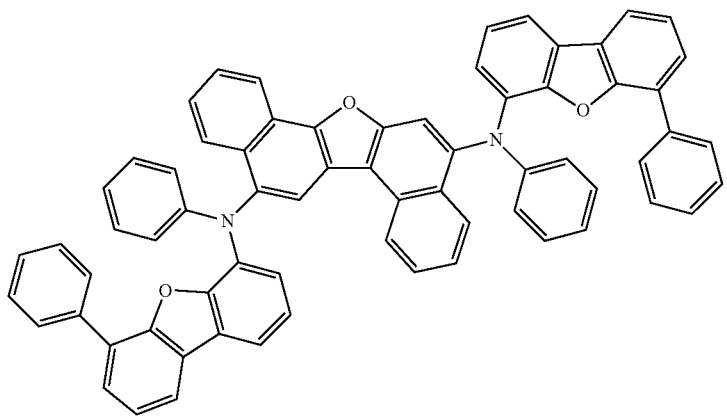
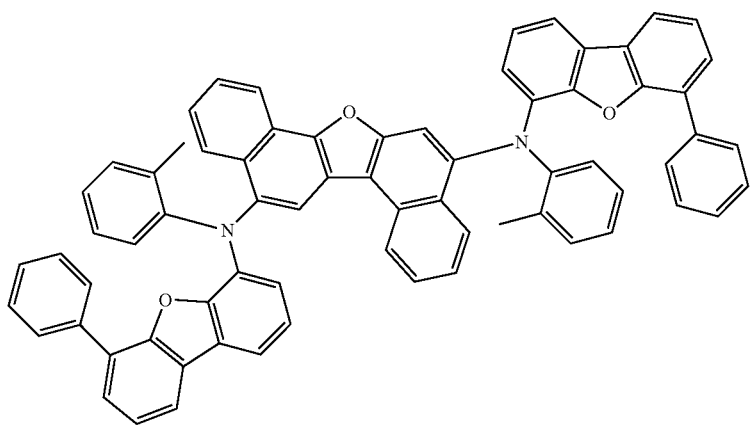
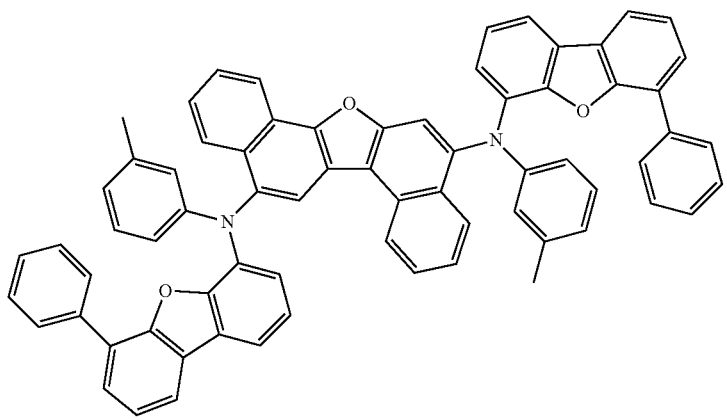
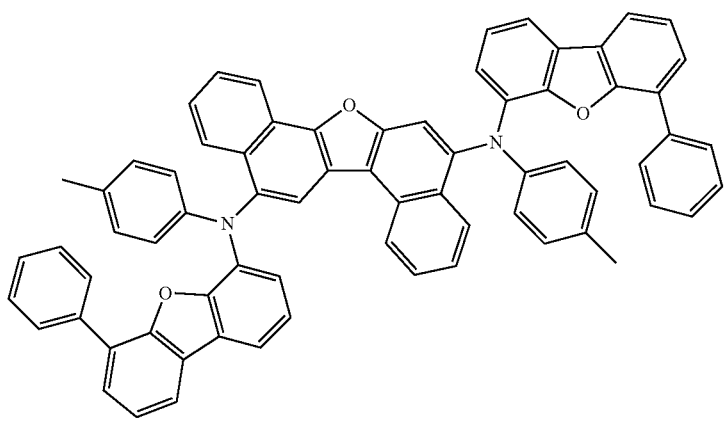

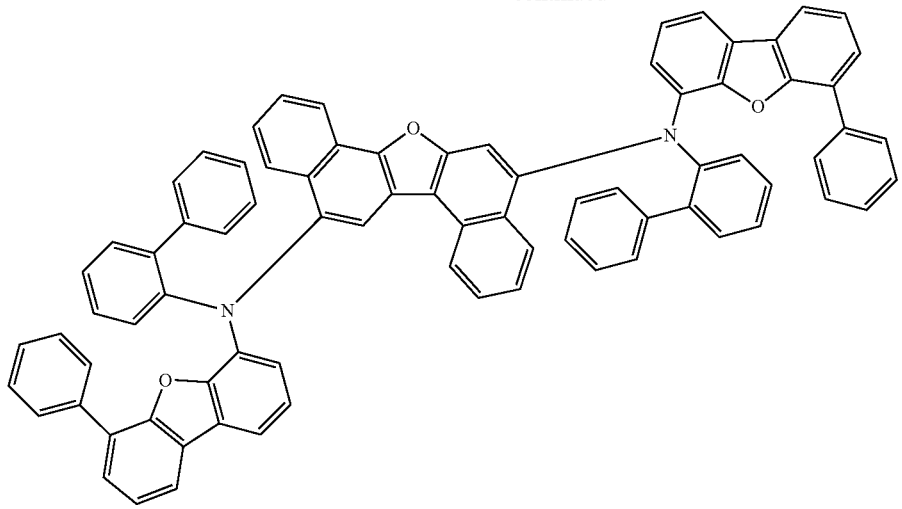
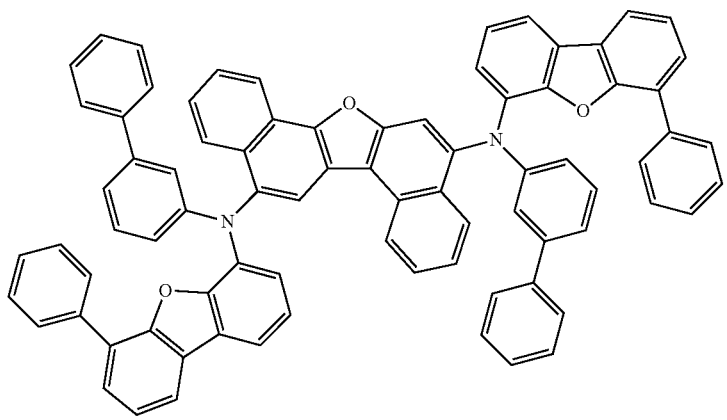
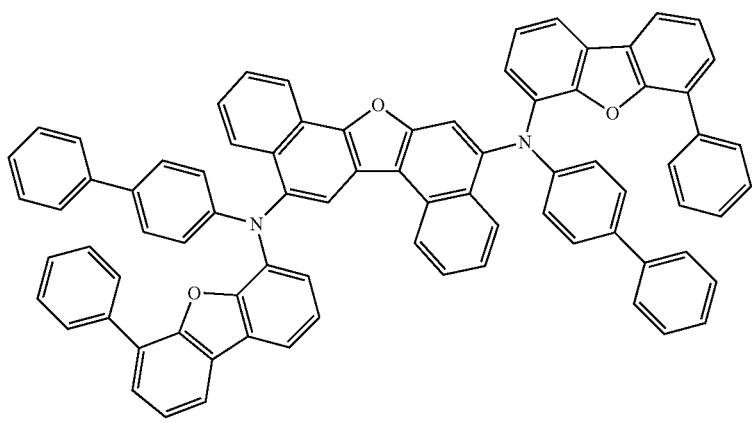

-continued
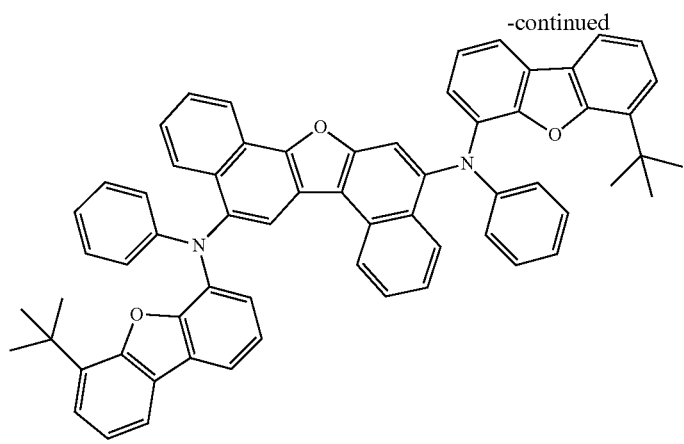
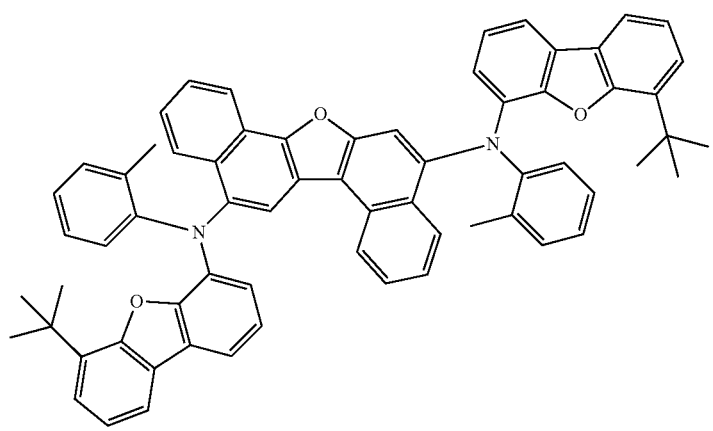
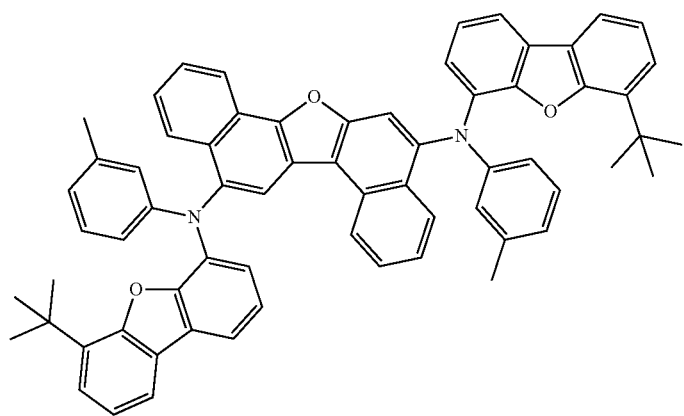

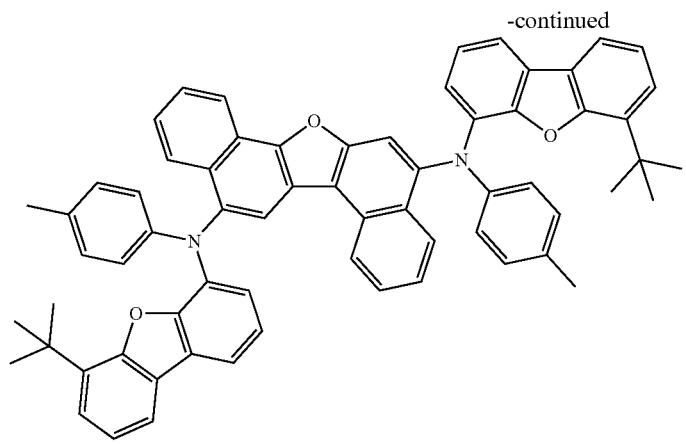
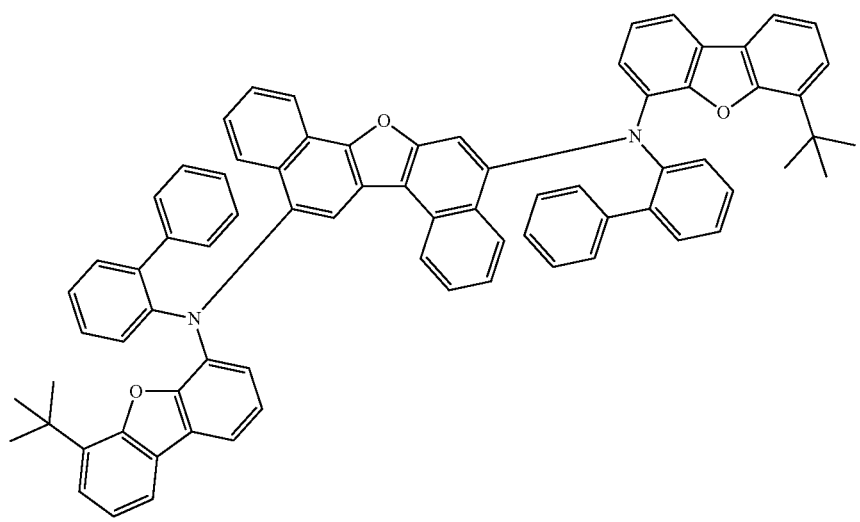
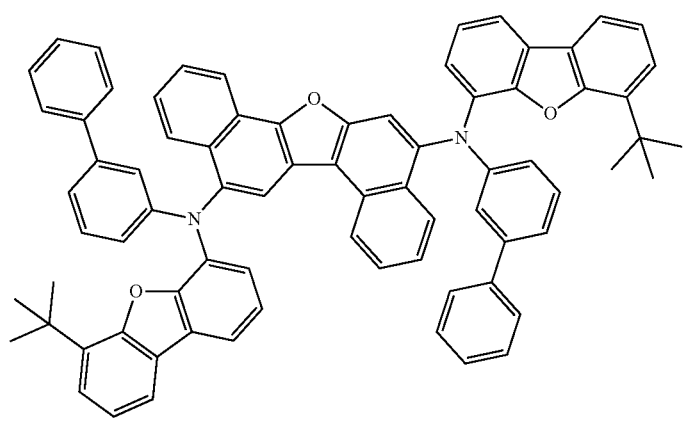

-continued
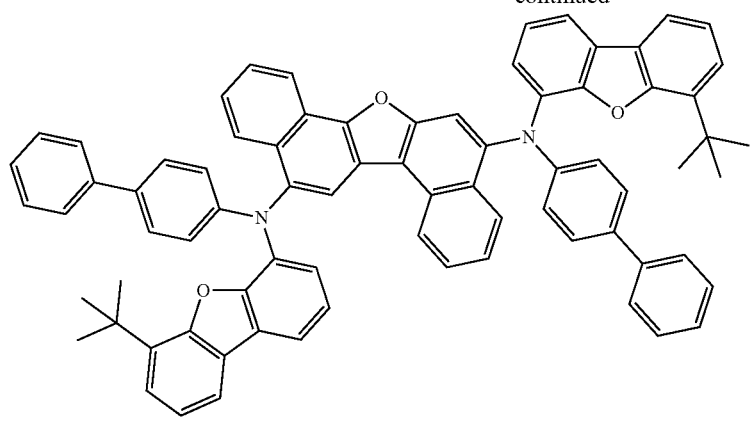
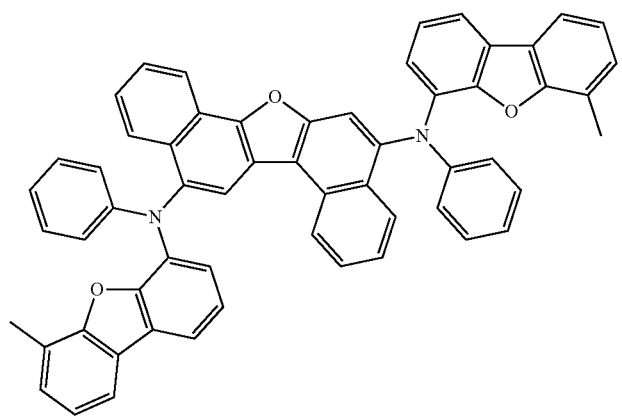
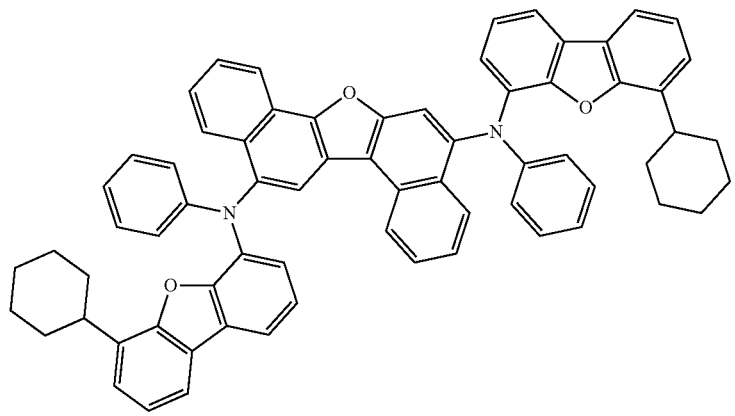
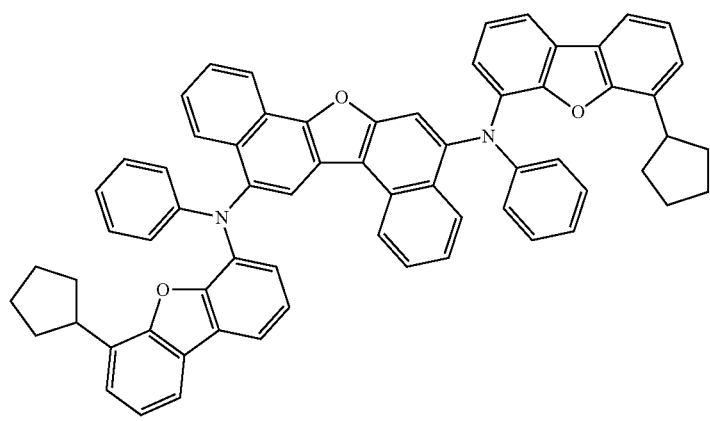

793 794
-continued
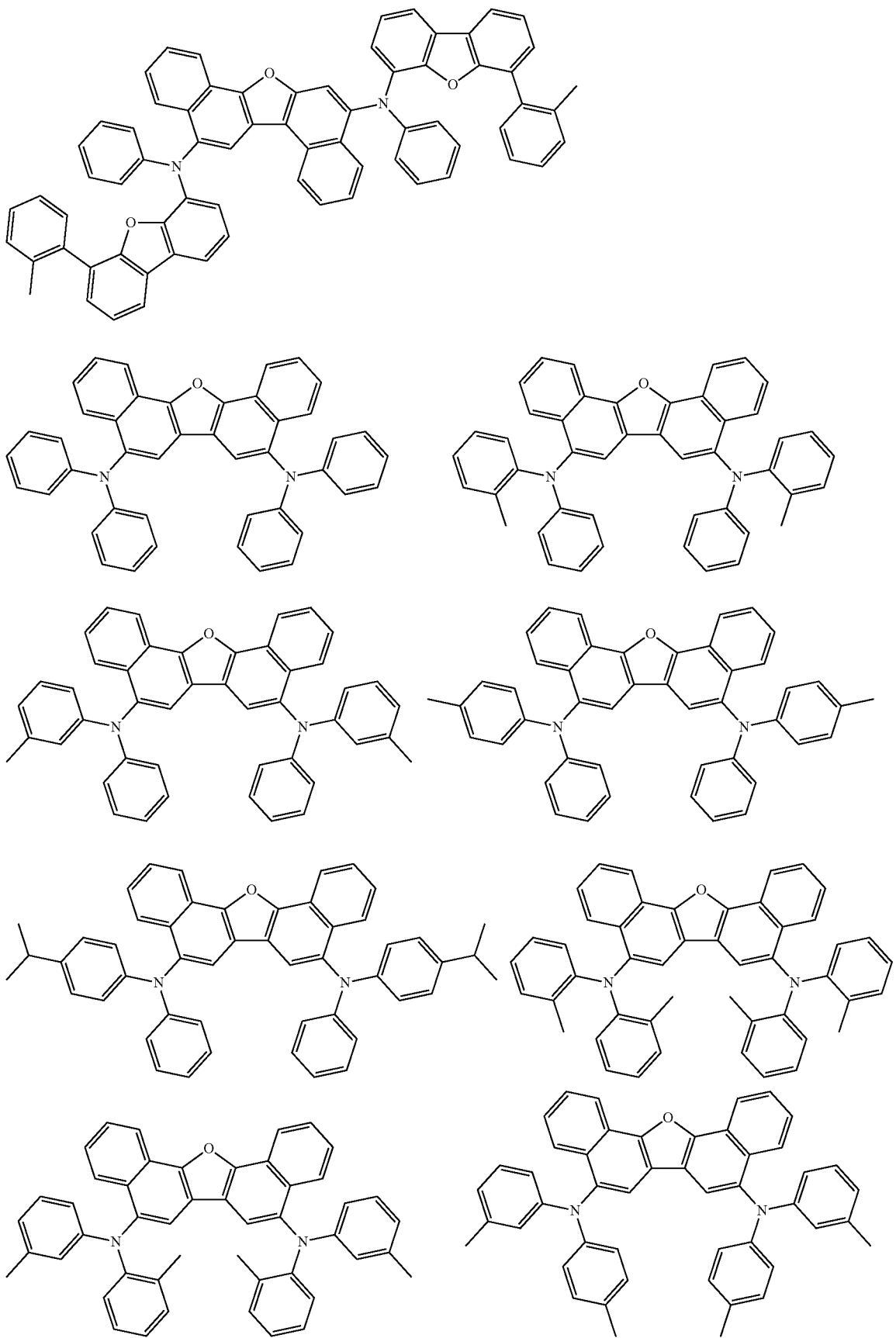

-continued
795    796
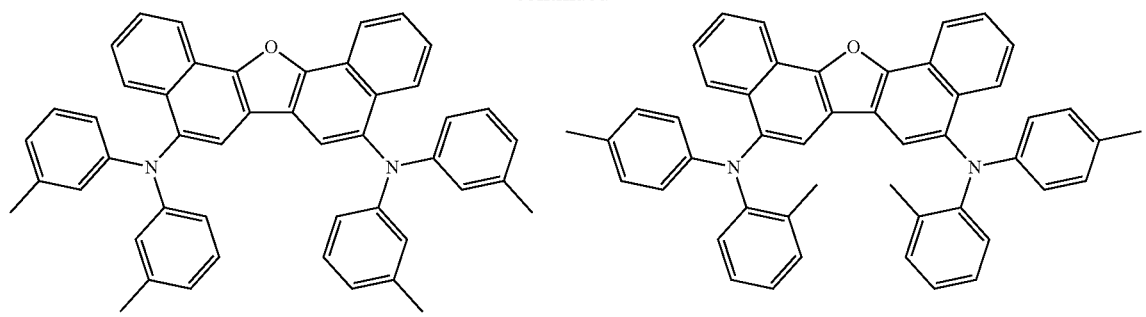
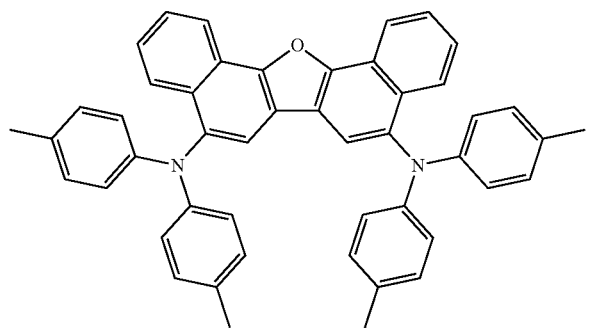
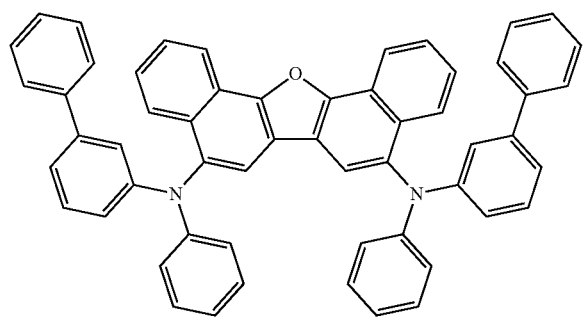
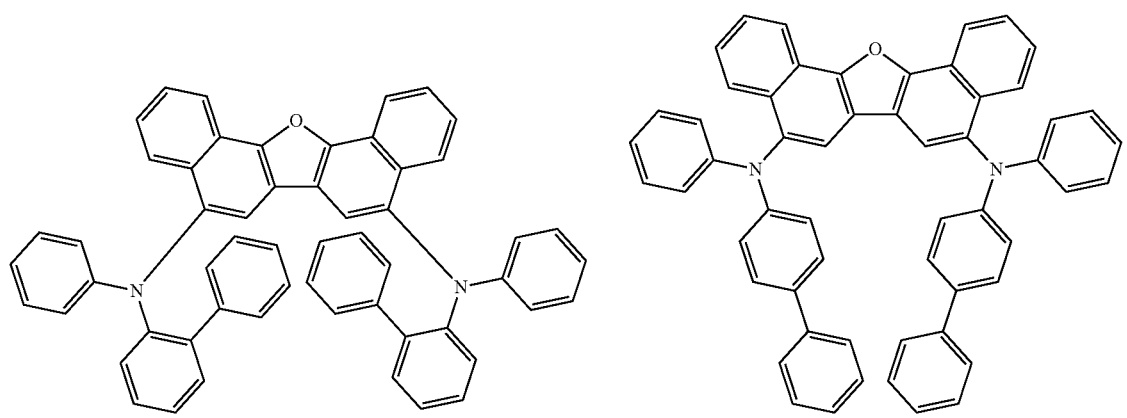
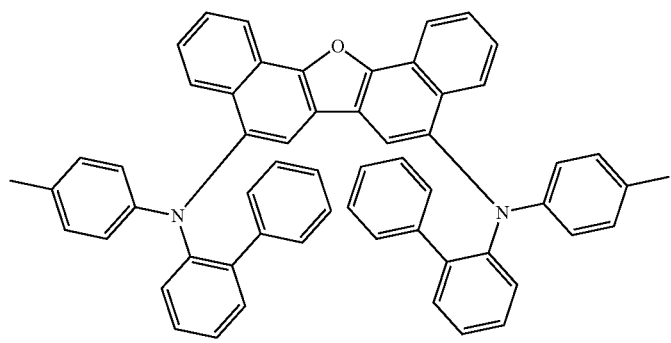

797 798
-continued
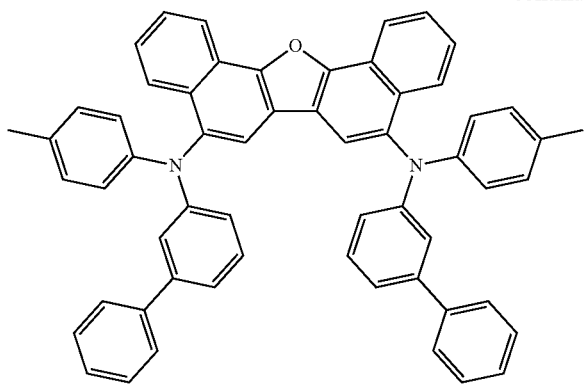
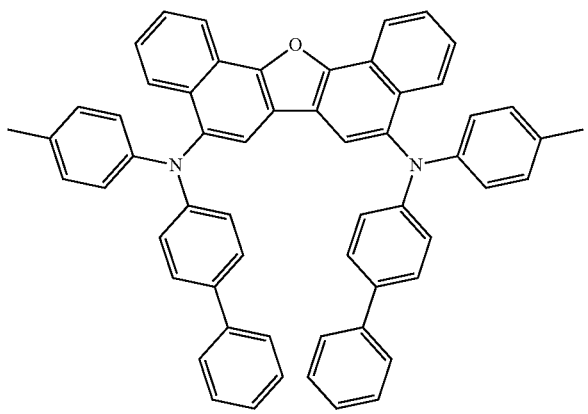
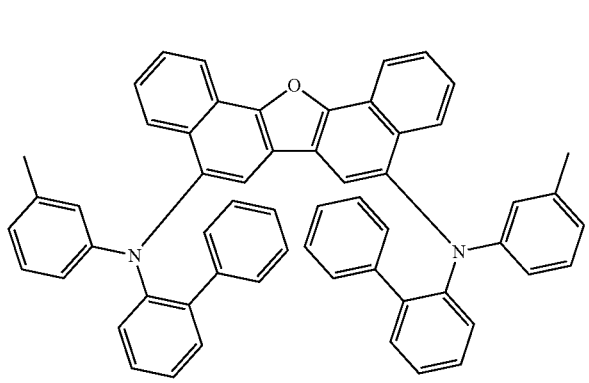
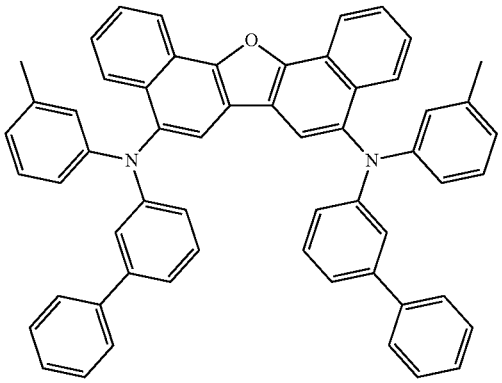
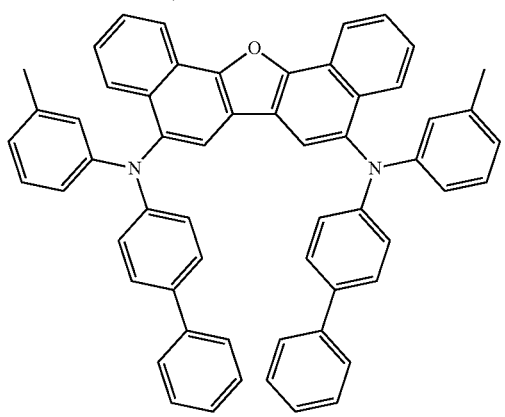
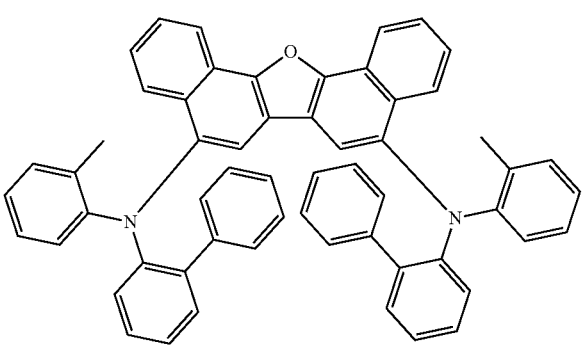

-continued
| 799 | 800 |
|---|---|
| 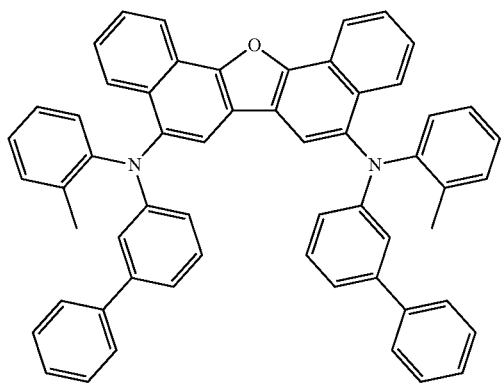 | 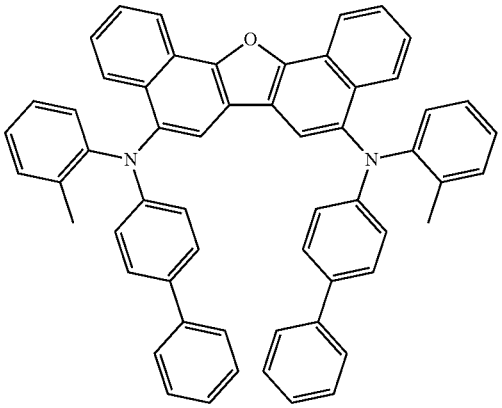 |
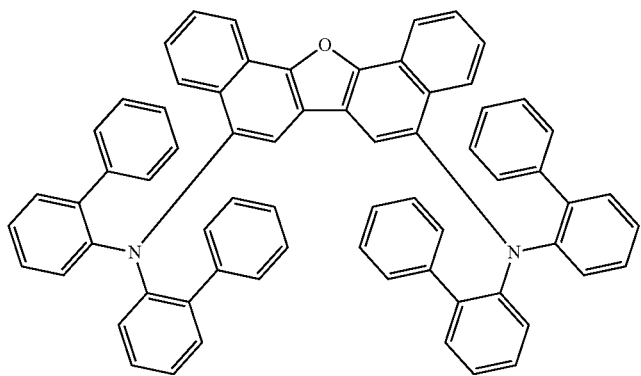
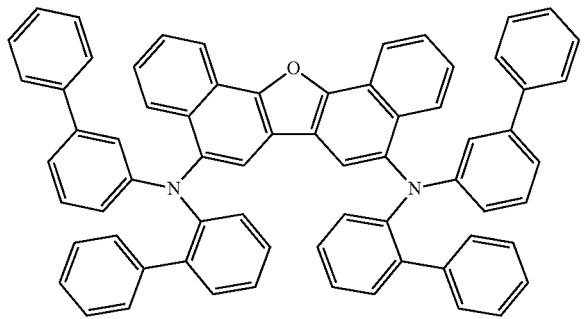
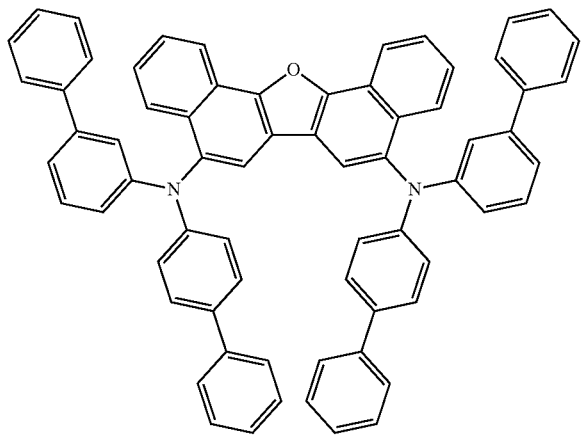

-continued
801
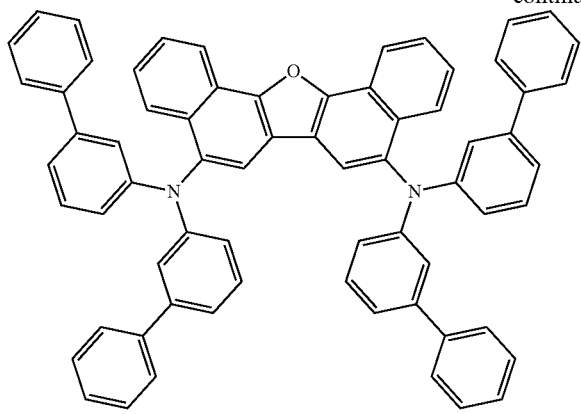
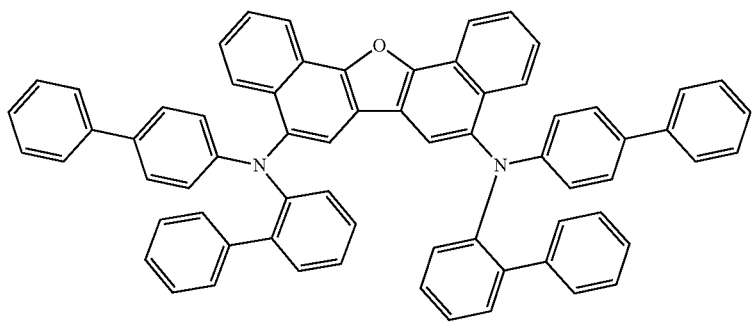
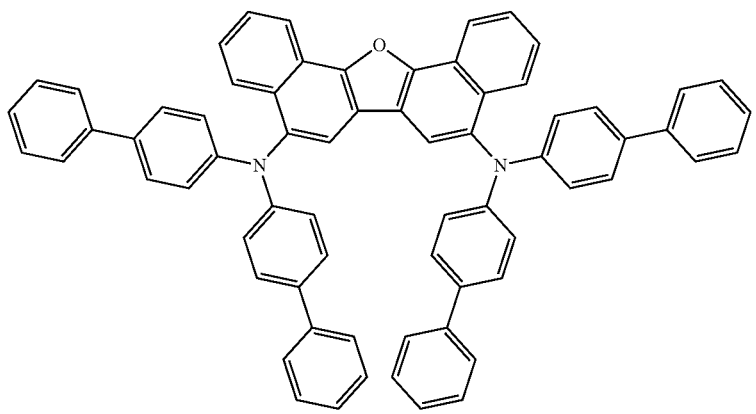
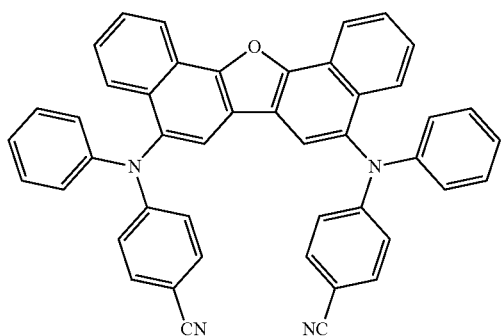
802
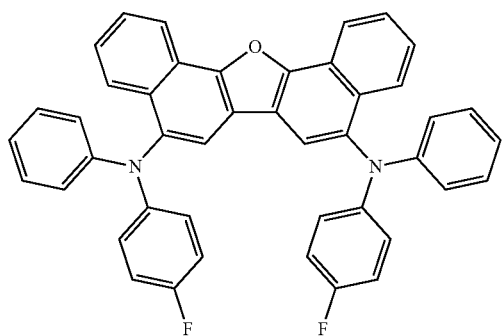

-continued
| 803 | 804 |
|---|---|
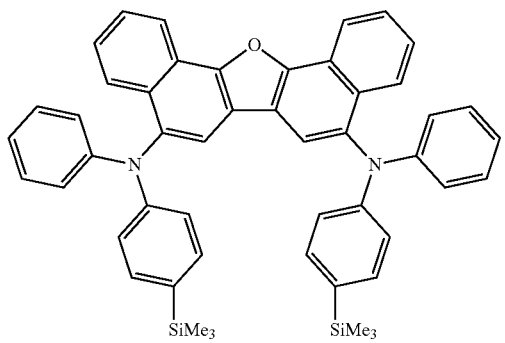
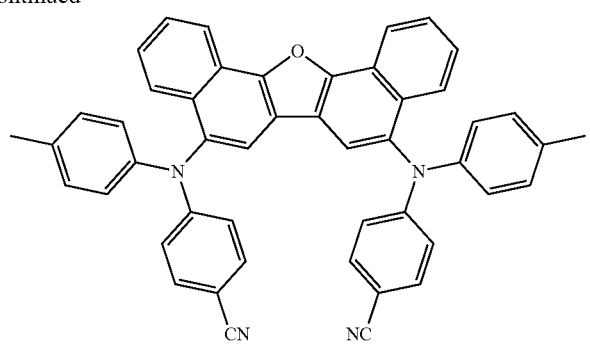
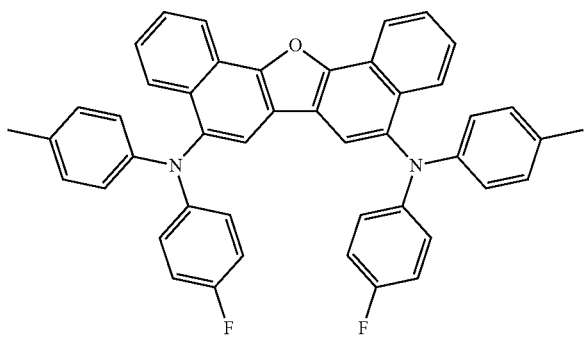
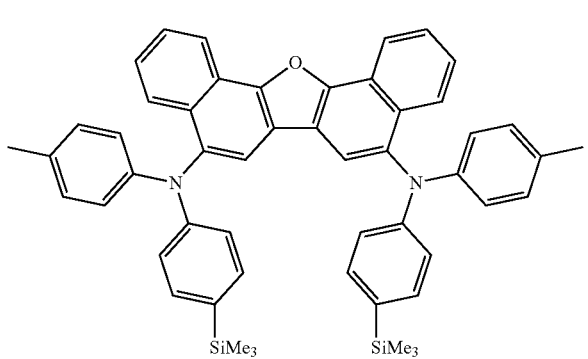
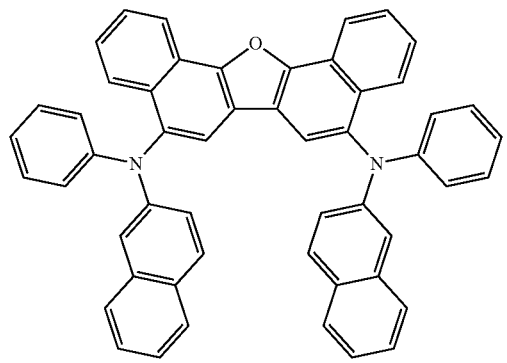
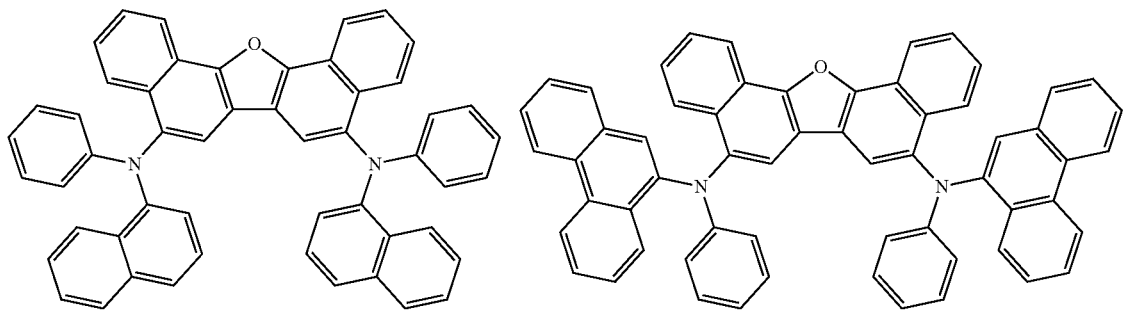

-continued
805
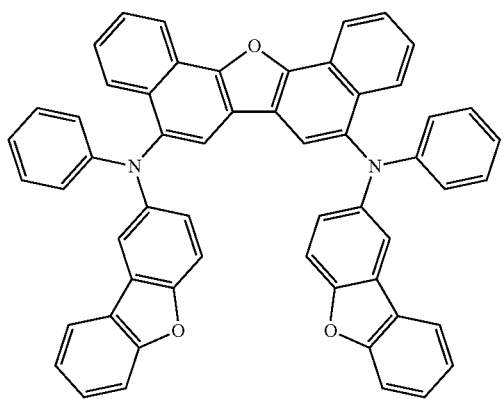
806
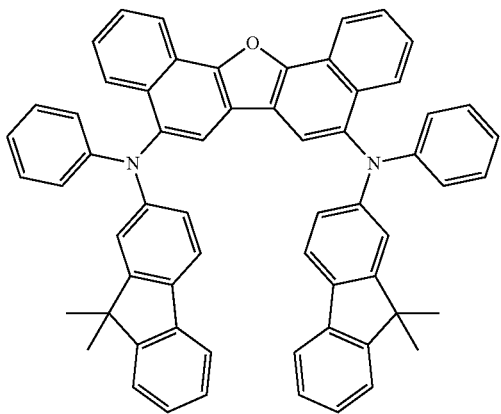
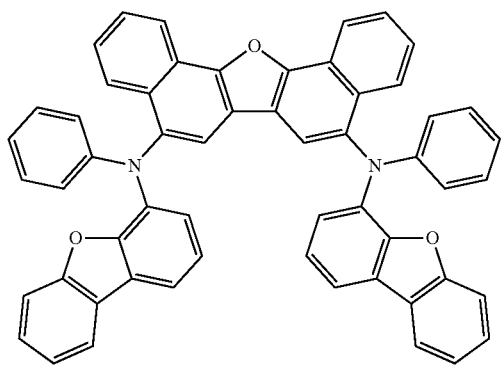
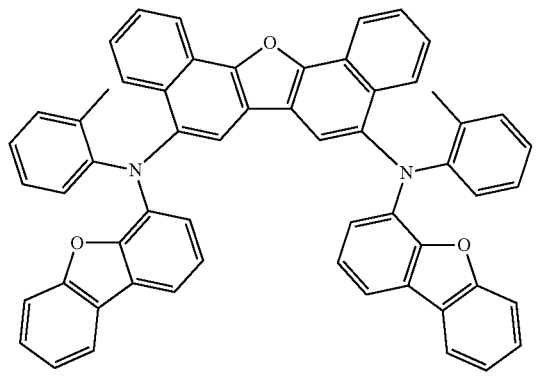
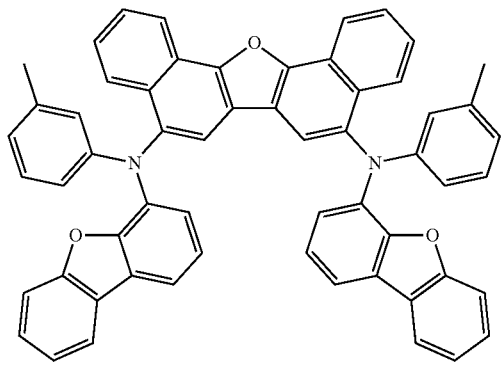
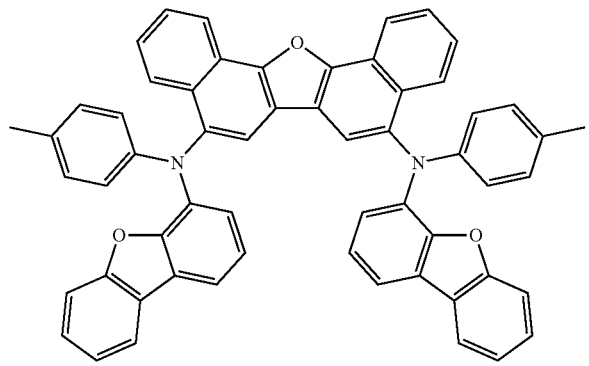
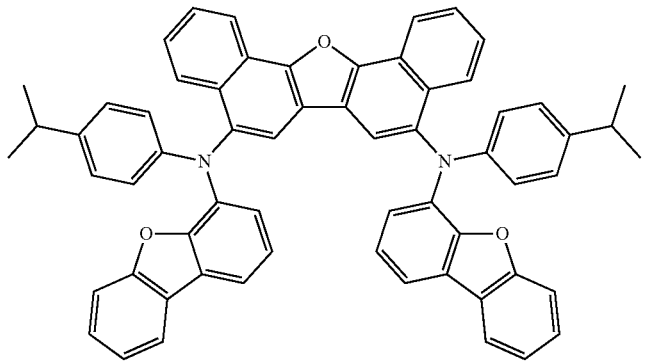

807                                                                                  808
-continued
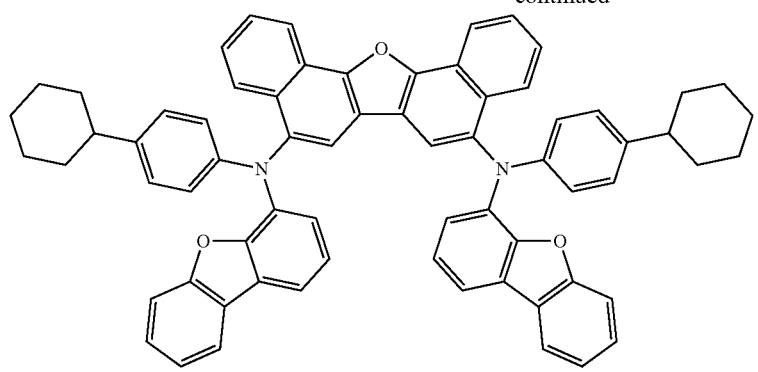
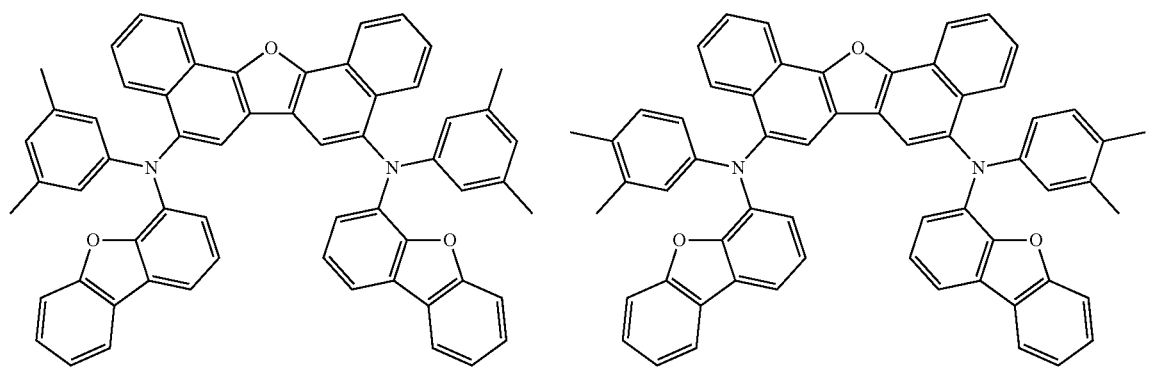
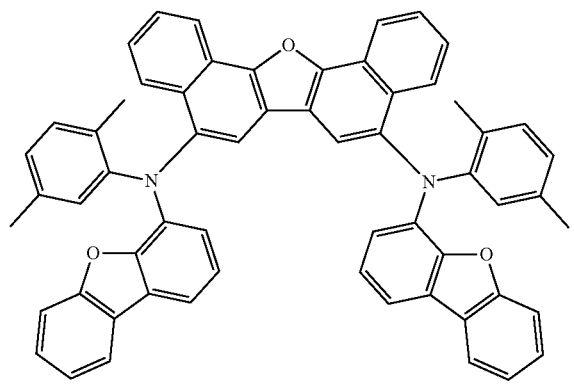
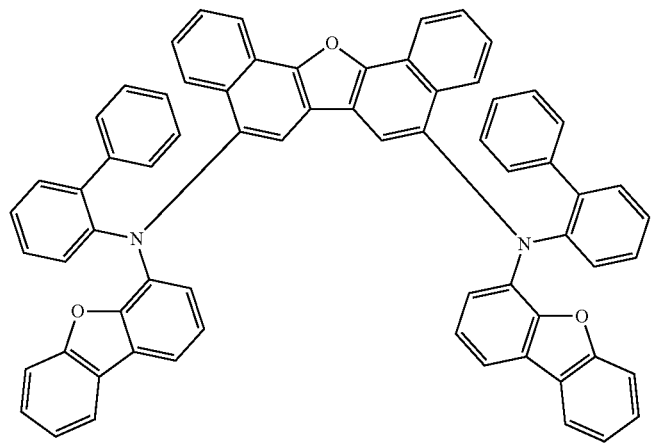

-continued
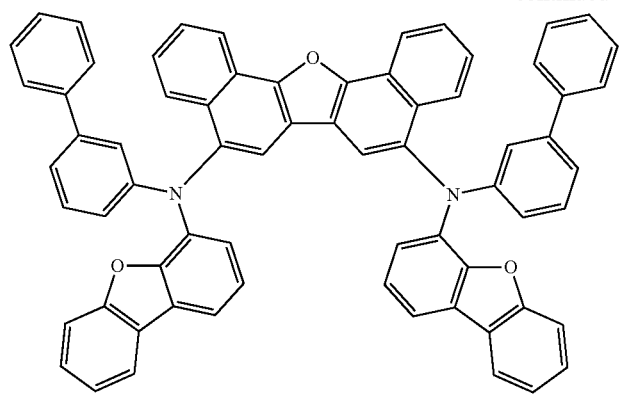
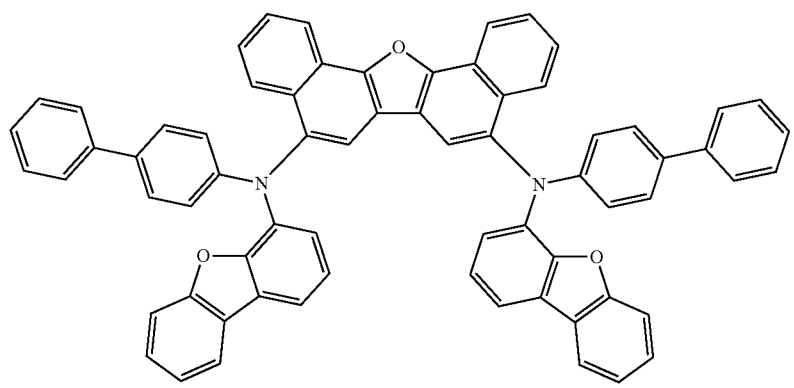
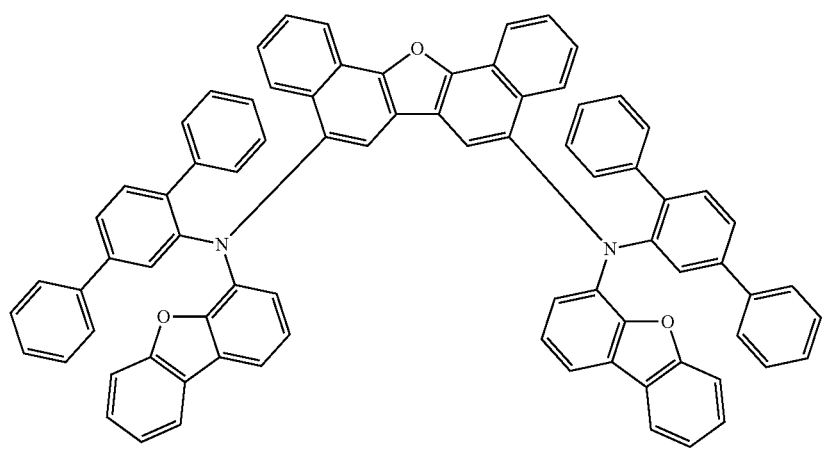
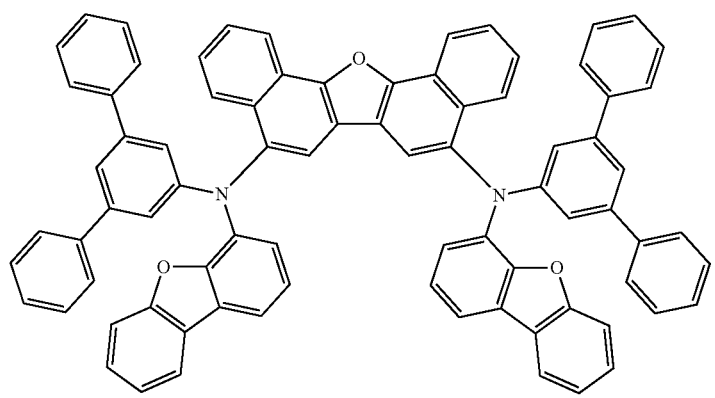

-continued
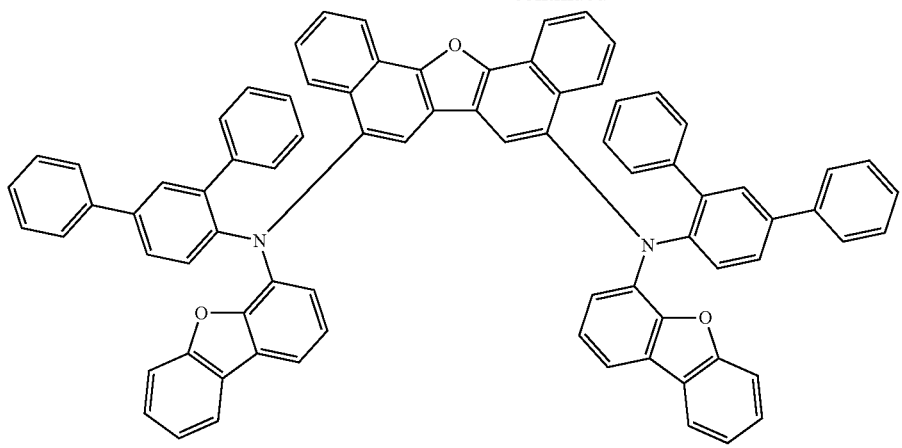
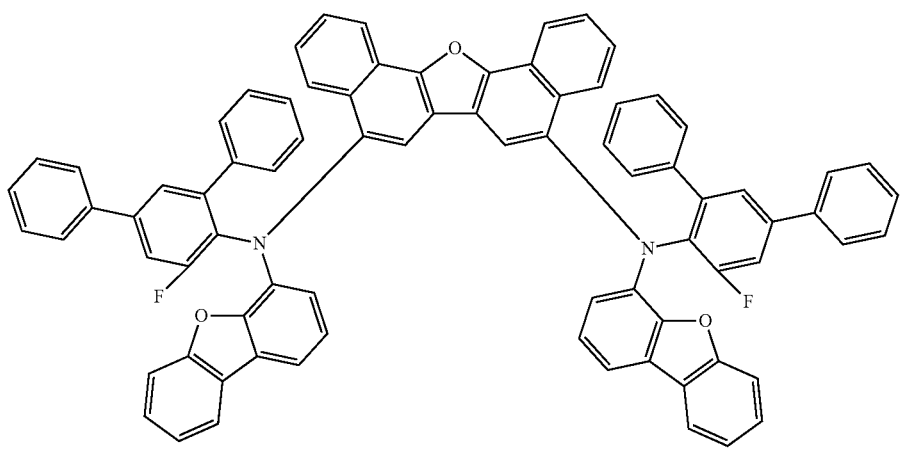
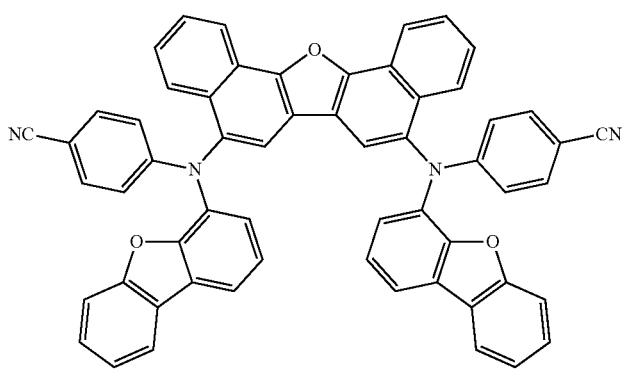
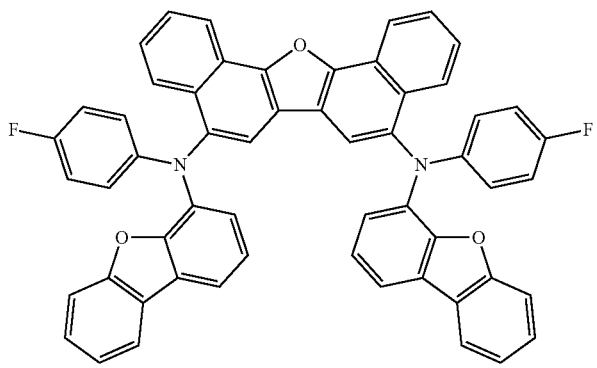

813
-continued
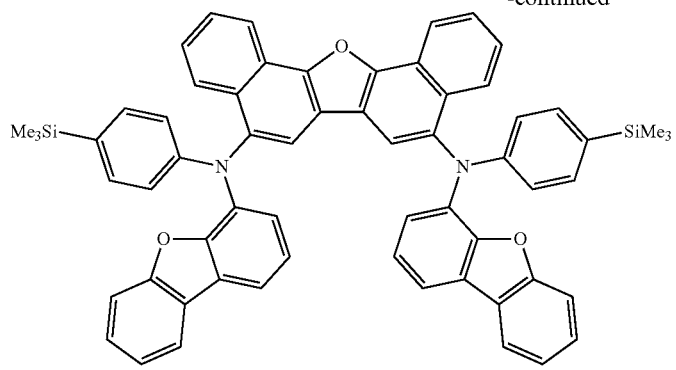
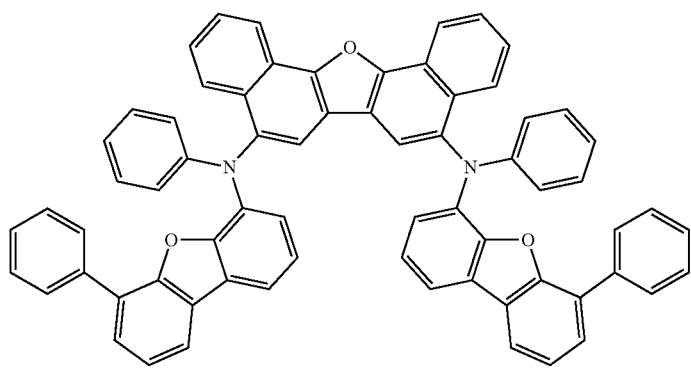
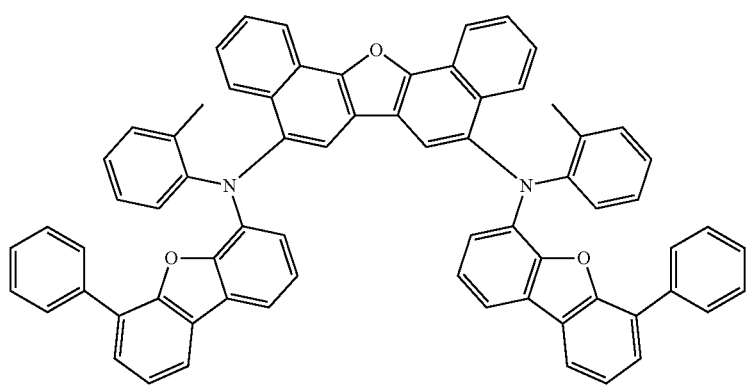
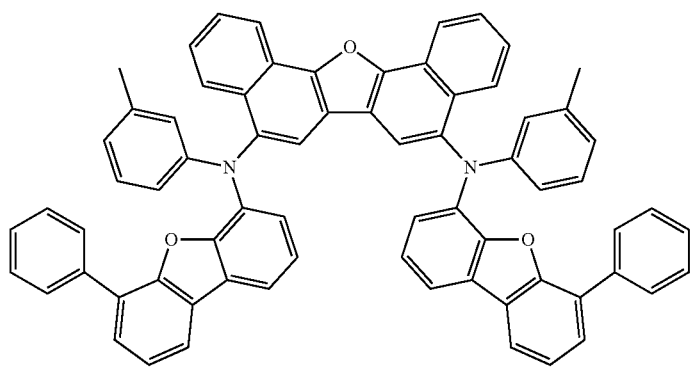
814

815
-continued
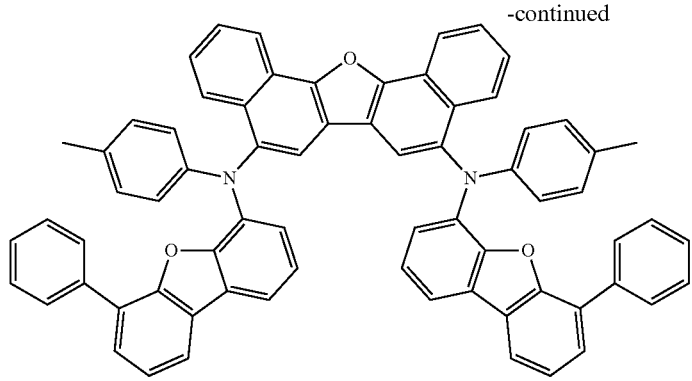
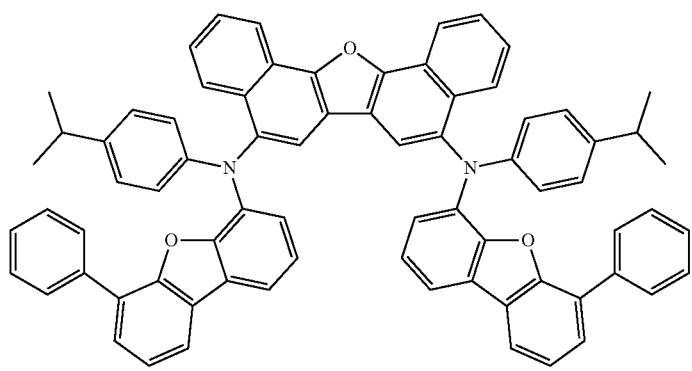
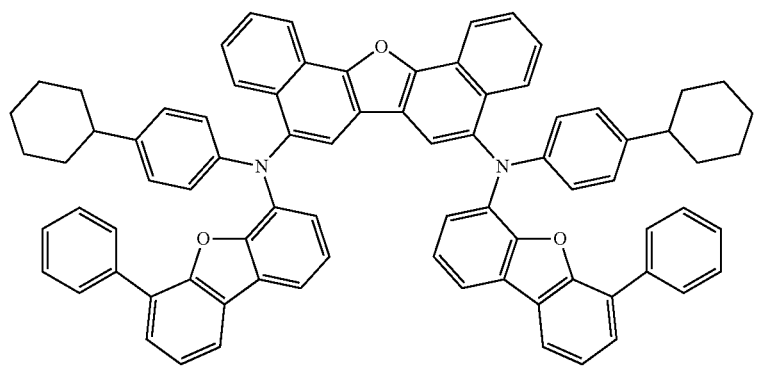
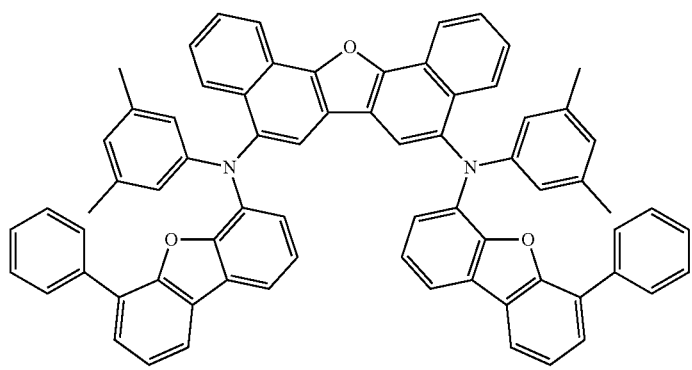
816

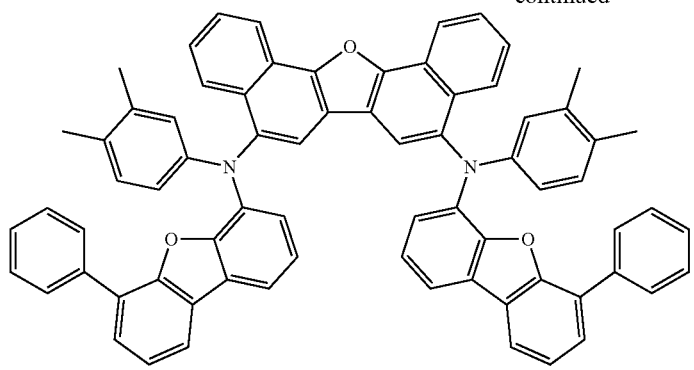
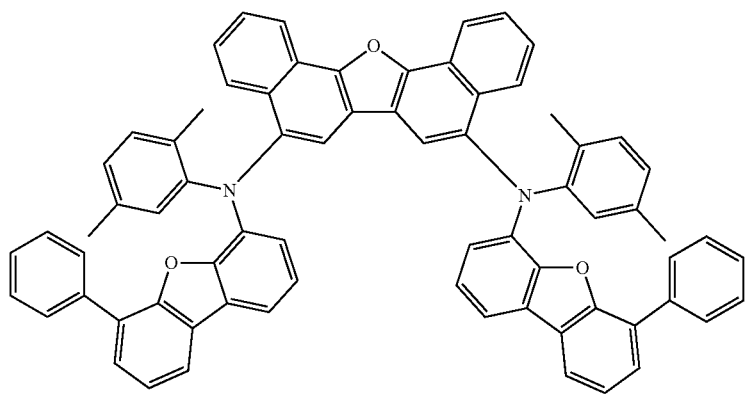
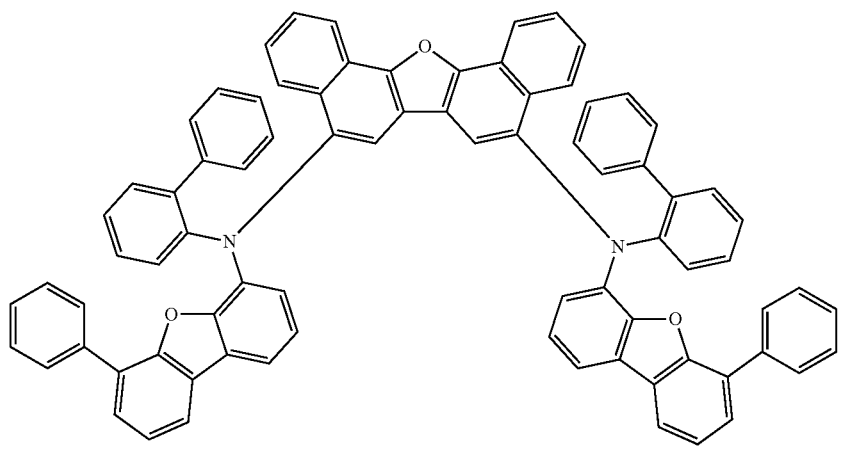
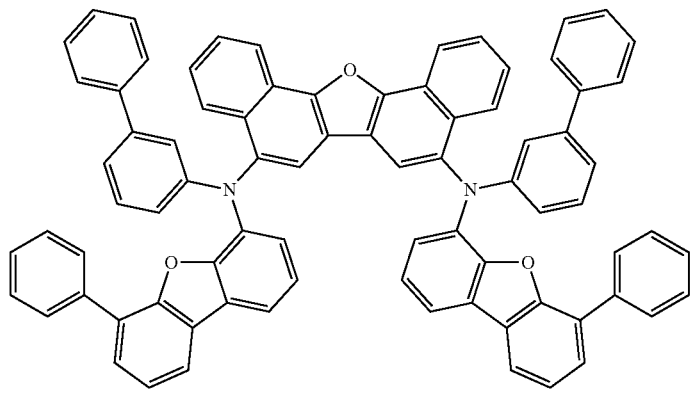

819
-continued
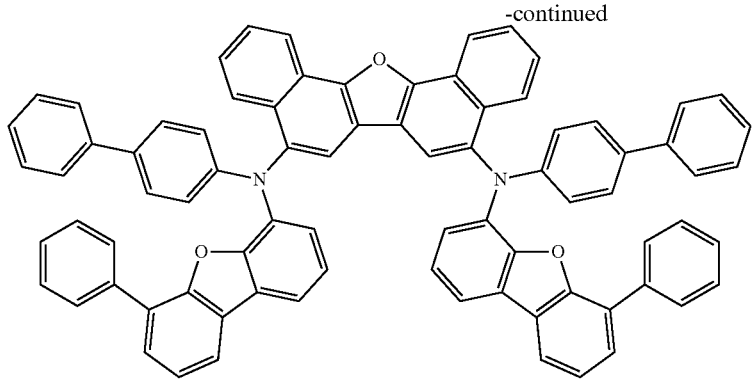
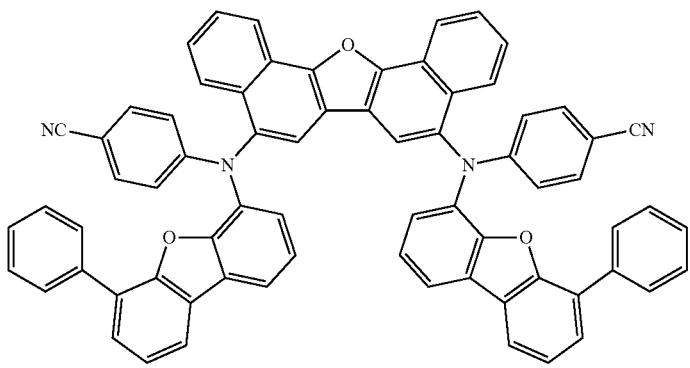
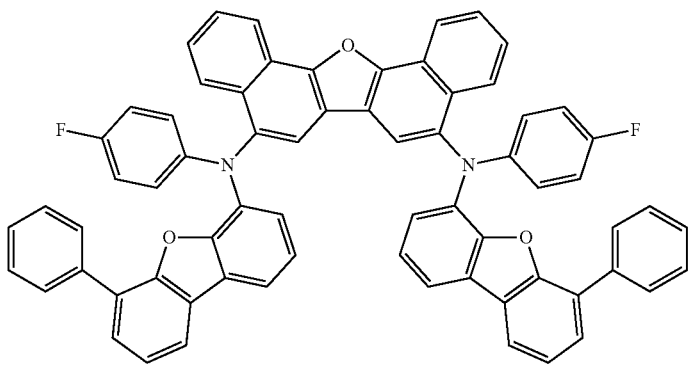
820
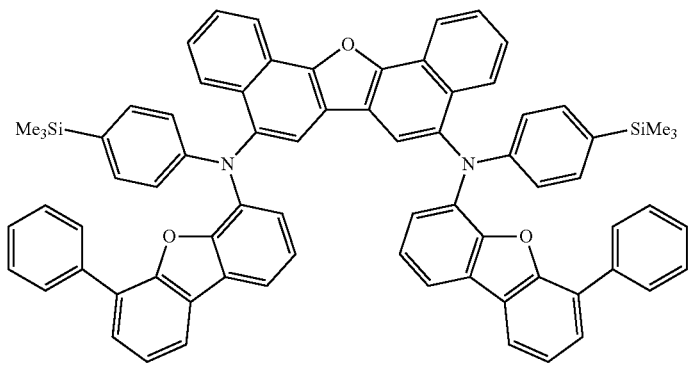

821
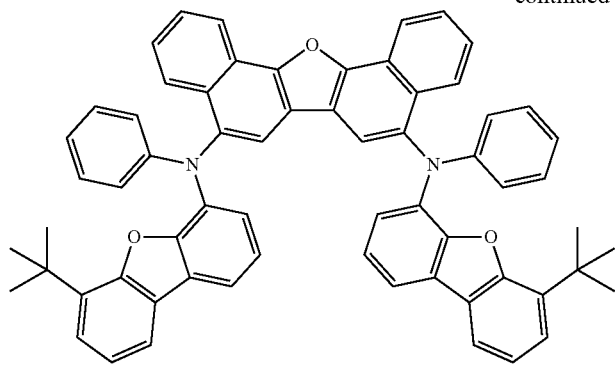
-continued
822
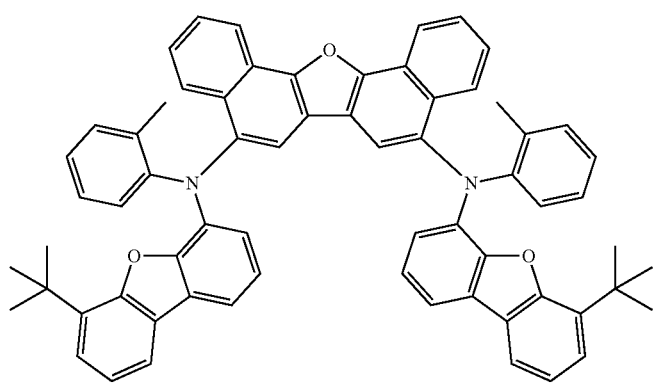
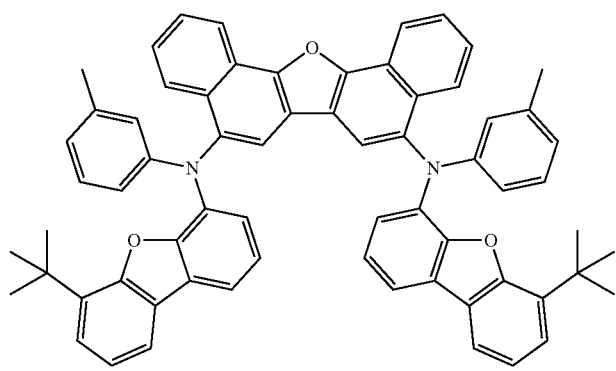
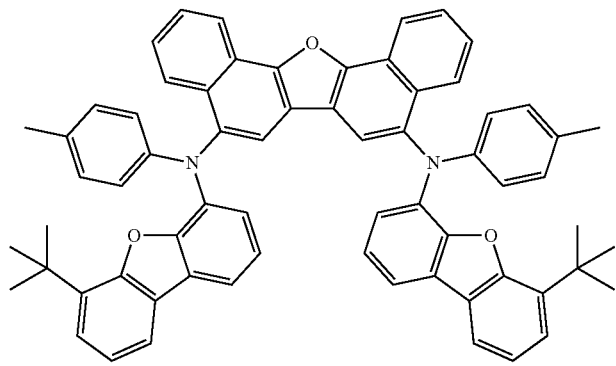

823
-continued
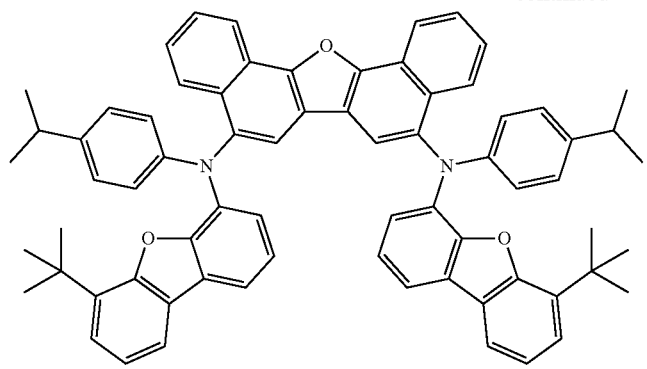
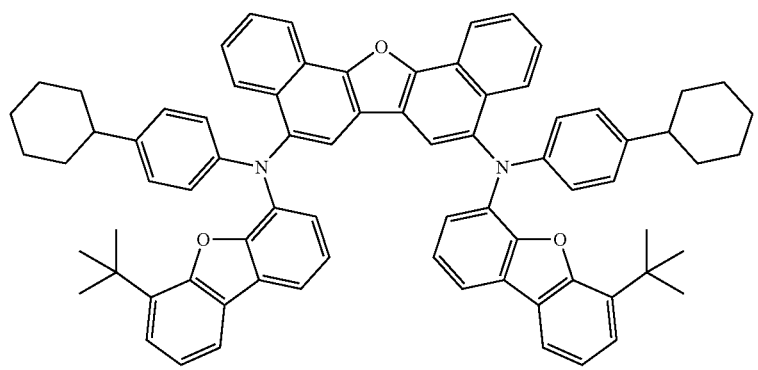
824
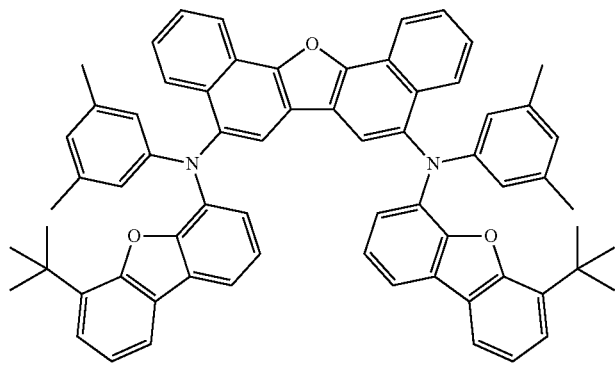
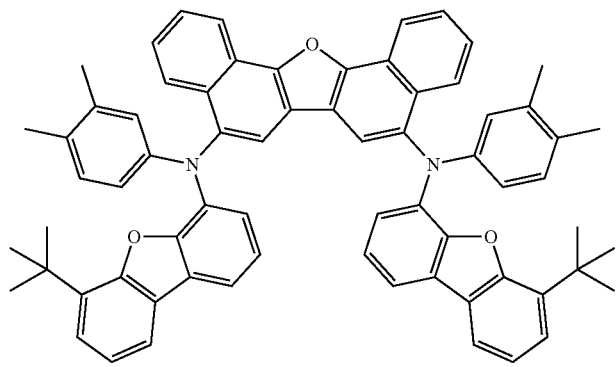

825
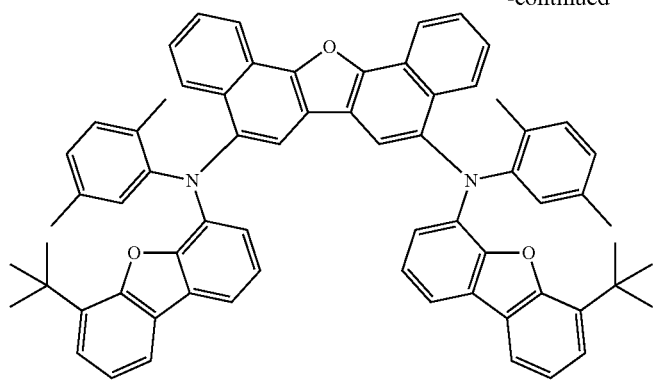
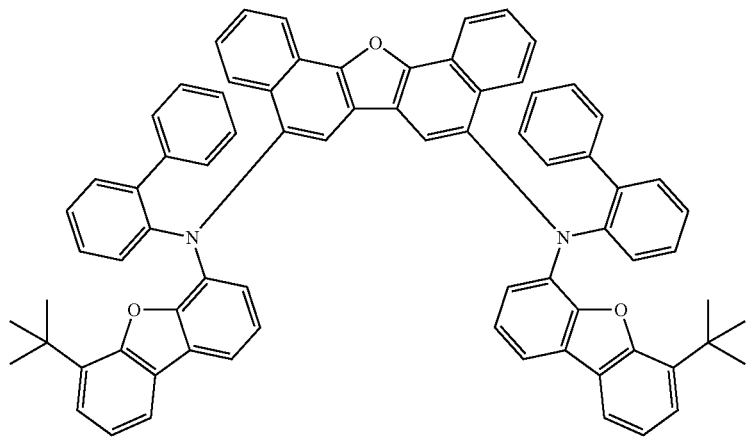
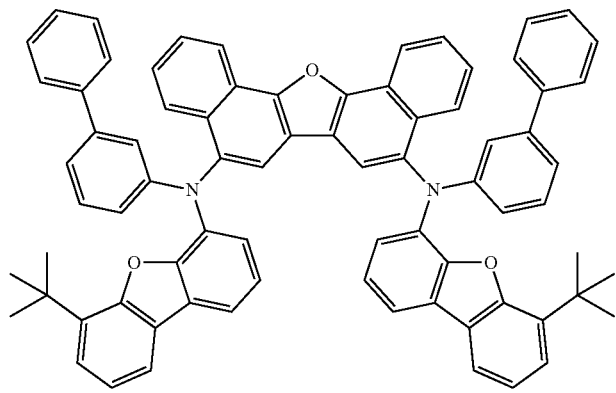
826
-continued
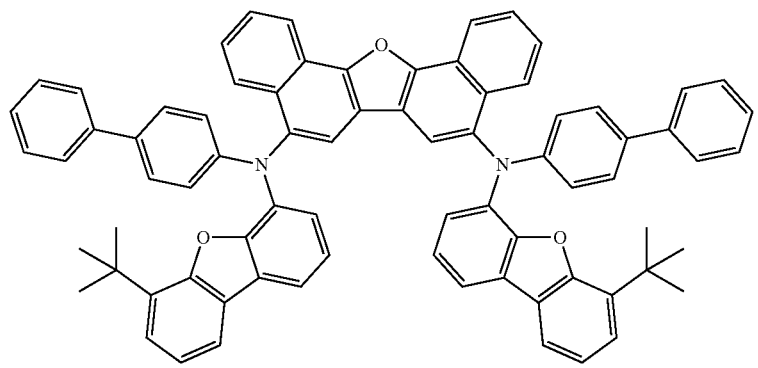

-continued
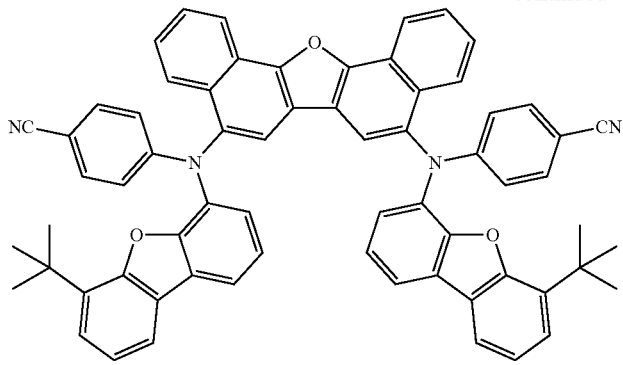
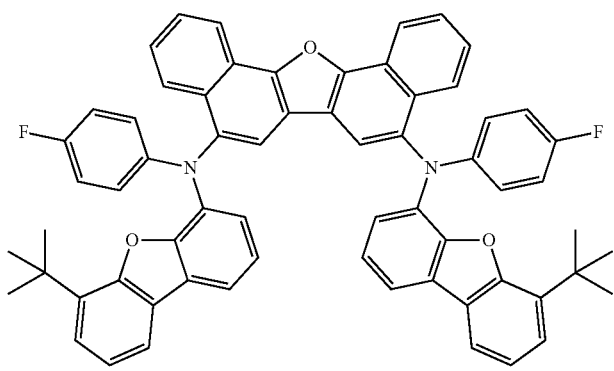
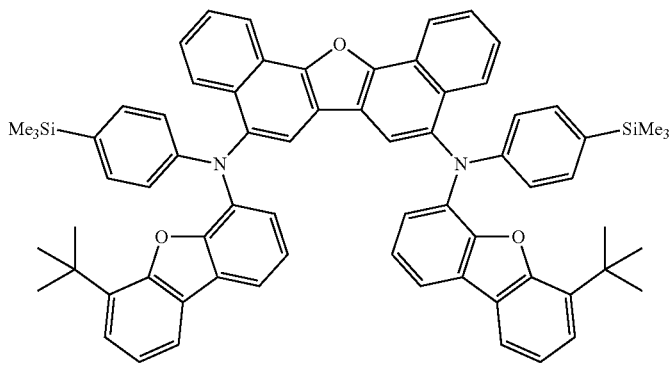
827
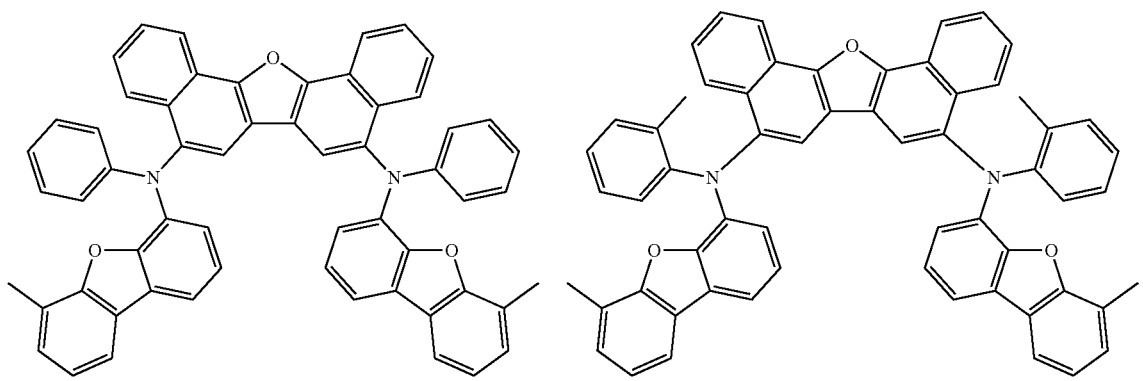
828

-continued
829 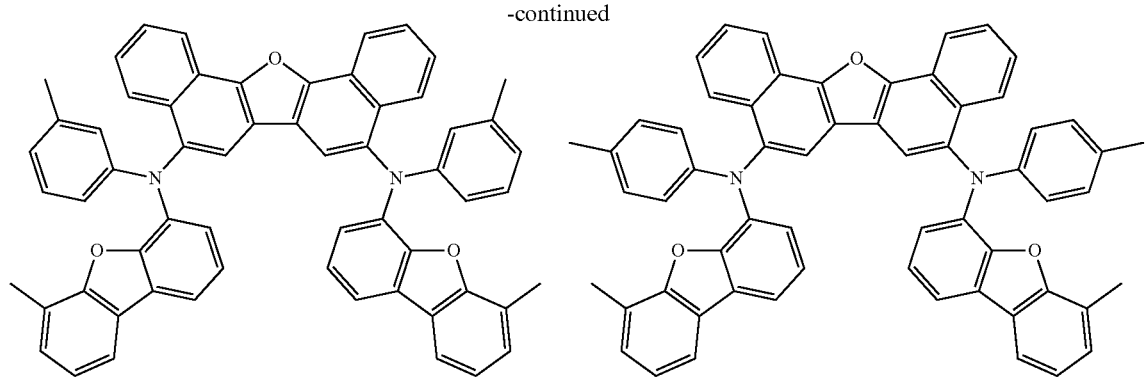 830
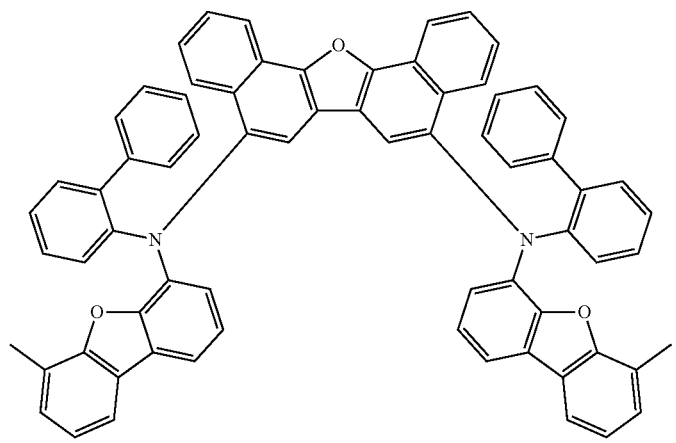
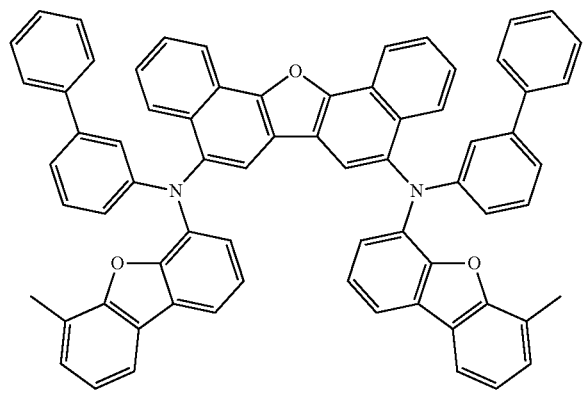
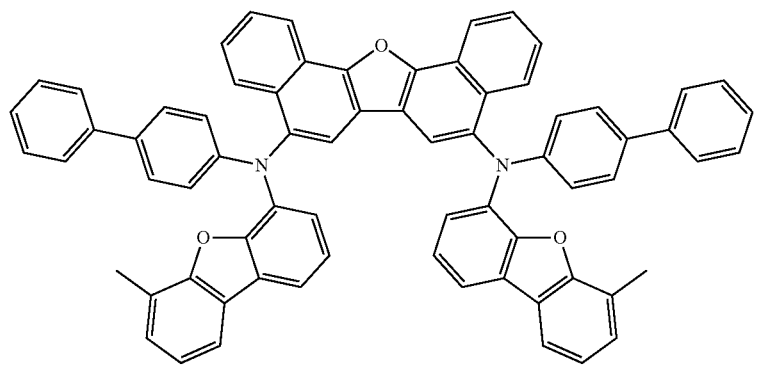

831
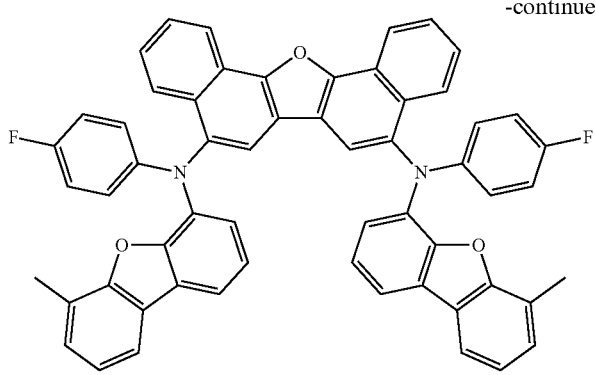
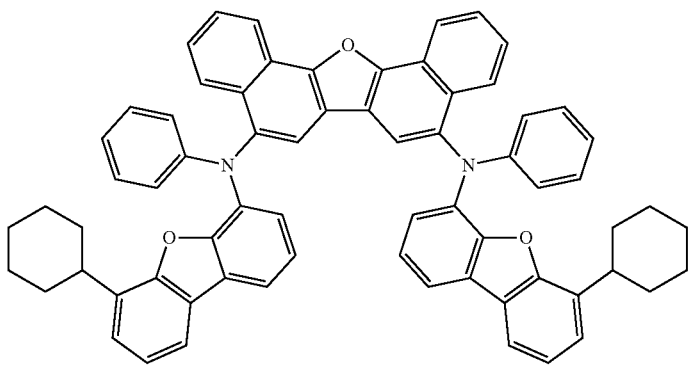
832
-continued
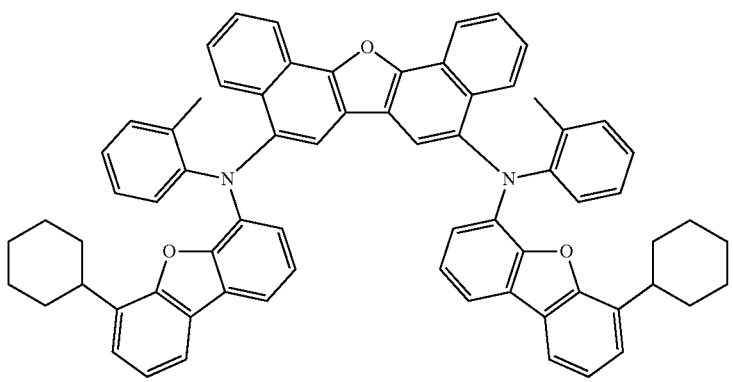
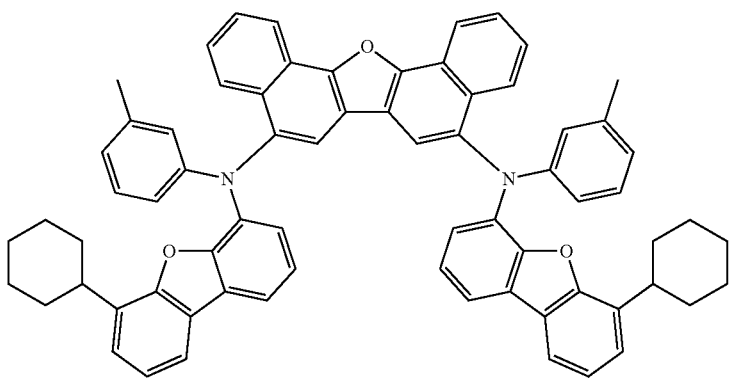

-continued
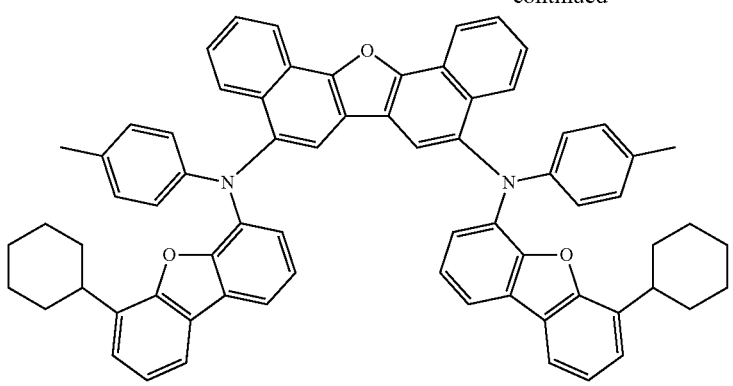
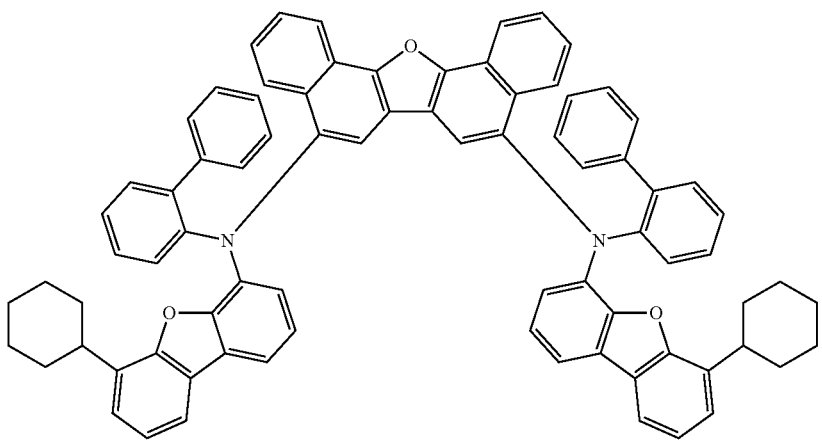
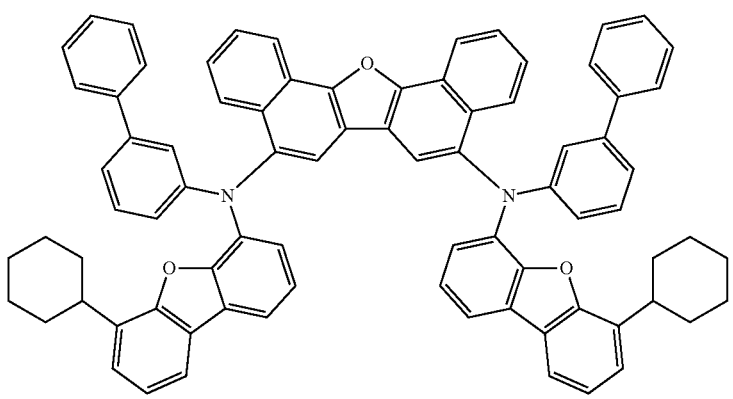
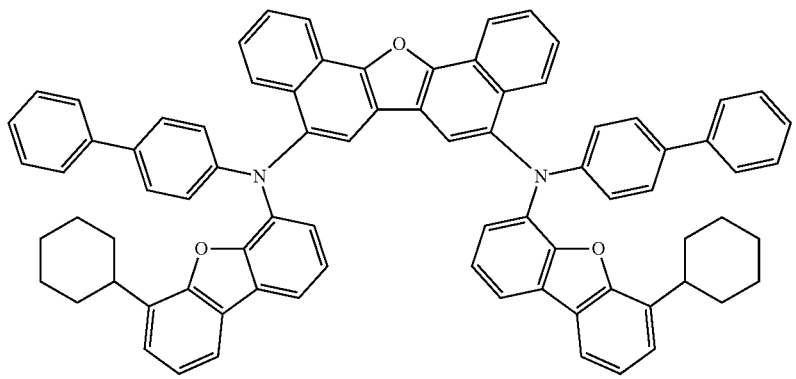

-continued
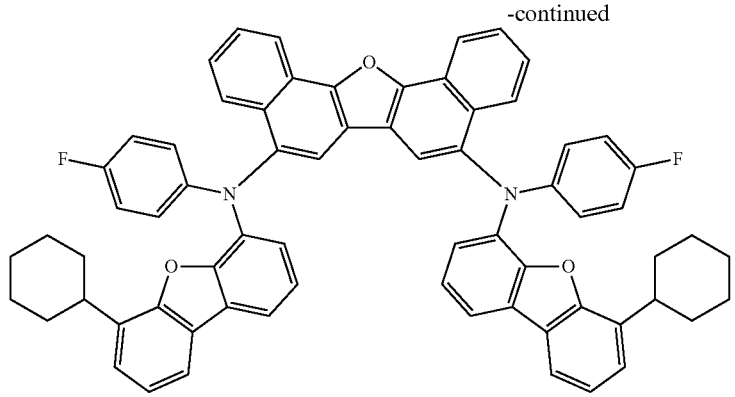
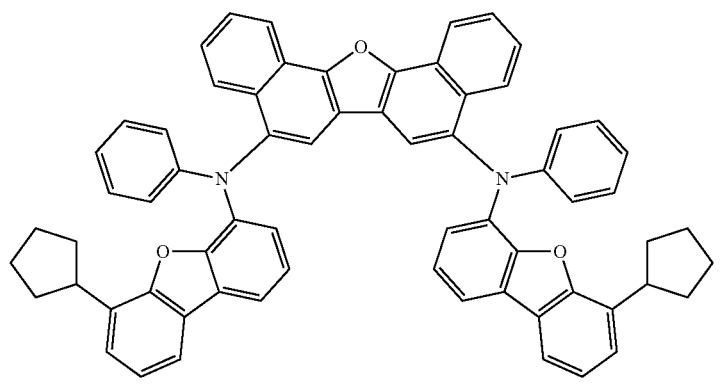
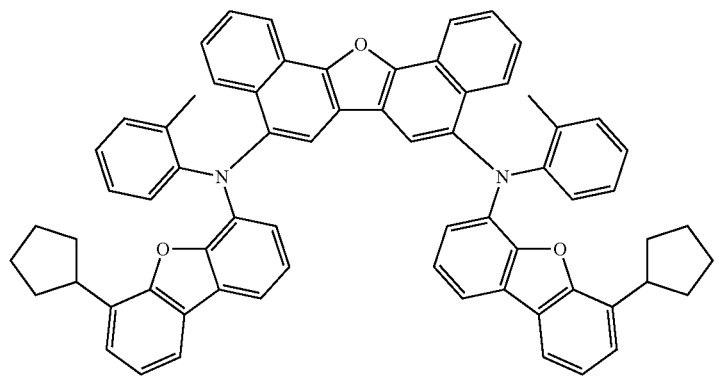
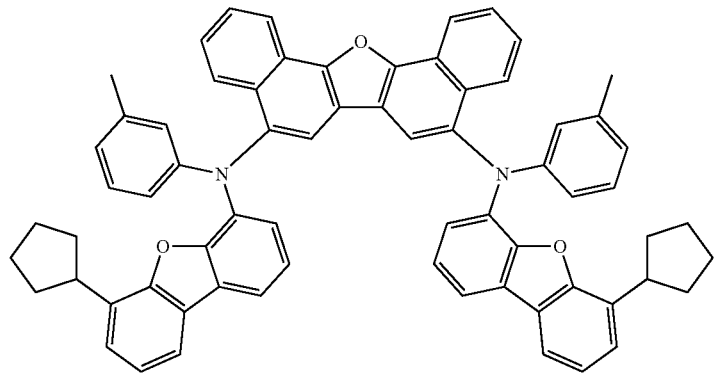

837
838
-continued
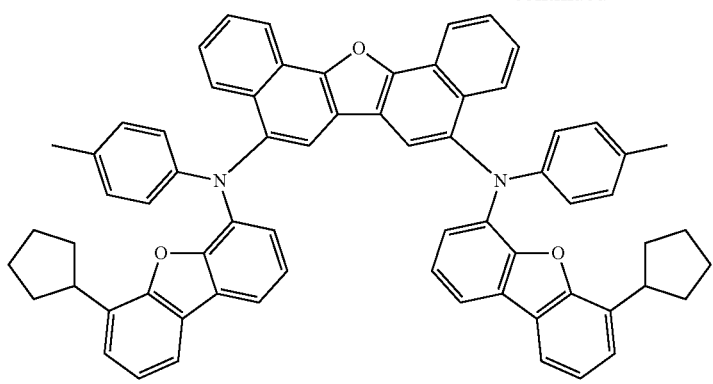
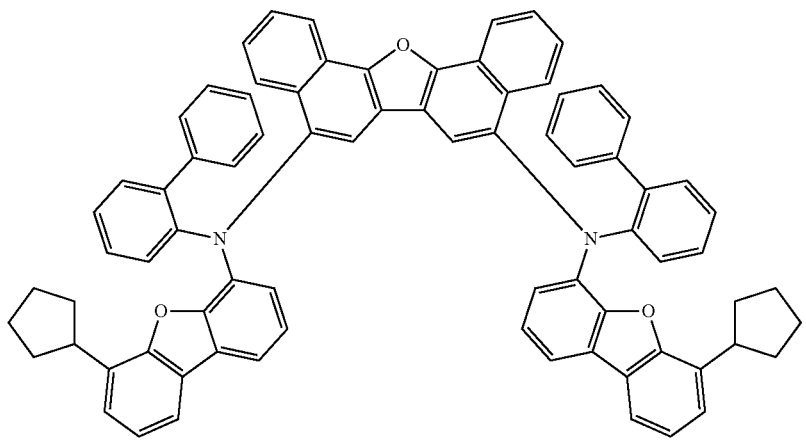
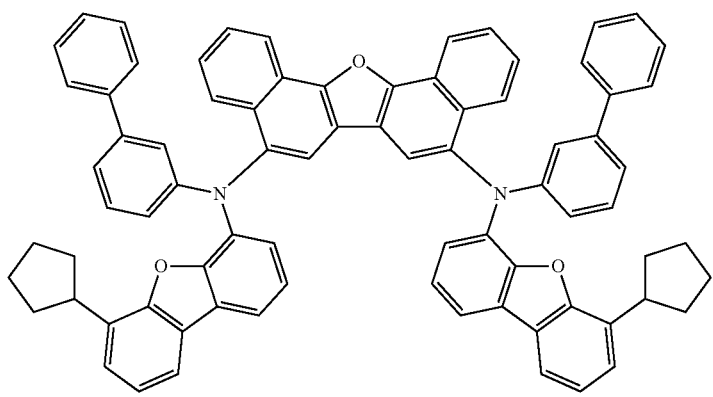
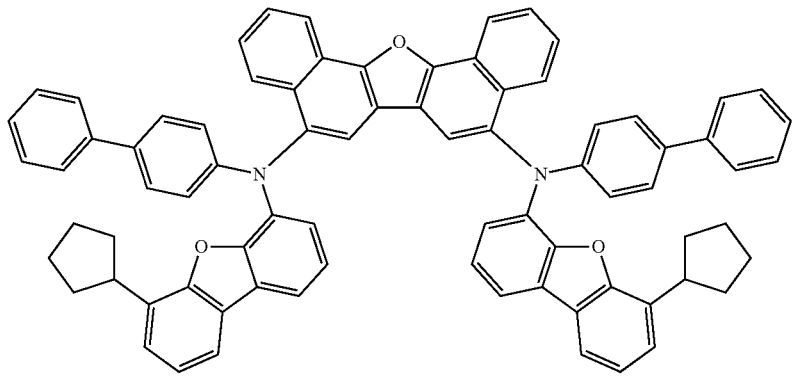

839
-continued
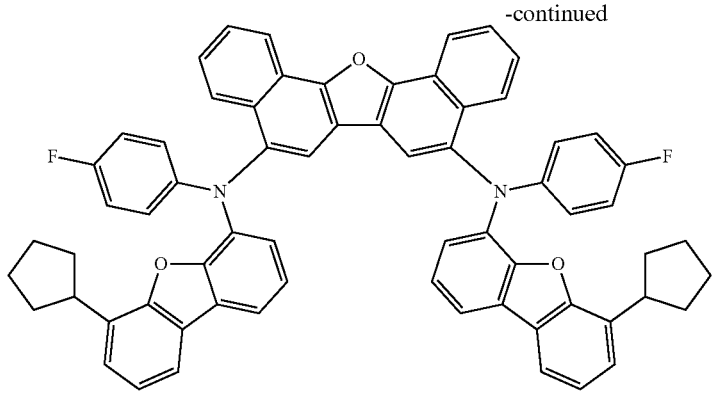
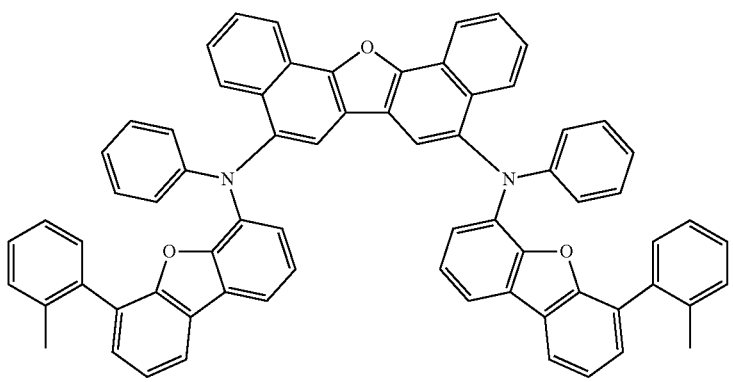
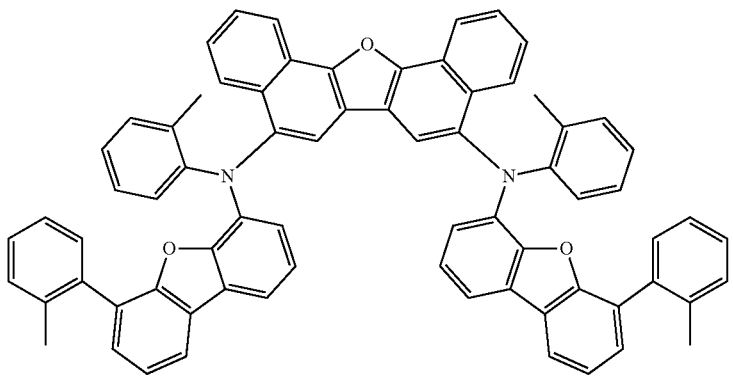 [SMILES: Cc1ccccc1-c1cccc2c1oc1c(N(c3ccccc3C)c3cc4c5cc(N(c6ccccc6C)c6cccc7c6oc6c(-c8ccccc8C)cccc67)c6ccccc6c5oc4c4ccccc34)cccc12]
840
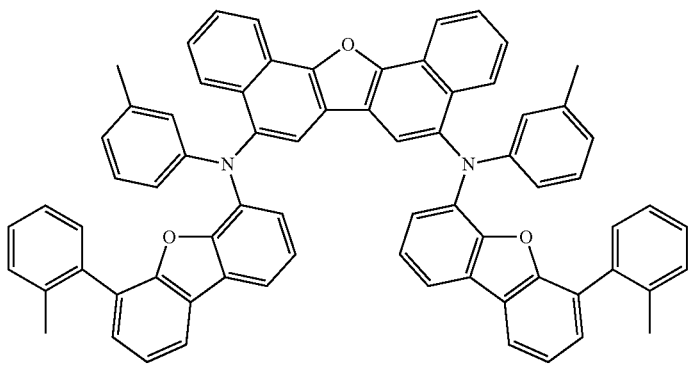

-continued
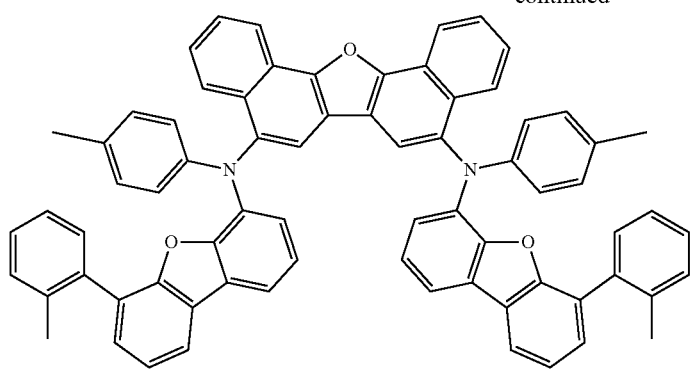
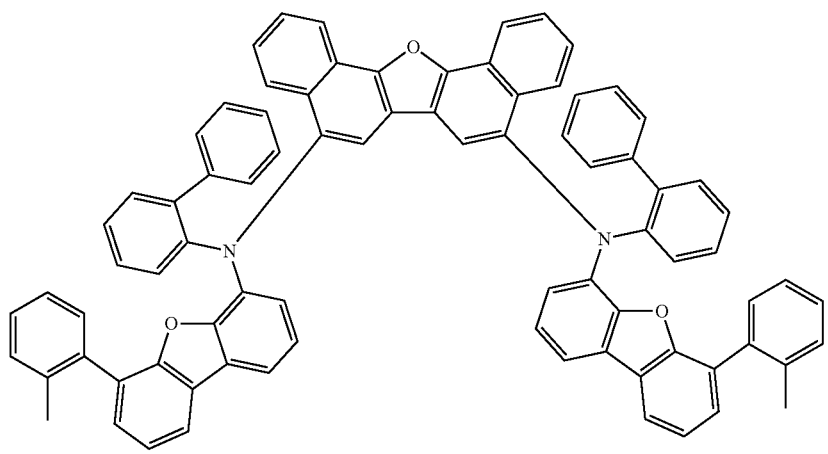
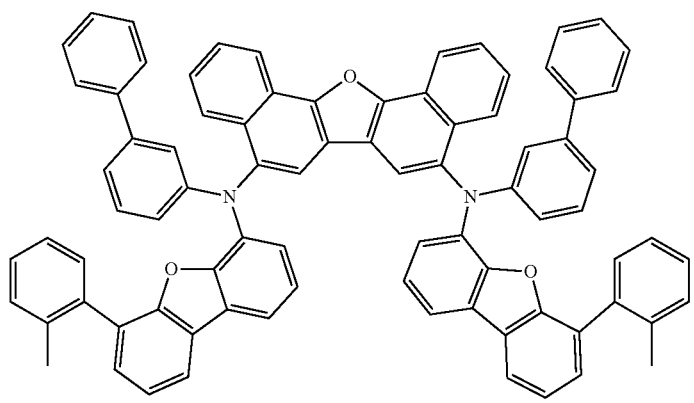
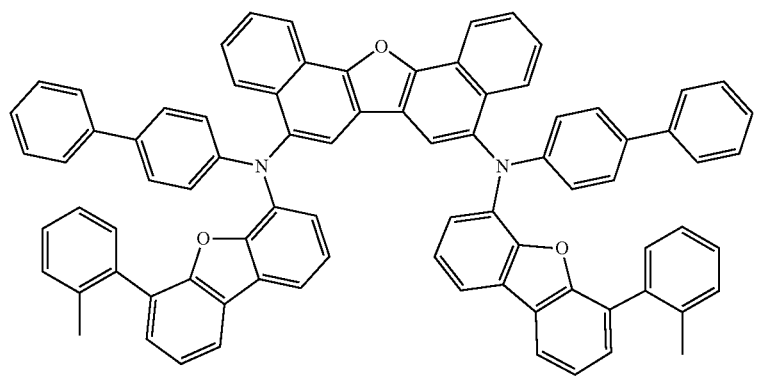

843
844
-continued
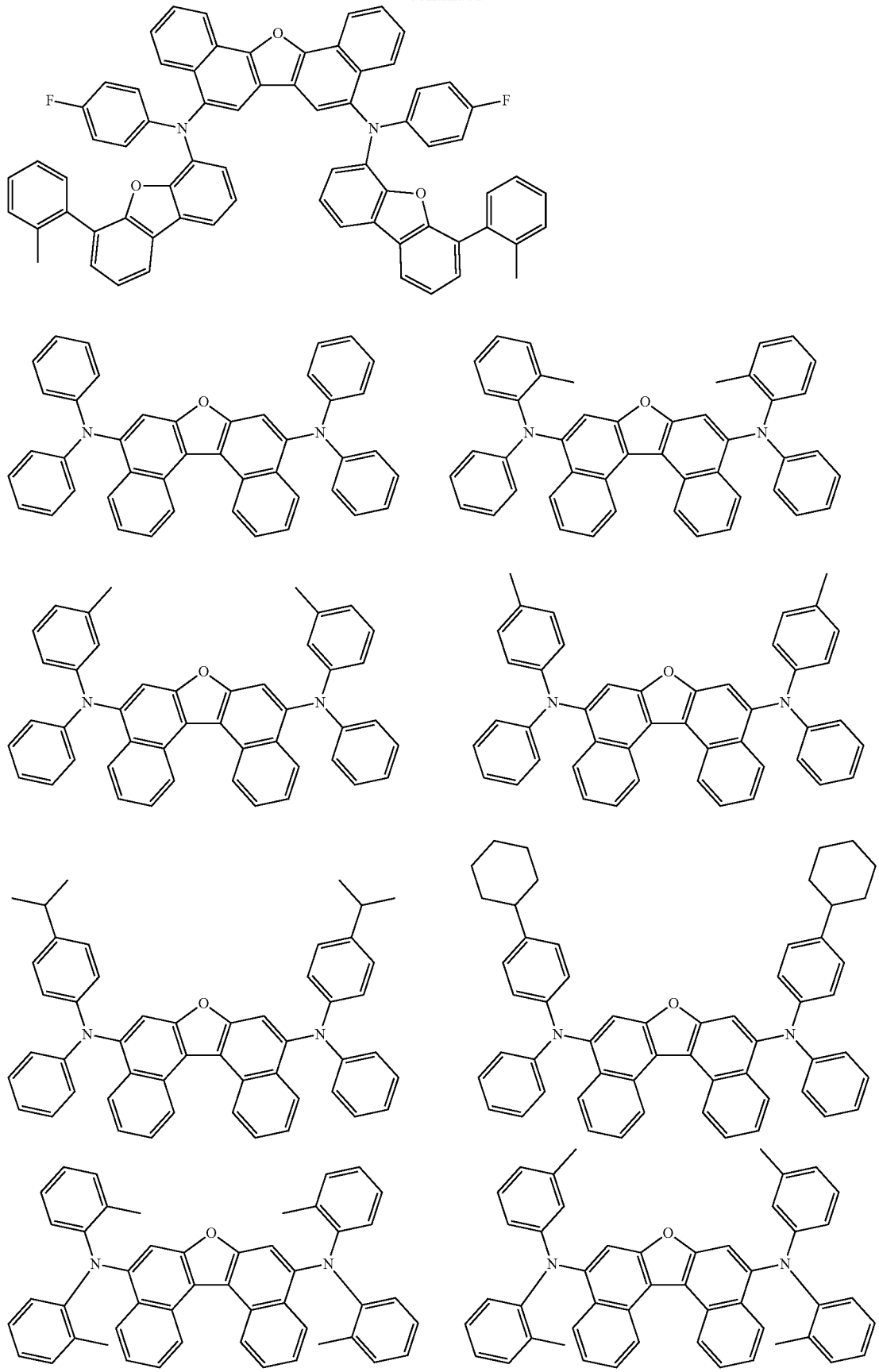

845 846
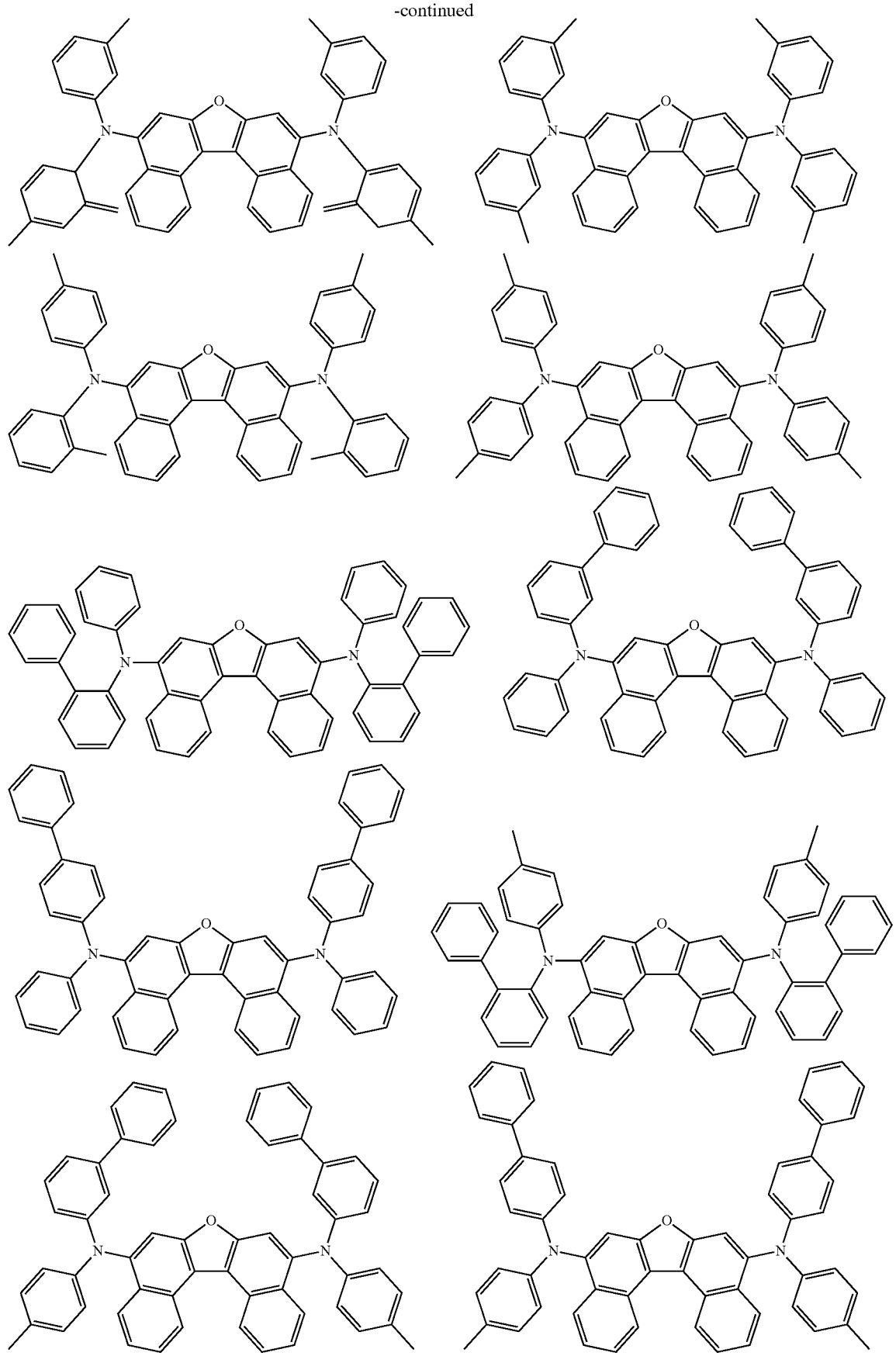
-continued 847
848
-continued
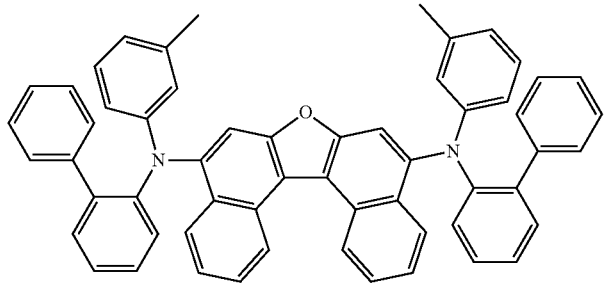
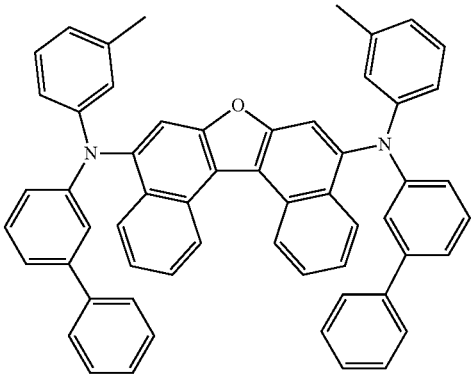
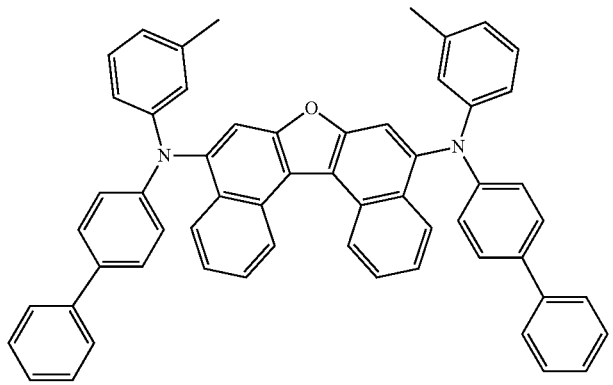
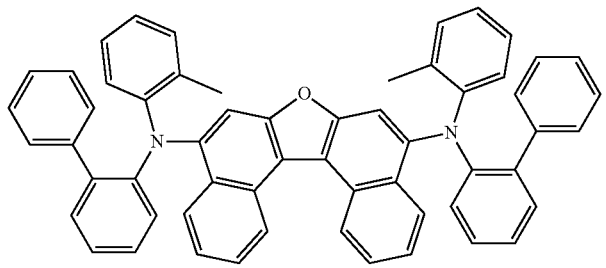
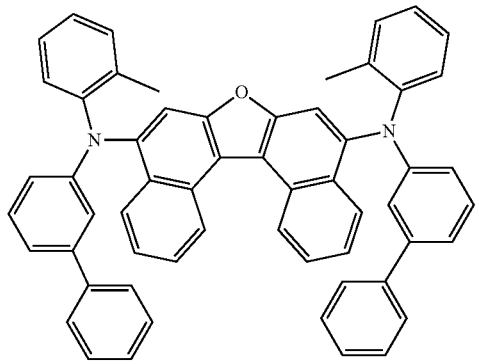
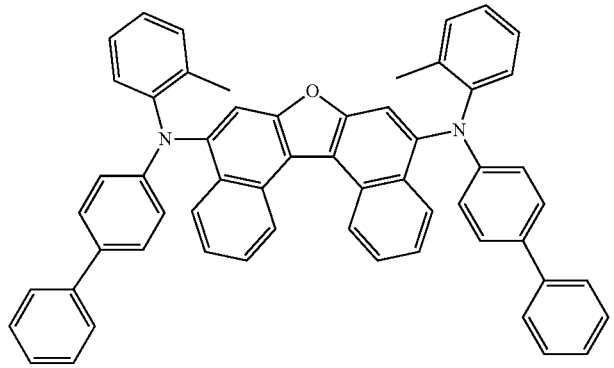
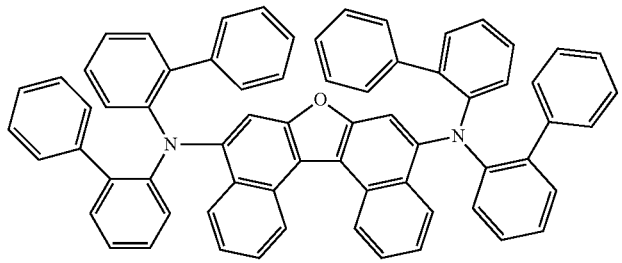

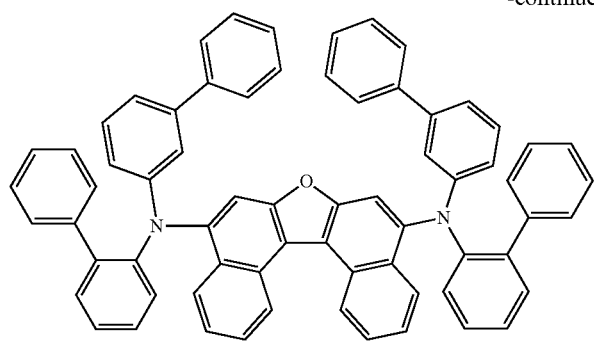
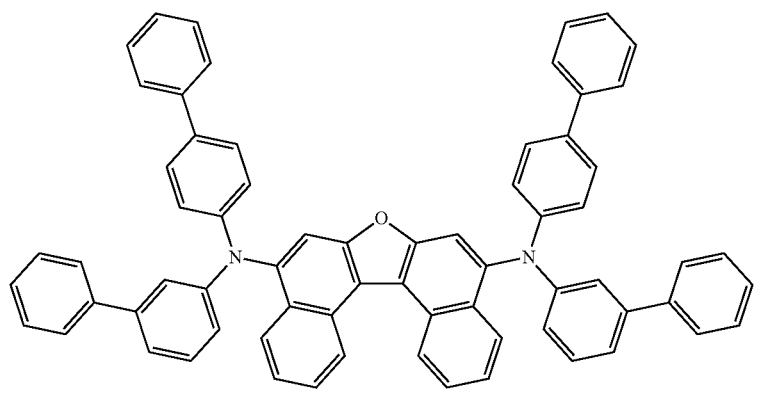
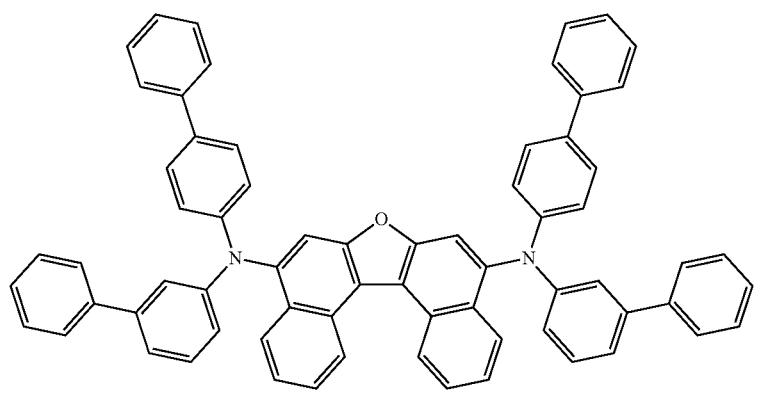
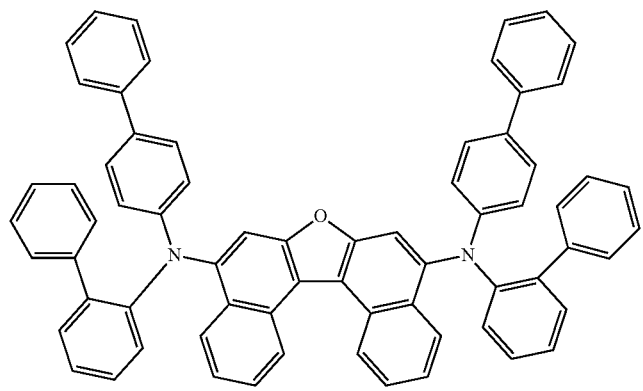

-continued
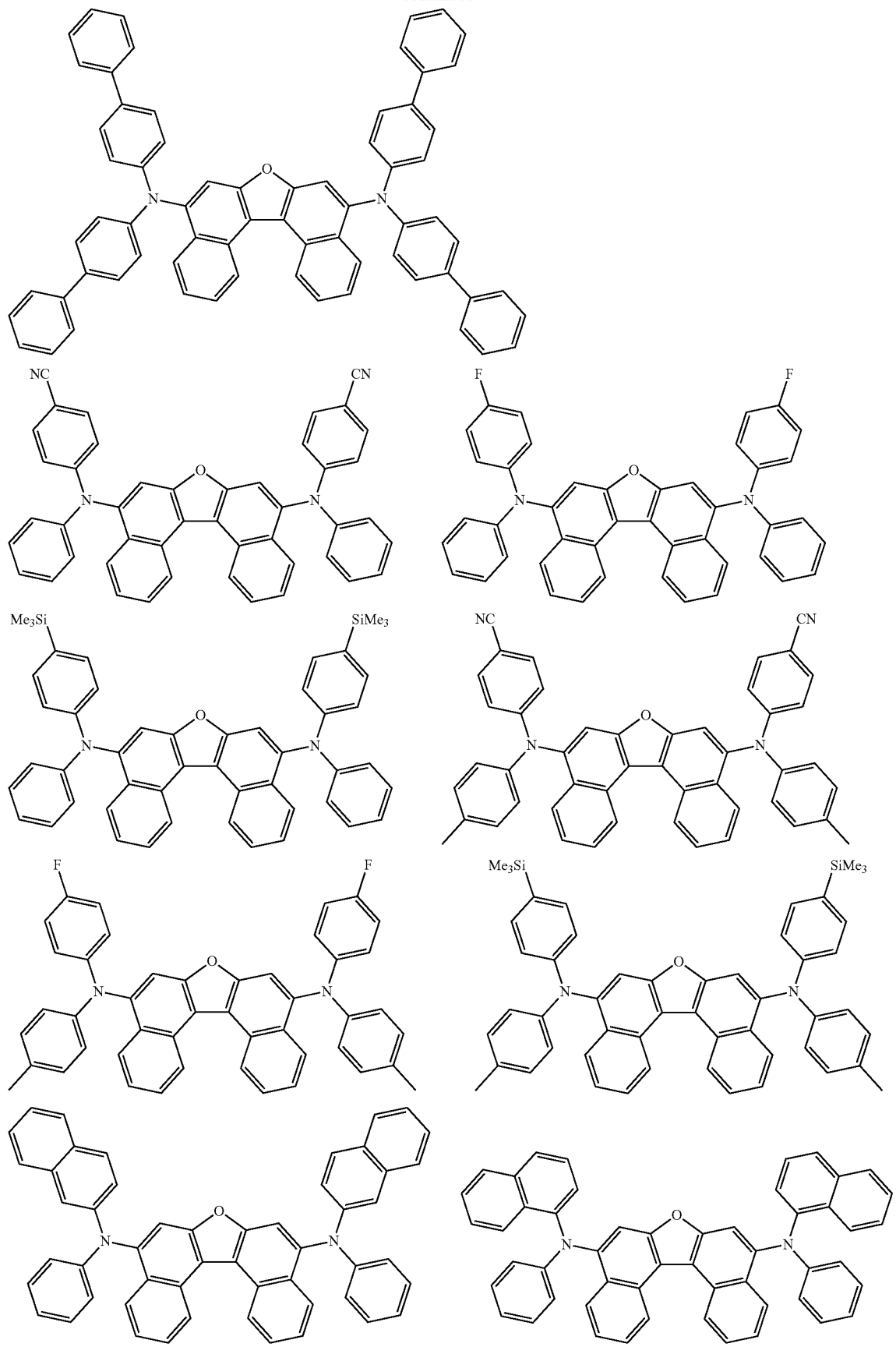

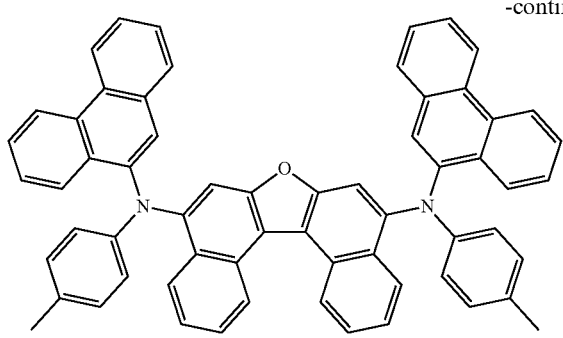
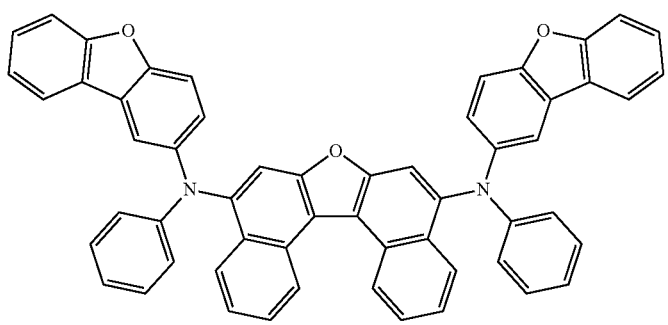
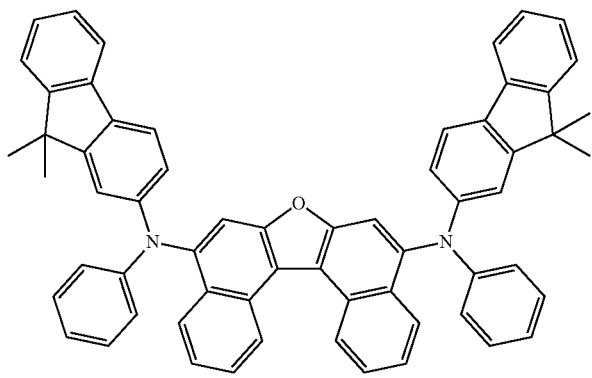
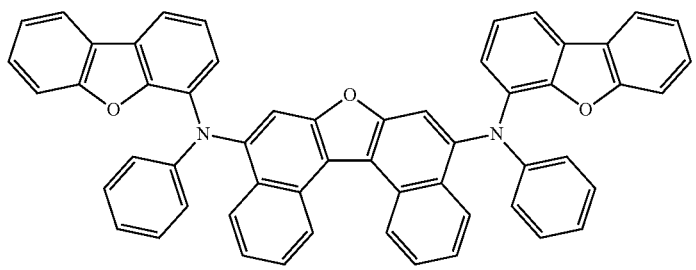
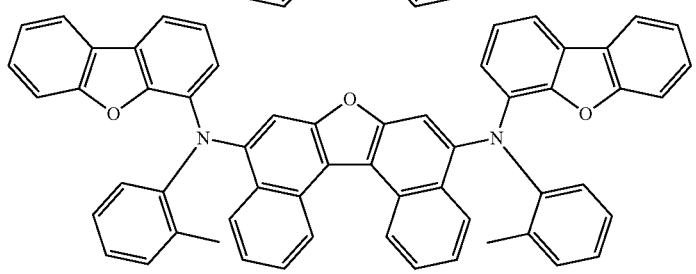

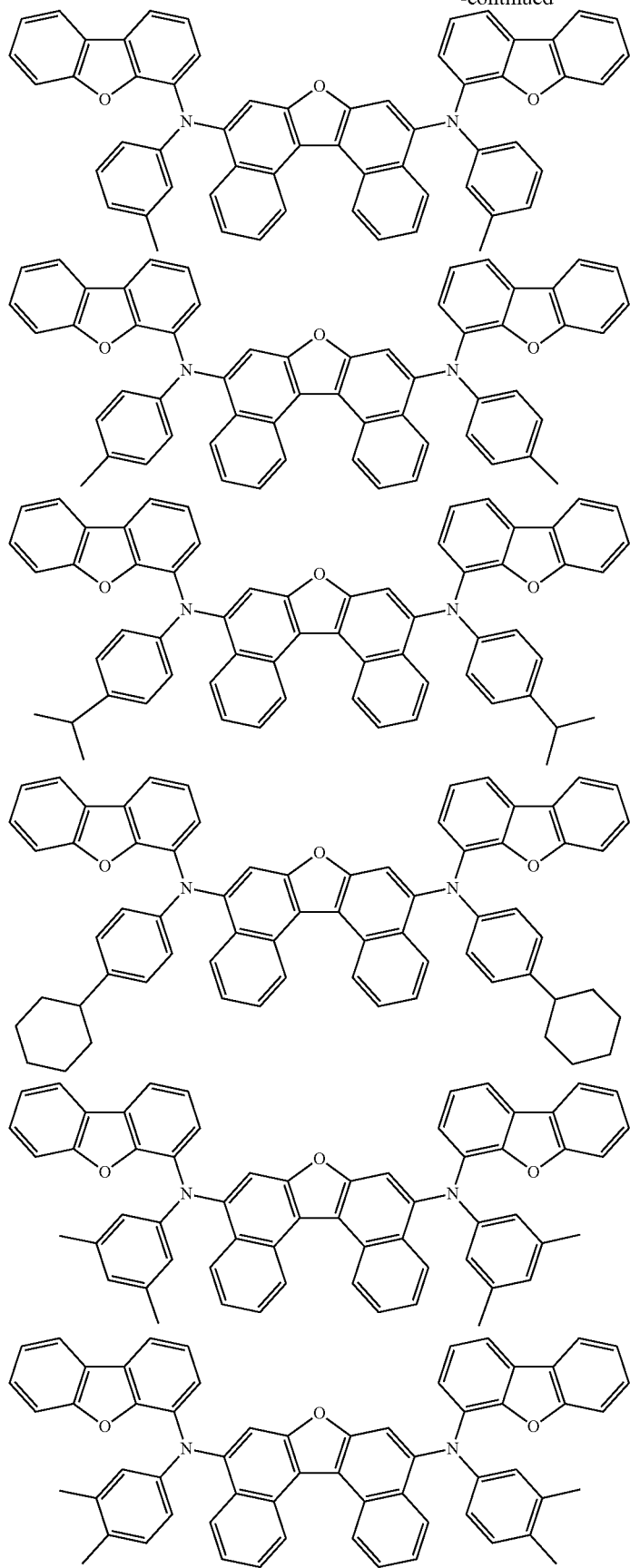

-continued
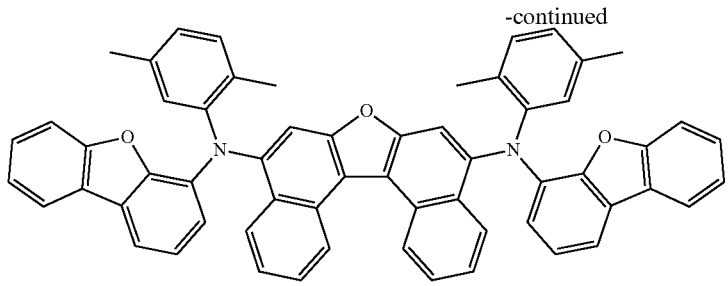
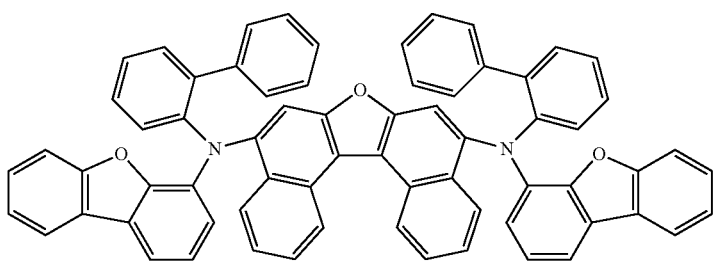
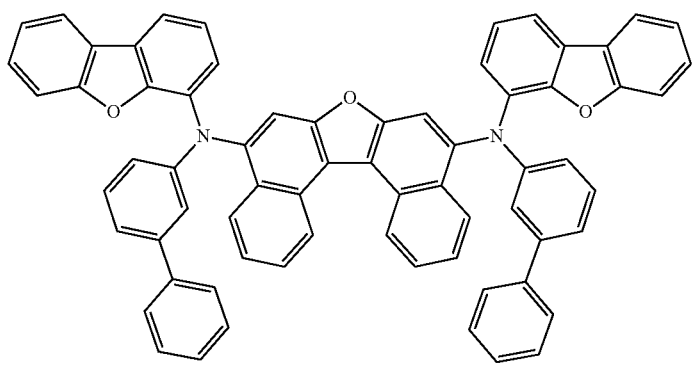
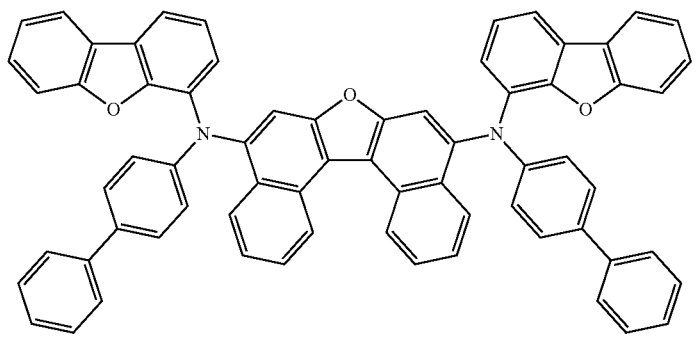
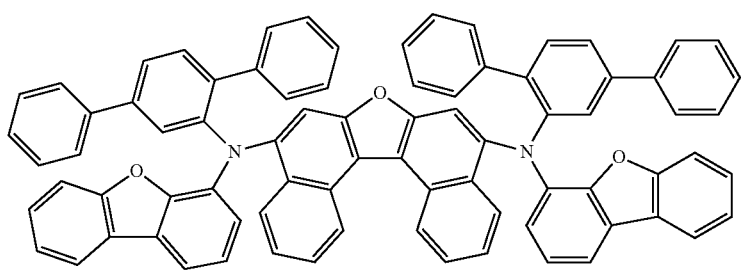

-continued
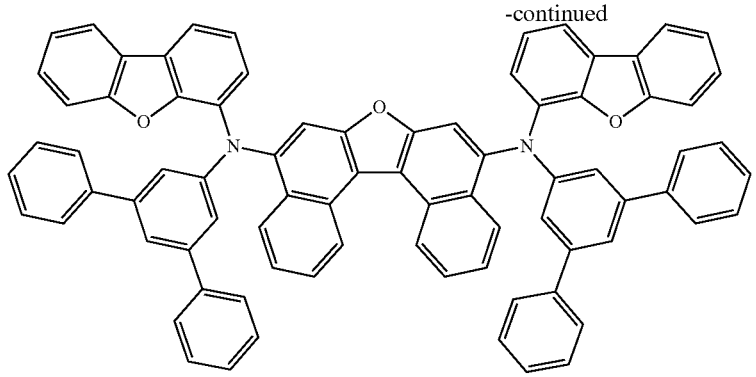
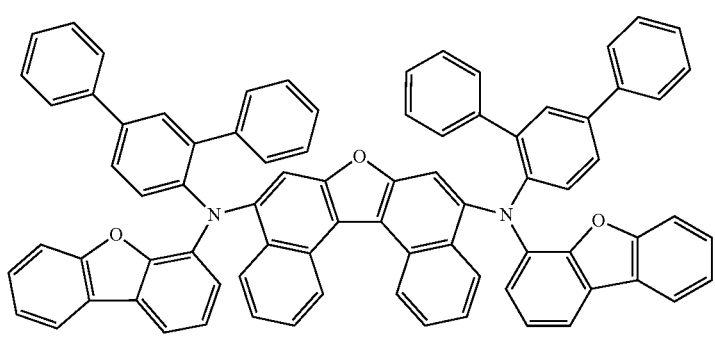
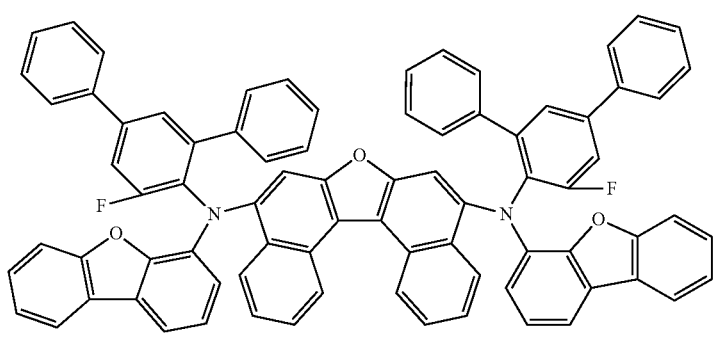
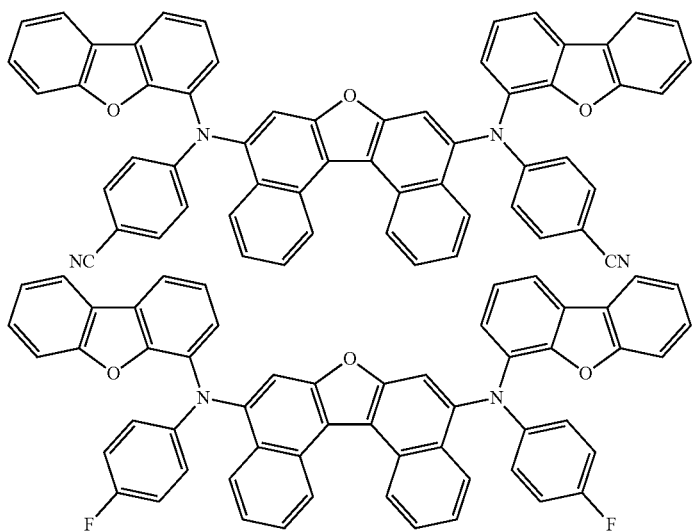

-continued
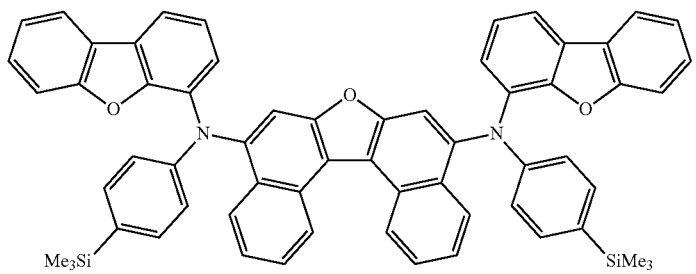
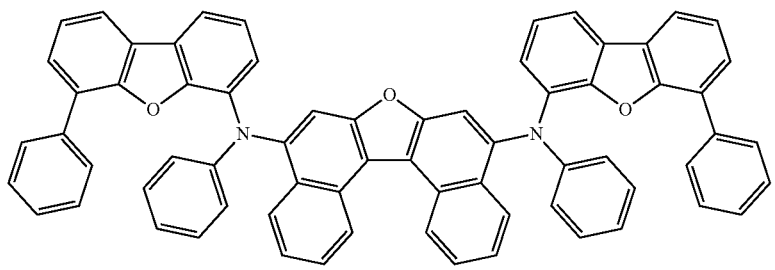
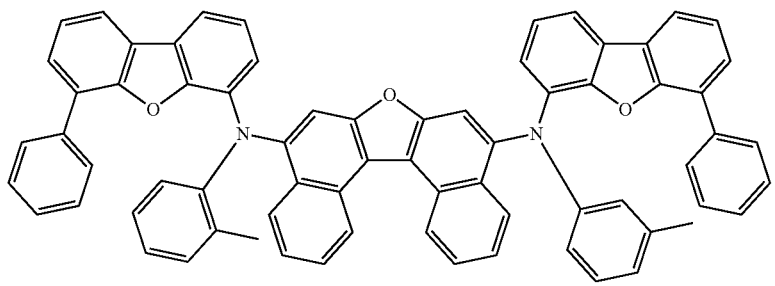
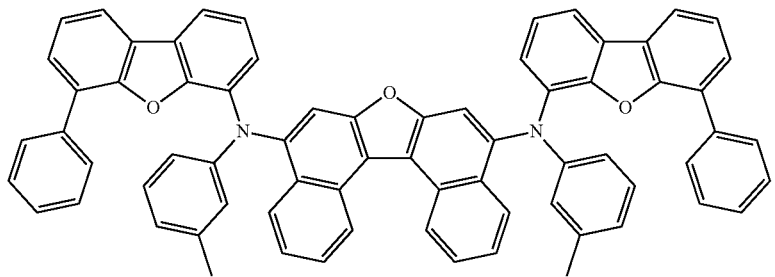
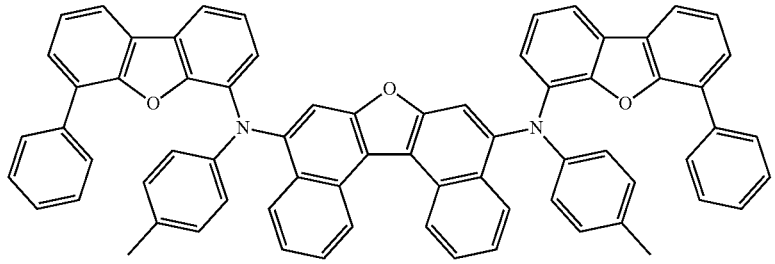
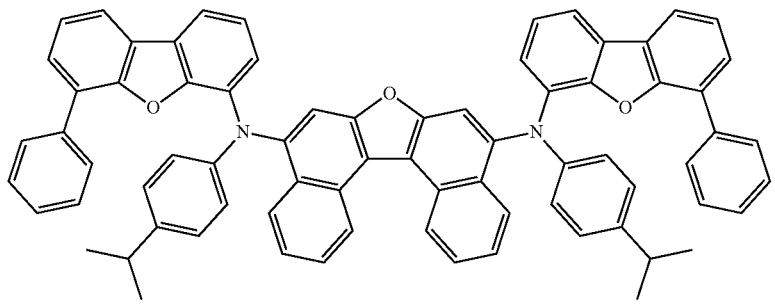

-continued
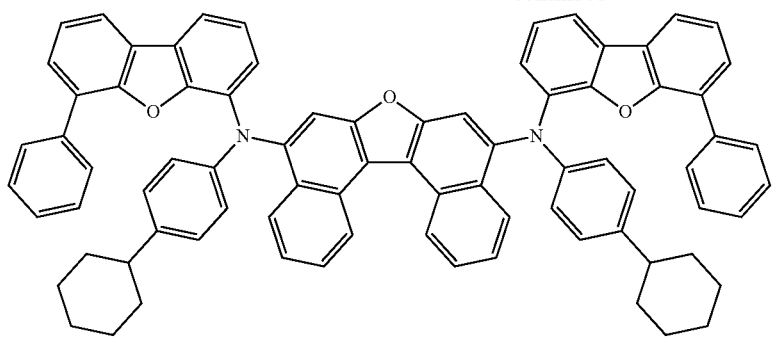
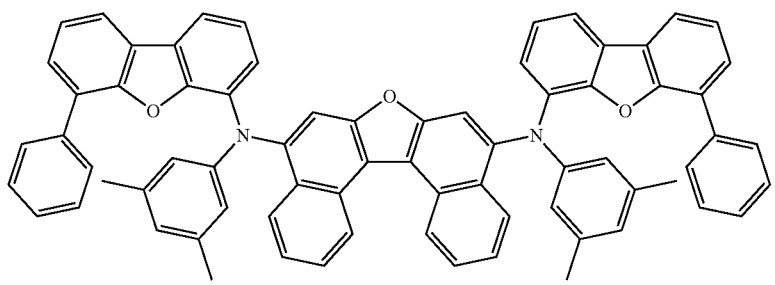
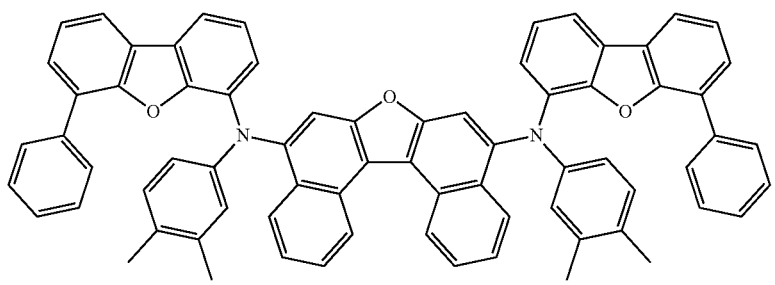
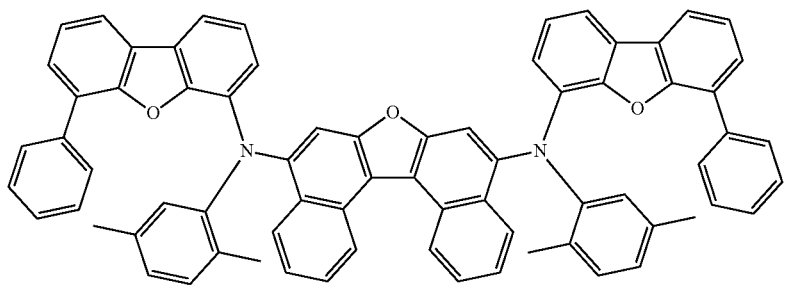
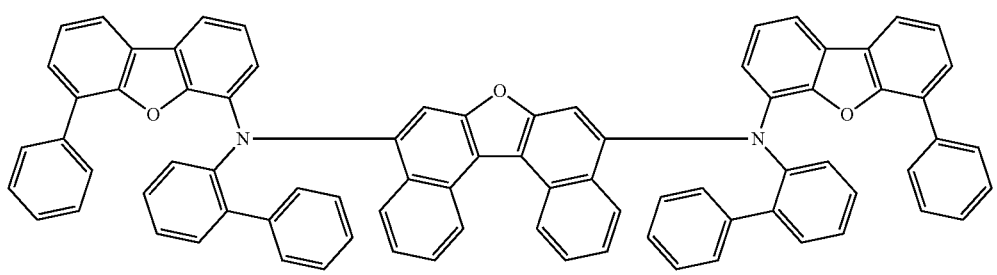

-continued
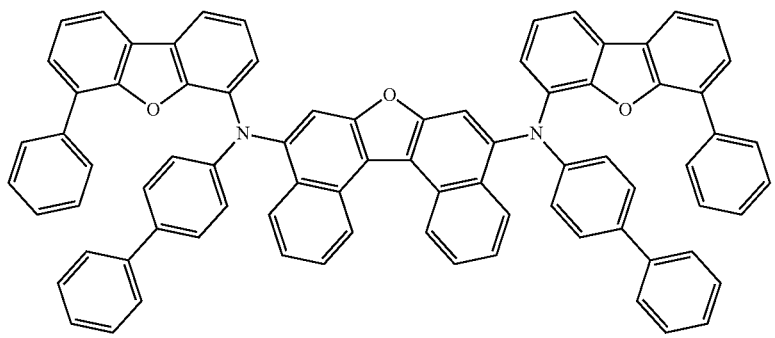
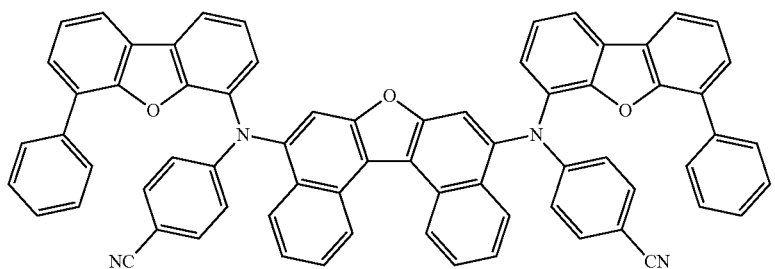
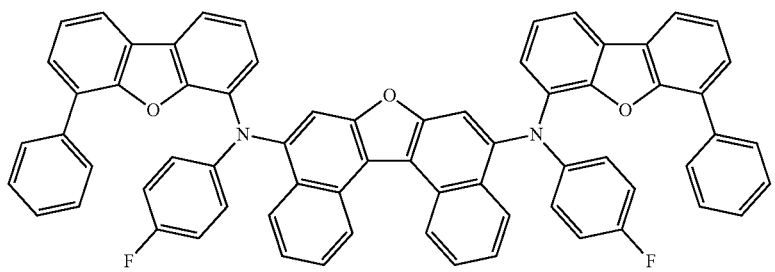
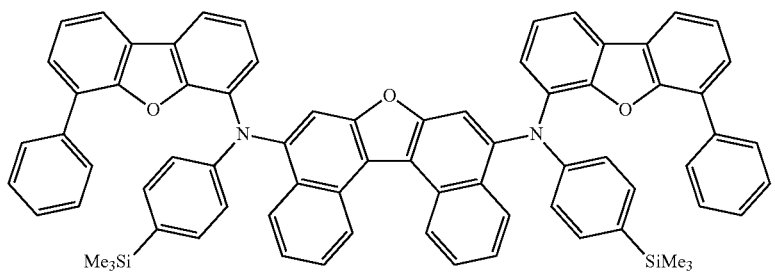

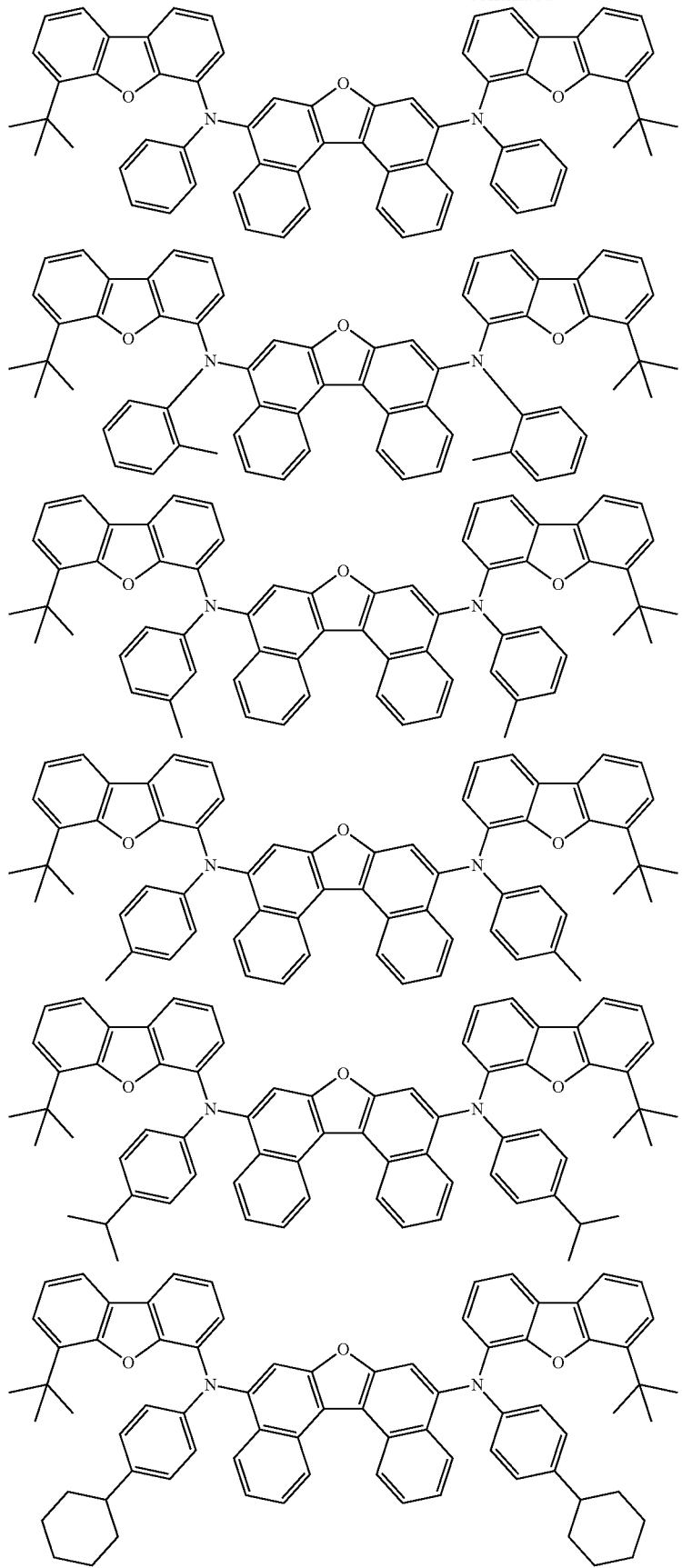

-continued
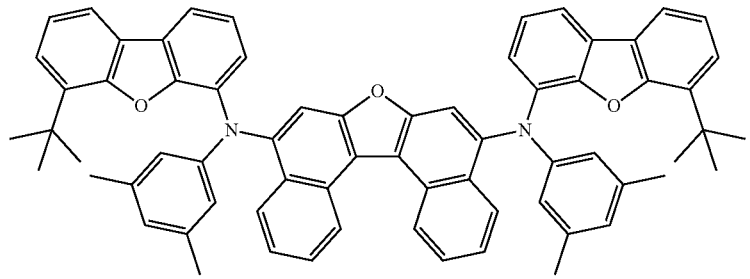
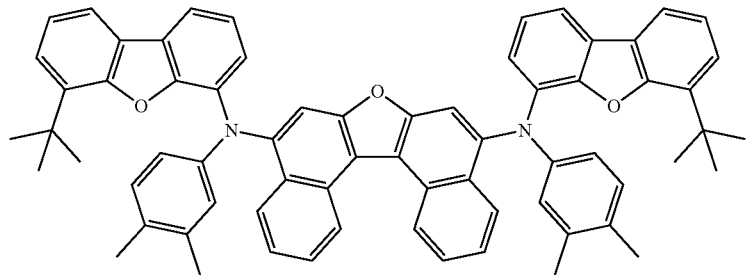
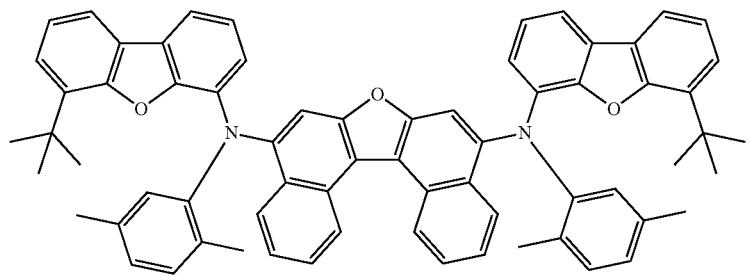
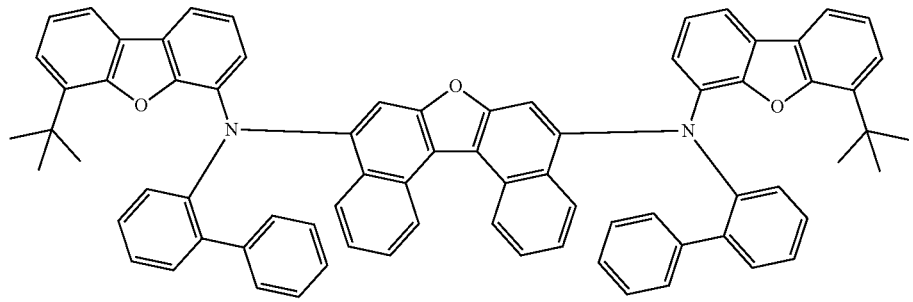
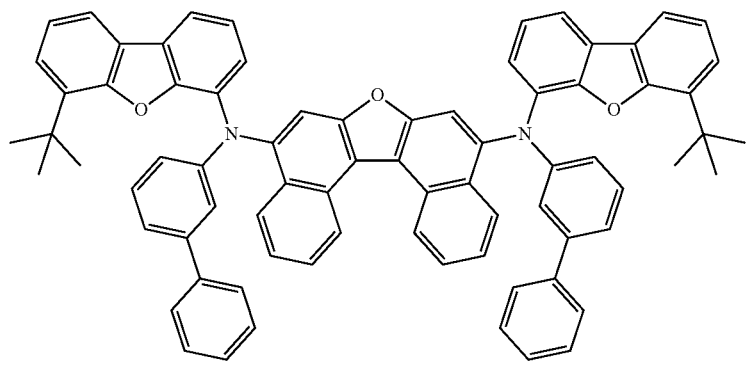

-continued
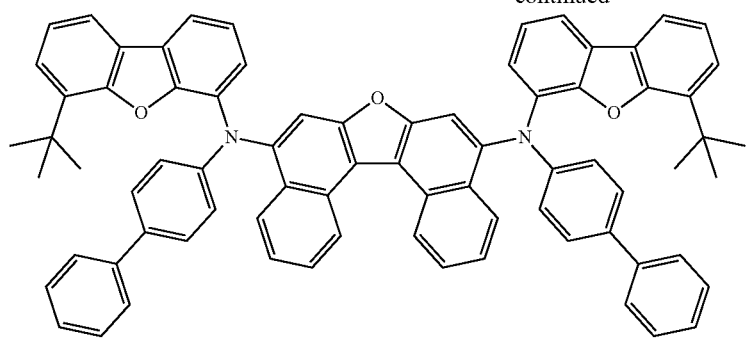
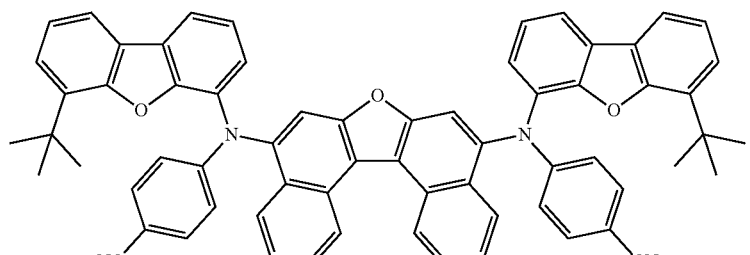
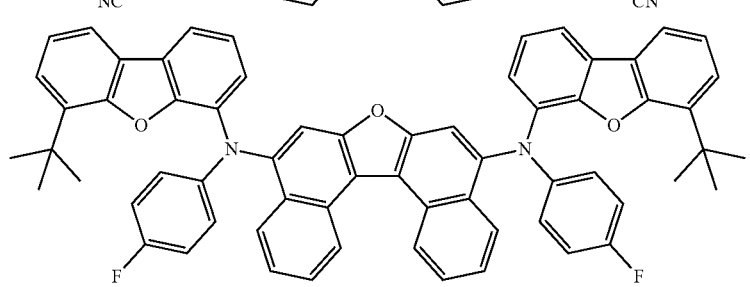
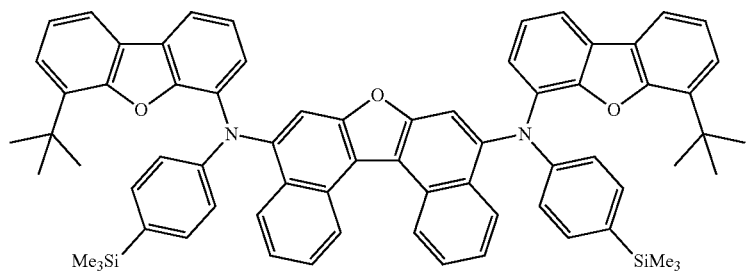
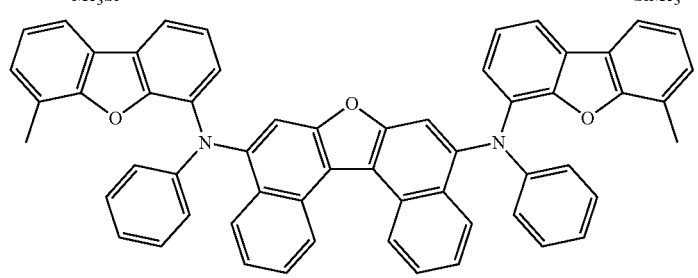
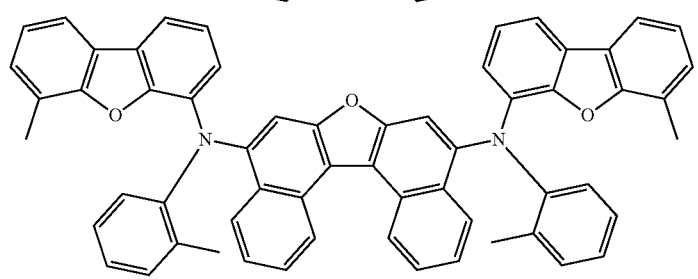

-continued
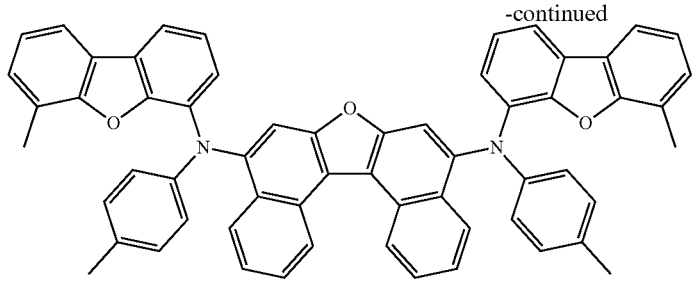
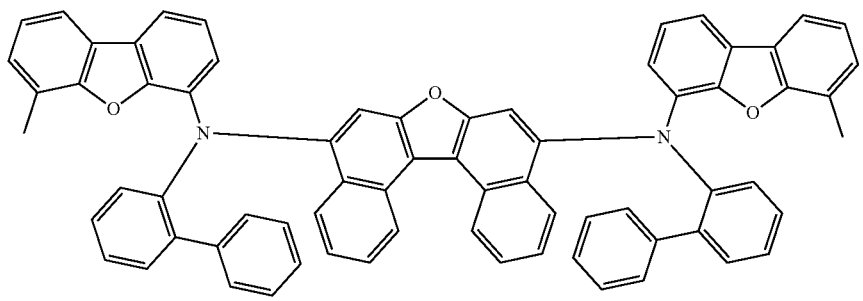
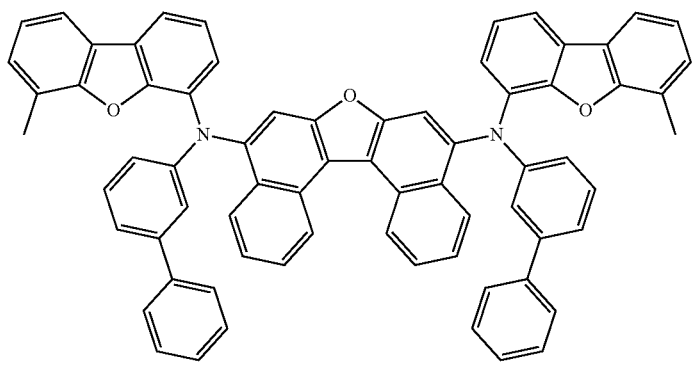
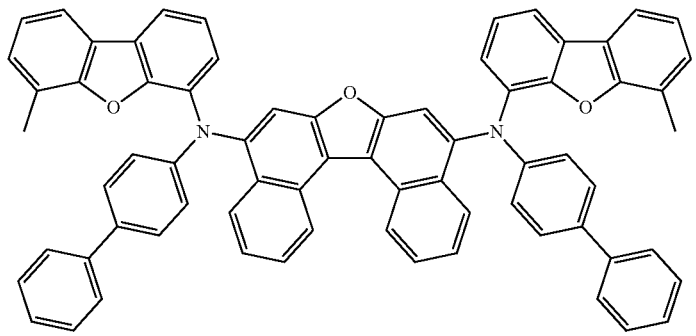
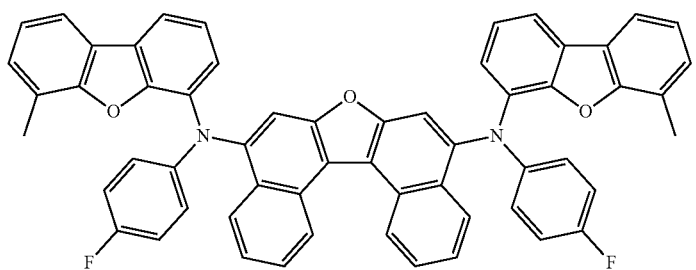

-continued
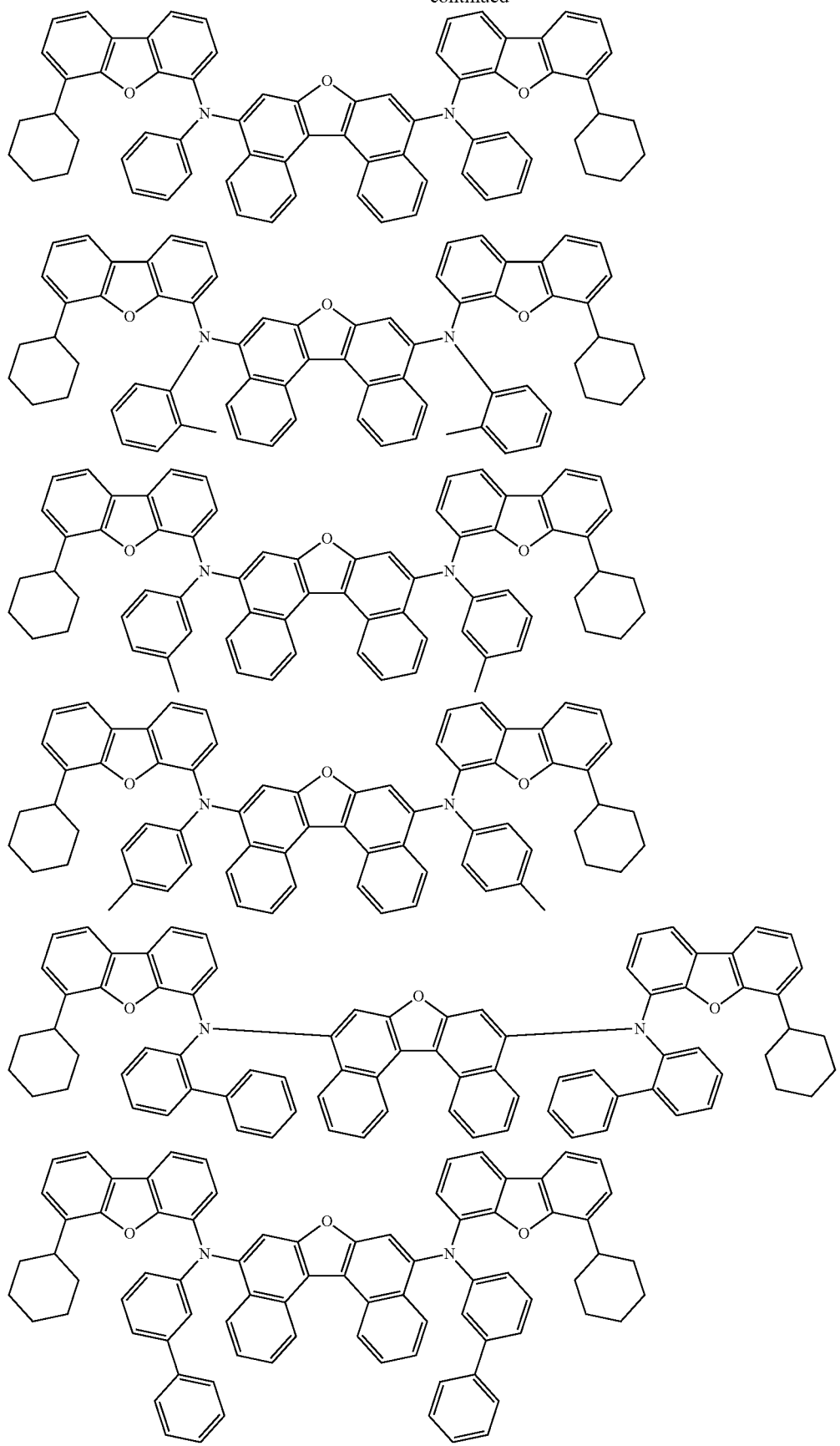

-continued
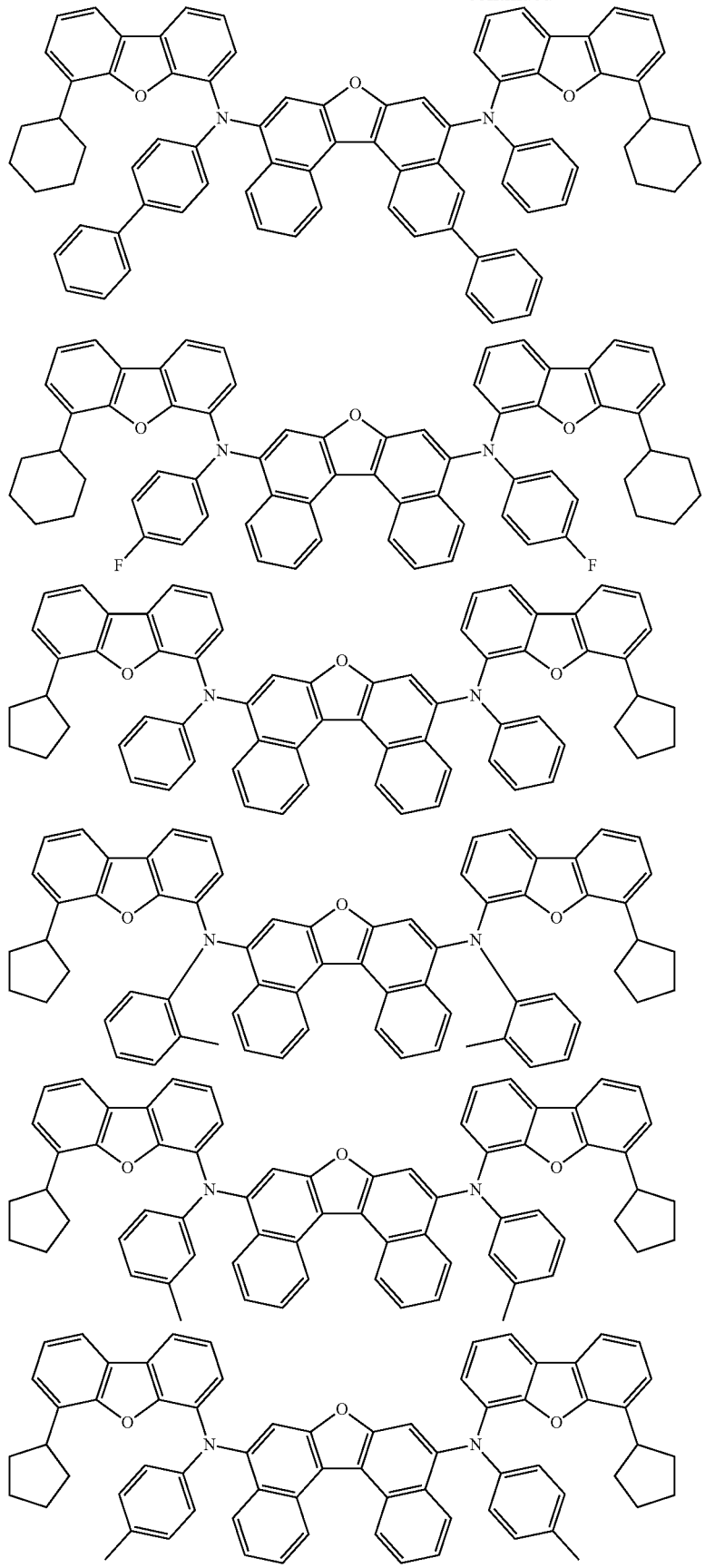

-continued
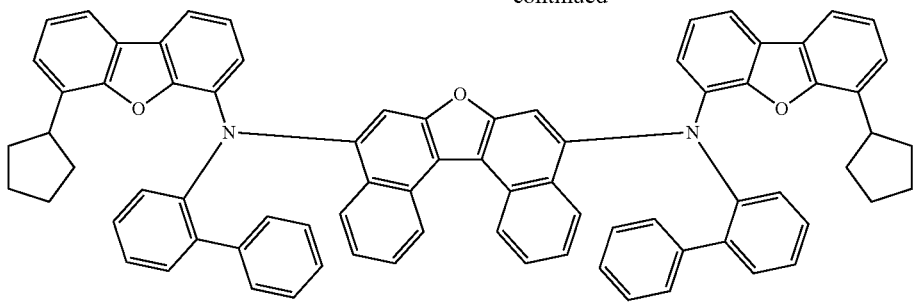
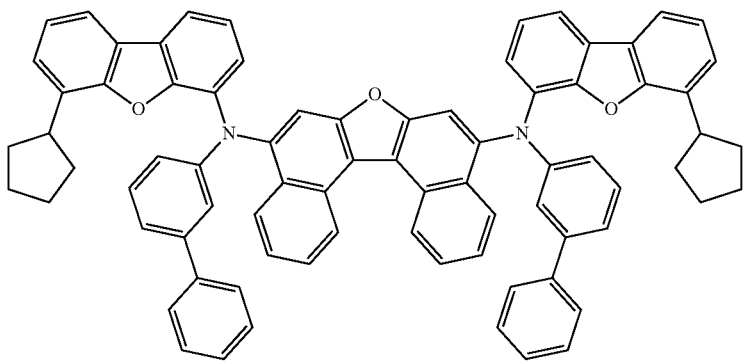
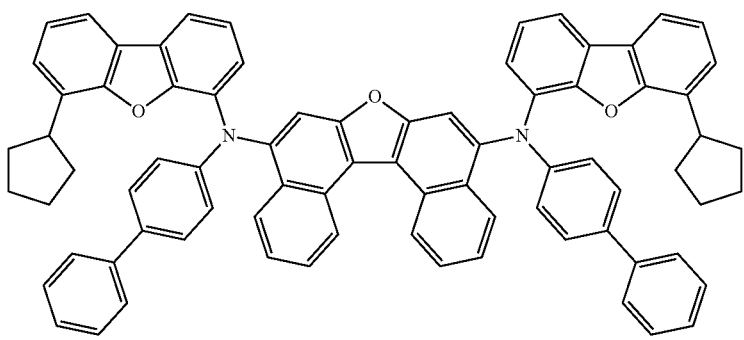
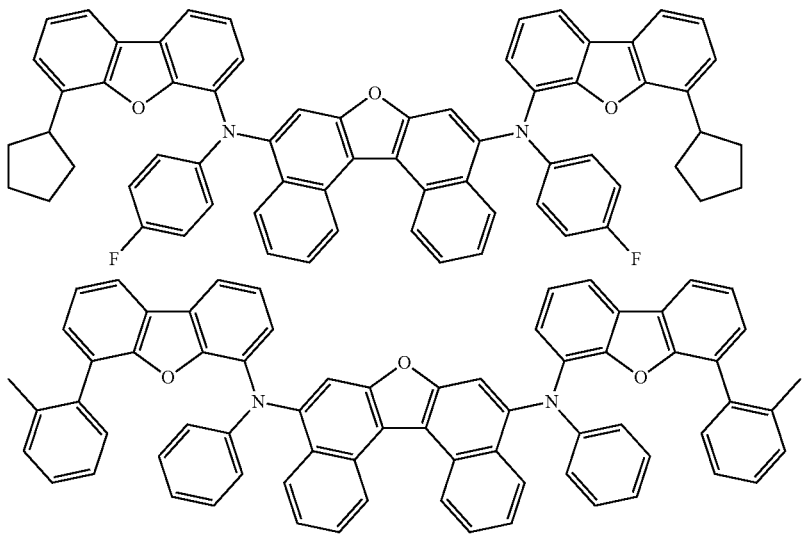

-continued
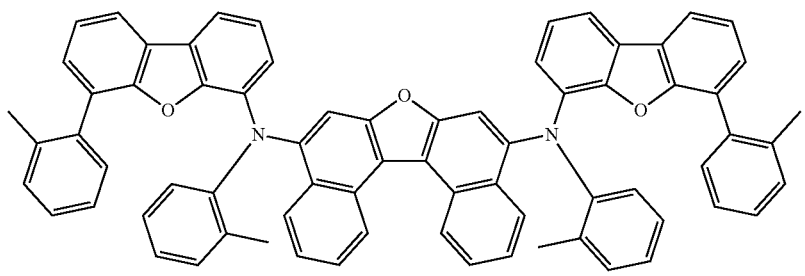
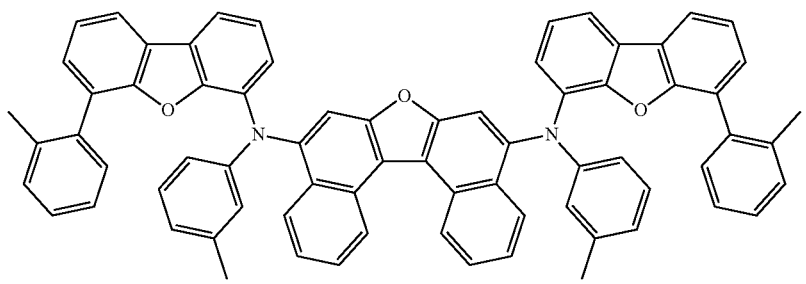
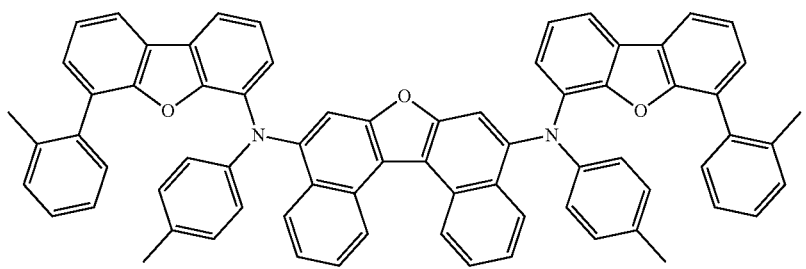
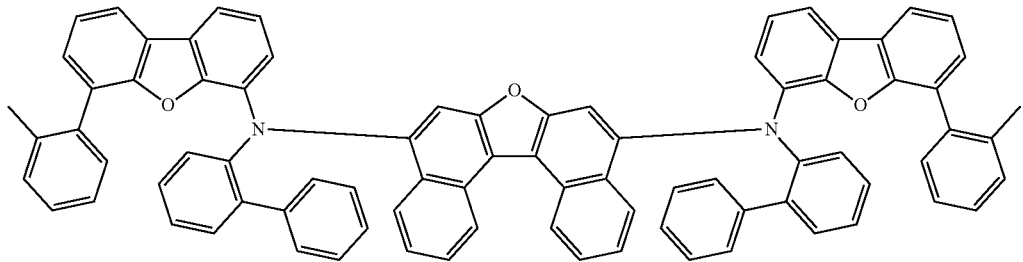
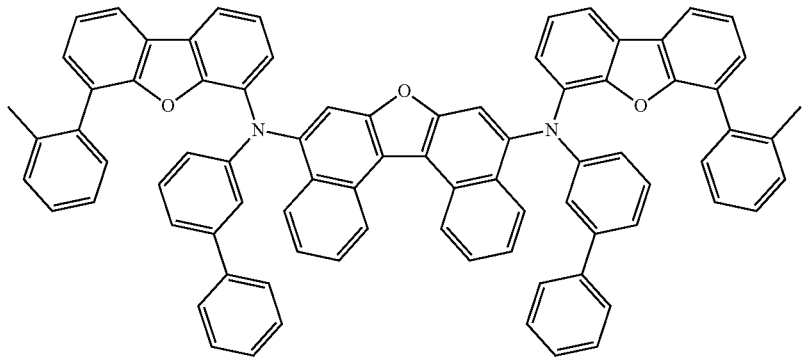

883    -continued    884
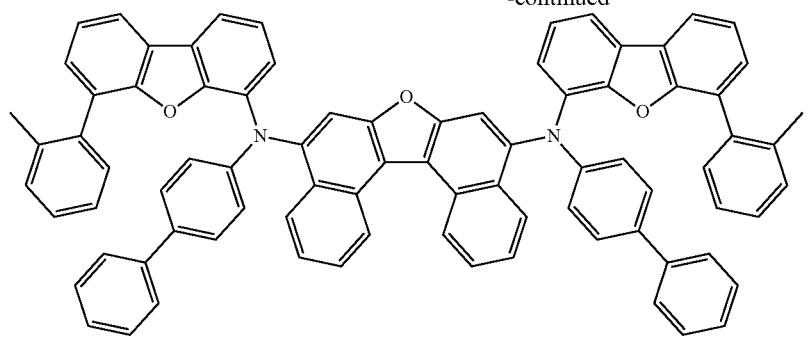
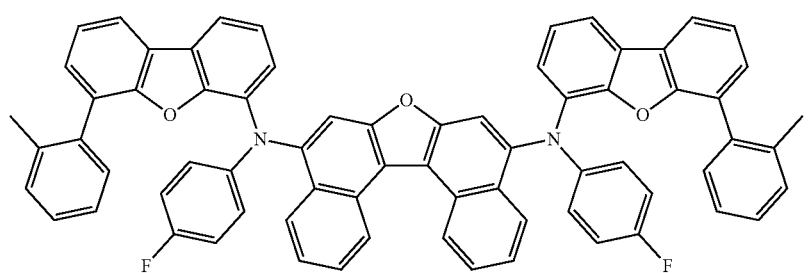
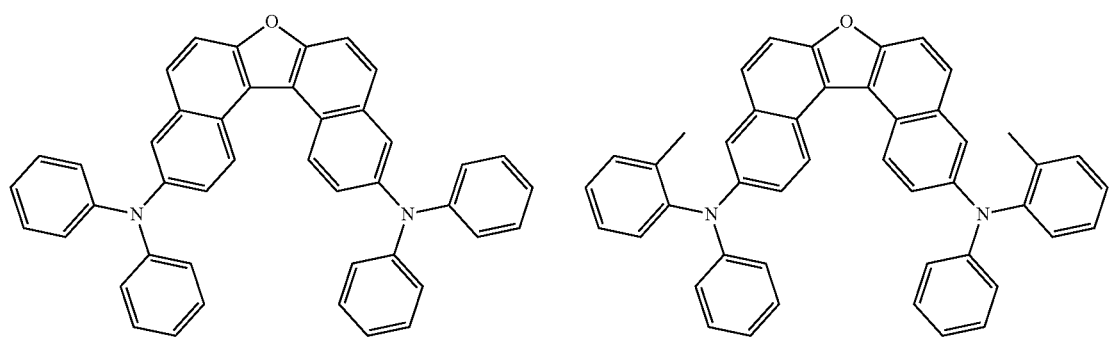
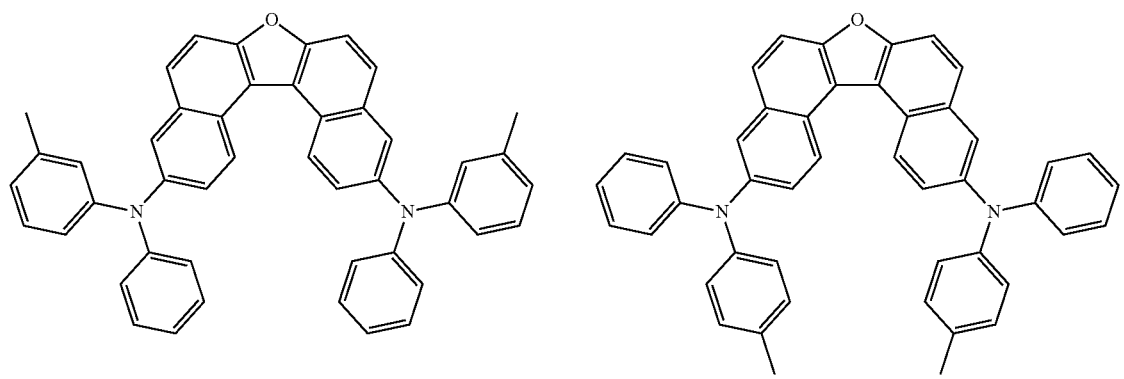

| 885 | 886 |
|---|---|
| 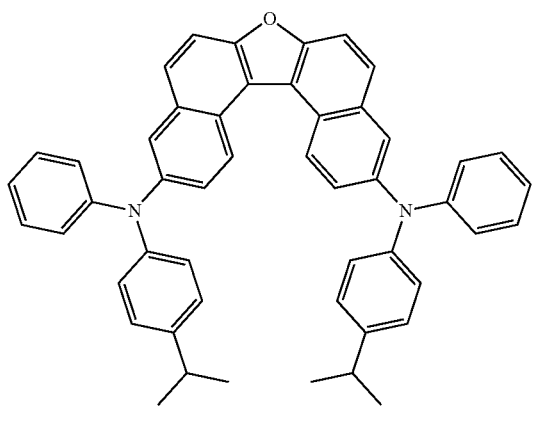 | 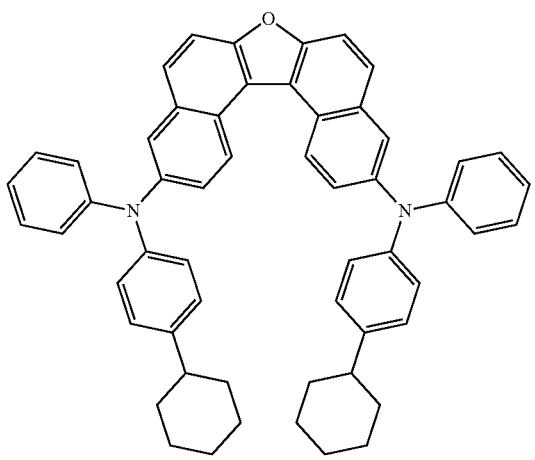 |
| 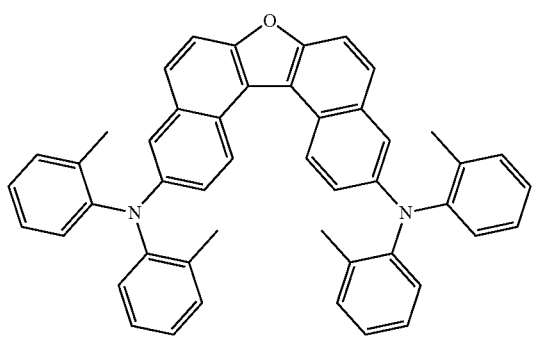 | 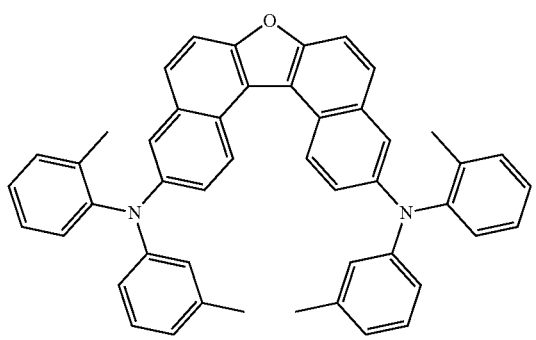 |
| 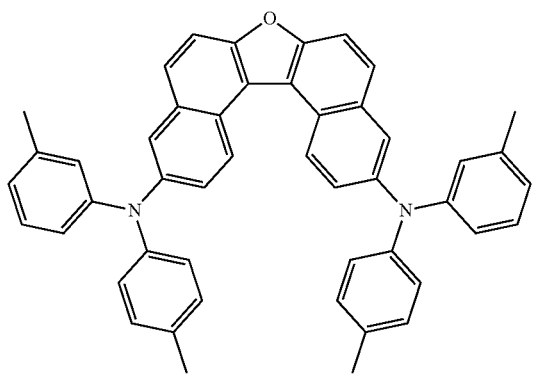 | 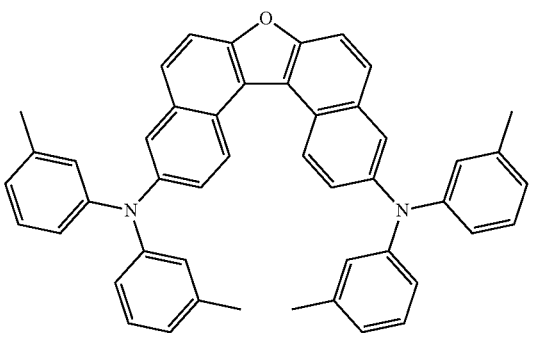 |
| 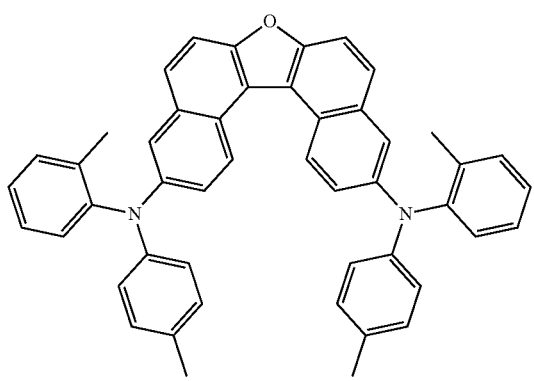 | |

-continued
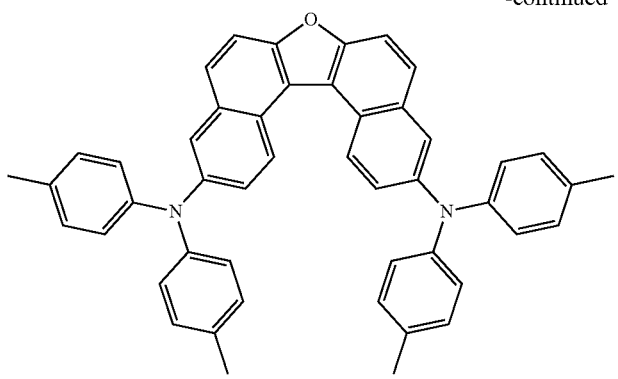
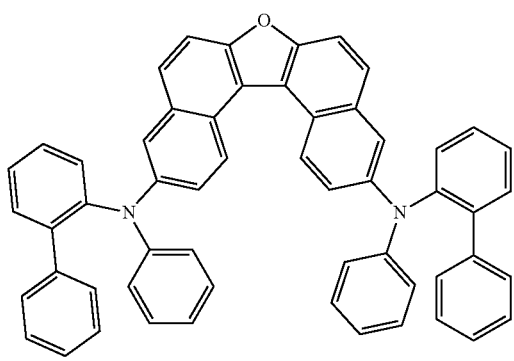
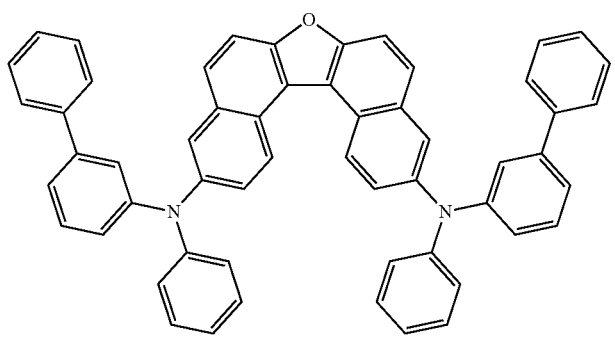
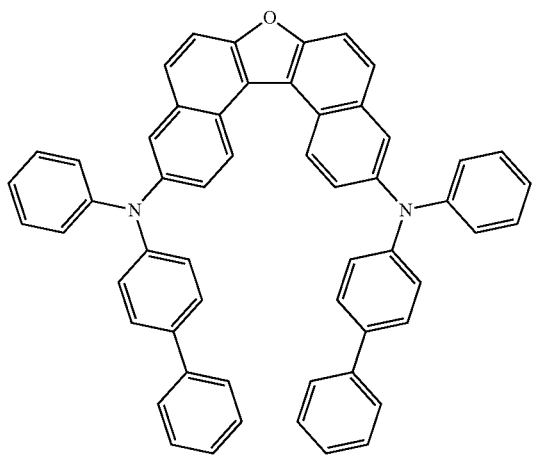

889 890
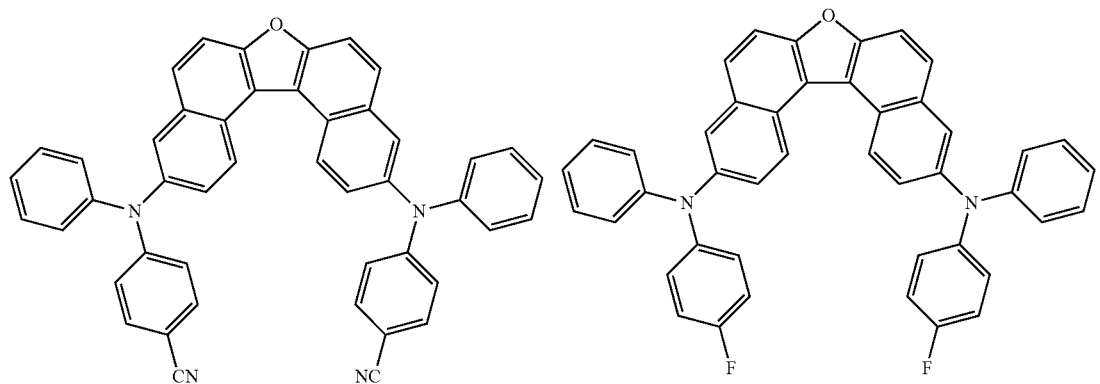
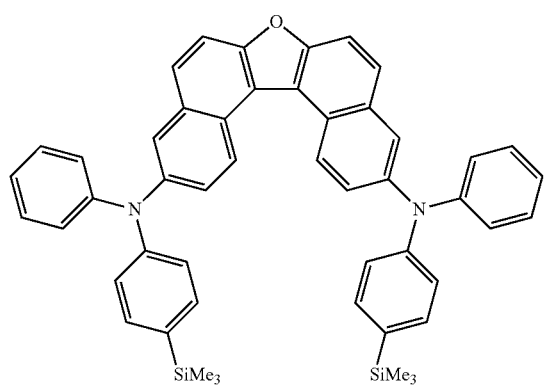
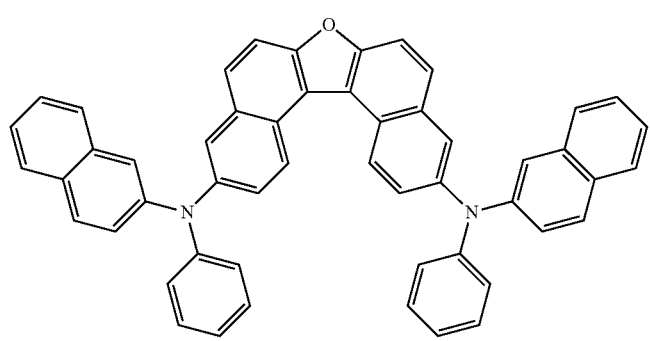
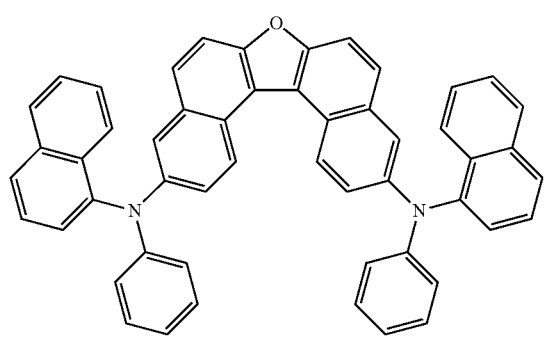

891                                      892
-continued
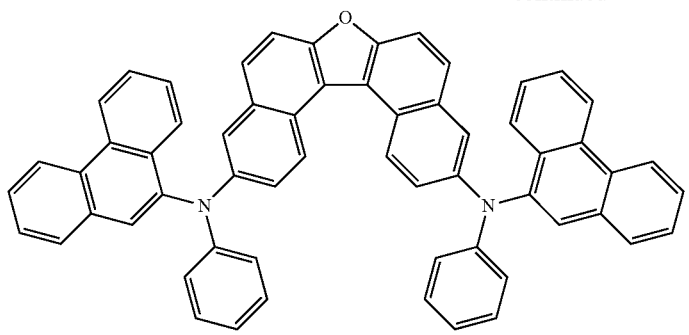
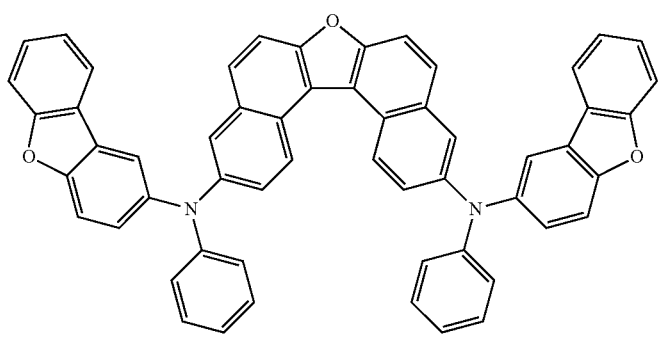
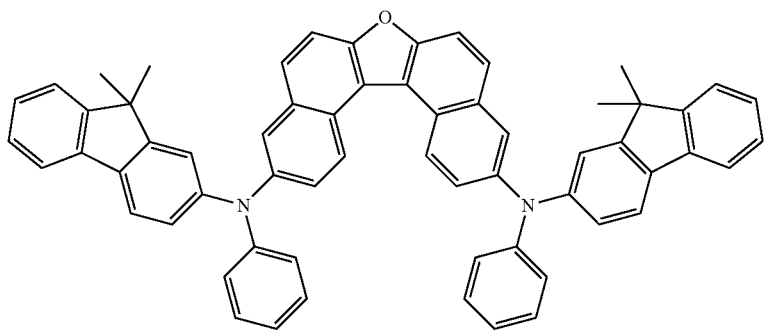
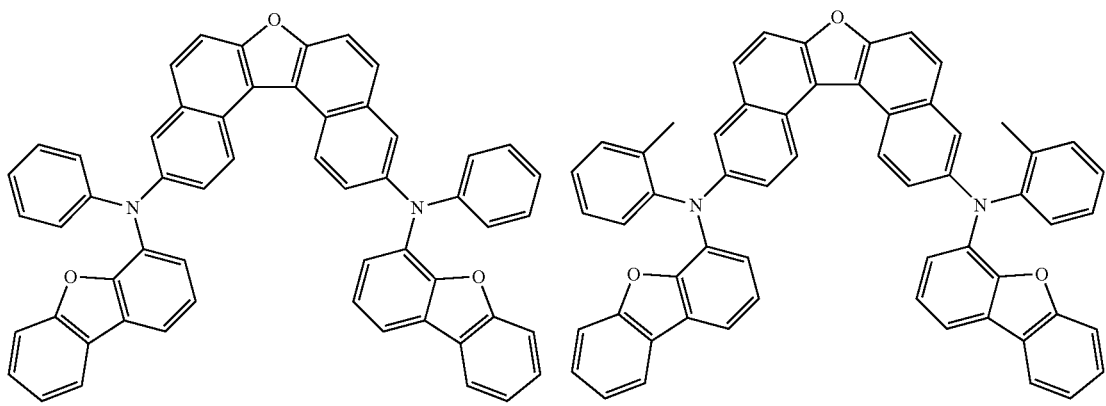

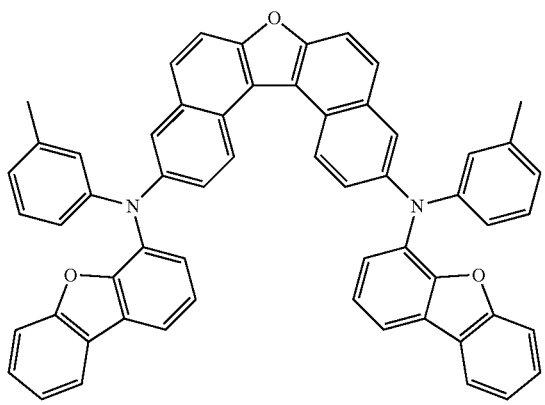
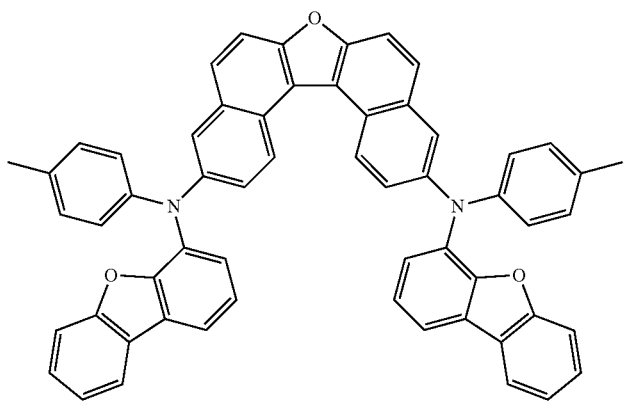
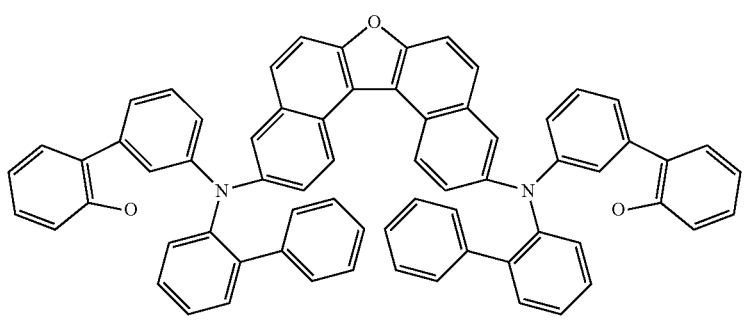
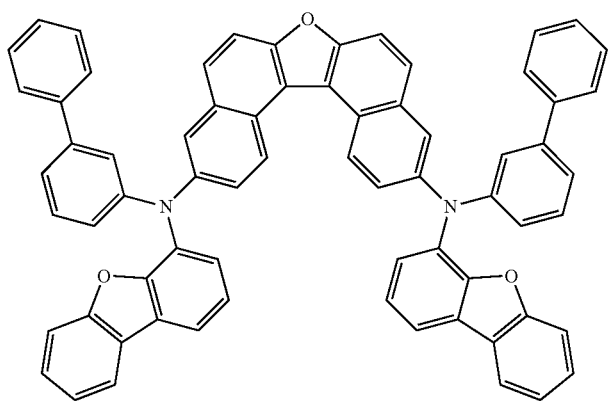

-continued
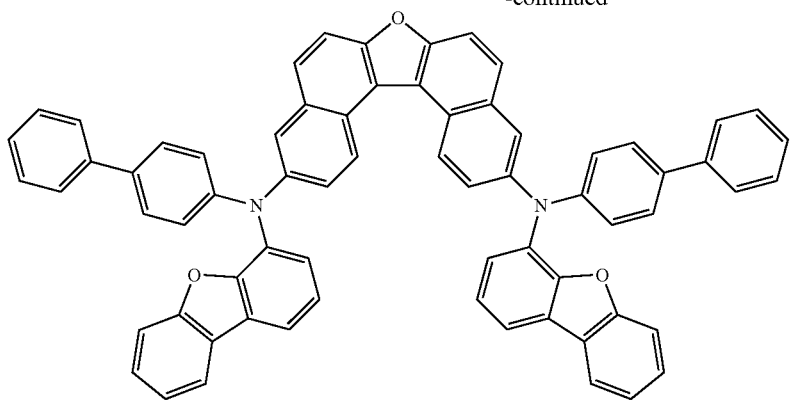
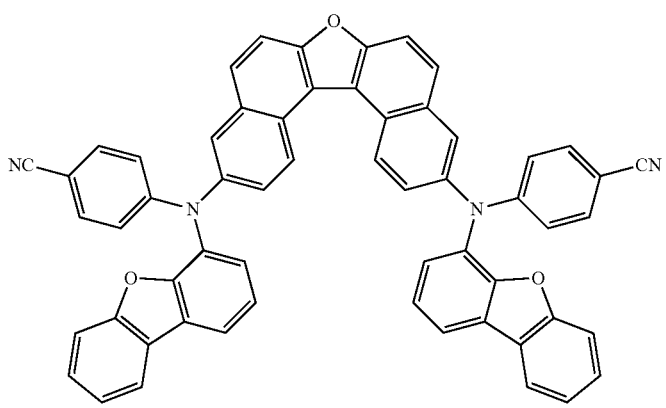
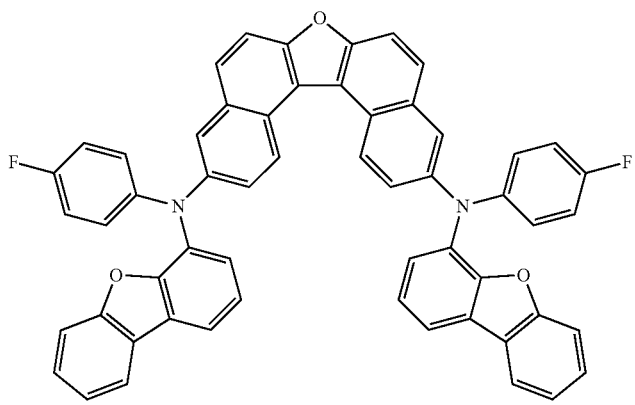
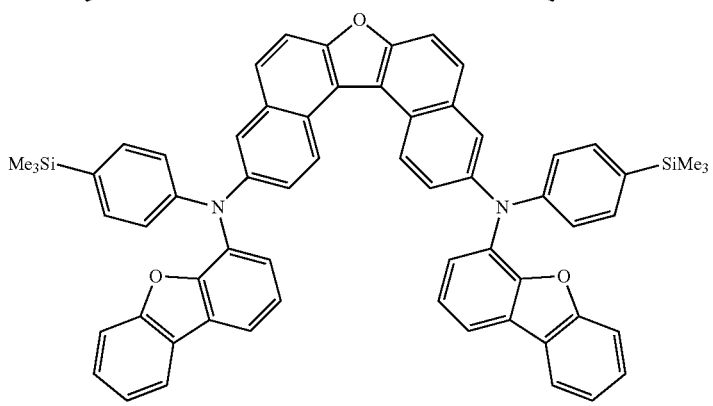

-continued
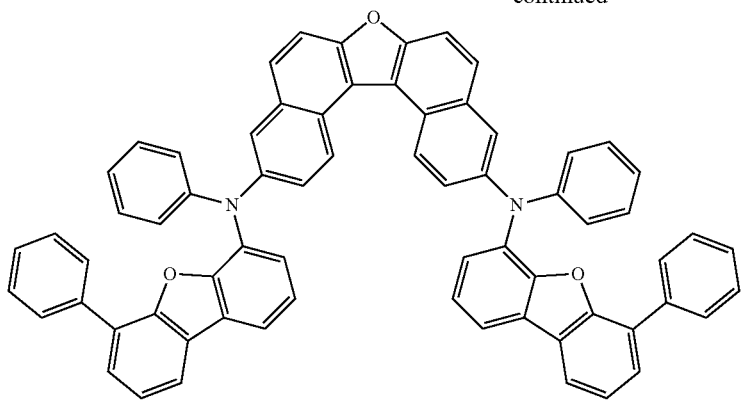
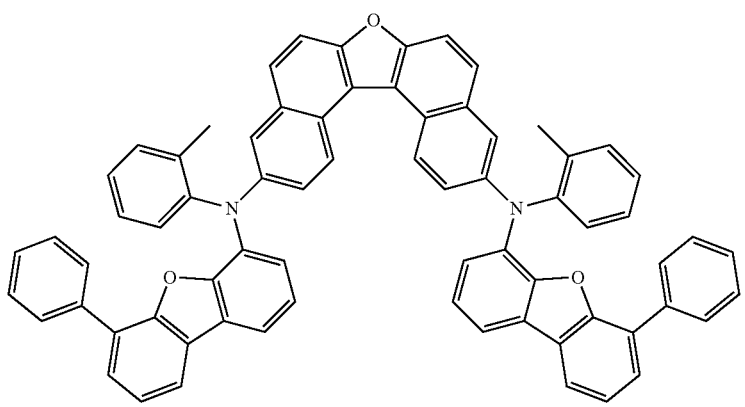
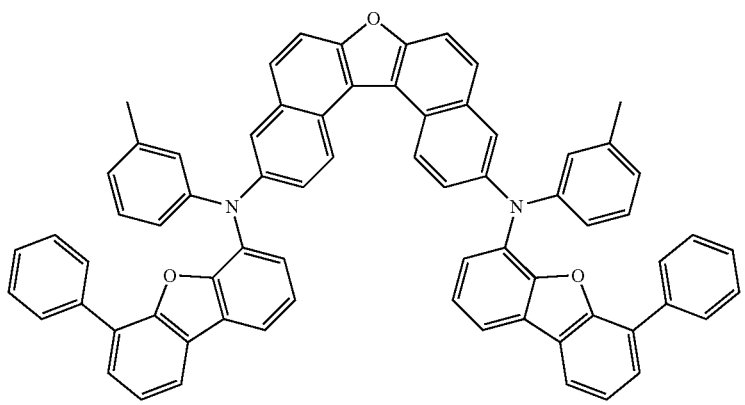
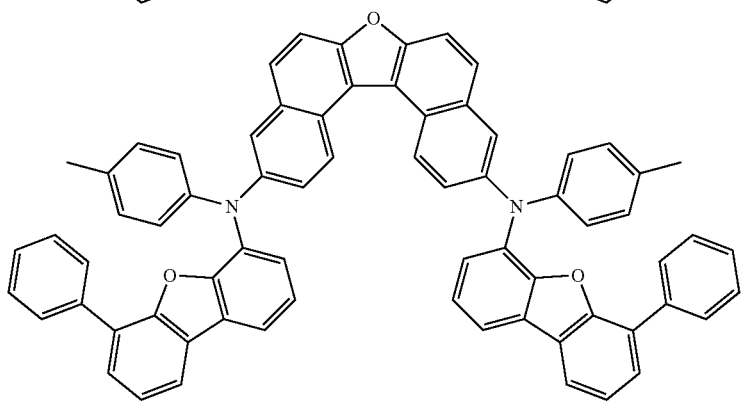

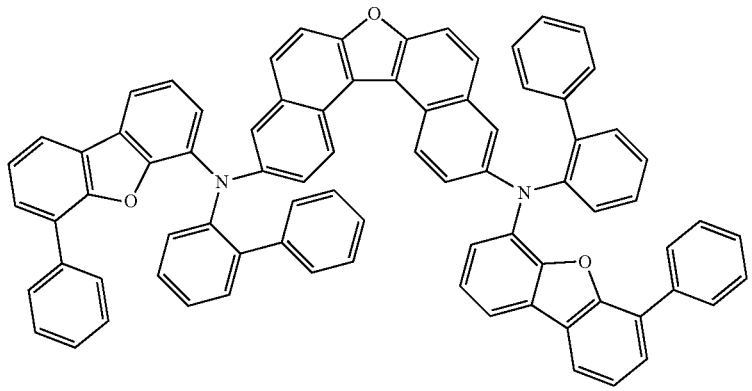
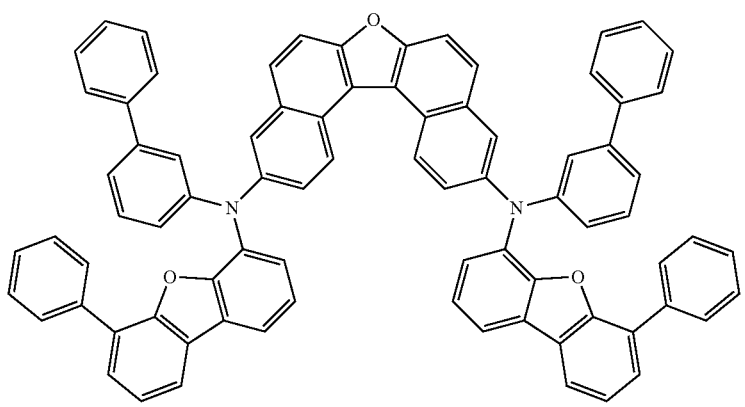
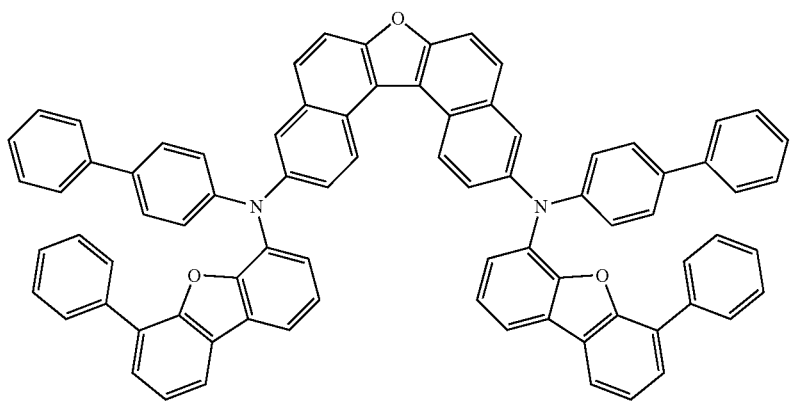
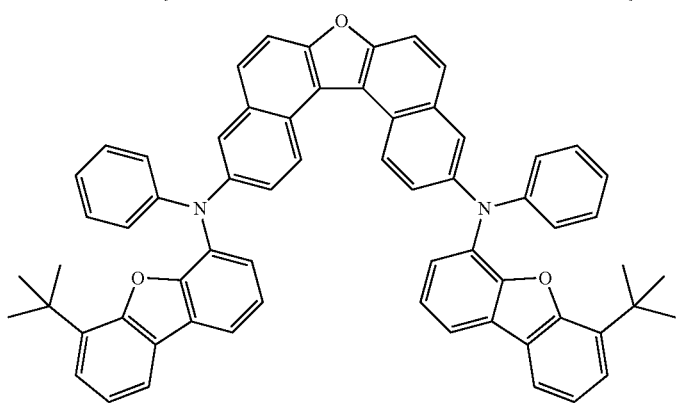

-continued
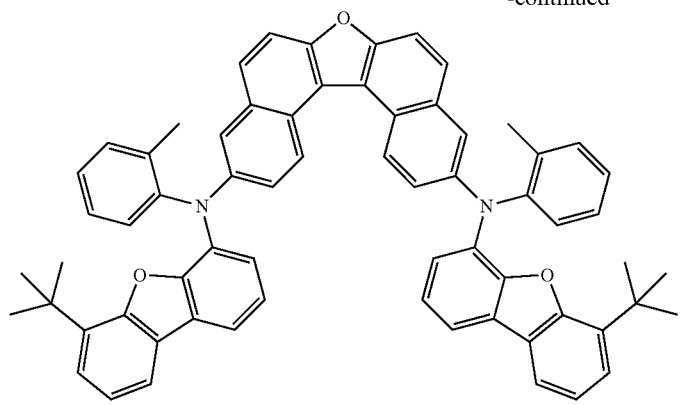
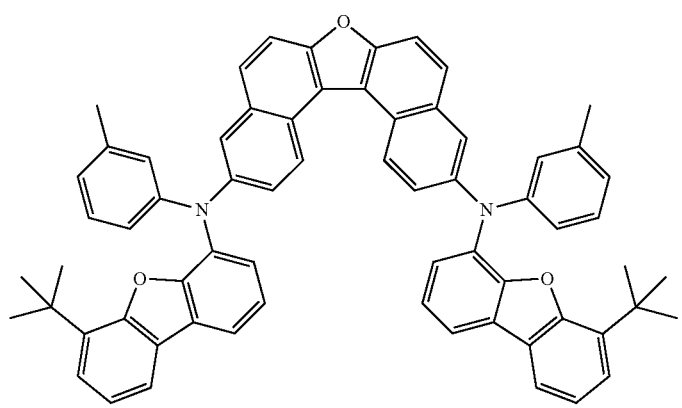
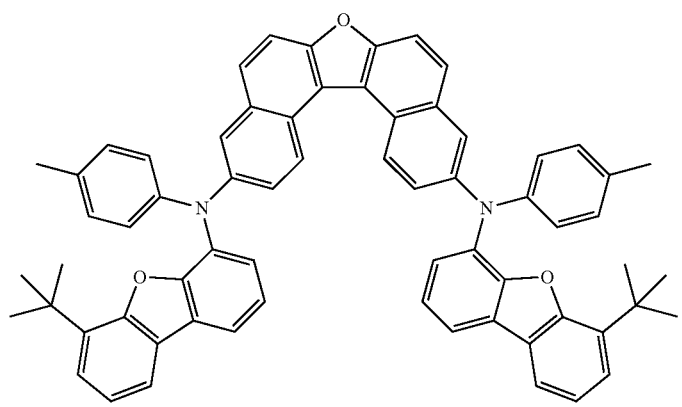
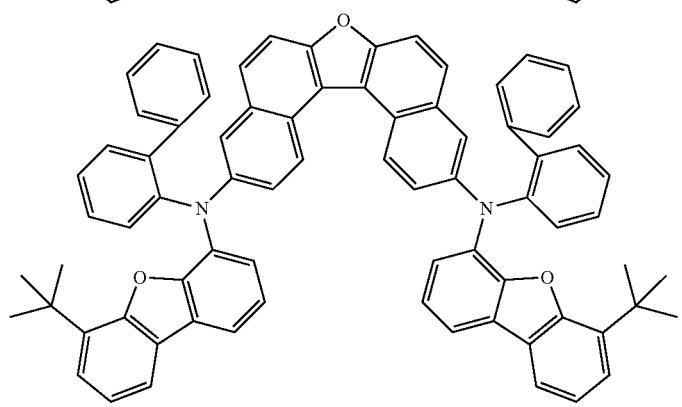

903
904
-continued
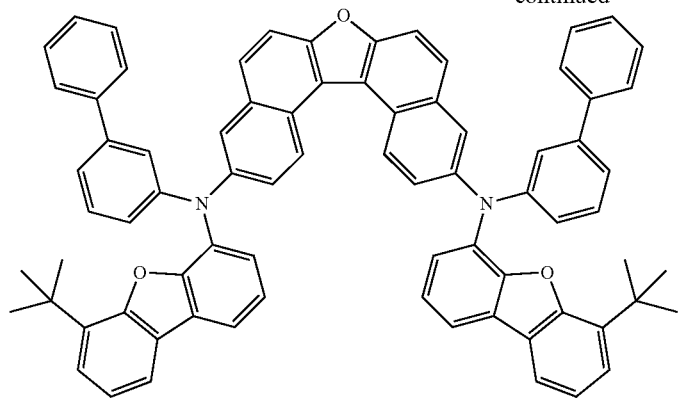
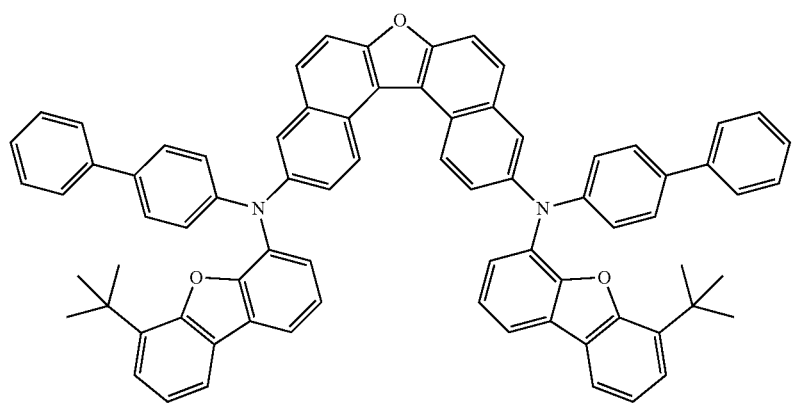
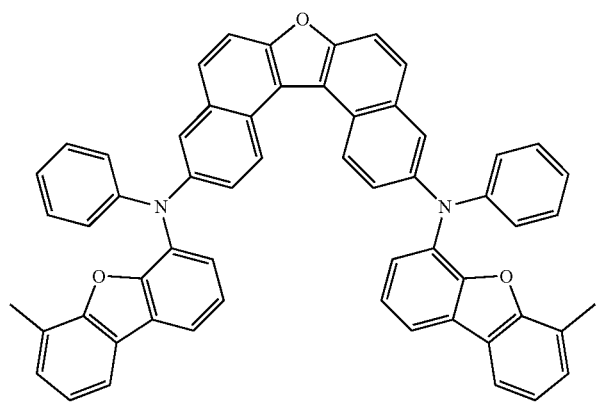
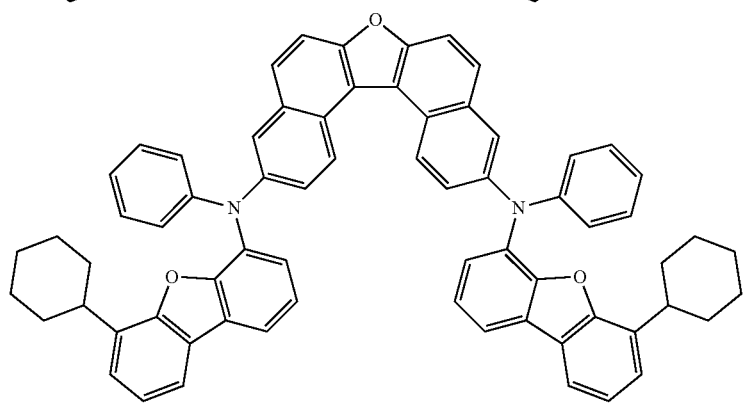

-continued
905
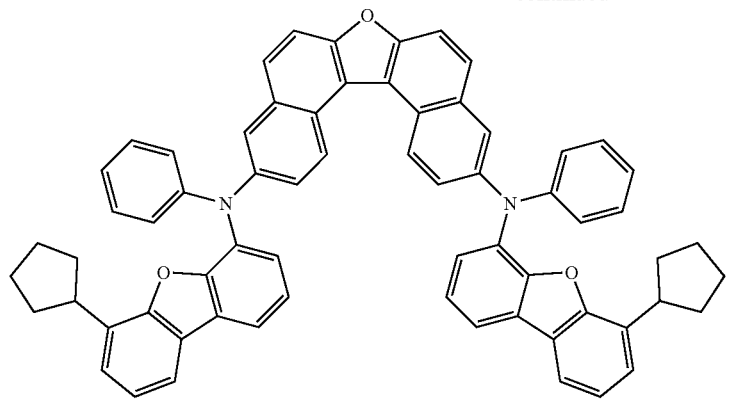
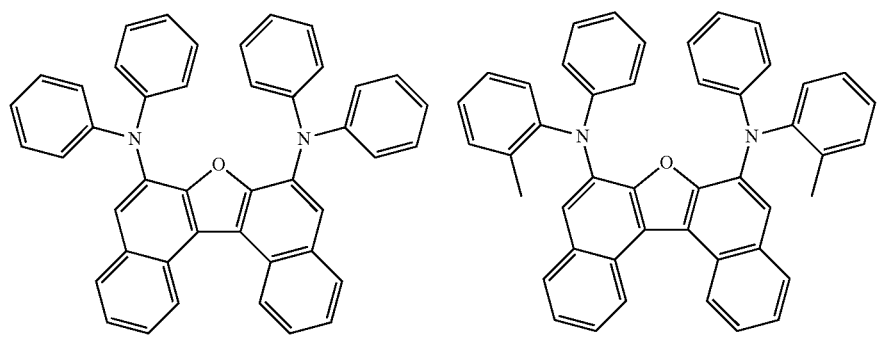
906
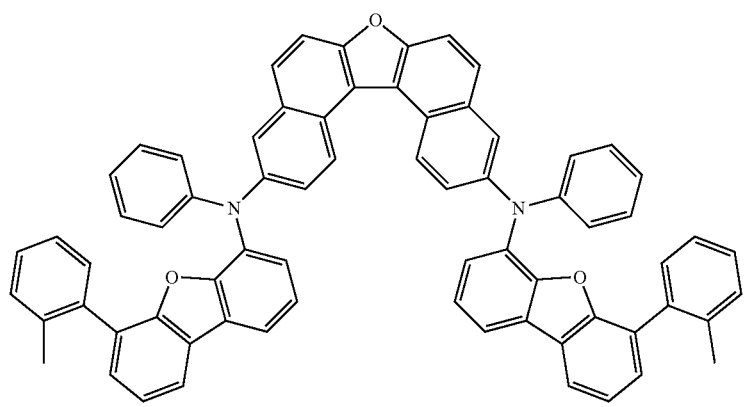
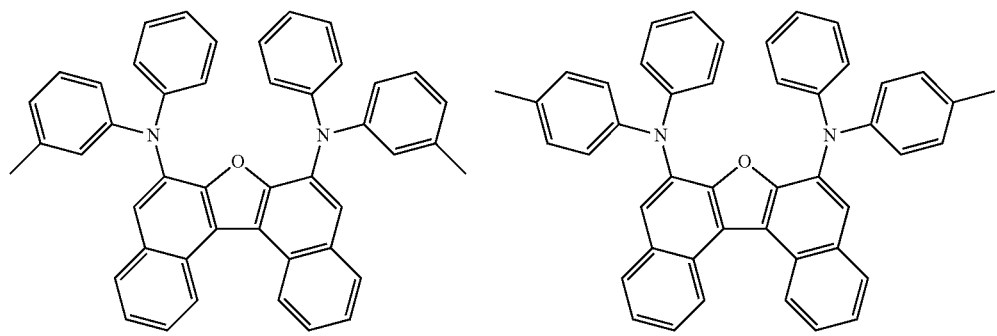

907 908
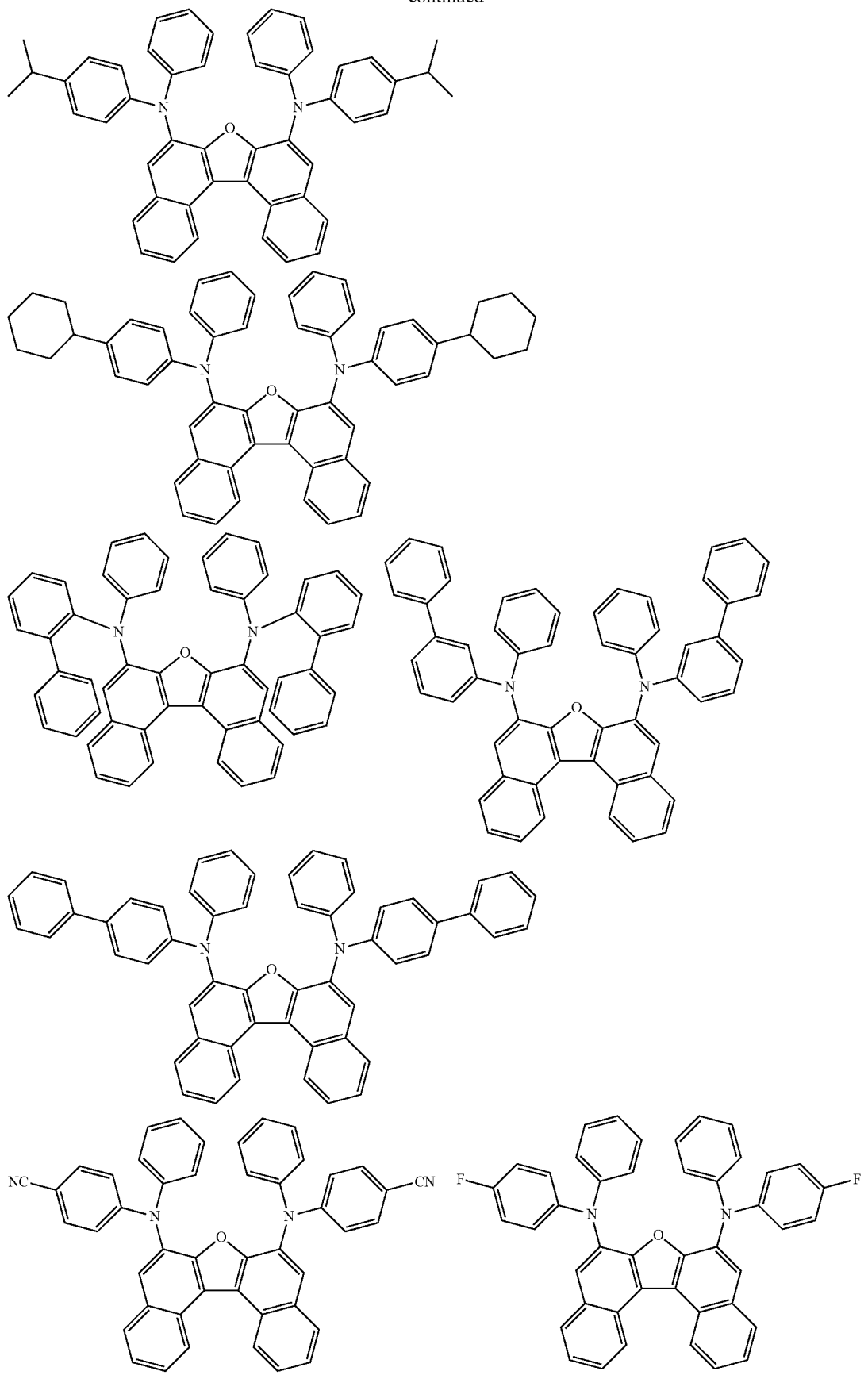

909 910
-continued
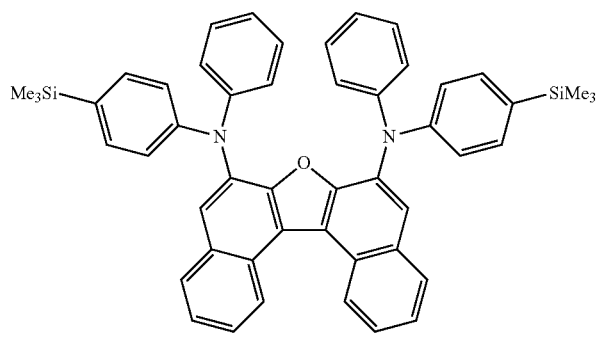
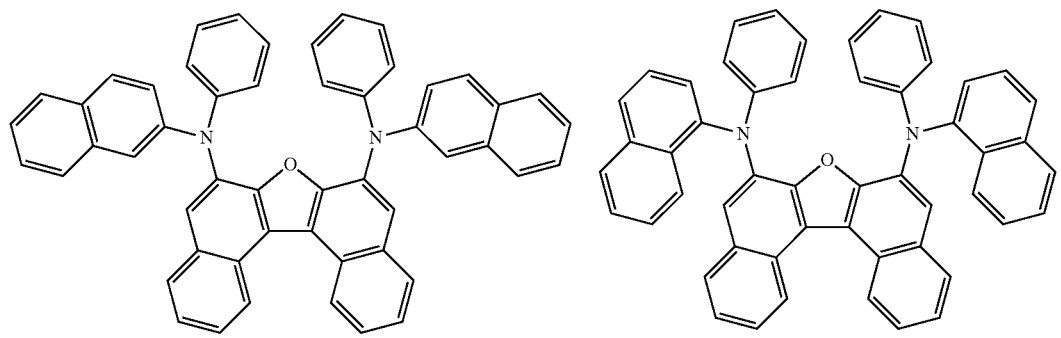
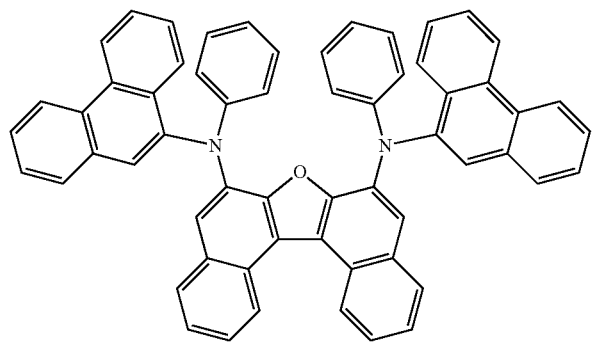
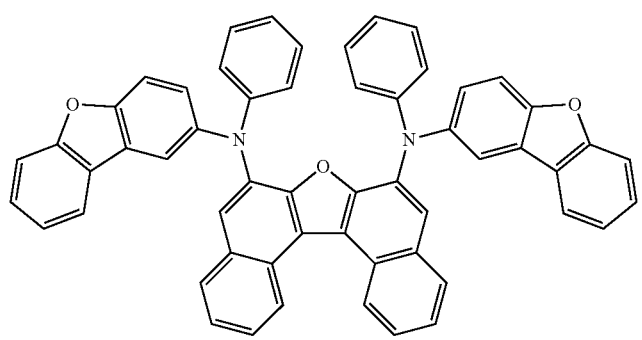
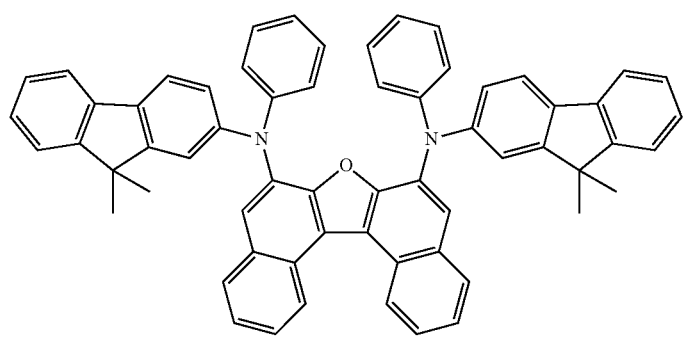

911 912
-continued
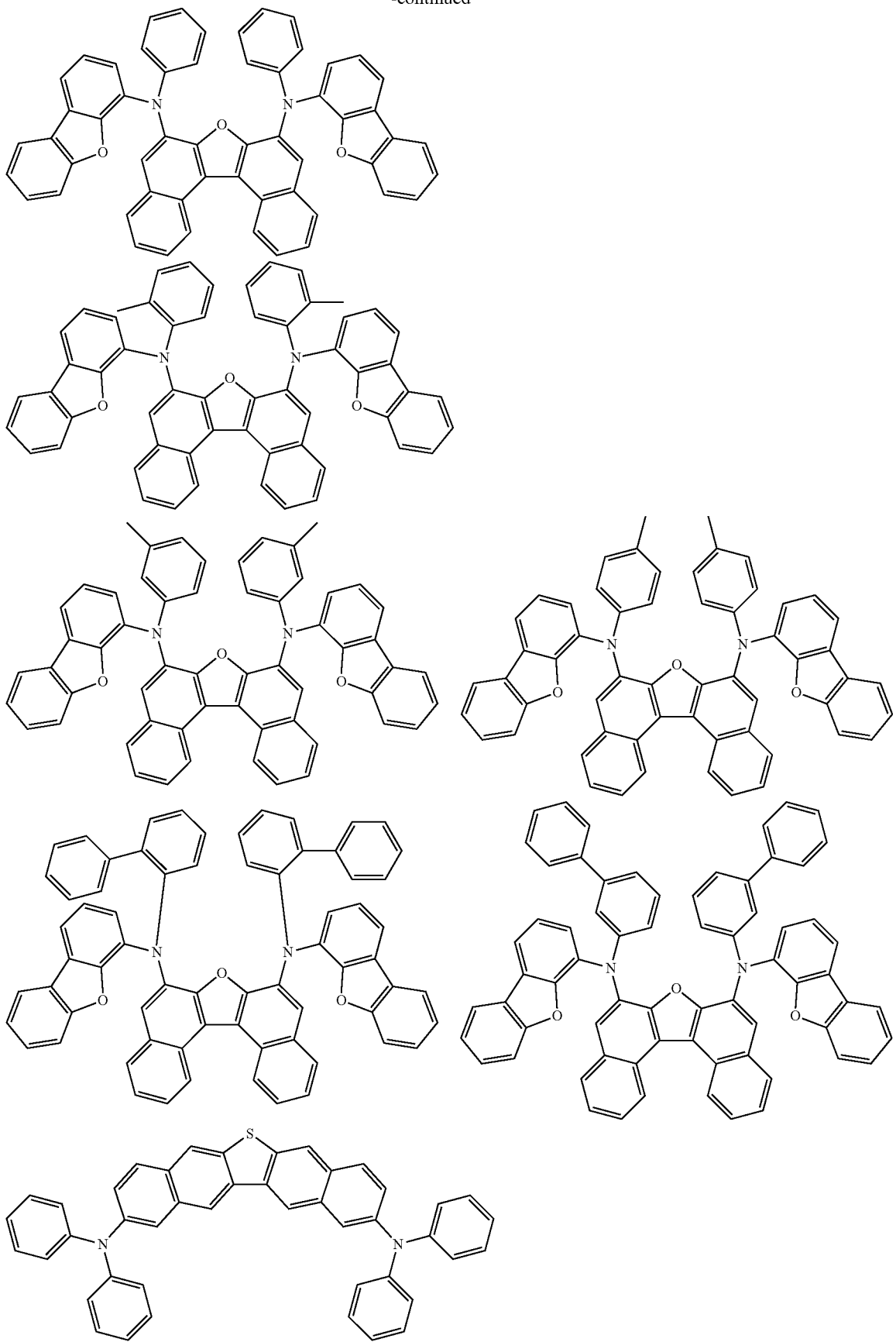

913
914
-continued
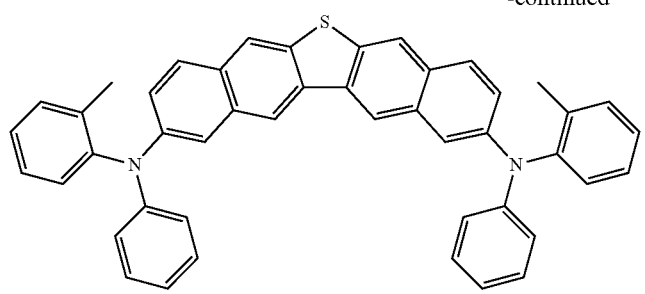
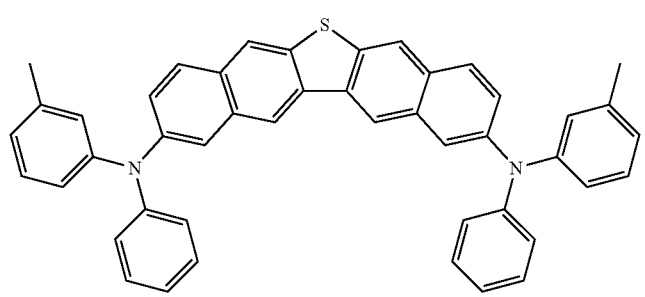
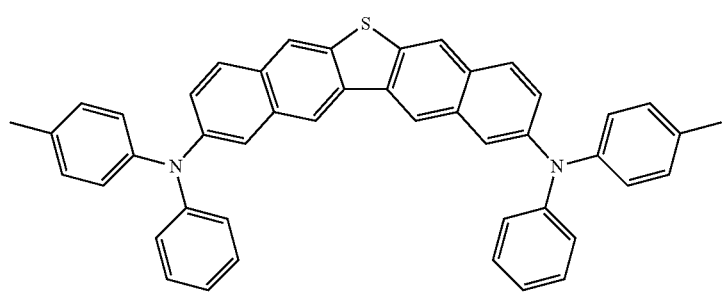
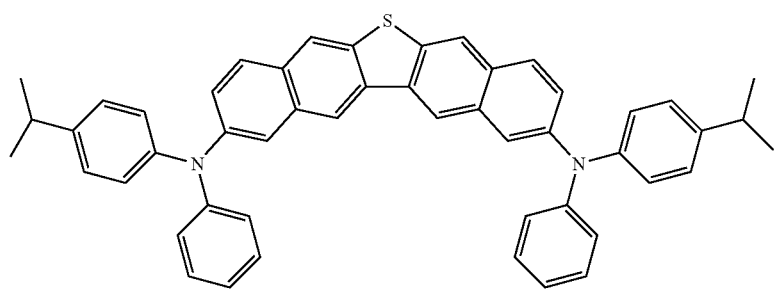
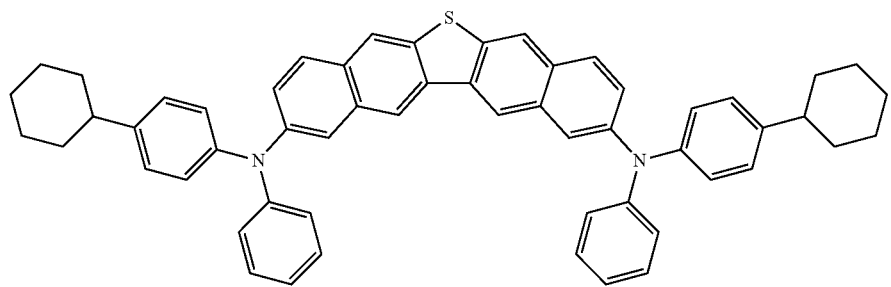

-continued
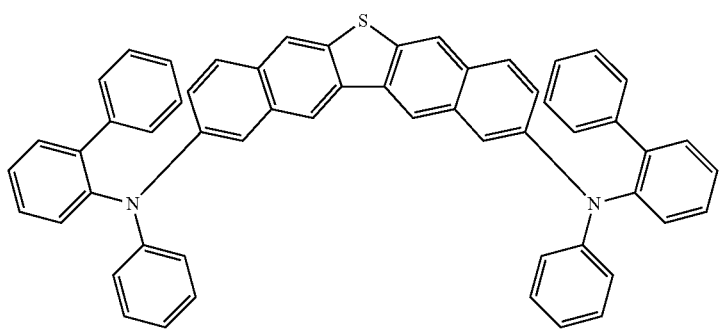
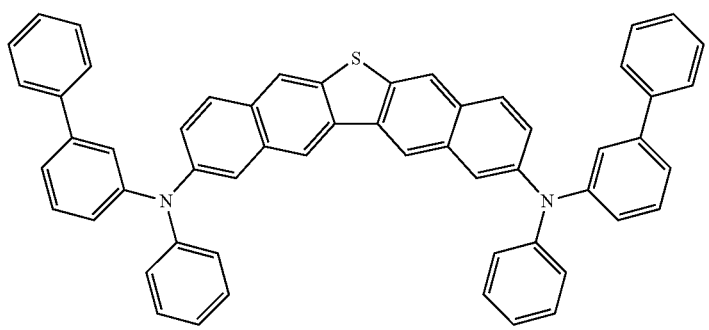
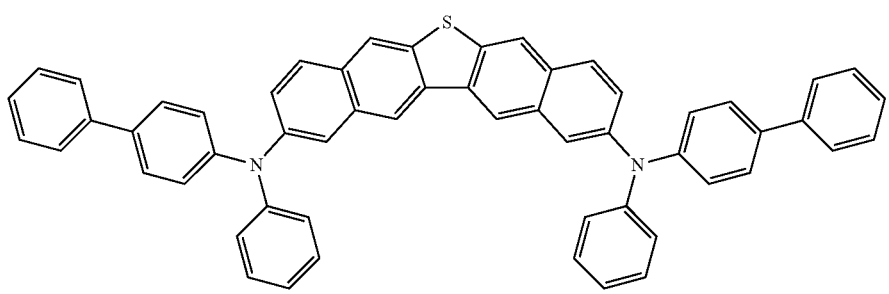
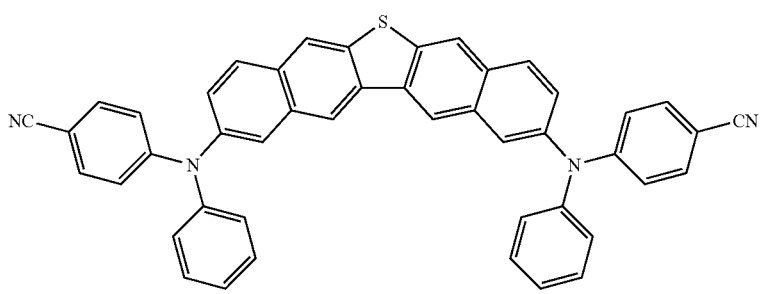
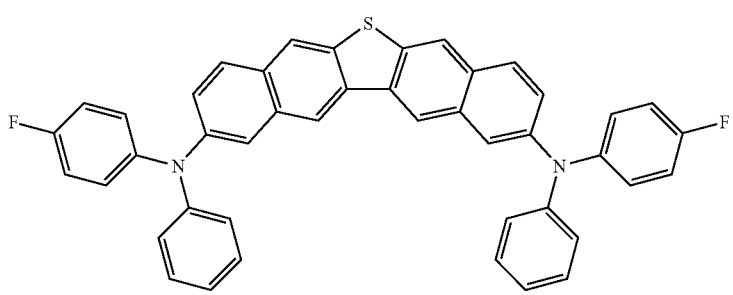

-continued
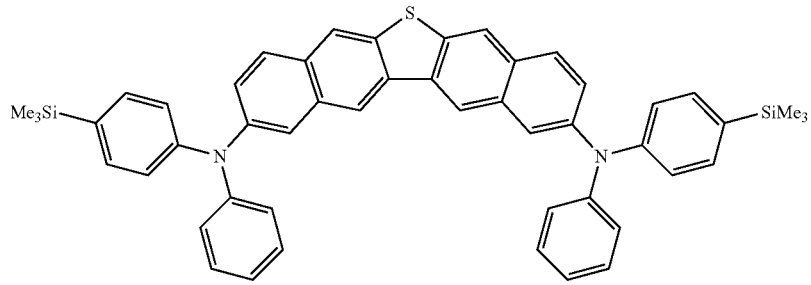

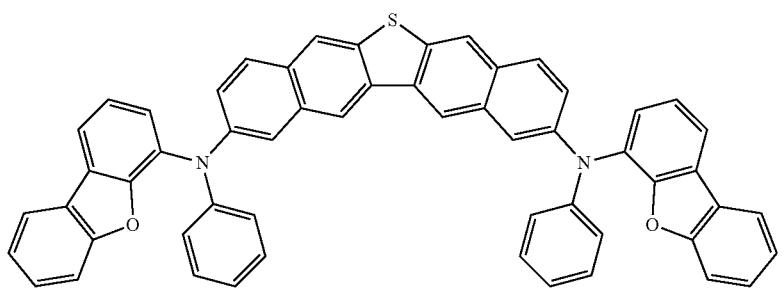
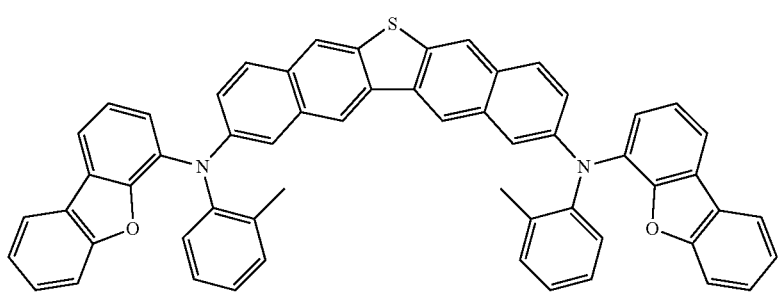
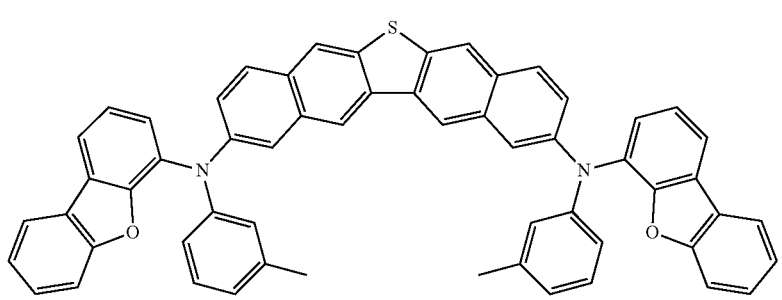
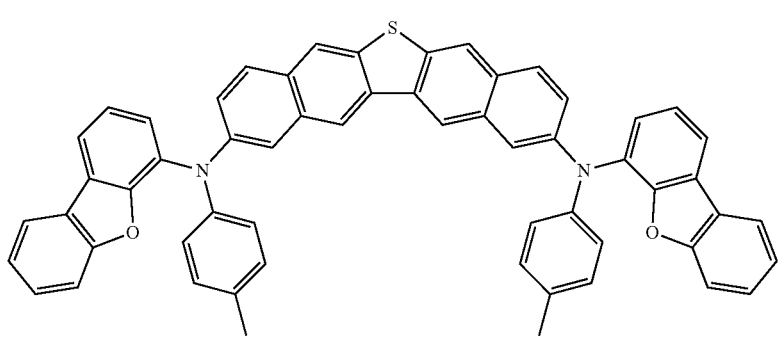
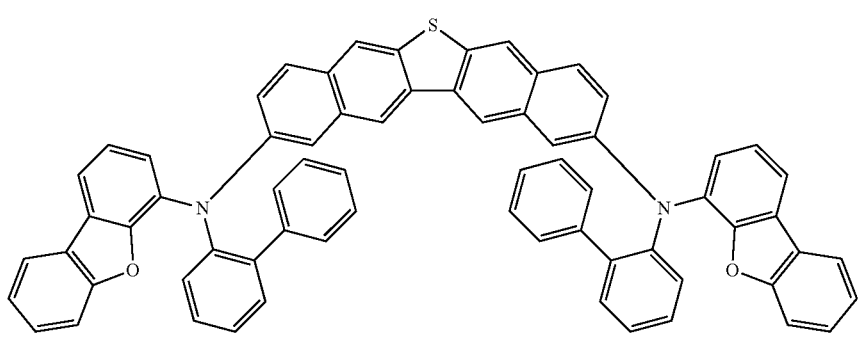

-continued
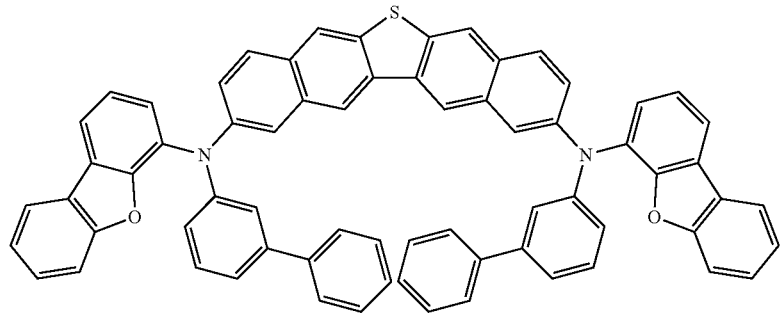
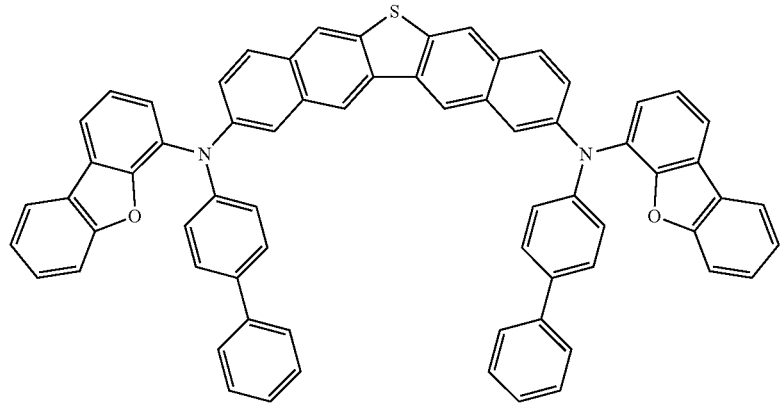
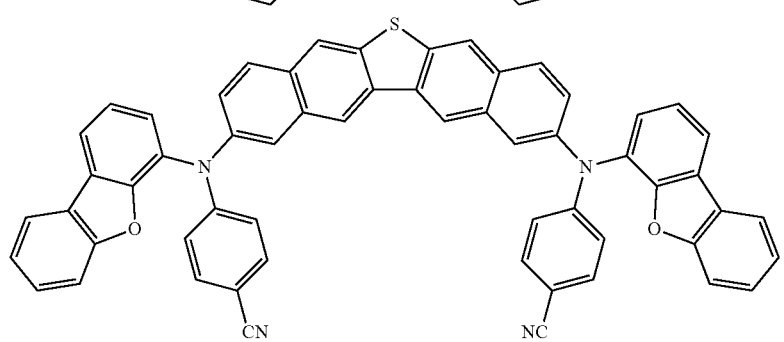
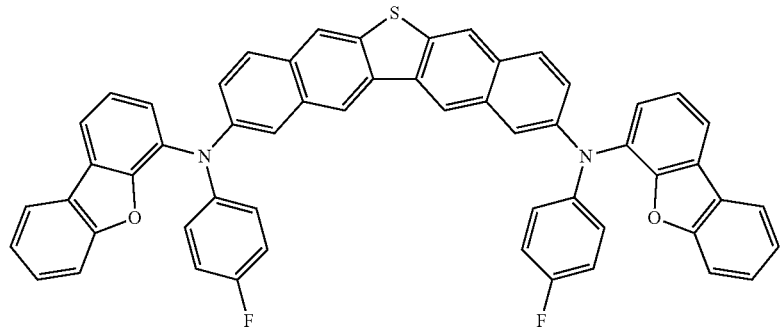
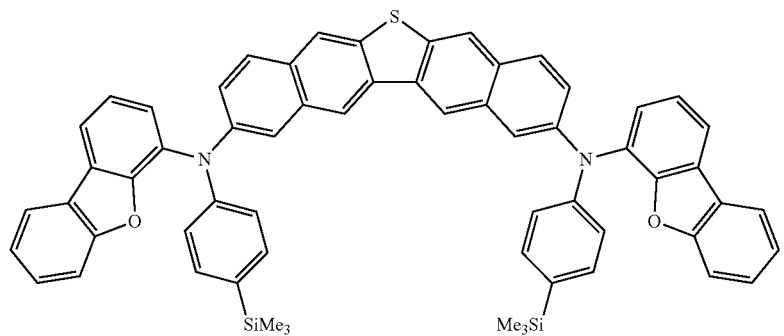

923 924
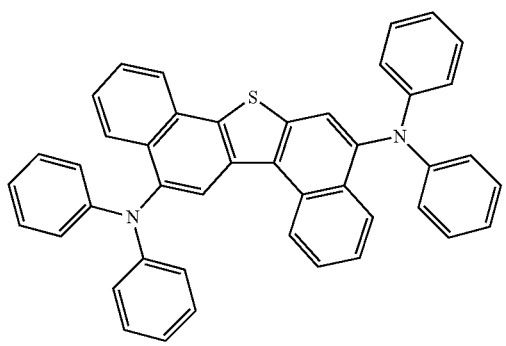
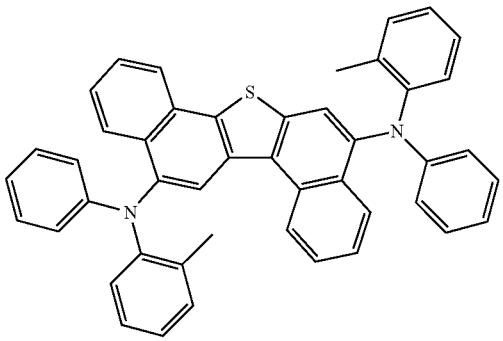
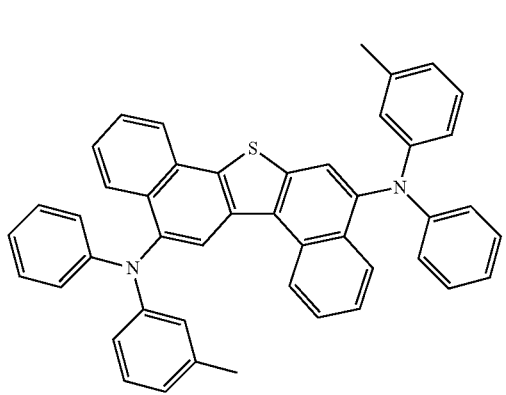
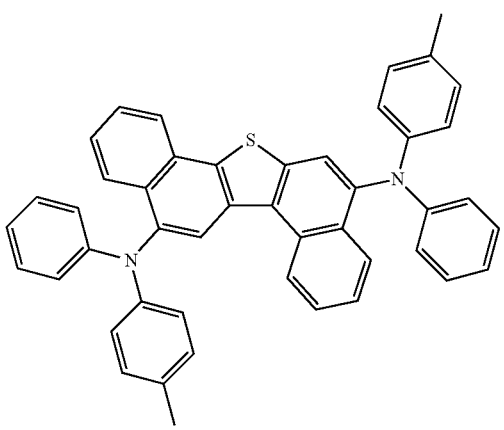
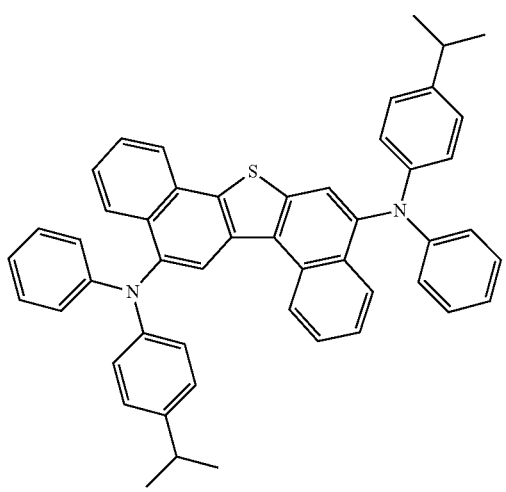
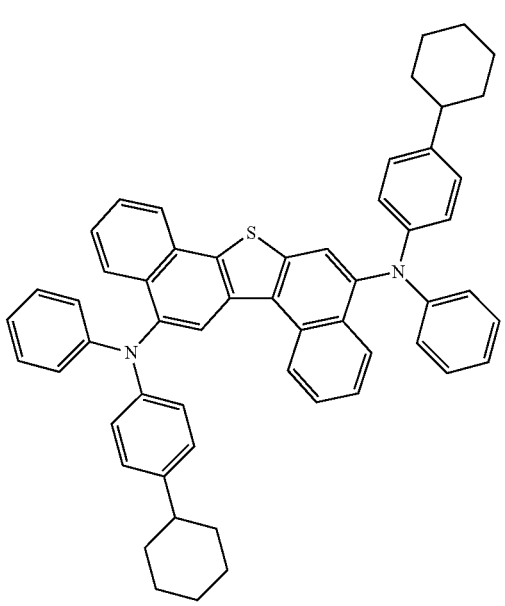

925
926
-continued
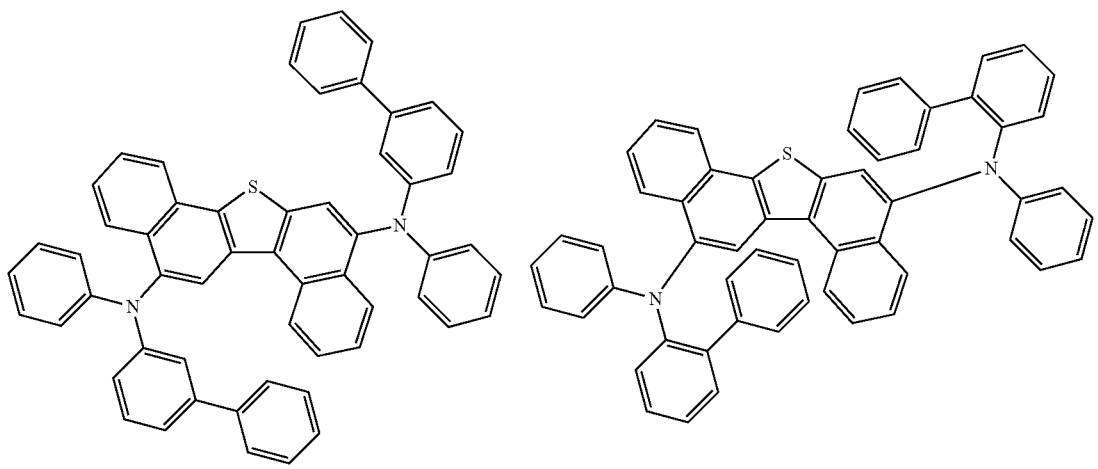
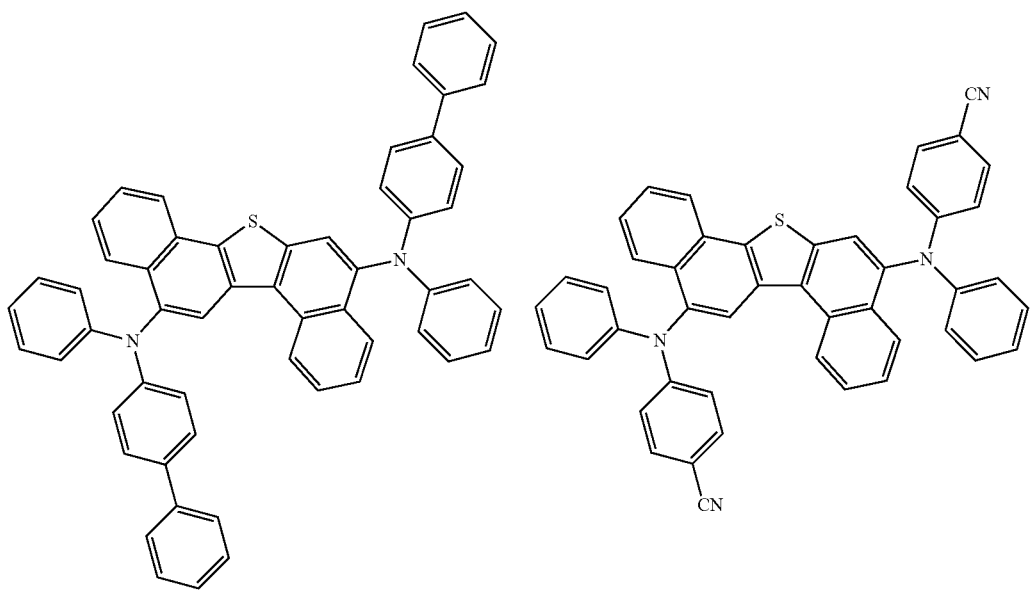
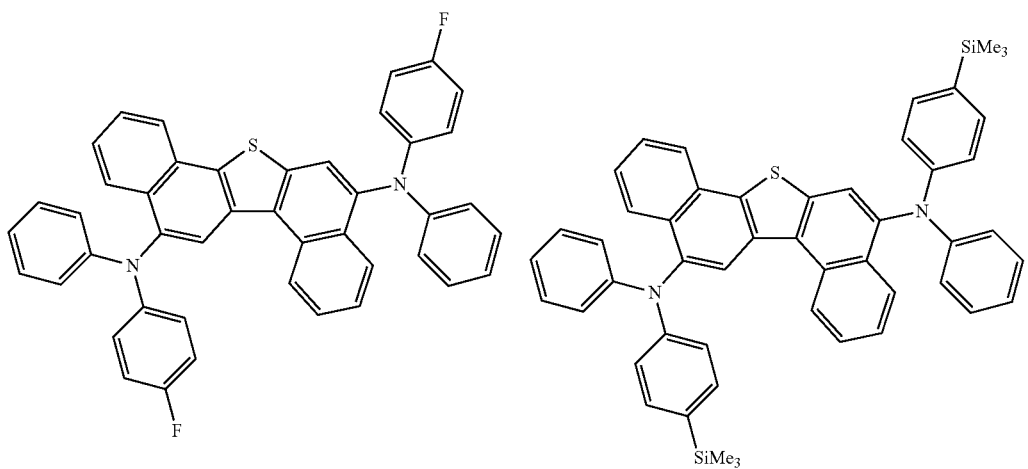

927 928
-continued
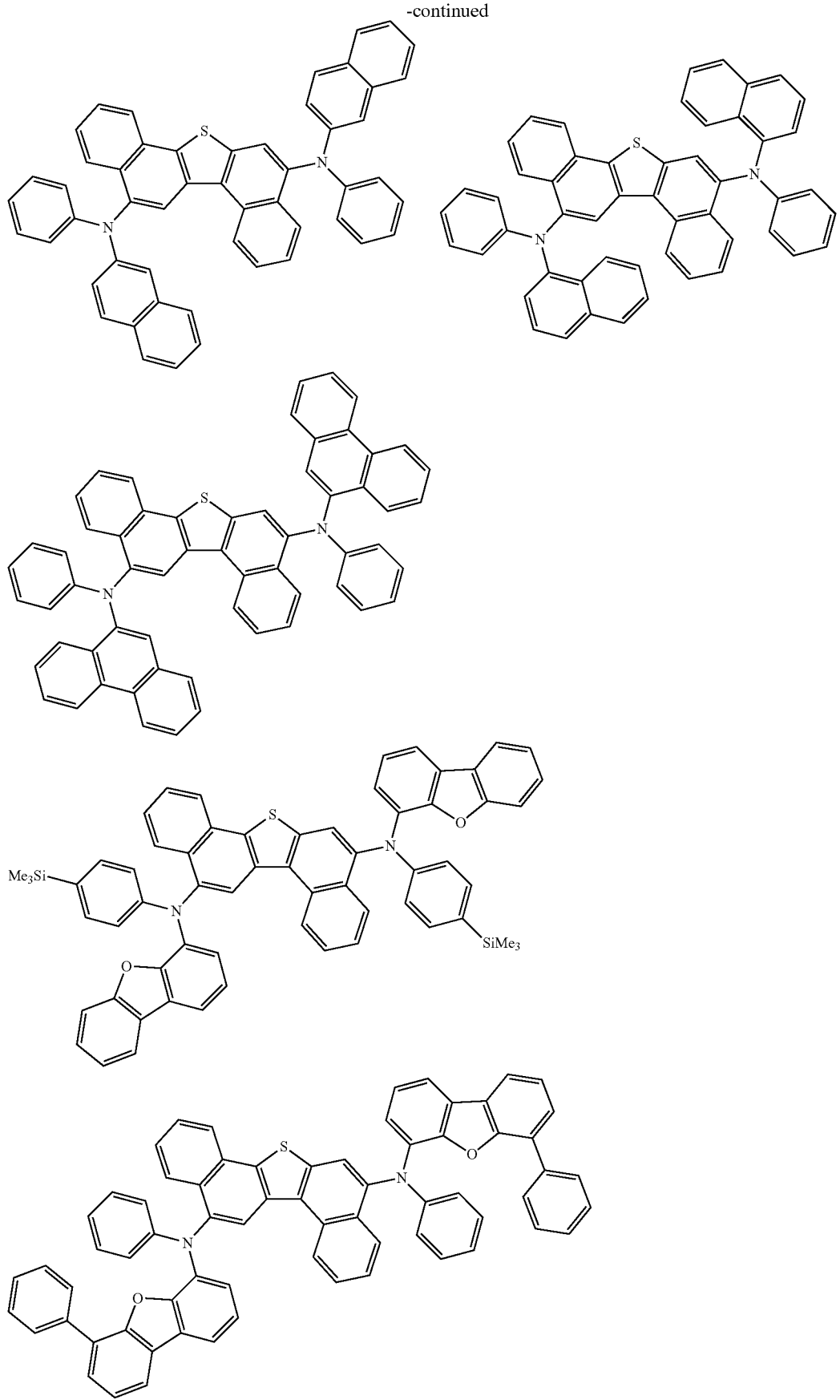

-continued
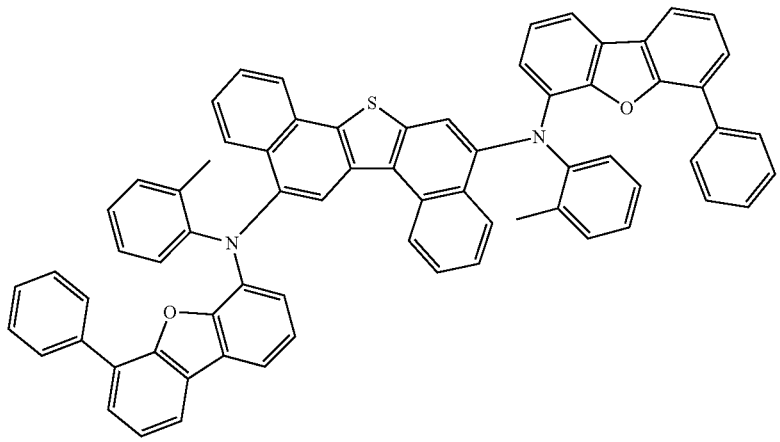
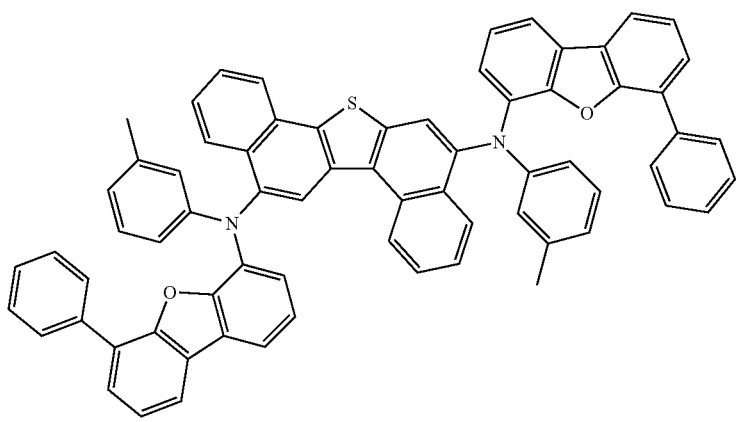
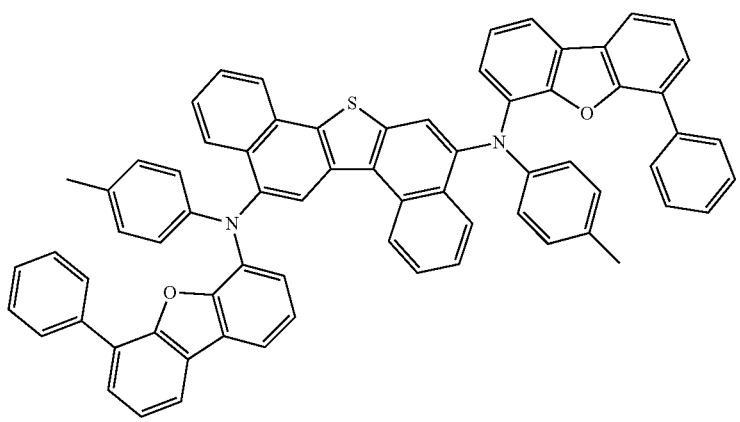

931 932
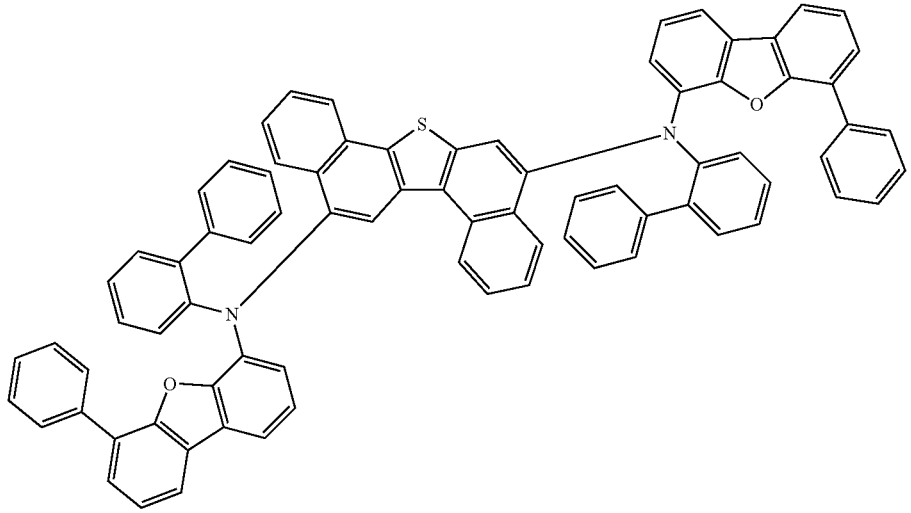
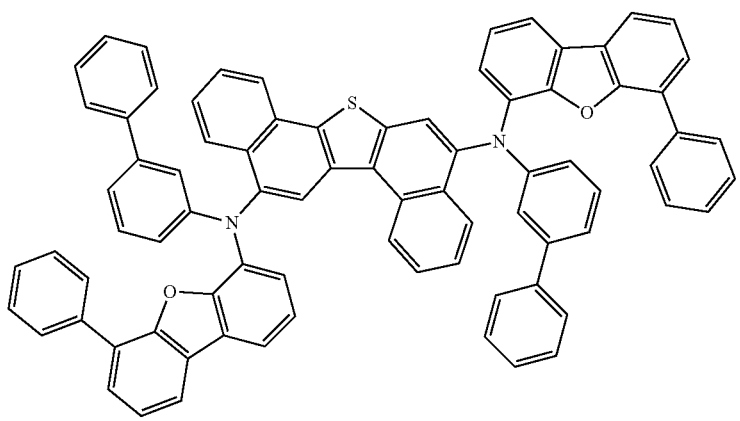
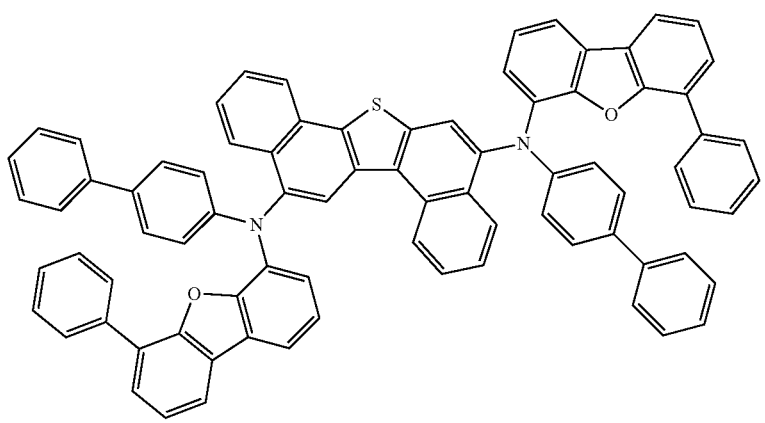

933
-continued
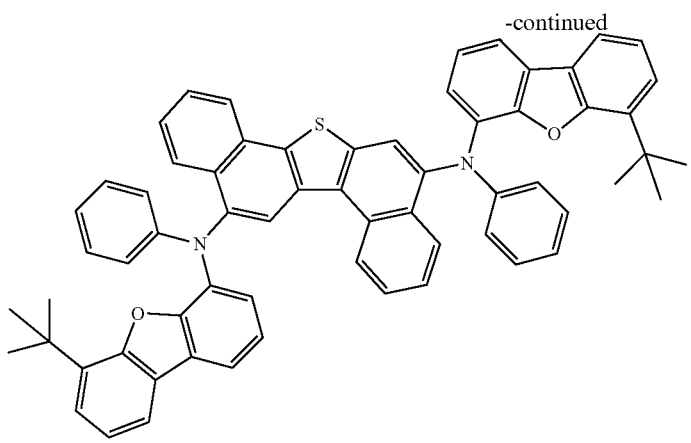
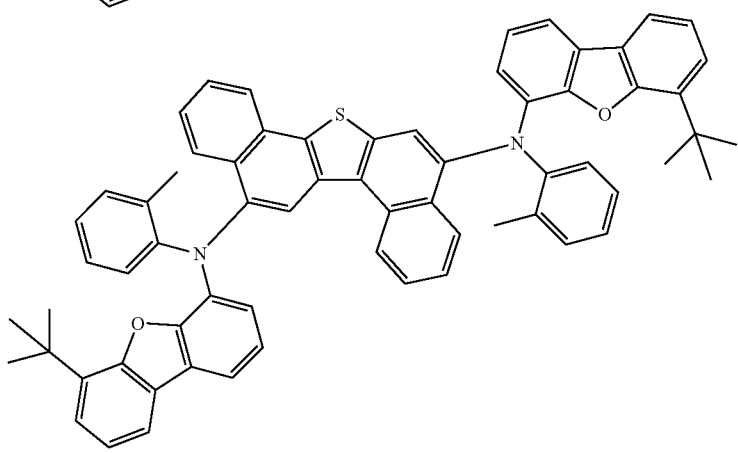
934
-continued
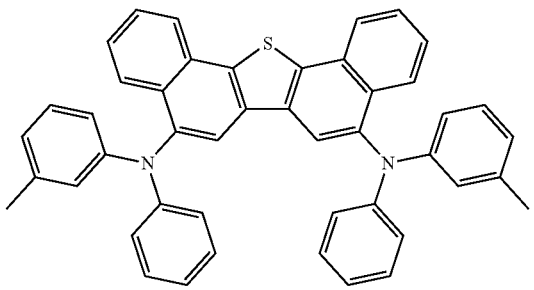
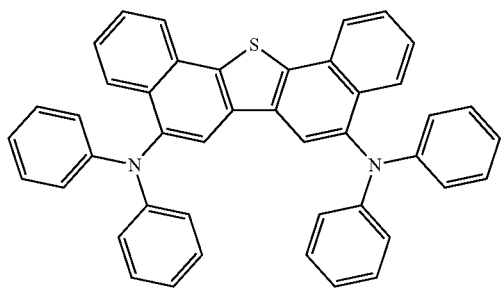
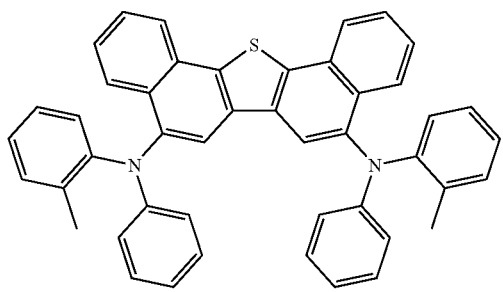
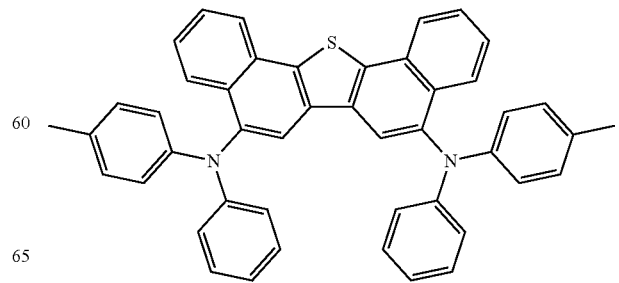

935
-continued
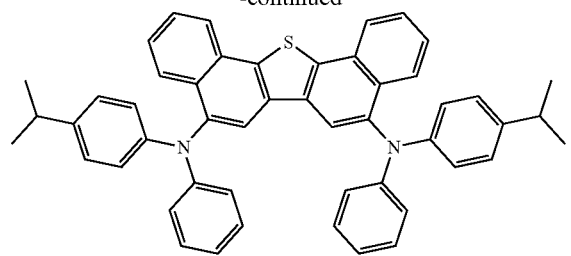
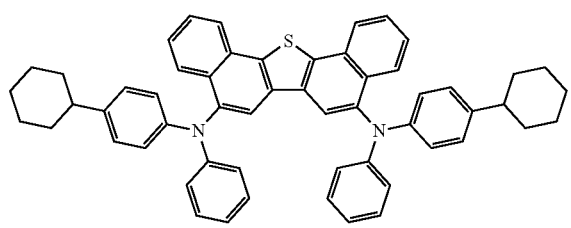
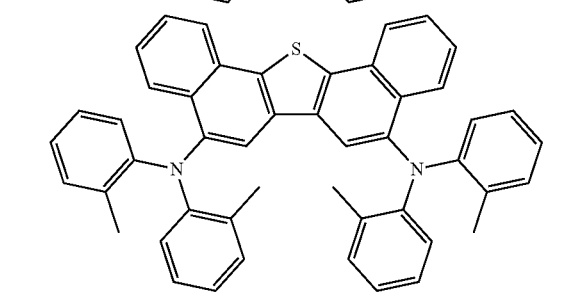
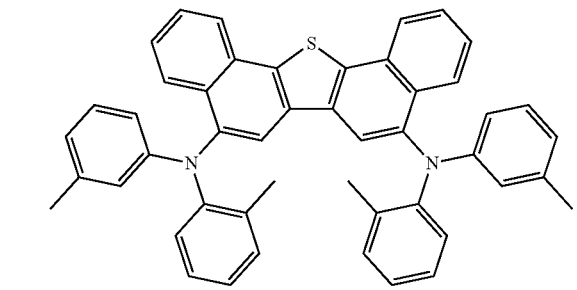
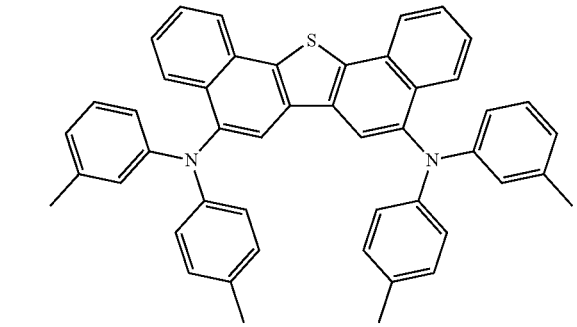
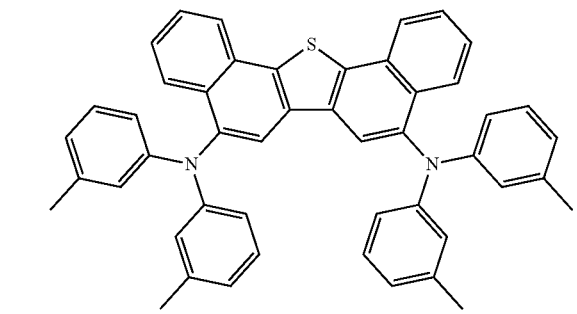
936
-continued
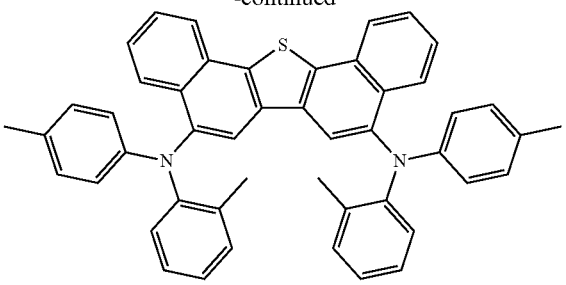
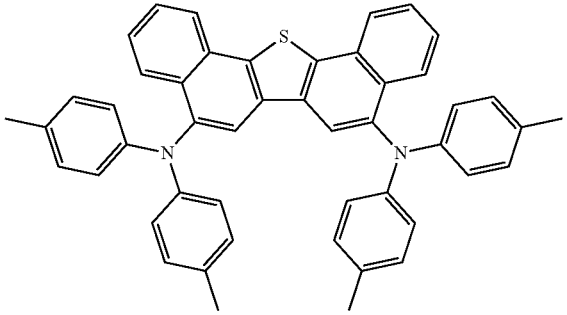
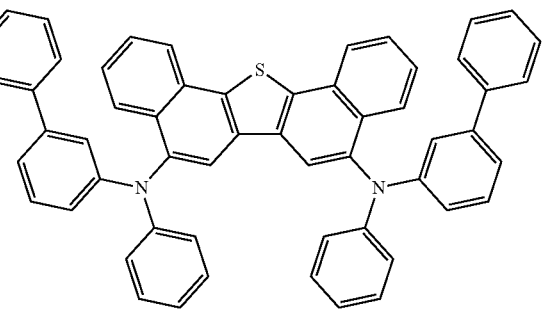
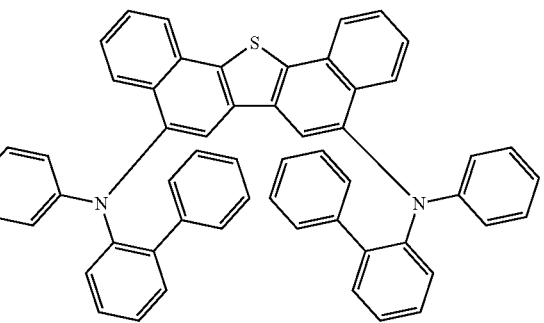
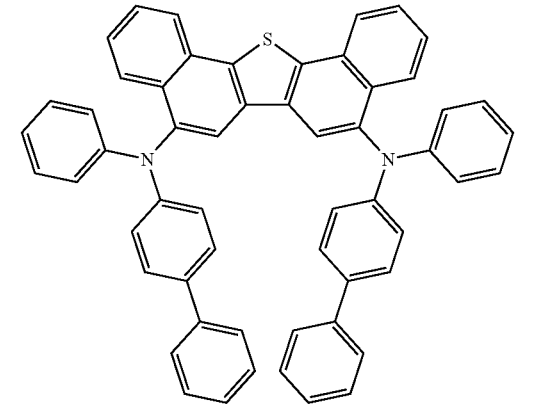

937
-continued
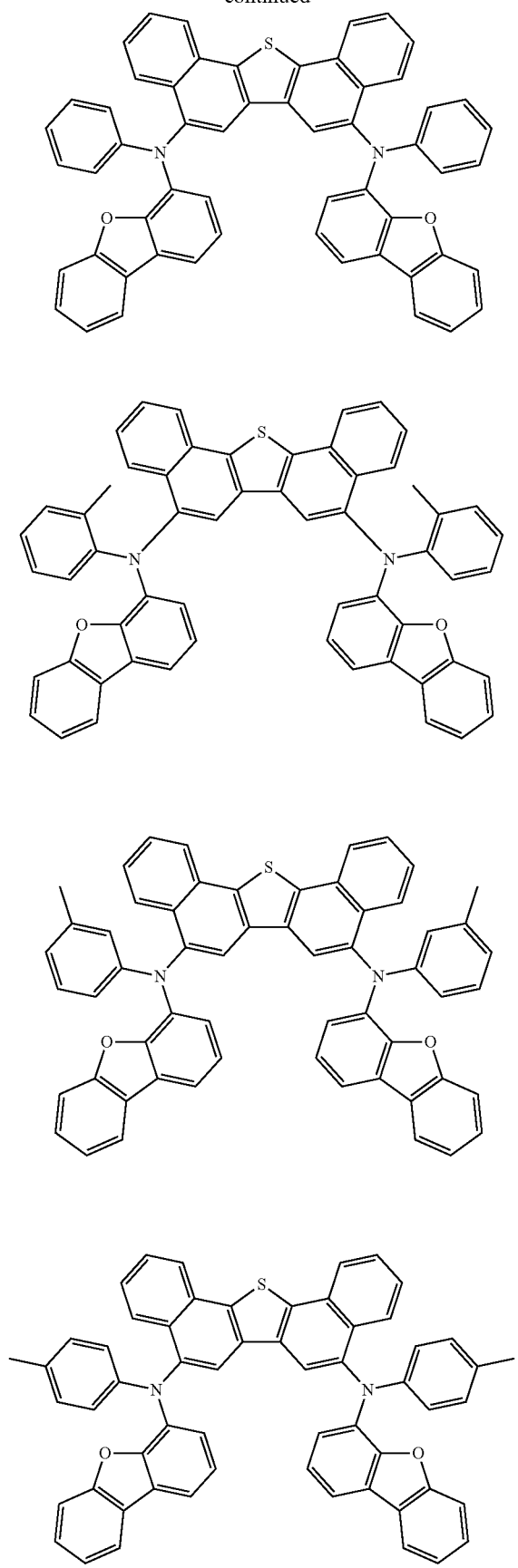
938
-continued
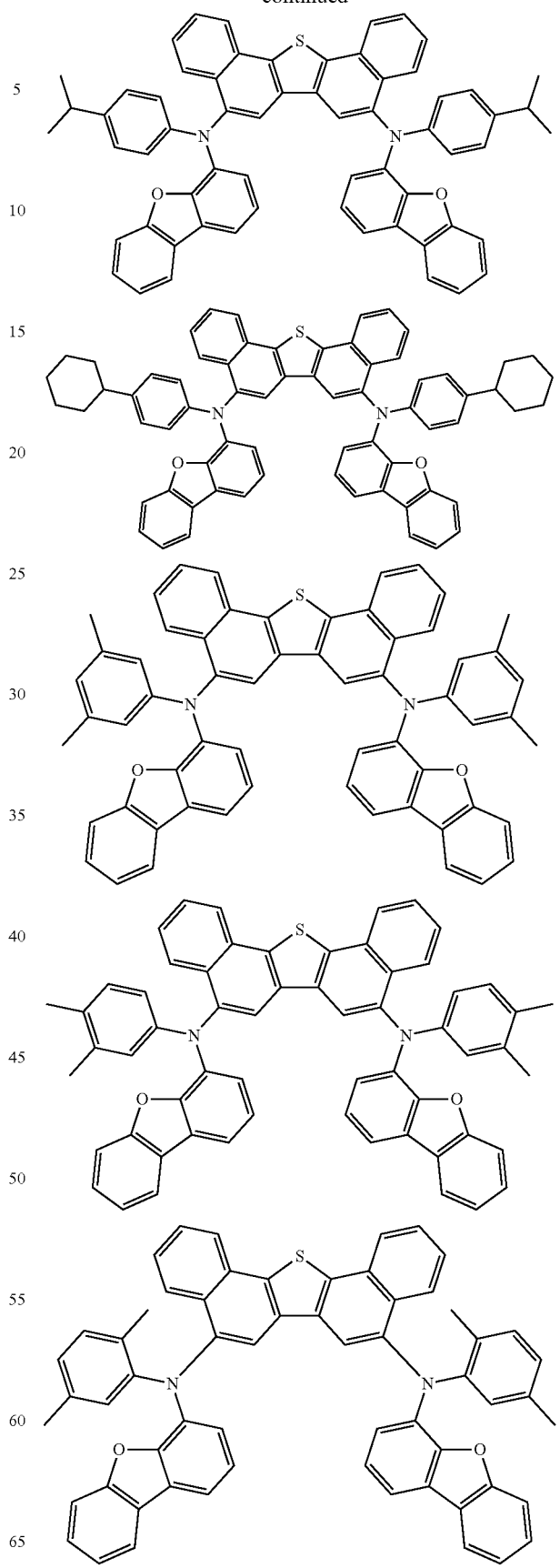

939
-continued
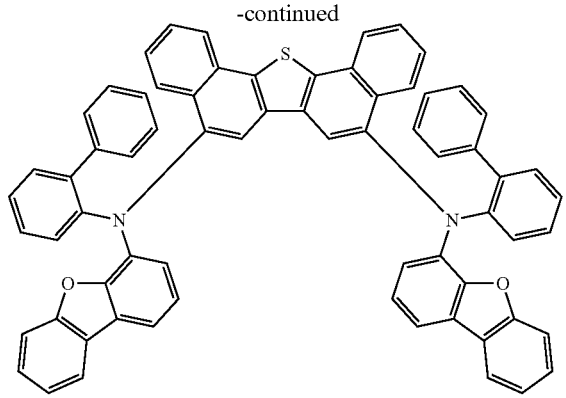
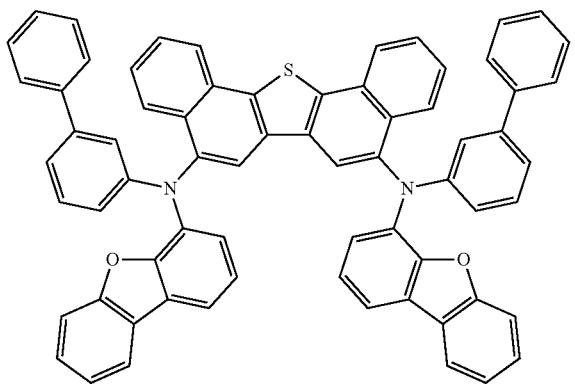
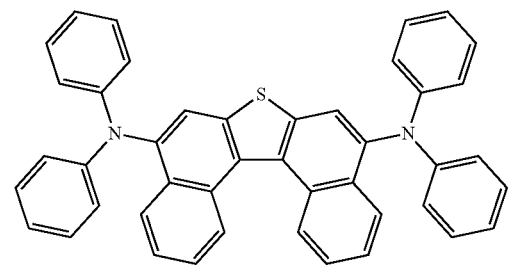
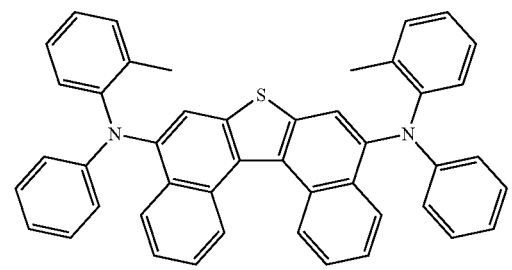
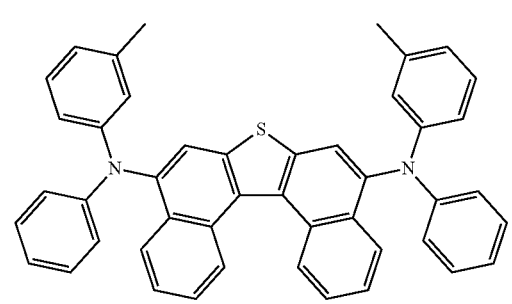
940
-continued
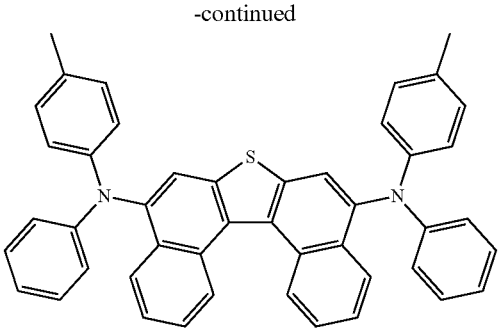
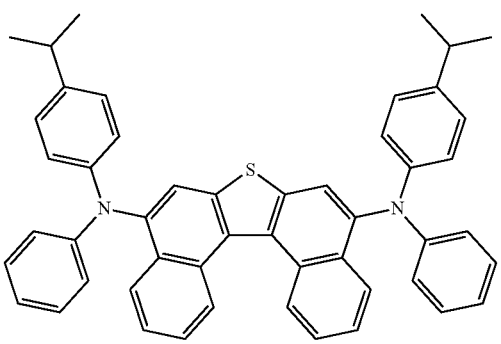
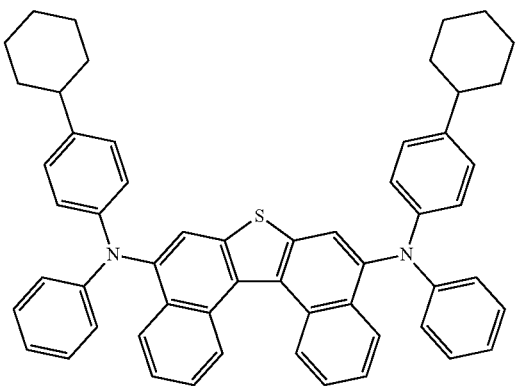
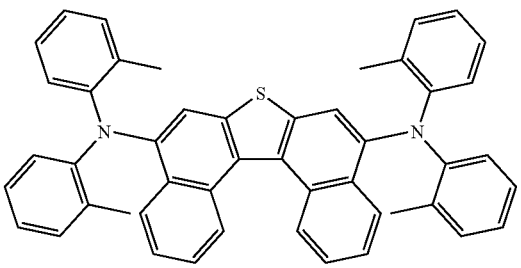
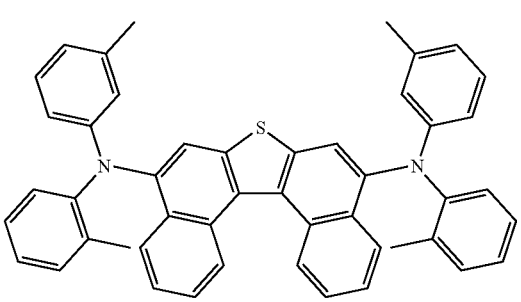

941
-continued
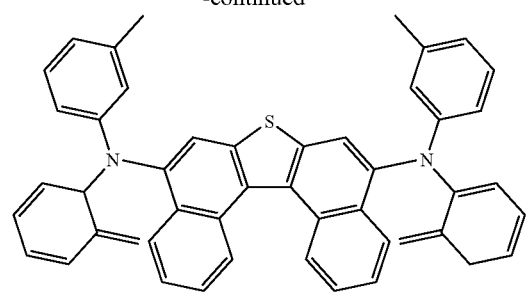
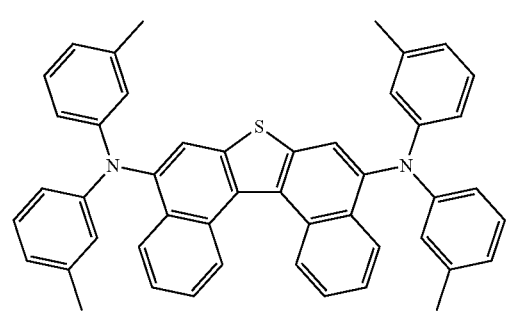
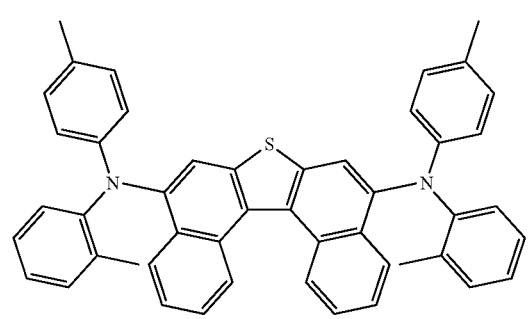
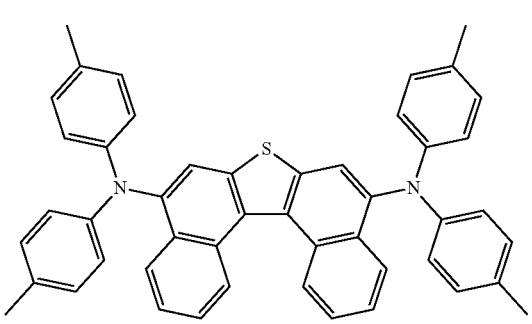
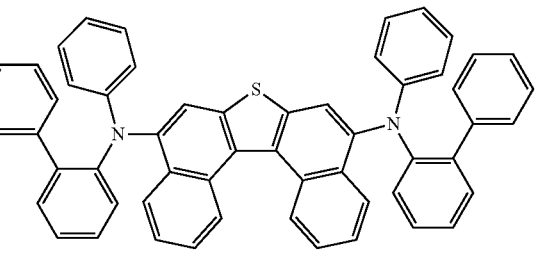
942
-continued
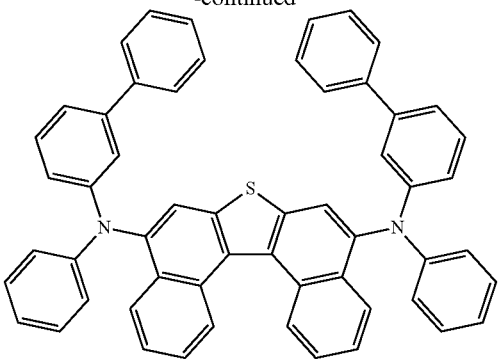
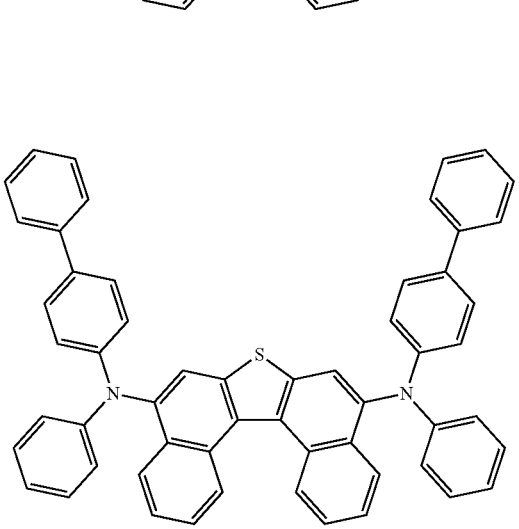
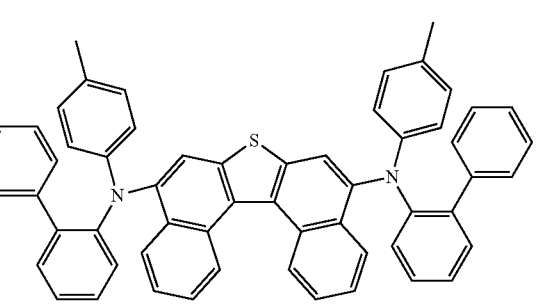
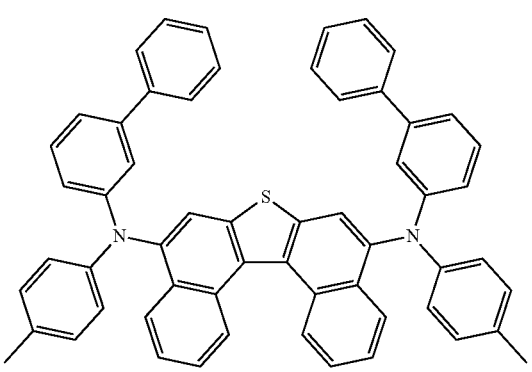

943
-continued
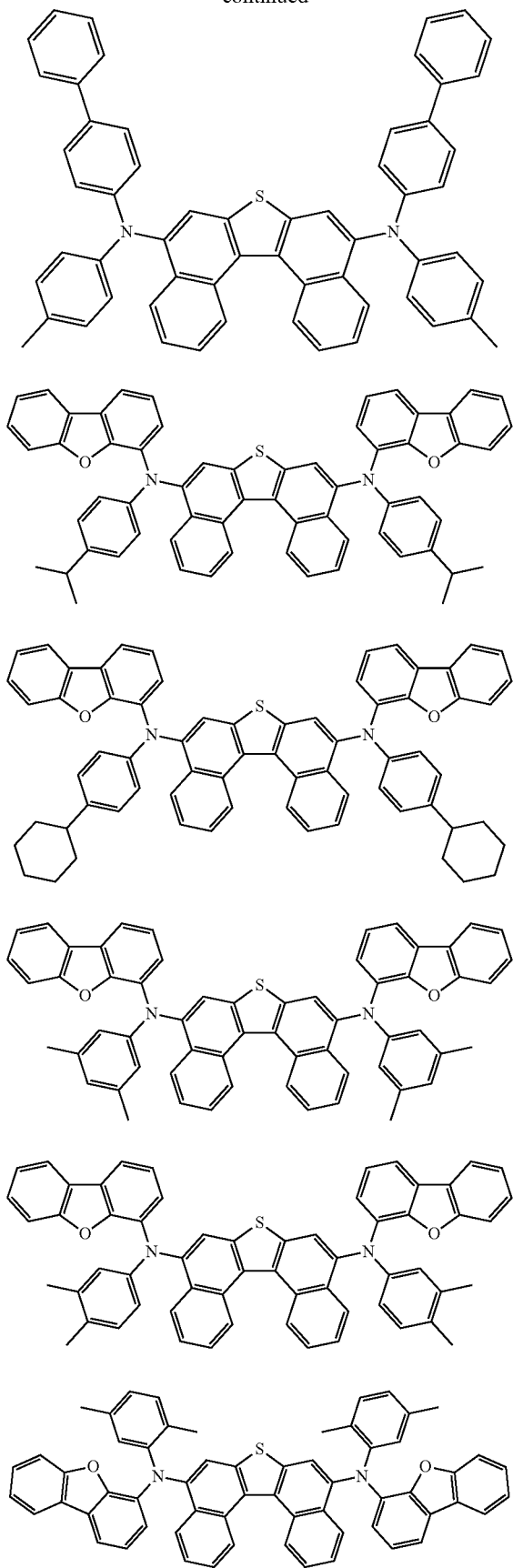
944
-continued
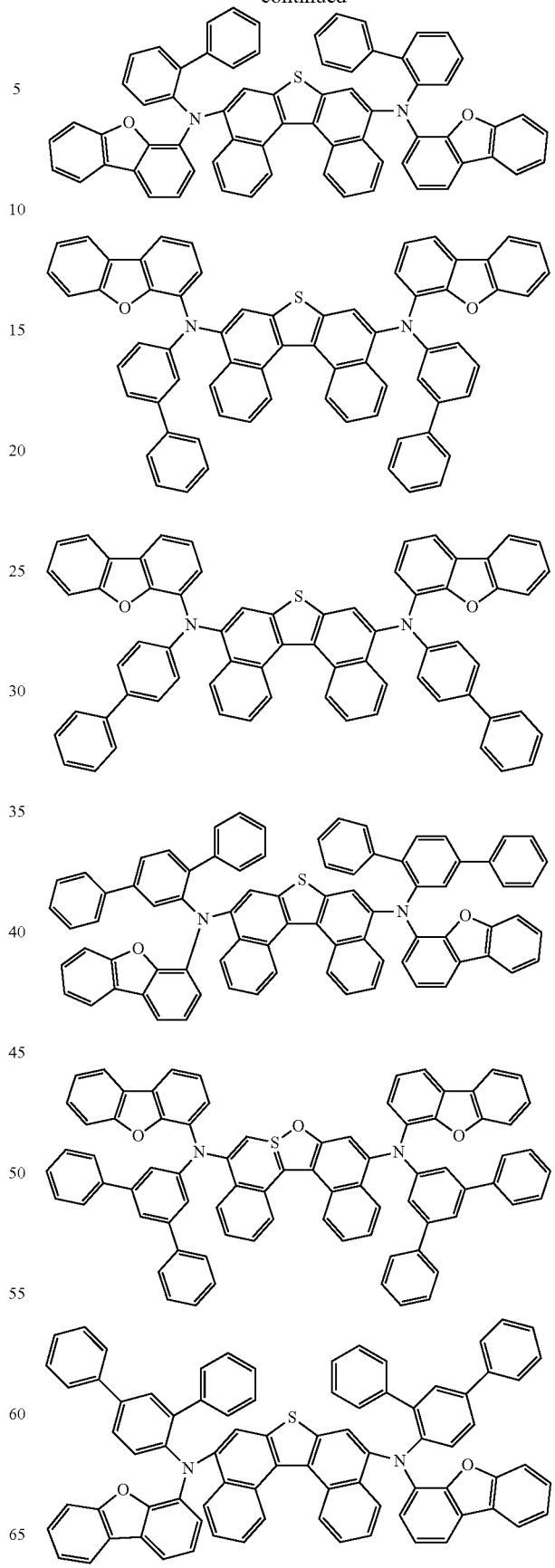

945
-continued
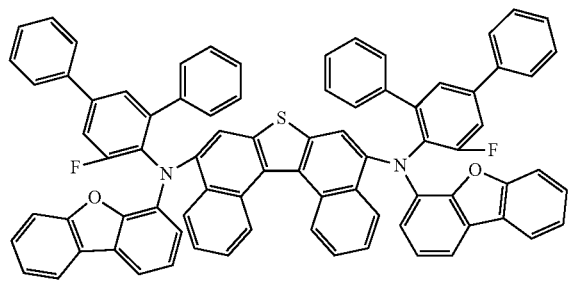
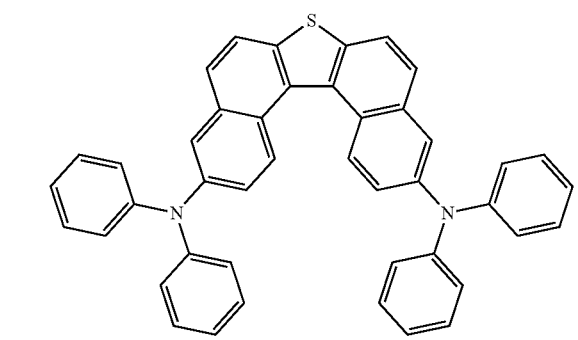
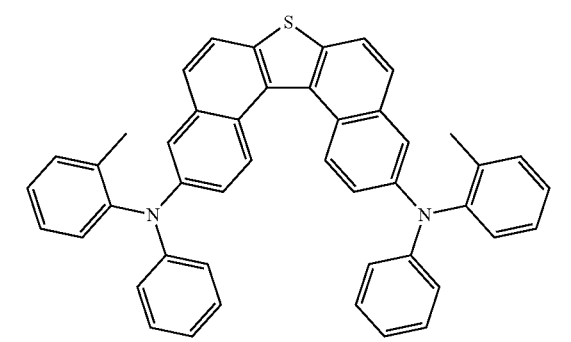
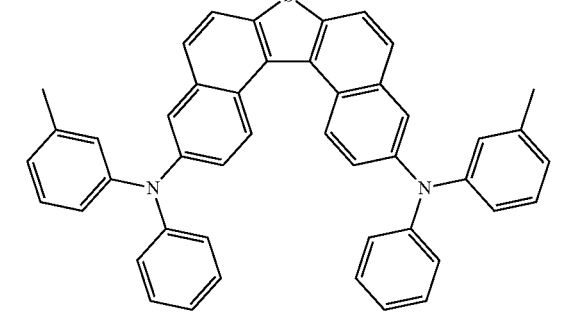
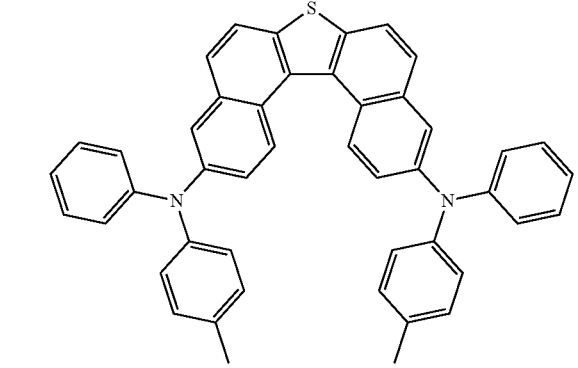
946
-continued
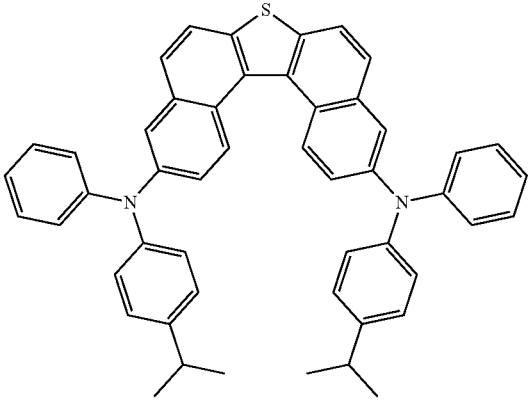
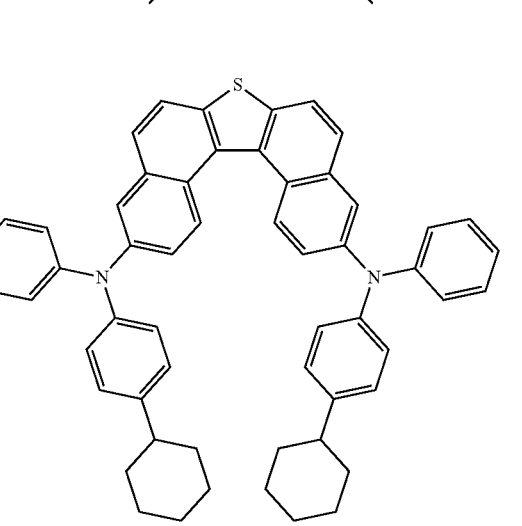
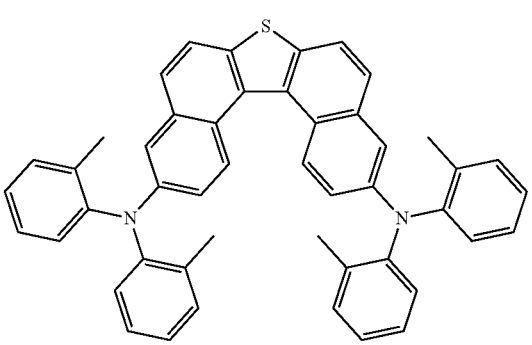
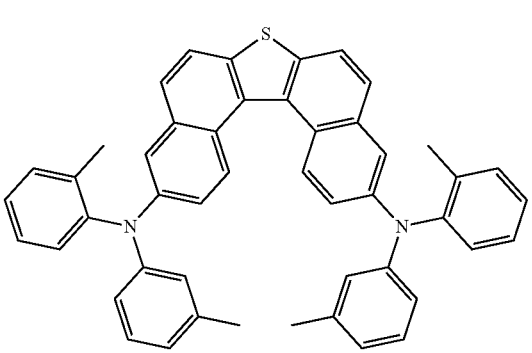

-continued

949
-continued
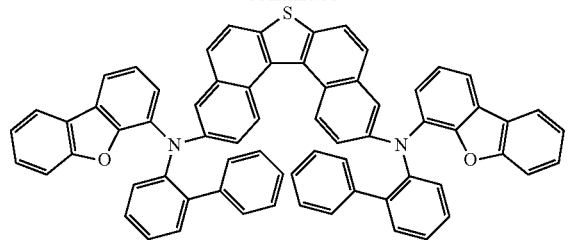
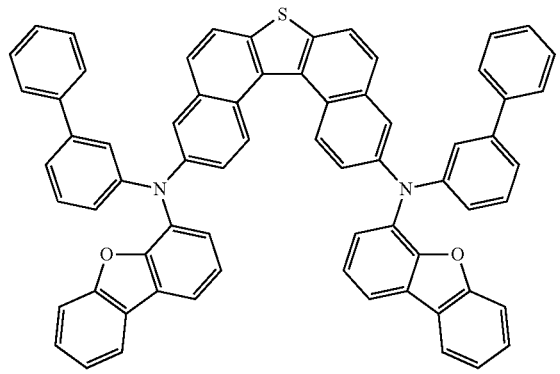
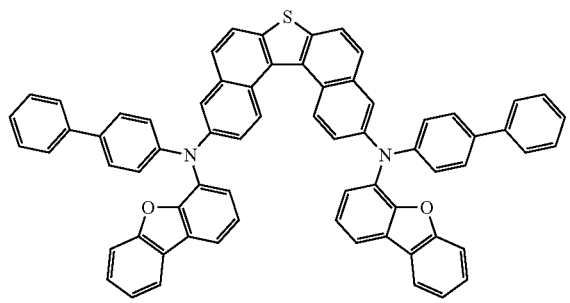
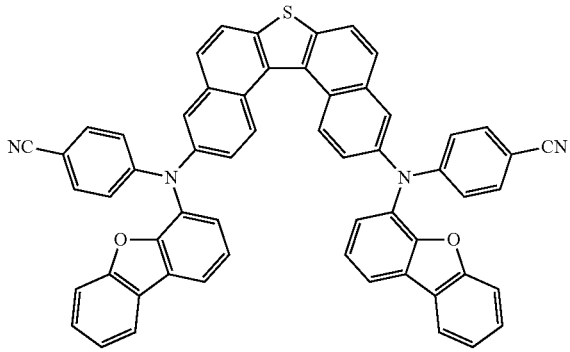
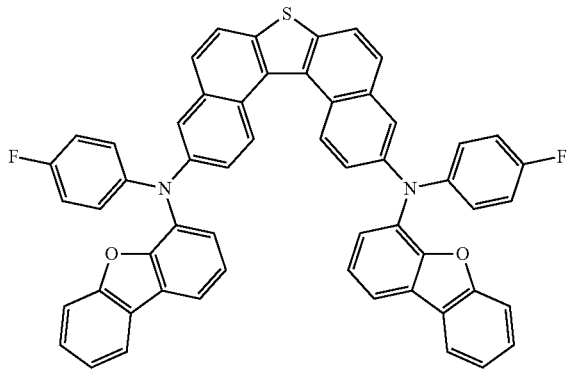
950
-continued
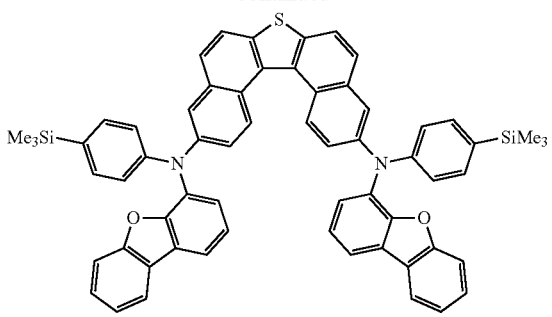
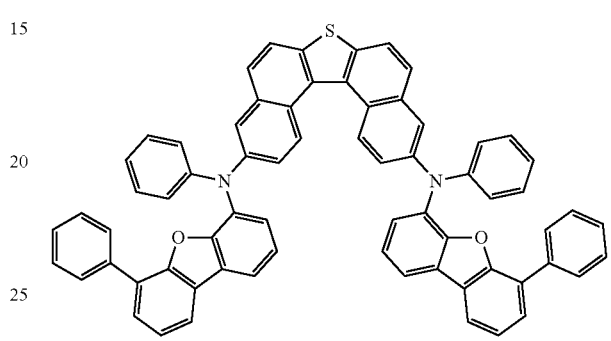
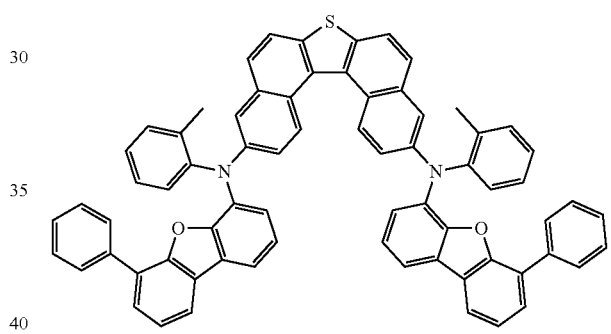
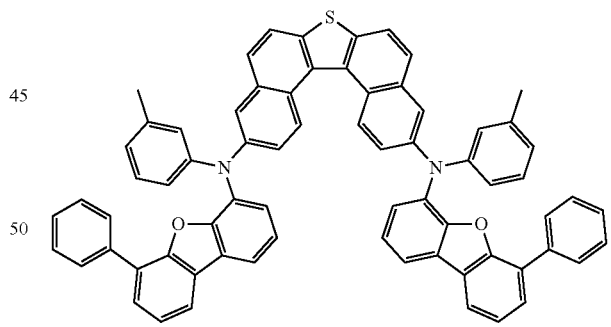
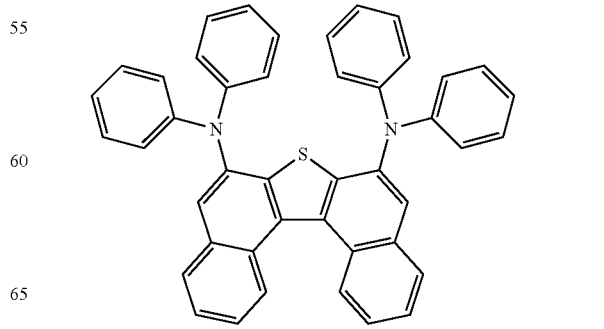

951
-continued
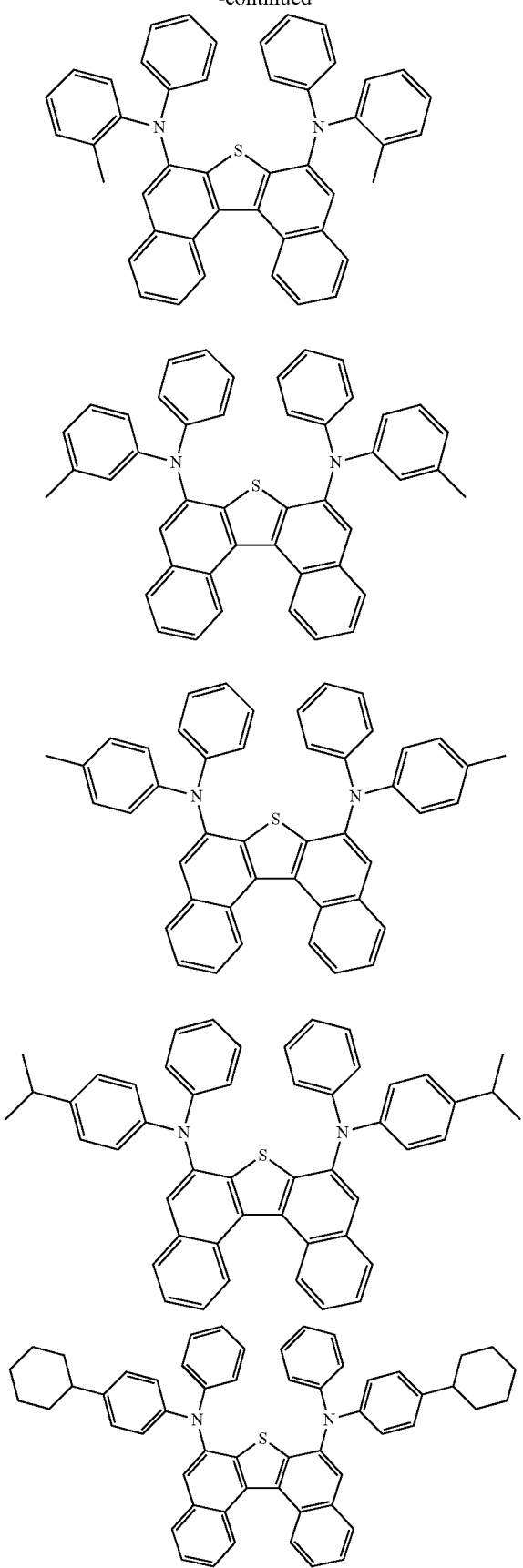
952
-continued
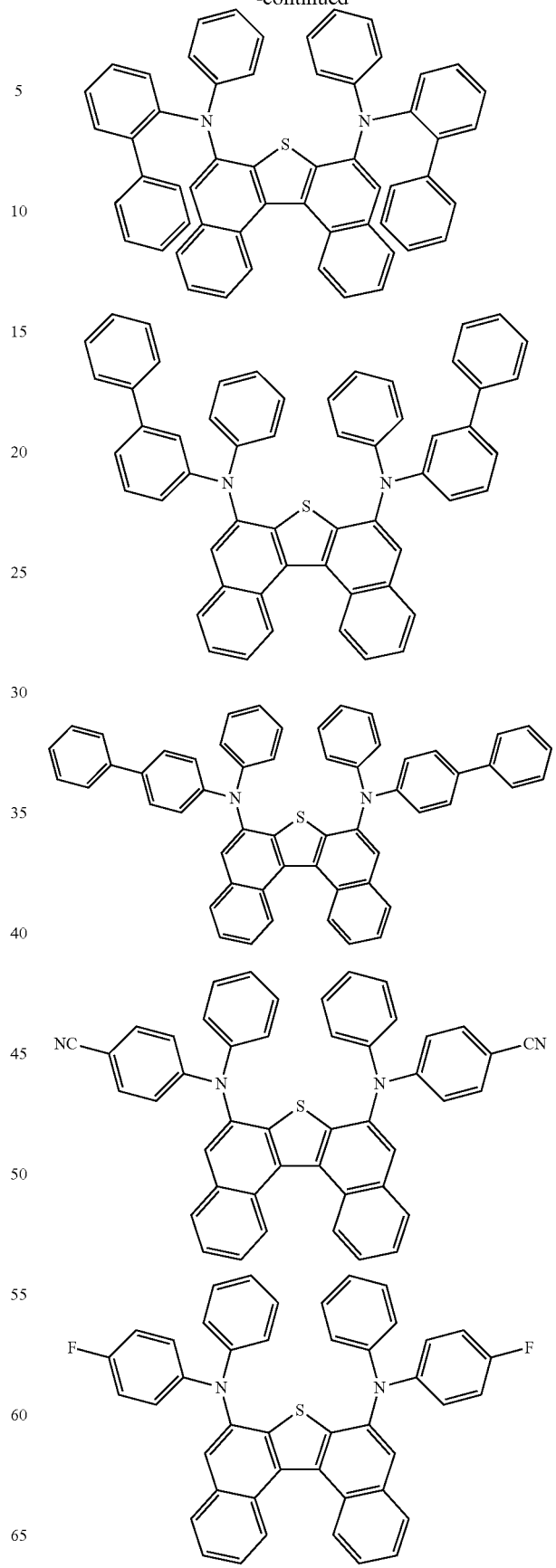

953
-continued
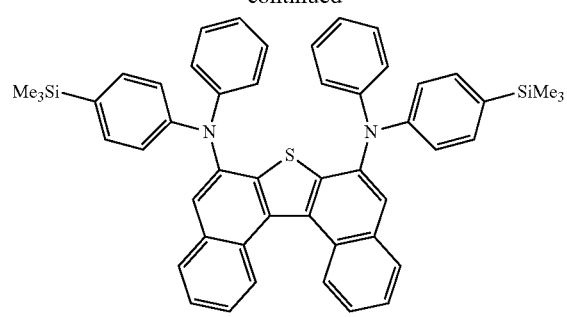
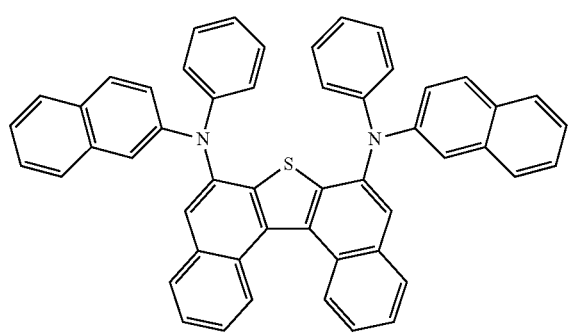
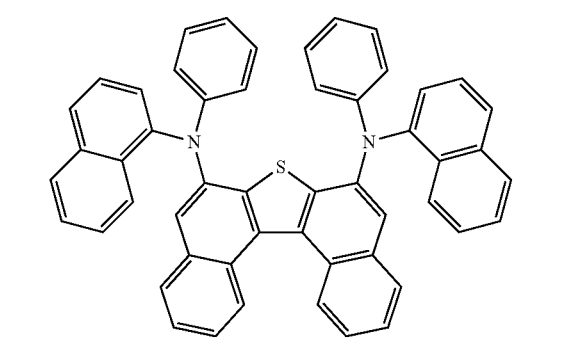
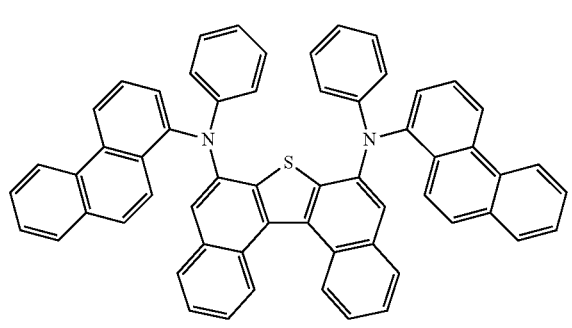
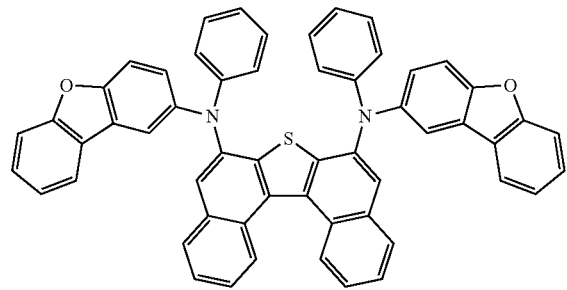
954
-continued
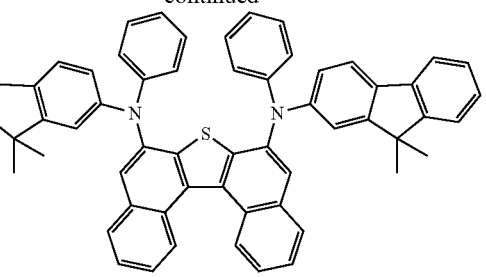
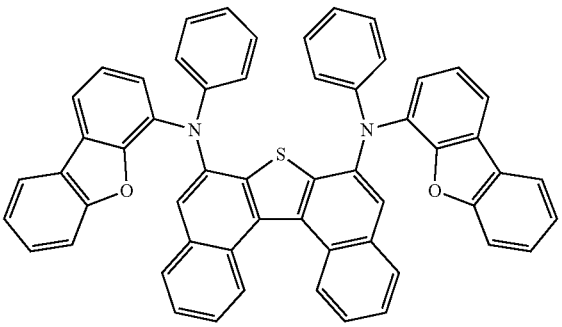
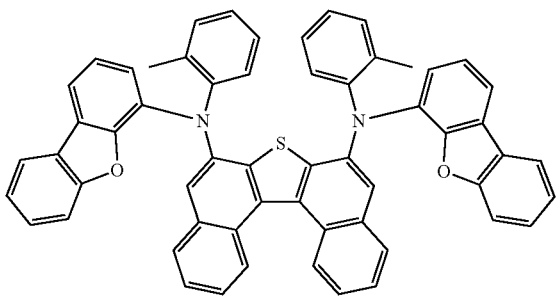
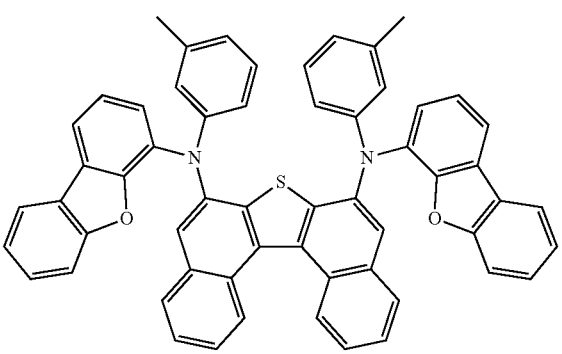
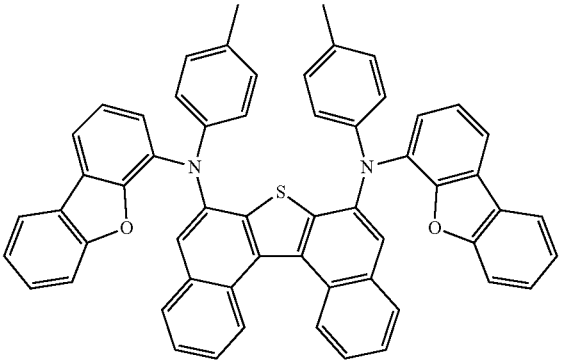

-continued

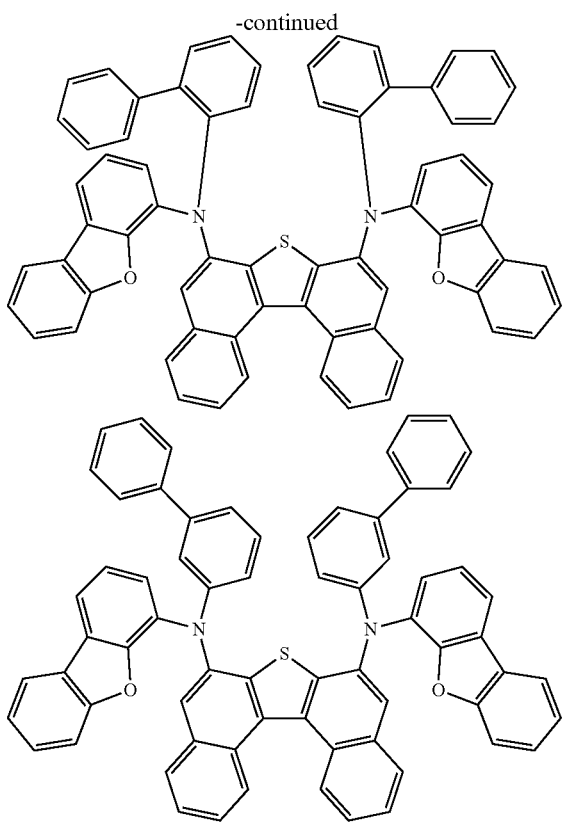

(Compound Represented by Formula (71))

The compound represented by the formula (71) is explained below.

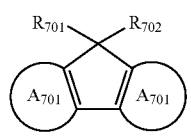

(71)

In the formula (71),
A701 ring and A7a2 ring are independently
a substituted or unsubstituted aromatic hydrocarbon ring including 6 to 50 ring carbon atoms, or
a substituted or unsubstituted heterocyclic ring including 5 to 50 ring atoms;

One or more rings selected from the group consisting of $A_{701}$ ring and $A_{702}$ ring are bonded to * of the structure represented by the following formula (72).

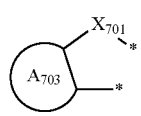

(72)

In the formula (72),
$A_{703}$ rings are independently
a substituted or unsubstituted aromatic hydrocarbon ring including 6 to 50 ring carbon atoms, or
a substituted or unsubstituted heterocyclic ring including 5 to 50 ring atoms;

$X_{701}$ is $NR_{703}$, $C(R_{704})(R_{705})$, $Si(R_{706})(R_{707})$, $Ge(R_{708})(R_{709})$, O, S or Se;

$R_{701}$ and $R_{702}$ are bonded with each other to form a substituted or unsubstituted, saturated or unsaturated ring or do not form a substituted or unsubstituted saturated or unsaturated ring;

$R_{701}$ and $R_{702}$ that do not form the substituted or unsubstituted, saturated or unsaturated ring, and $R_{703}$ to $R_{709}$ are independently a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—$Si(R_{901})(R_{902})(R_{903})$,
—O—$(R_{904})$,
—S—$(R_{905})$,
—$N(R_{906})(R_{907})$,
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are as defined in the formula (1).

One or more selected from the group consisting of $A_{701}$ ring and $A_{702}$ ring is bonded to * of the structure represented by the formula (72). That is, in one embodiment, the ring carbon atom of the aromatic hydrocarbon ring or the ring atom of the heterocyclic ring of $A_{701}$ ring is bonded to * in the structure represented by the formula (72). In one embodiment, the ring carbon atom of the aromatic hydrocarbon ring or the ring atom of the heterocyclic ring of $A_{702}$ ring is bonded to * in the structure represented by the formula (72).

In one embodiment, the group represented by the formula (73) is bonded to one or both of A70 ring and $A_{702}$ ring:

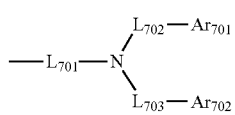

(73)

In the formula (73), $Ar_{701}$ and $Ar_{702}$ are independently
a substituted or unsubstituted aryl group including 6 to 50 ring carbon atoms, or
a substituted or unsubstituted monovalent heterocyclic group including 5 to 50 ring atoms; and
$L_{701}$ to $L_{703}$ are independently
a single bond,
a substituted or unsubstituted arylene group including 6 to 30 ring carbon atoms,
a substituted or unsubstituted divalent heterocyclic group including 5 to 30 ring atoms, or
a divalent linking group formed by bonding 2 to 4 above mentioned groups.

In one embodiment, in addition to A701 ring, the ring carbon atom of the aromatic hydrocarbon ring or the ring atom of the heterocyclic ring of $A_{702}$ ring is bonded to * in the structure represented by the formula (72). In this case, the structures represented by formula (72) may be the same or different.

In one embodiment, $R_{701}$ and $R_{702}$ are independently a substituted or unsubstituted aryl group including 6 to 50 ring carbon atoms.

In one embodiment, $R_{701}$ and $R_{702}$ are bonded with each other to form a fluorene structure.

In one embodiment, A70 ring and $A_{702}$ ring are substituted or unsubstituted aromatic hydrocarbon rings including 6 to 50 ring carbon atoms, and they are substituted or unsubstituted benzene rings, for example.

In one embodiment, $A_{703}$ ring is a substituted or unsubstituted aromatic hydrocarbon ring including 6 to 50 ring carbon atoms, and it is a substituted or unsubstituted benzene ring, for example.

In one embodiment, $X_{701}$ is O or S.

As specific example of the compound represented by the formula (71), the following compounds can be given, for example. In the following example compounds, Me represents methyl group.

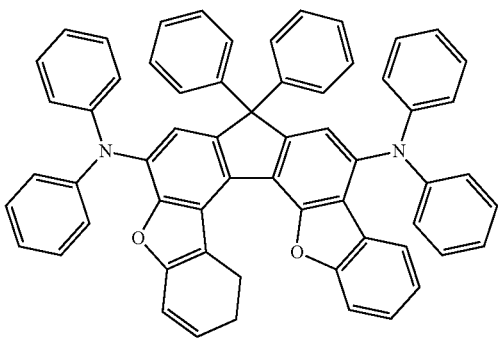

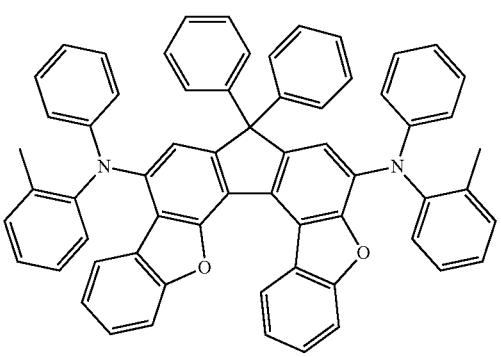

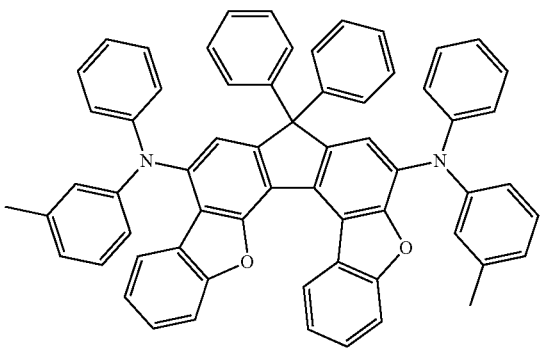

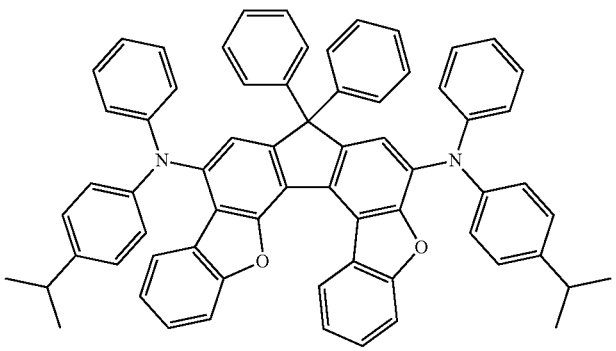

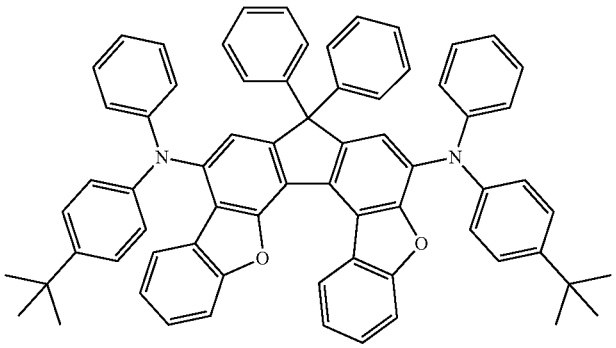

-continued
| 959 | 960 |
|---|---|
| 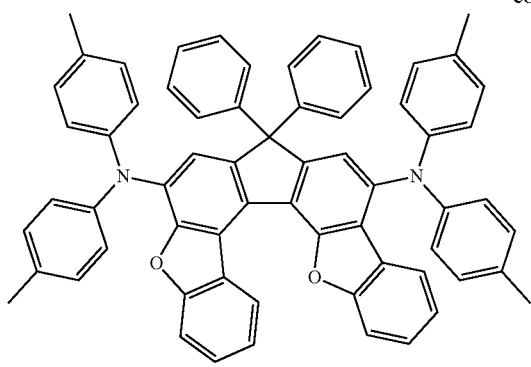 | 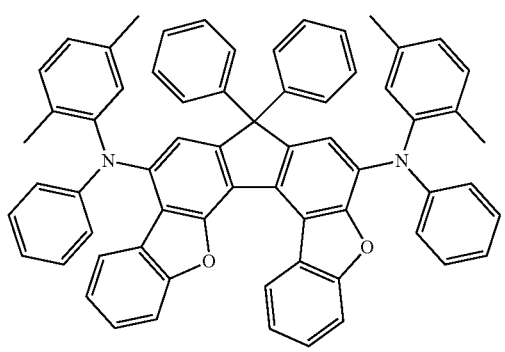 |
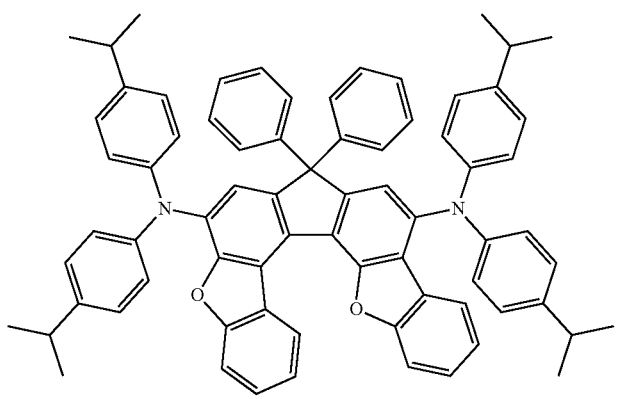
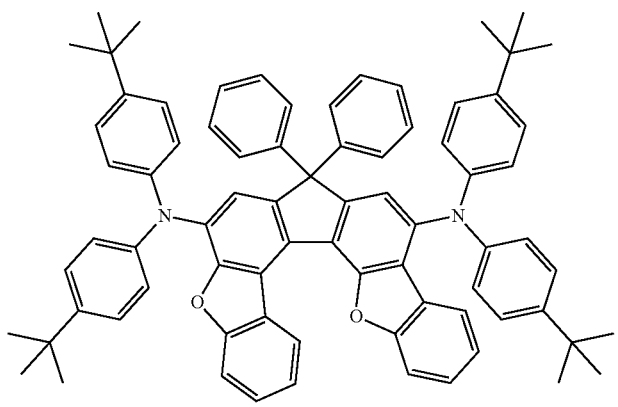
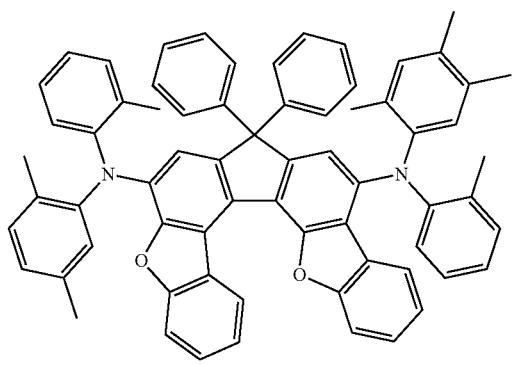
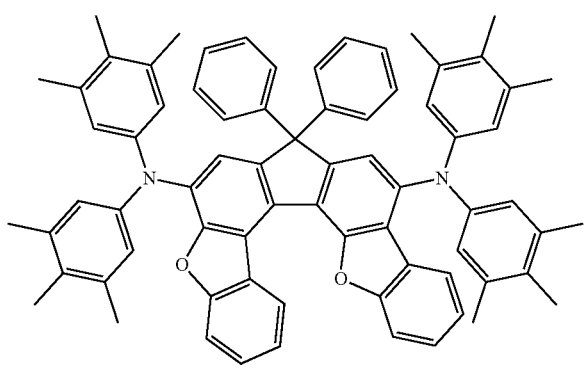

-continued
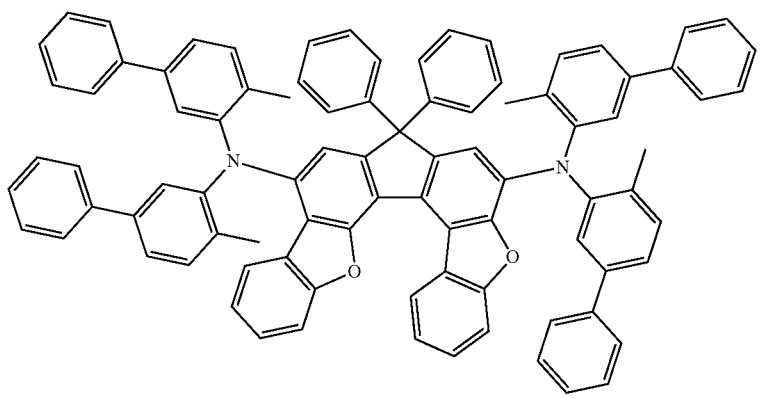
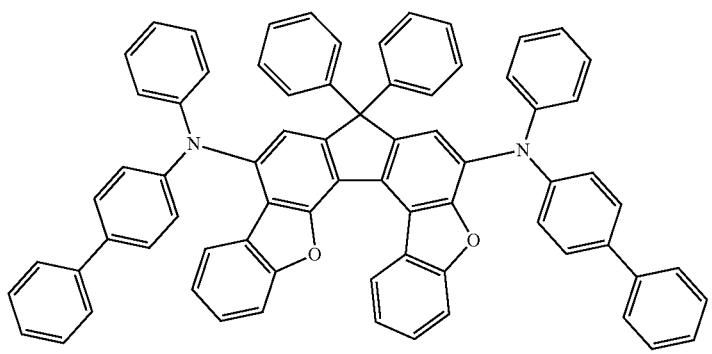
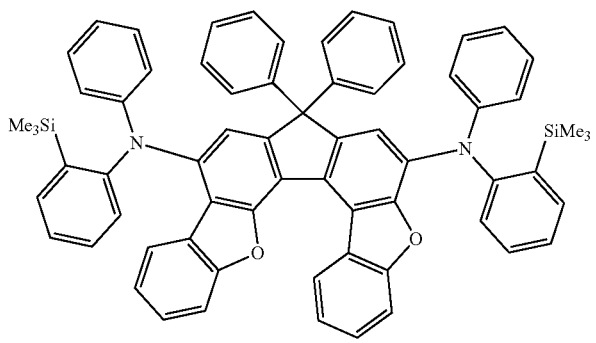
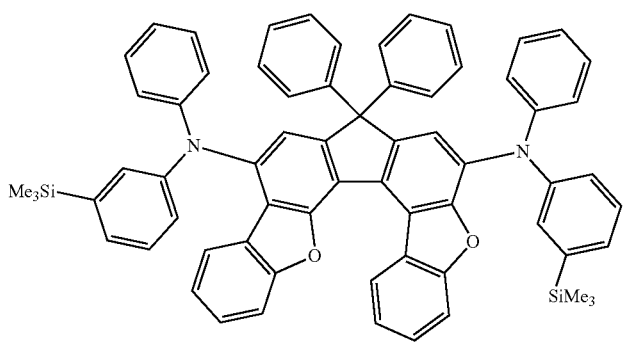

963
964
-continued
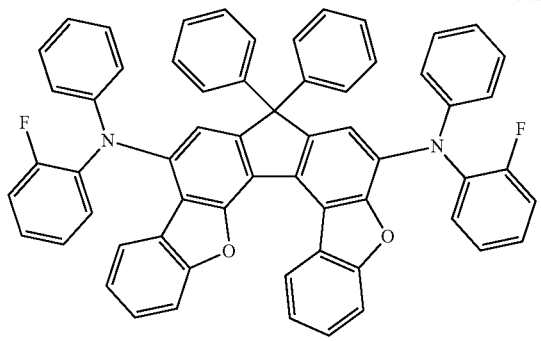
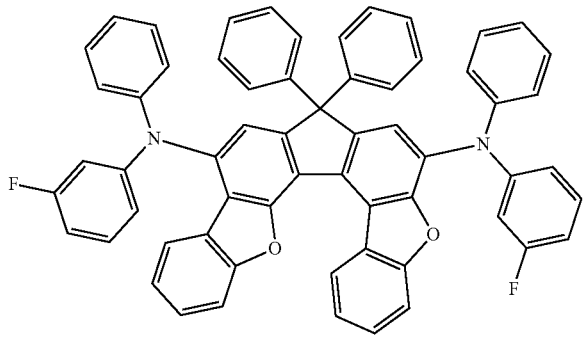
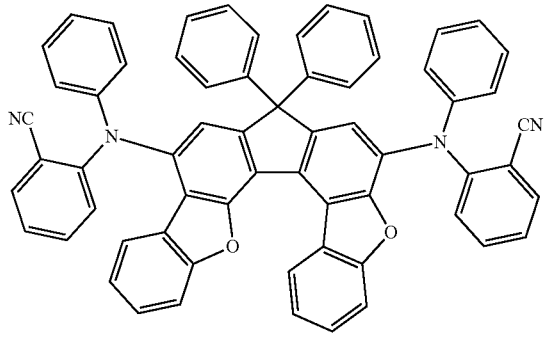
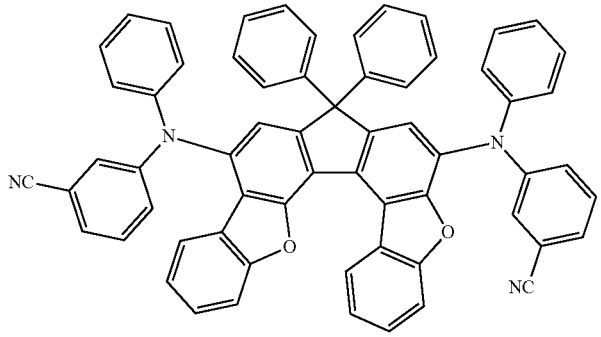
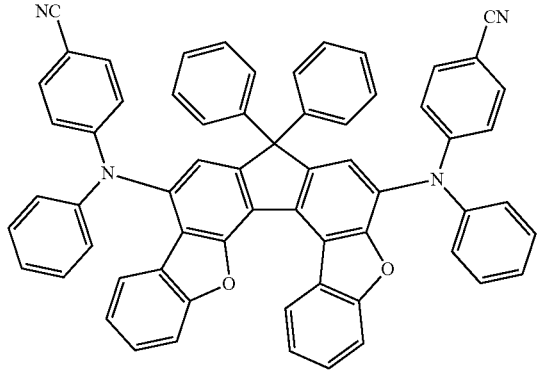

-continued
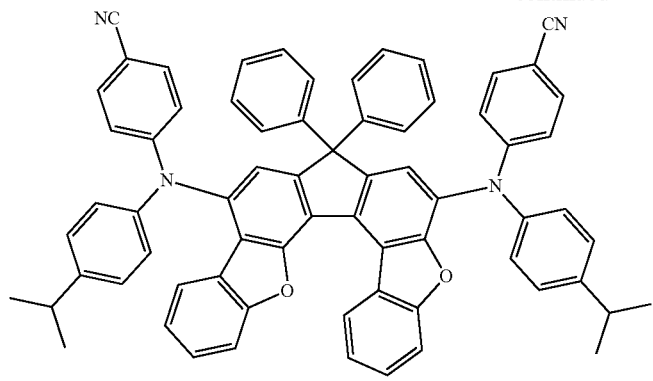
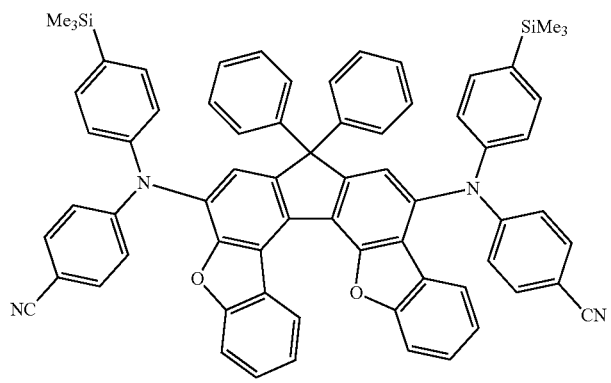
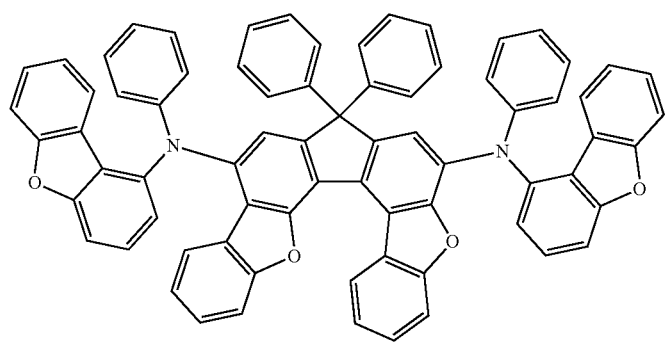
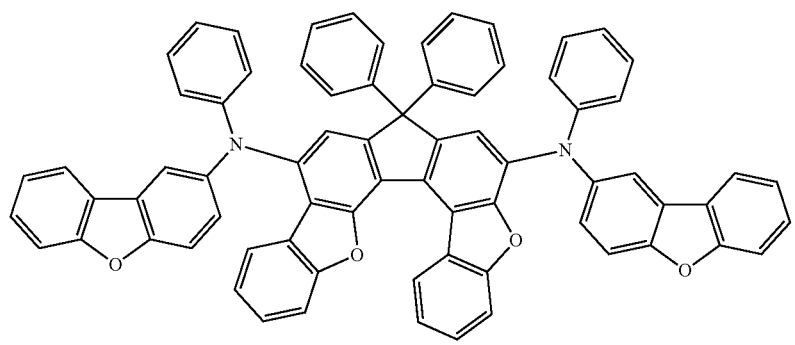

-continued
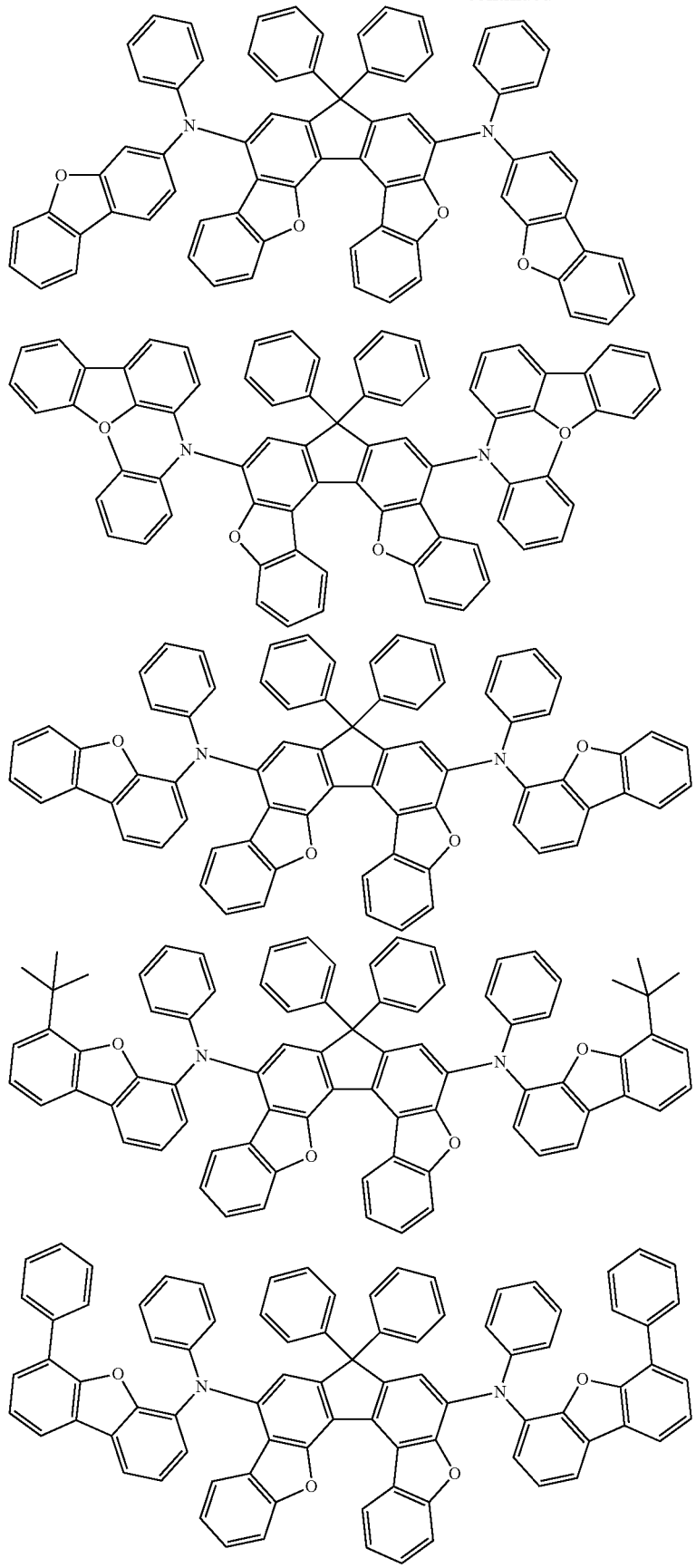

-continued
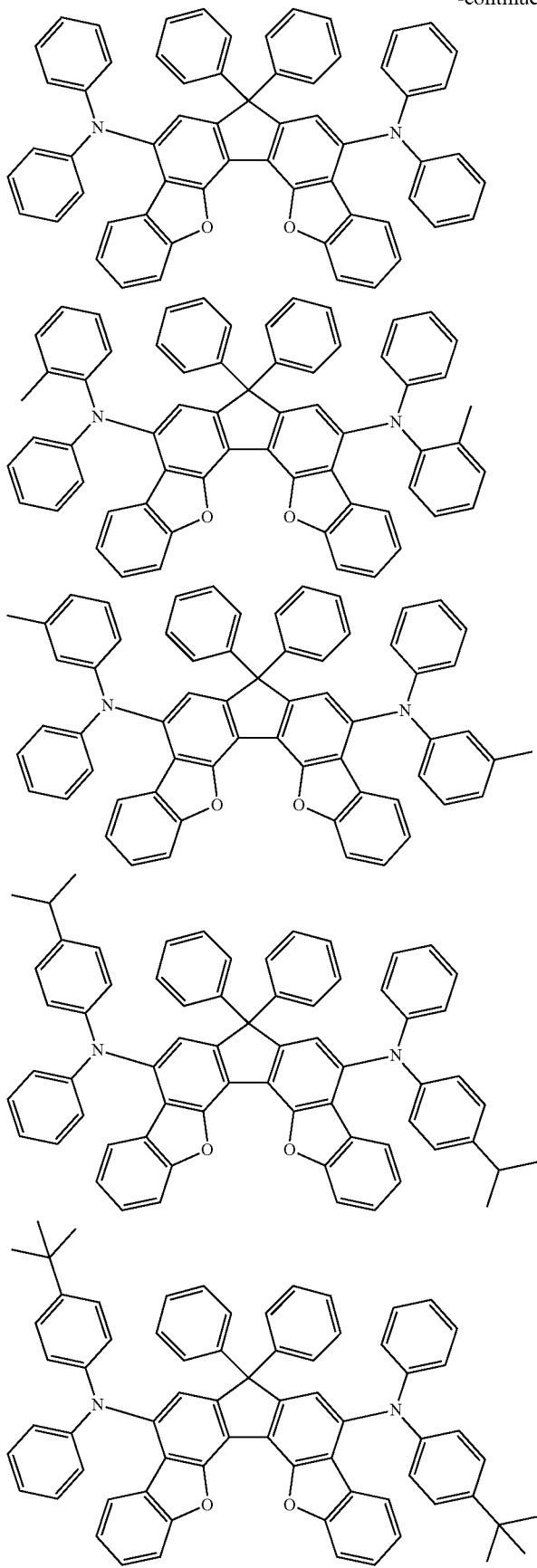

971 972
-continued
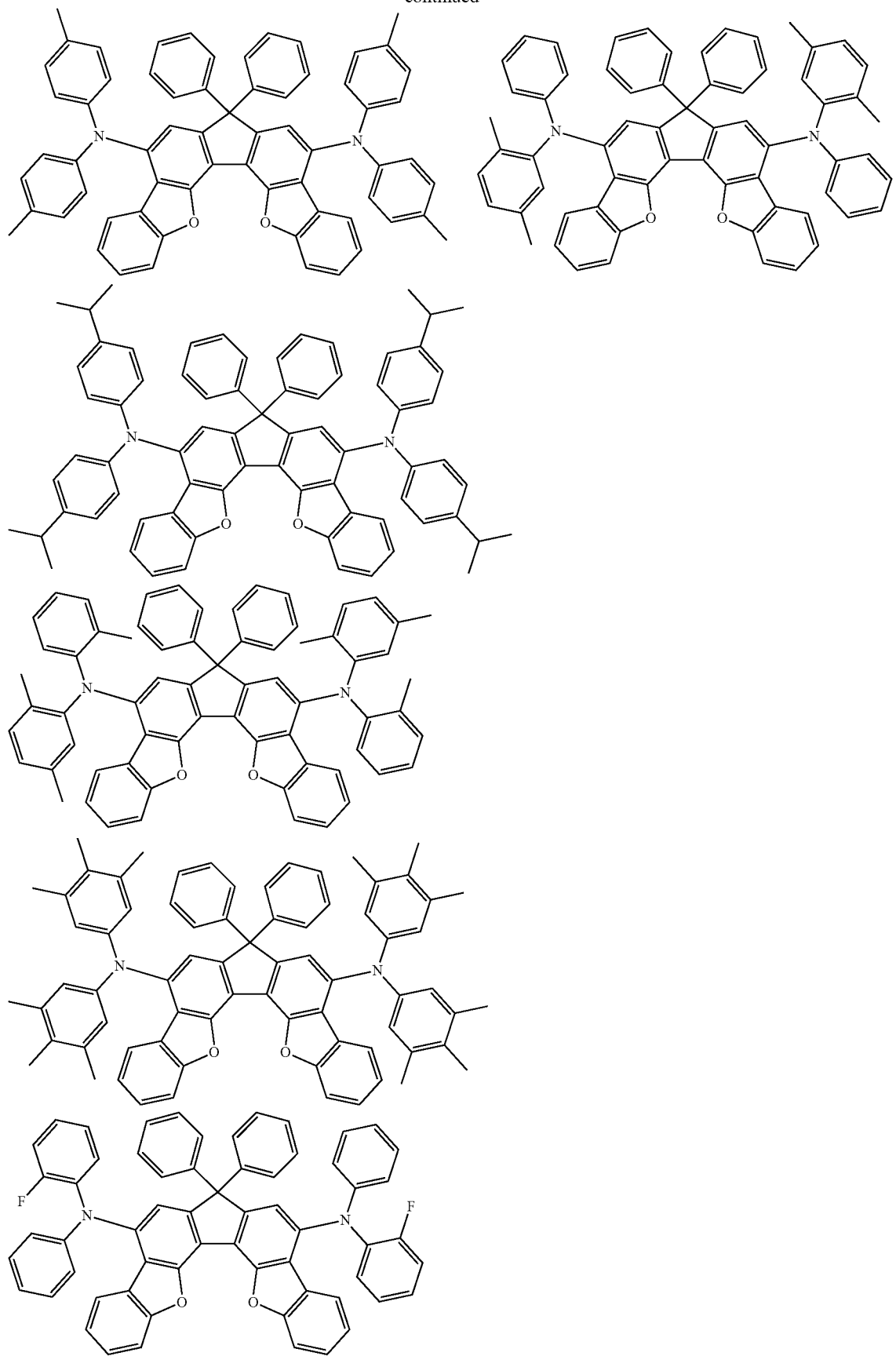

-continued
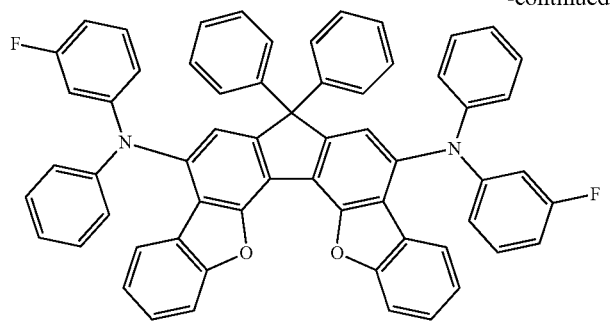
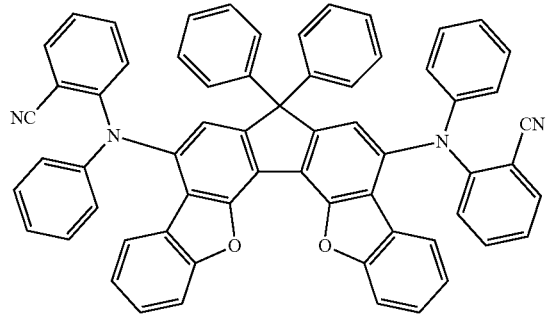
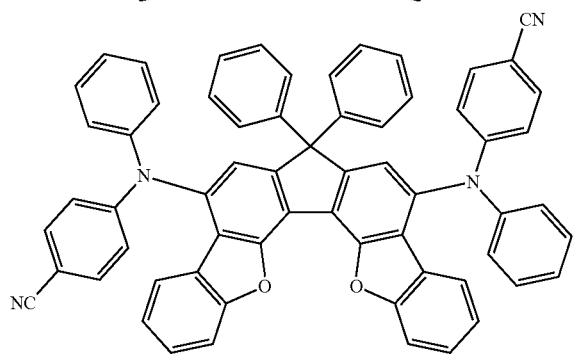
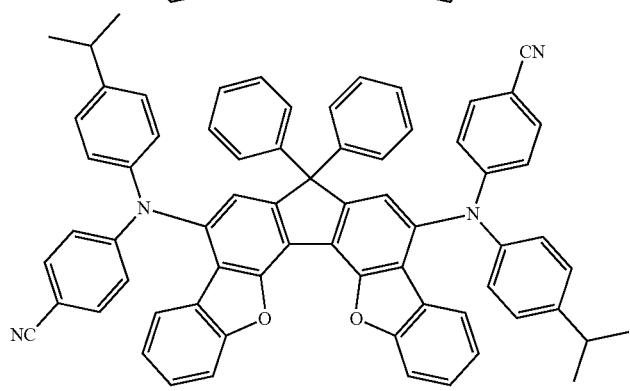
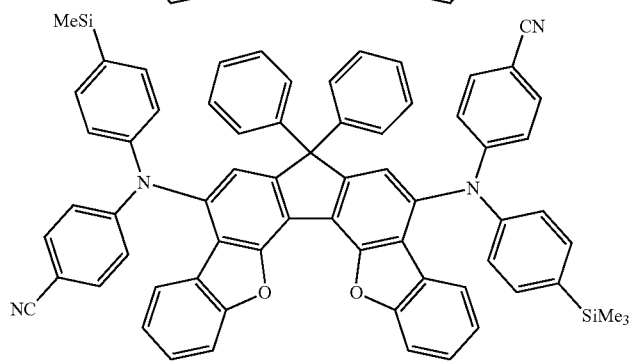

-continued
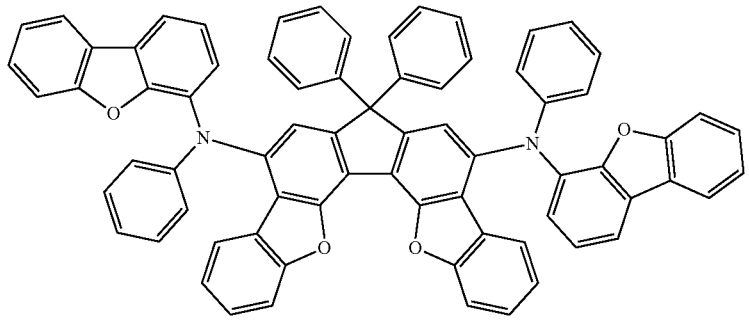
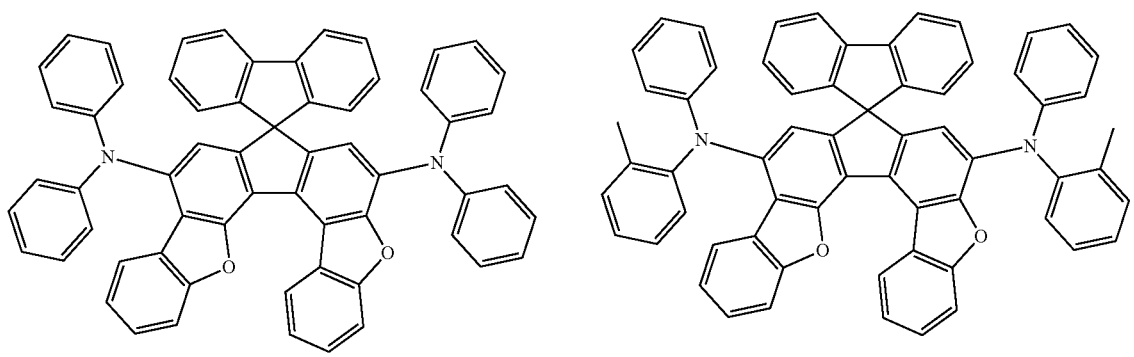
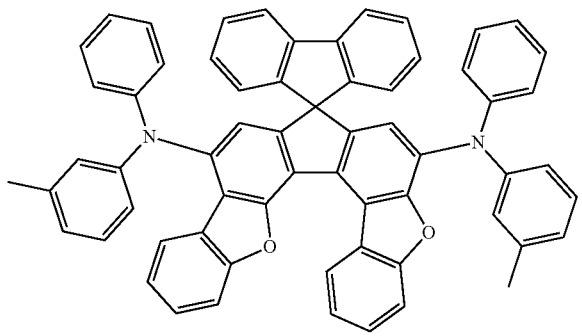
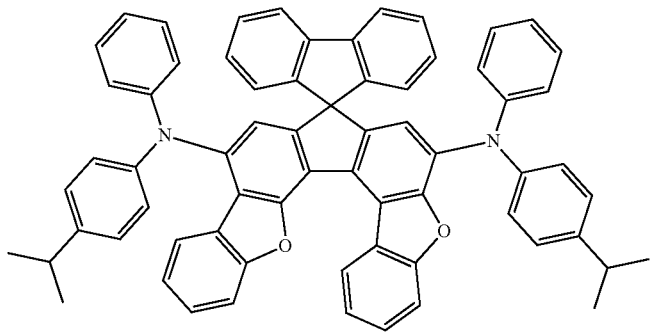
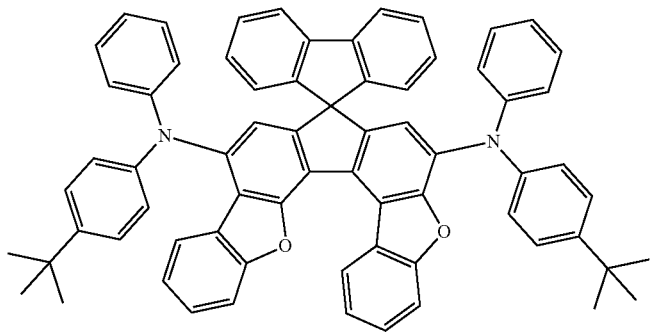

-continued
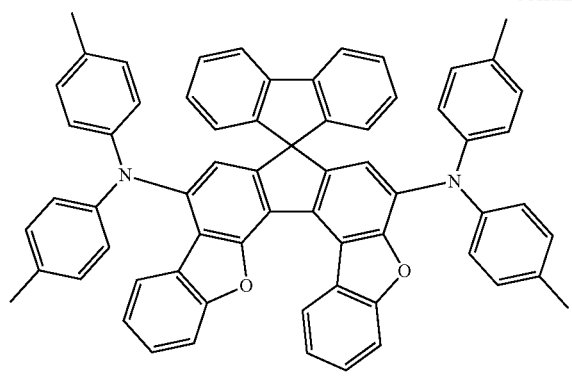
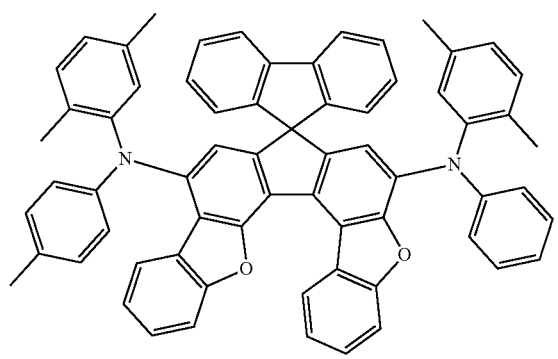
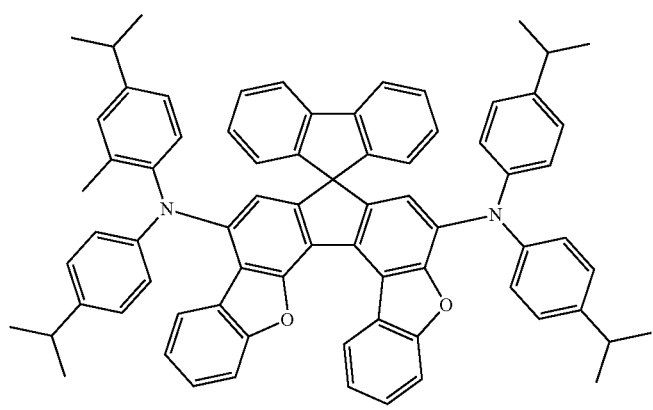
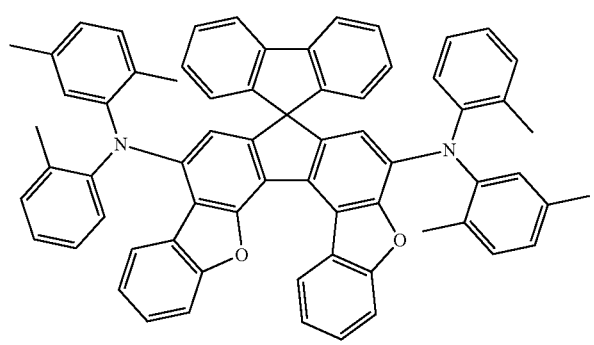

-continued
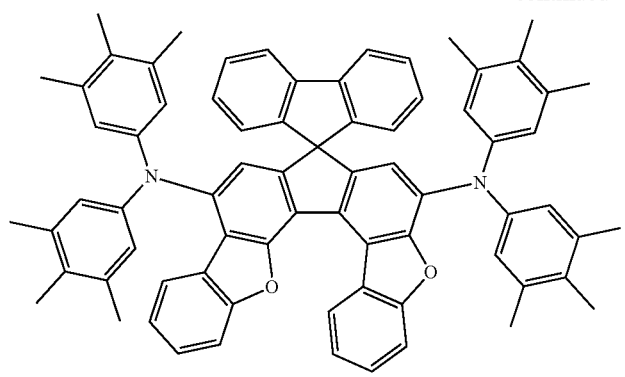
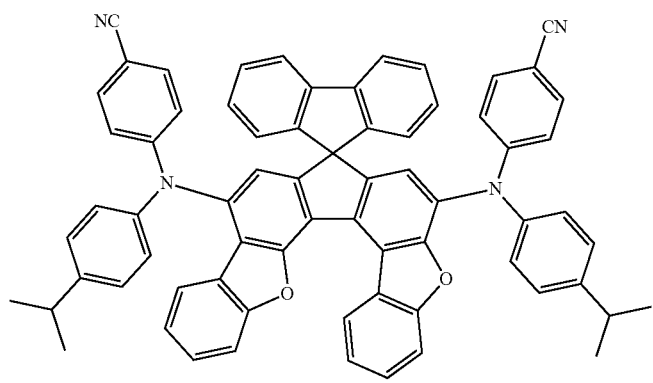
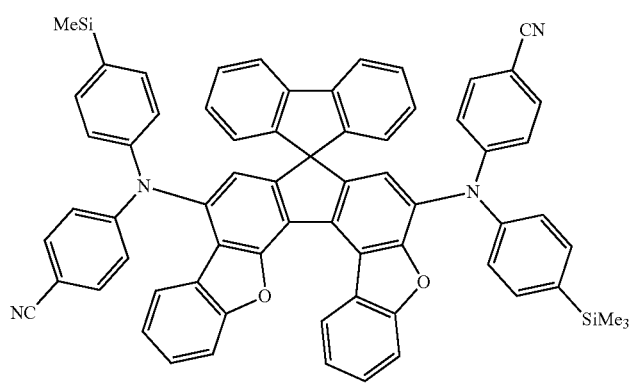
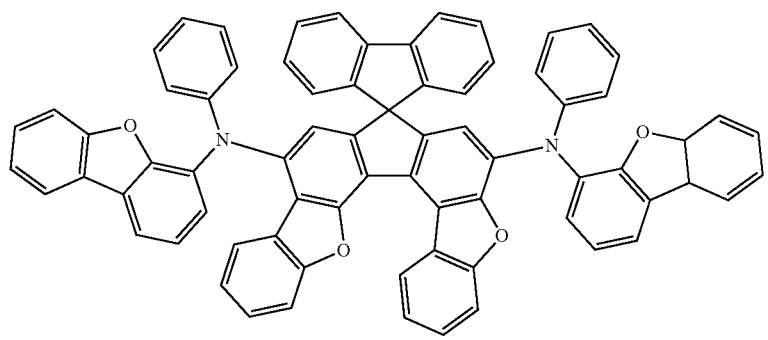

-continued
| 981 | 982 |
|---|---|
| 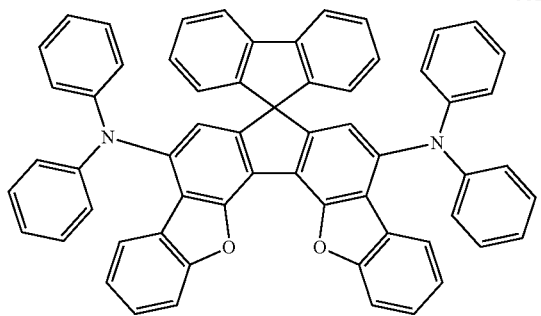 | 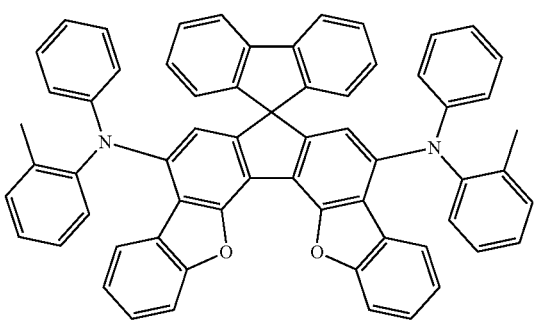 |
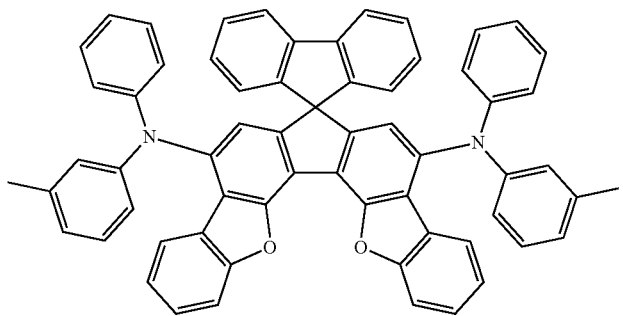
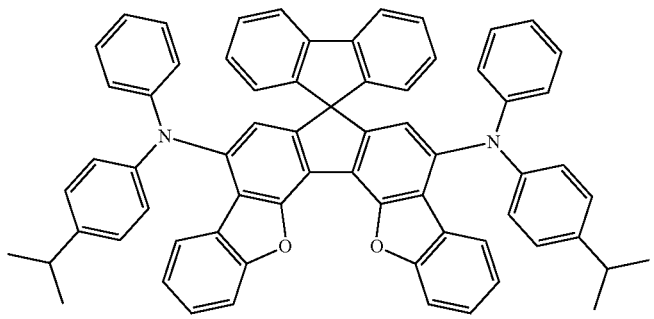
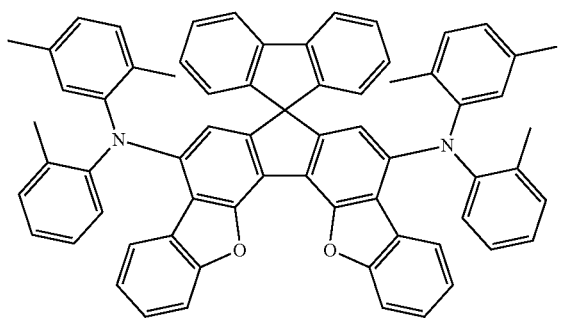
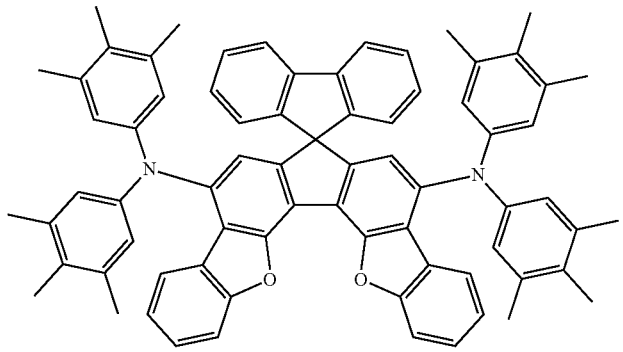

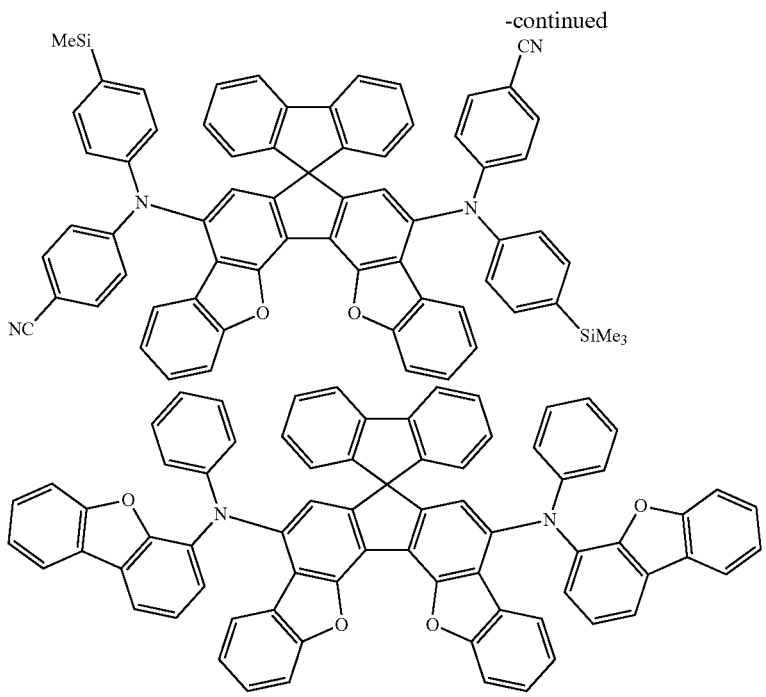

(Compound represented by formula (81))

The compound represented by the formula (81) is explained below.

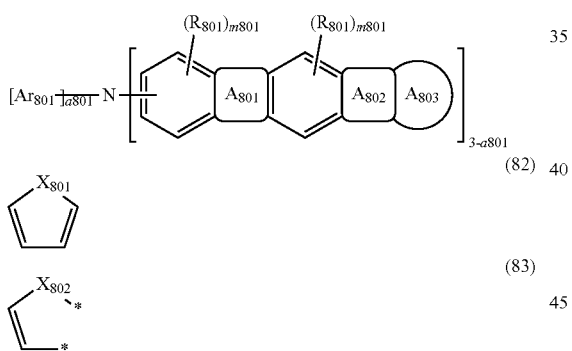

In the formula (81), $A_{801}$ ring is a ring represented by the formula (82) which is fused to an adjacent ring at an arbitrary position;

$A_{802}$ ring is a ring represented by the formula (83) which is fused to an adjacent ring at an arbitrary position;

two *'s bond to $A_{803}$ ring at an arbitrary position;

$X_{801}$ and $X_{802}$ are independently $C(R_{803})(R_{804})$, $Si(R_{805})(R_{806})$, an oxygen atom, or a sulfur atom;

$A_{803}$ ring is a substituted or unsubstituted aromatic hydrocarbon ring including 6 to 50 ring carbon atoms, or a substituted or unsubstituted heterocyclic ring including 5 to 50 ring atoms;

$Ar_{801}$ is a substituted or unsubstituted aryl group including 6 to 50 ring carbon atoms, or a substituted or unsubstituted monovalent heterocyclic group including 5 to 50 ring atoms;

$R_{801}$ to $R_{806}$ are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —$Si(R_{901})(R_{902})(R_{903})$,

—$O$—$(R_{904})$,

—$S$—$(R_{905})$,

—$N(R_{906})(R_{907})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms;

$R_{901}$ to $R_{907}$ are as defined in the formula (1);

m801 and m802 are independently an integer of 0 to 2; when these are 2, plural $R_{801}$'s or $R_{802}$'s may be the same or different;

a801 is an integer of 0 to 2; when a801 is 0 or 1, the structure in the parentheses indicated by "3-a801" may be the same or different from each other; when a801 is 2, $Ar_{801}$'s may be the same or different from each other.

In one embodiment, $Ar_{801}$ is a substituted or unsubstituted aryl group including 6 to 50 ring carbon atoms.

In one embodiment, $A_{803}$ ring is a substituted or unsubstituted aromatic hydrocarbon ring including 6 to 50 ring carbon atoms, and it is a substituted or unsubstituted benzene ring, a substituted or unsubstituted naphthalene ring, or a substituted or unsubstituted anthracene ring, for example.

In one embodiment, $R_{803}$ and $R_{804}$ are independently a substituted or unsubstituted alkyl group including 1 to 50 carbon atoms.

In one embodiment, a801 is 1.

As specific example of the compound represented by the formula (81), the following compounds can be given, for example.

985
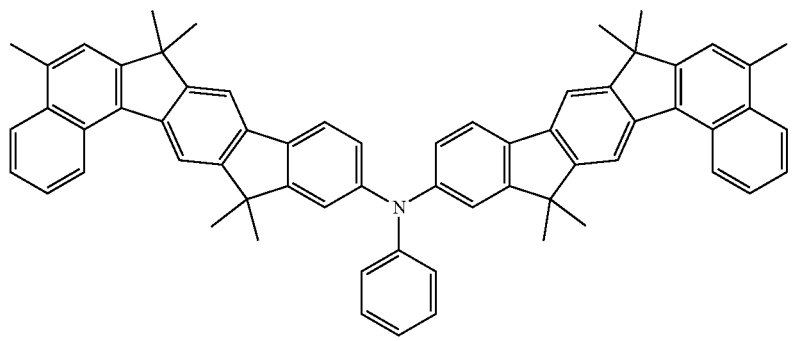
986
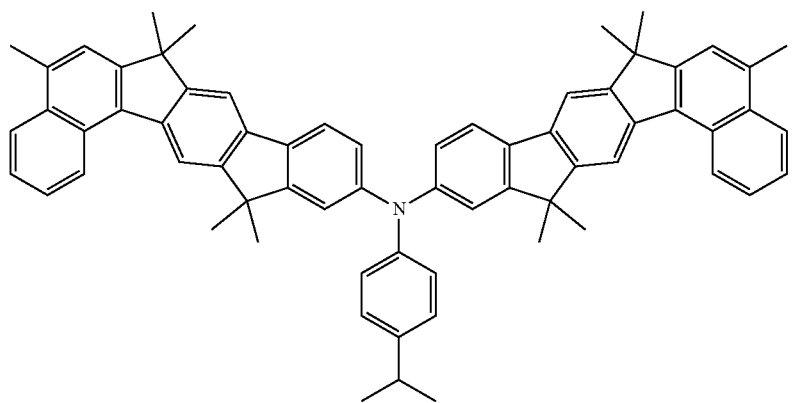
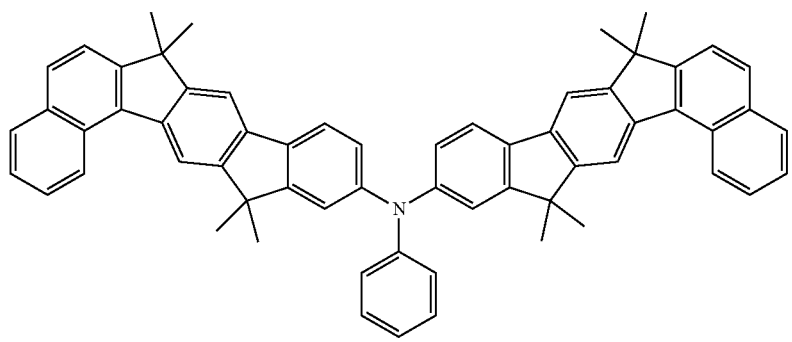
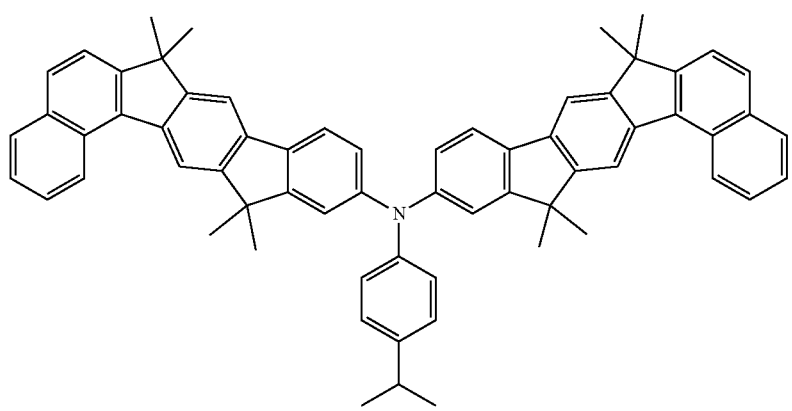

-continued
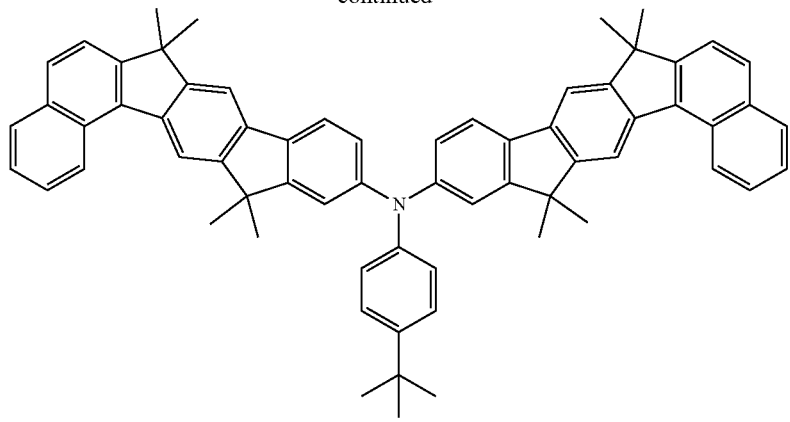
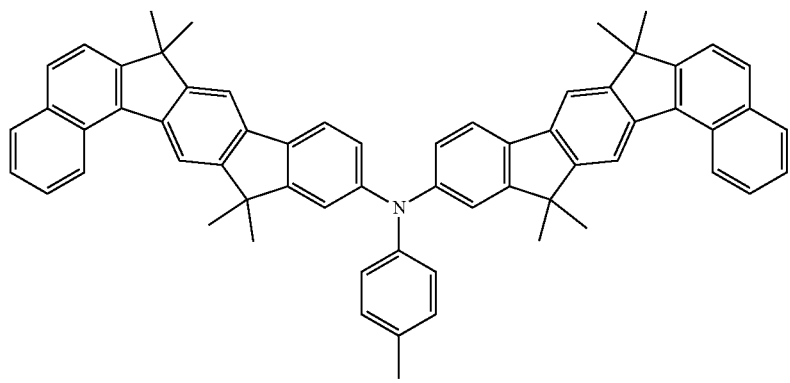
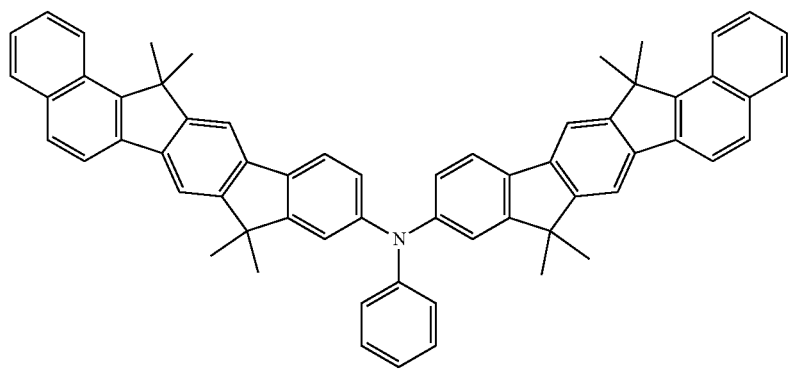
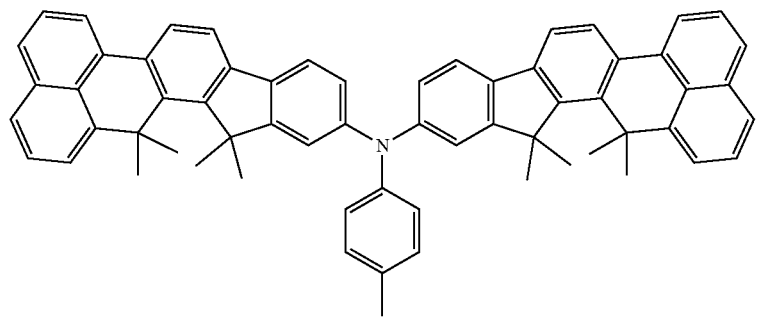

-continued

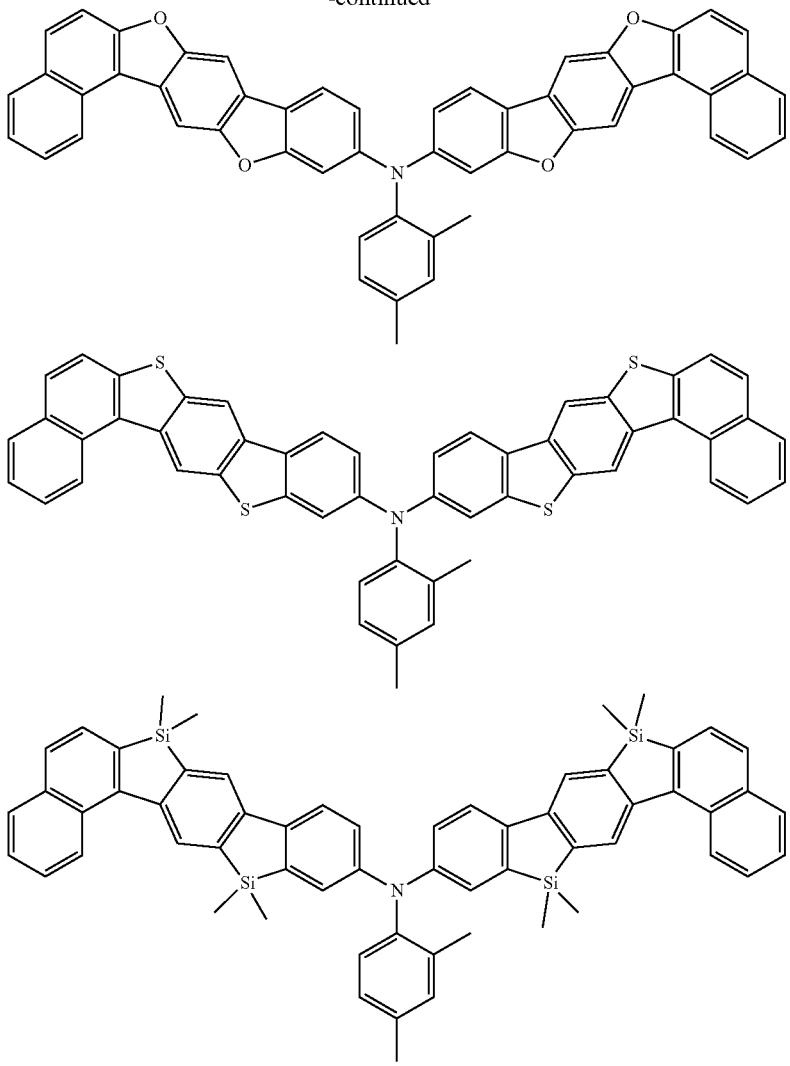

Specific examples of the above groups are as described in [Definition] of this specification.

In the organic EL device according to an aspect of the invention, known materials and device configurations may be applied as long as the device contains a cathode, an anode, and an emitting layer disposed between the cathode and the anode, and the emitting layer contains a compound represented by the formula (1), and as long as the effect of the invention is not impaired.

In one embodiment of the invention, known materials and device configurations may be applied as long as the emitting layer contains one or more compounds selected from the group consisting of compounds represented by the formulas (11), (21), (31), (41), (51), (61), (71) and (81) as a dopant material, and as long as the effect of the invention is not impaired.

The content of the compound represented by the formula (1) in the emitting layer is preferably 1 mass % or more and 20 mass % or less based on the total mass of the emitting layer. The content of the compound represented by the formula (11) is preferably 80 mass % or more and 99 mass % or less based on a total mass of the emitting layer.

An aspect of the organic EL device preferably has the hole-transporting layer between the anode and the emitting layer.

An aspect of the organic EL device preferably has the electron-transporting layer between the cathode and the emitting layer.

Hereinafter, a layer configuration of the organic EL device according to an aspect of the invention will be described.

The organic EL device according to an aspect of the invention has an organic layer between a pair of electrodes that are the cathode and the anode. The organic layer contains at least one layer containing an organic compound. Alternatively, the organic layer is formed by stacking a plurality of layers containing an organic compound. The organic layer is formed by stacking a plurality of layers containing an organic compound. The organic layer may have a layer consisting only of one or a plurality of organic compounds. The organic layer may have a layer containing an organic compound and an inorganic compound together. The organic layer may have a layer consisting only of one or a plurality of inorganic compounds.

At least one of the layers contained by the organic layer is an emitting layer. The organic layer may be formed, for example, as one layer of the emitting layer, or may contain other layers which can be adopted in the layer configuration of an organic EL device. Examples of the layers that may be employed in the layer configuration of the organic EL device include, but are not limited to, a hole-transporting region (e.g., a hole-transporting layer, a hole-injecting layer, an electron-blocking layer, an exciton-blocking layer, etc.) disposed between an anode and an emitting layer, an emitting layer, a space layer, and an electron-transporting region (e.g., an electron-transporting layer, an electron-injecting layer, a hole-blocking layer, etc.) disposed between a cathode and an emitting layer.

The organic EL device according to an aspect of the invention may be, for example, a monochromatic emitting device of a fluorescent or phosphorescent type, or a white emitting device of a fluorescent/phosphorescent hybrid type. In addition, it may be a simple type including a single light emitting unit or a tandem type including a plurality of light emitting units.

The "emitting unit" refers to the smallest unit which includes organic layers, in which at least one of the organic layers is an emitting layer, and which emits light by recombination of injected holes and electrons.

The "emitting layer" described in this specification is an organic layer having an emitting function. The emitting layer is, for example, a phosphorescent emitting layer, a fluorescent emitting layer, or the like, and may be a single layer or a plurality of layers.

The light-emitting unit may be of a stacked type including a plurality of a phosphorescent emitting layer and a fluorescent emitting layer, and in this case, for example, it may include a spacing layer between each emitting layer for preventing excitons generated by the phosphorescent emitting layer from diffusing into the fluorescent emitting layer.

The simple type organic EL device includes, for example, a device configuration such as anode/emitting unit/cathode.

Typical layer configurations of the emitting unit are shown below. The layers in parentheses are optional layers.

(a) (hole-injecting layer) hole-transporting layer/fluorescent emitting layer (/electron-transporting layer/electron-injecting layer)

(b) (hole-injecting layer) hole-transporting layer/phosphorescent emitting layer (/electron-transporting layer/electron-injecting layer)

(c) (hole-injecting layer/) hole-transporting layer/first fluorescent emitting layer/second fluorescent emitting layer (/electron-transporting layer/electron-injecting layer)

(d) (hole-injecting layer) hole-transporting layer/first phosphorescent emitting layer/second phosphorescent emitting layer (/electron-transporting layer/electron-injecting layer)

(e) (hole-injecting layer) hole-transporting layer/phosphorescent emitting layer/spacing layer/fluorescent emitting layer (/electron-transporting layer/electron-injecting layer)

(f) (hole-injecting layer/) hole-transporting layer/first phosphorescent emitting layer/second phosphorescent emitting layer/spacing layer/fluorescent emitting layer (/electron-transporting layer/electron-injecting layer)

(g) (hole-injecting layer) hole-transporting layer/first phosphorescent layer/spacing layer/second phosphorescent emitting layer/spacing layer/fluorescent emitting layer (/electron-transporting layer/electron-injecting layer)

(h) (hole-injecting layer) hole-transporting layer/phosphorescent emitting layer/spacing layer/first fluorescent emitting layer/second fluorescent emitting layer (/electron-transporting layer/electron-injecting layer)

(i) (hole-injecting layer/) hole-transporting layer/electron-blocking layer/fluorescent emitting layer (/electron-transporting layer/electron-injecting layer)

(j) (hole-injecting layer/) hole-transporting layer/electron-blocking layer/phosphorescent emitting layer (/electron-transporting layer/electron-injecting layer)

(k) (hole-injecting layer/) hole-transporting layer/exciton-blocking layer/fluorescent emitting layer (/electron-transporting layer/electron-injecting layer)

(l) (hole-injecting layer/) hole-transporting layer/exciton-blocking layer/phosphorescent emitting layer (/electron-transporting layer/electron-injecting layer)

(m) (hole-injecting layer/first hole-transporting layer/second hole-transporting layer/fluorescent emitting layer (/electron-transporting layer/electron-injecting layer)

(n) (hole-injecting layer) first hole-transporting layer/second hole-transporting layer/fluorescent emitting layer (/first electron-transporting layer/second electron-transporting layer/electron-injecting layer)

(o) (hole-injecting layer) first hole-transporting layer/second hole-transporting layer/phosphorescent emitting layer (/electron-transporting layer/electron-injecting layer)

(p) (hole-injecting layer/first hole-transporting layer/second hole-transporting layer/phosphorescent emitting layer (/first electron-transporting layer/second electron-transporting layer/electron-injecting layer)

(q) (hole-injecting layer/) hole-transporting layer/fluorescent emitting layer/hole-blocking layer (/electron-transporting layer/electron-injecting layer)

(r) (hole-injecting layer/) hole-transporting layer/phosphorescent emitting layer/hole-blocking layer (/electron-transporting layer/electron-injecting layer)

(s) (hole-injecting layer/) hole-transporting layer/fluorescent emitting layer/exciton-blocking layer (/electron-transporting layer/electron-injecting layer)

(t) (hole-injecting layer) hole-transporting layer/phosphorescent emitting layer/exciton-blocking layer (/electron-transporting layer/electron-injecting layer)

However, the layer configuration of the organic EL device according to one aspect of the invention is not limited thereto. For example, when the organic EL device has a hole-injecting layer and a hole-transporting layer, it is preferred that a hole-injecting layer be provided between the hole-transporting layer and the anode. Further, when the organic EL device has an electron-injecting layer and an electron-transporting layer, it is preferred that an electron-injecting layer be provided between the electron-transporting layer and the cathode. Further, each of the hole-injecting layer, the hole-transporting layer, the electron-transporting layer and the electron-injecting layer may be constituted of a single layer or of a plurality of layers.

The plurality of phosphorescent emitting layers, and the plurality of the phosphorescent emitting layer and the fluorescent emitting layer may be emitting layers that emit mutually different colors. For example, the emitting unit (f) may contain a hole-transporting layer/first phosphorescent layer (red light emission)/second phosphorescent emitting layer (green light emission)/spacing layer/fluorescent emitting layer (blue light emission)/electron-transporting layer.

An electron-blocking layer may be provided between each light emitting layer and the hole-transporting layer or the spacing layer. Further, a hole-blocking layer may be provided between each emitting layer and the electron-transporting layer. By providing the electron-blocking layer or the hole-blocking layer, it is possible to confine electrons or holes in the emitting layer, thereby to improve the recombination probability of carriers in the emitting layer, and to improve luminous efficiency.

As a representative device configuration of a tandem type organic EL device, for example, a device configuration such as anode/first emitting unit/intermediate layer/second emitting unit/cathode can be given.

The first emitting unit and the second emitting unit are independently selected from the above-mentioned emitting units, for example.

The intermediate layer is also generally referred to as an intermediate electrode, an intermediate conductive layer, a charge generating layer, an electron withdrawing layer, a connecting layer, a connector layer, or an intermediate insulating layer. The intermediate layer is a layer that supplies electrons to the first emitting unit and holes to the second emitting unit, and can be formed of known materials.

Only one of the first and second emitting units may be an emitting layer of an aspect of the invention, or both may be an emitting layer of an aspect of the invention.

Hereinbelow, an explanation will be made on function, materials, etc. of each layer constituting the organic EL device described in this specification.

(Substrate)

The substrate is used as a support of the organic EL device. The substrate preferably has a light transmittance of 50% or more in the visible light region within a wavelength of 400 to 700 nm, and a smooth substrate is preferable. Examples of the material of the substrate include soda-lime glass, aluminosilicate glass, quartz glass, plastic and the like. As the substrate, a flexible substrate can be used. The flexible substrate means a substrate that can be bent (flexible), and examples thereof include a plastic substrate and the like. Specific examples of the material for forming the plastic substrate include polycarbonate, polyallylate, polyether sulfone, polypropylene, polyester, polyvinyl fluoride, polyvinyl chloride, polyimide, polyethylene naphthalate and the like. Also, an inorganic vapor deposited film can be used.

(Anode)

As the anode, for example, it is preferable to use a metal, an alloy, a conductive compound, a mixture thereof or the like, which has a high work function (specifically, 4.0 eV or more). Specific examples of the material of the anode include indium oxide-tin oxide (ITO: Indium Tin Oxide), indium oxide-tin oxide containing silicon or silicon oxide, indium oxide-zinc oxide, indium oxide containing tungsten oxide or zinc oxide, graphene and the like. In addition, it is possible to use gold, silver, platinum, nickel, tungsten, chromium, molybdenum, iron, cobalt, copper, palladium, titanium, nitrides of these metals (e.g. titanium nitride) and the like.

The anode is normally formed by depositing these materials on the substrate by a sputtering method. For example, indium oxide-zinc oxide can be formed by a sputtering method by using a target in which 1 to 10 mass % zinc oxide is added to indium oxide. Further, indium oxide containing tungsten oxide or zinc oxide can be formed by a sputtering method by using a target in which 0.5 to 5 mass % of tungsten oxide or 0.1 to 1 mass % of zinc oxide is added to indium oxide.

As the other methods for forming the anode, a vacuum deposition method, a coating method, an inkjet method, a spin coating method or the like can be given. When silver paste or the like is used, it is possible to use a coating method, an inkjet method or the like.

The hole-injecting layer formed in contact with the anode is formed by using a material that allows easy hole injection regardless of the work function of the anode. For this reason, in the anode, it is possible to use a common electrode material, for example, a metal, an alloy, a conductive compound and a mixture thereof. Specifically, materials having a small work function such as alkaline metals such as lithium and cesium; magnesium; alkaline earth metals such as calcium and strontium; alloys containing these metals (for example, magnesium-silver and aluminum-lithium); rare earth metals such as europium and ytterbium; and an alloy containing rare earth metals can also be used for the anode.

(Hole-Injecting Layer)

A hole-injecting layer is a layer that contains a substance having a high hole-injecting property and has a function of injecting holes from the anode to the organic layer. As the substance having a high hole-injecting property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, an electron-attracting (acceptor) compound, a polymeric compound (oligomer, dendrimer, polymer, etc.) and the like can be given. Among these, an aromatic amine compound and an acceptor compound are preferable, with an acceptor compound being more preferable.

Specific examples of the aromatic amine compound include 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

The acceptor compound is preferably, for example, a heterocyclic ring derivative having an electron-attracting group, a quinone derivative having an electron-attracting group, an arylborane derivative, a heteroarylborane derivative, and the like, and specific examples include hexacyanohexaazatriphenylene, 2,3,5,6-tetrafluoro-7,7,8,8-tetracyanoquinodimethane (abbreviation: F4TCNQ), 1,2,3-tris[(cyano)(4-cyano-2,3,5,6-tetrafluorophenyl)methylene]cyclopropane, and the like.

When the acceptor compound is used, it is preferred that the hole-injecting layer further comprise a matrix material. As the matrix material, a material known as the material for an organic EL device can be used. For example, an electron-donating (donor) compound is preferable.

(Hole-Transporting Layer)

The hole-transporting layer is a layer that comprises a high hole-transporting property, and has a function of transporting holes from the anode to the organic layer.

As the substance having a high hole-transporting property, a substance having a hole mobility of 10-cm$^2$/(V·s) or more is preferable. For example, an aromatic amine compound, a carbazole derivative, an anthracene derivative, a polymeric compound, and the like can be given.

Specific examples of the aromatic amine compound include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluoren-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), and the like.

Specific examples of the carbazole derivative include 4,4'-di(9-carbazolyl)biphenyl (abbreviation: CBP), 9-[4-(9-carbazolyl)phenyl]-10-phenylanthracene (abbreviation: CzPA), 9-phenyl-3-[4-(10-phenyl-9-anthryl)phenyl]-9H-carbazole (abbreviation: PCzPA) and the like.

Specific examples of the anthracene derivative include 2-t-butyl-9,10-di(2-naphthyl)anthracene (t-BuDNA), 9,10-di(2-naphthyl)anthracene (DNA), 9,10-diphenylanthracene (DPAnth), and the like.

Specific examples of the polymeric compound include poly(N-vinylcarbazole) (abbreviation: PVK), poly(4-vinyltriphenylamine) (abbreviation: PVTPA) and the like.

As long as a compound other than those mentioned above, that has a higher hole-transporting property as compared with electron-transporting property, such a compound can be used for the hole-transporting layer.

The hole-transporting layer may be a single layer or may be a stacked layer of two or more layers. In this case, it is preferred to arrange a layer that contains a substance having a larger energy gap among substances having a higher hole-transporting property, on a side nearer to the emitting layer.

(Emitting Layer)

The emitting layer is a layer containing a substance having a high emitting property (dopant material). As the dopant material, various types of material can be used. For example, a fluorescent emitting compound (fluorescent dopant), a phosphorescent emitting compound (phosphorescent dopant) or the like can be used. A fluorescent emitting compound is a compound capable of emitting light from the singlet excited state, and an emitting layer containing a fluorescent emitting compound is called as a fluorescent emitting layer. Further, a phosphorescent emitting compound is a compound capable of emitting light from the triplet excited state, and an emitting layer containing a phosphorescent emitting compound is called as a phosphorescent emitting layer.

The emitting layer normally contains a dopant material and a host material that allows the dopant material to emit light efficiently. In some literatures, a dopant material may be called as a guest material, an emitter, or an emitting material. In some literatures, a host material is called as a matrix material.

A single emitting layer may include a plurality of dopant materials and a plurality of host materials. Further, a plurality of emitting layers may be present.

In this specification, a host material combined with the fluorescent dopant is referred to as a "fluorescent host" and a host material combined with the phosphorescent dopant is referred to as the "phosphorescent host". Note that the fluorescent host and the phosphorescent host are not classified only by the molecular structure. The phosphorescent host is a material for forming a phosphorescent emitting layer containing a phosphorescent dopant, but it does not mean that it cannot be used as a material for forming a fluorescent emitting layer. The same can be applied to the fluorescent host.

The content of the dopant material in the emitting layer is not particularly limited, but from the viewpoint of adequate luminescence and concentration quenching, it is preferable, for example, to be 0.1 to 70 mass %, more preferably 0.1 to 30 mass %, more preferably 1 to 30 mass %, still more preferably 1 to 20 mass %, and particularly preferably 1 to 10 mass %.

<Fluorescent Dopant>

As the fluorescent dopant, which can be used together with the fluorescent dopant used in an aspect of the invention, a fused polycyclic aromatic derivative, a styrylamine derivative, a fused ring amine derivative, a boron-containing compound, a pyrrole derivative, an indole derivative, a carbazole derivative can be given, for example. Among these, a fused ring amine derivative, a boron-containing compound, and a carbazole derivative are preferable.

As the fused ring amine derivative, a diaminopyrene derivative, a diaminochrysene derivative, a diaminoanthracene derivative, a diaminofluorene derivative, a diaminofluorene derivative with which one or more benzofuro skeletons are fused, and the like can be given.

As the boron-containing compound, a pyrromethene derivative, a triphenylborane derivative and the like can be given.

Examples of the blue fluorescent dopant, which can be used together with the fluorescent dopant used in an aspect of the invention, include a pyrene derivative, a styrylamine derivative, a chrysene derivative, a fluoranthene derivative, a fluorene derivative, a diamine derivative, a triarylamine derivative, and the like. Specifically, N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl) triphenylamine (abbreviation: PCBAPA) and the like can be given.

As the green fluorescent dopant, which can be used together with the fluorescent dopant used in an aspect of the invention, an aromatic amine derivative and the like can be given, for example. Specifically, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]—N-[4-(9H-carbazol-9-yl)phenyl]-N-phenylanthracene-2-amine (abbreviation: 2YGABPhA), N,N,9-triphenylanthracene-9-amine (abbreviation: DPhAPhA), and the like can be given.

As the red fluorescent dopant, a tetracene derivative, a diamine derivative or the like can be given. Specifically, N,N,N',N'-tetrakis(4-methylphenyl)tetracen-5,11-diamine (abbreviation: p-mPhTD), 7,14-diphenyl-N,N,N',N'-tetrakis(4-methylphenyl)acenaphtho[1,2-a]fluoranthen-3,10-diamine (abbreviation: p-mPhAFD) and the like can be given.

<Phosphorescent Dopant>

As the phosphorescent dopant, a phosphorescent light-emitting heavy metal complex and a phosphorescent light-emitting rare earth metal complex can be given.

As the heavy metal complex, an iridium complex, an osmium complex, a platinum complex and the like can be given. As the heavy metal complex, an ortho-metalated complex of a metal selected from iridium, osmium and platinum.

As the rare earth metal complexes include a terbium complex, a europium complex and the like. Specifically, tris(acetylacetonate)(monophenanthroline)terbium (III) (abbreviation: Tb(acac)$_3$(Phen)), tris(1,3-diphenyl-1,3-propandionate)(monophenanthroline)europium (III) (abbreviation: Eu(DBM)₃(Phen)), tris[1-(2-thenoyl)-3,3,3-trifluoroacetonate](monophenanthroline)europium (III) (abbreviation: Eu(TTA)₃(Phen)) and the like can be given. These rare earth metal complexes are preferable as phosphorescent dopants since rare earth metal ions emit light due to electronic transition between different multiplicity.

As the blue phosphorescent dopant, an iridium complex, an osmium complex, a platinum complex, or the like can be given, for example. Specific examples include bis[2-(4',6'-difluorophenyl)pyridinato-N,C2']iridium (III) tetrakis(1-pyrazolyl)borate (abbreviation: Flr6), bis[2-(4',6'-difluorophenyl)pyridinato-N,C2']iridium (III) picolinate (abbreviation: Flrpic), bis[2-(3',5'-bistrofluoromethylphenyl)pyridinato-N,C2']iridium (III) picolinate (abbreviation: Ir(CF₃ppy)₂(pic)), bis[2-(4',6'-difluorophenyl)pyridinato-N,C2']iridium (III) acetylacetonate (abbreviation: Flracac), and the like.

As the green phosphorescent dopant, an iridium complex or the like can be given, for example. Specific examples include tris(2-phenylpyridinato-N,C2')iridium (III) (abbreviation: Ir(ppy)₃), bis(2-phenylpyridinato-N,C2')iridium (III) acetylacetonate (abbreviation: Ir(ppy)₂(acac)), bis(1,2-diphenyl-1H benzimidazolate)iridium (III) acetylacetonate (abbreviation: Ir(pbi)₂(acac)), bis(benzo[h]quinolinato) iridium (III) acetylacetonate (abbreviation: Ir(bzq)₂(acac)), and the like.

As the red phosphorescent dopant, an iridium complex, a platinum complex, a terbium complex, a europium complex and the like can be given. Specifically, bis[2-(2'-benzo[4,5-a] thienyl)pyridinato-N,C3']iridium (III) acetylacetonate (abbreviation: lr(btp)₂(acac)), bis(1-phenylisoquinolinato-N,C2')iridium (III) acetylacetonate (abbreviation: lr(piq)₂(acac)), (acetylacetonate)bis[2,3-bis(4-fluorophenyl)quinoxalinato]iridium (III) (abbreviation: Ir(Fdpq)₂(acac)), 2,3,7,8,12,13,17,18-octaethyl-21H,23H-porphyrin platinum (II) (abbreviation: PtOEP), and the like.

<Host Material>

Examples of the host material, which can be used together with the host material used in an aspect of the invention, include metal complexes such as an aluminum complex, a beryllium complex, and a zinc complex; heterocyclic compounds such as an indole derivative, a pyridine derivative, a pyrimidine derivative, a triazine derivative, a quinoline derivative, an isoquinoline derivative, a quinazoline derivative, a dibenzofuran derivative, a dibenzothiophene derivative, an oxadiazole derivative, a benzimidazole derivative, a phenanthroline derivative; fused aromatic compounds such as a naphthalene derivative, a triphenylene derivative, a carbazole derivative, an anthracene derivative, a phenanthrene derivative, a pyrene derivative, a chrysene derivative, a naphthacene derivative, and a fluoranthene derivative; and aromatic amine compounds such as a triarylamine derivative, and a fused polycyclic aromatic amine derivative, and the like. Plural types of host materials can be used in combination.

Specific examples of the metal complex include tris(8-quinolinolato)aluminum(III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), bis[2-(2-benzothiazolyl) phenolato]zinc(II) (abbreviation: ZnBTZ), and the like.

Specific examples of the heterocyclic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), bathocuproine (abbreviation: BCP), and the like.

Specific examples of the fused aromatic compound include 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), 9,10-diphenylanthracene (abbreviation: DPAnth), 6,12-dimethoxy-5,11-diphenylchrysene, and the like.

Specific examples of the aromatic amine compound include N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 4,4'-bis[N-(1-naphthyl)-N-phenylamino]biphenyl (abbreviation: NPB ora-NPD), N,N'-bis(3-methylphenyl)-N,N'-diphenyl-[1,1'-biphenyl]-4,4'-diamine (abbreviation: TPD), 4,4'-bis[N-(9,9-dimethylfluoren-2-yl)-N-phenylamino]biphenyl (abbreviation: DFLDPBi), 4,4'-bis[N-(spiro-9,9'-bifluoren-2-yl)-N-phenylamino]biphenyl (abbreviation: BSPB), and the like.

As the fluorescent host material, a compound having a higher singlet energy level as compared with a fluorescent dopant is preferable. For example, a heterocyclic compound, a fused aromatic compound, and the like can be given. As fused aromatic compounds, for example, anthracene derivatives, pyrene derivatives, chrysene derivatives, and naphthacene derivatives are preferred.

As the phosphorescent host, a compound having a higher triplet energy level as compared with a phosphorescent dopant is preferable. For example, a metal complex, a heterocyclic compound, a fused aromatic compound and the like can be given. Among these, an indole derivative, a carbazole derivative, a pyridine derivative, a pyrimidine derivative, a triazine derivative, a quinoline derivative, an isoquinoline derivative, a quinazoline derivative, a dibenzofuran derivative, a dibenzothiophene derivative, a naphthalene derivative, a triphenylene derivative, a phenanthrene derivative, a fluoranthene derivative and the like are preferable.

(Electron-Transporting Layer)

An electron-transporting layer is a layer that comprises a substance having a high electron-transporting property. As the substance having a high electron-transporting property, a substance having an electron mobility of $10^{-6}$ cm²/Vs or more is preferable. For example, a metal complex, an aromatic heterocyclic compound, an aromatic hydrocarbon compound, a polymeric compound and the like can be given.

As the metal complex, an aluminum complex, a beryllium complex, a zinc complex and the like can be given. Specific examples of the metal complex include tris (8-quinolinolato) aluminum (III) (abbreviation: Alq), tris (4-methyl-8-quinolinolato)aluminum (abbreviation: Almq3), bis (10-hydroxybenzo[h]quinolinato) beryllium (abbreviation: BeBq2), bis (2-methyl-8-quinolinolato)(4-phenylphenolato)aluminum (III) (abbreviation: BAlq), bis (8-quinolinolato) zinc (II) (abbreviation: Znq), bis [2-(2-benzoxazolyl) phenolato]zinc (II) (abbreviation: ZnPBO), bis [2-(2-benzothiazolyl) phenolato] zinc(II) (abbreviation: ZnBTZ), and the like.

As the aromatic heterocyclic compound, imidazole derivatives such as a benzimidazole derivative, an imidazopyridine derivative and a benzimidazophenanthridine derivative; azine derivatives such as a pyrimidine derivative and a triazine derivative; compounds having a nitrogen-containing 6-membered ring structure such as a quinoline derivative, an isoquinoline derivative, and a phenanthroline derivative (also including one having a phosphine oxide-based substituent on the heterocyclic ring) and the like can be given. Specifically, 2-(4-biphenylyl)-5-(4-tert-butylphenyl)-1,3,4-oxadiazole (abbreviation: PBD), 1,3-bis [5-(p-tert-butylphenyl)-1,3,4-oxadiazol-2-yl] benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), 4,4'-bis (5-methylbenzoxazol-2-yl) stilbene (abbreviation: BzOs), and the like can be given.

As the aromatic hydrocarbon compound, an anthracene derivative, a fluoranthene derivative and the like can be given, for example.

As specific examples of the polymeric compound, poly [(9,9-dihexylfluoren-2,7-diyl)-co-(pyridine-3,5-diyl)] (abbreviation: PF-Py), poly [(9,9-dioctylfluoren-2,7-diyl)-co-(2,2'-bipyridin-6,6'-diyl)] (abbreviation: PF-BPy) and the like can be given.

As long as a compound other than those mentioned above, that has a higher electron-transporting property as compared with hole-transporting property, such a compound may be used in the electron-transporting layer.

The electron-transporting layer may be a single layer, or a stacked layer of two or more layers. In this case, it is preferable to arrange a layer that contains a substance having a larger energy gap, among substances having a high electron-transporting property, on the side nearer to the emitting layer.

The electron-transporting layer may contain a metal such as an alkali metal, magnesium, an alkaline earth metal, or an alloy containing two or more of these metals; a metal compound such as an alkali metal compound such as 8-quinolinolato lithium (Liq), or an alkaline earth metal compound. When a metal such as an alkali metal, magnesium, an alkaline earth metal, or an alloy containing two or more of these metals is contained in the electron-transporting layer, the content of the metal is not particularly limited, but is preferably from 0.1 to 50 mass %, more preferably from 0.1 to 20 mass %, further preferably from 1 to 10 mass %.

When a metal compound such as an alkali metal compound or an alkaline earth metal compound is contained in the electron-transporting layer, the content of the metal compound is preferably from 1 to 99 mass %, more preferably from 10 to 90 mass %. When plural electron-transporting layers are provided, the layer on the emitting layer side can be formed only from the metal compound as mentioned above.

(Electron-Injecting Layer)

The electron-injecting layer is a layer that contains a substance having a high electron-injecting property, and has the function of efficiently injecting electrons from a cathode to an emitting layer. Examples of the substance that has a high electron-injecting property include an alkali metal, magnesium, an alkaline earth metal, a compound thereof, and the like. Specific examples thereof include lithium, cesium, calcium, lithium fluoride, cesium fluoride, calcium fluoride, lithium oxide, and the like. In addition, a material in which an alkali metal, magnesium, an alkaline earth metal, or a compound thereof is incorporated to an electron-transporting substance having an electron-transporting property, for example, Alq incorporated with magnesium, may also be used.

Alternatively, a composite material that includes an organic compound and a donor compound may also be used in the electron-injecting layer. Such a composite material is excellent in the electron-injecting property and the electron-transporting property since the organic compound receives electrons from the donor compound.

The organic compound is preferably a substance excellent in transporting property of the received electrons, and specifically, for example, the metal complex, the aromatic heterocyclic compound, and the like, which are a substance that has a high electron-transporting property as mentioned above, can be used.

Any material capable of donating electrons to an organic compound can be used as the donor compound. Examples thereof include an alkali metal, magnesium, an alkaline earth metal, a rare earth metal and the like. Specific examples thereof include lithium, cesium, magnesium, calcium, erbium, ytterbium, and the like. Further, an alkali metal oxide and an alkaline earth metal oxide are preferred, and examples thereof include lithium oxide, calcium oxide, barium oxide, and the like. Lewis bases such as magnesium oxide can also be used. Alternatively, an organic compound such as tetrathiafulvalene (abbreviation: TTF) can be used.

(Cathode)

For the cathode, a metal, an alloy, an electrically conductive compound, and a mixture thereof, each having a small work function (specifically, a work function of 3.8 eV or less) are preferably used. Specific examples of the material for the cathode include alkali metals such as lithium and cesium; magnesium; alkaline earth metals such as calcium, and strontium; alloys containing these metals (for example, magnesium-silver, and aluminum-lithium); rare earth metals such as europium and ytterbium; alloys containing a rare earth metal, and the like.

The cathode is usually formed by a vacuum vapor deposition or a sputtering method. Further, in the case of using a silver paste or the like, a coating method, an inkjet method, or the like can be employed.

In the case where the electron-injecting layer is provided, a cathode can be formed from a substance selected from various electrically conductive materials such as aluminum, silver, ITO, graphene, indium oxide-tin oxide containing silicon or silicon oxide, regardless of the work function value. These electrically conductive materials are made into films by using a sputtering method, an inkjet method, a spin coating method, or the like.

(Insulating Layer)

In the organic EL device, pixel defects based on leakage or a short circuit are easily generated since an electric field is applied to a thin film. In order to prevent this, an insulating thin layer may be inserted between a pair of electrodes.

Examples of substances used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide, and the like. A mixture thereof may be used in the insulating layer, and a stacked body of a plurality of layers that include these substances can be also used for the insulating layer.

(Spacing Layer)

The spacing layer is a layer provided between a fluorescent emitting layer and a phosphorescent emitting layer when the fluorescent emitting layer and the phosphorescent emitting layer are stacked, in order to prevent diffusion of excitons generated in the phosphorescent emitting layer to the fluorescent emitting layer or in order to adjust the carrier balance. Further, the spacing layer can be provided between plural phosphorescent emitting layers.

Since the spacing layer is provided between the emitting layers, the material used for the spacing layer is preferably a substance that has both electron-transporting property and hole-transporting property. In order to prevent diffusion of the triplet energy in adjacent phosphorescent emitting layers, it is preferred that the material used for the spacing layer have a triplet energy of 2.6 eV or more.

As the material used for the spacing layer, the same materials as those used in the above-mentioned hole-transporting layer can be given.

(Electron-Blocking Layer, Hole-Blocking Layer, Exciton-Blocking Layer)

An electron-blocking layer, a hole-blocking layer, an exciton (triplet)-blocking layer, and the like may be provided in adjacent to the emitting layer.

The electron-blocking layer has a function of preventing leakage of electrons from the emitting layer to the hole-transporting layer. The hole-blocking layer has a function of preventing leakage of holes from the emitting layer to the electron-transporting layer. The exciton-blocking layer has a function of preventing diffusion of excitons generated in the emitting layer to the adjacent layers to confine the excitons within the emitting layer.

(Intermediate Layer)

In tandem-type organic EL device, an intermediate layer is provided.

(Method for Forming a Layer)

The method for forming each layer of the organic EL device is not particularly limited unless otherwise specified. As the film forming method, a known film-forming method such as a dry film-forming method, a wet film-forming method or the like can be used. Specific examples of the dry film-forming method include a vacuum deposition method, a sputtering method, a plasma method, an ion plating method, and the like. Specific examples of the wet film-forming method include various coating methods such as a spin coating method, a dipping method, a flow coating method, and an inkjet method.

(Film Thickness)

The film thickness of each layer of the organic EL device is not particularly limited unless otherwise specified. If the film thickness is too small, defects such as pinholes are likely to occur to make it difficult to obtain an enough luminance. On the other hand, if the film thickness is too large, a high driving voltage is required to be applied, leading to a lowering in efficiency. In this respect, the film thickness is preferably 1 nm to 10 μm, and more preferably 1 nm to 0.2 μm.

[Electronic Apparatus]

The electronic apparatus according to one aspect of the invention includes the above-described organic EL device according to one aspect of the invention. Examples of the electronic apparatus include display parts such as an organic EL panel module; display devices of television sets, mobile phones, smart phones, personal computers, and the like; and emitting devices of a lighting device and a vehicle lighting device.

EXAMPLES

Next, the invention will be described in more detail by referring to Examples and Comparative Examples, but the invention is not limited in any way to the description of these Examples.

<Compound>

The compounds having deuterium atoms represented by the formula (1)(host material) used for fabricating the organic EL devices of the following Examples are shown below.

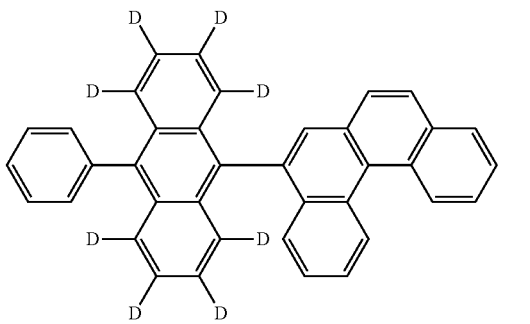

BH-1

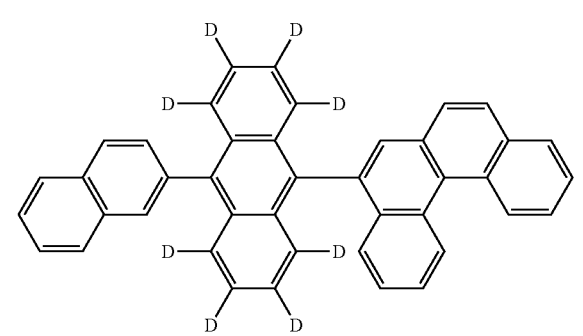

BH-2

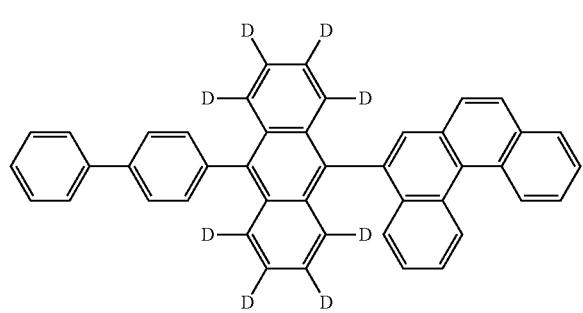

BH-3

BH-4
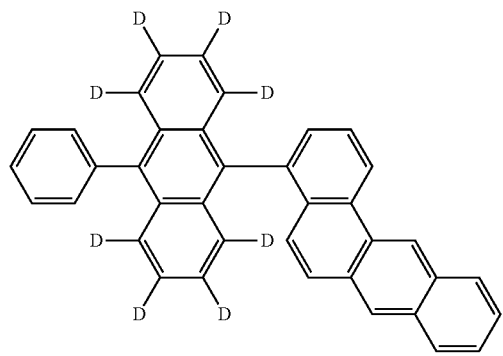
BH-5
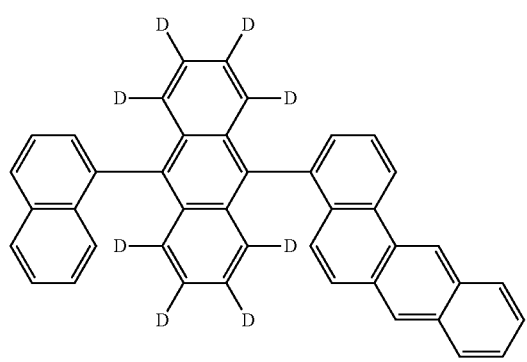
BH-6
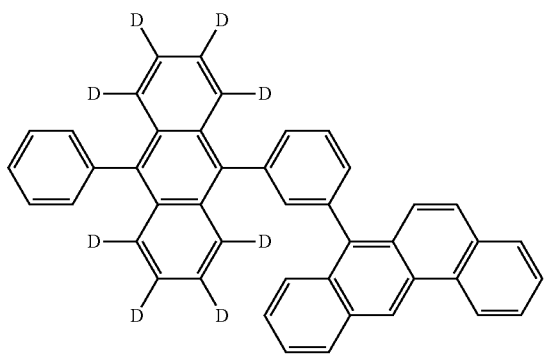
BH-7
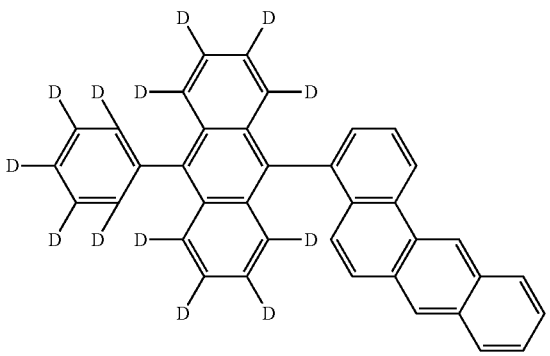
BH-8
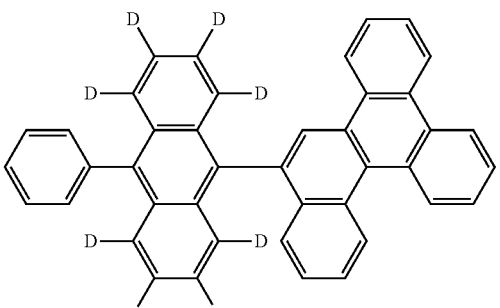
BH-9
The compounds having no deuterium atom used for fabricating the organic EL devices of the following Comparative Examples are shown below.
Comp BH-1
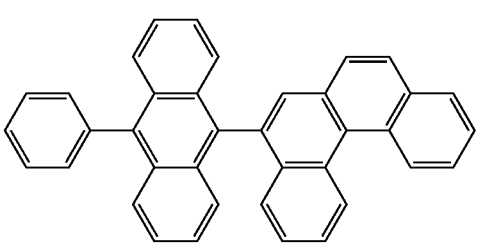
Comp BH-2
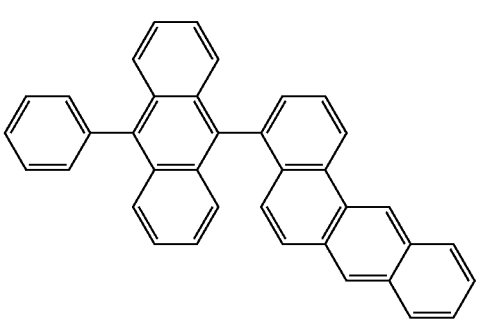
The dopant materials used for fabricating the organic EL devices of the following Examples and Comparative Examples are shown below.

1005
BD-1
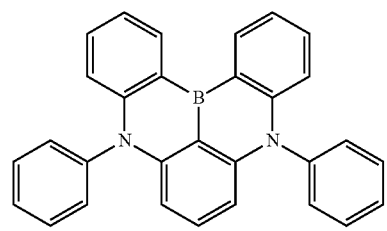
BD-2
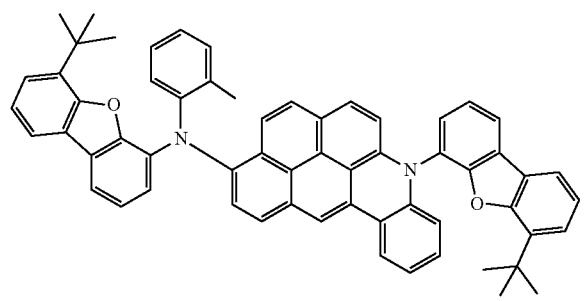
BD-3
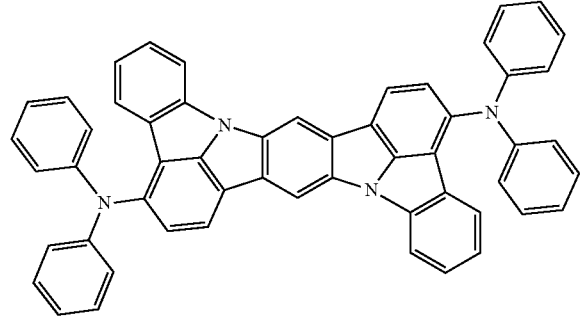
BD-4
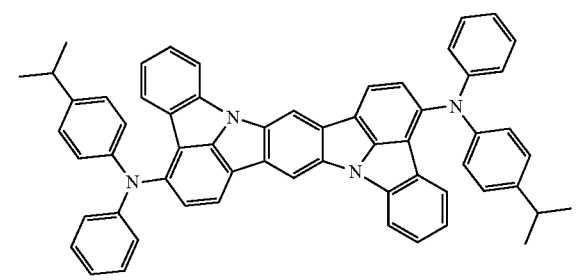
BD-5
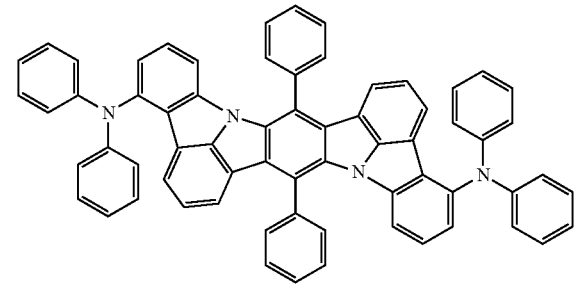
1006
-continued
BD-6
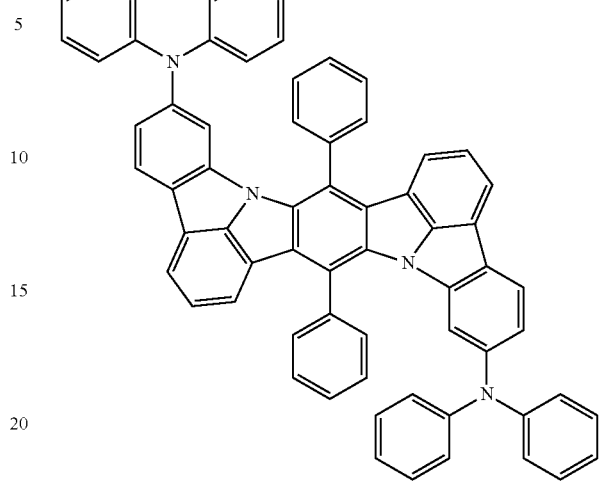
BD-7
BD-8

BD-9
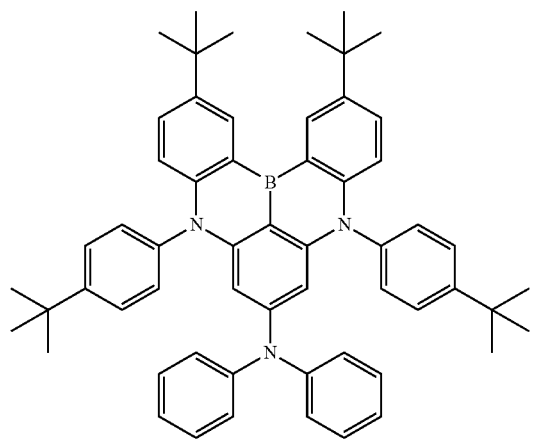
BD-10
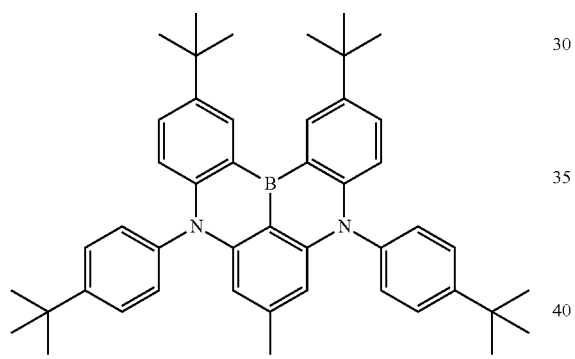
BD-11
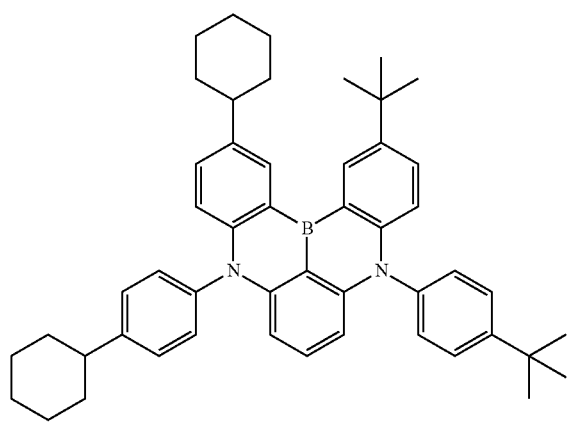
BD-12
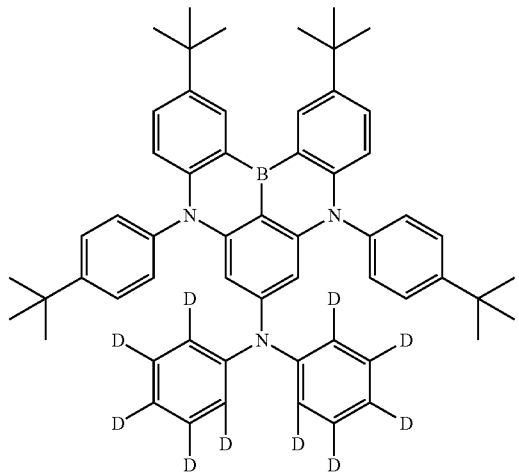
Other materials used for fabricating the organic EL devices of the following Examples and Comparative Examples are shown below.
HI-1
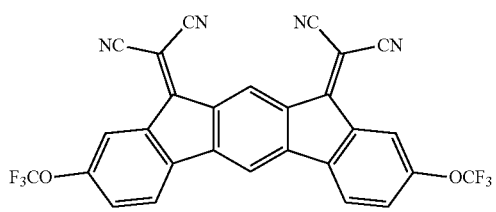
HT-1
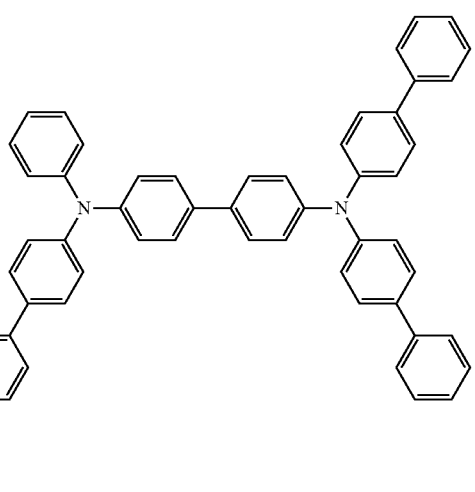

-continued

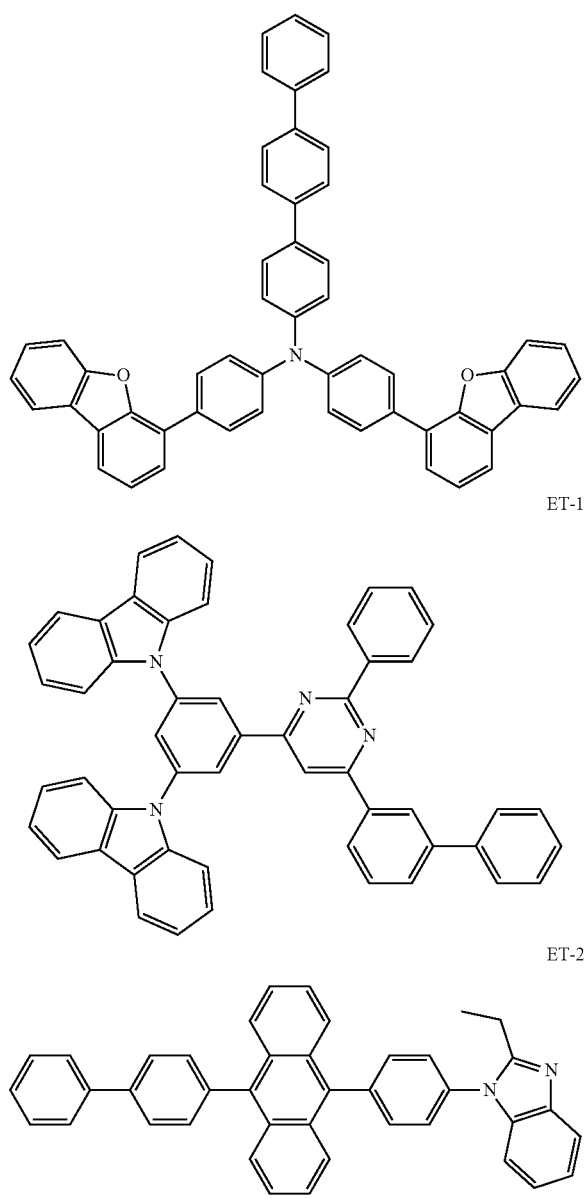

Fabrication of Organic EL Device

Example 1-1

A 25 mm×75 mm×1.1 mm-thick glass substrate with an ITO transparent electrode (anode) (manufactured by GEO-MATEC Co., Ltd.) was subjected to ultrasonic cleaning in isopropyl alcohol for 5 minutes, and then subjected to UV-ozone cleaning for 30 minutes. The thickness of the ITO film was 130 nm.

The glass substrate with the transparent electrode after being cleaned was mounted onto a substrate holder in a vacuum vapor deposition apparatus. First, a compound HI-1 was deposited on a surface on the side on which the transparent electrode was formed so as to cover the transparent electrode to form an HI-1 film having a thickness of 5 nm. The HI-1 film functions as a hole-injecting layer.

Subsequent to the formation of the HI-1 film, a compound HT-1 was deposited thereon to form an HT-1 film having a thickness of 80 nm on the HI-1 film. The HT-1 film functions as a hole-transporting layer (first hole-transporting layer).

Subsequent to the formation of the HT-1 film, a compound HT-2 was deposited thereon to form an HT-2 film having a thickness of 10 nm on the HT-1 film. The HT-2 film functions as an electron-blocking layer (second hole-transporting layer).

Compound BH-1 (host material) and Compound BD-1 (dopant material) were co-deposited on the HT-2 film so as to be 4 mass % in a proportion (mass ratio) of Compound BD-1, thereby forming a BH-1:BD-1 film having a thickness of 25 nm. The BH-1:BD-1 film functions as an emitting layer.

A compound ET-1 was deposited on the emitting layer to form an ET-1 film having a thickness of 10 nm. The ET-1 film functions as a hole barrier layer.

A compound ET-2 was deposited on the ET-1 film to form an ET-2 film having a thickness of 15 nm. The ET-2 film functions as an electron-transporting layer. LiF was deposited on the ET-2 film to form a LiF film having a thickness of 1 nm. Al metal was deposited on the LiF film to form a metal cathode having a thickness of 80 nm, thereby an organic EL device was fabricated.

The layer configuration of the obtained organic EL device is as follows. ITO(130)/HI-1(5)/HT-1(80)/HT-2(10)/BH-1:BD-1(25:4 mass %)/ET-1(10)/ET-2(15)/LiF(1)/Al(80)

Numerical values in parentheses indicate film thickness (unit: nm).

(Evaluation of Organic EL Device)

A voltage was applied to the obtained organic EL device so that the current density became 50 mA/cm$^2$, and the time until the luminance became 95% of the initial luminance (LT95 (unit: hours)) was measured. The results are shown in Table 1.

Examples 1-2 to 1-9 and Comparative Examples 1-1 to 1-2

The organic EL devices were fabricated and evaluated in the same manner as in Example 1-1 except that the host materials shown in Table 1 were used as the host material of the emitting layer. The results are shown in Table 1.

TABLE 1

| | Emitting layer | | LT95 |
|---|---|---|---|
| | Host material | Dopant material | (h) |
| Example 1-1 | BH-1 | BD-1 | 85 |
| Example 1-2 | BH-2 | BD-1 | 80 |
| Example 1-3 | BH-3 | BD-1 | 70 |
| Example 1-4 | BH-4 | BD-1 | 65 |
| Example 1-5 | BH-5 | BD-1 | 72 |
| Example 1-6 | BH-6 | BD-1 | 77 |
| Example 1-7 | BH-7 | BD-1 | 70 |
| Example 1-8 | BH-8 | BD-1 | 80 |
| Example 1-9 | BH-9 | BD-1 | 90 |
| Comparative Example 1-1 | Comp BH-1 | BD-1 | 30 |
| Comparative Example 1-2 | Comp BH-2 | BD-1 | 20 |

From the results shown in Table 1, it can be seen that the organic EL devices of Examples 1-1 to 1-9, in which the compounds BH-1 to BH-9 having deuterium atoms are used as a host material of the emitting layer, have significantly improved device lifetime as compared with the organic EL devices of Comparative Examples 1-1 and 1-2, in which the compound Comp BH-1 or Comp BH-2 having no deuterium atom are used.

From the comparison of Examples 1-1 and 1-9 with Comparative Example 1-1, and Examples 1-4 and 1-7 with Comparative Example 1-2, which use the compounds with the same chemical structure, differing only in whether or not the compound has deuterium atoms, and the same dopant materials shows that the device lifetime is greatly improved by using compounds having deuterium atoms as the host material.

Examples 2-1 to 2-9 and Comparative Examples 2-1 to 2-2

The organic EL devices were fabricated and evaluated in the same manner as in Example 1-1 except that the compound BD-2 was used as the dopant material for the emitting layer, and the compounds shown in Table 2 were used as the host materials, respectively. The results are shown in Table 2.

TABLE 2

| | Emitting layer | | LT95 |
|---|---|---|---|
| | Host material | Dopant material | (h) |
| Example 2-1 | BH-1 | BD-2 | 120 |
| Example 2-2 | BH-2 | BD-2 | 110 |
| Example 2-3 | BH-3 | BD-2 | 100 |
| Example 2-4 | BH-4 | BD-2 | 95 |
| Example 2-5 | BH-5 | BD-2 | 100 |
| Example 2-6 | BH-6 | BD-2 | 120 |
| Example 2-7 | BH-7 | BD-2 | 100 |
| Example 2-8 | BH-8 | BD-2 | 110 |
| Example 2-9 | BH-9 | BD-2 | 130 |
| Comparative Example 2-1 | Comp BH-1 | BD-2 | 75 |
| Comparative Example 2-2 | Comp BH-2 | BD-2 | 70 |

From the results shown in Table 2, it can be seen that, even when the compound BD-2 is used as the dopant material, the organic EL devices of Examples 2-1 to 2-9, in which the compounds BH-1 to BH-9 having deuterium atoms are used as a host material, have improved device lifetime as compared with the organic EL devices of Comparative Examples 2-1 and 2-2, in which the compounds Comp BH-1 and Comp BH-2 having no deuterium atom are respectively used as a host material.

Examples 3-1 to 3-9 and Comparative Examples 3-1 to 3-2

The organic EL devices were fabricated and evaluated in the same manner as in Example 1-1 except that the compound BD-3 was used as the dopant material for the emitting layer, and the compounds shown in Table 3 were used as the host materials, respectively. The results are shown in Table 3.

TABLE 3

| | Emitting layer | | LT95 |
|---|---|---|---|
| | Host material | Dopant material | (h) |
| Example 3-1 | BH-1 | BD-3 | 115 |
| Example 3-2 | BH-2 | BD-3 | 110 |
| Example 3-3 | BH-3 | BD-3 | 80 |

TABLE 3-continued

| | Emitting layer | | LT95 |
|---|---|---|---|
| | Host material | Dopant material | (h) |
| Example 3-4 | BH-4 | BD-3 | 75 |
| Example 3-5 | BH-5 | BD-3 | 90 |
| Example 3-6 | BH-6 | BD-3 | 95 |
| Example 3-7 | BH-7 | BD-3 | 93 |
| Example 3-8 | BH-8 | BD-3 | 100 |
| Example 3-9 | BH-9 | BD-3 | 120 |
| Comparative Example 3-1 | Comp BH-1 | BD-3 | 50 |
| Comparative Example 3-2 | Comp BH-2 | BD-3 | 25 |

Examples 4-1 to 4-9 and Comparative Examples 4-1 to 4-2

The organic EL devices were fabricated and evaluated in the same manner as in Example 1-1 except that the compound BD-4 was used as the dopant material for the emitting layer and the compounds shown in Table 4 were used as the host materials, respectively. The results are shown in Table 4.

TABLE 4

| | Emitting layer | | LT95 |
|---|---|---|---|
| | Host material | Dopant material | (h) |
| Example 4-1 | BH-1 | BD-4 | 125 |
| Example 4-2 | BH-2 | BD-4 | 120 |
| Example 4-3 | BH-3 | BD-4 | 90 |
| Example 4-4 | BH-4 | BD-4 | 85 |
| Example 4-5 | BH-5 | BD-4 | 100 |
| Example 4-6 | BH-6 | BD-4 | 105 |
| Example 4-7 | BH-7 | BD-4 | 103 |
| Example 4-8 | BH-8 | BD-4 | 110 |
| Example 4-9 | BH-9 | BD-4 | 128 |
| Comparative Example 4-1 | Comp BH-1 | BD-4 | 60 |
| Comparative Example 4-2 | Comp BH-2 | BD-4 | 35 |

Examples 5-1 to 5-9 and Comparative Examples 5-1 to 5-2

The organic EL devices were fabricated and evaluated in the same manner as in Example 1-1 except that the compound BD-5 was used as the dopant material for the emitting layer, and the compounds shown in Table 5 were used as the host materials, respectively. The results are shown in Table 5.

TABLE 5

| | Emitting layer | | LT95 |
|---|---|---|---|
| | Host material | Dopant material | (h) |
| Example 5-1 | BH-1 | BD-5 | 130 |
| Example 5-2 | BH-2 | BD-5 | 125 |
| Example 5-3 | BH-3 | BD-5 | 95 |
| Example 5-4 | BH-4 | BD-5 | 90 |
| Example 5-5 | BH-5 | BD-5 | 105 |
| Example 5-6 | BH-6 | BD-5 | 110 |
| Example 5-7 | BH-7 | BD-5 | 108 |
| Example 5-8 | BH-8 | BD-5 | 117 |
| Example 5-9 | BH-9 | BD-5 | 140 |

TABLE 5-continued

| | Emitting layer | | LT95 |
|---|---|---|---|
| | Host material | Dopant material | (h) |
| Comparative Example 5-1 | Comp BH-1 | BD-5 | 62 |
| Comparative Example 5-2 | Comp BH-2 | BD-5 | 33 |

Examples 6-1 to 6-9 and Comparative Examples 6-1 to 6-2

The organic EL devices were fabricated and evaluated in the same manner as in Example 1-1 except that the compound BD-6 was used as the dopant material for the emitting layer, and the compounds shown in Table 6 were used as the host materials, respectively. The results are shown in Table 6.

TABLE 6

| | Emitting layer | | LT95 |
|---|---|---|---|
| | Host material | Dopant material | (h) |
| Example 6-1 | BH-1 | BD-6 | 136 |
| Example 6-2 | BH-2 | BD-6 | 130 |
| Example 6-3 | BH-3 | BD-6 | 103 |
| Example 6-4 | BH-4 | BD-6 | 100 |
| Example 6-5 | BH-5 | BD-6 | 112 |
| Example 6-6 | BH-6 | BD-6 | 120 |
| Example 6-7 | BH-7 | BD-6 | 118 |
| Example 6-8 | BH-8 | BD-6 | 127 |
| Example 6-9 | BH-9 | BD-6 | 145 |
| Comparative Example 6-1 | Comp BH-1 | BD-6 | 60 |
| Comparative Example 6-2 | Comp BH-2 | BD-6 | 30 |

Examples 7-1 to 7-9 and Comparative Examples 7-1 to 7-2

The organic EL devices were fabricated and evaluated in the same manner as in Example 1-1 except that the compound BD-7 was used as the dopant material for the emitting layer, and the compounds shown in Table 7 were used as the host materials, respectively. The results are shown in Table 7.

TABLE 7

| | Emitting layer | | LT95 |
|---|---|---|---|
| | Host material | Dopant material | (h) |
| Example 7-1 | BH-1 | BD-7 | 157 |
| Example 7-2 | BH-2 | BD-7 | 150 |
| Example 7-3 | BH-3 | BD-7 | 121 |
| Example 7-4 | BH-4 | BD-7 | 118 |
| Example 7-5 | BH-5 | BD-7 | 134 |
| Example 7-6 | BH-6 | BD-7 | 140 |
| Example 7-7 | BH-7 | BD-7 | 138 |
| Example 7-8 | BH-8 | BD-7 | 147 |
| Example 7-9 | BH-9 | BD-7 | 162 |
| Comparative Example 7-1 | Comp BH-1 | BD-7 | 64 |
| Comparative Example 7-2 | Comp BH-2 | BD-7 | 44 |

Examples 8-1 to 8-9 and Comparative Examples 8-1 to 8-2

The organic EL devices were fabricated and evaluated in the same manner as in Example 1-1 except that the compound BD-8 was used as the dopant material for the emitting layer, and the compounds shown in Table 8 were used as the host materials, respectively. The results are shown in Table 8.

TABLE 8

| | Emitting layer | | LT95 |
|---|---|---|---|
| | Host material | Dopant material | (h) |
| Example 8-1 | BH-1 | BD-8 | 88 |
| Example 8-2 | BH-2 | BD-8 | 82 |
| Example 8-3 | BH-3 | BD-8 | 74 |
| Example 8-4 | BH-4 | BD-8 | 70 |
| Example 8-5 | BH-5 | BD-8 | 73 |
| Example 8-6 | BH-6 | BD-8 | 77 |
| Example 8-7 | BH-7 | BD-8 | 80 |
| Example 8-8 | BH-8 | BD-8 | 82 |
| Example 8-9 | BH-9 | BD-8 | 92 |
| Comparative Example 8-1 | Comp BH-1 | BD-8 | 40 |
| Comparative Example 8-2 | Comp BH-2 | BD-8 | 22 |

Examples 9-1 to 9-9 and Comparative Examples 9-1 to 9-2

The organic EL devices were fabricated and evaluated in the same manner as in Example 1-1 except that the compound BD-9 was used as the dopant material for the emitting layer, and the compounds shown in Table 9 were used as the host materials, respectively. The results are shown in Table 9.

TABLE 9

| | Emitting layer | | LT95 |
|---|---|---|---|
| | Host material | Dopant material | (h) |
| Example 9-1 | BH-1 | BD-9 | 105 |
| Example 9-2 | BH-2 | BD-9 | 100 |
| Example 9-3 | BH-3 | BD-9 | 85 |
| Example 9-4 | BH-4 | BD-9 | 80 |
| Example 9-5 | BH-5 | BD-9 | 87 |
| Example 9-6 | BH-6 | BD-9 | 92 |
| Example 9-7 | BH-7 | BD-9 | 85 |
| Example 9-8 | BH-8 | BD-9 | 95 |
| Example 9-9 | BH-9 | BD-9 | 110 |
| Comparative Example 9-1 | Comp BH-1 | BD-9 | 40 |
| Comparative Example 9-2 | Comp BH-2 | BD-9 | 33 |

Examples 10-1 to 10-9 and Comparative Examples 10-1 to 10-2

The organic EL devices were fabricated and evaluated in the same manner as in Example 1-1 except that the compound BD-10 was used as the dopant material for the emitting layer, and the compounds shown in Table 10 were used as the host materials, respectively. The results are shown in Table 10.

TABLE 10

| | Emitting layer | | LT95 |
|---|---|---|---|
| | Host material | Dopant material | (h) |
| Example 10-1 | BH-1 | BD-10 | 150 |
| Example 10-2 | BH-2 | BD-10 | 142 |
| Example 10-3 | BH-3 | BD-10 | 120 |
| Example 10-4 | BH-4 | BD-10 | 95 |
| Example 10-5 | BH-5 | BD-10 | 121 |
| Example 10-6 | BH-6 | BD-10 | 123 |
| Example 10-7 | BH-7 | BD-10 | 115 |
| Example 10-8 | BH-8 | BD-10 | 125 |
| Example 10-9 | BH-9 | BD-10 | 155 |
| Comparative Example 10-1 | Comp BH-1 | BD-10 | 55 |
| Comparative Example 10-2 | Comp BH-2 | BD-10 | 35 |

Examples 11-1 to 11-9 and Comparative Examples 11-1 to 11-2

The organic EL devices were fabricated and evaluated in the same manner as in Example 1-1 except that the compound BD-11 was used as the dopant material for the emitting layer, and the compounds shown in Table 11 were used as the host materials, respectively. The results are shown in Table 11.

TABLE 11

| | Emitting layer | | LT95 |
|---|---|---|---|
| | Host material | Dopant material | (h) |
| Example 11-1 | BH-1 | BD-11 | 155 |
| Example 11-2 | BH-2 | BD-11 | 143 |
| Example 11-3 | BH-3 | BD-11 | 121 |
| Example 11-4 | BH-4 | BD-11 | 96 |
| Example 11-5 | BH-5 | BD-11 | 123 |
| Example 11-6 | BH-6 | BD-11 | 124 |
| Example 11-7 | BH-7 | BD-11 | 117 |
| Example 11-8 | BH-8 | BD-11 | 127 |
| Example 11-9 | BH-9 | BD-11 | 157 |
| Comparative Example 11-1 | Comp BH-1 | BD-11 | 56 |
| Comparative Example 11-2 | Comp BH-2 | BD-11 | 34 |

Examples 12-1 to 12-9 and Comparative Examples 12-1 to 12-2

The organic EL devices were fabricated and evaluated in the same manner as in Example 1-1 except that the compound BD-12 was used as the dopant material for the emitting layer, and the compounds shown in Table 12 were used as the host materials, respectively. The results are shown in Table 12.

TABLE 12

| | Emitting layer | | LT95 |
|---|---|---|---|
| | Host material | Dopant material | (h) |
| Example 12-1 | BH-1 | BD-12 | 115 |
| Example 12-2 | BH-2 | BD-12 | 110 |
| Example 12-3 | BH-3 | BD-12 | 100 |
| Example 12-4 | BH-4 | BD-12 | 92 |
| Example 12-5 | BH-5 | BD-12 | 99 |
| Example 12-6 | BH-6 | BD-12 | 102 |

TABLE 12-continued

| | Emitting layer | | LT95 |
|---|---|---|---|
| | Host material | Dopant material | (h) |
| Example 12-7 | BH-7 | BD-12 | 95 |
| Example 12-8 | BH-8 | BD-12 | 105 |
| Example 12-9 | BH-9 | BD-12 | 119 |
| Comparative Example 12-1 | Comp BH-1 | BD-12 | 55 |
| Comparative Example 12-2 | Comp BH-2 | BD-12 | 40 |

The results of Tables 3-12 also confirmed the same trend as Tables 1 and 2. In other words, it can be seen that, even if the dopant material used is changed, the organic EL devices of Examples, in which the host material compounds BH-1 to BH-9 having deuterium atoms are used, have significantly improved device lifetime as compared with the organic EL devices of Comparative Examples, in which the host material compound Comp BH-1 or Comp BH-2 having no deuterium atom are used.

From the comparison of Examples and Comparative Examples, which use the compounds with the same chemical structure, differing only in whether or not the compound has deuterium atoms, and the same dopant materials shows that the device lifetime is greatly improved by using compounds having deuterium atoms.

Synthesis Example 1 [Synthesis of the Compound BH-1]

Synthetic Scheme of BH-1 is shown below

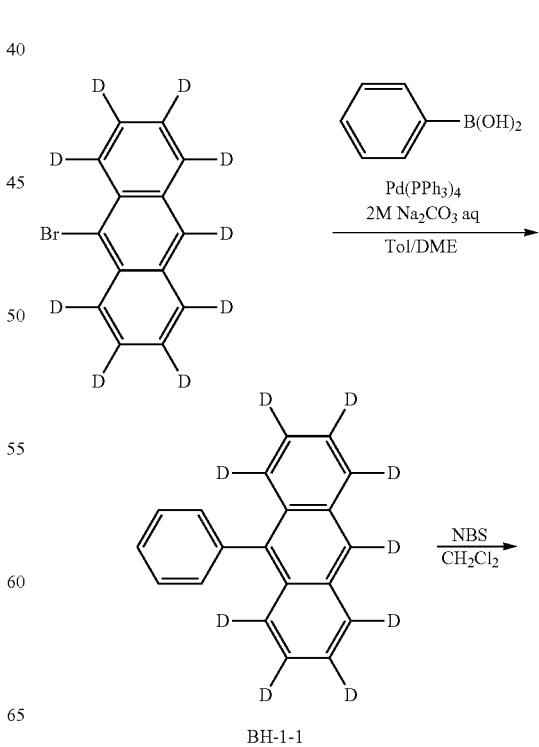

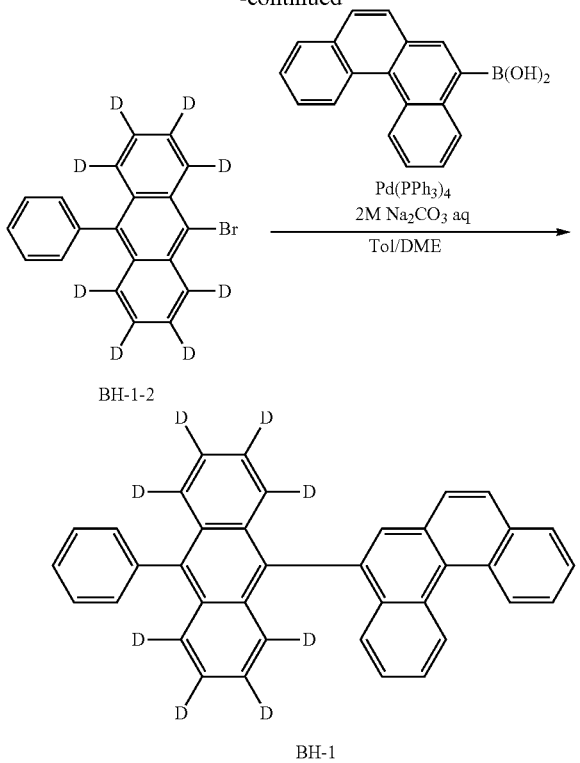

BH-1-2

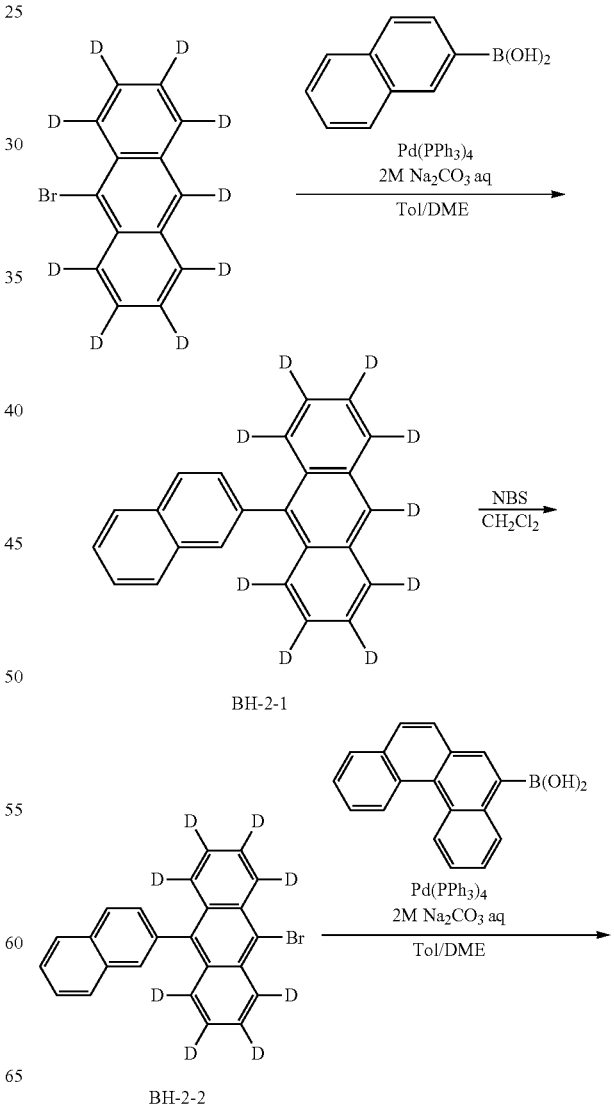

(1-1) Synthesis of BH-1-1

Under an argon atmosphere, 75 mL of toluene, 75 mL of dimethoxyethane (DME), and 75 mL of a 2M aqueous solution of $Na_2CO_3$ were added to 13.3 g (50.0 mmol) of 9-bromoanthracene-d9, 6.4 g (52.5 mmol) of phenylboronic acid, and 1.2 g (1.00 mmol) of Pd $[PPh_3]_4$, and the mixture was heated and stirred at about 80° C. for 10 hours.

After completion of the reaction, the reaction solution was cooled to room temperature and transferred to a separatory funnel and extracted with dichloromethane. The organic phase was dried over $MgSO_4$, filtered, and concentrated. The concentrated residue was purified by silica gel column chromatography to obtain 10.9 g of a white solid. The resulting compound was analyzed by FD-MS and identified as BH-1-1 (yield: 83%).

(1-2) Synthesis of BH-1-2

A solution obtained by dissolving 5.3 g (20.0 mmol) of BH-1-1 in 120 mL of dichloromethane was added dropwise to a solution obtained by dissolving 3.6 g (20.0 mmol) of N-bromosuccinimide (NBS) in 15 mL of dichloromethane at room temperature, and the mixture was stirred for 1 hour.

After completion of the reaction, the reaction solution was transferred to a separatory funnel and washed with a 2M aqueous solution of $Na_2S_2O_3$. The organic phase was further washed with 10% $Na_2CO_3$, and washed with water, and the separated organic phase was dried over $MgSO_4$, filtered, and concentrated.

The concentrated residue was dispersed in methanol (100 mL) and the precipitated crystals were collected by filtration to obtain 6.5 g of a white solid. The resulting compound was analyzed by FD-MS and identified as BH-1-2 (yield: 95%).

(1-3) Synthesis of BH-1

Under an argon atmosphere, 7.5 mL of toluene, 7.5 mL of dimethoxyethane, and 7.5 mL of an aqueous solution of 2M $Na_2CO_3$ were added to 1.7 g (5.0 mmol) of BH-1-2, 1.4 g (5.2 mmol) of benzophenanthrene-5-boronic acid, 0.1 g (0.1 mmol) of Pd $[PPh_3]_4$, and the mixture was heated and stirred at about 80° C. for 10 hours.

After completion of the reaction, the reaction solution was cooled to room temperature and transferred to a separatory funnel and extracted with dichloromethane. The organic phase was dried over $MgSO_4$, filtered, and concentrated. The concentrated residue was purified by silica gel column chromatography to obtain 1.7 g of a white solid. The resulting compound was analyzed by FD-MS and identified as compound BH-1 (70% yield).

Synthesis Example 2 [Synthesis of the Compound BH-2]

Synthetic scheme of BH-2 is shown below

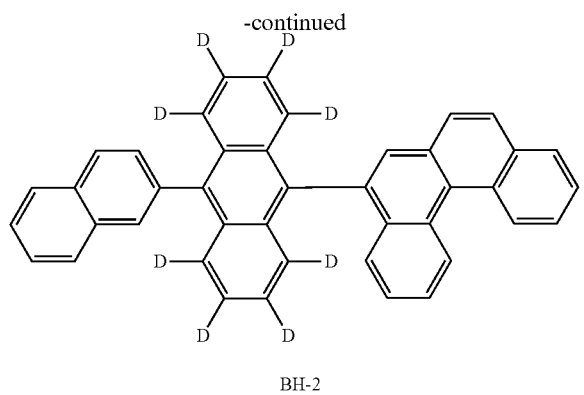

BH-2

(2-1) Synthesis of BH-2-1

Under an argon atmosphere, 75 mL of toluene, 75 mL of dimethoxyethane, and 75 mL of an aqueous solution of 2M $Na_2CO_3$ were added to 13.3 g (50.0 mmol) of 9-bromoanthracene-d9, 9.0 g (52.5 mmol) of 2-naphthylboronic acid, and 1.2 g (1.00 mmol) of Pd [$PPh_3$]$_4$, and the mixture was heated and stirred at about 80° C. for 10 hours.

After completion of the reaction, the reaction solution was cooled to room temperature and transferred to a separatory funnel and extracted with dichloromethane. The organic phase was dried over $MgSO_4$, filtered, and concentrated. The concentrated residue was purified by silica gel column chromatography to obtain 12.5 g of a white solid. The resulting compound was analyzed by FD-MS and identified as BH-2-1 (yield: 80%).

(2-2) Synthesis of BH-2-2

A solution obtained by dissolving 5.3 g (20.0 mmol) of BH-2-1 in 120 mL of dichloromethane was added dropwise to a solution obtained by dissolving 3.0 g (20.0 mmol) of N-bromosuccinimide (NBS) in 10 mL of dichloromethane at room temperature, and the mixture was stirred for 1 hour.

After completion of the reaction, the reaction solution was transferred to a separatory funnel and washed with a 2M aqueous solution of $Na_2S_2O_3$. The organic phase was further washed with 10% $Na_2CO_3$, and washed with water, and the separated organic phase was dried over $MgSO_4$, filtered, and concentrated.

The concentrated residue was dispersed in methanol (100 mL) and the precipitated crystals were collected by filtration to obtain 5.8 g of a white solid. The resulting compound was analyzed by FD-MS and identified as BH-2-2 (yield: 88%).

(2-3) Synthesis of BH-2

Under an argon atmosphere, 7.5 mL of toluene, 7.5 mL of dimethoxyethane, and 7.5 mL of an aqueous solution of 2M $Na_2CO_3$ were added to 1.7 g (5.0 mmol) of BH-2-2, 1.4 g (5.2 mmol) of benzophenanthrene-5-boronic acid, 0.1 g (0.1 mmol) of Pd [$PPh_3$]$_4$, and the mixture was heated and stirred at about 80° C. for 10 hours.

After completion of the reaction, the reaction solution was cooled to room temperature and transferred to a separatory funnel and extracted with dichloromethane. The organic phase was dried over $MgSO_4$, filtered, and concentrated. The concentrated residue was purified by silica gel column chromatography to obtain 1.5 g of a white solid. The resulting compound was analyzed by FD-MS and identified as compound BH-2 (yield: 66%).

Synthesis Example 3 [Synthesis of the Compound BH-3]

Synthetic scheme of BH-3 is shown below

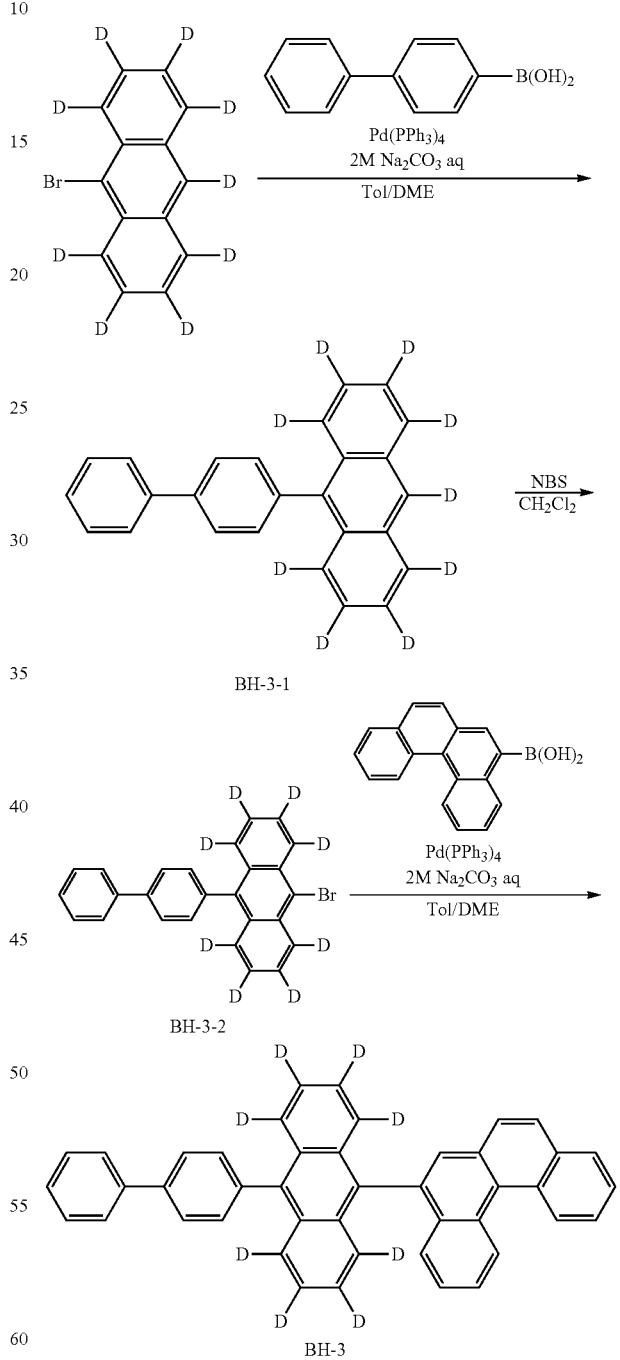

(3-1) Synthesis of BH-3-1

Under an argon atmosphere, 75 mL of toluene, 75 mL of dimethoxyethane, and 90 mL of an aqueous solution of 2M Na₂CO₃ were added to 13.3 g (50.0 mmol) of 9-bromoanthracene-d9, 10.4 g (52.5 mmol) of biphenylboronic acid, and 1.2 g (1.00 mmol) of Pd [PPh₃]₄, and the mixture was heated and stirred at about 80° C. for 10 hours.

After completion of the reaction, the reaction solution was cooled to room temperature and transferred to a separatory funnel and extracted with dichloromethane. The organic phase was dried over MgSO₄, filtered, and concentrated. The concentrated residue was purified by silica gel column chromatography to obtain 13.6 g of a white solid. The resulting compound was analyzed by FD-MS and identified as BH-3-1 (yield: 80%).

(3-2) Synthesis of BH-3-2

A solution obtained by dissolving 5.3 g (15.6 mmol) of BH-3-1 in 120 mL of dichloromethane was added dropwise to a solution obtained by dissolving 2.8 g (15.6 mmol) of N-bromosuccinimide (NBS) in 10 mL of dichloromethane at room temperature, and the mixture was stirred for 1 hour.

After completion of the reaction, the reaction solution was transferred to a separatory funnel and washed with a 2M aqueous solution of Na₂S₂O₃. The organic phase was further washed with 10% Na₂CO₃, and washed with water, and the separated organic phase was dried over MgSO₄, filtered, and concentrated.

The concentrated residue was dispersed in methanol (100 mL) and the precipitated crystals were collected by filtration to obtain 5.9 g of a white solid. The resulting compound was analyzed by FD-MS and identified as BH-3-2 (yield: 90%).

(3-3) Synthesis of BH-3

Under an argon atmosphere, 7.5 mL of toluene, 7.5 mL of dimethoxyethane, and 7.5 mL of an aqueous solution of 2M Na₂CO₃ were added to 1.5 g (3.6 mmol) of BH-3-2, 1.0 g (3.8 mmol) of benzophenanthrene-5-boronic acid, 0.1 g (0.1 mmol) of Pd [PPh₃]₄, and the mixture was heated and stirred at about 80° C. for 10 hours.

After completion of the reaction, the reaction solution was cooled to room temperature and transferred to a separatory funnel and extracted with dichloromethane. The organic phase was dried over MgSO₄, filtered, and concentrated. The concentrated residue was purified by silica gel column chromatography to obtain 1.4 g of a white solid. The resulting compound was subjected to FD-MS spectrometry and identified as compound BH-3 (yield: 70%).

Synthesis Example 4 [Synthesis of the Compound BH-4]

Synthetic scheme of BH-4 is shown below

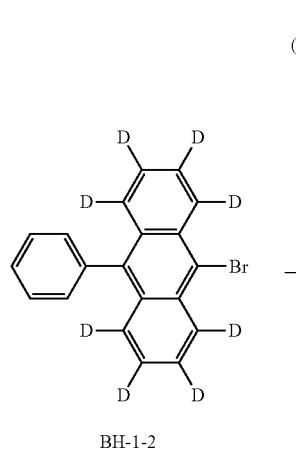

BH-1-2

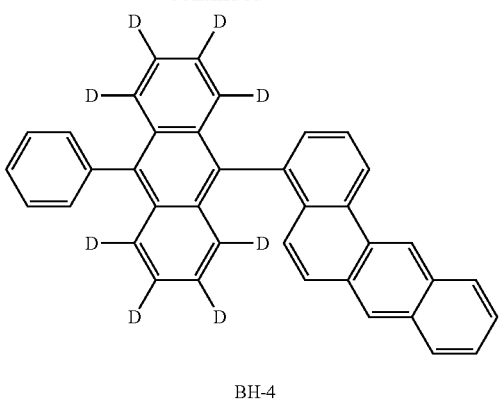

BH-4

(4-1) Synthesis of BH-4

Under an argon atmosphere, 7.5 mL of toluene, 7.5 mL of dimethoxyethane, and 7.5 mL of an aqueous solution of 2M Na₂CO₃ were added to 1.5 g (3.6 mmol) of BH-1-2, 1.0 g (3.8 mmol) of benzoanthracene-4-boronic acid, 0.1 g (0.1 mmol) of Pd [PPh₃]₄, and the mixture was heated and stirred at about 80° C. for 10 hours.

After completion of the reaction, the reaction solution was cooled to room temperature and transferred to a separatory funnel and extracted with dichloromethane. The organic phase was dried over MgSO₄, filtered, and concentrated. The concentrated residue was purified by silica gel column chromatography to obtain 1.2 g of a white solid. The resulting compound was analyzed by FD-MS and identified as compound BH-4 (yield: 60%).

Synthesis Example 5 [Synthesis of the Compound BH-5]

Synthetic scheme of BH-5 is shown below

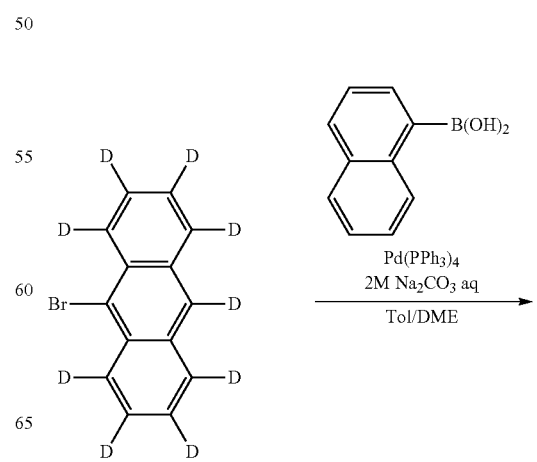

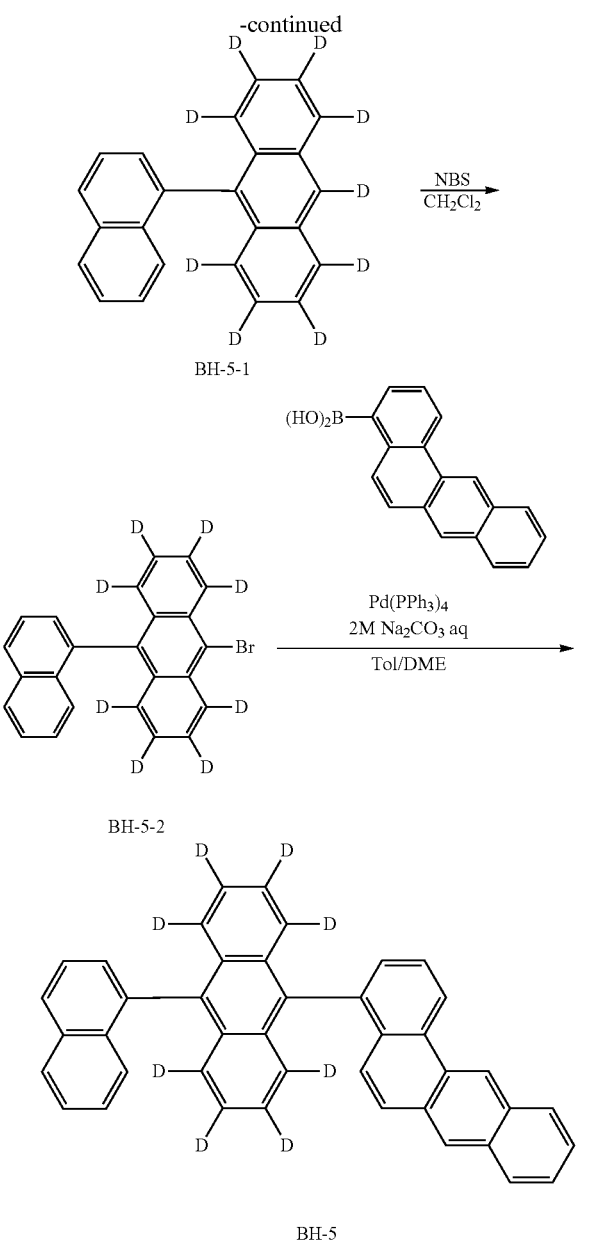

BH-5-1

BH-5-2

BH-5

(5-1) Synthesis of BH-5-1

Under an argon atmosphere, 75 mL of toluene, 75 mL of dimethoxyethane, and 75 mL of an aqueous solution of 2M $Na_2CO_3$ were added to 13.3 g (50.0 mmol) of 9-bromoanthracene-d9, 9.0 g (52.5 mmol) of 1-naphthylboronic acid, and 1.2 g (1.00 mmol) of Pd [$PPh_3$]$_4$, and the mixture was heated and stirred at about 80° C. for 10 hours.

After completion of the reaction, the reaction solution was cooled to room temperature and transferred to a separatory funnel and extracted with dichloromethane. The organic phase was dried over $MgSO_4$, filtered, and concentrated. The concentrated residue was purified by silica gel column chromatography to obtain 12.5 g of a white solid. The resulting compound was analyzed by FD-MS and identified as BH-5-1 (yield: 80%).

(5-2) Synthesis of BH-5-2

A solution obtained by dissolving 5.0 g (20.0 mmol) of BH-5-1 in 120 mL of dichloromethane was added dropwise to a solution obtained by dissolving 2.8 g (20.0 mmol) of N-bromosuccinimide (NBS) in 10 mL of dichloromethane at room temperature, and the mixture was stirred for 1 hour.

After completion of the reaction, the reaction solution was transferred to a separatory funnel and washed with a 2M aqueous solution of $Na_2S_2O_3$. The organic phase was further washed with 10% $Na_2CO_3$, and washed with water, and the separated organic phase was dried over $MgSO_4$, filtered, and concentrated.

The concentrated residue was dispersed in methanol (100 mL) and the precipitated crystals were collected by filtration to obtain 5.5 g of a white solid. The resulting compound was analyzed by FD-MS and identified as BH-5-2 (yield: 88%).

(5-3) Synthesis of BH-5

Under an argon atmosphere, 7.5 mL of toluene, 7.5 mL of dimethoxyethane, and 7.5 mL of an aqueous solution of 2M $Na_2CO_3$ were added to 1.5 g (3.8 mmol) of BH-5-2, 1.1 g (4.0 mmol) of benzoanthracene-4-boronic acid, 0.1 g (0.1 mmol) of Pd [$PPh_3$]$_4$, and the mixture was heated and stirred at about 80° C. for 10 hours.

After completion of the reaction, the reaction solution was cooled to room temperature and transferred to a separatory funnel and extracted with dichloromethane. The organic phase was dried over $MgSO_4$, filtered, and concentrated. The concentrated residue was purified by silica gel column chromatography to obtain 1.1 g of a white solid. The resulting compound was analyzed by FD-MS and identified as BH-5 (yield: 55%).

Synthesis Example 6 [Synthesis of the Compound BH-6]

Synthetic scheme of BH-6 is shown below

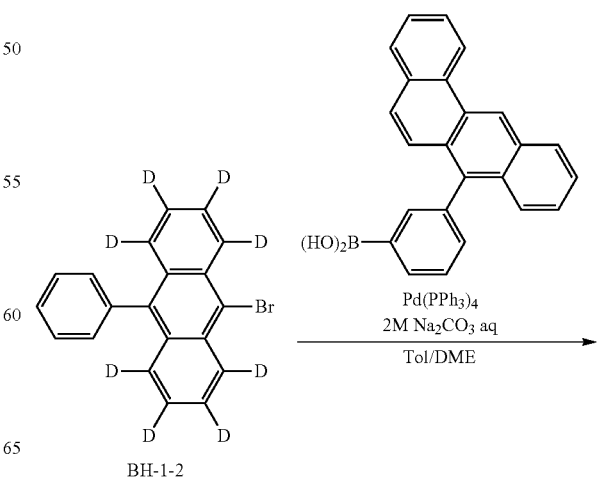

BH-1-2

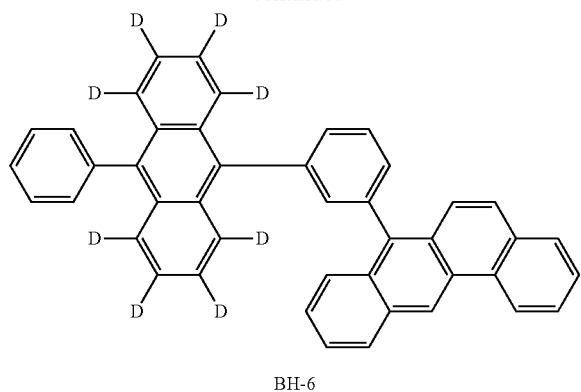

BH-6

(6-1) Synthesis of BH-6

Under an argon atmosphere, 7.5 mL of toluene, 7.5 mL of dimethoxyethane, and 7.5 mL of an aqueous solution of 2M $Na_2CO_3$ were added to 1.5 g (3.6 mmol) of BH-1-2, 1.6 g (4.6 mmol) of 3-(7-benzoanthracene)phenylboronic acid, 0.1 g (0.1 mmol) of Pd $[PPh_3]_4$, and the mixture was heated and stirred at about 80° C. for 10 hours.

After completion of the reaction, the reaction solution was cooled to room temperature and transferred to a separatory funnel and extracted with dichloromethane. The organic phase was dried over $MgSO_4$, filtered, and concentrated. The concentrated residue was purified by silica gel column chromatography to obtain 1.9 g of a white solid. The resulting compound was analyzed by FD-MS and identified as compound BH-6 (yield: 75%).

Synthesis Example 7 [Synthesis of the Compound BH-7]

Synthetic scheme of BH-7 is shown below

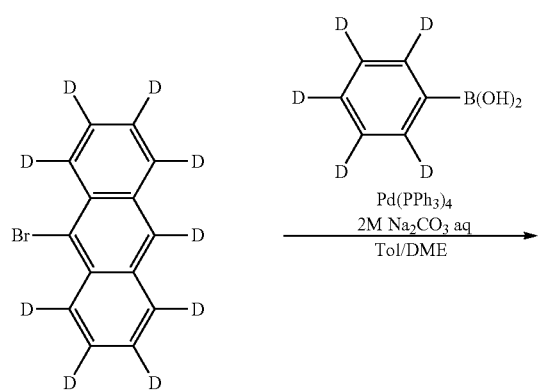

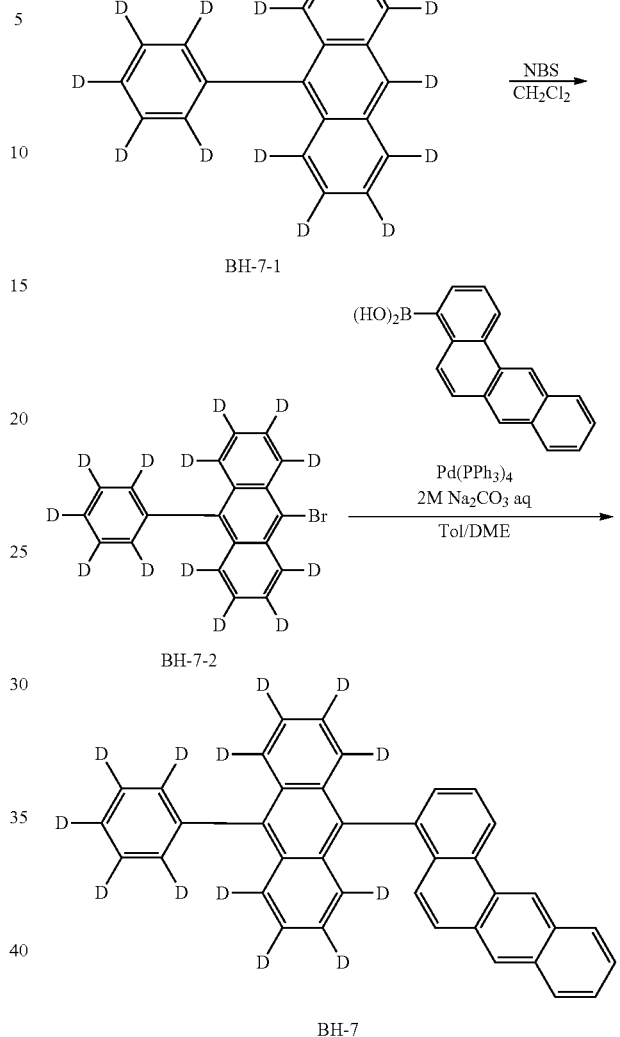

(7-1) Synthesis of BH-7-1

Under an argon atmosphere, 75 mL of toluene, 75 mL of dimethoxyethane, and 75 mL of a 2M aqueous solution of $Na_2CO_3$ were added to 13.3 g (50.0 mmol) of 9-bromoanthracene-d9, 6.7 g (52.5 mmol) of phenylboronic acid-d5, and 1.6 g (1.00 mmol) of Pd $[PPh_3]_4$, and the mixture was heated and stirred at about 80° C. for 10 hours.

After completion of the reaction, the reaction solution was cooled to room temperature and transferred to a separatory funnel and extracted with dichloromethane. The organic phase was dried over $MgSO_4$, filtered, and concentrated. The concentrated residue was purified by silica gel column chromatography to obtain 10.7 g of a white solid. The resulting compound was analyzed by FD-MS and identified as BH-7-1 (yield: 80%).

(7-2) Synthesis of BH-7-2

A solution obtained by dissolving 5.0 g (18.6 mmol) of BH-7-1 in 120 mL of dichloromethane was added dropwise to a solution obtained by dissolving 3.3 g (18.6 mmol) of N-bromosuccinimide (NBS) in 12 mL of dichloromethane at room temperature, and the mixture was stirred for 1 hour.

After completion of the reaction, the reaction solution was transferred to a separatory funnel and washed with a 2M aqueous solution of $Na_2S_2O_3$. The organic phase was further washed with 10% $Na_2CO_3$, and washed with water, and the separated organic phase was dried over $MgSO_4$, filtered, and concentrated.

The concentrated residue was dispersed in methanol (100 mL) and the precipitated crystals were collected by filtration to obtain 5.8 g of a white solid. The resulting compound was analyzed by FD-MS and identified as BH-7-2 (yield: 90%).

(7-3) Synthesis of BH-7

Under an argon atmosphere, 7.5 mL of toluene, 7.5 mL of dimethoxyethane, and 7.5 mL of an aqueous solution of 2M $Na_2CO_3$ were added to 1.7 g (5.0 mmol) of BH-7-2, 1.4 g (5.3 mmol) of benzoanthracene-4-boronic acid, 0.1 g (0.1 mmol) of Pd [PPh$_3$]$_4$, and the mixture was heated and stirred at about 80° C. for 10 hours.

After completion of the reaction, the reaction solution was cooled to room temperature and transferred to a separatory funnel and extracted with dichloromethane. The organic phase was dried over $MgSO_4$, filtered, and concentrated. The concentrated residue was purified by silica gel column chromatography to obtain 1.7 g of a white solid. The resulting compound was analyzed by FD-MS and identified as BH-7 (yield: 70%).

Synthesis Example 8 [Synthesis of the Compound BH-8]

Synthetic scheme of BH-8 is shown below

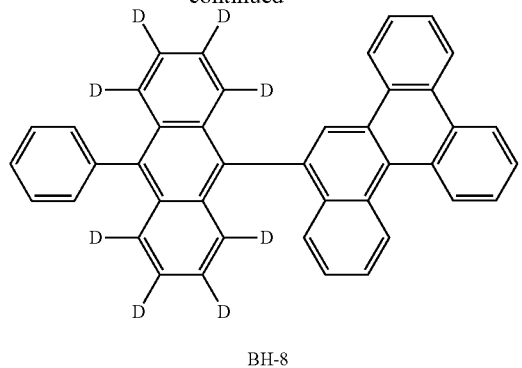

BH-8

(8-1) Synthesis of BH-8

Under an argon atmosphere, 7.5 mL of toluene, 7.5 mL of dimethoxyethane, and 7.5 mL of an aqueous solution of 2M $Na_2CO_3$ were added to 1.7 g (5.0 mmol) of BH-1-2, 1.7 g (5.3 mmol) of benzochrysen-6-boronic acid, 0.1 g (0.1 mmol) of Pd [PPh$_3$]$_4$, and the mixture was heated and stirred at about 80° C. for 10 hours.

After completion of the reaction, the reaction solution was cooled to room temperature and transferred to a separatory funnel and extracted with dichloromethane. The organic phase was dried over $MgSO_4$, filtered, and concentrated. The concentrated residue was purified by silica gel column chromatography to obtain 1.6 g of a white solid. The resulting compound was analyzed by FD-MS and identified as BH-8 (yield: 60%).

Synthesis Example 9 [Synthesis of the Compound BH-9]

Synthetic scheme of BH-9 is shown below

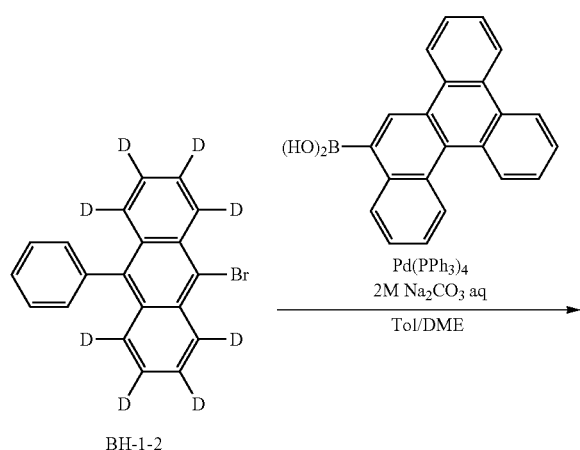

BH-1-2

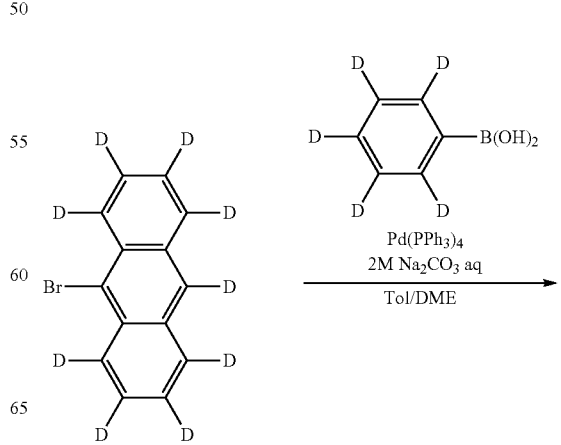

-continued

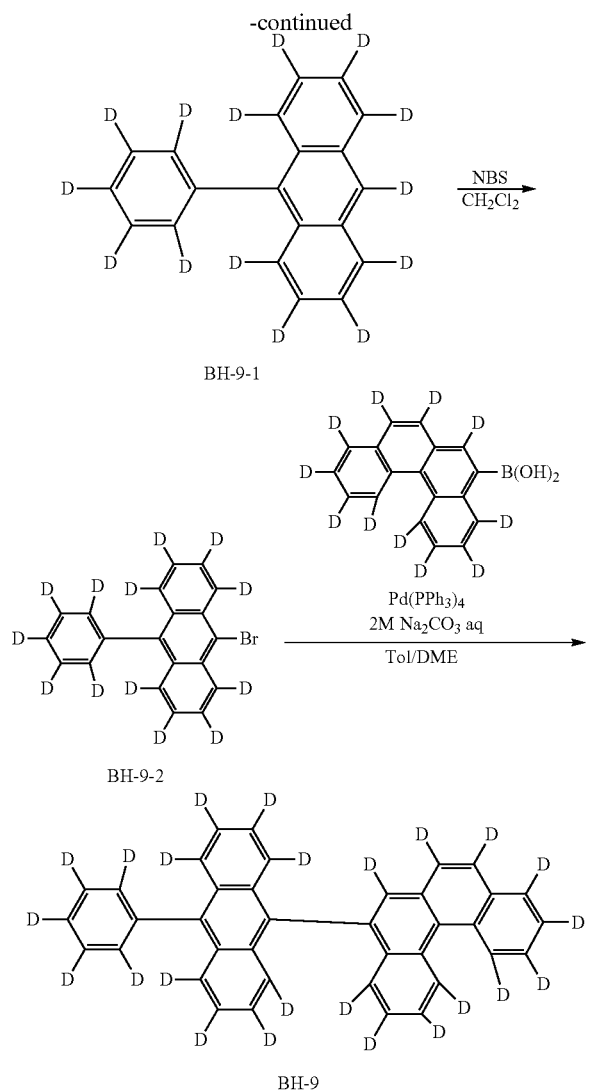

BH-9-1

BH-9-2

BH-9

(9-1) Synthesis of BH-9-1

Under an argon atmosphere, 75 mL of toluene, 75 mL of dimethoxyethane, and 75 mL of a 2M aqueous solution of $Na_2CO_3$ were added to 15.0 g (56.4 mmol) of 9-bromoanthracene-d9, 10.7 g (85.0 mmol) of phenylboronic acid-d5, and 1.3 g (1.13 mmol) of Pd $[PPh_3]_4$, and the mixture was heated and stirred at about 80° C. for 10 hours.

After completion of the reaction, the mixture was cooled to room temperature, and the sample was transferred to a separatory funnel and extracted with dichloromethane. The organic phase was dried over $MgSO_4$, filtered, and concentrated. The concentrated residue was purified by silica gel column chromatography to obtain 12.1 g of a white solid. The resulting compound was analyzed by FD-MS and identified as BH-9-1 (yield: 80%).

(9-2) Synthesis of BH-9-2

A solution obtained by dissolving 10.0 g (37.3 mmol) of BH-9-1 in 240 mL of dichloromethane was added dropwise to a solution obtained by dissolving 6.6 g (37.3 mmol) of N-bromosuccinimide (NBS) in 30 mL of dichloromethane at room temperature, and the mixture was stirred for 1 hour.

After completion of the reaction, the sample was transferred to a separatory funnel and washed with a 2M aqueous solution of $Na_2S_2O_3$. The organic phase was further washed with 10% $Na_2CO_3$, and washed with water, and the separated organic phase was dried over $MgSO_4$, filtered, and concentrated.

The concentrated residue was dispersed in methanol (200 mL) and the precipitated crystals were collected by filtration to obtain 7.7 g of a white solid. The resulting compound was analyzed by FD-MS and identified as BH-9-2 (yield: 60%).

(9-3) Synthesis of BH-9

Under an argon atmosphere, 15 mL of toluene, 15 mL of dimethoxyethane, and 15 mL of an aqueous solution of 2M $Na_2CO_3$ were added to 5.0 g (14.4 mmol) of BH-9-2, 4.1 g (14.4 mmol) of benzophenanthrene-5-boronic acid-d11, 0.3 g (0.3 mmol) of Pd $[PPh_3]_4$, and the mixture was heated and stirred at about 80° C. for 10 hours.

After completion of the reaction, the mixture was cooled to room temperature, and the sample was transferred to a separatory funnel and extracted with dichloromethane. The organic phase was dried over $MgSO_4$, filtered, and concentrated. The concentrated residue was purified by silica gel column chromatography to obtain 4.0 g of a white solid. The resulting compound was analyzed by FD-MS and identified as compound BH-9 (yield: 55%).

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The invention claimed is:

1. A compound represented by the following formula (1):

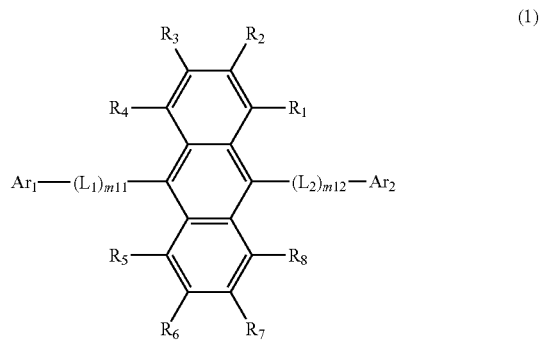

wherein in the formula (1),
$R_1$ to $R_8$ are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O-($R_{904}$), —S-(R$_{905}$),
—N(R$_{906}$)(R$_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
R$_{901}$ to R$_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms;
  when two or more of each of R$_{901}$ to R$_{907}$ are present, the two or more of each of R$_{901}$ to R$_{907}$ are the same or different;
  adjacent two or more of R$_1$ to R$_8$ do not form a ring by bonding with each other;
  provided that at least one of R$_1$ to R$_8$ is a deuterium atom;
  L$_1$ and L$_2$ are independently
a substituted or unsubstituted arylene group including 6 to 30 ring carbon atoms, or
a substituted or unsubstituted divalent heterocyclic group including 5 to 30 ring atoms;
  m11 and m12 are independently an integer of 0 to 4;
  when m11 and m12 are 0, (L$_1$)$_{m11}$ and (L$_2$)$_{m12}$ are single bonds;
  when m11 or m12 is 2 or more, the two or more m11 or m12 may be the same as or different from each other;
  Ar$_1$ and Ar$_2$ are independently
a substituted or unsubstituted aryl group including 6 to 50 ring carbon atoms, or
a substituted or unsubstituted monovalent heterocyclic group including 5 to 50 ring atoms;
  provided that at least one of Ar$_1$ and Ar$_2$ is a substituted or unsubstituted fused aryl group in which only four or more benzene rings are fused; and
  one or more hydrogen atoms possessed by one or more of the groups selected from L$_1$, L$_2$, Ar$_1$ and Ar$_2$ may be deuterium atoms, and
wherein the substituted or unsubstituted fused aryl group in which only four or more benzene rings are fused is a substituted or unsubstituted monovalent group derived from a polycyclic fused aromatic hydrocarbon selected from the group consisting of the following formulas (b1) to (b4):

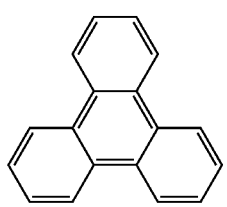
(b1)

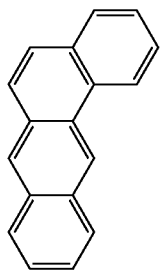
(b2)

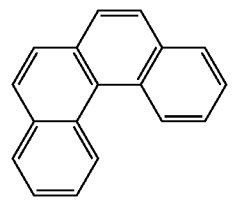
(b3)

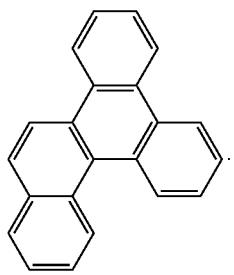
(b4)

2. The compound according to claim 1, wherein one of Ar$_1$ and Ar$_2$ is the fused aryl group in which only four or more benzene rings are fused.

3. The compound according to claim 1, wherein (L$_1$)$_{m11}$ and (L$_2$)$_{m12}$ are independently
a single bond,
a substituted or unsubstituted phenylene group,
a substituted or unsubstituted biphenylene group, or
a substituted or unsubstituted naphthylene group.

4. The compound according to claim 1, wherein m11 and m12 are 1 or more and (L$_1$)$_{m11}$ and (L$_2$)$_{m12}$ are independently selected from the group consisting of divalent groups represented by the following formulas (a1) to (a17):

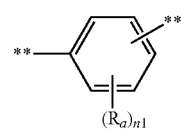
(a1)

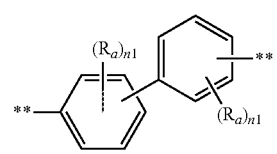
(a2)

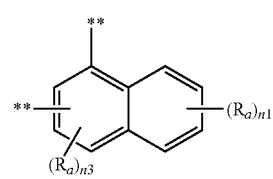
(a3)

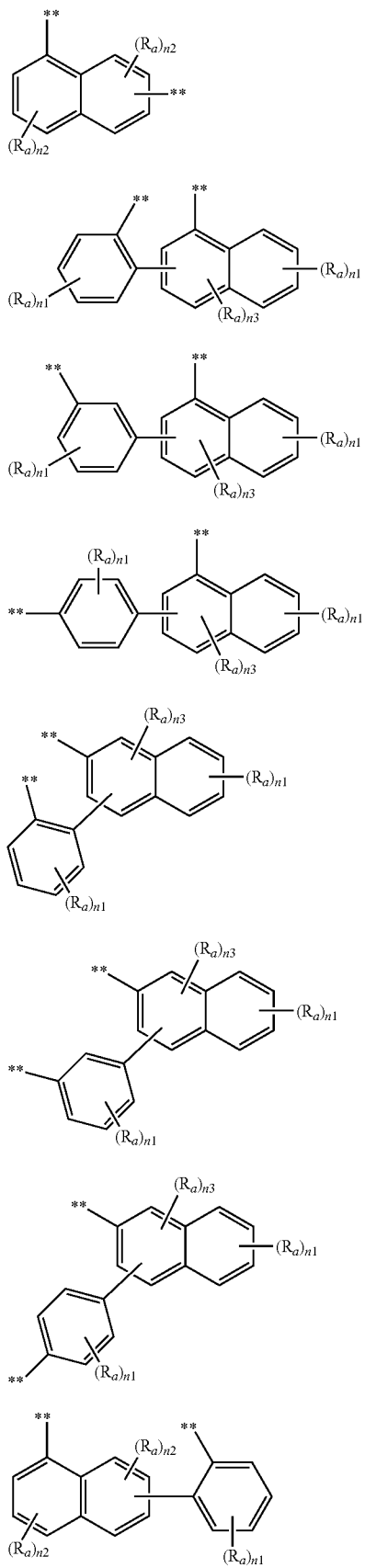

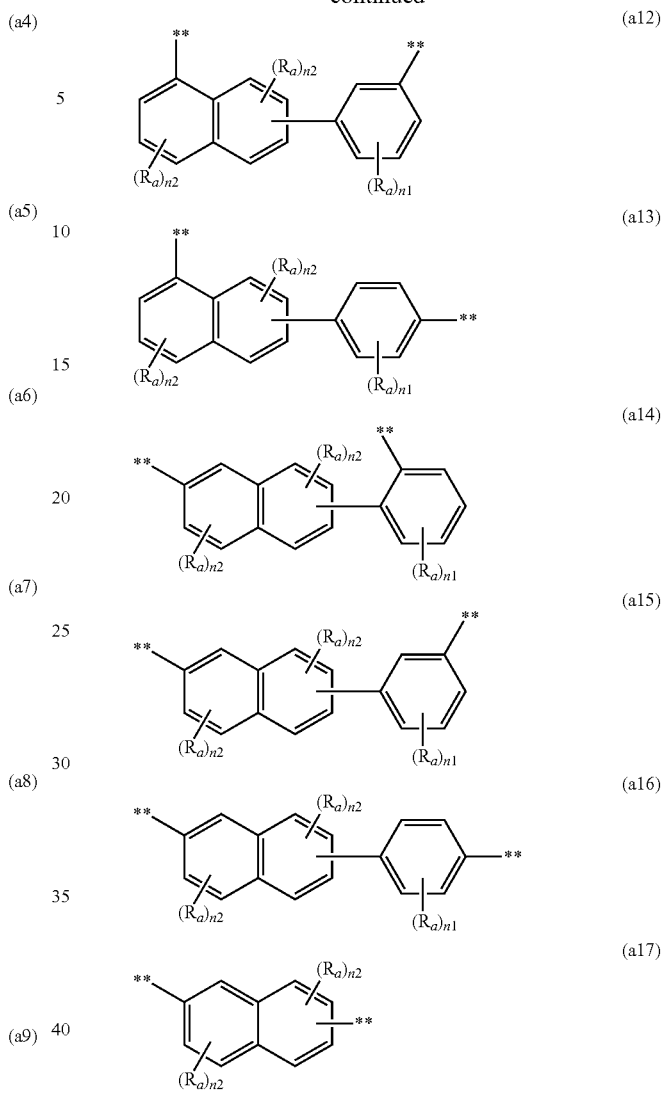

wherein in the formulas (a1) to (a17),

\*\*'s respectively represent binding positions with anthracene skeleton and $Ar_1$ or $Ar_2$;

$R_a$ is a substituent;

n1 is an integer of 0 to 4;

n2 is an integer of 0 to 3;

n3 is an integer of 0 to 2; and when n1, n2, and n3 are 2 or more, a plurality of $R_a$'s may be the same as or different from each other.

5. The compound according to claim 1, wherein m11 and m12 are 0.

6. The compound according to claim 1, wherein at least one of m11 and m12 is 2, $(L_1)_{m11}$ and $(L_2)_{m12}$ are independently represented by $(L_1)$-$(L_1)$ and $(L_2)$-$(L_2)$; and the plurality of each of $L_1$'s and $L_2$'s are independently a substituted or unsubstituted phenylene group, or a substituted or unsubstituted naphthylene group.

7. The compound according to claim 1, wherein the compound represented by the formula (1) is a compound represented by the following formula (1-1):

(1-1)

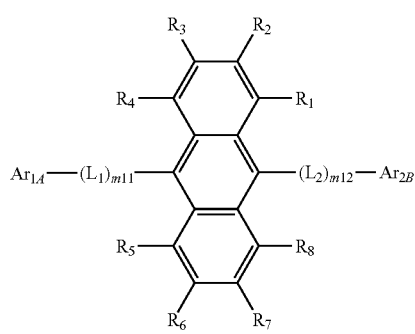

wherein in the formula (1-1), $R_1$ to $R_8$, $L_1$, $L_2$, m11, and m12 are as defined in the formula (1);

$Ar_{1A}$ is a substituted or unsubstituted aryl group including 6 to 50 ring carbon atoms other than a fused aryl group in which only four or more benzene rings are fused;

$Ar_{2B}$ is the fused aryl group selected from the group consisting of the following formulas (b1) to (b4):

(b1)

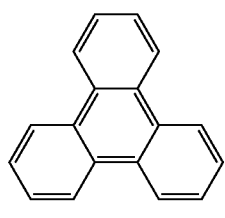

(b2)

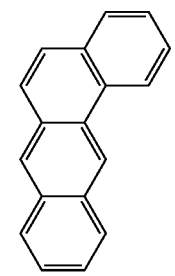

(b3)

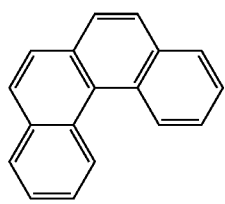

(b4)

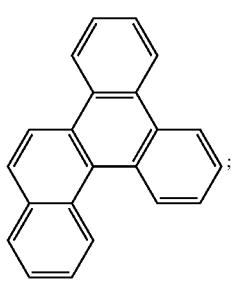

;

and one or more hydrogen atoms possessed by one or more of the groups selected from $L_1$, $L_2$, $Ar_{1A}$, and $Ar_{2B}$ may be deuterium atoms.

8. The compound according to claim 1, wherein the compound represented by the formula (1) is a compound represented by the following formula (1-2):

(1-2)

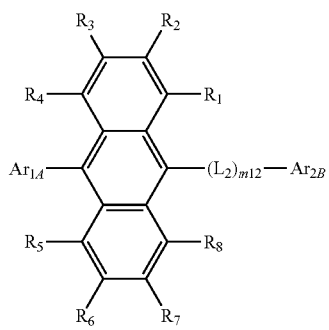

wherein in the formula (1-2), $R_1$ to $R_8$, $L_2$, and m12 are as defined in the formula (1);

$Ar_{1A}$ is a substituted or unsubstituted aryl group including 6 to 50 ring carbon atoms other than a fused aryl group in which only four or more benzene rings are fused;

$Ar_{2B}$ is the fused aryl group selected from the group consisting of the following formulas (b1) to (b4):

(b1)

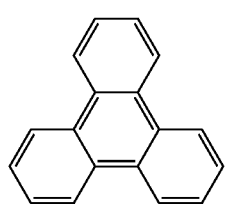

(b2)

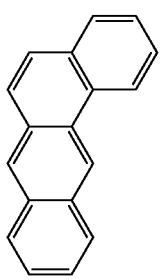

(b3)

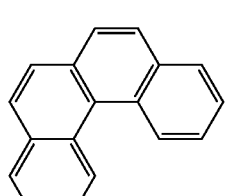

-continued (b4)
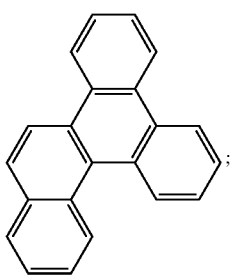

and
one or more hydrogen atoms possessed by one or more of the groups selected from $L_2$, $Ar_1$ A and $Ar_{2B}$ may be deuterium atoms.

9. The compound according to claim 1, wherein the compound represented by the formula (1) is a compound represented by the following formula (1-3):

(1-3)
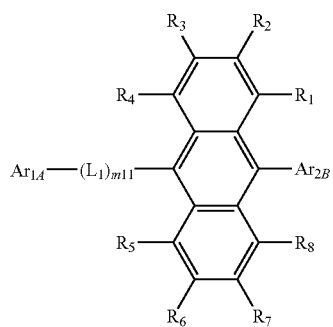

wherein in the formula (1-3), $R_1$ to $R_8$, $L_1$, and m11 are as defined in the formula (1);
$Ar_1$ A is a substituted or unsubstituted aryl group including 6 to 50 ring carbon atoms other than a fused aryl group in which only four or more benzene rings are fused;
$Ar_{2B}$ is the fused aryl group selected from the group consisting of the following formulas (b1) to (b4):

(b1)
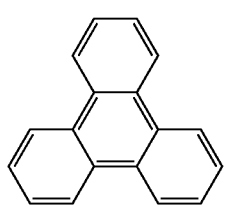

(b2)
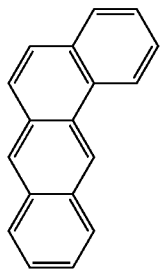

-continued (b3)
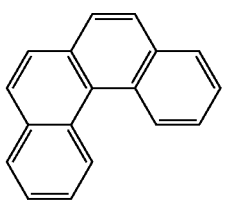

(b4)
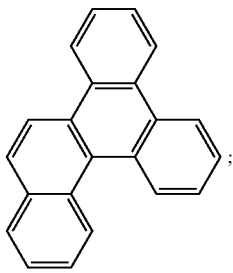

and
one or more hydrogen atoms possessed by one or more of the groups selected from $L_1$, $Ar_{1A}$ and $Ar_{2B}$ may be deuterium atoms.

10. The compound according to claim 7, wherein $Ar_{1A}$ is
a substituted or unsubstituted phenyl group,
a substituted or unsubstituted naphthyl group,
a substituted or unsubstituted biphenylyl group, or
a substituted or unsubstituted phenanthryl group.

11. The compound according to claim 1, wherein one or more hydrogen atoms possessed by one or more groups selected from $L_1$, $L_2$, $Ar_1$, and $Ar_2$ are deuterium atoms.

12. The compound according to claim 1, wherein one or more hydrogen atoms possessed by one or more groups selected from $Ar_1$ or $Ar_2$ which are not the fused aryl group in which only four or more benzene rings are fused are deuterium atoms.

13. The compound according to claim 1, wherein all hydrogen atoms possessed by $L_1$, $L_2$, $Ar_1$, and $Ar_2$ are protium atoms.

14. The compound according to claim 1, wherein one to eight of $R_1$ to $R_8$ are deuterium atoms.

15. The compound according to claim 1, wherein all of $R_1$ to $R_8$ are deuterium atoms.

16. A material for an organic electroluminescence device, comprising the compound according to claim 1.

17. A composition comprising a compound according to claim 1,
wherein the content ratio of a compound having the same structure as formula (1) except that only protium atoms are contained as hydrogen atoms to the total of the compound represented by the formula (1) and the compound having the same structure as formula (1) except that only protium atoms are contained as hydrogen atoms is 99 mol % or less.

18. An organic electroluminescence device comprising:
a cathode,
an anode, and
an emitting layer disposed between the cathode and the anode, wherein
the emitting layer comprises the compound according to claim 1.

19. The organic electroluminescence device according to claim 18, wherein the emitting layer further comprises a dopant material.

20. The organic electroluminescence device according to claim 19, wherein the dopant material is one or more compounds selected from the group consisting of a compound represented by the formula (11), a compound represented by the formula (21), a compound represented by the formula (31), a compound represented by the formula (41), a compound represented by the formula (51), a compound represented by the formula (61), a compound represented by the formula (71), and a compound represented by the formula (81):

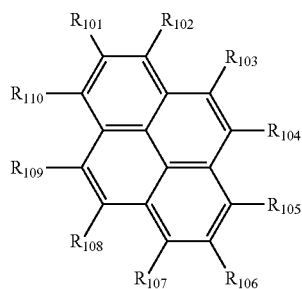

(11)

wherein in the formula (11),
one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;
at least one of $R_{101}$ to $R_{110}$ is a monovalent group represented by the formula (12);
$R_{101}$ to $R_{110}$ that do not form the substituted or unsubstituted, saturated or unsaturated ring and that are not a monovalent group represented by the following formula (12) are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O-($R_{904}$),
—S-($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are as defined in the formula (1);

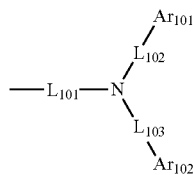

(12)

wherein in the formula (12), $Ar_{101}$ and $Ar_{102}$ are independently
a substituted or unsubstituted aryl group including 6 to 50 ring carbon atoms, or
a substituted or unsubstituted monovalent heterocyclic group including 5 to 50 ring atoms;
$L_{101}$ to $L_{103}$ are independently
a single bond,
a substituted or unsubstituted arylene group including 6 to 30 ring carbon atoms, or
a substituted or unsubstituted divalent heterocyclic group including 5 to 30 ring atoms;

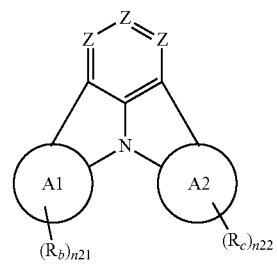

(21)

wherein in the formula (21),
Zs are independently $CR_a$ or N;
A1 ring and A2 ring are independently a substituted or unsubstituted aromatic hydrocarbon ring including 6 to 50 ring carbon atoms, or a substituted or unsubstituted heterocyclic ring including 5 to 50 ring atoms;
when plural $R_a$s exist, one or more pairs of two or more adjacent groups of $R_a$ are bonded with each other to form a substituted or unsubstituted, saturated or unsaturated ring, or do not form a substituted or unsubstituted, saturated or unsaturated ring;
when plural $R_b$s exist, one or more pairs of two or more adjacent groups of $R_b$ are bonded with each other to form a substituted or unsubstituted, saturated or unsaturated ring, or do not form a substituted or unsubstituted, saturated or unsaturated ring;
when plural Res exist, one or more pairs of two or more adjacent groups of $R_c$ are bonded with each other to form a substituted or unsubstituted, saturated or unsaturated ring, or do not form a substituted or unsubstituted, saturated or unsaturated ring;
n21 and n22 are independently an integer of 0 to 4;
$R_a$ to $R_c$ that do not form the substituted or unsubstituted, saturated or unsaturated ring are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O-($R_{904}$),
—S-($R_{905}$),
—N($R_{906}$)($R_{907}$),
a halogen atom, a cyano group, a nitro group,
a substituted or unsubstituted aryl group including 6 to 50 ring carbon atoms, or a substituted or unsubstituted monovalent heterocyclic group including 5 to 50 ring atoms; and
$R_{901}$ to $R_{907}$ are as defined in the formula (1);

(31)

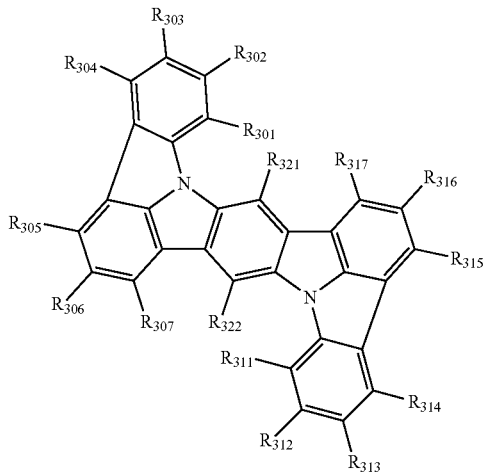

wherein in the formula (31),
one or more pairs of two or more adjacent groups of $R_{301}$ to $R_{307}$ and $R_{311}$ to $R_{317}$ form a substituted or unsubstituted, saturated or unsaturated ring, or do not form a substituted or unsubstituted, saturated or unsaturated ring;
$R_{301}$ to $R_{307}$ and $R_{311}$ to $R_{317}$ that do not form the substituted or unsubstituted, saturated or unsaturated ring are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O-($R_{904}$),
—S-($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
$R_{321}$ and $R_{322}$ are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O-($R_{904}$),
—S-($R_{905}$),
—N($R_{906}$)($R_{907}$),
a halogen atom, a cyano group, a nitro group, a substituted or unsubstituted aryl group including 6 to 50 ring carbon atoms, or
a substituted or unsubstituted monovalent heterocyclic group including 5 to 50 ring atoms; and
$R_{901}$ to $R_{907}$ are as defined in the formula (1);

(41)

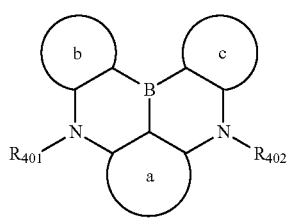

wherein in the formula (41),
a ring, b ring and c ring are independently
a substituted or unsubstituted aromatic hydrocarbon ring including 6 to 50 ring carbon atoms, or
a substituted or unsubstituted heterocyclic ring including 5 to 50 ring atoms;
$R_{401}$ and $R_{402}$ are independently bonded to the a ring, the b ring or the c ring to form a substituted or unsubstituted heterocyclic ring or do not form a substituted or unsubstituted heterocyclic ring;
$R_{401}$ and $R_{402}$ that do not form the substituted or unsubstituted heterocyclic ring are independently
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms;

(51)
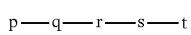
p—q—r—s—t

(52)
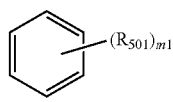
($R_{501}$)$_{m1}$

(53)
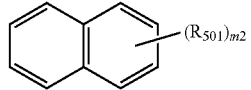
($R_{501}$)$_{m2}$

(54)
$X_{501}$

(55)
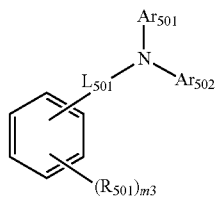
$Ar_{501}$
$L_{501}$—N—$Ar_{502}$
($R_{501}$)$_{m3}$

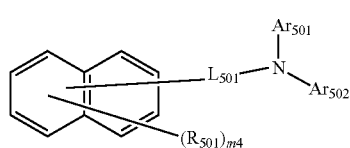

(56)

wherein in the formula (51),
r ring is a ring represented by the formula (52) or formula (53) which is fused to an adjacent ring at an arbitrary position;
q ring and s ring are independently a ring represented by the formula (54) which is fused to an adjacent ring at an arbitrary position;
p ring and t ring are independently a ring represented by the formula (55) or the formula (56) which is fused to an adjacent ring at an arbitrary position;
when plural $R_{501}$'s exist, adjacent plural $R_{501}$'s are bonded with each other to form a substituted or unsubstituted, saturated or unsaturated ring, or do not form a substituted or unsubstituted, saturated or unsaturated ring;
$X_{501}$ is an oxygen atom, a sulfur atom, or $NR_{502}$;
$R_{501}$ and $R_{502}$ that do not form the substituted or unsubstituted saturated or unsaturated ring are
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O-($R_{904}$),
—S-($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are as defined in the formula (1);
$Ar_{501}$ and $Ar_{502}$ are independently
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms;
$L_{501}$ is
a substituted or unsubstituted alkylene group including 1 to 50 carbon atoms,
a substituted or unsubstituted alkenylene group including 2 to 50 carbon atoms,
a substituted or unsubstituted alkynylene group including 2 to 50 carbon atoms,
a substituted or unsubstituted cycloalkylene group including 3 to 50 ring carbon atoms,
a substituted or unsubstituted arylene group including 6 to 50 ring carbon atoms, or
a substituted or unsubstituted divalent heterocyclic group including 5 to 50 ring atoms;
m1 is independently an integer of 0 to 2, m2 is independently an integer of 0 to 4, m3 is independently an integer of 0 to 3, and m4 is independently an integer of 0 to 5; when plural $R_{501}$'s exist, the plural $R_{501}$'s may be the same or different;

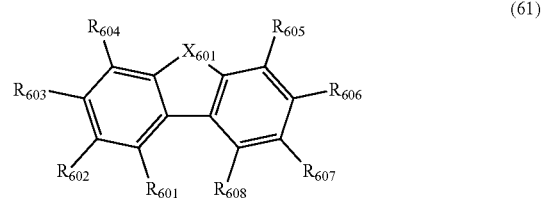

(61)

wherein in the formula (61),
at least one pair of $R_{601}$ and $R_{602}$, $R_{602}$ and $R_{603}$, and $R_{603}$ and $R_{604}$ are bonded with each other to form a divalent group represented by the formula (62);
at least one pair of $R_{605}$ and $R_{606}$, $R_{606}$ and $R_{607}$, and $R_{607}$ and $R_{608}$ are bonded with each other to form a divalent group represented by formula (63);

(62)

(63)

at least one of $R_{601}$ to $R_{604}$ that does not form the divalent group represented by the formula (62), and $R_{611}$ to $R_{614}$ is a monovalent group represented by the following formula (64);
at least one of $R_{605}$ to $R_{608}$ that do not form the divalent group represented by the formula (63), and $R_{621}$ to $R_{624}$ is a monovalent group represented by the following formula (64);
$X_{601}$ is an oxygen atom, a sulfur atom, or $NR_{609}$;
$R_{601}$ to $R_{608}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently
a hydrogen atom,
a substituted or unsubstituted alkyl group including 1 to 50 carbon atoms, a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O-($R_{904}$),
—S-($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are as defined in the formula (1);

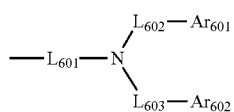

(64)

wherein in the formula (64), $Ar_{601}$ and $Ar_{602}$ are independently
a substituted or unsubstituted aryl group including 6 to 50 ring carbon atoms, or
a substituted or unsubstituted monovalent heterocyclic group including 5 to 50 ring atoms;
$L_{601}$ to $L_{603}$ are independently
a single bond,
a substituted or unsubstituted arylene group including 6 to 30 ring carbon atoms,
a substituted or unsubstituted divalent heterocyclic group including 5 to 30 ring atoms, or
a divalent linking group formed by bonding 2 to 4 above mentioned groups;

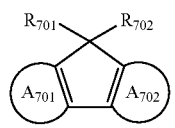

(71)

wherein in the formula (71),
$A_{701}$ ring and $A_{702}$ ring are independently
a substituted or unsubstituted aromatic hydrocarbon ring including 6 to 50 ring carbon atoms, or
a substituted or unsubstituted heterocyclic ring including 5 to 50 ring atoms;
One or more rings selected from the group consisting of $A_{701}$ ring and $A_{702}$ ring are bonded to the bond * of the structure represented by the following formula (72);

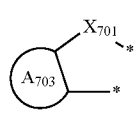

(72)

wherein in the formula (72),
$A_{703}$ rings are independently
a substituted or unsubstituted aromatic hydrocarbon ring including 6 to 50 ring carbon atoms, or
a substituted or unsubstituted heterocyclic ring including 5 to 50 ring atoms;
$X_{701}$ is $NR_{703}$, $C(R_{704})(R_{705})$, $Si(R_{706})(R_{707})$, $Ge(R_{708})(R_{709})$, O, S or Se;
$R_{701}$ and $R_{702}$ are bonded with each other to form a substituted or unsubstituted, saturated or unsaturated ring or do not form a substituted or unsubstituted saturated or unsaturated ring;
$R_{701}$ and $R_{702}$ that do not form the substituted or unsubstituted, saturated or unsaturated ring, and $R_{703}$ to $R_{709}$ are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O-($R_{904}$),
—S-($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are as defined in the formula (1);

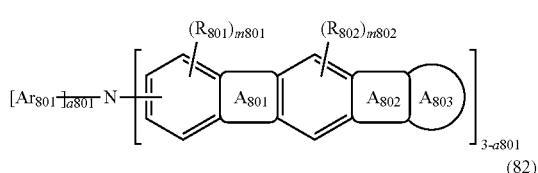

(81)

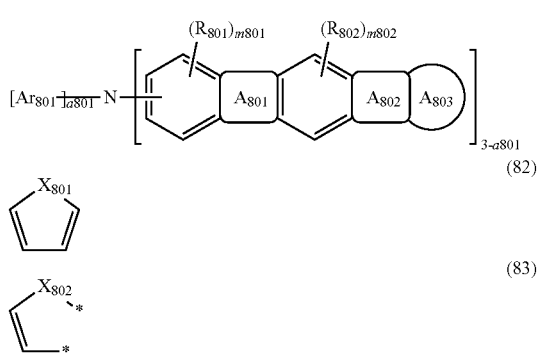

(82)

(83)

wherein in the formula (81),
$A_{801}$ ring is a ring represented by the formula (82) which is fused to an adjacent ring at an arbitrary position;
$A_{802}$ ring is a ring represented by the formula (83) which is fused to an adjacent ring at an arbitrary position; two bonds * bond to $A_{803}$ ring at an arbitrary position;
$X_{801}$ and $X_{802}$ are independently $C(R_{803})(R_{804})$, $Si(R_{805})(R_{806})$, an oxygen atom, or a sulfur atom;
$A_{803}$ ring is a substituted or unsubstituted aromatic hydrocarbon ring including 6 to 50 ring carbon atoms, or a substituted or unsubstituted heterocyclic ring including 5 to 50 ring atoms;
$Ar_{801}$ is a substituted or unsubstituted aryl group including 6 to 50 ring carbon atoms, or a substituted or unsubstituted monovalent heterocyclic group including 5 to 50 ring atoms;
$R_{801}$ to $R_{806}$ are independently
a hydrogen atom,
a substituted or unsubstituted alkyl group including 1 to 50 carbon atoms, a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O-($R_{904}$),
—S-($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are as defined in the formula (1);
m801 and m802 are independently an integer of 0 to 2; when these are 2, plural $R_{801}$'s or $R_{802}$'s may be the same or different;
a801 is an integer of 0 to 2; when a801 is 0 or 1, the structure in the parenthese indicated by "3-a801" may be the same or different from each other; when a801 is 2, $Ar_{801}$'s may be the same or different from each other.

21. The organic electroluminescence device according to claim 18, further comprising a hole-transporting layer between the anode and the emitting layer.

22. The organic electroluminescence device according to claim 18, further comprising an electron-transporting layer between the cathode and the emitting layer.

23. An electronic apparatus, wherein the organic electroluminescence device according to claim 18 is provided.

* * * * *